(12) United States Patent
Bentwich

(10) Patent No.: US 7,250,496 B2
(45) Date of Patent: Jul. 31, 2007

(54) BIOINFORMATICALLY DETECTABLE GROUP OF NOVEL REGULATORY GENES AND USES THEREOF

(75) Inventor: Isaac Bentwich, Kvuzat Shiler (IL)

(73) Assignee: Rosetta Genomics Ltd., Rehovot (IL)

( * ) Notice: Subject to any disclaimer, the term of this patent is extended or adjusted under 35 U.S.C. 154(b) by 714 days.

(21) Appl. No.: 10/310,914

(22) Filed: Dec. 6, 2002

(65) Prior Publication Data

US 2006/0003322 A1    Jan. 5, 2006

Related U.S. Application Data

(63) Continuation-in-part of application No. 10/293,338, filed on Nov. 14, 2002, now abandoned.

(51) Int. Cl.
  C07H 21/02  (2006.01)
  C07H 21/04  (2006.01)
  C12N 15/00  (2006.01)
  C12N 15/09  (2006.01)
  C12N 15/63  (2006.01)
  C12N 15/70  (2006.01)
  C12N 15/74  (2006.01)

(52) U.S. Cl. .................. 536/23.1; 435/320.1
(58) Field of Classification Search ............... 536/23.1; 435/320.1
See application file for complete search history.

(56) References Cited

U.S. PATENT DOCUMENTS

| | | | |
|---|---|---|---|
| 6,203,992 B1 * | 3/2001 | Granados et al. | 435/6 |
| 6,207,380 B1 * | 3/2001 | Billing-Medel et al. | 435/6 |
| 6,361,940 B1 * | 3/2002 | Van Ness et al. | 435/6 |
| 6,566,072 B1 * | 5/2003 | Watson et al. | 435/7.1 |
| 7,049,425 B2 * | 5/2006 | Wheeler et al. | 536/23.5 |
| 2002/0086356 A1 | 7/2002 | Tuschl et al. | |

FOREIGN PATENT DOCUMENTS

| | | |
|---|---|---|
| WO | WO 2001/068836 | 9/2001 |
| WO | WO 2002/044321 | 6/2002 |
| WO | WO 2002/094185 | 11/2002 |

OTHER PUBLICATIONS

Gallinaro, H., L. Domenjoud and M. Jacob. Structural study of the 5' end of a synthetic premessenger RNA from adenovirus. Evidence for a long-range exon-intron interaction J Mol Biol Jul. 15, 1994 205-225 240.
Lu, C. and R. Bablanian. Characterization of small nontranslated polyadenylylated RNAs in vaccinia virus-infected cells Proc Natl Acad Sci U S A Mar. 5, 1996 2037-2042 93.
Crawford, E. D., E. P. Deantoni, R. Etzioni, V. C. Schaefer, R. M. Olson and C. A. Ross. Serum prostate-specific antigen and digital rectal examination for early detection of prostate cancer in a national community-based program. The Prostate Cancer Education Council Urology Jun. 1996 863-869 47.
Engdahl HM, Hjalt TA, Wagner EG. A two unit antisense RNA cassette test system for silencing of target genes. Nucleic Acids Res. Aug. 15, 1997 3218-27 25.
Dsouza, M., N. Larsen and R. Overbeek. Searching for patterns in genomic data Trends Genet Dec. 1997, 497-498 13.
Moss, E. G., R. C. Lee and V. Ambros. The cold shock domain protein LIN-28 controls developmental timing in *C. elegans* and is regulated by the lin-4 RNA Cell 1997 637 88.
Fire, A., S. Xu, M. K. Montgomery, S. A. Kostas, S. E. Driver and C. C. Mello. Potent and specific genetic interference by double-stranded RNA in *Caenorhabditis elegans* Nature Feb. 19, 1998 806-811 391.
Waterhouse, P. M., M. W. Graham and M. B. Wang. Virus resistance and gene silencing in plants can be induced by simultaneous expression of sense and antisense RNA Proc Natl Acad Sci U S A Nov. 10 1998 13959-13964 95.
Ngo, H., C. Tschudi, K. Gull and E. Ullu. Double-stranded RNA induces mRNA degradation in *Trypanosoma brucei* Proc Natl Acad Sci U S A Dec. 8, 1998 14687-14692 95.
Verma, S. and F. Eckstein. Modified oligonucleotides: synthesis and strategy for users Annu Rev Biochem *No date in Pubmed* 1998 99-134 67.
Wuchty, S., W. Fontana, I. L. Hofacker and P. Schuster. Complete suboptimal folding of RNA and the stability of secondary structures Biopolymers Feb. 1999 145-165 49.
Mathews, D. H., J. Sabina, M. Zuker and D. H. Turner. Expanded sequence dependence of thermodynamic parameters improves prediction of RNA secondary structure J Mol Biol May 21, 1999 911-940 288.
Chang, P. L. Encapsulation for somatic gene therapy Ann N Y Acad Sci Jun. 18, 1999 146-158 875.
Zhang, M. Q. Large-scale gene expression data analysis: a new challenge to computational biologists Genome Res Aug. 1999 681-688 9.
Grisaru, D., M. Sternfeld, A. Eldor, D. Glick and H. Soreq. Structural roles of acetylcholinesterase variants in biology and pathology Eur J Biochem Sep. 1999 672-686 264.
Fire, A. RNA-triggered gene silencing Trends Genet Sep. 1999 358-363 15.
Tabara, H., M. Sarkissian, W. G. Kelly, J. Fleenor, A. Grishok, L. Timmons, A. Fire and C. C. Mello. The rde-1 gene, RNA interference, and transposon silencing in *C. elegans* Cell Oct. 15, 1999 123-132 99.

(Continued)

Primary Examiner—Brian Whiteman
(74) Attorney, Agent, or Firm—Polsinelli Shalton Welte Suelthaus PC; Teddy C. Scott, Jr.

(57) ABSTRACT

The present invention relates to a first group of novel genes, here identified as "genomic address messenger" or "GAM" genes, and a second group of novel operon-like genes, here identified as "genomic record" or "GR" genes. GAM genes selectively inhibit translation of known 'target' genes, many of which are known to be involved in various diseases. Nucleic acid molecules are provided respectively encoding 20600 GAM genes, and 6635 GR genes, as are vectors and probes both comprising the nucleic acid molecules, and methods and systems for detecting GAM and GR genes and specific functions and utilities thereof, for detecting expression of GAM and GR genes, and for selectively enhancing and selectively inhibiting translation of the respective target genes thereof.

4 Claims, 148 Drawing Sheets

OTHER PUBLICATIONS

Ryo, A., Y. Suzuki, K. Ichiyama, T. Wakatsuki, N. Kondoh, A. Hada, M. Yamamoto and N. Yamamoto. Serial analysis of gene expression in HIV-1-infected T cell lines FEBS Lett Nov. 26, 1999 182-186 462.

Olsen, P. H. and V. Ambros. The lin-4 regulatory RNA controls developmental timing in Caenorhabditis elegans by blocking LIN-14 protein synthesis after the initiation of translation Dev Biol Dec. 15, 1999 671-680 216.

Tuschl, T., P. D. Zamore, R. Lehmann, D. P. Bartel and P. A. Sharp. Targeted mRNA degradation by double-stranded RNA in vitro Genes Dev Dec. 15, 1999 3191-3197 13.

Reinhart, B. J., F. J. Slack, M. Basson, A. E. Pasquinelli, J. C. Bettinger, A. E. Rougvie, H. R. Horvitz and G. Ruvkun. The 21-nucleotide let-7 RNA regulates developmental timing in Caenorhabditis elegans Nature Feb. 24, 2000 901-906 403.

Pitt, J. N., J. A. Schisa and J. R. Priess. P granules in the germ cells of Caenorhabditis elegans adults are associated with clusters of nuclear pores and contain RNA Dev Biol Mar. 15, 2000 315-333 219.

Hammond, S. M., E. Bernstein, D. Beach and G. J. Hannon. An RNA-directed nuclease mediates post-transcriptional gene silencing in Drosophila cells Nature Mar. 16, 2000 293-296 404.

Slack, F. J., M. Basson, Z. Liu, V. Ambros, H. R. Horvitz and G. Ruvkun. The lin-41 RBCC gene acts in the C. elegans heterochronic pathway between the let-7 regulatory RNA and the LIN-29 transcription factor Mol Cell Apr. 2000 659-669 5.

Fortier, E. and J. M. Belote. Temperature-dependent gene silencing by an expressed inverted repeat in Drosophila Genesis Apr. 2000 240-244 26.

Mourrain, P., C. Beclin, T. Elmayan, F. Feuerbach, C. Godon, J. B. Morel, D. Jouette, A. M. Lacombe, S. Nikic, N. Picault, K. Remoue, M. Sanial, T. A. Vo and H. Vaucheret. Arabidopsis SGS2 and SGS3 genes are required for posttranscriptional gene silencing and natural virus resistance Cell May 26, 2000 533-542 101.

Sijen, T. and J. M. Kooter. Post-transcriptional gene-silencing: RNAs on the attack or on the defense? Bioessays Jun. 2000 520-531 22.

Brenner, S., M. Johnson, J. Bridgham, G. Golda, D. H. Lloyd, D. Johnson, S. Luo, S. McCurdy, M. Foy, M. Ewan, R. Roth, D. George, S. Eletr, G. Albrecht, E. Vermaas, S. R. Williams, K. Moon, T. Burcham, M. Pallas, R. B. Durbridge, J. Kirchner, K. Fearon, J. Mao and K. Corcoran. Gene expression analysis by massively parallel signature sequencing (MPSS) on microbead arrays Nat Biotechnol Jun. 2000 630-634 18.

Ryo, A., Y. Suzuki, M. Arai, N. Kondoh, T. Wakatsuki, A. Hada, M. Shuda, K. Tanaka, C. Sato, M. Yamamoto and N. Yamamoto. Identification and characterization of differentially expressed mRNAs in HIV type 1-infected human T cells AIDS Res Hum Retroviruses Jul. 1, 2000 995-1005 16.

Nilsson, M., G. Barbany, D. O. Antson, K. Gertow and U. Landegren. Enhanced detection and distinction of RNA by enzymatic probe ligation Nat Biotechnol Jul. 2000 791-793 18.

Kent, W. J. and A. M. Zahler. Conservation, regulation, synteny, and intons in a large-scale C. briggsae-C. elegans genomic alignment Genome Res Aug. 2000 1115-1125 10.

Kennerdell, J. R. and R. W. Carthew. Heritable gene silencing in Drosophila using double-stranded RNA Nat Biotechnol Aug. 2000 896-898 18.

Voinnet, O., C. Lederer and D. C. Baulcombe. A viral moment protein prevents spread of the gene silencing signal in Nicotiana benthamiana Cell Sep. 29, 2000 157-167 103.

Mette MF, Aufsatz W, van der Winden J, Matzke MA, Matzke AJ. Transcriptional silencing and promoter methylation triggered by double-stranded RNA. EMBO J. Oct. 2, 2000 5194-201 19.

Yang, D., H. Lu and J. W. Erickson. Evidence that processed small dsRNAs may mediate sequence-specific mRNA degradation during RNAi in Drosophila embryos Curr Biol Oct. 5, 2000 1191-1200 10.

Anandalakshmi, R., R. Marathe, X. Ge, J. M. Herr, Jr., C. Mau, A. Mallory, G. Pruss, L. Bowman and V. B. Vance. A calmodulin-related protein that suppresses posttranscriptional gene silencing in plants Science Oct. 6, 2000 142-144 290.

Fagard, M., S. Boutet, J. B. Morel, C. Bellini and H. Vaucheret. AGO1, QDE-2, and RDE-1 are related proteins required for post-transcriptional gene silencing in plants, quelling in fungi, and RNA interference in animals Proc Natl Acad Sci U S A Oct. 10, 2000 11650-11654 97.

Llave, C., K. D. Kasschau and J. C. Carrington. Virus-encoded suppressor of posttranscriptional gene silencing targets a maintenance step in the silencing pathway Proc Natl Acad Sci U S A Nov. 21, 2000 13401-13406 9.

Cogoni, C. and G. Macino. Post-transcriptional gene silencing across kingdoms Curr Opin Genet Dev Dec. 2000 638-643 10.

Elbashir, S. M., W. Lendeckel and T. Tuschl. RNA interference is mediated by 21- and 22- nucleotide RNAs Genes Dev Jan. 15, 2001 188-200 15.

Bernstein, E., A. A. Caudy, S. M. Hammond and G. J. Hannon. Role for a bidentate ribonuclease in the initiation step of RNA interference Nature Jan. 18, 2001 363-366 409.

Vaucheret, H. and M. Fagard. Transcriptional gene silencing in plants: targets, inducers and regulators Trends Genet Jan. 2001 29-35 17.

Thomas, C. L., L. Jones, D. C. Baulcombe and A. J. Maule. Size constraints for targeting post-transcriptional gene silencing and for RNA-directed methylation in Nicotiana benthamiana using a potato virus X vector Plant J Feb. 2001 417-425 25.

Galyam, N., D. Grisaru, M. Grifman, N. Melamed-Book, F. Eckstein, S. Seidman, A. Eldor and H. Soreq. Complex host cell responses to antisense suppression of ACHE gene expression Antisense Nucleic Acid Drug Dev Feb. 2001 51-57 11.

Sharp, P. A. RNA interference—2001 Genes Dev Mar. 1, 2001 485-490 15.

Mallory, A. C., L. Ely, T. H. Smith, R. Marathe, R. Anandalakshmi, M. Fagard, H. Vaucheret, G. Pruss, L. Bowman and V. B. Vance. HC-Pro suppression of transgene silencing eliminates the small RNAs but not transgene methylation or the mobile signal Plant Cell Mar. 2001 571-583 13.

Matzke, M. A., A. J. Matzke, G. J. Pruss and V. B. Vance. RNA-based silencing strategies in plants Curr Opin Genet Dev Apr. 2001 221-227 11.

Schisa, J. A., J. N. Pitt and J. R. Priess. Analysis of RNA associated with P granules in germ cells of C. elegans adults Development Apr. 2001 1287-1298 128.

Di Serio, F., H. Schob, A. Iglesias, C. Tarina, E. Bouldoires and F. Meins, Jr. Sense- and antisense-mediated gene silencing in tobacco is inhibited by the same viral suppressors and is associated with accumulation of small RNAs Proc Natl Acad Sci U S A May 22, 2001 6506-6510 98.

Piccin, A., A. Salameh, C. Benna, F. Sandrelli, G. Mazzotta, M. Zordan, E. Rosato, C. P. Kyriacou and R. Costa. Efficient and heritable functional knock-out of an adult phenotype in Drosophila using a GAL4-driven hairpin RNA incorporating a heterologous spacer Nucleic Acids Res Jun. 15, 2001 E55-55 29.

Vance, V. and H. Vaucheret. RNA silencing in plants—defense and couterdefense Science Jun. 22, 2001 2277-2280 292.

Argaman, L., R. Hershberg, J. Vogel, G. Bejerano, E. G. Wagner, H. Margalit and S. Altuvia. Novel small RNA-encoding genes in the intergenic regions of Escherichia coli Curr Biol Jun. 26, 2001 941-950 11.

Grishok, A., A. E. Pasquinelli, D. Conte, N. Li, S. Parrish, I. Ha, D. L. Baillie, A. Fire, G. Ruvkun and C. C. Mello. Genes and mechanisms related to RNA interference regulate expression of the small temporal RNAs that control C. elegans developmental timing Cell Jul. 13, 2001 23-34 106.

Hutvagner, G., J. McLachlan, A. E. Pasquinelli, E. Balint, T. Tuschl and P. D. Zamore. A cellular function for the RNA-interference enzyme Dicer in the maturation of the let-7 small temporal RNA Science Aug. 3, 2001 834-838 293.

Hammond, S. M., S. Boettcher, A. A. Caudy, R. Kobayashi and G. J. Hannon. Argonaute2, a link between genetic and biochemical analyses of RNAi Science Aug. 10, 2001 1146-1150 293.

Vaucheret, H., C. Beclin and M. Fagard. Post-transcriptional gene silencing in plants J Cell Sci Sep. 2001 3083-3091 114.

Wesley, S. V., C. A. Helliwell, N. A. Smith, M. B. Wang, D. T. Rouse, Q. Liu, P. S. Gooding, S. P. Singh, D. Abbott, P. A.

Stoutjesdijk, S. P. Robinson, A. P. Gleave, A. G. Green and P. M. Waterhouse. Construct design for efficient, effective and high-throughput gene silencing in plants Plant J Sep. 2001 581-590 27.

Mattick, J. S. and M. J. Gagen. The evolution of controlled multitasked gene networks: the role of introns and other noncoding RNAs in the development of complex organisms Mol Biol Evol Sep. 2001 1611-1630 18.

Carter, R. J., I. Dubchak and S. R. Holbrook. A computational approach to identify genes for functional RNAs in genomic sequences Nucleic Acids Res Oct. 1, 2001 3928-3938 29.

Ketting, R. F., S. E. Fischer, E. Bernstein, T. Sijen, G. J. Hannon and R. H. Plasterk. Dicer functions in RNA interference and in synthesis of small RNA involved in developmental timing in *C. elegans* Genes Dev Oct. 15, 2001 2654-2659 15.

Ruvkun, G. Molecular biology. Glimpses of a tiny RNA world Science Oct. 26, 2001 797-799 294.

Lee, R. C. and V. Ambros. An extensive class of small RNAs in *Caenorhabditis elegans* Science Oct. 26, 2001 862-864 294.

Lau, N. C., L. P. Lim, E. G. Weinstein and D. P. Bartel. An abundant class of tiny RNAs with probable regulatory roles in *Caenorhabditis elegans* Science Oct. 26, 2001 858-862 294.

Itaya, A., A. Folimonov, Y. Matsuda, R. S. Nelson and B. Ding. Potato spindle tuber viroid as inducer of RNA silencing in infected tomato Mol Plant Microbe Interact Nov. 2001 1332-1334 14.

Mattick, J. S. Non-coding RNAs: the architects of eukaryotic complexity EMBO Rep Nov. 2001 986-991 2.

Elbashir, S. M., J. Martinez, A. Patkaniowska, W. Lendeckel and T. Tuschl. Functional anatomy of siRNAs for mediating efficient RNAi in *Drosophila melanogaster* embryo lysate Embo J Dec. 3, 2001 6877-6888 20.

Ambros, V. microRNAs: tiny regulators with great potential Cell Dec. 28, 2001 823-826 107.

Blaszczyk, J., J. E. Tropea, M. Bubunenko, K. M. Routzahn, D. S. Waugh, D. L. Court and X. JI. Crystallographic and modeling studies of RNase III suggest a mechanism for double-stranded RNA cleavage Structure Dec. 2001 1225-1236 9.

Crete, P., S. Leuenberger, V. A. Iglesias, V. Suarez, H. Schob, H. Holtorf, S. Van Eeden and F. Meins. Graft transmission of induced and spontaneous post-transcriptional silencing of chitinase genes Plant J Dec. 2001 493-501 28.

Smallridge, R. A small fortune Nat Rev Mol Cell Biol Dec. 2001 867 2.

Eddy, S. R. Non-coding RNA genes and the modern RNA world Nat Rev Genet Dec. 2001 919-929 2.

Lu, C. M. miRNA bead detection Genaco Biomedical Products PHS 398 2001 1.

Matzke, M., A. J. Matzke and J. M. Kooter. RNA: guiding gene silencing 2001 1080 293.

Grosshans, H. and F. J. Slack. Micro-RNAs: small is plentiful J Cell Biol Jan. 7, 2002 17-21 156.

Meshorer, E., C. Erb, R. Gazit, L. Pavlovsky, D. Kaufer, A. Friedman, D. Glick, N. Ben-arie and H. Soreq. Alternative splicing and neuritic mRNA translocation under long-term neuronal hyper-sensitivity Science Jan. 18, 2002 508-512 295.

Paddison, P. J., A. A. Caudy and G. J. Hannon. Stable suppression of gene expression by RNAi in mammalian cells Proc Natl Acad Sci U S A Feb. 5, 2002 1443-1448 99.

Moss, E. G. MicroRNAs: hidden in the genome Curr Biol Feb. 19, 2002 R138-140 12.

Banerjee, D. and F. Slack. Control of developmental timing by small temporal RNAs: a paradigm for RNA-mediated regulation of gene expression Bioessays Feb. 2002 119-129 24.

Elbashir, S. M., J. Harborth, K. Weber and T. Tuschl. Analysis of gene function in somatic mammalian cells using small interfering RNAs Methods Feb. 2002 199-213 26

Han, Y. and D. Grierson. Relationship between small antisense RNAs and aberrant RNAs associated with sense transgene mediated gene silencing in tomato Plant J Feb. 2002 509-519 29.

Nicholson, R. H. and A. W. Nicholson. Molecular characterization of a mouse cDNA encoding Dicer, a ribonuclease III ortholog involved in RNA interference Mamm Genome Feb. 2002 67-73 13.

Puerta-Fernandez, E., A. Barroso-Deljesus and A. Berzal-Herranz. Anchoring hairpin ribozymes to long target RNAs by loop-loop RNA interactions Antisense Nucleic Acid Drug Dev Feb. 2002 1-9 12.

Giordano, E., R. Rendina, I. Peluso and M. Furia. RNAi triggered by symmetrically transcribed transgenes in *Drosophila melanogaster* Genetics Feb. 2002 637-648 160.

Martens, H., J. Novotny, J. Oberstrass, T. L. Steck, P. Postlethwait and W. Nellen. RNAi in Dictyostelium: the role of RNA-directed RNA polymerases and double-stranded RNase Mol Biol Cell Feb. 2002 445-453 13.

Mourelatos, Z., J. Dostie, S. Paushkin, A. Sharma, B. Charroux, L. Abel, J. Rappsilber, M. Mann and G. Dreyfuss. miRNPs: a novel class of ribnucleoproteins containing numerous microRNAs Genes Dev Mar. 15, 2002 720-728 16.

Seggerson, K., L. Tang and E. G. Moss. Two genetic circuits repress the *Caenorhabditis elegans* heterochronic gene lin-28 alter translation initiation Dev Biol Mar. 15, 2002 215-225 243.

Morel, J. B., C. Godon, P. Mourrain, C. Beclin, S. Boutet, F. Feuerbach, F. Proux and H. Vaucheret. Fertile hypomorphic Argonaute (ago1) mutants impaired in post-transcriptional gene silencing and virus resistance Plant Cell Mar. 2002 629-639 14.

Catalanotto, C., G. Azzalin, G. Macino and C. Cogoni. Involvement of small RNAs and role of the qde genes in the gene silencing pathway in Neurospora Genes Dev Apr. 1, 2002 790-795 16.

Boutla, A., K. Kalantidis, N. Tavernarakis, M. Tsagris and M. Tabler. Induction of RNA interference in *Caenorhabditis elegans* by RNAs derived from plants exhibiting post-transcriptional gene silencing Nucleic Acids Res Apr. 1, 2002 1688-1694 30.

Pasquinelli, A. E. and G. Ruvkun. Control of developmental timing by micrornas and their targets Annu Rev Cell Biol Epub Apr. 2, 2002 495-513 18.

Paddison, P. J., A. A. Caudy, E. Bernstein, G. J. Hannon and D. S. Conklin. Short hairpin RNAs (shRNAs) induce sequence-specific silencing in mammalian cells Genes Dev Apr. 15, 2002 948-958 16.

Beclin, C., S. Boutet, P. Waterhouse and H. Vaucheret. A branched pathway for transgene-induced RNA silencing in plants Curr Biol Apr. 16, 2002 684-688 12.

Eddy, S. R. Computational genomics of noncoding RNA genes Cell Apr. 19, 2002 137-140 109.

Lagos-Quintana, M., R. Rauhut, A. Yalcin, J. Meyer, W. Lendeckel and T. Tuschl. Identification of tissue-specific microRNAs from mouse Curr Biol Apr. 30, 2002 735-739 12.

Kent, W. J. Blat—the Blast-like alignment tool Genome Res Apr. 2002 656-664 12.

Hutvagner, G. and P. D. Zamore. RNAi: nature abhors a double-strand Curr Opin Genet Dev Apr. 2002 225-232 12.

Nilsson, M., J. Baner, M. Mendel-Hartvig, F. Dahl, D. O. Antson, M. Gullberg and U. Landegren. Making ends meet in genetic analysis using padlock probes Hum Mutat Apr. 2002 410-415 19.

Pasquinelli, A. E. MicroRNAs: deviants no longer Trends Genet Apr. 2002 171-173 18.

Lai, E. C. Micro RNAs are complementary to 3' UTR sequence motifs that mediate negative post-transcriptional regulation Nat Genet Apr. 2002 363-364 30.

Schwartz, D. S. and P. D. Zamore. Why do miRNAs live in the miRNP? Genes Dev May 1, 2002 1025-1031 16.

Brantl, S. Antisense-RNA regulation and RNA interference Biochim Biophys Acta May, 3, 2002 15-25 1575.

Li, H., W. X. Li and S. W. Ding. Induction and suppression of RNA silencing by an animal virus Science May 17, 2002 1319-1321 296.

Zamore, P. D. Ancient pathways programmed by small RNAs Science May 17, 2002 1265-1269 296.

Chen, S., E. A. Lesnik, T. A. Hall, R. Sampath, R. H. Griffey, D. J. Ecker and L. B. Blyn. A bioinformatics based approach to discover small RNA genes in the *Escherichia coli* genome Biosystems Mar.-May 2002 157-177 65.

Lee, N. S., T. Dohjima, G. Bauer, H. Li, M. J. Li, A. Ehsani, P. Salvaterra and J. Rossi. Expression of small interfering RNAs targeted against HIV-1 rev transcripts in human cells Nat Biotechnol May 2002 500-505 20.

Draghici, S. Statistical intelligence: effective analysis of high-density microarray data Drug Discov Today Jun. 1, 2002 S55-63 7.

Silhavy, D., A. Molnar, A. Lucioli, G. Szittya, C. Hornyik, M. Tavazza and J. Burgyan. A viral protein suppresses RNA silencing and binds silencing-generated, 21- to 25-nucleotide double-stranded RNAs Embo J Jun. 17, 2002 3070-3080 21.

Ayash-Rashkovsky, M., Z. Weisman, J. Diveley, R. B. Moss, Z. Bentwich and G. Borkow. Generation of Th1 immune responses to inactivated, gp120-depleted HIV-1 in mice with a dominant Th2 biased immune profile via immunostimulatory [correction of imunostimulatory] oligonucleotides—relevance to AIDS vaccines in developing countries Vaccine Jun. 21, 2002 2684-2692 20.

Tabara, H., E. Yigit, H. Siomi and C. C. Mello. The dsRNA binding protein RDE-4 interacts with RDE-1, DCR-1, and a DExH-box helicase to direct RNAi in C. elegans Cell Jun. 28, 2002 861-871 109.

Bettencourt, R., O. Terenius and I. Faye. Hemolin gene silencing by ds-RNA injected into Cecropia pupae is lethal to next generation embryos Insect Mol Biol Jun. 2002 267-271 11.

Hooper, N. M. and A. J. Turner. The search for alpha-secretase and its potential as a therapeutic approach to Alzheimer s disease Curr Med Chem Jun 2002 1107-1119 9.

Liu, Q., S. Singh and A. Green. High-oleic and high-stearic cottonseed oils: nutritionally improved cooking oils developed using gene silencing J Am Coll Nutr Jun. 2002 205S-211S 21.

Zeng, Y., E. J. Wagner and B. R. Cullen. Both natural and designed micro RNAs can inhibit the expression of cognate mRNAs when expressed in human cells Mol Cell Jun. 2002 1327-1333 9.

McManus, M. T., C. P. Petersen, B. B. Haines, J. Chen and P. A. Sharp. Gene silencing using micro-RNA designed hairpins Rna Jun. 2002 842-850 8.

Reinhart, B. J., E. G. Weinstein, M. W. Rhoades, B. Bartel and D. P. Bartel. MicroRNAs in plants Genes Dev Jul. 1, 2002 1616-1626 16.

McCaffrey, A. P., L. Meuse, T. T. Pham, D. S. Conklin, G. J. Hannon and M. A. Kay. RNA interference in adult mice Nature Jul. 4, 2002 38-39 418.

Hannon, G. J. RNA interference Nature Jul. 11, 2002 244-251 418.

Dennis, C. The brave new world of RNA Nature Jul. 11, 2002 122-124 418.

Jacque, J. M., K. Triques and M. Stevenson. Modulation of HIV-1 replication by RNA interference Nature Jul. 25, 2002 435-438 418.

Cullen, B. R. RNA interference: antiviral defense and genetic tool Nat Immunol Jul. 2002 597-599 3.

MA, C. and A. Mitra. Intrinsic direct repeats generate consistant post-transcriptional gene silencing in tobacco Plant J Jul. 2002 37-49 31.

Novina, C. D., M. F. Murray, D. M. Dykxhoorn, P. J. Beresford, J. Reiss, S. K. Lee, R. G. Collman, J. Lieberman, P. Shankar and P. A. Sharp. siRNA-directed inhibition of HIV-1 infection Nat Med Jul. 2002 681-686 8.

Pomerantz, R. J. RNA interference meets HIV-1: will silence be golden? Nat Med Jul. 2002 659-660 8.

Zeng, Y. and B. R. Cullen. RNA interference in human cells is restricted to cytoplasm Rna Jul. 2002 855-860 8.

Xiang, C. C., O. A. Kozhich, M. Chen, J. M. Inman, Q. N. Phan, Y. Chen and M. J. Brownstein. Amine-modified random primers to label probes for DNA microarrays Nat Biotechnol Jul. 2002 738-742 20.

Llave, C., K. D. Kasschau, M. A. Rector and J. C. Carrington. Endogenous and silencing-associated small RNAs in plants Plant Cell Jul. 2002 1605-1619 14.

Hipfner, D. R., K. Weigmann and S. M. Cohen. The bantam gene regulates Drosophila growth Genetics Aug. 2002 1527-1537 161.

Liu, Q., S. P. Singh and A. G. Green. High-stearic and High-oleic cottonseed oils produced by hairpin RNA-mediated post-transcriptional gene silencing Plant Physiol Aug. 2002 1732-1743 129.

Stoutjesdijk, P. A., S. P. Singh, Q. Liu, C. J. Hurlstone, P. A. Waterhouse and A. G. Green. hpRNA-mediated targeting of the Arabidopsis FAD2 gene gives highly efficient and stable silencing Plant Physiol Aug. 2002 1723-1731 129.

Suzuma, S., S. Asari, K. Bunai, K. Yoshino, Y. Ando, H. Kakeshita, M. Fujita, K. Nakamura and K. Yamane. Identification and characterization of novel small RNAs in the aspS-yrvM intergenic region of the Bacillus subtilis genome Microbiology Aug. 2002 2591-2598 148.

Milligan, L., T. Forne, E. Antoine, M. Weber, B. Hemonnot, L. Dandolo, C. Brunel and G. Cathala. Turnover of primary transcripts is a major step in the regulation of mouse H19 gene expression EMBO Rep Aug. 2002 774-779 3.

Hamilton, A., O. Voinnet, L. Chappell and D. Baulcombe. Two classes of short interfering RNA in RNA silencing Embo J Sep. 2, 2002 4671-4679 21.

Lee, Y., K. Jeon, J. T. Lee, S. Kim and V. N. Kim. MicroRNA maturation: stepwise processing and subcellular localization Embo J Sep. 2, 2002 4663-4670 21.

Klahre, U., P. Crete, S. A. Leuenberger, V. A. Iglesias and F. Meins, Jr. High Molecular weight RNAs and small interfering RNAs induce systemic posttreanscriptional gene silencing in plants Proc Natl Acad Sci U S A Sep. 3, 2002 11981-11986 99.

Park, W., J. Li, R. Song, J. Messing and X. Chen. Carpel Factory, a Dicer homolog, and Hen1, a novel protein, act in microRNA metabolism in Arabidopsis thaliana Curr Biol Sep. 3, 2002 1484-1495 12.

Jiang, M. and J. Milner. Selective silencing of viral gene expression in HPV-positive human cervical carcinoma cells treated with siRNA, a primer of RNA interference Oncogene Sep. 5, 2002 6041-6048 21.

Martinez, J., A. Patkaniowska, H. Urlaub, R. Luhrmann and T. Tuschl. Single-stranded antisense siRNAs guide target RNA cleavage in RNAi Cell Sep. 6, 2002 563-574 110.

Allshire, R. Molecular biology. RNAi and heterochromatin—a hushed-up affair Science Sep. 13, 2002 1818-1819 297.

Reinhart, B. J. and D. P. Bartel. Small RNAs correspond to centromere heterochromatic repeats Science Sep. 13, 2002 1831 297.

Volpe, T. A., C. Kidner, I. M. Hall, G. Teng, S. I. Grewal and R. A. Martienssen. Regulation of heterochromatic silencing and histone H3 lysine-9 methylation by RNAi Science Sep. 13, 2002 1833-1837 297.

Llave, C., Z. Xie, K. D. Kasschau and J. C. Carrington. Cleavage of Scarecrow-like mRNA targets directed by a class of Arabidopsis miRNA Science Sep. 20, 2002 2053-2056 297.

Mochizuki, K., N. A. Fine, T. Fujisawa and M. A. Gorovsky. Analysis of a piwi-related gene implicates small RNAs in genome rearrangement in tetrahymena Cell Sep. 20, 2002 689-699 110.

Hutvagner, G. and P. D. Zamore. A microRNA in a multiple-turnover RNAi enzyme complex Science Sep. 20, 2002 2056-2060 297.

Coburn, G. A. and B. R. Cullen. Potent and specific inhibition of human immunodeficiency virus type 1 replication by RNA interference J Virol Sep. 2002 9225-9231 76.

Caudy, A. A., M. Myers, G. J. Hannon and S. M. Hammond. Fragile X-related protein and VIG associate with the RNA interference machinery Genes Dev Oct. 1, 2002 2491-2496 16.

Ishizuka, A., M. C. Siomi and H. Siomi. A Drosophila fragile X protein interacts with components of RNAi and ribosomal proteins Genes Dev Oct. 1, 2002 2497-2508 16.

Voinnet, O. RNA silencing: small RNAs as ubiquitous regulators of gene expression Curr Opin Plant Biol Oct. 2002 444-451 5.

Golden, T. A., S. E. Schauer, J. D. Lang, S. Pien, A. R. Mushegian, U. Grossniklaus, D. W. Meinke and A. Ray. Short Integuments1/Suspensor1/Carpel Factory, a Dicer homolog, is a maternal effect gene required for embryo development in Arabidopsis Plant Physiol Oct. 2002 808-822 130.

Merkle, I., M. J. Van Ooij, F. J. Van Kuppeveld, D. H. Glaudemans, J. M. Galama, A. Henke, R. Zell and W. J. Melchers. Biological significance of a human enterovirus B-specific RNA element in the 3' nontranslated region J Virol Oct. 2002 9900-9909 76.

Froeyen, M. and P. Herdewijn. RNA as a target for drug design, the example of Tat-TAR interaction Curr Top Med Chem Oct. 2002 1123-1145 2.

Carmell, M. A., Z. Xuan, M. Q. Zhang and G. J. Hannon. The Argonaute family: tentacles that reach into RNAi, developmental control, stem cell maintenance, and tumorigenesis Genes Dev Nov. 1, 2002 2733-2742 16.

Provost, P., D. Dishart, J. Doucet, D. Frendewey, B. Samuelsson and O. Radmark. Ribonuclease activity and RNA binding of recombinant human Dicer Embo J Nov. 1, 2002 5864-5874 21.

Zhang, H., F. A. Kolb, V. Brondani, E. Billy and W. Filipowicz. Human Dicer preferentially cleaves dsRNAs at their termini without a requirement for ATP Embo J Nov. 1, 2002 5875-5885 21.

Mallory, A. C., B. J. Reinhart, D. Bartel, V. B. Vance and L. H. Bowman. A viral suppressor of RNA silencing differentially regulates the accumulation of short interfering RNAs and micro-RNAs in tobacco Proc Natl Acad Sci U S A Nov. 12, 2002 15228-15233 99.

Gottesman, S. Stealth regulation: biological circuits with small RNA switches Genes Dev Nov. 15, 2002 2829-2842 16.

Calin, G. A., C. D. Dumitru, M. Shimizu, R. Bichi, S. Zupo, E. Noch, H. Aldler, S. Rattan, M. Keating, K. Rai, L. Rassenti, T. Kipps, M. Negrini, F. Bullrich and C. M. Croce. Frequent deletions and down-regulation of micro- RNA genes miR15 and miR16 at 13q14 in chronic lymphocytic leukemia Proc Natl Acad Sci U S A Nov. 26, 2002 15524-15529 99.

Gaudilliere, B., Y. Shi and A. Bonni. RNA interference reveals a requirement for myocyte enhancer factor 2A in activity-dependent neuronal survival J Biol Chem Nov. 29, 2002 46442-46446 277.

Jones, L. Revealing micro-RNAs in plants Trnds Plant Sci Nov. 2002 473-475 7.

Schauer, S. E., S. E. Jacobsen, D. W. Meinke and A. Ray. Dicer-Like1: blind men and elephants in Arabidopsis development Trends Plant Sci Nov. 2002 487-491 7.

Okazaki, Y., M. Furuno, T. Kasukawa, J. Adachi, H. Bono, S. Kondo, et al. Analysis of the mouse transcriptome based on functional annotation of 60,770 full-length cDNAs Nature Dec. 5, 2002 563-573 420.

Huttenhofer, A., J. Brosius and J. P. Bachellerie. RNomics: identification and function of small, non-messenger RNAs Curr Opin Chem Biol Dec. 2002 835-843 6.

Wood, N. T. Unravelling the molecular basis of viral suppression of PTGS Trends Plant Sci 2002 384 7.

Cohen, O., C. Erb, D. Ginzberg, Y. Pollak, S. Seidman, S. Shoham, R. Yirmiya and H. Soreq. Neuronal overexpression of "readthrough" acetylcholinesterase is associated with antisense-suppressible behavioral impairments Mol Psychiatry *No date in pubmed* 2002 874-885 7.

Mlotshwa, S., O. Voinnet, M. F. Mette, M. Matzke, H. Vaucheret, S. W. Ding, G. Pruss and V. B. Vance. RNA silencing and the mobile silencing signal Plant Cell * No date in pubmed* 2002 S289-301 14 Suppl.

Lee, et al.; The *C. Elegans* Heterochronic Gene lin-r Encodes Small RNAs with Antisense Complementary to lin-14; *Cell*, 75:843-854 (Dec. 3, 1993).

Wightman, et al.; Posttranscriptional of the Heterochronic Gene lin-14 by lin-4 Mediates Temporal Pattern Formation of *C. elegans*; *Cell*, 75:855-862 (Dec. 3, 1993).

Smith, et al.; Total Silencing by Intron-Spliced Hairpin RNAs; *Nature*, 407:319-320 (Sep. 21, 2000).

Pasquinelli, et al.; Conservation of the Sequence and Temporal Expression of let-7 Heterochronic Regulatory RNA; *Nature*, 408:86-89 (Nov. 2, 2000).

Elbashir, et al.; Duplexes of 21-Nucleotide RNAs Mediate RNA Interference in Cultures Mammalian Cells; *Nature*, 411:498-498 (May 24, 2001).

Moss; RNA interference: It's a Small RNA World; *Curr. Biol.*, 11:R772-775 (Oct. 2, 2001).

Lagos-Quintana, et al.; Identification of Novel Genes Coding for Small Expressed RNAs; *Science*, 294:853-858 (Oct. 26, 2001).

Rhoades, et al.; Prediction of Plant MicroRNA Targets; *Cell*, 110:513-520 (Aug. 23, 2002).

* cited by examiner

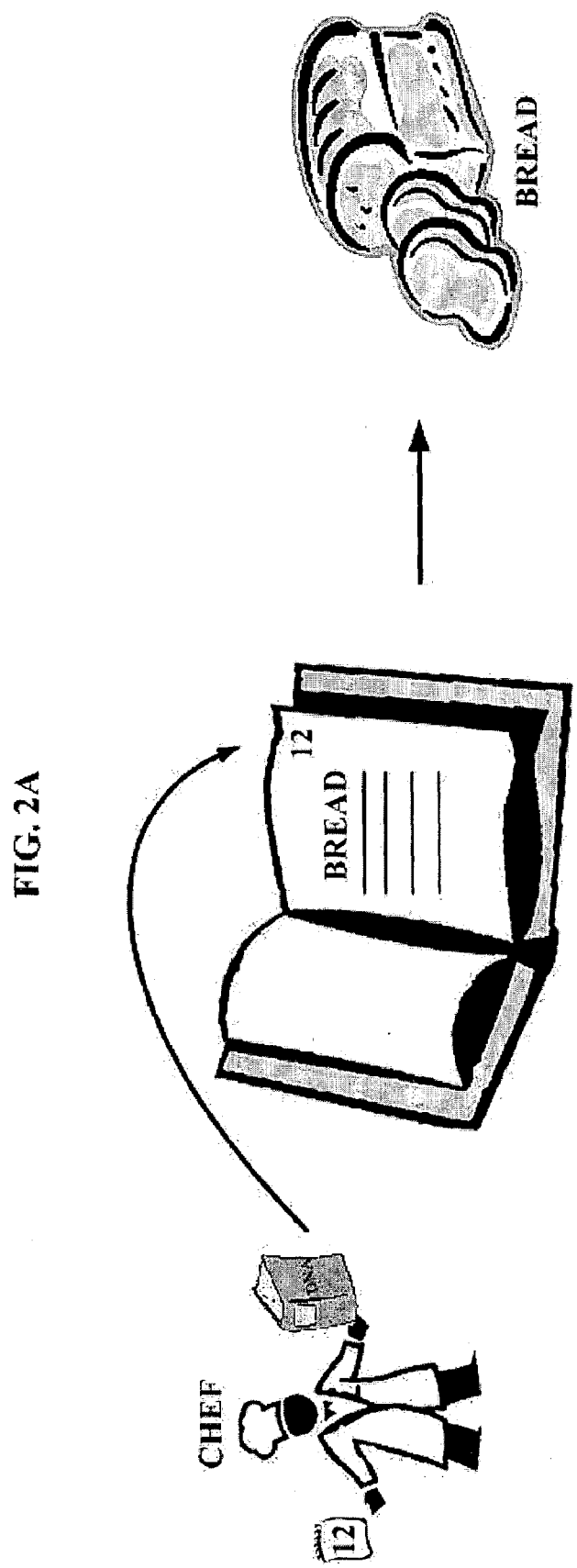

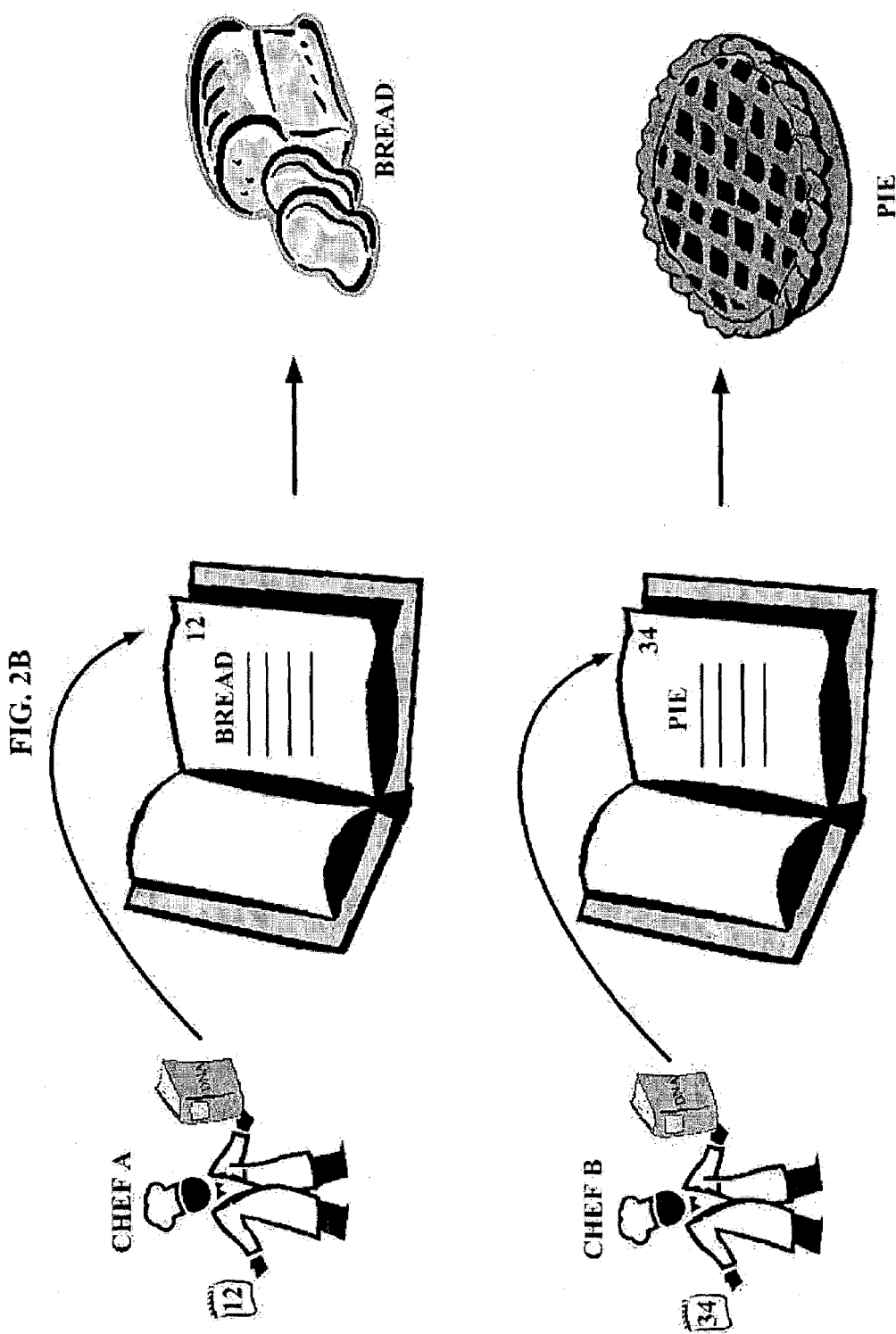

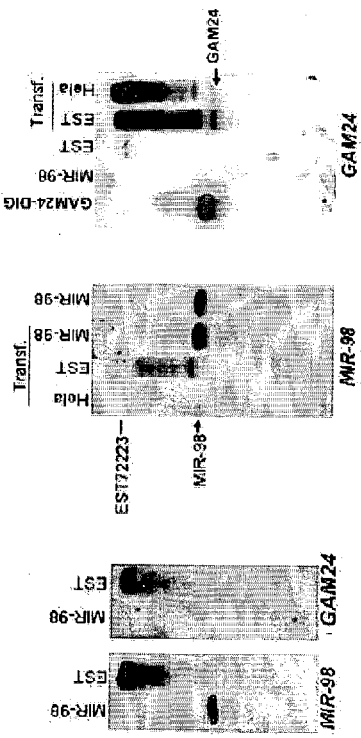
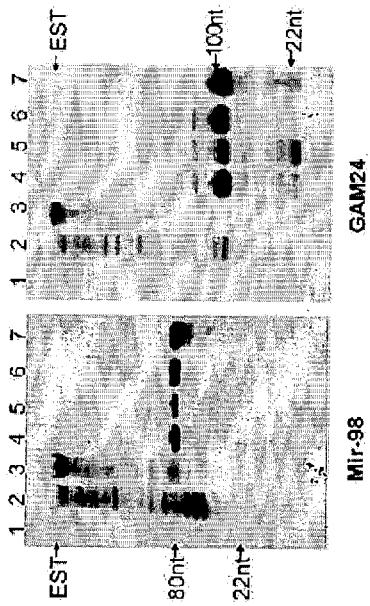
FIG. 21A
FIG. 21B
FIG. 21C
FIG. 21D

FIG. 22A dbEST Id.7929020(Image4514344) sequence:
GCAAAAACTGGAAGCATTCCCTTTGAAAACTGGCACAAGACAGGGATGCCCTCTCTCAC
CGCTCCTATTGAACATAGTGTTGGAAGTTCTGGCCAGGGCAATTAGGCAGGAGAAGGAA
ATAAAGGGTATTCAATTAGGAAAAGAGCAAGTCAAATTGTTCCTGTTTGCAGATGACAT
GATTGTATATCTAGAAAACCCCATTGTCTCAGCCCCAAATCTCCTTAAGCTGATAAGCA
ACTTCAGCAAAGTCTCAGGATACAAAATAAATGTACAAAAATCACAAGCATTCTTACAC
ACCAACAACAGAAAAACAGAGCCAAATCATGAGTGAACTCCCATTCACAATTGCTTCAA
AGAGAATAAAATACCTAGGAATCCAACTTACAAGGGATGTGAAGGACCTCTTCAAGGAG
AACTACAAACCACTGCTCAAGGAAATAAAAGAGGATACAAACAAATGGAAGAACATTCC
ATGCTCATGGGTAGGAAGAATCAATATTGTCAAAATGGCCATACTGCCCAAGGTAATTT
ACAGATTCAATGCCATCCCCATCAAGCTACCAATGACTTTCTTCACAGAATTGGAAAAA
ACTACTTTAAAGTTCATATGGAACCAAAAAGAGCCCGCATCGCCAAGTCAATCCTA**AG
CCAAAAGAACAAAGCTGGAGGCATCACACTACCTGACTTCAAACTTTACTACAAGGCTA** GAM23
CAGTAACCAAAACAGCATGGTACTGGTACCAAAACAGAGATATAGATCAATGGAACAGA
ACAGAGCCCTCAGAAATAACGCCGAATACCTACAACTATCTGATCTTTGACAAACCTGA
GAAAAACAAGCAATGGGGAAAGGATTCCCTATTTAATAAATGGTGCTGGGAAAACTGAC
TAGCCATATGTAGAAAGCTGAAACTGGATCCCTTCCTTACACCTTATACAAAAATCAAT
TCAAGATGGATTAAAGATTTAAACGTTAGACCTAAAACCATAAAAACCCTAGAAGAAAA
CCTAGGCATTACCATTCAGGACATAGGCATGGGCAAGGACTTCATGTCCAAAACACCAA
AAGCAATGGCAACAAAAGACAAAATTGACAAATGGGATCTAATTAAACTAAAGAGCTTC
TGCACAGCAAAAGAAACTACCA**TCAGAGTGAACAGGCAACCTACAAAATGGGAGAAAAT
TTTCGCAACCTACTCATCTGA**CAAAGGGCTAATATCCAGAATCTACAATGAACTCAAAC GAM25
AAATTTACAAAAAAAAAAAAAAA

FIG. 22B

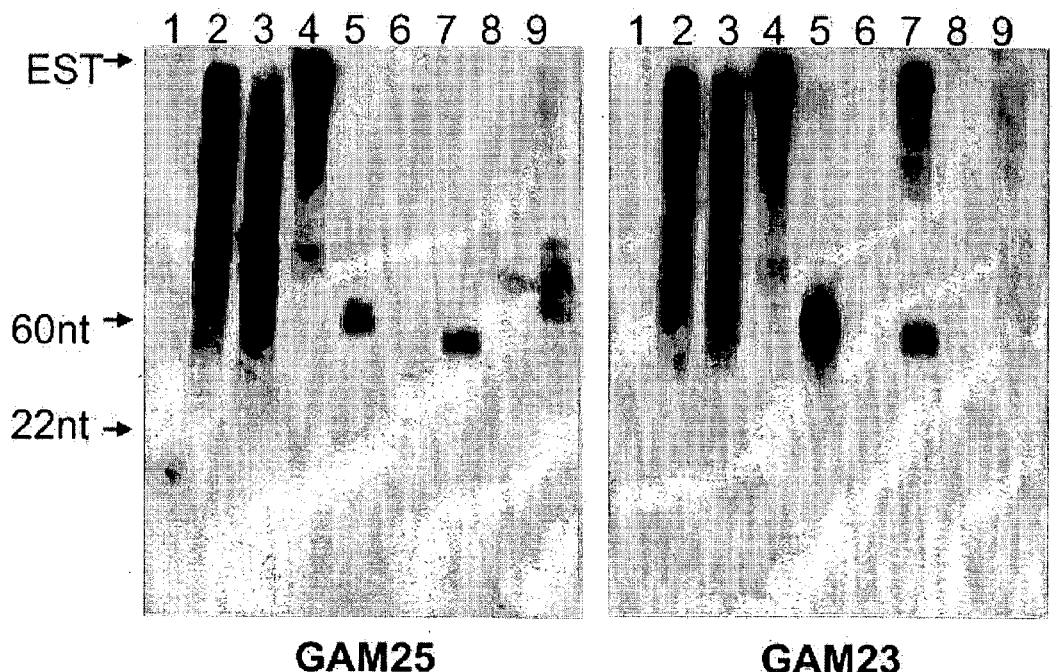

GAM25    GAM23

FIG. 23A dbEST Id.1388749 (Image1020185) Sequence:
ACTCCTATCAACAGTGTAAAAGCATTCCTGTTTCTCCATAATCTTGCCAGCATCTTTT
CATTTTTTTGAATTATAGCCATTCTGACTGTTGTGAGATGGTGTCTCATTGTGGTTTT
GATTTGCATTTCTCAGATGATCAGTGATGTTGAAGTTTTTTTGTTTGTTGGCTGCATG
TATGCCTTCTTTTGAAAAGTGTCTGTTTGTGTCCTTTGACCACTTTCTAATGGGGTTG
AGTTTTTTTTCTTGTAAATTTGTTTAAGTTCCTTGTAGATGCTGGATATTAGACCTT
TGTCAGATGGATAGAGTGCAAAAATTTTCTCCCATTCTGTAGGTTGTCGGTTTACTCT
GTTGATAGGTTCTTAATGCTGTGCAGAAGCTCTTTAGTTTAATTAGATCCCATTTGTC
AATTTTGGCTTTTGTTGCAATTGCTTTTGGCATCTTCGTCATGAAATCTTTGCCCTTG
CCTGTGTCCTGAATGGCATTGCCTAGGTTTTCTTCCAGGATTTTTATAGTTTTGGGTT
GTAGATTTAAGTCTTTAATCCATCTTGAGTTAACTTTTGTATATGGGTTAAGGAAGGG
GCCCGTTTCAATTTGCTGCAAATGGCTAGCCAGTTCTCCCAGCACCATTTATTAAATA
GGGAATCTTTTCCCCATTGCTTCCTTTTGTCAGGTTTGTCAAAGATCACATGGTTGTA
GGTGTGTGGTCTTATTTCTGGGTTCTCTATTCTGTTCCATTGGGCTATGGGCCGGTTC
TGTACCACCACTATGCTGTTTTGGGTACCATAGTCTTGTAGAATGTTTGAAGCTGGGT
AGCATGATGCCTCTAGCTTTGCTCTTCTTGCTAAGAAATGTCTTGGCTATTTGGGCTC
TTTTTTGGTTCCATATGAATTTTAAAATAGCTTTTTCTAGGTCTGTAAAGAATGTGAA
TAGTAGTTTAATGGGCCTAGCATTTAATTTACAGATTGCCTTGGGCAGTGTGGTCATT
TTCACGATATTGATCCTTCCTGTCTGTGAGCATATGTTT**TTCCATTTGTTTGTGTCAT
CTCTGATTTCTTTGAATAATGGTTTATAGTTATCCTTGAAAAGGTCCTTCACTTTTCT** GAM26
TGTTAGCTGTATTCCTAGATATTATACTCTTCTTGTGGCAATTGTGAATGGGAGTTAA
TTCATGAGTTTTCTCTCGGCTTGCCTGTTGTTGGTGTATAGGAATGCTAGTGACTTTT
GCACATTGATTTTGTATCCTGAGACTTTGTTGAAGTTGCTTATCAGCTAAGAAGTTTT
TGAGCTGAGATGATGGAGTTTTCTAGATATAGGATCATATCATCTGCAAACAAAGATA
GTTTGACTTCCTGTCTTCCTATTTGAATAGCTTTTCTTTCTTTCTCTTGCCTGATTGC
CTTGGTGAGAATTTCTAATACTGTGTTGAATAGGAGTGGTGAGCTCGTGCCAA

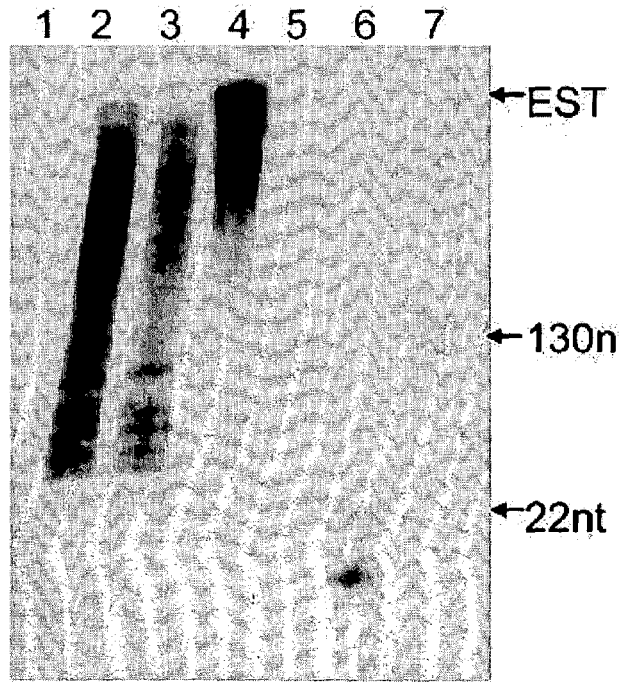

FIG. 23B

GAM26

ACTGTGGAATGCCTGCGGGGTGATGTTGATATTCTAATG  SEQ ID: 24
GAGTTCCTGCTCAATGTCACCA<u>CAGCACCAGAATTTCGT</u>
<u>CGT</u>

CAGCACCAGAATTTCGTCGT  SEQ ID: 1

```
        TG     GCC--    GG-            T-----     TA
     AC   TGGAAT    TGC   GGTGATGTTGA      ATTC   A         SEQ ID: 24
     ||   ||||||    |||   ||||||||||||     ||||
     TG   GCTTTA    ACG   CCACTGTAACT      TGAG   /
        CT     AGACC    ACA            CGTCCT     GT
```

Fig. 24D/1

```
                        TTC   C
              5' CAGCACCA GAAT    GT GT 3'      SEQ ID:20602
DCLRE1A          |||||||| ||||    || ||
BINDING SITE  3' GTCGTGGT CTTG    CA CA 5'      SEQ ID:507529
                        G    TA-  A

CA         TTC  -
              5'    GCACCAGAAT   G TCGT 3'      SEQ ID:20602
DKFZP586I2223       ||||||||||   | ||||
BINDING SITE  3'    CGTGGTCTTG   C AGCA 5'      SEQ ID:534456
                 GG         TCT G

CA    CCA        -
              5' GCA      GAATTTC GTCGT 3'      SEQ ID:20602
FLJ13725         |||      ||||||| |||||
BINDING SITE  3' CGT      CTTGAGG CAGCA 5'      SEQ ID:604594
                 AC    AC-       T

A          TC--  C
              5' AGC  CCAGAATT    GT GT 3'      SEQ ID:20602
PASK             |||  ||||||||    || ||
BINDING SITE  3' TCG  GGTCTTAA    CG CA 5'      SEQ ID:907327
                 G          TTGT  A

A         TC
              5' CAGC CCAGAATT    GTCGT 3'      SEQ ID:20602
TIGD5            |||| ||||||||    |||||
BINDING SITE  3' GTCG GGTCTTGG    CGGCA 5'      SEQ ID:993571
                  C         T-

-     C  C
              5' CAGCACCAGAA TTT  GT GT 3'      SEQ ID:20602
LOC151556        |||||||||||  |||  || ||
BINDING SITE  3' GTCGTGGTCTT AAA  CG CA 5'      SEQ ID:1151343
                             C    T  A

C         TT-   TC
              5' CAG ACCAGAAT     CG GT 3'      SEQ ID:20602
LOC196812        ||| ||||||||     || ||
BINDING SITE  3' GTC TGGTCTTA     GT CA 5'      SEQ ID:1214315
                  -         TCT   GA

AATT
              5' AGCACCAG    TCGTCGT 3'         SEQ ID:20602
LOC256158        ||||||||    |||||||
BINDING SITE  3' TCGTGGTC    GGCGGCA 5'         SEQ ID:1317257
                            CCTC

CA           G
              5'    GCACCAGAATTTC TCGT 3'       SEQ ID:20602
LOC90342            ||||||||||||| ||||
BINDING SITE  3'    TGTGGTCTTGGAG AGCA 5'       SEQ ID:1356067
                 A-              A
```

CCACCAGTCCTTGCACTGTTCTGACACTTTCCCCAGGAGG SEQ ID: 25
AAAACAAGTACAAAGGTTACGGTGG

GGAAAACAAGTACAAAGGTTACGG    SEQ ID: 2

```
     AGT-     GCAC   T  GACAC     CC
CCACC     CCTT    TGT CT     TTTCC  A
|||||     ||||    ||| ||     |||||         SEQ ID: 25
GGTGG     GGAA    ACA GA     AAAGG  G
     CATT     ----   T  ACA--     AG
```

Fig. 25D/1

```
                       A    A         TTACG
              5' GGAA ACA GTACAAAGG           3'      SEQ ID:29474
EED              ||||  ||| |||||||||
BINDING SITE  3' CCTT TGT CATGTTTCT           5'      SEQ ID:144323
                       C    -          TAC

A  A  AA      ACG
              5' GGAAAACA GT CA    GGTT       3'      SEQ ID:29474
MLPH             ||||||||  || ||   ||||
BINDING SITE  3' CCTTTTGT CA GT    CCGA       5'      SEQ ID:256513
                          -  C  C-      C

A  A      A
              5' GGAAAACA GT CA AGGTT CGG       3    SEQ ID:29474
NPY2R            ||||||||  || || ||||| |||
BINDING SITE  3' TCTTTTGT CA GT TCCGA GCC       5    SEQ ID:277186
                          C  C     C

A           A G   AC
              5' GG AAACAAGTACAA G TT   GG       3    SEQ ID:29474
NR1I2            || |||||||||||| | ||   ||
BINDING SITE  3' CC TTTGTTCATGTT C GA   CC       5    SEQ ID:277734
                    G           -  G   GA

AG A  A      TACGG
              5' GGAAAACA   T CA AGGT             3'   SEQ ID:29474
dJ383J4.3        ||||||||   | || ||||
BINDING SITE  3' CCTTTTGT   A GT TCTA             5'   SEQ ID:512554
                           CT  C   C      TC

GA         ACAA    TT    -
              5' G  AAACAAGT        AGG  AC GG          SEQ ID:29474
FLJ14280         |  ||||||||        |||  || ||
BINDING SITE  3' C  TTTGTTCA        TCC  TG CC          SEQ ID:610221
                    TC         CG--    TT   A

GGAAAAC        C      ---
              5'         AAGTA AA    AGGTTACGG          SEQ ID:29474
KIAA1678                 ||||| ||    |||||||||
BINDING SITE  3'         TTCAT TT    TCCAATGCC          SEQ ID:803886
                 CTT----        T      ATA

A      A  -       T
              5' GGAAA CAAGT CA AAGGT ACGG       3    SEQ ID:29474
KIAA1724         ||||| ||||| || ||||| ||||
BINDING SITE  3' CCTTT GTTCA GT TTTCA TGTC       5    SEQ ID:806213
                        -      A        -

A      -    AG-   ACGG
              5' GGAAA CAAGT ACAA    GTT              SEQ ID:29474
KIAA1949         ||||| ||||| ||||    |||
BINDING SITE  3' CCTTT GTTCA TGTT    CAA              SEQ ID:820868
                        C      A    CTA   CC
```

Fig. 25D/2

```
                        AAACA     CAAA-
                5' GGA      AGTA      GGTTACGG   3       SEQ ID:29474
RoXaN              ||       ||||      ||||||||
BINDING SITE    3' CCT      TCGT      CCAATGCC   5       SEQ ID:950975
                        C----     CCTAC

A          A  GT
                5' GGAAA CAAGTACA  AG   T        3'      SEQ ID:29474
SERP1              ||||| ||||||||  ||   |
BINDING SITE    3' CCTTT GTTCATGT  TC   A        5'      SEQ ID:963990
                        -        C   TG

-  C       TTACG
                5' GGAAAACAAG TA AAAGG            3'     SEQ ID:29474
SYNE-1             |||||||||| || |||||
BINDING SITE    3' CCTTTTGTTC AT TTTCC            5'     SEQ ID:986316
                             C  T       G

AAA          G
                5' GGA      CAAGTACAAA GTT        3'     SEQ ID:29474
TNRC4              |||      |||||||||| |||
BINDING SITE    3' CCT      GTTCATGTTT CGA        5'     SEQ ID:996086
                         CC-          G

G          ACAAA     T
                5' GAAAACAAGT          GGT ACGG     3    SEQ ID:29474
LOC196047          ||||||||||          ||| ||||
BINDING SITE    3' CTTTTGTTCA          TCG TGTC     5    SEQ ID:1210373
                         A          CG---     -

A   A  A-    TTACG
                5' GGAAAACA GT CAA  GG            3'     SEQ ID:29474
LOC221540          |||||||| || |||  ||
BINDING SITE    3' CCTTTTGT CA GTT  CC            5'     SEQ ID:1274947
                          A   C  GA    G

A   A  A-    TTACG
                5' GGAAAACA GT CAA  GG            3'     SEQ ID:29474
LOC257545          |||||||| || |||  ||
BINDING SITE    3' CCTTTTGT CA GTT  CC            5'     SEQ ID:1274947
                          A   C  GA    G

A   A  A-    TTACG
                5' GGAAAACA GT CAA  GG            3'     SEQ ID:29474
LOC257598          |||||||| || |||  ||
BINDING SITE    3' CCTTTTGT CA GTT  CC            5'     SEQ ID:1274947
                          A   C  GA    G

-  A  AA   TACGG
                5' GGAAAACAA GT CA   GGT          3      SEQ ID:29474
LOC63928           ||||||||| || ||   |||
BINDING SITE    3' CCTTTTGTT CA GT   CCA          5      SEQ ID:1347928
                           A  C  C-   CC
```

CGGCCGCCGAGTTCCGCGGCTCCGGGAGCGAAGCGCGCA  SEQ ID: 26
CCTGTGAGGCAGACGGCACCTCCTGCGACCGTCGCCGCC
ACCGCCGCCGCCGCCGCCGGGCGCCGAGGGGCTGGCGG
GCG

TCGCCGCCACCGCCGCCGCCGCCG                 SEQ ID: 3

```
     G     G     G    -    GA   AA   C   ACCT   A-    A     CACCT
  CG CCGCC AGTTCC CGGC TCCGG  GCG  GCG GC    GTG  GGC  GACGG     C
  || ||||| |||||| |||| |||||  |||  ||| ||    |||  |||  |||||     C    SEQ ID: 26
  GC GGCGG TCGGGG GCCG GGGCC  CGC  CGC CG    CAC  CCG  CTGCC     C
     G    -      A    C      GC   --   -    CCGC CG    -      AGCGT
```

Fig. 26D/1

```
                           5' GCCACCGCCGCCGCCGCCG      3'                SEQ ID:20604
ACVR1B                        ||||||||||||||||||
BINDING SITE               3' TGGTGGCGGCGGCGGCGGC      5'                SEQ ID:46182

A
                           5' CGCCGCC CCGCCGCCGCCG     3'                SEQ ID:20604
ACVR1B                        ||||||| |||||||||||||
BINDING SITE               3' GTGGCGG GGCGGCGGCGGC     5'                SEQ ID:46198
                                         C

A
                           5' CGCCGCC CCGCCGCCGCCG     3'                SEQ ID:20604
DLG3                          ||||||| |||||||||||||
BINDING SITE               3' GTGGCGG GGCGGCGGCGGC     5'                SEQ ID:46198
                                         C

C--    A    C
                           5' TCGC   GCC CCGC GCCGCCGCCG                  SEQ ID:20604
ADARB1                        ||||   ||| |||| |||||||||
BINDING SITE               3' GGCG   CGG GGCG CGGCGGCGGC                  SEQ ID:48568
                                   AAC    C    A

C--    A    C
                           5' TCGC   GCC CCGC GCCGCCGCCG                  SEQ ID:20604
ADARB1                        ||||   ||| |||| |||||||||
BINDING SITE               3' GGCG   CGG GGCG CGGCGGCGGC                  SEQ ID:48568
                                   AAC    C    A

A            CG
                           5' CGCCGCC CCGCCGCCGC   CC   3'                SEQ ID:20604
ADRBK1                        ||||||| |||||||||| ||
BINDING SITE               3' GCGGCGG GGCGGCGGCG  GG    5'                SEQ ID:51719
                                      C            A-

G   A-
                           5' GCC CC  CCGCCGCCGCCGCCG   3'                SEQ ID:20604
ADRBK1                        ||| ||  |||||||||||||||
BINDING SITE               3' CGG GG  GGCGGCGGCGGCGGC   5'                SEQ ID:51737
                                 A  AG

G   A-
                           5' GCC CC  CCGCCGCCGCCGCCG   3'                SEQ ID:20604
ADRBK1                        ||| ||  |||||||||||||||
BINDING SITE               3' CGG GG  GGCGGCGGCGGCGGC   5'                SEQ ID:51737
                                 A  AG

-   AC  C-
                           5! GC CGCC  CG  CGCCGCCG     3'                SEQ ID:20604
AKAP13                        || ||||  ||  ||||||||
BINDING SITE               3' CG GCGG  GC  GCGGCGGC     5'                SEQ ID:54490
                                  A    A-  CA
```

Fig. 26D/2

```
                         CA        C
                 5' CGC    CCGCCGCCGC GC  3'         SEQ ID:20604
AMD1                ||| |||||||||| ||
BINDING SITE     3' GCG    GGCGGCGGCG CG  5'         SEQ ID:57140
                         AC        A

CCG
                 5' CGCCGCCACCGCCGCCG    CC  3'      SEQ ID:20604
APP                 |||||||||||||||||    ||
BINDING SITE     3' GCGGCGGTGGCGGCGGC    GG  5'      SEQ ID:62063
                                         AGA

C  C
                 5' CGCCGC AC GCCGCCGCCG  3'         SEQ ID:20604
ARAF1               |||||| || |||||||||
BINDING SITE     3' GCGGCG TG CGGCGGCGGC  5'         SEQ ID:63732
                         A  T

C   A    -    G    CG
                 5' TCGC GCC CCGC CGCC CCGC          SEQ ID:20604
ASC                 |||| ||| |||| |||| ||||
BINDING SITE     3' GGCG CGG GGCG GTGG GGCG          SEQ ID:66821
                       A   C    A    -   AC

A   GCC
                 5' CGCCGCC CC    GCCGCCG  3'        SEQ ID:20604
ATF4                ||||||| ||    |||||||
BINDING SITE     3' GCGGCGG GG    CGGCGGC  5'        SEQ ID:67884
                            C     GA-

A    C---     C
                 5' CCGCC CCGC    GC GCCGCCG  3'     SEQ ID:20604
ATP1A1              ||||| ||||    || |||||||
BINDING SITE     3' GGCGG GGCG    CG CGGCGGC  5'     SEQ ID:68935
                         C    ACAA     A

CCA              C------
                 5' GCCG    CCGCCGCCGC        GCCG   SEQ ID:20604
ATP1A1              ||||    ||||||||||        ||||
BINDING SITE     3' CGGC    GGCGGCGGCG        CGGC   SEQ ID:68949
                        TAC          ACAACGA

CC   ACC
                 5' TCG    GCC    GCCGCCGCCGC  3'    SEQ ID:20604
ATP1A1              |||    |||    |||||||||||
BINDING SITE     3' AGC    CGG    CGGCGGCGGCG  5'    SEQ ID:68961
                        C-   CTA

ACC     C
                 5' TCGCCGCC    GCCGC GCCGC  3'      SEQ ID:20604
ATP2B2              ||||||||    ||||| |||||
BINDING SITE     3' GGCGGCGG    CGGCG CGGCG  5'      SEQ ID:69717
                           CGA       A
```

Fig. 26D/3

```
                            ACC        C
                      5' TCGCCGCC  GCCGC GCCGC 3'           SEQ ID:20604
DR1                      ||||||||  ||||| |||||
BINDING SITE          3' GGCGGCGG  CGGCG CGGCG 5'           SEQ ID:69717
                            CGA      A

CA   C     C
                      5' TCGCCGC CCGC GCCGC GCCG 3'         SEQ ID:20604
ATP2B2                   ||||||| |||| ||||| ||||
BINDING SITE          3' GGCGGCG GGCG CGGCG CGGC 5'         SEQ ID:69718
                            AC   A     A

A    C     C
                      5' GCCGCC CCGC GCCGC GCCG 3'          SEQ ID:20604
ATP2B2                   |||||| |||| ||||| ||||
BINDING SITE          3' CGGCGG GGCG CGGCG CGGC 5'          SEQ ID:69745
                            C    A     A

A    C     C
                      5' GCCGCC CCGC GCCGC GCCG 3'          SEQ ID:20604
DR1                      |||||| |||| ||||| ||||
BINDING SITE          3' CGGCGG GGCG CGGCG CGGC 5'          SEQ ID:69745
                            C    A     A

C  A      C
                      5' GC GCC CCGCCGC GCCGC 3'            SEQ ID:20604
ATP2B2                   || ||| ||||||| |||||
BINDING SITE          3' CG CGG GGCGGCG CGGCG 5'            SEQ ID:69749
                           A  C      A

CCAC
                      5' CCG      CGCCGCCGCCGCCG 3'         SEQ ID:20604
AUP1                     |||      |||||||||||||
BINDING SITE          3' GGC      GCGGCGGCGGCGGT 5'         SEQ ID:72273
                              A---

--  AC
                      5' CGCC  GCC  CGCCGCCGCCG 3'          SEQ ID:20604
AUP1                     ||||  |||  |||||||||||
BINDING SITE          3' GCGG  CGG  GCGGCGGCGG 5'           SEQ ID:72277
                              GC  CA

AC       C
                      5' TCGCCGCC  CGCCGC GCCGCCG 3'        SEQ ID:20604
BCL11B                   ||||||||  |||||| |||||||
BINDING SITE          3' GGCGGCGG  GCGGCG CGGCGGC 5'        SEQ ID:78295
                            C-       A

C  A    C
                      5' TCGC GCC CCGC GCCGCCGCCG 3'        SEQ ID:20604
BCL11B                   |||| ||| |||| ||||||||||
BINDING SITE          3' GGCG CGG GGCG CGGCGGCGGC 5'        SEQ ID:78304
                             A    C    A
```

Fig. 26D/4

```
                           C    A        C
                   5' TCGC GCC  CCGC GCCGCCGCCG    3        SEQ ID:20604
BCL11B                ||||  ||| ||||  ||||||||||
BINDING SITE       3' GGCG CGG  GGCG CGGCGGCGGC    5        SEQ ID:78304
                           A    C        A

CA          C
                   5' CGCCGC    CCGCCGC GCCGCCG    C        SEQ ID:20604
BCL11B                ||||||    ||||||| |||||||    |
BINDING SITE       3' GCGGCG    GGCGGCG CGGCGGC    G        SEQ ID:78310
                         AC          A

ACC
                   5' GCCGCC        GCCGCCGCCGCCG  3'       SEQ ID:20604
BCL11B                ||||||        |||||||||||||
BINDING SITE       3' CGGCGG        CGGCGGCGGCGGC  5'       SEQ ID:78336
                         CGA

A-
                   5' CGCCGCC    CCGCC GCCGCCGCCG  3        SEQ ID:20604
BCL7B                 |||||||    ||||| ||||||||||
BINDING SITE       3' GCGGCGG    GGCGG CGGCGGCGGC  5        SEQ ID:79353
                                  CG      G

A              G
                   5' CCGCC CCGCCGCCGCC CC           3'     SEQ ID:20604
BCR                   ||||| ||||||||||| ||
BINDING SITE       3' GGCGG GGCGGCGGCGG GG           5'     SEQ ID:79756
                          C              A

A              G
                   5' CCGCC CCGCCGCCGCC CC           3'     SEQ ID:20604
BCR                   ||||| ||||||||||| ||
BINDING SITE       3' GGCGG GGCGGCGGCGG GG           5'     SEQ ID:79756
                          C              A

A        C
                   5' CCGCC CCGCCGC GCCGCCG          3'     SEQ ID:20604
BCR                   ||||| ||||||| |||||||
BINDING SITE       3' GGCGG GGCGGCG CGGCGGC          5'     SEQ ID:79759
                          C        A

A      C
                   5' TCGCCGCC CCGC GCCGCCGCCG       3'     SEQ ID:20604
BCR                   |||||||| |||| ||||||||||
BINDING SITE       3' GGCGGCGG GGCG CGGCGGCGGC       5'     SEQ ID:79761
                            C      A

A      C
                   5' TCGCCGCC CCGC GCCGCCGCCG       3'     SEQ ID:20604
BCR                   |||||||| |||| ||||||||||
BINDING SITE       3' GGCGGCGG GGCG CGGCGGCGGC       5'     SEQ ID:79761
                            C      A
```

Fig. 26D/5

```
                              A         C
                     5' CCGCC CCGCCGC GCCGCCG  C  3'     SEQ ID:20604
BCR                     ||||| ||||||| |||||||  |
BINDING SITE         3' GGCGG GGCGGCG CGGCGGC  G  5'     SEQ ID:79762
                              C         A

ACC
                     5' TCGCCGCC    GCCGCCGCCGCCG  3'    SEQ ID:20604
BCR                     ||||||||    |||||||||||||
BINDING SITE         3' GGCGGCGG    CGGCGGCGGCGGC  5'    SEQ ID:79766
                                    CGA

ACC
                     5' TCGCCGCC    GCCGCCGCCGCCG  3'    SEQ ID:20604
BCR                     ||||||||    |||||||||||||
BINDING SITE         3' GGCGGCGG    CGGCGGCGGCGGC  5'    SEQ ID:79766
                                    CGA

ACC
                     5' TCGCCGCC    GCCGCCGCCGCCG  3'    SEQ ID:20604
ZNF6                    ||||||||    |||||||||||||
BINDING SITE         3' GGCGGCGG    CGGCGGCGGCGGC  5'    SEQ ID:79766
                                    CGA

A           ---
                     5' TCGCCGCC CCGCCGC CGCCGCCG       SEQ ID:20604
BCRP2                   |||||||| ||||||| ||||||||
BINDING SITE         3' GGCGGCGG GGCGGCG GCGGCGGC       SEQ ID:79919
                                C        AGC

CGCC
                     5' GC     ACCGCCGCCGCCGCCG  3'     SEQ ID:20604
BCRP2                   ||     |||||||||||||||
BINDING SITE         3' CG     TGGCGGCGGCGGCGGC  5'     SEQ ID:79941
                           ACCT

-      C
                     5' CCA CCGC GCCGCCGCCG  3'         SEQ ID:20604
BSG                     ||| |||| ||||||||||
BINDING SITE         3' GGT GGCG CGGCGGCGGC  5'         SEQ ID:83983
                            T    A

C    A      C
                     5' TCG CGCC CCGC GCCGCCG  3'       SEQ ID:20604
BSN                     ||| |||| |||| |||||||
BINDING SITE         3' AGC GCGG GGCG CGGCGGC  5'       SEQ ID:84199
                            C    C    A

CACC
                     5' CGCCGC     GCCGCCGCCGC  3'      SEQ ID:20604
BTG3                    ||||||     |||||||||||
BINDING SITE         3' GCGGCG     CGGCGGCGGCG  5'      SEQ ID:84854
                              A---
```

Fig. 26D/6

```
                              CACC
                    5' CGCCGC       GCCGCCGCCGC  3'        SEQ ID:20604
CHS1                   ||||||       |||||||||||
BINDING SITE        3' GCGGCG       CGGCGGCGGCG  5'        SEQ ID:84854
                          A---

G      ACC   C
                    5' TC CCGCC  GC GCCGCCGCCG   3'        SEQ ID:20604
BTG3                   || |||||  || ||||||||||
BINDING SITE        3' AG GGCGG  CG CGGCGGCGGC   5'        SEQ ID:84863
                       -    ---  A

-  CCACC
                    5' CGC CG       GCCGCCGCCGCC  3'       SEQ ID:20604
HIRA                   ||| ||       ||||||||||||
BINDING SITE        3' GCG GC       CGGCGGCGGCGG  5'       SEQ ID:85041
                        A  -----

-  C  C
                    5' GCCACCGCC GC GC GC   3'             SEQ ID:20604
CACNA1A                ||||||||| || || ||
BINDING SITE        3' CGGTGGCGG CG CG CG   5'             SEQ ID:87774
                                 A  A  A

----   CACC
                    5' CGC     CGC     GCCGCCGCCGCCG       SEQ ID:20604
CALM1                  |||     |||     ||||||||||||
BINDING SITE        3' GCG     GCG     CGGCGGCGGCGGC       SEQ ID:89443
                       ACAC    ATA-

A          ---
                    5' GCCGCC CCGCCGCC     GCCGCCG  3      SEQ ID:20604
CALM1                  |||||| ||||||||     |||||||
BINDING SITE        3' CGGCGG GGCGGCGG     CGGCGGC  5      SEQ ID:89450
                            C          ACG

A
                    5' TCGCCGCC CCGCCGCCGCCGCCG  3'        SEQ ID:20604
CACNA1A                |||||||| |||||||||||||||
BINDING SITE        3' GGCGGCGG GGCGGCGGCGGCGGC  5'        SEQ ID:94853
                                C

A
                    5' TCGCCGCC CCGCCGCCGCCGCCG  3'        SEQ ID:20604
CBL                    |||||||| |||||||||||||||
BINDING SITE        3' GGCGGCGG GGCGGCGGCGGCGGC  5'        SEQ ID:94853
                                C

A
                    5' TCGCCGCC CCGCCGCCGCCGCCG  3'        SEQ ID:20604
CBL                    |||||||| |||||||||||||||
BINDING SITE        3' GGCGGCGG GGCGGCGGCGGCGGC  5'        SEQ ID:94853
                                C
```

Fig. 26D/7

```
                    A
              5' TCGCCGCC CCGCCGCCGCCGCCG 3'      SEQ ID:20604
CBL              |||||||| |||||||||||||||
BINDING SITE  3' GGCGGCGG GGCGGCGGCGGCGGC 5'      SEQ ID:94853
                    C

A
              5' TCGCCGCC CCGCCGCCGCCGCCG 3'      SEQ ID:20604
CBL              |||||||| |||||||||||||||
BINDING SITE  3' GGCGGCGG GGCGGCGGCGGCGGC 5'      SEQ ID:94853
                    C

A
              5' TCGCCGCC CCGCCGCCGCCGCCG 3'      SEQ ID:20604
FGF18            |||||||| |||||||||||||||
BINDING SITE  3' GGCGGCGG GGCGGCGGCGGCGGC 5'      SEQ ID:94853
                    C

A
              5' TCGCCGCC CCGCCGCCGCCGCCG 3'      SEQ ID:20604
FGF18            |||||||| |||||||||||||||
BINDING SITE  3' GGCGGCGG GGCGGCGGCGGCGGC 5'      SEQ ID:94853
                    C

A
              5' TCGCCGCC CCGCCGCCGCCGCCG 3'      SEQ ID:20604
FMR1             |||||||| |||||||||||||||
BINDING SITE  3' GGCGGCGG GGCGGCGGCGGCGGC 5'      SEQ ID:94853
                    C

A
              5' TCGCCGCC CCGCCGCCGCCGCCG 3'      SEQ ID:20604
FMR1             |||||||| |||||||||||||||
BINDING SITE  3' GGCGGCGG GGCGGCGGCGGCGGC 5'      SEQ ID:94853
                    C

A
              5' TCGCCGCC CCGCCGCCGCCGCCG 3'      SEQ ID:20604
FMR1             |||||||| |||||||||||||||
BINDING SITE  3' GGCGGCGG GGCGGCGGCGGCGGC 5'      SEQ ID:94853
                    C

A
              5' TCGCCGCC CCGCCGCCGCCGCCG 3'      SEQ ID:20604
FMR1             |||||||| |||||||||||||||
BINDING SITE  3' GGCGGCGG GGCGGCGGCGGCGGC 5'      SEQ ID:94853
                    C

A
              5' TCGCCGCC CCGCCGCCGCCGCCG 3'      SEQ ID:20604
FMR1             |||||||| |||||||||||||||
BINDING SITE  3' GGCGGCGG GGCGGCGGCGGCGGC 5'      SEQ ID:94853
                    C
```

Fig. 26D/8

```
                          A
            5' TCGCCGCC CCGCCGCCGCCGCCG 3'      SEQ ID:20604
FMR1           |||||||| ||||||||||||||||
BINDING SITE 3' GGCGGCGG GGCGGCGGCGGCGGC 5'      SEQ ID:94853
                          C

A
            5' TCGCCGCC CCGCCGCCGCCGCCG 3'      SEQ ID:20604
FMR1           |||||||| ||||||||||||||||
BINDING SITE 3' GGCGGCGG GGCGGCGGCGGCGGC 5'      SEQ ID:94853
                          C

A
            5' TCGCCGCC CCGCCGCCGCCGCCG 3'      SEQ ID:20604
GSPT1          |||||||| ||||||||||||||||
BINDING SITE 3' GGCGGCGG GGCGGCGGCGGCGGC 5'      SEQ ID:94853
                          C

A
            5' TCGCCGCC CCGCCGCCGCCGCCG 3'      SEQ ID:20604
GSPT1          |||||||| ||||||||||||||||
BINDING SITE 3' GGCGGCGG GGCGGCGGCGGCGGC 5'      SEQ ID:94853
                          C

A
            5' TCGCCGCC CCGCCGCCGCCGCCG 3'      SEQ ID:20604
GSPT1          |||||||| ||||||||||||||||
BINDING SITE 3' GGCGGCGG GGCGGCGGCGGCGGC 5'      SEQ ID:94853
                          C

A
            5' TCGCCGCC CCGCCGCCGCCGCCG 3'      SEQ ID:20604
MLLT1          |||||||| ||||||||||||||||
BINDING SITE 3' GGCGGCGG GGCGGCGGCGGCGGC 5'      SEQ ID:94853
                          C

A
            5' TCGCCGCC CCGCCGCCGCCGCCG 3'      SEQ ID:20604
MLLT1          |||||||| ||||||||||||||||
BINDING SITE 3' GGCGGCGG GGCGGCGGCGGCGGC 5'      SEQ ID:94853
                          C

A
            5' TCGCCGCC CCGCCGCCGCCGCCG 3'      SEQ ID:20604
NTRK3          |||||||| ||||||||||||||||
BINDING SITE 3' GGCGGCGG GGCGGCGGCGGCGGC 5'      SEQ ID:94853
                          C

A
            5' TCGCCGCC CCGCCGCCGCCGCCG 3'      SEQ ID:20604
PPP3CA         |||||||| ||||||||||||||||
BINDING SITE 3' GGCGGCGG GGCGGCGGCGGCGGC 5'      SEQ ID:94853
                          C
```

Fig. 26D/9

```
                     A
             5' TCGCCGCC CCGCCGCCGCCGCCG 3'      SEQ ID:20604
PPP3CA          |||||||| ||||||||||||||
BINDING SITE 3' GGCGGCGG GGCGGCGGCGGCGGC 5'      SEQ ID:94853
                     C

A
             5' TCGCCGCC CCGCCGCCGCCGCCG 3'      SEQ ID:20604
PPP3CA          |||||||| ||||||||||||||
BINDING SITE 3' GGCGGCGG GGCGGCGGCGGCGGC 5'      SEQ ID:94853
                     C

A
             5' TCGCCGCC CCGCCGCCGCCGCCG 3'      SEQ ID:20604
RELN            |||||||| ||||||||||||||
BINDING SITE 3' GGCGGCGG GGCGGCGGCGGCGGC 5'      SEQ ID:94853
                     C

A
             5' TCGCCGCC CCGCCGCCGCCGCCG 3'      SEQ ID:20604
RGS19IP1        |||||||| ||||||||||||||
BINDING SITE 3' GGCGGCGG GGCGGCGGCGGCGGC 5'      SEQ ID:94853
                     C

A
             5' TCGCCGCC CCGCCGCCGCCGCCG 3'      SEQ ID:20604
RGS19IP1        |||||||| ||||||||||||||
BINDING SITE 3' GGCGGCGG GGCGGCGGCGGCGGC 5'      SEQ ID:94853
                     C

A
             5' TCGCCGCC CCGCCGCCGCCGCCG 3'      SEQ ID:20604
RGS19IP1        |||||||| ||||||||||||||
BINDING SITE 3' GGCGGCGG GGCGGCGGCGGCGGC 5'      SEQ ID:94853
                     C

A
             5' TCGCCGCC CCGCCGCCGCCGCCG 3'      SEQ ID:20604
RGS19IP1        |||||||| ||||||||||||||
BINDING SITE 3' GGCGGCGG GGCGGCGGCGGCGGC 5'      SEQ ID:94853
                     C

A
             5' TCGCCGCC CCGCCGCCGCCGCCG 3'      SEQ ID:20604
UBE2B           |||||||| ||||||||||||||
BINDING SITE 3' GGCGGCGG GGCGGCGGCGGCGGC 5'      SEQ ID:94853
                     C

A
             5' TCGCCGCC CCGCCGCCGCCGCCG 3'      SEQ ID:20604
UBE2B           |||||||| ||||||||||||||
BINDING SITE 3' GGCGGCGG GGCGGCGGCGGCGGC 5'      SEQ ID:94853
                     C
```

Fig. 26D/10

```
                        A
                  5' TCGCCGCC CCGCCGCCGCCGCCG 3'         SEQ ID:20604
UBE2B                 |||||||| ||||||||||||||
BINDING SITE      3' GGCGGCGG GGCGGCGGCGGCGGC 5'         SEQ ID:94853
                                C

A
                  5' TCGCCGCC CCGCCGCCGCCGCCG 3'         SEQ ID:20604
UBE2B                 |||||||| ||||||||||||||
BINDING SITE      3' GGCGGCGG GGCGGCGGCGGCGGC 5'         SEQ ID:94853
                                C

A
                  5' GCCGCC CCGCCGCCGCCGCCG  C           SEQ ID:20604
CAMK4                 |||||| ||||||||||||||  |
BINDING SITE      3' CGGCGG GGCGGCGGCGGCGGC  G           SEQ ID:94860
                               C

A
                  5' GCCGCC CCGCCGCCGCCGCCG  C           SEQ ID:20604
CBL                   |||||| |||||||||||||   |
BINDING SITE      3' CGGCGG GGCGGCGGCGGCGGC  G           SEQ ID:94860
                               C

CAC--
                  5' TCGCCGC    CGCCGCCGCCGCCG           SEQ ID:20604
CD47                  |||||||   ||||||||||||||
BINDING SITE      3' GGCGGCG    GCGGCGGCGGCGGC           SEQ ID:97660
                       CCCCA

---   A
                  5' TCGCC   GCC CCGCCGCCGCCGCCG         SEQ ID:20604
CDC2L1                |||||   ||| ||||||||||||||
BINDING SITE      3' GGCGG   CGG GGCGGCGGCGGCGGC         SEQ ID:99045
                       GCA   C

A---
                  5' TCGCCGCC    CCGCCGCCGCCGCCG         SEQ ID:20604
CDC2L1                ||||||||   ||||||||||||||
BINDING SITE      3' GGCGGCGG    GGCGGCGGCGGCGGC         SEQ ID:99046
                         GCAC

GCCAC
                  5' CC     CGCCGCCGCCGCCG 3'            SEQ ID:20604
CDC34                 ||     ||||||||||||||
BINDING SITE      3' GG     GCGGCGGCGGCGGC 5'            SEQ ID:99180
                       AGAC-

G  CCACC
                  5' TC CCG    GCCGCCGCCGCCG 3'          SEQ ID:20604
CDH23                 || |||   ||||||||||||||
BINDING SITE      3' AG GGC    CGGCGGCGGCGGC 5'          SEQ ID:100443
                       -  T----
```

Fig. 26D/11

```
                          A         ---
                5' CCGCC CCGCCGCCGC    CGCCG  3'       SEQ ID:20604
CDH6               ||||| ||||||||||    |||||
BINDING SITE    3' GGCGG GGCGGCGGCG    GCGGC  5'       SEQ ID:100628
                          C            CCA

A
                5' CGCC  CCGCCGCCGCC  3'               SEQ ID:20604
CDH6               ||||  |||||||||||
BINDING SITE    3' GCGG  GGCGGCGGCGG  5'               SEQ ID:100637
                         C

A
                5' CGCC  CCGCCGCCGCC  3'               SEQ ID:20604
PEA15              ||||  |||||||||||
BINDING SITE    3' GCGG  GGCGGCGGCGG  5'               SEQ ID:100637
                         C

G A
                5' GCC CC CCGCCGCCGCCG  3'             SEQ ID:20604
CDH6               ||| || ||||||||||||
BINDING SITE    3' CGG GG GGCGGCGGCGGC  5'             SEQ ID:100646
                        A C

A ----     C   C
                5' TCGCCGCC CC    GC GC GCCGCCG        SEQ ID:20604
CDK9               |||||||| ||    || || |||||||
BINDING SITE    3' GGCGGCGG GG    CG CG CGGCGGC        SEQ ID:101419
                            G TCAG A   A

A G ----    C  C
                5' TCGCCGCC CC CC    GC GC GCCG        SEQ ID:20604
CDK9               |||||||| || ||    || || ||||
BINDING SITE    3' GGCGGCGG GG GG    CG CG CGGC        SEQ ID:101421
                            C G TCAG  A  A

A       G    C-
                5' CGCCGCC CCGCC  CCG  CGC  3'         SEQ ID:20604
CDK9               ||||||| |||||  |||  |||
BINDING SITE    3' GCGGCGG GGCGG  GGT  GCG  5'         SEQ ID:101424
                          C       G    CA

C  CACC           CG
                5' TCGC GC      GCCGCCGC CC  3'        SEQ ID:20604
CDK9               |||| ||      |||||||| ||
BINDING SITE    3' AGCG CG      CGGCGGCG GG  5'        SEQ ID:101437
                     A  A---            A-

A       C---    C
                5' CCGCC CCGCCGC    GC GCCG  3'        SEQ ID:20604
CDKN2D             ||||| |||||||    || ||||
BINDING SITE    3' GGCGG GGCGGCG    CG CGGC  5'        SEQ ID:102195
                        C    ACTC    T
```

Fig. 26D/12

```
                        GCC    AC
                    5'  TC  GCC    CGCCGCCGCCGCCG              SEQ ID:20604
    CDKN2D              ||  |||    ||||||||||||||
    BINDING SITE    3'  AG  CGG    GCGGCGGCGGCGGC              SEQ ID:102235
                        ACT    AC                GA

A  C       GC
                    5'  CGCCGCC CCGC GCC    CG  3'             SEQ ID:20604
    CHN2                ||||||| |||| |||    ||
    BINDING SITE    3'  GCGGCGG GGCG CGG    GC  5'             SEQ ID:105797
                             C  A        GA

G   CAC
                    5'  TC CCGC    CGCCGCCGC   3'              SEQ ID:20604
    CHRNA3              || ||||    |||||||||
    BINDING SITE    3'  AG GGCG    GCGGCGGCG   5'              SEQ ID:106136
                          A   AA-

CCA    C
                    5'  GCCG    CCGC GCCGCCGCCG  3'            SEQ ID:20604
    CHS1                ||||    |||| ||||||||||
    BINDING SITE    3'  CGGC    GGCG CGGCGGCGGC  5'            SEQ ID:106651
                          TGC    A

CA
                    5'  CCGC    CCGCCGCCGCCGC  3'              SEQ ID:20604
    CKAP1               ||||    |||||||||||||
    BINDING SITE    3'  GGCG    GGCGGCGGCGGCG  5'              SEQ ID:107655
                             TC

CA
                    5'  CCGC    CCGCCGCCGCCGC  3'              SEQ ID:20604
    CKAP1               ||||    |||||||||||||
    BINDING SITE    3'  GGCG    GGCGGCGGCGGCG  5'              SEQ ID:107655
                             TC

A   C  C   C
                    5'  TCGCCGCC CCGC GC GC GC  3'             SEQ ID:20604
    CKAP1               |||||||| |||| || || ||
    BINDING SITE    3'  GGCGGCGG GGCG CG CG CG  5'             SEQ ID:107659
                              C   A  A   A

A    G    C
                    5'  TCGCCGCC CCGCC CCGC GCC  3'             SEQ ID:20604
    COL5A1              |||||||| ||||| |||| |||
    BINDING SITE    3'  AGCGGCGG GGCGG GGCG TGG  5'             SEQ ID:114312
                                 C     -    C

G   A     GC
                    5'  TCGCC CC CC    CGCCGCCGCCG  3'          SEQ ID:20604
    COL5A1              ||||| || ||    |||||||||||
    BINDING SITE    3'  AGCGG GG GG    GCGGCGGCGGC  5'          SEQ ID:114314
                            A   A  A-
```

Fig. 26D/13

```
                         -- CA
                  5' CGC  CGC  CCGCCGCCGCCG 3'        SEQ ID:20604
CPE               |||  |||  ||||||||||||
BINDING SITE      3' GCG  GCG  GGCGGCGGCGGC 5'        SEQ ID:116431
                         AC  A-

A   C  CG
                  5' CGCCGCC CCGC GC  CCG 3'          SEQ ID:20604
CSNK1D            ||||||| |||| ||  |||
BINDING SITE      3' GCGGCGG GGCG CG  GGC 5'          SEQ ID:120331
                        C   A  A-

A   GC   C
                  5' TCGCCGCC CCGCC CGC GC 3'         SEQ ID:20604
CUGBP1            |||||||| ||||| ||| ||
BINDING SITE      3' GGCGGCGG GGCGG GCG CG 5'         SEQ ID:122870
                         C   A-   A

CA-            C
                  5' CCGC    CCGCCGCCGC GCCG 3'       SEQ ID:20604
CUGBP1            ||||    |||||||||| ||||
BINDING SITE      3' GGCG    GGCGGCGGCG CGGC 5'       SEQ ID:122874
                       CAG            A

CG  G
                  5' CGCCGCCACCGCCGC CC CCG 3'        SEQ ID:20604
DAG1              ||||||||||||||| || |||
BINDING SITE      3' GCGGCGGTGGCGGCG GG GGC 5'        SEQ ID:127812
                                   A-  -

C   CACC  C
                  5' TCG CGC   GC GCCGCCGCCG  3       SEQ ID:20604
DAG1              ||| |||   || ||||||||||
BINDING SITE      3' AGC GCG   CG CGGCGGCGGC  5       SEQ ID:127882
                        C   CTT-  A

A    C
                  5' CGCC CCGC GCCGCCGCCG 3'          SEQ ID:20604
DDEF2             |||| |||| ||||||||||
BINDING SITE      3' GTGG GGCG CGGCGGCGGC 5'          SEQ ID:129959
                        C    A

-----          C
                  5' TCGCCGC    CACCGCCGC GCCGCC      SEQ ID:20604
DDEF2             |||||||    |||||||| ||||||
BINDING SITE      3' GGCGGCG    GTGGCGGCG CGGCGG      SEQ ID:129968
                               AGCCT         A

CA        CG
                  5' CGCCGC CCGCCGCCGC CCG 3'         SEQ ID:20604
DDEF2             |||||| |||||||||| |||
BINDING SITE      3' GCGGCG GGCGGCGGCG GGC 5'         SEQ ID:129973
                        AC        A-
```

Fig. 26D/14

```
                                G   A  -  C
                    5' TC CCGCC CC GC GCCGCCG 3'          SEQ ID:20604
DHFR                   || |||||| || || |||||||
BINDING SITE        3' AG GGCGG GG CG CGGCGGC 5'          SEQ ID:133111
                        -      -  T  A

5' TCGCCGCCACCGCCGCCGCCG 3'           SEQ ID:20604
DLG3                   |||||||||||||||||||||
BINDING SITE        3' GGCGGCGGTGGTGGCGGCGGC 5'           SEQ ID:134695

5' TCGCCGCCACCGCCGCCGCCG 3'           SEQ ID:20604
DLG3                   |||||||||||||||||||||
BINDING SITE        3' GGCGGCGGTGGCGGCGGTGGC 5'           SEQ ID:134697

G    CA     C
                    5' C CCGC CCGC GCCGCCGCCG 3'          SEQ ID:20604
DR1                    | |||| |||| ||||||||||
BINDING SITE        3' G GGCG GGCG CGGCGGCGGC 5'          SEQ ID:138522
                         G    AC     A

CA    C    C
                    5' TCGCCGC CCGC GCCGC GC 3'           SEQ ID:20604
DR1                    ||||||| |||| ||||| ||
BINDING SITE        3' GGCGGCG GGCG CGGCG CG 5'           SEQ ID:138525
                            AC    A    A

C   A      C
                    5' TCGC GCC CCGCCGC GCCGC 3'          SEQ ID:20604
DR1                    |||| ||| ||||||| |||||
BINDING SITE        3' GGCG CGG GGCGGCG CGGCG 5'          SEQ ID:138526
                           A   C      A

CA         C
                    5' GCCGC CCGCCGCCG GCCG 3'            SEQ ID:20604
DR1                    ||||| ||||||||| ||||
BINDING SITE        3' CGGCG GGCGGCGGC CGGC 5'            SEQ ID:138546
                            AC         A

A-
                    5' TCGCCGCC  CCGCCGCCGCCGCCG 3        SEQ ID:20604
DSCAM                  ||||||||  ||||||||||||||
BINDING SITE        3' GGCGGCGG  GGCGGCGGCGGCGGC 5        SEQ ID:139794
                               GC

A-
                    5' TCGCCGCC  CCGCCGCCGCCGCCG          SEQ ID:20604
DSCAM                  ||||||||  ||||||||||||||
BINDING SITE        3' GGCGGCGG  GGCGGCGGCGGCGGC          SEQ ID:139795
                               GC
```

Fig. 26D/15

```
                          A       C       --
               5' CGCCGCC CCGCCGC GCC   GCCG  3'        SEQ ID:20604
DSCAM             ||||||| ||||||| |||   ||||
BINDING SITE   3' GCGGCGG GGCGGCG CGG   CGGC  5'        SEQ ID:139808
                          C       A     AT

A  GC   -
               5' TCGCCGCC CC  CG CCG  3'               SEQ ID:20604
DSCR1             |||||||| ||  || |||
BINDING SITE   3' AGCGGCGG GG  GC GGC  5'               SEQ ID:139913
                           C  GA  A

A        C  C
               5' TCGCCGCC CCGCCGC GC GC  3'            SEQ ID:20604
DUSP5             |||||||| ||||||| || ||
BINDING SITE   3' GGCGGCGG GGCGGCG CG CG  5'            SEQ ID:141448
                           C       -  T

AC
               5' CGCCGCC  CGCCGCCGCCG  3'              SEQ ID:20604
DVL3              |||||||  |||||||||||
BINDING SITE   3' GCGGCGG  GCGGCGGCGGC  5'              SEQ ID:141937

CG  ACC
               5' GC  CC    GCCGCCGCCG  3'              SEQ ID:20604
DXYS155E          ||  ||    ||||||||||
BINDING SITE   3' CG  GG    CGGCGGCGGC  5'              SEQ ID:142341
                     CA  GTC

C    AC
               5' GC GCC  CGCCGCCGCCG  3'               SEQ ID:20604
DYRK2             || |||  |||||||||||
BINDING SITE   3' CG CGG  GCGGCGGCGGC  5'               SEQ ID:142933
                     A    CA

GCC  CACC
               5' TC GC      GCCGCCGCCGCCG  3'          SEQ ID:20604
DYRK2             || ||      |||||||||||||
BINDING SITE   3' AG CG      CGGCGGCGGCGGC  5'          SEQ ID:142953
                     AC-  C---

A           G
               5' CCGCC CCGCCGCCGCC CC  3'              SEQ ID:20604
EFNA3             ||||| ||||||||||| ||
BINDING SITE   3' GGCGG GGCGGCGGCGG GG  5'              SEQ ID:144685
                        C           G

CCA
               5' CCG    CCGCCGCCGCCG  3'               SEQ ID:20604
EFNA3             |||    |||||||||||||
BINDING SITE   3' GGC    GGCGGCGGCGGCGGC  5'            SEQ ID:144687
                        CTC
```

Fig. 26D/16

```
                          A        GCC
              5' GCCGCC CCGCCGCC    GC      3'          SEQ ID:20604
EGLN1            ||||||  ||||||||   ||
BINDING SITE  3' CGGCGG GGCGGCGG    CG      5'          SEQ ID:145984
                          C        AGT

5' TCGCCGCCACCGCCGCCGCCG      3'          SEQ ID:20604
EGR3             ||||||||||||||||||||||
BINDING SITE  3' GGCGGCGGTGGCGGCGGTGGCGGC   5'          SEQ ID:146843

5' TCGCCGCCACCGCCGCCGC CG     3'          SEQ ID:20604
EGR3             ||||||||||||||||||| ||
BINDING SITE  3' GGCGGCGGTGGCGGCGGCG GC     5'          SEQ ID:146845
                                    A

A
              5' GCCGCC CCGCCGCCGCCGCCG     3'          SEQ ID:20604
EGR3             ||||||  |||||||||||||||
BINDING SITE  3' CGGCGG GGCGGCGGTGGCGGC     5'          SEQ ID:146876
                       C

G  CCACC
              5' TC CCG       GCCGCCGCCGCCG  3'         SEQ ID:20604
EGR3             || |||       ||||||||||||
BINDING SITE  3' AG GGC       CGGCGGCGGCGGC  5'         SEQ ID:146919
                   -   TCGA-

CCA            C--
              5' CCG    CCGCCGCCGC    GCC   3'          SEQ ID:20604
EIF2C1           |||    ||||||||||    |||
BINDING SITE  3' GGC    GGCGGCGGCG    CGG   5'          SEQ ID:148159
                    AAC            CCT

C          C  C
              5' TCGC GCCACCGCCGC GC GCCG   3'          SEQ ID:20604
EIF4G1           ||||  ||||||||||  ||  ||||
BINDING SITE  3' GGTG CGGTGGCGGCG CG CGGC   5'          SEQ ID:148798
                    A           A  A

CACC   C         G
              5' TCGCCGC    GC GCCGCC CC     3'         SEQ ID:20604
EIF4G1           |||||||    || ||||||  ||
BINDING SITE  3' GGCGGCG    CG CGGCGG GG     5'         SEQ ID:148812
                         A---  A       G

C  CACC  C              -
              5' TCGC GC    GC GCCGCCGC CG   3           SEQ ID:20604
EIF4G2           |||| ||    || |||||||| ||
BINDING SITE  3' AGCG CG    CG CGGCGGTG GC   5           SEQ ID:148906
                    A  A---  T              A
```

Fig. 26D/17

```
                              A          ---
                     5' TCGCCGCC CCGCCGCC    GCCGCCG       SEQ ID:20604
EIF5A                   |||||||| ||||||||    |||||||
BINDING SITE         3' GGCGGCGG GGCGGCGG    TGGCGGC       SEQ ID:148944
                              C          AGA

A     ---
                     5' TCGCCGCC CCGCC    GCCGCCGCCG       SEQ ID:20604
EIF5A                   |||||||| |||||    ||||||||||
BINDING SITE         3' GGCGGCGG GGCGG    TGGCGGCGGC       SEQ ID:148945
                              C     AGA

CA
                     5' CCGC    CCGCCGCCGCCGCC    C  3     SEQ ID:20604
EIF5A                   ||||    ||||||||||||||       |
BINDING SITE         3' GGCG    GGCGGCGGCGGCGGC    G  5    SEQ ID:148952
                           AC

CA-    C
                     5' TCGCCGC    CCGC GCCGCCGCCG         SEQ ID:20604
EP300                   |||||||    |||| ||||||||||
BINDING SITE         3' GGCGGCG    GGCG CGGCGGCGGC         SEQ ID:151947
                                CGA    -

-    A
                     5' TCGC CGCC CCGCCGCCGCCGCCG  3       SEQ ID:20604
EZH2                    |||| |||| |||||||||||||||
BINDING SITE         3' GGCG GCGG GGCGGCGGCGGCGGC  5       SEQ ID:156540
                            C    C

G    AC-
                     5' TCGCC CC    CGCCGCCGCCGCCG  3      SEQ ID:20604
EZH2                    ||||| ||    ||||||||||||||
BINDING SITE         3' AGCGG GG    GCGGCGGCGGCGGC  5      SEQ ID:156546
                            G    CGC

G    A----
                     5' TCGCC CC       CCGCCGCCGCCGCCG     SEQ ID:20604
EZH2                    ||||| ||       |||||||||||||||
BINDING SITE         3' AGCGG GG       GGCGGCGGCGGCGGC     SEQ ID:156547
                            G    CGCGC

A            C
                     5' TCGCCGCC CCGCCGCCGC GC  3'         SEQ ID:20604
FGF18                   |||||||| |||||||||| ||
BINDING SITE         3' GGCGGCGG GGCGGCGGCG CG  5'         SEQ ID:163374
                              C            A

A            C
                     5' TCGCCGCC CCGCCGCCGC GC  3'         SEQ ID:20604
SERPINB8                |||||||| |||||||||| ||
BINDING SITE         3' GGCGGCGG GGCGGCGGCG CG  5'         SEQ ID:163374
                              C            A
```

Fig. 26D/18

```
                          A       C  C
             5' TCGCCGCC CCGCCGC GC GC    3'         SEQ ID:20604
FGF18           |||||||| ||||||| || ||
BINDING SITE 3' GGCGGCGG GGCGGCG CG CG    5'         SEQ ID:163376
                          C       A  A

G    A
             5' TC CCGCC CCGCCGCCGCCGCCG  3'         SEQ ID:20604
FGF18           || ||||| |||||||||||||||
BINDING SITE 3' GG GGCGG GGCGGCGGCGGCGGC  5'         SEQ ID:163380
                   A    C

C  CA      ---
             5' GC GC  CC     GCCGCCGCCG  3          SEQ ID:20604
FKRP            || ||  ||     ||||||||||
BINDING SITE 3' CG CG  GG     CGGCGGCGGC  5          SEQ ID:166297
                   -  AG      CGA

CG  A--           C
             5' TCGC  CC    CCGCCGCCGC GCCG          SEQ ID:20604
FLT1            ||||  ||    |||||||||| ||||
BINDING SITE 3' GGCG  GG    GGCGGCGGCG CGGC          SEQ ID:167123
                     A-  CTC           A

A   CC   G
             5' TCGCCGCC CCG GCC CCG      3'         SEQ ID:20604
FLT1            |||||||| ||| ||| |||
BINDING SITE 3' AGCGGCGG GGC CGG GGC      5'         SEQ ID:167194
                         C   --  -

A         ---
             5' TCGCCGCC CCGCCGCC    GCCGCCG         SEQ ID:20604
FMR1            |||||||| ||||||||    |||||||
BINDING SITE 3' GGCGGCGG GGCGGCGG    CGGCGGC         SEQ ID:167700
                         C          AGG

A         ---
             5' TCGCCGCC CCGCCGCC    GCCGCCG         SEQ ID:20604
FMR1            |||||||| ||||||||    |||||||
BINDING SITE 3' GGCGGCGG GGCGGCGG    CGGCGGC         SEQ ID:167700
                         C          AGG

A       G
             5' CCGCC CCGCC CCGCCGCCG     3'         SEQ ID:20604
SMURF1          ||||| ||||| |||||||||
BINDING SITE 3' GGCGG GGCGG GGCGGCGGC     5'         SEQ ID:167709
                    C     A

A
             5' TCGCCGCC CCGCCGCCGCCGCCG  3'         SEQ ID:20604
FMR1            |||||||| |||||||||||||||
BINDING SITE 3' GGCGGCGG GGCGGCGGCGGCGGC  5'         SEQ ID:167713
                         A
```

Fig. 26D/19

```
                          A
              5' TCGCCGCC  CCGCCGCCGCCGCCG  3'        SEQ ID:20604
FMR1             ||||||||  |||||||||||||||
BINDING SITE  3' GGCGGCGG  GGCGGCGGCGGCGGC  5'        SEQ ID:167713
                          A

G    A
              5' TCGCC  CC  CCGCCGCCGCCGCCG  3'       SEQ ID:20604
FMR1             |||||  ||  |||||||||||||||
BINDING SITE  3' GGCGG  GG  GGCGGCGGCGGCGGC  5'       SEQ ID:167717
                     A    C

G    A
              5' TCGCC  CC  CCGCCGCCGCCGCCG  3'       SEQ ID:20604
FMR1             |||||  ||  |||||||||||||||
BINDING SITE  3' GGCGG  GG  GGCGGCGGCGGCGGC  5'       SEQ ID:167717
                     A    C

A              G
              5' CGCCGCC  CCGCCGCCGCC  CCG  3'        SEQ ID:20604
FMR1             |||||||  |||||||||||  |||
BINDING SITE  3' GCGGCGG  GGCGGCGGCGG  GGC  5'        SEQ ID:167722
                        C              A

A              G
              5' CGCCGCC  CCGCCGCCGCC  CCG  3'        SEQ ID:20604
FMR1             |||||||  |||||||||||  |||
BINDING SITE  3' GCGGCGG  GGCGGCGGCGG  GGC  5'        SEQ ID:167722
                        C              A

A              G
              5' CGCCGCC  CCGCCGCCGCC  CCG  3'        SEQ ID:20604
GNB1             |||||||  |||||||||||  |||
BINDING SITE  3' GCGGCGG  GGCGGCGGCGG  GGC  5'        SEQ ID:167722
                        C              A

A              G
              5' CGCCGCC  CCGCCGCCGCC  CCG  3'        SEQ ID:20604
ZNF6             |||||||  |||||||||||  |||
BINDING SITE  3' GCGGCGG  GGCGGCGGCGG  GGC  5'        SEQ ID:167722
                        C              A

A            C--
              5' CGCCGCC  CCGCCGCCGC     GCCG  3      SEQ ID:20604
FMR1             |||||||  ||||||||||     ||||
BINDING SITE  3' GCGGCGG  GGCGGCGGCG     CGGC  5      SEQ ID:167723
                        C            CGA

A     GC   -
              5' TCGCCGCC  CCGCC  CGC  CGCCG  3       SEQ ID:20604
FMR1             ||||||||  |||||  |||  |||||
BINDING SITE  3' AGTGGCGG  GGCGG  GCG  GCGGC  5       SEQ ID:167756
                         C     GC    A
```

Fig. 26D/20

```
                             CACC
                    5' GCCGC       GCCGCCGCCGCCG  3'        SEQ ID:20604
FOXD2                  |||||       |||||||||||||
BINDING SITE        3' CGGCG       CGGCGGCGGCGGC  5'        SEQ ID:169035
                             A---

A---
                    5' CGCCGCC      CCGCCGCCGCCGCCG          SEQ ID:20604
FOXF1                  |||||||      |||||||||||||||
BINDING SITE        3' GCGGCGG      GGCGGCGGCGGCGGC          SEQ ID:169360
                                  AGGG

CACC
                    5' CGC        GCCGCCGCCGCCG  3'          SEQ ID:20604
FUS1                   |||        |||||||||||||
BINDING SITE        3' GCG        CGGCGGCGGCGGC  5'          SEQ ID:170829
                          TCCA

A              GCCG
                    5' GCCGCC CCGCCGCC         CCG  3'       SEQ ID:20604
FUS1                   |||||| ||||||||         |||
BINDING SITE        3' CGGCGG GGCGGCGG         GGC  5'       SEQ ID:170846
                           C             AA--

C  CACC  C         G  G
                    5' TCGC GC    GC GCCGCC CC  3'           SEQ ID:20604
FZD2                   |||| ||    || ||||||  ||
BINDING SITE        3' AGCG CG    CG CGGCGG GG  5'           SEQ ID:172450
                          A  C---  A         A

C  A
                    5' GC GCC CCGCCGCCGCCGCCG  3'            SEQ ID:20604
GABRB3                 || ||| |||||||||||||||
BINDING SITE        3' CG CGG GGCGGCGGCGGCGGC  5'            SEQ ID:173934
                          A   C

C  A
                    5' GC GCC CCGCCGCCGCCGCCG  3'            SEQ ID:20604
NPAS2                  || ||| |||||||||||||||
BINDING SITE        3' CG CGG GGCGGCGGCGGCGGC  5'            SEQ ID:173934
                          A   C

C  A
                    5' GC GCC CCGCCGCCGCCGCCG  3'            SEQ ID:20604
REPS2                  || ||| |||||||||||||||
BINDING SITE        3' CG CGG GGCGGCGGCGGCGGC  5'            SEQ ID:173934
                          A   C

C  A
                    5' GC GCC CCGCCGCCGCCGCCG  3'            SEQ ID:20604
SERPINB8               || ||| |||||||||||||||
BINDING SITE        3' CG CGG GGCGGCGGCGGCGGC  5'            SEQ ID:173934
                          A   C
```

Fig. 26D/21

```
                         C
               5' TCGCCGCCACCGCCGCCGC GC  3'        SEQ ID:20604
GAL               ||||||||||||||||||| ||
BINDING SITE   3' GGCGGCGGTGGCGGCGGCG CG  5'        SEQ ID:174735
                                     A

A
               5' GCCGCC CCGCCGCCGCC  3'            SEQ ID:20604
GAL               |||||| ||||||||||||
BINDING SITE   3' CGGCGG GGTGGCGGCGGCG  5'          SEQ ID:174743
                         C

A
               5' TCGCCGCC CCGCCGCCGCCGCCG  3'      SEQ ID:20604
GDI1              |||||||| |||||||||||||||
BINDING SITE   3' AGCGGCGG GGTGGCGGCGGCGGC  5'      SEQ ID:178360
                           C

G   CA
               5' TC CCGC   CCGCCGCCGCCGCC         SEQ ID:20604
GNB1              || ||||   ||||||||||||||
BINDING SITE   3' AG GGCG   GGCGGCGGCGGCGGC        SEQ ID:182802
                   -    AG                 G

ACC  C    CC
               5' GCCGCC   GC GCCG   GCCG  3'       SEQ ID:20604
GPRK5             ||||||   || ||||   ||||
BINDING SITE   3' CGGCGG   CG CGGC   CGGC  5'       SEQ ID:186691
                       CGA  A    CT

A  ------
               5' TCGCCGCC CC         GCCGCCGCGC   SEQ ID:20604
GSPT1             |||||||| ||         ||||||||||
BINDING SITE   3' GGCGGCGG GG         CGGCGGCGGCG  SEQ ID:189737
                           C  TCCCTT

A
               5' CGCCGCC CCGCCGCCGCCG  3'          SEQ ID:20604
GSPT1             ||||||| |||||||||||||
BINDING SITE   3' GCGGCGG GGCGGCGGCGGTG  5'         SEQ ID:189752
                           C

A    ------
               5' GCCGCC CCGCC        GCCGCCGCCG    SEQ ID:20604
GSPT1             |||||| |||||        ||||||||||
BINDING SITE   3' CGGCGG GGCGG        CGGCGGCGGC    SEQ ID:189763
                         C   TCCCTT

CACC  CG
               5' GCCGC    GC  CCGCCGCCG  3'        SEQ ID:20604
GSPT1             |||||    ||  |||||||||
BINDING SITE   3' CGGCG    CG  GGCGGCGGC  5'        SEQ ID:189764
                       ACGA  AG
```

Fig. 26D/22

```
                         C  CA
                     5' GC GC    CCGCCGCCGCCGCCG  3'        SEQ ID:20604
GSPT1                   || ||    |||||||||||||||
BINDING SITE         3' CG CG    GGCGGCGGCGGCGGC  5'        SEQ ID:189765
                         A  AG

G     A
                     5' TC CCGCC CCGCCGCCGCCGCCG  3'        SEQ ID:20604
GSPT1                   || ||||| |||||||||||||||
BINDING SITE         3' AG GGCGG GGCGGCGGCGGCGGC  5'        SEQ ID:189777
                           -     C

GC-          C--
                     5' CC    CACCGCCGC     GCCG  3'        SEQ ID:20604
GTF2I                   ||    |||||||||     ||||
BINDING SITE         3' GG    GTGGCGGCG     CGGC  5'        SEQ ID:190454
                           ACA          TAC

A        G
                     5' CGCCGCC CCGCCGCC CCG  3'            SEQ ID:20604
HCCS                    ||||||| |||||||| |||
BINDING SITE         3' GCGGCGG GGCGGCGG GGC  5'            SEQ ID:192464
                                C        -

C--     A
                     5' GC    GCC CCGCCGCCGCCGCCG  3'       SEQ ID:20604
HCN2                    ||    ||| |||||||||||||||
BINDING SITE         3' CG    CGG GGCGGCGGCGGCGGC  5'       SEQ ID:192735
                          CCT     C

C  CACC            C   -
                     5' GC GC     GCCGCCGC GC CG  3'        SEQ ID:20604
HDAC2                   || ||     |||||||| || ||
BINDING SITE         3' CG CG     CGGCGGCG CG GC  5'        SEQ ID:193593
                         A  A---           C  A

C  CACC    C  C
                     5' GC GC    GC GC GCCGCCG  3'          SEQ ID:20604
HDAC2                   || ||    || || |||||||
BINDING SITE         3' CG CG    CG CG CGGCGGC  5'          SEQ ID:193594
                         A  A--- A  A

C  CACC    C  C
                     5' GC GC    GC GC GCCGCCG  3'          SEQ ID:20604
IRS1                    || ||    || || |||||||
BINDING SITE         3' CG CG    CG CG CGGCGGC  5'          SEQ ID:193594
                         A  A--- A  A

CCACC       C
                     5' CCG         GCCGC GCCGCCG  3'       SEQ ID:20604
HIC1                    |||         ||||| |||||||
BINDING SITE         3' GGC         CGGCG CGGCGGC  5'       SEQ ID:195147
                             CCGA-        A
```

Fig. 26D/23

```
                          A            C
               5' TCGCCGCC  CCGCCGCCGC  GCCG  3'      SEQ ID:20604
HIRA              ||||||||  ||||||||||  ||||
BINDING SITE   3' GGCGGCGG  GGCGGTGGTG  CGGC  5'      SEQ ID:195839
                          C            T

CCA
               5' CG     CCGCCGCCGCCGCCG  3'          SEQ ID:20604
HIRA              ||     |||||||||||||||
BINDING SITE   3' GC     GGCGGCGGCGGCGGC  5'          SEQ ID:195850
                  C--

C           C  C
               5' TCGCCGC  ACCGCCGC  GC  GCCG  3'     SEQ ID:20604
HMGA2             |||||||  ||||||||  ||  ||||
BINDING SITE   3' GGCGGCG  TGGCGGCG  CG  CGGC  5'     SEQ ID:197765
                          A         A  T

G    A    CG         CG
               5' TC CCGCC CCGC    CCGCCGC      3     SEQ ID:20604
HMGA2             || ||||| ||||    |||||||
BINDING SITE   3' AG GGCGG GGCG    GGCGGCG      5     SEQ ID:197853
                   -       C    AT       AC

CA-
               5' CCGC     CCGCCGCCGCCG  3'           SEQ ID:20604
HPCAL1            ||||     ||||||||||||
BINDING SITE   3' GGCG     GGCGGCGGCGGC  5'           SEQ ID:201019
                    ACG

CC  C
               5' TCG  GC  ACCGCCGCCGCCGCCG  3        SEQ ID:20604
HRB               |||  ||  ||||||||||||||||
BINDING SITE   3' GGC  TG  TGGCGGCGGCGGCGGC  5        SEQ ID:201812
                      CC  T

-  CA         C   C
               5' GCC GC  CCGCCGC  GC  GC  3'         SEQ ID:20604
HS3ST3B1          ||| ||  |||||||  ||  ||
BINDING SITE   3' CGG CG  GGCGGCG  CG  CG  5'         SEQ ID:202532
                    G   CC         A   A

CCAC           G
               5' CGCCG     CGCCGCCGCC  CCG  3'       SEQ ID:20604
ING1L             |||||     ||||||||||  |||
BINDING SITE   3' GCGGC     GCGGCGGCGG  GGC  5'       SEQ ID:213784
                       A---            A

--  AC         C
               5' GCCG   CC  CGCCG  CGCCGCCG  3'      SEQ ID:20604
ING1L             ||||   ||  |||||  ||||||||
BINDING SITE   3' CGGC   GG  GCGGC  GCGGCGGC  5'      SEQ ID:213788
                       TA  C-         A
```

Fig. 26D/24

```
                        C   CACC   C
                  5' GC  GC      GC GCCGCCGCC 3'        SEQ ID:20604
IRS1                 ||  ||      || |||||||||
BINDING SITE      3' CG  CG      CG CGGCGGCGG 5'        SEQ ID:215707
                     A   A---    A

CA              C
                  5' CGC   CCGCCGCCGC GC 3'             SEQ ID:20604
KCNA6                |||   |||||||||| ||
BINDING SITE      3' GCG   GGCGGCGGCG CG 5'             SEQ ID:221336
                        AC            T

A         G  -
                  5' TCGCCGCC  CCGCCGCC CC GCC 3'       SEQ ID:20604
KCNA7                ||||||||  |||||||| || |||
BINDING SITE      3' GGCGGCGG  GGCGGCGG GG CGG 5'       SEQ ID:221548
                              C         -  T

--    A
                  5' GCC  GCC  CCGCCGCCGCCGCCG 3'       SEQ ID:20604
KCNA7                |||  |||  |||||||||||||||
BINDING SITE      3' CGG  CGG  GGCGGCGGCGGCGGC 5'       SEQ ID:221616
                             GA    -

A---
                  5' GCCGCC       CCGCCGCCGCCGCCG 3     SEQ ID:20604
KCNA7                ||||||       |||||||||||||||
BINDING SITE      3' CGGCGG       GGCGGCGGCGGCGGC 5     SEQ ID:221618
                                AGCC

A          C
                  5' GCCGCC CCGCCGC GCCGC 3'            SEQ ID:20604
KCNF1                |||||| ||||||| |||||
BINDING SITE      3' CGGCGG GGCGGCG CGGCG 5'            SEQ ID:222269
                            C          A

CACC    C    C    G
                  5' TCGCCGC      GC GC GCC CC 3'       SEQ ID:20604
KCNK3                |||||||      || || ||| ||
BINDING SITE      3' GGCGGCG      CG CG CGG GG 5'       SEQ ID:223599
                          A---   A  A     -

G    ACC         CC
                  5' TC CCGCC    GCCGCCGCCG 3'          SEQ ID:20604
KCNK3                || |||||    ||||||||||
BINDING SITE      3' AG GGCGG    CGGCGGCGGC 5'          SEQ ID:223678
                          -      GCC

CC   A    -         C
                  5' TCG   GCC  CCG  CCGCCGC  GC 3'     SEQ ID:20604
KCNK3                |||   |||  |||  |||||||  ||
BINDING SITE      3' AGC   CGG  GGC  GGCGGCG  CG 5'     SEQ ID:223685
                         --    -        C        A
```

Fig. 26D/25

```
                    5' TCGCCGCCACCGCCGCCGCCGC 3'          SEQ ID:20604
KCNMB4                 ||||||||||||||||||||||
BINDING SITE        3' GGCGGCGGTGGCGGCGGCGGCG 5'          SEQ ID:224477

A
                    5' TCGCCGCC CCGCCGCCGCCGCCG 3'         SEQ ID:20604
KCNMB4                 |||||||| |||||||||||||||
BINDING SITE        3' GGCGGCGG GGTGGCGGCGGCGGC 5'         SEQ ID:224480
                              C

A    - C  C
                    5' CGCCGCC CCGCC GC GC GCCG 3'         SEQ ID:20604
KCNS2                  ||||||| ||||| || || ||||
BINDING SITE        3' GCGGCGG GGCGG CG CG CGGC 5'         SEQ ID:224998
                           C     G T  A

GC
                    5' TCGCCGCCACC CGCCGCCG 3'             SEQ ID:20604
KRAS2                  ||||||||||| ||||||||
BINDING SITE        3' GGCGGCGGTGG GCGGCGGC 5'             SEQ ID:229032
                                AA

ACC  C   G
                    5' TCGCCGCC   GC GCC CCGCCG 3'         SEQ ID:20604
KRAS2                  ||||||||   || ||| ||||||
BINDING SITE        3' GGCGGCGG   CG CGG GGCGGC 5'         SEQ ID:229035
                             CGA  A   A

CACC    G
                    5' TCGCCGC    GCC CCGCCGCCG 3'         SEQ ID:20604
KRAS2                  |||||||    ||| |||||||||
BINDING SITE        3' GGCGGCG    CGG GGCGGCGGC 5'         SEQ ID:229036
                            ACGA   A

A    C  C   G
                    5' GCCGCC CCGC GC GCC CCG 3'           SEQ ID:20604
KRAS2                  |||||| |||| || ||| |||
BINDING SITE        3' CGGCGG GGCG CG CGG GGC 5'           SEQ ID:229050
                          C    A  A   A

A    C
                    5' TCGCCGCC CCGC GCCGCCGCCG 3'         SEQ ID:20604
KRAS2                  |||||||| |||| ||||||||||
BINDING SITE        3' AGCGGCGG GGTG CGCGGCGGC 5'          SEQ ID:229059
                             C    A

CC  CA
                    5' TCG GC  CCGCCGCCGCCGCCG 3'          SEQ ID:20604
LASS1                  ||| ||  ||||||||||||||
BINDING SITE        3' GGC CG  GGCGGCGGCGGCGGC 5'          SEQ ID:231693
                          CC  AC
```

Fig. 26D/26

```
                          AC
              5' CCGCC    CGCCGCCGCCGCCG  3'          SEQ ID:20604
LASS2            |||||    ||||||||||||||
BINDING SITE  3' GGCGG    GCGGCGGCGGCGGC  5'          SEQ ID:231822
                          CC

A              C
              5' TCGCCGCC CCGCCGCCG CGCCG  3'         SEQ ID:20604
LMO2             |||||||| ||||||||| |||||
BINDING SITE  3' GGCGGCGG GGCGGCGGC GCGGC  5'         SEQ ID:236309
                         C              A

A        C
              5' TCGCCGCC CCGCCG CGCCGCCG  3'         SEQ ID:20604
LMO2             |||||||| |||||| ||||||||
BINDING SITE  3' GGCGGCGG GGCGGC GCGGCGGC  5'         SEQ ID:236311
                         C        A

AC          CG
              5' CGCCGCC CGCCGCCGC  CC   3'           SEQ ID:20604
LMO2             ||||||| |||||||||  ||
BINDING SITE  3' GCGGCGG GCGGCGGCG  GG   5'           SEQ ID:236328
                        CA          A-

ACCG  -       G
              5' TCGCCGCC    CC GCC CCG  3'           SEQ ID:20604
LMO2             ||||||||    || ||| |||
BINDING SITE  3' AGCGGCGG    GG CGG GGC  5'           SEQ ID:236380
                       CGA-  A       A

-    CAC      CCG
              5' TCGC CGC    CGCCG    CCG  3'         SEQ ID:20604
LMO2             |||| |||    |||||    |||
BINDING SITE  3' AGCG GCG    GCGGC    GGC  5'         SEQ ID:236383
                      C    ACA       CGA

C-      A
              5' TCG    CGCC CCGCCGCCGCCGCCG  3       SEQ ID:20604
LMO2             |||    |||| ||||||||||||||
BINDING SITE  3' AGC    GCGG GGCGGCGGCGGCGGC  5       SEQ ID:236384
                        CC    C

C-      A
              5' TCG    CGCC CCGCCGCCGCCGCCG         SEQ ID:20604
LMO2             |||    |||| ||||||||||||||
BINDING SITE  3' AGC    GCGG GGCGGCGGCGGCGGC         SEQ ID:236385
                        CC    C

G    A
              5' TC CCGCC CCGCCGCCGCCGCCG  3'        SEQ ID:20604
LRP8             || ||||| ||||||||||||||
BINDING SITE  3' GG GGCGG GGCGGCGGCGGCGGC  5'        SEQ ID:238167
                     G    C
```

Fig. 26D/27

```
                    G    A
               5'  TC CCGCC CCGCCGCCGCCGCCG  3'        SEQ ID:20604
LRP8               || ||||| ||||||||||||||
BINDING SITE   3'  GG GGCGG GGCGGCGGCGGCGGC  5'        SEQ ID:238167
                    G    C

G    A
               5'  TC CCGCC CCGCCGCCGCCGCCG             SEQ ID:20604
LRP8               || ||||| ||||||||||||||
BINDING SITE   3'  GG GGCGG GGCGGCGGCGGCGGC             SEQ ID:238168
                    G    C                 GA

A         C
               5'  CGCC CCGCCGC GCCGCC  3'              SEQ ID:20604
LRP8               |||| ||||||| ||||||
BINDING SITE   3'  GCGG GGCGGCG CGGCGG  5'              SEQ ID:238188
                    C         A

G  A
               5'  GCC CC CCGCCGCCGCCGCCG     C         SEQ ID:20604
LRP8               ||| || ||||||||||||||      |
BINDING SITE   3'  CGG GG GGCGGCGGCGGCGGC     G         SEQ ID:238204
                   G  C

CA    G
               5'  GCCGC CC CCGCCGCCGCCG  3'            SEQ ID:20604
LRP8               ||||| || ||||||||||||
BINDING SITE   3'  CGGCG GG GGCGGCGGCGGC  5'            SEQ ID:238208
                        AC    G

G     CACC
               5'  TC CCGC      GCCGCCGCCGCC  3'        SEQ ID:20604
LRP8               || ||||      |||||||||||
BINDING SITE   3'  AG GGCG      CGGCGGCGGCGG  5'        SEQ ID:238239
                      G        ----

C    A      CC
               5'  TCGC GCC CCGCCG GCCGC  3'            SEQ ID:20604
MAD                |||| ||| |||||| |||||
BINDING SITE   3'  AGCG CGG GGCGGC TGGCG  5'            SEQ ID:241104
                     A    C      C-

C       CC  C-
               5'  TCGC GCCA GC  GCCGCCGCC             SEQ ID:20604
MAD1L1             |||| |||| ||  |||||||||
BINDING SITE   3'  AGCG CGGT CG  CGGCGGCGGC             SEQ ID:241126
                     T       --  AA

A         CG
               5'  CGCCGCC CCGCCGCCGC CCG  3'           SEQ ID:20604
MAF                ||||||| |||||||||| |||
BINDING SITE   3'  GCGGCGG GGCGGCGGCG GGC  5'           SEQ ID:241961
                        C         A-
```

Fig. 26D/28

```
                            A
                  5' GCCGCC CCGCCGCCGCCGCCG 3'      SEQ ID:20604
ADARB1               ||||||  ||||||||||||||||
BINDING SITE      3' CGGCGG GGCGGCGGCGGCGGC 5'      SEQ ID:241978
                            C

A
                  5' GCCGCC CCGCCGCCGCCGCCG 3'      SEQ ID:20604
BCL11B               ||||||  ||||||||||||||||
BINDING SITE      3' CGGCGG GGCGGCGGCGGCGGC 5'      SEQ ID:241978
                            C

A
                  5' GCCGCC CCGCCGCCGCCGCCG 3'      SEQ ID:20604
FMR1                 ||||||  ||||||||||||||||
BINDING SITE      3' CGGCGG GGCGGCGGCGGCGGC 5'      SEQ ID:241978
                            C

A
                  5' GCCGCC CCGCCGCCGCCGCCG 3'      SEQ ID:20604
MAF                  ||||||  ||||||||||||||||
BINDING SITE      3' CGGCGG GGCGGCGGCGGCGGC 5'      SEQ ID:241978
                            C

A
                  5' GCCGCC CCGCCGCCGCCGCCG 3'      SEQ ID:20604
NPAS2                ||||||  ||||||||||||||||
BINDING SITE      3' CGGCGG GGCGGCGGCGGCGGC 5'      SEQ ID:241978
                            C

A
                  5' GCCGCC CCGCCGCCGCCGCCG 3'      SEQ ID:20604
RELN                 ||||||  ||||||||||||||||
BINDING SITE      3' CGGCGG GGCGGCGGCGGCGGC 5'      SEQ ID:241978
                            C

A
                  5' GCCGCC CCGCCGCCGCCGCCG 3'      SEQ ID:20604
ZNF6                 ||||||  ||||||||||||||||
BINDING SITE      3' CGGCGG GGCGGCGGCGGCGGC 5'      SEQ ID:241978
                            C

G   ACC
                  5' CC CC    GCCGCCGCCGCCG  3'     SEQ ID:20604
MAFK                 || ||    ||||||||||||
BINDING SITE      3' GG GG    CGGCGGCGGCGGC  5'     SEQ ID:242287
                       -  AGC

-           G
                  5' CC GCCACCGCCGCC CCG  3'        SEQ ID:20604
MAN2A1               || ||||||||||||  |||
BINDING SITE      3' GG CGGTGGCGGCGG  GGT  5'       SEQ ID:243405
                       A
```

Fig. 26D/29

```
                              -    AC     GC
                        5' TCGC CGCC  CGCC  CGCCGCCG   3      SEQ ID:20604
MAP3K5                     |||| ||||  ||||  ||||||||
BINDING SITE            3' AGCG GCGG  GCGG  GCGGCGGC   5      SEQ ID:244540
                                C     C-    GA

A             C
                        5' TCGCCGCC CCGCCGC GCCGC    3'        SEQ ID:20604
MAP4K5                     |||||||| ||||||| |||||
BINDING SITE            3' GGCGGCGG GGCGGCG TGGTG    5'        SEQ ID:245274
                                C              -

CCA---     C
                        5' CCG      CCG CGCCGCCGCCG   3'       SEQ ID:20604
MAP4K5                     |||      ||| |||||||||||
BINDING SITE            3' GGC      GGC GCGGCGGCGGC   5'       SEQ ID:245277
                              CCAAAC     A

A           - -
                        5' TCGCCGCC CCGCCGC C GCCGC   3'       SEQ ID:20604
MAP4K5                     |||||||| ||||||| | |||||
BINDING SITE            3' AGCGGCGG GGCGGTG G CGGCG   5'       SEQ ID:245293
                                C           A T

A
                        5' TCGCCGCC CCGCCGCCGCCG   3'          SEQ ID:20604
MAP4K5                     |||||||| ||||||||||||
BINDING SITE            3' AGCGGCGG GGCGGCGGCGGC   5'          SEQ ID:245294
                                C

A  CC  C
                        5' CGCCGCC CCG  GC GCCGCCG   3'        SEQ ID:20604
MAPK1                      ||||||| |||  || ||||||||
BINDING SITE            3' GCGGCGG GGC  CG CGGCGGC   5'        SEQ ID:245382
                                  C  CA  T

C   ACC
                        5' GC GCC     GCCGCCGCCG   3'          SEQ ID:20604
MAPK1                      || |||     |||||||||
BINDING SITE            3' CG CGG     CGGCGGCGGC   5'          SEQ ID:245394
                              A   CC-

G    CA-
                        5' TC CCGC    CCGCCGCCGCCGCCG  3       SEQ ID:20604
MATK                       || ||||    |||||||||||||||
BINDING SITE            3' GG GGCG    GGCGGCGGCGGCGGC  5       SEQ ID:247365
                              A .   CGC

G   CCAC
                        5' C CCG     CGCCGCCGCCGCCG   3'       SEQ ID:20604
MID2                       | |||     ||||||||||||||
BINDING SITE            3' G GGC     GCGGCGGCGGCGGC   5'       SEQ ID:254906
                              G   CA--
```

Fig. 26D/30

```
                          AC----            C
              5' TCGCCGCC        CGCCGCCGC GCCG           SEQ ID:20604
MID2             ||||||||        ||||||||| ||||
BINDING SITE  3' GGCGGCGG        GCGGCGGCG CGGC           SEQ ID:254911
                          GCGGAA           A

C    C     C
              5' GCCGC ACCG CGCCG CGCCG    3'             SEQ ID:20604
MID2             ||||| |||| ||||| |||||
BINDING SITE  3' CGGCG TGGC GCGGC GCGGC    5'             SEQ ID:254918
                       A    A     T

A           CG
              5' TCGCCGCC CCGCCGC    CCGC   3'            SEQ ID:20604
MID2             |||||||| |||||||    ||||
BINDING SITE  3' AGCGGCGG GGCGGCG    GGTG   5'            SEQ ID:254922
                          C          AT

A---    CG    C
              5' TCGCCGCC      CCGC  CCG CGCCG            SEQ ID:20604
MID2             ||||||||      ||||  ||| |||||
BINDING SITE  3' AGCGGCGG      GGCG  GGC GCGGC            SEQ ID:254923
                          CGAC     AT    A

A         -    C
              5' TCGCCGCC CCGCCGC CG CGCCG    3           SEQ ID:20604
MLLT1            |||||||| ||||||| || |||||
BINDING SITE  3' GGCGGCGG GGCGGCG GT GCGGC    5           SEQ ID:255942
                          C        A  T

A
              5' CGCCGCC CCGCCGCCGCCGCCG    CG            SEQ ID:20604
MLLT1            ||||||| ||||||||||||||||   ||
BINDING SITE  3' GCGGCGG GGCGGCGGCGGCGGC    GC            SEQ ID:255948
                         C

A
              5' CGCCGCC CCGCCGCCGCCGCCG    CG            SEQ ID:20604
NTRK3            ||||||| ||||||||||||||||   ||
BINDING SITE  3' GCGGCGG GGCGGCGGCGGCGGC    GC            SEQ ID:255948
                         C

C  A
              5' GC GCC CCGCCGCCGCCGCCG      C            SEQ ID:20604
MLLT1            || ||| ||||||||||||||||     |
BINDING SITE  3' CG CGG GGCGGCGGCGGCGGC      G            SEQ ID:255952
                     -  C

-      A
              5' TCGC CGCC CCGCCGCCGCCGCCG               SEQ ID:20604
MLLT1            |||| |||| |||||||||||||||
BINDING SITE  3' AGCG GCGG GGCGGCGGCGGCGGC               SEQ ID:255957
                      A    C
```

Fig. 26D/31

```
                       ACC         CG
                  5' CGCCGCC    GCCGCCGC   CCG  3'      SEQ ID:20604
MPP6                 |||||||    ||||||||   |||
BINDING SITE      3' GCGGCGG    CGGCGGCG   GGC  5'      SEQ ID:259906
                       CGA         AG

A-----              C
                  5' GCCGCC       CCGCCGC GCCGCCG        SEQ ID:20604
MPP6                 ||||||       ||||||| |||||||
BINDING SITE      3' CGGCGG       GGCGGCG CGGCGGC       SEQ ID:259910
                     AGGCGC              A

G  -  AC    CGC
                  5' TC CCG CC   CGC    CGCCGCCG  3     SEQ ID:20604
MTA1L1               || ||| ||   |||    ||||||||
BINDING SITE      3' AG GGC GG   GCG    GCGGCGGC  5     SEQ ID:261852
                     -   C  GC    ACA

----          A
                  5' TCGC    CGCC CCGCCGCCGCCGCCG       SEQ ID:20604
MTMR1                ||||    |||| |||||||||||||||
BINDING SITE      3' AGCG    GCGG GGCGGCGGCGGCGGC       SEQ ID:262287
                     TCGG        C

A         G G
                  5' GCCGCC CCGCCGCC CC CCG  3'         SEQ ID:20604
MVK                  |||||| ||||||||  || |||
BINDING SITE      3' CGGCGG GGCGGCGG GG GGC  5'         SEQ ID:264118
                           C         A -

CGCCA
                  5' GC          CCGCCGCCGCCGCCG  3'    SEQ ID:20604
NCKAP1               ||          |||||||||||||||
BINDING SITE      3' CG          GGCGGCGGCGGCGGC  5'    SEQ ID:268447
                         ACCAC

-         C
                  5' CCA  CCGCCGC GCCGCCG  3'           SEQ ID:20604
NFYA                 |||  |||||||  |||||||
BINDING SITE      3' GGT  GGCGGCG CGGCGGC  5'           SEQ ID:272973
                          C         A

CA           C
                  5' TCGCCGC  CCGCCGCCGC GCCG  3'       SEQ ID:20604
NFYA                 |||||||  ||||||||||  ||||
BINDING SITE      3' GGCGGCG  GGCGGCGGTG CGGC  5'       SEQ ID:272979
                           AC           A

A            C
                  5' CGCCGCC CCGCCGCCG GC  3'           SEQ ID:20604
NPAS2                ||||||| |||||||||  ||
BINDING SITE      3' GCGGCGG GGCGGCGGCG CG  5'          SEQ ID:275935
                          C            C
```

Fig. 26D/32

```
                              C  CA
                         5' GC GC   CCGCCGCCGCCGCCG    C     SEQ ID:20604
NPAS2                       || ||   |||||||||||||||    |
BINDING SITE             3' CG CG   GGCGGCGGCGGCGGC    G     SEQ ID:275947
                              A  AC

-  CC
                         5' TCGCCGC CA  GCCGCCGCC   3'       SEQ ID:20604
NRG2                        ||||||| ||  |||||||||
BINDING SITE             3' GGCGGCG GT  CGGCGGCGC   5'       SEQ ID:279264
                                A  --

CC     C
                         5' CG   ACCG CGCCGCCGCCG   3'       SEQ ID:20604
NUP98                       ||   |||| |||||||||||
BINDING SITE             3' GC   TGGC GCGGCGGCGGC   5'       SEQ ID:281811
                              TT     A

A    CG    G
                         5' TCGCCGCC CCGC  CCGCC CC  3'      SEQ ID:20604
NUP98                       |||||||| ||||  ||||| ||
BINDING SITE             3' AGCGGCGG GGCG  GGTGG GG  5'      SEQ ID:281839
                                  C    AT    -

C   A
                         5' GC GCC  CCGCCGCCGCCGCCG  3'      SEQ ID:20604
OSR1                        || |||  |||||||||||||||
BINDING SITE             3' TG CGG  GGCGGCGGCGGCGGC  5'      SEQ ID:285281
                               T   C

A
                         5' TCGCCGCC CCGCCGCCGCCGCCG  3'     SEQ ID:20604
PACE4                       ||||||||  ||||||||||||||
BINDING SITE             3' GGCGGCGG GGCGGTGGCGGCGGC  5'     SEQ ID:287686
                                       C

A
                         5' CGCCGCC CCGCCGCCGCCGCCG  3'      SEQ ID:20604
PACE4                       |||||||  ||||||||||||||
BINDING SITE             3' GCGGCGG GGCGGCGGTGGCGGC  5'      SEQ ID:287698
                                      C

CA
                         5' CGC   CCGCCGCCGCC    3'          SEQ ID:20604
PACSIN1                     |||   ||||||||||||
BINDING SITE             3' GCG   GGCGGCGGTGGCG 5'           SEQ ID:287889
                                 AC

G    C         C
                         5' TC CCGC ACCGCCGCCGC GCCG 3'      SEQ ID:20604
PAPOLA                      || |||| ||||||||||| ||||
BINDING SITE             3' GG GGCG TGGCGGCGGCG CGGC 5'      SEQ ID:288993
                              G    T         A
```

Fig. 26D/33

```
                         A    ------
                    5' TCGCCGCC CCGCC         GCCGCCGC      SEQ ID:20604
PEA15                  |||||||| |||||         ||||||||
BINDING SITE        3' GGCGGCGG GGCGG         CGGCGGCG      SEQ ID:301501
                         C       CGAAGA

CACC
                    5' TCGCCGC       GCCGCCGCCGCCG  3'      SEQ ID:20604
PEA15                  |||||||       |||||||||||||
BINDING SITE        3' GGCGGCG       CGGCGGCGGCGGC  5'      SEQ ID:301508
                                AAGA

A          GCCG
                    5' GCCGCC CCGCCGCC    CCG   3'          SEQ ID:20604
PEA15                  |||||| ||||||||    |||
BINDING SITE        3' CGGCGG GGCGGCGG    GGC   5'          SEQ ID:301547
                           C         AGAA

- CG A
                    5' TCG C  CC CCGCCGCCGCCGCCG    3       SEQ ID:20604
PEA15                  ||| |  || |||||||||||||||
BINDING SITE        3' AGC G  GG GGCGGCGGCGGCGGC    5       SEQ ID:301572
                         C AG C

CCA
                    5' GCCG    CCGCCGCCGCCGC   3'           SEQ ID:20604
PIM1                   ||||    |||||||||||||
BINDING SITE        3' CGGC    GGCGGCGGCGGCG   5'           SEQ ID:305922
                              CAG

G      A      C
                    5' TC CCGCC CCGCCGC GCCGCCG    3        SEQ ID:20604
PIM1                   || ||||| ||||||| |||||||
BINDING SITE        3' AG GGCGG GGCGGCG CGGTGGC    5        SEQ ID:305956
                       -       C       A

CAC       C
                    5' TCGCCGC    CGCCGC GCCG  3'           SEQ ID:20604
PITPN                  |||||||    |||||| ||||
BINDING SITE        3' AGCGGCG    GCGGCG CGGC  5'           SEQ ID:306515
                              CCA       -

GCCG  AC  C  C
                    5' TC    CC CG CG CGCCGCCG  3'          SEQ ID:20604
POLI                   ||    || || || ||||||||
BINDING SITE        3' AG    GG GC GC GCGGCGGC  5'          SEQ ID:312045
                          AA-- A-  A  A

CAC---
                    5' CGCCGC       CGCCGCCGCCG             SEQ ID:20604
POLRMT                 ||||||       |||||||||||
BINDING SITE        3' GCGGCG       GCGGCGGCGGC             SEQ ID:312593
                              AGGTCC
```

Fig. 26D/34

```
                        CCA-    -
                  5' GCCG    CC GCCGCCGCGC 3'          SEQ ID:20604
PP                   ||||    || ||||||||||
BINDING SITE      3' CGGC    GG CGGCGGCGGCG 5'         SEQ ID:313812
                        CTCA   A

A
                  5' CGCCGCC CCGCCGCCGCCGCCG   C       SEQ ID:20604
CACNA1A              ||||||| ||||||||||||||    |
BINDING SITE      3' GCGGCGG GGCGGCGGCGGCGGC   G       SEQ ID:317209
                             C

A
                  5' CGCCGCC CCGCCGCCGCCGCCG   C       SEQ ID:20604
CACNA1A              ||||||| ||||||||||||||    |
BINDING SITE      3' GCGGCGG GGCGGCGGCGGCGGC   G       SEQ ID:317209
                             C

A
                  5' CGCCGCC CCGCCGCCGCCGCCG   C       SEQ ID:20604
PPP3CA               ||||||| ||||||||||||||    |
BINDING SITE      3' GCGGCGG GGCGGCGGCGGCGGC   G       SEQ ID:317209
                             C

A         C
                  5' CGCCGCC CCGCCGCCGC GC   3'        SEQ ID:20604
GABRB3               ||||||| |||||||||| ||
BINDING SITE      3' GCGGCGG GGCGGCGGCG CG   5'        SEQ ID:317210
                             C         -

A         C
                  5' CGCCGCC CCGCCGCCGC GC   3'        SEQ ID:20604
PPP3CA               ||||||| |||||||||| ||
BINDING SITE      3' GCGGCGG GGCGGCGGCG CG   5'        SEQ ID:317210
                             C         -

C    A
                  5' TCG CGCC CCGCCGCCGCCGCCG 3'       SEQ ID:20604
PPP3CA               ||| |||| |||||||||||||||
BINDING SITE      3' AGT GCGG GGCGGCGGCGGCGGC 5'       SEQ ID:317246
                         T    C

CA------
                  5' GCCGC        CCGCCGCCGCCGCCG      SEQ ID:20604
PRKAA2               |||||        |||||||||||||||
BINDING SITE      3' CGGCG        GGCGGCGGCGGCGGC      SEQ ID:318787
                         AGGCGATC

CG       -    CCGC
                  5' TCGC CCACCGCC GCCG       3'       SEQ ID:20604
PRKAA2               |||| |||||||| ||||
BINDING SITE      3' AGCG GGTGGCGG CGGC       5'       SEQ ID:318794
                         A-       A
```

Fig. 26D/35

```
                              A    C
                     5' TCGCCGCC CCGC GCCGCCG    3'      SEQ ID:20604
PSEN1                   ||||||||  ||||  |||||||
BINDING SITE         3' GGCGGCGG GGCG CGGCGGC    5'      SEQ ID:322696
                                 -  A

CA
                     5' TCGCCGC    CCGCCGCCGCCGCCG  3'   SEQ ID:20604
PTEN                    |||||||    |||||||||||||||
BINDING SITE         3' GGCGGCG    GGCGGCGGCGGCGGC  5'   SEQ ID:324380
                                CC

A      C
                     5' CGCC CCGC GCCGCCGCCG   3'        SEQ ID:20604
PTEN                    ||||  ||||  ||||||||||
BINDING SITE         3' GCGG GGCG CGGCGGCGGC   5'        SEQ ID:324398
                          C    A

CA             C-
                     5' CGCCGC  CCGCCGCCGC   GCCG   3'   SEQ ID:20604
PTEN                    ||||||  ||||||||||   ||||
BINDING SITE         3' GCGGCG  GGCGGCGGCG   CGGC   5'   SEQ ID:324399
                            AC             TC

A
                     5' GCCGCC CCGCCGCCGCCG    3'        SEQ ID:20604
PTEN                    ||||||  |||||||||||||
BINDING SITE         3' CGGCGG GGCGGCGGCGGC    5'        SEQ ID:324417
                              C

A
                     5' GCCGCC CCGCCGCCGCCG    3'        SEQ ID:20604
PTEN                    ||||||  |||||||||||||
BINDING SITE         3' CGGCGG GGCGGCGGCGGC    5'        SEQ ID:324417
                              C

G  GCCA----
                     5' TC  CC          CCGCCGCCGCCGCCG  SEQ ID:20604
PTEN                    ||  ||           ||||||||||||||
BINDING SITE         3' AG  GG          GGCGGCGGCGGCGGC  SEQ ID:324452
                            -  ACCTACAC

CACC     CG   -
                     5' TCGCCGC    GCGC  CC GCCG   3     SEQ ID:20604
PTP4A2                  |||||||    ||||  ||  ||||
BINDING SITE         3' GGCGGCG    CGCG  GG CGGC   5     SEQ ID:326495
                              A---     A-  T

CA  G     C
                     5' TCGCCGC  CC CCGC GCCGCCG    C    SEQ ID:20604
PTP4A2                  |||||||  || ||||  |||||||   |
BINDING SITE         3' GGCGGCG  GG GGCG CGGCGGC    G    SEQ ID:326499
                              AC  A     A
```

Fig. 26D/36

```
                        CACCG-- - C
               5' TCGCCGC       CC GC GCCGCCG          SEQ ID:20604
PTP4A2            |||||||       || || |||||||
BINDING SITE   3' GGCGGCG       GG CG CGGCGGC          SEQ ID:326500
                        ACGCAGA  A  A

C  A   C           CG
               5' TCGC GCC CCGC GCCGCCGC    3          SEQ ID:20604
PTP4A2            |||| ||| |||| ||||||||
BINDING SITE   3' GGCG CGG GGCG CGGCGGCG    5          SEQ ID:326502
                     A   A   A         AC

-  CA         C  G
               5' CC GC CCGCCGC GCC CCG    3'          SEQ ID:20604
PTP4A2            || || ||||||| ||| |||
BINDING SITE   3' GG CG GGCGGCG CGG GGC    5'          SEQ ID:326511
                  A  AC         A   A

CCA    -         C
               5' CGCCG   CCG CCGCCGC GCCG    3'       SEQ ID:20604
PTP4A2            |||||   ||| ||||||| ||||
BINDING SITE   3' GCGGC   GGC GGCGGCG CGGC    5'       SEQ ID:326515
                      ACG  C          A

ACC     C
               5' TCGCCGCC    GCCGC GC    3'           SEQ ID:20604
PTPN1             ||||||||    ||||| ||
BINDING SITE   3' GGCGGCGG    CGGCG CG    5'           SEQ ID:326697
                          GAT    A

CG
               5' TCGCCGCCACCGC  CCGCCG    3'          SEQ ID:20604
PTPRF             |||||||||||||  ||||||
BINDING SITE   3' GGCGGCGGTGGCG  GGCGGC    5'          SEQ ID:327695
                              AG

CA    C
               5' CCGC   CCGC GCCGCCGCCG    3'         SEQ ID:20604
PURA              ||||   |||| ||||||||||
BINDING SITE   3' GGCG   GGCG CGGCGGCGGC    5'         SEQ ID:328884
                      AC

A
               5' CGCC CCGCCGCC GCCG    3'             SEQ ID:20604
PURA              |||| |||||||| ||||
BINDING SITE   3' GCGG GGCGGCGG CGGC    5'             SEQ ID:328886
                            C    A

------- CA
               5' CGCC      GC CCGCCGCCGCCGCC          SEQ ID:20604
PX19              ||||      || ||||||||||||
BINDING SITE   3' GCGG      CG GGCGGCGGCGGCGG          SEQ ID:329171
                      GTTCGT  AC
```

Fig. 26D/37

```
                          A
              5' CGCCGCC CCGCCGCCGCCG 3'              SEQ ID:20604
PX19             ||||||| ||||||||||||
BINDING SITE  3' GCGGCGG GGCGGCGGCGGT 5'              SEQ ID:329172
                          C

C  A
              5' GC GCC CCGCCGCCGCCGCCG    C          SEQ ID:20604
PX19             || ||| ||||||||||||||||   |
BINDING SITE  3' CG CGG GGCGGCGGCGGCGGC    G          SEQ ID:329182
                  A   C

GCC
              5' TCGCCGCCACCGCCGCC    GC 3'           SEQ ID:20604
RAB1A            ||||||||||||||||     ||
BINDING SITE  3' GGCGGCGGTGGCGGCGG    CG 5'           SEQ ID:330375
                                GAA

A
              5' GCGCC CCGCCGCCGCCG 3'                SEQ ID:20604
RAB1A            |||||| ||||||||||||
BINDING SITE  3' CGGCGG GGCGGTGGCGGC 5'               SEQ ID:330388
                        C

C  CACC   C
              5' TCGC GC     GC GCCGCCGCCG 3'         SEQ ID:20604
RAB1A            |||| ||     || |||||||||||
BINDING SITE  3' AGTG CG     CG CGGCGGCGGC 5'         SEQ ID:330410
                     A  T---   A

C  CA  -
              5' CGC GC  CC GCCGCCGCCG 3'             SEQ ID:20604
RAB33A           ||| ||  || |||||||||||
BINDING SITE  3' GCG CG  GG CGGCGGCGGC 5'             SEQ ID:330765
                    A  A-  T

G   A       C  CC
              5' TC CCGCC CCGCCGC GCCG 3'             SEQ ID:20604
RAD21            || ||||| |||||||| ||||
BINDING SITE  3' AG GGCGG GGCGGTG CGGC 5'             SEQ ID:333078
                    -      C    T

G  A
              5' TCGCC CC CCGCCGCCGCCGCCG 3'          SEQ ID:20604
RASGRP1          ||||| || ||||||||||||||||
BINDING SITE  3' AGCGG GG GGTGGTGGCGGCGGC 5'          SEQ ID:336440
                        G  C

C
              5' TCGCCGC ACCGCCGCCGCCG 3'             SEQ ID:20604
LAF4             ||||||| ||||||||||||
BINDING SITE  3' GGCGGCG TGGCGGCGGCGGC 5'             SEQ ID:338574
                         A
```

Fig. 26D/38

```
                           C
                   5' TCGCCGC ACCGCCGCCGCCG 3'       SEQ ID:20604
RECK                  ||||||| |||||||||||||
BINDING SITE       3' GGCGGCG TGGCGGCGGCGGC 5'       SEQ ID:338574
                           A

C
                   5' TCGCCGC ACCGCCGCCGCCG 3'       SEQ ID:20604
RECK                  ||||||| |||||||||||||
BINDING SITE       3' GGCGGCG TGGCGGCGGCGGC 5'       SEQ ID:338574
                           A

CACC       C
                   5' GCCGC    GCCGC GCCGCCG 3'      SEQ ID:20604
RECK                  |||||    ||||| |||||||
BINDING SITE       3' CGGCG    CGGCG CGGCGGC 5'      SEQ ID:338585
                         T---       A

--   A         C
                   5' GCC  GCC CCGCCGC GCCGCCG 3'    SEQ ID:20604
RENT1                 |||  ||| ||||||| |||||||
BINDING SITE       3' CGG  CGG GGCGGCG CGGCGGC 5'    SEQ ID:339175
                        CT  C         A

A
                   5' TCGCCGCC CCGCCGCCGCCGCCG 3'    SEQ ID:20604
REPS2                 |||||||| |||||||||||||||
BINDING SITE       3' GGCGGCGG GGCGGTGGTGGCGGC 5'    SEQ ID:339240
                              C

A   C     G
                   5' CCGCC CCGC GCCGCC CCG 3'       SEQ ID:20604
REPS2                 ||||| |||| |||||| |||
BINDING SITE       3' GGCGG GGCG CGGCGG GGT 5'       SEQ ID:339246
                         C   A     A

CA      C
                   5' GCCGC  CCGC GCCGCCGCCG 3'      SEQ ID:20604
REPS2                 |||||  |||| ||||||||||
BINDING SITE       3' CGGCG  GGCG CGGCGGCGGC 5'      SEQ ID:339265
                       AC     A

-  GC   CC-
                   5' TCG CC CA    GCCGCCGCCGCCG 3'  SEQ ID:20604
REPS2                 ||| || ||    |||||||||||||
BINDING SITE       3' AGC GG GT    CGGCGGCGGCGGC     SEQ ID:339278
                       C  A-  CGA

-  ---  CA
                   5' TCG CC   GC  CCGCCGCCGCCGCCG 3' SEQ ID:20604
REPS2                 ||| ||   ||  |||||||||||||||
BINDING SITE       3' AGC GG   CG  GGCGGCGGCGGCGGC 5' SEQ ID:339279
                       C  AGT  AC
```

Fig. 26D/39

```
                          C    C
                    5' GCCGCCAC GC GCCGCCGCCG 3'         SEQ ID:20604
REV3L                  |||||||| || ||||||||||
BINDING SITE        3' CGGCGGTG CG CGGTGGCGGC 5'         SEQ ID:339991
                          A    -

A
                    5' CCGCC CCGCCGCCGCCGCCG 3'          SEQ ID:20604
RGS19IP1               ||||| ||||||||||||||
BINDING SITE        3' GGCGG GGCGGCGGCGGCGGC 5'          SEQ ID:341338
                          C

A          C      G
                    5' CGCCGCC CCGCCGC GCC CCG 3'        SEQ ID:20604
RGS19IP1               ||||||| ||||||| ||| |||
BINDING SITE        3' GCGGCGG GGCGGCG CGG GGC 5'        SEQ ID:341352
                          C       A   A

-    C              -
                    5' CC GCCA CGCCGCC GCCG 3'           SEQ ID:20604
RNF14                  || |||| ||||||| ||||
BINDING SITE        3' GG CGGT GCGGCGG CGGC 5'           SEQ ID:342895
                       A  A       T

C    CCGC       CCG
                    5' TCGC GCCA      CGCCGCCG 3'        SEQ ID:20604
ROCK2                  |||| ||||      ||||||||
BINDING SITE        3' GGCG CGGT      GCGGCGGC 5'        SEQ ID:344223
                            A   ACCA

C
                    5' CGCCGCCACCGCCGC GCC 3'            SEQ ID:20604
ROCK2                  |||||||||||||| |||
BINDING SITE        3' GCGGCGGTGGCGGCG CGG 5'            SEQ ID:344231
                                       C

A    C
                    5' GCCGCC CCGC GCCGCCGCCG 3'         SEQ ID:20604
RORA                   |||||| |||| ||||||||||
BINDING SITE        3' CGGCGG GGCG CGGCGGCGGC 5'         SEQ ID:344515
                          C   -

CCA
                    5' CCG    CCGCCGCCGCCGCC 3'          SEQ ID:20604
RPS6KA1                |||    ||||||||||||||
BINDING SITE        3' GGC    GGCGGCGGCGGCGG 5'          SEQ ID:346249
                              A--

C   C         C
                    5' CGCCACCGC GC GC GCC 3'            SEQ ID:20604
RRAS                   ||||||||| || || |||
BINDING SITE        3' GCGGTGGCG CG CG CGG 5'            SEQ ID:346568
                                 A  A  A
```

Fig. 26D/40

```
                     C   ACC            C
                 5' GC GCC     GCCGCCGC GCCG  3'      SEQ ID:20604
RRAS2               || |||     |||||||| ||||
BINDING SITE     3' CG CGG     CGGCGGCG CGGC  5'      SEQ ID:346598
                      -  CT-           A

C   CACC
                 5' GC GC       GCCGCCGCCGCCG 3'      SEQ ID:20604
RTN4                || ||       |||||||||||||
BINDING SITE     3' CG CG       CGGCGGCGGCGGC 5'      SEQ ID:347317
                     T  ACGA

C   A     CC
                 5' GC GCC CCGCCGCC  GCCG  3'         SEQ ID:20604
RTN4                || ||| ||||||||  ||||
BINDING SITE     3' CG CGG GGCGGCGG  CGGC  5'         SEQ ID:347318
                         A  C       CC
                       ˎ
                         CCA
                 5' CCG     CCGCCGCCGCCGCCG  3'       SEQ ID:20604
SAS                 |||     |||||||||||||||
BINDING SITE     3' GGC     GGCGGCGGCGGCGGC  5'       SEQ ID:349188
                         C--

A     C  C
                 5' CGCC CCGCCGC GC GC  3'            SEQ ID:20604
SERPINB8            |||| ||||||| || ||
BINDING SITE     3' GCGG GGCGGCG CG CG  5'            SEQ ID:353985
                         C      A  A

A
                 5' GCCGCC CCGCCGCCGCCGC  3'          SEQ ID:20604
REPS2               |||||| |||||||||||||
BINDING SITE     3' CGGCGG GGCGGCGGCGGCG  5'          SEQ ID:353987
                            C

A
                 5' GCCGCC CCGCCGCCGCCGC  3'          SEQ ID:20604
SERPINB8            |||||| |||||||||||||
BINDING SITE     3' CGGCGG GGCGGCGGCGGCG  5'          SEQ ID:353987
                            C

C  CA
                 5' GC GC   CCGCCGCCGCCGCCG  3'       SEQ ID:20604
GABRB3              || ||   |||||||||||||||
BINDING SITE     3' CG CG   GGCGGCGGCGGCGGC  5'       SEQ ID:353989
                     A  AC

C  CA
                 5' GC GC   CCGCCGCCGCCGCCG  3'       SEQ ID:20604
SERPINB8            || ||   |||||||||||||||
BINDING SITE     3' CG CG   GGCGGCGGCGGCGGC  5'       SEQ ID:353989
                     A  AC
```

Fig. 26D/41

```
                        --    A
                   5' GCC   GCC  CCGCCGCCGCCGCCG  3'         SEQ ID:20604
SFRP5                 |||   |||  |||||||||||||||
BINDING SITE       3' TGG   CGG  GGCGGCGGCGGCGGC  5'         SEQ ID:355430
                        GT    C

G    CA
                   5' TC CCGC     CCGCCGCCGCCG  3'           SEQ ID:20604
SGCB                  || ||||     ||||||||||||
BINDING SITE       3' AG GGCG     GGCGGCGGCGGC  5'           SEQ ID:356034
                         -    CG

ACC
                   5' CCGCC      GCCGCCGCCGCC  3'            SEQ ID:20604
SLC1A1                |||||      ||||||||||||
BINDING SITE       3' GGCGG      CGGCGGCGGTGG  5'            SEQ ID:362965
                              CAA

---            ---
                   5' TCGCCGCC    ACCGCCGCC    GCCGC         SEQ ID:20604
SLC1A1                ||||||||    |||||||||    |||||
BINDING SITE       3' AGCGGCGG    TGGTGGCGG    CGGCG         SEQ ID:362996
                                  CAG         CAA

GC   -
                   5' CC  CA  CCGCCGCCGCCGCCG  3'            SEQ ID:20604
SMARCB1               ||  ||  |||||||||||||||
BINDING SITE       3' GG  GT  GGCGGCGGCGGCGGC  5'            SEQ ID:370333
                        A-   C

C      CG
                   5' GCCGCCAC  GCCGC   CC   3'              SEQ ID:20604
SMARCC1               ||||||||  |||||   ||
BINDING SITE       3' CGGCGGTG  CGGCG   GG   5'              SEQ ID:370474
                              A       AA

CGCCACC   C
                   5' TCGC         GC  GCCGCCGCC    3        SEQ ID:20604
SNX3                  ||||         ||  |||||||||
BINDING SITE       3' AGCG         CG  CGGCGGCGG    5        SEQ ID:373083
                          ACATCGA   A

A           GCC
                   5' CCGCC  CCGCCGCC     GCCG  3'           SEQ ID:20604
SOX10                 |||||  ||||||||     ||||
BINDING SITE       3' GGCGG  GGCGGCGG     CGGC  5'           SEQ ID:374793
                         C           AGC

G  A-
                   5' TCGCC CC  CCGCCGCCGCCGCCG  3           SEQ ID:20604
SOX10                 ||||| ||  |||||||||||||||
BINDING SITE       3' AGCGG GG  GGCGGCGGCGGCGGC  5           SEQ ID:374849
                         G  CC
```

Fig. 26D/42

```
                            C   AC              CC
              5' TCGC GCC    CGCCGCCGCCG    3'         SEQ ID:20604
SOX11            |||| |||    |||||||||||
BINDING SITE  3' AGCG CGG    GCGGCGGCGGC    5'         SEQ ID:375242
                       - GC

C   A         CC    G
              5' TCGC GCC    CCGCCGCCG   GCC           SEQ ID:20604
SPG4             |||| |||    |||||||||   |||
BINDING SITE  3' AGTG CGG    GGCGGCGGT   TGG           SEQ ID:376880
                       A  C              AT GC

C   A    C         CC
              5' TCGC GCC    CCGC  GCCGCCG    3'       SEQ ID:20604
ST7              |||| |||    ||||  |||||||
BINDING SITE  3' AGCG CGG    GGCG  CGGCGGC    5'       SEQ ID:380179
                       -      C     -

C  CACC        C    CG
              5' TCGC GC        GCCGCCGC  GC       3   SEQ ID:20604
STAR             |||| ||        ||||||||  ||
BINDING SITE  3' GGCG CG        CGGCGGCG  CG       5   SEQ ID:380380
                       A  ACGA        A   AC

CACC    C
              5' GCCGC      GC GCCGCCGC      3'        SEQ ID:20604
STAR             |||||      || ||||||||
BINDING SITE  3' CGGCG      CG CGGCGGCG      5'        SEQ ID:380387
                    ACGA   A

C  CACC    C   C
              5' CGC GC          GC  GC  GCCGCCG  3'   SEQ ID:20604
STC1             ||| ||          ||  ||  |||||||
BINDING SITE  3' GCG CG          CG  CG  CGGTGGC  5'   SEQ ID:381482
                    A   ACGA   A   A

C              C   C
              5' GC GCCACCGCCGC GC GC       3'         SEQ ID:20604
STC1             || ||||||||||| || ||
BINDING SITE  3' CG CGGTGGCGGCG CG CG       5'         SEQ ID:381506
                    A            A   A

C   A    C    C   C
              5' GC GCC  CCGC  GC  GC  GC   3'         SEQ ID:20604
STC1             || |||  ||||  ||  ||  ||
BINDING SITE  3' CG CGG  GGCG  CG  CG  CG   5'         SEQ ID:381507
                     A   C     A   A   A

C   CA       C    C
              5' GC GC    CCGCCGC  GC  GC   3'         SEQ ID:20604
STAR             || ||    |||||||  ||  ||
BINDING SITE  3' CG CG    GGCGGCG  CG  CG   5'         SEQ ID:381508
                     A  AC         A   A
```

Fig. 26D/43

```
                              C  CA         C   C
                        5' GC GC  CCGCCGC  GC  GC  3'      SEQ ID:20604
STC1                       || ||  |||||||  ||  ||
BINDING SITE            3' CG CG  GGCGGCG  CG  CG  5'      SEQ ID:381508
                           A  AC           A   A

CG-       CC               CC
                        5' TCGC    CCA    GCCGCCGCCG          3'      SEQ ID:20604
SYK                        ||||    |||    ||||||||||
BINDING SITE            3' AGCG    GGT    CGGCGGCGGC          5'      SEQ ID:384918
                                   AGA    --

C    A      C
                        5' TCG CGCC CCGC GCCGCCGCCG    3      SEQ ID:20604
SYNGR2                     ||| |||| |||| ||||||||||
BINDING SITE            3' GGC GCGG GGCG CGGCGGCGGC    5      SEQ ID:385461
                               A    C    A

ACC
                        5' TCGCCGCC    GCCGCCGCCGC    3'     SEQ ID:20604
SYNGR2                     ||||||||    |||||||||||
BINDING SITE            3' AGCGGCGG    CGGCGGCGGCG    5'     SEQ ID:385484
                               CGA

CCA          C
                        5' TCGCCG    CCGCCGC GCCGCCG    3'     SEQ ID:20604
SYNGR2                     ||||||    ||||||| |||||||
BINDING SITE            3' AGCGGC    GGCGGCG CGGCGGC    5'     SEQ ID:385485
                                AGC         A

A       CG    -
                        5' GCCGCC  CCGCCGC  CC  GC   3'      SEQ ID:20604
TBL3                       ||||||  |||||||  ||  ||
BINDING SITE            3' CGGCGG  GGCGGCG  GG  CG   5'      SEQ ID:388909
                               C        A-   T

5' TCGCCGCCACCGCCGCCGCC    3'      SEQ ID:20604
TCF4                       ||||||||||||||||||||
BINDING SITE            3' GGCGGCGGTGGCGGCGGCGG    5'      SEQ ID:390926

A
                        5' CCGCC CCGCCGCCGCCGCCG    3'      SEQ ID:20604
TCF4                       ||||| |||||||||||||||
BINDING SITE            3' GGCGG GGCGGTGGCGGCGGC    5'      SEQ ID:390929
                                 C

G  A
                        5' GCC CC CCGCCGCCGCCGCCG    3'      SEQ ID:20604
TCF4                       ||| || |||||||||||||||
BINDING SITE            3' CGG GG GGCGGCGGCGGCGGC    5'      SEQ ID:390953
                               A  -
```

Fig. 26D/44

```
                        G     A
              5' TC CCGCC  CCGCCGCCGCCG      C       SEQ ID:20604
TCF4             || |||||  ||||||||||||      |
BINDING SITE  3' AG GGCGG  GGCGGCGGCGGC      G       SEQ ID:390956
                        G     C

C
              5' TCGCCGCCACCGCCGCCGC GCCG  3'        SEQ ID:20604
THOP1            |||||||||||||||||||| ||||
BINDING SITE  3' GGCGGCGGTGGCGGCGGTG CGGC  5'        SEQ ID:396604
                                         C

-   ACC
              5' CC GCC    GCCGCCGCCG  3'            SEQ ID:20604
TIF1             || |||    ||||||||||
BINDING SITE  3' GG CGG    CGGCGGCGGC  5'            SEQ ID:397065
                    A    GAA

CACC           C
              5' GCCGC    GCCGCCGC GCCG  3'          SEQ ID:20604
TIMP3            |||||    |||||||| ||||
BINDING SITE  3' CGGCG    CGGCGGCG CGGC  5'          SEQ ID:397666
                   ACGA           A

C  A   C   CC
              5' GC GCC CCGC GCCG  GC  3'            SEQ ID:20604
TIMP3            || ||| |||| ||||  ||
BINDING SITE  3' CG CGG GGCG CGGC  CG  5'            SEQ ID:397672
                 A   C   A   CC

A    -   C
              5' GCCGCC CCGC CGC GCCG  3'            SEQ ID:20604
TMPO             |||||| |||| ||| ||||
BINDING SITE  3' CGGCGG GGCG GTG CGGC  5'            SEQ ID:400315
                      C    A   -

G   A-          C
              5' TC CCGCC  CCGCCGCCG GCCG  3         SEQ ID:20604
U2AF1            || |||||  ||||||||| ||||
BINDING SITE  3' AG GGTGG  GGCGGCGGC CGGC  5         SEQ ID:411863
                     -     GC         A

CGCCAC-
              5' TCGC       CGCCGCCGCCG              SEQ ID:20604
UBE2B            ||||       |||||||||||
BINDING SITE  3' AGTG       GCGGCGGCGGC              SEQ ID:412149
                     ACACCTA

A
              5' TCGCCGCC CCGCCGCCGCCGCCG   C        SEQ ID:20604
MLLT1            |||||||| |||||||||||||||   |
BINDING SITE  3' AGCGGCGG GGCGGCGGCGGCGGC   G        SEQ ID:412156
                                        C
```

Fig. 26D/45

```
                              A
                 5' TCGCCGCC CCGCCGCCGCCG       C      SEQ ID:20604
UBE2B               |||||||| ||||||||||||      |
BINDING SITE     3' AGCGGCGG GGCGGCGGCGGC       G      SEQ ID:412156
                              C

A          CCG
                 5' TCGCCGCC CCGCCGCCG         C       SEQ ID:20604
UBE2B               |||||||| |||||||||         |
BINDING SITE     3' AGCGGCGG GGCGGCGGC         G       SEQ ID:412157
                              C         G

ACC      C
                 5' GCCGCC    GCCGC GCCGCCG    C       SEQ ID:20604
UFD1L               ||||||    ||||| |||||||    |
BINDING SITE     3' CGGCGG    CGGCG CGGCGGC    G       SEQ ID:414051
                         CGA      A

CA       C       --
                 5' GCCGC  CCGCCGC GCC  GCCG  3'       SEQ ID:20604
UFD1L               |||||  ||||||| |||  ||||
BINDING SITE     3' CGGCG  GGCGGCG CGG  CGGC  5'       SEQ ID:414052
                       AC       -       TT

G  -  A    C       C
                 5' TC CC GCC CCGC GCCGC GCCG          SEQ ID:20604
UFD1L               || || ||| |||| ||||| ||||
BINDING SITE     3' AG GG CGG GGCG CGGCG CGGC          SEQ ID:414064
                       -  T  C    A       A

C   A    C    GC
                 5' GC GCC CCGC GCC  CGCCG   3'        SEQ ID:20604
UNC119              || ||| |||| |||  |||||
BINDING SITE     3' CG CGG GGCG CGG  GCGGC   5'        SEQ ID:414673
                       A   C    A    AC

C  CACC          C
                 5' GC GC       GCCGCCG GCC   3'       SEQ ID:20604
UNC119              || ||       ||||||| |||
BINDING SITE     3' CG CG       CGGCGGCG CGG  5'       SEQ ID:414674
                       A  A---          A

-  CACC   C
                 5' TCGCC GC   GC GCCGCCGC  3'         SEQ ID:20604
UNC119              ||||| ||   || ||||||||
BINDING SITE     3' AGCGG CG   CG CGGCGGCG  5'         SEQ ID:414696
                       A  A--- A

A    CC
                 5' GCCGCC CCG  GCCGCCG   3'           SEQ ID:20604
USP11               |||||| |||  |||||||
BINDING SITE     3' CGGCGG GGT  CGGCGGC   5'           SEQ ID:415547
                            C   AT
```

Fig. 26D/46

```
                          ACC         C
                  5' TCGCCGCC    GCCGCCGC GCCG  3'        SEQ ID:20604
UVRAG                ||||||||    |||||||| ||||
BINDING SITE      3' GGCGGCGG    CGGCGGCG CGGC  5'        SEQ ID:416390
                                 CGA         A

CA         C
                  5' TCGCCGC  CCGCCGC GCCGCCG  3'         SEQ ID:20604
UVRAG                |||||||  ||||||| |||||||
BINDING SITE      3' GGCGGCG  GGCGGCG CGGCGGC  5'         SEQ ID:416391
                           AC        A

CA         CC
                  5' TCGCCGC  CCGCC  GCCGCCG  3'          SEQ ID:20604
UVRAG                |||||||  |||||  |||||||
BINDING SITE      3' GGCGGCG  GGCGG  CGGCGGC  5'          SEQ ID:416392
                           AC        AA

CA          C
                  5' CCGC  CCGCCGC GCCGCCG  3'            SEQ ID:20604
UVRAG                ||||  ||||||| |||||||
BINDING SITE      3' GGCG  GGCGGCG CGGCGGC  5'            SEQ ID:416394
                        AC         A

C   A   CC         CG
                  5' TCGC GCC CCG    GCCGCCGC   3         SEQ ID:20604
UVRAG                |||| ||| |||    ||||||||
BINDING SITE      3' GGCG CGG GGC    CGGCGGCG   5         SEQ ID:416396
                        A   C   AA         AC

A       C
                  5' GCCGCC CCGC GCCGCCGC  3'             SEQ ID:20604
UVRAG                |||||| |||| ||||||||
BINDING SITE      3' CGGCGG GGCG CGGCGGCG  5'             SEQ ID:416411
                           C       A

ACC         CC
                  5' GCCGCC    GCCGCCG  GCCG   3'         SEQ ID:20604
UVRAG                ||||||    |||||||  ||||
BINDING SITE      3' CGGCGG    CGGCGGC  CGGC   5'         SEQ ID:416412
                           CGA         AA

C  CACC
                  5' CGC GC       GCCGCCGCCGCC  3'        SEQ ID:20604
VAMP5                ||| ||       ||||||||||||
BINDING SITE      3' GCG CG       CGGCGGCGGCGG  5'        SEQ ID:416481
                         A A---

A---       CG-
                  5' TCGCCGCC    CCGC    CCGCCGCCG        SEQ ID:20604
VEGF                 ||||||||    ||||    |||||||||
BINDING SITE      3' AGCGGCGG    GGTG    GGCGGCGGC        SEQ ID:417797
                             CGCA       ACA
```

Fig. 26D/47

```
                            A      ------
                  5' TCGCCGCC CCGCC      GCCGCCGC          SEQ ID:20604
WHSC1L1              ||||||||  |||||     ||||||||
BINDING SITE      3' GGCGGCGG GGCGG      CGGCGGCG          SEQ ID:422800
                            C      AGAGGG

A      G---
                  5' TCGCCGCC CCGCC      CCGCCGCCG         SEQ ID:20604
WHSC1L1              ||||||||  |||||    |||||||||
BINDING SITE      3' GGCGGCGG GGCGG     GGCGGCGGC          SEQ ID:422801
                            C      AGAG

CACC           C
                  5' TCGCCGC     GCCGCCGC GC    3'         SEQ ID:20604
WHSC1L1              |||||||     ||||||||  ||
BINDING SITE      3' AGCGGCG     CGGCGGCG CG    5'         SEQ ID:422875
                       ----            A

C  CACC           CCG
                  5' TCGC GC     GCCGCCGCCG    3'          SEQ ID:20604
YWHAH                |||| ||     ||||||||||
BINDING SITE      3' AGCG CG     CGGCGGCGGC    5'          SEQ ID:426949
                       A  CCTC

A     G    CC
                  5' TCGCCGCC CCGCC CCG  GCCG  3'          SEQ ID:20604
ZNF6                 ||||||||  |||||  |||  ||||
BINDING SITE      3' GGCGGCGG GGCGG GGC  CGGC  5'          SEQ ID:432632
                            C     A    A-

ACC
                  5' TCGCCGCC    GCCGCCGCCGC   3'          SEQ ID:20604
ZNF6                 ||||||||    ||||||||||
BINDING SITE      3' GGCGGCGG    CGGCGGCGGCG   5'          SEQ ID:432637
                              CGA

CA
                  5' TCGCCGC   CCGCCGCCGCCGCCG  3'         SEQ ID:20604
ADARB1               |||||||   |||||||||||||||
BINDING SITE      3' GGCGGCG   GGCGGCGGCGGCGGC  5'         SEQ ID:432641
                              AC

CA
                  5' TCGCCGC   CCGCCGCCGCCGCCG  3'         SEQ ID:20604
BCL11B               |||||||   |||||||||||||||
BINDING SITE      3' GGCGGCG   GGCGGCGGCGGCGGC  5'         SEQ ID:432641
                              AC

CA
                  5' TCGCCGC   CCGCCGCCGCCGCCG  3'         SEQ ID:20604
BCR                  |||||||   |||||||||||||||
BINDING SITE      3' GGCGGCG   GGCGGCGGCGGCGGC  5'         SEQ ID:432641
                              AC
```

Fig. 26D/48

```
                          CA
                   5' TCGCCGC   CCGCCGCCGCCGCCG 3'      SEQ ID:20604
BCR                   |||||||   |||||||||||||||
BINDING SITE       3' GGCGGCG   GGCGGCGGCGGCGGC 5'      SEQ ID:432641
                          AC

CA
                   5' TCGCCGC   CCGCCGCCGCCGCCG 3'      SEQ ID:20604
ZNF6                  |||||||   |||||||||||||||
BINDING SITE       3' GGCGGCG   GGCGGCGGCGGCGGC 5'      SEQ ID:432641
                          AC

CA            C
                   5' TCGCCGC   CCGCCGCCGC GCCG 3'      SEQ ID:20604
ZNF6                  |||||||   |||||||||| ||||
BINDING SITE       3' GGCGGCG   GGCGGCGGCG CGGC 5'      SEQ ID:432642
                          AC             A

C   A
                   5' TCGC GCC CCGCCGCCGCCGCCG  3      SEQ ID:20604
ADARB1                |||| ||| |||||||||||||||
BINDING SITE       3' GGCG CGG GGCGGCGGCGGCGGC  5      SEQ ID:432644
                        A   C

C   A
                   5' TCGC GCC CCGCCGCCGCCGCCG  3      SEQ ID:20604
BCL11B                |||| ||| |||||||||||||||
BINDING SITE       3' GGCG CGG GGCGGCGGCGGCGGC  5      SEQ ID:432644
                        A   C

C   A
                   5' TCGC GCC CCGCCGCCGCCGCCG  3      SEQ ID:20604
BCR                   |||| ||| |||||||||||||||
BINDING SITE       3' GGCG CGG GGCGGCGGCGGCGGC  5      SEQ ID:432644
                        A   C

C   A
                   5' TCGC GCC CCGCCGCCGCCGCCG  3      SEQ ID:20604
BCR                   |||| ||| |||||||||||||||
BINDING SITE       3' GGCG CGG GGCGGCGGCGGCGGC  5      SEQ ID:432644
                        A   C

C   A
                   5' TCGC GCC CCGCCGCCGCCGCCG  3      SEQ ID:20604
REPS2                 |||| ||| |||||||||||||||
BINDING SITE       3' GGCG CGG GGCGGCGGCGGCGGC  5      SEQ ID:432644
                        A   C

C   A
                   5' TCGC GCC CCGCCGCCGCCGCCG  3      SEQ ID:20604
ZNF6                  |||| ||| |||||||||||||||
BINDING SITE       3' GGCG CGG GGCGGCGGCGGCGGC  5      SEQ ID:432644
                        A   C
```

Fig. 26D/49

```
                      C   A        C
              5' TCGC GCC CCGCCGC GCCGCCG      3'        SEQ ID:20604
ZNF6             |||| |||  ||||||| |||||||
BINDING SITE  3' GGCG CGG GGCGGCG CGGCGGC      5'        SEQ ID:432645
                      A   C        A

A       C
              5' GCCGCC CCGC GCCGCCGCCG        3'        SEQ ID:20604
ZNF6             |||||| ||||  ||||||||||
BINDING SITE  3' CGGCGG GGCG CGGCGGCGGC        5'        SEQ ID:432654
                        C   A

A       C
              5' GCCGCC CCGC GCCGCCGCCG        3'        SEQ ID:20604
ZNF6             |||||| ||||  ||||||||||
BINDING SITE  3' CGGCGG GGCG CGGCGGCGGC        5'        SEQ ID:432654
                        C   A

C   A        C
              5' GC GCC CCGCCGC GCCGCCG        3'        SEQ ID:20604
ZNF6             || ||| ||||||| |||||||
BINDING SITE  3' CG CGG GGCGGCG CGGCGGC        5'        SEQ ID:432655
                    A   C        A

A         C
              5' CCGCC CCGCCGCCGC GC           3'        SEQ ID:20604
RELN             ||||| |||||||||| ||
BINDING SITE  3' GGCGG GGCGGCGGCG CG           5'        SEQ ID:547115
                           C       -

CA    C
              5' CCGC CCGC GCCGCCGCCG          3'        SEQ ID:20604
DR1              |||| ||||  ||||||||||
BINDING SITE  3' GGCG GGCG CGGCGGCGGC          5'        SEQ ID:625767
                      AC   A

A          GC
              5' CCGCC CCGCCGCCGCC C           3'        SEQ ID:20604
SOX10            ||||| |||||||||||| |
BINDING SITE  3' GGCGG GGCGGCGGCGG G           5'        SEQ ID:717573
                         C          A

G   A
              5' TC CCGCC CCGCCGCCGCCGCCG      C         SEQ ID:20604
ADRBK1           || |||||  ||||||||||||||||   |
BINDING SITE  3' AG GGCGG GGCGGCGGCGGCGGC      G         SEQ ID:816521
                         -       C

G   A
              5' TC CCGCC CCGCCGCCGCCGCCG      C         SEQ ID:20604
PEA15            || |||||  ||||||||||||||||   |
BINDING SITE  3' AG GGCGG GGCGGCGGCGGCGGC      G         SEQ ID:816521
                         -       C
```

Fig. 26D/50

```
                           A
                  5' TCGCCGCC CCGCCGCCGCCGCCG   C      SEQ ID:20604
ADRBA1               |||||||| |||||||||||||||   |
BINDING SITE      3' GGCGGCGG GGCGGCGGCGGCGGC   G      SEQ ID:844404
                           C

A
                  5' TCGCCGCC CCGCCGCCGCCGCCG   C      SEQ ID:20604
FOXF1                |||||||| |||||||||||||||   |
BINDING SITE      3' GGCGGCGG GGCGGCGGCGGCGGC   G      SEQ ID:844404
                           C

5' TCGCCGCCACCGCCGCCG   3'          SEQ ID:20604
CHIC2                ||||||||||||||||||
BINDING SITE      3' AGCGGCGGTGGCGGCGGC   5'          SEQ ID:893635

A
                  5' TCGCCGCC CCGCCGCCGCCGC   3'      SEQ ID:20604
MAP4K5               |||||||| |||||||||||||
BINDING SITE      3' AGCGGCGG GGCGGCGGCGGCG   5'      SEQ ID:918189
                           C

CA   C     C
                  5' CCGC  CCGC GCCGC GCCG   3'       SEQ ID:20604
ATP2B2               ||||  |||| ||||| ||||
BINDING SITE      3' GGCG  GGCG CGGCG CGGC   5'       SEQ ID:947819
                         AC   A     A

C    CACC
                  5' GC GC       GCCGCCGCCGCCG   3'   SEQ ID:20604
SERPINB8             || ||       |||||||||||||
BINDING SITE      3' CG CG       CGGCGGCGGCGGC   5'   SEQ ID:950359
                        A    ACGA

C    CACC   C
                  5' GC GC      GC GCCGCCGCCG   3'    SEQ ID:20604
SERPINB8             || ||      || ||||||||||
BINDING SITE      3' CG CG      CG CGGCGGCGGC   5'    SEQ ID:950360
                        A    ACGA  A

G    A
                  5' TC CCGCC CCGCCGCCGCCGCCG   C     SEQ ID:20604
FOXF1                || ||||| |||||||||||||||   |
BINDING SITE      3' GG GGCGG GGCGGCGGCGGCGGC   G     SEQ ID:969275
                        G    C

G    A
                  5' TC CCGCC CCGCCGCCGCCGCCG   C     SEQ ID:20604
MMP2                 || ||||| |||||||||||||||   |
BINDING SITE      3' GG GGCGG GGCGGCGGCGGCGGC   G     SEQ ID:969275
                        G    C
```

Fig. 26D/51

```
                              A
                5' TCGCCGCC CCGCCGCCGCCGC 3'         SEQ ID:20604
CACNA1A            |||||||| |||||||||||||
BINDING SITE    3' GGCGGCGG GGCGGCGGCGGCG 5'         SEQ ID:969284
                              C

A
                5' TCGCCGCC CCGCCGCCGCCGC 3'         SEQ ID:20604
CAMK4              |||||||| |||||||||||||
BINDING SITE    3' GGCGGCGG GGCGGCGGCGGCG 5'         SEQ ID:969284
                              C

A
                5' TCGCCGCC CCGCCGCCGCCGC 3'         SEQ ID:20604
FGF18              |||||||| |||||||||||||
BINDING SITE    3' GGCGGCGG GGCGGCGGCGGCG 5'         SEQ ID:969284
                              C

A
                5' TCGCCGCC CCGCCGCCGCCGC 3'         SEQ ID:20604
RGS19IP1           |||||||| |||||||||||||
BINDING SITE    3' GGCGGCGG GGCGGCGGCGGCG 5'         SEQ ID:969284
                              C

A         C
                5' TCGCCGCC CCGCCGCCGC GCCG 3'       SEQ ID:20604
LRP8               |||||||| |||||||||| ||||
BINDING SITE    3' GGCGGCGG GGCGGCGGCG CGGC 5'       SEQ ID:969288
                              C         A

A         C
                5' TCGCCGCC CCGCCGCCGC GCCG 3'       SEQ ID:20604
REPS2              |||||||| |||||||||| ||||
BINDING SITE    3' GGCGGCGG GGCGGCGGCG CGGC 5'       SEQ ID:969288
                              C         A

A           C
                5' CGCC CCGCCGCCGC GC 3'             SEQ ID:20604
CRAT               |||| |||||||||| ||
BINDING SITE    3' GCGG GGCGGCGGCG CG 5'             SEQ ID:982983
                          C           C

A
                5' CCGCC CCGCCGCCGCCG 3'             SEQ ID:20604
PX19               ||||| |||||||||||||
BINDING SITE    3' GGCGG GGCGGCGGCGGT 5'             SEQ ID:993966
                              C

C   ACC
                5' TCGC GCC    GCCGCCGCCGG 3'        SEQ ID:20604
ADAM10             |||| |||    |||||||||||
BINDING SITE    3' GGCG CGG    CGGCGGCGGCC 5'        SEQ ID:993970
                       A   CGA
```

Fig. 26D/52

```
                         C   ACC
                      5' TCGC GCC    GCCGCCGCCGCCG      3        SEQ ID:20604
REPS2                    |||| |||    |||||||||||||
BINDING SITE          3' GGCG CGG    CGGCGGCGGCGGC      5        SEQ ID:993970
                         A    CGA

A
                      5' CCGCC CCGCCGCCGCCGCC    C   3           SEQ ID:20604
EXTL3                    ||||| |||||||||||||||   |
BINDING SITE          3' GGCGG GGCGGCGGCGGCGGC   G   5           SEQ ID:1065873
                               C

A              C
                      5' CGCC CCGCCGCCGC GCC    3'                SEQ ID:20604
CAMK4                    |||| |||||||||| |||
BINDING SITE          3' GCGG GGCGGCGGCG CGG    5'                SEQ ID:1295963
                            C              A

A
                      5' CGCC CCGCCGCCGCCGCC    3'                SEQ ID:20604
EXTL3                    |||| ||||||||||||||
BINDING SITE          3' GCGG GGCGGCGGCGGCGG    5'                SEQ ID:1310953
                            C

CA
                      5' GCCGC    CCGCCGCCGCCGCCG    3'           SEQ ID:20604
REPS2                    |||||    |||||||||||||||
BINDING SITE          3' CGGCG    GGCGGCGGCGGCGGC    5'           SEQ ID:1323750
                              AC

A
                      5' CGCCGCC CCGCCGCCGCCG    3'               SEQ ID:20604
FAF1                     ||||||| ||||||||||||
BINDING SITE          3' GTGGCGG GGCGGCGGCGGC    5'               SEQ ID:46198
                             C

A
                      5' CGCCGCC CCGCCGCCGCCG    3'               SEQ ID:20604
FLJ12377                 ||||||| ||||||||||||
BINDING SITE          3' GTGGCGG GGCGGCGGCGGC    5'               SEQ ID:46198
                             C

A
                      5' TCGCCGCC CCGCCGCCGCCGCCG    3'           SEQ ID:20604
CHSY1                    |||||||| |||||||||||||||
BINDING SITE          3' GGCGGCGG GGCGGCGGCGGCGGC    5'           SEQ ID:94853
                              C

A
                      5' TCGCCGCC CCGCCGCCGCCGCCG    3'           SEQ ID:20604
CHSY1                    |||||||| |||||||||||||||
BINDING SITE          3' GGCGGCGG GGCGGCGGCGGCGGC    5'           SEQ ID:94853
                              C
```

Fig. 26D/53

```
                              A
              5' TCGCCGCC CCGCCGCCGCCGCCG 3'        SEQ ID:20604
FLJ21588         |||||||| ||||||||||||||||
BINDING SITE  3' GGCGGCGG GGCGGCGGCGGCGGC 5'        SEQ ID:94853
                              C

A
              5' TCGCCGCC CCGCCGCCGCCGCCG 3'        SEQ ID:20604
MGC10702         |||||||| ||||||||||||||||
BINDING SITE  3' GGCGGCGG GGCGGCGGCGGCGGC 5'        SEQ ID:94853
                              C

A
              5' TCGCCGCC CCGCCGCCGCCGCCG 3'        SEQ ID:20604
QKI              |||||||| ||||||||||||||||
BINDING SITE  3' GGCGGCGG GGCGGCGGCGGCGGC 5'        SEQ ID:94853
                              C

A
              5' TCGCCGCC CCGCCGCCGCCGCCG 3'        SEQ ID:20604
STK39            |||||||| ||||||||||||||||
BINDING SITE  3' GGCGGCGG GGCGGCGGCGGCGGC 5'        SEQ ID:94853
                              C

A
              5' TCGCCGCC CCGCCGCCGCCGCCG 3'        SEQ ID:20604
STK39            |||||||| ||||||||||||||||
BINDING SITE  3' GGCGGCGG GGCGGCGGCGGCGGC 5'        SEQ ID:94853
                              C

A
              5' TCGCCGCC CCGCCGCCGCCGCCG 3'        SEQ ID:20604
STK39            |||||||| ||||||||||||||||
BINDING SITE  3' GGCGGCGG GGCGGCGGCGGCGGC 5'        SEQ ID:94853
                              C

A
              5' GCCGCC CCGCCGCCGCCGCCG   C        SEQ ID:20604
FLJ10996         |||||| ||||||||||||||||  |
BINDING SITE  3' CGGCGG GGCGGCGGCGGCGGC   G        SEQ ID:94860
                            C

A
              5' GCCGCC CCGCCGCCGCCGCCG   C        SEQ ID:20604
FLJ21588         |||||| ||||||||||||||||  |
BINDING SITE  3' CGGCGG GGCGGCGGCGGCGGC   G        SEQ ID:94860
                            C

A
              5' GCCGCC CCGCCGCCGCCGCCG   C        SEQ ID:20604
MGC4796          |||||| ||||||||||||||||  |
BINDING SITE  3' CGGCGG GGCGGCGGCGGCGGC   G        SEQ ID:94860
                            C
```

Fig. 26D/54

```
                          G    A
                     5' TC CCGCC CCGCCGCCGCCGCCG 3'      SEQ ID:20604
OATPRP4                 || ||||| |||||||||||||||
BINDING SITE         3' GG GGCGG GGCGGCGGCGGCGGC 5'      SEQ ID:163380
                          A         C

A                G
                     5' CGCCGCC CCGCCGCCGCC CCG 3'       SEQ ID:20604
FLJ10996                ||||||| |||||||||||| |||
BINDING SITE         3' GCGGCGG GGCGGCGGCGG GGC 5'       SEQ ID:167722
                             C              A

C  CACC   C  C
                     5' GC GC    GC GC GCCGCCG 3'        SEQ ID:20604
KIAA1483                || ||    || || |||||||
BINDING SITE         3' CG CG    CG CG CGGCGGC 5'        SEQ ID:193594
                        A  A---  A  A

A
                     5' GCCGCC CCGCCGCCGCCGCCG 3'        SEQ ID:20604
FLJ20539                |||||| |||||||||||||||
BINDING SITE         3' CGGCGG GGCGGCGGCGGCGGC 5'        SEQ ID:241978
                               C

A
                     5' GCCGCC CCGCCGCCGCCGCCG 3'        SEQ ID:20604
MGC2599                 |||||| |||||||||||||||
BINDING SITE         3' CGGCGG GGCGGCGGCGGCGGC 5'        SEQ ID:241978
                               C

A
                     5' GCCGCC CCGCCGCCGCCGCCG 3'        SEQ ID:20604
TSLL2                   |||||| |||||||||||||||
BINDING SITE         3' CGGCGG GGCGGCGGCGGCGGC 5'        SEQ ID:241978
                               C

A
                     5' TCGCCGCC CCGCCGCCGCCG 3'         SEQ ID:20604
KIAA0995                |||||||| ||||||||||||
BINDING SITE         3' AGCGGCGG GGCGGCGGCGGC 5'         SEQ ID:245294
                                 C

A
                     5' TCGCCGCC CCGCCGCCGCCG 3'         SEQ ID:20604
PMX2B                   |||||||| ||||||||||||
BINDING SITE         3' AGCGGCGG GGCGGCGGCGGC 5'         SEQ ID:245294
                                 C

A
                     5' GCCGCC CCGCCGCCGCCG 3'           SEQ ID:20604
CLSTN1                  |||||| ||||||||||||
BINDING SITE         3' CGGCGG GGCGGCGGCGGC 5'           SEQ ID:324417
                               C
```

Fig. 26D/55

```
                        A
              5' GCCGCC CCGCCGCCGCCG    3'              SEQ ID:20604
FLJ10996         ||||||  ||||||||||||
BINDING SITE  3' CGGCGG GGCGGCGGCGGC    5'              SEQ ID:324417
                        C

A
              5' GCCGCC CCGCCGCCGCCG    3'              SEQ ID:20604
MGC4170          ||||||  ||||||||||||
BINDING SITE  3' CGGCGG GGCGGCGGCGGC    5'              SEQ ID:324417
                        C

A
              5' TCGCCGCC CCGCCGCCGCCG     C            SEQ ID:20604
SSBP3            ||||||||  ||||||||||||    |
BINDING SITE  3' AGCGGCGG GGCGGCGGCGGCGG   G            SEQ ID:412156
                          C

G  C  -
              5' TC CCG CA CCGCCGCCGC   3'              SEQ ID:20604
ADAR3            || ||| || ||||||||||||
BINDING SITE  3' AG GGC GT GGCGGCGGCGGCG  5'            SEQ ID:436814
                 -    C  C

A -----  C
              5' GCCGCC CCG     CCG CGCCGCCG            SEQ ID:20604
ADPRTL2          ||||||  |||     |||  ||||||||
BINDING SITE  3' CGGCGG GGC     GGC GCGGCGGC            SEQ ID:437139
                         C CACGA  A

GC    ACC         CC
              5' TC  CGCC    GCCGCCGCCG    3'           SEQ ID:20604
ADPRTL2          ||  ||||    ||||||||||
BINDING SITE  3' AG  GCGG    CGGCGGCGGC    5'           SEQ ID:437144
                    A-    GA-

C
              5' CGCCG CACCGCCGCCGCCGCCG    C           SEQ ID:20604
AKAP9            |||||  |||||||||||||||||   |
BINDING SITE  3' GCGGC GTGGCGGCGGCGGCGGC    G           SEQ ID:439691
                      A

A    CG     C
              5' CGCCGCC CCGC   CCGC GCCG   3'          SEQ ID:20604
ALTE             |||||||  ||||   ||||  ||||
BINDING SITE  3' GCGGCGG GGCG   GGCG CGGC   5'          SEQ ID:440959
                          C    AA     -

CACC     GC
              5' GCCGC    GCC   CGCCGCCG    3'          SEQ ID:20604
AP1GBP1          |||||     |||   ||||||||
BINDING SITE  3' CGGCG    CGG   GCGGCGGC    5'          SEQ ID:442346
                      A---    AA
```

Fig. 26D/56

```
                           A      ------
                     5' CGCCGCC CCGCC       GCCGCCGCC
AP4E1                   ||||||| |||||       |||||||||       SEQ ID:20604
BINDING SITE         3' GCGGCGG GGCGG          CGGCGGCGG
                           C      GCGCTA                    SEQ ID:443308

A         C--
                     5' CGCCGCC CCGCCGC    GCCG  3'
ARF6                    ||||||| |||||||    ||||              SEQ ID:20604
BINDING SITE         3' GCGGCGG GGCGGCG    TGGC  5'
                           C         CTT                     SEQ ID:445874

C  C
                     5' GCCG CA CGCCGCCGCCGCCG  3'
ARF6                    |||| || ||||||||||||||                SEQ ID:20604
BINDING SITE         3' CGGT GT GCGGCGGCGGCGGC  5'
                          T  T                                SEQ ID:445885

C
                     5' TCGCCGCCACCGCCGC GCCGCCG  3'
ARTS-1                  ||||||||||||||||| |||||||            SEQ ID:20604
BINDING SITE         3' GGCGGCGGTGGTGGTG CGGCGGC  5'
                                       A                     SEQ ID:449602

C   CAC   C
                     5' CG CGC    CGC GCCGCCGCCG  3'
ATE1                    || |||    ||| ||||||||||              SEQ ID:20604
BINDING SITE         3' GC GCG    GCG CGGCGGCGGC  5'
                            A   ATC   C                      SEQ ID:450724

G  A  G  GC
                     5' TCGCC CC CC CC    CGCCGCCG  3'
ATP6V1B2                ||||| || || ||    ||||||||           SEQ ID:20604
BINDING SITE         3' AGCGG GG GG GG    GCGGCGGC  5'
                            -  C  G  AA                      SEQ ID:451749

A    CC-
                     5' CGCCGCC CCG    GCCGCCG  3'
AWP1                    ||||||| |||    |||||||               SEQ ID:20604
BINDING SITE         3' GCGGCGG GGC    CGGCGGC  5'
                           C    CAT                          SEQ ID:452398

C  CAC
                     5' CGC GC    CGCCGCCGCCG  3'
AWP1                    ||| ||    |||||||||||                SEQ ID:20604
BINDING SITE         3' GCG CG    GCGGCGGCGGC  5'
                         A  C--                              SEQ ID:452399

A   CGC
                     5' GCC CCGC    CGCCGCCG  3'
BA108L7.2               ||| ||||    ||||||||                 SEQ ID:20604
BINDING SITE         3' CGG GGCG    GCGGCGGC  5'
                           A   ACA                           SEQ ID:453226
```

Fig. 26D/57

```
                          CCG   AC-
                   5' TCG    CC    CGCCGCCGCCG 3'        SEQ ID:20604
BC-2                  |||    ||    |||||||||||
BINDING SITE       3' AGC    GG    GCGGCGGCGGC 5'        SEQ ID:454363
                          CA-   ACA

CACCGC
                   5' TCGCCGC       CGCCGCC 3'           SEQ ID:20604
BEX1                  |||||||       |||||||
BINDING SITE       3' AGCGGTG       GCGGCGG 5'           SEQ ID:455564
                            CTCCAC

CGC      CC-
                   5' TCGCCGCCAC    CGCCG    GCCG 3      SEQ ID:20604
BLCAP                 ||||||||||    |||||    ||||
BINDING SITE       3' GGCGGCGGTG    GCGGC    CGGC 5      SEQ ID:457198
                                ACA      AGA

A       CGC
                   5' CGCCGCC CCGC     CGCCG 3'          SEQ ID:20604
BLCAP                 ||||||| ||||     |||||
BINDING SITE       3' GCGGCGG GGTG     GCGGC 5'          SEQ ID:457204
                            C       ACA

C      GCC
                   5' TCGCCGCCA CGCC     GCCG 3'         SEQ ID:20604
BTBD1                 |||||||||| ||||    ||||
BINDING SITE       3' GGCGGCGGT GCGG     CGGC 5'         SEQ ID:460514
                              A      GTC

CA                 ---
                   5' CCGC    CCGCCGCCGCC    GCC 3'      SEQ ID:20604
C12orf22              ||||    |||||||||||    |||
BINDING SITE       3' GGCG    GGCGGCGGCGG    CGG 5'      SEQ ID:463154
                         AC                 GAT A      C
                   5' GCCGCC CCGC GCCGCCGCCG 3'          SEQ ID:20604
C12orf22              |||||| |||| ||||||||||
BINDING SITE       3' CGGCGG GGCG CGGCGGCGGC 5'          SEQ ID:463178
                           G      A CCG   C-  C-         CCG
                   5' TCG    CCA  CG    CGCCGCCG         SEQ ID:20604
C20orf124             |||    |||  ||    ||||||||
BINDING SITE       3' AGC    GGT  GC    GCGGCGGC         SEQ ID:468753
                         AA-   AA  CC ACC    -
                   5' GCCGCC    GC CGCCGCCG 3'           SEQ ID:20604
C20orf139             ||||||    || |||||||||
BINDING SITE       3' CGGCGG    CG GCGGCGGC 5'           SEQ ID:469119
                         GA-    C
```

Fig. 26D/58

```
                       CA    -
              5' TCGCCGC  CC GCCGCCG 3'              SEQ ID:20604
C20orf178       |||||||  || |||||||
BINDING SITE  3' GGCGGCG  GG CGGCGGC 5'              SEQ ID:470891
                       AG  A A        -  C
              5' TCGCCGCC CCGCCGC CG CG 3'           SEQ ID:20604
C2orf7          |||||||| ||||||| || ||
BINDING SITE  3' AGCGGCGG GGCGGCG GC GC 5'           SEQ ID:476575
                         -       C  A C   AC  -
              5' TCGC GCC  C GCCGCCGCCGCCG           SEQ ID:20604
C4S-2           |||| |||  | ||||||||||||
BINDING SITE  3' AGCG CGG  G CGGCGGCGGCGGC           SEQ ID:477108
                      -   GC T

-      ----
              5' GC CGCC     ACCGCCGCCGCCGCCG        SEQ ID:20604
CAMTA1           || ||||     ||||||||||||||||
BINDING SITE  3' CG GCGG     TGGCGGCGGCGGCGGC        SEQ ID:483028
                    C        AGCA

--   A
              5' CC  GCC  CCGCCGCCGCCGCCG 3'         SEQ ID:20604
CARM1           ||  |||  |||||||||||||||
BINDING SITE  3' GG  CGG  GGCGGCGGCGGCGGC 5'         SEQ ID:483979
                     TC  -

A       C  C
              5' CGCCGCC CCGCCGC GC GCC 3'           SEQ ID:20604
CARM1           ||||||| ||||||| || |||
BINDING SITE  3' GCGGCGG GGCGGCG CG CGG 5'           SEQ ID:483989
                         C       A  -

CCA    C  C
              5' CG   CCGC GC GCCGCCG 3'             SEQ ID:20604
CBLN1           ||   |||| || |||||||
BINDING SITE  3' GC   GGCG CG CGGCGGC 5'             SEQ ID:485030
                  CAG    A  A

G    CACC         G  G
              5' TC CCGC      GCCGCCGCC CC  3        SEQ ID:20604
CBLN1           || ||||      ||||||||| ||
BINDING SITE  3' AG GGCG      CGGCGGCGG GG  5        SEQ ID:485054
                  -     ACGA            A  A

C  CA
              5' GC GC  CCGCCGCCGCCG 3'              SEQ ID:20604
CDC14A          || ||  ||||||||||||
BINDING SITE  3' CG CG  GGCGGCGGCGGC 5'              SEQ ID:487263
                    A  A-
```

Fig. 26D/59

```
                         C  CA
                 5' GC GC    CCGCCGCCGCCG    3'         SEQ ID:20604
CDC14A              || ||    ||||||||||||
BINDING SITE     3' CG CG    GGCGGCGGCGGC    5'         SEQ ID:487263
                    A  A-

-   CACC
                 5' GCC GC      GCCGCCGCCGCCG  3'       SEQ ID:20604
CDC16               ||| ||      |||||||||||||
BINDING SITE     3' CGG CG      CGGCGGCGGCGGC  5'       SEQ ID:487765
                    A  T---

A  -     C C  C
                 5' TCGCCGCC CCG CCGC G CG CG   3       SEQ ID:20604
CDC42BPB            |||||||| ||| ||||  | || ||
BINDING SITE     3' AGCGGCGG GGC GGCG C GC GC   5       SEQ ID:487991
                          -      A   - A  A

CA      -----
                 5' TCGCCGC   CCGCCG       CCGCCGC      SEQ ID:20604
CDCA4               |||||||   ||||||       |||||||
BINDING SITE     3' GGCGGCG   GGCGGT       GGCGGCG      SEQ ID:488095
                           AC         CGAAG

G   CACC  C              -
                 5' TC CCGC     GC GCCGCCGC CG   3      SEQ ID:20604
CECR2               || ||||     || |||||||| ||
BINDING SITE     3' AG GGCG     CG CGGCGGCG GC   5      SEQ ID:489555
                        -       A---         A

C   CA       C
                 5' TCG CGC    CCGCCG CGCCGCCG   3      SEQ ID:20604
CGGBP1              ||| |||    |||||| ||||||||
BINDING SITE     3' GGC GCG    GGCGGC GCGGCGGC   5      SEQ ID:492176
                        A   AC       A

C    A   C
                 5' TCGC GCC CCG CGCCGCCG    3'         SEQ ID:20604
CGGBP1              |||| ||| ||| ||||||||
BINDING SITE     3' AGCG CGG GGC GCGGCGGC    5'         SEQ ID:492221
                        A   C   A

A        C-    G
                 5' TCGCCGCC CCGCCGC   GCC CCG    3     SEQ ID:20604
CHSY1               |||||||| |||||||   ||| |||
BINDING SITE     3' GGCGGCGG GGCGGCG   CGG GGC    5     SEQ ID:494504
                                   C       TC  -

--    A
                 5' TCGCC   GCC  CCGCCGCCGCCGCCG        SEQ ID:20604
CHSY1               |||||   |||  |||||||||||||||
BINDING SITE     3' GGCGG   CGG  GGCGGCGGCGGCGGC        SEQ ID:494516
                         CC    C
```

Fig. 26D/60

```
                              A     C- -
                    5' CGCCGCC CCGCCGC  GCC GCCG  3'      SEQ ID:20604
CHSY1                  ||||||| |||||||  ||| ||||
BINDING SITE        3' GCGGCGG GGCGGCG  CGG CGGC  5'      SEQ ID:494532
                                         CC   G

CC    AC          CCG
                    5'   TCG  GCC   CGCCGCCGCCG    3'     SEQ ID:20604
CHSY1                    |||  |||   |||||||||||
BINDING SITE        3'   AGC  CGG   GCGGCGGCGGC    5'     SEQ ID:494603
                              AT    CC

A             C--
                    5' CGCCGCC CCGCCGCC     CGC   3'      SEQ ID:20604
CLSTN1                 ||||||| ||||||||     |||
BINDING SITE        3' GCGGCGG GGCGGCGG     GCG   5'      SEQ ID:496944
                              C             ACT

CGCCACCGC
                    5' TCGC             CGCCGCCGCCG  3'   SEQ ID:20604
CNNM3                  ||||             |||||||||||
BINDING SITE        3' AGCG             GCGGCGGCGGC  5'   SEQ ID:498002
                       ACATCCCCA

CG-   ACC         C
                    5' GC    CC    GCCGCCGCC CG   3'      SEQ ID:20604
COASTER                ||    ||    ||||||||| ||
BINDING SITE        3' CG    GG    CGGCGGCGG GC   5'      SEQ ID:498924
                          ACA   GAA         A

C  -           ---
                    5' GCCG CA CCGCCGCCGCC    GCCG    SEQ ID:20604
COL4A3BP               |||| || |||||||||||    ||||
BINDING SITE        3' CGGC GT GGCGGCGGCGG    CGGC    SEQ ID:499352
                            A  C            CAG

A       C
                    5' CGCCGCC CCGCCGC GCCG   3'          SEQ ID:20604
CTCF                   ||||||| ||||||| ||||
BINDING SITE        3' GTGGCGG GGCGGCG CGGC   5'          SEQ ID:503528
                              C       A

-
                    5' CGCCG CCACCGCCGCCGCCGC    3'       SEQ ID:20604
CTCF                   ||||| |||||||||||||||||
BINDING SITE        3' GTGGC GGTGGCGGCGGCGGCG    5'       SEQ ID:503529
                              C

A    G G
                    5' TCGCCGCC CCGCCGCC CC CCG   3'      SEQ ID:20604
DDM36                  |||||||| |||||||| || |||
BINDING SITE        3' GGCGGCGG GGCGGCGG GG GGC   5'      SEQ ID:508506
                              C          A -
```

Fig. 26D/61

```
                    CC   A
              5' TCG   GCC  CCGCCGCCGCCGCCG  3'         SEQ ID:20604
DDM36            |||   |||  |||||||||||||||
BINDING SITE  3' AGC   CGG  GGCGGCGGCGGCGGC  5'         SEQ ID:508575
                       C-   C

A           CG   -
              5' CGCCGCC  CCGCCGC  CC GC     3'         SEQ ID:20604
DKFZP434D1335    |||||||  |||||||  || ||
BINDING SITE  3' GCGGCGG  GGCGGCG  GG CG     5'         SEQ ID:516151
                    C           AG T

AC  C-
              5' TCGCCGCC  CG  CGCCG         3'         SEQ ID:20604
DKFZP434J154     |||||||  ||  |||||
BINDING SITE  3' AGCGGCGG  GC  GCGGC         5'         SEQ ID:520474
                       A-  CA

CC-
              5' TCGCCGCCA    GCGCCG         3'         SEQ ID:20604
DKFZP434N093     |||||||||    ||||||
BINDING SITE  3' GGCGGCGGT    CGGCGGC        5'         SEQ ID:522414
                          ACA

ACC    -   C
              5' GCCGCC   GC CGC GCCGCCG      3'        SEQ ID:20604
DKFZP434P106     ||||||   || |||  |||||||
BINDING SITE  3' CGGCGG   CG GTG CGGCGGC      5'        SEQ ID:523992
                          ---  A  T

ACCG
              5' GCCGCC      CCGCCGCCGCCG     3'        SEQ ID:20604
DKFZP566A1524    ||||||      ||||||||||||
BINDING SITE  3' CGGCGG      GGCGGCGGCGGC     5'        SEQ ID:531199
                        GCGA

CCAC           -
              5' CGCCG      CGCCGCCG CCG      3'        SEQ ID:20604
DKFZP566K1924    |||||      |||||||| |||
BINDING SITE  3' GCGGC      GCGGCGG  GGC      5'        SEQ ID:532863
                        A---        A

G    A            CC
              5' TC CCGCC  CCGCCGCCGCCG       3'        SEQ ID:20604
DKFZp761B0514    || |||||  ||||||||||||
BINDING SITE  3' AG GGCGG  GGCGGCGGCGGC       5'        SEQ ID:536448
                        -          -

C--  CA     C
              5' GC    GC   CCGC GCCGCCG      3'        SEQ ID:20604
DKFZp762E1511    ||    ||   |||| |||||||
BINDING SITE  3' CG    CG   GGCG CGGCGGCG     5'        SEQ ID:539970
                     ACC  AC     A
```

Fig. 26D/62

```
                        C   C
                5' GCCA CGC GCCGCCGCCG 3'          SEQ ID:20604
Dlc2               |||| ||| ||||||||||
BINDING SITE    3' CGGT GCG CGGCGGCGGT 5'          SEQ ID:540962
                        A   A

A         C  C
                5' CCGCC CCGCCGC GC GCC 3'         SEQ ID:20604
E46L               ||||| ||||||| || |||
BINDING SITE    3' GGCGG GGCGGCG CG CGG 5'         SEQ ID:545962
                        C         A  T

GCC
                5' CC    ACCGCCGCCGCCGC 3'         SEQ ID:20604
E46L               ||    ||||||||||||||
BINDING SITE    3' GG    TGGCGGCGGCGGCG 5'         SEQ ID:545966
                      AT-

A         C
                5' CCGCC CCGCCGCCG GC 3'           SEQ ID:20604
EHM2               ||||| ||||||||| ||
BINDING SITE    3' GGCGG GGCGGCGGCG CG 5'          SEQ ID:547115
                                   C         -

CA    C  C
                5' GCCGC  CCGC GC GCCGCCG 3'       SEQ ID:20604
EHM2               |||||  |||| || |||||||
BINDING SITE    3' CGGCG  GGCG CG CGGCGGC 5'       SEQ ID:547149
                     AC       A  -

-  A-
                5' GCCG CC  CCGCCGCCGCCGCCG 3'     SEQ ID:20604
EHM2               |||| ||  |||||||||||||||
BINDING SITE    3' CGGC GG  GGCGGCGGCGGCGGC 5'     SEQ ID:547151
                     A  GC

CG
                5' TCGCCGCCAC   CCGCCGCCGCCG   C  SEQ ID:20604
ELKS               ||||||||||   ||||||||||||   |
BINDING SITE    3' GGCGGCGGTG   GGCGGCGGCGGC   G  SEQ ID:548280
                             AT

C   CAC
                5' TCGC GC   CGCCGCCGCCG 3'        SEQ ID:20604
ELKS               |||| ||   |||||||||||
BINDING SITE    3' GGCG CG   GCGGCGGCGGC 5'        SEQ ID:548281
                        - ACA

---     A     C
                5' CGC   CGCC CCGCCGC GCCG 3'      SEQ ID:20604
ELKS               |||   |||| ||||||| ||||
BINDING SITE    3' GCG   GCGG GGCGGCG CGGC 5'      SEQ ID:548286
                   ACA        C       C
```

Fig. 26D/63

```
                                AC--
                       5' GCCGCC      CGCCGCCGCCGCCG    C       SEQ ID:20604
ELKS                      ||||||      ||||||||||||||   |
BINDING SITE           3' CGGCGG      GTGGCGGCGGCGGC    G       SEQ ID:548299
                                GCCC

A              CG
                       5' GCCGCC CCGCCGCCGC     CCG  3'         SEQ ID:20604
ELL2                      |||||| ||||||||||     |||
BINDING SITE           3' CGGCGG GGCGGCGGCG     GGC  5'         SEQ ID:548421
                                 C              A-

G    CCA--
                       5' TC CCG        CCGCCGCCGCCGCCG         SEQ ID:20604
ELL2                      || |||        |||||||||||||||
BINDING SITE           3' AG GGC        GGCGGCGGCGGCGGC         SEQ ID:548442
                             G    CCCAC

A             C-
                       5' CGCCGCC CCGCCGCC    CGCCG  3'         SEQ ID:20604
FAF1                      ||||||| ||||||||    |||||
BINDING SITE           3' GCGGCGG GGCGGCGG    GCGGC  5'         SEQ ID:552942
                                 C             CC

5' TCGCCGCCACCGCCGCCGCCGCCG    C         SEQ ID:20604
FAF1                      |||||||||||||||||||||||||   |
BINDING SITE           3' AGCGGCGGTGGCGGCGGCGGCGGC    G         SEQ ID:552963

C  C   C
                       5' CGCCACCGC GC GC GCCG  3'              SEQ ID:20604
FEM1B                     |||||||| || || ||||
BINDING SITE           3' GCGGTGGCG CG CG CGGC  5'              SEQ ID:556003
                                  A  T   A

C  A     CGCC-
                       5' GC GCC CCGCCGC     GCCG  3'           SEQ ID:20604
FJX1                      || ||| |||||||     ||||
BINDING SITE           3' CG CGG GGCGGCG     CGGC  5'           SEQ ID:557158
                             -  C     AAGTT

----                    C
                       5' CC     GCCACCGCCGCCGCCG CG  3         SEQ ID:20604
FLJ10211                  ||     ||||||||||||||| ||
BINDING SITE           3' GG     CGGTGGCGGCGGCGGC GC  5         SEQ ID:562466
                            AGTC                 A

-
                       5' TCGCCGCCACCGCCGCCGC CG  3'             SEQ ID:20604
FLJ10211                  |||||||||||||||||||| ||
BINDING SITE           3' AGCGGCGGTGGCGGCGGCG GC  5'            SEQ ID:562496
                                                A
```

Fig. 26D/64

```
                                    CCGCC
                    5'  TCGCCGCCACCGCCGCCG        3'       SEQ ID:20604
FLJ10211                |||||||||||||||||
BINDING SITE        3'  AGCGGCGGTGGCGGCGGC        5'       SEQ ID:562509
                          A                G

A         C
                    5' TCGCCGCC CCGCCGC GCCGC      3'       SEQ ID:20604
FLJ10244               |||||||| ||||||| |||||
BINDING SITE        3' GGCGGCGG GGCGGCG CGGCG      5'       SEQ ID:562895
                                C         A

A     C      C
                    5' TCGCCGCC CCGC GCCGC GCCG    3'       SEQ ID:20604
FLJ10244               |||||||| |||| ||||| ||||
BINDING SITE        3' GGCGGCGG GGCG CGGCG CGGC    5'       SEQ ID:562897
                                C    A     A

CACC       C             -
                    5' CGCCGC     GCCGC GCCGC CG    3'       SEQ ID:20604
FLJ10244               ||||||     ||||| ||||| ||
BINDING SITE        3' GCGGCG     CGGCG CGGCG GC    5'       SEQ ID:562906
                         A---       A     A

A            C
                    5' GCCGCC CCGCCGCCGC GCCG      C        SEQ ID:20604
FLJ10244               |||||| |||||||||| ||||      |
BINDING SITE        3' CGGCGG GGCGGCGGCG CGGC      G        SEQ ID:562923
                          C         A

C
                    5' TCGCCGCCAC GCCGCCGCCG      3'        SEQ ID:20604
FLJ10244               |||||||||| ||||||||||
BINDING SITE        3' AGTGGCGGTG CGGCGGCGGC      5'        SEQ ID:562943
                                  C

CA      C   G
                    5' CCGC  CCGCCGC GCC CCG      3'        SEQ ID:20604
FLJ10342               ||||  ||||||| ||| |||
BINDING SITE        3' GGCG  GGCGGCG CGG GGC      5'        SEQ ID:564347
                        AC          A   A

C  A---   G
                    5' TCGC GCC   CC CCGCCGCCGCCG           SEQ ID:20604
FLJ10648               |||| |||   || ||||||||||||
BINDING SITE        3' GGCG CGG   GG GGCGGCGGCGGC           SEQ ID:569200
                        A   CAGC  A

A    CG
                    5' TCGCCGCC CCGC CCGCCGCCG    3'        SEQ ID:20604
FLJ10709               |||||||| |||| |||||||||
BINDING SITE        3' GGCGGCGG GGCG GGCGGCGGC    5'        SEQ ID:570431
                                C    AT
```

Fig. 26D/65

```
                              CA
                  5' CGCCGC   CCGCCGCCGCCGCCG    C        SEQ ID:20604
FLJ10856             ||||||   |||||||||||||||    |
BINDING SITE      3' GCGGCG   GGCGGCGGCGGCGG     G        SEQ ID:574295
                              AC

CCAC           G
                  5' TCGCCG       CGCCGCCGCC CC  3'       SEQ ID:20604
FLJ10925             ||||||       |||||||||| ||
BINDING SITE      3' AGCGGC       GCGGCGGCGG GG  5'       SEQ ID:575621
                              C---           G

CGC          CC       -
                  5' GC      CACCGCCG    GCC GC  3'       SEQ ID:20604
FLJ10996             ||      ||||||||    ||| ||
BINDING SITE      3' CG      GTGGTGGT    CGG CG  5'       SEQ ID:576651
                         ACA          T-    A

--       C
                  5' GCCA  CCGCCGC GCCGCCG   3'           SEQ ID:20604
FLJ11700             ||||  ||||||| |||||||
BINDING SITE      3' CGGT  GGCGGCG CGGCGGC   5'           SEQ ID:582367
                         CC        A

A            C
                  5' CGCC  CCGCCGC  GCCGC   3'            SEQ ID:20604
FLJ12363             ||||  |||||||  |||||
BINDING SITE      3' GCGG  GGCGGCG  CGGCG   5'            SEQ ID:587504
                         C            A

CA            C
                  5' CGCCGC   CCGCCGCCGC  GCCG   3'       SEQ ID:20604
FLJ12363             ||||||   ||||||||||  ||||
BINDING SITE      3' GCGGCG   GGCGGCGGCG  CGGC   5'       SEQ ID:587507
                              C-            A

5' TCGCCGCCACCGCCGCCGCCGCCG    3'       SEQ ID:20604
FLJ12377             ||||||||||||||||||||||||
BINDING SITE      3' GGCGGTGGTGGCGGCGGCGGCGGC    5'       SEQ ID:587654

G ----     A
                  5' TC CC     GCC  CCGCCGCCGCCGCCG       SEQ ID:20604
FLJ12697             || ||     |||  |||||||||||||||
BINDING SITE      3' AG GG     CGG  GGCGGCGGCGGCGGC       SEQ ID:592585
                         G    GAGC   C

CCAC
                  5' GCCG     CGCCGCCGCCGC   3'           SEQ ID:20604
FLJ12750             ||||     ||||||||||||
BINDING SITE      3' CGGC     GCGGTGGCGGCG   5'           SEQ ID:593299
                              AGCA
```

Fig. 26D/66

```
                          -  A  GC-
                   5' GCCG CC CC    CGCCGCCGCCG 3'        SEQ ID:20604
FLJ13189              |||| || ||    |||||||||||
BINDING SITE       3' CGGC GG GG    GCGGCGGCGGC 5'        SEQ ID:599594
                          A  -  AAA

A     GC
                   5' TCGCCGCC CCGCC CGCCG 3'             SEQ ID:20604
FLJ13189              |||||||| ||||| |||||
BINDING SITE       3' AGCGGCGG GGCGG GTGGC 5'             SEQ ID:599628
                            C        --

G    A    C C---
                   5' TC CCGCC CCGC GC    GCCGCCG         SEQ ID:20604
FLJ13194              || ||||| |||| ||    |||||||
BINDING SITE       3' AG GGCGG GGCG CG    CGGCGGC         SEQ ID:600122
                         -    C    - AACA

CC             C
                   5' CCG  ACCGCCGCCGC GCCG 3'            SEQ ID:20604
FLJ13340              |||  |||||||||||| ||||
BINDING SITE       3' GGC  TGGCGGCGGCG CGGC 5'            SEQ ID:601522
                        --             A

CC             C
                   5' CCG  ACCGCCGCCGC GCCG 3'            SEQ ID:20604
TBDN100               |||  |||||||||||| ||||
BINDING SITE       3' GGC  TGGCGGCGGCG CGGC 5'            SEQ ID:601522
                        --             A

CCA             C
                   5' CCG    CCGCCGCCGC GCCG 3'           SEQ ID:20604
FLJ13855              |||    |||||||||| ||||
BINDING SITE       3' GGC    GGCGGCGGCG CGGC 5'           SEQ ID:605857
                        TTG            A

ACC-
                   5' CCGCC    GCCGCCGCCG 3'              SEQ ID:20604
FLJ13855              |||||    ||||||||||
BINDING SITE       3' GGCGG    CGGCGGCGGC 5'              SEQ ID:605858
                        GCGA

A
                   5' TCGCCGCC CCGCCGCCGCCGC 3'           SEQ ID:20604
FLJ14299              |||||||| ||||||||||||
BINDING SITE       3' GGCGGCGG GGCGGTGGCGGCG 5'           SEQ ID:610393
                                     C

A  CC--- C  C
                   5' TCGCCGCC CCG    GC GC GCCG          SEQ ID:20604
FLJ14451              |||||||| |||    || || ||||
BINDING SITE       3' GGCGGCGG GGC    CG CG CGGC          SEQ ID:612603
                            C  ATCAA  A  A
```

Fig. 26D/67

```
                         C  CACC----
                  5' CGC GC      GCCGCCGCCGCCG       SEQ ID:20604
FLJ14451             ||| ||      |||||||||||||
BINDING SITE      3' GCG CG      CGGCGGCGGCGGC       SEQ ID:612607
                         A  ACCCAAGA

CA    C
                  5' GCCGC  CCGC GCCGCCGCC 3'        SEQ ID:20604
FLJ20288             |||||  |||| |||||||||
BINDING SITE      3' TGGCG  GGCG CGGCGGCGGC 5'       SEQ ID:625741
                         AC    A

CA
                  5' CCGC    CCGCCGCCGCC 3'          SEQ ID:20604
FLJ20288             ||||    |||||||||||
BINDING SITE      3' GGCG    GGCGGCGGCGGCG 5'        SEQ ID:625764
                         AC

CA    C
                  5' CCGC    CCGC GCCGCCGCCG 3'      SEQ ID:20604
PCAF                 ||||    |||| |||||||||
BINDING SITE      3' GGCG    GGCG CGGCGGCGGC 5'      SEQ ID:625767
                         AC    A

A     C  C
                  5' GCCGCC CCGCCGC GC GCCG 3'       SEQ ID:20604
FLJ20288             |||||| ||||||| || ||||
BINDING SITE      3' CGGCGG GGCGGCG CG CGGC 5'       SEQ ID:625783
                           C       A  A

CA
                  5' GCCGC    CCGCCGCCGCCGC 3'       SEQ ID:20604
FLJ20288             |||||    |||||||||||||
BINDING SITE      3' CGGCG    GGCGGCGGCGGCG 5'       SEQ ID:625785
                           AC

CGC
                  5' TCGC    CACCGCCGCCGC 3'         SEQ ID:20604
FLJ20288             ||||    |||||||||||
BINDING SITE      3' AGCG    GTGGCGGCGGCG 5'         SEQ ID:625802
                           CCA

G    A   C
                  5' TC CCGCC CCG CGCCGCCGCCG  C     SEQ ID:20604
FLJ20400             || ||||| ||| |||||||||||  |
BINDING SITE      3' AG GGCGG GGC GCGGCGGCGGC  G     SEQ ID:629258
                        -     C   A

C    A-
                  5' TCG CGCC  CCGCCGCCGCCGCCG 3     SEQ ID:20604
FLJ20421             ||| ||||  |||||||||||||||
BINDING SITE      3' GGT GCGG  GGCGGCGGCGGCGGC 5     SEQ ID:629645
                          C    GC
```

Fig. 26D/68

```
                       A             C
              5' TCGCCGCC CCGCCGC GCCGCCG  3'        SEQ ID:20604
FLJ20421         ||||||||  |||||||  |||||||
BINDING SITE  3' GGCGGCGG GGCGGCG CGGCGGC  5'       SEQ ID:629655
                              C       T

A              C
              5' CGCCGCC CCGCCGCCGC GCCG  3'        SEQ ID:20604
FLJ20421         |||||||  ||||||||||  ||||
BINDING SITE  3' GCGGCGG GGCGGCGGCG CGGC  5'       SEQ ID:629660
                              C       T

A   -  GC-
              5' TCGCCGCC CC GCC    CGCCG  3'        SEQ ID:20604
FLJ20425         ||||||||  ||  |||       |||||
BINDING SITE  3' AGCGGCGG GG CGG    GCGGC  5'       SEQ ID:629739
                          C  T  GTC

G  -  A
              5' TC CCG CC CCGCCGCCGCCGCCG  3       SEQ ID:20604
FLJ20539         ||  |||  ||  ||||||||||||||||
BINDING SITE  3' AG GGC GG GGCGGCGGCGGCGGC   5      SEQ ID:632084
                      -   C  C

ACC   C         GC
              5' TCGCCGCC    GC GCCGCC    C  3'     SEQ ID:20604
FLJ20718         ||||||||    ||  ||||||    |
BINDING SITE  3' AGCGGCGG    CG CGGCGG    G  5'    SEQ ID:635286
                         ---    T         A

A              CCG
              5' GCCGCC CCGCCGCCGCCG        C       SEQ ID:20604
FLJ21588         ||||||  ||||||||||||         |
BINDING SITE  3' CGGCGG GGCGGCGGCGGC        G      SEQ ID:641646
                      C                    GC

ACC
              5' CGCCGCC    GCCGCCGCCG  3'          SEQ ID:20604
FLJ21613         |||||||    ||||||||||
BINDING SITE  3' GCGGCGG    CGGCGGCGGC  5'         SEQ ID:641999
                            AGC

ACC---
              5' CGCC          GCCGCCGCCGCCG  3'    SEQ ID:20604
FLJ22393         ||||           |||||||||||||
BINDING SITE  3' GCGG          CGGCGGCGGCGGC  5'   SEQ ID:649088
                       GCCCCA

A GC    G
              5' TCGCCGCC CC CGCC CCGC  3'          SEQ ID:20604
FLJ23251         ||||||||  ||   ||||  ||||
BINDING SITE  3' AGCGGCGG GG   GCGG GGTG  5'       SEQ ID:657789
                          C AA       -
```

Fig. 26D/69

```
                          CAC
                  5' CGCCGC      CGCCGCCGCCGCCG 3'         SEQ ID:20604
FLJ31564             ||||||      ||||||||||||||
BINDING SITE      3' GCGGCG      GCGGCGGCGGTGGC 5'         SEQ ID:665686
                          ACA

-  -  A              CCG
                  5' TCG CCG CC CCGCCGCCGCCG               SEQ ID:20604
FLJ31978             ||| ||| || ||||||||||||
BINDING SITE      3' AGC GGC GG GGCGGCGGCGGC               SEQ ID:666546
                       T   C  -

G   CCAC
                  5' TC CCG      CGCCGCCGCCGCCG 3'         SEQ ID:20604
FOXO3A               || |||      ||||||||||||||
BINDING SITE      3' AG GGC      GCGGCGGCGGCGGC 5'         SEQ ID:669368
                       -   CC--

G  A        ---
                  5' TCGCC CC CCGCC    GCCGCCGCCG          SEQ ID:20604
FUBP3                ||||| || |||||    ||||||||||
BINDING SITE      3' GGCGG GG GGCGG    CGGCGGCGGC          SEQ ID:670361
                          G  C        CAG

A      C
                  5' TCGCCGCC CCGCCG CGCCG 3'              SEQ ID:20604
FUBP3                |||||||| |||||| |||||
BINDING SITE      3' AGCGGCGG GGCGGC GCGGC 5'              SEQ ID:670394
                            C      T

C  C      GCC      CC
                  5' TCG CG CACCGCC    GCCG 3'             SEQ ID:20604
GIOT-3               ||| || |||||||    ||||
BINDING SITE      3' GGC GC GTGGCGG    CGGC 5'             SEQ ID:674988
                     A  A              GC-

A       C  C
                  5' CGCC CCGCCG CG CGCCG 3'               SEQ ID:20604
GIOT-3               |||| |||||| || |||||
BINDING SITE      3' GCGG GGCGGC GC GTGGC 5'               SEQ ID:674995
                        A       A  A

A
                  5' GCCGCC CCGCCGCCGCC 3'                 SEQ ID:20604
MGC14425             |||||| |||||||||||
BINDING SITE      3' CGGCGG GGCGGCGGCGG 5'                 SEQ ID:676856
                            C

A          --
                  5' GCCGCC CCGCCGCCGCC   GCCG 3'          SEQ ID:20604
GNA13                |||||| |||||||||||   ||||
BINDING SITE      3' CGGCGG GGCGGCGGCGG   CGGC 5'          SEQ ID:676857
                            C              AG
```

Fig. 26D/70

```
                            CGCCA              CC
                   5' TCGC       CCGCCGCCGCCG      3'        SEQ ID:20604
GOLPH2                || ||       ||||||||||||
BINDING SITE       3' AGCG       GGCGGCGGCGGC      5'        SEQ ID:677940
                            AGAG-

CA         G  G
                   5' TCGCCGC   CCGCCGCC CC  CCG   3'        SEQ ID:20604
GSK3A                 |||||||   |||||||| ||  |||
BINDING SITE       3' GGCGGCG   GGCGGCGG GG  GGC   5'        SEQ ID:681389
                               AC         A  G

---      A          C
                   5' GCC    GCC CCGCCGC GCCGCCG   3         SEQ ID:20604
GSK3A                 |||    ||| ||||||| |||||||
BINDING SITE       3' CGG    CGG GGCGGCG CGGCGGC   5         SEQ ID:681400
                      GGT     C          A

C   A     C
                   5' GC GCC CCGC GCCGCCGCCG       3'        SEQ ID:20604
GTF2A1                || ||| |||| ||||||||||
BINDING SITE       3' CG CGG GGCG CGGCGGTGGC       5'        SEQ ID:681625
                           - C    A

CA ---         C
                   5' TCGCCGC  CC    GCCGCCGC GCCG           SEQ ID:20604
GTF2A1                |||||||  ||    |||||||| ||||
BINDING SITE       3' AGTGGCG  GG    CGGCGGCG CGGC           SEQ ID:681632
                            AG ACG            A

C   A--       C
                   5' TCGC GCC    CCGC GCCGCCGCCG  SEQ ID:20604
H2AV                  |||| |||    |||| ||||||||||
BINDING SITE       3' GGCG CGG    GGCG CGGCGGCGGC  SEQ ID:683857
                           A   CTG      -

C  C            -
                   5' TCGC GC ACCG CCGCCGCCGCCG    SEQ ID:20604
H2AV                  |||| || |||| ||||||||||||
BINDING SITE       3' AGCG CG TGGC GGCGGCGGCGGC    SEQ ID:683934
                           T        -    T

CCAC--        C
                   5' CCG     CGCCG CGCCGCCG       3'        SEQ ID:20604
HNRPA0                |||     ||||| ||||||||
BINDING SITE       3' GGC     GCGGC GCGGCGGC       5'        SEQ ID:689726
                      TCCAAA        A

A            G
                   5' CCGCC CCGCCGCCGCC CC         3'        SEQ ID:20604
HRIHFB2122            ||||| ||||||||||| ||
BINDING SITE       3' GGCGG GGCGGCGGCGG GG         5'        SEQ ID:691356
                            C              -
```

Fig. 26D/71

```
                        CACC    C
                    5'  GCCGC     GC GCCGCCGCCG  3'           SEQ ID:20604
HS6ST1                  |||||     || ||||||||||
BINDING SITE        3'  CGGCG     CG CGGCGGCGGC  5'           SEQ ID:691939
                             ----  C

AC       C--
                    5'  TCGCCGCC  CGCCGC     GCCG  3'          SEQ ID:20604
HSPC195                 ||||||||  ||||||     ||||
BINDING SITE        3'  GGCGGCGG  GCGCGC     CGGC  5'          SEQ ID:696302
                               CA       CTC

C
                    5'  GCCGCCACCGCCGCCG CGCCG    CG           SEQ ID:20604
HSPC195                 ||||||||||||||| |||||    ||
BINDING SITE        3'  CGGCGGTGGCGGCGGC GCGGC    GC           SEQ ID:696329
                                          A

A        -
                    5'  GCCGCC  CCGCCGC  CGCC  3'              SEQ ID:20604
HSPC195                 ||||||  |||||||  ||||
BINDING SITE        3'  CGGCGG  GGCGGCG  GCGG  5'              SEQ ID:696330
                                C        C

ACC
                    5'  GCCGCC      GCCGCCGCCGCCG  3'          SEQ ID:20604
HSPC195                 ||||||      |||||||||||||
BINDING SITE        3'  CGGCGG      CGGCGGCGGCGGC  5'          SEQ ID:696332
                              AGA

ACC   C
                    5'  GCCGCC      GC GCCGCCG  3'             SEQ ID:20604
HSPC195                 ||||||      || |||||||
BINDING SITE        3'  CGGCGG      CG CGGCGGC  5'             SEQ ID:696333
                              AGA   A

CC  C  CG
                    5'  TCGCCG   AC GC   CCGCCGCCG  3'         SEQ ID:20604
HUMAGCGB                ||||||   || ||   |||||||||
BINDING SITE        3'  AGCGGC   TG CG   GGCGGCGGC  5'         SEQ ID:698714
                              --    A  AG

-    CACC
                    5'  TCG CCGC      GCCGCCGCCG  3            SEQ ID:20604
ILF3                    ||| ||||      ||||||||||
BINDING SITE        3'  AGC GGCG      CGGCGGCGGC  5            SEQ ID:701811
                             T    T---

-   CA--
                    5'  GC CGC      CCGCCGCCGCCG  3            SEQ ID:20604
ITPK1                   || |||      ||||||||||||
BINDING SITE        3'  CG GCG      GGCGGCGGCGGC  5            SEQ ID:704065
                            C   TCAG
```

Fig. 26D/72

```
                         C   A       G
                  5' GC GCC CCGCC CCGCCGCCG 3'        SEQ ID:20604
KCNT1                || ||| ||||| |||||||||
BINDING SITE      3' CG CGG GGCGG GGTGGCGGC 5'        SEQ ID:707411
                         A   G

C    CGC
                  5' GCCG CAC    CGCCGCCG 3'          SEQ ID:20604
KIAA0082             |||| |||    ||||||||
BINDING SITE      3' CGGC GTG    GCGGCGGCG 5'         SEQ ID:710416
                         T   ACA

ACC      CC
                  5' TCGCCGCC    GCCG  GCCGCCG 3'     SEQ ID:20604
KIAA0082             ||||||||    ||||  |||||||
BINDING SITE      3' AGCGGCGG    CGGT  CGGCGGC 5'     SEQ ID:710439
                         CGA      CT

A       -  -
                  5' TCGCCGCC CCGCCGC CG CCGCCG       SEQ ID:20604
KIAA0084             |||||||| ||||||| || ||||||
BINDING SITE      3' GGCGGCGG GGCGGCG GC GGCGGC       SEQ ID:710507
                                     C   C  A

C   A
                  5' CGC GCC CCGCCGCCGCCGCCG 3'       SEQ ID:20604
KIAA0084             ||| ||| |||||||||||||||
BINDING SITE      3' GCG CGG GGCGGCGGCGGCGGC 5'       SEQ ID:710522
                         -    G

AC        C
                  5' TCGCCGCC  CGCCGC GCCGCCG 3'      SEQ ID:20604
KIAA0191             ||||||||  |||||| |||||||
BINDING SITE      3' GGCGGCGG  GCGGCG CGGCGGC 5'      SEQ ID:715434
                                CA    A

AC         C
                  5' CCGCC  CGCCGC GCCGCCG 3'         SEQ ID:20604
KIAA0191             |||||  |||||| |||||||
BINDING SITE      3' GGCGG  GCGGCG CGGCGGC 5'         SEQ ID:715436
                              CA    A

A  -   C
                  5' CCGCC CC GC GCCGCCGCCG 3'        SEQ ID:20604
KIAA0191             ||||| || || ||||||||||
BINDING SITE      3' GGCGG GG CG CGGCGGCGGC 5'        SEQ ID:715438
                           A  A  A

CA       CGCC-
                  5' CCGC CCGCCGC      GCCG 3'        SEQ ID:20604
KIAA0191             |||| |||||||      ||||
BINDING SITE      3' GGCG GGCGGCG      CGGC 5'        SEQ ID:715439
                        AC       ACCTC
```

Fig. 26D/73

```
                      A    C      C
          5' GCCGCC CCG CGCCGC GCCG 3'        SEQ ID:20604
KIAA0191     ||||||  |||  ||||||| ||||
BINDING SITE 3' CGGCGG GGC GCGGCG CGGC 5'     SEQ ID:715444
                      C    A      A

C  A      C
          5' GC GCC CCGCCG CGCCGC 3'          SEQ ID:20604
KIAA0191     ||  |||  ||||||  ||||||
BINDING SITE 3' CG CGG GGCGGC GCGGCG 5'       SEQ ID:715447
                   A  C      A

A        GC
          5' CCGCC CCGCCGCCGCC  C  3'         SEQ ID:20604
KIAA0227     |||||  |||||||||||  |
BINDING SITE 3' GGCGG GGCGGCGGCGG  G  5'      SEQ ID:717573
                   C           A

A    GC  C-
          5' TCGCCGCC CCGCC  CG  CGCCG  3     SEQ ID:20604
KIAA0227     ||||||||  |||||   ||  |||||
BINDING SITE 3' GGCGGCGG GGCGG  GC  GCGGC  5  SEQ ID:717578
                        C    A-  CT

CG       -
          5' GC  CCA -CCGCCGCCGCCGCCG  3'     SEQ ID:20604
KIAA0227     ||   |||  |||||||||||||||
BINDING SITE 3' CG  GGT  GGCGGCGGCGGCGGC  5'  SEQ ID:717615
                A-       C

C
          5' GCCGCCAC GCCGCCGCCGCCG  3'       SEQ ID:20604
KIAA0252     ||||||||  |||||||||||||
BINDING SITE 3' TGGCGGTG CGGCGGCGGCGGC  5'    SEQ ID:718931
                         A

C  A       CG
          5' TCGC GCC CCGCCGCCGCCGC    3      SEQ ID:20604
KIAA0252     ||||  |||  ||||||||||||||
BINDING SITE 3' GGTG CGG GGCGGCGGCGGCG    5   SEQ ID:718993
                     A  C        AC

A       C  -
          5' CGCCGCC CCGCCGC GC CG  3'        SEQ ID:20604
KIAA0252     |||||||  ||||||| ||  ||
BINDING SITE 3' GCGGCGG GGCGGCG CG GC  5'     SEQ ID:719014
                    C        A A

G       CCG      CC
          5' TC CCGCCA    CCGCCGCCG   3'      SEQ ID:20604
KIAA0336     ||  ||||||   |||||||||
BINDING SITE 3' AG GGCGGT    GGCGGCGGC   5'   SEQ ID:724234
                 A        CG-
```

Fig. 26D/74

```
                              G  - A-
                     5' TC CCG CC  CCGCCGCCGCCGCCG          SEQ ID:20604
KIAA0397                || ||| ||  |||||||||||||||
BINDING SITE         3' AG GGC GG  GGCGGCGGCGGCGGC          SEQ ID:726863
                            -  C  GC

C       GCC-       CCG
                     5' TCGC GCCACCGCC      GCCG       3    SEQ ID:20604
KIAA0406                |||| ||||||||       ||||
BINDING SITE         3' GGCG CGGTGGCGG      CGGC       5    SEQ ID:726937
                        A            ATAC

CG AC
                     5' GC  CC  CGCCGCCGCCG  3'             SEQ ID:20604
KIAA0441                ||  ||  |||||||||||
BINDING SITE         3' CG  GG  GCGGCGGCGGC  5'             SEQ ID:730328
                        A-  AC

A   -
                     5' TCGCCGCC CC GCCGCCGCCGCCG  3        SEQ ID:20604
KIAA0475                |||||||| || |||||||||||||
BINDING SITE         3' AGTGGCGG GG CGGCGGCGGCGGC  5        SEQ ID:734620
                                 G  T

C
                     5' TCGCCGCCACCGC GCCG  3'              SEQ ID:20604
KIAA0633                |||||||||||| ||||
BINDING SITE         3' GGCGGCGGTGGCG CGGC  5'              SEQ ID:744516
                                      A

ACC           G
                     5' CGCCGCC    GCCGCCGCC CCG  3'        SEQ ID:20604
KIAA0649                |||||||    ||||||||| |||
BINDING SITE         3' GCGGCGG    CGGCGGCGG GGC  5'        SEQ ID:745411
                                CGA           -

G  CA-        C
                     5' TC CCGC   CCGCCGC GCCGCCG           SEQ ID:20604
KIAA0649                || ||||   ||||||| |||||||
BINDING SITE         3' AG GGCG   GGCGGCG CGGCGGC           SEQ ID:745444
                           G   CGC        A

C         C     CCG
                     5' TCGC GCCACCGC GCCGCCG      3'       SEQ ID:20604
KIAA0700                |||| |||||||| |||||||
BINDING SITE         3' GGCG CGGTGGCG CGGTGGC      5'       SEQ ID:747790
                             A        A

C  CACC  C  C
                     5' GC GC    GC GC GCCGCCG  3'          SEQ ID:20604
KIAA0844                || ||    || || |||||||
BINDING SITE         3' CG CG    CG CG CGGCGGC  5'          SEQ ID:754642
                        A  A---  A  T
```

Fig. 26D/75

```
                            CCA       C
                    5' GCCG    CCGC GCCGCCGCCG 3'        SEQ ID:20604
KIAA0960               ||||    |||| ||||||||||
BINDING SITE        3' CGGC    GGCG CGGCGGCGGC 5'        SEQ ID:760740
                            ACC       A

C  CA          -    CG
                    5' TCGC GC CCGCCGC CGC  CCG          SEQ ID:20604
KIAA0963               |||| || ||||||| |||  |||
BINDING SITE        3' AGCG CG GGCGGCG GTG  GGC          SEQ ID:761105
                          T  AC        A    AA

G   CCA-
                    5' TC CCG     CCGCCGCCGCCG  3        SEQ ID:20604
KIAA0979               || |||     ||||||||||||
BINDING SITE        3' AG GGC     GGCGGCGGCGGC  5        SEQ ID:762065
                          A   CCTA

AC
                    5' TCGCCGCC  CGCCGCCGCCGCCG 3'       SEQ ID:20604
FUBP3                  ||||||||  ||||||||||||||
BINDING SITE        3' GGCGGCGG  GCGGCGGCGGCGGC 5'       SEQ ID:763022
                                 CA

AC
                    5' TCGCCGCC  CGCCGCCGCCGCCG 3'       SEQ ID:20604
KIAA0995               ||||||||  ||||||||||||||
BINDING SITE        3' GGCGGCGG  GCGGCGGCGGCGGC 5'       SEQ ID:763022
                                 CA

CCA
                    5' TCGCCG    CCGCCGCCGCCGCCG 3'      SEQ ID:20604
KIAA0995               ||||||    |||||||||||||||
BINDING SITE        3' GGCGGC    GGCGGCGGCGGCGGC 5'      SEQ ID:763026
                             AGC

C    A     C
                    5' TCG CGCC CCGCCG CGCCGCCG 3'       SEQ ID:20604
KIAA0995               ||| |||| |||||| ||||||||
BINDING SITE        3' GGC GCGG GGCGGC GCGGCGGC 5'       SEQ ID:763030
                          C    C      A

C    A
                    5' TCG CGCC CCGCCGCCGCCGCCG 3        SEQ ID:20604
KIAA0995               ||| |||| ||||||||||||||
BINDING SITE        3' GGC GCGG GGCGGCGGCGGCGGC 5        SEQ ID:763031
                          A    C

A  C
                    5' CGCCGCC CCG CGCCGCCGCCG  C        SEQ ID:20604
KIAA0995               ||||||| ||| |||||||||||  |
BINDING SITE        3' GCGGCGG GGC GCGGCGGCGGC  G        SEQ ID:763039
                             C  A
```

Fig. 26D/76

```
                          C                    G
              5' TCGC  GCCACCGCCGCCGCC            SEQ ID:20604
KIAA1016         ||||  |||||||||||||||
BINDING SITE  3' GGCG  CGGTGGCGGCGGTGGTGG         SEQ ID:764057
                    A                 GC

C    CACC
              5' TCGC GC        GCCGCCGCCGCC  3'  SEQ ID:20604
KIAA1061         |||| ||        ||||||||||||
BINDING SITE  3' GGCG CG        CGGTGGCGGCGGC 5'  SEQ ID:768364
                     A  ACA-

-    AC
              5' TCGCC GCC   CGCCGCCGCCGCCG    3  SEQ ID:20604
KIAA1079         ||||| |||   ||||||||||||||
BINDING SITE  3' GGCGG CGG   GCGGCGGCGGCGGC    5  SEQ ID:769234
                       G     AC

G    A      CG
              5' TC CCGCC CCGCCGC   CCG       3'  SEQ ID:20604
KIAA1091         || ||||| |||||||   |||
BINDING SITE  3' AG GGCGG GGCGGCG   GGC       5'  SEQ ID:769882
                  -       C         AT

C   A
              5' CGC GCC CCGCCGCCGCCGC         3' SEQ ID:20604
KIAA1140         ||| ||| ||||||||||||||
BINDING SITE  3' GCG CGG GGCGGCGGCGGCG         5' SEQ ID:771839
                      A   C

C  CA
              5' GC GC   CCGCCGCCGCCGCCG       3' SEQ ID:20604
KIAA1140         || ||   |||||||||||||||
BINDING SITE  3' CG CG   GGCGGCGGCGGCGGC       5' SEQ ID:771842
                   - AC

G  A--         C
              5' TCGCC CC   CCGCCG CGCCGCCG       SEQ ID:20604
KIAA1194         ||||| ||   |||||| ||||||||
BINDING SITE  3' AGCGG GG   GGCGGC GCGGCGGC       SEQ ID:776042
                      A  CGC        A

CAC
              5' CGCCGC    CGCCGCCGCCGCCG      3' SEQ ID:20604
KIAA1233         ||||||    |||||||||||||||
BINDING SITE  3' GCGGCG    GCGGCGGCGGCGGC      5' SEQ ID:779098
                           TCA

A       C  C
              5' CGCCGCC CCGCCGC GC GC         3' SEQ ID:20604
KIAA1332         ||||||| ||||||| || ||
BINDING SITE  3' GCGGCGG GGCGGCG CG CG         5' SEQ ID:785691
                         C       T  A
```

Fig. 26D/77

```
                         A          G
              5' TCGCCGCC CCGCCGCC CCGCCG 3'       SEQ ID:20604
KIAA1458         |||||||| |||||||| ||||||
BINDING SITE  3' GGCGGCGG GGCGGCGG GGCGGC 5'       SEQ ID:791465
                         C          A

-  A
              5' CCG CC CCGCCGCCGCCGCCG 3'         SEQ ID:20604
KIAA1458         ||| || |||||||||||||||
BINDING SITE  3' GGC GG GGCGGCGGCGGCGGC 5'         SEQ ID:791473
                   C  -

CG-  A  G
              5' GC   CC CC CCGCCGCCGCCG 3'        SEQ ID:20604
KIAA1483         ||   || || ||||||||||||
BINDING SITE  3' CG   GG GG GGCGGCGGCGGC 5'        SEQ ID:792995
                    ACA  A  -

C  CACC   C   C   C
              5' TCGC GC   GC  GC  GC GCCG    C    SEQ ID:20604
KIAA1483         |||| ||   ||  ||  || ||||    |
BINDING SITE  3' AGCG CG   CG  CG  CG CGGC    G    SEQ ID:793014
                    A  ACGA   A   A   A

A    GCC
              5' TCGCCGCC CC    GCCGCCGCCG 3'      SEQ ID:20604
KIAA1542         |||||||| ||    ||||||||||
BINDING SITE  3' GGCGGCGG GG    CGGCGGCGGC 5'      SEQ ID:795954
                         C    AGA

CAC        -
              5' CGC   CGC CGCCGCCGC 3'            SEQ ID:20604
KIAA1542         |||   ||| |||||||||
BINDING SITE  3' GCG   GCG GCGGCGGCG 5'            SEQ ID:795958
                    CTC        A

ACC    C   -   -
              5' TCGCCGCC  GC  GC  CG CCG 3'       SEQ ID:20604
KIAA1542         ||||||||  ||  ||  || |||
BINDING SITE  3' AGCGGCGG  CG  CG  GC GGC 5'       SEQ ID:795963
                    ---    A   T   T

A          G
              5' TCGCCGCC CCGCCGCC CCG 3'          SEQ ID:20604
KIAA1608         |||||||| |||||||| |||
BINDING SITE  3' AGCGGCGG GGCGGCGG GGT 5'          SEQ ID:799200
                         C          A

CG   AC
              5' TCGC  CC CCGCCGCCGCCG 3'         SEQ ID:20604
KIAA1608         ||||  || ||||||||||||
BINDING SITE  3' AGCG  GG GCGGCGGCGGCGG 5'        SEQ ID:799201
                    A-   GA
```

Fig. 26D/78

```
                              AC
                      5' TCGCCGCC  CGCCGCCGCCG   3'         SEQ ID:20604
KIAA1766                 ||||||||  |||||||||||
BINDING SITE          3' AGCGGCGG  GCGGCGGCGGC   5'         SEQ ID:808833
                              GA

G       A
                      5' TC CCGCC CCGCCGCCGCCG   C          SEQ ID:20604
KIAA1893                 || |||||  ||||||||||||  |
BINDING SITE          3' AG GGCGG GGCGGCGGCGGC   G          SEQ ID:816521
                          -    C

CA
                      5' TCGCCGC  CCGCCGCCGCCG   3'         SEQ ID:20604
KIAA1966                 |||||||  ||||||||||||
BINDING SITE          3' GGCGGCG  GGTGGCGGCGGC   5'         SEQ ID:822274
                              AC

C
                      5' TCGC GCCACCGCCGCCGC   3'           SEQ ID:20604
KIAA1966                 |||| ||||||||||||||
BINDING SITE          3' GGCG CGGTGGCGGCGGCG   5'           SEQ ID:822277
                            A

G
                      5' TCGCCGCCACCGCC CCGC   3'           SEQ ID:20604
KIAA1981                 ||||||||||||| ||||
BINDING SITE          3' AGTGGCGGTGGCGG GGCG   5'           SEQ ID:823610
                                   G

A        G
                      5' CGCC CCGCCGCCGCC CC   3'           SEQ ID:20604
LANCL2                   |||| ||||||||||| ||
BINDING SITE          3' GCGG GGCGGCGGCGG GG   5'           SEQ ID:828560
                          -              A

CCA       G
                      5' TCGCCG  CCGCC CCGCCGCCG   3'       SEQ ID:20604
LANO                     ||||||  ||||| |||||||||
BINDING SITE          3' AGCGGC  GGCGG GGCGGCGGC   5'       SEQ ID:828789
                             AGC     G

AC  C   C   C
                      5' TCGCCGCC  CG CG CGC GC   3'        SEQ ID:20604
LAP1B                    ||||||||  || || ||| ||
BINDING SITE          3' GGCGGCGG  GC GC GCG CG   5'        SEQ ID:828926
                              AC  A   A   A

-    CG
                      5' TCGCCG CCAC  CCGCCGCCGCC  3        SEQ ID:20604
LSM4                     |||||| ||||  ||||||||||||
BINDING SITE          3' AGCGGC GGTG  GGCGGCGGCGGC 5        SEQ ID:834693
                              C    AA
```

Fig. 26D/79

```
                    5' TCGCCGCCACCGCCGCCG    3'              SEQ ID:20604
MAP2K7                 ||||||||||||||||||
BINDING SITE        3' GGCGGCGGTGGCGGCGGC    5'              SEQ ID:838581

C   G
                    5' GCCGCCACCGC GCC CCG   3'              SEQ ID:20604
MAPK8IP3               |||||||||||  |||  |||
BINDING SITE        3' CGGCGGTGGCG CGG GGC   5'              SEQ ID:839431
                             A   -

CA    C      ---
                    5' TCGCCGC  CCGC GCC    GCCGCCG          SEQ ID:20604
MESDC1                 |||||||  |||| |||    |||||||
BINDING SITE        3' GGCGGCG  GGCG CGG    CGGCGGC          SEQ ID:842805
                          AC    C      TGA

CGCCAC
                    5' GC        CGCCGCCGCCGCCG  3'          SEQ ID:20604
MESDC1                 ||        ||||||||||||||
BINDING SITE        3' CG        GCGGCGGCGGCGGC  5'          SEQ ID:842838
                          ACCAA-

A
                    5' TCGCCGCC CCGCCGCCGCCGCCG   C          SEQ ID:20604
OATPRP4                |||||||| ||||||||||||||||  |
BINDING SITE        3' GGCGGCGG GGCGGCGGCGGCGGC   G          SEQ ID:844404
                                C

A
                    5' TCGCCGCC CCGCCGCCGCCGCCG   C          SEQ ID:20604
SLC21A11               |||||||| ||||||||||||||||  |
BINDING SITE        3' GGCGGCGG GGCGGCGGCGGCGGC   G          SEQ ID:844404
                                C

G    C
                    5' TC CCGC ACCGCCGCCGCCGCCG   C          SEQ ID:20604
MGC10702               || |||| ||||||||||||||||   |
BINDING SITE        3' GG GGCG TGGCGGCGGCGGCGGC   G          SEQ ID:844408
                          A    A

ACC  C  C
                    5' TCGCCGCC   GC GC GCCG   3'            SEQ ID:20604
MGC13159               ||||||||   || || ||||
BINDING SITE        3' AGCGGCGG   CG CG CGGC   5'            SEQ ID:851324
                              CCT  A  A

.    G    CA
                    5' TC CCGC   CCGCCGCCGCCGCCG   C         SEQ ID:20604
MGC14425               || ||||   ||||||||||||||||  |
BINDING SITE        3' AG GGCG   GGCGGCGGCGGCGGC   G         SEQ ID:852921
                             -   AC
```

Fig. 26D/80

```
                      AC       C
              5' TCGCCGCC  CGCCGC GCC    3'           SEQ ID:20604
MGC15396         |||||||| |||||| |||
BINDING SITE  3' GGCGGCGG  GCGGCG CGG    5'           SEQ ID:853827
                      CA       C

C    A        C
              5' TCG CGCC CCGCCG CGCCG    3'          SEQ ID:20604
MGC15396         ||| |||| |||||| |||||
BINDING SITE  3' AGT GCGG GGCGGC GCGGC    5'          SEQ ID:853851
                      C   C        A

ACC
              5' CGCCGCC    GCCGCCGCCGCCG    3'       SEQ ID:20604
MGC17347         ||||||| |||||||||||||
BINDING SITE  3' GCGGCGG    CGGCGGCGGTGGC    5'       SEQ ID:858358
                         CGA

A     C
              5' GCCGCC CCGC GCCGCC    3'             SEQ ID:20604
MGC17347         |||||| |||| ||||||
BINDING SITE  3' CGGCGG GGCG CGGCGG    5'             SEQ ID:858360
                      C     A

G              C  CG
              5' TC CCGCCACCGCCGCCGC GC         3    SEQ ID:20604
MGC1842          || |||||||||||||||| ||
BINDING SITE  3' AG GGCGGTGGCGGCGGCG CG         5    SEQ ID:858800
                   A                A  C

G   AC  CC  C
              5' TC CCGCC  CG  GC GCCGCCG   3'       SEQ ID:20604
MGC22679         || |||||  ||  || |||||||
BINDING SITE  3' AG GGCGG  GC  CG CGGCGGC   5'       SEQ ID:861565
                       -   CA  --  T

ACC
              5' TCGCCGCC    GCCGCCG    3'           SEQ ID:20604
MGC2594          ||||||||    |||||||
BINDING SITE  3' AGCGGCGG    CGGCGGC    5'           SEQ ID:864289
                         AGC

5' TCGCCGCCACCGCCGCCGCCG    3'          SEQ ID:20604
MGC26684         |||||||||||||||||||||
BINDING SITE  3' GGCGGCGGTGGCGGTGGCGGC    5'          SEQ ID:865556

C   A      GC   C
              5' TCGC GCC CCGCC CGC GC    3'          SEQ ID:20604
MGC3222          |||| ||| ||||| ||| ||
BINDING SITE  3' AGCG CGG GGCGG GCG CG    5'          SEQ ID:870434
                      A   C     A-   -
```

Fig. 26D/81

```
                              A       GCC
                     5' TCGCCGCC CCGCCGCC  GC  3'         SEQ ID:20604
MGC4170                 |||||||| ||||||||  ||
BINDING SITE         3' GGCGGCGG GGCGGCGG  CG  5'         SEQ ID:872011
                              C       AGT

CA-  -
                     5' CCGC    CC GCCGCCGCCGCCG  3'      SEQ ID:20604
MGC4172                 ||||    || |||||||||||||
BINDING SITE         3' GGCG    GG CGGCGGCGGCGGC  5'      SEQ ID:872115
                        AGA  A

C        CG   CC
                     5' TCGC GCCACCGC  CCG  GCCG  3'      SEQ ID:20604
MGC4172                 |||| ||||||||  |||  ||||
BINDING SITE         3' AGCG CGGTGGCG  GGT  CGGC  5'      SEQ ID:872142
                                       A-   A-

C          C
                     5' TCGCCG CACCGCCGC GCCG  3'         SEQ ID:20604
MGC5466                 |||||| ||||||||| ||||
BINDING SITE         3' GGCGGC GTGGTGGCG CGGC  5'         SEQ ID:877031
                              A         A

A--      C
                     5' TCGCCGCC    CCGC GCCGCCGCCG       SEQ ID:20604
MIP-T3                  ||||||||    |||| ||||||||||
BINDING SITE         3' GGCGGCGG    GGCG CGGCGGCGGC       SEQ ID:879055
                                    CCG  -

CACC        C
                     5' GCCGC     GCCGCCGC GCCG  3'       SEQ ID:20604
MIR                     |||||     |||||||| ||||
BINDING SITE         3' CGGCG     CGGCGGTG CGGC  5'       SEQ ID:879086
                           A---            T

C   A
                     5' GC GCC CCGCCGCCGCCGCCG  3'        SEQ ID:20604
MOV34-34KD              || ||| |||||||||||||||
BINDING SITE         3' CG CGG GGCGGCGGCGGCGGC  5'        SEQ ID:881891
                           T   C

C   CA
                     5' GC GC   CCGCCGCCGCCGCCG  3'       SEQ ID:20604
MOV34-34KD              || ||   |||||||||||||||
BINDING SITE         3' CG CG   GGCGGCGGCGGCGGC  5'       SEQ ID:881892
                          A   TC

CC   CACC
                     5' TCG  GC        GCCGCCGCCGCCG  3'  SEQ ID:20604
MOV34-34KD              |||  ||        |||||||||||||
BINDING SITE         3' AGC  CG        CGGCGGCGGCGGC  5'  SEQ ID:881894
                          AT   ACGT
```

Fig. 26D/82

```
                              C  CA---
                         5' TCGC GC      CCGCCGCCGCCGCCG         SEQ ID:20604
MPZL1                       |||| ||      |||||||||||||||
BINDING SITE             3' GGTG CG      GGCGGCGGCGGCGGC         SEQ ID:882046
                            A   TCAGC

A            CG
                         5' CCGCC CCGCCGCCGC  CC   3'            SEQ ID:20604
MPZL1                       ||||| ||||||||||  ||
BINDING SITE             3' GGCGG GGCGGCGGCG  GG   5'            SEQ ID:882049
                                 C            CA

A        C  C
                         5' TCGCCGCC CCGCCGC GC GC    3'         SEQ ID:20604
NCOR1                       |||||||| ||||||| || ||
BINDING SITE             3' GGCGGCGG GGCGGCG CG CG    5'         SEQ ID:889437
                                     C        C  A

CG   -
                         5' TCGC   CCA  CCGCCGCCGCCGCCG          SEQ ID:20604
NCOR1                       ||||   |||  ||||||||||||||
BINDING SITE             3' AGTG   GGT  GGCGGCGGCGGCGGC          SEQ ID:889452
                                A-     C

5' TCGCCGCCACCGCCGCCGCCGC    3'         SEQ ID:20604
NFAT5                       |||||||||||||||||||||||
BINDING SITE             3' AGCGGCGGTGGCGGCGGCGGCG    5'         SEQ ID:892135

AC    C
                         5' CGCC  CGC  GCCGCCGCC    3'           SEQ ID:20604
NIR1                        ||||  |||  |||||||||
BINDING SITE             3' GCGG  GCG  CGGCGGTGG    5'           SEQ ID:893156
                                A-    A

C
                         5' GCCGCCACCGC GCCGCCGCCG    3'         SEQ ID:20604
NIR1                        |||||||||||| |||||||||
BINDING SITE             3' CGGCGGTGGCG CGGCGGCGGC    5'         SEQ ID:893162
                                        T

5' TCGCCGCCACCGCCGCCG    3'             SEQ ID:20604
NKX2B                       |||||||||||||||||||
BINDING SITE             3' AGCGGCGGTGGCGGCGGC    5'             SEQ ID:893635

CAC    C
                         5' TCGCCGC   CGC  GCCGCCGCCG    3'      SEQ ID:20604
NS1-BP                      |||||||   |||  |||||||||||
BINDING SITE             3' AGTGGTG   GCG  CGGCGGCGGC    5'      SEQ ID:896538
                                  CAC    A
```

Fig. 26D/83

```
                            C    AC    C           CG
                    5' TCG CGCC  CGC GCCGCCGC    3'              SEQ ID:20604
NTN4                    ||| ||||  ||| ||||||||
BINDING SITE        3' AGC GCGG  GCG CGGCGGCG    5'              SEQ ID:896979
                            C    --    T           A

A        C   -
                    5' CGCCGCC CCGC GC CGCCG     3'               SEQ ID:20604
OAZ1                    ||||||| |||| || |||||
BINDING SITE        3' GCGGCGG GGCG CG GCGGC     5'               SEQ ID:899518
                               C     A A

G    CACC
                    5' TC CCGC      GCCGCCGCCGC  3'              SEQ ID:20604
OAZ1                    || ||||     |||||||||||
BINDING SITE        3' AG GGCG      CGGCGGCGGCG  5'              SEQ ID:899526
                        A          ----

C
                    5' GCCG CACCGCCGCCGCCGCCG      C             SEQ ID:20604
OAZ2                   |||| ||||||||||||||||||      |
BINDING SITE        3' CGGC GTGGCGGCGGCGGCGG      G             SEQ ID:899599
                            A

A
                    5' TCGCCGCC CCGCCGCCGCCGCCG  3'             SEQ ID:20604
OAZ2                   |||||||| |||||||||||||||
BINDING SITE        3' AGTGGCGG GGCGGCGGCGGCGGC  5'             SEQ ID:899619
                                C

C   A  G
                    5' CGC GCC CC CCGCCGCCGC     3'              SEQ ID:20604
OSBPL1A                ||| ||| || ||||||||||
BINDING SITE        3' GCG CGG GG GGCGGCGGCG     5'              SEQ ID:902150
                                A   -  A

CC-
                    5' TCGCCGCCACCGCCG       GC   3'             SEQ ID:20604
PARG1                  ||||||||||||||||      ||
BINDING SITE        3' GGCGGCGGTGGCGGC       CG   5'             SEQ ID:907038
                                             TCC

CA
                    5' CCGC    CCGCCGCCGCCGC    3'               SEQ ID:20604
PCAF                   ||||    |||||||||||||
BINDING SITE        3' GGCG    GGCGGCGGCGGTG    5'               SEQ ID:908148
                               AC

CAC
                    5' GC    CGCCGCCGCCGCCG     3'               SEQ ID:20604
PCCX2                  ||    |||||||||||||||
BINDING SITE        3' CG    GCGGCGGCGGCGGC     5'               SEQ ID:908515
                       CC-
```

Fig. 26D/84

```
                        A     C
              5' CGCCGCC CCG CGCCGCCG 3'            SEQ ID:20604
PELI2            ||||||| ||| ||||||||
BINDING SITE  3' GCGGCGG GGC GCGGCGGC 5'            SEQ ID:912193
                         C   T

AC
              5' GCCGCC    CGCCGCCGCCG 3'           SEQ ID:20604
PELI2            ||||||    |||||||||||
BINDING SITE  3' CGGCGG    GCGGCGGCGGC 5'           SEQ ID:912206
                           CT

AC-
              5' CCGCC    CGCCGCCGCCGCCG 3'         SEQ ID:20604
PF1              |||||    ||||||||||||||
BINDING SITE  3' GGCGG    GCGGCGGCGGCGGC 5'         SEQ ID:912812
                          AGA

G    A      GCC-
              5' TC CCGCC CCGCC    GCCGCCG          SEQ ID:20604
PLCL2            || ||||| |||||    |||||||
BINDING SITE  3' AG GGCGG GGCGG    CGGCGGC          SEQ ID:917013
                      G    C      AGCC

A       CC
              5' CCGCC CCGCCG  GCCGCCG 3'           SEQ ID:20604
PM5              |||||  ||||||  |||||||
BINDING SITE  3' GGCGG  GGCGGT  CGGCGGC 5'          SEQ ID:917719
                        C       CT

CA---
              5' CCGC      CCGCCGCCGCCGCCG 3'       SEQ ID:20604
PMX2B            ||||      ||||||||||||||
BINDING SITE  3' GGCG      GGCGGCGGCGGCGGC 5'       SEQ ID:918145
                    ACAGC

-  CAC
              5' TCGCC GC   CGCCGCCGCCGCCG          SEQ ID:20604
PMX2B            ||||| ||   ||||||||||||||
BINDING SITE  3' AGCGG CG   GCGGCGGCGGCGGC          SEQ ID:918187
                      G ACA

A
              5' TCGCCGCC CCGCCGCCGCCGC 3'          SEQ ID:20604
PMX2B            |||||||| ||||||||||||||
BINDING SITE  3' AGCGGCGG GGCGGCGGCGGCG 5'          SEQ ID:918189
                          C

A-   CC  C--    C
              5' GCCGCC CCG GC  GCCG CG 3           SEQ ID:20604
PRDM8            ||||||  |||  ||  ||||  ||
BINDING SITE  3' CGGCGG GGC  CG  CGGC GC 5          SEQ ID:924600
                         CG  AC  CTA  A
```

Fig. 26D/85

```
                        CA           CC
              5' CGCCGC  CCGCCGCCG  GC  3'         SEQ ID:20604
PSIP2            ||||||  |||||||||  ||
BINDING SITE  3' GCGGCG  GGCGGCGGC  CG  5'         SEQ ID:933689
                        AC           AT

-----    A      C
              5' TCGC      CGCC  CCGC  GCCGCCGCC   SEQ ID:20604
PSIP2            ||||      ||||  ||||  |||||||||
BINDING SITE  3' AGCG      GCGG  GGCG  CGGCGGCGG   SEQ ID:933709
                   TTGGC    C     A

A      C
              5' CCGCC CCGC GCCGCCGCCG 3'          SEQ ID:20604
PTR4             ||||| |||| ||||||||||
BINDING SITE  3' GGCGG GGCG CGGCGGCGGC 5'          SEQ ID:937407
                       C    C

-     A
              5' TCGCC GCC CCGCCGCCGCCGCCG  3      SEQ ID:20604
QKI              ||||| |||  ||||||||||||||
BINDING SITE  3' GGCGG CGG GGCGGCGGCGGCGGC  5      SEQ ID:938140
                       G   C

A       GCC
              5' CGCCGCC CCGCC    GCCG  3'         SEQ ID:20604
QKI              ||||||| |||||    ||||
BINDING SITE  3' GCGGCGG GGCGG    CGGC  5'         SEQ ID:938170
                        C       ACA

ACC       C
              5' CGCC    GCCGC GCCGCCG  3'         SEQ ID:20604
QKI              ||||    ||||| |||||||
BINDING SITE  3' GCGG    CGGCG CGGCGGC  5'         SEQ ID:938172
                   AGA       A

CA         C  CG
              5' GCCGC  CCGCCGC GC  CCG  3'        SEQ ID:20604
QKI              |||||  ||||||| ||  |||
BINDING SITE  3' CGGCG  GGCGGCG CG  GGC  5'        SEQ ID:938196
                    AC         -  A-

CACC    C   C----
              5' TCGCCGC    GC GC    GCCGCCG       SEQ ID:20604
RAB2             |||||||    || ||    |||||||
BINDING SITE  3' GGCGGCG    CG CG    CGGCGGC       SEQ ID:939662
                    A---    A  A  ACAGT

AC
              5' CGCCGCC  CGCCGCCGCCGC  3'         SEQ ID:20604
RAB2             |||||||  ||||||||||||
BINDING SITE  3' GCGGCGG  GCGGCGGCGGCG  5'         SEQ ID:939672
                           --
```

Fig. 26D/86

```
                        AC
              5' CGCCGCC   CGCCGCCGCCGC  3'         SEQ ID:20604
RAB2             |||||||   ||||||||||||
BINDING SITE  3' GCGGCGG   GCGGCGGCGGCG  5'         SEQ ID:939672
                        --

CCACC
              5' CCG        GCCGCCGCCGCCG  3'       SEQ ID:20604
RAB22A           |||        |||||||||||||
BINDING SITE  3' GGC        CGGCGGCGGCGGC  5'       SEQ ID:939920
                     CCT--

CACC              -
              5' CGCCGC     GCCGCCGC  CG  3'        SEQ ID:20604
RAB22A           ||||||     ||||||||  ||
BINDING SITE  3' GCGGCG     CGGCGGCG  GC  5'        SEQ ID:939925
                   A---              T

-     CCA
              5' TCG CCG    CCGCCGCCGCCGCCG  3      SEQ ID:20604
RAB5EP           ||| |||    |||||||||||||||
BINDING SITE  3' AGT GGC    GGCGGCGGCGGCGGC  5      SEQ ID:941423
                   T   TC-

C    AC
              5' TCG CGCC  CGCCGCCGC  3'            SEQ ID:20604
RALY             ||| ||||  |||||||||
BINDING SITE  3' AGC GCGG  GCGGCGGCG  5'            SEQ ID:943042
                     A    CA

C    AC        CG
              5' TCG CGCC  CGCCGCCGC  CCG  3        SEQ ID:20604
RALY             ||| ||||  |||||||||  |||
BINDING SITE  3' AGC GCGG  GCGGCGGCG  GGC  5        SEQ ID:943043
                     A    CA        AT

C  CCAC    C
              5' TCG CG    CGCCG CGCCGCCG  3        SEQ ID:20604
RALY             ||| ||    ||||| ||||||||
BINDING SITE  3' AGC GC    GCGGC GCGGCGGC  5        SEQ ID:943044
                     A  AGCA    A

GCC
              5' CC    ACCGCCGCCGCCG  3'            SEQ ID:20604
RC3              ||    ||||||||||||||
BINDING SITE  3' GG    TGGCGGCGGCGGC  5'            SEQ ID:945022
                       AGC

C  CACC
              5' GC GC      GCCGCCGCCGCCG  3'       SEQ ID:20604
RNPC2            || ||      |||||||||||||
BINDING SITE  3' CG CG      CGGCGGCGGCGGC  5'       SEQ ID:950359
                     A  ACGA
```

Fig. 26D/87

```
                        C  CACC      C
                   5' GC GC       GC GCCGCCGCCG  3'      SEQ ID:20604
RNPC2                 || ||       || ||||||||||
BINDING SITE       3' CG CG       CG CGGCGGCGGC  5'      SEQ ID:950360
                      A  ACGA     A

ACC
                   5' TCGCCGCC     GCCGCCGCCG  3'        SEQ ID:20604
RPS6KC1               ||||||||     ||||||||||
BINDING SITE       3' GGCGGCGG     CGGCGGCGGC  5'        SEQ ID:952575
                            AGA

---   A    C---
                   5' TCGCC   GCC  CCGC    GCCGCCGC      SEQ ID:20604
SERP1                 |||||   |||  ||||    ||||||||
BINDING SITE       3' GGCGG   CGG  GGCG    CGGCGGCG      SEQ ID:963975
                         CAG    C     AAAC

AC
                   5' CGCCGCC   CGCCGCCGC  3'            SEQ ID:20604
SERP1                 |||||||   |||||||||
BINDING SITE       3' GCGGCGG   GCGGCGGCG  5'            SEQ ID:963978
                             CA

GC    CA        C
                   5' TC  CGC   CCGCCG CGCCGCCG  3'      SEQ ID:20604
SERP1                 ||  |||   |||||| ||||||||
BINDING SITE       3' AG  GCG   GGCGGC GCGGCGGC  5'      SEQ ID:964015
                         A-    C-       A

CA-       --
                   5' TCGCCGC   CCGC   CGCCGCCGCCG       SEQ ID:20604
SFRS9                 |||||||   ||||   |||||||||||
BINDING SITE       3' GGCGGCG   GGTG   GCGGCGGCGGC       SEQ ID:964985
                          TCG       CA

CAC              - C
                   5' CCGC    CGCCGCCG C GCC  3'         SEQ ID:20604
SH2D3C                ||||    |||||||| | |||
BINDING SITE       3' GGCG    GCGGCGGC G TGG  5'         SEQ ID:965802
                         ACA              C T

C-  CACC      C
                   5' TCGC  GC      GC GCCGCCGCCG        SEQ ID:20604
SHANK3                ||||  ||      || ||||||||||
BINDING SITE       3' AGCG  CG      CG CGGCGGCGGC        SEQ ID:966276
                        CC  CTT-    A

- C          C
                   5' GCCG C ACCGCCGC GC  3'             SEQ ID:20604
SHARP                 |||| | |||||||| ||
BINDING SITE       3' CGGC G TGGCGGCG CG  5'             SEQ ID:966487
                         C C          A
```

Fig. 26D/88

```
                        A-    C  C
              5' TCGCCGCC  CCGC GC GC   3'          SEQ ID:20604
SIAT8A           ||||||||  |||| || ||
BINDING SITE  3' AGCGGCGG  GGCG CG CG   5'          SEQ ID:966899
                        AG    -  A

AC        -
              5' CCGCC   CGCC GCCGCCGC  3'          SEQ ID:20604
SLC16A3          |||||   |||| ||||||||
BINDING SITE  3' GGCGG   GTGG CGGCGGCG  5'          SEQ ID:968639
                   A-        A

G     A
              5' TC CCGCC CCGCCGCCGCCG      C       SEQ ID:20604
SLC21A11         || ||||| |||||||||||||     |
BINDING SITE  3' GG GGCGG GGCGGCGGCGGCGGC   G       SEQ ID:969275
                    G     C

A                )
              5' TCGCCGCC CCGCCGCCGCCGC  3'         SEQ ID:20604
OATPRP4          |||||||| |||||||||||||
BINDING SITE  3' GGCGGCGG GGCGGCGGCGGCG  5'         SEQ ID:969284
                         C

A
              5' TCGCCGCC CCGCCGCCGCCGC  3'         SEQ ID:20604
SLC21A11         |||||||| |||||||||||||
BINDING SITE  3' GGCGGCGG GGCGGCGGCGGCG  5'         SEQ ID:969284
                         C

A          C
              5' TCGCCGCC CCGCCGCCGC GCCG  3'       SEQ ID:20604
SLC21A11         |||||||| |||||||||| ||||
BINDING SITE  3' GGCGGCGG GGCGGCGGCG CGGC  5'       SEQ ID:969288
                         C          A

A   C    CG-
              5' CCGCC CCGC GCCGC    CC  3'         SEQ ID:20604
SLC21A11         ||||| |||| |||||    ||
BINDING SITE  3' GGCGG GGCG CGGCG    GG  5'         SEQ ID:969292
                   C   A    AAA

A            )
              5' TCGCCGCC CCGCCGCCG  3'             SEQ ID:20604
SLC21A11         |||||||| |||||||||
BINDING SITE  3' AGCGGCGG GGCGGCGGC  5'             SEQ ID:969328
                          C

CA    CC
              5' TCGCCGC CCG GCCGCCG  3'            SEQ ID:20604
SLC21A11         ||||||| ||| |||||||
BINDING SITE  3' AGCGGCG GGC CGGCGGC  5'            SEQ ID:969329
                       A-    --
```

Fig. 26D/89

```
                            CA      C
                    5' CGC  CCGC GCCGCCGC   3'           SEQ ID:20604
SRF                    |||  |||| ||||||||
BINDING SITE        3' GCG  GGCG CGGCGGCG   5'           SEQ ID:979150
                            AC      C

--   A--
                    5' CGCC   GCC     CCGCCGCCGCCGCCG    SEQ ID:20604
SSBP3                  ||||   |||     |||||||||||||||
BINDING SITE        3' GCGG   CGG     GGCGGCGGCGGCGGC    SEQ ID:980403
                           CT    AGC

A              CG
                    5' CGCCGCC CCGCCGCCGC   CCG   3'     SEQ ID:20604
SSBP3                  ||||||| ||||||||||   |||
BINDING SITE        3' GCGGCGG GGCGGCGGCG   GGC   5'     SEQ ID:980404
                              C              AT

A             CCG
                    5' TCGCCGCC CCGCCGCCGCCG       C     SEQ ID:20604
SSBP3                  |||||||| ||||||||||||       |
BINDING SITE        3' AGCGGCGG GGCGGCGGCGGC       G     SEQ ID:980415
                              C             GC

CG   C
                    5' GC   CCAC GCCGCCGCCGCCG   3'      SEQ ID:20604
SSBP4                  ||   |||| ||||||||||||
BINDING SITE        3' CG   GGTG CGGCGGCGGCGGC   5'      SEQ ID:980450
                           A-   -

A          C
                    5' CGCC  CCGCCGCCGC GC   3'          SEQ ID:20604
STIM2                  ||||  |||||||||| ||
BINDING SITE        3' GCGG  GGCGGCGGCG CG   5'          SEQ ID:982983
                             C          C

-   A
                    5' TCGCC GCC CCGCCGCCGCCGCCG         SEQ ID:20604
STK39                  ||||| ||| |||||||||||||||
BINDING SITE        3' GGCGG CGG GGCGGCGGCGGCGGC         SEQ ID:983798
                            G   C

A       - G
                    5' TCGCCGCC CCGCCG CC CCGCCG  3      SEQ ID:20604
STK39                  |||||||| |||||| || ||||||
BINDING SITE        3' GGCGGCGG GGCGGC GG GGCGGC  5      SEQ ID:983808
                              C       A -

A          G
                    5' CGCCGCC CCGCCGCCG CC CCG   3'     SEQ ID:20604
KIAA0995               ||||||| ||||||||| || |||
BINDING SITE        3' GCGGCGG GGCGGCGGC GG GGC   5'     SEQ ID:983814
                             C          A -
```

Fig. 26D/90

```
                          A      -  G
              5' CGCCGCC CCGCCGCCG CC CCG   3'        SEQ ID:20604
STK39            ||||||  |||||||||  ||  |||
BINDING SITE  3' GCGGCGG GGCGGCGGC GG GGC   5'        SEQ ID:983814
                          C         A  -

G    CA           CC
              5' TC CCGC  CCGCCGCCGCCG      3'        SEQ ID:20604
STRBP            || ||||  ||||||||||||
BINDING SITE  3' AG GGCG  GGCGGCGGCGGC      5'        SEQ ID:984349
                   -    A-

AC      C
              5' TCGCCGCC   CGCCG CGCCGCCG  3'        SEQ ID:20604
SULT4A1          ||||||||   |||||  ||||||||
BINDING SITE  3' GGCGGCGG   GCGGC GCGGCGGC  5'        SEQ ID:985480
                         CA      A

CCA      C
              5' TCGCCG    CCG CGCCGCCGCCG  3'        SEQ ID:20604
SULT4A1          ||||||    |||  ||||||||||||
BINDING SITE  3' GGCGGC    GGC GCGGCGGCGGC  5'        SEQ ID:985482
                       AGC    A

A    C     C
              5' GCCGCC CCG CGCCG CGCCG     3'        SEQ ID:20604
SULT4A1          ||||||  |||  |||||  |||||
BINDING SITE  3' CGGCGG GGC GCGGC GCGGC     5'        SEQ ID:985499
                         C    A     A

CCAC
              5' TCGCCG       CGCCGCCGCCGCC 3'        SEQ ID:20604
SULT4A1          ||||||       ||||||||||||||
BINDING SITE  3' AGCGGC       GCGGCGGCGGCGG 5'        SEQ ID:985516
                          A---

A
              5' TCGCCGCC CCGCCGCCG         3'        SEQ ID:20604
TBLR1            ||||||||  ||||||||
BINDING SITE  3' AGCGGCGG GGCGGTGGC         5'        SEQ ID:989703
                            C

A    C  -  C
              5' TCGCCGCC CCGC GC CG CGCCG  3        SEQ ID:20604
TIEG             ||||||||  ||||  ||  ||  |||||
BINDING SITE  3' GGCGGCGG GGCG CG GT GCGGC  5        SEQ ID:993412
                          C    -  A  C

CA
              5' CGCCGC  CCGCCGCCGCCG       3'        SEQ ID:20604
TIEG             ||||||  ||||||||||||
BINDING SITE  3' GCGGCG  GGCGGCGGCGGC       5'        SEQ ID:993414
                   AG
```

Fig. 26D/91

```
                              C   ACC
                         5' TCGC GCC    GCCGCCGCCGCCG 3'         SEQ ID:20604
FLJ20288                    |||| |||    |||||||||||||
BINDING SITE             3' GGCG CGG    CGGCGGCGGCGGC 5'         SEQ ID:993970
                              A   CGA

C   ACC
                         5' TCGC GCC    GCCGCCGCCGCCG 3'         SEQ ID:20604
TIP120A                     |||| |||    |||||||||||||
BINDING SITE             3' GGCG CGG    CGGCGGCGGCGGC 5'         SEQ ID:993970
                              A   CGA

-  CA   C
                         5' GCC GC  CCGC GCCGCCGCCG 3'            SEQ ID:20604
TIP120A                     ||| ||  |||| ||||||||||
BINDING SITE             3' CGG CG  GGCG CGGCGGCGGC 5'            SEQ ID:993979
                              G  AC   A

A
                         5' GCCGCC CCGCCGCCGCCGC 3'               SEQ ID:20604
TIP120A                     |||||| |||||||||||||
BINDING SITE             3' CGGCGG GGCGGCGGCGGTG 5'               SEQ ID:993980
                                   C

CA
                         5' GC  CCGCCGCCGCCGCCG 3'                SEQ ID:20604
TLK2                        ||  |||||||||||||||
BINDING SITE             3' CG  GGCGGCGGCGGCGGC 5'                SEQ ID:994634
                              AC

GC   C  -
                         5' TC CGC AC CGCCGCCGCCGCCG               SEQ ID:20604
TPARL                       || ||| || ||||||||||||||
BINDING SITE             3' AG GTG TG GCGGCGGCGGCGGC               SEQ ID:997782
                              GA   C  A

A           C--
                         5' CCGCC CCGCCGCCGC    GCCG 3'           SEQ ID:20604
TRIM28                      ||||| ||||||||||    ||||
BINDING SITE             3' GGCGG GGCGGCGGCG    CGGC 5'           SEQ ID:1000325
                                C           CTC

CA
                         5' GCCGC    CCGCCGCCGCCGCCG    C         SEQ ID:20604
TRIM28                      |||||    |||||||||||||||    |
BINDING SITE             3' CGGCG    GGCGGCGGCGGCGGC    G         SEQ ID:1000339
                              AC

CC------          C
                         5' TCGCCGCCA        GCCGC GCCGC          SEQ ID:20604
TRIM28                      |||||||||        ||||| |||||
BINDING SITE             3' AGCGGCGGT        CGGCG CGGCG          SEQ ID:1000350
                                TGACGACC       A
```

Fig. 26D/92

```
                           AC--
              5' TCGCCGCC    CGCCGCCGCCGCCG        SEQ ID:20604
TRIM33           ||||||||    ||||||||||||||
BINDING SITE  3' GGCGGCGG    GCGGCGGCGGCGGC        SEQ ID:1000528
                           GGCA

A          G
              5' TCGCCGCC CCGCCGCC CCG        3'   SEQ ID:20604
TRIM33           |||||||| |||||||| |||
BINDING SITE  3' AGCGGCGG GGCGGCGG GGT        5'   SEQ ID:1000533
                         C          G

CA
              5' GC   CCGCCGCCGCCGCCG         3'   SEQ ID:20604
TRIP10           ||   |||||||||||||||
BINDING SITE  3' CG   GGCGGCGGCGGCGGC         5'   SEQ ID:1001537
                 AG

CA
              5' GC   CCGCCGCCGCCGCCG         3'   SEQ ID:20604
ZDHHC3           ||   |||||||||||||||
BINDING SITE  3' CG   GGCGGCGGCGGCGGC         5'   SEQ ID:1001537
                 AG

G   ACC         C
              5' CGCC CC   GCCGCCGC GC         3'  SEQ ID:20604
WBSCR21          |||| ||   |||||||| ||
BINDING SITE  3' GCGG GG   CGGCGGCG CG         5'  SEQ ID:1012104
                     G   AGC         A

C    A  ---       C  CG
              5' TCG CGCC CC    GCCGCCGC GC        SEQ ID:20604
WBSCR21          ||| |||| ||    |||||||| ||
BINDING SITE  3' AGC GCGG GG    CGGCGGCG CG        SEQ ID:1012156
                     C    G  AGC       A  ACG

AC    CCGC
              5' CCGCC CG     CGCCGCCG       3'    SEQ ID:20604
ZDHHC5           ||||| ||     ||||||||
BINDING SITE  3' GGCGG GC     GTGGCGGC       5'    SEQ ID:1016404
                    CA    AACA

CCGC         G-
              5' TCG    CACCGCCGCC  CCG      3'    SEQ ID:20604
ZDHHC5           |||    ||||||||||  |||
BINDING SITE  3' AGC    GTGGCGGCGG  GGC      5'    SEQ ID:1016478
                        AACA         AG

CA         C
              5' CGCCGC CCGCCGC GCCGCCG       3'   SEQ ID:20604
ZER6             |||||| ||||||| |||||||
BINDING SITE  3' GCGGCG GGCGGCG CGGTGGC       5'   SEQ ID:1016788
                        AC       A
```

Fig. 26D/93

```
                             ACC       C
                    5' TCGCCGCC  GCCGCCGC  GCC  3'        SEQ ID:20604
ZER6                   ||||||||  ||||||||  |||
BINDING SITE        3' AGCGGCGG  CGGCGGCG  CGG  5'        SEQ ID:1016846
                             CGA       A

C   ACCGC--
                    5' GC GCC           CGCCGCCGCCG  3'   SEQ ID:20604
ZF                     || |||           |||||||||||
BINDING SITE        3' CG CGG           GCGGCGGCGGC  5'   SEQ ID:1016945
                           C·  CCCTCTA

CGCCAC
                    5' GC           CGCCGCCGCCGCC  3'     SEQ ID:20604
ZNF364                 ||           |||||||||||||
BINDING SITE        3' CG           GCGGCGGCGGCGG  5'     SEQ ID:1023294
                             TCAGCA

C   A           GC
                    5' TCG CGCC CCGCCGCCGCC  CG   3       SEQ ID:20604
ZNF364                 ||| |||| |||||||||||  ||
BINDING SITE        3' AGC GCGG GGCGGCGGCGG  GC   5       SEQ ID:1023303
                          A   C           A-

C         C
                    5' GCCGCCAC GCCGCCG CGCCG  3'         SEQ ID:20604
ZTL1                   |||||||| ||||||| |||||
BINDING SITE        3' CGGCGGTG CGGCGGC GCGGC  5'         SEQ ID:1023979
                              A         A

C         C
                    5' GCCGCCAC GCCGCCG CGCCG  3'         SEQ ID:20604
ZTL1                   |||||||| ||||||| |||||
BINDING SITE        3' CGGCGGTG CGGCGGC GCGGC  5'         SEQ ID:1023979
                              A         A

A     C
                    5' CCGCC CCGC GCCGCCG  3'             SEQ ID:20604
CTCF                   ||||| |||| |||||||
BINDING SITE        3' GGCGG GGCG CGGCGGT  5'             SEQ ID:1037665
                             C     A

A
                    5' CCGCC CCGCCGCCGCCGCC  C   3        SEQ ID:20604
ERIHFB2122             ||||| |||||||||||||||  |
BINDING SITE        3' GGCGG GGCGGCGGCGGCGGC  G   5       SEQ ID:1065873
                                             C

A
                    5' CCGCC CCGCCGCCGCCGCC  C   3        SEQ ID:20604
KIAA0397               ||||| |||||||||||||||  |
BINDING SITE        3' GGCGG GGCGGCGGCGGCGGC  G   5       SEQ ID:1065873
                                             C
```

Fig. 26D/94

```
                           A     C
                  5' TCGCCGCC CCGCCG CGCCGCCG 3'          SEQ ID:20604
FUBP3                ||||||||  ||||||  ||||||||
BINDING SITE      3' AGCGGCGG GGCGGC GCGGCGGC 5'          SEQ ID:1190283
                           C      T

-  AC
                  5' GCCG CC  CGCCGCCGCCGCCG 3'           SEQ ID:20604
H2AV                 |||| ||  ||||||||||||||
BINDING SITE      3' CGGC GG  GCGGCGGCGGCGGC 5'           SEQ ID:1303366
                        T  GC

A
                  5' CGCC CCGCCGCCGCCGCC 3'               SEQ ID:20604
FLJ20539             |||| |||||||||||||||
BINDING SITE      3' GCGG GGCGGCGGCGGCGG 5'               SEQ ID:1310953
                        C

A
                  5' CGCC CCGCCGCCGCCGCC 3'               SEQ ID:20604
KIAA1893             |||| |||||||||||||||
BINDING SITE      3' GCGG GGCGGCGGCGGCGG 5'               SEQ ID:1310953
                        C

A
                  5' CGCC CCGCCGCCGCCGCC 3'               SEQ ID:20604
RINZF                |||| |||||||||||||||
BINDING SITE      3' GCGG GGCGGCGGCGGCGG 5'               SEQ ID:1310953
                        C

CA
                  5' GCCGC  CCGCCGCCGCCGCCG 3'            SEQ ID:20604
TIP120A              |||||  |||||||||||||||
BINDING SITE      3' CGGCG  GGCGGCGGCGGCGGC 5'            SEQ ID:1323750
                        AC

A
                  5' TCGCCGCC CCGCCGCCGCCGCCG 3'          SEQ ID:20604
LOC146223            ||||||||  |||||||||||||||
BINDING SITE      3' GGCGGCGG GGCGGCGGCGGCGGC 5'          SEQ ID:94853
                               C

A
                  5' TCGCCGCC CCGCCGCCGCCGCCG 3'          SEQ ID:20604
LOC255426            ||||||||  |||||||||||||||
BINDING SITE      3' GGCGGCGG GGCGGCGGCGGCGGC 5'          SEQ ID:94853
                               C

A
                  5' TCGCCGCC CCGCCGCCGCCGCCG 3'          SEQ ID:20604
LOC255426            ||||||||  |||||||||||||||
BINDING SITE      3' GGCGGCGG GGCGGCGGCGGCGGC 5'          SEQ ID:94853
                               C
```

Fig. 26D/95

```
                         A
                5' TCGCCGCC CCGCCGCCGCCGCCG 3'        SEQ ID:20604
LOC255426          ||||||||  |||||||||||||||
BINDING SITE    3' GGCGGCGG GGCGGCGGCGGCGGC 5'        SEQ ID:94853
                         C

A
                5' TCGCCGCC CCGCCGCCGCCGCCG 3'        SEQ ID:20604
LOC255426          ||||||||  |||||||||||||||
BINDING SITE    3' GGCGGCGG GGCGGCGGCGGCGGC 5'        SEQ ID:94853
                         C

A
                5' TCGCCGCC CCGCCGCCGCCGCCG 3'        SEQ ID:20604
LOC255426          ||||||||  |||||||||||||||
BINDING SITE    3' GGCGGCGG GGCGGCGGCGGCGGC 5'        SEQ ID:94853
                         C

A
                5' TCGCCGCC CCGCCGCCGCCGCCG 3'        SEQ ID:20604
LOC255426          ||||||||  |||||||||||||||
BINDING SITE    3' GGCGGCGG GGCGGCGGCGGCGGC 5'        SEQ ID:94853
                         C

C  A
                5' GC GCC CCGCCGCCGCCGCCG 3'          SEQ ID:20604
LOC122525          ||  |||  |||||||||||||||
BINDING SITE    3' CG CGG GGCGGCGGCGGCGGC 5'          SEQ ID:173934
                    A   C

A
                5' GCCGCC CCGCCGCCGCCGCCG 3'         SEQ ID:20604
LOC122525          ||||||  |||||||||||||||
BINDING SITE    3' CGGCGG GGCGGCGGCGGCGGC 5'         SEQ ID:241978
                         C

GCCA
                5' CC   CCGCCGCCGCCGCC 3'            SEQ ID:20604
LOC146057          ||   ||||||||||||||
BINDING SITE    3' GG   GGCGGCGGCGGCGG 5'            SEQ ID:264106
                   AC--

A
                5' CGCCGCC CCGCCGCCGCCGCCG    C      SEQ ID:20604
LOC203197          |||||||  ||||||||||||||    |
BINDING SITE    3' GCGGCGG GGCGGCGGCGGCGGC    G      SEQ ID:317209
                         C

A
                5' TCGCCGCC CCGCCGCCGCCGCCG    C     SEQ ID:20604
LOC146223          ||||||||  |||||||||||||||   |
BINDING SITE    3' AGCGGCGG GGCGGCGGCGGCGGC    G     SEQ ID:412156
                         C
```

Fig. 26D/96

```
                         C   A
              5' TCGC GCC  CCGCCGCCGCCGCCG    3'      SEQ ID:20604
LOC256905        ||||  |||  ||||||||||||||| 
BINDING SITE  3' GGCG CGG  GGCGGCGGCGGCGGC    5'      SEQ ID:432644
                         A   C

G  A        ---
              5' TCGCC CC CCGCC      GCCGCCGCCG       SEQ ID:20604
LOC158301        |||||  || |||||      ||||||||||
BINDING SITE  3' GGCGG GG GGCGG      CGGCGGCGGC       SEQ ID:670361
                   G  C         CAG

A     C
              5' TCGCCGCC CCGCCG CGCCG     3'         SEQ ID:20604
LOC158301        ||||||||  ||||||  |||||
BINDING SITE  3' AGCGGCGG GGCGGC GCGGC     5'         SEQ ID:670394
                              C      T

C   A--      C
              5' TCGC GCC    CCGC GCCGCCGCCG          SEQ ID:20604
LOC254573        ||||  |||    ||||  ||||||||||
BINDING SITE  3' GGCG CGG    GGCG CGGCGGCGGC          SEQ ID:683857
                      A   CTG       -

AC
              5' TCGCCGCC   CGCCGCCGCCGCCG   3'       SEQ ID:20604
LOC158301        ||||||||   |||||||||||||||
BINDING SITE  3' GGCGGCGG   GCGGCGGCGGCGGC   5'       SEQ ID:763022
                          CA

5' TCGCCGCCACCGCCGCCGCCG        3'      SEQ ID:20604
LOC57795         ||||||||||||||||||||||
BINDING SITE  3' GGCGGCGGTGGCGGTGGCGGC        5'      SEQ ID:865556

A
              5' TCGCCGCC  CCGCCGCCGCCGC     3'       SEQ ID:20604
LOC122525        ||||||||   |||||||||||||
BINDING SITE  3' GGCGGCGG  GGCGGCGGCGGCG     5'       SEQ ID:969284
                           C

C-   CA
              5' CGC  GC   CCGCCGCCGCCGCCG    3'      SEQ ID:20604
LOC112609        |||   ||   |||||||||||||||
BINDING SITE  3' GCG  CG   GGCGGCGGCGGCGGC    5'      SEQ ID:1024445
                 CT   C-

A         C
              5' TCGCCGCC CCGCCGC GCCGCG     3'       SEQ ID:20604
LOC121536        ||||||||  |||||||  |||||||
BINDING SITE  3' GGCGGCGG GGTGGCG CGGCGGC    5'       SEQ ID:1036323
                          G       A
```

Fig. 26D/97

```
                         CC    AC  C
                     5' TCG   GCC  CG CGCCGCCGC 3'        SEQ ID:20604
LOC121536               |||   |||  || |||||||||
BINDING SITE         3' GGC   CGG  GC GCGGCGGCG 5'        SEQ ID:1036334
                         AT    GA  A

CA      G
                     5' GC   CCGCC CCGCCGCCG 3'           SEQ ID:20604
LOC121536               ||   ||||| |||||||||
BINDING SITE         3' CG   GGCGG GGCGGCGGC 5'           SEQ ID:1036375
                           AC      G

CA    C
                     5' TCGCCGC   CCG CGCCGCCGCCG 3'      SEQ ID:20604
LOC122525               |||||||   ||| |||||||||||
BINDING SITE         3' GGCGGCG   GGC GCGGCGGCGGC 5'      SEQ ID:1036926
                              TG    A

A        CG -
                     5' CGCCGCC CCGCCGC  C CG 3'          SEQ ID:20604
LOC124944               ||||||| |||||||  | ||
BINDING SITE         3' GCGGCGG GGCGGCG  G GC 5'          SEQ ID:1041522
                            C        AT T

A        CG-
                     5' CCGCC CCGCCGC   CCGCCG 3'         SEQ ID:20604
LOC125228               ||||| |||||||   ||||||
BINDING SITE         3' GGCGG GGCGGCG   GGCGGC 5'         SEQ ID:1042173
                           C        AAG

CACC
                     5' CGC     GCCGCCGCCGCCG 3'          SEQ ID:20604
LOC125228               |||     |||||||||||||
BINDING SITE         3' GCG     CGGCGGCGGCGGC 5'          SEQ ID:1042179
                          ACCT

ACC  C
                     5' TCGCCGCC  GC GCCGCCG 3'           SEQ ID:20604
LOC126432               ||||||||  || |||||||
BINDING SITE         3' AGCGGCGG  CG CGGCGGC 5'           SEQ ID:1044359
                            ---  T

A     GCC  C
                     5' CGCCGCC CCGCC  GC GCCG 3'         SEQ ID:20604
LOC126917               ||||||| |||||  || ||||
BINDING SITE         3' GCGGCGG GGCGG  CG CGGC 5'         SEQ ID:1045771
                            C     GCA  -

A    C    C
                     5' CCGCC CCGC GCCGC GCCG 3'          SEQ ID:20604
LOC130367               ||||| |||| ||||| ||||
BINDING SITE         3' GGCGG GGCG CGGTG CGGC 5'          SEQ ID:1051475
                           C    A     -
```

Fig. 26D/98

```
                              A
                     5' CCGCC CCGCCGCCGCCG    C  3       SEQ ID:20604
LOC143243               ||||| ||||||||||||    |
BINDING SITE         3' GGCGG GGCGGCGGCGGC    G  5       SEQ ID:1065873
                              C

CACC     C
                     5' GCCGC     GC GCCGCCGCCG  3'      SEQ ID:20604
LOC143891               |||||     || ||||||||||
BINDING SITE         3' CGGCG     CG CGGCGGCGGC  5'      SEQ ID:1068561
                              CGA-   A

C   A          --
                     5' TCGC GCC CCGCCGCC GCCGCCG        SEQ ID:20604
LOC145173               |||| ||| |||||||| |||||||
BINDING SITE         3' GGCG CGG GGCGGCGG CGGCGGC        SEQ ID:1077948
                          A   C          GA

CA          --
                     5' CGCCGC  CCGCCGCCGCC  GCCG  3     SEQ ID:20604
LOC145173               ||||||  |||||||||||  ||||
BINDING SITE         3' GCGGCG  GGCGGCGGCGG  CGGC  5     SEQ ID:1077952
                              AC          GA

-    C         C
                     5' CC GCCAC GCCGCCGC GCC  3'        SEQ ID:20604
LOC145581               || ||||| |||||||| |||
BINDING SITE         3' GG CGGTG CGGCGGCG CGG  5'        SEQ ID:1081817
                              A        A    A

5' TCGCCGCCACCGCCGCCGCCGCCG   C     SEQ ID:20604
LOC145990               |||||||||||||||||||||||||  |
BINDING SITE         3' GGTGGCGGTGGCGGCGGCGGCGGC   G     SEQ ID:1089127

A         G
                     5' CCGCC CCGCCGCCGCC CCG  3'        SEQ ID:20604
LOC145990               ||||| ||||||||||| |||
BINDING SITE         3' GGCGG GGCGGCGGCGG GGC  5'        SEQ ID:1089148
                              C         A

GCC
                     5' GCCGCCACCGCCGCC    GCCG  3'      SEQ ID:20604
LOC145990               |||||||||||||||    ||||
BINDING SITE         3' CGGCGGTGGCGGCGG    CGGC  5'      SEQ ID:1089170
                                   AGA

G    A     G
                     5' TC CCGCC CCGCC CCGCCG  3'        SEQ ID:20604
LOC145990               || ||||| ||||| ||||||
BINDING SITE         3' AG GGCGG GGCGG GGCGGC  5'        SEQ ID:1089181
                          G    C     G
```

Fig. 26D/99

```
                          G  A   -
                      5'  CC CC CC GCCGCCGCCGCCG   3'         SEQ ID:20604
LOC146057                 || || ||  ||||||||||||
BINDING SITE          3'  GG GG GG CGGCGGCGGCGGC   5'         SEQ ID:1089542
                          G  A  A

-  G         CG   C
                      5'  TCG CC CCACCGC   CCG CGCCG          SEQ ID:20604
LOC146057                 ||| || |||||||   ||| |||||
BINDING SITE          3'  AGC GG GGTGGCG   GGT GCGGC          SEQ ID:1089568
                          A   -        AG    A   GA

CAC
                      5'  TCGCCGC   CGCCGCCGCCGCCG   3'       SEQ ID:20604
LOC146223                 |||||||   ||||||||||||||
BINDING SITE          3'  GGCGGCG   GCGGCGGCGGCGGC   5'       SEQ ID:1090768
                                 TA-

GCCA    C--
                      5'  TCGCC    CCG   CGCCGCCG    3'       SEQ ID:20604
LOC147057                 |||||    |||   ||||||||
BINDING SITE          3'  AGCGG    GGC   GCGGCGG     5'       SEQ ID:1102464
                             AAG-    CCA

GCCAC    C
                      5'  GCC     CGC  GCCGCCGCC    3'        SEQ ID:20604
LOC147409                 |||     |||  |||||||||
BINDING SITE          3'  CGG     GCG  CGGCGGCGGC   5'        SEQ ID:1105742
                             ATTTT    A

C  CA
                      5'  TCGC GC   CCGCCGCCGCCGCCG   3       SEQ ID:20604
LOC147808                 |||| ||   |||||||||||||||
BINDING SITE          3'  GGCG CG   GGCGGCGGCGGCGGC   5       SEQ ID:1108755
                               A   CG

CG     C-
                      5'  TCGCCGCCACCGC  CCGC  GC    3'       SEQ ID:20604
LOC150984                 |||||||||||||  ||||  ||
BINDING SITE          3'  GGCGGCGGTGGCG  GGCG  CG    5'       SEQ ID:1144920
                                    A-     AT

-         C    C
                      5'  CC GCCAC GC GCCGCCG        3'       SEQ ID:20604
LOC151517                 || ||||| || |||||||
BINDING SITE          3'  GG CGGTG CG CGGCGGC        5'       SEQ ID:1151083
                          A        -     A

C     A      C  CG
                      5'  TCG CGCC CCGC GC   CCG     3'       SEQ ID:20604
LOC152048                 ||| |||| |||| ||   |||
BINDING SITE          3'  AGC GCGG GGCG CG   GGC     5'       SEQ ID:1155173
                              A      C      C  AG
```

Fig. 26D/100

```
                         C   A
              5' TCGC GCC CCGCCGCCGCCGCCG 3'          SEQ ID:20604
LOC154743        ||||  |||  ||||||||||||||||
BINDING SITE  3' AGCG CGG GGCGGCGGCGGCGGC  5'         SEQ ID:1174818
                         T   C

-----     A
              5' TCGCCG      CC CCGCCGCCGCCGCC        SEQ ID:20604
LOC154807        ||||||      ||  ||||||||||||||
BINDING SITE  3' GGCGGT      GG GGCGGCGGCGGCGG        SEQ ID:1175671
                    AGAAG   C

G
              5' TCGCCGCCACCGCCGCC CCG  3'            SEQ ID:20604
LOC154807        |||||||||||||||||  |||
BINDING SITE  3' GGCGGCGGTGGCGGCGG GGC  5'            SEQ ID:1175672
                                    A

A            C
              5' GCCGCC CCGCCGCCG CGCCG  3'           SEQ ID:20604
LOC158301        ||||||  ||||||||| |||||
BINDING SITE  3' TGGCGG GGCGGCGGC GCGGC  5'           SEQ ID:1190223
                       G            A

A         C
              5' TCGCCGCC CCGCCG CGCCGCCG 3'          SEQ ID:20604
LOC158301        ||||||||  ||||||  ||||||||
BINDING SITE  3' AGCGGCGG GGCGGC GCGGCGGC  5'         SEQ ID:1190283
                                C       T

--      A---
              5' GCC GCC     CCGCCGCCGCCGCCG          SEQ ID:20604
LOC158856        |||  |||    ||||||||||||||||
BINDING SITE  3' CGG CGG     GGCGGCGGCGGCGGC          SEQ ID:1195246
                     CC    AAGC

C        C   C CCG
              5' TCGC GCCACCGC GCCG CG    3'          SEQ ID:20604
LOC161635        ||||  ||||||||  ||||  ||
BINDING SITE  3' GGCG CGGTGGTG CGGC GC    5'          SEQ ID:1199731
                      A        A    A

AC        C
              5' TCGCCGCC  CGCCGCCGC GC   3'          SEQ ID:20604
LOC162417        ||||||||  ||||||||| ||
BINDING SITE  3' AGCGGCGG  GCGGCGGCG CG   5'          SEQ ID:1201175
                                     --  -

CA-  GC   C
              5' CCGC  CC  CGC GCCGCCG   3'           SEQ ID:20604
LOC162762        ||||   ||  |||  |||||||
BINDING SITE  3' GGCG  GG  GCG CGGCGGC   5'           SEQ ID:1201432
                    ACA  A-   A
```

Fig. 26D/101

```
                        C   A        G
                 5' TCGC GCC CCGCCGCC CCG 3'          SEQ ID:20604
LOC162762           |||| ||| |||||||| |||
BINDING SITE     3' AGCG CGG GGCGGTGG GGT 5'          SEQ ID:1201436
                        A   C        -

G  ACC   C
                 5' CC CC    GC GCCGCCGCC 3'          SEQ ID:20604
LOC163126           || ||    || |||||||||
BINDING SITE     3' GG GG    CG CGGCGGCGG 5'          SEQ ID:1201784
                      -  AC-  A

G   GCCA
                 5' TC CC     CCGCCGCCGCCGCCG 3'      SEQ ID:20604
LOC163126           || ||     |||||||||||||||
BINDING SITE     3' AG GG     GGCGGCGGCGGCGGC 5'      SEQ ID:1201817
                     -   ACC-

A    C     C
                 5' CGCCGCC CCGC GCCGC GCCG 3'        SEQ ID:20604
LOC165257           ||||||| |||| ||||| ||||
BINDING SITE     3' GCGGCGG GGCG CGGTG CGGC 5'        SEQ ID:1205008
                            C    A     T

C  CCACC              C
                 5' TCG CG     GCCGCCGCCG 3'          SEQ ID:20604
LOC165333           ||| ||     ||||||||||
BINDING SITE     3' AGC GC     CGGCGGCGGC 5'          SEQ ID:1205096
                     A  AT---

CA    C
                 5' GC   CCGC GCCGCCGCC 3'            SEQ ID:20604
LOC165552           ||   |||| |||||||||
BINDING SITE     3' CG   GGCG CGGCGGCGG 5'            SEQ ID:1205248
                       AC    A

A     C
                 5' CGCC CCG CGCCGCCGCC 3'            SEQ ID:20604
LOC196549           |||| ||| ||||||||||
BINDING SITE     3' GCGG GGC GCGGCGGCGG 5'            SEQ ID:1213581
                        -     C

CA         G  -
                 5' CGC  CCGCCGCC CC GC 3'            SEQ ID:20604
LOC202020           |||  |||||||| || ||
BINDING SITE     3' GCG  GGTGGCGG GG CG 5'            SEQ ID:1240261
                     AG         -  T

---    A
                 5' TCGCC   GCC CCGCCGCCGCCGCCG       SEQ ID:20604
LOC203197           |||||   ||| |||||||||||||||
BINDING SITE     3' GGCGG   CGG GGCGGCGGCGGCGGC       SEQ ID:1245216
                           GCG   C
```

Fig. 26D/102

```
                            A           G
                    5' TCGCCGCC  CCGCCGCCGCC CCG 3'        SEQ ID:20604
LOC203197              ||||||||  ||||||||||| |||
BINDING SITE        3' GGCGGCGG  GGCGGCGGTGG GGC 5'        SEQ ID:1245218
                            C                -

AC
                    5' GCCGCC  CGCCGCCGCCGCCG 3'           SEQ ID:20604
LOC203197              ||||||  ||||||||||||||
BINDING SITE        3' CGGCGG  GCGGCGGCGGCGGC 5'           SEQ ID:1245270
                            GC

CGCCACC-             CG
                    5' TCGC        GCCGCCGCC           3'  SEQ ID:20604
LOC203668              ||||        |||||||||
BINDING SITE        3' AGCG        CGGCGGCGG           5'  SEQ ID:1249923
                       CCACAACT             AC

CA    C  C
                    5' TCGCCGC  CCG CG CGCCGCCG 3'         SEQ ID:20604
LOC219333              |||||||  ||| || |||||||||
BINDING SITE        3' GGCGGCG  GGC GC GCGGCGGC 5'         SEQ ID:1253262
                         AC    A  A

CACC         C   G
                    5' CCGC     GCCGCCGC GCC    C  3      SEQ ID:20604
LOC219333              ||||     |||||||| |||    |
BINDING SITE        3' GGCG     CGGCGGCG CGG    G  5      SEQ ID:1253264
                       ACC-          A   CA-

CACC      C
                    5' GCCGC     GCCGC GCCGCCG 3'          SEQ ID:20604
LOC219654              |||||     ||||| |||||||
BINDING SITE        3' CGGCG     CGGCG CGGCGGC 5'          SEQ ID:1256056
                       A---          A

CAC              - -
                    5' CCGC     CGCCGCCGC C GCC 3'         SEQ ID:20604
LOC219899              ||||     ||||||||| | |||
BINDING SITE        3' GGCG     GCGGCGGCG G CGG 5'         SEQ ID:1258777
                       ACA              A T

G    -          CGC
                    5' TC CCG CCACCGC    CGCCGCCG 3       SEQ ID:20604
LOC219899              || ||| |||||||    ||||||||
BINDING SITE        3' AG GGC GGTGGCG    GCGGCGGC 5       SEQ ID:1258810
                       -    C             ACA

--   CA
                    5' CC GC    CCGCCGCCGCC 3'             SEQ ID:20604
LOC220058              || ||    |||||||||||
BINDING SITE        3' GG CG    GGCGGCGGCGGC 5'            SEQ ID:1261177
                       AC A-
```

Fig. 26D/103

```
                           ACC    C   C
              5' TCGCCGCC     GC GC GCCG   3'        SEQ ID:20604
LOC245726        ||||||||     || || ||||
BINDING SITE  3' AGCGGCGG     CG CG CGGC   5'        SEQ ID:1287683
                           AA-   T   -

-  A              C
              5' CC GCC  CCGCCGC GCCGCCG   3'        SEQ ID:20604
LOC253943        || |||  ||||||| |||||||
BINDING SITE  3' GG CGG  GGCGGCG CGGCGGC   5'        SEQ ID:1295954
                      T  C              A

CCA-
              5' CCG      CCGCCGCCGCCGCCG  3'        SEQ ID:20604
LOC253943        |||      |||||||||||||||
BINDING SITE  3' GGC      GGCGGCGGCGGCGGC  5'        SEQ ID:1295956
                     TCTC

A            C
              5' CGCC CCGCCGCCGC GCC   3'            SEQ ID:20604
LOC253943        |||| |||||||||| |||
BINDING SITE  3' GCGG GGCGGCGGCG CGG   5'            SEQ ID:1295963
                         C            A

ACC       C-
              5' CGCCGCC    GCCGCCG   CGC   3'       SEQ ID:20604
LOC253943        |||||||    |||||||   |||
BINDING SITE  3' GCGGCGG    CGGCGGC   GCG   5'       SEQ ID:1295964
                        CGA       AA

CACC          C---
              5' CCGC      GCCGCCG      GCC   3'     SEQ ID:20604
LOC254102        ||||      |||||||      |||
BINDING SITE  3' GGCG      CGGCGGCG     CGG   5'     SEQ ID:1298522
                      A---          ACCC

CA-    C
              5' CGC    CCGC GCCGCCGC   3'           SEQ ID:20604
LOC254102        |||    |||| ||||||||
BINDING SITE  3' GCG    GGCG CGGCGGCG   5'           SEQ ID:1298528
                     AGA    A

G    ACC          CC
              5' TC CCGCC     GCCGCCGCC    3'        SEQ ID:20604
LOC254107        || |||||     |||||||||
BINDING SITE  3' AG GGCGG     CGGCGGCGG    5'        SEQ ID:1298621
                     -         GT-

-  AC
              5' GCCG  CC  CGCCGCCGCCGCCG   3'       SEQ ID:20604
LOC254573        ||||  ||  ||||||||||||||
BINDING SITE  3' CGGC  GG  GCGGCGGCGGCGGC   5'       SEQ ID:1303366
                     T  GC
```

Fig. 26D/104

```
                          G    CACC    C           CCG
                 5' TC CCGC      GC GCCGCCG      3'         SEQ ID:20604
LOC255028           || ||||      || ||||||||
BINDING SITE     3' AG GGCG      CG CGGCGGC      5'         SEQ ID:1306373
                          G    CCCA    A

C    ACC---                 C
                 5' GC GCC         GCCGCCGCCG CG   3          SEQ ID:20604
LOC255056           || |||         |||||||||| ||
BINDING SITE     3' CG CGG         CGGCGGCGGC GC   5          SEQ ID:1307405
                          A    GCTCCC              A

A-
                 5' CGCCGCC    CCGCCGCCGCCG      3'         SEQ ID:20604
LOC255426           |||||||    ||||||||||||
BINDING SITE     3' GCGGCGG    GGCGGCGGCGGC      5'         SEQ ID:1310952
                               GC

A-
                 5' CGCCGCC    CCGCCGCCGCCG      3'         SEQ ID:20604
LOC255426           |||||||    ||||||||||||
BINDING SITE     3' GCGGCGG    GGCGGCGGCGGC      5'         SEQ ID:1310952
                               GC

A
                 5' CGCC    CCGCCGCCGCC       3'            SEQ ID:20604
LOC146223           ||||    |||||||||||
BINDING SITE     3' GCGG    GGCGGCGGCGG       5'            SEQ ID:1310953
                                C

A
                 5' CGCC    CCGCCGCCGCC       3'            SEQ ID:20604
LOC255426           ||||    |||||||||||
BINDING SITE     3' GCGG    GGCGGCGGCGG       5'            SEQ ID:1310953
                                C

AC  C     CCGCC
                 5' TCGCCGCC  CG CG        GCC   3'         SEQ ID:20604
LOC201780           ||||||||  || ||        |||
BINDING SITE     3' AGCGGCGG  GC GC        CGG   5'         SEQ ID:1317863
                            -- A     AAGA-

AC  C     CCGCC
                 5' TCGCCGCC  CG CG        GCC   3'         SEQ ID:20604
LOC256160           ||||||||  || ||        |||
BINDING SITE     3' AGCGGCGG  GC GC        CGG   5'         SEQ ID:1317863
                            -- A     AAGA-

G              C    CCG
                 5' TC CCGCCACCGCCGC GCCG        3'         SEQ ID:20604
LOC256537           || |||||||||||||| ||||
BINDING SITE     3' AG GGCGGTGGCGGCG CGGC        5'         SEQ ID:1321461
                          A              C
```

Fig. 26D/105

```
                            G  A
                      5' CC CC CCGCCGCCGCCGCCG 3'              SEQ ID:20604
LOC256586                || ||  |||||||||||||||
BINDING SITE          3' GG GG GGCGGCGGCGGCGGC 5'              SEQ ID:1321729
                            A  A

A       GC
                      5' CGCCGCC CCGCC  CGCCG 3'               SEQ ID:20604
LOC256812                |||||||  |||||  |||||
BINDING SITE          3' GCGGCGG GGCGG  GCGGC 5'               SEQ ID:1322939
                                 C       A-

A
                      5' CGCCGCC CCGCCGCCGCCGCCG 3'            SEQ ID:20604
LOC256905                |||||||  |||||||||||||||
BINDING SITE          3' GCGGCGG GGCGGCGGCGGTGGC 5'            SEQ ID:1323732
                                 C

A-  ---
                      5' GCCGCC  CC  GCCGCCGCCGCCG             SEQ ID:20604
LOC256905                ||||||  ||  |||||||||||||
BINDING SITE          3' CGGCGG  GG  CGGCGGCGGCGGC             SEQ ID:1323749
                            AC  CGA

CA
                      5' GCCGC  CCGCCGCCGCCGCCG 3'             SEQ ID:20604
LOC256905                |||||  |||||||||||||||
BINDING SITE          3' CGGCG  GGCGGCGGCGGCGGC 5'             SEQ ID:1323750
                               AC

A    C  C
                      5' GCCGCC CCGC GC GCCGC 3'               SEQ ID:20604
LOC257222                ||||||  ||||  ||  |||||
BINDING SITE          3' CGGCGG CGCG CG CGGTG 5'               SEQ ID:1326885
                              C    A  A

CA    --   C-
                      5' CCGC CCGC CGC GCCGC 3'                SEQ ID:20604
LOC257479                ||||  ||||  |||  |||||
BINDING SITE          3' GGCG GGCG GCG CGGCG 5'                SEQ ID:1330681
                            AC    AC   AC

A    C    C
                      5' CGCC CCGC GCCGC GC 3'                 SEQ ID:20604
LOC257479                ||||  ||||  |||||||  ||
BINDING SITE          3' GCGG GGCG CGGCG CG 5'                 SEQ ID:1330687
                             C    A    A

G   ACC  C       CG
                      5' TC CCGCC   GC GCCGCCGC 3'             SEQ ID:20604
LOC257479                ||  |||||| || |||||||||
BINDING SITE          3' AG GGCGG   CG CGGCGGCG 5'             SEQ ID:1330706
                             -   C-- C        A
```

Fig. 26D/106

```
                          CA              G   G
                    5' TCGCCGC  CCGCCGCC  CC  CCG  3'      SEQ ID:20604
LOC257479              |||||||  ||||||||  ||  |||
BINDING SITE        3' AGCGGCG  GGCGGCGG  GG  GGC  5'      SEQ ID:1330708
                          A-              A   A

- CACC-
                    5' TCGCCG  C         GCCGCCGCCGCCG      SEQ ID:20604
LOC51061               ||||||  |         |||||||||||||
BINDING SITE        3' AGCGGC  G         TGGCGGCGGCGGC      SEQ ID:1335336
                            C  AAATA

A
                    5' GCCGCC  CCGCCGCCGCCG   3'            SEQ ID:20604
LOC55829               ||||||  ||||||||||||
BINDING SITE        3' TGGCGG  GGCGGCGGCGGC   5'            SEQ ID:1343670
                           C

A              --
                    5' CCGCC  CCGCCGCCGCC  GCC  3'          SEQ ID:20604
LOC55829               |||||  |||||||||||  |||
BINDING SITE        3' GGCGG  GGCGGCGGCGG  CGG  5'          SEQ ID:1343683
                          C                GT

CC     A
                    5' TCG  GCC  CCGCCGCCGCCGCCG   3        SEQ ID:20604
LOC57795               |||  |||  |||||||||||||||
BINDING SITE        3' AGC  CGG  GGCGGCGGCGGTGGC   5        SEQ ID:1347000
                        CA     C

C    AC
                    5' TCG  CGCC  CGCCGCCGCCGCCG   3        SEQ ID:20604
LOC84548               |||  ||||  |||||||||||||||
BINDING SITE        3' GGC  GCGG  GCGGCGGCGGCGGC   5        SEQ ID:1349247
                         A    CA

C    AC   C
                    5' TCG  CGCC  CGCCG  CGCCGCCG   3       SEQ ID:20604
LOC84548               |||  ||||  |||||  ||||||||
BINDING SITE        3' GGC  GCGG  GCGGC  GCGGCGGC   5       SEQ ID:1349248
                         A    CA   A

CCA
                    5' TCGCCG    CCGCCGCCGCCGCCG   3'       SEQ ID:20604
LOC84548               ||||||    |||||||||||||||
BINDING SITE        3' AGCGGC    GGCGGCGGCGGCGGC   5'       SEQ ID:1349283
                            AGC

CCA   C
                    5' TCGCCG    CCG  CGCCGCCGCCG   3'      SEQ ID:20604
LOC84548               ||||||    |||  |||||||||||
BINDING SITE        3' AGCGGC    GGC  GCGGCGGCGGC   5'      SEQ ID:1349284
                            AGC   A
```

Fig. 26D/107

```
                         -- AC
                   5' CGCC  GCC   CGCCGCCGCCGCCG 3       SEQ ID:20604
LOC86010              ||||  |||   ||||||||||||||
BINDING SITE       3' GCGG  CGG   GCGGCGGCGGCGGC 5       SEQ ID:1349829
                         CT  A-

A       CG
                   5' TCGCCGCC CCGCCGC  CCG 3'           SEQ ID:20604
LOC86010              |||||||| |||||||  |||
BINDING SITE       3' AGCGGCGG GGCGGCG  GGC 5'           SEQ ID:1349832
                               C        AT

G  ACC
                   5' CC CC   GCCGCCGCCGCCG 3'           SEQ ID:20604
LOC90379              || ||   |||||||||||||
BINDING SITE       3' GG GG   CGGCGGCGGCGGC 5'           SEQ ID:1356590
                         G  CCC

-     CAC
                   5' TCG CCGC   CGCCGCCGCCGCCG          SEQ ID:20604
LOC90835              ||| ||||   ||||||||||||||
BINDING SITE       3' AGT GGCG   GCGGCGGCGGCGGC          SEQ ID:1362330
                         A  AAA              AG

A      C    -
                   5' TCGCCGCC CCGCCG CG CCGC 3'         SEQ ID:20604
LOC90835              |||||||| |||||| || ||||
BINDING SITE       3' AGCGGCGG GGCGG  GC GGTG 5'         SEQ ID:1362338
                               C      A A

A  G    C
                   5' CGCCGCC CC CCGC GCCGC 3'           SEQ ID:20604
LOC90874              ||||||| || |||| |||||
BINDING SITE       3' GCGGCGG GG GGCG CGGCG 5'           SEQ ID:1362769
                               C  G    -

CAC
                   5' CGC    CGCCGCCGCCGCC 3'            SEQ ID:20604
LOC91050              |||    ||||||||||||
BINDING SITE       3' GCG    GCGGCGGCGGCGG 5'            SEQ ID:1364688
                         CA-

A     GCC  G
                   5' TCGCCGCC CCGCC   GCC CCG 3'        SEQ ID:20604
LOC91050              |||||||| |||||   ||| |||
BINDING SITE       3' AGCGGCGG GGCGG   CGG GGC 5'        SEQ ID:1364726
                               C       GCC -

C CAC    --
                   5' TCGC GC   CGC  CGCCGCCGCCG         SEQ ID:20604
LOC91050              |||| ||   |||  ||||||||||
BINDING SITE       3' AGCG TG   GCG  GCGGCGGCGGC         SEQ ID:1364727
                         C CA-   CA
```

Fig. 26D/108

```
                       -     CAC
                  5' TCGC CGC    CGCCGCCGCCGCCG        SEQ ID:20604
LOC91300             |||| |||    ||||||||||||||
BINDING SITE     3' AGCG GCG    GCGGCGGCGGCGGC        SEQ ID:1367936
                       T     ACA

-     CAC
                  5' TCGC CGC    CGCCGCCGCCGCCG        SEQ ID:20604
LOC91300             |||| |||    ||||||||||||||
BINDING SITE     3' AGCG GCG    GCGGCGGCGGCGGC        SEQ ID:1367936
                       T     ACA

ACC  CG--      C
                  5' GCCGCC   GC    CCGC GCCG  3'     SEQ ID:20604
LOC91978             ||||||   ||    |||| ||||
BINDING SITE     3' CGGCGG   CG    GGTG CGGC  5'     SEQ ID:1375053
                          ---  AAGA     A

-     CCA
                  5' TCG CCG    CCGCCGCCGCCGCCG  3    SEQ ID:20604
LOC92181             ||| |||    ||||||||||||||
BINDING SITE     3' AGC GGC    GGCGGCGGCGGCGGC  5    SEQ ID:1376487
                       A     CCG

CACC
                  5' TCGCCGC    GCCGCCGCCG  3'        SEQ ID:20604
LOC92299             |||||||    ||||||||||
BINDING SITE     3' GGCGGCG    CGGCGGCGGT  5'        SEQ ID:1377998
                         A---
```

CTGCGGAGCCCGCGTCGCAGCAGCCCGGACAGGAAGATT  SEQ ID: 27
GGTCTGGATGTGGGTCCGGT<u>CTTACAGTCGCGGGCCAGG</u>
<u>ATGAG</u>GGCAGGTTGCGACAGCGCGCACCCGG

CTTACAGTCGCGGGCCAGGATGAG                SEQ ID: 4

```
      C  A  C  -           A-   GGA  GGAAGA              -  -   TC
   CTG GG GC CGC GTCGCAGC  GCCC      CA      TTGGTCTG GA TGTGG3  C
   ||| || || ||| ||||||||  ||||      ||      ''||||'|| || ||||||        SEQ ID: 27
   GGC CC CG GCG CAGCGTTG  CGGG      GT      GACCGGGC CT ACATTC  G
      -  A  C  A           GA   A--  AG----             G  G    TG
```

Fig. 27D/1

```
                      GC---           A
              5' GTC      GGGCCAGG TGAG   3'        SEQ ID:20605
DEC1             |||      |||||||| ||||
BINDING SITE  3' CAG      CCCGGTCC ACTC   5'        SEQ ID:131107
                   AAGGA           C

TCGC     C
              5' CAG    GGGC AGGATGAG     3'        SEQ ID:20605
HD               |||    |||| ||||||||
BINDING SITE  3' GTC    TTCG TCCTACTC     5'        SEQ ID:193353
                   CTTT    A

T  AG GC         A  AG
              5' CT AC TC GGGCCAGG TG      3        SEQ ID:20605
HPN              || || || |||||||| ||
BINDING SITE  3' GA TG GG CCCGGTCC AC      5        SEQ ID:201170
                 C  GA A-         C  CC

A             CAGGA
              5' CTT CAGTCGCGGGC      TGAG  3       SEQ ID:20605
C20orf11         ||| |||||||||||      ||||
BINDING SITE  3' GAA GTCAGCGTCCG      ACTC  5       SEQ ID:468069
                     C             ACTAG 5' CTTACAGTCGCGGGCCAGGATGAG  3'       SEQ ID:20605
FAF1             ||||||||||||||||||||||||
BINDING SITE  3' GAATGTCAGCGCCCGGTCCTACTC  5'       SEQ ID:552947

A  GT--  C   CCA  A
              5' CTT CA   CG GGG   GG TGAG          SEQ ID:20605
FLJ23878         ||| ||   || |||   || ||||
BINDING SITE  3' GAA GT   GC CCC   CC ACTC          SEQ ID:662582
                   A ACTC  A   AAC  C

-  GGGC
              5' AGTC GC     CAGGATGAG  3'          SEQ ID:20605
ODZ2             |||| ||     ||||||||
BINDING SITE  3' TCAG TG     GTCCTACTC  5'          SEQ ID:900303
                     A  AA--

TC   -
              5' AG  GC GGGCCAGGATG  3'             SEQ ID:20605
LOC144231        ||  || |||||||||||
BINDING SITE  3' TC  CG CCCGGTCCTAC  5'             SEQ ID:1069942
                   TC  A

CGC    C
              5' ACAGT    GGGC AGGATGAG  3'         SEQ ID:20605
LOC158156        |||||    |||| ||||||||
BINDING SITE  3' TGTCG    TTCG TCCTACTC  5'         SEQ ID:1187897
                      T--    A
```

FIG. 28A
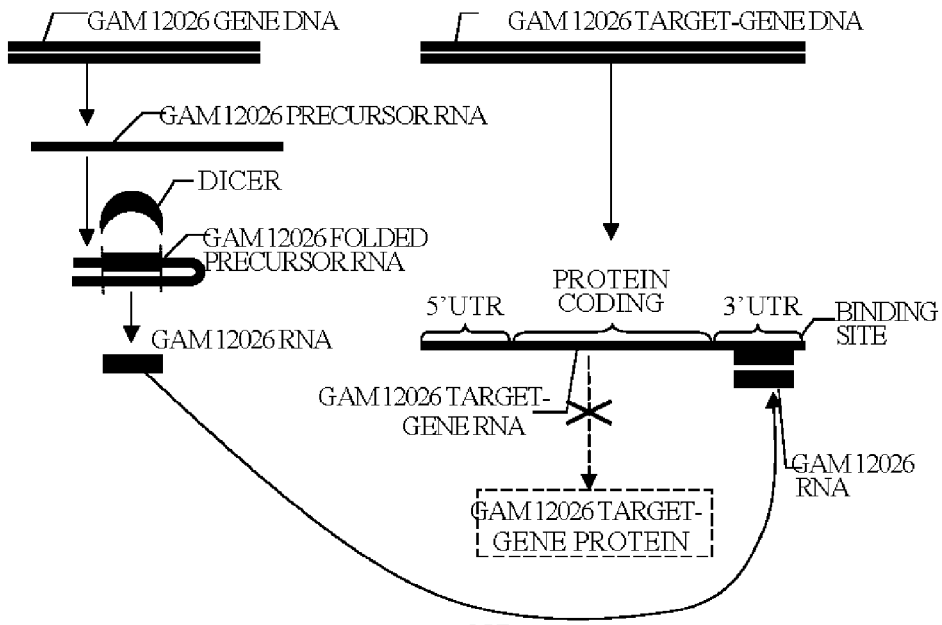
FIG. 28B
GACCUGCGGGACAAGAUUCUUGGUGCCACCAU<u>UGAGAAC</u>  SEQ ID NO: 12003
<u>UCCAGGAUUGUCCUGCAGAUC</u>
UGAGAACUCCAGGAUUGUCCUGCA  SEQ ID NO: 42079
FIG. 28C
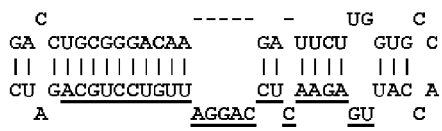
SEQ ID NO: 12003

Fig. 28D/1

```
                              CA   AT   TC
                  5' TGAGAACTC  GG  TG  CTGCA 3'        SEQ ID:28678
ABCC5                ||||||||   ||  ||  |||||
BINDING SITE      3' ACTCTTGAG  CC  GC  GACGT 5'        SEQ ID:42985
                              TG   --   GA

AAC        CCTGCA
                  5' TGAG    TCCAGGATTGT          3'    SEQ ID:28678
AIM1                 ||||    ||||||||||||
BINDING SITE      3' ACTC    AGGTTCTAACG          5'    SEQ ID:53607
                              CTA        AAC

A   C   AT
                  5' GAGA CTC AGG  TGTCCTGC 3'          SEQ ID:28678
AIPL1                |||| ||| |||  ||||||||
BINDING SITE      3' CTCT GAG TTC  ACAGGACG 5'          SEQ ID:53676
                         C   A   --

CCA   TT   C
                  5' TGAGAACT   GGA  GTC TGC 3'         SEQ ID:28678
BSG                  ||||||||   |||  ||| |||
BINDING SITE      3' ACTCTTGA   CCT  TAG ACG 5'         SEQ ID:84013
                              A--   --   A

CA
                  5' TGAGAACTC   GGATTGT 3'             SEQ ID:28678
C7                   |||||||||   |||||||
BINDING SITE      3' ACTTTTGAG   CCTGACA 5'             SEQ ID:86945
                              AC

AA             GTCC
                  5' GAG   CTCCAGGATT      TGCA 3'      SEQ ID:28678
CCND1                |||   ||||||||||      ||||
BINDING SITE      3' CTC   GAGGTCCTGA      ACGT 5'      SEQ ID:95252
                         C-             A---

G      ATTG      C
                  5' TGA  AACTCCAGG    TCCTG 3'         SEQ ID:28678
EPHA8                |||  ||||||||||   |||||
BINDING SITE      3' ACT  TTGAGGTCC    AGGAC 5'         SEQ ID:152819
                         A      ----

GA     A TG C    CA
                  5' TGA   ACTCCAGG T  T CTG    3       SEQ ID:28678
HUNK                 |||   ||||||||| |  | |||
BINDING SITE      3' ACT   TGAGGTCC  G  A GAC   5       SEQ ID:204846
                         TC     - GT A    AT

AA       TT   CC
                  5' TGAG   CTCCAGGA  GT  TGC 3'        SEQ ID:28678
IGFBP3               ||||   ||||||||  ||  |||
BINDING SITE      3' ACTC   GAGGTCCT  CG  ACG 5'        SEQ ID:208615
                              --       --   T-
```

Fig. 28D/2

```
                              ATT   CC
               5' TGAGAACTCCAGG   GT  TG  3'        SEQ ID:28678
JAG1              ||||||||||||   ||  ||
BINDING SITE   3' ACTCTTGAGGTCT   CA  AC  5'        SEQ ID:219150
                              ACT   AA

-      TTGTC
               5' GAA CTCCAGGA     CTGC  3'         SEQ ID:28678
RRP22             ||| ||||||||     ||||
BINDING SITE   3' CTT GAGGTCCT     GACG  5'         SEQ ID:346965
                   C           CGTCC

C        TTGT
               5' TGAGAA TCCAGGA     CCTG  3'       SEQ ID:28678
DKFZP4340125      |||||| |||||||     ||||
BINDING SITE   3' ACTCTT AGGTCTT     GGAC  5'       SEQ ID:523373
                       A           ----

CA   ATTG
               5' TGAGAACTC  GG    TCCT  3'         SEQ ID:28678
DKFZP434P0721     |||||||||  ||    ||||
BINDING SITE   3' ACTCTTGAG  CC    AGGA  5'         SEQ ID:523926
                            AC   GA--

CAGGATT
               5' TGAGAACTC       GTCCTGC  3'       SEQ ID:28678
FLJ20457          |||||||||       |||||||
BINDING SITE   3' ACTCTTGAG       CAGGACG  5'       SEQ ID:630483
                            TT-----

CTC        TC
               5' TGAGAA   CAGGATTG   CTGCA  3'     SEQ ID:28678
FLJ20485          ||||||   ||||||||   |||||
BINDING SITE   3' ACTCTT   GTCCTAAC   GACGT  5'     SEQ ID:630888
                       AAC        GT

CCA-  A
               5' AGAACT    GG  TTGTCCTG  3'        SEQ ID:28678
FLJ21820          ||||||    ||  ||||||||
BINDING SITE   3' TCTTGA    CC  AACAGGAC  5'        SEQ ID:643418
                        ACGA  -

AA     AGGAT
               5' GAG   CTCC    TGTCCTGCA  3'       SEQ ID:28678
HRIHFB2122        |||   ||||    |||||||||
BINDING SITE   3' CTC   GAGG    ACAGGACGT  5'       SEQ ID:691379
                        C-     GG---

AA  CCAGG
               5' TGAG  CT      ATTGTCCTGCA  3'     SEQ ID:28678
KIAA0596          ||||  ||      |||||||||||
BINDING SITE   3' ACTC  GA      TGACAGGACGT  5'     SEQ ID:742690
                        CC  A----
```

Fig. 28D/3

```
                         A    C        TG   TGC
                    5' TG GAA TCCAGGAT  TCC      3'        SEQ ID:28678
MGC23284               || ||| ||||||||  |||
BINDING SITE        3' AC CTT AGGTCTTA  AGG      5'        SEQ ID:861987
                         C    A        --   T

AA           T   -
                    5' GAG   CTCCAGGAT GTC CTGC   3'        SEQ ID:28678
NCK1                   |||   |||||||||  ||| ||||
BINDING SITE        3' CTC   GAGGTCCTG CGG GACG   5'        SEQ ID:889147
                         CC           -   T

C    A
                    5' TGAGAACT CAGG TTGT       3'          SEQ ID:28678
NFASC                  |||||||| |||| ||||
BINDING SITE        3' ACTCTTGA GTCC GACG       5'          SEQ ID:891644
                              C    A

A   C    TT       A
                    5' TGAG ACT CAGGA GTCCTGC   3'          SEQ ID:28678
NUBP2                  |||| ||| ||||| |||||||
BINDING SITE        3' ACTC TGA GTCTT CAGGACG   5'          SEQ ID:897170
                         C   C    --

AAC      ATT   C   CA
                    5' TGAG    TCCAGG   GTC  TG    3'       SEQ ID:28678
SPIB                   ||||    ||||||   |||  ||
BINDING SITE        3' ACTC    GGGTCC   CAG  AC    5'       SEQ ID:976787
                              CTA      CT-   -   A

A      ATTGTC
                    5' TGAG ACTCCAGG      CTGCA    3'       SEQ ID:28678
TIP47                  |||| ||||||||      |||||
BINDING SITE        3' ACTC TGAGGTCT      GACGT    5'       SEQ ID:994148
                              C          CGTGTC

A    C      CCTGC
                    5' TG GAACT CAGGATTGT          3'       SEQ ID:28678
WDR7                   || ||||| |||||||||
BINDING SITE        3' AC CTTGA GTCCTAACG          5'       SEQ ID:1012964
                          C    T          T

A    T
                    5' ACTCCAGG TTG CCTGCA    3'            SEQ ID:28678
ZFPL1                  |||||||| ||| ||||||
BINDING SITE        3' TGAGGTCC GAC GGACGT    5'            SEQ ID:1018178
                               G    C

A        G   GTC
                    5' GAG ACTCCAG ATT   CTG   3'           SEQ ID:28678
KIAA0563               ||| |||||||| |||   |||
BINDING SITE        3' CTC TGAGGTT TAA   GAC   5'           SEQ ID:1235064
                         C        -   AA-
```

Fig. 28D/4

```
                              T  A   -    TCC
                    5' TGAGAAC CC GGA TTG    TGCA    3       SEQ ID:28678
LOC143308              ||||||| || ||| |||    ||||
BINDING SITE        3' ACTCTTG GG CCT GAC    ACGT    5       SEQ ID:1066389
                              -  C   C    CT-

A-    GGA       CC
                    5' TGAGA  CTCCA    TTGT   TGC    3'      SEQ ID:28678
LOC145844              |||||  |||||    ||||   |||
BINDING SITE        3' ACTTT  GGGGT    GACA   ACG    5'      SEQ ID:1087357
                              AA     AG-      AA

CA     ATT
                    5' GAACTC    GG  GTCCTGCA    3'          SEQ ID:28678
LOC146733              ||||||    ||  ||||||||
BINDING SITE        3' CTTGAG    CC  CAGGACGT    5'          SEQ ID:1097577
                                 AC     GGC

AA   C     ATTG
                    5' GAG CTC AGG    TCCTGCA   3'           SEQ ID:28678
LOC146909              ||| ||| |||    |||||||
BINDING SITE        3' TTC GAG TCC    GGGACGT   5'           SEQ ID:1100335
                           CC   A     ----

A   CT     GGATT
                    5' TG GAA   CCA        GTCCTGC   3'      SEQ ID:28678
LOC157931              || |||   |||        |||||||
BINDING SITE        3' AC CTT   GGT        CGGGACG   5'      SEQ ID:1186324
                            C   AC     -----

A       G    GTC
                    5' GAG ACTCCAG ATT    CTG   3'           SEQ ID:28678
LOC201173              ||| |||||||| |||    |||
BINDING SITE        3' CTC TGAGGTT TAA    GAC   5'           SEQ ID:1235064
                            C       -    AA-

A       G    GTC
                    5' GAG ACTCCAG ATT    CTG   3'           SEQ ID:28678
LOC201220              ||| |||||||| |||    |||
BINDING SITE        3' CTC TGAGGTT TAA    GAC   5'           SEQ ID:1235064
                            C       -    AA-
``` ately also
BIOINFORMATICALLY DETECTABLE GROUP OF NOVEL REGULATORY GENES AND USES THEREOF This application is continuation in part of U.S. patent application Ser. No. 10/293,338, filed Nov. 14, 2002, now abandoned entitled "Bioinformatically Detectable Group of Novel Regulatory Genes and Uses Thereof", the disclosure of which application is hereby incorporated by reference, and claims priority therefrom.

FIELD OF THE INVENTION

The present invention relates to a group of bioinformatically detectable novel genes, here identified as "genomic address messenger" or "GAM" genes, which are believed to be related to the micro RNA (miRNA) group of genes.

BRIEF DESCRIPTION OF SEQUENCE LISTING

Reference is made to the appendix submitted on the compact disc. The compact disc contains SEQUENCE LISTING.TXT (201,325 KB, Feb. 14, 2006), which is a replacement Sequence Listing in accordance with 37 C.F.R §§ 1.821-1.825, the contents of which are incorporated by reference herein.

BACKGROUND OF THE INVENTION

Small RNAs are known to perform diverse cellular functions, including post-transcriptional gene expression regulation. The first two such RNA genes, Lin-4 and Let-7, were identified by genetic analysis of *Caenorhabditis Elegans* (*Elegans*) developmental timing, and were termed short temporal RNA (stRNA) (Wightman, B., Ha, I., Ruvkun, G., Cell 75, 855 (1993); Erdmann, V. A. et al., Nucleic Acids Res. 29, 189 (2001); Lee, R. C., Feinbaum, R. L., Ambros, V., Cell 75, 843 (1993); Reinhart, B. et al., Nature 403, 901 (2000)).

Lin-4 and Let-7 each transcribe a ~22 nucleotide (nt) RNA, which acts a post transcriptional repressor of target mRNAs, by binding to elements in the 3'-untranslated region (UTR) of these target mRNAs, which are complimentary to the 22 nt sequence of Lin-4 and Let-7 respectively. While Lin-4 and Let-7 are expressed at different developmental stage, first larval stage and fourth larval stage respectively, both specify the temporal progression of cell fates, by triggering post-transcriptional control over other genes (Wightman, B., Ha, I., Ruvkun, G., Cell 75, 855 (1993); Slack et al., Mol. Cell 5, 659 (2000)). Let-7 as well as its temporal regulation have been demonstrated to be conserved in all major groups of bilaterally symmetrical animals, from nematodes, through flies to humans (Pasquinelli, A., et al. Nature 408, 86 (2000)).

The initial transcription product of Lin-4 and Let-7 is a ~60-80 nt RNA, the nucleotide sequence of the first half of which is partially complimentary to that of its second half, therefore allowing this RNA to fold onto itself, forming a 'hairpin structure'. The final gene product is a ~22 nt RNA, which is 'diced' from the above mentioned 'hairpin structure', by an enzyme called Dicer, which also apparently also mediates the complimentary binding of this ~22 nt segment to a binding site in the 3' UTR of its target gene.

Recent studies have uncovered 93 new genes in this class, now referred to as micro RNA or miRNA genes, in genomes of *Elegans*, Drosophilea, and Human (Lagos-Quintana, M., Rauhut, R., Lendeckel, W., Tuschl, T., Science 294, 853 (2001); Lau, N. C., Lim, L. P., Weinstein, E. G., Bartel, D. P., Science 294, 858 (2001); Lee, R. C., Ambros, V., Science 294, 862 (2001). Like the well studied Lin-4 and Let-7, all newly found MIR genes produce a ~60-80 nt RNA having a nucleotide sequence capable of forming a 'hairpin structure'. Expressions of the precursor ~60-80 nt RNA and of the resulting diced ~22 nt RNA of most of these newly discovered MIR genes have been detected.

Based on the striking homology of the newly discovered MIR genes to their well-studied predecessors Lin-4 and Let-7, the new MIR genes are believed to have a similar basic function as that of Lin-4 and Let-7: modulation of target genes by complimentary binding to the UTR of these target genes, with special emphasis on modulation of developmental control processes. This is despite the fact that the above mentioned recent studies did not find target genes to which the newly discovered MIR genes complementarily bind. While existing evidence suggests that the number of regulatory RNA genes "may turn out to be very large, numbering in the hundreds or even thousands in each genome", detecting such genes is challenging (Ruvkun G., 'Perspective: Glimpses of a tiny RNA world', Science 294, 779 (2001)).

The ability to detect novel RNA genes is limited by the methodologies used to detect such genes. All RNA genes identified so far either present a visibly discernable whole body phenotype, as do Lin-4 and Let-7 (Wightman et. al., Cell 75, 855 (1993); Reinhart et al., Nature 403, 901 (2000)), or produce significant enough quantities of RNA so as to be detected by the standard biochemical genomic techniques, as do the 93 recently detected miRNA genes. Since a limited number clones were sequenced by the researchers discovering these genes, 300 by Bartel and 100 by Tuschl (Bartel et. al., Science 294, 858 (2001); Tuschl et. al., Science 294, 853 (2001)), the RNA genes found can not be much rarer than 1% of all RNA genes. The recently detected miRNA genes therefore represent the more prevalent among the miRNA gene family.

Current methodology has therefore been unable to detect RNA genes which either do not present a visually discernable whole body phenotype, or are rare (e.g. rarer than 0.1% of all RNA genes), and therefore do not produce significant enough quantities of RNA so as to be detected by standard biochemical technique.

SUMMARY OF THE INVENTION

The present invention relates to a novel group of regulatory, non-protein coding genes, which are functional in specifically inhibiting translation of other genes, some of which are known to be involved in various diseases. Each gene in this novel group of genes, here identified as "GAM" or "Genomic Address Messengers", specifically inhibits translation of one of more other 'target' genes by means of complimentary hybridization of a segment of the RNA transcript encoded by GAM2, to an inhibitor site located in the 3' untranslated region of the mRNA of the one or more 'target' genes.

In various preferred embodiments, the present invention seeks to provide improved method and system for specific modulation of expression of specific known 'target' genes involved in significant human diseases, and improved method and system for detection of expression of these target genes.

Accordingly, the invention provides several substantially pure DNAs (e.g., genomic DNA, cDNA or synthetic DNA) each encoding a novel gene of the GAM group of gene, vectors comprising the DNAs, probes comprising the DNAs, a method and system for selectively modulating translation of known 'target' genes utilizing the vectors, and a method and system for detecting expression of known 'target' genes utilizing the probe.

By "substantially pure DNA" is meant DNA that is free of the genes which, in the naturally-occurring genome of the organism from which the DNA of the invention is derived, flank the genes discovered and isolated by the present invention. The term therefore includes, for example, a recombinant DNA which is incorporated into a vector, into an autonomously replicating plasmid or virus, or into the genomic DNA of a prokaryote or eukaryote at a site other than its natural site, or which exists as a separate molecule (e.g., a cDNA or a genomic or cDNA fragment produced by PCR or restriction endonuclease digestion) independent of other sequences. It also includes a recombinant DNA which is part of a hybrid gene encoding additional polypeptide sequence.

"Inhibiting translation" is defined as the ability to prevent synthesis of a specific protein encoded by a respective gene, by means of inhibiting the translation of the mRNA of this gene. "Translation inhibitor site" is defined as the minimal DNA sequence sufficient to inhibit translation.

There is thus provided in accordance with a preferred embodiment of the present invention a bioinformatically detectable novel gene encoding substantially pure DNA wherein: RNA encoded by the bioinformatically detectable novel gene is about 18 to about 24 nucleotides in length, and originates from an RNA precursor, which RNA precursor is about 50 to about 120 nucleotides in length, a nucleotide sequence of a first half of the RNA precursor is a partial inversed-reversed sequence of a nucleotide sequence of a second half thereof, a nucleotide sequence of the RNA encoded by the novel gene is a partial inversed-reversed sequence of a nucleotide sequence of a binding site associated with at least one target gene, the novel gene cannot be detected by either of the following: a visually discernable whole body phenotype, and detection of 99.9% of RNA species shorter than 25 nucleotides expressed in a tissue sample, and a function of the novel gene is bioinformatically deducible.

There is further provided in accordance with another preferred embodiment of the present invention a bioinformatically detectable novel gene encoding substantially pure DNA wherein: RNA encoded by the bioinformatically detectable novel gene includes a plurality of RNA sections, each of the RNA sections being about 50 to about 120 nucleotides in length, and including an RNA segment, which RNA segment is about 18 to about 24 nucleotides in length, a nucleotide sequence of a first half of each of the RNA sections encoded by the novel gene is a partial inversed-reversed sequence of nucleotide sequence of a second half thereof, a nucleotide sequence of each of the RNA segments encoded by the novel gene is a partial inversed-reversed sequence of the nucleotide sequence of a binding site associated with at least one target gene, and a function of the novel gene is bioinformatically deducible from the following data elements: the nucleotide sequence of the RNA encoded by the novel gene, a nucleotide sequence of the at least one target gene, and function of the at least one target gene.

There is still further provided in accordance with another preferred embodiment of the present invention a bioinformatically detectable novel gene encoding substantially pure DNA wherein: RNA encoded by the bioinformatically detectable novel gene is about 18 to about 24 nucleotides in length, and originates from an RNA precursor, which RNA precursor is about 50 to about 120 nucleotides in length, a nucleotide sequence of a first half of the RNA precursor is a partial inversed-reversed sequence of a nucleotide sequence of a second half thereof, a nucleotide sequence of the RNA encoded by the novel gene is a partial inversed-reverse sequence of a nucleotide sequence of a binding site associated with at least one target gene, a function of the novel gene is modulation of expression of the at least one target gene, and the at least one target gene does not encode a protein.

There is additionally provided in accordance with another preferred embodiment of the present invention A bioinformatically detectable novel gene encoding substantially pure DNA wherein: the bioinformatically detectable novel gene does not encode a protein, RNA encoded by the bioinformatically detectable novel gene is maternally transferred by a cell to at least one daughter cell of the cell, a function of the novel gene includes modulation of a cell type of the daughter cell, and the modulation is bioinformatically deducible.

There is moreover provided in accordance with another preferred embodiment of the present invention a bioinformatically detectable novel gene encoding substantially pure DNA wherein: the bioinformatically detectable novel gene does not encode a protein, a function of the novel gene is promotion of expression of the at lease one target gene, and the at least one target gene is bioinformatically deducible.

Further in accordance with a preferred embodiment of the present invention the function of the novel gene is bioinformatically deducible from the following data elements: the nucleotide sequence of the RNA encoded by the bioinformatically detectable novel gene, a nucleotide sequence of the at least one target gene, and a function of the at least one target gene.

Still further in accordance with a preferred embodiment of the present invention the RNA encoded by the novel gene complementarily binds the binding site associated with the at least one target gene, thereby modulating expression of the at least one target gene.

Additionally in accordance with a preferred embodiment of the present invention the binding site associated with at least one target gene is located in an untranslated region of RNA encoded by the at least one target gene.

Moreover in accordance with a preferred embodiment of the present invention the function of the novel gene is selective inhibition of translation of the at least one target gene, which selective inhibition includes complementary hybridization of the RNA encoded by the novel gene to the binding site.

Further in accordance with a preferred embodiment of the present invention the invention includes a vector including the DNA.

Still further in accordance with a preferred embodiment of the present invention the invention includes a method of selectively inhibiting translation of at least one gene, including introducing the vector.

Moreover in accordance with a preferred embodiment of the present invention the introducing includes utilizing RNAi pathway.

Additionally in accordance with a preferred embodiment of the present invention the invention includes a gene expression inhibition system including: the vector, and a vector inserter, functional to insert the vector into a cell, thereby selectively inhibiting translation of at least one gene.

Further in accordance with a preferred embodiment of the present invention the invention includes a probe including the DNA.

Still further in accordance with a preferred embodiment of the present invention the invention includes a method of selectively detecting expression of at least one gene, including using the probe.

Additionally in accordance with a preferred embodiment of the present invention the invention includes a gene expression detection system including: the probe, and a gene expression detector functional to selectively detect expression of at least one gene.

BRIEF DESCRIPTION OF DRAWINGS

FIGS. 2 through 4 are schematic diagrams which when taken together provide an analogy that illustrates a conceptual model of the present invention, addressing the genomic differentiation enigma;

FIG. 21A is an annotated sequence of EST72223 (SEQ ID NO: 1388403) comprising miRNA gene MIR98 and novel gene GAM24 detected by the gene detection system of the present invention;

FIGS. 21B and 21C are pictures of laboratory results, which when taken together demonstrate laboratory confirmation of expression of the bioinformatically detected novel gene GAM24 of FIG. 21A;

FIG. 21D provides pictures of laboratory results, which when taken together demonstrate further laboratory confirmation of expression of the bioinformatically detected novel gene GAM24 of FIG. 21A;

FIG. 22A is an annotated sequence of an EST7929020 (SEQ ID NO: 1388404) comprising novel genes GAM23 and GAM25 detected by the gene detection system of the present invention;

FIG. 22B is a picture of laboratory results, which confirm expression of bioinformatically detected novel genes GAM23 and GAM25 of FIG. 22A;

FIG. 23A is an annotated sequence of an EST1388749 (SEQ ID NO: 1388405) comprising novel gene GAM26 detected by the gene detection system of the present invention;

FIG. 23B are a picture of laboratory results, which confirm expression of the bioinformatically detected novel gene GAM26 of FIG. 23A;

FIGS. 24A through 28D are schematic diagrams illustrating sequences, functions and utilities of 5 specific genes of the novel group of genes of the present invention, detected using the bioinformatic gene detection system described hereinabove with reference to FIGS. 8 through 15.

DETAILED DESCRIPTION OF A PREFERRED EMBODIMENT

Figure 1:
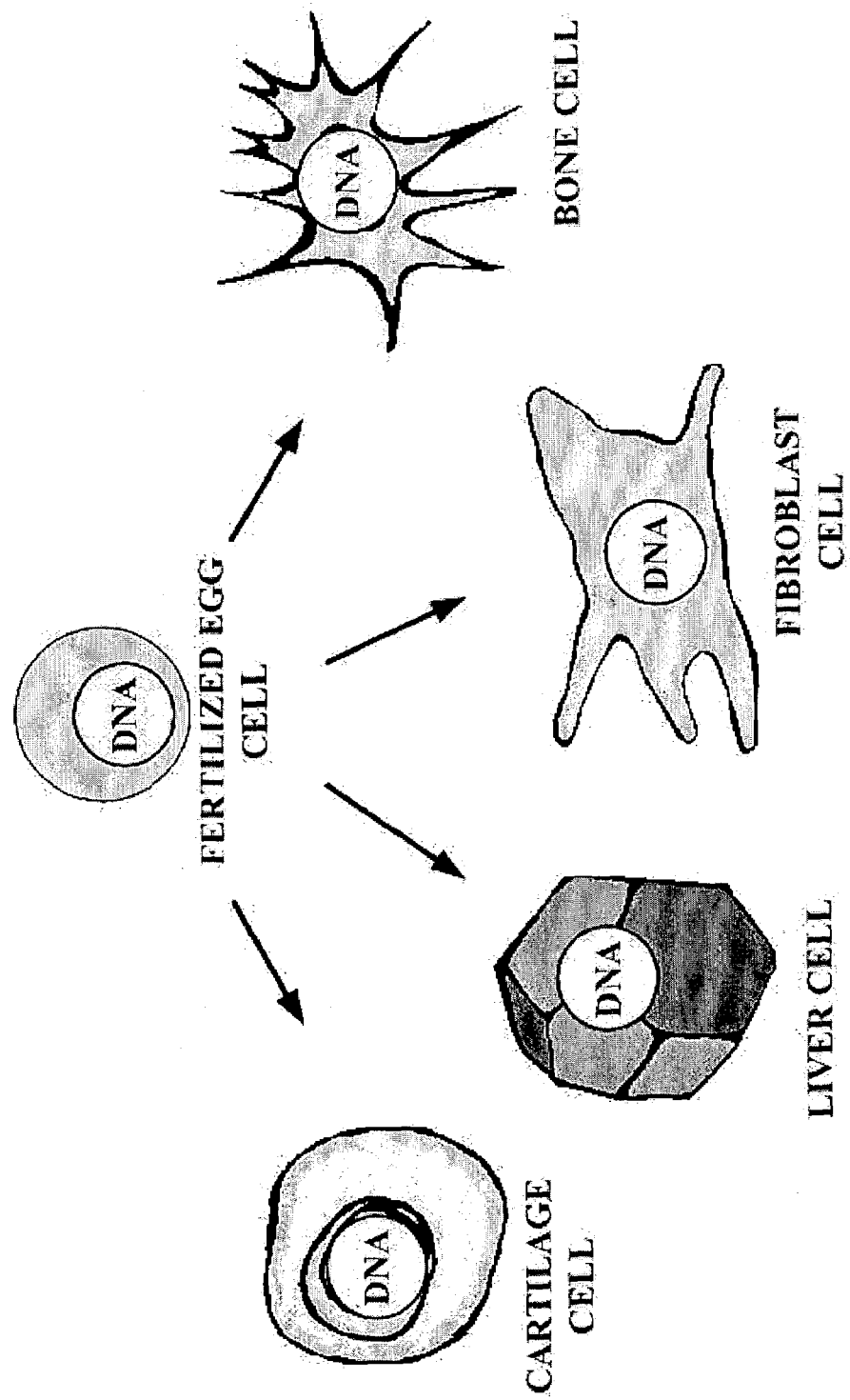
FIG. 1 is a simplified diagram illustrating the genomic differentiation enigma that the present invention addresses.

Reference is now made to FIG. 1, which is a simplified diagram providing a conceptual explanation of a genomic differentiation enigma, which the present invention addresses.

FIG. 1 depicts different cell types in an organism, such as CARTILAGE CELL, LIVER CELL, FIBROBLAST CELL and BONE CELL all containing identical DNA, and deriving from the initial FERTILIZED EGG CELL, and yet each of these cells expressing different proteins, and hence acquiring different shape and function.

The present invention proposes that the inevitable conclusion from this constraint is, however, strikingly simple: the coding system used must be modular. It must comprise multiple modules, or records, one for each cell-type, and a mechanism whereby each cell at its inception is instructed which record to open, and behaves according to instructions in that record.

This modular code concept is somewhat difficult to grasp, since we are strongly habituated to viewing things from an external viewpoint. An architect, for example, looks at a blueprint of a building, which details exactly where each element (block, window, door, electrical switch, etc.) is to be placed relative to all other elements, and then instructs builders to place these elements in their designated places. This is an external viewpoint: the architect is external to the blueprint, which itself is external to the physical building, and its different elements. The architect may therefore act as an 'external organizing agent': seeing the full picture and the relationships between all elements, and being able to instruct from the outside where to place each of them.

Genomics differentiation coding evidently works differently, without any such external organizing agent. It comprises only one smart block (the first cell), which is the architect and the blueprint, and which continuously duplicates itself, somehow knowing when to manifest itself as a block and when as a window, door, or electrical switch.

Figure 3:
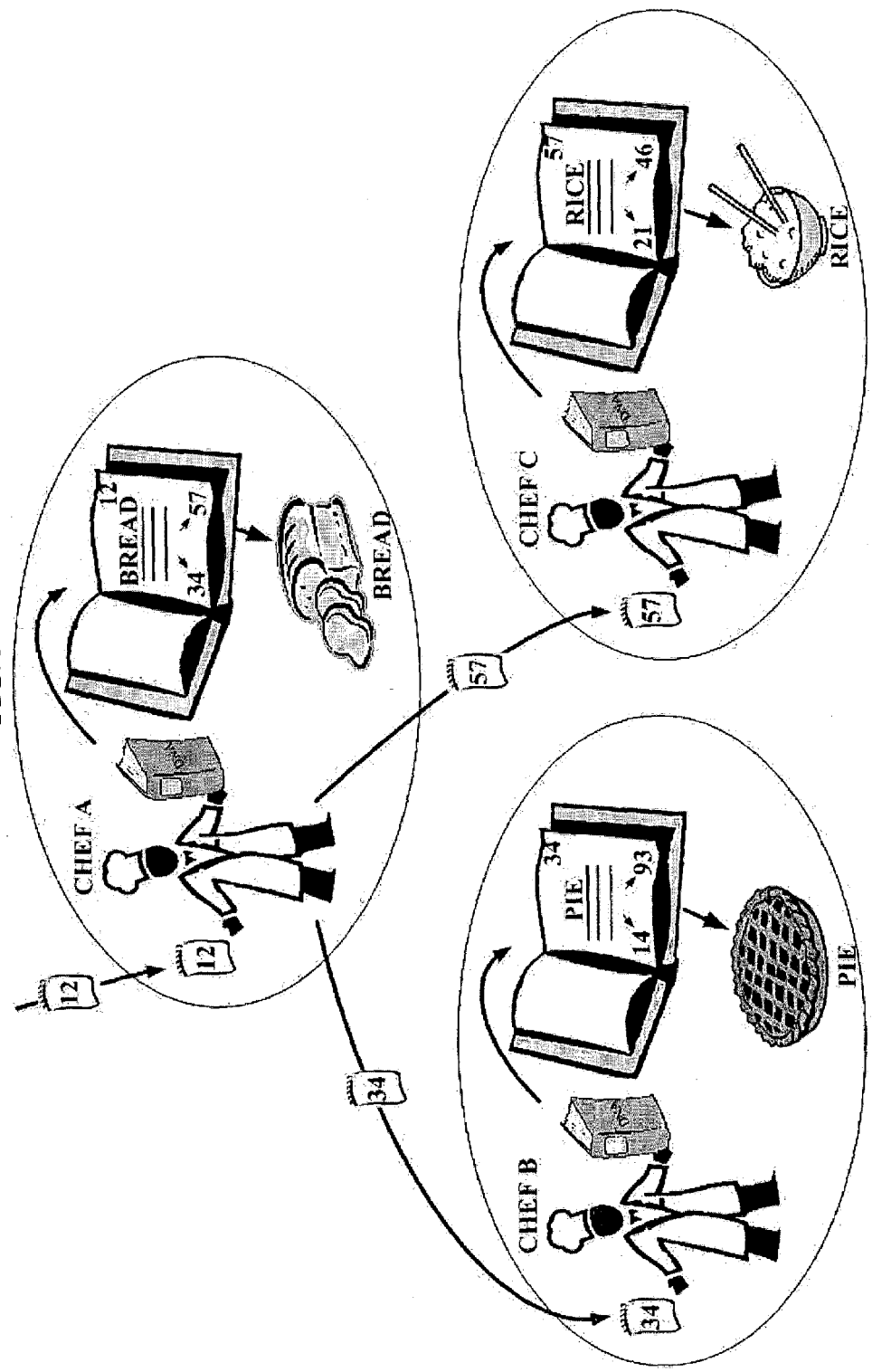
Figure 4:
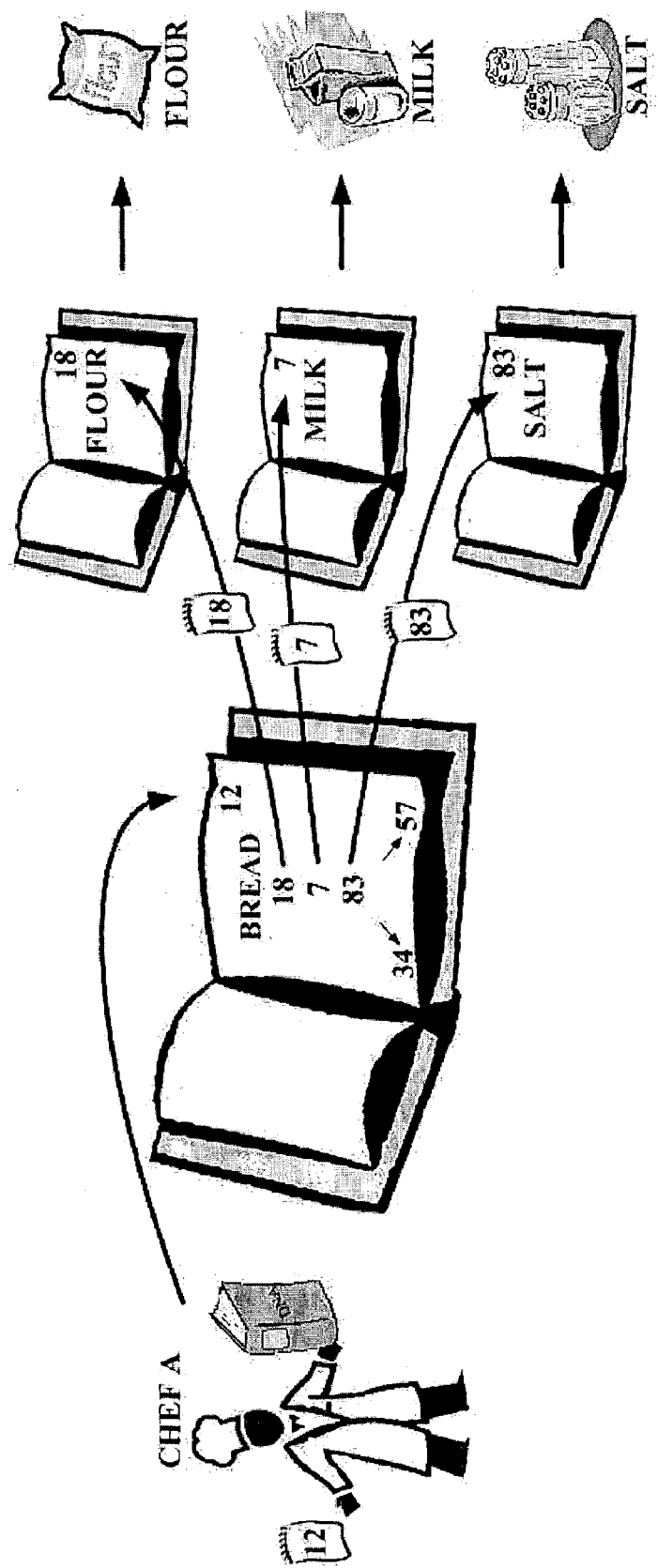

Reference is now made to FIGS. 2 through 4 which are schematic diagrams which when taken together provide an analogy that illustrates a conceptual model of the present invention, addressing the genomic differentiation enigma.

Reference is now made to FIG. 2A. Imagine a very talented chef, capable of preparing any meal provided the is given specific written cooking instructions. This chef is equipped with two items: (a) a thick recipe book, and (b) a small note with a number scribbled on it. The book comprises multiple pages, each page detailing how to prepare a specific meal. The small note indicates the page to be opened, and therefore the meal to be prepared. The chef looks at the page-number written on the note, opens the recipe book at the appropriate page, and prepares the meal according to the written instructions on this page. As an example, FIG. 2A depicts a CHEF holding a note with the number 12 written on it, he opens the book on page 12, and since that page contains the recipe for preparing BREAD, the CHEF prepares a loaf of BREAD.

Reference is now made to FIG. 2B, which depicts two identical chefs, CHEF A and CHEF B, holding an identical recipe book. Despite their identity, and the identity of their recipe book, since CHEF A holds a note numbered 12, and therefore opens the book on page 12 and prepares BREAD, whereas CHEF B holds a note numbered 34 and therefore opens the book on page 34 and prepares a PIE.

Reference is now made to FIG. 3. Imagine the chef of the analogy is also capable of duplicating himself once he has finished preparing the specified meal. The format of the book is such that at the bottom of each page, two numbers are written. When he has finished preparing the meal specified on that page, the chef is trained to do the following: (i) divide himself into two identical duplicate chefs, (ii) duplicate the recipe book and hand a copy to each of his duplicate chefs, and (iii) write down the two numbers found at the bottom of the page of the meal he prepared, on two small notes, handing one note to each of his two duplicate chefs.

Each of the two resulting duplicate chefs are now equipped with the same book, and have the same talent to prepare any meal, but since each of them received a different note, they will now prepare different meals.

FIG. 3 depicts CHEF A holding a recipe book and receiving a note numbered 12. CHEF A therefore opens the book on page 12 and prepares BREAD. When he is finished making bread, CHEF A performs the following actions: (i) divides himself into two duplicate chefs, designated CHEF B and CHEF C, (ii) duplicates his recipe book handing a copy to each of CHEF B and CHEF C, (iii) writes down the numbers found at the bottom of page 12, numbers 34 and 57, on two notes, handing note numbered 34 to CHEF B and note numbered 57 to CHEF C.

Accordingly, CHEF B receives a note numbered 34 and therefore opens the recipe book on page 34 and prepares PIE, whereas CHEF C receives a note numbered 57 and therefore opens the book on page 57 and therefore prepares RICE.

It is appreciated that while CHEF A, CHEF B & CHEF C are identical and hold identical recipe books, they each prepare a different meal. It is also appreciated that the meals prepared by CHEF B and CHEF C are determined CHEF A, and are mediated by the differently numbered notes passed on from CHEF A to CHEF B and CHEF C.

It is further appreciated that the mechanism illustrated by FIG. 3 enables an unlimited lineage of chefs to divide into duplicate, identical chefs and to determine the meals those duplicate chefs would prepare. For example, having been directed to page 34, when CHEF B divides into duplicate chefs (not shown), he will instruct its two duplicate chefs to prepare meals specified on pages 14 and 93 respectively, according to the numbers at the bottom of page 34 to which he was directed. Similarly, CHEF C will instruct its duplicate chefs to prepare meals specified on pages 21 and 46 respectively, etc.

Reference is now made to FIG. 4. Imagine that the cooking instructions on each page of the recipe book are written in shorthand format. The main meal-page to which the chef was directed by the scribbled note, merely contains a list of numbers which direct him to multiple successive pages, each specifying how to prepare an ingredient of that meal.

As an example, FIG. 4 depicts CHEF A of FIGS. 2 and 3, holding a recipe book and a note numbered 12. Accordingly, CHEF A opens the recipe book on page 12, which details the instructions for preparing BREAD. However, the 'instructions' on making BREAD found on page 12 comprise only of 3 numbers, 18, 7 and 83, which 'refer' CHEF A to pages detailing preparation of the ingredients of BREAD-FLOUR, MILK and SALT, respectively.

As illustrated in FIG. 4, turning from the main 'meal page' (—e.g. 12) to respective 'ingredients pages' (e.g. pages 18, 7 & 83) is mediated by scribbled notes with the page-numbers written on them. In this analogy, the scribbled notes are required for seeking the target pages to be turned to—both when turning to main 'meal pages' (e.g. page 12), as well as when turning to 'ingredient pages' (e.g. pages 18, 7 & 83).

The chef in the given analogy, schematically depicted in FIGS. 2 through 4, represents a cell; the thick recipe book represents the DNA; preparing a meal in the given analogy represents the cell manifesting itself as a specific cell-type; and ingredients of a meal represent proteins expressed by that cell-type. Like the chef equipped with the thick recipe book in the given analogy, all cells in an organism contain the same DNA and are therefore each potentially capable of manifesting itself as any cell-type, expressing proteins typical of that cell type.

Figure 5A:
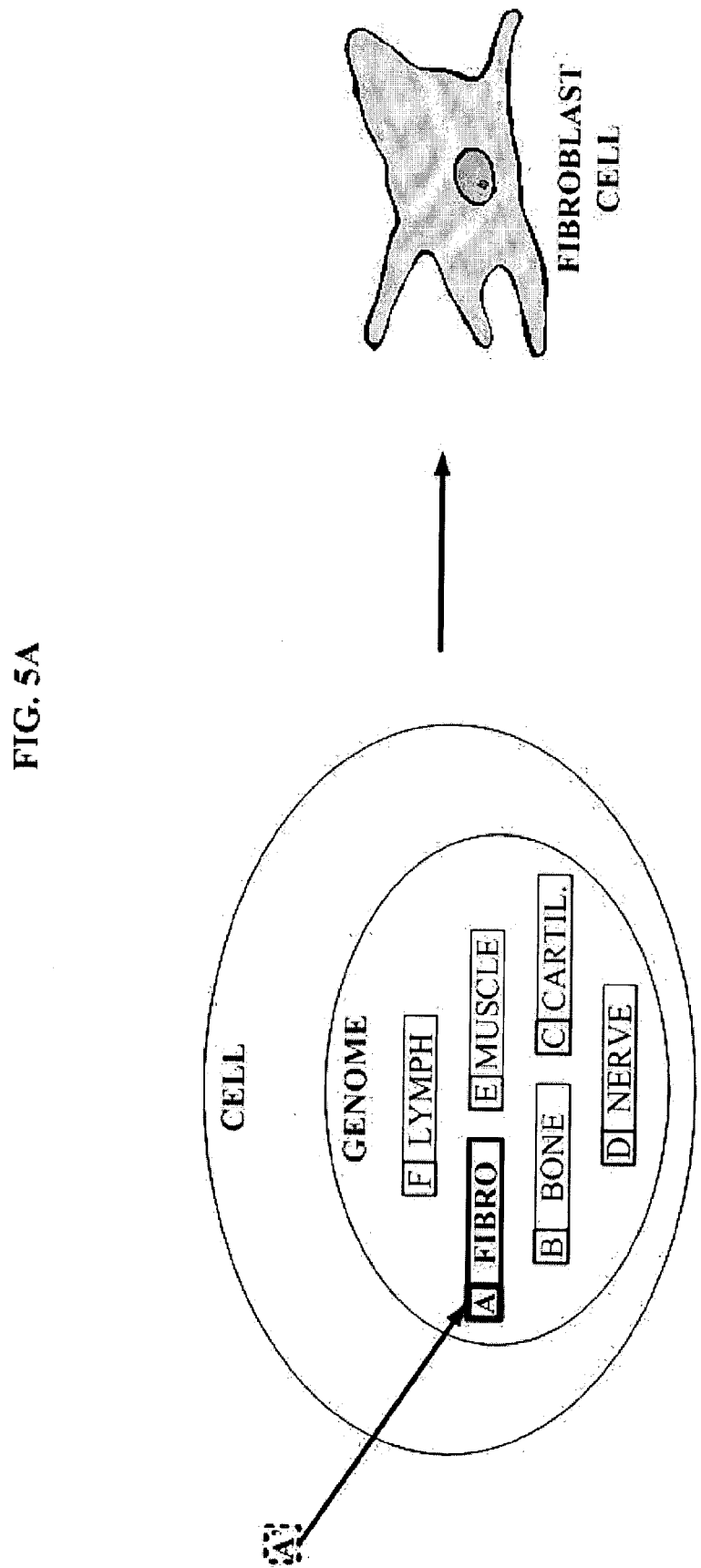
FIGS. 5A and 5B are schematic diagrams, which when taken together illustrate a 'genomic records' concept of the conceptual model of the present invention, addressing the genomic differentiation enigma.
Figure 5B:
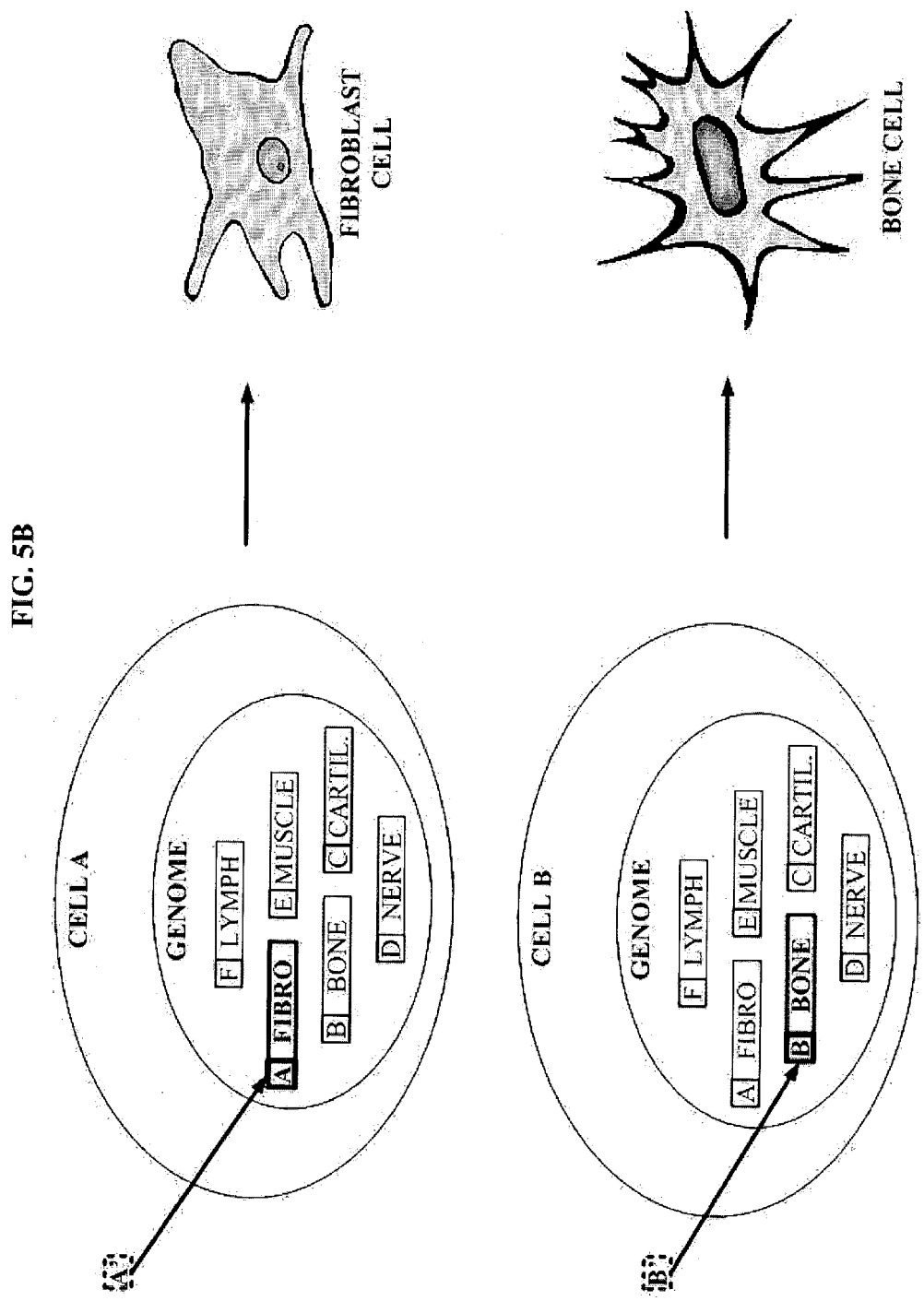

Reference is now made to FIGS. 5A and 5B which are schematic diagrams, which when taken together illustrate a 'genomic records' concept of the conceptual model of the present invention, addressing the genomic differentiation enigma.

The Genomic Records concept asserts that the DNA (the thick recipe book in the illustration) comprises a very large number of Genomic Records (analogous to pages in the recipe book), each containing the instructions for differentiation of a different cell-type, or developmental process. Each Genomic Record is headed by a very short genomic sequence which functions as a 'Genomic Address' of that Genomic Record (analogous to the page number in the recipe book). At its inception, in addition to the DNA, each cell also receives a short RNA segment (the scribbled note in the illustration). This short RNA segment binds complementarily to a 'Genomic Address' sequence of one of the Genomic Records, thereby activating that Genomic Record, and accordingly determining the cell's-fate (analogous to opening the book on the page corresponding to the number on the scribbled note, thereby determining the meal to be prepared).

Reference is now made to FIG. 5A. a CELL is illustrated which comprises a GENOME. The GENOME comprises a plurality of GENOMIC RECORDS, each of which correlates to a specific cell type (for clarity only 6 sample genomic records are shown). Each genomic record comprises genomic instructions on differentiation into a specific cell-type, as further elaborated below with reference to FIG. 7. At cell inception, the CELL receives a maternal short RNA segment, which activates one of the GENOMIC RECORDS, causing the cell to differentiate according to the instructions comprised in that genomic record. As an example, FIG. 5A illustrates reception of a maternal short RNA segment designated A' and outlined by a broken line, which activates the FIBRO genomic record, causing the cell to differentiate into a FIBROBLAST CELL.

Reference is now made to FIG. 5B, which is a simplified schematic diagram, illustrating cellular differentiation mediated by the 'Genomic Records' concept. FIG. 5B depicts 2 cells in an organism, designated CELL A and CELL B, each having a GENOME. It is appreciated that since CELL A and CELL B are cells in the same organism, the GENOME of CELL A is identical to that of CELL B. Despite having an identical GENOME, CELL A differentiates differently from CELL B, due to activation of different genomic records in these two cells. In CELL A the FIBRO GENOMIC RECORD is activated, causing CELL A to differentiate into a FIBROBLAST CELL, whereas in CELL B the BONE GENOMIC RECORD is activated, causing the CELL B to differentiate into a BONE CELL. The cause for activation of different genomic records in these two cells is the different maternal short RNA which they both received: CELL A received a maternal short RNA segment designated A' which activated genomic record FIBRO, whereas CELL B received a maternal short RNA segment designated B' which activated genomic record BONE.

Figure 6:
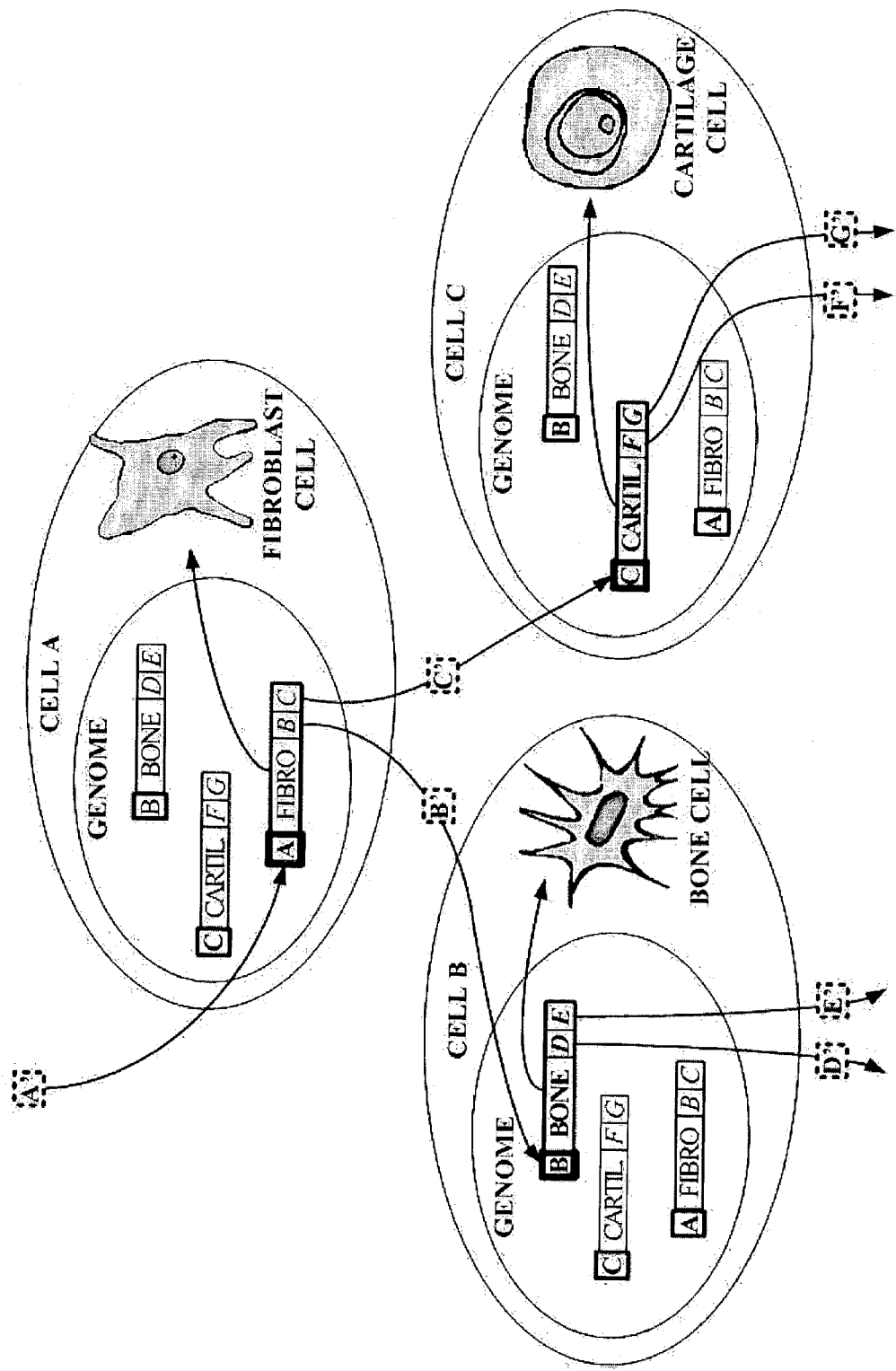
FIG. 6 is a schematic diagram illustrating a 'genomically programmed cell differentiation' concept of the conceptual model of the present invention, addressing the genomic differentiation enigma.

Reference is now made to FIG. 6 which is a schematic diagram illustrating a 'genomically programmed cell differentiation' concept of the conceptual model of the present invention, addressing the genomic differentiation enigma.

A cell designated CELL A divides into 2 cells designated CELL B and CELL C. CELL A, CELL B and CELL C each comprise a GENOME, which GENOME comprises a plurality of GENOMIC RECORDS. It is appreciated that since CELL A, CELL B and CELL C are cells in the same organism, the GENOME of these cells, and the GENOMIC RECORDS comprised therein, are identical.

As described above with reference to FIG. 5B, at its inception, CELL A receives a maternal short RNA segment, designated A' and marked by a broken line, which activates the FIBRO genomic record, thereby causing CELL A to differentiate into a FIBROBLAST CELL. However, FIG. 6 shows further details of the genomic records: each cell genomic record also comprises two short genomic sequences, referred to here as Daughter Cell Genomic Addresses. Blocks designated B and C are Daughter Cell Genomic Addresses of the FIBRO Genomic Record. At cell division, each parent cell transcribes two short RNA segments, corresponding to the two Daughter Cell Genomic Addresses of the Genomic Record of that parent cell, and transfers one to each of its two daughter cells. CELL A of FIG. 6 transcribes and transfers to its two respective daughter cells, two short RNA segments, outlined by a broken line and designated B' and C', corresponding to daughter cell genomic addresses designated B and C comprised in the FIBRO genomic record.

CELL B therefore receives the above mentioned maternal short RNA segment designated B', which binds complementarily to genomic address designated B of genomic record BONE, thereby activating this genomic record, which in turn causes CELL B to differentiate into a BONE CELL. Similarly, CELL C receives the above mentioned maternal short RNA segment designated C', which binds complementarily to genomic address designated C of genomic record CARTIL, thereby activating this genomic record, which in turn causes CELL C to differentiate into a CARTILAGE CELL.

It is appreciated that the mechanism illustrated by FIG. 6 enables an unlimited lineage of cells to divide into daughter cells containing the same DNA, and to determine the cell-fate of these daughter cells. For example, when CELL B and CELL C divide into their respective daughter cells (not shown), they will transfer short RNA segments designated D' & E', and F' & G' respectively, to their respective daughter cells. The cell fate of each of these daughter cells would be determined by the identity of the maternal short RNA segment they receive, which would determine the genomic record activated.

Figure 7:
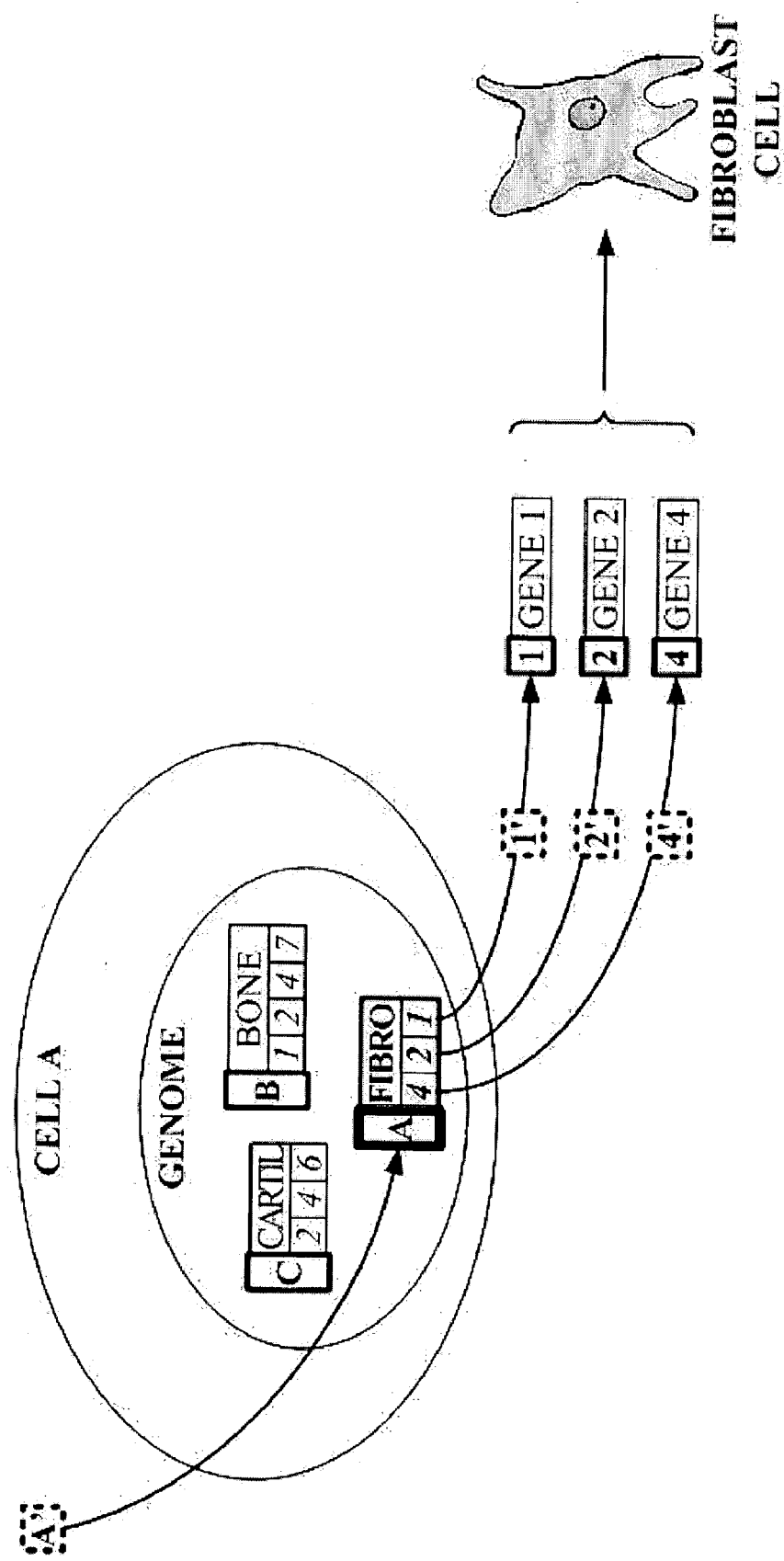
FIG. 7 is a schematic diagram illustrating a 'genomically programmed cell-specific protein expression modulation' concept of the conceptual model of the present invention, addressing the genomic differentiation enigma.

Reference is now made to FIG. 7 which is a schematic diagram illustrating a 'genomically programmed cell-specific protein expression modulation' concept of the conceptual model of the present invention, addressing the genomic differentiation enigma.

Cell A receives a maternal short RNA segment designated A', which activates a genomic record designated FIBRO, by anti-sense binding to a binding site 'header' of this genomic record, designated A. Genomic record FIBRO encodes 3 short RNA segments, designated 1, 2 and 4 respectively, which modulate expression of target genes designated GENE1, GENE2 and GENE4 respectively. Modulation of expression of these genes results in CELL A differentiating into a FIBROBLAST CELL.

Figure 8:
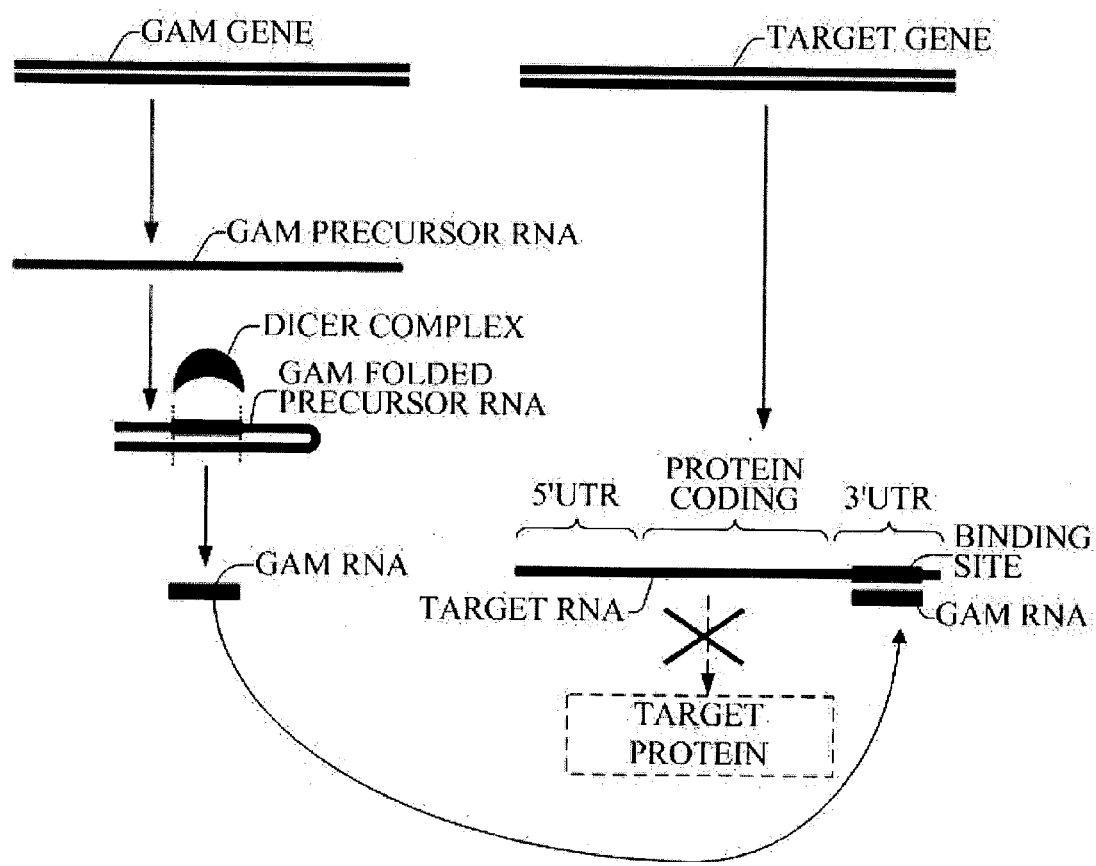
FIG. 8 is a simplified diagram illustrating a mode by which genes of a novel group of genes of the present invention, modulate expression of known target genes.

Reference is now made to FIG. 8 which is a simplified diagram illustrating a mode by which genes of a novel group of genes of the present invention, modulate expression of known target genes.

The novel genes of the present invention are micro RNA (miRNA)-like, regulatory RNA genes, modulating expression of known target genes. This mode of modulation is common to other known miRNA genes, as described hereinabove with reference to the background of the invention section.

GAM GENE and TARGET GENE are two human genes contained in the DNA of the human genome.

GAM GENE encodes a GAM PRECURSOR RNA. However, similar to other miRNA genes, and unlike most ordinary genes, its RNA, GAM PRECURSOR RNA, does not encode a protein.

GAM PRECURSOR RNA folds onto itself, forming GAM FOLDED PRECURSOR RNA. As FIG. 8 illustrates, GAM FOLDED PRECURSOR RNA forms a 'hairpin structure', folding onto itself. As is well known in the art, this 'hairpin structure', is typical genes of the miRNA genes, and is due to the fact that nucleotide sequence of the first half of the RNA of a gene in this group is an accurate or partial inversed-reversed sequence of the nucleotide sequence of its second half. By "inversed-reversed" is meant a sequence which is reversed and wherein each nucleotide is replaced by a complimentary nucleotide, as is well known in the art (—e.g. ATGGC is the inversed-reversed sequence of GCCAT).

An enzyme complex, designated DICER COMPLEX, 'dices' the GAM FOLDED PRECURSOR RNA into a single stranded RNA segment, about 22 nucleotides long, designated GAM RNA. As is known in the art, 'dicing' of the hairpin structured RNA precursor into shorter RNA segments about 22 nucleotides long by a Dicer type enzyme is catalyzed by an enzyme complex comprising an enzyme called Dicer together with other necessary proteins.

TARGET GENE encodes a corresponding messenger RNA, designated TARGET RNA. This TARGET RNA comprises 3 regions: a 5' untranslated region, a protein coding region and a 3' untranslated region, designated 5'UTR, PROTEIN CODING and 3'UTR respectively.

GAM RNA binds complementarily a BINDING SITE, located on the 3'UTR segment of TARGET RNA. This complementarily binding is due to the fact that the nucleotide sequence of GAM RNA is an accurate or partial inversed-reversed sequence of the nucleotide sequence of BINDING SITE.

The complimentary binding of GAM RNA to BINDING SITE inhibits translation of TARGET RNA into TARGET PROTEIN. TARGET PROTEIN is therefore outlined by a broken line.

It is appreciated by one skilled in the art that the mode of transcriptional inhibition illustrated by FIG. 8 with specific reference to GAM genes of the present invention, is in fact common to all other miRNA genes. A specific complimentary binding site has been demonstrated only for Lin-4 and Let-7. All the other 93 newly discovered miRNA genes are also believed by those skilled in the art to modulate expression of other genes by complimentary binding, although specific complimentary binding sites for these genes have not yet been found (Ruvkun G., 'Perspective: Glimpses of a tiny RNA world', Science 294, 779 (2001)). The present invention discloses a novel group of genes, the GAM genes, belonging to the miRNA genes group, and for which a specific a complimentary binding has been determined.

Figure 9:
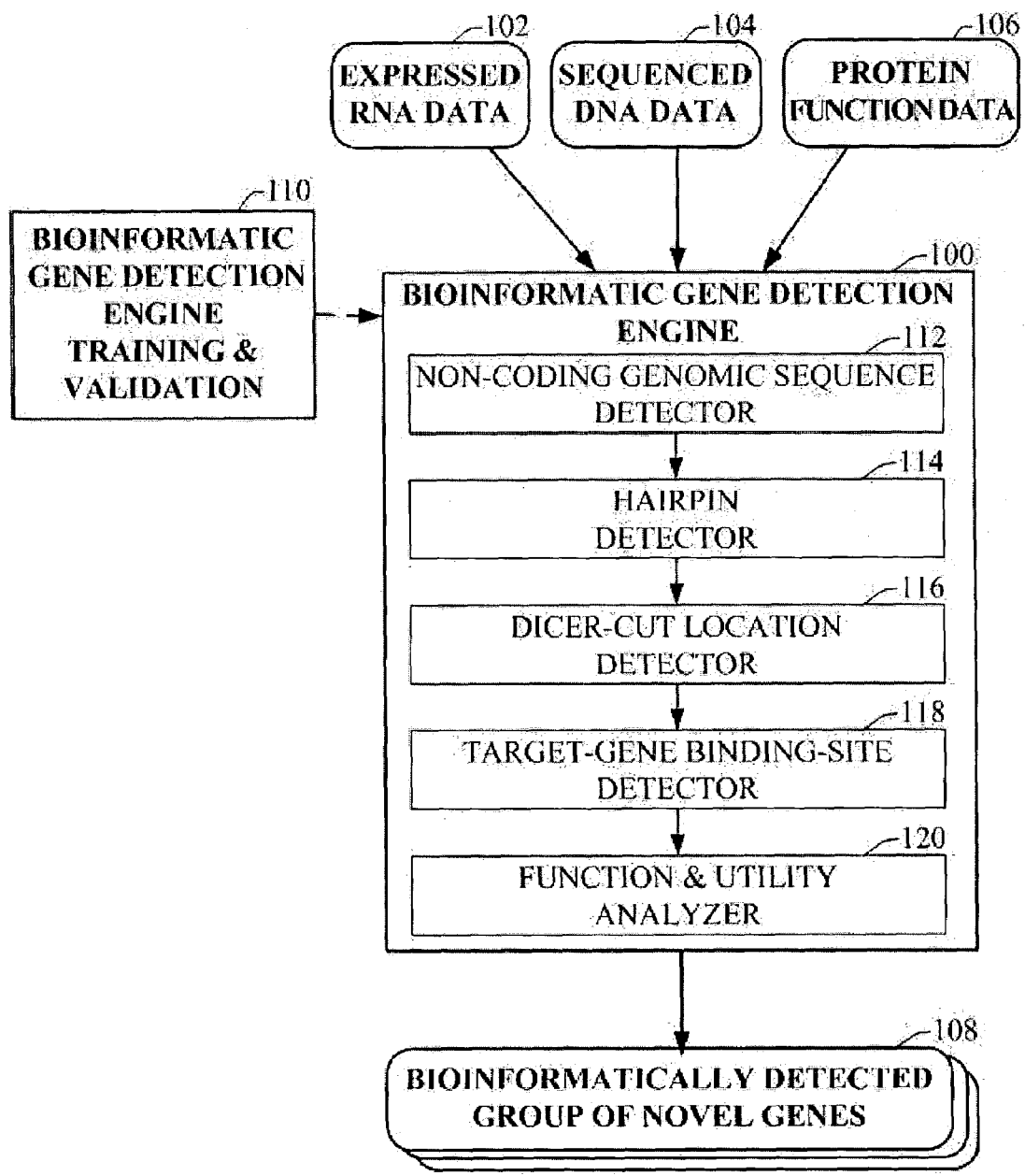
FIG. 9 is a simplified block diagram illustrating a bioinformatic gene detection system capable of detecting genes of the novel group of genes of the present invention, which system is constructed and operative in accordance with a preferred embodiment of the present invention.

Reference is now made to FIG. 9 which is a simplified block diagram illustrating a bioinformatic gene detection system capable of detecting genes of the novel group of genes of the present invention, which system is constructed and operative in accordance with a preferred embodiment of the present invention.

A centerpiece of the present invention is a bioinformatic gene detection engine 100, which is a preferred implementation of a mechanism capable of bioinformatically detecting genes of the novel group of genes of the present invention.

The function of the bioinformatic gene detection engine 100 is as follows: it receives three types of input, expressed RNA data 102, sequenced DNA data 104, and protein function data 106, performs a complex process of analysis of this data as elaborated below, and based on this analysis produces output of a bioinformatically detected group of novel genes designated 108.

Expressed RNA data 102 comprises published expressed sequence tags (EST) data, published mRNA data, as well as other sources of published RNA data. Sequenced DNA data 104 comprises alphanumeric data describing sequenced genomic data, which preferably includes annotation data such as location of known protein coding regions relative to the sequenced data. Protein function data 106 comprises scientific publications reporting studies which elucidated physiological function known proteins, and their connection, involvement and possible utility in treatment and diagnosis of various diseases. Expressed RNA data 102, sequenced DNA data 104 may preferably be obtained from data published by the National Center for Bioinformatics (NCBI) at the National Institute of Health (NIH), as well as from various other published data sources. Protein function data 106 may preferably be obtained from any one of numerous relevant published data sources, such as the Online Mendelian Inherited Disease In Man (OMIM) database developed by John Hopkins University, and also published by NCBI.

Prior to actual detection of bioinformatically detected novel genes 108 by the bioinformatic gene detection engine 100, a process of bioinformatic gene detection engine training & validation designated 110 takes place. This process uses the known miRNA genes as a training set (some 200 such genes have been found to date using biological laboratory means), to train the bioinformatic gene detection engine 100 to bioinformatically recognize miRNA-like genes, and their respective potential target binding sites. Bioinformatic gene detection engine training & validation 110 is further described hereinbelow with reference to FIG. 10.

The bioinformatic gene detection engine 100 comprises several modules which are preferably activated sequentially, and are described as follows:

A non-coding genomic sequence detector 112 operative to bioinformatically detect non-protein coding genomic sequences. The non-coding genomic sequence detector 112 is further described hereinbelow with reference to FIGS. 11A and 11B.

A hairpin detector 114 operative to bioinformatically detect genomic 'hairpin-shaped' sequences, similar to GAM FOLDED PRECURSOR of FIG. 8. The hairpin detector 114 is further described hereinbelow with reference to FIGS. 12A and 12B.

A dicer-cut location detector 116 operative to bioinformatically detect the location on a hairpin shaped sequence which is enzymatically cut by DICER COMPLEX of FIG.

8. The dicer-cut location detector 116 is further described hereinbelow with reference to FIG. 13A.

A target-gene binding-site detector 118 operative to bioinformatically detect target genes having binding sites, the nucleotide sequence of which is partially complementary to that of a given genomic sequence, such as a sequence cut by DICER COMPLEX of FIG. 8. The target-gene binding-site detector 118 is further described hereinbelow with reference to FIGS. 14A and 14B.

A function & utility analyzer 120 operative to analyze function and utility of target genes, in order to identify target genes which have a significant clinical function and utility. The function & utility analyzer 120 is further described hereinbelow with reference to FIG. 15.

Hardware implementation of the bioinformatic gene detection engine 100 is important, since significant computing power is preferably required in order to perform the computation of bioinformatic gene detection engine 100 in reasonable time and cost. As an example, it is estimated that using one powerful 8-processor PC Server, over 30 months of computing time (at 24 hours per day) would be required in order to detect all miRNA genes in human EST data, and their respective binding sites.

For example, in order to address this challenge at reasonable time and cost, a preferred embodiment of the present invention may comprise a cluster of a large number of personal computers (PCs), such as 100 PCs (Pentium IV, 1.7 GHz, with 40 GB storage each), connected by Ethernet to several strong servers, such as 4 servers (2-CPU, Xeon 2.2 GHz, with 200 GB storage each), combined with an 8-processor server (8-CPU, Xeon 550 Mhz w/8 GB RAM) connected via 2 HBA fiber-channels to an EMC Clariion 100-disks, 3.6 Terabyte storage device. Additionally, preferably an efficient database computer program, such as Microsoft™ SQL-Server database computer program is used and is optimized to the specific requirements of bioinformatic gene detection engine 100. Furthermore, the PCs are preferably optimized to operate close to 100% CPU usage continuously, as is known in the art. Using suitable hardware and software may preferably reduce the required calculation time in the abovementioned example from 30 months to 20 days.

It is appreciated that the abovementioned hardware configuration is not meant to be limiting, and is given as an illustration only. The present invention may be implemented in a wide variety of hardware and software configurations.

The present invention discloses 527 novel genes of the GAM group of genes, which have been detected bioinformatically, as described hereinbelow with reference to FIGS. 24 through 550. Laboratory confirmation of 4 genes of the GAM group of genes is described hereinbelow with reference to FIGS. 21A through 23.

Figure 10:
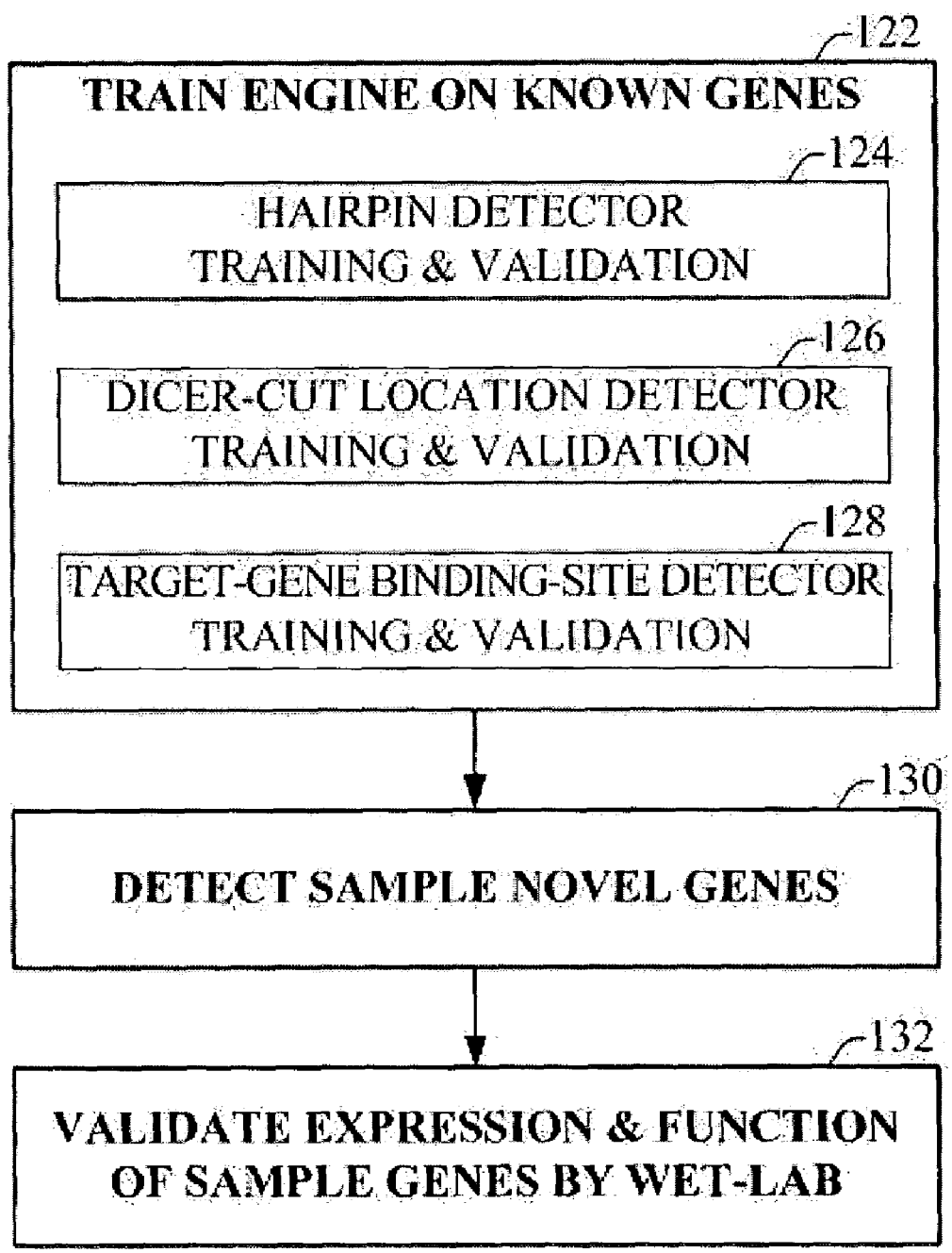
FIG. 10 is a simplified flowchart illustrating operation of a mechanism for training of a computer system to recognize the novel genes of the present invention, which mechanism is constructed and operative in accordance with a preferred embodiment of the present invention.

Reference is now made to FIG. 10 which is a simplified flowchart illustrating operation of a mechanism for training of a computer system to recognize the novel genes of the present invention. This mechanism is a preferred implementation of the bioinformatic gene detection engine training & validation 110 described hereinabove with reference to FIG. 9.

Bioinformatic gene detection engine training & validation 110 of FIG. 9 begins by training the bioinformatic gene detection engine to recognize known miRNA genes, as designated by numeral 122. This training step comprises hairpin detector training & validation 124, further described hereinbelow with reference to FIG. 12A, dicer-cut location detector training & validation 126, further described hereinbelow with reference to FIGS. 13A and 13B, and target-gene binding-site detector training & validation 128, further described hereinbelow with reference to FIG. 14A.

Next, the bioinformatic gene detection engine 100 is used to bioinformatically detect sample novel genes, as designated by numeral 130. An example of a sample novel gene thus detected is described hereinbelow with reference to FIG. 21.

Finally, wet lab experiments are preferably conducted in order to validate expression and preferably function the sample novel genes detected by the bioinformatic gene detection engine 100 in the previous step. An example of wet-lab validation of the abovementioned sample novel gene bioinformatically detected by the system is described hereinbelow with reference to FIGS. 22A and 22B.

Figure 11A:
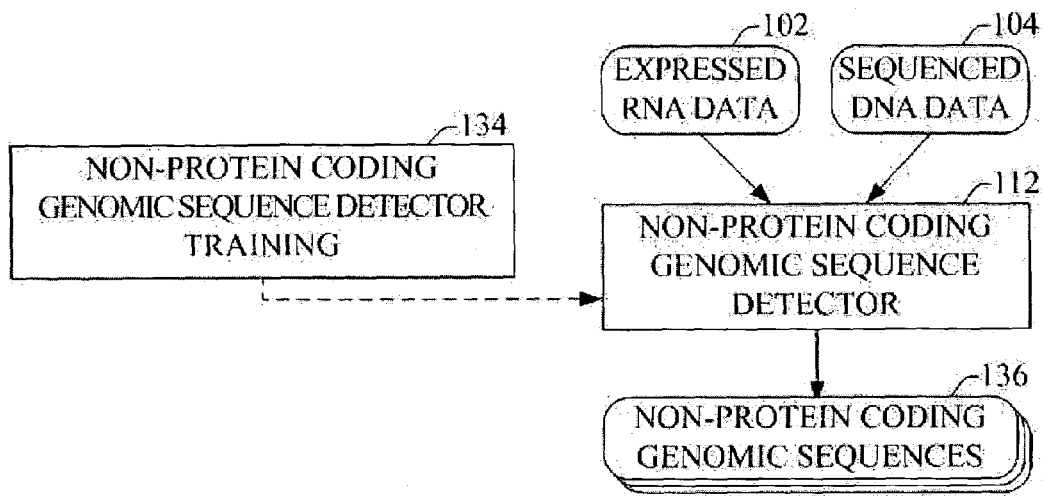
FIG. 11A is a simplified block diagram of a non-coding genomic sequence detector constructed and operative in accordance with a preferred embodiment of the present invention.

Reference is now made to FIG. 11A which is a simplified block diagram of a preferred implementation of the non-coding genomic sequence detector 112 described hereinabove with reference to FIG. 9. Non-protein coding genomic sequence detector 112 of FIG. 9 preferably receives as input at least two types of published genomic data: expressed RNA data 102, including EST data and mRNA data, and sequenced DNA data 104. After its initial training, indicated by numeral 134, and based on the abovementioned input data, the non-protein coding genomic sequence detector 112 produces as output a plurality of non-protein coding genomic sequences 136. Preferred operation of the non-protein coding genomic sequence detector 112 is described hereinbelow with reference to FIG. 11B.

Figure 11B:
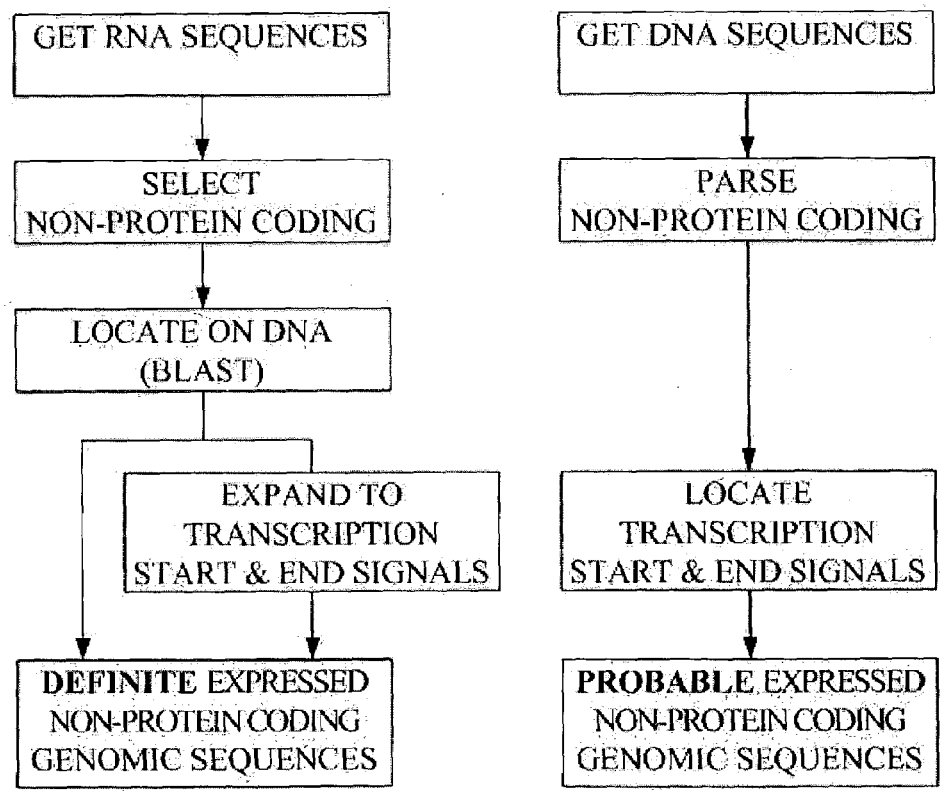
FIG. 11B is a simplified flowchart illustrating operation of a non-coding genomic sequence detector constructed and operative in accordance with a preferred embodiment of the present invention.

Reference is now made to FIG. 11B which is a simplified flowchart illustrating a preferred operation of the non-coding genomic sequence detector 112 of FIG. 9. Detection of non-protein coding genomic sequences to be further analyzed by the system generally preferably progresses in one of the following two paths.

A first path for detecting non-protein coding genomic sequences begins by receiving a plurality of known RNA sequences, such as EST data. Each RNA sequence is first compared to all known protein-coding sequences, in order to select only those RNA sequences which are non-protein coding. This can preferably be performed by BLAST comparison of the RNA sequence to known protein coding sequences. The abovementioned BLAST comparison to the DNA preferably also provides the localization of the RNA on the DNA.

Optionally, an attempt may be made to 'expand' the non-protein RNA sequences thus found, by searching for transcription start and end signals, upstream and downstream of location of the RNA on the DNA respectively, as is well known in the art.

A second path for detecting non-protein coding genomic sequences starts by receiving DNA sequences. The DNA sequences are parsed into non protein coding sequences, based on published DNA annotation data: extracting those DNA sequences which are between known protein coding sequences. Next, transcription start and end signals are sought. If such signals are found, and depending on their 'strength', probable expressed non-protein coding genomic sequences are yielded.

Figure 12A:
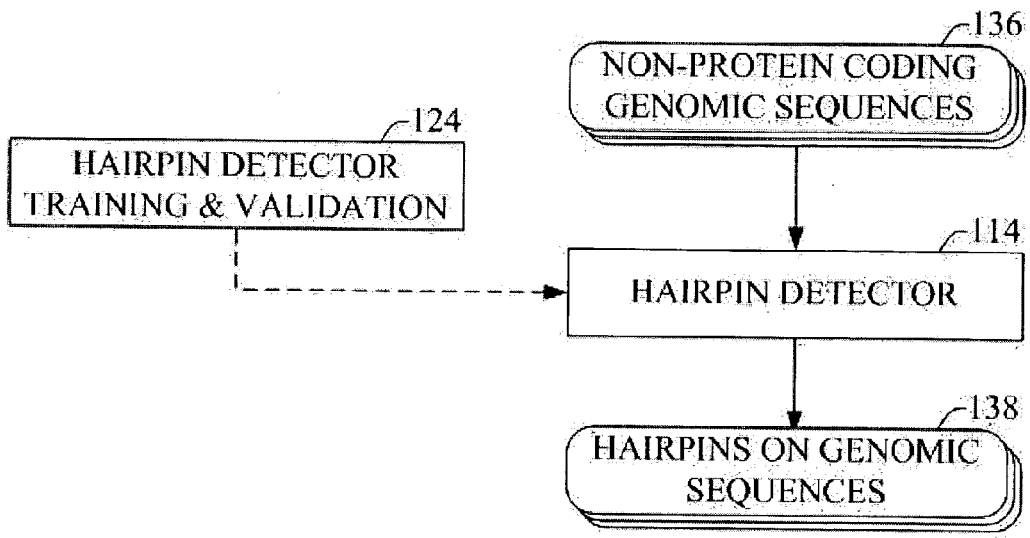
FIG. 12A is a simplified block diagram of a hairpin detector constructed and operative in accordance with a preferred embodiment of the present invention.

Reference is now made to FIG. 12A which is a simplified block diagram of a preferred implementation of the hairpin detector 114 described hereinabove with reference to FIG. 9.

The goal of the hairpin detector 114 is to detect 'hairpin' shaped genomic sequences, similar to those of known miRNA genes. As mentioned hereinabove with reference to FIG. 8, a 'hairpin' genomic sequence refers to a genomic sequence which 'folds onto itself' forming a hairpin like shape, due to the fact that nucleotide sequence of the first half of the nucleotide sequence is an accurate or The hairpin detector 114 of FIG. 9 receives as input a plurality of non-protein coding genomic sequences 136 of FIG. 11A, and after a phase of hairpin detector training & validation 124 of FIG. 10, is operative to detect and output 'hairpin shaped' sequences found in the input expressed non-protein coding sequences, designated by numeral 138.

The phase of hairpin detector training & validation 124 is an iterative process of applying the hairpin detector 114 to known hairpin shaped miRNA genes, calibrating the hairpin detector 114 such that it identifies the training set of known hairpins, as well as sequences which are similar thereto. Preferred operation of the hairpin detector 114 is described hereinbelow with reference to FIG. 12B.

Figure 12B:
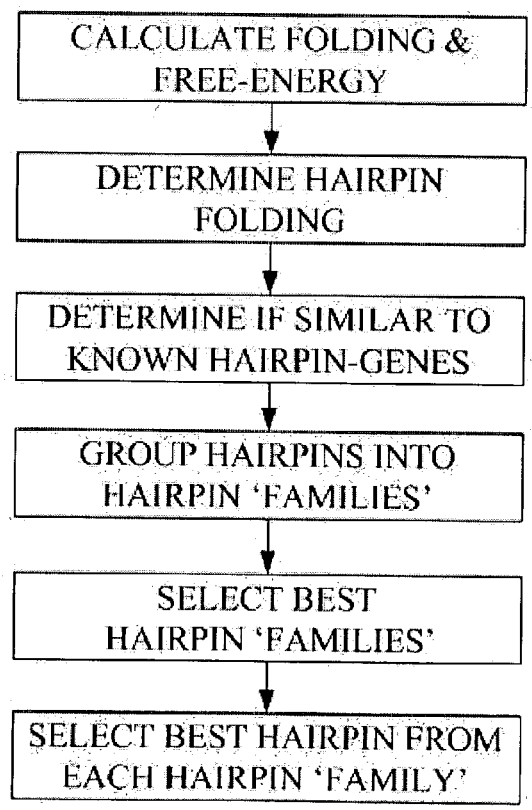
FIG. 12B is a simplified flowchart illustrating operation of a hairpin detector constructed and operative in accordance with a preferred embodiment of the present invention.

Reference is now made to FIG. 12B which is a simplified flowchart illustrating a preferred operation of the hairpin detector 114 of FIG. 9.

A hairpin structure is a two dimensional folding structure, resulting from the nucleotide sequence pattern: the nucleotide sequence of the first half of the hairpin sequence is an inversed-reversed sequence of the second half thereof. Different methodologies are known in the art for detection of various two dimensional and three dimensional hairpin structures.

In a preferred embodiment of the present invention, the hairpin detector 114 initially calculates possible 2-dimensional (2D) folding patterns of a given one of the non-protein coding genomic sequences 136, preferably using a 2D folding algorithm based on free-energy calculation, such as the Zucker algorithm, as is well known in the art.

Next, the hairpin detector 114 analyzes the results of the 2D folding, in order to determine the presence, and location of hairpin structures. A 2D folding algorithm typically provides as output a listing of the base-pairing of the 2D folded shape, i.e. a listing of which all two pairs of nucleotides in the sequence which will bond. The goal of this second step is to assess this base-pairing listing, in order to determine if it describes a hairpin type bonding pattern.

The hairpin detector 114 then assess those hairpin structures found by the previous step, comparing them to hairpins of known miRNA genes, using various parameters such as length, free-energy, amount and type of mismatches, etc. Only hairpins that bear statistically significant resemblance of the population of hairpins of known miRNAs, according to the abovementioned parameters are accepted.

Lastly, the hairpin detector 114 attempts to select those hairpin structures which are as stable as the hairpins of know miRNA genes. This may be achieved in various manners. A preferred embodiment of the present invention utilizes the following methodology comprising three steps.

First, the hairpin detector 114 attempts to group potential hairpins into 'families' of closely related hairpins. As is known in the art, a free-energy calculation algorithm, typically provides multiple 'versions' each describing a different possible 2D folding pattern for the given genomic sequence, and the free energy of such possible folding. The hairpin detector 114 therefore preferably assesses all hairpins found on all 'versions', grouping hairpins which appear in different versions, but which share near identical locations into a common 'family' of hairpins. For example, all hairpins in different versions, the center of which is within 7 nucleotides of each other may preferably be grouped to a single 'family'.

Next, hairpin 'families' are assessed, in order to select only those families which represent hairpins that are as stable as those of known miRNA hairpins. For example, preferably only families which are represented in at least 65% of the free-energy calculation 2D folding versions are considered stable.

Finally, an attempt is made to select the most suitable hairpin from each selected family. For example, preferably the hairpin which appears in more versions than other hairpins, and in versions the free-energy of which is lower, may be selected.

Figure 13A:
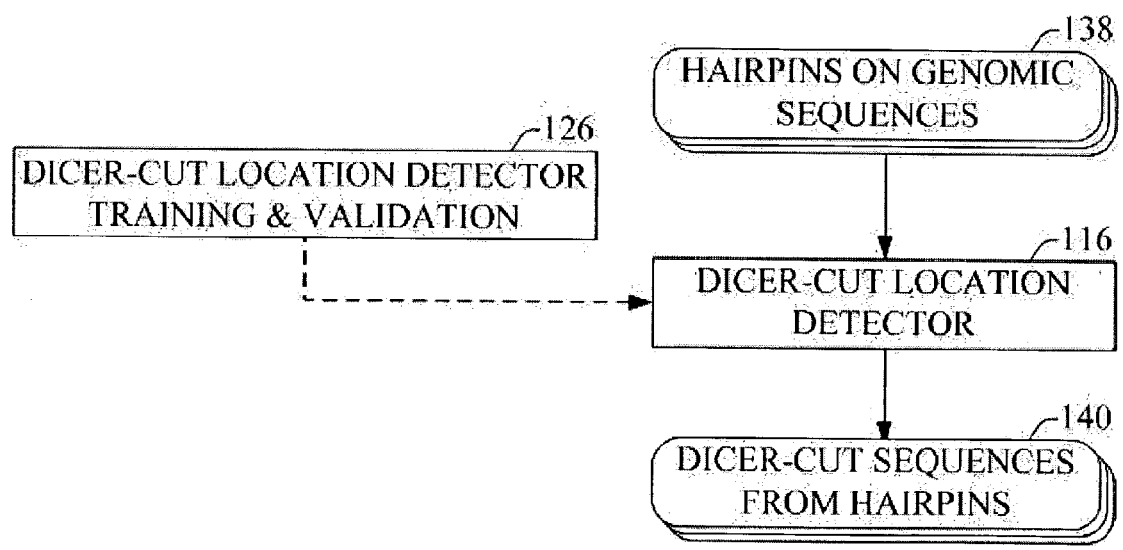
FIG. 13A is a simplified block diagram of a dicer-cut location detector constructed and operative in accordance with a preferred embodiment of the present invention.

Reference is now made to FIG. 13A which is a simplified block diagram of a preferred implementation of the dicer-cut location detector 116 described hereinabove with reference to FIG. 9.

The goal of the dicer-cut location detector 116 is to detect the location in which DICER COMPLEX of FIG. 8, comprising the enzyme Dicer, would 'dice' the given hairpin sequence, similar to GAM FOLDED PRECURSOR RNA, yielding GAM RNA both of FIG. 8.

The dicer-cut location detector 116 of FIG. 9 therefore receives as input a plurality of hairpins on genomic sequences 138 of FIG. 12A, which were calculated by the previous step, and after a phase of dicer-cut location detector training & validation 126 of FIG. 10, is operative to detect a respective plurality of dicer-cut sequences from hairpins 140, one for each hairpin.

In a preferred embodiment of the present invention, the dicer-cut location detector 116 preferably uses a combination of neural networks, Bayesian networks, Markovian modeling, and Support Vector Machines (SVMs) trained on the known dicer-cut locations of known miRNA genes, in order to detect dicer-cut locations. Dicer-cut location detector training & validation 126, which is further described hereinbelow with reference to FIG. 13B.

Figure 13B:
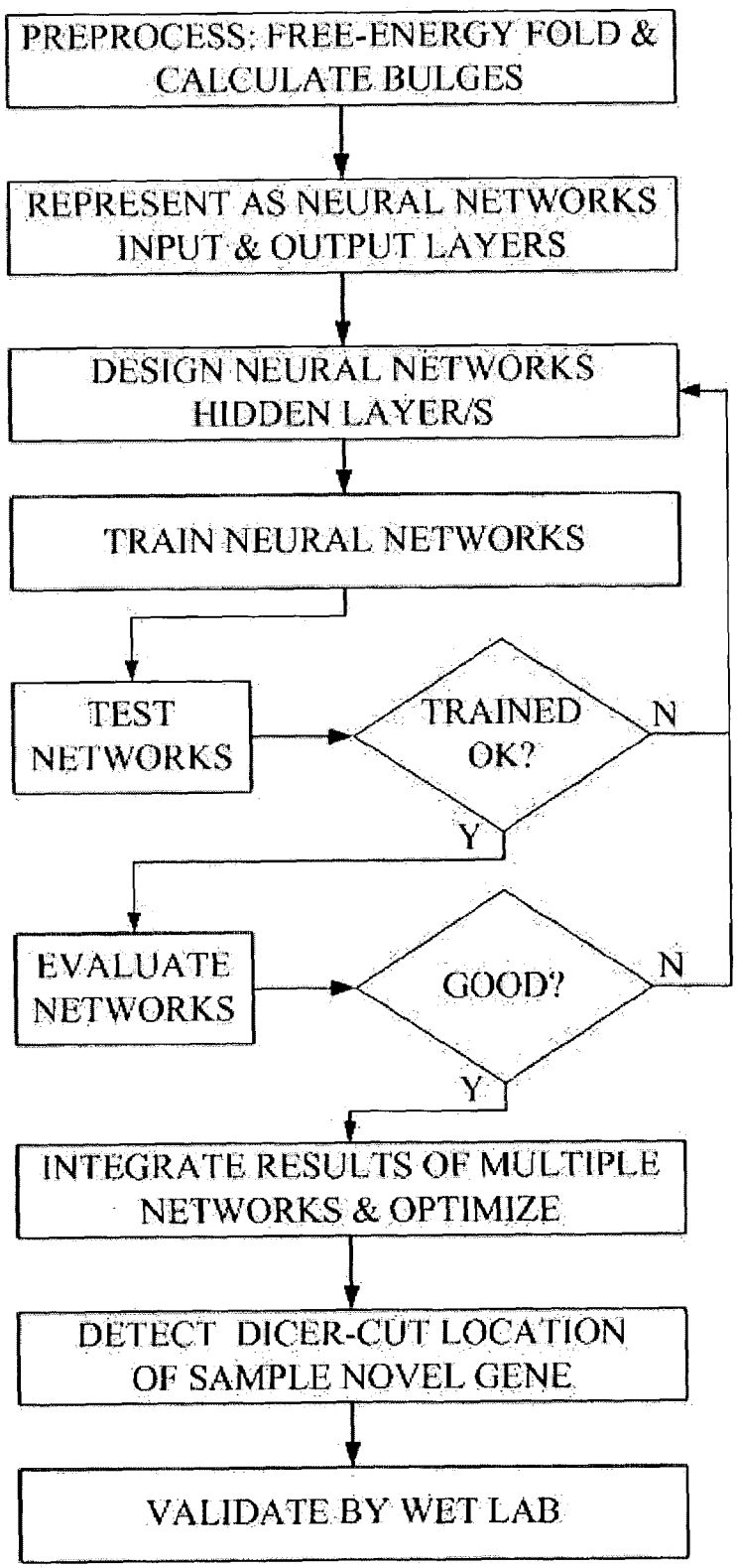
FIG. 13B is a simplified flowchart illustrating training of a dicer-cut location detector constructed and operative in accordance with a preferred embodiment of the present invention.

Reference is now made to FIG. 13B which is a simplified flowchart illustrating a preferred implementation of dicer-cut location detector training & validation 126 of FIG. 10. Dicer-cut location detector 116 first preprocesses known miRNA hairpins and their respective dicer-cut locations, so as to be able to properly analyze them and train the detection system accordingly.

The folding pattern is calculated for each known miRNA, preferably based on free-energy calculation, and the size of the hairpin, the size of the loop at the center of the hairpin, and 'bulges' (i.e. mismatched base-pairs) in the folded hairpin are noted.

The dicer-cut location, which is known for known miRNA genes, is noted relative to the above, as well as to the nucleotides in each location along the hairpin. Frequency of identity of nucleotides, and nucleotide-pairing, relative to their location in the hairpin, and relative to the known dicer-cut location in the known miRNA genes is analyzed and modeled.

Different techniques are well known in the art for analysis of existing pattern from a given 'training set' of species belonging to a genus, which techniques are then capable, to a certain degree, to detect similar patterns in other species not belonging to the training-set genus. Such techniques include, but are not limited to neural networks, Bayesian networks, Support Vector Machines (SVM), Genetic Algorithms, Markovian modeling, and others, as is well known in the art.

Using such techniques, preferably a combination of several of the above techniques, the known hairpins are represented as a several different networks (such as neural, Bayesian, or SVM) input and output layers. Both nucleotide, and 'bulge' (i.e. nucleotide pairing or mismatch) are represented for each position in the hairpin, at the input layer, and a corresponding true/false flag at each position, indicating whether it was diced by dicer at the output layer. Multiple networks are preferably used concurrently, and the results therefrom are integrated and further optimized. Markovian modeling may also be used to validate the results and enhance their accuracy. Finally, the bioinformatic detection of dicer-cut location of a sample novel is confirmed by wet-lab experimentation.

Figure 14A:
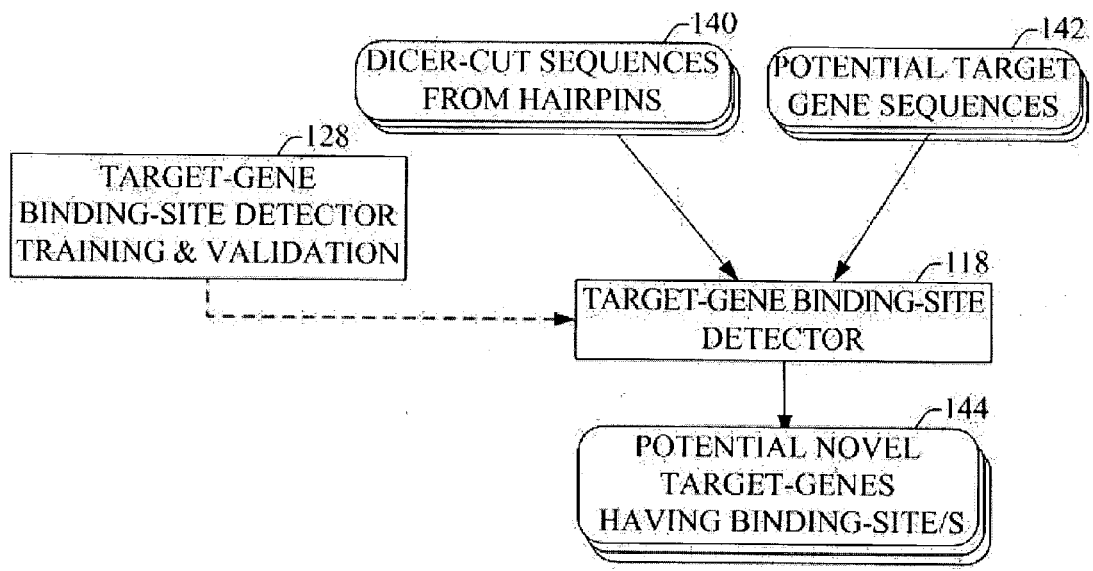
FIG. 14A is a simplified block diagram of a target-gene binding-site detector constructed and operative in accordance with a preferred embodiment of the present invention.

Reference is now made to FIG. 14A which is a simplified block diagram of a preferred implementation of the target-gene binding-site detector 118 described hereinabove with reference to FIG. 9. The goal of the target-gene binding-site detector 118 is to detect a BINDING SITE of FIG. 8, located in an untranslated region of the RNA of a known gene, the nucleotide sequence of which BINDING SITE is at least partially complementary to that of a GAM RNA of FIG. 8, thereby determining that the abovementioned known gene is a target gene of GAM of FIG. 8.

The target-gene binding-site detector 118 of FIG. 9 therefore receives as input a plurality of dicer-cut sequences from hairpins 140 of FIG. 13A which were calculated by the previous step, and a plurality of potential target gene sequences 142 which derive sequence DNA data 104 of FIG. 9, and after a phase of target-gene binding-site detector training & validation 128 of FIG. 10, is operative to detect target-genes having binding site/s 144 the nucleotide sequence of which is at least partially complementary to that of each of the plurality of dicer-cut sequences from hairpins 140. Preferred operation of the target-gene binding-site detector is further described hereinbelow with reference to FIG. 14B.

Figure 14B:
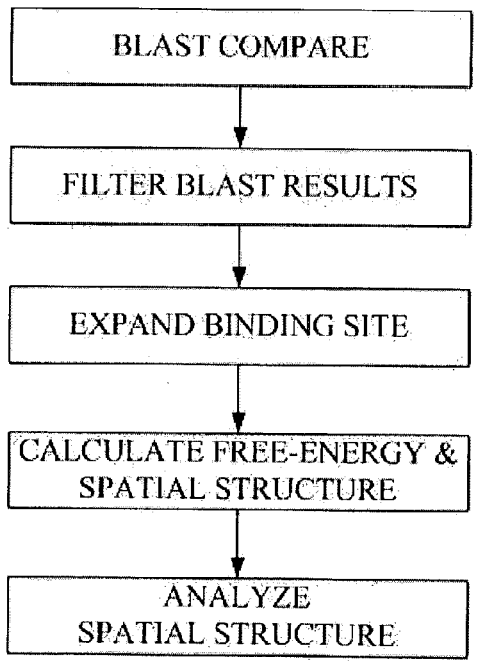
FIG. 14B is a simplified flowchart illustrating operation of a target-gene binding-site detector constructed and operative in accordance with a preferred embodiment of the present invention.

Reference is now made to FIG. 14B which is a simplified flowchart illustrating a preferred operation of the target-gene binding-site detector 118 of FIG. 9. In a preferred embodiment of the present invention, the target-gene binding-site detector 118 first performs a BLAST comparison of the nucleotide sequence of each of the plurality of dicer-cut sequences from hairpins 140, to the potential target gene sequences 142, in order to find crude potential matches. Blast results are then filtered to results which are similar to those of known binding sites (e.g. binding sites of miRNA genes Lin-4 and Let-7 to target genes Lin-14, Lin-41, Lin 28 etc.). Next the binding site is expanded, checking if nucleotide sequenced immediately adjacent to the binding site found by BLAST, may improve the match. Suitable binding sites, then are computed for free-energy and spatial structure. The results are analyzed, selecting only those binding sites, which have free-energy and spatial structure similar to that of known binding sites.

Figure 15:
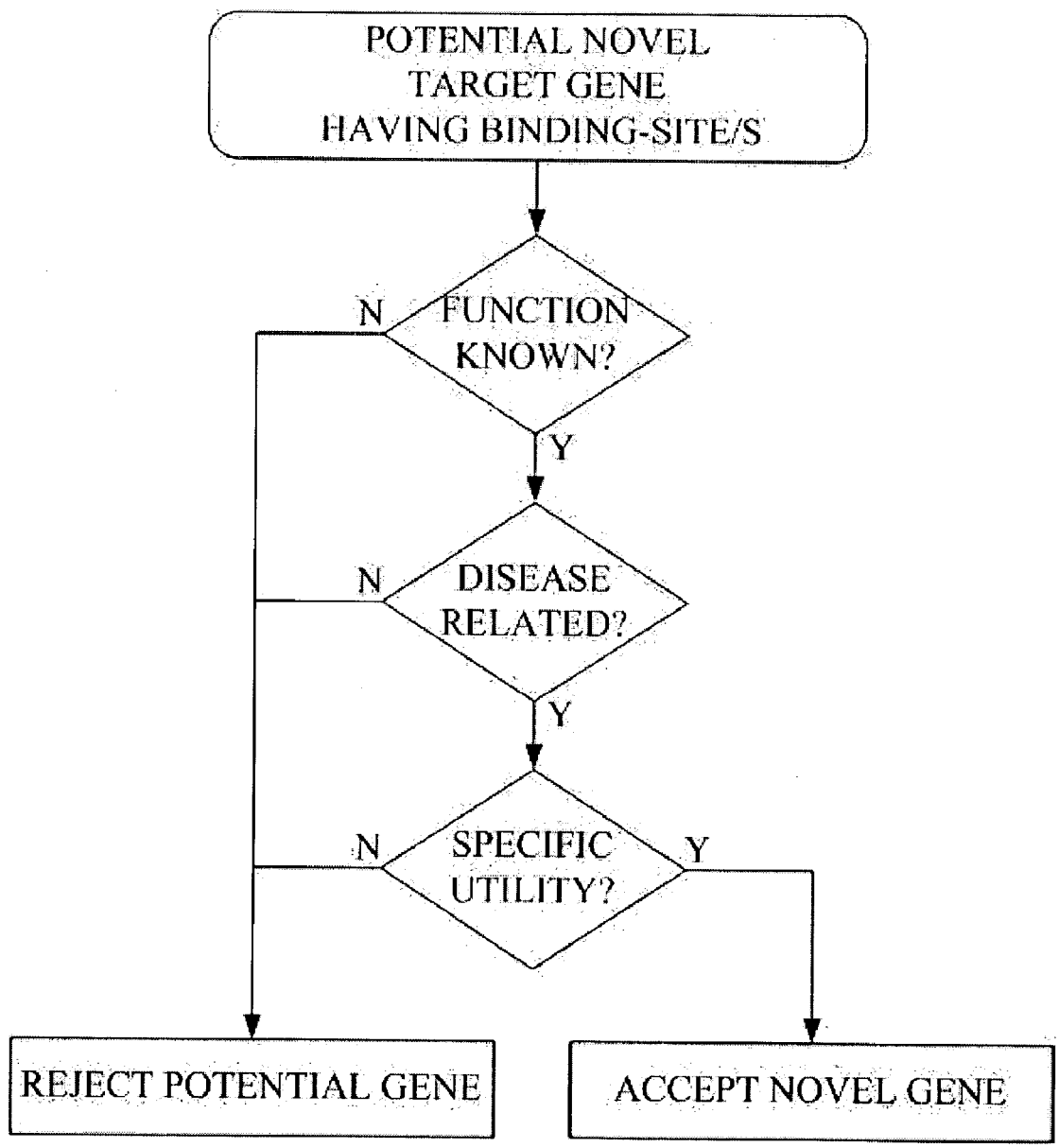
FIG. 15 is a simplified flowchart illustrating operation of a function & utility analyzer constructed and operative in accordance with a preferred embodiment of the present invention.

Reference is now made to FIG. 15 which is a simplified flowchart illustrating a preferred operation of the function & utility analyzer 120 described hereinabove with reference to FIG. 9. The goal of the function & utility analyzer 120 is to determine if a potential target gene is in fact a valid clinically useful target gene. Since a potential novel GAM gene binding a binding site in the UTR of a target gene is understood to inhibit expression of that target gene, and if that target gene is shown to have a valid clinical utility, then in such a case it follows that the potential novel gene itself also has a valid useful function—which is the opposite of that of the target gene.

The function & utility analyzer 120 preferably receives as input a plurality of potential novel target genes having binding-site/s 144, generated by the target-gene binding-site detector 118, both of FIG. 14A. Each potential gene, is evaluated as follows:

First the system first checks to see if the function of the potential target gene is scientifically well established. Preferably, this can be achieved bioinformatically by searching various published data sources presenting information on known function of proteins. Many such data sources exist and are published as is well known in the art.

Next, for those target genes the function of which is scientifically known and is well documented, the system then checks if scientific research data exists which links them to known diseases. For example, a preferred embodiment of the present invention utilizes the OMIM™ database published by NCBI, which summarizes research publications relating to genes which have been shown to be associated with diseases.

Finally, the specific possible utility of the target gene is evaluated. While this process too may be facilitated by bioinformatic means, it might require human evaluation of published scientific research regarding the target gene, in order to determine the utility of the target gene to the diagnosis and or treatment of specific disease. Only potential novel genes, the target-genes of which have passed all three examinations, are accepted as novel genes.

Figure 16:
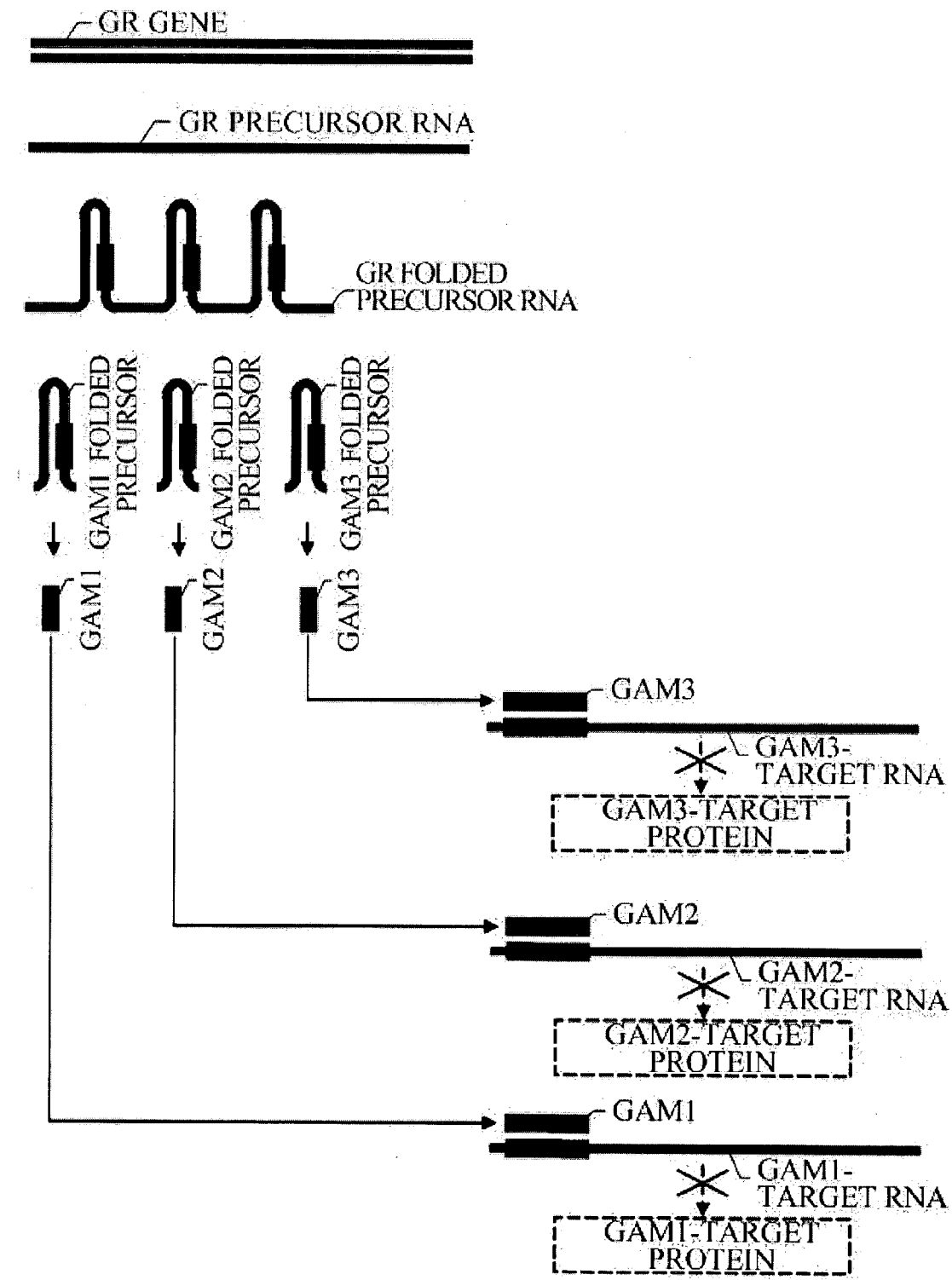
FIG. 16 is a simplified diagram describing a novel bioinformatically detected group of regulatory genes, referred to here as Genomic Record (GR) genes, each of which encodes an 'operon-like' cluster of novel miRNA-like genes, which in turn modulates expression of a plurality of target genes.

Reference is now made to FIG. 16, which is a simplified diagram describing a novel bioinformatically detected group of regulatory genes, referred to here as Genomic Record (GR) genes, that encode an 'operon-like' cluster of novel miRNA-like genes, each modulating expression of a plurality of target genes, the function and utility of which target genes is known.

GR GENE (Genomic Record Gene) is gene of a novel, bioinformatically detected group of regulatory, non protein coding, RNA genes. The method by which GR is detected is described hereinabove with reference to FIGS. 6-15.

GR GENE encodes an RNA molecule, typically several hundred nucleotides long, designated GR PRECURSOR RNA.

GR PRECURSOR RNA folds spatially, as illustrated by GR FOLDED PRECURSOR RNA, into a plurality of what is known in the art as 'hair-pin' structures. The nucleotide sequence of GR PRECURSOR RNA comprises a plurality of segments, the first half of each such segment having a nucleotide sequence which is at least a partial inversed-reversed sequence of the second half thereof, thereby causing formation of a plurality of 'hairpin' structures, as is well known in the art.

GR FOLDED PRECURSOR RNA is naturally processed by cellular enzymatic activity, into 3 separate hairpin shaped RNA segments, each corresponding to GAM PRECURSOR RNA of FIG. 8, designated GAM1 PRECURSOR, GAM2 PRECURSOR and GAM3 PRECURSOR respectively.

The above mentioned GAM precursors, are diced by Dicer of FIG. 8, yielding short RNA segments of about 22 nucleotides in length, each corresponding to GAM RNA of FIG. 8, designated GAM1, GAM2 and GAM3 respectively.

GAM1, GAM2 and GAM3 each bind complementarily to binding sites located in untranslated regions of respective target genes, designated GAM1-TARGET RNA, GAM2-TARGET RNA and GAM3-TARGET RNA respectively. This binding inhibits translation of the respective target proteins designated GAM1-TARGET PROTEIN, GAM2-TARGET PROTEIN and GAM3-TARGET PROTEIN respectively.

The structure of GAM genes comprised in a GR GENE, and their mode of modulation of expression of their respective target genes is described hereinabove with reference to FIG. 8. The bioinformatic approach to detection of GAM genes comprised in a GR GENE is described hereinabove with reference to FIGS. 9 through 15. The present invention discloses 147 novel genes of the GR group of genes, which have been detected bioinformatically, as described hereinbelow with reference to FIGS. 551 through 697. Laboratory confirmation of 3 genes of the GR group of genes is described hereinbelow with reference to FIGS. 21A through 23.

In summary, the current invention discloses a very large number of novel GR genes, each of which encodes a plurality of GAM genes, which in turn may modulate expression of a plurality of target proteins. It is appreciated therefore that the function of GR genes is in fact similar to that of the Genomic Records concept of the present invention addressing the differentiation enigma, described hereinabove with reference to FIG. 7.

Figure 17:
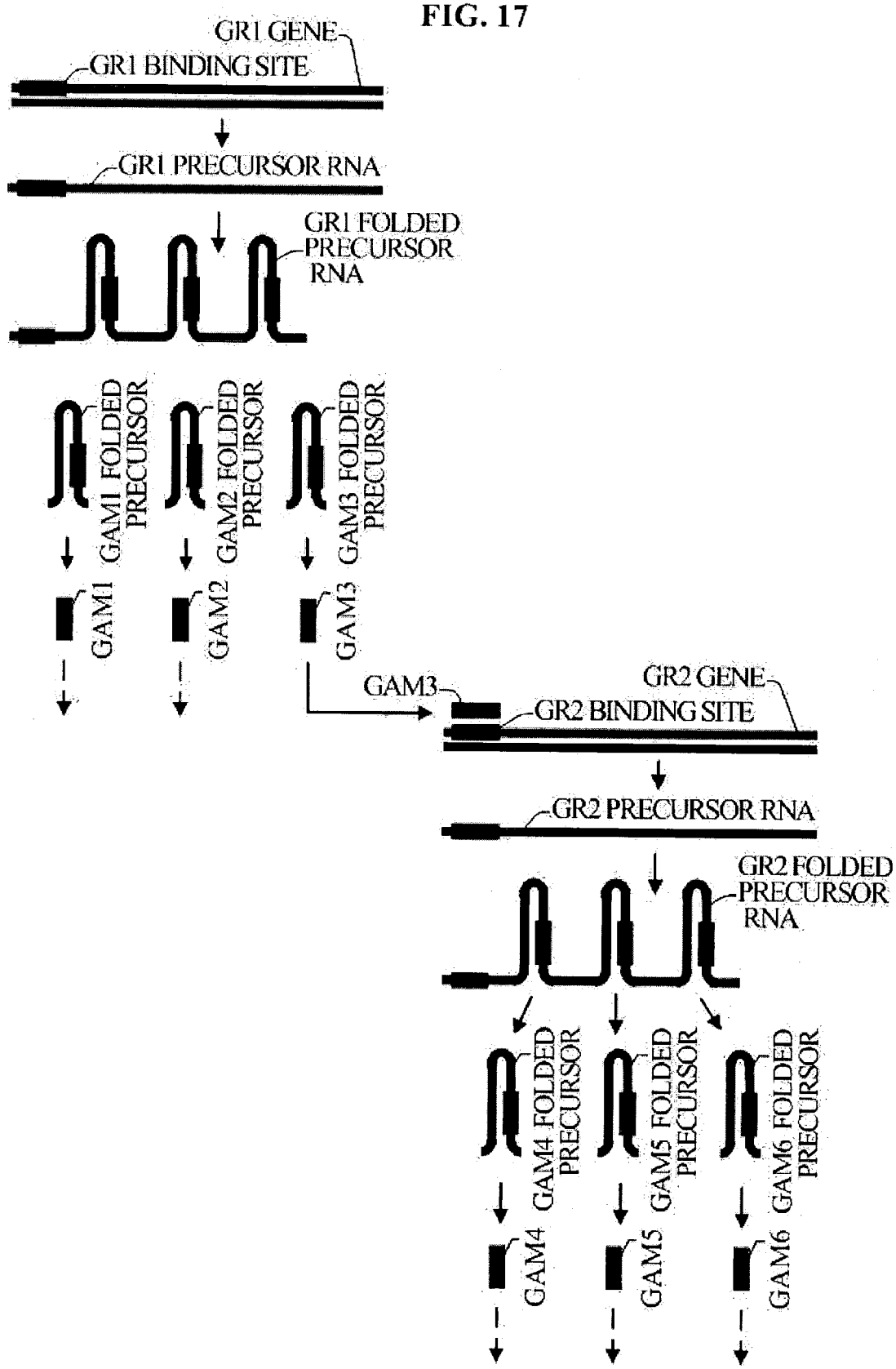
FIG. 17 is a simplified diagram illustrating a mode by which genes of a novel group of operon-like genes of the present invention, modulate expression of other such genes, in a cascading manner.

Reference is now made to FIG. 17 which is a simplified diagram illustrating a mode by which genes of a novel group of operon-like genes, described hereinabove with reference to FIG. 16 of the present invention, modulate expression of other such genes, in a cascading manner.

GR1 GENE and GR2 GENE are two genes of the novel group of operon-like genes designated GR of FIG. 16. As is typical of genes of the GR group of genes, GR1 and GR2 each encode a long RNA precursor, which in turn folds into a folded RNA precursor comprising multiple hairpin shapes, and is cut into respective separate hairpin shaped RNA segments, each of which RNA segments being diced to yield a gene of a group of genes designated GAM of FIG. 8. In this manner GR1 yields GAM1, GAM2 and GAM3, and GR2 yields GAM4, GAM5 and GAM6.

As FIG. 17 shows, GAM 3 which derives from GR1, binds a binding site located adjacent to GR2 GENE, thus modulating expression of GR2, thereby invoking expression of GAM4, GAM5 and GAM6 which derive from GR2.

It is appreciated that the mode of modulation of expression presented by FIG. 17 enables an unlimited 'cascading effect' in which a GR gene comprises multiple GAM genes, each of which may modulate expression of other GR genes, each such GR gene comprising additional GAM genes, etc., whereby eventually certain GAM genes modulate expression of target proteins. This mechanism is in accord with the conceptual model of the present invention addressing the differentiation enigma, described hereinabove with specific reference to FIGS. 6 and 7.

Figure 18:
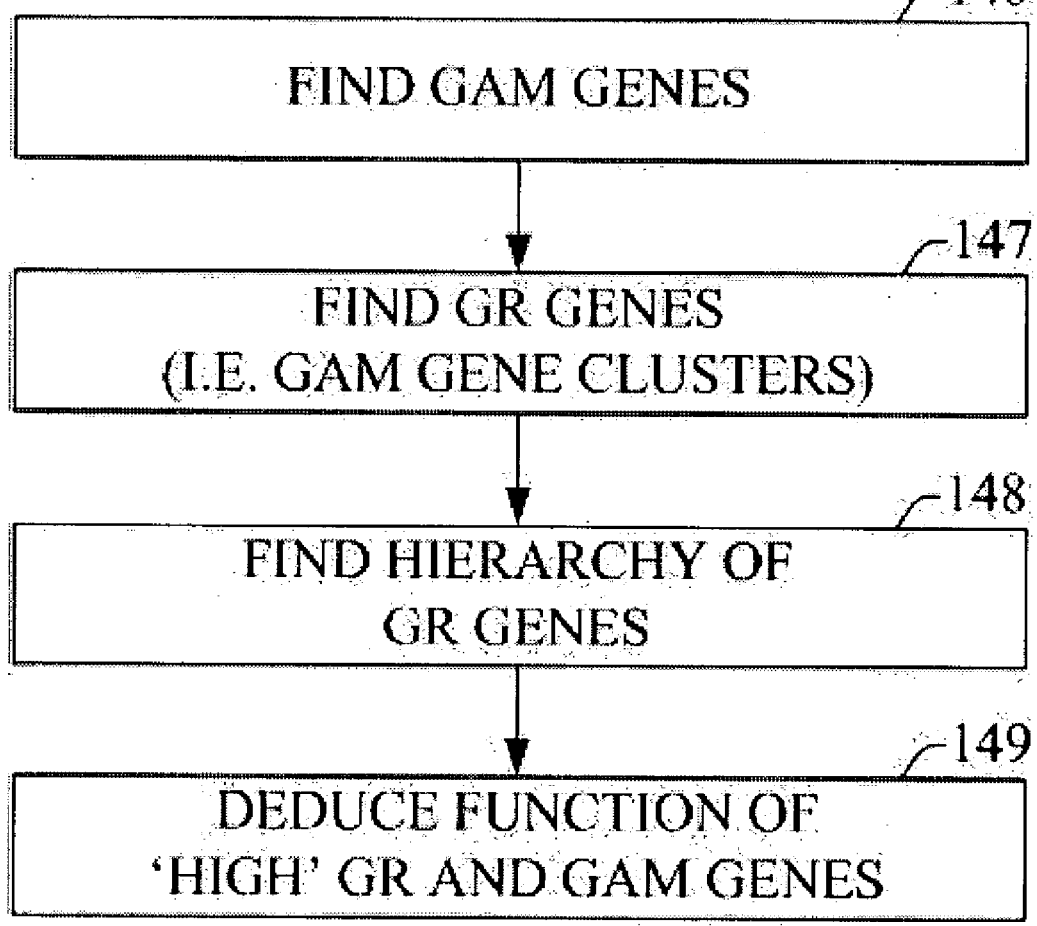
FIG. 18 is a block diagram illustrating an overview of a methodology for finding novel genes and operons of the present invention, and their respective functions.

Reference is now made to FIG. 18 which is a block diagram illustrating an overview of a methodology for finding novel genes and operon-like genes of the present invention, and their respective functions.

According to a preferred embodiment of the present invention, the methodology to finding novel genes of the present invention and their function comprises of the following major steps:

First, genes of the novel group of genes of the present invention, referred to here as GAM genes, are located and their function elicited by detecting target proteins they bind and the function of those target proteins, as described hereinabove with reference to FIGS. 9 through 15.

Next, genes of a novel group of operon-like genes of the present invention, referred to here as GR genes, are located, by locating clusters of proximally located GAM genes, based on the previous step.

Consequently, the hierarchy of GR and GAM genes is elicited: binding sites for non-protein-binding GAM genes comprised in each GR gene found are sought adjacent to other GR genes. When found, such a binding site indicates that the connection between the GAM and the GR the expression of which it modulates, and thus the hierarchy of the GR genes and the GAM genes they comprise.

Lastly, the function of GR genes and GAM genes which are 'high' in the hierarchy, i.e. GAM genes which modulate expression of other GR genes rather than directly modulating expression of target proteins, may be deduced. A preferred approach is as follows: The function of protein-modulating GAM genes is deducible from the proteins which they modulate, provided that the function of these target proteins is known. The function of 'higher' GAM genes may be deduced by comparing the function of protein-modulating GAM genes, with the hierarchical relationships by which the 'higher' GAM genes are connected to the protein-modulating GAM genes. For example, given a group of several protein-modulating GAM genes, which collectively cause a protein expression pattern typical of a certain cell-type, then a 'higher' GAM gene is sought which modulates expression of GR genes which perhaps modulate expression of other genes which eventually modulate expression of the given group of protein-modulating GAM genes. The 'higher' GAM gene found in this manner is taken to be responsible for differentiation of that cell-type, as per the conceptual model of the invention described hereinabove with reference to FIG. 6.

Figure 19:
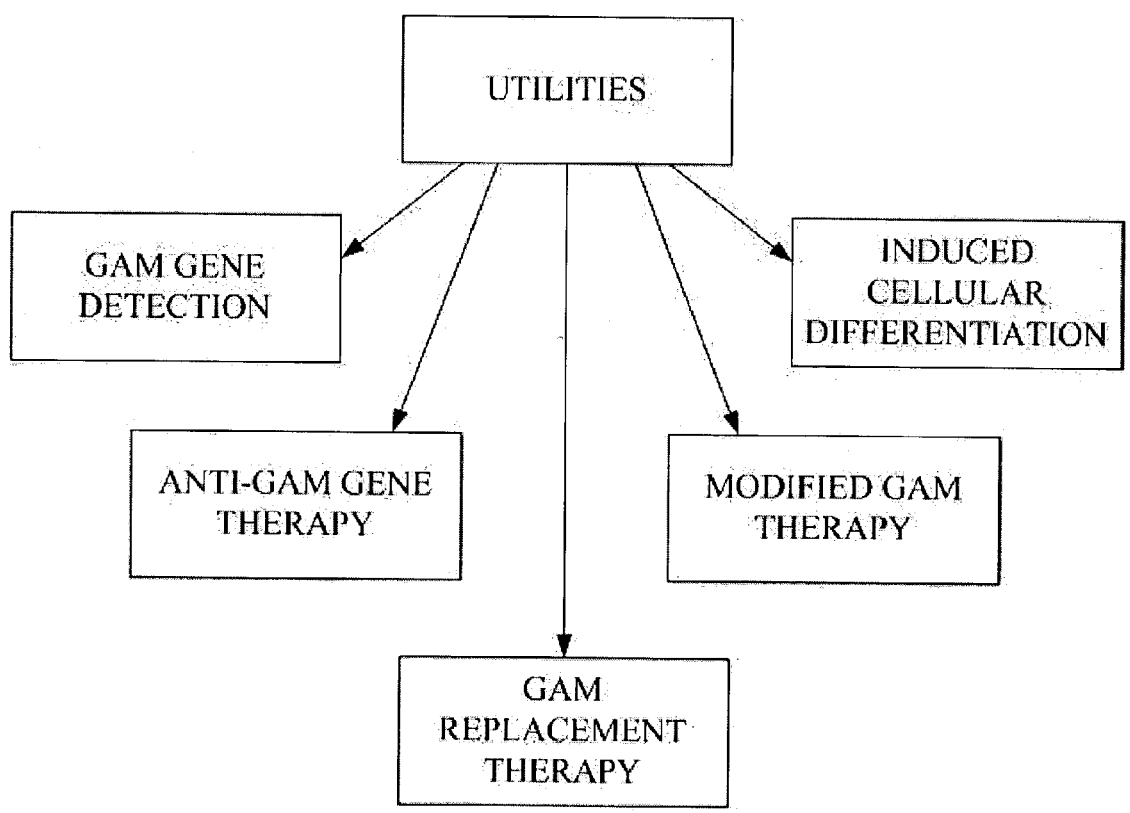
FIG. 19 is a block diagram illustrating different utilities of genes of a novel group of genes, and operons of a novel group of operons, both of the present invention.

Reference is now made to FIG. 19 which is a block diagram illustrating different utilities of genes of the novel group of genes of the present invention referred to here as GAM genes and GR genes.

The present invention discloses a first plurality of novel genes referred to here as GAM genes, and a second plurality of operon-like genes referred to here as GR genes, each of the GR genes encoding a plurality of GAM genes. The present invention further discloses a very large number of known target-genes, which are bound by, and the expression of which is modulated by each of the novel genes of the present invention. Published scientific data referenced by the present invention provides specific, substantial and credible evidence that the abovementioned target genes modulated by novel genes of the present invention, are associated with various diseases. Specific novel genes of the present invention, target genes thereof and diseases associated therewith, are described hereinbelow with reference to FIGS. 24 through 27260. It is therefore appreciated that a function of GAM genes and GR genes of the present invention is modulation of expression of target genes related to known diseases, and that therefore utilities of novel genes of the present invention include diagnosis and treatment of the abovementioned diseases. FIG. 19 describes various types of diagnostic and therapeutic utilities of novel genes of the present invention.

A utility of novel genes of the present invention is detection of GAM genes and of GR genes. It is appreciated that since GAM genes and GR genes modulate expression of disease related target genes, that detection of expression of GAM genes in clinical scenarios associated with said diseases is a specific, substantial and credible utility. Diagnosis of novel genes of the present invention may preferably be implemented by RNA expression detection techniques, including but not limited to biochips, as is well known in the art. Diagnosis of expression of genes of the present invention may be useful for research purposes, in order to further understand the connection between the novel genes of the present invention and the abovementioned related diseases, for disease diagnosis and prevention purposes, and for monitoring disease progress.

Another utility of novel genes of the present invention is anti-GAM gene therapy, a mode of therapy which allows up regulation of a disease related target-gene of a novel GAM gene of the present invention, by lowering levels of the novel GAM gene which naturally inhibits expression of that target gene. This mode of therapy is particularly useful with respect to target genes which have been shown to be under-expressed in association with a specific disease. Anti-GAM gene therapy is further discussed hereinbelow with reference to FIGS. 20A and 20B.

A further utility of novel genes of the present invention is GAM replacement therapy, a mode of therapy which achieves down regulation of a disease related target-gene of a novel GAM gene of the present invention, by raising levels of the GAM gene which naturally inhibits expression of that target gene. This mode of therapy is particularly useful with respect to target genes which have been shown to be over-expressed in association with a specific disease. GAM replacement therapy involves introduction of supplementary GAM gene products into a cell, or stimulation of a cell to produce excess GAM gene products. GAM replacement therapy may preferably be achieved by transfecting cells with an artificial DNA molecule encoding a GAM gene, which causes the cells to produce the GAM gene product, as is well known in the art.

Yet a further utility of novel genes of the present invention is modified GAM therapy. Disease conditions are likely to exist, in which a mutation in a binding site of a GAM gene prevents natural GAM gene to effectively bind inhibit a disease related target-gene, causing up regulation of that target gene, and thereby contributing to the disease pathology. In such conditions, a modified GAM gene is designed which effectively binds the mutated GAM binding site, i.e. is an effective anti-sense of the mutated GAM binding site, and is introduced in disease effected cells. Modified GAM therapy is preferably achieved by transfecting cells with an artificial DNA molecule encoding the modified GAM gene, which causes the cells to produce the modified GAM gene product, as is well known in the art.

An additional utility of novel genes of the present invention is induced cellular differentiation therapy. As aspect of the present invention is finding genes which determine cellular differentiation, as described hereinabove with reference to FIG. 18. Induced cellular differentiation therapy comprises transfection of cell with such GAM genes thereby determining their differentiation as desired. It is appreciated that this approach may be widely applicable, inter alia as a means for auto transplantation—harvesting cells of one cell-type from a patient, modifying their differentiation as desired, and then transplanting them back into the patient. It is further appreciated that this approach may also be utilized to modify cell differentiation in vivo, by transfecting cells in a genetically diseased tissue with a cell-differentiation determining GAM gene, thus stimulating these cells to differentiate appropriately.

Figure 20A:
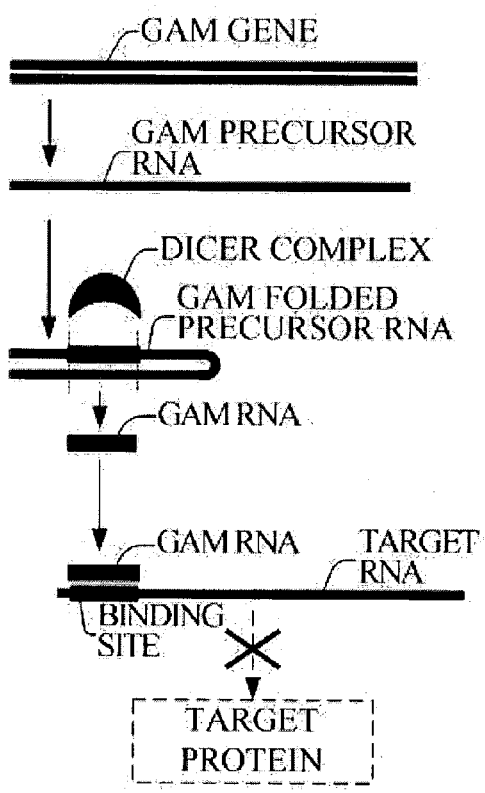
FIGS. 20A and 20B are simplified diagrams, which when taken together illustrate a mode of gene therapy applicable to genes of the novel group of genes of the present invention.
Figure 20B:
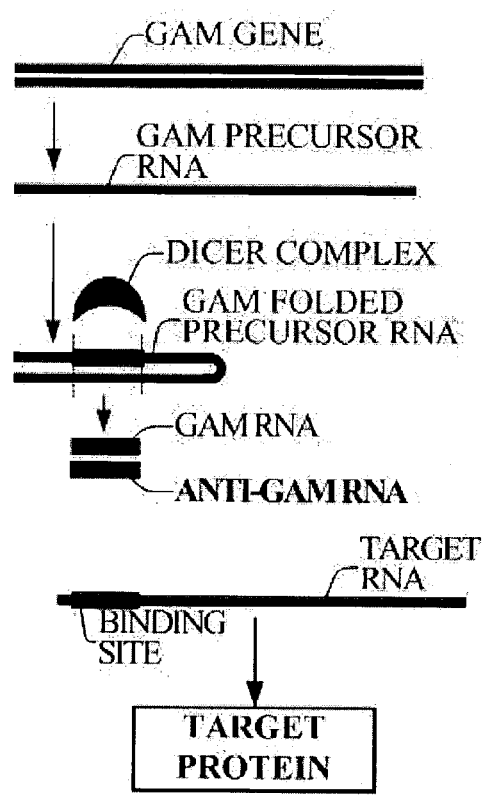

Reference is now made to FIGS. 20A and 20B, simplified diagrams which when taken together illustrate anti-GAM gene therapy mentioned hereinabove with reference to FIG. 19. A utility of novel genes of the present invention is anti-GAM gene therapy, a mode of therapy which allows up regulation of a disease related target-gene of a novel GAM gene of the present invention, by lowering levels of the novel GAM gene which naturally inhibits expression of that target gene. FIG. 20A shows a normal GAM gene, inhibiting translation of a target gene of GAM gene, by binding to a BINDING SITE found in an untranslated region of TARGET RNA, as described hereinabove with reference to FIG. 8.

FIG. 20B shows an example of anti-GAM gene therapy. ANTI-GAM RNA is short artificial RNA molecule the sequence of which is an anti-sense of GAM RNA. Anti-GAM treatment comprises transfecting diseased cells with ANTI-GAM RNA, or with a DNA encoding thereof. The ANTI-GAM RNA binds the natural GAM RNA, thereby preventing binding of natural GAM RNA to its BINDING SITE. This prevents natural translation inhibition of TARGET RNA by GAM RNA, thereby up regulating expression of TARGET PROTEIN.

It is appreciated that anti-GAM gene therapy is particularly useful with respect to target genes which have been shown to be under-expressed in association with a specific disease.

Reference is now made to FIG. 21A which is an annotated sequence of an EST comprising a novel gene detected by the gene detection system of the present invention. FIG. 21A shows the nucleotide sequence of a known human non-protein coding EST (Expressed Sequence Tag), identified as EST72223. It is appreciated that the sequence of this EST comprises sequences of one known miRNA gene, identified as MIR98, and of one novel GAM gene, referred to here as GAM24, detected by the bioinformatic gene detection system of the present invention, described hereinabove with reference to FIG. 9.

Reference is now made to FIGS. 21B and 21C that are pictures of laboratory results, which when taken together demonstrate laboratory confirmation of expression of the bioinformatically detected novel gene of FIG. 21A. Reference is now made to FIG. 21B which is a Northern blot analysis of MIR-98 and EST72223 transcripts. MIR-98 and EST72223 were reacted with MIR-98 and GAM24 probes as indicated in the figure. It is appreciated that the probes of both MIR-98 and GAM24 reacted with EST72223, indicating that EST72223 contains the sequences of MIR-98 and of GAM24. It is further appreciated that the probe of GAM24 does not cross-react with MIR-98.

Reference is now made to FIG. 21C. A Northern blot analysis of EST72223 and MIR-98 transfections were performed, subsequently marking RNA by the MIR-98 and GAM24 probes. Left, Northern reacted with MIR-98, Right, Northern reacted with GAM24. The molecular Sizes of EST72223, MIR-98 and GAM24 are indicated by arrows. Hela are control cells that have not been introduced to exogenous RNA. EST and MIR-98 Transfections are RNA obtained from Hela transfected with EST72223 and MIR-98, respectively. MIR-98 and EST are the transcripts used for the transfection experiment. The results indicate that EST72223, when transfected into Hela cells, is cut yielding known miRNA gene MIR-98 and novel miRNA gene GAM24.

Reference is now made to FIG. 21D, which is a Northern blot of a lisate experiment with MIR-98 and GAM24. Northern blot analysis of hairpins in EST72223. Left, Northern reacted with predicted Mir-98 hairpin probe. Right, Northern reacted with predicted GAM24 hairpin probe. The molecular size of EST is indicated by arrow. The molecular sizes of Mir-98 and GAM24 are 80 nt and 100 nt, respectively as indicated by arrows. The 22 nt molecular marker is indicated by arrow. 1-Hela lysate; 2-EST incubated 4 h with Hela lysate; 3-EST without lysate; 4-Mir transcript incubated 4 h with Hela lysate; 5-Mir transcript incubated overnight with Hela lysate; 6-Mir transcript without lysate; 7-RNA extracted from Hela cells following transfection with Mir transcript.

Technical methods used in experiments, the results of which are depicted in FIGS. 21B, 21C and 21D are as follows:

Transcript preparations: Digoxigenin (DIG) labeled transcripts were prepared from EST72223 (TIGER), MIR98 and predicted precursor hairpins by using a DIG RNA labeling kit (Roche Molecular Biochemicals) according to the manufacture's protocol. Briefly, PCR products with T7 promoter at the 5' end or T3 promoter at the 3'end were prepared from each DNA in order to use it as a template to prepare sense and antisense transcripts, respectively.

MIR-98 was amplified using EST72223 as a template with T7 miR98 forward primer:
5-'TAATACGACTCACTATAGGGTGAGGTAG-TAAGTTGTATTGTT-3' (SEQ ID NO: 1388406) and T3miR98 reverse primer:
5'-AATTAACCCTCACTAAAGGGAAAGTAG-TAAGTTGTATAGTT-3' (SEQ ID NO: 1388407) EST72223 was amplified with T7-EST 72223 forward primer:
5'-TAATACGACTCACTATAGGCCCTTATTA-GAGGATTCTGCT-3' (SEQ ID NO: 1388408) and T3-EST72223 reverse primer:
5'-AATTAACCCTCACTAAAG-GTTTTTTTTTCCTGAGACAGAGT-3'
(SEQ ID NO: 1388409) Bet-4 was amplified using EST72223 as a template with Bet-4 forward primer: 5'-GAGGCAGGAGAATTGCTTGA-3' (SEQ ID NO: 1388410) and T3-EST7223 reverse primer:
5'-AATTAACCCTCACTAAAGGCCTGAGACA-GAGTCTTGCTC-3' (SEQ ID NO: 1388411)

The PCR products were cleaned and used for DIG-labeled or unlabeled transcription reactions with the appropriate polymerase. For transfection experiments, CAP reaction was performed by using a mMassage mMachine kit (Ambion).

Transfection procedure: Transfection of Hela cells was performed by using TransMessenger reagent (Qiagen) according to the manufacture's protocol. Briefly, Hela cells were seeded to 1-2×10^6 cells per plate a day before transfection. Two μg RNA transcripts were mixed with 8 μl Enhancer in a final volume of 100 μl, mixed and incubated at room temperature for 5 min. 16 μl TransMessenger reagent was added to the RNA-Enhancer, mixed and incubated for additional 10 min. Cell plates were washed with sterile PBS twice and then incubated with the transfection mix with 2.5 ml DMEM medium without serum. Cells were incubated with transfection mix for three hours under their normal growth condition (370 C and 5% CO2) before the transfection mix was removed and a fresh DMEM medium containing serum was added to the cells. Cells were left to grow 48 hours before harvesting.

Target RNA cleavage assay: Cap-labeled target RNAs were generated using mMessage mMachine™ (Ambion). Caped RNA transcripts were preincubated at 30° C. for 15 min in supplemented Hela S100 obtained from Computer Cell Culture, Mos, Belgium. After addition of all components, final concentrations were 100 mM target RNA, 1 m M ATP, 0.2 mM GTP, 10 U/ml RNasin, 30 μg/ml creatine kinase, 25 mM creatine phosphate, and 50% S100 extract. Incubation was continued for 4 hours to overnight. Cleavage reaction was stopped by the addition of 8 volumes of proteinase K buffer (200 Mm Tris-Hcl, pH 7.5, 25 m M EDTA, 300 mM NaCl, and 2% SDS). Proteinase K, dissolved in 50 mM Tris-HCl, pH 8, 5 m M CaCl2, and 50% glycerol, was added to a final concentration of 0.6 mg/ml. Sample were subjected to phenol/chloroform extraction and kept frozen until analyzed by urea-TBE PAGE.

Northern analysis: RNAs were extracted from cells by using Tri-reagent according to the manufacture's protocol. The RNAs were dissolved in water and heated to 650 C to disrupt any association of the 25 nt RNA with larger RNA molecules. RNA were placed on ice and incubated for 30 min with PEG (MW=8000) in a final concentration of 5% and NaCl in a final concentration of 0.5M to precipitate high molecular weight nucleic acid. The RNAs were centrifuged at 10,000×g for 10 min to pellet the high molecular weight nucleic acid. The supernatant containing the low molecular weight RNAs was collected and three volumes of ethanol was added. The RNAs were placed at −200 C for at least two hours and then centrifuged at 10,000×g for 10 min. The pellets were dissolved in Urea-TBE buffer (1Xtbe, 7M urea) for further analysis by a Northern blot.

RNA samples were boiled for 5 min before loading on 15%-8% polyacrylamide (19:1) gels containing 7M urea and 1×TBE. Gels were run in 1×TBE at a constant voltage of 300V and then transferred into a nylon membrane. The membrane was exposed to 3 min ultraviolet light to cross link the RNAs to the membrane. Hybridization was performed overnight with DIG-labeled probes at 420 C. Membranes were washed twice with SSC×2 and 0.2% SDS for 10 min. at 420 C and then washed twice with SSC×0.5 for 5 min at room temperature. The membrane was then developed by using a DIG luminescent detection kit (Roche) using anti DIG and CSPD reaction, according to the manufacture's protocol.

It is appreciated that the data presented in FIGS. 21B, 21C and 21D, when taken together validate the function of the bioinformatic gene detection engine 100 of FIG. 9. FIG. 21A shows a novel GAM gene bioinformatically detected by the bioinformatic gene detection engine 100, and FIGS. 21B, 21C and 21D show laboratory confirmation of the expression of this novel gene. This is in accord with the engine training and validation methodology described hereinabove with reference to FIG. 10.

Reference is now made to FIG. 22A which is an annotated sequence of an EST comprising a novel gene detected by the gene detection system of the present invention. FIG. 22A shows the nucleotide sequence of a known human non-protein coding EST (Expressed Sequence Tag), identified as EST 7929020. It is appreciated that the sequence of this EST comprises sequences of two novel GAM genes, referred to here as GAM23 and GAM25, detected by the bioinformatic gene detection system of the present invention, described hereinabove with reference to FIG. 9.

Reference is now made to FIG. 22B which presents pictures of laboratory results that demonstrate laboratory confirmation of expression of the bioinformatically detected novel gene of FIG. 22A. Northern blot analysis of hairpins in EST7929020. Left, Northern reacted with predicted GAM25 hairpin probe, Right, Northern reacted with predicted GAM23 hairpin probe. The molecular size of EST is indicated by arrow. The molecular sizes of GAM23 and GAM25 are 60 nt, as indicated by arrow. The 22 nt molecular marker is indicated by arrow. 1-Hela lysate; 2-EST incubated 4 h with Hela lysate; 3-EST incubated overnight with Hela lysate; 4-EST without lysate; 5-GAM transcript; 6-GAM 22 nt marker; 7-GAM PCR probe; 8-RNA from control Hela cells; 9-RNA extracted from Hela cells following transfection with EST.

Figure 22C:
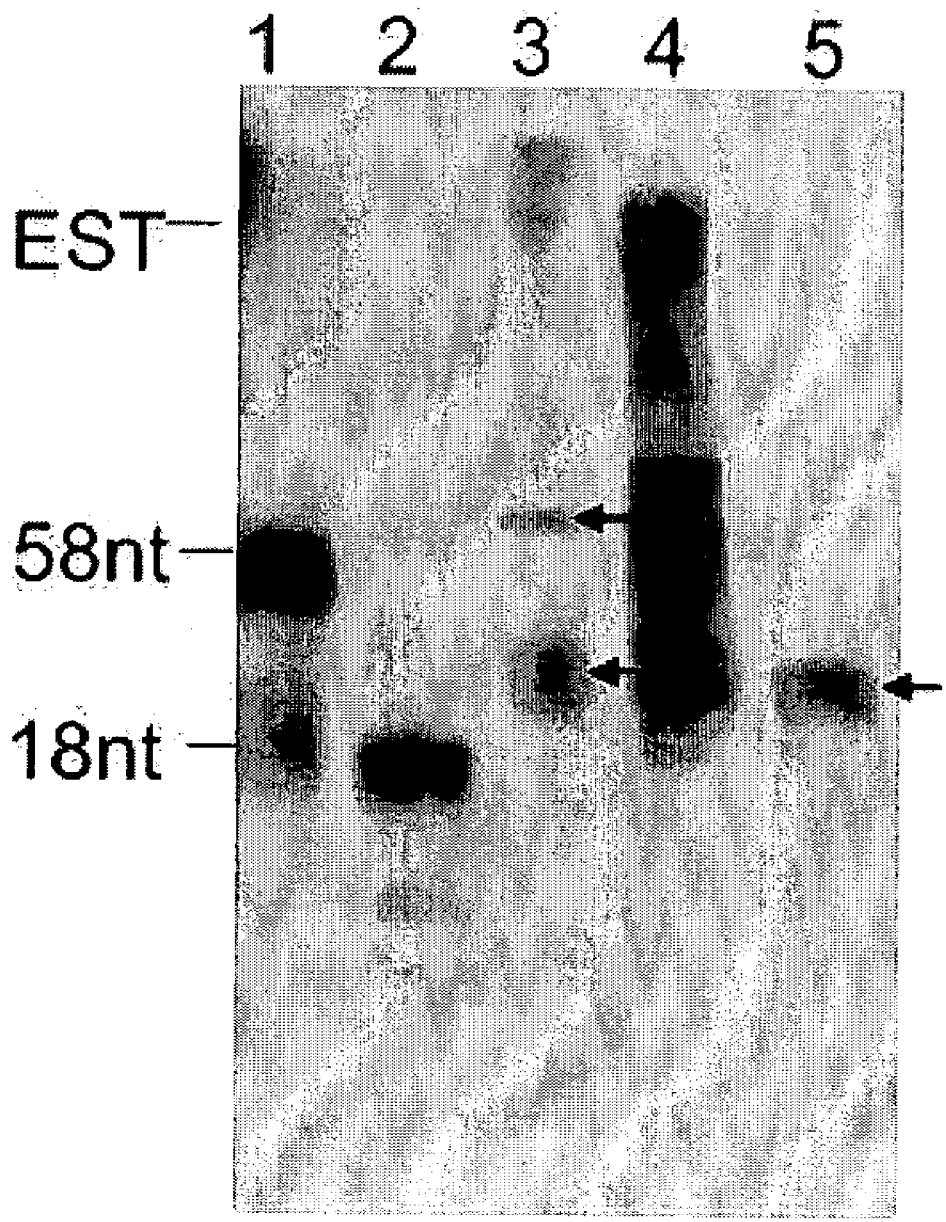
FIG. 22C is a picture of laboratory results, which confirm endogenous expression of bioinformatically detected novel gene GAM25 of FIG. 22A.

Reference is now made to FIG. 22C which is a picture of a Northern blot confirming Endogenous expression of bio-informatically detected gene GAM25 of FIG. 22A from in Hela cells. Northern was reacted with a predicted GAM25 hairpin probe. The molecular size of EST7929020 is indicated. The molecular sizes of GAM25 are 58 nt, as indicated. A 19 nt DNA oligo molecular marker is indicated. Endogenous expression of GAM25 in Hela total RNA fraction and in S-100 fraction is indicated by arrows. 1-GAM25 transcript; 2-GAM25 DNA oligo marker; 3-RNA from control Hela cells; 4-RNA extracted from Hela cells following transfection with EST; 5-RNA extracted from S-100 Hela lysate.

Reference is now made to FIG. 23A which is an annotated sequence of an EST comprising a novel gene detected by the gene detection system of the present invention. FIG. 23A shows the nucleotide sequence of a known human non-protein coding EST (Expressed Sequence Tag), identified as EST 1388749. It is appreciated that the sequence of this EST comprises sequence of a novel GAM gene, referred to here as GAM26, detected by the bioinformatic gene detection system of the present invention, described hereinabove with reference to FIG. 9.

Reference is now made to FIG. 23B which is a picture of Northern blot analysis, confirming expression of novel bioinformatically detected gene GAM26, and natural processing thereof from EST1388749. Northern reacted with predicted GAM26 hairpin probe. The molecular size of EST is indicated by arrow. The molecular sizes of GAM26 are 130 nt, as indicated by arrow. The 22 nt molecular marker is indicated by arrow. 1-Hela lysate; 2-EST incubated 4 h with Hela lysate; 3-EST incubated overnight with Hela lysate; 4-EST without lysate; 5-GAM transcript; 6-GAM 22 nt marker; 7-GAM PCR probe.

Figures 24A, 24B, 24C:
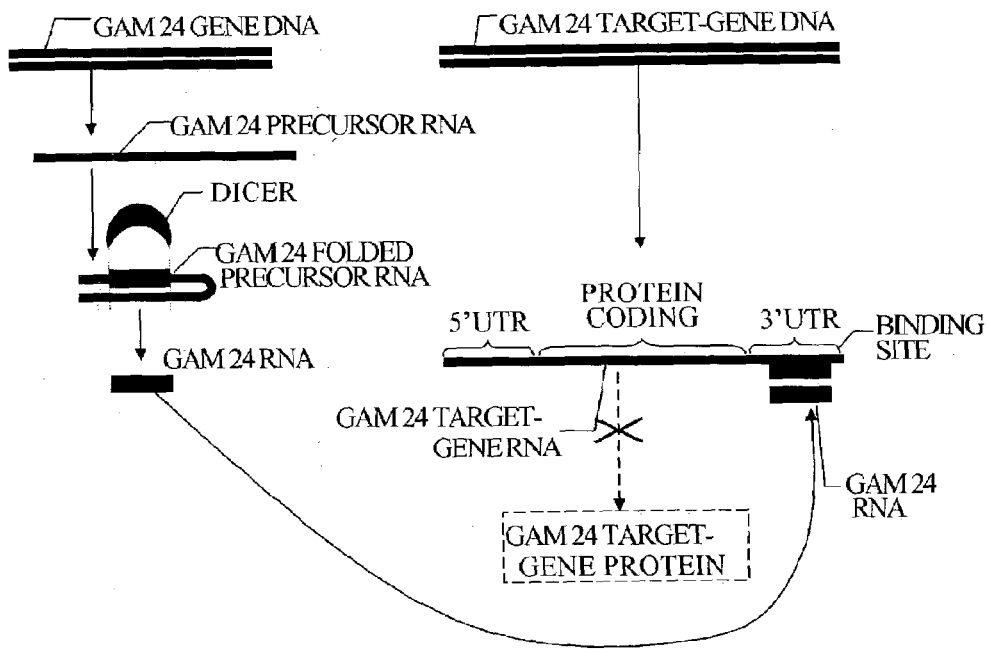

Reference is now made to FIG. 24A, which is a simplified diagram providing a conceptual explanation of the mode by which a novel bioinformatically detected gene, referred to here as GAM24 modulates expression of target genes thereof, the function and utility of which target genes is known in the art.

GAM24 (Genomic Address Messenger 24) is a novel bioinformatically detected regulatory, non protein coding, micro RNA (miRNA) gene. The method by which GAM24 was detected is described hereinabove with reference to FIGS. 6-15.

GAM24 GENE and GAM24-TARGET GENE are two human genes contained in the human genome.

GAM24 GENE encodes a GAM24 PRECURSOR RNA. Similar to other miRNA genes, and unlike most ordinary genes, the RNA transcribed by GAM24, GAM24 PRECURSOR RNA, does not encode a protein.

GAM24 PRECURSOR RNA folds onto itself, forming GAM24 FOLDED PRECURSOR RNA. As FIG. 24 illustrates, GAM24 FOLDED PRECURSOR RNA forms a 'hairpin structure', folding onto itself. As is well known in the art, this 'hairpin structure', is typical of RNA encoded by miRNA genes, and is due to the fact that the nucleotide sequence of the first half of the RNA encoded by a miRNA gene is an accurate or partial inversed-reversed sequence of the nucleotide sequence of the second half thereof, By "inversed-reversed" is meant a sequence which is reversed and wherein each nucleotide is replaced by a complimentary nucleotide, as is well known in the art (e.g. ATGGC is the inversed-reversed sequence of GCCAT).

An enzyme complex designated DICER COMPLEX, 'dices' the GAM24 FOLDED PRECURSOR RNA into a single stranded ~22 nt long RNA segment, designated GAM24 RNA. As is known in the art, 'dicing' of a hairpin structured RNA precursor product into short a ~22 nt RNA segment is catalyzed by an enzyme complex comprising an enzyme called Dicer together with other necessary proteins.

GAM24-TARGET GENE encodes a corresponding messenger RNA, designated GAM24-TARGET RNA. GAM24-TARGET RNA comprises three regions, as is typical of mRNA of a protein coding gene: a 5' untranslated region, a protein coding region and a 3' untranslated region, designated 5'UTR, PROTEIN CODING and 3'UTR respectively.

GAM24 RNA binds complimentarily to a BINDING SITE, located on an untranslated region of GAM24-TARGET RNA. This complimentarily binding is due to the fact that the nucleotide sequence of GAM24 RNA is an accurate or a partial inversed-reversed sequence of the nucleotide sequence of BINDING SITE. It is appreciated that while FIG. 24A depicts the BINDING SITE on the 3'UTR region, this is meant as an example only—the BINDING SITE may be located on the 5'UTR region as well.

The complimentary binding of GAM24 RNA to BINDING SITE inhibits translation of GAM24-TARGET RNA into GAM24-TARGET PROTEIN GAM24-TARGET PROTEIN is therefore outlined by a broken line.

It is appreciated that GAM24-TARGET GENE in fact represents a plurality of target genes of GAM24. The mRNA of each of this plurality of target genes of GAM24 comprises a BINDING SITE, having a nucleotide sequence which is at least partly complementary to GAM24 RNA, and which when bound by GAM24 RNA causes inhibition of translation one of a plurality of target proteins of GAM24. The plurality of target genes of GAM24 and their respective binding sites are described hereinbelow with reference to FIG. 24D.

It is appreciated by one skilled in the art that the mode of translational inhibition illustrated by FIG. 24 with specific reference to translational inhibition exerted by GAM24 on one or more target genes of GAM24 is in fact common to other known miRNA genes. As mentioned hereinabove with reference to the background section, although a specific complimentary binding site has been demons only for miRNA genes Lin-4 and Let-7, all other recently discovered miRNA genes are also believed by those skilled in the art to modulate expression of other genes by complimentary binding, although specific complimentary binding sites of these genes have not yet been found (Ruvkun G., 'Perspective: Glimpses of a tiny RNA world', Science 294, 779 (2001)).

Reference is now made to FIG. 24B which shows the nucleotide sequence of GAM24 PRECURSOR RNA of FIG. 24A, designated SEQ ID:1, and a probable nucleotide sequence of GAM24 RNA of FIG. 24A, designated SEQ ID:20602. The nucleotide sequence of SEQ ID:20602, which is highly likely (over 0.878955%) to be identical or highly similar to that of GAM24, is marked by an underline within the sequence of GAM24 PRECURSOR RNA.

Reference is now made to FIG. 24C, which shows the secondary folding of GAM24 PRECURSOR RNA, forming a 'hairpin structure' designated GAM24 FOLDED PRECURSOR RNA, both of FIG. 24A. A probable (>0.878955%) nucleotide sequence of GAM24 RNA, designated SEQ ID:20602 of FIG. 24B, is marked by an underline on GAM24 FOLDED PRECURSOR RNA. It is appreciated that the complimentary base-paring is not perfect, with 'bulges', as is well known in the art with respect to the RNA folding of all known miRNA genes.

Reference is now made to FIG. 24D, which is a table showing binding sites found in untranslated regions of a plurality of target genes of GAM24, each binding site corresponding to BINDING SITE of FIG. 24A, and their complementarity to SEQ ID:20602, which is highly likely (>0.878955%) to be identical or highly similar to the nucleotide sequence of GAM24 RNA of FIG. 24A.

It is appreciated that the functions, and accordingly the utilities, of GAM24 correlate with, and may be deduced from, the identity of the target genes which GAM24 binds and inhibits, and the function of these target genes, as elaborated hereinbelow.

Reference is now made to DCLRE1A BINDING SITE. DCLRE1A is a target gene of GAM24, corresponding to GAM24-TARGET GENE of FIG. 24A. DCLRE1A BINDING SITE is a binding site found in an untranslated region of DCLRE1A, corresponding to BINDING SITE of FIG. 24A. FIG. 24D illustrates the complementarity of the nucleotide sequence of DCLRE1A BINDING SITE, designated SEQ ID:507529, to the nucleotide sequence of GAM24 RNA of FIG. 24A, designated SEQ ID:20602 a function of GAM24 is therefore inhibition of (DCLRE1A). Accordingly, utilities of GAM24 include diagnosis and treatment diseases and clinical conditions with which DCLRE1A is associated.

Reference is now made to DKFZP586I2223 BINDING SITE. DKFZP586I2223 is a target gene of GAM24, corresponding to GAM24-TARGET GENE of FIG. 24A. DKFZP586I2223 BINDING SITE is a binding site found in an untranslated region of DKFZP586I223, corresponding to BINDING SITE of FIG. 24A. FIG. 24D illustrates the complementarity of the nucleotide sequence of DKFZP586I2223 BINDING SITE, designated SEQ ID:534456, to the nucleotide sequence of GAM25 RNA of FIG. 24A, designated SEQ ID:20602. Yet another function of GAM24 is therefore inhibition of (DKFZP586I2223). Accordingly, utilities of GAM24 include diagnosis and treatment of diseases and clinical conditions with which DKFZP586I2223 is associated.

Reference is now made to FLJ13725 BINDING SITE. FLJ13725 is a target gene of GAM24, corresponding to GAM24-TARGET GENE of FIG. 24A. FLJ13725 BINDING SITE is a binding site found in an untranslated region of FLJ13725, corresponding to BINDING SITE of FIG. 24A. FIG. 24D illustrates the complementarity of the nucleotide sequence of FLJ13725 BINDING SITE, designated SEQ ID:604594, to the nucleotide sequence of GAM24 RNA of FIG. 24A, designated SEQ ID:20602. An additional function of GAM24 is therefore inhibition of (FLJ13725). Accordingly, utilities of GAM24 include diagnosis and treatment of diseases and clinical conditions with which FLJ13725 is associated.

Reference is now made to PASK BINDING SITE. PASK is a target gene of GAM24, corresponding to GAM24-TARGET GENE of FIG. 24A. PASK BINDING SITE is a binding site found in an untranslated region of PASK, corresponding to BINDING SITE of FIG. 24A. FIG. 24D illustrates the complementarity of the nucleotide sequence of PASK BINDING SITE, designated SEQ ID:907327, to the nucleotide sequence of GAM24 RNA of FIG. 24A, designated SEQ ID:20602. A further function of GAM24 is therefore inhibition of (PASK). Accordingly, utilities of GAM24 include diagnosis and treatment of diseases and clinical conditions with which PASK is associated.

Reference is now made to TIGD5 BINDING SITE. TIGD5 is a target gene of GAM24, corresponding to GAM24-TARGET GENE of FIG. 24A. TIGD5 BINDING SITE is a binding site found in an untranslated region of TIGD5, corresponding to BINDING SITE of FIG. 24A FIG. 24D illustrates the complementarity of the nucleotide sequence of TIGD5 BINDING SITE, designated SEQ ID:993571, to the nucleotide sequence of GAM24 RNA of FIG. 24A, designated SEQ ID:20602. Yet a further function of GAM24 is therefore inhibition of (TIGD5). Accordingly, utilities of GAM24 include diagnosis and treatment of diseases and clinical conditions with which TIGD5 is associated.

Reference is now made to LOC151556 BINDING SITE. LOC151556 is a target gene of GAM24, corresponding to GAM24-TARGET GENE of FIG. 24A. LOC151556 BINDING SITE is a binding site found in an untranslated region of LOC151556, corresponding to BINDING SITE of FIG. 24A. FIG. 24D illustrates the complementarity of the nucleotide sequence of LOC151556 BINDING SITE, designated SEQ ID:1151343, to the nucleotide sequence of GAM24 RNA of FIG. 24A, designated SEQ ID:20602. Another function of GAM24 is therefore inhibition of (LOC151556). Accordingly, utilities of GAM24 include diagnosis and treatment of diseases and clinical conditions with which LOC151556 is associated.

Reference is now made to LOC196812 BINDING SITE. LOC196812 is a target gene of GAM24, corresponding to GAM24-TARGET GENE of FIG. 24A. LOC196812 BINDING SITE is a binding site found in an untranslated region of LOC196812, corresponding to BINDING SITE of FIG. 24A. FIG. 24D illustrates the complementarity of the nucleotide sequence of LOC196812 BINDING SITE, designated SEQ ID:1214315, to the nucleotide sequence of GAM24 RNA of FIG. 24A, designated SEQ ID:20602. Yet another function of GAM24 is therefore inhibition of (LOC196812). Accordingly, utilities of GAM24 include diagnosis and treatment of diseases and clinical conditions with which LOC196812 is associated.

Reference is now made to LOC256158 BINDING SITE. LOC256158 is a target gene of GAM24, corresponding to GAM24-TARGET GENE of FIG. 24A LOC256158 BINDING SITE is a binding site found in an untranslated region of LOC256158, corresponding to BINDING SITE of FIG. 24A. FIG. 24D illustrates the complementarity of the nucleotide sequence of LOC256158 BINDING SITE, designated SEQ ID:1317257, to the nucleotide sequence of GAM24 RNA of FIG. 24A, designated SEQ ID:20602. An additional function of GAM24 is therefore inhibition of (LOC256158). Accordingly, utilities of GAM24 include diagnosis and treatment of diseases and clinical conditions with which LOC256158 is associated.

Reference is now made to LOC90342 BINDING SITE. LOC90342 is a target gene of GAM24, corresponding to GAM24-TARGET GENE of FIG. 24A. LOC90342 BINDING SITE is a binding site found in an untranslated region of LOC90342, corresponding to BINDING SITE of FIG. 24A. FIG. 24D illustrates the complementarity of the nucleotide sequence of LOC90342 BINDING SITE, designated SEQ ID:1356067, to the nucleotide sequence of GAM24 RNA of FIG. 24A, designated SEQ ID:20602. A further function of GAM24 is therefore inhibition of (LOC90342). Accordingly, utilities of GAM24 include diagnosis and treatment of diseases and clinical conditions with which LOC90342 is associated.

Figures 25A, 25B, 25C:
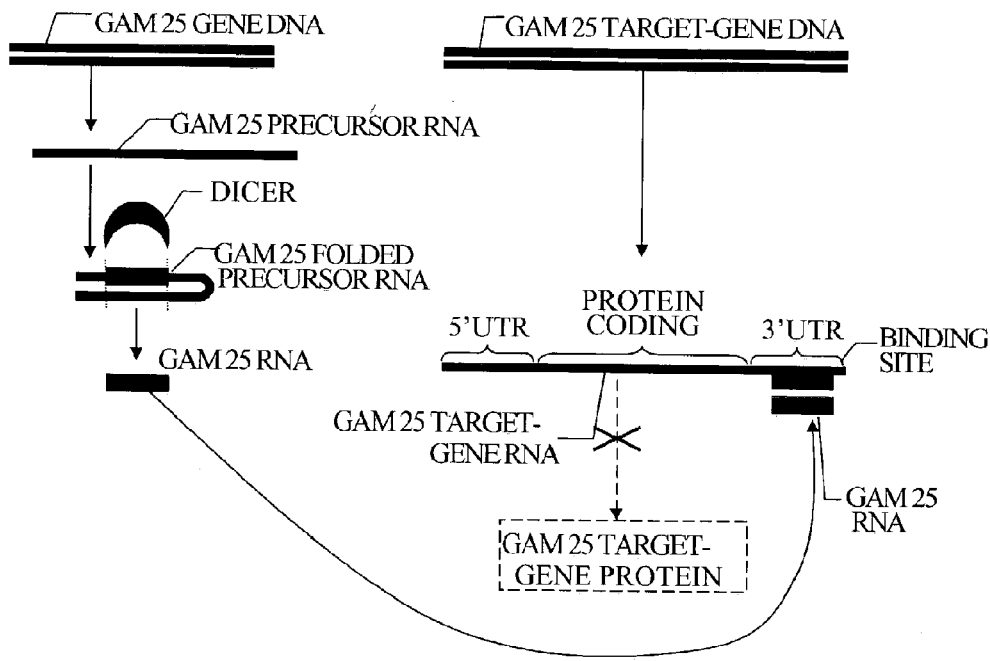

Reference is now made to FIG. 25A, which is a simplified diagram providing a conceptual explanation of the mode by which a novel bioinformatically detected gene, referred to here as GAM25 modulates expression of target genes thereof, the function and utility of which target genes is known in the art.

GAM25 (Genomic Address Messenger 25) is a novel bioinformatically detected regulatory, non protein coding, micro RNA (miRNA) gene. The method by which GAM25 was detected is described hereinabove with referent to FIGS. 6-15.

GAM25 GENE and GAM25-TARGET GENE are two human genes contained in the human genome.

GAM25 GENE encodes a GAM25 PRECURSOR RNA. Similar to other miRNA genes, and unlike most ordinary genes, the RNA transcribed by GAM25, GAM25 PRECURSOR RNA, does not encode a protein.

GAM25 PRECURSOR RNA folds onto itself, forming GAM25 FOLDED PRECURSOR RNA. As FIG. 25 illustrates, GAM25 FOLDED PRECURSOR RNA forms a 'hairpin structure', folding onto itself. As is well known in the art, this 'hairpin structure', is typical of RNA encoded by miRNA genes, and is due to the fact that the nucleotide sequence of the first half of the RNA encoded by a miRNA gene is an accurate or partial inversed-reversed sequence of the nucleotide sequence of the second half thereof. By "inversed-reversed" is meant a sequence which is reversed and wherein each nucleotide is replaced by a complimentary nucleotide, as is well known in the art (e.g. ATGGC is the inversed-reversed sequence of GCCAT).

An enzyme complex designated DICER COMPLEX 'dices' the GAM25 FOLDED PRECURSOR RNA into a single stranded ~22 long RNA segment, designated GAM25 RNA. As is known in the art, 'dicing' of a hairpin structured RNA precursor product into short a ~22 nt RNA segment is catalyzed by an enzyme complex comprising an enzyme called Dicer together with other necessary proteins.

GAM25-TARGET GENE encodes a corresponding messenger RNA, designated GAM25-TARGET RNA. GAM25-TARGET RNA comprises three regions, as is typical of mRNA of a protein coding gene: a 5' untranslated region, a protein coding region and a 3' untranslated region, designated 5'UTR, PROTEIN CODING and 3'UTR respectively.

GAM25 RNA binds complimentarily to a BINDING SITE, located on an untranslated region of GAM25-TARGET RNA. This complimentarily binding is due to the fact that the nucleotide sequence of GAM25 RNA is an accurate or a partial inversed-reversed sequence of the nucleotide sequence of BINDING SITE. It is appreciated that while FIG. 25A depicts the BINDING SITE on the 3'UTR region, this is meant as an example only—the BINDING SITE may be located on the 5'UTR region as well.

The complimentary binding of GAM25 RNA to BINDING SITE inhibits translation of GAM25-TARGET RNA into GAM25-TARGET PROTEIN. GAM25-TARGET PROTEIN is therefore outlined by a broken line.

It is appreciated that GAM25-TARGET GENE in fact represents a plurality of target genes of GAM25. The mRNA of each of this plurality of target genes of GAM25 comprises a BINDING SITE, having a nucleotide sequence which is at least partly complementary to GAM25 RNA, and which when bound by GAM25 RNA causes inhibition of translation of one of a plurality of target proteins of GAM25. The plurality of target genes of GAM25 and their respective binding sites are described hereinbelow with reference to FIG. 25D.

It is appreciated by one skilled in the art that the mode of translational inhibition illustrated by FIG. 25 with specific reference to translational inhibition exerted by GAM25 on one or more target genes of GAM25 is in fact common to other known miRNA genes. As mentioned hereinabove with reference to the background section, although a specific complimentary binding site has been demonstrated only for miRNA genes Lin-4 and Let-7, all other recently discovered miRNA genes are also believed by those skilled in the art to modulate expression of other genes by complimentary binding, although specific complimentary binding sites of these genes have not yet been found (Ruvkun G., 'Perspective: Glimpses of a tiny RNA world', Science 294, 779 (2001)).

Reference is now made to FIG. 25B which shows the nucleotide sequence of GAM25 PRECURSOR RNA of FIG. 25A, designated SEQ ID:2, and a probable nucleotide sequence of GAM25 RNA of FIG. 25A, designated SEQ ID:29474. The nucleotide sequence of SEQ ID:29474, which is highly likely (over 0.25%) to be identical or highly similar to that of GAM25, is marked by an underline within the sequence of GAM25 PRECURSOR RNA.

Reference is now made to FIG. 25C, which shows the secondary folding of GAM25 PRECURSOR RNA, forming a 'hairpin structure' designated GAM25 FOLDED PRECURSOR RNA, both of FIG. 25A. A probable (>0.25%) nucleotide sequence of GAM25 RNA, designated SEQ ID:29474 of FIG. 25B, is marked by an underline on GAM25 FOLDED PRECURSOR RNA. It is appreciated that the complimentary base-paring is not perfect, with 'bulges', as is well known in the art with respect to the RNA folding of all known miRNA genes.

Reference is now made to FIG. 25D, which is a table showing binding sites found in untranslated regions of a plurality of target genes of GAM25, each binding site corresponding to BINDING SITE of FIG. 25A, and their complementarity to SEQ ID:29474, which is highly likely (>0.25%) to be identical or highly similar to the nucleotide sequence of GAM25 RNA of FIG. 25A.

It is appreciated that the functions, and accordingly the utilities, of GAM25 correlate with, and may be deduced from, the identity of the target genes which GAM25 binds and inhibits, and the function of these target genes, as elaborated hereinbelow.

Reference is now made to EED BINDING SITE. Embryonic ectoderm development (EED) is a target gene of GAM25, corresponding to GAM25-TARGET GENE of FIG. 25A. EED BINDING SITE is a binding site found in an untranslated region of EED, corresponding to BINDING SITE of FIG. 25A. FIG. 25D illustrates the complementarity of the nucleotide sequence of EED BINDING SITE, designated SEQ ID:144323, to the nucleotide sequence of GAM25 RNA of FIG. 25A, designated SEQ ID:29474.

A function of GAM25 is therefore inhibition of embryonic ectoderm development (EED), a gene which encodes a transcription factor that may be a transcriptional repressor involved in embryonic development. Accordingly, utilities of GAM25 include diagnosis and treatment of the above-mentioned diseases and clinical conditions.

The function of EED has been established by previous studies. In *Drosophila*, the Polycomb-group (PcG) and trithorax-group (trxG) genes are part of a cellular memory system responsible for the stable inheritance of gene activity. PcG and trxG genes are repressors and activators, respectively, of *Drosophila* homeotic gene expression. ENX1 (EZH2; 601573) is a mammalian homolog of the *Drosophila* 'enhancer of zest' gene and has domains with sequence homology to both PcG and trxG genes. Using a yeast 2-hybrid screen with ENX1 as bait, followed by screening a fetal brain cDNA library, Sewalt et al. (1998) isolated a cDNA encoding EED. EED is the human homolog of Eed, a murine PcG gene homologous to the *Drosophila* homeotic gene, 'extra sex combs.' The predicted 535-amino acid human EED protein is 100% identical to the murine protein. The N-terminal region of EED contains a putative PEST sequence, which is implicated in protein degradation, and there are 5 WD40 domains throughout the EED protein. WD40 domains are involved in protein-protein interactions, and Sewalt et al. (1998) showed that all 5 are necessary for the ENX1-EED interaction to occur. Northern blot analysis detected 1.5- and 2.0-kb EED transcripts in all tissues and cell lines tested; larger transcripts were detected in normal human tissues only, but at much lower levels. Highest expression was found in testis, spleen, prostate, ovary, and small intestine, as well as in colorectal adenocarcinoma, chronic myeloid leukemia, and osteosarcoma cell lines, with lower levels in thymus, colon, and peripheral blood leukocytes.

Animal model experiments lend further support to the function of EED. In marsupials and the extraembryonic region of the mouse, X inactivation is imprinted: the paternal X chromosome is preferentially inactivated whereas the maternal X is always active. Having more than 1 active X chromosome is deleterious to extraembryonic development in the mouse. Wang et al. (2001) showed that the eed gene is required for primary and secondary trophoblast giant cell development in female embryos. Results from mice carrying a paternally inherited X-linked GFP transgene implicated eed in the stable maintenance of imprinted X inactivation in extraembryonic tissues. Based on the recent finding that the EED protein interacts with histone deacetylases, Wang et al. (2001) suggested that this maintenance activity involves hypoacetylation of the inactivated paternal X chromosome in the extraembryonic tissues.

It is appreciated that the abovementioned animal model for EED is acknowledged by those skilled in the art as a scientifically valid animal model, as can be further appreciated from the publications sited hereinbelow.

Full details of the abovementioned studies are described in the following publications, the disclosure of which are hereby incorporated by reference:

Sewalt, R. G. A. B.; van der Vlag, J.; Gunster, M. J.; Hamer, K. M.; den Blaauwen, J. L.; Satijn, D. P. E.; Hendrix, T.; van Driel, R.; Otte, A. P.: Characterization of interactions between the mammalian Polycomb-group proteins Enx1/EZH2 and EED suggests the existence of different mammalian Polycomb-group protein complexes. Molec. Cell. Biol. 18: 3586-3595, 1998. PubMed ID: 9584199 5. Wang, J.; Mager, J.; Chen, Y.; Schneider, E.; Cross, J. C.; Nagy, A.; Magnuson, T.: Imprinted X inactivation maintained by a mouse Polycomb group gene. Nature Genet. 28: 371-375, 2001.

Further studies establishing the function and utilities of EED are found in John Hopkins OMIM database record ID 605984, and in references numbered 1-5 listed hereinbelow.

Reference is now made to MLPH BINDING SITE. (MLPH) is a target gene of GAM25, corresponding to GAM25-TARGET GENE of FIG. 25A. MLPH BINDING SITE is a binding site found in an untranslated region of MLPH, corresponding to BINDING SITE of FIG. 25A. FIG. 25D illustrates the complementarity of the nucleotide sequence of MLPH BINDING SITE, designated SEQ ID:256513, to the nucleotide sequence of GAM25 RNA of FIG. 25A, designated SEQ ID:29474.

Yet another function of GAM25 is therefore inhibition of (MLPH), a gene which encodes a transcription factor that is a member of the Rab effector family, and is associated with Griscelli syndrome. Accordingly, utilities of GAM25 include diagnosis and treatment of the abovementioned diseases and clinical conditions.

The function of MLPH has been established by previous studies. In 3 pigment mutations of the mouse, dilute (d), ashen (ash), and leaden (ln), melanin synthesis is normal but melanosome transport is impaired, resulting the clumping of the melanosomes in the Perinuclear region of the cell (Silvers, 1979). Genetic evidence suggested that these loci encode proteins that function in the same or overlapping pathways. All 3 mutations have identical phenotypes. In addition, Matesic et al. (2001) stated that the doubly and triply homozygous mutant combinations on a nonagouti background have phenotypes that are indistinguishable from any of the single mutations alone. Furthermore, all 3 mutations are suppressed by the cell autonomous, semidominant 'dilute suppressor' (dsu). By positional cloning, Matesic et al. (2001) identified in mouse a gene, which they designated melanophilin (Mlph), encoding a novel member of the Rab effector family. Northern blot analysis demonstrated expression of 3 Mlph transcripts in most adult tissues, with highest expression in epithelial-enriched tissues such as kidney, lung, skin, small intestine, and stomach. Matesic et al. (2001) determined that the Mlph gene is mutated in leaden mice. Mutations in ashen and dilute in the Rab27a (603868) and myosin Va (160777) genes, respectively. Matesic et al. (2001) suggested that Mlph may function as part of a transport complex with MyoVa and Rab27a. Matesic et al. (2001) noted that all characterized patients with Griscelli syndrome (214450) carry mutations in the MYOVA or the RAB27A gene. Thus, it would not be surprising to find patients with Griscelli syndrome, or patients with other hypopigmentation disorders, with mutations in the MLPH gene.

Full details of the abovementioned studies are described in the following publications, the disclosure of which are hereby incorporated by reference:

Matesic, L. E.; Yip, R.; Reuss, A. E.; Swing, D. A.; O'Sullivan, T. N.; Fletcher, C. F.; Copeland N. G.; Jenkins, N. A.: Mutations in Mlph, encoding a member of the Rab effector family, cause the melanosome transport defects observed in leaden mice. Proc. Nat. Acad. Sci. 98: 10238-10243, 2001. PubMed ID: 1504925 2. Silvers, W. K.: The Coat Colors of Mice. New York: Springer, 1979.

Further studies establishing the function and utilities of MLPH are found in John Hopkins OMIM database record ID 606526, and in references numbered 6-7 listed hereinbelow.

Reference is now made to NPY2R BINDING SITE. Neuropeptide Y receptor Y2 (NPY2R) is a target gene of GAM25, corresponding to GAM25-TARGET GENE of FIG. 25A. NPY2R BINDING SITE is a binding site found in an untranslated region of NPY2R, corresponding to BINDING SITE of FIG. 25A. FIG. 25D illustrates the complementarity of the nucleotide sequence of NPY2R BINDING SITE, designated SEQ ID:277186, to the nucleotide sequence of GAM25 RNA of FIG. 25A, designated SEQ ID:29474.

An additional function of GAM25 is therefore inhibition of neuropeptide Y receptor Y2 (NPY2R), a gene which encodes a receptor that stimulates intracellular calcium flux and may modulate psychomotor activity, food intake, endocrine secretion and vasoconstriction. Accordingly, utilities of GAM25 include diagnosis and treatment of the abovementioned diseases and clinical conditions.

The function of NPY2R has been established by previous studies. Neuropeptide Y (NPY) signals through a family of G protein-coupled receptors present in the brain and sympathetic neurons. At least 3 types of neuropeptide Y receptor have been defined on the basis of pharmacologic criteria, tissue distribution, and structure of the encoding gene; see 162641 and 162643. Rose et al. (1995) reported the expression cloning in COS cells of a cDNA for the human type 2 receptor, NPY2R. Transfected cells showed high affinity for NPY (162640), peptide YY (PYY; 600781), and a fragment of NPY including amino acids 13 to 36. The predicted 381-amino acid protein has 7 transmembrane domains characteristic of G protein-coupled receptors and is only 31% identical to the human Y1 receptor (NPY1R; 162641). A 4-kb mRNA was detected on Northern blots of tissue samples from several regions of the nervous system. Gerald et al. (1995) cloned the cDNA corresponding to the human Y2 receptor from a human hippocampal cDNA expression library using a radiolabeled PYY-binding assay. They expressed the Y2 gene in COS-7 cells and performed a hormone binding assay which showed that the Y2 receptor binds (from highest to lowest affinity) PYY, NPY, and pancreatic polypeptide (PP; 167780) hormones.

Full details of the abovementioned studies are described in the following publications, the disclosure of which are hereby incorporated by reference:

Gerald, C.; Walker, M. W.; Vaysse, P. J. -J.; He, C.; Branchek, T. A.; Weinshank, R. L.: Expression cloning and pharmacological characterization of a human hippocampal neuropeptide Y/peptide YY Y2 receptor subtype. J. Biol. Chem. 270: 26758-26761, 1995. PubMed ID: 7592910 4. Rose, P. M.; Fernandes, P.; Lynch, J. S.; Frazier, S. T.; Fisher, S. M.; Kodukula, K.; Kienzle, B.; Seethala, R.: Cloning and functional expression of a cDNA encoding a human type 2 neuropeptide Y receptor. J. Biol. Chem. 270: 22661-22664, 1995.

Further studies establishing the function and utilities of NPY2R are found in John Hopkins OMIM database record ID 162642, and in references numbered 8-11 listed hereinbelow.

Reference is now made to NR1I2 BINDING SITE. Nuclear receptor subfamily 1, group I, member 2 (NR1I2) is a target gene of GAM25, corresponding to GAM25-TARGET GENE of FIG. 25A. NR1I2 BINDING SITE is a binding site found in an untranslated region of NR1I2, corresponding to BINDING SITE of FIG. 25A. FIG. 25D illustrates the complementarity of the nucleotide sequence of NR1I2 BINDING SITE, designated SEQ ID:277734, to the nucleotide sequence of GAM5 RNA of FIG. 25A, designated SEQ ID:29474.

A further function of GAM25 is therefore inhibition of nuclear receptor subfamily 1, group I, member 2 (NR1I2), a gene which encodes a protein that binds to a response element in the cyp3a4 gene promoter and activates its expression in response to a wide variety of endobiotics and xenobiotics. Accordingly, utilities of GAM25 include diagnosis and treatment of the abovementioned diseases and clinical conditions.

The function of NR1I2 has been established by previous studies. Lehmann et al. (1998) identified a nuclear receptor, termed PXR, that binds to the rifampicin/dexamethasone response element in the CYP3A4 (124010) promoter as a heterodimer with the 9-cis retinoic acid receptor RXR (see 180245). The human PXR is related to the mouse Pxr1, which they had cloned and shown to be activated by dexamethasone, pregnenolone 16-alpha-carbonitrile (PCN), and other compounds known to induce expression of the CYP3A1 gene, the predominant form of CYP3A in rat liver and intestine. Lehmann al. (1998) isolated PXR clones from a human liver cDNA library. Amino acid sequence comparison showed that human PXR shared 96% and 76% sequence identity with mouse Pxr1 in the DNA-binding and ligand-binding domains, respectively. Initiation of translation at a CUG initiation codon would yield a protein of 434 amino acids. Northern blot analysis detected most abundant expression in liver, colon, and small intestine; transcripts of 2.6, 4.3, and 5 kb were present in each of these tissues. Lehmann et al. (1998) provided several lines of evidence indicating that human PXR serves as a key transcriptional regulator of the CYP3A4 gene.

Animal model experiments lend further support to the function of NR1I2. The induction of CYP3A enzymes is species-specific and believed to involve 1 or more cellular factors, or receptor-like xenosensors. Xie et al. (2000) identified one such factor as the nuclear receptor Pxr and its human homolog SXR. Xie et al. (2000) showed that targeted disruption of the mouse Pxr gene abolished induction of CYP3A by prototypic inducers such as dexamethasone or pregnenolone-16-alpha-carbonitrile. In Pxr-null mice carrying a transgene for an activated form of human SXR, there was constitutive upregulation of CYP3A gene expression and enhanced protection against toxic xenobiotic compounds. Xie et al. (2000) demonstrated that species origin of the receptor, rather than the promoter structure of the CYP3A genes, dictates the species-specific pattern of CYP3A inducibility. Thus, they could generate 'humanized' transgenic mice that were responsive to human-specific inducers such as the antibiotic rifampicin. Xie et al. (2000) concluded that the SXR/Pxr genes encode the primary species-specific xenosensors that mediate the adaptive hepatic response, and may represent the critical biochemical mechanism of human xenoprotection.

It is appreciated that the abovementioned animal model for NR1I2 is acknowledged by those skilled in the art as a scientifically valid animal model, as can be further appreciated from the publications sited hereinbelow.

Full details of the abovementioned studies are described in the following publications, the disclosure of which are hereby incorporated by reference:

Lehmann, J. M.; McKee, D. D.; Watson, M. A.; Wilson, T. M.; Moore, J. T.; Kliewer, S. A.: The human orphan nuclear receptor PXR is activated by compounds that regulate CYP3A4 gene expression and cause drug interactions. J. Clin. Invest 102: 1016-1023, 1998. PubMed ID: 9727070 6. Xie, W.; Barwick, J. L.; Downes, M.; Blumberg, B.; Simon, C. M.; Nelson, M. C.; Neuschwander-Tetri, B. A.; Brunt, E. M.; Guzelian, P. S.; Evans, R. M.: Humanized xenobiotic response in mice expressing nuclear receptor SXR. Nature 406: 435-439, 2000.

Further studies establishing the function and utilities of NR1I2 are found in John Hopkins OMIM database record ID 603065, and in references numbered 12-18 listed hereinbelow.

Reference is now made to dJ383J4.3 BINDING SITE. DJ383J4.3 is a target gene of GAM25, corresponding to GAM25-TARGET GENE of FIG. 25A. DJ383J4.3 BINDING SITE is a binding site found in an untranslated region of dJ383J4.3, corresponding to BINDING SITE of FIG. 25A. FIG. 25D illustrates the complementarity of the nucleotide sequence of dJ383J4.3 BINDING SITE, designated SEQ ID:512554, to the nucleotide sequence of GAM25 RNA of FIG. 25A, designated SEQ ID:29474. Yet a further function of GAM25 is therefore inhibition of (dJ383J4.3). Accordingly, utilities of GAM25 include diagnosis and treatment of diseases and clinical conditions with which dJ383J4.3 is associated.

Reference is now made to FLJ4280 BINDING SITE. FLJ14280 is a target gene of GAM25, corresponding to GAM25-TARGET GENE of FIG. 25A. FLJ14280 BINDING SITE is a binding site found in an untranslated region of FLJ14280, corresponding to BINDING SITE of FIG. 25A. FIG. 25D illustrates the complementarity of the nucleotide sequence of FLJ14280 BINDING SITE, designated SEQ ID:610221, to the nucleotide sequence of GAM25 RNA of FIG. 25A, designated SEQ ID:29474. Another function of GAM25 is therefore inhibition of (FLJ14280). Accordingly, utilities of GAM25 include diagnosis and treatment of diseases and clinical conditions with which FLJ14280 is associated.

Reference is now made to KIAA1678 BINDING SITE. KIAA1678 is a target gene of GAM25, corresponding to GAM25-TARGET GENE of FIG. 25A. KIAA1678 BINDING SITE is a binding site found in an untranslated region of KIAA1678, corresponding to BINDING SITE of FIG. 25A. FIG. 25D illustrates the complementarity of the nucleotide sequence of KIAA1678 BINDING SITE, designated SEQ ID:803886, to the nucleotide sequence of GAM25 RNA of FIG. 25A, designated SEQ ID:29474. Yet another function of GAM25 is therefore inhibition of (KIAA1678). Accordingly, utilities of GAM25 include diagnosis and treatment of diseases and clinical conditions with which KIAA1678 is associated.

Reference is now made to KIAA1724 BINDING SITE. KIAA1724 is a target gene of GAM25, corresponding to GAM25-TARGET GENE of FIG. 25A. KIAA1724 BINDING SITE is a binding site found in an untranslated region of KIAA1724, corresponding to BINDING SITE of FIG. 25A. FIG. 25D illustrates the complementarity of the nucleotide sequence of KIAA1724 BINDING SITE, designated SEQ ID:806213, to the nucleotide sequence of GAM25 RNA of FIG. 25A, designated SEQ ID:29474. An additional function of GAM25 is therefore inhibition of (KIAA1724). Accordingly, utilities of GAM25 include diagnosis and treatment of diseases and clinical conditions with which KIAA1724 is associated.

Reference is now made to KIAA1949 BINDING SITE. KIAA1949 is a target gene of GAM25, corresponding to GAM25-TARGET GENE of FIG. 25A. KIAA1949 BINDING SITE is a binding site found in an untranslated region of KIAA1949, corresponding to BINDING SITE of FIG. 25A. FIG. 25D illustrates the complementarity of the nucleotide sequence of KIAA1949 BINDING SITE, designated SEQ ID:820868, to the nucleotide sequence of GAM25 RNA of FIG. 25A, designated SEQ ID:29474. A further function of GAM25 is therefore inhibition of (KIAA1949). Accordingly, utilities of GAM25 include diagnosis and treatment of diseases and clinical conditions with which KIAA1949 is associated.

Reference is now made to RoXaN BINDING SITE. RoXaN is a target gene of GAM25, corresponding to GAM25-TARGET GENE of FIG. 25A. RoXaN BINDING SITE is a binding site found in an untranslated region of RoXaN, corresponding to BINDING SITE of FIG. 25A. FIG. 25D illustrate the complementarity of the nucleotide sequence of RoXaN BINDING SITE, designated SEQ ID:950975, to the nucleotide sequence of GAM25 RNA of FIG. 25A, designated SEQ ID:29474. Yet a further function of GAM25 is therefore inhibition of (RoXaN). Accordingly, utilities of GAM25 include diagnosis and treatment of diseases and clinical conditions with which RoXaN is associated.

Reference is now made to SERP1 BINDING SITE. SERP1 is a target gene of GAM25; corresponding to GAM25-TARGET GENE of FIG. 25A. SERP1 BINDING SITE is a binding site found in an untranslated region of SERP1, corresponding to BINDING SITE of FIG. 25A. FIG. 25D illustrates the complementarity of the nucleotide sequence of SERP1 BINDING SITE, designated SEQ ID:963990, to the nucleotide sequence of GAM25 RNA of FIG. 25A, designated SEQ ID:29474. Another function of GAM25 is therefore inhibition of (SERP1). Accordingly, utilities of GAM25 include diagnosis and treatment of diseases and clinical conditions with which SERP1 is associated.

Reference is now made to SYNE-1 BINDING SITE. SYNE-1 is a target gene of GAM25, corresponding to GAM25-TARGET GENE of FIG. 25A. SYNE-1 BINDING SITE is a binding site found in an untranslated region of SYNE-1, corresponding to BINDING SITE of FIG. 25A. FIG. 25D illustrates the complementarity of the nucleotide sequence of SYNE-1 BINDING SITE, designated SEQ ID:986316, to the nucleotide sequence of GAM25 RNA of FIG. 25A, designated SEQ ID:29474. Yet another function of GAM25 is therefore inhibition of (SYNE-1). Accordingly, utilities of GAM25 include diagnosis and treatment of diseases and clinical conditions with which SYNE-1 is associated.

Reference is now made to TNRC4 BINDING SITE. TNRC4 is a target gene of GAM25, corresponding to GAM25-TARGET GENE of FIG. 25A. TNRC4 BINDING SITE is a binding site found in an untranslated region of TNRC4, corresponding to BENDING SITE of FIG. 25A. FIG. 25D illustrates the complementarity of the nucleotide sequence of TNRC4 BINDING SITE, designate SEQ ID:996086, to the nucleotide sequence of GAM25 RNA of FIG. 25A, designate SEQ ID:29474. An additional function of GAM25 is therefore inhibition of (TNRC4). Accordingly, utilities of GAM25 include diagnosis and treatment of diseases and clinical conditions with which TNRC4 is associated.

Reference is now made to LOC196047 BINDING SITE. LOC196047 is a target gene of GAM25, corresponding to GAM25-TARGET GENE of FIG. 25A. LOC196047 BINDING SITE is a binding site found in an untranslated region of LOC196047, corresponding to BINDING SITE of FIG. 25A. FIG. 25D illustrates the complementarity of the nucleotide sequence of LOC196047 BINDING SITE, designated SEQ ID:1210373, to the nucleotide sequence of GAM25 RNA of FIG. 25A, designated SEQ ID:29474. A further function of GAM25 is therefore inhibition of (LOC196047). Accordingly, utilities of GAM25 include diagnosis and treatment of diseases and clinical conditions with which LOC196047 is associated.

Reference is now made to LOC221540 BINDING SITE. LOC221540 is a target gene of GAM25, corresponding to GAM25-TARGET GENE of FIG. 25A. LOC221540 BINDING SITE is a binding site found in an untranslated region of LOC221540, corresponding to BINDING SITE of FIG. 25A. FIG. 25D illustrates the complementarity of the nucleotide sequence of LOC221540 BINDING SITE, designated SEQ ID:1274947, to the nucleotide sequence of GAM25 RNA of FIG. 25A, designated SEQ ID:29474. Yet a further function of GAM25 is therefore inhibition of (LOC221540). Accordingly, utilities of GAM25 include diagnosis and treatment of diseases and clinical conditions with which LOC221540 is associated.

Reference is now made to LOC257545 BINDING SITE. LOC257545 is a target gene of GAM25, corresponding to GAM25-TARGET GENE of FIG. 25A. LOC257545 BINDING SITE is a binding site found in an untranslated region of LOC257545, corresponding to BINDING SITE of FIG. 25. FIG. 25D illustrates the complementarity of the nucleotide sequence of LOC257545 BINDING SITE, designated SEQ ID:1274947, to the nucleotide sequence of GAM25 RNA of FIG. 25A, designated SEQ ID:29474. Another function of GAM25 is therefore inhibit of (LOC257545). Accordingly, utilities of GAM25 include diagnosis and treatment of diseases and clinical conditions with which LOC257545 is associated.

Reference is now made to LOC257598 BINDING SITE. LOC257598 is a target gene of GAM25, corresponding to GAM25-TARGET GENE of FIG. 25A. LOC257598 BINDING SITE is a binding site found in an untranslated region of LOC257598, corresponding to BINDING SITE of FIG. 25A. FIG. 25D illustrates the complementarity of the nucleotide sequence of LOC257598 BINDING SITE, designated SEQ ID:1274947, to the nucleotide sequence of GAM25 RNA of FIG. 25A, designated SEQ ID:29474. Yet another function of GAM25 is therefore inhibition of (LOC257598). Accordingly, utilities of GAM25 include diagnosis and treatment of diseases and clinical conditions with which LOC257598 is associated.

Reference is now made to LOC63928 BINDING SITE. LOC63928 is a target gene of GAM25, corresponding to GAM25-TARGET GENE of FIG. 25A. LOC63928 BINDING SITE is a binding site found in an untranslated region of LOC63928, corresponding to BINDING SITE of FIG. 25A. FIG. 25D illustrates the complementarity of the nucleotide sequence of LOC63928 BINDING SITE, designated SEQ ID:1347928, to the nucleotide sequence of GAM25 RNA of FIG. 25A, designated SEQ ID:29474. An additional function of GAM25 is therefore inhibition of (LOC63928). Accordingly, utilities of GAM25 include diagnosis and treatment of diseases and clinical conditions with which LOC63928 is associated.

Figures 26A, 26B, 26C:
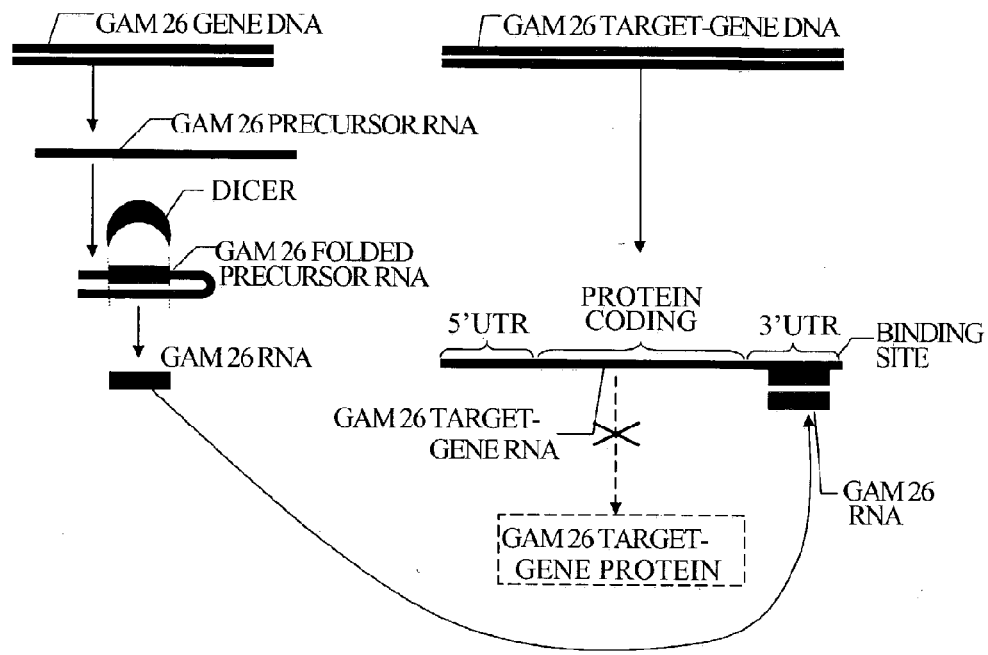

Reference is now made to FIG. 26A, which is a simplified diagram providing a conceptual explanation of the mode by which a novel bioinformatically detected gene, referred to here as GAM26 modulates expression of target genes thereof, the function and utility of which target genes is known in the art.

GAM26 (Genomic Address Messenger 26) is a novel bioinformatically detected regulatory, non protein coding, micro RNA (miRNA) gene. The method by which GAM26 was detected is described hereinabove with reference to FIGS. 6-15.

GAM26 GENE and GAM26-TARGET GENE are two human genes contained in the human genome.

GAM26 GENE encodes a GAM26 PRECURSOR RNA. Similar to other miRNA genes, and unlike most ordinary genes, the RNA transcribed by GAM26, GAM26 PRECURSOR RNA, does not encode a protein.

GAM26 PRECURSOR RNA folds onto itself, forming GAM26 FOLDED PRECURSOR RNA. As FIG. 26 illustrates, GAM26 FOLDED PRECURSOR RNA forms a 'hairpin structure', folding onto itself. As is well known in the art, this 'hairpin structure', is typical of RNA encoded by miRNA genes, and is due to the fact that the nucleotide sequence of the first half of the RNA encoded by a mRNA gene is an accurate or partial inversed-reversed sequence of the nucleotide sequence of the second half thereof. By "inversed-reversed" is meant a sequence which is reversed and wherein each nucleotide is replaced by a complimentary nucleotide, as is well known in the art (e.g. ATGGC is the inversed-reversed sequence of GCCAT).

An enzyme complex designated DICER COMPLEX, 'dices' the GAM26 FOLDED PRECURSOR RNA into a single stranded ~22 nt long RNA segment, designated GAM26 RNA. As is known in the art, 'dicing' of a hairpin structured RNA precursor product into short a ~22 nt RNA segment is catalyzed by an enzyme complex comprising an enzyme called Dicer together with other necessary proteins.

GAM26-TARGET GENE encodes a corresponding messenger RNA, designated GAM26-TARGET RNA. GAM26-TARGET RNA comprises three regions, as is typical of mRNA of a protein coding gene: a 5' untranslated region, a protein coding region and a 3' untranslated region, designated 5'UTR, PROTEIN CODING and 3'UTR respectively.

GAM26 RNA binds complimentarily to a BINDING SITE, located on an untranslated region of GAM26-TARGET RNA. This complimentarily binding is due to the fact that the nucleotide sequence of GAM26 RNA is an accurate or a partial inversed-reversed sequence of the nucleotide sequence of BINDING SITE. It is appreciated that while FIG. 26A depicts the BINDING SITE on the 3'UTR region this is meant as an example only—the BINDING SITE may be located on the 5'UTR region as well.

The complimentary binding of GAM26 RNA to BINDING SITE inhibits translation of GAM26-TARGET RNA into GAM26-TARGET PROTEIN. GAM26-TARGET PROTEIN is therefore outlined by a broken line.

It is appreciated that GAM26-TARGET GENE in fact represents a plurality of target genes of GAM26. The mRNA of each of this plurality of target genes of GAM26 comprises a BINDING SITE, having a nucleotide sequence which is at least partly complementary to GAM26 RNA, and which when bound by GAM26 RNA causes inhibition of translation of one of a plurality of target proteins of GAM26. The plurality of target genes of GAM26 and their respective binding sites are described hereinbelow with reference to FIG. 26D.

It is appreciated by one skilled in the art that the mode of translational inhibition illustrated by FIG. 26 with specific reference to translational inhibition exerted by GAM26 on one or more target genes of GAM26 is in fact common to other known miRNA genes. As mentioned hereinabove with reference to the background section, although a specific complimentary binding site has been demonstrated only for miRNA genes Lin-4 and Let-7, all other recently discovered miRNA genes are also believed by those skilled in the art to modulate expression of other genes by complimentary binding, although specific complimentary binding sites of these genes have not yet been found (Ruvkun G., 'Perspective: Glimpses of a tiny RNA world', Science 294, 779 (2001)).

Reference is now made to FIG. 26B which shows the nucleotide sequence of GAM26 PRECURSOR RNA of FIG. 26A, designated SEQ ID:3, and a probable nucleotide sequence of GAM26 RNA of FIG. 26A, designated SEQ ID:20604. The nucleotide sequence of SEQ ID:20604, which is highly likely (over 0.801122%) to be identical or highly similar to that of GAM26, is marked by an underline within the sequence of GAM26 PRECURSOR RNA.

Reference is now made to FIG. 26C, which shows the secondary folding of GAM26 PRECURSOR RNA, forming a 'hairpin structure' designed GAM26 FOLDED PRECURSOR RNA, both of FIG. 26A. A probable (>0.801122%) nucleotide sequence of GAM26 RNA, designated SEQ ID:20604 of FIG. 26B, is marked by an underline on GAM26 FOLDED PRECURSOR RNA. It is appreciated that the complimentary base-paring is not perfect, with 'bulges', as is well known in the art with respect to the RNA folding of all known miRNA genes.

Reference is now made to FIG. 26D, which is a table showing binding sites found in untranslated regions of a plurality of target genes of GAM26, each binding site corresponding to BINDING SITE of FIG. 26A, and their complementarity to SEQ ID:20604, which is highly likely (>0.801122%) to be identical or highly similar to the nucleotide sequence of GAM26 RNA of FIG. 26A.

It is appreciated that the functions, and accordingly the utilities, of GAM26 correlate with, and may be deduced from, the identity of the target genes which GAM26 binds and inhibits, and the function of these target genes, as elaborated hereinbelow.

Reference is now made to ACVR1B BINDING SITE. Activin A receptor, type IB (ACVR1B) is a target gene of GAM26, corresponding to GAM26-TARGET GENE of FIG. 26A. ACVR1B BINDING SITE is a binding site found in an untranslated region of ACVR1B, corresponding to BINDING SITE of FIG. 26A. FIG. 26D illustrates the complementarity of the nucleotide sequence of ACVR1B BINDING SITE, designated SEQ ID:46182, to the nucleotide sequence of GAM26 RNA of FIG. 26A, designated SEQ ID:20604.

A function of GAM26 is therefore inhibition of activin A receptor, type IB (ACVR1B), a gene which encodes a receptor that Activin receptor-like kinase; similar to activin, TGF-beta, and *C. elegans* daf-1 receptors. Accordingly utilities of GAM26 include diagnosis and treatment of the abovementioned diseases and clinical conditions.

The function of ACVR1B has been established by previous studies. See ACVRL1 (601284). Human cDNA clones encoding 4 putative transmembrane ser/thr kinases were identified by ten Dijke et al. (1993). Using degenerate DNA primers based on the human activin receptor type II (see 102581) and *C. elegans* Daf-1 gene products, they PCR-amplified mRNA from human erythroleukemia (HEL) cells, a cell type known to respond both to activin (147290) and TGF-beta (190180). Their partial clone of the ALK4 gene encodes a 383-amino acid polypeptide with a truncated extracellular domain but sequence and structural domain similarities with the other 3 ALK genes they cloned. ALK1, ALK2 (102576), ALK3 (601299), and ALK4 share approximately 40% sequence identity with activin receptors type II and IIB, TGF-beta receptor (see 190181), and Daf-1 in their kinase domains but share 60 to 790% sequence identity among themselves, suggesting to ten Dijke et al. (1993) that the ALK gene products form a subfamily of receptor ser/thr kinases. By Northern analysis, ten Dijke et al. (1993) showed that ALK4 is expressed in many tissues, most strongly in human kidney, pancreas, brain, lung, and liver. Su et al. (2001) described the gene structure and novel somatic mutations of the activin type IB receptor in pancreatic cancer. This was the first description of ACVR1B as a tumor suppressor gene.

Full details of the abovementioned studies are described in the following publications, the disclosure of which are hereby incorporated by reference:

Ten Dijke, P.; Ichijo, H.; Franzen, P.; Schulz, P.; Saras, J.; Toyoshima, H.; Heldin, C. -H.; Miyazono, K.: Activin receptor-like kinases: a novel subclass of cell-surface receptors with predicted serine/threonine kinase activity. Oncogene 8: 2879-2887, 1993. PubMed ID: 8397373 3.

Su, G. H.; Bansal, R.; Murphy, K. M.; Montgomery, E.; Yeo, C. J.; Hruban, R. H.; Kern, S. E.: ACVR1B (ALK4, activin receptor type 1B) gene mutations in pancreatic carcinoma. Proc. Nat. Acad. Sci. 98: 3254-3257, 2001.

Further studies establishing the function and utilities of ACVR1B are found in John Hopkins OMIM database record ID 601300, and in references numbered 19-24 listed hereinbelow.

Referring now to ACVR1B BINDING SITE. Activin A receptor, type IB (ACVR1B) is target gene of GAM26, corresponding to GAM26-TARGET GENE of FIG. 26A. ACVR1B BINDING SITE is a binding site found in an untranslated region of ACVR1B, corresponding to BINDING SITE of FIG. 26A. FIG. 26D illustrates the complementarity of the nucleotide sequence of ACVR1B BINDING SITE, designated SEQ ID:46198, to the nucleotide sequence of GAM26 RNA of FIG. 26A, designated SEQ ID:20604.

Yet another function of GAM26 is therefore inhibition of activin A receptor, type IB (ACVR1B), a gene which encodes a receptor that Activin receptor-like kinase; similar to activin, TGF-beta, and *C. elegans* daf-1 receptors. Accordingly, utilities of GAM26 include diagnosis and treatment of the abovementioned diseases and clinical conditions. The function and utilities of ACVR1B have been established by previous studies, as described hereinabove with reference to FIG. 26D.

Reference is now made to DLG3 BINDING SITE. Discs large (*Drosophila*) homolog (neuroendocrine-dlg) (DLG3) is a target gene of GAM26, corresponding to GAM26-TARGET GENE of FIG. 26A. DLG3 BINDING SITE is a binding site found in an untranslated region of DLG3, corresponding to BINDING SITE of FIG. 26. FIG. 26D illustrates the complementarity of the nucleotide sequence of DLG3 BINDING SITE, designated SEQ ID:46198, to the nucleotide sequence of GAM26 RNA of FIG. 26A, designated SEQ ID:20604.

An additional function of GAM26 is therefore inhibition of discs, large (Drosophila) homolog 3 (neuroendocrine-dlg) (DLG3), a gene which encodes a protein that mediates protein-protein interactions at the cytoplasmic surface of the cell membrane. Accordingly, utilities of GAM26 include diagnosis and treatment of the abovementioned diseases and clinical conditions.

The function of DLG3 has been established by previous studies. The discs-large family is a collection of proteins first described in *Drosophila* that have a common structural organization and are thought to be involved in signal transduction and mediating protein-protein interactions at the cytoplasmic surface of the cell membrane. Each protein has 3 distinct structural domains: an N-terminal segment comprising 1 or more discs-large homologous regions (DHRs); a SRC oncogene (190090) homology motif 3 (SH3); and a C-terminal domain with homology to guanylate kinase (139270). The defining member of this group of proteins is the gene product of the *Drosophila* lethal (1) discs-large 1 locus (601014), which was originally identified by the analysis of recessive lethal mutants. Germline mutations in the *Drosophila* gene dlg result in loss of apical-basal lateral polarity, disruption of normal cell-cell adhesion, and neoplastic overgrowth of the imaginal disc epithelium. The DLG1 gene maps to human 3q29; the MPP2 gene (600723) maps to 17q12-21. Smith et al. (1996) isolated and characterized another human gene, MPP3, which they called DLG3, with the structural characteristics of the discs-large family. The putative MPP3 gene product has a molecular weight of 66 kD and is located on chromosome 17 in the same segment, 17q12-q21, as MPP2. The products of the MPP2 and MPP3 genes show 36% identity and 58% similarity to each other, and both show nearly 60% sequence similarity to the EMP55 (305360) gene which encodes an erythroid phosphoprotein that is a component of the red cell membrane.

Full details of the abovementioned studies are described in the following publications, the disclosure of which are hereby incorporated by reference:

Smith, S. A.; Holik, P.; Stevens, J.; Mazoyer, S.; Melis, A.; Williams, B.; White, R.; Albertsen, H.: Isolation of a gene (DLG3) encoding a second member of the discs-large family on chromosome 17q12-q21. Genomics 31: 145-150, 1996.

Further studies establishing the function and utilities DLG3 are found in John Hopkins OMIM database record ID 601114, and in reference numbered 26 listed hereinbelow.

Reference is now made to ADARB1 BINDING SITE. Adenosine deaminase, RNA-specific, B1 (homolog of rat RED1) (ADARB1) is a target gene of GAM26, corresponding to GAM26-TARGET GENE of FIG. 26A. ADARB1 BINDING SITE is a binding site found in an untranslated region of ADARB1, corresponding to BINDING SITE of FIG. 6A FIG. 26D illustrates the complementarity of the nucleotide sequence of ADARB1 BINDING SITE, designated SEQ ID:48568, to the nucleotide sequence of GAM26 RNA of FIG. 26A, designated SEQ ID:20604.

A further function of GAM26 is therefore inhibition of adenosine deaminase, RNA-specific, B1 (homolog of rat RED1) (ADARB1), a gene which encodes enzyme that RNA editing involves the deamination of adenosines at specific sites. Accordingly, utilizes of GAM26 include diagnosis and treatment of the abovementioned diseases and clinical conditions.

The function of ADARB1 has been established by previous studies. RNA editing involves the deamination of adenosines at specific sites, the result of which can be a change in the amino acid sequence of the protein so that it differs from that predicted by the sequence of the DNA. Editing of the glutamate receptor B (GluRB; 138247) pre-mRNA has been shown to alter a codon (referred to as the Q/R site) for a channel determinant that controls the calcium permeability of the AMPA glutamate receptors. Melcher et al. (1996) tested the candidate dsRNA adenosine deaminase DRADA (601059) and showed that when coexpressed with a GluR-B minigene in HEK 293 cells, DRADA produced low-level editing at the GluR-B Q/R site. The authors then screened a rat brain cDNA library with the predicted catalytic domain of rat DRADA to identify other potential editing enzymes. A cDNA encoding a predicted 711 amino acid protein was isolated that gave about 90% of the expected activity in their editing assay. Melcher et al. (1996) designated this novel mammalian RNA editing protein RNA-editing enzyme-1 (RED1). Rat RED1 and DRADA share about 31% overall identity primarily due to their conservation in the C-terminal catalytic domain. Northern blots showed highest expression of RED1 in rat brain. Melcher et al. (1996) further observed that while RED1 was more efficient at deaminating some sites, DRADA had stronger activity at others. They speculated that a combination of these and perhaps other editing enzymes may be involved in determining the overall editing process for a give transcript. Higuchi et al. (2000) studied ADAR2-mediated RNA editing by generating mice that were homozygous for a targeted functional null allele. Editing in Adar2 −/− mice was substantially reduced at most of 25 positions in diverse transcripts; the mutant mice became prone to seizures and died young. The impaired phenotype appeared to result entirely from a single underedited position, since it reverted to normal when both alleles for the underedited transcript were substituted with alleles encoding the edited version exonically. The critical position specifies an ion channel determinant, the Q/R site, in AMPA receptor GluRB premessenger RNA. Higuchi et al. (2000) concluded that this transcript is physiologically the most important substrate of ADAR2.

Full details of the abovementioned studies are described in the following publications, the disclosure of which are hereby incorporated by reference:

Melcher, T.; Maas, S.; Herb, A.; Sprengel, R.; Seeburg, P. H.; Higuchi, M.: A mammalian RNA editing enzyme. Nature 379: 460-463, 1996. PubMed ID: 8559253 1. Higuchi, M.; Maas, S.; Single, F. N.; Hartner, J.; Rozov, A.; Burnashev, N.; Feldmeyer, D.; Sprengel, R.; Seeburg, P. H.: Point mutation in an AMPA receptor gene rescues lethality in mice deficient in the RNA-editing enzyme ADAR2. Nature 406: 78-81, 2000.

Further studies establishing the function and utilities of ADARB1 are found in John Hopkins OMIM database record ID 601218, and in references numbered 28-34 listed hereinbelow.

Referring now to ADARB1 BINDING SITE. Adenosine deaminase, RNA-specific, B1 (homolog of rat RED1) (ADARB1) is a target gene of GAM26, corresponding to GAM26-TARGET GENE of FIG. 26A. ADARB1 BINDING SITE is a binding site found in an untranslated region of ADARB1, corresponding to BINDING SITE of FIG. 26A. FIG. 26D illustrates the complementarity of the nucleotide sequence of ADARB1 BINDING SITE, designated SEQ ID:48568, to the nucleotide sequence of GAM26 RNA of FIG. 26A, designated SEQ ID:20604.

Yet a further function of GAM26 is therefore inhibition of adenosine deaminase, RNA-specific B1 (homolog of rat RED1) (ADARB1), a gene which encodes enzyme that RNA editing involves the deamination of adenosines at specific sites. Accordingly, utilities of GAM26 include diagnosis and treatment of the abovementioned diseases and clinical conditions. The function and utilities of ADARB1 have been established by previous studies, as described hereinabove with reference to FIG. 26D.

Reference is now made to ADRBK1 BINDING SITE. Adrenergic, beta, receptor kinase 1 (ADRBK1) is a target gene of GAM26, corresponding to GAM26-TARGET GENE of FIG. 26A. ADRBK1 BINDING SITE is a binding site found in an untranslated region of ADRBK1, corresponding to BINDING SITE of FIG. 26A. FIG. 26 illustrates the complementarity of the nucleotide sequence of ADRBK1 BINDING SITE, designated SEQ ID:51719, to the nucleotide sequence of GAM26 RNA of FIG. 26A, designated SEQ ID:20604.

Another function of GAM26 is therefore inhibition of adrenergic, beta, receptor kinase 1 (ADRBK1), a gene which encodes an enzyme that regulates desensitization of b-adrenergic receptors and related GPCRs. Accordingly, utilities of GAM26 include diagnosis and treatment of the abovementioned diseases and clinical conditions.

The function of ADRBK1 has been established by previous studies. Beta-adrenergic receptor kinase (BARK) phosphorylates the beta-2-adrenergic receptor (109690) and appears to mediate agonist-specific desensitization observed at high agonist concentrations. BARK is a ubiquitous cytosolic enzyme that specifically phosphorylates the activated form of the beta-adrenergic and related G protein-coupled receptors. Benovic et al. (1991) used the bovine BARK cDNA to screen a human retina library and isolate the human cDNA. They showed that it encodes a protein of 689 amino acids with an overall 98% amino acid and 92.5% nucleotide identity with bovine BARK. By study of rodent/human hybrid cells retaining various human chromosomes and parts of chromosomes, Benovic et al. (1991) demonstrated that the ADRBK1 gene segregates with the long arm of chromosome 11, centromeric to 11q13, i.e., 11cen-q13. Benovic et al. (1991) mapped the homologous gene to mouse chromosome 19.

Animal model experiments lend further support to the function of ADRBK1. Rockman et al. (1998) mated transgenic mice with cardiac-restricted overexpression of either a peptide inhibitor of beta-ARK1 or the beta-2-AR into a genetic model of murine heart failure. They found that overexpression of the inhibitor prevented the development of cardiomyopathy in this murine model of heart failure.

It is appreciated that the abovementioned animal model for ADRBK1 is acknowledged by those skilled in the art as a scientifically valid animal model, as can be further appreciated from the publications sited hereinbelow.

Full details of the abovementioned studies are described in the following publications, the disclosure of which are hereby incorporated by reference:

Enovic, J. L.; Stone, W. C.; Huebner, K.; Croce, C.; Caron, M. G.; Lefkowitz, R. J.: cDNA cloning and chromosomal localization of the human beta-adrenergic receptor kinase. FEBS Lett. 283: 122-126, 1991. PubMed ID: 2037065 4.

Rockman, H. A.; Chien, K. R.; Choi, D. -J.; Iaccarino, G.; Hunter, J. J.; Ross, J., Jr.; Lefkowitz, R. J.; Koch, W. J.: Expression of a beta-adrenergic receptor kinase 1 inhibitor prevents the development of myocardial failure in gene-targeted mice. Proc. Nat. Acad. Sci. 95: 7000-7005, 1998.

Further studies establishing the function and utilities of ADRBK1 are found in John Hopkins OMIM database record ID 109635, and in references numbered 35-39 listed hereinbelow.

Referring now to ADRBK1 BINDING SITE. Adrenergic beta, receptor kinase 1 (ADRBK1) is a target gene of GAM26, corresponding to GAM26-TARGET GENE of FIG. 26A. ADRBK1 BINDING SITE is a binding site found in an untranslated region of ADRBK1, corresponding to BINDING SITE of FIG. 26A. FIG. 26D illustrates the complementarity of the nucleotide sequence of ADRBK1 BINDING SITE, designated SEQ ID:51737, to the nucleotide sequence of GAM2 RNA of FIG. 26A, designated SEQ ID:20604.

Yet another function of GAM26 is therefore inhibition of adrenergic, beta, receptor kinase 1 (ADRBK1), a gene which encodes an enzyme that regulates desensitization of b-adrenergic receptors and related GPCRs. Accordingly, utilities of GAM26 include diagnosis and treatment of the abovementioned diseases and clinical conditions. The function and utilities of ADRBK1 have been established by previous studies, as described hereinabove with reference to FIG. 26D.

Referring now to ADRBK1 BINDING SITE. Adrenergic beta, receptor kinase 1 (ADRBK1) is a target gene of GAM26, corresponding to GAM26-TARGET GENE of FIG. 26A. ADRBK1 BINDING SITE is a binding site found in an untranslated region of ADRBK1, corresponding to BINDING SITE of FIG. 26A. FIG. 26D illustrates the complementarity of the nucleotide sequence of ADRBK1 BINDING SITE, designated SEQ ID:51737, to the nucleotide sequence of GAM26 RNA of FIG. 26A, designated SEQ ID:20604.

An additional function of GAM26 is therefore inhibition of adrenergic, beta, receptor kinase 1 (ADRBK1), a gene which encodes an enzyme that regulates desensitization of b-adrenergic receptors and related GPCRs. Accordingly, utilities of GAM26 include diagnosis and treatment of the abovementioned diseases and clinical conditions. The function and utilities of ADRBK1 have been established by previous studies, as described hereinabove with reference to FIG. 26D.

Reference is now made to AKAP13 BINDING SITE. A kinase (PRKA) anchor protein 13 (AKAP13) is a target gene of GAM26, corresponding to GAM26-TARGET GENE of FIG. 26A. AKAP13 BINDING SITE is a binding site found in an untranslated region of AKAP13, corresponding to BINDING SITE of FIG. 26A. FIG. 26D illustrates the complementarity of the nucleotide sequence of AKAP13 BINDING SITE, designated SEQ ID:54490, to the nucleotide sequence of GAM26 RNA of FIG. 26A, designated SEQ ID:20604.

A further function of GAM26 is therefore inhibition of A kinase (PRKA) anchor protein 13 (AKAP13), a gene which encodes a protein that regulates subcellular localization of type II cAMP-dependent PKA. Accordingly, utilities of GAM26 include diagnosis and treatment of the abovementioned diseases and clinical conditions.

The function of AKAP13 has been established by previous studies. Gene map locus 15q24q25 A-kinase anchor proteins (AKAPs; see 602449), such as AKAP13, direct the activity of protein kinase A (PKA; see 176911) by tethering the enzyme near its physiologic substrates. AKAP13 is also known as LBC. Catalytic GDP-GTP exchange factors (GEFs), such as LBC, play an important role in regulating the Rho/Rac GTPase cycle. The Rho/Rac family of small GTPases mediates cytoskeletal reorganization, gene transcription, and cell cycle progression through unique signal transduction pathways. By probing a breast cancer expression library using an interaction cloning strategy for proteins that bind RXR (see 180245), Rubino et al. (1998) obtained a full-length cDNA encoding LBC, which they called BRX (breast cancer cDNA-encoded nuclear receptor-binding auxiliary protein). The deduced 1,428-amino acid BRX protein contains a region of identity to the LBC sequence identified by Toksoz and Williams (1994) that is preceded by 3 novel regions. A fifth, C-terminal region binds the estrogen receptor (ESR1; 133430). In addition to the tissues detected by Toksoz and Williams (1994), Northern blot analysis by Rubino et al. (1998) revealed BRX mRNA expression in reproductive tissues (ovary and placenta), and a 5.3-kb BRX transcript was detected in breast cancer cell lines, normal breast, and testis. Western blot and immunohistochemic analysis showed that BRX is expressed as a 170-kD protein in mammary epithelial cell lobules and terminal ducts. Binding analysis determined that BRX binds to ESR1, RXR, PPAR (170998), and THR (see 190120). Regions 4 and 5 of BRX were shown to bind independently to the ligand-binding domain near the C terminus of ESR1 without the requirement of other bridging proteins. Overexpression of BRX in the presence of estrogen augmented the activity of an estrogen response element. ESR activation by BRX could be inhibited by a dominant-negative mutant of CDC42 (116952). By genomic sequence and somatic cell hybrid analyses, Sterpetti et al. (1999) determined that proto-LBC and onco-LBC both contain N-terminal DH and PH domains; however, proto-LBC has a distinct C terminus absent in the oncoprotein. FISH with onco-LBC probes localized the LBC gene to 15q24-q25 and showed that onco-LBC represents a chimera derived from fusion with an unrelated sequence on 7q36. Northern blot analysis detected variably sized LBC transcripts and extended the known tissue distribution to spleen and a number of cancer cell lines. Immunoblot and thin-layer chromatography analysis showed that both proto- and onco-LBC can promote the formation of GTP-bound RHOA (ARHA; 165390). Mutation analysis indicated that the transforming activity of proto-LBC is increased by truncation of the C terminus, and that the DH and PH domains, but not the chromosome 7 sequence, are required for transformation. Immunoblot analysis determined that the proto-LBC form is in the membrane fraction, while the majority of the onco-LBC product is cytosolic, indicating that the C terminus may play a major role in the subcellular localization and regulation of LBC. Using FISH with onco-LBC probes, Sterpetti et al. (1999) localized the LBC gene to 15q24-q25 and showed that onco-LBC represents a chimera derived from fusion with an unrelated sequence on 7q36.

Full details of the abovementioned studies are described in the following publications, the disclosure of which are hereby incorporated by reference:

Rubino, D.; Driggers, P.; Arbit, D.; Kemp, L.; Miller, B.; Coso, O.; Pagliai, K.; Gray, K.; Gutkind, S.; Segars, J.: Characterization of Brx, a novel Dbl family member that modulates estrogen receptor action. Oncogene 16: 2513-2526, 1998. PubMed ID: 96271174. Sterpetti, P.; Hack, A. A.; Bashar, M. P.; Park, B.; Cheng, S. -D.; Knoll, J. H. M.; Urano, T.; Feig, L. A.; Toksoz, D.: Activation of the Lbc Rho exchange factor proto-oncogene by truncation of an extended C terminus that regulates transformation and targeting. Molec. Cell. Biol. 19: 1334-1345, 1999.

Further studies establishing the function and utilities of AKAP13 are found in John Hopkins OMIM database record ID 604686, and in references numbered 40-44 listed hereinbelow.

Reference is now made to AMD1 BINDING SITE. S-adenosylmethionine decarboxylase 1 (AMD1) is a target gene of GAM26, corresponding to GAM26-TARGET GENE of FIG. 26A. AMD1 BINDING SITE is a binding site found in an untranslated region of AMD1, corresponding to BINDING SITE of FIG. 26A. FIG. 26D illustrates the complementarity of the nucleotide sequence of AMD1 BINDING SITE, designated SEQ ID:57140, to the nucleotide sequence of GAM26 RNA of FIG. 26A, designated SEQ ID:20604.

Yet a further function of GAM26 is therefore inhibition of S-adenosylmethionine decarboxylase 1 (AMD1), a gene which encodes an enzyme that catalyzes the removal of the carboxylate group of S-adenosylmethionine in the polyamine biosynthesis pathway. Accordingly, utilities of GAM26 include diagnosis and treatment of the abovementioned diseases and clinical conditions.

The function of AMD1 has been established by previous studies. The polyamines spermine, spermidine, and putrescine are low molecular weight aliphatic amines essential for cellular proliferation and tumor promotion. Omithine decarboxylase (ODC; 165640) and S-adenosylmethionine decarboxylase (AdoMetDC) catalyze the rate-limiting steps in polyamine biosynthesis. A concordant rise in ODC and AdoMetDC activity is seen in various neoplastic conditions including colon cancer and benign colonic polyps. A rat cDNA clone for AdoMetDC was used by Radford et al (1987, 1989) in mouse-human somatic cell hybrid experiments to map the AMD gene to chromosomes 6 and X. They demonstrated that the gene on chromosome 6, symbolized AMD1, is not amplified in colon neoplasia. The sequence on X, symbolized AMD2, was localized to Xq22-q28 and may represent a pseudogene. That AMD2 is indeed a pseudogene was indicated by the findings of Maric et al. (1992) that the X-chromosome gene lacks introns which are present in the chromosome 6 gene. The gene on chromosome 6 encompasses at least 22 kb and comprises 9 exons and 8 introns, in contrast to the corresponding rat gene that has only 8 exons. Other aspects of the structure and organization were presented by Maric et al. (1992). Pulkka et al. (1993) characterized 2 AMD genes in the rat and localized both to rat chromosome 20 by mouse-rat somatic cell hybrids. They showed a high degree of conservation of sequence and structural organization in the coding portions but the 5-prime flanking regions were totally different Maric et al. (1995) characterized the AMD pseudogene on the X chromosome. It lacks all the introns present in AMD1 and has numerous mutations in the protein-coding region. By fluorescence in situ hybridization, they mapped AMD1 to 6q21-q22 and the pseudogene, which they referred to as AMD2, to Xq28.

Full details of the abovementioned studies are described in the following publications, the disclosure of which are hereby incorporated by reference:

Maric, S. C.; Crozat, A.; Janne, O. A.: Structure and organization of the human S-adenosylmethionine decarboxylase gene. J. Biol. Chem. 267: 18915-18923, 1992. PubMed ID: 1527020 2. Maric, S. C.; Crozat, A.; Louhimo, J.; Knuutila, S.; Janne, O. A.: The human S-adenosylmethionine decarboxylase gene: nucleotide sequence of a pseudogene and chromosomal localization of the active gene (AMD1) and the pseudogene (AMD2). Cytogenet. Cell Genet. 70: 195-199, 1995.

Further studies establishing the function and utilities of AMD1 are found in John Hopkins OMIM database record ID 180980, and in references numbered 45-49 listed hereinbelow.

Reference is now made to APP BINDING SITE. Amyloid beta (A4) precursor protein (protease nexin-II, Alzheimer dise (APP) is a target gene of GAM26, corresponding to GAM26-TARGET GENE of FIG. 26A. APP BINDING SITE is a binding site found in an untranslated region of APP, corresponding to BINDING SITE of FIG. 26A. FIG. 26D illustrates the complementarity of the nucleotide sequence of APP BINDING SITE, designated SEQ ID:62063, to the nucleotide sequence of GAM26 RNA of FIG. 26A, designated SEQ ID:20604.

Another function of GAM26 is therefore inhibition of amyloid beta (A4) precursor protein (protease nexin-II, Alzheimer dise (APP), a gene which encodes a protein that is associated with amyloidosis. Accordingly, utilities of GAM26 include diagnosis and treatment of the abovementioned diseases and clinical conditions.

The function of APP has been established by previous studies. APP, a widely expressed cell surface protein, is cleaved in the transmembrane region by gamma-secretase. Gamma-cleavage of APP produces the extracellular amyloid beta peptide of Alzheimer disease and releases an intracellular tail fragment Cao and Sudhof (2001) demonstrated that the cytoplasmic tail of APP forms a multimeric complex with the nuclear adaptor protein Fe65 (602709) and the histone acetyltransferase TIP60 (601409). This complex potently stimulates transcription via heterologous Gal4 or LexA DNA binding domains, suggesting that release of the cytoplasmic tail of APP by gamma-cleavage may function in gene expression.

Animal model experiments lend further support to the function of APP. Calhoun et al. (1998) studied the pattern of neuron loss in transgenic mice expressing mutant human APP with the 'Swedish mutation' (104760.0008). These mice develop APP-immunoreactive plaques, primarily in neocortex and hippocampus, progressively with age (Sturchler-Pierrat et al., 1997). Calhoun et al. (1998) showed that formation of amyloid plaques can lead to region-specific loss of neurons in the transgenic mouse. Neuron loss was observed primarily in the vicinity of plaques, but intraneuronal amyloidogenic APP processing could not be excluded as an additional cause. The extent of the observed loss was less than that reported in end-stage AD, possibly because overexpression of APP in the transgenic mouse has a neuroprotective effect. It is also likely that neuron loss would increase in these mice with further aging.

It is appreciated that the abovementioned anima model for APP is acknowledged by those skilled in the art as a scientifically valid animal model, as can be further appreciated from the publications sited hereinbelow.

Full details of the abovementioned studies are described in the following publications, the disclosure of which are hereby incorporated by reference:

Calhoun, E.; Wiederhold, K. -H.; Abramowski, D.; Phinney, A. L.; Probst, A.; Sturchler-Pierrat, C.; Staufenbiel, M.; Sommer, B.; Jucker, M.: Neuron loss in APP transgenic mice. Nature 395: 765-766, 1998.

Further studies establishing the function and utilities of APP are found in John Hopkins OMIM database record ID 104760, and in references numbered 50-148 listed hereinbelow.

Reference is now made to ARAF1 BINDING SITE. v-raf murine sarcoma 3611 viral oncogene homolog 1 (ARAF1) is a target gene of GAM26, corresponding to GAM26-TARGET GENE of FIG. 26A. ARAF1 BINDING SITE is a binding site found in an untranslated region of ARAF1, corresponding to BINDING SITE of FIG. 26A. FIG. 26D illustrates the complementarity of the nucleotide sequence of ARAF1 BINDING SITE, designated SEQ ID:63732, to the nucleotide sequence of GAM26 RNA of FIG. 26A, designated SEQ ID:20604.

Yet another function of GAM26 is therefore inhibition of v-raf murine sarcoma 3611 viral oncogene homolog 1 (ARAF1), a gene which encodes an enzyme that may play a critical role in cell growth and development, and is associated with angioimmunoblastic lymphadenopathy. Accordingly, utilities of GAM26 include diagnosis and treatment of the abovementioned diseases and clinical conditions.

The function of ARAF1 has been established by previous studies. By screening a mouse cDNA library with a v-raf oncogene probe, Huebner et al. (1986) also isolated a transforming raf-related cDNA, A-raf, that represented a gene distinct from RAF1. As an initial step in the analysis of this RAF1 related DNA, they isolated a human ARAF cDNA and used it to map the genes in mouse and man. The mouse gene cosegregated with the X chromosome in Chinese hamster-mouse hybrid cells. In humans, 2 independently segregating loci, designated ARAF1 and ARAF2, were mapped to chromosomes X and 7, respectively. (Huebner et al. (1986) had not conclusively shown that the ARAF2 locus on chromosome 7 is transcribed, and indeed the ARAF2 locus, now designated ARAF2P, has been shown to be a pseudogene (Lee et al., 1994).) The single X-linked ARAF locus of the mouse and the ARAF1 locus of man are actively transcribed in several mouse and human cell lines. Because of an 80% homology to RAF1 in its kinase domain, the authors speculated that the ARAF1 gene product may have serine/threonine-specific kinase activity. By in situ hybridization, ARAF1 was mapped to Xp21-q11, probably Xp13-p11. Popescu and Mark (1989) regionalized the gene to Xp11.4-p11.2 by in situ hybridization. Beck et al. (1987) deduced the complete 606-amino acid sequence of the human ARAF1 oncogene from the 2,453-nucleotide sequence of the cDNA. Avner et al (1987) found that in the mouse the A-raf oncogene is on the X chromosome, 10 to 17 cM proximal to the Hprt gene. The localization was considered compatible with the presence of the ARAF oncogene on the short arm of the X chromosome between the centromere and Xp21 in man. The RAF protooncogenes encode cytoplasmic protein serine/threonine kinases that play a critical role in cell growth and development. Araf1 in the mouse is expressed predominantly in urogenital tissues. Lee et al. (1994) demonstrated that the ARAF1 gene in the human comprises 16 exons encoded by a minimum of 10,776 nucleotides.

Full details of the abovementioned studies are described in the following publications, the disclose of which are hereby incorporated by reference:

Beck, T.; Huleihel M.; Gunnell, M.; Bonner, T. I.; Rapp, U. R.: The complete coding sequence of the human A-raf-1 oncogene and transforming activity of a human A-raf carrying retrovirus. Nucleic Acids Res. 15: 595-609, 1987. PubMed ID: 3029685 4. Lee, J. -E.; Beck, T. W.; Brennscheidt, U.; DeGennaro, L. J.; Rapp, U. R.: The complete sequence and promoter activity of the human A-raf-1 gene (ARAF1). Genomics 20: 43-55, 1994.

Further studies establishing the function and utilities of ARAF1 are found in John Hopkins OMIM database record ID 311010, and in numbered 149-154 listed hereinbelow.

Reference is now made to ASC BINDING SITE. Apoptosis-associated speck-like protein containing (ASC) is a target gene of GAM26, corresponding to GAM26-TARGET GENE of FIG. 26A. ASC BINDING SITE is a binding site found in an untranslated region of ASC, corresponding to BINDING SITE of FIG. 26A. FIG. 26D illustrates the complementarity of the nucleotide sequence of ASC BINDING SITE, designated SEQ ID:66821, to the nucleotide sequence of GAM26 RNA of FIG. 26A, designated SEQ ID:20604.

An additional function of GAM26 is therefore inhibition of apoptosis-associated speck-like protein containing (ASC), a gene which encodes a protein that is an adaptor protein with a caspase-associated recruitment domain motif; may act to promote apoptosis induced by etoposide. Accordingly, utilities, of GAM26 include diagnosis and treatment of the abovementioned diseases and clinical conditions.

The function of ASC has been established by previous studies. Western blot analysis by Masumoto et al. (1999) indicated that ASC may have proapoptotic activity by increasing the susceptibility of leukemia cell lines to apoptotic stimuli by anticancer drugs. Methylation-sensitive restriction PCR and methylation-specific PCR (MSP) analyses by Conway et al. (2000) indicated that silencing of TMS1 correlates with hypermethylation of the CpG island surrounding exon 1 and that overexpression of DNMT1 promotes hypermethylation and silencing of TMS1. Breast cancer cell lines, but not normal breast tissue, exhibited complete methylation of TMS1 and expressed no TMS1 message. Express ion of TMS1 in breast cancer cell lines inhibited growth and reduced the number of surviving colonies. Conway et al. (2000) concluded that TMS1 functions in the promotion of caspase-dependent apoptosis and that overexpression of TMS1 inhibits the growth of breast cancer cells. Using bisulfite genomic sequencing, Dnase I-hypersensitive site mapping, and chromatin immunoprecipitation, Stimson and Vertino (2002) showed that in normal fibroblasts, the TMS1 CpG island is composed of an unmethylated domain with distinct 5-prime and 3-prime boundaries. De novo methylation of the CpG island in cells overexpressing DNMT1 was accompanied by a loss of CpG island-specific hypersensitive site formation, localized hypoacetylation of histone H3 (see 601128) and H4 (see 602822), and gene silencing. Stimson and Vertino (2002) proposed the existence of protein-binding sites that demarcate the boundaries of TMS1 CpG islands in normal cells and that the boundaries are overcome by aberrant methylation, resulting in gene silencing.

Full details of the abovementioned studies are described in the following publications, the disclosure of which are hereby incorporated by reference:

Martinon, F.; Hofmann, K.; Tschopp, J.: The pyrin domain: a possible member of the death domain-fold family implicated in apoptosis and inflammation. Curr. Biol. 10: R118-R120, 2001. 3. Masumoto, J.; Taniguchi, S.; Ayukawa, K.; Sarvotham, H.; Kishino, T.; Niikawa, N.; Hidaka, E.; Katsuyama, T.; Higuchi, T.; Sagara, J.: ASC, a novel 22-kDa protein, aggregates during apoptosis of human promyelocytic leukemia HL-60 cells. J. Biol. Chem. 274: 33835-33838, 1999.

Further studies establishing the function and utilities of ASC are found in John Hopkins OMIM database record ID 606838, and in references numbered 155-159 listed hereinbelow.

Reference is now made to ATF4 BINDING SITE. Activating transcription factor 4 (tax-responsive enhancer element B67 (ATF4) is a target gene of GAM26, corresponding to GAM26-TARGET GENE of FIG. 26A. ATF4 BINDING SITE is a binding site found in an untranslated region of ATF4, corresponding to BINDING SITE of FIG. 26A. FIG. 26D illustrates the complementarity of the nucleotide sequence of ATF4 BINDING SITE, designated SEQ ID:67884, to the nucleotide sequence of GAM26 RNA of FIG. 26A, designated SEQ ID:20604.

A further function of GAM26 is therefore inhibition of activating transcription factor 4 (tax-responsive enhancer element B67 (ATF4), a gene which encodes a transcription factor that functions as a specific repressor of CRE-dependent transcription. Accordingly, utilities of GAM26 include diagnosis and treatment of the abovementioned diseases and clinical conditions.

The function of ATF4 has been established by previous studies. The cAMP response element (CRE) is an octanucleotide motif that mediates diverse transcriptional regulatory effects. By screening a Jurkat T-cell line expression library for the ability to bind CRE, Karpinski et al. (1992) isolated and characterized a full-length cDNA corresponding to ATF4, which they called CREB2 (CRE-binding protein-2). The predicted protein contains 351-amino acids. Northern blot analysis revealed that the 1.5-kb CREB2 mRNA was expressed in all human tumor cell lines and mouse organs tested. Unlike CREB (123810), which activates transcription from CRE-containing promoters, CREB2 functions as a specific repressor of CRE-dependent transcription. The transcriptional repressor activity resides within the C-terminal leucine zipper and basic domain region of the CREB2 protein.

Animal model experiments lend further support to the function of ATF4. Tanaka et al. (1998) used gene targeting to generate mice lacking Atf4. They found that Atf4-deficient mice exhibited severe microphthalmia. The Atf4-deficient eyes revealed a normal gross lens structure up to embryonic day 14.5, after which the lens degenerated due to apoptosis without the formation of lens secondary fiber cells. Retinal development was normal in the mutant mice. The lens-specific expression of Atf4 in the mutant mice led not only to the recovery of lens secondary fibers but also to the induction of hyperplasia of these fibers. Tanaka et al. (1998) concluded that ATF4 is essential for the later stages of lens fiber cell differentiation.

It is appreciated that the abovementioned animal model for ATF4 is acknowledged by those skilled in the art as a scientifically valid animal model, as can be further appreciated from the publications sited hereinbelow.

Full details of the abovementioned studies are described in the following publications, the disclosure of which are hereby incorporated by reference:

Karpinski, B. A.; Morle, G. D.; Huggenvik, J.; Uhler, M. D.; Leiden, J. M.: Molecular cloning of human CREB-2: an ATF/CREB transcription factor that can negatively regulate transcription from the cAMP response element Proc. Nat. Acad. Sci. 89: 4820-4824, 1992. PubMed ID: 1534408 3. Tanaka, T.; Tsujimura, T.; Takeda, K.; Sugihara, A.; Maekawa, A.; Terada, N.; Yoshida, N.; Akira, S.: Targeted disruption of ATF4 discloses its essential role in the formation of eye lens fibres. Genes Cells 3; 801-810, 1998.

Further studies establishing the function and utilities of ATF4 are found in John Hopkins OMIM database record ID 604064, and in references numbered 160-163 listed hereinbelow.

Reference is now made to ATP1A1 BINDING SITE. ATPase, Na+/K+transporting, alpha 1 polypeptide (ATP1A1) is a target gene of GAM26, corresponding to GAM26-TARGET GENE of FIG. 26A. ATP1A1 BINDING SITE is a binding site found in an untranslated region of ATP1A1, corresponding to BINDING SITE of FIG. 26A. FIG. 26D illustrates the complementarity of the nucleotide sequence of ATP1A1 BINDING SITE, designated SEQ ID:68935, to the nucleotide sequence of GAM26 RNA of FIG. 26A, designated SEQ ID:20604.

Yet a further function of GAM26 is therefore inhibition of ATPase, Na+/K+ transporting, alpha 1 polypeptide (ATP1A1), a gene which encodes an enzyme that catalyzes the hydrolysis of ATP coupled with the exchange of Na+/K+ ions across the plasma membrane. Accordingly, utilities of GAM26 include diagnosis and treatment of the abovementioned diseases and clinical conditions.

The function of ATP1A1 has been established by previous studies. Na,K-ATPase (Na(+),K(+)-activated ATP phosphohydrolase; EC 3.6.1.3) is an integral membrane protein responsible for establishing and maintaining the electrochemical gradients of Na and K ions across the plasma membrane. As these gradients are essential for osmoregulation, for sodium-coupled transport of a variety of organic and inorganic molecules, and for electrical excitability of nerve and muscle, the enzyme plays an essential role in cellular physiology. It is composed of 2 subunits, a large catalytic subunit (alpha) and a smaller glycoprotein subunit (beta) of unknown function. (See 182330.) Biochemical studies have demonstrated the existence of 2 isoforms of the catalytic subunit, alpha and alpha(+). Kidney contains predominantly the alpha form, whereas both alpha and alpha(+) are found in brain, adipose tissue, and skeletal muscle. A third isoform, alpha-III, has been identified in rat brain. Studies by Shull and Lingrel (1987) demonstrated that the catalytic subunit of Na,K-ATPase is encoded by multiple genes. Shull and Lingrel (1987) identified separate genes encoding the alpha and alpha(+) isoforms. These genes were called alpha-A and alpha-B (ATP1A2; 182340), respectively. In addition, they isolated 2 other genes, termed alpha-C and alpha-D, one of which is physically linked to the alpha(+) gene; these genes showed nucleotide and deduced amino acid homology to the catalytic subunit cDNA sequences but did not correspond to any previously identified isoforms.

Animal model experiments lend further support to the function of ATP1A1. To determine the functional roles of the ATP1A1 and ATP1A2 proteins, James et al. (1999) generated mice with targeted disruption of either the Atp1a1 or Atp1a2 gene. Hearts from heteroygous Atp1a2 mice were hypercontractile as a result of increased calcium transients during the contractile cycle. In contrast, hearts from heterozygous Atp1a1 mice were hypocontractile. The different functional roles of these 2 proteins were further demonstrated since inhibition of the Atp1a2 protein with ouabain increased the contractility of heterozygous Atp1a1 hearts.

These results illustrated specific role for the ATP1A2 protein in calcium signaling during cardiac contraction.

It is appreciated that the abovementioned animal model for ATP1A1 is acknowledged by those skilled in the art as a scientifically valid animal model as can be further appreciated from the publications sited hereinbelow.

Full details of the abovementioned studies are described in the following publications, the disclosure of which are hereby incorporated by reference:

Shull, M. M.; Lingrel, J. B.: Multiple genes encode the human Na+,K+-ATPase catalytic subunit. Proc. Nat. Acad. Sci. 84: 4039-4043, 1987. PubMed ID: 3035563 8.

James, P. F.; Grupp, I. L.; Grupp, G.; Woo, A. L.; Askew, G. R.; Croyle, M. L.; Walsh, R. A.; Lingrel, J. B.: Identification of a specific role for the Na,K-ATPase alpha-2 isoform as a regulator of calcium in the heart Molec. Cell 3: 555-563, 1999.

Further studies establishing the function and utilities of ATP1A1 are found in John Hopkins OMIM database record ID 182310, and in references numbered 164-178 listed hereinbelow.

Referring now to ATP1A1 BINDING SITE. ATPase, Na+/K+ transporting, alpha 1 polypeptide (ATP1A1) is a target gene of GAM26, corresponding to GAM26-TARGET GENE of FIG. 26A. ATP1A1 BINDING SITE is a binding site found in an untranslated region of ATP1A1, corresponding to BINDING SITE of FIG. 26A. FIG. 26D illustrates the complementarity of the nucleotide sequence of ATP1A1 BINDING SITE, designated SEQ ID:68949, to the nucleotide sequence of GAM26 RNA of FIG. 26A, designated SEQ ID:20604.

Another function of GAM26 is therefore inhibition of ATPase, Na+/K+ transporting, alpha 1 polypeptide (ATP1A1), a gene which encodes a Enzyme that catalyzes the hydrolysis of ATP coupled with the exchange of Na+/K+ ions across the plasma membrane. Accordingly, utilities of GAM26 include diagnosis and treatment of the abovementioned diseases and clinical conditions. The function and utilities of ATP1A1 have been established by previous studies, as described hereinabove with reference to FIG. 26D.

Referring now to ATP1A1 BINDING SITE. ATPase, Na+/K+ transporting, alpha 1 polypeptide (ATP1A1) is a target gene of GAM26, corresponding to GAM26-TARGET GENE of FIG. 26A. ATP1A1 BINDING SITE is a binding site found in an untranslated region of ATP1A1, corresponding to BINDING SITE of FIG. 26A. FIG. 26D illustrates the complementarity of the nucleotide sequence of ATP1A1 BINDING SITE, designated SEQ ID:68961, to the nucleotide sequence of GAM26 RNA of FIG. 26A, designated SEQ ID:20604.

Yet another function of GAM26 is therefore inhibition of ATPase, Na+/K+ transporting, alpha 1 polypeptide (ATP1A1), a gene which encodes a Enzyme that catalyzes the hydrolysis of ATP coupled with the exchange of Na+/K+ ions across the plasma membrane. Accordingly, utilities of GAM26 include diagnosis and treatment of the abovementioned diseases and clinical conditions. The function and utilities of ATP1A1 have been established by previous studies, as described hereinabove with reference to FIG. 26D.

Reference is now made to ATP2B2 BINDING SITE. ATPase, Ca++ transporting, plasma membrane 2 (NOTE: redefinition of sy (ATP2B2) is a target gene of GAM26, corresponding to GAM26-TARGET GENE of FIG. 26A. ATP2B2 BINDING SITE is a binding site found in an untranslated region of ATP2B2, corresponding to BINDING SITE of FIG. 26A. FIG. 26D illustrates the complementarity of the nucleotide sequence of ATP2B2 BINDING SITE, designated SEQ ID:69717, to the nucleotide sequence of GAM26 RNA of FIG. 26A, designated SEQ ID:20604.

An additional function of GAM26 is therefore inhibition of ATPase, Ca++ transporting, plasma membrane 2 (NOTE: redefinition of sy (ATP2B2), a gene which encodes an enzyme that catalyzes the hydrolysis of ATP coupled with the transport of calcium out of the cell. Accordingly, utilities of GAM126 include diagnosis and treatment of the abovementioned diseases and clinical conditions.

The function of ATP2B2 has been established by previous studies. The plasma membrane Ca(2+)-transporting ATPase designated as PMCA4 was mapped to 1q25-q32 by Olson et al. (1991) by 3 independent methods: Southern analysis of human-rodent somatic cell hybrids, in situ hybridization of human metaphase spreads, and genetic linkage analysis in the CEPH pedigrees. No evidence was obtained for multiple copies of the gene at this locus; however, a cross-hybridizing sequence was detected on Xq13-qter at low stringency. Further studies were required to determine whether the X-chromosomal sequence represented another member of the PMCA gene family.

Full details of the abovementioned studies are described in the following publications, the disclosure of which are hereby incorporated by reference:

Olson, S.; Wang, M. G.; Carafoli, E.; Strehler, E. E.; McBride, O. W.: Localization of two genes encoding plasma membrane Ca(2+)-transporting ATPases to human chromosomes 1q25-32 and 12q21-23. Genomics 9: 629-641, 1991.

Further studies establishing the function and utilities of ATP2B2 are found in John Hopkins OMIM database record ID 108732, and in references numbered 180 listed hereinbelow.

Reference is now made to DR1 BINDING SITE. Down-regulator of transcription 1, TBP-binding (negative cofactor 2) (DR1) is a target gene of GAM26, corresponding to GAM26-TARGET GENE of FIG. 26A. DR1 BINDING SITE is a binding site found in an untranslated region of DR1, corresponding to BINDING SITE of FIG. 26A. FIG. 26D illustrates the complementarity of the nucleotide sequence of DR1 BINDING SITE, designated SEQ ID:69717, to the nucleotide sequence of GAM26 RNA of FIG. 26A, designated SEQ ID:20604.

A further function of GAM26 is therefore inhibition of down-regulator of transcription 1, TBP-binding (negative cofactor 2) (DR1), a gene which encodes a protein that influences functional repression of both activated and basal transcription of class II genes. Accordingly, utilities of GAM26 include diagnosis and treatment of the abovementioned diseases and clinical conditions.

The function of DR1 has been established by previous studies. Several phosphoproteins are known to interact with TBP, the TATA box-binding protein (600075). Among them, DR1 is a TBP-associated phosphoprotein that represses both basal and activated levels of transcription. Inostroza et al. (1992) biochemically characterized DR1 purified from HeLa cells and cloned the human gene from a HeLa cell cDNA library. The gene encodes a 176-amino acid polypeptide of 19 kD. They showed that DR1 is phosphorylated in vivo and that phosphorylation of DR1 affected its interaction with TBP. The DR1 protein contains 3 domains: a histone fold motif at the N terminus, a TBP-binding domain, and a glutamine- and alanine-rich region. Mermelstein et al. (1996) showed that the histone fold motif of DR1 is required for DR1-DRAP1 interaction. Both the TBP-binding domain and the glutamine- and alanine-rich region are required for DR1-mediated repression of transcription. Yeung et al. (1997) demonstrated that the TBP-binding domain has 2 functions: it tethers the DR1 repressor complex to the promoter by interacting with TBP, and it is required for the coepression activity of DRAP1, although it is nor required for DR1-DRAP1 interaction. Yeung et al. (1997) determined that the glutamine- and alanine-rich region is the repressor domain of DR1 and that this domain interacts with TBP. Goppelt et al. (1996) proposed that binding of DR1 repressor complexes to TBP-promoter complexes establishes a mechanism in which an altered DNA conformation, together with the formation of hi her order complexes, inhibits the assembly or the preinitiation complex and controls the rate of RNA polymerase II transcription.

Full details of the abovementioned studies are described in the following publications, the disclosure of which are hereby incorporated by reference:

Nostroza, nostroza, J. A.; Mermeistein, F. H.; Ha, I.; Lane, W. S.; Reinberg, D.: Dr1, a TATA-binding protein-associated phosphoprotein and inhibitor of class II gene transcription. Cell 70: 477-489, 1992. PubMed ID: 1339312 5. Mermelstein, F.; Yeung, K.; Cao, J.; Inostroza, J. A.; Erdjument-Bromage, H.; Eagelson, K.; Landsman, D.; Levitt, P.; Tempst, P.; Reinberg, D.: Requirement of a corepressor for Dr1-mediated repression of transcription. Genes Dev. 10: 1033-1048, 1996.

Further studies establishing the function and utilities of DR1 are found in John Hopkins OMIM database record ID 601482, and in references numbered 185-193 listed hereinbelow.

Referring now to ATP2B2 BINDING SITE. ATPase, Ca++ transporting, plasma membrane 2. (NOTE: redefinition of sy (ATP2B2) is a target gene of GAM26, corresponding to GAM26-TARGET GENE of FIG. 26A. ATP2B2 BINDING SITE is a binding site found in an untranslated region of ATP2B2, corresponding to BINDING SITE of FIG. 26A. FIG. 26D illustrates the complementarity of the nucleotide sequence of ATP2B2 BINDING SITE, designated SEQ ID:69718, to the nucleotide sequence of GAM26 RNA of FIG. 26A, designated SEQ ID:20604.

Yet a further function of GAM26 is therefore inhibit on of ATPase, Ca++ transporting, plasma membrane 2 (NOTE: redefinition of sy (ATP2B2), a gene which encodes an enzyme that catalyzes the hydrolysis of ATP coupled with the transport of calcium out of the cell. Accordingly, utilities of GAM26 include diagnosis and treatment of the abovementioned diseases and clinical conditions. The function and utilities of ATP2B2 have been established by previous studies, as described hereinabove with reference to FIG. 26D.

Referring now to ATP2B2 BINDING SITE. ATPase, Ca++ transporting, plasma membrane 2 (NOTE: redefinition of sy (ATP2B2) is a target gene of GAM26, corresponding to GAM26-TARGET GENE of FIG. 26A. ATP2B2 BINDING SITE is a binding site found in an untranslated region of ATP2B2, corresponding to BINDING SITE of FIG. 26A. FIG. 26D illustrates the complementarity of the nucleotide sequence of ATP2B2 BINDING SITE, designated SEQ ID:69745, to the nucleotide sequence of GAM26 RNA of FIG. 26A, designated SEQ ID:20604.

Another function of GAM26 is therefore inhibition of ATPase, Ca++ transporting, plasma membrane 2 (NOTE: redefinition of sy (ATP2B2), a gene which encodes an enzyme that catalyzes the hydrolysis of ATP coupled with the transport of calcium out of the cell. Accordingly, utilities of GAM126 include diagnosis and treatment of the abovementioned diseases and clinical conditions. The function and utilities of ATP2B2 have been established by previous studies, as described hereinabove with reference to FIG. 26D.

Referring now to DR1 BINDING SITE. Down-regulator of transcription 1, TBP-binding (negative cofactor 2) (DR1) is a target gene of GAM26, corresponding to GAM26-TARGET GENE of FIG. 26A. DR1 BINDING SITE is a binding site found in an untranslated region of DR1, corresponding to BINDING SITE of FIG. 26A. FIG. 26D illustrates the complementarity of the nucleotide sequence of DR1 BINDING SITE, designated SEQ ID:69745, to the nucleotide sequence of GAM26 RNA of FIG. 26A, designated SEQ ID:20604.

Yet another function of GAM26 is therefore inhibition of down-regulator of transcription 1, TBP-1-binding (negative cofactor 2) (DR1), a gene which encodes a protein that influences functional repression of both activated and basal transcription of class II genes. Accordingly, utilities of GAM26 include diagnosis and treatment of the abovementioned diseases and clinical conditions. The function and utilities of DR1 have been established by previous studies, as described hereinabove with reference to FIG. 26D.

Referring now to ATP2B2 BINDING SITE. ATPase, Ca++ transporting, plasma membrane 2 (NOTE: redefinition of sy (ATP2B2) is a target gene of GAM26, corresponding to GAM26-TARGET GENE of FIG. 26A. ATP2B2 BINDING SITE is a binding site found in an untranslated region of ATP2B2, corresponding to BINDING SITE of FIG. 26A. FIG. 26D illustrates the complementarity of the nucleotide sequence of ATP2B2 BINDING SITE, designated SEQ ID:69749, to the nucleotide sequence of GAM26 RNA of FIG. 26A, designated SEQ ID:20604.

An additional function of GAM26 is therefore inhibition of ATPase, Ca++ transporting, plasma membrane 2 (NOTE: redefinition of sy (ATP2B2), a gene which encodes an enzyme that catalyzes the hydrolysis of ATP coupled with the transport of calcium out of the cell. Accordingly, utilities of GAM26 include diagnosis and treatment of the abovementioned diseases and clinical conditions. The function and utilities of ATP2B2 have been established by previous studies, as described hereinabove with reference to FIG. 26D.

Reference is now made to AUP1 BINDING SITE. Ancient ubiquitous protein 1 (AUP1) is a target gene of GAM26, corresponding to GAM26-TARGET GENE of FIG. 26A. AUP1 BINDING SITE is a binding site found in an untranslated region of AUP1, corresponding to BINDING SITE of FIG. 26A. FIG. 26D illustrates the complementarity of the nucleotide sequence of AUP1 BINDING SITE, designated SEQ ID:72273, to the nucleotide sequence of GAM26 RNA of FIG. 26A, designated SEQ ID:20604.

A further function of GAM26 is therefore inhibition of ancient ubiquitous protein 1 (AUP1), a gene which encodes a protein that is an ubiquitously expressed protein. Accordingly, utilities of GAM26 include diagnosis and treatment of the abovementioned diseases and clinical conditions.

The function of AUP1 has been established by previous studies. While searching for genes on mouse chromosome 6 between microsatellite markers D6Mit5 and D6Mit21, Jang et al. (1996) found a nonrepetitive 0.7-kb fragment that hybridized to human, cat, and dog DNAs on a zoo blot. Using this fragment as a probe, they cloned cDNAs from mouse neonatal brain and adult mouse testis cDNA libraries. Jang et al. (1996) sequenced overlapping cDNAs and found an open reading frame of 410 amino acids with putative secretion signal sequence at the N terminals and a domain with homology to the 'ancient conserved region' of the ARCN1 (600820) gene. They called the new gene AUP1, for ancient ubiquitous protein-1. Northern blot analysis in the mouse revealed a 1.5-kb Aup1 transcript in all adult tissues tested and in fetal samples from days E10 to E14. By database analysis, Jang et al. (1996) revealed the existence of a *Caenorhabditis elegans* homolog, hypothetical protein F44b9, which has 35% amino acid identity to mouse Aup1. With numerous overlapping EST sequences, Jang et al. (1996) identified a human homolog of mouse Aup1.

Full details of the abovementioned studies are described in the following publications, the disclosure of which are hereby incorporated by reference:

Jang, W.; Weber, J. S.; Bashir, R.; Bushby, K.; Meisler, M. H.: Aup1, a novel gene on mouse chromosome 6 and human chromosome 2p13. Genomics 36: 366-368, 1996.

Further studies establishing the function and utilities of AUP1 are found in John Hopkins OMIM database record ID 602434, and in references numbered 194 listed hereinbelow.

Referring now to AUP1 BINDING SITE. Ancient ubiquitous protein 1 (AUP1) is a target gene of GAM26, corresponding to GAM26-TARGET GENE of FIG. 26A. AUP1 BINDING SITE is a binding site found in an untranslated region of AUP1, corresponding to BINDING SITE of FIG. 26A. FIG. 26D illustrates the complementarity of the nucleotide sequence of AUP1 BINDING SITE, designated SEQ ID:72277, to the nucleotide sequence of GAM26 RNA of FIG. 26A, designated SEQ ID:20604.

Yet a further function of GAM26 is therefore inhibition of ancient ubiquitous protein 1 (AUP1), a gene which encodes a protein that is a ubiquitously expressed protein. Accordingly, utilities of GAM26 include diagnosis and treatment of the abovementioned diseases and clinical conditions. The function and utilities of AUP1 have been established by previous studies, as described hereinabove with reference to FIG. 26D.

Reference is now made to BCL11B BINDING SITE. B-cell CLL/lymphoma 11B (zinc finger protein) (BCL11B) is a target gene of GAM26, corresponding to GAM26-TARGET GENE of FIG. 26A. BCL11B BINDING SITE is a binding site found in an untranslated region of BCL11B, corresponding to BINDING SITE of FIG. 26A. FIG. 26D illustrates the complementarity of the nucleotide sequence of BCL11B BINDING SITE, designated SEQ ID:78295, to the nucleotide sequence of GAM26 RNA of FIG. 26, designated SEQ ID:20604.

Another function of GAM26 is therefore inhibition of B-cell CLL/lymphoma 11B (zinc finger protein) (BCL11B), a gene which encodes a protein that is implicated in mouse and human leukemias and is associated with T-cell leukemia/lymphoma. Accordingly, utilities of GAM26 include diagnosis and treatment of the abovementioned diseases and clinical conditions.

The function of BCL11B has been established by previous studies. BCL11A (606558) is a highly conserved gene across a wide range of species and is implicated in mouse and human leukemias. By database analysis, Satterwhite et al. (2001) identified a human homolog of BCL11A, designated BCL11B. The deduced 823-amino acid BCL11B protein is 61% identical to BCL11A overall but 95% identical in the zinc finger domains. It is as 86% identical to mouse Ctip2. Like BCL11A, BCL11B has a large 5-prime CpG island. Northern blot analysis detected expression in malignant T-cell lines derived from patients with adult T-cell leukemia/lymphoma but not in any malignant B-cell lines examined.

Full details of the abovementioned studies are described in the following publications, the disclosure of which are hereby incorporated by reference:

Satterwhite, E.; Sonoki, T.; Willis, T. G.; Harder, L.; Nowak, R.; Arriola, E. L.; Liu, H.; Price, H. P.; Gesk, S.; Steinemann, D.; Schlegelberger, B.; Oscier, D. G.; Siebert, R.; Tucker, P. A.; Dyer, M. J. S.: The BCL11 gene family: involvement of BCL11A in lymphoid malignancies. Blood 98: 3413-3420, 2001.

Further studies establishing the function and utilities of BCL11B are found in John Hopkins OMIM database record ID 606558, and in references numbered 195 listed hereinbelow.

Referring now to BCL11B BINDING SITE. B-cell CLL/lymphoma 11B (zinc finger protein) (BCL11B) is a target gene of GAM26, corresponding to GAM26-TARGET GENE of FIG. 26A. BCL11B BINDING SITE is a binding site found in an untranslated region of BCL11B, corresponding to BINDING SITE of FIG. 26A. FIG. 26D illustrates the complementarity of the nucleotide sequence of BCL11B BINDING SITE, designated SEQ ID:78304, to the nucleotide sequence of GAM26 RNA of FIG. 26A, designated SEQ ID:20604.

Yet another function of GAM26 is therefore inhibition of B-cell CLL/lymphoma 11B (zinc finger protein) (BCL11B), a gene which encodes a protein that is implicated in mouse and human leukemias is associated with T-cell leukemia/lymphoma. Accordingly, utilities of GAM26 include diagnosis and treatment of the abovementioned diseases and clinical conditions. The function and utilities of BCL11B have been established by previous studies, as described hereinabove with reference to FIG. 26D.

Referring now to BCL11B BINDING SITE. B-cell CLL/lymphoma 11B (zinc finger protein) (BCL11B) is a target gene of GAM26, corresponding to GAM26-TARGET GENE of FIG. 26A. BCL11B BINDING SITE is a binding site found in an untranslated region of BCL11B, corresponding to BINDING SITE of FIG. 26A. FIG. 26D illustrates the complementarity of the nucleotide sequence of BCL11B BINDING SITE, designated SEQ ID:78304, to the nucleotide sequence of GAM26 RNA of FIG. 26A, designated SEQ ID:20604.

An additional function of GAM26 is therefore inhibition of B-cell CLL/lymphoma 11B (zinc finger protein) (BCL11B), a gene which encodes a protein that is implicated in mouse and human leukemias and is associated with T-cell leukemia/lymphoma. Accordingly, utilities of GAM26 include diagnosis and treatment of the abovementioned diseases and clinical conditions. The function and utilities of BCL11B have been established by previous studies, as described hereinabove with reference to FIG. 26D.

Referring now to BCL11B BINDING SITE. B-cell CLL/lymphoma 11B (zinc finger protein) (BCL11B) is a target gene of GAM26, corresponding to GAM26-TARGET GENE of FIG. 26A. BCL11B BINDING SITE is a binding site found in an untranslated region of BCL11B, corresponding to BINDING SITE of FIG. 26A. FIG. 26D illustrates the complementarity of the nucleotide sequence of BCL11B BINDING SITE, designated SEQ ID:78310, to the nucleotide sequence of GAM26 RNA of FIG. 26A, designated SEQ ID:20604.

A further function of GAM26 is therefore inhibition of B-cell CLL/lymphoma 11B (zinc finger protein) (BCL11B), a gene which encodes a protein that is implicated in mouse and human leukemias and is associated with T-cell leukemia/lymphoma. Accordingly, utilities of GAM26 include diagnosis and treatment of the abovementioned diseases and clinical conditions. The function and utilities of BCL11B have been established by previous studies, as described hereinabove with reference to FIG. 26D.

Referring now to BCL11B BINDING SITE. B-cell CLL/lymphoma 11B (zinc finger protein) (BCL11B) is a target gene of GAM26, corresponding to GAM26-TARGET GENE of FIG. 26A. BCL11B BINDING SITE is a binding site found in an untranslated region of BCL11B, corresponding to BINDING SITE of FIG. 26A. FIG. 26D illustrates the complementarity of the nucleotide sequence of BCL11B BINDING SITE, designated SEQ ID:78336, to the nucleotide sequence of GAM26 RNA of FIG. 26A, designated SEQ ID:20604.

Yet a further function of GAM26 is therefore inhibition of B-cell CLL/lymphoma 11B (zinc finger protein) (BCL11B), a gene which encodes a protein that is implicated in mouse and human leukemias and is associated with T-cell leukemia/lymphoma. Accordingly, utilities of GAM26 include diagnosis and treatment of the abovementioned diseases and clinical conditions. The function and utilities of BCL11B have been established by previous studies, as described hereinabove with reference to FIG. 26D.

Reference is now made to BCL7B BINDING SITE. B-cell CLL/lymphoma 7B (BCL7B) is a target gene of GAM26, corresponding to GAM26-TARGET GENE of FIG. 26A. BCL7B BINDING SITE is a binding site found in an untranslated region of BCL7B, corresponding to BINDING SITE of FIG. 26A. FIG. 26D illustrates the complementarity of the nucleotide sequence of BCL7B BINDING SITE, designated SEQ ID:79353, to the nucleotide sequence of GAM26 RNA of FIG. 26A, designated SEQ ID:20604.

Another function of GAM26 is therefore inhibition of B-cell CLL/lymphoma 7B (BCL7B), a gene which encodes a protein that is of yet unknown function and is associated with Williams-Beuren syndrome. Accordingly, utilities of GAM26 include diagnosis and treatment of the abovementioned diseases and clinical conditions.

The function of BCL7B has been established by previous studies. Meng et al. (1998) constructed a physical map encompassing the 1.5-Mb region of chromosome 7q11.23 that is commonly deleted in Williams-Beuren syndrome (WBS; 194050). They identified 3 genes in this region, including BCL7B, which contains 6 exons. By EST database searching, screening of a liver cDNA library, and sequencing, they cloned a BCL7B cDNA encoding deduced 202-amino acid protein that shows high homology to the BCL7A gene (601406) which was cloned from a complex chromosomal translocation in Burkitt lymphoma cell lines. BCL7B is highly conserved from C. elegans to human, suggesting that it has been conserved through evolution.

Full detail of the abovementioned studies are described in the following publications, the disclosure of which are hereby incorporated by reference:
Jadayel, D. M.; Osborne, L. R.; Coignet, L. J. A.; Zani, V. J.; Tsui L. -C.; Scherer, S. W.; Dyer, M. J. S.: The BCL7 gene family: deletion of BCL7B in Williams syndrome. Gene 224: 35-44, 1998; PubMed ID: 9931421 2. Meng, X.; Lu, X.; Li, Z.; Green, E. D.; Massa, H.; Trask, B. J.; Morris, C. A.; Keating, M. T.: Complete physical map of the common deletion region in Williams syndrome and identification and characterization of three novel genes. Hum. Genet. 103: 590-599, 1998.

Further studies establishing the function and utilities of BCL7B are found in John Hopkins OMIM database record ID 605846, and in references numbered 196-197 listed hereinbelow.

Reference is now made to BCR BINDING SITE. Breakpoint cluster region (BCR) is a target gene of GAM26, corresponding to GAM26-TARGET GENE of FIG. 26A. BCR BINDING SITE is a binding site found in an untranslated region of BCR, corresponding to BINDING SITE of FIG. 26A. FIG. 26D illustrates the complementarity of the nucleotide sequence of BCR BINDING SITE, designated SEQ ID:79756, to the nucleotide sequence of GAM26 RNA of FIG. 26A, designated SEQ ID:20604.

Yet another function of GAM26 is therefore inhibition of breakpoint cluster region (BCR), a gene which encodes a protein that is a serine/threonine kinase that involves in the t(9;22) translocation (Philadelphia chromosome) and is associated with chronic myeloid leukemia (cml), acute myeloid leukemia (aml), acute lymphoblastic leukemia (all). Accordingly, utilities of GAM26 include diagnosis and treatment of the abovementioned diseases and clinical conditions.

The function of BCR has been established by previous studies. The normal BCR gene occupies a region of about 135 kb on chromosome 22. It is expressed as mRNAs of 4.5- and 6.7-kb, which apparently encode for the same cytoplasmic 160-kD protein, and contains 23 exons as well as an unusual inverted repeat flanking the first exon. The BCR protein reportedly contains a unique serine/threonine kinase activity and at least two SH2 binding sites encoded in its first exon and a C-terminal domain that functions as a GTPase activating protein for p21(rac) (Diekmann et al., 1991); see rac serine/threonine protein kinase (164730). Chissoe et al. (1995) sequenced the complete BCR gene and greater than 80% of the human ABL gene, which are both involved in the t(9;22) translocation (Philadelphia chromosome) associated with more than 90% of chronic myelogenous leukemia, 25 to 30% of adult and 2 to 10% of childhood acute lymphoblastic leukemia, and rare cases of acute myelogenous leukemia. Comparison of the gene with its cDNA sequence revealed the positions of 23 BCR exons and putative alternative BCR first and second exons. From the sequence of 4 newly studied Philadelphia chromosome translocations and a review of several other previously sequenced breakpoints, Chissoe et al. (1995) could discern no consistent breakpoint features. No clear-cut mechanism for Philadelphia chromosome translocation was evident. Because tyrosine kinase activity is essential to the transforming function of BCR-ABL, Druker et al. (2001) reasoned that an inhibitor of the kinase may be an effective treatment for CML. They found that indeed a tyrosine kinase inhibitor (STI571) was well tolerated and had significant antileukemic activity in patients with CML in whom treatment with standard chemotherapy had failed. This experience demonstrated the potential for the development of anticancer drugs based on the specific molecular abnormality present in a human cancer.

Animal model experiments lend further support to the function of BCR. Cancer is thought to arise from multiple genetic events that establish irreversible malignancy. A different mechanism might be present in certain leukemias initiated by a chromosomal translocation. Huettner et al. (2000) adopted a new approach to determine if ablation of the genetic abnormality is sufficient for reversion. They generated a conditional transgenic model of BCR-ABL-induced leukemia. The most common form of the product of the fusion gene, p210 BCR-ABL1, is found in more than 90% of patients with chronic myelogenous leukemia and in up to 15% of adult patients with de novo acute lymphoblastic leukemia. Efforts to establish a useful transgenic model had been hampered by embryonic lethality when the oncogene is expressed during embryogenesis, by reduced penetrance, or by extremely long latency. Huettner et al. (2000) used the 'knock-in' approach to induce leukemia by p190 BCR-ABL1 (Castellanos et al., 1997). Lethal leukemia developed within an acceptable time frame in all animals, and complete remission was achieved by suppression of BCR-ABL1 expression, even after multiple rounds of induction and reversion. The results demonstrated that BCR-ABL1 is required for both induction and maintenance of leukemia. The findings suggested that complete and lasting remissions can be achieved if the genetic abnormality is abolished or silenced before secondary mutations are acquired. The results have implications for therapies that directly target leukemia oncogenes, with a relevant example being the use of BCR-ABL1-specific tyrosine kinase inhibitors.

It is appreciated that the abovementioned animal model for BCR is acknowledged by those skilled in the art as a scientifically valid animal model, as can be further appreciated from the publications sited hereinbelow.

Full details of the abovementioned studies are described in the following publications, the disclosure of which are hereby incorporated by reference:

Chissoe, S. L.; Bodenteich, A.; Wang, Y. -F.; Wang, Y. -P.; Burian, D.; Clifton, S. W.; Crabtree, J.; Freeman, A.; Iyer, K.; Jian, L.; Ma, Y.; McLaury, H. -J.; Pan, H. -Q.; Sarhan, O. H.; Toth, S.; Wang, Z.; Zhang, G.; Heisterkamp, N.; Groffen, J.; Roe, B. A.: Sequence and analysis of the human ABL gene, the BCR gene, and regions involved in the Philadelphia chromosomal translocation. Genomics 27: 67-82, 1995. PubMed ID: 7665185 31. Huettner, C. S.; Zhang, P.; Van Etten, R. A.; Tenen, D. G.: Reversibility of acute B-c ell leukaemia induced by BCR-ABL1. Nature Genet. 24: 57-60, 2000.

Further studies establishing the function and utilities of BCR are found in John Hopkins OMIM database record ID 151410, and in references numbered 198-267 listed hereinbelow.

Referring now to BCR BINDING SITE. Breakpoint cluster region (BCR) is a target gene of GAM26, corresponding to GAM26-TARGET GENE of FIG. 26A. BCR BINDING SITE is a binding site found in an untranslated region of BCR, corresponding to BINDING SITE of FIG. 26A. FIG. 26D illustrates the complementarity of the nucleotide sequence of BCR BINDING SITE, designated SEQ ID:79756, to the nucleotide sequence of GAM26 RNA of FIG. 26A, designated SEQ ID:20604.

An additional function of GAM26 is therefore inhibition of breakpoint cluster region (BCR), a gene which encodes a protein that is a serine/threonine kinase that involves in the t(9;22) translocation (Philadelphia chromosome) and is associated with chronic myeloid leukemia (cml), acute myeloid leukemia (aml), acute lymphoblastic leukemia (all). Accordingly, utilities of GAM26 include diagnosis and treatment of the abovementioned diseases and clinical conditions. The function and utilities of BCR have been established by previous studies, as described hereinabove with reference to FIG. 26D.

Referring now to BCR BINDING SITE. Breakpoint cluster region (BCR) is a target gene of GAM26, corresponding to GAM26-TARGET GENE of FIG. 26A. BCR BINDING SITE is a binding site found in an untranslated region of BCR, corresponding to BINDING SITE of FIG. 26A. FIG. 26D illustrates the complementarity of the nucleotide sequence of BCR BINDING SITE, designated SEQ ID:79759, to the nucleotide sequence of GAM26 RNA of FIG. 26A, designated SEQ ID:20604.

A further function of GAM26 is therefore inhibition of breakpoint cluster region (BCR), a gene which encodes a protein that is a serine/threonine kinase that involves in the t(9;22) translocation (Philadelphia chromosome) and is associated with chronic myeloid leukemia (cml), acute myeloid leukemia (aml), acute lymphoblastic leukemia (all). Accordingly, utilities of GAM26 include diagnosis and treatment of the abovementioned disease and clinical conditions. The function and utilities of BCR have been established by previous studies, as described hereinabove with reference to FIG. 26D.

Referring now to BCR BINDING SITE. Breakpoint cluster region (BCR) is a target gene of GAM26, corresponding to GAM26-TARGET GENE of FIG. 26A. BCR BINDING SITE is a binding site found in an untranslated region of BCR, corresponding to BINDING SITE of FIG. 26A. FIG. 26D illustrates the complementarity of the nucleotide sequence of BCR BINDING SITE, designated SEQ ID:79761, to the nucleotide sequence of GAM26 RNA of FIG. 26A, designated SEQ ID:20604.

Yet a further function of GAM26 is therefore inhibition of breakpoint cluster region (BCR), a gene which encodes a protein that is a serine/threonine kinase that involves in the t(9;22) translocation (Philadelphia chromosome) and is associated with chronic myeloid leukemia (cml), acute myeloid leukemia (aml), acute lymphoblastic leukemia (all). Accordingly, utilities of GAM26 include diagnosis and treatment of the abovementioned diseases and clinical conditions. The function and utilities of BCR have been established by previous studies, as described hereinabove with reference to FIG. 26D.

Referring now to BCR BINDING SITE. Breakpoint cluster region (BCR) is a target gene of GAM26, corresponding to GAM26-TARGET GENE of FIG. 26A. BCR BINDING SITE is a binding site found in an untranslated region of BCR, corresponding to BINDING SITE of FIG. 26A. FIG. 26D illustrates the complementarity of the nucleotide sequence of BCR BINDING SITE, designated SEQ ID:79761, to the nucleotide sequence of GAM26 RNA of FIG. 26A, designated SEQ ID:20604.

Another function of GAM26 is therefore inhibition of breakpoint cluster region (BCR), a gene which encodes a protein that is a serine/threonine kinase that involves in the t(9;22) translocation (Philadelphia chromosome) and is associated with chronic myeloid (cml), acute myeloid leukemia (aml) acute lymphoblastic leukemia (all). Accordingly, utilities of GAM26 include diagnosis and treatment of the abovementioned diseases and clinical conditions. The function ant utilities of BCR have been established by previous studies, as described hereinabove with reference to FIG. 26D.

Referring now to BCR BINDING SITE. Breakpoint cluster region (BCR) is a target gene of GAM26, corresponding to GAM26-TARGET GENE of FIG. 26A. BCR BINDING SITE is a binding site found in an untranslated region of BCR, corresponding to BINDING SITE of FIG. 26A. FIG. 26D illustrates the complementarity of the nucleotide sequence of BCR BINDING SITE, designated SEQ ID:79762, to the nucleotide sequence of GAM26 RNA of FIG. 26A, designated SEQ ID:20604.

Yet another function of GAM26 is therefore inhibition of breakpoint cluster region (BCR), a gene which encodes a protein that is a serine/threonine kinase that involves in the t(9;22) translocation (Philadelphia chromosome) and is associated with chronic myeloid leukemia (cml), acute myeloid leukemia (aml), acute lymphoblastic leukemia (all). Accordingly, utilities of GAM26 include diagnosis and treatment of the abovementioned disease and clinical conditions. The function and utilities of BCR have been established by previous studies, as described hereinabove with reference to FIG. 26D.

Referring now to BCR BINDING SITE. Breakpoint cluster region (BCR) is a target gene of GAM26, corresponding to GAM26-TARGET GENE of FIG. 26A. BCR BINDING SITE is a binding site found in an untranslated region of BCR, corresponding to BINDING SITE of FIG. 26A. FIG. 26D illustrates the complementarity of the nucleotide sequence of BCR BINDING SITE, designated SEQ ID:79766, to the nucleotide sequence of GAM26 RNA of FIG. 26A, designated SEQ ID:20604.

An additional function of GAM26 is therefore inhibition of breakpoint cluster region (BCR), a gene which encodes a protein that is a serine/threonine kinase that involves in the t(9;22) translocation (Philadelphia chromosome) and is associated with chronic myeloid leukemia (cml), acute myeloid leukemia (aml), acute lymphoblastic leukemia (all). Accordingly, utilities of GAM26 include diagnosis and treatment of the abovementioned diseases and clinical conditions. The function and utilities of BCR have been established by previous studies, as described hereinabove with reference to FIG. 26D.

Referring now to BCR BINDING SITE. Breakpoint cluster region (BCR) is a target gene of GAM26, corresponding to GAM26-TARGET GENE of FIG. 26A. BCR BINDING SITE is a binding site found in an untranslated region of BCR, corresponding to BINDING SITE of FIG. 26A. FIG. 26D illustrate the complementarity of the nucleotide sequence of BCR BINDING SITE, designated SEQ ID:79766, to the nucleotide sequence of GAM26 RNA of FIG. 26A, designated SEQ ID:20604.

A further function of GAM26 is therefore inhibition breakpoint cluster region (BCR), a gene which encodes a protein that is a serine/threonine kinase that involves in the t(9;22) translocation (Philadelphia chromosome) and is associated with chronic myeloid leukemia (cml), acute myeloid leukemia (aml), acute lymphoblastic leukemia (all). Accordingly, utilities of GAM26 include diagnosis and treatment of the abovementioned diseases and clinical conditions. The function and utilities of BCR have been established by previous studies, as described hereinabove with reference to FIG. 26D.

Reference is now made to ZNF6 BINDING SITE. Zinc finger protein 6 (CMPX1) (ZNF6) is a target gene of GAM26, corresponding GAM26-TARGET GENE of FIG. 26A. ZNF6 BINDING SITE is a binding site found in an untranslated region of ZNF6, corresponding to BINDING SITE of FIG. 26A. FIG. 26D illustrates the complementarity of the nucleotide sequence of ZNF6 BINDING SITE, designated SEQ ID:79766, to the nucleotide sequence of GAM26 RNA of FIG. 26A, designated SEQ ID:20604.

Yet a further function of GAM26 is therefore inhibition of zinc finger protein 6 (CMPX1) (ZNF6), a gene which encodes a protein that is probably a transcriptional activator. Accordingly, utilities of GAM26 include diagnosis and treatment of the abovementioned diseases and clinical conditions.

The function of ZNF6 has been established by previous studies. See 194520. This gene was originally called CMPX1 and later ZNF6 by the Human Gene Mapping Workshop nomenclature committee. Lloyd et al. (1991) mapped the ZNF6 gene to the region in the proximal long arm of the X chromosome that shows homology to a region of the Y chromosome. It was mapped to Xq21.1-q21.3 by in situ hybridization, analysis of somatic cell hybrids, and study of males carrying deleted X chromosomes. The ZNF6 gene is highly conserved across species. Dosage in male mice indicated that it is also X linked in that species. ZFX (314980), ZFY, and ZNF6 may be derived from a common ancestral gene.

Full details of the abovementioned studies are described in the following publications, the disclosure of which are hereby incorporated by reference:

Lloyd, S. L.; Sargent, C. A.; Chalmers, J.; Lim, E.; Habeebu, S. S. M.; Affara, N. A.: An X-linked zinc finger gene mapping to Xq21.1-21.3 closely related to ZFX and ZFY: possible origins from a common ancestral gene. Nucleic Acids Res. 19: 4835-4841, 1991.

Further studies establishing the function and utilities of ZNF6 are found in John Hopkins OMIM database record ID 314990, and in references numbered 268 listed hereinbelow.

Reference is now made to BCRP2 BINDING SITE. Breakpoint cluster region protein, uterine leiomyo (BCRP2) is a target gene of GAM26, corresponding to GAM26-TARGET GENE of FIG. 26A. BCRP2 BINDING SITE is a binding site found in an untranslated region of BCRP2, corresponding to BINDING SITE of FIG. 26A. FIG. 26D illustrates the complementarity of the nucleotide sequence of BCRP2 BINDING SITE, designated SEQ ID:79919, to the nucleotide sequence of GAM26 RNA of FIG. 26A, designated SEQ ID:20604.

Another function of GAM26 is therefore inhibition of Breakpoint cluster region protein, uterine leiomyo (BCRP2), a gene which encodes a protein that accelerates osteoblast differentiation. Accordingly, utilities of GAM26 include diagnosis and treatment of the abovementioned diseases and clinical conditions.

The function of BCRP2 has been established by previous studies. In a t(12;14) breakpoint cluster region, Lynch et al. (1998) identified 4 expressed genes: REC2 (602948), cytoskeletal alpha-actinin (102575), D14S1460E (BCRP1), and D14S1461E (BCRP2). All map to the 14q24.1-q24.2 region. Northern blot analysis revealed BCRP2 expression in all human tissues tested.

Full details of the abovementioned studies are described in the following publications, the disclosure of which are hereby incorporated by reference:

Lynch, R. A.; Piper, M.; Bankier, A.; Bhugra, B.; Surti, U.; Liu, J.; Buckler, A.; Dear, P. H.; Menon, A. G.: Genomic and functional map of the chromosome 14 t(12;14) breakpoint cluster region in uterine leiomyoma. Genomics 52: 17-26, 1998.

Further studies establishing the function and utilities of BCRP2 are found in John Hopkins OMIM database record ID 603812, and in references numbered 269 listed hereinbelow.

Referring now to BCRP2 BINDING SITE. Breakpoint cluster region protein, uterine leiomyo (BCRP2) is a target gene of GAM26, corresponding to GAM26-TARGET GENE of FIG. 26A. BCRP2 BINDING SITE is a binding site found in an untranslated region of BCRP2, corresponding to BINDING SITE of FIG. 26A. FIG. 26D illustrates the complementarity of the nucleotide sequence of BCRP2 BINDING SITE, designated SEQ ID:79941, to the nucleotide sequence of GAM26 RNA of FIG. 26A, designated SEQ ID:20604.

Yet another function of GAM26 is therefore inhibition of Breakpoint cluster region protein, uterine leiomyo (BCRP2), a gene which encodes a protein that accelerates osteoblast differentiation. Accordingly, utilities of GAM26 include diagnosis and treatment of the abovementioned diseases and clinical conditions. The function and utilities of BCRP2 have been established by previous studies, as described hereinabove with reference to FIG. 26D.

Reference is now made to BSG BINDING SITE. Basigin (OK blood group) (BSG) is a target gene of GAM26, corresponding GAM26-TARGET GENE of FIG. 26A. BSG BINDING SITE is a binding site found in an untranslated region of BSG, corresponding to BINDING SITE of FIG. 26A. FIG. 26D illustrates the complementarity of the nucleotide sequence of BSG BINDING SITE, designated SEQ ID:83983, to the nucleotide sequence of GAM26 RNA of FIG. 26A, designated SEQ ID:20604.

An additional function of GAM26 is therefore inhibition of basigin (OK blood group) (BSG), a gene which encodes a protein that is a LEUKOCYTE ACTIVATION ANTIGEN and a member of the immunoglobulin superfamily. Accordingly, utilities of GAM26 include diagnosis and treatment of the abovementioned diseases and clinical conditions.

The function of BSG has been established by previous studies. Basigin is a member of the immunoglobulin superfamily, with a structure related to the putative primordial form of the family. It was cloned as a carrier of an oncodevelopmental carbohydrate marker expressed in teratocarcinoma stem cells. It is expressed broadly in both embryos and adults (4,5:Miyauchi et al., 1990, 1991; Kanekura et al., 1991). As members of the immunoglobulin superfamily play fundamental roles in intercellular recognition involved in various immunologic phenomena, differentiation, and development, basigin is thought also to play a role in intercellular recognition.

Animal model experiments lend further support to the function of BSG. Naruhashi et al. (1997) generated mice deficient in basigin by targeted disruption. Bsg −/− mice showed worse performance than their wildtype and heterozygous littermates in the Y-maze task, which assesses short-term memory, and in the water-finding task, which examines latent learning, without any motor dysfunction. Moreover, the mutant mice showed less acclimation in the habituation task compared with the wildtype mice. The mutant mice were also more sensitive to electric foot shock. Naruhashi et al. (1997) found these findings consistent with the expression profile of basigin in the central nervous system and suggested that basigin may play an important role in learning and memory as well as in sensory functions.

It is appreciated that the abovementioned anima model for BSG is acknowledged by those skilled in the art as a scientifically valid animal model, as can be further appreciated from the publications sited hereinbelow.

Full details of the abovementioned studies are described in the following publications, the disclosure of which are hereby incorporated by reference:

Kanekura, T.; Miyauchi, T.; Tashiro, M.; Muramatsu, T.: Basigin, a new member of the immunoglobulin superfamily: genes in different mammalian species, glycosylation changes in the molecule from adult organs and possible variation in the N-terminal sequences. Cell Struct. Funct. 16: 23-30, 1991. PubMed ID: 2032306 6.

Naruhashi, K.; Kadomatsu, K.; Igakura, T.; Fan, Q. -W.; Kuno, N.; Muramatsu, H.; Miyauchi, T.; Hasegawa, T.; Itoh, A.; Muramatsu, T.; Nabeshima T.: Abnormalities of sensory and memory functions in mice lacking Bsg gene. Biochem. Biophys. Res. Commun. 236: 733-737, 1997.

Further studies establishing the function and utilities of BSG are found in John Hopkins OMIM database record ID 109480, and in references numbered 270-277 listed hereinbelow.

Reference is now made to BSN BINDING SITE. Bassoon (presynaptic cytomatrix protein) (BSN) is a target gene of GAM26, corresponding to GAM26-TARGET GENE of FIG. 26A. BSN BINDING SITE is a binding site found in an untranslated region of BSN, corresponding to BINDING SITE of FIG. 26A. FIG. 26D illustrates the complementarity of the nucleotide sequence of BSN BINDING SITE, designated SEQ ID:84199, to the nucleotide sequence of GAM26 RNA of FIG. 26A, designated SEQ ID:20604.

A further function of GAM26 is therefore inhibition of bassoon (presynaptic cytomatrix protein) (BSN), a gene which encodes a protein that may be involved in cytomatrix organization at the site of neurotransmitter release and is associated with Multiple system atrophy (MSA). Accordingly, utilities of GAM26 include diagnosis and treatment of the abovementioned diseases and clinical conditions.

The function of BSN has been established by previous studies. Both the presynaptic terminal and the postsynaptic compartment of neuronal synapses comprise a highly specialized cytoskeleton underlying the synaptic membranes. The presynaptic nerve terminal is the principal site of regulated neurotransmitter release. The active zone is the region of the presynaptic plasmalemma over which synaptic vesicles dock, fuse, and release neurotransmitter. Piccolo (PCLO; 604918), a 420-kD protein, is 1 component of the presynaptic cytomatrix. Tom Dieck et al. (1998) isolated a large (greater than 400 kD) protein in mouse that is also found in the presynaptic compartments of rat brain synapses. They designated the protein Bassoon because it, along with Piccolo, is part of the ensemble of presynaptic proteins that are involved in orchestrating events at the nerve terminal. Bassoon is found in axon terminals of hippocampal neurons where it is highly concentrated in the vicinity of the active zone. Piccolo has a similar distribution and colocalizes with Bassoon in cultured hippocampal cells. Tom Dieck et al. (1998) suggested that Bassoon may be involved in cytomatrix organization at the site of neurotransmitter release multiple system atrophy (MSA) is a sporadic progressive neurodegenerative disease. By differential hybridization to high-density cDNA filters, Hashida et al. (1998) identified human frontal lob with altered expression patterns in patients. One partial cDNA whose expression was elevated 2-fold in MSA cerebella encoded a protein that the authors designated ZNF231 (zinc finger protein-231). By screening additional libraries with the partial cDNA, they assembled a full-length ZNF231 cDNA. The predicted 3,926-amino acid protein contains 2 glycine-proline dipeptide repeats, a pair of homologous C8 double zinc finger motifs, a leucine zipper motif, an SH3 domain-binding motif, 2 nuclear targeting sequences, 2 glutamine-rich domains, and a histidine-rich domain. Northern blot analysis of rat tissues indicated that the ZNF231 gene was expressed as a 16-kb mRNA specifically in brain. By RT-PCR of human brain cell lines and tissue, Hashida et al. (1998) determined that ZNF231 was expressed in the cerebellum and in a neuroblastoma cell line, but not in the white matter. Ishikawa et al. (1997) recovered a ZNF231 cDNA, designated KIAA0434, as 1 of 78 brain cDNAs that may encode large proteins. Gundelfinger 1999) stated that ZNF231 is the human homolog of Bassoon.

Full details of the abovementioned studies are described in the following publications, the disclosure of which are hereby incorporated by reference:

Tom Dieck, S.; Sanmarti-Vila, L.; Langnaese, K.; Richter, K.; Kindler, S.; Soyke, A.; Wex, H.; Smalla, K. -H.; Kampf, U.; Franzer, J. -T.; Stumm, M.; Garner, C. C.; Gundelfinger, E. D.: Bassoon, a novel zinc-finger CAG/glutamine-repeat protein selectively localized at the active zone of presynaptic nerve terminals. J. Cell Biol.

142: 499-509, 1998. PubMed ID: 9679147 2. Hashida, H.; Goto, J.; Zhao, N.; Takahashi, N.; Hirai, M.; Kanazawa, I.; Sakaki, Y.: Cloning and mapping of ZNF231, a novel brain-specific gene encoding neuronal double zinc finger protein whose expression is enhanced in a neurodegenerative disorder, multiple system atrophy (MSA). Genomics 54: 50-58, 1998.

Further studies establishing the function and utilities of BSN are found in John Hopkins OMIM database record ID 604020, and in references numbered 278-282 listed hereinbelow.

Reference is now made to BTG3 BINDING SITE. BTG family, member 3 (BTG3) is a target gene of GAM26, corresponding to GAM26-TARGET GENE of FIG. 26A. BTG3 BINDING SITE is a binding site found in an untranslated region of BTG3, corresponding to BINDING SITE of FIG. 26A. FIG. 26D illustrate complementarity of the nucleotide sequence of BTG3 BINDING SITE, designated SEQ ID:84854, to the nucleotide sequence of GAM26 RNA of FIG. 26A, designated SEQ ID:20604.

Yet a further function of GAM26 is therefore inhibition of BTG family, member 3 (BTG3), a gene which encodes a protein that may inhibit cell cycle progression from the g0/g1 to s phase. Accordingly, utilities of GAM26 include diagnosis and treatment of the abovementioned diseases and clinical conditions.

The function of BTG3 has been established by previous studies. Using the RT-PCR-mediated cloning procedure, Yoshida et al. (1998) identified BTG3, a novel member of the PC3/BTG/TOB family of growth inhibitory genes. They obtained full-length sequences of the human and mouse cDNAs by screening a Daudi cell cDNA library and a testis cDNA library, respectively. The human BTG3 cDNA, which the authors called ANA, encodes a deduced 252-amino acid protein that shares 93% sequence identity with the mouse protein. Northern blot analysis detected a 1.5-kb transcript in various human tissues, with relatively high expression in testis, prostate, ovary, thymus, and lung, and low expression in skeletal muscle and spleen. Further analysis in mouse revealed that BTG3 expression was high in the ventricular zone of the developing central nervous system. Overexpression of BTG3 impaired serum-induced cell cycle progression from the G0/G1 to S phase.

Full details of the abovementioned studies are described in the following publications, the disclose of which are hereby incorporated by reference:

Yoshida, Y.; Matsuda, S.; Ikematsu, N.; Kawamura-Tsuzuku, J.; Inazawa, J.; Umemori, H.; Yamamoto, T.: ANA, a novel member of Tob/BTG1 family, is expressed in the ventricular zone of the developing central nervous system. Oncogene 16: 2687-2693, 1998.

Further studies establishing the function and utilities of BTG3 are found in John Hopkins OMIM database record ID 605674, and in references numbered 283 listed hereinbelow.

Reference is now made to CHS1 BINDING SITE. Chediak-Higashi syndrome 1 (CHS1) is target gene of GAM26, corresponding to GAM26-TARGET GENE of FIG. 26A. CHS1 BINDING SITE is a binding site found in an untranslated region of CHS1, corresponding to BINDING SITE of FIG. 26A. FIG. 26D illustrates the complementarity of the nucleotide sequence of CHS1 BINDING SITE, designated SEQ ID:84854, to the nucleotide sequence of GAM26 RNA of FIG. 26A, designated SEQ ID:20604.

Another function of GAM26 is therefore inhibition of Chediak-Higashi syndrome 1 (CHS1), a gene which encodes a protein that is associated with chediak-Higashi syndrome. Accordingly, utilities of GAM26 include diagnosis and treatment of the abovementioned diseases and clinical conditions.

The function of CHS1 has been established by previous studies. Barbosa et al. (1997) identified novel mutations within the region of the coding domain common to both CHS1 isoforms in 3 CHS patients: C-to-T transitions that generated stop codons (R50X; 606897.0006 and Q1029X; 606897.0007) were found in 2 patients, and a novel frameshift mutation (deletion of nucleotides 3073 and 3074 of the coding domain) was found in a third. Northern blots of lymphoblastoid mRNA from HS patients revealed loss of the largest transcript (approximately 13.5 kb) in 2 of 7 CHS patients, while the small mRNA was undiminished in abundance. These results suggested that the small isoform alone cannot complement Chediak-Higashi syndrome. All beige and CHS1 mutations that had been identified were predicted to result in either truncated or absent proteins. Although Perou et al. (1996) and Barbosa et al. (1996) reported identification of the 'beige' gene, the 2 cDNAs were quite different. Nagle et al. (1996) described the sequence of a human cDNA homologous to mouse 'beige,' identified pathologic mutations in patients with Chediak-Higashi syndrome, and clarified the discrepancies of the previous reports of sequence. Analysis of the CHS1 polypeptide demonstrated that its modular architecture is similar to that of the yeast vacuolar sorting VPS15. Nagle et al. (1996) screened human cDNA libraries with mouse 'beige' probes to yield the human 'beige' cDNA homolog, and found 87.9% amino acid identity between the 2 sequences. The predicted human protein comprises 3,801 amino acids, with a molecular mass of approximately 43 kD. Barbosa et al. (1997) reported the sequences of 2 major mRNA isoforms of the CHS1 gene in human and mouse. These isoforms differ both in size and in sequence at the 3-prime end of their coding domains, with a small isoform (approximately 5.8 kb) arising from incomplete splicing and reading through an intron. These mRNAs also differ in tissue distribution of transcription and in predicted biologic properties.

Full details of the abovementioned studies are described in the following publications, the disclosure of which are hereby incorporated by reference:

Karim, M. A.; Nagle, D. L.; Kandil, H. H.; Burger, J.; Moore, K. J.; Spritz, R. A.: Mutations in the Chediak-Higashi syndrome gene (CHS1) indicate requirement for the complete 3801 amino acid CHS protein. Hum. Molec. Genet. 6: 1087-1089, 1997. PubMed ID: 9215679 1. Barbosa, M. D. F. S.; Barrat, F. J.; Tchernev, V. T.; Nguyen, Q. A.; Mishra, V. S.; Colman, S. D.; Pastural, E.; Dufourcq-Lagelouse, R.; Fischer, A.; Holcombe, R. F.; Wallace, M. R.; Brandt, S. J.; de Saint Basile, G.; Kingsmore S. F.: Identification of mutations in two major mRNA isoforms of the Chediak-Higashi syndrome gene in human and mouse. Hum. Molec. Genet. 6: 1091-1098, 1997.

Further studies establishing the function and utilities of CHS1 are found in John Hopkins OMIM database record ID 606897, and in references numbered 284-296 listed hereinbelow.

Referring now to BTG3 BINDING SITE. BTG family, member 3 (BTG3) is a target gene of GAM26, corresponding to GAM26-TARGET GENE of FIG. 26A. BTG3 BINDING SITE is a binding site found in an untranslated region of BTG3, corresponding to BINDING SITE of FIG. 26A. FIG. 26D illustrates the complementarity of the nucleotide sequence of BTG3 BINDING SITE, designated SEQ ID:84863, to the nucleotide sequence of GAM26 RNA of FIG. 26A, designated SEQ ID:20604.

Yet another function of GAM26 is therefore inhibition of BTG family, member 3 (BTG3), a gene which encodes a protein that may inhibit cell cycle progression from the g0/g1 to s phase. Accordingly, utilities of GAM26 include diagnosis and treatment of the abovementioned diseases and clinical conditions. The function and utilities of BTG3 have been established by previous studies, as described hereinabove with reference to FIG. 26D.

Reference is now made to HIRA BINDING SITE. HIR (histone cell cycle regulation defective, *S. cerevisiae*) homolog A (HIRA) is a target gene of GAM26, corresponding to GAM26-TARGET GENE of FIG. 26A. HIRA BINDING SITE is a binding site found in an untranslated region of HIRA, corresponding to BINDING SITE of FIG. 26A. FIG. 26D illustrates the complementarity of the nucleotide sequence of HIRA BINDING SITE, designated SEQ ID:85041, to the nucleotide sequence of GAM26 RNA of FIG. 26A, designated SEQ ID:20604.

An additional function of GAM26 is therefore inhibition of HIR (histone cell cycle regulation defective, *S. cerevisiae*) homolog A (HIRA), a gene which encodes a transcription factor that have a part in mechanisms of transcriptional regulation similar to that played by yeast hir1 and hir2 together and is associated with DiGeorge syndrome. Accordingly, utilities of GAM26 include diagnosis and treatment of the abovementioned diseases and clinical conditions.

The function of HIRA has been established by previous studies. The human TUPLE1 gene encodes a putative transcription regulator with a sequence similar to that of the yeast TUP1 gene (Halford et al., 1993). The protein product of the TUPLE1 gene contains WD40 domain, motifs thought to be involved in protein-protein interactions. Halford et al. (1993) demonstrated that the TUPLE1 gene maps to chromosome 22 and to the shortest region of deletion overlap in a series of over 100 patients with the DiGeorge syndrome (DGS; 188400), velocardiofacial syndrome (VCFS; 92430), or a related disorder. It is expressed in a range of fetal tissues. Halford et al. (1993) cloned the murine Tuple1 gene and showed that it has strong sequence similarity to the human gene. Since TUPLE1 is a candidate gene for DGS through the mechanism of haploinsufficiency and it might be possible to produce models of this disorder by creating mutations in the mouse gene, Mattei et al. (1994) mapped the gene to mouse chromosome 16 by isotopic in situ hybridization. The experiments were carried out using metaphase spreads from a WMP male mouse in which all of the autosomes, except 19, were the form of metacentric Robertsonian translocations. In the human, TUPLE1 is centromeric to COMT (116790), which in turn is centromeric to IGLC1 (147220); all of these expressed sequences map to mouse chromosome 16. Magnaghi et al. (1998) reported an interaction between HIRA and the transcription factor PAX3 (606597). PAX3 haploinsufficiency results in the mouse 'splotch' and human Waardenburg syndrome (see 193500) phenotypes. Mice homozygous for PAX3 mutations die in utero with a phenocopy of DiGeorge syndrome, or neonatally with neural tube defects. HIRA was also found to interact with core histones. Thus, altered stoichiometry of complexes containing HIRA may be important for the development of structures affected in Waardenburg syndrome and DiGeorge syndrome.

Full details of the abovementioned studies are described in the following publications, the disclosure of which are hereby incorporated by reference:

Halford, S.; Wilson, D. I.; Daw, S. C. M.; Roberts, C.; Wadey, R.; Kamath, S.; Wickremasinghe, A.; Burn, J.; Goodship, J.; Mattei, M. -G.; Moorman, A. F. M.; Scambler, P. J.: Isolation of a gene expressed during early embryogenesis from the region of 22q11 commonly deleted in DiGeorge syndrome. Hum. Molec. Genet 2: 1577-1582, 1993. PubMed ID: 8268909 5. Magnaghi, P.; Roberts, C.; Lorain, S.; Lipinski, M.; Scambler, P. J.: HIRA, a mammalian homologue of *Saccharomyces cerevisiae* transcriptional co-repressors, interacts with Pax3. Nature Genet. 20: 74-77, 1998.

Further studies establishing the function and utilities HIRA are found in John Hopkins OMIM database record ID 600237, and in references numbered 297-304 listed hereinbelow.

Reference is now made to CACNA1A BINDING SITE. Calcium channel, voltage-dependent, P/Q type, alpha 1A subunit (CACNA11) is a target gene of GAM26, corresponding to GAM26-TARGET GENE of FIG. 26A. CACNA1A BINDING SITE is a binding site found in an untranslated region of CACNA1A, corresponding to BINDING SITE of FIG. 26D illustrates the complementarity of the nucleotide sequence of CACNA1A BINDING SITE, designated SEQ ID:87774, to the nucleotide sequence of GAM26 RNA of FIG. 26A, designated SEQ ID:20604.

A further function of GAM26 is therefore inhibition of calcium channel, voltage-dependent, P/Q type, alpha 1A subunit (CACNA1A), a gene which encodes a protein that is associated with episodic ataxia type 2, familial hemiplegic migraine, spinocerebellar ataxia type 6, and idiopathic generalized epilepsy. Accordingly, utilities of GAM26 include diagnosis and treatment of the abovementioned diseases and clinical conditions.

The function of CACNA1A has been established by previous studies. Ca(2+) currents have been described on the basis of their biophysical and pharmacologic properties and include L-, N-, T-, P-, Q-, and R-types. The distinctive properties of these Ca(2+) channel types are related primarily to the expression of a variety of alpha-1 isoforms (Dunlap et al., 1995). The alpha-1A isoform is abundantly expressed in neuronal tissue and corresponds to the P/Q Ca(2+) channel type. The B and E isoforms are also expressed in neuronal tissue and correspond to the N-type and R-type of Ca(2+) channels, respectively (Lehmann-Horn and Jurkat-Rott, 1999). The genes encoding the alpha-1A, B, and E isoforms are symbolized CACNL1A4 or CACNA1A, CACNL1A5 (601012), and CACNL1A6 (601013) and are located on 19p13, 9q34 and 1q25-q31, respectively (Diriong et al., 1995).

Animal model experiments lend further support to the function of CACNA1A. By a position al cloning approach, Fletcher et al. (1996) identified an alpha-1 voltage-sensitive Ca(2+) channel gene that is mutated in the 'tottering' mutations in tg and tg(1a) mice. The tg mutation is a well-studied mutation that gives rise to behavioral arrest seizures, which may be compared to human absence (or petit mal) epilepsy (600131) and cerebellar ataxia. The tottering phenotype also includes motor seizures. Fletcher et al. (1996) noted that the tg leaner mice, tg(1a), suffer from absence seizures but do not have motor seizures. These mice are severely ataxic. Fletcher et al. (1996) mapped the tg phenotype to mouse chromosome 8 in the vicinity of the Junb gene (165161). Fletcher et al. (1996) evaluated the C (2+) channel gene as a candidate for the tg locus using RT-PCR and sequencing.

In the tg(1a) mice they demonstrated a single G-to-A change in a splice donor site in the portion of the mouse gene encoding the putative regulatory C-terminal domain of the channel. This mutation resulted in several aberrant mRNA species, including insertion of 98 nucleotides at position 5901/2 and deletion of nucleotides 5763-5901, either of which altered the reading frame 3-prime to the mutations. The tg transcript contained a C-to-A change at position 1802 relative to the control sequence. Fletcher et al. (1996) reported that this alteration leads to a nonconservative proline-to-leucine amino acid substitution that may affect the pore function of the Ca(2+) channel. Fletcher et al. (1996) noted that this is the first gene identified as being involved in absence epilepsy.

It is appreciated that the abovementioned animal model for CACNA1A is acknowledged by those skilled in the art as a scientifically valid animal model, as can be further appreciated from the publications sited hereinbelow.

Full details of the abovementioned studies are described in the following publications, the disclosure of which are hereby incorporated by reference:

Dunlap, K.; Luebke, J. I.; Turner, T. J.: Exocytotic Ca(2+) channels in mammalian central neurons. Trends Neurosci. 18: 89-98, 1995. PubMed ID: 7537420 8. Fletcher, C. F.; Lutz, C. M.; O'Sullivan, T. N.; Shaughnessy, J. D, Jr.; Hawkes, R.; Frankel, W. N.; Copeland, N. G.; Jenkins, N. A.: Absence epilepsy in tottering mutant mice is associated with calcium channel defects. Cell 87: 607-617, 1996.

Further studies establishing the function and utilities of CACNA1A are found in John Hopkins OMIM database record ID 601011, and in numbered 305-335 listed hereinbelow.

Reference is now made to CALM1 BINDING SITE. Calmodulin 1 (phosphorylase kinase, delta) (CALM1 is a target gene of GAM26, corresponding to GAM26-TARGET GENE of FIG. 26A. CALM1 BINDING SITE is a binding site found in an untranslated region of CALM1, corresponding to BINDING SITE of FIG. 26A. FIG. 26D illustrates the complementarity of the nucleotide sequence of CALM1 BINDING SITE, designated SEQ ID:89443, to the nucleotide sequence of GAM26 RNA of FIG. 26A, designated SEQ ID:20604.

Yet a further function of GAM26 is therefore inhibition of calmodulin 1 (phosphorylase kinase, delta) (CALM1), a gene which encodes a protein that plays roles in growth and the cell cycle as well as in signal transduction and the synthesis and release of neurotransmitters. Accordingly, utilities of GAM26 include diagnosis and treatment of the abovementioned diseases and clinical conditions.

The function of CALM1 has been established by previous studies. Calmodulin is the archetype of the family of calcium-modulated proteins of which nearly 20 members have been found. They are identified by their occurrence in the cytosol or on membranes facing the cytosol and by a high affinity for calcium. Calmodulin contains 149 amino acids and has 4 calcium-binding domains. Its functions include roles in growth and the cell cycle as well as in signal transduction and the synthesis and release of neurotransmitters. To determine how calcium/calmodulin activate calcium/calmodulin-dependent protein kinase I (CAMK1; 604998), Chin et al. (1997) characterized CAMK1 activation by calmodulin mutants with substitutions at hydrophobic residues. They found that CAMK1 activity is dependent on met124 within the C-terminal domain of calmodulin as well as on N-terminal hydrophobic residues of calmodulin.

Full details of the abovementioned studies are described in the following publications, the disclosure of which are hereby incorporated by reference:

Rhyner, J. A.; Ottiger, M.; Wicki, R.; Greenwood, T. M.; Strehler, E. E.: Structure of the human CALM1 calmodulin gene and identification of two CALM1-related pseudogenes CALM1P1 and CALM1P2. Europ. J. Biochem. 225: 71-82, 1994. PubMed ID: 7925473 2. Chin, D.; Winkler, K. E.; Means, A. R.: Characterization of substrate phosphorylation and use of calmodulin mutants to address implications from the enzyme crystal structure of calmodulin-dependent protein kinase I. J. Biol. Chem. 272: 31235-31240, 1997.

Further studies establishing the function and utilities of CALM1 are found in John Hopkins OMIM database record ID 114180, and in references numbered 336-347 listed hereinbelow.

Referring now to CALM1 BINDING SITE. Calmodulin 1 (phosphorylase kinase, delta) (CALM1) is a target gene of GAM26, corresponding to GAM26-TARGET GENE of FIG. 26A. CALM1 BINDING SITE is a binding site found in an untranslated region of CALM1, corresponding to BINDING SITE of FIG. 26A. FIG. 26D illustrates the complementarity of the nucleotide sequence CALM1 BINDING SITE, designated SEQ ID:89450, to the nucleotide sequence of GAM26 RNA of FIG. 26A, designated SEQ ID:20604.

Another function of GAM26 is therefore inhibition of calmodulin 1 (phosphorylase kinase, delta) (CALM1), a gene which encodes a protein that plays roles in growth and the cell cycle as well as in signal transduction and the synthesis and release of neurotransmitters. Accordingly, utilities of GAM26 include diagnosis and treatment of the abovementioned diseases and clinical conditions. The function and utilities of CALM1 have been established by previous studies, as described hereinabove with reference to FIG. 26D.

Referring now to CACNA1A BINDING SITE. Calcium channel, voltage-dependent, P/Q type, alpha 1A subunit (CACNA1A) is a target gene of GAM26, corresponding to GAM26-TARGET GENE of FIG. 26A. CACNA1A BINDING SITE is a binding site found in an untranslated region of CACNA1A, corresponding to BINDING SITE of FIG. 26A. FIG. 26D illustrates the complementarity of the nucleotide sequence of CACNA1A BINDING SITE, designated SEQ ID:94853, to the nucleotide sequence of GAM26 RNA of FIG. 26A, designated SEQ ID:20604.

Yet another function of GAM26 is therefore calcium channel, voltage-dependent, P/Q type, alpha 1A subunit (CACNA1A), a gene which encodes a protein that is associated with episodic ataxia type 2, familial hemiplegic migraine, spinocerebellar ataxia type 6, and idiopathic generalized epilepsy. Accordingly, utilities of GAM26 include diagnosis and treatment of the abovementioned diseases and clinical conditions. The function and utilities of CACNA1A have been established by previous studies, as described hereinabove with reference to FIG. 26D.

Reference is now made to CBL BINDING SITE. Cas-Br-M (murine) ecotropic retroviral transforming sequence (CBL) is a target gene of GAM26, corresponding to GAM26-TARGET GENE of FIG. 26A. CBL BINDING SITE is a binding site found in an untranslated region of CBL, corresponding to BINDING SITE of FIG. 26A. FIG. 26D illustrates the complementarity of the nucleotide sequence of CBL BINDING SITE, designated SEQ ID:94853, to the nucleotide sequence of GAM26 RNA of FIG. 26A, designated SEQ ID:20604.

An additional function of GAM26 is therefore inhibition of Cas-Br-M (murine) ecotropic retroviral transforming sequence (CBL), a gene which encodes a protein that may modify receptor tyrosine kinase-mediated signal transduction and is associated with B-lineage lymphomas. Accordingly, utilities of GAM26 include diagnosis and treatment of the abovementioned diseases and clinical conditions.

The function of CBL has been established by previous studies. Cas NS-1 is an acutely transforming murine retrovirus that induces pre-B and pro-B cell lymphomas. Molecular cloning showed that it was generated from the ecotropic Cas-Br-M virus by sequential recombinations with endogenous retroviral sequences and a cellular oncogene. Langdon et al. (1989) found that the oncogene sequence shows no homology with known oncogenes, but some similarity to the yeast transcriptional activator GCN4. A 100-kD gag-cbl fusion protein, with no detectable kinase activity, is responsible for the cellular transformation. The cellular homolog of v-cbl, present in mouse and human DNA, is expressed in a range of homopoietic lineages. Wei et al. (1990) mapped the CBL2 gene to 11q23.3-qter by molecular characterization of the breakpoints in 2 somatic cell hybrids. Savage et al. (1991) studied the relation of CBL2 to the breakpoints in malignancies with translocations involving chromosome 11. CBL2 was translocated from chromosome 11 to 4 in an acute leukemia cell line possessing a t(4;11)(q21;q23) and from chromosome 11 to 14 in a B-cell lymphoma with a t(11;14)(q23;q32). CBL2 remained on chromosome 11 in a Ewing sarcoma cell line (133450) with a t(11;22)(q23;q12). Other studies indicated that NCAM (116930) and the genes for the 3 subunits of CD3 were all proximal to the tightly clustered THY1 (188230), ETS1 (164720), and CBL2 in 11q23. Vulval induction during development of *Caenorhabditis elegans* is mediated by LET-23, a homolog of the mammalian epidermal growth factor receptor tyrosine kinase (131550). The sli-1 gene is a negative regulator of LET-23 and was shown by Yoon et al. (1995) to encode a protein similar to the mammalian protooncoprotein CBL2. The sli-1 and CBL2 proteins share approximately 55% amino acid identity over a stretch of 390 residues, which includes a C(3)HC(4) zinc-binding motif known as the RING finger, and multiple consensus binding sites for SRC homology 3 (SH3) domains. The authors stated that sli-1 and CBL2 may define a new class of proteins that modify receptor tyrosine kinase-mediated signal transduction.

Full details of the abovementioned studies are described in the following publications, the disclosure of which are hereby incorporated by reference:

Savage, P. D.; Shapiro, M.; Langdon, W. Y.; Geurts van Kessel, A. D.; Seuanez, H. N.; Akao, Y.; Croce, C.; Morse, H. C., III; Kersey, J. H.: Relationship of the human protooncogene CBL2 on 11q23 to the t(4;11), t(11;22), and t(11;4) breakpoints. Cytogenet Cell Genet 56: 112-115, 1991. PubMed ID: 2013228 12. Yoon, C. H.; Lee, J.; Jongeward, G. D.; Sternberg, P. W.: Similarity of sli-1, a regulator of vulval development in *C. elegans*, to the mammalian proto-oncogene c-cbl. Science 269: 1102-1105, 1995.

Further studies establishing the function and utilities of CBL are found in John Hopkins OMIM database record ID 165360, and in references numbered 348-359 listed hereinbelow.

Referring now to CBL BINDING SITE. Cas-Br-M (murine) ecotropic retroviral transforming sequence (CBL) is a target gene of GAM26, corresponding to GAM26-TARGET GENE of FIG. 26A. CBL BINDING SITE is a binding site found in an untranslated region of CBL, corresponding to BINDING SITE of FIG. 26A. FIG. 26D illustrates the complementarity of the nucleotide sequence of CBL BINDING SITE, designated SEQ ID:94853, to the nucleotide sequence of GAM26 RNA of FIG. 26A, designated SEQ ID: 20604.

A further function of GAM26 is therefore inhibition of Cas-Br-M (murine) ecotropic retroviral transforming sequence (CBL), a gene which encodes a protein that may modify receptor tyrosine kinase-mediated signal transduction, and is associated with B-lineage lymphomas. Accordingly, utilities of GAM26 include diagnosis and treatment of the abovementioned diseases and clinical conditions. The function and utilities of CBL have been established by previous studies, as described hereinabove with reference to FIG. 26D.

Referring now to CBL BINDING SITE. Cas-Br-M (murine) ecotropic retroviral transforming sequence (CBL) is a target gene of GAM26, corresponding to GAM26-TARGET GENE of FIG. 26A. CBL BINDING SITE is a binding site found in an untranslated region of CBL, corresponding to BINDING SITE FIG. 26A. FIG. 26D illustrates the complementarity of the nucleotide sequence of CBL BINDING SITE, designated SEQ ID:94853, to the nucleotide sequence of GAM26 RNA of FIG. 26A, designated SEQ ID:20604.

Yet a further function of GAM26 is therefore inhibition of Cas-Br-M (murine) ecotropic retroviral transforming sequence (CBL), a gene which encodes a protein that may modify receptor tyrosine kinase-mediated signal transduction and is associated with B lineage lymphomas. Accordingly, utilities of GAM26 include diagnosis and treatment of the abovementioned diseases and clinical conditions. The function and utilities of CBL have been established by previous studies, as described hereinabove with reference to FIG. 26D.

Referring now to CBL BINDING SITE. Cas-Br-M (murine) ecotropic retroviral transforming sequence (CBL) is a target gene of GAM26, corresponding to GAM26-TARGET GENE of FIG. 26A. CBL BINDING SITE is a binding site found in an untranslated region of CBL, corresponding to BINDING SITE of FIG. 26A. FIG. 26D illustrates the complementarity of the nucleotide sequence of CBL BINDING SITE, designated SEQ ID:94853, to the nucleotide sequence of GAM26 RNA of FIG. 26A, designated SEQ ID:20604.

Another function of GAM26 is therefore inhibition of Cas-Br-M (murine) ecotropic retroviral transforming sequence (CBL), a gene which encodes a protein that may modify receptor tyrosine kinase-mediated signal transduction and is associated with B-lineage lymphomas. Accordingly, utilities of GAM26 include diagnosis and treatment of the abovementioned diseases and clinical conditions. The function and utilities of CBL have been established by previous studies, as described hereinabove with reference to FIG. 26D.

Reference is now made to FGF18 BINDING SITE. Fibroblast growth factor 18 (FGF18) is a target gene of GAM26, corresponding to GAM26-TARGET GENE of FIG. 26A. FGF18 BINDING SITE is a binding site found in an untranslated region of FGF18, corresponding to BINDING SITE of FIG. 26A. FIG. 26D illustrates the complementarity of the nucleotide sequence of FGF18 BINDING SITE, designated SEQ ID:94853, to the nucleotide sequence of GAM26 RNA of FIG. 26A, designated SEQ ID:20604.

Yet another function of GAM26 is therefore inhibition of fibroblast growth factor 18 (FGF18), a gene which encodes a protein that stimulates hepatic and intestinal proliferation.

Accordingly, utilities of GAM26 include diagnosis and treatment of the abovementioned diseases and clinical conditions.

The function of FGF18 has been established by previous studies. The fibroblast growth factors (FGFs; e.g., FGF2; 134920) are a family of growth factors and oncogenes that contain a conserved, approximately 120-amino acid core. Individual FGFs play important roles in embryonic development, cell growth, morphogenesis, tissue repair, inflammation, angiogenesis, and tumor growth and invasion. Ohbayashi et al. (1998) isolated human, mouse, and rat cDNAs encoding a novel member of the FGF family, FGF18. The deduced 207-amino acid human and rat FGF18 proteins are 99% identical. FGF18 contains a typical hydrophobic signal sequence at its N terminus, and the authors demonstrated that recombinant rat Fgf18 can be efficiently secreted by High Five insect cells. Recombinant rat Fgf18 induced neurite outgrowth in PC12 cells. Northern blot analysis of rat adult tissues showed abundant expression of Fgf18 in lung but did not detect Fgf18 expression in other tissues. In rat 14.5- and 19.5-day embryos, in situ hybridization showed Fgf18 expression in several discrete regions. Independently, Hu et al. (1998) isolated human and mouse FGF18 cDNAs. Among known FGF family members, the FGF18 protein is most similar to FGF8 (600483) and FGF17 (603725), with human FGF18 showing 60% and 58% identity with human FGF8 and FGF17, respectively. The authors demonstrated that recombinant mouse Fgf18 is glycosylated and can stimulate proliferation of NIH 3T3 cells in vitro in a heparan sulfate-dependent manner. Northern blot analysis of mouse adult tissues showed highest Fgf18 expression in the lung and kidney, and in situ hybridization of mouse 15.5-day embryos detected Fgf18 transcripts primarily in the lung. However, injection of recombinant mouse Fgf18 into normal mice induced proliferation in a wide variety of tissues, with the liver and small intestine appearing to be the primary targets. Hu et al. (1998) showed that transgenic mice overexpressing Fgf18 in the liver exhibited an increase in liver weight and hepatocellular proliferation. By radiation hybrid analysis and FISH, Whitmore et al. (2000) mapped the FGF18 gene to chromosome 5q34.

Full details of the abovementioned studies are described in the following publications, the disclosure of which are hereby incorporated by reference:

Ohbayashi, N.; Hoshikawa, M.; Kimura, S.; Yamasaki, M.; Fukui, S.; Itoh, N.: Structure and expression of the mRNA encoding a novel fibroblast growth factor, FGF-18. J. Biol. Chem. 273: 18161-18164, 1998. PubMed ID: 9660775 3. Whitmore, T. E.; Maurer, M. F.; Sexson, S.; Raymond, F.; Conklin, D.; Deisher, T. A.: Assignment of fibroblast growth factor 18 (FGF18) to human chromosome 5q34 by use of radiation hybrid mapping and fluorescence in situ hybridization. Cytogenet. Cell Genet 90: 231-233, 2000.

Further studies establishing the function and utilities of FGF18 are found in John Hopkins OMIM database record ID 603726, and in references numbered 360-362 listed hereinbelow.

Referring now to FGF18 BINDING SITE. Fibroblast growth factor 18 (FGF18) is a target gene of GAM26, corresponding to GAM26-TARGET GENE of FIG. 26A. FGF18 BINDING SITE is a binding site found in an untranslated region of FGF18, corresponding to BINDING SITE of FIG. 26A. FIG. 26D illustrates the complementarity of the nucleotide sequence of FGF18 BINDING SITE, designated SEQ ID:94853, to the nucleotide sequence of GAM26 RNA of FIG. 26A, designated SEQ ID:20604.

An additional function of GAM26 is therefore inhibition of fibroblast growth factor 18 (FGF18) a gene which encodes a protein that stimulates hepatic and intestinal proliferation. Accordingly, utilities of GAM26 include diagnosis and treatment of the abovementioned diseases and clinical condition. The function and utilities of FGF18 have been established by previous studies, as described hereinabove with reference to FIG. 26D.

Reference is now made to FMR1 BINDING SITE. Fragile X mental retardation 1 (FMR1) is a target gene of GAM26, corresponding to GAM26-TARGET GENE of FIG. 26A. FMR1 BINDING SITE is a binding site found in an untranslated region of FMR1, corresponding to BINDING SITE of FIG. 26A. FIG. 26D illustrates the complementarity of the nucleotide sequence of FMR1 BINDING SITE, designated SEQ ID:94853, to the nucleotide sequence of GAM26 RNA of FIG. 26A, designated SEQ ID:20604.

A further function of GAM26 is therefore inhibition of fragile X mental retardation 1 (FMR1), a gene which encodes a protein that is associated with fragile x syndrome. Accordingly, utilities of GAM26 include diagnosis and treatment of the abovementioned diseases and clinical conditions.

The function of FMR1 has been established by previous studies. X-linked mental retardation associated with marXq28, or fragile X syndrome, is characterized by moderate to severe mental retardation, macroorchidism, large ears, prominent jaw, and high-pitched jocular speech. Expression is variable, with mental retardation being the most common feature. This phenotype is associated with mutations in the FMR1 gene. McCabe et al. (1999) summarized the proceedings of a workshop on the fragile X syndrome held in December 1998. Filippi et al. (1983) studied linkage with G6PD and colorblindness in 18 Sardinian pedigrees. In 6 informative pedigrees the fragile X syndrome showed close linkage with G6PD deficiency and deutan colorblindness. The maximum likelihood estimate of recombination was 6% with 90% fiducial limits between 2.5 and 19.5% and odds favoring linkage of 428:1. No hint of linkage of G6PD and the Renpenning form of X-linked mental retardation (309500) or other unspecified type of X-linked mental retardation was found. Patients with the Renpenning form not only lack the facial features and macroorchidism typical of the fragile X syndrome but also have microcephaly. Brown et al. (1988) performed a multilocus linkage analysis of the fragile X syndrome in 147 families using 4 flanking markers. As previously observed by Giannelli et al. (1987), significant variation in the recombination distance between F9 and FRAXA was found also in this group of families. Heterogeneity testing showed that 20% of the families had tight F9-FRAXA linkage, whereas 80% demonstrated loose linkage, with an average recombination distance of 0.35. On average, the multipoint distances found were DXS51-F9, 6.9%; F9-FRAXA, 22.4%; FRAXA-DXS52, 12.7%; and DXS52-DXS15, 2.2%. Thibodeau et al. (1988) also reported on linkage data between the fragile X locus and 4 polymorphic markers: DXS51, F9, DXS98, and DXS52. The markers were studied in 14 families with fragile X and 9 normal pedigrees from the CEPH collection. In this set of families, as has been previously observed, there was evidence for genetic heterogeneity between the fragile X locus and the F9 site. The observed recombination frequencies were as follows: DXS51-F9, 0%; F9-DXS52, 45%; DXS51-FRAXA, 15%; F9-FRAXA, 18%; DXS8-FRAXA, 36%; and DXS52-FRAXA, 15%. The authors proposed the following relative order for the 5 loci, based on multipoint linkage analysis: (DXS51, F9, DXS98)--FRAXA--DXS52. Laggerbauer et al. (2001) showed that FMR1 strongly inhibited translation of various mRNAs at nanomolar in both rabbit reticulocyte lysate and microinjected *Xenopus laevis* oocytes. The effect was specific for FMR1, since other proteins with similar RNA-binding domains, including the autosomal homologs of FMR1, FXR1 and FXR2, failed to suppress translation in the same concentration range. Initial studies addressing the underlying mechanism of inhibition suggested that FMR1 may inhibit the assembly of 80S ribosomes on the target mRNAs. A disease-causing substitution, ile304 to asn (I304N; 309550.0001), rendered FMR1 incapable of interfering with translation in both test systems, and severely impaired homooligomerization of FMR1. The failure of FMR1 I304N to suppress translation was not due to its reduced affinity for mRNA or its interacting proteins FXR1 and FXR2. The authors hypothesized that inhibition of translation may be a function of FMR1 in vivo, and that failure of mutant FMR1 protein to oligomerize may contribute to the pathophysiologic events leading to fragile X syndrome.

Animal model experiments lend further support to the function of FMR1. Zhang et al. (2001) developed a *Drosophila* model of fragile X syndrome using loss-of-function mutants and overexpression of the FMR1 homolog, Dfxr (*Drosophila* fragile X-related gene). Dfxr nulls displayed enlarged synaptic terminals, whereas neuronal overexpression resulted in fewer and larger synaptic boutons. Synaptic structural defects were accompanied by altered neurotransmission, with synapse type-specific regulation in central and peripheral synapses.

It is appreciated that the abovementioned animal model for FMR1 is acknowledged by those skilled in the art as a scientifically valid animal model, as can be further appreciated from the publications sited hereinbelow.

Full details of the abovementioned studies are described in the following publications, the disclosure of which are hereby incorporated by reference:

Zhang Y. Q.; Bailey, A. M.; Matthies, H. J. G.; Renden, R. B.; Smith, M. A.; Speese, S. D.; Rubin, G. M.; Broadie, K.: Drosophila fragile X-related gene regulates the MAP1B homolog Futsch to control synaptic structure and function. Cell 107: 591-603, 2001. PubMed ID: 11733059

139. McCabe, E. R. B.; de la Cruz, F.; Clapp, K.: Workshop on Fragile X: future research directions. Am. J. Med. Genet 85: 317-322, 1999.

Further studies establishing the function and utilities of FMR1 are found in John Hopkins OMIM database record ID 309550, and in references numbered 363-461 listed hereinbelow.

Referring now to FMR1 BINDING SITE. Fragile X mental retardation 1 (FMR1) is a target gene of GAM26, corresponding to GAM26-TARGET GENE of FIG. 26A. FMR1 BINDING SITE is a binding site found in an untranslated region of FMR1, corresponding to BINDING SITE of FIG. 26A. FIG. 26D illustrates the complementarity of the nucleotide sequence of FMR1 BINDING SITE, designated SEQ ID:94853, to the nucleotide sequence of GAM26 RNA of FIG. 26A, designated SEQ ID:20604.

Yet a further function of GAM26 is therefore inhibition of fragile X mental retardation 1 (FMR1), a gene which encodes a protein that is associated with fragile x syndrome. Accordingly, utilities of GAM26 include-diagnosis and treatment of the abovementioned diseases and clinical conditions. The function and utilities of FMR1 have been established by previous studies, as described hereinabove with reference to FIG. 26D.

Referring now to FMR1 BINDING SITE. Fragile X mental retardation 1 (FMR1) is a target gene of GAM26, corresponding to GAM26-TARGET GENE of FIG. 26A. FMR1 BINDING SITE is a binding site found in an untranslated region of FMR1, corresponding to BINDING SITE of FIG. 26A. FIG. 26D illustrates the complementarity of the nucleotide sequence of FMR1 BINDING SITE, designated SEQ ID:94853, to the nucleotide sequence of GAM26 RNA of FIG. 26A, designated SEQ ID:20604.

Another function of GAM26 is therefore inhibition of fragile X mental retardation 1 (FMR1), a gene which encodes a protein that is associated with fragile x syndrome. Accordingly, utilities of GAM26 include diagnosis and treatment of the abovementioned diseases and clinical conditions. The function and utilities of FMR1 have been established by previous studies, as described hereinabove with reference to FIG. 26D.

Referring now to FMR1 BINDING SITE. Fragile X mental retardation 1 (FMR1) is a target gene of GAM26, corresponding to GAM26-TARGET GENE of FIG. 26A. FMR1 BINDING SITE is a binding site found in an untranslated region of FMR1, corresponding to BINDING SITE of FIG. 26A. FIG. 26D illustrates the complementarity of the nucleotide sequence of FMR1 BINDING SITE, designated SEQ ID:94853, to the nucleotide sequence of GAM26 RNA of FIG. 26A, designated SEQ ID:20604.

Yet another function of GAM26 is therefore inhibition of fragile X mental retardation 1 (FMR1), a gene which encodes a protein that is associated with fragile x syndrome. Accordingly, utilities of GAM26 include diagnosis and treatment of the abovementioned diseases and clinical conditions. The function and utilities of FMR1 have been established by previous studies, as described hereinabove with reference to FIG. 26D.

Referring now to FMR1 BINDING SITE. Fragile X mental retardation 1 (FMR1) is a target gene of GAM26, corresponding to GAM26-TARGET GENE of FIG. 26A. FMR1 BINDING SITE is a binding site found in an untranslated region of FMR1, corresponding to BINDING SITE of FIG. 26A. FIG. 26D illustrates the complementarity of the nucleotide sequence of FMR1 BINDING SITE, designated SEQ ID:94853, to the nucleotide sequence of GAM26 RNA of FIG. 26A, designated SEQ ID:20604.

An additional function of GAM26 is therefore inhibition of fragile X mental retardation 1 (FMR1), a gene which encodes a protein that is associated with fragile x syndrome. Accordingly, utilities of GAM26 include diagnosis and treatment of the abovementioned diseases and clinical conditions. The function and utilities of FMR1 have been established by previous studies, as described hereinabove with reference to FIG. 26D.

Referring now to FMR1 BINDING SITE. Fragile X mental retardation 1 (FMR1) is a target gene of GAM26, corresponding GAM26-TARGET GENE of FIG. 26A. FMR1 BINDING SITE is a binding site found in an untranslated region of FMR1, corresponding to BINDING SITE of FIG. 26A. FIG. 26D illustrates the complementarity of the nucleotide sequence of FMR1 BINDING SITE, designated SEQ ID:94853, to the nucleotide sequence of GAM26 RNA of FIG. 26A, designated SEQ ID:20604.

A further function of GAM26 is therefore inhibition of fragile X mental retardation 1 (FMR1), a gene which encodes a protein that is associated with fragile x syndrome. Accordingly utilities of GAM26 include diagnosis and treatment of the abovementioned diseases and clinical conditions. The function and utilities of FMR1 have been established by previous studies, as described hereinabove with reference to FIG. 26D.

Referring now to FMR1 BINDING SITE. Fragile X mental retardation 1 (FMR1) is a target gene of GAM26, corresponding to GAM26-TARGET GENE of FIG. 26A. FMR1 BINDING SITE is a binding site found in an untranslated region of FMR1, corresponding to BINDING SITE of FIG. 26A. FIG. 26D illustrates the complementarity of the nucleotide sequence of FMR1 BINDING SITE, designated SEQ ID:94853, to the nucleotide sequence of GAM26 RNA of FIG. 26A, designated SEQ ID:20604.

Yet a further function of GAM26 is therefore inhibition of fragile X mental retardation 1 (FMR1), a gene which encodes a protein that is associated with fragile x syndrome. Accordingly, utilities of GAM26 include diagnosis and treatment of the abovementioned diseases and clinical conditions. The function and utilities of FMR1 have been established by previous studies, as described hereinabove with reference to FIG. 26D.

Reference is now made to GSPT1 BINDING SITE. G1 to S phase transition 1 (GSPT1) is a target gene of GAM26, corresponding to GAM26-TARGET GENE of FIG. 26A. GSPT1 BINDING SITE is a binding site found in an untranslated region of GSPT1, corresponding to BINDING SITE of FIG. 26A. FIG. 26D illustrates the complementarity of the nucleotide sequence of GSPT1 BINDING SITE, designated SEQ ID:94853, to the nucleotide sequence of GAM26 RNA of FIG. 26A, designated SEQ ID:20604.

Another function of GAM26 is therefore inhibition of G1 to S phase transition 1 (GSPT1), a gene which encodes a protein that involves in regulation of mammalian cell growth. Accordingly, utilities of GAM26 include diagnosis and treatment of the abovementioned diseases and clinical conditions.

The function of GSPT1 has been established by previous studies. Kikuchi et al. (1988) isolated a gene from a yeast genomic library that could complement a temperature-sensitive mutant of Saccharomyces cerevisiae. The gene, termed GST1, seemed to be essential for the G1-to-S phase transition in the yeast cell cycle. The gene product appeared to be a GTP-binding protein of molecular mass 76,565 Da, with 38% identity in amino acid sequence with the alpha subunit of elongation factor-1 (130590). Hoshino et al. (1989) cloned the human equivalent from a cDNA library. By nonradioactive in situ hybridization, Ozawa et al. (1992) mapped the GSPT1 gene, the human homolog of the yeast gene GST1-Hs, to human chromosome 16p13.1. Southern blot hybridization with a panel of human-rodent somatic cells confirmed the localization of the GSPT1 gene on chromosome 16 and also showed the existence of a homologous gene on the X chromosome. They pointed out that a breakpoint for nonrandom chromosome rearrangements has been found in the region of GSPT1 in patients with acute nonlymphocytic leukemia.

Full details of the abovementioned studies are described in the following publications, the disclosure of which are hereby incorporated by reference:

Ozawa, K.; Murakami, Y.; Eki, T.; Yokoyama, K.; Soeda, E.; Hoshino, S.; Ui, M.; Hanaoka, F.: Mapping of the human GSPT1 gene, a human homolog of the yeast GST1 gene, to chromosomal band 16p13.1. Somat. Cell Molec. Gene 18: 189-194, 1992. PubMed ID: 1574740 1. Hoshino, S.; Miyazawa, H.; Enomoto, T.; Hanaoka, F.; Kikuchi, Y.; Kikuchi, A.; Ui, M.: A human homologue of the yeast GST1 gene codes for a GTP-binding protein and is expressed in a proliferation-dependent manner in mammalian cells. EMBO J. 8: 3807-3814, 1989.

Further studies establishing the function and utilities of GSPT1 are found in John Hopkins OMIM database record ID 139259, and in references numbered 462-464 listed hereinbelow.

Referring now to GSPT1 BINDING SITE. G1 to S phase transition 1 (GSPT1) is a target gene of GAM26, corresponding to GAM26-TARGET GENE of FIG. 26A. GSPT1 BINDING SITE is a binding site found in an untranslated region of GSPT1, corresponding to BINDING SITE of FIG. 26A. FIG. 26D illustrates the complementarity of the nucleotide sequence of GSPT1 BINDING SITE, designated SEQ ID:94853, to the nucleotide sequence of GAM26 RNA of FIG. 26A, designated SEQ ID:20604.

Yet another function of GAM26 is therefore inhibition of G1 to S phase transition 1 (GSPT1), a gene which encodes a protein that involves in regulation of mammalian cell growth. Accordingly, utilities of GAM26 include diagnosis and treatment of the abovementioned diseases and clinical conditions. The function and utilities of GSPT1 have been established by previous studies, as described hereinabove with reference to FIG. 26D.

Referring now to GSPT1 BINDING SITE. G1 to S phase transition 1 (GSPT1) is a target gene of GAM26, corresponding to GAM26-TARGET GENE of FIG. 26A. GSPT1 BINDING SITE is a binding site found in an untranslated region of GSPT1, corresponding to BINDING SITE of FIG. 26A. FIG. 26D illustrates the complementarity of the nucleotide sequence of GSPT1 BINDING SITE, designated SEQ ID:94853, to the nucleotide sequence of GAM26 RNA of FIG. 26A, designated SEQ ID:20604.

An additional function of GAM26 is therefore inhibition of G1 to S phase transition 1 (GSPT1), a gene which encodes a protein that involves in regulation of mammalian cell growth. Accordingly, utilities of GAM26 include diagnosis and treatment of the abovementioned diseases and clinical conditions. The function and utilities of GSPT1 have been established by previous studies, as described hereinabove with reference to FIG. 26D.

Reference is now made to MLLT1 BINDING SITE. Myeloid/lymphoid or mixed-lineage leukemia (trithorax (Drosophila) hom (MLLT1) is a target gene of GAM26, corresponding to GAM26-TARGET GENE of FIG. 26A. MLLT1 BINDING SITE is a binding site found in an untranslated region of MLLT1, corresponding to BINDING SITE of FIG. 26A. FIG. 26D illustrates the complementarity of the nucleotide sequence of MLLT1 BINDING SITE, designated SEQ ID:94853, to the nucleotide sequence of GAM26 RNA of FIG. 26A, designated SEQ ID:20604.

A further function of GAM26 is therefore inhibition of myeloid/lymphoid or mixed-lineage leukemia (trithorax (Drosophila) hom (MLLT1), a gene which encodes a protein that is associated with acute leukemias. Accordingly, utilities of GAM26 include diagnosis and treatment of the abovementioned diseases and clinical conditions.

The function of MLLT1 has been established by previous studies. Tkachuk et al. (1992) showed that the gene involved in recurring 11q23 leukemogenic translocations codes for an unusually large protein that is a homolog of Drosophila 'trithorax' and is involved in homeotic gene regulation (MLL; 159555). In studies of a t(11;19) translocation, they identified a chimeric protein containing the amino-terminal 'AT-hook' motifs of the MLL gene on chromosome 11 fused to a previously undescribed protein from chromosome 19. The nucleotide sequence determinations demonstrated an open reading frame that coded for a predicted 62-kD protein, which Tkachuk et al. (1992) named ENL for 'eleven-nineteen leukemia.' Nakamura et al. (1993) showed that the gene on chromosome 19 that is fused to the MLL gene (also known as ALL1 gene) in patients with leukemia and translocation t(11;19)(q23;p13) shows high sequence homology to the genes on chromosome 4 (159557) and chromosome 9 (159558) that are fused with the ALL1 gene in patient with translocation t(4;11)(q21;q23) and t(9;11)(p22;q23), respectively. The 3 protein gene products contained nuclear targeting sequences as well as serine-rich and proline-rich regions. The results suggested that the different proteins fused to ALL1 polypeptides. These leukemias provide similar functional domains. Thirman et al. (1994) pointed out that the breakpoint that results in the fusion of MLL to the ENL gene is located at 19p13.3. Another translocation t(11;19)(q23;p13.1) results in fusion of the MLL gene with the ELL gene (600284) in acute myeloid leukemia. This gene is also symbolized MLLT1.

Full details of the abovementioned studies are described in the following publications, the disclosure of which are hereby incorporated by reference:

Takamura, T.; Alder, H.; Gu, Y.; Prasad, R.; Canaani, O.; Kamada, N.; Gale, R. P.; Lange, B.; Crist, W. M.; Nowell, P. C.; Croce, C. M.; Canaani, E.: Genes on chromosomes 4, 9, and 19 involved in 11q23 abnormalities in acute leukemia share sequence homology and/or common motifs. Proc. Nat. Acad. Sci. 90: 4631-4635, 1993. PubMed ID: 8506309 3. Thirman, M. J.; Levitan, D. A.; Kobayashi, H.; Simon, M. C.; Rowley, J. D.: Cloning of ELL, a gene that fuses to MLL in a t(11;19)(q23;p13.1) in acute myeloid leukemia. Proc. Nat. Acad. Sci. 91: 12110-12114, 1994.

Further studies establishing the function and utilities of MLLT1 are found in John Hopkins OMIM database record ID 159556, and in references numbered 465-468 listed hereinbelow.

Referring now to MLLT1 BINDING SITE. Myeloid/lymphoid or mixed-lineage leukemia (trithorax (*Drosophila*) hom (MLLT1) is a target gene of GAM26, corresponding to GAM26-TARGET GENE of FIG. 26A. MLLT1 BINDING SITE is a binding site found in an untranslated region of MLLT1, corresponding BINDING SITE of FIG. 26A. FIG. 26D illustrates the complementarity of the nucleotide sequence of MLLT1 BINDING SITE, designated SEQ ID:94853, to the nucleotide sequence of GAM26 RNA of FIG. 26A, designated SEQ ID:20604.

Yet a further function of GAM26 is therefore inhibition of myeloid/lymphoid or mixed-lineage leukemia (trithorax (*Drosophila*) hom (MLLT1), a gene which encodes a protein that is associated with acute leukemias. Accordingly, utilities of GAM26 include diagnosis and treatment of the abovementioned diseases and clinical conditions. The function and utilities of MLLT1 have been established by previous studies, as described hereinabove with reference to FIG. 26D.

Reference is now made to NTRK3 BINDING SITE. Neurotrophic tyrosine kinase, receptor, type 3 (NTRK3) is a target gene of GAM26, corresponding to GAM26-TARGET GENE of FIG. 26A. NTRK3 BINDING SITE is a binding site found in an untranslated region of NTRK3, corresponding to BINDING SITE of FIG. 26A. FIG. 26D illustrates the complementarity of the nucleotide sequence of NTRK3 BINDING SITE, designated SEQ ID:94853, to the nucleotide sequence of GAM26 RNA of FIG. 26A, designated SEQ ID:20604.

Another function of GAM26 is therefore inhibition of neurotrophic tyrosine kinase, receptor, type 3 (NTRK3), a gene which encodes a protein that is a tyrosine-protein kinase receptor. Accordingly, utilities of GAM26 include diagnosis and treatment of the abovementioned diseases and clinical conditions.

The function of NTRK3 has been established by previous studies. Bothwell (1996), Carter and Lewin (1997), and Bibel and Barde (2000) reviewed neurotrophins and their receptors. Nerve growth factor receptor (NGFR; 162010) is also referred to as p75(NTR) due to its molecular mass and its ability to bind at low affinity not only NGF (see 162030), but also other neurotrophins, including brain-derived neurotrophic factor (BDNF; 113505), neurotrophin-3 (NTF3; 162660), and neurotrophin-4/5 (NTF5; 162662). As a monomer, NGFR binds NGF with low affinity. Higher affinity binding is achieved by association with higher molecular mass, low-affinity neurotrophin receptors, namely the tropomyosin receptor kinases, TRKA (NTRK1; 191315), TRKB (NTRK2; 600456), and TRKC (NTRK3). TRKA, TRKB, and TRKC are specific for or 'preferred by' NGF, NTF5 and BDNF, and NTF3, respectively (Ip et al., 1993). NTF3 also binds to TRKA and TRKB, but with significantly lower affinity. Lamballe et al. (1991) isolated and characterized TRKC, a member of the TRK family of tyrosine protein kinase genes. They found that TRKC is preferentially expressed in the brain; in situ hybridization studies showed transcripts in the hippocampus, cerebral cortex, and the granular cell layer of the cerebellum. The product of the TRKC gene is a glycoprotein of 145 kD, gp145(trkC), which is equally related to the previously characterize gp140(trk) (TRKA) and gp145(trkB) (TRKB) tyrosine kinases. Lamballe et al. (1991) demonstrated that gp145(trkC) is a receptor for NTF3, a factor important in the development of certain areas of the central nervous system, but does not bind NGF or BDNF.

Full details of the abovementioned studies are described in the following publications, the disclosure of which are hereby incorporated by reference:

Bibel, M.; Barde, Y. A.: Neurotrophins: key regulators of cell fate and cell shape in the vertebrate nervous system. Genes Dev. 14: 2919-2937, 2000. PubMed ID: 11114882 6. Lamballe, F.; Klein, R.; Barbacid, M.: TRKC, a new member of the TRK family of tyrosine protein kinases, is a receptor for neurotrophin-3. Cell 66: 967-979, 1991.

Further studies establishing the function and utilities of NTRK3 are found in John Hopkins OMIM database record ID 191316, and in references numbered 469-477 listed hereinbelow.

Reference is now made to PPP3CA BINDING SITE. Protein phosphatase 3 (formerly 2B), catalytic subunit, alpha isoform (PPP3CA) is a target gene of GAM26, corresponding to GAM26-TARGET GENE of FIG. 26. PPP3CA BINDING SITE is a binding site found in an untranslated region of PPP3CA, corresponding to BINDING SITE of FIG. 26A. FIG. 26D illustrates the complementarity of the nucleotide sequence of PPP3CA BINDING SITE, designated SEQ ID:94853, to the nucleotide sequence of GAM26 of FIG. 26A, designated SEQ ID:20604.

Yet another function of GAM26 is therefore inhibition of protein phosphatase 3 (formerly 2B), catalytic subunit, alpha isoform (PPP3CA), a gene which encodes enzyme that is the catalytic subunit of calcium-dependent, calmodulin-stimulated protein phosphatase. Accordingly, utilities of GAM26 include diagnosis and treatment of the abovementioned diseases and clinical conditions.

The function of PPP3CA has been established previous studies. Semsarian et al. (1999) and Musaro et al. (1999) independently showed that IGF1 (147440) stimulates skeletal muscle hypertrophy and a switch to glycolytic metabolism by activating calcineurin A and inducing the nuclear translocation of transcription factor NFATC1 (600489). Semsarian et al. (1999) found that hypertrophy was suppressed by the calcineurin inhibitors cyclosporin A or FK506, but not by inhibitors of the MAP kinase or phosphatidylinositol-3-OH kinase pathways. Musaro et al. (1999) showed that expression of a dominant-negative calcineurin mutant also repressed myocyte differentiation and hypertrophy. Musaro et al. (1999) demonstrated that either IGF1 or activated calcineurin induces expression of transcription factor GATA2 (137295), which accumulates in a subset of myocyte nuclei, where it associates with calcineurin and a specific dephosphorylated isoform of NFATC1.

Animal model experiments lend further support to the function of PPP3CA. Winder et al. (1998) generated transgenic mice that overexpressed a truncated form of the murine calcineurin A-alpha catalytic subunit under the control of the CaMKII-alpha promoter. Mice expressing this transgene show increased calcium-dependent phosphatase activity in the hippocampus. Physiologic studies and pharmacologic experiments revealed a novel, intermediate phase of long-term potentiation (I-LTP) in the CA1 region of the hippocampus. This I-LTP differs from the E-LTP (early component of LTP) by requiring multiple trains for induction and in being dependent on PKA (cAMP-dependent protein kinase). It also differs from the L-LTP (late component of LTP) in not requiring new protein synthesis. These data suggested to Winder et al. (1998) that calcineurin acts as an inhibitory constraint on I-LTP that is relieved by PKA, and that this inhibitory constraint acts as a gate to regulate the synaptic induction of L-LTP.

It is appreciated that the abovementioned animal model for PPP3CA is acknowledged by those skilled in the art as a scientifically valid animal model, as can be further appreciated from the publications sited hereinbelow.

Full details of the abovementioned studies are described in the following publications, the disclosure, of which are hereby incorporated by reference:
Winder, D. G.; Mansuy, I. M.; Osman, M.; Moallem, T. M.; Kandel, E. R.: Genetic and pharmacological evidence for a novel, intermediate phase of long-term potentiation suppressed by calcineurin. Cell 92: 25-37, 1998. PubMed ID:9489697 2. Fuentes, J. J.; Genesca, L.; Kingsbury, T. J.; Cunningham, K. W.; Perez-Riba, M.; Estivill, X.; de la Luna, S.: DSCR1, overexpressed in Down syndrome, is an inhibitor of calcineurin-mediated signaling pathways. Hum. Molec. Genet 9: 681-1690, 2000.

Further studies establishing the function and utilities of PPP3CA are found in John Hopkins OMIM database record ID 114105, and in references numbered 478-490 listed hereinbelow.

Referring now to PPP3CA BINDING SITE. Protein phosphatase 3 (formerly 2B), catalytic subunit, alpha isoform (PPP3CA) is a target gene of GAM26, corresponding to GAM26-TARGET GENE of FIG. 26A. PPP3CA BINDING SITE is a binding site found in an untranslated region of PPP3CA, corresponding to BINDING SITE of FIG. 26A. FIG. 26D illustrates the complementarity of the nucleotide sequence of PPP3CA BINDING SITE, designated SEQ ID:94853, to the nucleotide sequence of GAM26 RNA of FIG. 26A, designated SEQ ID:20604.

An additional function of GAM26 is therefore inhibition of protein phosphatase 3 (formerly 2B), catalytic subunit, alpha isoform (PPP3CA), a gene which encodes enzyme that is the catalytic subunit of calcium-dependent, calmodulin-stimulated protein phosphatase. Accordingly, utilities of GAM26 include diagnosis and treatment of the abovementioned diseases and clinical conditions. The function and utilities of PPP3CA have been established by previous studies, as described hereinabove with reference to FIG. 26D.

Referring now to PPP3CA BINDING SITE. Protein phosphatase 3 (formerly 2B), catalytic subunit, alpha isoform (PPP3CA) is a target gene of GAM26, corresponding to GAM26-TARGET GENE of FIG. 26A. PPP3CA BINDING SITE is a binding site found in an untranslated region of PPP3CA, corresponding to BINDING SITE of FIG. 26A. FIG. 26D illustrates the complementarity of the nucleotide sequence of PPP3CA BINDING SITE designated SEQ ID:94853, to the nucleotide sequence of GAM26 RNA of FIG. 26A, designated SEQ ID:20604.

A further function of GAM26 is therefore inhibition of protein phosphatase 3 (formerly 2B), catalytic subunit, alpha isoform (PPP3CA), a gene which encodes enzyme that is the catalytic subunit of calcium-dependent, calmodulin-stimulated protein phosphatase. Accordingly, utilities of GAM26 include diagnosis and treatment of the abovementioned diseases and clinical conditions. The function and utilities of PPP3CA have been established by previous studies, as described hereinabove with reference to FIG. 26D.

Reference is now made to RELN BINDING SITE. Reelin (RELN) is a target gene of GAM26, corresponding to GAM26-TARGET GENE of FIG. 26A. RELN BINDING SITE is a binding site found in an untranslated region of RELN, corresponding to BINDING SITE of FIG. 26A. FIG. 26D illustrates the complementarity of the nucleotide sequence of RELN BINDING SITE, designated SEQ ID:94853, to the nucleotide sequence of GAM26 RNA of FIG. 26A, designated SEQ ID:20604.

Yet a further function of GAM26 is therefore inhibition of reelin (RELN), a gene which encodes transcription factor that is associated with Norman-Roberts syndrome. Accordingly, utilities of GAM26 include diagnosis and treatment of the abovementioned diseases and clinical conditions.

The function of RELN has been established by previous studies. Normal development of the cerebral cortex requires long-range migration of cortical neurons from proliferative regions deep in the brain. Lissencephaly ('smooth brain,' from 'lissos,' meaning 'smooth,' and 'encephalos,' meaning 'brain') is a severe developmental disorder in which neuronal migration is impaired, leading to a thickened cerebral cortex whose normally folded contour is simplified and smooth. X-linked lissencephaly (300067) is caused by mutation in the gene encoding doublecortin (DCX; 300121). Deletion of or mutation in the LIS1 gene (601545), located on 17p, causes isolated lissencephaly sequence (ILS), and haploinsufficiency of this and other neighboring genes is responsible for the Miller-Dieker lissencephaly syndrome (247200), a contiguous gene deletion syndrome. Lissencephaly is a feature of a number of syndromes, such as the Walker-Warburg syndrome (236670). Hong et al. (2000) studied an autosomal recessive form of lissencephaly associated with severe abnormalities of the cerebellum, hippocampus, and brainstem; see lissencephaly syndrome, Norman-Roberts type (257320). They tested for linkage to markers near RELN on chromosome 7 and DAB1 on 1p32-p31, because mutations in the mouse homologs of these 2 genes cause brain defects in mice that resemble lissencephaly, including hypoplasia of the cerebellum, brainstem abnormalities, and a neuronal migration disorder of the neocortex and hippocampus. In 2 unrelated pedigrees, they found substantial regions of homozygosity in affected children near the RELN locus on 7q22. In these 2 families, they demonstrated different splice site mutations in the RELN gene. The study of these human patients pointed to several previously unsuspected functions of reelin in and outside of the brain. Although abnormalities of RELN mRNA had been reported in postmortem rains of schizophrenic humans (Impagnatiello et al., 1998), no evidence of schizophrenia was found in individuals with heterozygous or homozygous RELN mutations. On the other hand, one of the lissencephaly patients studied with a muscle biopsy showed evidence of abnormal neuromuscular connectivity (Hourihane et al., 1993). Moreover, at least 3 patients had persistent lymphedema neonatally, and one showed accumulation of chlyous (i.e., fatty) ascites fluid that required peritoneal shunting (Hourihane et al., 1993). The apparent role for reelin in serum homeostasis may reflect reelin interactions with LDL superfamily receptors outside the brain, as well as in the brain.

Animal model experiments lend further support to the function of RELN. To investigate Reln function, Magdaleno et al. (2002) generated transgenic mice using the nestin (NES; 600915) promoter to drive ectopic expression of Reln in the ventricular zone during early brain development. Ectopic Reln expression in transgenic reelin mice, which lack endogenous Reln expression, induced tryosine phosphorylation of Dab1 in the ventricular zone. The transgene also rescued some, but not all, of the neuroanatomic and behavioral abnormalities characteristic of the reeler phenotype, including ataxia and the migration of Purkinje cells. Magdaleno et al. (2002) hypothesized that Reln functions in concert with other positional cues to promote cell-cell interactions that are required for layer formation during development.

It is appreciated that the abovementioned animal model for RELN is acknowledged by those skilled in the art as a scientifically valid animal model, as can be further appreciated from the publications sited hereinbelow.

Full details of the abovementioned studies are described in the following publications, the disclosure of which are hereby incorporated by reference:

Hong, S. E.; Shugart, Y. Y.; Huang, D. T.; Al Shahwan, S.; Grant, P. E.; Hourihane, J. O.; Martin, N. D. T.; Walsh, C. A.: Autosomal recessive lissencephaly with cerebellar hypoplasia is associated with human RELN mutations. Nature Genet. 26: 93-96, 2000. Note: Erratum: Nature Genet. 27: 225 only, 2001. PubMed ID:10973257 12. Magdaleno, S.; Keshvara, L.; Curran, T.: Rescue of ataxia and preplate splitting by ectopic expression of reelin in reeler mice. Neuron 33: 573-586, 2002.

Further studies establishing the function and utilities of RELN are found in John Hopkins OMIM data base record ID 600514, and in references numbered 491-505 listed hereinbelow.

Reference is now made to RGS19IP1 BINDING SITE. (RGS19IP1) is a target gene of GAM26, corresponding to GAM26-TARGET GENE of FIG. 26A. RGS19IP1 BINDING SITE is a binding site found in an untranslated region of RGS19IP1, corresponding to BINDING SITE of FIG. 26A. FIG. 26D illustrates the complementarity of the nucleotide sequence of RGS19IP1 BINDING SITE, designated SEQ ID:94853, to the nucleotide sequence of GAM26 RNA of FIG. 26A, designated SEQ ID:20604.

Another function of GAM26 is therefore inhibition of (RGS19IP1), a gene which encodes a protein that is involved in g protein-linked signaling. Accordingly, utilities of GAM26 include diagnosis and treatment the abovementioned diseases and clinical conditions.

The function of RGS19IP1 has been established by previous studies. Northern blot analysis detected a 1.8-kb C19ORF3 transcript in all tissues tested, with strongest expression in pancreas, followed by skeletal muscle, brain, kidney, placenta, lung, liver, and lowest expression in heart. Expression levels did not correlate with those of GAIP. Immunoblot analysis demonstrated the presence of C19ORF3 primarily in cytosolic fractions but also in membrane fractions. Immunofluorescence analysis showed expression of endogenous C19ORF3 in both a diffuse and a punctate staining pattern throughout the cytoplasm. Using a yeast 2-hybrid system, Bunn et al. (1999) isolated a cDNA encoding C19ORF3, which they called GLUT1CBP (GLUT1 (SLC2A1; 138140) C-terminus-binding protein). SDS-PAGE and Western blot analyses determined that C19ORF3 is expressed as a 39-kD protein in all tissues tested except small intestine. Yeast 2-hybrid analysis showed that C19ORF3 binds SLC2A1 through its PDZ domain. Northern blot analysis revealed similar expression patterns for C19ORF3 and SLC2A1, with both being expressed most strongly in brain. Using a yeast 2-hybrid screen for brain-interacting proteins, the authors determined that only SLC2A1, KIF1B, and alpha actinin-1 (ACTN1; 102575) bind C19ORF3 through its PDZ domain; myosin VI (MYO6; 600970) was shown to interact with C19ORF3 but not via the PDZ domain.

Full details of the abovementioned studies are described in the following publications, the disclosure of which are hereby incorporated by reference.

Bunn, R. C.; Jensen, M. A.; Reed, B. C.: Protein interactions with the glucose transporter binding protein GLUT1CBP that provides a link between GLUT1 and the cytoskeleton. Molec. Biol. Cell 10: 819-832, 1999. PubMed ID: 10198040 Von Kap-Herr, C.; Kandala, G.; Mann, S. S.; Hart, T. C.; Pettenati, M. J.; Setaluri, V.: Assignment of PDZ domain-containing protein GIPC gene (C19orf3) to human chromosome band 19p13.1 by in situ hybridization and radiation hybrid mapping. Cytogenet Cell Genet. 89: 234-235, 2000.

Further studies establishing the function and utilities of RGS19IP1 are found in John Hopkins OMIM database record ID 605072, and in references numbered 506-508 listed hereinbelow.

Referring now to RGS19IP1 BINDING SITE. (RGS19IP1) is a target gene of GAM26, corresponding to GAM26-TARGET GENE of FIG. 26A. RGS19IP1 BINDING SITE is a binding site found in an untranslated region of RGS19IP1, corresponding to BINDING SITE of FIG. 26A. FIG. 26D illustrates the complementarity of the nucleotide sequence of RGS19IP1 BINDING SITE, designated SEQ ID:94853, to the nucleotide sequence of GAM26 RNA of FIG. 26A, designated ID:20604.

Yet another function of GAM26 is therefore inhibition of (RGS19IP1), a gene which encodes a protein that is involved in g protein-linked signaling. Accordingly, utilities of GAM26 include diagnosis and treatment the abovementioned diseases and clinical conditions. The function and utilities of RGS19IP1 have been established by previous studies, as described hereinabove with reference to FIG. 26D.

Referring now to RGS19IP1 BINDING SITE. RGS19IP1) is a target gene of GAM26, corresponding to GAM26-TARGET GENE of FIG. 26A. RGS19IP1 BINDING SITE is a binding site found in an untranslated region of RGS19IP1, corresponding to BINDING SITE of FIG. 26A. FIG. 26D illustrates the complementarity of the nucleotide sequence of RGS19IP1 BINDING SITE, designated SEQ ID:94853, to the nucleotide sequence of GAM26 RNA of FIG. 26A, designated SEQ ID:20604.

An additional function of GAM26 is therefore inhibition of (RGS19IP1), a gene which encodes a protein that is involved in g protein-linked signaling. Accordingly, utilities of GAM26 include diagnosis and treatment of the abovementioned diseases and clinical conditions. The function and utilities of RGS19IP1 have been established by previous studies, as described hereinabove with reference to FIG. 26D.

Referring now to RGS19IP1 BINDING SITE. (RGS19IP1) is a target gene of GAM26, corresponding to GAM26-TARGET GENE of FIG. 26A. RGS19IP1 BINDING SITE is a binding site found in an untranslated region of RGS19IP1, corresponding to BIND NG SITE of FIG. 26A. FIG. 26D illustrates the complementarity of the nucleotide sequence of RGS19IP1 BINDING SITE, designated SEQ ID:94853, to the nucleotide sequence of GAM26 RNA of FIG. 26A, designated SEQ ID:20604.

A further function of GAM26 is therefore inhibition of (RGS19IP1), a gene which encodes a protein that is involved in g protein-linked signaling. Accordingly, utilities of GAM26 include diagnosis and treatment of the abovementioned diseases and clinical conditions. The function and utilities of RGS19IP1 have been established by previous studies, as described hereinabove with reference to FIG. 26D.

Reference is now made to UBE2B BINDING SITE. Ubiquitin-conjugating enzyme E2B (RAD6 homolog) (UBE2B) is a target gene of GAM26, corresponding to GAM26-TARGET GENE of FIG. 26A. UBE2B BINDING SITE is a binding site found in an untranslated region of UBE2B, corresponding to BINDING SITE of FIG. 26A. FIG. 26D illustrates the complementarity of the nucleotide sequence of UBE2B BINDING SITE, designated SEQ ID:94853, to the nucleotide sequence of GAM26 RNA of FIG. 26A, designated SEQ ID:20604.

Yet a further function of GAM26 is therefore inhibition of ubiquitin-conjugating enzyme E2B (RAD6 homolog) (UBE2B), a gene which encodes an enzyme that catalyzes the covalent attachment of ubiquitin to other proteins and is required for postreplication repair of uv-damaged DNA. Accordingly, utilities of GAM26 include diagnosis and treatment of the abovementioned diseases and clinical conditions.

The function of UBE2B has been established by previous studies. The RAD6 pathway is central to postreplicative DNA repair in eukaryotic cells. Two principal elements of this pathway are the ubiquitin-conjugating enzymes RAD6 and the MMS2 (603001)-UBC13 (603679) heterodimer, which are recruited to chromatin by the RING-finger proteins RAD18 (6015256) and RAD5 (607266), respectively. Hoege et al. (2002) showed that UBC9 (601661), a small ubiquitin-related modifier (SUMO)-conjugating enzyme, is also affiliated with this pathway and that proliferating cell nuclear antigen (PCNA; 176740), a DNA polymerase sliding clamp involved in DNA synthesis and repair, is a substrate. PCNA is monoubiquitinated through RAD6 and RAD18, modified by lys63-linked multiubiquitination, which additionally requires MMS2, UBC13, and RAD5, and is conjugated to SUMO by UBC9. All 3 modifications affect the same lysine residue of PCNA, K164, suggesting that they label PCNA for alternative functions. Hoege et al. (2002) demonstrated that these modifications differentially affect resistance to DNA damage, and that damage-induced PCNA ubiquitination is elementary for DNA repair and occurs at the same conserved residue in yeast and humans.

Animal model experiments lend further support to the function of UBE2B. Roest et al. (1996) reported the phenotype of the first animal mutant in the ubiquitin pathway. Experimental inactivation of the RAD6B gene in mice caused male infertility. Derailment of spermatogenesis became overt during the postmeiotic condensation of chromatin in spermatids. In yeast the gene is not only implicated in postreplication repair and damage-induced mutagenesis but is also required for sporulation and may modulate chromatin structure via histone ubiquitination. The authors stated that the findings in the 'knock-out' mice provided a parallel between yeast sporulation and mammalian spermatogenesis and strongly implicated RAD6-dependent ubiquitination in chromatin remodeling in the human. Since heterozygous male mice and even knockout female mice are completely normal and fertile and thus able to transmit the defect, similar RAD6B mutations may cause male infertility in man. The fact that the RAD6B mice are viable and phenotypically normal is presumably due to functional redundancy with RAD6A (312180).

It is appreciated that the abovementioned animal model for UBE2B is acknowledged by those skilled in the art as a scientifically valid animal model, as can be further appreciated from the publications sited hereinbelow.

Full details of the abovementioned studies are described in the following publications, the disclosure of which are hereby incorporated by reference:

Hoege, C.; Pfander, B.; Moldovan, G. -L.; Pyrowolakis, G.; Jentsch, S.: RAD6-dependent DNA repair is linked to modification of PCNA by ubiquitin and SUMO. Nature 419: 135-141, 2002. PubMed ID: 12226657 Roest, H. P.; van Klaveren, J.; de Wit, J.; van Gurp, C. G.; Koken, M. H. M.; Vermey, M.; van Roijen, J. H.; Hoogerbrugge, J. W.; Vreeburg, J. T. M.; Baarends, W. M.; Bootsma, D.; Grootegoed, J. A.; Hoeijmakers, J. H. J.: Inactivation of the HR6B ubiquitin-conjugating DNA repair enzyme in mice causes male sterility associated with chromatin modification. Cell 86: 799-810, 1996.

Further studies establishing the function and utilities of UBE2B are found in John Hopkins OMIM database record ID 179095, and in references numbered 509-513 listed hereinbelow.

Referring now to UBE2B BINDING SITE. Ubiquitin-conjugating enzyme E2B (RAD6 homolog) (UBE2B) is a target gene of GAM26, corresponding to GAM26-TARGET GENE of FIG. 26A. UBE2B BINDING SITE is a binding site found in an untranslated region of UBE2B, corresponding to BINDING SITE of FIG. 26A. FIG. 26D illustrates the complementarity of the nucleotide sequence of UBE2B BINDING SITE, designated SEQ ID:94853, to the nucleotide sequence of GAM26 RNA of FIG. 26A, designated SEQ ID:20604.

Another function of GAM26 is therefore inhibition of ubiquitin-conjugating enzyme E2B (RAD6 homolog) (UBE2B), a gene which encodes an enzyme that catalyzes the covalent attachment of ubiquitin to other proteins and is required for postreplication repair of uv-damaged DNA. Accordingly, utilities of GAM26 include diagnosis and treatment of the abovementioned diseases and clinical conditions. The function and utilities of UBE2B have been established by previous studies, as described hereinabove with reference to FIG. 26D.

Referring now to UBE2B BINDING SITE. Ubiquitin-conjugating enzyme E2B (RAD6 homolog) (UBE2B) is a target gene of GAM26, corresponding to GAM26-TARGET GENE of FIG. 26A. UBE2B BINDING SITE is a binding site found in an untranslated region of UBE2B, corresponding to BINDING SITE of FIG. 26A. FIG. 26D illustrates the complementarity of the nucleotide sequence of UBE2B BINDING SITE, designated SEQ ID:94853, to the nucleotide sequence of GAM26 RNA of FIG. 26A, designated SEQ ID:20604.

Yet another function of GAM26 is therefore inhibition of ubiquitin-conjugating enzyme (RAD6 homolog) (UBE2B), a gene which encodes an enzyme that catalyzes the covalent attachment of ubiquitin to other proteins and is required for postreplication repair of uv-damaged DNA. Accordingly, utilities of GAM26 include diagnosis and treatment of the abovementioned diseases and clinical conditions. The function and utilities of UBE2B have been established by previous studies, as described hereinabove with reference to FIG. 26D.

Referring now to UBE2B BINDING SITE. Ubiquitin-conjugating enzyme E2B (RAD6 homolog) (UBE2B) is a target gene of GAM26, corresponding to GAM26-TARGET GENE of FIG. 26A. UBE2B BINDING SITE is a binding site found in an untranslated region of UBE2B, corresponding to BINDING SITE of FIG. 26A. FIG. 26D illustrates the complementarity of the nucleotide sequence of UBE2B BINDING SITE, designated SEQ ID:94853, to the nucleotide sequence of GAM26 RNA of FIG. 26A, designated SEQ ID:20604.

An additional function of GAM26 is therefore inhibition of ubiquitin-conjugating enzyme E2B (RAD6 homolog) (UBE2B), a gene which encodes an enzyme that catalyzes the covalent attachment of ubiquitin to other proteins and is required for postreplication repair of uv-damaged DNA. Accordingly, utilities of GAM26 include diagnosis and treatment of the abovementioned diseases and clinical conditions. The function and utilities of UBE2B have been established by previous studies, as described hereinabove with reference to FIG. 26D.

Reference is now made to CAMK4 BINDING SITE calcium/calmodulin-dependent protein kinase IV (CAMK4) is a target gene of GAM26, corresponding to GAM26-TARGET GENE of FIG. 26A. CAMK4 BINDING SITE is a binding site found in an untranslated region of CAMK4, corresponding to BINDING SITE of FIG. 26A. FIG. 26D illustrates the complementarity of the nucleotide sequence of CAMK4 BINDING SITE, designated SEQ ID:94860; to the nucleotide sequence of GAM26 RNA of FIG. 26A, designated SEQ ID 20604.

A further function of GAM26 is therefore inhibition of calcium/calmodulin-dependent protein kinase IV (CAMK4), a gene which encodes an enzyme that is a heat-stable, acidic, calmodulin-binding protein. Accordingly, utilities of GAM26 include diagnosis and treatment of the abovementioned diseases and clinical conditions.

The function of CAMK4 has been established by previous studies. Protein phosphorylation, a prominent activity in the brain, apparently plays an important role in several neural functions such as neural transmitter release, ion channel modulation, and axoplasmic transport. Sikela et al. (1989) identified cDNA clones corresponding to a brain Ca(2+)/calmodulin-dependent protein kinase, which they referred to as brain CaM kinase IV (CAMK4). On the basis of Western blot analysis, this kinase appeared to be restricted to brain in the rat; interestingly, it was not detected in the brain of the newborn, but became detectable within a few days after birth.

Animal model experiments lend further support to the function of CAMK4. Camk4 is a multifunctional serine/threonine protein kinase with limited tissue distribution that has been implicated in transcriptional regulation in lymphocytes, neurons, and male germ cells. In the mouse testis, however, Camk4 is expressed in spermatids and associated with chromatin and nuclear matrix. Elongating spermatids are not transcriptionally active, rising the possibility that Camk4 has a novel function in male germ cells. To investigate the role of Camk4 in spermatogenesis, Wu et al. (2000) generated mice with a targeted deletion of the Camk4 gene. Male Camk4 −/− mice were infertile with impairment of spermiogenesis in late elongating spermatids. The sequential deposition of sperm basic nuclear proteins on chromatin was disrupted, with a specific loss of protamine-2 (182890) and prolonged retention of transition protein-2 (190232) in step-15 spermatids. Protamine-2 is phosphorylated by Camk4 in vitro implicating a connection between Camk4 signaling and the exchange of basic nuclear proteins in mammalian male germ cells. Defects in protamine-2 have been identified in sperm of infertile men, suggesting that the results of Wu et al. (2000) may have clinical implications for the understanding of human male infertility.

It is appreciated that the abovementioned animal model for CAMK4 is acknowledged by those skilled in the art as a scientifically valid animal model, as can be further appreciated from the publications sited hereinbelow.

Full details of the abovementioned studies are described in the following publications, the disclosure of which are hereby incorporated by reference:

Sikela, J. L.; Law, M. L.; Kao, F. -T.; Hartz, J. A.; Wei, Q.; Han, W. E.: Chromosomal localization of the human gene for brain Ca(2+)/calmodulin-dependent protein kinase type IV. Genomics 4: 21-27, 1989. PubMed ID: 6634 7.

Wu, J. Y.; Ribar, T. J.; Cummings D. E.; Burton, K. A.; McKnight, G. S.; Means, A. R.: Spermiogenesis and exchange of basic nuclear proteins are impaired in male germ cells lacking Camk4 Nature Genet. 25: 448-452, 2000.

Further studies establishing the function and utilities of CAMK4 are found in John Hopkins OMIM database record ID 114080, and in references numbered 514-520 listed hereinbelow.

Referring now to CBL BINDING SITE. Cas-B-M (murine) ecotropic retroviral transforming sequence (CBL) is a target gene of GAM26, corresponding to GAM26-TARGET GENE of FIG. 26A. CBL BINDING SITE is a binding site found in an untranslated region of CBL, corresponding to BINDING SITE of FIG. 26A. FIG. 26D illustrates the complementarity of the nucleotide sequence of CBL BINDING SITE, designated SEQ ID:94860, to the nucleotide sequence of GAM26 RNA of FIG. 26A, designated SEQ ID:20604.

Yet a further function of GAM26 is therefore inhibition of Cas-Br-M (murine) ecotropic retroviral transforming sequence (CBL), a gene which encodes a protein that may modify receptor tyrosine kinase-mediated signal transduction, and is associated with B-lineage lymphomas. Accordingly, utilities of GAM26 include diagnosis and treatment of the abovementioned diseases and clinical conditions. The function and utilities of CBL have been established by previous studies, as described hereinabove with reference to FIG. 26D.

Reference is now made to CD47 BINDING SITE. CD47 antigen (Rh-related antigen, integrin-associated signal transduce (CD47) is a target gene of GAM26, corresponding to GAM26-TARGET GENE of FIG. 26A. CD47 BINDING SITE is a binding site found in an untranslated region of CD47, corresponding to BINDING SITE of FIG. 26A. FIG. 26D illustrates the complementarity of the nucleotide sequence of CD47 BINDING SITE, designated SEQ ID:97660, to the nucleotide sequence of GAM26 RNA of FIG. 26A, designated SEQ ID:20604.

Another function of GAM26 is therefore inhibition of CD47 antigen (Rh-related antigen, integrin-associated signal transduce (CD47), a gene which encodes a protein that may be involved in membrane permeability changes induced following virus infection. Accordingly, utilities of GAM26 include diagnosis and treatment of the abovementioned diseases and clinical conditions.

The function of CD47 has been established by previous studies. By testing hybrids containing various deletions of chromosome 3, Miller et al (1987) described an IgM monoclonal antibody, 1D8, that recognized an antigen coded by a gene located in the region 3cen-q22. The monoclonal antibody was designated MER6. The antigen was absent in the Rh deficiency syndrome, Rh-null hemolytic anemia (268150). This antigen probably had no pathogenetic role in the Rh deficiency, which was shown by Cherif-Zahar et al. (1996) to be due to mutation in the Rh50 gene (190297) on chromosome 6. They noted that many cell Animal model experiments lend further support to the function of CD47. By testing hybrids containing various deletions of chromosome 3, Miller et al. (1987) described an IgM monoclonal antibody, 1D8, that recognized an antigen coded by a gene located in the region 3cen-q22. The monoclonal antibody was designated MER6. The antigen was absent in the Rh deficiency syndrome, Rh-null hemolytic anemia (268150). This antigen probably had no pathogenetic role in the Rh deficiency, which was shown by Cherif-Zahar et al. (1996) to be due to mutation in the Rh50 gene (180297) on chromosome 6. They noted that many cell It is appreciated that the abovementioned animal model for CD47 is acknowledged by those skilled in the art as a scientifically valid animal model, as can be further appreciated from the publications sited hereinbelow.

Full details of the abovementioned studies are described in the following publications, the disclosure of which are hereby incorporated by reference:

By testing hybrids containing various deletions of chromosome 3, Miller et al. (1987) described an IgM monoclonal antibody, 1D8, that recognized an antigen coded by a gene located in the region 3cen-q22. The monoclonal antibody was designated MER6. The antigen was absent in the Rh deficiency syndrome, Rh-null hemolytic anemia (268150). This antigen probably had no pathogenetic role in the Rh deficiency, which was shown by Cherif-Zahar et al. (1996) to be due to mutation in the Rh50 gene (180297) on chromosome 6. They noted that many cell.

Further studies establishing the function and utilities of CD47 are found in John Hopkins OMIM database record ID 601028, and in references numbered 521-527 listed hereinbelow.

Reference is now made to CDC2L1 BINDING SITE. cell division cycle 2-like 1 (PITSLRE proteins) (CDC2L1) is a target gene of GAM26, corresponding to GAM26-TARGET GENE of FIG. 26A. CDC2L1 BINDING SITE is a binding site found in an untranslated region of CDC2L1, corresponding to BINDING SITE of FIG. 26A. FIG. 26D illustrates the complementarity of the nucleotide sequence of CDC2L1 BINDING SITE, designated SEQ ID:99045, to the nucleotide sequence of GAM26 RNA of FIG. 26A, designated SEQ ID:20604.

Yet another function of GAM26 is therefore inhibition of cell division cycle 2-like 1 (PITSLRE proteins) (CDC2L1), a gene which encodes a protein that is a negative regulator of normal cell cycle progression. Accordingly, utilities of GAM26 include diagnosis and treatment of the abovementioned diseases and clinical conditions.

The function of CDC2L1 has been established by previous studies. Bunnell et al. (1990) identified a human cell division control (CDC)-related protein kinase, p58, that is structurally and functionally related to p34(cdc2) (CDC2; 116940). Abnormal expression of the p58 protein kinase in eukaryotic cells had effects suggesting that it is a negative regulator of normal cell cycle progression. The gene is well conserved evolutionarily. Its expression is regulated during murine embryogenesis, and its activity is coordinately regulated with that of p34(cdc2) during the cell cycle. Eipers et al. (1991) assigned the expressed p58 gene to 1p36 by somatic cell hybrid analysis, in situ hybridization, and nested PCR amplification of microdissected chromosomes. The authors stated that this gene, tentatively symbolized PK58, may be implicated in the pathogenesis of tumors that have deletion in the region of 1p36. Eipers et al. (1992) detailed the complete structure of the CDC2L1 gene including its putative promoter region, transcriptional start sites, exonic sequences, and intron/exon boundary sequences. The gene is 10 kb in size and contains 12 exons and 11 introns.

Full details of the abovementioned studies are described in the following publications, the disclosure of which are hereby incorporated by reference:

Bunnell, B.; Heath, L. S.; Adams, D. E.; Lahti, J. M.; Kidd, V. J.: Elevated expression of a p58 protein kinase leads to changes in the CHO cell cycle. Proc. Nat. Acad. Sci. 87: 7467-747, 1990. PubMed ID: 2217177 2. Cornelis, S.; Bruynooghe, Y.; Denecker, G.; Van Huffel, S.; Tinton, S.; Beyaert, R.: Identification and characterization of a novel cell cycle-regulated internal ribosome entry site. Molec. Cell 5: 597-605, 2000.

Further studies establishing the function and utilities of CDC2L1 are found in John Hopkins OMIM database record ID 176873, and in references numbered 528-535 listed hereinbelow.

Referring now to CDC2L1 BINDING SITE. Cell division cycle 2-like 1 (PITSLRE proteins) (CDC2L1) is a target gene of GAM26, corresponding to GAM26-TARGET GENE of FIG. 26A. CDC2L1 BINDING SITE is a binding site found in an untranslated region of CDC2L1, corresponding to BINDING SITE of FIG. 26A. FIG. 26D illustrates the complementarity of the nucleotide sequence of CDC2L1 BINDING SITE, designated SEQ ID:99046, to the nucleotide sequence of GAM26 RNA of FIG. 26A, designated SEQ ID:20604.

An additional function of GAM26 is therefore inhibition of cell division cycle 2-like 1 (PITSLRE proteins) (CDC2L1), a gene which encode a protein that is a negative regulator of normal cell cycle progression. Accordingly, utilities of GAM26 include diagnosis and treatment of the abovementioned diseases ad clinical conditions. The function and utilities of CDC2L1 have been established by previous studies, as described hereinabove with reference to FIG. 26D.

Reference is now made to CDC34 BINDING SITE. Cell division cycle 34 (CDC34) is a target gene of GAM26, corresponding to GAM26-TARGET GENE of FIG. 26A. CDC34 BINDING SITE is a binding site found in an untranslated region of CDC34, corresponding to BINDING SITE of FIG. 26A. FIG. 26D illustrates the complementarity of the nucleotide sequence of CDC34 BINDING SITE, designated SEQ ID:99180, to the nucleotide sequence of GAM26 RNA of FIG. 26A, designated SEQ ID:20604.

A further function of GAM26 is therefore inhibition of cell division cycle 34 (CDC34), a gene which encodes a protein that catalyzes the covalent attachment of ubiquitin to other proteins. Accordingly, utilities of GAM26 include diagnosis and treatment of the abovementioned diseases and clinical conditions.

The function of CDC34 has been established by previous studies. Genomic instability with aneuploidy and chromosomal rearrangement is a hallmark of human malignancies. Normal eukaryotes from yeasts to humans have a conserved checkpoint mechanism in cell division for maintenance of genomic stability. After DNA strand breaks, checkpoint genes induce rest in the G1 and G2 phases of the cell cycle until the damage is repaired. The tumor suppressor gene p53 (191170) is a checkpoint gene required for the G1 arrest after DNA damage. Plon et al. (1993) isolated a putative human G2 checkpoint gene, a homolog of the CDC34 gene of *Saccharomyces cerevisiae*. Human CDC34 could substitute efficiently for yeast CDC34. Plon et al. (1993) demonstrated by in situ hybridization that the CDC34 gene is located in the far telomeric region of 19p13.3, in a region of homology between human 19p and mouse 11.

Full details of the abovementioned studies are described in the following publications, the disclosure of which are hereby incorporated by reference:

Plon, S. E.; Leppig, K. A.; Do, H. -N.; Groudine, M.: Cloning of the human homolog of the CDC34 cell cycle gene by complementation in yeast. Proc. Nat. Acad. Sci. 90: 10484-10488, 1993.

Further studies establishing the function and utilities of CDC34 are found in John Hopkins OMIM database record ID 116948, and in references numbered 536 listed hereinbelow.

Reference is now made to CDH23 BINDING SITE. Cadherin related 23 (CDH23) is a target gene of GAM26, corresponding to GAM26-TARGET GENE of FIG. 26A. CDH23 BINDING SITE is a binding site found in an untranslated region of CDH23, corresponding to BINDING SITE of FIG. 26A. FIG. 26D illustrates the complementarity of the nucleotide sequence of CDH23 BINDING SITE, designated SEQ ID:100443, to the nucleotide sequence of GAM26 RNA of FIG. 26A, designated SEQ ID:20604.

Yet a further function of GAM26 is therefore inhibition of cadherin related 23 (CDH23), a gene which encodes a protein that is associated with usher syndrome type 1d (ush1d). Accordingly, utilities of GAM26 include diagnosis and treatment of the abovementioned diseases and clinical conditions.

The function of CDH23 has been established by previous studies. Bolz et al. (2001) identified a Cuban pedigree in which type I Usher syndrome was linked to the USH1D locus on chromosome 10. Affected individuals presented with congenital deafness and a highly variable degree of retinal degeneration as an autosomal recessive trait. Using a positional candidate approach, Bolz et al. (2001) identified CDH23 as the gene responsible for USH1D in these individuals. CDH23 encodes a predicted protein of 3,354 amino acids with a single transmembrane domain and 27 cadherin repeats. In the Cuban family, the authors detected 2 different CDH23 mutations. A severe course of the retinal disease was observed in individuals homozygous for a presumed truncating splice-site mutation (605516.0001), whereas mild retinitis pigmentosa was present in individuals carrying a homozygous missense mutation (605516.0002). Variable expression of the retinal phenotype was seen in patients with a combination of the 2 mutations. Bolz et al. (2001) also identified 2 mutations in the CDH23 gene in a German patient with Usher syndrome (see 605516.0003). Only missense mutations of CDH23 have been observed in families with nonsyndromic deafness, whereas nonsense, frameshift, splice-site, and missense mutations have been identified in families with Usher syndrome. Astuto et al. (2002) screened a panel of 69 probands with Usher syndrome and 38 probands with recessive nonsyndromic deafness for the presence of mutations in the entire coding region of CDH23, by heteroduplex, SSCP, and direct sequence analyses. Thirty-six different CDH23 mutations were detected in 45 families; 33 of these mutations were novel, including 18 missense, 3 nonsense, 5 splicing defects, 5 microdeletions, and 2 insertions. Seven mutations were common to more than 1 family. Ophthalmologic examination of patients with nonsyndromic deafness revealed asymptomatic manifestations similar to retinitis pigmentosa (RP; 268000), which indicated that missense mutations may have a subtle effect in the retina. Furthermore, patients with mutations in CDH23 displayed a wide range of hearing loss and RP phenotypes, differing in severity, age at onset, type, and the presence or absence of vestibular areflexia. Astuto et al. (2002) also presented a comprehensive catalog of CDH23 mutations identified both in their study and in patients reported elsewhere with either recessive nonsyndromic deafness or Usher syndrome type I.

Full details of the abovementioned studies are described in the following publications, the disclosure of which are hereby incorporated by reference:

Bolz, H.; von Brederlow, B.; Ramirez, A.; Bryda, E. C.; Kutsche, K.; Nothwang, H. G.; Seeliger, M.; Cabrera, M. C. -S.; Vila, M. C.; Molina, O. P.; Gal, A.; Kubisch, C.: Mutation of CDH23, encoding a new member of the cadherin gene family, causes Usher syndrome type 1D. Nature Genet. 27: 108-112, 2001. PubMed ID: 11138009

1. Astuto, L. M.; Bork, J. M.; Weston, M. D.; Askew, J. W.; Fields, R. R.; Orten, D. J.; Ohliger, S. J.; Riazuddin, S.; Morell, R. J.; Khan, S.; Riazuddin, S.; Kremer, H.; and 15 others: CDH23 mutation and phenotype heterogeneity: a profile of 107 diverse families with Usher syndrome and nonsyndromic deafness. Am. J. Hum. Genet. 71: 262-275, 2002.

Further studies establishing the function and utilities of CDH23 are found in John Hopkins OMIM database record ID 605516, and in references numbered 537-541 listed hereinbelow.

Reference is now made to CDH6 BINDING SITE. Cadherin 6, type 2, K-cadherin (fetal kidney) (CDH6) is a target gene of GAM26, corresponding to GAM26-TARGET GENE of FIG. 26A. CDH6 BINDING SITE is a binding site found in an untranslated region of CDH6, corresponding to BINDING SITE of FIG. 26A. FIG. 26D illustrates the complementarity of the nucleotide sequence of CDH6 BINDING SITE, designated SEQ ID:100628, to the nucleotide sequence of GAM26 RNA of FIG. 26A, designated SEQ ID:20604.

Another function of GAM26 is therefore inhibition of cadherin 6, type 2, K-cadherin (fetal kidney) (CDH6), a gene which encodes a protein that is a calcium dependent cell adhesion protein. Accordingly, utilities of GAM26 include diagnosis and treatment of the abovementioned diseases and clinical conditions.

The function of CDH6 has been established by previous studies. Cadherins are calcium-dependent cell-cell adhesion molecules that mediate cell-cell binding in a homophilic manner. They play key roles in morphogenesis and in the maintenance of orderly structures such as epithelium, and may be involved in the metastasis and invasion of cancer. Mature cadherin proteins are composed of a large N-terminal extracellular domain, a single membrane-spanning domain, and a small C-terminal cytoplasmic domain. The extracellular domain consists of 5 subdomains, each containing a cadherin motif, and appears to determine the specificity of the homophilic cell adhesion activity of the cadherin; the amino acid sequence of the cytoplasmic domain is highly conserved among cadherins. CLONING By PCR using degenerate oligonucleotides based on highly conserved sequences of the cadherin cytoplasmic domain, followed by screening of a human fetal brain cDNA library, Suzuki et al. (1991) isolated a partial cDNA encoding CDH6. Using this partial CDH6 cDNA to screen a human hepatocellular carcinoma cell cDNA library, Shimoyama et al. (1995) cloned a full-length CDH6 cDNA. The deduced 790-amino acid CDH6 protein contains a signal sequence, prosequence, extracellular domain, transmembrane sequence, and cytoplasmic domain. The predicted 737-amino acid mature CDH6 protein has 97% amino acid similarity with rat K-cadherin, 64% with human CDH12 (600562), and 60% with human CDH8 (603008) and CDH11 (600023). Northern blot analysis detected multiple CDH6 transcripts in a variety of normal human tissues, with highest levels in kidney, brain, and cerebellum; no expression was found in liver, heart or colonic mucosa. Four of 6 hepatocellular carcinoma cell lines and 3 of 4 renal carcinoma cell lines showed strong expression of CDH6 transcripts. Among small cell lung carcinoma lines, all 11 CDH6-positive lines were of the classic type, whereas all 4 CDH6-negative lines were of the variant type.

Full details of the abovementioned studies are described in the following publications, the disclosure of which are hereby incorporated by reference:

Shimoyama, Y.; Gotoh, M.; Terasaki, T.; Kitajima, M.; Hirohashi, S.: Isolation and sequence analysis of human cadherin-6 complementary DNA for the full coding sequence and its expression in human carcinoma cells. Cancer Res. 55: 2206-2211, 1995. PubMed ID: 7743525 3. Suzuki, S.; Sano, K.; Tanihara, H.: Diversity of the cadherin family: evidence for eight new cadherins in nervous tissue. Cell Regul. 2: 261-270, 1991.

Further studies establishing the function and utilities of CDH6 are found in John Hopkins OMIM database record ID 603007, and in references numbered 542-544 listed hereinbelow.

Referring now to CDH6 BINDING SITE. Cadherin 6, type 2, K-cadherin (fetal kidney) (CDH6) is a target gene of GAM26, corresponding to GAM26-TARGET GENE of FIG. 26A. CDH6 BINDING SITE is a binding site found in an untranslated region of CDH6, corresponding to BINDING SITE FIG. 26A. FIG. 26D illustrates the complementarity of the nucleotide sequence of CDH6 BINDING SITE, designated SEQ ID:100637, to the nucleotide sequence of GAM26 RNA of FIG. 26A, designated SEQ ID:20604.

Yet another function of GAM26 is therefore inhibition of cadherin 6, type 2, K-cadherin (fetal kidney) (CDH6), a gene which encodes a protein that is a calcium dependent cell adhesion protein. Accordingly, utilities of GAM26 include diagnosis and treatment of the abovementioned diseases and clinical conditions. The function and utilities of CDH6 have been established by previous studies, as described hereinabove with reference to FIG. 26D.

Reference is now made to PEA15 BINDING SITE. Phosphoprotein enriched in astrocytes 15 (PEA15) is a target gene of GAM26, corresponding to GAM26-TARGET GENE of FIG. 26. PEA15 BINDING SITE is a binding site found in an untranslated region of PEA15, corresponding to BINDING SITE of FIG. 26A. FIG. 26D illustrates the complementarity of the nucleotide sequence of PEA15 BINDING SITE, designated SEQ ID:100637, to the nucleotide sequence of GAM26 RNA of FIG. 26A, designated SEQ ID:20604.

An additional function of GAM26 is therefore inhibition of phosphoprotein enriched in astrocytes 15 (PEA15), a gene which encodes a protein that is a phosphoprotein and involved in glucose uptake. Accordingly, utilities of GAM26 include diagnosis and treatment of the abovementioned diseases and clinical conditions.

The function of PEA15 has been established by previous studies. Astrocytes are involved in a variety of functions, including storage of glycogen and support for the migration and differentiation of neurons. They express membrane receptors which allow them to respond to extracellular signals. Activation of the receptors induces a cascade of events, such as the stimulation of protein kinases and the subsequent phosphorylation of target proteins. Araujo et al. (1993) identified a unique 15-kD protein in astrocytes that exists as a nonphosphorylated form and as 2 increasingly phosphorylated varieties. This protein, which they called PEA15, contains a consensus site for protein kinase C (PKC; e.g., 176960) and is an endogenous substrate for PKC. Using differential display to identify genes whose expressions are altered in tissues derived from type II diabetes mellitus (125853) patients compared with nondiabetic individuals, Condorelli et al. (1998) cloned cDNAs encoding PEA15, which they named PED for 'phosphoprotein enriched in diabetes'. The ubiquitously expressed 2.8-kb PED mRNA was overexpressed in fibroblasts, skeletal muscle, and adipose tissue from type II diabetics. Levels of the 15-kD PED phosphoprotein were also elevated in type II diabetic tissues. The authors demonstrated that transfection of a PED cDNA into differentiating L6 skeletal muscle cells increases the content of glucose transporter-1 (GLUT1; 138140) on the plasma membrane and inhibits insulin-stimulated glucose transport and cell surface recruitment of glucose transporter-4 (GLUT4; 138190). These effects were reversed by blocking PKC activity.

Full details, of the abovementioned studies are described in the following publications, the disclosure of which are hereby incorporated by reference:

Araujo, H.; Danziger, N.; Cordier, J.; Glowinski, J.; Chneiweiss, H.: Characterization of PEA-15, a major substrate for protein kinase C in astrocytes. J. Biol. Chem. 268: 5911-5920, 1993. PubMed ID: 8449955 3. Condorelli, G.; Vigliotta, G.; Iavarone, C.; Caruso, M.; Tocchetti, C. G.; Andreozzi, F.; Cafieri, A.; Tecce, M. F.; Formisano, P.; Beguinot, L.; Beguinot, F.: PED/PEA-15 gene controls glucose transport and is overexpressed in type 2 diabetes mellitus. EMBO J. 17: 3858-3866, 1998.

Further studies establishing the function and utilities of PEA15 are found in John Hopkins OMIM database record ID 603434, and in references numbered 545-551 listed hereinbelow.

Referring now to CDH6 BINDING SITE. Cadherin 6, type 2, K-cadherin (fetal kidney) (CDH6) is a target gene of GAM26, corresponding to GAM26-TARGET GENE of FIG. 26A. CDH6 BINDING SITE is a binding site found in an untranslated region of CDH6, corresponding to BINDING SITE of FIG. 26A. FIG. 26D illustrates the complementarity of the nucleotide sequence of CDH6 BINDING SITE, designated SEQ ID:100646, to the nucleotide sequence of GAM26 RNA of FIG. 26A, designated SEQ ID:20604.

A further function of GAM26 is therefore inhibition of cadherin 6, type 2, K-cadherin (fetal kidney) (CDH6), a gene which encodes a protein that is a calcium dependent cell adhesion protein. Accordingly, utilities of GAM26 include diagnosis and treatment of the abovementioned diseases and clinical conditions. The function and utilities of CDH6 have been established by previous studies, as described hereinabove with reference to FIG. 26D.

Reference is now made to CDK9 BINDING SITE. Cyclin-dependent kinase 9 (CDC2-related kinase) (CDK9) is a target gene of GAM26, corresponding to GAM26-TARGET GENE of FIG. 26A. CDK9 BINDING SITE is a binding site found in an untranslated region of CDK9, corresponding to BINDING SITE of FIG. 26A. FIG. 26D illustrates the complementarity of the nucleotide sequence of CDK9 BINDING SITE, designated SEQ ID:101419, to the nucleotide sequence of GAM26 RNA of FIG. 26A, designated SEQ ID:20604.

Yet a further function of GAM26 is therefore inhibition of cyclin-dependent kinase 9 (CDC2-related kinase) (CDK9), a gene which encodes a protein that is a positive transcription elongation factor band. Accordingly, utilities of GAM26 include diagnosis and treatment of the abovementioned diseases and clinical conditions.

The function of CDK9 has been established by previous studies. Cyclin-dependent kinases (CDKs) are CDC2 (116940)-related kinases that bind to cyclin to form active holoenzymes that play a pivotal role in the regulation of the eukaryotic cell cycle. To identify additional CDC2 family members, Grana et al. (1994) performed PCR on a mouse embryonic cDNA library using degenerate oligonucleotides based on regions conserved among CDC2-related proteins. They used a resulting PCR product to screen a human cDNA library and isolated a CDK9 cDNA. The predicted 372-amino acid protein contains the 11 conserved regions characteristic of the protein kinase catalytic domain, a putative nuclear localization signal, and a putative ATP-binding site. The authors called the protein PITALRE because it contains a pro-ile-thr-ala-leu-arg-glu motif that is similar to the PSTAIRE motif found in prototypic CDC2 kinases. CDK9 shares 41 to 43% amino acid sequence identity with CDC2, CDK2 (116953), CDK3 (123828), and CDK5 (123831). Subcellular fractionation and Western blot analyses demonstrated that CDK9 has a molecular mass of 43 kD and is located primarily in the nucleus. Three cellular proteins coimmunoprecipitated with CDK9, and CDK9 immunocomplexes had an RB1 (180200) kinase activity. Northern blot analysis indicated that CDK9 was expressed as 2.8- and 3.2-kb mRNAs in all tissues tested, with the highest levels in liver and placenta. Yang et al. (2001) identified 7SK snRNA (606515) as a specific P-TEFb-associated factor. 7SK inhibits general and HIV-1 Tat-specific transcriptional activities of P-TEFb in vivo and in vitro by inhibiting the kinase activity of CDK9 and preventing recruitment of P-TEFb to the HIV-1 promoter. 7SK is efficiently dissociated from P-TEFb (the CDK9/cyclin T1 heterodimer) by treatment of cells with ultraviolet irradiation and actinomycin D. As these 2 agents have been shown to enhance significantly HIV-1 transcription and phosphorylation of Pol-II, Yang et al. (2001) concluded that their data provide a mechanistic explanation for this stimulatory effect. Yang et al. (2001) further suggested that the 7SK/P TEFb interaction may serve as a principal control point for the induction of cellular and HIV-1 viral gene expression during stress-related responses. The study demonstrated the involvement of a snRNA in controlling the activity of CDK/cyclin kinase.

Full details of the abovementioned studies are described in the following publications, the disclosure of which are hereby incorporated by reference:

Yang, Z.; Zhu, Q.; Luo, K.; Zhou, Q.: The 7SK small nuclear RNA inhibits the CDK9/cyclin T1 kinase to control transcription. Nature 414: 317-322, 2001. PubMed ID: 11713532 5. Grana, X.; De Luca, A.; Sang, N.; Fu, Y.; Claudio, P. P.; Rosenblatt, J.; Morgan, D. O.; Giordano, A.: PITALRE, a nuclear CDC2-related protein kinase that phosphorylates the retinoblastoma protein in vitro. Proc. Nat. Acad. Sci. 91: 3834-3838, 1994.

Further studies establishing the function and utilities of CDK9 are found in John Hopkins OMIM database record ID 603251, and in references numbered 552-559 listed hereinbelow.

Referring now to CDK9 BINDING SITE. Cyclin-dependent kinase 9 (CDC2-related kinase) (CDK9) is a target gene of GAM26, corresponding to GAM25-TARGET GENE of FIG. 26A. CDK9 BINDING SITE is a binding site found in an untranslated region of CDK9, corresponding to BINDING SITE of FIG. 26A. FIG. 26D illustrates the complementarity of the nucleotide sequence of CDK9 BINDING SITE, designated SEQ ID:101421, to the nucleotide sequence of GAM26 RNA of FIG. 26A, designated SEQ ID:20604.

Another function of GAM26 is therefore inhibition of cyclin-dependent kinase 9 (CDC2-related kinase) (CDK9), a gene which encodes a protein that is a positive transcription elongation factor band. Accordingly, utilities of GAM26 include diagnosis and treatment of the abovementioned diseases and clinical conditions. The function and utilities of CDK9 have been established by previous studies, as described hereinabove with reference to FIG. 26D.

Referring now to CDK9 BINDING SITE. Cyclin-dependent kinase 9 (CDC2-related kinase) (CDK9) is a target gene of GAM26, corresponding to GAM26-TARGET GENE of FIG. 26A. CDK9 BINDING SITE is a binding site found in an untranslated region of CDK9, corresponding to BINDING SITE of FIG. 26A. FIG. 26D illustrates the complementarity of the nucleotide sequence of CDK9 BINDING SITE, designated SEQ ID:101424, to the nucleotide sequence of GAM26 RNA of FIG. 26A, designated SEQ ID:20604.

Yet another function of GAM26 is therefore inhibition of cyclin-dependent kinase 9 (CDC2-related kinase) (CDK9), a gene which encodes a protein that is a positive transcription elongation factor band. Accordingly, utilities of GAM26 include diagnosis and treatment of the abovementioned diseases and clinical conditions. The function and utilities of CDK9 have been established by previous studies, as described hereinabove with reference to FIG. 26D.

Referring now to CDK9 BINDING SITE. Cyclin-dependent kinase 9 (CDC2-related kinase) (CDK9) is a target gene of GAM26, corresponding to GAM26-TARGET GENE of FIG. 26A. CDK9 BINDING SITE is a binding site found in an untranslated region of CDK9, corresponding to BINDING SITE of FIG. 26A. FIG. 26D illustrates the complementarity of the nucleotide sequence of CDK9 BINDING SITE, designated SEQ ID:101437, to the nucleotide sequence of GAM26 RNA of FIG. 26A, designated SEQ ID:20604.

An additional function of GAM26 is therefore inhibition of cyclin-dependent kinase 9 (CDC2-related kinase) (CDK9), a gene which encodes a protein that is a positive transcription elongation factor band. Accordingly, utilities of GAM26 include diagnosis and treatment of the abovementioned diseases and clinical conditions. The function and utilities of CDK9 have been established by previous studies, as described hereinabove with reference to FIG. 26D.

Reference is now made to CDKN2D BINDING SITE. Cyclin-dependent kinase inhibitor 2D (p19, inhibits CDK4) (CDKN2D) is a target gene of GAM26, corresponding to GAM26-TARGET GENE of FIG. 26A. CDKN2D BINDING SITE is a binding site found in an untranslated region of CDKN2D, corresponding to BINDING SITE of FIG. 26A. FIG. 26D illustrates the complementarity of the nucleotide sequence of CDKN2D BINDING SITE, designated SEQ ID:102195, to the nucleotide sequence of GAM26 RNA of FIG. 26A, designated SEQ ID:20604.

A further function of GAM26 is therefore inhibition of cyclin-dependent kinase inhibitor 2D (p19, inhibits CDK4) (CDKN2D), a gene which encodes a protein that interacts strongly with cdk4 and cdk6. Accordingly, utilities of GAM26 include diagnosis and treatment of the abovementioned diseases and clinical conditions.

The function of CDKN2D has been established by previous studies. Cyclins are important in regulating the cell cycle through their formation of enzymatic complexes with various cyclin-dependent kinases. The D type cyclins complex with CDK4 (123829) and CDK6 to govern progression through the G1 phase of the cell cycle and later are involved with inactivating phosphorylation of the RB protein (180200) which results in release of RB-associated transcription factors that are needed for entry into S phase (Okuda et al., 1995). The activity of the cyclin D-dependent kinases is, in part, controlled by inhibitors such as the INK4 family (which includes INK4a (CDKN2A; 600160), 4b (CDKN2B; 600431), 4c (CDKN2C), and 4d (CDKN2D)). INK4a has been shown to act by competing with CDK4 and CDK6 and functions as a tumor suppressor in a variety of cancers. The INK4d protein was first identified in a yeast 2 hybrid system screened for CDK4 binding proteins (Hirai et al., 1995). The mouse INK4d protein interacts with cdk6 as well. In fibroblasts and macrophages it is rapidly induced at the G1-to-S transition. Overexpression of INK4d caused NIH 3T3 cells to arrest in G1 phase and inhibited cyclin D1-CDK4 kinase activity (Hirai et al., 1995 Okuda et al. (1995) described the cloning and mapping of the human INK4d gene (CDKN2D). The predicted 166-amino acid protein is 86% identical to the mouse protein and about 45% identical to other human INK4 family members. Northern blots showed that the 1.4-kb transcript is ubiquitously expressed with the highest levels in tissues with the most rapidly dividing cells. Lowest expression occurs at mid G1 phase and is highest during S phase. Okuda et al. (1995) obtained a P1-phage genomic clone including the gene and mapped it by fluorescence in situ hybridization to 19p13

Full details of the abovementioned studies are described in the following publications, the disclosure of which are hereby incorporated by reference:

Hirai, H.; Roussel, M. F.; Kato, J. -Y.; Ashmun, R. A.; Sherr, C. J.: Novel INK4 proteins, p19 and p18, are specific inhibitors of cyclin D-dependent kinases CDK4 and CDK6. Molec. Cell. Biol. 15: 2672-2681, 1995. PubMed ID:7739547 2. Okuda, T.; Hirai, H.; Valentine, V. A.; Shurtleff, S. A.; Kidd, V. J.; Lahti, J. M.; Sherr, C. J.; Downing, J. R.: Molecular cloning, expression pattern, and chromosomal localization of human CDKN2D/INK4d, an inhibitor of cyclin D-dependent kinases. Genomics 29: 623-630, 1995.

Further studies establishing the function and utilities of CDKN2D are found in John Hopkins OMIM database record ID 600927, and in references numbered 560-561 listed hereinbelow.

Referring now to CDKN2D BINDING SITE. Cyclin-dependent kinase inhibitor 2D (p19, inhibits CDK4) (CDKN2D) is a target gene of GAM26, corresponding to GAM26-TARGET GENE of FIG. 26A. CDKN2D BINDING SITE is a binding site found in an untranslated region of CDKN2D, corresponding to BINDING SITE of FIG. 26A. FIG. 26D illustrates the complementarity of the nucleotide sequence of CDKN2D BINDING SITE, designated SEQ ID 102235, to the nucleotide sequence of GAM26 RNA of FIG. 26A, designated SEQ ID:20604.

Yet a further function of GAM26 is therefore inhibition of cyclin-dependent kinase inhibitor 2D (p19, inhibits CDK4) (CDKN2D), gene which encodes a protein that strongly with cdk4 and cdk6. Accordingly, utilities of GAM26 include diagnosis and treatment of the abovementioned diseases and clinical conditions. The function and utilities of CDKN2D have been established by previous studies, as described hereinabove with reference to FIG. 26D.

Reference is now made to CHN2 BINDING SITE. Chimerin (chimaerin) 2 (CHN2) is a target gene of GAM26, corresponding to GAM26-TARGET GENE of FIG. 26A. CHN2BINDING SITE is a binding site found in an untranslated region of CHN2, corresponding to BINDING SITE of FIG. 26A. FIG. 26D illustrates the complementarity of the nucleotide sequence of CHN2 BINDING SITE, designated SEQ ID:105797, to the nucleotide sequence of GAM26 RNA of FIG. 26A, designated SEQ ID:20604.

Another function of GAM26 is therefore inhibition of chimerin (chimaerin) 2 (CHN2), a gene which encodes a receptor that plays a role in the progression from low-grade to high-grade tumors. Accordingly, utilities of GAM26 include diagnosis and treatment of the abovementioned diseases and clinical conditions.

The function of CHN2 has been established by previous studies. The Rho family of GTP-binding proteins is believed to play a role in membrane/cytoskeletal reorganization events. These proteins cycle between active GTP-bound and inactive GDP-bound forms. Activation to the GTP-bound state is mediated by specific guanine nucleotide dissociation stimulators, whereas acceleration of GTP hydrolysis can be accomplished by GTPase-activating proteins (GAPs). Leung et al., (1993) isolated a rat testis cDNA that encodes a 30-kD GAP, which they named beta-chimerin, or beta-1-chimerin. The 1.35-kb beta-1 chimerin transcript is present exclusively in testicular germ cells. The beta-1-chimerin protein contains a phorbol ester-binding region and a GAP domain, and is selective for Rac (see RAC1; 602048). Leung et al. (1994) detected a 46-kD RacGAP in soluble rat cerebellar extracts, using antibodies against beta-1 chimerin. By screening a human cerebellar cDNA library with a rat beta-1-chimerin cDNA, they cloned a 2.45-kb cDNA corresponding to the cerebellar chimerin, which they named beta-2 chimerin. The encoded 466-amino acid beta-2-chimerin protein is identical to beta-1-chimerin, in both the phorbol ester binding and GAP domains, but it contains an additional N-terminal SH2 domain which is strikingly similar to that of alpha-2-chimerin (CHN1; 118423). Based on Southern blot and cDNA analyses, the authors concluded that beta-1- and beta-2-chimerin are derived from the same gene by alternative splicing. In situ hybridization of rat, brain showed that beta-2-chimerin mRNA is expressed only in the cerebellum, mainly in granule cells. Beta-2-chimerin protein is enriched in the particulate/synaptosomal fractions of rat cerebellum. Signaling in response to the second messenger diacylglycerol (DAG) is thought to proceed through the activation of protein kinase C (PKC) isozymes. Binding of this lipid second messenger and its related analogs, the phorbol esters, occurs at the C1 domain (also called cysteine-rich regions or zinc fingers) present in PKCs. The phorbol ester receptor family was expanded with the discovery of the chimerins. The several chimerin isoforms each possess a single C1 domain with approximately 40% homology to those present in PKCs. Having previously demonstrated that beta-2-chimerin binds phorbol esters with high affinity, Caloca et al. (1999) analyzed its properties as a DAG receptor by using a series of conformationally constrained cyclic DAG analogs (DAG lactones) as probes. They identified analogs that bind to beta-2-chimerin with high affinity. Cellular studies revealed that these DAG analogs induced translocation of beta-2-chimerin from cytosolic (soluble) to particulate fractions, and specifically to the perinuclear region. Binding and translocation were prevented by mutation of the conserved cys246 in the C1 domain. The results demonstrated that beta-2-chimerin is indeed a high affinity receptor for DAG through binding to its C1 domain and supported the concept that multiple pathways transduce signaling through DAG and the phorbol esters Full details of the abovementioned studies are described in the following publications, the disclosure of which are hereby incorporated by reference:

Leung, T.; How, B. -E.; Manser, E.; Lim, L.: Cerebellar beta-2-chimaerin, a GTPase-activating protein for p21 Ras-related Rac is specifically expressed in granule cells and has a unique N-terminal SH2 domain J. Biol. Chem. 269: 12888-12892, 1994. PubMed ID: 8175705 1. Caloca, M. J.; Garcia Bermejo, M. L.; Blumberg, P. M.; Lewin, N. E.; Kremmer, E.; Mischak, H.; Wang, S.; Nacro, K.; Bienfait, B.; Marquez, V. E.; Kazanietz, M. G.: Beta-2-chimaerin is a novel target for diacylglycerol: binding properties and changes in subcellular localization mediated by ligand binding to its C1 domain. Proc. Nat. Acad. Sci. 96: 11854-11859, 1999.

Further studies establishing the function and utilities of CHN2 are found in John Hopkins OMIM database record ID 602857, and in references numbered 562-565 listed hereinbelow.

Reference is now made to CHRNA3 BINDING SITE. Cholinergic receptor, nicotinic, alpha polypeptide 3 (CHRNA3) is a target gene of GAM26, corresponding to GAM26-TARGET GENE of FIG. 26A. CHRNA3 BINDING SITE is a binding site found in an untranslated region of CHRNA3, corresponding to BINDING SITE of FIG. 26A. FIG. 26D illustrates the complementarity of the nucleotide sequence of CHRNA3 BINDING SITE, designated SEQ ID:106136, to the nucleotide sequence of GAM26 RNA of FIG. 26A, designated SEQ ID:20604.

Yet another function of GAM26 is therefore inhibition of cholinergic receptor, nicotinic, alpha polypeptide 3 (CHRNA3), a gene which encodes a protein that binds acetylcholine and opens an ion-conducting channel across the plasma membrane and is associated with myasthenia gravis. Accordingly, utilities of GAM26 include diagnosis and treatment of the abovementioned diseases and clinical conditions.

The function of CHRNA3 has been established by previous studies. To examine the role of thymic AChRs in the anti-AChR response seen in myasthenia gravis (254200), Mihovilovic and Roses (1991) independently isolated the human alpha-3 subunit from a thymus cDNA library. The open reading frame coded for a 503-amino acid protein with a 29-amino acid putative signal peptide. On Northern blots, alpha-3 was transcribed as a major 3.0-kb mRNA with other minor bands in thymus but not in muscle or liver. Groot Kormelink and Luyten (1997) reported that alpha-3 was transcribed as a 3.0-kb mRNA on Northern blots of a neuroblastoma cell line. Prompted by the finding that mutations in the CHRNA4 gene (118504) are responsible for some cases of autosomal dominant nocturnal frontal lobe epilepsy (600513), Rempel et al. (1998) determined the genomic structure of the CHRNA3 gene necessary or mutational analysis of this gene as a candidate in families with epilepsy unlinked to CHRNA4.

Animal model experiments lend further support to the function of CHRNA3. The alpha-3 subunit of the neuronal nicotinic acetylcholine receptor is widely expressed in autonomic ganglia and in some parts of the brain. The alpha-3 subunit can form heteromultimeric ion channels with other alpha subunits and with beta-2 and beta-4 subunits. To understand better the function of CHRNA3 in vivo, Xu et al. (1999) prepared a null mutation the alpha-3 gene by the deletion of exon 5 and found that homozygous –/– mice lacked detectable mRNA on Northern blotting. The null mice survived to birth but had impaired growth and increased mortality before and after weaning. The null mice had extreme bladder enlargement, dribbling urination, bladder infection, urinary stones, and widely dilated ocular pupils that did not contract in response to light. Detailed histologic studies of null mice showed no significant abnormalities in brain or peripheral tissues except urinary bladder, where inflammation was prominent. Ganglion cells and axons were present in bladder and bowel. Bladder strips from null mice failed to contract in response to 0.1 mM nicotine, but did contract in response to electrical field stimulation or carbamoylcholine. The number of acetylcholine-activated single-channel currents was severely reduced in the neurons of superior cervical ganglia in null mice with 5 physiologically distinguishable nicotinic acetylcholine receptor subtypes with different conductance and kinetic properties in wildtype mice, all of which were reduced in null mice. The findings in the alpha-3-null mice suggested that this subunit is an essential component of the nicotinic receptors mediating normal function of the autonomic nervous system. Xu et al. (1999) suggested that the phenotype in null mice may be similar to that of the rare megacystis-microcolon-intestinal hypoperistalsis syndrome (MMIH; 249210).

It is appreciated that the abovementioned animal model for CHRNA3 is acknowledged by those skilled in the art as a scientifically valid animal model, as can be further appreciated from the publications sited hereinbelow.

Full details of the abovementioned studies are described in the following publications, the disclose of which are hereby incorporated by reference:

Groot Kormelink, P. J.; Luyten, W. H. M. L.: Cloning and sequence of full-length cDNAs encoding the human neuronal nicotinic acetylcholine receptor (nAChR) subunits beta-3 and beta-4 and expression of seven nAChR subunits in the human neuroblastoma cell line SH-SY5Y and/or IMR-32. FEBS Lett. 400: 309-314, 1997. PubMed ID: 9009220 12. Rempel, N.; Heyers, S.; Engels, H.; Sleegers, E.; Steinlein, O. K.: The structures of the human neuronal nicotinic acetylcholine receptor beta-2- and alpha-3-subunit genes (CHRNB2 and CHRNA3). Hum. Genet. 103: 645-653, 1998.

Further studies establishing the function and utilities of CHRNA3 are found in John Hopkins OMIM database record ID 118503, and in references numbered 566-578 listed hereinbelow.

Referring now to CHS1 BINDING SITE. Chediak-Higashi syndrome 1 (CHS1) is a target gene of GAM26, corresponding to GAM26-TARGET GENE of FIG. 26A. CHS1 BINDING SITE is a binding site found in an untranslated region of CHS1, corresponding to BINDING SITE of FIG. 26A. FIG. 26D illustrates the complementarity of the nucleotide sequence of CHS1 BINDING SITE, designated SEQ ID:106651, to the nucleotide sequence of GAM26 RNA of FIG. 26A, designated SEQ ID:20604.

An additional function of GAM26 is therefore inhibition of Chediak-Higashi syndrome 1 (CHS1), a gene which encodes a protein that is associated with chediak-Higashi syndrome. Accordingly, utilities of GAM26 include diagnosis and treatment of the abovementioned diseases and clinical conditions. The function and utilities of CHS1 have been established by previous studies, as described hereinabove with reference to FIG. 26D.

Reference is now made to CKAP1 BINDING SITE. Cytoskeleton-associated protein 1 (CKAP1) is a tar et gene of GAM26, corresponding to GAM26-TARGET GENE of FIG. 26A. CKAP1 BINDING SITE is a binding site found in an untranslated region of CKAP1, corresponding to BINDING SITE of FIG. 26A. FIG. 26D illustrates the complementarity of the nucleotide sequence of CKAP1 BINDING SITE, designated SEQ ID:107655, to the nucleotide sequence of GAM26 RNA of FIG. 26A, designated SEQ ID:20604.

A further function of GAM26 is therefore inhibition of cytoskeleton-associated protein 1 (CKAP1), a gene which encodes a protein that binds to alpha-tubulin folding intermediates. Accordingly, utilities of GAM26 include diagnosis and treatment of the abovementioned diseases and clinical conditions.

The function of CKAP1 has been established by previous studies. The cytoskeleton is composed of 3 structural elements: actin filaments, microtubules, and intermediate filaments. Cytoskeletal activity is modulated by many cytoskeleton-associated proteins (CAPs). One group of CAPs is characterized by a highly conserved glycine motif, the CAP-GLY domain, which may contribute to its association with microtubules. Members of the group of CAPs include dynactin (601143), the dynein-associated protein. Watanabe et al. (1996) isolated a novel member of this family, which they called CKAPI (for cytoskeleton-associated protein I, glycine motif). The cDNA was isolated from a human fetal-brain cDNA library and found to contain an open reading frame of 579 nucleotides encoding a 193-amino acid polypeptide. Three transcripts of different sizes were expressed in all tissues examined. By fluorescence in situ hybridization, Watanabe et al. (1996) assigned the gene to 19q13.11-q13.12.

Full details of the abovementioned studies are described in the following publications, the disclosure of which are hereby incorporated by reference:

Watanabe, T. K.; Shimizu, F.; Nagata, M.; Kawai, A.; Fujiwara, T.; Nakamura, Y.; Takahashi, E.; Hirai, Y.: Cloning, expression, and mapping of CKAP1, which encodes a putative cytoskeleton-associated protein containing a CAP-GLY domain. Cytogenet. Cell Genet. 72: 208-211, 1996.

Further studies establishing the function and utilities of CKAP1 are found in John Hopkins OMIM database record ID 601303, and in references numbered 579 listed hereinbelow.

Referring now to CKAP1 BINDING SITE. Cytoskeleton-associated protein 1 (CKAP1) is a target gene of GAM26, corresponding to GAM26-TARGET GENE of FIG. 26A. CKAP1 BINDING SITE is a binding site found in an untranslated region of CKAP1, corresponding to BINDING SITE of FIG. 26A. FIG. 26D illustrates the complementarity of the nucleotide sequence of CKAP1 BINDING SITE, designated SEQ ID:107655, to the nucleotide sequence of GAM26 RNA of FIG. 26A, designated SEQ ID:20604.

Yet a further function of GAM26 is therefore inhibition of cytoskeleton-associated protein 1 (CKAP1), a gene which encodes a protein that binds to alpha-tubulin folding intermediates. Accordingly, utilities of GAM26 include diagnosis and treatment of the abovementioned diseases and clinical conditions. The function and utilities of CKAP1 have been established by previous studies, as described hereinabove with reference to FIG. 26D.

Referring now to CKAP1 BINDING SITE. Cytoskeleton-associated protein 1 (CKAP1) is a target gene of GAM26, corresponding to GAM26-TARGET GENE of FIG. 26A. CKAP1 BINDING SITE is a binding site found in an untranslated region of CKAP1, corresponding to BINDING SITE of FIG. 26A. FIG. 26D illustrates the complementarity of the nucleotide sequence of CKAP1 BINDING SITE, designated SEQ ID:107659, to the nucleotide sequence of GAM26 RNA of FIG. 26A, designated SEQ ID:20604.

Another function of GAM26 is therefore inhibition of cytoskeleton-associated protein 1 (CKAP1), a gene which encodes a protein that binds to alpha-tubulin folding intermediates. Accordingly, utilities of GAM26 include diagnosis and treatment of the abovementioned diseases and clinical conditions. The function and utilities of CKAP1 have been established by previous studies, as described hereinabove with reference to FIG. 26D.

Reference is now made to COL5A1 BINDING SITE. Collagen type V, alpha 1 (COL5A1) is a target gene of GAM26, corresponding to GAM26-TARGET GENE of FIG. 26A. COL5A1 BINDING SITE is a bi ding site found in an untranslated region of COL5A1, corresponding to BINDING SITE of FIG. 26A. FIG. 26D illustrates the complementarity of the nucleotide sequence of COL5A1 BINDING SITE, designated SEQ ID:114312, to the nucleotide sequence of GAM26 RNA of FIG. 26A, designated SEQ ID:20604.

Yet another function of GAM26 is therefore inhibition of collagen, type V, alpha 1 (COL5A1), a gene which encodes a protein that is associated with EHLERS-DANLOS SYNDROME. Accordingly, utilities of GAM26 include diagnosis and treatment of the above mentioned diseases and clinical conditions.

The function of COL5A1 has been established by previous studies. Type V collagen was first identified in human placenta and adult skin, but later studies showed that it is present in many other tissues and organs as a minor collagen component. Type V collagen occurs as heterotrimers of 3 different polypeptide chains, alpha-1, alpha-2 (COL5A2, 120190), and alpha-3 (COL5A3, 120216), or 2 copies of alpha-1 and 1 copy of alpha-2; it also occurs as a homotrimer of alpha-1 polypeptides. Takahara et al. (1991) reported the sequence of cDNA encoding the complete prepro-alpha-1 (V) chain. The collagenous region and COOH-terminal noncollagenous region closely resembled that of the alpha-1(XI) (120280) chain; however, codon usage differed, that the COL5A1 gene is evolutionarily distinct Similarly, Wenstrup et al. (2000) found that 8 of 28 probands with classic EDS, who were heterozygous for expressed polymorphisms in COL5A1, showed complete or nearly complete loss of expression 1 COL5A1 allele. Reduced levels of COL5A1 mRNA relative to levels of COL5A2 mRNA were also observed in the cultured fibroblasts from EDS probands. Products of the 2 COL5A1 alleles were approximately equal after the addition of cycloheximide to the fibroblast cultures.

After harvesting of mRNAs from cycloheximide-treated cultured fibroblasts, heteroduplex analysis of overlapping RT-PCR segments spanning the complete COL5A1 cDNA showed anomalies in 4 of the 8 probands, leading to identification of causative mutations; in the remaining 4 probands, targeting of CGA-to-TGA, mutations in genomic DNA revealed a premature stop codon in one of them. Wenstrup et al. (2000) estimated that one-third of persons with classic EDS have mutations of the COL5A1 gene that result in haploinsufficiency. These findings indicated that normal formation of the heterotypic collagen fibrils that contain types I, III, and V collagen require the expression of both COL5A1 alleles Full details of the abovementioned studies are described in the following publications, the disclosure of which are hereby incorporated by reference:

Takahara, K.; Sato, Y.; Okazawa, K.; Okamoto, N.; Noda, A.; Yaoi, Y.; Kato, I.: Complete primary structure of human collagen alpha-1(V) chain. J. Biol. Chem. 266: 13124-13129, 1991. PubMed ID: 2071595 17. Wenstrup, R. J.; Florer, J. B.; Willing, M. C.; Giunta, C.; Steinmann, B.; Young, F.; Susic, M.; Cole, W. G.: COL5A1 haploinsufficiency is a common molecular mechanism underlying the classical form of EDS. Am. J. Hum. Genet. 66: 1766-1776, 2000.

Further studies establishing the function and utilities of COL5A1 are found in John Hopkins OMIM database record ID 120215, and in references numbered 580-597 listed hereinbelow.

Referring now to COL5A1 BINDING SITE. Collagen type V, alpha 1 (COL5A1) is a target gene of GAM26, corresponding to GAM26-TARGET GENE of FIG. 26A. COL5A1 BINDING SITE is a binding site found in an untranslated region of COL5A1, corresponding to BINDING SITE of FIG. 26A. FIG. 26D illustrates the complementarity of the nucleotide sequence of COL5A1 BINDING SITE, designated SEQ ID:114314, to the nucleotide sequence of GAM26 RNA of FIG. 26A, designated SEQ ID:20604.

An additional function of GAM26 is therefore inhibition of collagen, type V, alpha 1 (COL5A1), a gene which encodes a protein that is associated with EHLERS-DANLOS SYNDROME. Accordingly, utilities of GAM26 include diagnosis and treatment of the abovementioned diseases and clinical conditions. The function and utilities of COL5A1 have been established by previous studies, as described hereinabove with reference to FIG. 26D.

Reference is now made to CPE BINDING SITE. Carboxypeptidase E (CPE) is a target gene of GAM126, corresponding to GAM26-TARGET GENE of FIG. 26A. CPE BINDING SITE is a binding site found in an untranslated region of CPE, corresponding to BINDING SITE of FIG. 26A. FIG. 26D illustrates the complementarity of the nucleotide sequence of (CPE BINDING SITE, designated SEQ ID:116431, to the nucleotide sequence of GAM26 RNA of FIG. 26A, designated SEQ ID:20604.

A further function of GAM26 is therefore inhibition of carboxypeptidase E (CPE), a gene which encodes a enzyme that removes residual c-terminal arg or lys remaining after initial endoprotease cleavage, and is associated with hyperproinsulinemia and diabetes. Accordingly, utilities of GAM26 include diagnosis and treatment of the abovementioned diseases and clinical conditions.

The function of CPE has been established by previous studies. Naggert et al. (1995) stated that mice homozygous for the 'fat' mutation develop obesity and hyperglycemia that can be suppressed by treatment with exogenous insulin. The 'fat' mutation maps to mouse chromosome 8, very close to the gene for carboxypeptidase E (Cpe), which encodes an enzyme (CPE) that processes prohormone intermediates such as proinsulin. Naggert et al. (1995) demonstrated a defect in proinsulin processing associated with the virtual absence of CPE activity in extracts of fat/fat pancreatic islets and pituitaries. A single ser202-to-pro mutation distinguished the mutant Cpe allele and abolished enzymatic activity in vitro. Thus, the 'fat' mutation represents the first demonstration of an obesity-diabetes syndrome elicited by a genetic defect in a prohormone processing pathway. As indicated, CPE is involved in the biosynthesis of peptide hormones and neurotransmitters, including insulin. One of the features of type II diabetes mellitus (125853) is an elevation in the proinsulin level and/or molar ratio of proinsulin to insulin, suggesting that mutations in proinsulin processing enzymes may contribute to the development of this form of diabetes. Chen et al. (2001) scanned the CPE gene for mutations in a collection of Ashkenazi type II diabetes families and identified 5 novel single-nucleotide polymorphisms. One of these, C-to-T transition at nucleotide 847, changed arginine to tryptophan (arg283 to trp; R283W). The arg283 residue is conserved among CPE orthologs as well as most enzymatically active metallocarboxypeptidases. Of the 272 Ashkenazi pedigrees with type II diabetes, Chen et al. (2001) found 4 families segregating R283W. Within these 4 families, patients who inherited one copy of this variant had much earlier age of onset of type II diabetes. The R283W CPE protein was found to cleave peptide substrates with substantially lower efficiencies and was, furthermore, less stable at elevated temperature. In addition, the R283W CPE variant had a narrower pH optimum and was much less active at pH 6.0 to 6.5, indicating that the R283W CPE variant would be substantially less active than wildtype CPE in the trans-Golgi network and immature secretory vesicles where the enzyme functions in vivo. Chen et al. (2001) predicted that in the homozygous state this mutant could cause hyperproinsulinemia and diabetes.

Full details of the abovementioned studies are described in the following publications, the disclosure of which are hereby incorporated by reference:

Naggert, J. K.; Fricker, L. D.; Varlamov, O.; Nishina, P. M.; Rouille, Y.; Steiner, D. F.; Carroll, R. J.; Paigen, B. J.; Leiter, E. H.: Hyperproinsulinaemia in obese fat/fat mice associated with a carboxypeptidase E mutation which reduces enzyme activity. Nature Genet 10: 135-142, 1995. PubMed ID: 7663508 1. Chen, H.; Jawahar, S.; Qian, Y.; Duong, Q.; Chan, G.; Parker, A.; Meyer, J. M.; Moore, K. J.; Chayen, S.; Gross, D. J.; Glaser, B.; Permutt, M. A.; Fricker, L. D.: Missense polymorphism in the human carboxypeptidase E gene alters enzymatic activity. Hum. Mutat. 18: 120-131, 2001.

Further studies establishing the function and utilities of CPE are found in John Hopkins OMIM database record ID 114855, and in references numbered 598-602 listed hereinbelow.

Reference is now made to CSNK1D BINDING SITE. Casein kinase 1, delta (CSNK1D) is a target gene of GAM26, corresponding to GAM26-TARGET GENE of FIG. 26A. CSNK1D BINDING SITE is a binding site found in an untranslated region of CSNK1D, corresponding to BINDING SITE of FIG. 26A. FIG. 26D illustrates the complementarity of the nucleotide sequence of CSNK1D BINDING SITE, designated SEQ ID:120331, to the nucleotide sequence of GAM26 RNA of FIG. 26A, designated SEQ ID:20604.

Yet a further function of GAM26 is therefore inhibition of casein kinase 1, delta (CSNK1D), a gene which encodes a protein that can phosphorylate a large number of proteins. Accordingly, utilities of GAM26 include diagnosis and treatment of the abovementioned diseases and clinical conditions.

The function of CSNK1D has been established by previous studies. Casein kinase I is a ubiquitous serine/threonine-specific protein kinase that constitutes most of the kinase activity in eukaryotic cells, where it is distributed in the nucleus, cytoplasm, and membrane fraction. The monomeric enzyme (34 to 55 kD) phosphorylates hierarchically a variety of substrates without the involvement or the so-called second messenger in signal transduction. A full-length rat CKI-delta cDNA was cloned by Graves et al. (1993). Fish et al. (1995) mapped the human CKI-delta locus to 17q25 by fluorescence in situ hybridization. Kusuda et al. (1996) isolated and sequenced a cDNA clone for human casein kinase I. An open reading frame of 415 amino acids was identified, showing 97% homology to rat CKI-delta; within the kinase domain of 284 amino acids the 2 were completely identical. The amino acid sequence of the kinase domain of human CSNK1D to yeast enzymes that are involved in the repair of DNA strand breaks supported speculation that the human gene product acts in DNA metabolism through excision and recombinational repair. By fluorescence in situ hybridization and PCR analysis of human/rodent hybrid cell panels, Kusuda et al. (1996) mapped CSNK1D to 17q25.2-q25.3.

Full details of the abovementioned studies are described in the following publications, the disclosure of which are hereby incorporated by reference:

Graves, P. R.; Haas, D. W.; Hagedorn, C. H.; DePaoli-Roach, A. A.; Roach, P. J.: Molecular cloning, expression, and characterization of a 49-kilodalton casein kinase I isoform from rat testis. J. Biol. Chem. 268: 6394-6401, 1993. PubMed ID: 8454611 3. Kusuda, J.; Hidari, N.; Hirai, M.; Hashimoto, K.: Sequence analysis of the cDNA for the human casein kinase 1-delta (CSNK1D) gene and its chromosomal localization. Genomics 32: 140-143, 1996.

Further studies establishing the function and utilities of CSNK1D are found in John Hopkins OMIM database record ID 600864, and in references numbered 603-605 listed hereinbelow.

Reference is now made to CUGBP1 BINDING SITE. CUG triplet repeat, RNA-binding protein 1 (CUGBP1) is a target gene of GAM26, corresponding to GAM26-TARGET GENE of FIG. 26A. CUGBP1 BINDING SITE is a binding site found in an untranslated region of CUGBP1, corresponding to BINDING SITE of FIG. 26A. FIG. 26D illustrates the complementarity of the nucleotide sequence of CUGBP1 BINDING SITE, designated SEQ ID:122870, to the nucleotide sequence of GAM26 RNA of FIG. 26A, designated SEQ ID:20604.

Another function of GAM26 is therefore inhibition of CUG triplet repeat, RNA-binding protein 1 (CUGBP1), a gene which encodes a receptor that regulates splicing and translation of various RNAs, and is associated with myotonic dystrophy. Accordingly, utilities of GAM26 include diagnosis and treatment the abovementioned diseases and clinical conditions.

The function of CUGBP1 has been established by previous studies. While an unstable CTG triplet repeat expansion is responsible for myotonic dystrophy (DM; 160900), the mechanism whereby this genetic defect induces the disease is unknown. To detect proteins that bind to CTG triplet repeats, Timchenko et al. (1996) performed bandshift analysis using as probes double-stranded DNA fragments having CTG repeats and single-stranded oligonucleotides having CTG repeats or CUG repeats. The proteins were derived from nuclear and cytoplasmic extracts of HeLa cells, fibroblasts, and myotubes. Proteins binding to the double-stranded DNA repeat were inhibited by the nonlabeled repeat but not by a nonspecific DNA fragment. Another protein binding to the single-stranded CTG probe and the RNA CUG probe was inhibited by nonlabeled CTG(8) and CUG(8) repeats. The protein binding only to the RNA repeat (CUG)8 was inhibited by nonlabeled (CUG)8 but not by nonlabeled single- or double-stranded CTG repeats. Furthermore, the protein, designated CUG-binding protein (CUGBP) by the authors, exhibited no binding to an RNA oligonucleotide of triplet repeats of the same length but having a different sequence, CGG. The CUG-binding protein was localized to the cytoplasm, whereas double-stranded DNA binding proteins were localized to the nuclear extract. Thus, Timchenko et al. (1996) concluded that several trinucleotide-binding proteins exist and their specificity is determined by the triplet sequence. CTG trinucleotide repeats encode CUG repeat regions in the corresponding mRNAs. Timchenko et al. (1996) identified 2 proteins, termed CUGBP1 and CUGBP2, that bind specifically to CUG repeats in RNA. They suggested that these 2 proteins, with masses of 49 kD and 51 kD, respectively, are isoforms encoded by the same gene. Timchenko et al. (1996) cloned a gene, termed NAB50 by them, based on the interaction between its protein product and the yeast Nab2 protein. The authors stated that the NAB50 gene encodes the CUGBP1 and CUGBP2 proteins because anti-Nab50 antibodies cross-reacted with both CUGBP isoforms. The gene predicts a 482-amino acid protein with a calculated molecular mass of 52 kD. The predicted protein contains 3 RNA-binding domains and is homologous to the hnRNPs Full detail of the abovementioned studies are described in the following publications, the disclosure of which are hereby incorporated by reference:

Timchenko L. T.; Miller, J. W.; Timchenko, N. A.; DeVore, D. R.; Datar, K. V.; Lin, L.; Roberts, R.; Caskey, C. T.; Swanson, M. S.: Identification of a (CUG)n triplet repeat RNA-binding protein and its expression in myotonic dystrophy. Nucleic Acids Res. 24: 4407-4414, 1996. PubMed ID: 8948631 1. Good, P. J.; Chen, Q.; Warner, S. J.; Herring, D. C.: A family of human RNA-binding proteins related to the *Drosophila* Bruno transcriptional regulator. J. Biol. Chem. 275: 28583-28592, 2000.

Further studies establishing the function and utilities of CUGBP1 are found in John Hopkins OMIM database record ID 601074, and in references numbered 606-609 listed hereinbelow.

Referring now to CUGBP1 BINDING SITE. CUG triplet repeat, RNA-binding protein 1 (CUGBP1) is a target gene of GAM26, corresponding to GAM26-TARGET GENE of FIG. 26A. CUGBP1 BINDING SITE is a binding site found in an untranslated region of CUGBP1, corresponding to BINDING SITE of FIG. 26A. FIG. 26D illustrates the complementarity of the nucleotide sequence of CUGBP1 BINDING SITE, designated SEQ ID: 122874, to the nucleotide sequence of GAM26 RNA of FIG. 26A, designated SEQ ID:20604.

Yet another function of GAM26 is therefore inhibition of CUG triplet repeat, RNA-binding protein 1 (CUGBP1), a gene which encodes a receptor that regulates splicing and translation of various RNAs, and is associated with myotonic dystrophy. Accordingly, utilities of GAM26 include diagnosis and treatment of the abovementioned diseases and clinical conditions. The function and utilities of CUGBP1 have been established by previous studies, as described hereinabove with reference to FIG. 26D.

Reference is now made to DAG1 BINDING SITE. Dystroglycan 1 (dystrophin-associated glycoprotein 1) (DAG1) is a target gene of GAM26, corresponding to GAM26-TARGET GENE of FIG. 26A. DAG1 BINDING SITE is a binding site found in an untranslated region of DAG1, corresponding to BINDING SITE of FIG. 26A. FIG. 26D illustrates the complementarity of the nucleotide sequence of DAG1 BINDING SITE, designated SEQ ID:127812, to the nucleotide sequence of GAM26 RNA of FIG. 26A, designated SEQ ID:20604.

An additional function of GAM26 is therefore inhibition of dystroglycan 1 (dystrophin-associated glycoprotein 1) (DAG1), a gene which encodes a protein that may provide linkage between the sarcolemma and extracellular matrix (ECM) and is associated with Fukuyama-type congenital muscular dystrophy. Accordingly, utilities of GAM26 include diagnosis and treatment of the abovementioned diseases and clinical conditions.

The function of DAG1 has been established by previous studies. Ibraghimov-Beskrovnaya et al. (1992) demonstrated that the transmembrane 43-kD and extracellular 156-kD dystrophin (300377)-associated glycoproteins are encoded by a single messenger RNA and that the extracellular 156-kD DAG binds laminin. Thus, the 156-kD DAG is a laminin-binding glycoprotein that may provide linkage between the sarcolemma and extracellular matrix (ECM). The dramatic reduction in the 156K DAG in Duchenne muscular dystrophy (310200) led to a loss of linkage between the sarcolemma and extracellular matrix, rendering muscle fibers more susceptible to necrosis. Ibraghimov-Beskrovnaya et al. (1992, 1992, 1993) mapped the DAG gene to chromosome 3 by Southern blot analysis of human/Chinese hamster somatic cell hybrid DNAs. One hybrid cell line with an isochromosome 3q was negative, suggesting location of the gene on 3p. The regional assignment was confirmed and further refined by fluorescence in situ hybridization, the localization being 3p21. The coding sequence of the DAG1 gene is organized into 2 exons, separated by a large intron (Ibraghimov-Beskrovnaya et al., 1993). The predicted amino acid sequence of human and rabbit dystroglycan are 93% identical, with predicted glycosylation sites being conserved. Human dystroglycan is expressed in a variety of fetal and adult tissues. The muscle and nonmuscle isoforms of dystroglycan differ by carbohydrate moities but not protein sequence. Using PCR, immunohistochemistry, and immunoblotting to analyze samples from patients with Fukuyama congenital muscular dystrophy (FCMD; 253800), Hayashi et al. (2001) confirmed a deficiency of fukutin and found marked deficiency of highly glycosylated DAG1 in skeletal and cardiac muscle and reduced mounts of DAG1 in brain tissue. Beta-dystroglycan was normal in all tissues examined. These findings supported the suggestion that fukutin deficiency affects the modification of glycosylation of DAG1, which then cannot localize or function properly and may be degraded or eluted from the extracellular surface membrane of the muscle fiber. Hayashi et al. (2001) concluded that this disruption underlies the developmental, structural, and functional damage to muscles in patients with FCMD.

Animal model experiments lend further support to the function of DAG1. Cohn et al. (2002) found that striated muscle-specific disruption of the Dag1 gene in mice resulted in loss of the dystrophin-glycoprotein complex in differentiated muscle and a remarkably mild muscular dystrophy with hypertrophy and without tissue fibrosis. They found that satellite cells, expressing dystroglycan, supported continued efficient regeneration of skeletal muscle along with transient expression of dystroglycan in regenerating muscle fibers. Cohn et al. (2002) demonstrated a similar phenomenon of reexpression of functional dystroglycan in regenerating muscle fibers in a mild form of human muscular dystrophy caused by disruption of posttranslational dystroglycan processing. They concluded that maintenance of regenerative capacity by satellite cells expressing dystroglycan is likely responsible for mild disease progression in mice and possibly humans. Cohn et. al. (2002) suggested that inadequate repair of skeletal muscle by satellite cells represents an important mechanism affecting the pathogenesis of muscular dystrophy.

It is appreciated that the abovementioned animal model for DAG1 is acknowledged by those skilled in the art as a scientifically valid animal model, as can be further appreciated from the publications sited hereinbelow.

Full details of the abovementioned studies are described in the following publications, the disclosure of which are hereby incorporated by reference:

Ibraghimov Beskrovnaya, O.; Ervasti, J. M.; Leveille, C. J.; Slaughter, C. A.; Sernett, S. W.; Campbell, K. P.: Primary structure of dystrophin-associated glycoproteins linking dystrophin to the extracellular matrix. Nature 355: 696-702, 1992. PubMed ID: 1741056 8. Hayashi, Y. K.; Ogawa, M.; Tagawa, K.; Noguchi, S.; Ishihara, T.; Nonaka, I.; Arahata, K.: Selective deficiency of alpha-dystroglycan in Fukuyama-type congenital muscular dystrophy. Neurology 57: 115-121, 2001.

Further studies establishing the function and utilities of DAG1 are found in John Hopkins OMIM database record ID 128239, and in references numbered 610-634 listed hereinbelow.

Referring now to DAG1 BINDING SITE. Dystroglycan 1 (dystrophin-associated glycoprotein 1) (DAG1) is a target gene of GAM26, corresponding to GAM26-TARGET GENE of FIG. 26A. DAG1 BINDING SITE is a binding site found in an untranslated region of DAG1, corresponding to BINDING SITE of FIG. 26A. FIG. 26D illustrates the complementarity of the nucleotide sequence of DAG1 BINDING SITE, designated SEQ ID:127882, to the nucleotide sequence of GAM26 RNA of FIG. 26A, designated SEQ ID:20604.

A further function of GAM26 is therefore inhibition of dystroglycan 1 (dystrophin-associated glycoprotein 1) (DAG1), a gene which encodes a protein that may provide linkage between the sarcolemma and extracellular matrix (ECM) and is associated with Fukuyama-type congenital muscular dystrophy. Accordingly, utilities of GAM26 include diagnosis and treatment of the abovementioned diseases and clinical conditions. The function and utilities of DAG1 have been established by previous studies, as described hereinabove with reference to FIG. 26D.

Reference is now made to DDEF2 BINDING SITE. Development and differentiation enhancing factor 2 (DDEF2) is a target gene of GAM26, corresponding to GAM26-TARGET GENE of FIG. 26A. DDEF2 BINDING SITE is a binding site found in an untranslated region of DDEF2, corresponding to BINDING SITE of FIG. 26A. FIG. 26D illustrates the complementarity of the nucleotide sequence of DDEF2 BINDING SITE, designated SEQ ID:129959, to the nucleotide sequence of GAM26 RNA of FIG. 26A, designated SEQ ID:20604.

Yet a further function of GAM26 is therefore inhibition of development and differentiation enhancing factor 2 (DDEF2), a gene which encodes a protein that interacts with members of the Arf and Src family. Accordingly, utilities of GAM26 include diagnosis and treatment of the abovementioned diseases and clinical conditions.

The function of DDEF2 has been established by previous studies. By screening human brain cDNAs for those encoding large proteins, Ishikawa et al. (1997) identified a cDNA, which they called KIAA0400, encoding development- and differentiation-enhancing factor-2. They found that the deduced 1,006-amino acid DDEF2 protein contains a 60-amino acid zinc finger motif thought to be associated with GTPase activating protein (GAP) activity. Using PYK2 (601212) as bait in a yeast 2-hybrid screen, Andreev et al. (1999) isolated DDEF2, a PYK2-binding protein which they designated PAP. DDEF2 is a multidomain protein composed of an N-terminal alpha-helical region with a coiled-coil motif, followed by a pleckstrin homology domain, an Arf-GAP domain, an ankyrin homology region, a proline-rich region, and a C-terminal SH3 domain. DDEF2 shares 95% sequence identity with the mouse homolog and 68% sequence identity with human DDEF1 (605953). Andreev et al. (1999) identified 2 DDEF2 isoforms, designated PAP-alpha and PAP-beta, which differ by deletion of 45 amino acids from the proline-rich region and 172 amino acids from the N terminus. Northern blot analysis detected expression of an approximately 5.7-kb transcript at high levels in brain, kidney, and heart, and at lower levels in placenta, lung, and pancreas. Immunofluorescence studies demonstrated that DDEF2 is localized in the Golgi apparatus and at the plasma membrane, where it is colocalized with PYK2. DDEF2 forms a stable complex with PYK2 and activation of PYK2 leads to tyrosine phosphorylation of DDEF2 in vivo. The interaction of DDEF2 and PYK2 appears to be mediated by binding of the SH3 domain of DDEF2 to the proline-rich region in the C terminus of PYK2. In addition, in vitro recombinant DDEF2 exhibits strong GAP activity towards the small GTPases ARF1 (103180) and ARF5 (103188) and weak activity towards ARF6 (600464).

Full details of the abovementioned studies are described in the following publications, the disclosure of which are hereby incorporated by reference:

Andreev, J.; Simon, J. -P.; Sabatini, D. D.; Kam, J.; Plowman, G.; Randazzo, P. A.; Schlessinger, J.: Identification of a new Pyk2 target protein with Arf-GAP activity. Molec. Cell. Biol. 19: 2338-2350, 1999. PubMed ID: 10022920 2. Ishikawa, K.; Nagase, T. Nakajima, D.; Seki, N.; Ohira, M.; Miyajima, N.; Tanaka, A.; Kotani, H.; Nomura, N.; Ohara, O.: Prediction of the coding sequences of unidentified human genes. VIII. 78 new cDNA clones from brain which code for large proteins in vitro. DNA Res. 4: 307-313, 1997.

Further studies establishing the function and utilities of DDEF2 are found in John Hopkins OMIM database record ID 603817, and in references numbered 635 listed hereinbelow.

Referring now to DDEF2 BINDING SITE. Development and differentiation enhancing factor 2 (DDEF2) is a target gene of GAM26, corresponding to GAM26-TARGET GENE of FIG. 26A. DDEF2 BINDING SITE is a binding site found in an untranslated region of DDEF2, corresponding to BINDING SITE of FIG. 26A. FIG. 26D illustrates the complementarity of the nucleotide sequence of DDEF2 BINDING SITE, designated SEQ ID:129968, to the nucleotide sequence of GAM26 RNA of FIG. 26A, designated SEQ ID:20604.

Another function of GAM26 is therefore inhibition of development and differentiation enhancing factor 2 (DDEF2), a gene which encodes a protein that interacts with members of the Arf and Src family. Accordingly, utilities of GAM26 include diagnosis and treatment of the abovementioned diseases and clinical conditions. The function and utilities of DDEF2 have been established by previous studies, as described hereinabove with reference to FIG. 26D.

Referring now to DDEF2 BINDING SITE. Development and differentiation enhancing factor 2 (DDEF2) is a target gene of GAM26, corresponding to GAM26-TARGET GENE of FIG. 26A. DDEF2 BINDING SITE is a binding site found in an untranslated region of DDEF2, corresponding to BINDING SITE of FIG. 26A. FIG. 26D illustrates the complementarity of the nucleotide sequence of DDEF2 BINDING SITE, designated SEQ ID:129973, to the nucleotide sequence of GAM26 RNA of FIG. 26A, designated SEQ ID:20604.

Yet another function of GAM26 is therefore inhibition of development and differentiation enhancing factor 2 (DDEF2), a gene which encode a protein that interacts with members of the Arf and Src family. Accordingly, utilities of GAM26 include diagnosis and treatment of the abovementioned diseases and clinical conditions. The function and utilities of DDEF2 have been established by previous studies, as described hereinabove with reference to FIG. 26D.

Reference is now made to DHFR BINDING SITE. Dihydrofolate reductase (DHFR) is a target gene of GAM26, corresponding to GAM26-TARGET GENE of FIG. 26A. DHFR BINDING SITE is a binding site found in an untranslated region of DHFR, corresponding to BINDING SITE of FIG. 26A. FIG. 26D illustrates the complementarity of the nucleotide sequence of DHFR BINDING SITE, designated SEQ ID:133111, to the nucleotide sequence of GAM26 RNA of FIG. 26A, designated SEQ ID:20604.

An additional function of GAM26 is therefore inhibition of dihydrofolate reductase (DHFR), a gene which encodes an enzyme that converts dihydrofolate into tetrahydrofolate. Accordingly, utilities of GAM26 include diagnosis and treatment of the abovementioned diseases and clinical conditions.

The function of DHFR has been established by previous studies. Dihydrofolate reductase (EC 1.5.1.3) converts dihydrofolate into tetrahydrofolate, a methyl group shuttle required for the de novo synthesis of purines, thymidylic acid, and certain amino acids. DHFR is inhibited by methotrexate (MTX), a folate analog used as an antineoplastic and immunosuppressive agent. From comparisons of eukaryotic gene sequences and protein sequences of homologous enzymes from bacterial and mammalian organisms, Craik et al. (1983) noted that intron-exon junctions often coincide with variable surface loops of the protein structure. Proteins studied included DHFR, trypsin, and chymotrypsin. They pointed out that altered surface structures can account for functional differences among the members of a family, e.g., the serine proteases. 'Sliding' of the intron-exon junctions may constitute a mechanism for generating length polymorphisms and divergent sequences. Different function can thus be achieved without disrupting the stability of the protein core. DNA sequence amplification is one of the most frequent manifestations of genomic instability in human tumors. In most human tumor cells, amplified DNA sequences are borne on unstable, extrachromosomal double minutes (DMs). Singer et al. (2000) isolated a large number of independent methotrexate-resistant human cell lines, all of which contained DHFR-bearing DMs. All but one of these also had suffered partial or complete loss of one of the parental DHFR-bearing chromosomes. Cells in a few populations displayed what could be transient intermediates in the amplification process, including an initial homogeneously staining chromosome region (HSR), its subsequent breakage, the appearance of DHFR-containing fragments, and, finally, DMs. The studies suggested that both HSRs and DMs are initiated by chromosome breaks, but that cell types differ in how the extra sequences ultimately are processed and/or maintained.

Full details of the abovementioned studies are described in the following publications, the disclosure of which are hereby incorporated by reference:

Singer, M. J.; Mesner, L. D.; Friedman, C. L.; Trask B. J.; Hamlin, J. L.: Amplification of the human dihydrofolate reductase gene via double minutes is initiated by chromosome breaks. Proc. Nat. Acad. Sci. 97: 7921-7926, 2000. PubMed ID: 10859355 7. Craik, C. S.; Rutter, W. J.; Fletterick, R.: Splice junctions: association with variation in protein structure. Science 220: 1125-1129, 1983.

Further studies establishing the function and utilities of DHFR are found in John Hopkins OMIM database record ID 126060, and in references numbered 636-653 listed hereinbelow.

Referring now to DLG3 BINDING SITE. Discs large (*Drosophila*) homolog 3 (neuroendocrine-dlg) (DLG3) is a target gene of GAM26, corresponding to GAM26-TARGET GENE of FIG. 26A. DLG3 BINDING SITE is a binding site found in an untranslated region of DLG3, corresponding to BINDING SITE of FIG. 26A. FIG. 26D illustrates the complementarity of the nucleotide sequence of DLG3 BINDING SITE, designated SEQ ID:134695, to the nucleotide sequence of GAM26 RNA of FIG. 26A, designated SEQ ID:20604.

A further function of GAM26 is therefore inhibition of discs, large (*Drosophila*) homolog 3 (neuroendocrine-dlg) (DLG3), a gene which encodes a protein that mediates protein-protein interactions at the cytoplasmic surface of the cell membrane. Accordingly, utilities of GAM26 include diagnosis and treatment of the abovementioned diseases and clinical conditions. The function and utilities of DLG3 have been established by previous studies, as described hereinabove with reference to FIG. 26D.

Referring now to DLG3 BINDING SITE. Discs large (*Drosophila*) homolog 3 (neuroendocrine-dlg) (DLG3) is a target gene of GAM26, corresponding to GAM26-TARGET GENE of FIG. 26A. DLG3 BINDING SITE is a binding site found in an untranslated region of DLG3, corresponding to BINDING SITE of FIG. 26A. FIG. 26D illustrates the complementarity of the nucleotide sequence of DLG3 BINDING SITE, designated SEQ ID:134697, to the nucleotide sequence of GAM26 RNA of FIG. 26A, designated SEQ ID:20604.

Yet a further function of GAM26 is therefore inhibition of discs, large (*Drosophila*) homolog 3 (neuroendocrine-dig) (DLG3), a gene which encodes a protein that mediates protein-protein interactions at the cytoplasmic surface of the cell membrane. Accordingly, utilities of GAM26 include diagnosis and treatment of the abovementioned diseases and clinical conditions. The function and utilities of DLG3 have been established by previous studies, as described hereinabove with reference to FIG. 26D.

Referring now to DR1 BINDING SITE. Down-regulator of transcription 1, TBP-binding (negative cofactor 2) (DR1) is a target gene of GAM26, corresponding to GAM26-TARGET GENE of FIG. 26A. DR1 BINDING SITE is a binding site found in an untranslated region of DR1, corresponding to BINDING SITE of FIG. 26A. FIG. 26D illustrates the complementarity of the nucleotide sequence of DR1 BINDING SITE, designated SEQ ID:138522, to the nucleotide sequence of GAM26 RNA of FIG. 26A, designated SEQ ID:20604.

Another function of GAM26 is therefore inhibition of down-regulator of transcription 1, TBP-binding (negative cofactor 2) (DR1), a gene which encodes a protein that influences functional repression of both activated and basal transcription of class II genes. Accordingly, utilities of GAM26 include diagnosis and treatment of the abovementioned diseases and clinical conditions. The function and utilities of DR1 have been established by previous studies, as described hereinabove with reference to FIG. 26D.

Referring now to DR1 BINDING SITE. Down-regulator of transcription 1, TBP-binding (negative cofactor 2) (DR1) is a target gene of GAM26, corresponding to GAM26-TARGET GENE of FIG. 26A. DR1 BINDING SITE is a binding site found in an untranslated region of DR1, corresponding to BINDING SITE of FIG. 26A. FIG. 26D illustrates the complementarity of the nucleotide sequence of DR1 BINDING SITE, designated SEQ ID:138525, to the nucleotide sequence of GAM26 RNA of FIG. 26A, designated SEQ ID:20604.

Yet another function of GAM26 is therefore inhibition of down-regulator of transcription 1, TBP-binding (negative cofactor 2) (DR1), a gene which encodes a protein that influences functional repression of both activated and basal transcription of class II genes. Accordingly, utilities of GAM26 include diagnosis and treatment of the abovementioned diseases and clinical conditions. The function and utilities of DR1 have been established by previous studies, as described hereinabove with reference to FIG. 26D.

Referring now to DR1 BINDING SITE. Down-regulator of transcription 1, TBP-binding (negative cofactor 2) (DR1) is a target gene of GAM26, corresponding to GAM26-TARGET GENE of FIG. 26A. DR1 BINDING SITE is a binding site found in an untranslated region of DR1, corresponding to BINDING SITE of FIG. 26A. FIG. 26D illustrates the complementarity of the nucleotide sequence of DR1 BINDING SITE, designated SEQ ID:138526, to the nucleotide sequence of GAM26 RNA of FIG. 26A, designated SEQ ID:20604.

An additional function of GAM26 is therefore inhibition of down-regulator of transcription 1, TBP-binding (negative cofactor 2) (DR1), a gene which encodes a protein that influences functional repression of both activated and basal transcription of class II genes. Accordingly, utilities of GAM26 include diagnosis and treatment of the abovementioned diseases and clinical conditions. The function and utilities of DR1 have been established by previous studies, as described hereinabove with reference to FIG. 26D.

Referring now to DR1 BINDING SITE. Down-regulator of transcription 1, TBP-binding (negative cofactor 2) (DR1) is a target gene of GAM26, corresponding to GAM26-TARGET GENE of FIG. 26A. DR1 BINDING SITE is a binding site found in an untranslated region of DR1, corresponding to BINDING SITE of FIG. 26A. FIG. 26D illustrates the complementarity of the nucleotide sequence of DR1 BINDING SITE, designated SEQ ID:138546, to the nucleotide sequence of GAM26 RNA of FIG. 26A, designated SEQ ID:20604.

A further function of GAM26 is therefore inhibition of down-regulator of transcription 1, TBP-binding (negative cofactor 2) (DR1), a gene which encodes a protein that influences functional repression of both activated and basal transcription of class II genes. Accordingly, utilities of GAM26 include diagnosis and treatment of the abovementioned diseases and clinical conditions. The function and utilities of DR1 have been established by previous studies, as described hereinabove with reference to FIG. 26D.

Reference is now made to DSCAM BINDING SITE. Down syndrome cell adhesion molecule (DSCAM is a target gene of GAM26, corresponding to GAM26-TARGET GENE of FIG. 26A. DSCAM BINDING SITE is a binding site found in an untranslated region of DSCAM, corresponding to BINDING SITE of FIG. 26A. FIG. 26D illustrates the complementarity of the nucleotide sequence of DSCAM BINDING SITE, designated SEQ ID: 139794, to the nucleotide sequence of GAM26 RNA of FIG. 26A, designated SEQ ID:20604.

Yet a further function of GAM26 is therefore inhibition of Down syndrome cell adhesion molecule (DSCAM), a gene which encodes a protein that is a cell adhesion molecule that can mediate cation-independent homophilic binding activity. Accordingly, utilities of GAM26 include diagnosis and treatment other abovementioned diseases and clinical conditions.

The function of DSCAM has been established by previous studies. Schmucker et al. (2000) isolated a *Drosophila* homolog of the human DSCAM gene by its affinity to Dock (see DOCK1; 601403), an SH3/SH2 adaptor protein required for axon guidance. Dscam binds directly to both the SH2 and SH3 domains of Dock. Genetic studies revealed that Dscam, Dock, and Pak (see 602590), a serine/threonine kinase, act together to direct pathfinding of Bolwig's nerve, which contains a subclass of sensory axons, to an intermediate target in the embryo. Dscam also is required for the formation of axon pathways in the embryonic central nervous system. cDNA and genomic analyses revealed the existence of multiple forms of Dscam with a conserved architecture containing variable immunoglobulin and transmembrane domains. Alternative splicing can potentially generate more than 38,000 Dscam isoforms in *Drosophila*. The authors suggested that this molecular diversity may contribute to the specificity of neuronal connectivity. Barlow et al. (2001) studied a panel of 19 individuals with partial trisomy 21 (see 190685) and evaluated them using quantitative Southern blot dosage analysis and fluorescence in situ hybridization with subsets of 32 BACs spanning the region defined by D21S16 through the telomere. Fourteen individuals were duplicated for the candidate region, of whom 8 (57%) had the characteristic spectrum of Down syndrome-congenital heart disease (DS-CHD). Combining the results from these 8 individuals suggests that the candidate region for DS-CHD is demarcated by D21S3 (defined by ventricular septal defect), through PFKL (defined by tetralogy of Fallot). Barlow et al. (2001) concluded that the presence of 3 copies of gene(s) from this region is sufficient for the production of subsets of DS-CHD. This region does not include genes located near D21S55, previously proposed as a Down syndrome critical region, or the genes encoding collagens VI (see 120220) and XVIII (120328). Of the potential gene candidates in the narrowed DS-CHD region, DSCAM is notable in that it encodes a cell adhesion molecule, spans more than 840 kb of the candidate region, and is expressed in the heart during cardiac development. Given these properties, Barlow et al. (2001) proposed DSCAM as a candidate for DS-CHD.

Full details of the abovementioned studies are described in the following publications, the disclosure of which are hereby incorporated by reference:

Barlow G. M.; Chen, X. -N.; Shi, Z. Y.; Lyons, G. E.; Kurnit, D. M.; Celle, L.; Spinner, N. B.; Zackai, E.; Pettenati, M. J.; Van Riper, A. J.; Vekemans, M. J.; Mjaatvedt, C. H.; Korenberg, J. R.: Down syndrome congenital heart disease: a narrowed region and a candidate gene. Genet. Med. 3: 91-101, 2001. PubMed ID: 11280955 2. Schmucker, D.; Clemens, J. C.; Shu, H.; Worby, C. A.; Xiao, J.; Muda, M.; Dixon, J. E.; Zipursky, S. L.: *Drosophila* Dscam is an axon guidance receptor exhibiting extraordinary molecular diversity. Cell 101: 671-684, 2000.

Further studies establishing the function and utilities of DSCAM are found in John Hopkins OMIM database record ID 602523, and in references numbered 654-656 listed hereinbelow.

Referring now to DSCAM BINDING SITE. Down syndrome cell adhesion molecule (DSCAM) is target gene of GAM26, corresponding GAM26-TARGET GENE of FIG. 26A. DSCAM BINDING SITE is a binding site found in an untranslated region of DSCAM, corresponding to BINDING SITE of FIG. 26A. FIG. 26D illustrates the complementarity of the nucleotide sequence of DSCAM BINDING SITE, designated SEQ ID:139795, to the nucleotide sequence of GAM26 RNA of FIG. 26A, designated SEQ ID:20604.

Another function of GAM26 is therefore inhibition of Down syndrome cell adhesion molecule (DSCAM), a gene which encodes a protein that is a cell adhesion molecule that can mediate cation-independent homophilic binding activity. Accordingly, utilities of GAM26 include diagnosis and treatment the abovementioned diseases and clinical conditions. The function and utilities of DSCAM have been established by previous studies, as described hereinabove with reference to FIG. 26D.

Referring now to DSCAM BINDING SITE. Down syndrome cell adhesion molecule (DSCAM) is a target gene of GAM26, corresponding to GAM26-TARGET GENE of FIG. 26A. DSCAM BINDING SITE is a binding site found in an untranslated region of DSCAM, corresponding to BINDING SITE of FIG. 26A. FIG. 26D illustrates the complementarity of the nucleotide sequence of DSCAM BINDING SITE, designated SEQ ID:139808, to the nucleotide sequence of GAM26 RNA of FIG. 26A, designated SEQ ID:20604.

Yet another function of GAM26 is therefore inhibition of Down syndrome cell adhesion molecule (DSCAM), a gene which encodes a protein that is a cell adhesion molecule that can mediate cation-independent homophilic binding activity. Accordingly, utilities of GAM26 include diagnosis and treatment of the abovementioned diseases and clinical conditions. The function and utilities of DSCAM have been established by previous studies, as described hereinabove with reference to FIG. 26D.

Reference is now made to DSCR1 BINDING SITE. Down syndrome critical region gene 1 (DSCR1) is a target gene of GAM26, corresponding to GAM26-TARGET GENE of FIG. 26A. DSCR1 BINDING SITE is a binding site found in an untranslated region of DSCR1, corresponding to BINDING SITE of FIG. 26A. FIG. 26D illustrates the complementarity of the nucleotide sequence of DSCR1 BINDING SITE, designated SEQ ID:139913, to the nucleotide sequence of GAM26 RNA of FIG. 26A, designated SEQ ID:20604.

An additional function of GAM26 is therefore inhibition of Down syndrome critical region gene 1 (DSCR1), a gene which encode a protein that inhibits calcineurin-dependent transcriptional responses. Accordingly, utilities of GAM26 include diagnosis and treatment of the abovementioned diseases and clinical conditions.

The function of DSCR1 has been established by previous studies. The study of patients with partial trisomy 21 has defined an area of approximately 3 Mb at chromosomal region 21q22 as the minimal candidate region for the Down syndrome phenotype (190685). Using a novel exon cloning strategy, Fuentes et al. (1995) identified several putative exons from region 21q22.1-q22.2. One exon was used to isolate fetal brain cDNAs corresponding to a gene that the authors designated DSCR1. The predicted 171-amino acid protein contains 2 proline-rich regions, a putative DNA-binding domain, and an acidic region. Northern blot analysis revealed that the 2.2-kb DSCR1 transcript is expressed at the highest levels in fetal brain and adult heart and at lower levels in various other tissues. An addition 2-kb mRNA was detected in fetal and adult liver. Increased expression in the brains of young rats compared with adults suggested to Fuentes et al. (1995) that DSCR1 plays a role during central nervous system development. Fuentes et al. (1997) determined that DSCR1 spans nearly 45 kb and contain 7 exons, 4 of which are alternative first exons. They found tissue-specific express on patterns for the alternative transcripts. Kingsbury and Cunningham (2000) referenced to the proteins encoded by the MCIP genes as calcipressins. Functional analysis showed that when expressed in yeast, DSCR1 and ZAKI4 inhibited calcineurin function. The authors proposed that increased expression of DSCR1 in trisomy-21 individuals may contribute to the neurologic, cardiac, or immunologic defects of Down syndrome.

Full details of the abovementioned studies are described in the following publications, the disclosure of which are hereby incorporated by reference:

Fuentes, J. J.; Pritchard, M. A.; Estivill, X.: Genomic organization, alternative splicing, and expression patterns of the DSCR1 (Down syndrome candidate region 1) gene. Genomics 44: 358-361, 1997. PubMed ID: 9325060 4. Kingsbury, T. J.; Cunningham, K. W.: A conserved family of calcineurin regulators. Genes Dev. 14: 1595-1604, 2000.

Further studies establishing the function and utilities of DSCR1 are found in John Hopkins OMIM database record ID 602917, and in references numbered 657 and 658-662 listed hereinbelow.

Reference is now made to DUSP5 BINDING SITE. Dual specificity phosphatase 5 (DUSP5) is a target gene of GAM26, corresponding to GAM26-TARGET GENE of FIG. 26A. DUSP5 BINDING SITE is a binding site found in an untranslated region of DUSP5, corresponding to BINDING SITE of FIG. 26A. FIG. 26D illustrates the complementarity of the nucleotide sequence of DUSP5 BINDING SITE, designated SEQ ID:141448, to the nucleotide sequence of GAM26 RNA of FIG. 26A, designated SEQ ID:20604.

A further function of GAM26 is therefore inhibition of dual specificity phosphatase 5 (DUSP5), a gene which encodes a protein that displays phosphatase activity toward several substrates. Accordingly, utilities of GAM26 include diagnosis and treatment of the abovementioned diseases and clinical conditions.

The function of DUSP5 has been established by previous studies. The VH1 phosphatase encoded by vaccinia virus is a dual-specificity protein-tyrosine phosphatase (PTPase) which hydrolyzes substrates phosphorylated on both tyrosine and serine/threonine residues VH1-like PTPases have been identified in humans and other organisms. See DUSP1 (500714). To identify additional human dual-specificity PTPases, Martell et al. (1994) screened a genomic library with a partial DUSP1 cDNA. They isolated several novel PTPase genes, including 1 which they designated HVH3 for human VH1-like PTPase-3. Kwak and Dixon (1995) cloned human placental HVH3 cDNAs and reported that the predicted protein has 384 amino acids. Using immunofluorescence, they determined that epitope-tagged HVH3 is localized primarily in the nucleus of mammalian cells. Ishibashi et al. (1994) isolated HVH3 cDNAs from a human mammary epithelial cell cDNA library and found that the predicted protein has 397 amino acids. In vitro, recombinant protein containing the catalytic domain of HVH3 displayed phosphatase activity toward several substrates. The highest relative activity was toward ERK1 (601795), suggesting that it may be a target for HVH3 activity in vivo. Northern blot analysis revealed that HVH3 is expressed as a 2.5-kb mRNA in a variety of tissues, with the highest levels in pancreas and brain. HVH3 expression was induced by serum stimulation of fibroblasts and by heat shock, with similar kinetics to those observed with DUSP1. As has been proposed for other dual-specificity PTPases like DUSP1 and DUSP2 (603068), Ishibashi et al. (1994) suggested that the induction of HVH3 may lead to the deactivation of mitogen- or stress-activated protein kinases, hereby restoring these signaling pathways to their mitogen- or stress-sensitive state. By fluorescence in situ hybridization, Martell et al. (1994) mapped the HVH3 gene to 10q25

Full details of the abovementioned studies are described in the following publications, the disclosure of which are hereby incorporated by reference:

Ishibashi, T.; Bottaro, D. P.; Michieli, P.; Kelley, C. A.; Aaronson, S. A.: A novel dual specificity phosphatase induced by serum stimulation and heat shock. J. Biol. Chem. 269: 29897-29902, 1994. PubMed ID: 7961985 3. Martell, K. J.; Kwak, S.; Hakes, D. J.; Dixon, J. E.; Trent, J. M.: Chromosomal localization of four human VH1-like protein-tyrosine phosphatases. Genomics 22: 462-464, 1994.

Further studies establishing the function and utilities of DUSP5 are found in John Hopkins OMIM database record ID 603069, and in references numbered 663-665 listed hereinbelow.

Reference is now made to DVL3 BINDING SITE. Dishevelled 3 (homologous to *Drosophila* dsh) (DVL3) is a target gene of GAM26, corresponding to GAM26-TARGET GENE of FIG. 26A. DVL3 BINDING SITE is a binding site found in an untranslated region of DVL3, corresponding to BINDING SITE of FIG. 26A. FIG. 26D illustrates the complementarity of the nucleotide sequence of DVL3 BINDING SITE, designated SEQ ID:141937, to the nucleotide sequence of GAM26 RNA of FIG. 26A, designated SEQ ID:20604.

Yet a further function of GAM26 is therefore inhibition of dishevelled 3 (homologous to *Drosophila* dsh) (DVL3), a gene which encodes a protein that regulates cell proliferation. Accordingly, utilities of GAM26 include diagnosis and treatment of the abovementioned diseases and clinical conditions.

The function of DVL3 has been established by previous studies. The *Drosophila* dishevelled gene (dsh) encodes a cytoplasmic phosphoprotein (Klingensmith et al., 1994) that regulates cell proliferation, acting as a transducer molecule for developmental processes, including segmentation and neuroblast specification. Pizzuti et al. (1996) noted that dsh is required for the function of the wingless gene product wg, a segment polarity gene homologous to the mammalian protooncogene WNT1 (164820). Pizzuti et al. (1996) reported the isolation and chromosomal mapping of 2 human dsh homologs, designated DVL1 (601365) and DVL3 by them. The human dsh homologs were isolated from a fetal brain cDNA library. DVL3 encodes a predicted 716-amino acid polypeptide that shows 74% nucleotide homology with human DVL1 and 71% homology with the mouse Dvl1 gene. DVL1 and DVL3 share 64% amino acid identity. Pizzuti et al. (1996) reported that homology is particularly high in the N-terminal region and that there is more divergence in the C-terminal regions. PCR carried out using DNA from rodent human somatic cell hybrids and DVL3 specific primers led to the assignment of DVL3 to human chromosome 3. Pizzuti et al. (1996) regionally assigned DVL3 to band 3q27 using fluorescence in situ hybridization. Hybridization of poly(A) mRNA with the DVL3 cDNA revealed a 2.9-kb transcript with abundant expression in skeletal muscle, pancreas and heart. They also detected 5.9-kb and 5.0-kb transcripts in skeletal muscle, adult liver, adult heart, pancreas, and placenta. The 5.9-kb form was abundant in fetal tissues but the 5.0 kb form was absent from these tissues. Pizzuti et al. (1996) noted that Charcot-Marie-Tooth type 2B (600882) maps to chromosome 3q. Bui et al. (1997) also isolated human DVL3, which shares 98% amino acid identity with mouse Dvl3 and 49% with *Drosophila* dsh. The authors confirmed the chromosomal localization at 3p27. Semenov and Snyder (1997) isolated 3 human genes encoding proteins homologous to *Drosophila* dsh. The cDNA sequence of DVL3 reported by Semenov and Snyder (1997) differs from the previously reported sequences deposited in GenBank. Bui et al. (1997) detected expression of DVL3 mRNA in B cells, breast, kidney, bladder, endometrium, and 2 primary endometrial cultures. It was detected equally in normal human breast tissues and tumors and in colorectal samples of normal tissues, polyps, and tumors.

Full details of the abovementioned studies are described in the following publications, the disclosure of which are hereby incorporated by reference:

Pizzuti, A.; Amati, F.; Calabrese, G.; Mari, A.; Colosimo, A.; Silani, V.; Giardino, L.; Ratti, A.; Penso, D.; Calza, L.; Palka, G.; Scarlato, G.; Novelli, G.; Dallapicolla, B.: cDNA characterization and chromosomal mapping of two human homologs of the *Drosophila* dishevelled polarity gene. Hum. Molec. Genet. 5: 953-958, 1996. PubMed ID: 8817329 4. Semenov, M. V.; Snyder, M.: Human dishevelled genes constitute a DHR-containing multigene family. Genomics 42: 302-310, 1997.

Further studies establishing the function and utilities of DVL3 are found in John Hopkins OMIM database record ID 601368, and in references numbered 666-669 listed hereinbelow.

Reference is now made to DXYS155E BINDING SITE. (DXYS155E) is a target gene of GAM26, corresponding to GAM26-TARGET GENE of FIG. 26A. DXYS155E BINDING SITE is a binding site found in an untranslated region of DXYS155E, corresponding to BINDING SITE of FIG. 26A. FIG. 26D illustrates the complementarity of the nucleotide sequence of DXYS155E BINDING SITE, designated SEQ ID:142341, to the nucleotide sequence of GAM26 RNA of FIG. 26A, designated SEQ ID:20604.

Another function of GAM26 is therefore inhibition of (DXYS155E), a gene which encodes a protein that may be involved in b-cell activation, may also be involved in sign al transduction and gene regulation. Accordingly, utilities of GAM26 include diagnosis and treatment of the abovementioned diseases and clinical conditions.

The function of DXYS155E has been established by previous studies. In the 2.6-megabase segment of the distal short arms of the X and Y chromosomes, called the pseudoautosomal region, Ellison et al. (1992) identified an expressed gene designated XE7. (See also 465000.) They reported the structure of the XE7 gene and its expression in various human tissues. The analysis of genomic and cDNA clones showed that alternative RNA splicing results in the production of 2 protein isoforms, one containing 385 amino acids and the other containing 695 residues. The smaller polypeptide is a truncated version of the larger and results from the inclusion of a cassette exon that has an in-frame stop codon. The XE7 gene appears to be ubiquitously expressed, and the production of both protein isoforms was predicted in each of the several tissues examined.

Full details of the abovementioned studies are described in the following publications, the disclosure of which are hereby incorporated by reference:

Ellison, J.; Passage, M.; Yu, L. -C.; Yen, P.; Mohandas, T. K.; Shapiro, L.: Directed isolation of human genes that escape X inactivation. Somat. Cell Molec. Genet 18: 259-268, 1992. PubMed ID: 1496421 2. Ellison, J. W.; Ramos, C.; Yen, P. H.; Shapiro, L. J.: Structure and expression of the human pseudoautosomal gene XE7. Hum. Molec. Genet 1: 691-696, 1992.

Further studies establishing the function and utilities of DXYS155E are found in John Hopkins OMIM database record ID 312095, and in references numbered 670-671 listed hereinbelow.

Reference is, now made to DYRK2 BINDING SITE. Dual-specificity tyrosine-(Y)-phosphorylation regulated kinase 2 (DYRK2) is a target gene of GAM26, corresponding to GAM26-TARGET GENE of FIG. 26A. DYRK2 BINDING SITE is a binding site found in an untranslated region of DYRK2, corresponding to BINDING SITE of FIG. 26A. FIG. 26D illustrates the complementarity of the nucleotide sequence of DYRK2 BINDING SITE, designated SEQ ID:142933, to the nucleotide sequence of GAM26 RNA of FIG. 26A, designated SEQ ID:20604.

Yet another function of GAM26 is therefore inhibition of dual-specificity tyrosine (Y)-phosphorylation regulated kinase 2 (DYRK2), a gene which encodes a protein that can phosphorylate histones h3 and h2b on ser and thr residues. Accordingly, utilities of GAM26 include diagnosis and treatment of the abovementioned diseases and clinical conditions.

The function of DYRK2 has been established by previous studies. DYRK1 (600855) is a dual-specificity protein kinase that catalyzes its autophosphorylation on serine/threonine and tyrosine residues and is presumably involved in brain development. By PCR using sequences conserved between DYRK1 and the related proteins MNB of *Drosophila* and Yak1 of *S. cerevisiae*, Becker et al. (1998) identified DYRK2 and DYRK3 (603497), kinases related to DYRK1. Human fetal brain DYRK2 (GenBank Y13493) cDNAs encode 2 isoforms: a deduced 528-amino acid protein and a protein containing 73 additional amino acids at the N terminus. The DYRK2 proteins contain a canonical kinase domain located between a large N-terminal re ion and a short C-terminal extension, and features specific to DYRK-related kinases DYRK2 shares 46% identity with DYRK1 in the catalytic domain, but lacks the striking sequence motifs identified in DYRK1. The DYRK2 and DYRK3 proteins are related over their entire sequences except for the N-terminal region. Northern blot analysis of rat tissues detected Dyrk2 expression in testis, only after the onset of spermatogenesis. Recombinant DYRK2 was found predominantly in the cytoplasm of transfected mammalian cells. DYRK2 expressed in *E. coli* demonstrated tyrosine autophosphorylation and catalyzed phosphorylation of histones H3 and H2B in vitro. Based on sequence similarity to EST Z25301, Becker et al. (1998) tentatively mapped the DYRK2 gene to chromosome 12.

Full details of the abovementioned studies are described in the following publications, the disclosure of which are hereby incorporated by reference:

Becker, W.; Weber, Y.; Wetzel, K.; Eirmbter, K.; Tejedor, F. J.; Joost, H. G.: Sequence characteristics, subcellular localization, and substrate specificity of DYRK-related kinases, a novel family of dual specificity protein kinases J. Biol. Chem. 273: 25893-25902, 1998.

Further studies establishing the function and utilities of DYRK2 are found in John Hopkins OMIM database record ID 603496, and in references numbered 672 listed hereinbelow.

Referring now to DYRK2 BINDING SITE. Dual-specificity tyrosine-(Y)-phosphorylation regulated kinase 2 (DYRK2) is a target gene of GAM26, corresponding to GAM2-TARGET GENE of FIG. 26A. DYRK2 BINDING SITE is a binding site found in an untranslated region of DYRK2, corresponding to BINDING SITE of FIG. 26A. FIG. 26D illustrates the complementarity of the nucleotide sequence of DYRK2 BINDING SITE, designated SEQ ID:142953, to the nucleotide sequence of GAM26 RNA of FIG. 26A, designated SEQ ID:20604.

An additional function of GAM26 is therefore inhibition of dual-specificity tyrosine-(Y)-phosphorylation regulated kinase 2 (DYRK2), a gene which encodes a protein that can phosphorylate histones h3 and h2b on ser and thr residues. Accordingly, utilities of GAM26 include diagnosis and treatment of the abovementioned diseases and clinical conditions. The function and utilities of DYRK2 have been established by previous studies, as described hereinabove with reference to FIG. 26D.

Reference is now made to EFNA3 BINDING SITE. Ephrin-A3 (EFNA3) is a target gene of GAM26, corresponding to GAM26-TARGET GENE of FIG. 26A. EFNA3 BINDING SITE is a binding site found in an untranslated region of EFNA3, corresponding to BINDING SITE of FIG. 26A. FIG. 26D illustrates the complementarity of the nucleotide sequence of EFNA3 BINDING SITE, designated SEQ ID:144685, to the nucleotide sequence of GAM26 RNA of FIG. 26A, designated SEQ ID:20604.

A further function of GAM26 is therefore inhibition of ephrin-A3 (EFNA3), a gene which encodes a protein that is a ligand of Eph-related receptor tyrosine kinases. Accordingly, utilities of GAM26 include diagnosis and treatment of the abovementioned diseases and clinical conditions.

The function of EFNA3 has been established by previous studies. Proteins in the LERK subfamily of ligands, called ephrins, bind to members of the EPH group of receptor tyrosine kinases. The various ephrins are characterized by sequence similarities and the fact that they are attached to the cell membrane by glycosylphosphatidylinositol (GPI) anchors or by a single transmembrane domain. See 179610 for additional information on ephrins and the Eph receptor family. By fluorescence in situ hybridization, Cerretti et al. (1996) mapped the EPLG3 gene to a cluster on chromosome 1q21-q22, together with EPLG1 (EFNA1; 191164) and EPLG4 (EFNA4; 601380). By interspecific backcross analysis, they mapped the mouse EPLG3 homolog (Epl3: to the central region of mouse chromosome 3. Cerretti and Nelson (1998) reported that the mouse Efna3 gene has 5 exons. The gene structures of human EFNA2 (602756) and mouse Efna3, Efna4 (601380), and Efnb1 (300035) are conserved through the first 3 exons.

Full details of the abovementioned studies are described in the following publications, the disclosure of which are hereby incorporated by reference:

Cerretti, D. P.; Lyman, S. D.; Kozlosky, C. J.; Copeland, N. G.; Gilbert, D. J.; Jenkins, N. A.; Valentine, V.; Kirstein, M. N.; Shapiro, D. N.; Morris, S. W.: The genes encoding the Eph-related receptor tyrosine kinase ligands LERK-1 (EPLG1, Epl1), LERK-3 (EPLG3, Epl3, and LERK-4 (EPLG4, Epl4) are clustered on human chromosome 1 and mouse chromosome 3. Genomics 33: 277-282, 1996. PubMed ID: 8660976 2. Cerretti D. P.; Nelson, N.: Characterization of the genes for mouse LERK-3/Ephrin-A3 (Epl3), mouse LERK-4Ephrin-A4 (Epl4), and human LERK-6/Ephrin-A2 (EPLG6): conservation of intron/exon structure. Genomics 47: 131-135, 1998.

Further studies establishing the function and utilities of EFNA3 are found in John Hopkins OMIM database record ID 601381, and in references numbered 673-674 listed hereinbelow.

Referring now to EFNA3 BINDING SITE. Ephrin-A3 (EFNA3) is a target gene of GAM26, corresponding to GAM26-TARGET GENE of FIG. 26A. EFNA3 BINDING SITE is a binding site found in an untranslated region of EFNA3, corresponding to BINDING SITE of FIG. 26A. FIG. 26D illustrates the complementarity of the nucleotide sequence of EFNA3 BINDING SITE, designated SEQ ID:144687, to the nucleotide sequence of GAM26 RNA of FIG. 26A, designated SEQ ID:20604.

Yet a further function of GAM26 is therefore inhibition of ephrin-A3 (EFNA3), a gene which encodes a protein that is a ligand of Eph-related receptor tyrosine kinases. Accordingly, utilities of GAM26 include diagnosis and treatment of the abovementioned diseases and clinical conditions. The function and utilities of EFNA3 have been established by previous studies, as described hereinabove with reference to FIG. 26D.

Reference is now made to EGLN1 BINDING SITE. egl nine homolog 1 (*C. elegans*) (EGLN1) is a target gene of GAM26, corresponding to GAM26-TARGET GENE of FIG. 26A. EGLN1 BINDING SITE is a binding site found in an untranslated region of EGLN1, corresponding to BINDING SITE of FIG. 26A. FIG. 26D illustrates the complementarity of the nucleotide sequence of EGLN1 BINDING SITE, designated SEQ ID:145984, to the nucleotide sequence of GAM26 RNA of FIG. 26A, designated SEQ ID:20604.

Another function of GAM26 is therefore inhibition of egl nine homolog 1 (*C. elegans*) (EGLN1), a gene which encodes a protein that is expressed in the cytoplasm of arterial smooth muscle cells. Accordingly, utilities of GAM26 include diagnosis and treatment of the abovementioned diseases and clinical conditions.

The function of EGLN1 has been established by previous studies. HIF is a transcriptional complex that plays a central role in mammalian oxygen homeostasis. Posttranslational modification by prolyl hydroxylation is a key regulatory event that targets HIF-alpha (HIF1; 603348) subunits for proteasomal destruction via the von Hippel-Lindau (VHL; 193300) ubiquitylation complex. Epstein et al. (2001) defined a conserved HIF-VHL-prolyl hydroxylase pathway in *C. elegans* and identified Egl9 as a dioxygenase that regulates HIF by prolyl hydroxylation. In mammalian cells, they showed that the HIF-prolyl hydroxylases are represented by 3 proteins with a conserved 2-histidine-1-carboxylate iron coordination motif at the catalytic site. The genes encoding these proteins were cloned and termed PHD1 (606424), PHD2, and PHD3 (606426) by the authors. Direct modulation of recombinant enzyme activity by graded hypoxia, iron chelation, and cobaltous ions mirrored the characteristics of HIF induction in vivo, fulfilling requirements for these enzymes being oxygen sensors that regulate HIF. In cultured mammalian cells, Bruick and McKnight (2001) found that the inappropriate accumulation of HIF caused by forced expression of the HIF1-alpha (603348) subunit under normoxic conditions was attenuated by coexpression of HPH. Suppression of HPH in cultured *Drosophila melanogaster* cells by RNA interference resulted in elevated expression of the hypoxia inducible gene LDH (see 150000) under normoxic conditions. Bruick and McKnight (2001) concluded that HPH is an essential component of the pathway through which cells sense oxygen.

Full details of the abovementioned studies are described in the following publications, the disclosure of which are hereby incorporated by reference:

Bruick, R. K.; McKnight, S. L.: A conserved family of prolyl-4-hydroxylases that modify HIF. Science 294: 1337-1340, 2001. PubMed ID: 11598268 3. Epstein, A. C. R.; Gleadle J. M.; McNeill, L. A.; Hewitson, K. S.; O'Rourke, J.; Mole, D. R.; Mukherji, M.; Metzen E.; Wilson, M. I.; Dhanda, A.; Tian, Y. -M.; Masson, N.; Hamilton, D. L.; Jaakkola, P.; Barstead, R.; Hodgkin, J.; Maxwell, P. H.; Pugh, C. W.; Schofield, C. J.; Ratcliffe, P. J.: *C. elegans* EGL-9 and mammalian homologs define a family of dioxygenases that regulate HIF by prolyl hydroxylation. Cell 107: 43-54, 2001.

Further studies establishing the function and utilities, EGLN1 are found in John Hopkins OMIM database record ID 606425, and in referent numbered 675-677 listed hereinbelow.

Reference is now made to EGR3 BINDING SITE. early growth response 3 (EGR3) is a target gene of GAM26, corresponding to GAM26-TARGET GENE of FIG. 26A. EGR3 BINDING SITE is a binding site found in an untranslated region of EGR3, corresponding to BINDING SITE of FIG. 26A. FIG. 26D illustrates the complementarity of the nucleotide sequence of EGR3 BINDING SITE, designated SEQ ID:146843, to the nucleotide sequence of GAM26 RNA of FIG. 26A, designated SEQ ID:20604.

Yet another function of GAM26 is therefore inhibition of early growth response 3 (EGR3) a gene which encodes a protein that is a putative transcription factor. Accordingly, utilities of GAM26 include diagnosis and treatment of the abovementioned diseases and clinical conditions.

The function of EGR3 has been established by previous studies. The human EGR3 gene was described by Patwardhan et al. (1991) as predicting a 387-amino acid protein containing 3 C2H2 zinc fingers nearly identical to those of EGR1 and EGR2. The EGR3 gene has a single intron. The gene was known to be induced in various brain regions in response to stress or following focal brain injury. Morris et al. (1998) stated that, in the SCN, it probably participates in the transcriptional regulation of genes in response to retinal input, as had been proposed for FOS. Muscle spindles are skeletal muscle sensory organs that provide axial and limb position information (proprioception) to the central nervous system. Spindles consist of encapsulated muscle fibers (intrafusal fibers) that are innervated by specialized motor and sensory axons. Tourtellotte and Milbrandt (1998) found that mice rendered deficient in Egr3 by gene targeting had gait ataxia, increased frequency of perinatal mortality, scoliosis, resting tremors, and ptosis. Although extrafusal skeletal muscle fibers appeared normal, Egr3-deficient animals lacked muscle spindles, a finding that is consistent with their profound gait ataxia. Egr3 was highly expressed in developing muscle spindles, but not in IIa afferent neurons or their terminals during developmental periods that coincided with the induction of spindle morphogenesis by sensory afferent axons. These results indicated that type I myotubes are dependent upon Egr3-mediated transcription for proper spindle development.

Full details of the abovementioned studies are described in the following publications, the disclosure of which are hereby incorporated by reference:

Morris M. E.; Viswanathan, N.; Kuhlman, S.; Davis, F. C.; Weitz, C. J.: A screen for genes induced in the suprachiasmatic nucleus by light. Science 279: 1544-1547, 1998. PubMed ID:9488654 3. Tourtellotte, W. G.; Milbrandt, J.: Sensory ataxia and muscle spindle agenesis in mice lacking the transcription factor Egr3. Nature Genet. 20: 87-91, 1998.

Further studies establishing the function and utilities of EGR3 are found in John Hopkins OMIM database record ID 602419, and in referent numbered 678-680 listed hereinbelow.

Referring now to EGR3 BINDING SITE. Early growth response 3 (EGR3) is a target gene of GAM26, corresponding to GAM26-TARGET GENE of FIG. 26A. EGR3 BINDING SITE is a binding site found in an untranslated region of EGR3, corresponding to BINDING SITE of FIG. 26A. FIG. 26 illustrates the complementarity of the nucleotide sequence of EGR3 BINDING SITE, designated SEQ ID:146845, to the nucleotide sequence of GAM26 RNA of FIG. 26A, designated SEQ ID:20604.

An additional function of GAM26 is therefore inhibition of early growth response 3 (EGR3), a genie which encodes a protein that is a putative transcription factor. Accordingly, utilities of GAM26 include diagnosis and treatment of the abovementioned diseases and clinical conditions. The function and utilities of EGR3 have been established by previous studies, as described hereinabove with reference to FIG. 26D.

Referring now to EGR3 BINDING SITE. Early growth response 3 (EGR3) is a target gene of GAM26, corresponding to GAM26-TARGET GENE of FIG. 26A. EGR3 BINDING SITE is a binding site found in an untranslated region of EGR3, corresponding to BINDING SITE of FIG. 26A. FIG. 26D illustrates the complementarity of the nucleotide sequence of EGR3 BINDING SITE, designated SEQ ID:146876, to the nucleotide sequence of GAM26 RNA of FIG. 26A, designated SEQ ID:20604.

A further function of GAM26 is therefore inhibition of early growth response 3 (EGR3), a gene which encodes a protein that is a putative transcription factor. Accordingly, utilities of GAM26 include diagnosis and treatment of the abovementioned diseases and clinical conditions. The function and utilities of EGR3 have been established by previous studies, as described hereinabove with reference to FIG. 26D.

Referring now to EGR3 BINDING SITE. Early growth response 3 (EGR3) is a target gene of GAM26, corresponding to GAM26-TARGET GENE of FIG. 26A, EGR3 BINDING SITE is a binding site found in an untranslated region of EGR3, corresponding to BINDING SITE of FIG. 26A. FIG. 26D illustrates the complementarity of the nucleotide sequence of EGR3 BINDING SITE, designated SEQ ID:146919, to the nucleotide sequence of GAM26 RNA of FIG. 26A, designated SEQ ID:20604.

Yet a further function of GAM26 is therefore inhibition of early growth response 3 (EGR3), a gene which encodes a protein that is a putative transcription factor. Accordingly, utilities of GAM26 include diagnosis and treatment of the abovementioned diseases and clinical conditions. The function and utilities of EGR3 have been established by previous studies, as described hereinabove with reference to FIG. 26D.

Reference is now made to EIF2C1 BINDING SITE. Eukaryotic translation initiation factor 2C, 1 (EIF2C1) is a target gene of GAM26, corresponding to GAM26-TARGET GENE of FIG. 26A. EIF2C1 BINDING SITE is a binding site found in an untranslated region of EIF2C1, corresponding to BINDING SITE of FIG. 26A. FIG. 26D illustrates the complementarity of the nucleotide sequence of EIF2C1 BINDING SITE, designated SEQ ID:148159, to the nucleotide sequence of GAM26 RNA of FIG. 26A, designated SEQ ID:20604.

Another function of GAM26 is therefore inhibition of eukaryotic translation initiation factor 2C, 1 (EIF2C1), a gene which encode a protein that plays an important role in the eukaryotic peptide chain initiation process. Accordingly, utilities of GAM26 include diagnosis and treatment of the abovementioned diseases and clinical conditions.

The function of EIF2C1 has been established by previous studies. Koesters et al. (1999) isolated an EIF2C1 cDNA from a human fetal kidney cDNA library. To obtain genomic sequence information, they isolated a P1 genomic clone containing the EIF2C1 locus. The human EIF2C1 gene encodes a protein of 857 amino acids. The 2,571-bp open reading frame is flanked by 238 bp of 5-prime sequence and an extremely large 3-prime untranslated region with multiple short repeated segments composed of mono-, tri-, or quatronucleotides interspersed throughout. Northern blot analysis demonstrated that the human EIF2C1 gene is ubiquitously expressed at low to medium levels. Differential polyadenylation and splicing resulted in a complex transcriptional pattern. Martinez et al. (2002) demonstrated that a single-stranded small interfering RNA (siRNA) resides in the human RNA-induced silencing complex (RISC) together with the EIF2C1 and/or EIF2C2 (606229) proteins. RISC could be rapidly formed in HeLa cell cytoplasmic extract supplemented with 21-nucleotide siRNA duplexes, but also by adding single-stranded antisense RNAs, which range in size between 19 and 29 nucleotides.

Full details of the abovementioned studies are described in the following publications, the disclosure of which are hereby incorporated by reference:

Koesters, R.; Adams, V.; Betts, D.; Moos, R.; Schmid, M.; Siermann, A.; Hassam, S.; Weitz, S.; Lichter, P.; Heitz, P. U.; von Knebel Doeberitz, M.; Briner, J.: Human eukaryotic initiation factor EIF2C1 gene: cDNA sequence, genomic organization, localization to chromosomal bands 1q34p35, and expression. Genomics 61: 210-218, 1999. PubMed ID: 105344062. Martinez, J.; Patkaniowska, A.; Urlaub, H.; Luhrmann, R.; Tuschi, T.: Single-stranded antisense siRNAs guide target RNA cleavage in RNAi. Cell 110: 563-574, 2002.

Further studies establishing the function and utilities of EIF2C1 are found in John Hopkins OMIM database record ID 606228, and in references numbered 681-682 listed hereinbelow.

Reference is now made to EIF4G1 BINDING SITE. Eukaryotic translation initiation fact or 4 gamma, 1 (EIF4G1) is a target gene of GAM26, corresponding to GAM26-TARGET GENE of FIG. 26A. EIF4G1 BINDING SITE is a binding site found in an untranslated region of EIF4G1, corresponding to BINDING SITE of FIG. 26A. FIG. 26D illustrates the complementarity of the nucleotide sequence of EIF4G1 BINDING SITE, designated SEQ ID:148798, to the nucleotide sequence of GAM26 RNA of FIG. 26A, designated SEQ ID:20604.

Yet another function of GAM26 is therefore inhibition of eukaryotic translation initiation factor 4 gamma, 1 (EIF4G1), a gene which encodes a protein that is a Translation initiation factor. Accordingly, utilities of GAM26 include diagnosis and treatment of the above mentioned diseases and clinical conditions.

The function of EIF4G1 has been established by previous studies. Gradi et al. (1998) identified a second human eIF4G gene. They designated the original gene eIF4GI and the novel gene eIF4GII (EIF4G3; 603929). Imataka et al. (1998) found that the human eIF4GI protein contains an additional 156 N-terminal amino acids compared to the sequence published by Yan et al. (1992). They demonstrated that this N-terminal region binds poly(A)-binding protein (PABP; 604679). In an in vitro translation system, an N-terminal fragment of eIF4GI that included the PABP-binding site inhibited poly(A)-dependent translation, but had no effect on translation of a deadenylated mRNA. Imataka et al. (1998) concluded that eIF4G probably functions in poly(A)-dependent translation in mammalian cells. By screening a rabbit brain library with oligonucleotide probes based on the sequence of rabbit eIF4-gamma peptides, Yan et al. (1992) identified partial eIF4-gamma cDNAs. They used the rabbit cDNAs as probes and isolated human brain cDNAs encoding eIF4-gamma. The predicted human protein contains 1,396 amino acids. Western blot analysis of poliovirus-infected Hela cell extracts revealed that eIF4-gamma has an apparent molecular weight of 200 to 220 kD and is cleaved by this picornavirus. Imataka and Sonenberg (1997) stated that the N-terminal region of eIF4G contains a binding site for eIF4E. They demonstrated that the central third of eIF4G contains an eIF3 (see 602039)-binding region and an eIF4A-binding domain. A second, separate eIF4A-binding site is present in the C-terminal third. Neither eIF4A-binding domain alone activates translation. In contrast to eIF4G, the eIF4G-related translation regulator p97 (602325) binds eIF4A only through its N-terminal domain, which is homologous to the central domain of eIF4G Full details of the abovementioned studies are described in the following publications, the disclosure of which are hereby incorporated by reference:

Imataka, H.; Gradi, A.; Sonenberg, N.: A newly identified N-terminal amino acid sequence of human eIF4G binds poly(A)-binding protein and functions in poly(A)-dependent translation. EMBO J. 17: 7480-7489, 1998. PubMed ID: 9857202 4. Imataka, H.; Sonenberg, N.: Human eukaryotic translation initiation factor 4G (eIF4G) possesses two separate and independent binding sites for eIF4A. Molec. Cell. Biol. 17: 6940-6947, 1997.

Further studies establishing the function and utilities of EIF4G1 are found in John Hopkins OMIM database record ID 600495, and in references numbered 683-690 listed hereinbelow.

Referring now to EIF4G1 BINDING SITE. Eukaryotic translation initiation factor 4 gamma, 1 (EIF4G1) is a target gene of GAM26, corresponding to GAM26-TARGET GENE of FIG. 26A. EIF4G1 BINDING SITE is a binding site found in an untranslated region of EIF4G1, corresponding to BINDING SITE of FIG. 26A. FIG. 26D illustrates the complementarity of the nucleotide sequence of EIF4G1 BINDING SITE, designated SEQ ID:148812, to the nucleotide sequence of GAM26 RNA of FIG. 26, designated SEQ ID:20604.

An additional function of GAM26 is therefore inhibition of eukaryotic translation initiation factor 4 gamma, 1

(EIF4G1), a gene which encodes a protein that is a Translation initiation factor. Accordingly, utilities of GAM26 include diagnosis and treatment of the abovementioned diseases and clinical conditions. The function and utilities of EIF4G1 have been established by previous studies, as described hereinabove with reference to FIG. 26D.

Reference is now made to EIF4G2 BINDING SITE. Eukaryotic translation initiation factor 4 gamma, 2 (EIF4G2) is a target gene of GAM26, corresponding to GAM26-TARGET GENE of FIG. 26A. EIF4G2 BINDING SITE is a binding site found in an untranslated region of EIF4G2, corresponding to BINDING SITE of FIG. 26A. FIG. 26D illustrates the complementarity of the nucleotide sequence of EIF4G2 BINDING SITE, designated SEQ ID:148906, to the nucleotide sequence of GAM26 RNA of FIG. 26A, designated SEQ ID:20604.

A further function of GAM26 is therefore inhibition of eukaryotic translation initiation factor 4 gamma, 2 (EIF4G2), a gene which encodes a protein that is a repressor of translation. Accordingly, utilities of GAM26 include diagnosis and treatment of the abovementioned diseases and clinical conditions.

The function of EIF4G2 has been established by previous studies. Imataka et al. (1997) used immunoprecipitation studies with HA- or FLAG-tagged proteins to show that p97 specifically binds to EIF4A and EIF3, but not to EIF4E (133440) in vitro. Transient transfection experiments showed that p97 suppressed both cap-dependent and independent translation, and that overexpression of p97 reduced overall protein synthesis. Imataka et al. (1997) suggested that p97 is a general repressor of translation that acts by forming translationally inactive complexes. Levy-Strumpf et al. (1997) showed that while a fragment of DAP5 cDNA from the C-terminal region (encoding a 28-kD 'miniprotein') protected cells from IFNG-induced programmed cell death at low levels of expression, higher levels of express ion were toxic. They proposed that the miniprotein may be a dominant-negative inhibitor of the essential DAP5 protein, and that DAP5 may play a specific role in apoptosis.

Full details of the abovementioned studies are described in the following publications, the disclosure of which are hereby incorporated by reference:

Imataka, H.; Olsen, H. S.; Sonenberg, N.: A new translational regulator with homology to eukaryotic translation initiation factor 4G. EMBO J. 16: 817-825, 1997. PubMed ID: 9049310 2. Levy-Strumpf, N.; Deiss, L. P.; Berissi, H.; Kimchi, A.: DAP-5, a novel homolog of eukaryotic translation initiation factor 4G isolated as a putative modulator of gamma interferon-induced programmed cell death. Molec. Cell. Biol. 17: 1615-1625, 1997.

Further studies establishing the function and utilities of EIF4G2 are found in John Hopkins OMIM database record ID 602325, and in references numbered 691-692, 688 and 693-694 listed hereinbelow.

Reference is now made to EIF5A BINDING SITE. Eukaryotic translation initiation factor 5A (EIF5A) is a target gene of GAM26, corresponding to GAM26-TARGET GENE of FIG. 26A. EIF5A BINDING SITE is a binding site found in an untranslated region of EIF5A, corresponding to BINDING SITE of FIG. 26A. FIG. 26D illustrates the complementarity of the nucleotide sequence of EIF5A BINDING SITE, designated SEQ ID:148944, to the nucleotide sequence of GAM26 RNA of FIG. 26A, designated SEQ ID:20604.

Yet a further function of GAM26 is therefore inhibition of eukaryotic translation initiation factor 5A (EIF5A), a gene which encodes a protein that is an initiation factor. Accordingly, utilities of GAM26 include diagnosis and treatment of the abovementioned diseases and clinical conditions.

The function of EIF5A has been established by previous studies. The eukaryotic initiation factor 5A is an 18-kD protein composed of 154 amino acids. It contains a unique amino acid residue, hypusine, which is formed posttranslationally via the transfer and hydroxylation of the butylamino-group from the polyamine spermidine to a lys50 within the EIF5A protein. Koettnitz et al. (1994) isolated and characterized the human EIF5A pseudogene. Subsequently, Koettnitz et al. (1995) identified a genomic clone with an EIF5A containing 3 introns and spanning about 4.8 kb. The authors showed that this sequence would successfully complement yeast carrying the HYP2 mutation (the homolog of EIF5A), whereas the pseudogenes could not. Steinkasserer et al. (1995) mapped the EIF5A gene to 17p13-p12 by fluorescence in situ hybridization. Three pseudogenes were mapped to 10q23.3, 17q25, and 19q13.2.

Full details of the abovementioned studies are described in the following publications, the disclosure of which are hereby incorporated by reference:

Koettnitz, K.; Wohl, T.; Kappel, B.; Lottspeich, F.; Hauber, J.; Bevec, D.: Identification of a new member of the human eIF-5A gene family. Gene 159: 283-284, 1995. PubMed ID: 7622067 3. Steinkasserer, A.; Jones, T.; Sheer, D.; Koettnitz, K.; Hauber, J.; Bevec, D.: The eukaryotic cofactor for the human immunodeficiency virus type 1 (HIV-1) rev protein, eIF-5A, maps to chromosome 17p12-p13: three eIF-5A pseudogenes map to 10q23.3, 17q25, and 19q13.2. Genomics 25: 749-752, 1995.

Further studies establishing the function and utilities of EIF5A are found in John Hopkins OMIM database record ID 600187, and in references numbered 695-697 listed hereinbelow.

Referring now to EIF5A BINDING SITE. Eukaryotic translation initiation factor 5A (EIF5A) is a target gene of GAM26, corresponding to GAM26-TARGET GENE of FIG. 26A. EIF5A BINDING SITE is a binding site found in an untranslated region of EIF5A, corresponding to BINDING SITE a FIG. 26A. FIG. 26D illustrates the complementarity of the nucleotide sequence of EIF5A BINDING SITE, designated SEQ ID:148945, to the nucleotide sequence of GAM26 RNA of FIG. 26A, designated SEQ ID:20604.

Another function of GAM26 is therefore inhibition of eukaryotic translation initiation facto 5A (EIF5A), a gene which encodes a protein that is an initiation factor. Accordingly, utilities of GAM26 include diagnosis and treatment of the abovementioned diseases and clinical conditions. The function and utilities of EIF5A have been established by previous studies, as described hereinabove with reference to FIG. 26D.

Referring now to EIF5A BINDING SITE. Eukaryotic translation initiation factor 5A (EIF5A) is a target gene of GAM26, corresponding to GAM26-TARGET GENE of FIG. 26A. EIF5A BINDING SITE is a binding site found in an untranslated region of EIF5A, corresponding to BINDING SITE of FIG. 26A. FIG. 26D illustrates the complementarity of the nucleotide sequence of EIF5A BINDING SITE, designated SEQ ID:148952, to the nucleotide sequence of GAM26 RNA of FIG. 26A, designated SEQ ID:20604.

Yet another function of GAM26 is therefore inhibition of eukaryotic translation initiation factor 5A (EIF5A), a gene which encodes a protein that is an initiation factor. Accordingly, utilities of GAM26 include diagnosis and treatment of the abovementioned diseases and clinical conditions. The function and utilities of EIF5A have been established by previous studies, as described hereinabove with reference to FIG. 26D.

Reference is now made to EP300 BINDING SITE. E1A binding protein p300 (EP300) is a target gene of GAM26, corresponding to GAM26-TARGET GENE of FIG. 26A. EP300 BINDING SITE is a binding site found in an untranslated region of EP300, corresponding to BINDING SITE of FIG. 26A. FIG. 26D illustrates the complementarity of the nucleotide sequence of EP300 BINDING SITE, designated SEQ ID:151947, to the nucleotide sequence of GAM26 RNA of FIG. 26A, designated SEQ ID:20604.

An additional function of GAM26 is therefore inhibition of E1A binding protein p300 (EP300), a gene which encodes a protein that may have a function in cell cycle regulation, and is associated with COLORECTAL CANCER. Accordingly, utilities of GAM26 include diagnosis and treatment of the abovementioned diseases and clinical conditions.

The function of EP300 has been established by previous studies. The growth-controlling functions of the adenovirus E1A oncoprotein depend on its ability to interact with a set of cellular proteins. Among these are the retinoblastoma protein, p107, p130, and p300. Eckner et al. (1994) isolated a cDNA encoding full-length human p300. p300 contains 3 cysteine- and histidine-rich regions of which the most carboxy-terminal region interacts specifically with E1A. In its center, p300 contains a bromodomain, a hallmark of certain transcriptional coactivators. p300 and CREB-binding protein (CREBBP, or CBP; 600140) are highly related in primary structure (Arany et al., 1994). Several protein motifs such as a bromodomain, a KIX domain, and 3 regions rich in cys/his residues are well conserved between these 2 proteins.

Animal model experiments lend further support to the function of EP300. The EP300 protein is a histone acetyltransferase that regulates transcription via chromatin remodeling and is important in the processes of cell proliferation and differentiation. A role for EP300 in cancer had been implied by the fact that it is targeted by viral oncoproteins (Arany et al., 1995), it is fused to MLL (159555) in leukemia (Ida et al., 1997), and 2 missense sequence alterations in EP300 were identified in epithelial malignancies (Muraoka et al., 1996). Gayther et al. (2000) described EP300 mutations that predicted a truncated protein in 6 (3%) of 193 epithelial cancer analyzed. Of these 6 mutations, 2 were in primary tumors (a colorectal cancer and a breast cancer) and 4 were in cancer cell lines (colorectal, breast, and pancreatic). In addition, they identified a somatic in-frame insertion in a primary breast cancer and missense alterations in a primary colorectal cancer and 2 cell lines (breast and pancreatic). Inactivation of the second allele was demonstrated in 5 of the 6 cases with truncating mutations and in 2 other cases. The data shored that EP300 is mutated in epithelial cancers and provided the first evidence that it behaves as a classic tumor suppressor gene.

It is appreciated that the abovementioned anima model for EP300 is acknowledged by those skilled in the art as a scientifically valid a mal model, as can be further appreciated from the publications sited hereinbelow.

Full detail the abovementioned studies are described in the following publications, the disclosure of which are hereby incorporated by reference:

Tini, M.; Benecke, A.; Um, S. -I.; Torchia, J.; Evans, R. M.; Chambon, P.: Association of CBP/p300 acetylase and thymine DNA glycosylase links DNA repair and transcription. Molec. Cell 9: 265-277, 2002. PubMed ID: 11864601 8. Lin, C. H.; Hare, B. J.; Wagner, G.; Harrison, S. C.; Maniatis, T.; Fraenkel, E.: A small domain of CBP/p300 binds diverse proteins: solution structure and functional studies. Molec. Cell 8: 581-590, 2001.

Further studies establishing the function and utilities of EP300 are found in John Hopkins OMIM database record ID 602700, and in referent numbered 698-710 listed hereinbelow.

Reference is now made to EZH2 BINDING SITE. Enhancer of zeste (*Drosophila*) homolog 2 (EZH2) is a target gene of GAM26, corresponding to GAM26-TARGET GENE of FIG. 26A. EZH2 BINDING SITE is a binding site found in an untranslated region of EZH2, corresponding to BINDING SITE of FIG. 26A. FIG. 26D illustrates the complementarity of the nucleotide sequence of EZH2 BINDING SITE, designated SEQ ID:156540, to the nucleotide sequence of GAM26 RNA of FIG. 26A, designated SEQ ID:20604.

A further function of GAM26 is therefore inhibition of enhancer of zeste (*Drosophila*) homolog 2 (EZH2), a gene which encodes a protein that may be involved in the regulation of gene transcription and chromatin structure and is associated with this protein may pray a role in the hematopoietic and central nervous systems. Accordingly, utilities of GAM26 include diagnosis and treatment of the abovementioned diseases and clinical conditions.

The function of EZH2 has been established by previous studies. To identify genes that map on human chromosome 21 that may contribute to the phenotype of Down syndrome, Chen et al. (1996) applied exon trapping to cosmid DNA from a chromosome 21-specific library. One of the potential exons that was cloned and partially characterized showed strong homology to the *Drosophila* 'enhancer of zeste' protein from amino acid 665 to amino acid 694. The *Drosophila* protein is a member of the Polycomb group, which maintains homeotic gene repression and is thought to control gene expression by regulating chromatin. Chen et al. (1996) cloned the full-length cDNA for this human homolog, termed EZH2. Chen et al. (1996) mapped the human EZH2 cDNA within YACs between marker D21S65 and ERG (165080) on 21q22.2. However, Cardoso et al. (2000) later showed by FISH that the functional EZH2 gene map to 7q35, not 21q22, and that the sequence isolated from the chromosome 21 cosmid corresponds to a pseudogene. By FISH, Laible et al. (1999) mapped the mouse Ezh2 gene to chromosome 6. Varambally et al. (2002) demonstrated through gene expression profiling that EZH2 is overexpressed in hormone-refractory, metastatic prostate cancer. Small interfering RNA (siRNA) duplexes targeted against EZH2 reduced the amounts of EZH2 protein present in prostate cells and also inhibited cell proliferation in vitro. Ectopic expression of EZH2 in prostate cells induced transcriptional repression of a specific cohort of genes. Gene silencing mediated by EZH2 requires the SET domain and is attenuated by inhibiting histone deacetylase activity. Amounts of both EZH2 mRNA an EZH2 protein were increased in metastatic prostate cancer. In addition, clinically localized prostate cancers that expressed higher concentrations of EZH2 showed a poorer prognosis. Thus, Varambally et al. (2002, concluded that dysregulated expression of EZH2 may be involved in the progression of prostate cancer as well as being a marker that distinguishes indolent prostate cancer from those at risk of lethal progression.

Full details of the abovementioned studies are described in the following publications, the disclosure of which are hereby incorporated by reference:

Chen, H.; Rossier, C.; Antonarakis, S. E.: Cloning of a human homolog of the *Drosophila* enhancer of zeste gene (EZH2) that maps to chromosome 21q22.2. Genomics 38: 30-37, 1996. PubMed ID: 8954776 6. Varambally, S.; Dhanasekaran, S. M.; Zhou, M.; Barrette, T. R.; Kumar-Sinha, C.; Sanda, M. G.; Ghosh, D.; Pienta, K. J.; Sewalt, R. G. A. B.; Otte, A. P.; Rubin, M. A.; Chinnaiyan, A. M.: The polycomb group protein EZH2 is involved in progression of prostate cancer. Nature 419: 624-629, 2002.

Further studies establishing the function and utilities of EZH2 are found in John Hopkins OMIM database record ID 601573, and in references numbered 711-712, 712-713, 713-714, 714-715, 715-716 and 716 listed hereinbelow.

Referring now to EZH2 BINDING SITE. Enhancer of zeste (*Drosophila*) homolog 2 (EZH2) is a target gene of GAM26, corresponding to GAM26-TARGET GENE of FIG. 26A. EZH2 BINDING SITE is a binding site found in an untranslated region of EZH2, corresponding to BINDING SITE of FIG. 26A. FIG. 26D illustrates the complementarity of the nucleotide sequence of EZH2 BINDING SITE, designated SEQ ID:156546, to the nucleotide sequence of GAM26 RNA of FIG. 26A, designated SEQ ID:20604.

Yet a further function of GAM26 is therefore inhibition of enhancer of zeste (*Drosophila*) homolog 2 (EZH2), a gene which encodes a protein that may be involved in the regulation of gene transcription and chromatin structure, and is associated with This protein may play a role in the hematopoietic and central nervous systems. Accordingly, utilities of GAM26 include diagnosis and treatment of the abovementioned diseases and clinical conditions. The function and utilities of EZH2 have been established by previous studies, as described hereinabove with reference to FIG. 26D.

Referring now to EZH2 BINDING SITE. Enhancer of zeste (*Drosophila*) homolog 2 (EZH2) is a target gene of GAM26, corresponding to GAM26-TARGET GENE of FIG. 26A. EZH2 BINDING SITE is a binding site found in an untranslated region of EZH2, corresponding to BINDING SITE of FIG. 26A. FIG. 26D illustrates the complementarity of the nucleotide sequence of EZH2 BINDING SITE, designated SEQ ID:156547, to the nucleotide sequence of GAM26 RNA of FIG. 26A, designated SEQ ID:20604.

Another function of GAM26 is therefore inhibition of enhancer of zeste (*Drosophila*) homolog 2 (EZH2), a gene which encodes a protein that may be involved in the regulation of gene transcription and chromatin structure and is associated with This protein may play a role in the hematopoietic and central nervous systems. Accordingly, utilities of GAM26 include diagnosis and treatment of the abovementioned diseases and clinical conditions. The function and utilities of EZH2 have been established by previous studies, as described hereinabove with reference to FIG. 26D.

Referring now to FGF18 BINDING SITE. Fibroblast growth factor 18 (FGF18) is a target gene of GAM26, corresponding to GAM26-TARGET GENE of FIG. 26A. FGF18 BINDING SITE is a binding site found in an untranslated region of FGF18, corresponding to BINDING SITE of FIG. 26A. FIG. 26D illustrates the complementarity of the nucleotide sequence of FGF18 BINDING SITE, designated SEQ ID:163374, to the nucleotide sequence of GAM26 RNA of FIG. 26A, designated SEQ ID:20604.

Yet another function of GAM26 is therefore inhibition of fibroblast growth factor 18 (FGF18), a gene which encodes a protein that stimulates hepatic and intestinal proliferation. Accordingly, utilities of GAM26 include diagnosis and treatment of the abovementioned diseases and clinical conditions. The function and utilities of FGF18 have been established by previous studies, as described hereinabove with reference to FIG. 26D.

Reference is now made to SERPINB8 BINDING SITE. Serine (or cysteine) proteinase inhibitor, clade B (ovalbumin), member (SERPINB8) is a target gene of GAM26, corresponding to GAM26-TARGET GENE of FIG. 26A. SERPINB8 BINDING SITE is a binding site found in an untranslated region of SERPINB8, corresponding to BINDING SITE of FIG. 26A. FIG. 26D illustrates the complementarity of the nucleotide sequence of SERPINB8 BINDING SITE, designated SEQ ID:163374, to the nucleotide sequence of GAM26 RNA of FIG. 26A, designated SEQ ID:20604.

An additional function of GAM26 is therefore inhibition of serine (or cysteine) proteinase inhibitor, clade B (ovalbumin), member (SERPINB18), a gene which encodes a protein that protease inhibitors; may be a serpin serine protease inhibitor that binds thrombin. Accordingly, utilities of GAM26 include diagnosis and treatment of the abovementioned diseases and clinical conditions.

The function of SERPINB8 has been established by previous studies. High molecular weight serine proteinase inhibitors (serpins) are a large superfamily of proteins which bind to and inactivate serine proteinases. These interactions are involved in many cellular processes including coagulation, fibrinolysis, complement fixation, matrix remodeling, and apoptosis. Sprecher et al. (1995) cloned 2 novel serpins, termed PI8 and PI9 (601799), from a human placenta cDNA library. Sequence analysis showed that PI8 encodes a 376-amino acid polypeptide with over 60% identity to PI6 (173321). Using Northern blotting, they observed that PI8 was expressed as 2 transcripts of 1.4 and 3.8 kb. The 1.4-kb transcript was most abundant in liver and lung while the 3.8-kb transcript was most abundant in skeletal muscle and heart. They showed that PI8 was localized to the cytoplasm of transfected cells and that it was able to form an SDS-insoluble complex with human thrombin (176930)). Serpins are characterized by a well-conserved tertiary structure that consists of 3 beta sheets and 8 or 9 alpha helices (Huber and Carrell, 1989). A critical portion of the molecule, the reactive center loop, connects beta sheets A and C and, in most cases, serves as bait for a target serine proteinase. Bartuski et al. (1997) stated that more than 100 members of the serpin superfamily are known, including C1 esterase inhibitor (C1NH; 606860), antithrombin III (AT3; 107300), protease inhibitor 7 (PI7; 177010), and maspin (PI5; 154790), which are involved in complement activation, coagulation, cell differentiation, and tumor suppression, respectively, as well as many others. The ovalbumin-type serpins (ov-serpins) are a subset of the serpin superfamily and are characterized by their high degree of homology to chicken ovalbumin, the lack of N- and C-terminal extensions, the absence of a signal peptide, and a serine rather than an asparagine residue at the penultimate position. Four members of the ov-serpin family had been mapped to a 300-kb region within 18q21.3: PI5, SCCA1 (600517), SCCA2 (600518), and PAI2 (173390). Using a panel of 18q21.3 AC clones, PCR, and DNA blotting, Bartuski et al. (1997) mapped 2 additional ov-serpins, cytoplasmic antiproteinase 2 (CAP2 or PI8) and bone marrow-associated serpin bomapin (PI10; 602058), to the same region. Three of the serpins (PI8, PI10, and PAI2) mapped to the same YACs. Bartuski et al. (1997) estimated that the size of the 18q21.3 serpin cluster spans approximately 500 kb and contains at least 6 serpin genes. The gene order is cen--PI5--SCCA2--SCCA1--PAI2--PI10--PI8--tel. The characterization the serpin gene cluster at 18q21 provided new opportunities to study coordinate gene regulation and the evolution of gene families.

Full details of the abovementioned studies are described in the following publications, the disclosure of which are hereby incorporated by reference:

Bartuski, A. J.; Kamachi, Y.; Schick, C.; Overhauser, J.; Silverman, G. A.: Cytoplasmic antiproteinase 2 (PI8) and bomapin (PI10) map to the serpin cluster at 18q21.3. Genomics 43: 321-328, 1997. PubMed ID: 9268635 3. Sprecher, C. A.; Morgenstern, K. A.; Mathewes, S.; Dahlen, J. R.; Schrader, S. K.; Foster, D. C.; Kisiel, W.: Molecular cloning, expression, and partial characterization of two members of the ovalbumin family of serine proteinase inhibitors. J. Biol. Chem. 270: 29854-29861, 1995.

Further studies establishing the function and utilities of SERPINB8 are found in John Hopkins OMIM database record ID 601697, and in references numbered 717-718, 718-719 and 715 listed hereinbelow.

Referring now to FGF18 BINDING SITE. Fibroblast growth factor 18 (FGF18) is a target gene of GAM26, corresponding GAM26-TARGET GENE of FIG. 26A. FGF18 BINDING SITE is a binding site found in an untranslated region of FGF18, corresponding to BINDING SITE of FIG. 26A. FIG. 26D illustrates the complementarity of the nucleotide sequence of FGF18 BINDING SITE, designated SEQ ID:163376, to the nucleotide sequence of GAM26 RNA of FIG. 26A, designated SEQ ID:20604.

A further function of GAM26 is therefore inhibition of fibroblast growth factor 18 (FGF18), a gene which encodes a protein that stimulates hepatic and intestinal proliferation. Accordingly, utilities of GAM26 include diagnosis and treatment of the abovementioned diseases and clinical conditions. The function and utilities of FGF18 have been established by previous studies, as described hereinabove with reference to FIG. 26D.

Referring now to FGF18 BINDING SITE. Fibroblast growth factor 18 (FGF18) is a target gene of GAM26, corresponding to GAM26-TARGET GENE of FIG. 26A. FGF18 BINDING SITE is a binding site found in an untranslated region of FGF18, corresponding to BINDING SITE of FIG. 26A. FIG. 26D illustrates the complementarity of the nucleotide sequence of FGF18 BINDING SITE, designated SEQ ID:163380, to the nucleotide sequence of GAM26 RNA of FIG. 26A, designated SEQ ID:20604.

Yet a further function of GAM26 is therefore inhibition of fibroblast growth factor 18 (FGF18), a gene which encodes a protein that stimulates hepatic and intestinal proliferation. Accordingly, utilities of GAM26 include diagnosis and treatment of the abovementioned diseases and clinical conditions. The function and utilities of FGF18 have been established by previous studies, as described hereinabove with reference to FIG. 26D.

Reference is now made to FKRP BINDING SITE. FUKUTIN-RELATED PROTEIN (FKRP) is a target gene of GAM26, corresponding to GAM26-TARGET GENE of FIG. 26A. FKRP BINDING SITE is a binding site found in an untranslated region of FKRP, corresponding to BINDING SITE of FIG. 26A. FIG. 26D illustrates the complementarity of the nucleotide sequence of FKRP BINDING SITE, designated SEQ ID:166297, to the nucleotide sequence of GAM26 RNA of FIG. 26A, designated SEQ ID:20604.

Another function of GAM26 is therefore inhibition of FUKUTIN-RELATED PROTEIN (FKRP), a gene which encodes a protein that is associated with congenital muscular dystrophies MDC1C. Accordingly, utilities of GAM26 include diagnosis and treatment of the abovementioned diseases and clinic conditions.

The function of FKRP has been established by previous studies. Brockington et al. (2001) identified the fukutin-related protein gene (FKRP) by database screening using the mouse fukutin sequence. The human version of the sequence was determined by a combination of EST assembly, RT-PCR, and RACE. The cDNA had a 1,488-bp open reading frame that encoded a 495-amino acid protein. Sequence analysis predicted a molecular organization similar to that found in several Golgi-resident glycosyltransferases. Northern blot analysis detected a 4.0 kb FKRP transcript expressed predominantly in skeletal muscle, placenta, and heart and relatively weakly in other tissues. Brockington et al (2001) determined that the 12-kb FKRP gene is composed of 3 noncoding exons and a single large exon of 3.8 kb that contained part of the 5-prime untranslated region and the entire open reading frame and 3-prime untranslated region. By radiation hybrid mapping, Brockington et al. (2001) localized the FKRP gene to chromosome 19q13.3. Driss et al. (2000) demonstrated that autosomal recessive limb-girdle muscular dystrophy type 2I (LGMD2I; 607155), a mild later-onset muscular dystrophy, maps to chromosome 19q13.3. The congenital muscular dystrophies (CMD) are a heterogeneous group of autosomal recessive disorders presenting in infancy with muscle weakness, contractures, and dystrophic changes on skeletal muscle biopsy. Structural brain defects, with or without mental retardation, are additional features of several CMD syndromes. Approximately 40% of patients with CMD have a primary deficiency (MDC1A) of the laminin alpha-2 chain of merosin (laminin-2) due to mutations in the LAMA2 gene (156225), which maps to 6q. In addition, a secondary deficiency of laminin alpha-2 is apparent in some CMD syndromes, including MDC1B (604801), which is mapped to chromosome 1q42, and both muscle-eye-brain disease (MEB; 253280), which maps to 1p, and Fukuyama CMD (FCMD; 253800) on 9q31, both of which are forms with severe brain involvement. The FCMD gene encodes a protein, fukutin, predicted through sequence analysis to be a phosphoryl-ligand transferase. Brockington et al. (2001) identified a member of the fukutin-related-protein family, which was found to be mutated in a severe form of CMD that they called MDC1C (606612). Patients harboring mutations in this gene had a secondary deficiency of laminin alpha-2 and a profound reduction in alpha-dystroglycan immunostaining. In addition, the molecular weight of alpha-dystroglycan was reduced in muscle. Together, these findings suggested that this protein is abnormally glycosylated in MDC1C and is central to the pathogenesis of the disorder. Brockington et al. (2001) identified mutations in the FKRP gene in 7 families with CMD characterized by disease onset in the first weeks of life and a severe phenotype with inability to walk, muscle hypertrophy, marked elevation of serum creatine kinase, and normal brain structure and function. Nine of the mutations were missense mutation and 2 were nonsense mutations. In 4 families, the affected individuals were compound heterozygotes; in the other 3 the patients were homozygous for the particular mutation. The 11 mutations were all different Brockington et al. (2001) found FKRP mutations in 17 of 25 LGMD2I families, including some with a severe and early-onset phenotype. Affected individuals from 15 of 17 families had an identical C826A (leu276-to-ile; 606596.0004) mutation, and individual in 5 families were homozygous for this recurrent mutation. Linkage analysis identified at least 2 possible haplotypes in linkage disequilibrium with this mutation. Patients with the C826A change had the clinically less severe LGMD2I phenotype, suggesting that this is a less disruptive FKRP mutation than those found in MDC1C. A variable reduction of alpha-dystroglycan (DAG1; 128239) expression was observed in the skeletal muscle biopsy of all individuals studied. In addition, several cases showed a deficiency of laminin 2 (LAMA2; 156225) either by immunocytochemistry or western blotting.

Full details of the abovementioned studies are described in the following publications, the disclosure of which are hereby incorporated by reference:

Brockington, M.; Blake, D. J.; Prandini, P.; Brown, S. C.; Torelli, S.; Benson, M. A.; Ponting, C. P.; Estournet, B.; Romero, N. B.; Mercuri, E.; Voit, T.; Sewry, C. A.; Guicheney, P.; Muntoni, F.: Mutations in the fukutin-related protein gene (FKRP) cause a form of congenital muscular dystrophy with secondary laminin alpha-2 deficiency and abnormal glycosylation of alpha-dystroglycan. Am. J. Hum. Genet. 69: 1198-1209, 2001. PubMed ID: 11592034 4. Mercuri, E.; Sewry, C. A.; Brown, S. C.; Brockington, M.; Jungbluth, H. DeVile, C.; Counsell, S.; Manzur, A.; Muntoni, F.: Congenital muscular dystrophy with secondary merosin deficiency and normal brain MRI: a novel entity? Neuropediatrics 31: 186-189, 2000.

Further studies establishing the function and utilities of FKRP are found in John Hopkins OMIM data base record ID 606596, and in references numbered 720-723 listed hereinbelow.

Reference is now made to FLT1 BINDING SITE. Fms-related tyrosine kinase 1 (vascular endothelial growth factor/vasc (FLT1) is a target gene of GAM26, corresponding to GAM26-TARGET GENE of FIG. 26A. FLT1 BINDING SITE is a binding site found in an untranslated region of FLT1, corresponding to BINDING SITE of FIG. 26A. FIG. 26D illustrates the complementarity of the nucleotide sequence of FLT1 BINDING SITE, designated SEQ ID:167123, to the nucleotide sequence of GAM26 RNA of FIG. 26A, designated SEQ ID:20604.

Yet another function of GAM26 is therefore inhibition of fms-related tyrosine kinase 1 (vascular endothelial growth factor/vasc (FLT1), a gene which encodes a receptor that receptor for vegf, vegfb and pgf has a tyrosine-protein kinase activity. Accordingly, utilities of GAM26 include diagnosis and treatment of the abovementioned diseases and clinical conditions.

The function of FLT1 has been established by previous studies. Oncogene FLT belongs to the src gene family and is related to oncogene ROS (165020). Like other members of this family, it shows tyrosine protein kinase activity that is important for the control of cell proliferation and differentiation. The sequence structure of the FLT gene resembles that of the FMS gene (164770); hence, Yoshida et al. (1987) proposed the name FLT as an acronym for FMS-like tyrosine kinase. Satoh et al. (1987) and Yoshida et al. (1987) mapped FLT to 13q12 by probing of DNA from a panel of human-mouse somatic cell hybrids and by in situ hybridization. By the isolation and analysis of a YAC containing the FLT1 and (136351) genes, Imbert et al. (1994) confirmed their close physical linkage. FLT1 and FLT3 are linked in a head-to-tail configuration and are separated by about 150 kb. Imbert et al. (1994) found that the region contains 3 CpG islands, 2 of which were thought to correspond to FLT1 and FLT3 and the third to a putative, unidentified receptor-type tyrosine kinase (RTK) gene. They referred to studies performed by fluorescence in situ hybridization using the YAC as a probe. Wiesmann et al. (1997) reported the crystal structure to 1.7-angstrom resolution of the complex between the receptor-binding domain of VEGF and FLT1 domain 2. The crystal structure of the complex between VEGF and the second domain of FLT1 shows domain 2 in a predominantly hydrophobic interaction with the 'poles' of the VEGF dimer. Based on this structure and on mutational data, Wiesmann et al. (1997) presented a model of VEGF bound to the first 4 domains of FLT1.

Animal model experiments lend further support to the function of FLT1. VEGF and its high-affinity binding receptors, the tyrosine kinases FLK1 and FLT1, are thought to be important for the development of embryonic vasculature. Studying transgenic mice in whom the Flk1 gene was disrupted, Shalaby et al (1995) demonstrated a total failure of embryonic mice to develop blood vessels and failure of blood island formation in the yolk sac. Fong et al. (1995) reported that in mice Flt1 is essential for the organization of embryonic vasculature, but is not essential for endothelial cell differentiation. Transgenic mouse embryos homozygous for a targeted mutation in the Flt1 locus formed endothelial cells in both embryonic and extraembryonic regions, but assembled these cells into abnormal vascular channels and died in utero at mid-somite stages. At earlier stages, the blood islands of homozygous mice were abnormal with angioblasts in the interior as well as on the periphery. Fong et al. (1995) suggested that the Flt1 signaling pathway may regulate normal endothelial cell-cell or cell-matrix interactions during vascular development.

It is appreciated that the abovementioned animal model for FLT1 is acknowledged by those skilled in the art as a scientifically valid animal model as can be further appreciated from the publications sited hereinbelow.

Full details of the abovementioned studies are described in the following publications, the disclosure of which are hereby incorporated by reference:

Yoshida, M. C.; Satoh, H.; Matsushime, H.; Shibuya, M.; Sasaki, M.: Two ros-related protooncogenes, c-ros-1 and flt, are regionally mapped on human chromosomes 6q22 and 13q12, respectively. (Abstract) Cytogen. Cell Genet. 46: 724 only, 1987. 3. Imbert, A.; Rosnet, O.; Marchetto, S.; Ollendorff, V.; Birnbaum, D.; Pebusque, M.-J.: Characterization of a yeast artificial chromosome from human chromosome band 13q12 containing the FLT1 and FLT3 receptor-type tyrosine kinase genes. Cytogenet. Cell Genet. 67: 175-177, 1994.

Further studies establishing the function and utilities of FLT1 are found in John Hopkins OMIM database record ID 165070, and in references numbered 724-732 listed hereinbelow.

Referring now to FLT1 BINDING SITE. Fms-related tyrosine kinase 1 (vascular endothelial growth factor/vasc (FLT1) is a target gene of GAM26, corresponding to GAM26-TARGET GENE of FIG. 26A. FLT1 BINDING SITE is a binding site found in an untranslated region of FLT1, correspond to BINDING SITE of FIG. 26A. FIG. 26D illustrates the complementarity of the nucleo de sequence of FLT1 BINDING SITE, designated SEQ ID:167194, to the nucleotide sequence of GAM26 RNA of FIG. 26A, designated SEQ ID:20604.

An additional function of GAM26 is therefore inhibition of fms-related tyrosine kinase 1 (vascular endothelial growth factor/vasc (FLT1), a gene which encodes a receptor that receptor for vegf, vegfb and pgf. has a tyrosine-protein kinase activity. Accordingly, utilities of GAM26 include diagnosis and treatment of the abovementioned diseases and clinical conditions. The function and utilities of FLT1 have been established by previous studies, as described hereinabove with reference to FIG. 26D.

Referring now to FMR1 BINDING SITE. Fragile X mental retardation 1 (FMR1) is a target gene of GAM26, corresponding to GAM26-TARGET GENE of FIG. 26A. FMR1 BINDING SITE is a binding site found in an untranslated region of FMR1, corresponding to BINDING SITE of FIG. 26A. FIG. 26D illustrates the complementarity of the nucleotide sequence of FMR1 BINDING SITE, designated SEQ ID:167700, to the nucleotide sequence of GAM26 RNA of FIG. 26A, designated SEQ ID:20604.

A further function of GAM26 is therefore inhibition of fragile X mental retardation 1 (FMR1), a gene which encodes a protein that is associated with fragile x syndrome. Accordingly, utilities of GAM26 include diagnosis and treatment of the abovementioned diseases and clinical conditions. The function and utilities of FMR1 have been established by previous studies, as described hereinabove with reference to FIG. 26D.

Referring now to FMR1 BINDING SITE. Fragile X mental retardation 1 (FMR1) is a target gene of GAM26, corresponding to GAM26-TARGET GENE of FIG. 26A. FMR1 BINDING SITE is a binding site found in an untranslated region of FMR1, corresponding to BINDING SITE of FIG. 26A. FIG. 26D illustrates the complementarity of the nucleotide sequence of FMR1 BINDING SITE, designated SEQ ID:167700, to the nucleotide sequence of GAM26 RNA of FIG. 26A, designated SEQ ID:20604.

Yet a further function of GAM26 is therefore inhibition of fragile X mental retardation 1 (FMR1), a gene which encodes a protein that is associated with fragile x syndrome. Accordingly, utilities of GAM26 include diagnosis and treatment of the abovementioned diseases and clinical conditions. The function and utilities of FMR1 have been established by previous studies, as described hereinabove with reference to FIG. 26D.

Reference is now made to SMURF1 BINDING SITE. SMAD UBIQUITINATION REGULATORY FACTOR 1 (SMURF1) is a target gene of GAM26, corresponding to GAM26-TARGET GENE of FIG. 26A. SMURF1 BINDING SITE is a binding site found in an untranslated region of SMURF1, corresponding to BINDING SITE of FIG. 26A. FIG. 26D illustrates the complementarity of the nucleotide sequence of SMURF1 BINDING SITE, designated SEQ ID:167709, to the nucleotide sequence of GAM26 RNA of FIG. 26A, designated SEQ ID:20604.

Another function of GAM26 is therefore inhibition of SMAD UBIQUITINATION REGULATORY FACTOR 1 (SMURF1), a gene which encodes enzyme that triggers ubiquitination and degradation of smads specific for the BMP pathway. Accordingly, utilities of GAM26 include diagnosis and treatment of the abovementioned diseases and clinical conditions.

The function of SMURF1 has been established by previous studies. Using a yeast 2-hybrid screen with frog Smad1 as bait, Zhu et al. (1999) identified cDNAs encoding frog and human SMURF1 (SMAD ubiquitination regulatory factor-1). Sequence analysis predicted that frog and human SMURF1 contain 731 amino acids, share 91% identity, are most closely related to yeast Pub1, and have significant homology to the Hect subclass of E3 ubiquitin ligases. Expression of SMURF1 caused a dose-dependent decrease in expression of SMAD1 and SMAD5, which function in BMP signaling, but not in expression of SMAD2 or SMAD3, which function in TGFB signaling. Pulse-chase analysis demonstrated that degradation of SMAD proteins occurs by ubiquitination of the SMAD Hect domain and transport to the proteasome. Mutational analysis indicated that the WW motif of SMURF1 associates with SMAD1 and SMAD5 through their PY motifs. In frog eggs, Smurf1 mRNA was localized to the animal pole; ectopic Smurf1 in frog embryos inhibited the transmission of BMP signals, affecting pattern formation.

Full detail of the abovementioned studies are described in the following publications, the disclosure of which are hereby incorporated by reference:

Zhu H.; Kavsak, P.; Abdollah, S.; Wrana, J. L.; Thomsen, G. H.: A SMAD ubiquitin ligase targets the BMP pathway and affect embryonic pattern formation. Nature 400: 687-693, 1999.

Further studies establishing the function and utilities SMURF1 are found in John Hopkins OMIM database record ID 605568, and in references numbered 733-734 listed hereinbelow.

Referring now to FMR1 BINDING SITE. Fragile X mental retardation 1 (FMR1) is target gene of GAM26, corresponding to GAM26-TARGET GENE of FIG. 26A. FMR1 BINDING SITE is a binding site found in an untranslated region of FMR1, corresponding to BINDING SITE of FIG. 26A. FIG. 26D illustrates the complementarity of the nucleotide sequence of FMR1 BINDING SITE, designated SEQ ID:167713, to the nucleotide sequence of GAM26 RNA of FIG. 26A, designated SEQ ID:20604.

Yet another function of GAM26 is therefore inhibition of fragile X mental retardation 1 (FMR1), a gene which encodes a protein that is associated with fragile x syndrome. Accordingly, utilities of GAM26 include diagnosis and treatment of the abovementioned diseases and clinical conditions. The function and utilities of FMR1 have been established by previous studies, as described hereinabove with reference to FIG. 26D.

Referring now to FMR1 BINDING SITE. Fragile X mental retardation 1 (FMR1) is a target gene of GAM26, correspond to GAM26-TARGET GENE of FIG. 26A. FMR1 BINDING SITE is a binding site found in an untranslated region of FMR1, corresponding to BINDING SITE of FIG. 26A. FIG. 26D illustrates the complementarity of the nucleotide sequence of FMR1 BINDING SITE, designated SEQ ID:167713, to the nucleotide sequence of GAM26 RNA of FIG. 26A, designated SEQ ID:20604.

An additional function of GAM26 is therefore inhibition of fragile X mental retardation 1 (FMR1), a gene which encodes a protein that is associated with fragile x syndrome. Accordingly, utilities of GAM26 include diagnosis and treatment of the abovementioned diseases and clinical conditions. The function and utilities of FMR1 have been established by previous studies, as described hereinabove with reference to FIG. 26D.

Referring now to FMR1 BINDING SITE. Fragile X mental retardation 1 (FMR1) is a target gene of GAM26, corresponding to GAM26-TARGET GENE of FIG. 26A. FMR1 BINDING SITE is a binding site found in an untranslated region of FMR1, corresponding to BINDING SITE of FIG. 26A. FIG. 26D illustrates the complementarity of the nucleotide sequence of FMR1 BINDING SITE, designated SEQ ID:167717, to the nucleotide sequence of GAM26 RNA of FIG. 26A, designated SEQ ID:20604.

A further function of GAM26 is therefore inhibition of fragile X mental retardation 1 (FMR1), a gene which encodes a protein that is associated with fragile x syndrome. Accordingly, utilities of GAM26 include diagnosis and treatment of the abovementioned diseases and clinical conditions. The function and utilities of FMR1 have been established by previous studies, as described hereinabove with reference to FIG. 26D.

Referring now to FMR1 BINDING SITE. Fragile X mental retardation 1 (FMR1) is a target gene of GAM26, corresponding to GAM26-TARGET GENE of FIG. 26A. FMR1 BINDING SITE is a binding site found in an untranslated region of FMR1, corresponding to BINDING SITE of FIG. 26A. FIG. 26D illustrates the complementarity of the nucleotide sequence of FMR1 BINDING SITE, designated SEQ ID:167717, to the nucleotide sequence of GAM26 RNA of FIG. 26A, designated SEQ ID:20604.

Yet a further function of GAM26 is therefore inhibition of fragile X mental retardation 1 (FMR1), a gene which encodes a protein that is associated with fragile x syndrome. Accordingly, utilities of GAM26 include diagnosis and treatment of the abovementioned diseases and clinical conditions. The function and utilities of FMR1 have been established by previous studies, as described hereinabove with reference to FIG. 26D.

Referring now to FMR1 BINDING SITE. Fragile X mental retardation 1 (FMR1) is a target gene of GAM26, corresponding to GAM26-TARGET GENE of FIG. 26A. FMR1 BINDING SITE is a binding site found in an untranslated region of FMR1, corresponding to BINDING SITE of FIG. 26A. FIG. 26D illustrates the complementarity of the nucleotide sequence of FMR1 BINDING SITE, designated SEQ ID:167722, to the nucleotide sequence of GAM26 RNA of FIG. 26A, designated SEQ ID:20604.

Another function of GAM26 is therefore inhibition of fragile X mental retardation 1 (FMR1), a gene which encodes a protein that is associated with fragile x syndrome. Accordingly, utilities of GAM26 include diagnosis and treatment of the abovementioned diseases and clinical conditions. The function and utilities of FMR1 have been established by previous studies, as described hereinabove with reference to FIG. 26D.

Referring now to FMR1 BINDING SITE. Fragile X mental retardation 1 (FMR1) is a target gene of GAM26, corresponding to GAM26-TARGET GENE of FIG. 26A. FMR1 BINDING SITE is a binding site found in an untranslated region of FMR1, corresponding to BINDING SITE of FIG. 26A. FIG. 26D illustrates the complementarity of the nucleotide sequence of FMR1 BINDING SITE, designated SEQ ID:167722, to the nucleotide sequence of GAM26 RNA of FIG. 26A, designated SEQ ID:20604.

Yet another function of GAM26 is therefore inhibition of fragile X mental retardation 1 (FMR1), a gene which encodes a protein at is associated with fragile x syndrome. Accordingly, utilities of GAM26 include diagnosis and treatment of the abovementioned diseases and clinical conditions. The function and utilities of FMR1 have been established by previous studies, as described hereinabove with reference to FIG. 26D.

Reference is now made to GNB1 BINDING SITE. Guanine nucleotide binding protein (G protein), beta polypeptide 1 (GNB1) is a target gene of GAM26, corresponding to GAM26-TARGET GENE of FIG. 26A. GNB1 BINDING SITE is a binding site found in an untranslated region of GNB1, corresponding to BINDING SITE of FIG. 26A. FIG. 26D illustrates the complementarity of the nucleotide sequence of GNB1 BINDING SITE, designated SEQ ID:167722, to the nucleotide sequence of GAM26 RNA of FIG. 26A, designated SEQ ID:20604.

An additional function of GAM26 is therefore inhibition of guanine nucleotide binding protein (G protein), beta polypeptide 1 (GNB1), a gene which encodes a protein that transduces signals from G protein-coupled receptors to intracellular effectors. Accordingly, utilities of GAM26 include diagnosis and treatment of the abovementioned diseases and clinical conditions.

The function of GNB1 has been established by previous studies. Heterotrimeric guanine nucleotide-binding proteins (G proteins) transduce extracellular signals received by transmembrane receptors to effector proteins. Each subunit of the G protein complex is encoded by a member of 1 of 3 corresponding gene families. Hurowitz et al. (2000) counted 16 different members of the alpha-subunit family, 5 different members of the beta-subunit family, and 11 different members of the gamma-subunit family, as described in mammals. They identified and characterized BACs containing the human homologs of each of the alpha-, beta-, and gamma-subunit genes. The gene structure and chromosome location of each gene was determined, as were the orientations of paired genes. Using a cDNA probe against a mouse/human somatic cell hybrid panel, Sparkes et al. (1987) mapped the human beta-1 polypeptide of protein to human chromosome 1. Levine et al. (1990) confirmed the assignment to chromosome 1 by Southern analysis of somatic cell hybrids, and Levine et al. (1990) and Modi et al. (1991) regionalized the assignment to 1pter-p31.2 by in situ hybridization. Although Sparkes et al. (1987) had mapped the mouse Gnb1 gene to chromosome 19, later studies showed that Gnb1 is located on distal mouse chromosome 4 (Danciger et al., 199).

Full details of the abovementioned studies are descried in the following publications, the disclosure of which are hereby incorporated by reference:

Hurowitz, E. H.; Melnyk, J. M.; Chen, Y. -J.; Kouros-Mehr, H.; Simon, M. I.; Shizuya, H.: Genomic characterization of the human heterotrimeric G protein alpha, beta, and gamma subunit genes. DNA Res. 7: 111-120, 2000. 6.

Sparkes, R. S.; Cohn, V. H.; Mohandas, T.; Zollman, S.; Cire-Eversole, P.; Amatatruda, T. T.; Reed, R. R.; Lochrie, M. A.; Simon, M. I.: Mapping of genes encoding the subunits of guanine nucleotide-binding protein (G-proteins) in humans. (Abstract) Cytogenet. Cell Genet. 46: 696 only, 1987.

Further studies establishing the function and utilities of GNB1 are found in John Hopkins OMIM database record ID 139380, and in references numbered 735-740 listed hereinbelow.

Referring now to ZNF6 BINDING SITE. Zinc finger protein 6 (CMPX1) (ZNF6) is a target gene of GAM26, corresponding to GAM26-TARGET GENE of FIG. 26A. ZNF6 BINDING SITE is a binding site found in an untranslated region of ZNF6, corresponding to BINDING SITE of FIG. 26A. FIG. 26D illustrates the complementarity of the nucleotide sequence of ZNF6 BINDING SITE, designated SEQ ID:167722, to the nucleotide sequence of GAM26 RNA of FIG. 26A, designated SEQ ID:20604.

A further function of GAM26 is therefore inhibition of zinc finger protein 6 (CMPX1) (ZNF6), a gene which encodes a protein that is probably a transcriptional activator. Accordingly, utilities of GAM26 include diagnosis and treatment of the abovementioned diseases and clinical conditions. The function and utilities of ZNF6 have been established by previous studies, as described hereinabove with reference to FIG. 26D.

Referring now to FMR1 BINDING SITE. Fragile X mental retardation 1 (FMR1) is a target gene of GAM26, corresponding to GAM26-TARGET GENE of FIG. 26A. FMR1 BINDING SITE is a binding site found in an untranslated region of FMR1, corresponding to BINDING SITE of FIG. 26A. FIG. 26D illustrates the complementarity of the nucleotide sequence of FMR1 BINDING SITE, designated SEQ ID:167723, to the nucleotide sequence of GAM26 RNA of FIG. 26A, designated SEQ ID:20604.

Yet a further function of GAM26 is therefore inhibition of fragile X mental retardation 1 (FMR1), a gene which encodes a protein that is associated with fragile x syndrome. Accordingly, utilities of GAM26 include diagnosis and treatment of the abovementioned diseases and clinical conditions. The function and utilities of FMR1 have been established by previous studies, as described hereinabove with reference to FIG. 26D.

Referring now to FMR1 BINDING SITE. Fragile X mental retardation 1 (FMR1) is a target gene of GAM26, corresponding to GAM26-TARGET GENE of FIG. 26A. FMR1 BINDING SITE is a binding site found in an untranslated region of FMR1, corresponding to BINDING SITE of FIG. 26A. FIG. 26D illustrates the complementarity of the nucleotide sequence of FMR1 BINDING SITE, designated SEQ ID:167756, to the nucleotide sequence of GAM26 RNA of FIG. 26A, designated SEQ ID:20604.

Another function of GAM26 is therefore inhibition of fragile X mental retardation 1 (FMR1), a gene which encodes a protein that is associated with fragile x syndrome. Accordingly, utilities of GAM26 include diagnosis and treatment of the abovementioned diseases and clinical conditions. The function and utilities of FMR1 have been established by previous studies, as described hereinabove with reference to FIG. 26D.

Reference is now made to FOXD2 BINDING SITE. Forkhead box D2 (FOXD2) is a tare gene of GAM26, corresponding to GAM26-TARGET GENE of FIG. 26A. FOXD2 BINDING SITE is a binding site found in an untranslated region of FOXD2, corresponding to BINDING SITE of FIG. 26A. FIG. 26D illustrates the complementarity of the nucleotide sequence of FOXD2 BINDING SITE, designated SEQ ID:169035, to the sequence of GAM26 RNA of FIG. 26A, designated SEQ ID:20604.

Yet another function of GAM26 is therefore inhibition of forkhead box D2 (FOXD2), a gene which encodes a transcription factor that is a probable transcription factor. Accordingly, utilities of GAM26 include diagnosis and treatment of the abovementioned diseases and clinical conditions.

The function of FOXD2 has been established by previous studies. Ernstsson et al. (1997) described the cloning of a nearly full-length 4,258-bp cDNA encoding the human forkhead gene FREAC9 (FKHL17). The 5-prime untranslated region is unusual since it is very long (2,127 bp) and contains 15 upstream AUG codons. Hybridization to a panel consisting of RNA derived from 50 different tissues showed that the FKHL17 gene is transcribed exclusively in the kidney. By a combination of fluorescence in situ hybridization and somatic cell hybrid analyses, they localized the FKHL17 gene to 1p32. The conceptual translation produce predicts a protein of 372 amino acids within a N-terminal domain rich in acidic amino acids and with a high likelihood of forming an amphipathic helix, a DNA binding forkhead domain, and a C-terminal region that has a high probability of forming an amphipathic beta-sheet. The amino acid sequence of the DNA binding forkhead motif of this protein is identical to that of another forkhead protein, FREAC4 (601091), whereas 12 substitutions are present at the nucleotide level. There are no similarities in region outside of the DNA binding domains of FREAC9 and FREAC4, and since the gene encoding the latter protein maps to 5q12-q13, it is likely that evolutionary selection has acted to maintain identical DNA binding domains between these 2 kidney-expressed transcript on factors. Ernstsson et al. (1997) tabulated the chromosomal localization of 15 human forkhead genes in their Table 1

Full details of the abovementioned studies are described in the following publications, the disclosure of which are hereby incorporated by reference:

Ernstsson, S.; Betz, R.; Lagercrantz, S.; Larsson C.; Ericksson, S.; Cederberg, A.; Carlsson, P.; Enerback, S.: Cloning and characterization of freac-9 (FKHL17), a novel kidney-expressed human forkhead gene that maps to chromosome 1p32-p34. Genomics 46: 78-85, 1997.

Further studies establishing the function and utilities of FOXD2 are found in John Hopkins OMIM database record ID 602211, and in references numbered 741 listed hereinbelow.

Reference is now made to FOXF1 BINDING SITE. Forkhead box F1 (FOXF1) is a target gene of GAM26, corresponding to GAM26-TARGET GENE of FIG. 26A. FOXF1 BINDING SITE is a binding site found in an untranslated region of FOXF1, corresponding to BINDING SITE of FIG. 26A. FIG. 26D illustrates the complementarity of the nucleotide sequence of FOXF1 BINDING SITE, designated SEQ ID:169360, to the nucleotide sequence of GAM26 RNA of FIG. 26A, designated SEQ ID:20604.

An additional function of GAM26 is therefore inhibition of forkhead box F1 (FOXF1), a gene which encodes a transcription factor that is a probable transcription activator for a number of lung-specific genes. Accordingly, utilities of GAM26 include diagnosis and treatment of the abovementioned diseases and clinical conditions.

The function of FOXF1 has been established by previous studies. The forkhead genes are transcription factors distinguished by a characteristic 100-amino acid motif that was originally identified in *Drosophila* (see 164874). Pierrou et al. (1994) identified 7 human genes containing forkhead domains and designated them forkhead related activators (FREAC) 1 through 7. Northern blot analysis revealed that the FREAC1, or FKHL5, gene is expressed as a 2.6-kb mRNA in placenta and adult and fetal lung. Hellqvist et al. (1996) reported the FREAC1 cDNA sequence. The predicted 354-amino acid protein is nearly identical to FREAC2 (FKHL6; 603250) within a 112-residue region containing the forkhead domain and adjacent sequences, and within the C-terminal region. Using a reporter gene construct containing FREAC2 binding sequences in the promoter, Hellqvist et al. (1996) demonstrated that both FREAC1 and FREAC2 have C-terminal transcriptional activation domains. FREAC1/FREAC2 binding sequences are present in the promoters of several lung-specific genes, including CC10 (192020) and SPB (SFTPB; 178640). While both FREAC1 and FREAC2 transactivated an SPB promoter construct, CC10 was activated only by FREAC1. CC10 activation occurred specifically in a lung cell line with Clara cell-like characteristics. Hellqvist et al. (1996) reported that the mouse HFH8 gene and FREAC1 share 90% nucleotide sequence identity. By resequencing of HFH8, these authors demonstrated that 5 frameshifts in the HFH8 sequence reported by Clevidence et al. (1994) were due to sequencing errors.

Full details of the abovementioned studies are described in the following publications, the disclosure of which are hereby incorporated by reference:

Clevidence, D. E.; Overdier; D. G.; Peterson, R. S.; Porcella, A.; Ye, H.; Paulson, K. E.; Costa, R. H.: Members of the HNF-3/forkhead family of transcription factors exhibit distinct cellular expression patterns in lung and regulate the surfactant protein B promoter. Dev. Biol. 166: 195-

209, 1994. PubMed ID: 7958446 2. Hellqvist, M.; Mahlapuu, M.; Blixt, A.; Enerback, S.; Carlsson, P.: The human forkhead protein FREAC-2 contains two functionally redundant activation domains and interacts with TBP and TFIIB. J. Biol. Chem. 273: 23335-23343, 1998.

Further studies establishing the function and utilities of FOXF1 are found in John Hopkins OMIM database record ID 601089, and in references numbered 742-746 listed hereinbelow.

Reference is now made to FUS1 BINDING SITE. FUS1 GENE (FUS1) is a target gene of GAM26, corresponding to GAM26-TARGET GENE of FIG. 26A. FUS1 BINDING SITE is a binding site found in an untranslated region of FUS1, corresponding to BINDING SITE of FIG. 26A. FIG. 26D illustrates the complementarity of the nucleotide sequence of FUS1 BINDING SITE, designated SEQ ID:170829, to the nucleotide sequence of GAM26 RNA of FIG. 26A, designated SEQ ID:20604.

A further function of GAM26 is therefore inhibition of FUS1 GENE (FUS1), a gene which encodes a protein that may function as a tumor suppressor and is associated with lung cancer. Accordingly, utilities of GAM26 include diagnosis and treatment of the abovementioned diseases and clinical conditions.

The function of FUS1 has been established by previous studies. Lerman and Minna (2000) identified a FUS1 mutation in 2 nonsmall cell lung cancer (NSCLC) cell lines that resulted in a 28-bp truncation at the 3-prime end of exon 2 and a predicted protein of only 82 amino acids. Using SSCP and CpG island promoter methylation analyses, Kondo et al. (2001) failed to detect mutations, polymorphisms, or methylation of FUS1 in lung cancer specimens. Western blot analysis indicated low or no expression of FUS1 in lung cancer cell lines. Overexpression of transfected wildtype but not mutant FUS1 in NSCLCs led to the detection of an approximately 20-kD protein and a dramatic reduction in colony-forming cells. Ecdysone-induced expression of FUS1 had the same effects. Flow cytometric analysis indicated that the arrest occurred in G1 phase.

Full details of the abovementioned studies are described in the following publications, the disclosure of which are hereby incorporated by reference:

Kondo, M.; Ji, L.; Kamibayashi, C.; Tomizawa, Y.; Randle, D.; Sekido, Y.; Yokota, J.; Kashuba, V.; Zabarovsky, E.; Kuzmin, I.; Lerman, M.; Roth, J.; Minna, J. D.: Overexpression of candidate tumor suppressor gene FUS1 isolated from the 3p21.3 homozygous deletion region leads to G1 arrest and growth inhibition of lung cancer cells. Oncogene 20: 6258-6262, 2001. PubMed ID: 11593436 2. Lerman, M. I.; Minna, J. D.: The 630-kb lung cancer homozygous deletion region on human chromosome 3p21.3: identification and evaluation of the resident candidate tumor suppressor genes. Cancer Res. 60: 6116-6133, 2000.

Further studies establishing the function and utilities of FUS1 are found in John Hopkins OMIM database record ID 607052, and in reference numbered 747-748 listed hereinbelow.

Referring now to FUS1 BINDING SITE. FUS1 GENE (FUS1) is a target gene of GAM26, corresponding to GAM26-TARGET GENE of FIG. 26A. FUS1 BINDING SITE is a binding site found in an untranslated region of FUS1, corresponding to BINDING SITE of FIG. 26A. FIG. 26D illustrates the complementarity of the nucleotide sequence of FUS1 BINDING SITE, designated SEQ ID:170846, to the nucleotide sequence of GAM26 RNA of FIG. 26A, designated SEQ ID:20604.

Yet a further function of GAM26 is therefore inhibition of FUS1 GENE (FUS1), a gene which encodes a protein that may function as a tumor suppressor and is associated with lung cancer. Accordingly, utilities of GAM26 include diagnosis and treatment of the abovementioned diseases and clinical conditions. The function and utilities of FUS1 have been established by previous studies, as described hereinabove with reference to FIG. 26D.

Reference is now made to FZD2 BINDING SITE. Frizzled (*Drosophila*) homolog 2 (FZD2) is a target gene of GAM26, corresponding to GAM26-TARGET GENE of FIG. 26A. FZD2 BINDING SITE is a binding site found in an untranslated region of FZD2, corresponding to BINDING SITE FIG. 26A. FIG. 26D illustrates the complementarity of the nucleotide sequence of FZD2 BINDING SITE, designated SEQ ID:172450, to the nucleotide sequence of GAM26 RNA of FIG. 26A, designated SEQ ID:20604.

Another function of GAM26 is therefore inhibition of frizzled (*Drosophila*) homolog 2 (FZD2), a gene which encodes a protein that is aputative receptor with a role in transmembrane signal transmission. Accordingly, utilities of GAM26 include diagnosis and treatment of the abovementioned diseases and clinical conditions.

The function of FZD2 has been established by previous studies. Following up on the identification of trinucleotide repeat expansions as the basis of many inherited human disorders, Zhao et al. (1995) isolated and characterized cDNAs containing trinucleotide repeats. In the course of these studies, they discovered a human homolog of the *Drosophila* polarity gene 'frizzled' (fz). The fz locus in *Drosophila* is required for the transmission of polarity signals across the plasma membrane in epidermal cells. The *Drosophila* fz gene encodes a protein with 7 putative transmembrane domains that is thought to function as a G protein-coupled receptor. Zhao et al. (1995) isolated a human homolog, symbolized FZD2, from a human ovarian cDNA library and mapped this gene to 17q21.1 by fluorescence in situ hybridization using a corresponding cosmid. The full-length cDNA of FZD2 encodes a protein of 565 amino acids that shares 56% sequence identity with *Drosophila* fz protein. Zhao et al. (1995) found that the expression of the FZD2 gene appears to be developmentally regulated, with high levels of expression in fetal kidney and lung and in adult colon and ovary. The structure of FZD2 suggests that it has a role in transmembrane signal transmission, although its precise physiologic function and associated pathways have yet to be determined. Wang et al. (1996) showed that a large family of frizzled homologs exists in mammals. They mapped FZD2 to mouse chromosome 11, syntenic to human chromosome 17q, by interspecific backcross analysis. Another human homolog termed 'frizzled 5,' (601723) was also isolated by Wang et al. (1996).

Full details of the abovementioned studies are described in the following publications, the disclosure of which are hereby incorporated by reference:

Wang, Y.; Macke, J. P.; Abella, B. S.; Andreasson, K.; Worley, P.; Gilbert, D. J.; Copeland, N. G.; Jenkins, N. A.; Nathans, J.: A large family of putative transmembrane receptors homologous to the product of the *Drosophila* tissue polarity gene frizzled. J. Biol. Chem. 271: 4468-4476, 1996. PubMed ID: 8626800 2. Zhao, Z. Y.; Lee, C. C.; Baldini, A.; Caskey, C. T.: A human homologue of the *Drosophila* polarity gene frizzled has been identified and mapped to 17q21.1. Genomics 27: 370-373, 1995.

Further studies establishing the function and utilities of FZD2 are found in John Hopkins OMIM database record ID 600667, and in references numbered 749-750 listed hereinbelow.

Reference is now made to GABRB3 BINDING SITE. Gamma-aminobutyric acid (GABA) A receptor, beta 3 (GABRB3) is a target gene of GAM26, corresponding to GAM26-TARGET GENE of FIG. 26A. GABRB3 BINDING SITE is a binding site found in an untranslated region of GABRB3, corresponding to BINDING SITE of FIG. 26A. FIG. 26D illustrates the complementarity of the nucleotide sequence of GABRB3 BINDING SITE, designated SEQ ID:173934, to the nucleotide sequence of GAM26 RNA of FIG. 26A, designated SEQ ID:20604.

Yet another function of GAM26 is therefore inhibition of gamma-aminobutyric acid (GABA) A receptor, beta 3 (GABRB3), a gene which encodes a receptor that mediates neuronal inhibition by binding to the gaba/benzodizepine receptor and opening an integral chloride channel, and is associated with Angelman syndrome and Prader-Willi syndrome. Accordingly, utilities GAM26 include diagnosis and treatment of the abovementioned diseases and clinical conditions.

The function of GABRB3 has been established by previous studies. Wagstaff et al. (1991) showed that the gene encoding the beta-3 subunit of the GABA-A receptor (GABRB3) maps to the region of 15q involved in Angelman syndrome (AS; 105830) and Prader-Willi syndrome (PWS; 176270). Deletion of the gene was found in patients of both types with interstitial cytogenetic deletions. The gene was also deleted in an Angelman syndrome patient with an unbalanced 13;15 translocation but not in a PWS patient with an unbalanced 9;15 translocation. Wagstaff et al. (1991) suggested that this receptor gene may be involved in the pathogenesis of one or both of these syndromes. This is the first gene to be mapped to this region. Wagstaff et al. (1991) showed that the gene is located on mouse chromosome 7, very closely linked to 2 other genes that in the human have been mapped to the 15q11-q13 region. Saitoh et al. (1992) studied a highly informative family in which 3 sibs had Angelman syndrome and a deletion of one GABRB3 gene. The mother had the same deletion which she had inherited from her father. The finding supposed the possibility that GABRB3 is the Angelman gene and indicated that the genes for AS and PWS are different since transmission of the deletion from the grandfather to the mother of the affected children did not result in PWS. Using the combined techniques of field-inversion gel electrophoresis (FIGE) and phage genomic library screening, Sinnett et al. (1993) constructed a high-resolution physical map covering nearly 1.0 Mb in the proximal region of 15q. The map showed that GABRB3 and GABRA5 (gamma-aminobutyric acid receptor alpha-5 subunit gene; 137142) are separated by less than 100 kb and are arranged in a head-to-head configuration. GABRB3 encompasses approximately 250 kb, while GABRA5 is contained within 70 kb. The difference in size is due largely to an intron of 150 kb within GABRB3. Chromosomal rearrangement breakpoints in 2 patients with Angelman syndrome were located within the large GABRB3 intron. Russek and Farb (1994) stated that the gene encoding the gamma-3 form of the GABA-A receptor (GABRG3; 600233) is located on 15q11-q13 in a cluster with GABRA5 and GAB B3.

Full details of the abovementioned studies are described in the following publications, the disclosure of which are hereby incorporated by reference:

Saitoh, S.; Kubota, T.; Ohta, T.; Jinno, Y.; Niikawa, N.; Sugimoto, T.; Wagstaff, J.; Lalande, M.: Familial Angelman syndrome caused by imprinted submicroscopic deletion encompassing GABA(A) receptor beta(3)-subunit gene. (Letter) Lancet 339: 366-367, 1992. PubMed ID: 1346439 15. Wagstaff, J.; Knoll, J. H. M.; Fleming, J.; Kirkness, E. F.; Martin-Gallardo, A.; Greenberg, F.; Graham, J. M., Jr.; Menninger, J.; Ward, D.; Venter, J. C.; Lalande, M.: Localization of the gene encoding the GABA(A) receptor beta-3 subunit to the Angelman/Prader-Willi region of human chromosome 15. Am. J. Hum. Genet. 49: 330-337, 1991.

Further studies establishing the function and utilities of GABRB3 are found in John Hopkins OMIM database record ID 137192, and in references numbered 751-765 listed hereinbelow.

Reference is now made to NPAS2 BINDING SITE. Neuronal PAS domain protein 2 (NPAS2) is a target gene of GAM26, corresponding to GAM26-TARGET GENE of FIG. 26A. NPAS2 BINDING SITE is a binding site found in an untranslated region of NPAS2, corresponding to BINDING SITE of FIG. 26A. FIG. 26D illustrates the complementarity of the nucleotide sequence of NPAS2 BINDING SITE, designated SEQ ID:173934, to the nucleotide sequence of GAM26 RNA of FIG. 26A, designated SEQ ID:20604.

An additional function of GAM26 is therefore inhibition of neuronal PAS domain protein 2 (NPAS2), a gene which encodes a protein that is a member of basic helix-loop-helix-PAS family of transcription factors. Accordingly, utilities of GAM26 include diagnosis and treatment of the abovementioned diseases and clinical conditions.

The function of NPAS2 has been established by previous studies. Members of the bHLH-PAS family are transcription factors that contain a basic helix-loop-helix (bHLH) DNA-recognition motif located N-terminal to a PAS do main composed of 2 imperfect direct repeats. See BMAL1 (602550). By searching an EST database, Zhou et al. (1997) identified hum an and mouse cDNAs encoding 2 novel bHLH-PAS proteins, NPAS1 (603346) and NPAS2. The predicted 824-amino acid human NPAS2 protein shares 87% sequence identity with mouse Npas2. Northern blot analysis of mouse tissues revealed that Npas2 is expressed predominantly in brain. In situ hybridization indicated that the pattern of Npas2 mRNA distribution in mouse brain is broad and complex, and is largely nonoverlapping with that of Npas1. Hogenesch et al. (1997) identified NPAS2 as MOP4 (member of the PAS superfamily 4). McNamara et al. (2001) reported a hormone-dependent interaction of the nuclear receptors RARA (180240) and RXRA (180245) with CLOCK (601851) and MOP4. They found that these interactions negatively regulate CLOCK-BMAL1 and MOP4-BMAL1 heterodimer-mediated transcriptional activation of clock gene expression in vascular cells. MOP4 exhibited a robust rhythm in the vasculature, and retinoic acid could phase shift PER2 (603426) mRNA rhythmicity in vivo and in serum-induced smooth muscle cells in vitro, providing a molecular mechanism for hormonal control of clock gene expression. McNamara et al. (2001) proposed that circadian or periodic availability of nuclear hormones may play a critical role in resetting a peripheral vascular clock.

Full details of the abovementioned studies are described in the following publications, the disclosure of which are hereby incorporated by reference:

McNamara P.; Seo, S.; Rudic, R. D.; Sehgal, A.; Chakravarti, D.; FitzGerald, G. A.: Regulation of CLOCK and MOP4 by nuclear receptors in the vasculature: a humoral mechanism to reset a peripheral clock. Cell 105: 877-889, 2001. PubMed ID: 114391846. Zhou, Y. -D.; Barnard, M.; Tian, H.; Li, X.; Ring, H. Z.; Francke, U.; Shelton, J.; Richardson, J.; Russell, D. W.; McKnight, S. L.: Molecular characterization of two mammalian bHLH-PAS domain proteins selectively expressed in the central nervous system. Proc. Nat. Acad. Sci. 94: 713-718, 1997.

Further studies establishing the function and utilities are found in John Hopkins OMIM database record ID 603347, and in references numbered 766-771 listed hereinbelow.

Reference is now made to REPS2 BINDING SITE, RALBP1 associated Eps domain containing 2 (REPS2) is a target gene of GAM26, corresponding to GAM26-TARGET GENE of FIG. 26A. REPS2 BINDING SITE is a binding site found in an untranslated region of REPS2, corresponding to BINDING SITE of FIG. 26A. FIG. 26D illustrates the complementarity of the nucleotide sequence of REPS2 BINDING SITE, designated SEQ ID:173934, to the nucleotide sequence of GAM26 RNA of FIG. 26A, designated SEQ ID:20604.

A further function of GAM26 is therefore inhibition RALBP1 associated Eps domain containing 2 (REPS2), a gene which encodes a protein that interacts with the active form of RAS with adaptor protein GRB2 and binds calcium. Accordingly, utilities of GAM26 include diagnosis and treatment of the abovementioned diseases and clinical conditions.

The function of REPS2 has been established by previous studies. Small G proteins have GDP-bound inactive and GTP-bound active forms; RAL proteins (e.g., RALA; 179550) shift from the inactive to the active state through the actions of RALGDS (601619). RALGDS interacts with the active form of RAS (see HRAS; 190020). Using RALA-binding protein-1 (RALBP1; 605801) as bait in a yeast 2-hybrid screen of a brain cDNA library, Ikeda et al. (1998) isolated cDNAs encoding REPS2, which they termed POB1 Sequence analysis predicted that the 521-amino acid protein has 2 potential initiator methionines in its N terminus, a central EPS15 (600051)-like domain, and 2 proline-rich regions and a putative coiled-coil structure in its C terminus. Northern blot analysis revealed strong expression in rat cerebrum cerebellum, lung, and testis, with weak expression in kidney and no expression in heart, thymus, liver, spleen, or adrenal gland. Immunoprecipitation and immunoblot analyses confirmed that the C-terminal 146 amino acids of REPS2 and the C-terminal 147 residues of RALBP1 interact in intact cells. RAL interacts with a distinct region of RALBP1, just N terminal of the REPS2-binding domain, and both proteins can interact simultaneously with RALBP1. Immunoblot analysis established that REPS2 is tyrosine phosphorylated in response to epidermal growth factor (EGF; 131530) and interacts with the EGF receptor (EGFR; 131550), possibly through the adaptor protein GRB2 (108355) with which REPS2 interacts specifically. Using nuclear magnetic resonance spectroscopy, Koshiba et al. (1999) showed that the EPS15 homology domain of REPS2 consists of 2 EF-hand structures, the second of which binds calcium.

Full details of the abovementioned studies are described in the following publications, the disclosure of which are hereby incorporated by reference:

Ikeda, M.; Ishida, O.; Hinoi, T.; Kishida, S.; Kikuchi, A.: Identification and characterization of a novel protein interacting with Ral-binding protein 1, a putative effector protein of Ral. J. Biol. Chem. 273: 814-821, 1998. PubMed ID: 9422736 2. Koshiba, S.; Kigawa, T.; Iwahara, J.; Kikuchi, A.; Yokoyama, S.: Solution structure of the Eps15 homology domain of a human POB1 (partner of RalBP1). FEBS Lett. 442: 138-142, 1999.

Further studies establishing the function and utilities of REPS2 are found in John Hopkins OMIM database record ID 300317, and in references numbered 772-773 listed hereinbelow.

Referring now to SERPINB8 BINDING SITE. Serine (or cysteine) proteinase inhibitor, clade B (ovalbumin), member (SERPINB8) is a target gene of GAM26, corresponding to GAM26-TARGET GENE of FIG. 26A. SERPINB8 BINDING SITE is a binding site found in an untranslated region of SERPINB8, corresponding to BINDING SITE of FIG. 26A. FIG. 26D illustrates the complementarity of the nucleotide sequence of SERPINB8 BINDING SITE, designated SEQ ID:173934, to the nucleotide sequence of GAM26 RNA of FIG. 26A, designated SEQ ID:20604.

Yet a further function of GAM26 is therefore inhibition of serine (or cysteine) proteinase inhibitor, lade B (ovalbumin), member (SERPINB8), a gene which encodes a protein that protease inhibitors; may be a serpin serine protease inhibitor that binds thrombin. Accordingly, utilities of GAM26 include diagnosis and treatment of the abovementioned diseases and clinical conditions. The function and utilities of SERPINB8 have been established by previous studies, as described hereinabove with reference to FIG. 26D.

Reference is now made to GAL BINDING SITE. Galanin (GAL) is a target gene of GAM26, corresponding to GAM26-TARGET GENE of FIG. 26A. GAL BINDING SITE is a binding site found in an untranslated region of GAL, corresponding to BINDING SITE of FIG. 26A. FIG. 26D illustrates the complementarity of the nucleotide sequence of GAL BINDING SITE, designated SEQ ID:174735, to the nucleotide sequence of GAM26 RNA of FIG. 26A, designated SEQ ID:20604.

Another function of GAM26 is therefore inhibition of galanin (GAL), a gene which encodes a hormone that stimulates LH secretion and enhances LHRH-induced LH release from dispersed anterior pituitary cells in vitro. Accordingly, utilities of GAM26 include diagnosis and treatment of the abovementioned diseases and clinical conditions.

The function of GAL has been established by previous studies. Galanin is a 29-amino acid peptide widely distributed in the peripheral and cent al nervous systems. In the brain, the highest concentrations are observed in the hypothalamus and particularly in the nerve terminals of the median eminence. Since the establishment of the neurovascular concept in the regulation of the hypothalamus-pituitary axis (Harris, 1948), it is well known that the median eminence represents a key area for neuroendocrine regulation. Hypothalamic releasing and inhibiting factors are secreted from median eminence terminals into the portal circulation to reach the adenohypophyseal cells where they exert specific actions. Lopez et al. (1991) presented evidence that galanin meets the criteria to be considered a hypothalamic-hypophysiotropic hormone. They found a possibly meaningful colocalization and cosecretion of galanin and LHRH (152760). Galanin stimulates LH secretion and enhances LHRH-induced LH release from dispersed anterior pituitary cells in vitro. Galanin is important to gastrointestinal function also (Rattan, 1991).

Animal model experiments lend further support to the function of GAL. The neuropeptide galanin is predominantly expressed by the lactotrophs (the prolactin-secreting cell type) in the rodent anterior pituitary and in the median eminence and paraventricular nucleus of the hypothalamus. Prolactin (PRL; 76760) and galanin colocalize in the same secretory granule, and the expression of both proteins is extremely sensitive to the estrogen status of the animal. Administration of estradiol-17-beta induces pituitary hyperplasia followed by adenoma formation and causes a 3,000-fold increase in the galanin mRNA content of the lactotroph. To further study the role of galanin in prolactin release and lactotroph growth, Wynick et al. (1998) generated mice carrying a loss-of-function mutation of the endogenous galanin gene. There was no evidence of embryonic lethality and the mutant mice grew normally. The specific endocrine abnormalities identified related to the expression of prolactin. Pituitary prolactin message levels and protein content of adult female mutant mice were reduced by 30 to 40% compared with wildtype controls. Mutant females failed to lactate and pups died of starvation/dehydration unless fostered onto wildtype mothers. Prolactin secretion in mutant females was markedly reduced at 7 days postpartum compared with wildtype controls with an associated failure in mammary gland maturation. There was almost complete abrogation of the proliferative response of the lactotroph to high doses of estrogen, with a failure to upregulate prolactin release and STAT5 (601511) expression or to increase pituitary cell number. These data supported the hypothesis that galanin acts as a paracrine regulator of prolactin expression and as a growth factor to the lactotroph.

It is appreciated that the abovementioned animal model for GAL is acknowledged by those skilled in the art as a scientifically valid animal model, as can be further appreciated from the publications sited hereinbelow.

Full details of the abovementioned studies are described in the following publications, the disclosure of which are hereby incorporated by reference:

Wynick, D.; Small, C. J.; Bacon, A.; Holmes, F. E.; Norman, M.; Ormandy, C. J.; Kilic, E.; Kerr, N. C. H.; Ghatei, M.; Talamantes, F.; Bloom, S. R.; Pachnis, V.: Galanin regulates prolactin release and lactotroph proliferation. Proc. Nat. Acad. Sci. 95: 12671-12676, 1998. PubMed ID: 9770544 6. Lopez, F. J.; Merchenthaler, I.; Ching, M.; Wisniewski, M. G.; Negro-Vilar, A.: Galanin: a hypothalmic-hypophysiotropic hormone modulating reproductive functions. Proc. Nat. Acad. Sci. 88: 4508-4512, 1991.

Further studies establishing the function and utilities of GAL are found in John Hopkins OMIM database record ID 137035, and in referent numbered 774-785 listed hereinbelow.

Referring now to GAL BINDING SITE. Galanin (GAL) is a target gene of GAM26, corresponding to GAM26-TARGET GENE of FIG. 26A. GAL BINDING SITE is a binding site found in an untranslated region of GAL, corresponding to BINDING SITE of FIG. 26A. FIG. 26D illustrates the complementarity of the nucleotide sequence of GAL BINDING SITE, designated SEQ ID:174743, to the nucleotide sequence of GAM26 RNA of FIG. 26A, designated SEQ ID:20604.

Yet another function of GAM26 is therefore inhibition of galanin (GAL), a gene which encodes a hormone that stimulates LH secretion and enhances LHRH-induced LH release from dispersed anterior pituitary cells in vitro. Accordingly, utilities of GAM26 include diagnosis and treatment of the abovementioned diseases and clinical conditions. The function and utilities of GAL have been established by previous studies, as described hereinabove with reference to FIG. 26D.

Reference is now made to GDI1 BINDING SITE. GDP dissociation inhibitor 1 (GDI1) is a target gene of GAM26, corresponding to GAM26-TARGET GENE of FIG. 26A. GDI1 BINDING SITE is a binding site found in an untranslated region of GDI1, corresponding to BINDING SITE of FIG. 26A. FIG. 26D illustrates the complementarity of the nucleotide sequence of GDI1 BINDING SITE, designated SEQ ID:178360, to the nucleotide sequence of GAM26 RNA of FIG. 26A, designated SEQ ID:20604.

An additional function of GAM26 is therefore inhibition of GDP dissociation inhibitor 1 (GDI1), a gene which encodes a protein that is associated with x-linked nonspecific mental retardation (xlmr) types 41 (mrx41) and 48 (mrx48). Accordingly, utilities of GAM26 include diagnosis and treatment of the abovementioned diseases and clinical conditions.

The function of GDI1 has been established by previous studies. GDI binds to the small G proteins of the Rab family, particularly the brain-specific form RAB3A (179490), and modulates their activity and vesicle-mediated transport D'Adamo et al. (1997) noted that GDI is expressed in all parts of the adult brain and, by in situ hybridization analysis, it is detectable in post-mitotic neural cells during mouse development, with the same timing and in the same cell type as Rab3a. Since the RABGDIA gene has these properties and maps to Xq28, it is a plausible candidate gene for one or more forms of X-linked nonspecific mental retardation (MRX) that map to this chromosomal region. Five families with X-linked nonspecific mental retardation had been mapped to Xq28; these families, which are reviewed in 309541, were designated MRX3, MRX25, MRX28, MRX41, and MRX48. D'Adamo et al. (1997) found unique mutations in the RABGDIA gene in affected members of the MRX41 (300104.0001) and MRX48 (300104.0002) families. Chelly (1999) referred to the protein mutant in MRX41 as oligophrenin-2 (OPHN2). Bienvenu et al. (1998) carried out mutation screening of the whole coding region of the GDI1 gene, using a combination of denaturing gradient gel electrophoresis and direct sequencing, in 164 patients found negative for expansions across the FRAXA GCC repeat. In addition to the nonsense mutation found in the MRX48 family (300104.002), they identified a novel missense mutation in exon 11 of the GDI1 gene in a family with nonspecific mental retardation. In this large French family, all affected allowed moderate to severe mental retardation. X-linked semidominant inheritance was strongly suggested by the severe phenotypes in males in comparison to mildly affected females or unaffected obligate carriers. The study suggested that the prevalence of GDI1 mutations in nonspecific mental retardation may be 0.5 to 1%. One of the families included in the study by Bienvenu et al. (1998) was the so-designated MRX16 family reported by Moraine et al. (1994), known to be located in Xq28, in a genetic interval encompassing GDI1. Gendrot et al. (1999) found no mutation in the GDI1 gene in a large MRX16 family.

Full details of the abovementioned studies are described in the following publications, the disclosure of which are hereby incorporated by reference:

Bienvenu, T.; des Portes, V.; Saint Martin, A.; McDonell, N.; Billuart, P.; Carrie, A.; Vinet, M. -C.; Couvert, P.; Toniolo, D.; Ropers, H. -H.; Moraine, C.; van Bokhoven, H.; Fryns, J. -P.; Kahn, A.; Beldjord, C.; Chelly, J.: Nonspecific X-linked semidominant mental retardation by mutations in a Rab GDP-dissociation inhibitor. Hum. Molec. Genet. 7: 1311-1315, 1998. PubMed ID: 9668174
4. D'Adamo, P.; Gulisano, M.; Oostra, B. A.; Chelly, J.; Toniolo, D.: GDI is responsible for X-linked mental retardation. (Abstract) Am. J. Hum. Genet. 61 (suppl.): A11 only, 1997.

Further studies establishing the function and utilities of GDI1 are found in John Hopkins OMIM database record ID 300104, and in references numbered 786-799 listed hereinbelow.

Referring now to GNB1 BINDING SITE. Guanine nucleotide binding protein (G protein), beta polypeptide 1 (GNB1) is a target gene of GAM26, corresponding to GAM26-TARGET GENE of FIG. 26A. GNB1 BINDING SITE is a binding site found in an untranslated region of GNB1, corresponding to BINDING SITE of FIG. 26A. FIG. 26D illustrates the complementarity of the nucleotide sequence of GNB1 BINDING SITE, designated SEQ ID:182802, to the nucleotide sequence of GAM26 RNA of FIG. 26A, designated SEQ ID:20604.

A further function of GAM26 is therefore inhibition of guanine nucleotide binding protein (G protein), beta polypeptide 1 (GNB1), a gene which encodes a protein that transduces signals from G protein-coupled receptors to intracellular effectors. Accordingly, utilities of GAM26 include diagnosis and treatment of the abovementioned diseases and clinical conditions. The function and utilities of GNB1 have been established by previous studies, as described hereinabove with reference to FIG. 26D.

Reference is now made to GPRK5 BINDING SITE. G protein-coupled receptor kinase 5 (GPRK5) is a target gene of GAM26, corresponding to GAM26-TARGET GENE of FIG. 26A. GPRK5 BINDING SITE is a binding site found in an untranslated region of GPRK5, corresponding to BINDING SITE of FIG. 26A. FIG. 26D illustrates the complementarity of the nucleotide sequence of GPRK5 BINDING SITE, designated SEQ ID:186691, to the nucleotide sequence of GAM26 RNA of FIG. 26A, designated SEQ ID:20604.

Yet a further function of GAM26 is therefore inhibition of G protein-coupled receptor kinase 5 (GPRK5) a gene which encodes an enzyme that regulates the activity of G protein-coupled receptors. Accordingly, utilities of GAM26 include diagnosis and treatment of the abovementioned diseases and clinical conditions.

The function of GPRK5 has been established by previous studies. By PCR on neutrophil cDNA using primers based on sequences of known receptor kinases, Haribabu and Snyderman (1993) identified GPRK5 and GPRK6 (600869) sequences. Bullrich et al. (1995) used a rodent-human hybrid panel to map 2 newly identified members of the GRK family: GPRK5 and GPRK6 (600869) to 10q24-qter and 5q35, respectively. The hybrid cells containing parts of chromosomes 10 and 5 were used for the regionalization.

Full details of the abovementioned studies are described in the following publications, the disclosure of which are hereby incorporated by reference:

Bullrich, F.; Druck, T.; Kunapuli, P.; Gomez, J.; Gripp, K. W.; Schlegelberger, B.; Lasota, J.; Aronson, M.; Cannizzaro, L. A.; Huebner, K.; Benovic, J. L.: Chromosomal mapping of the genes GPRK5 and GPRK6 encoding G protein-coupled receptor kinases GRK5 and GRK6. Cytogenet. Cell Genet. 70: 250-254, 1995. PubMed ID: 7789183 2. Haribabu, B.; Snyderman, R.: Identification of additional members of human G-protein-coupled receptor kinase multigene family. Proc. Nat. Acad. Sci. 90: 9398-9402, 1993.

Further studies establishing the function and utilities of GPRK5 are found in John Hopkins OMIM database record ID 600870, and in references numbered 800-801 listed hereinbelow.

Referring now to GSPT1 BINDING SITE. G1 to S phase transition 1 (GSPT1) is a target gene of GAM26, corresponding to GAM26-T GET GENE of FIG. 26A. GSPT1 BINDING SITE is a binding site found in an untranslated region of GSPT1, corresponding to BINDING SITE of FIG. 26A. FIG. 26D illustrates the complementarity of the nucleotide sequence of GSPT1 BINDING SITE, designated SEQ ID:189737, to the nucleotide sequence of GAM26 RNA of FIG. 26A, designated SEQ ID:20604.

Another function of GAM26 is therefore inhibition of G1 to S phase transition 1 (GSPT1), a gene which encodes a protein that involves in regulation of mammalian cell growth. Accordingly, utilities of GAM26 include diagnosis and treatment of the abovementioned diseases and clinical conditions. The function and utilities of GSPT1 have been established by previous studies, as, described hereinabove with reference to FIG. 26D.

Referring now to GSPT1 BINDING SITE. G1 to S phase transition 1 (GSPT1) is a target gene of GAM26, corresponding to GAM26-TARGET GENE of FIG. 26A. GSPT1 BINDING SITE is a binding site found in an untranslated region of GSPT1, corresponding to BINDING SITE of FIG. 26A. FIG. 26D illustrates the complementarity of the nucleotide sequence of GSPT1 BINDING SITE, designated SEQ ID:189752, to the nucleotide sequence of GAM26 RNA of FIG. 26A, designated SEQ ID:20604.

Yet another function of GAM26 is therefore inhibition of G1 to S phase transition 1 (GSPT1), a gene which encodes a protein that involves in regulation of mammalian cell growth. Accordingly, utilities of GAM26 include diagnosis and treatment of the abovementioned diseases and clinical conditions. The function and utilities of GSPT1 have been established by previous studies, as described hereinabove with reference to FIG. 26D.

Referring now to GSPT1 BINDING SITE. G1 to S transition 1 (GSPT1) is a target gene of GAM26, corresponding to GAM26-TARGET GENE of FIG. 26A. GSPT1 BINDING SITE is a binding site found in an untranslated region of GSPT1, corresponding to BINDING SITE of FIG. 26A. FIG. 26D illustrates the complementarity of the nucleotide sequence of GSPT1 BINDING SITE, designated SEQ ID:189763, to the nucleotide sequence of GAM26 RNA of FIG. 26A, designated SEQ ID:20604.

An additional function of GAM26 is therefore inhibition of G1 to S phase transition 1 (GSPT1), a gene which encodes a protein that involves in regulation of mammalian cell growth. Accordingly, utilities of GAM261 include diagnosis and treatment of the abovementioned diseases and clinical conditions. The function and utilities of GSPT1 have been established by previous studies, as described hereinabove with reference to FIG. 26D.

Referring now to GSPT1 BINDING SITE. G1 to S phase transition 1 (GSPT1) is a target gene of GAM26, corresponding to GAM26-TARGET GENE of FIG. 26A. GSPT1 BINDING SITE is a binding site found in an untranslated region of GSPT1, corresponding to BINDING SITE of FIG. 26A. FIG. 26D illustrates the complementarity of the nucleotide sequence of GSPT1 BINDING SITE, designated SEQ ID:189764, to the nucleotide sequence of GAM26 RNA of FIG. 26A, designated SEQ ID:20604.

A further function of GAM26 is therefore inhibition of G1 to S phase transition 1 (GSPT1), a gene which encodes a protein that involves in regulation of mammalian cell growth. Accordingly, utilities of GAM26 include diagnosis and treatment of the abovementioned diseases and clinical conditions. The function and utilities of GSPT1 have been established by previous studies, as described hereinabove with reference to FIG. 26D.

Referring now to GSPT1 BINDING SITE. G1 to S phase transition 1 (GSPT1) is a target gene of GAM26, corresponding to GAM26-TARGET GENE of FIG. 26A. GSPT1 BINDING SITE is a binding site found in an untranslated region of GSPT1, corresponding to BINDING SITE of FIG. 26A. FIG. 26D illustrates the complementarity of the nucleotide sequence of GSPT1 BINDING SITE, designated SEQ ID:189765, to the nucleotide sequence of GAM26 RNA FIG. 26A, designated SEQ ID:20604.

Yet a further function of GAM26 is therefore inhibition of G1 to S phase transition 1 (GSPT1 a gene which encodes a protein that involves in regulation of mammalian cell growth. Accordingly, utilities of GAM26 include diagnosis and treatment of the abovementioned diseases and clinical conditions. The function and utilities of GSPT1 have been established by previous studies, as described hereinabove with reference to FIG. 26D.

Referring now to GSPT1 BINDING SITE. G1 to S transition 1 (GSPT1) is a target gene of GAM26, corresponding to GAM26-TARGET GENE of FIG. 26A. GSPT1 BINDING SITE is a binding site found in an untranslated region of GSPT1, corresponding to BINDING SITE of FIG. 26A. FIG. 26D illustrates the complementarity of the nucleotide sequence of GSPT1 BINDING SITE, designated SEQ ID:189777, to the nucleotide sequence of GAM26 RNA of FIG. 26A, designated SEQ ID:20604.

Another function of GAM26 is therefore inhibition of G1 to S phase transition 1 (GSPT1), a gene which encodes a protein that involves in regulation of mammalian cell growth. Accordingly, utilities of GAM26 include diagnosis and treatment of the abovementioned diseases and clinical conditions. The function and utilities of GSPT1 have been established by previous studies, as described hereinabove with reference to FIG. 26D.

Reference is now made to GTF2I BINDING SITE. General transcription factor II, I (GTF2I) is a target gene of GAM26, corresponding to GAM26-TARGET GENE of FIG. 26A. GTF2I BINDING SITE is a binding site found in an untranslated region of GTF2I, corresponding to BINDING SITE of FIG. 26A. FIG. 26D illustrates the complementarity of the nucleotide sequence of GTF2I BINDING SITE, designated SEQ ID:190454, to the nucleotide sequence of GAM26 RNA of FIG. 26A, designated SEQ ID:20604.

Yet another function of GAM26 is therefore inhibition of general transcription factor II, I (GTF2I), a gene which encodes a transcription factor that interacts with the basal transcription machinery by coordinating the formation of a multiprotein complex at the c-fos promoter, and linking specific signal responsive activator complexes and is associated with Williams-Beuren syndrome. Accordingly, utilities of GAM26 include diagnosis and treatment of the abovementioned diseases and clinical conditions.

The function of GTF2I has been established by previous studies. Through transfection experiments, Roy et al. (1997) found that GTF21 is capable of binding to both a pyrimidine-rich initiator (Inr) and an E-box for upstream stimulatory factor-1 (USF1; 191523). GTF2I and USF1 can also act synergistically to activate transcription through both Inr and the E-box elements of the adenovirus major late promoter. By in vitro cotranslation followed by coimmunoprecipitation studies, Roy et al. (1997) confirmed direct protein interaction between GTF2I and USF1. Williams-Beuren syndrome (WBS; 194050) is a neurodevelopmental disorder with multisystemic manifestations caused by heterozygosity for a partial deletion of 7q11.23. The breakpoints luster within regions located approximately 1 cM at either side of the elastin locus (ELN; 130160). Perez Jurado et al. (1998) characterized a duplicated region near the common deletion breakpoints, which includes a transcribed gene. The centromeric (C) and telomeric (T) copies are almost identical in the duplicated 3-prime portions but diverge at the 5-prime ends. C-specific 4.3-kb mRNA and T-specific 5.4-kb mRNA are widely expressed in embryonic and adult tissues. The telomeric gene gives rise to several tandemly spliced forms and is deleted in all WBS individuals who have documented ELN deletions. Database searches show that this gene encodes BAP135, a protein phosphorylated by BTK in B cells, as well as the multifunctional transcription factor TFII-I; hence, the gene name GTF2I. The centromeric gene is not deleted in WBS and appears to be a partially truncated expressed pseudogene (GTF2IP1) with no protein product. Both loci map to different genomic clone contigs that also contain other deleted and nondeleted loci. The duplicated region containing GTF2I and GTF2IP1, respectively, is located close to the deletion breakpoints and may predispose to unequal meiotic recombination between chromosome 7 homologs and/or to intrachromosomal rearrangements. Hemizygosity for GTF2I may also contribute to the WBS phenotype.

Full details of the abovementioned studies are described in the following publications, the disclosure of which are hereby incorporated by reference:

Perez Jurado, L. A.; Wang, Y. -K.; Peoples, R.; Coloma, A.; Cruces, J.; Francke, U.: A duplicated gene in the breakpoint regions of the 7q11.23 Williams-Beuren syndrome deletion encodes the initiator binding protein TFII-I and BAP-135, a phosphorylation target of BTK Hum. Molec. Genet 7: 325-334, 1998. PubMed ID: 9466987 2. Roy, A. L.; Du, H.; Gregor, P. D.; Novina, C. D.; Martinez, E.; Roeder, R. G.: Cloning of an Inr- and E-box binding protein, TFII-I, that interacts physically and functionally with USF1. EMBO J. 16: 7091-7104, 1997.

Further studies establishing the function and utilities of GTF2I are found in John Hopkins OMIM database record ID 601679, and in references numbered 802-804 listed hereinbelow.

Reference is now made to HCCS BINDING SITE. Holocytochrome c synthase (cytochrome c heme-lyase) (HCCS) is a target gene of GAM26, corresponding to GAM26-TARGET GENE of FIG. 26A. HCCS BINDING SITE is a binding site found in an untranslated region of HCCS, corresponding to BINDING SITE of FIG. 26A. FIG. 26D illustrates the complementarity of the nucleotide sequence of HCCS BINDING SITE, designated SEQ ID:192464, to the nucleotide sequence of GAM26 RNA of FIG. 26A, designated SEQ ID:20604.

An additional function of GAM26 is therefore inhibition of holocytochrome c synthase (cytochrome c heme-lyase) (HCCS), a gene which encodes a enzyme that catalyzes the covalent addition of a heme group onto c-type cytochromes in mitochondria and is associated with Microphthalmia with linear skin defects syndrome and Rett syndrome. Accordingly, utilities of GAM26 include diagnosis and treatment of the abovementioned diseases and clinical conditions.

The function of HCCS has been established by previous studies. Microphthalmia with linear skin defects syndrome (MLS; 309801) is an X-linked male-lethal disorder associated with X-chromosomal rearrangements resulting in monosomy from Xpter to Xp22. Features include microphthalmia, sclerocornea, linear skin defects, and agenesis of the corpus callosum. Using a cross-species conservation strategy, Schaefer et al. (1996) isolated an expressed sequence from the 450- to 550-kb MLS critical region on Xp22 by screening a human embryo cDNA library. Northern analysis demonstrated a transcript of approximately 2.6 kb in all tissues examined, with weaker expression of 1.2- and 5.2-kb transcripts. The strongest expression was observed in heart and skeletal muscle. Sequence analysis of a 3-kb cDNA contig revealed an 807-bp open reading frame encoding putative 268-amino acid protein. Comparison of the sequence with sequences in databases revealed homology with holocytochrome c-type synthetases, which catalyze the covalent addition of a heme group onto c-type cytochromes in mitochondria. The c-type cytochromes are required for proper functioning of the electron transport pathway. The human gene, symbolized HCCS, and the corresponding murine gene characterized by Schaefer et al. (1996) share 83% nucleotide sequence identity and 85% amino acid identity. The authors stated that, because of the lack of a neuromuscular phenotype in MLS, it is uncertain how the deletion of a mitochondrial holocytochrome synthetase would contribute to phenotype seen in MLS. The expression pattern of the gene and knowledge of the function of holocytochrome synthetase suggested, however, that it is a good candidate for X-linked encephalomyopathies typically associated with mitochondrial dysfunction. Based on its chromosomal location and its role in the mitochondrial respiratory chain, HCCS was considered a candidate gene for Rett syndrome (RTT; 312750). The genomic structure of the gene, which occupies an 11-kb region and consists of 7 exons, was determined. No mutational abnormality of the gene was found in 20 RTT patients (Van den Veyver et al., 1998).

Full details of the abovementioned studies are described in the following publications, the disclosure of which are hereby incorporated by reference:

Schaefer, L.; Ballabio, A.; Zoghbi, H. Y.: Cloning and characterization of a putative human holocytochrome c-type synthetase gene (HCCS) isolated from the critical region for microphthalmia with linear skin defects (MLS). Genomics 34: 166-172, 1996. PubMed ID: 8661044 2. Van den Veyver, I. B.; Subramanian, S.; Zoghbi, H. Y.: Genomic structure of a human holocytochrome c-type synthetase gene in Xp22.3 and mutation analysis in patients with Rett syndrome. Am. J. Med. Genet. 78: 179-181, 1998.

Further studies establishing the function and utilities of HCCS are found in John Hopkins OMIM database record ID 300056, and in references numbered 805-806 listed hereinbelow.

Reference is now made to HCN2 BINDING SITE. Hyperpolarization activated cyclic nucleotide-gated potassium channel (HCN2) is a target gene of GAM26, corresponding to GAM26-TARGET GENE of FIG. 26A. HCN2 BINDING SITE is a binding site found in an untranslated region of HCN2, corresponding to BINDING SITE of FIG. 26A. FIG. 26D illustrate the complementarity of the nucleotide sequence of HCN2 BINDING SITE, designated SEQ ID:192735, to the nucleotide sequence of GAM26 RNA of FIG. 26A, designated SEQ ID:20604.

A further function of GAM26 is therefore inhibition of hyperpolarization activated cyclic nucleotide-gated potassium channel (HCN2), a gene which encodes a channel that is hyperpolarization-activated cyclic nucleotide-gated cation channel 2 and may act as a pacemaker in the brain and the heart. Accordingly, utilities of GAM26 include diagnosis and treatment of the abovementioned diseases and clinical conditions.

The function of HCN2 has been established by previous studies. Ludwig et al. (1999) observed that when expressed in HEK293 cells, HCN2 gives rise to hyperpolarization-activated cation currents with the hallmark features of the native cation current. HCN2 has fast activation kinetics, and Ludwig et al. (1999) concluded that HCN2 may underlie the fast component of the cardiac hyperpolarization-activated cation current. By constructing truncation mutants, Wainger et al. (2001) demonstrated that the CNBD inhibits activation of the core transmembrane domain of HCN family members. Cyclic AMP binding relieves this inhibition. Differences in activation gating and extent of cAMP modulation between the HCN1 and HCN2 isoforms result largely from differences in the efficacy of CNBD inhibition.

Full details of the abovementioned studies are described in the following publications, the disclosure of which are hereby incorporated by reference:

Ludwig, A.; Zong, X.; Stieber, J.; Hullin, R.; Hofmann, F.; Biel, M.: Two pacemaker channels from human heart with profoundly different activation kinetics. EMBO J. 18: 2323-2329, 1999. PubMed ID: 10228147 2. Santoro, B.; Grant, S. G. N.; Bartsch, D.; Kandel, E. R.: Interactive cloning with the SH3 domain of N-src identifies a new brain specific ion channel protein, with homology to Eag and cyclic nucleotide-gated channels. Proc. Nat. Acad. Sci. 94: 14815-14820, 1997.

Further studies establishing the function and utilities of HCN2 are found in John Hopkins OMIM database record ID 602781, and in references numbered 807-810 listed hereinbelow.

Reference is now made to HDAC2 BINDING SITE. Histone deacetylase 2 (HDAC2) is a target gene of GAM26, corresponding to GAM26-TARGET GENE of FIG. 26A. HDAC2 BINDING SITE is a binding site found in an untranslated region of HDAC2, corresponding to BINDING SITE of FIG. 26A. FIG. 26D illustrates the complementarity of the nucleotide sequence of HDAC2 BINDING SITE, designated SEQ ID:193593, to the nucleotide sequence of GAM26 RNA of FIG. 26A, designated SEQ ID:20604.

Yet a further function of GAM26 is therefore inhibition of histone deacetylase 2 (HDAC2), gene which encodes an enzyme that is responsible for the deacetylation of lysine residues on the n-terminal part of the core histones and mediates transcriptional repression. Accordingly, utilities of GAM26 include diagnosis and treatment of the abovementioned diseases and clinical conditions.

The function of HDAC2 has been established by previous studies. Zhang et al. (1998) identified the SIN3-associated 30-kD protein SAP30 (603378) as a novel component of the human histone deacetylase complex which is conserved among eukaryotic organisms. This complex includes SIN3, SAP18 (02949), the histone deacetylases HDAC1 (601241) and HDAC2, the histone-binding proteins RbAp46 (RBBP7; 602922) and RbAp48 (RBBP4; 602923), as well as other polypeptides. Yarden and Brody (1999) reported that BRCA1 (113705) interacts in vivo and in vitro with RBBP7 and RBBP4, with RB1 (180200), and that the BRCT domain of BRCA1 associates with HDAC1 and HDAC2. Rountree et al. (2000) showed that DNMT1 (126375) can establish a repressive transcription complex consisting of DNMT1, HDAC2, and DMAP1 (605077). The noncatalytic amino terminus of DNMT1 binds to HDAC2 and to DMAP1 and can mediate transcriptional repression. DMAP1 is targeted to replication foci through interaction with the far N terminus of DNMT1 throughout S phase, whereas HDAC2 joins DNMT1 and DMAP1 only during late S phase, providing a platform for how histones may become deacetylated in heterochromatin following replication.

Full details of the abovementioned studies are described in the following publications, the disclosure of which are hereby incorporated by reference:

Yarden, R. I.; Brody, L. C.: BRCA1 interacts with components of the histone deacetylase complex. Proc. Nat. Acad. Sci. 96: 4983-4988, 1999. PubMed ID: 10220405 4. Rountree, M. R.; Bachman, K. E.; Baylin, S. B.: DNMT1 binds HDAC2 and a new co-repressor, DMAP1, to form a complex at replication foci. Nature Genet. 25: 269-277, 2000.

Further studies establishing the function and utilities of HDAC2 are found in John Hopkins OMIM database record ID 605164, and in references numbered 811-817 listed hereinbelow.

Referring now to HDAC2 BINDING SITE. Histone deacetylase 2 (HDAC2) is a target gene of GAM26, corresponding to GAM26-TARGET GENE of FIG. 26A. HDAC2 BINDING SITE is a binding site found in an untranslated region of HDAC2, corresponding to BINDING SITE of FIG. 26A. FIG. 2 illustrates the complementarity of the nucleotide sequence of HDAC2 BINDING SITE, designated SEQ ID:193594, to the nucleotide sequence of GAM26 RNA of FIG. 26A, designated SEQ ID:20604.

Another function of GAM26 is therefore inhibition of histone deacetylase 2 (HDAC2), a gene which encodes an enzyme that is responsible for the deacetylation of lysine residues on the n-terminal part of the core histones and mediates transcriptional repression. Accordingly, utilities of GAM26 include diagnosis and treatment of the abovementioned diseases and clinical conditions. The function and utilities of HDAC2 have been established by previous studies, as described hereinabove with reference to FIG. 26D.

Reference is now made to IRS1 BINDING SITE. Insulin receptor substrate 1 (IRS1) is a target gene of GAM26, corresponding GAM26-TARGET GENE of FIG. 26A. IRS1 BINDING SITE is a binding site found in an untranslated region of IRS1, corresponding to BINDING SITE of FIG. 26A. FIG. 26D illustrates the complementarity of the nucleotide sequence of IRS1 BINDING SITE, designated SEQ ID:193594, to the nucleotide sequence of GAM26 RNA of FIG. 26A, designated SEQ ID:20604.

Yet another function of GAM26 is therefore inhibition of insulin receptor substrate 1 (IRS1), a gene which encodes a receptor that may mediate the control of various cellular processes by insulin and is associated with DIABETES MELLITUS, TYPE II. Accordingly, utilities of GAM26 include diagnosis and treatment of the abovementioned diseases and clinical conditions.

The function of IRS1 has been established by previous studies. Sun et al. (1991) isolated cDNAs encoding a 160- to 185-kD phosphotyrosyl protein that is a substrate of the insulin receptor tyrosine kinase and a putative participant in insulin (INS; 176730) signaling. This protein, designated insulin receptor substrate-1 (IRS1), is found in a variety of insulin responsive cells and tissues. It exhibits no intrinsic enzyme activity but is believed to serve as a docking protein involved in binding and activating other signal transduction molecules after being phosphorylated on tyrosine by the insulin receptor kinase Almind et al. (1996) examined insulin-stimulated processes in a cultured myeloid progenitor cell stably overexpressing the insulin receptor when transfected with either wildtype human IRS1 or the gly972-to-arg common variant (numbering according to Nishiyama and Wands, 1992). They showed that the mutation in codon 972 of the IRS1 gene impairs insulin-stimulated signaling, especially along the phosphatidylinositol 3-kinase (171834) pathway, and may contribute to insulin resistance in normal and diabetic populations.

Animal model experiments lend further support to the function of IRS1. Clancy et al. (2001) found that mutation of chico extends fruit fly lifespan by up to 48% in homozygotes and 36% in heterozygotes. Extension of lifespan was not a result of impaired oogenesis in chico females, nor was it consistently correlated with increased stress resistance. The dwarf phenotype of chico homozygotes was also unnecessary for extension of lifespan. The role of insulin/IGF signaling in regulating animal aging is therefore evolutionarily conserved.

It is appreciated that the abovementioned animal for IRS1 is acknowledged by those skilled in the art as a scientifically valid an animal model, as can be further appreciated from the publications sited hereinbelow.

Full details of the abovementioned studies are described in the following publications, the disclosure of which are hereby incorporated by reference:

Esposito, D. L.; Mammarella, S.; Ranieri, A.; Loggia, F. D.; Capani, F.; Consoli, A.; Marani-Costantini, R.; Caramia, F. G.; Cama, A.; Battista, P.: Deletion of gly723 in the insulin receptor substrate-1 of a patient with noninsulin-dependent diabetes mellitus. Hum. Mutat. 7: 364-366, 1996. PubMed ID: 8723689 4. Almind, K.; Inoue, G.; Pedersen, O.; Kahn, C. R.: A common amino acid polymorphism in insulin receptor substrate-1 causes impaired insulin signaling: evidence from transfection studies. J. Clin. Invest. 97: 2569-2575, 1996.

Further studies establishing the function and utilities of IRS1 are found in John Hopkins OMIM record ID 147545, and in referent numbered 818-839 listed hereinbelow.

Reference is now made to HIC1 BINDING SITE. Hypermethylated in cancer 1 (HIC1) is a target gene of GAM26, corresponding to GAM26-TARGET GENE of FIG. 26A. HIC1 SITE is a binding site found in an untranslated region of HIC1, corresponding to BINDING SITE of FIG. 26A. FIG. 26D illustrates the complementarity of the nucleotide sequence of HIC1 BINDING SITE, designated SEQ ID:195147, to the nucleotide sequence of GAM26 RNA of FIG. 26A, designated SEQ ID:20604.

An additional function of GAM26 is therefore inhibition of hypermethylated in cancer 1 (HIC1), a gene which encodes a transcription factor that is a transcriptional repressor and may act as a tumor suppressor, and is associated with miller-dieker syndrome. Accordingly, utilities of GAM26 include diagnosis and treatment of the abovementioned diseases and clinical conditions.

The function of HIC1 has been established by previous studies. The human HIC1 (hypermethylated in cancer) gene maps to 17p13.3 and is deleted in the contiguous gene disorder Miller-Dieker syndrome (MDS; 247200) (Makos Wales et al., 1995; Chong et al., 1996). Grimm et al. (1999) isolated the murine Hic1 gene, which encodes a zinc finger protein with a poxvirus and zinc finger (POZ) domain. Comparison of genomic and cDNA sequences predicted 2 exons for the murine Hic1 gene. The second exon exhibits 88% identity at the DNA level to the corresponding region of the human HIC1 gene. During embryonic development, Hic1 is expressed in mesenchymes of the sclerotomes, lateral body wall, limb, and craniofacial regions embedding the outgrowing peripheral nerves during their differentiation. During fetal development, Hic1 is also expressed in mesenchymes apposed to the precartilaginous condensations, at many interfaces to budding epithelia of inner and weakly in muscles. Grimm et al. (1999) observed activation of Hic1 expression in the embryonic anlagen of many tissues displaying anomalies in MDS patients. Besides lissencephaly, MDS patients exhibit facial dysmorphism and frequently additional birth defects, e.g., anomalies of the heart, kidney, gastrointestinal tract, and the limbs. Thus, HIC1 activity may correlate with the defective development of the nose, jaws, extremities, gastrointestinal tract, and kidney in MDS patients.

Animal model experiments lend further support to the function of HIC1. The location of HIC1 in the Miller-Dieker syndrome critical dele on region on 17p13.3 makes it a candidate gene for involvement in the MDS gene deletion syndrome. To study the function of murine Hic1 in development, Carter et al. (2000) created Hic1-deficient mice. They found that these animals died perinatally and exhibited varying combinations of gross developmental defects throughout the second half of development, including acrania, exencephaly, cleft palate, limb anomalies, and omphalocele. These abnormalities demonstrated a role for Hic1 in the development of structures affected in the Miller-Dieker syndrome, and provided functional evidence to strengthen its candidacy as a gene involved in that disorder.

It is appreciated that the abovementioned animal model for HIC1 is acknowledged by those skilled in the art as a scientifically valid animal model, as can be further appreciated from the publications sited hereinbelow.

Full details of the abovementioned studies are described in the following publications, the disclosure of which are hereby incorporated by reference:

Carter, M. G.; Johns, M. A.; Zeng, X.; Zhou, L.; Zink, M. C.; Mankowski, J. L.; Donovan, D. M.; Baylin, S. B.: Mice deficient in the candidate tumor suppressor gene Hic1 exhibit developmental defects of structures affected the Miller-Dieker syndrome. Hum. Molec. Genet. 9: 413-419, 2000. PubMed ID: 10655551 3. Grimm, C.; Sporle, R.; Schmid, T. E.; Adler, I. -D.; Adamski, J.; Schughart, K.; Graw, J.: Isolation and embryonic expression of the novel mouse gene Hic1, the homologue of HIC1, a candidate gene for the Miller-Dieker syndrome. Hum. Molec. Genet. 8: 697-710, 1999.

Further studies establishing the function and utilities of HIC1 are found in John Hopkins OMIM database record ID 603825, and in references numbered 840-843 listed hereinbelow.

Referring now to HIRA BINDING SITE. HIR (histone cell cycle regulation defective, S. cerevisiae) homolog A (HIRA) is a target gene of GAM26, corresponding to GAM26-TARGET GENE of FIG. 26A. HIRA BINDING SITE is a binding site found in an untranslated region of HIRA, corresponding to BINDING SITE of FIG. 26A. FIG. 26D illustrates the complementarity of the nucleotide sequence of BINDING SITE, designated SEQ ID:195839, to the nucleotide sequence of GAM26 RNA of FIG. 26A, designated SEQ ID:20604.

A further function of GAM26 is therefore inhibition of HIR (histone cell cycle regulation defective, S. cerevisiae) homolog A (HIRA), a gene which encodes a transcription factor that could have a part in mechanisms of transcriptional regulation similar to that played by yeast hir1 and hir2 together and is associate with DiGeorge syndrome. Accordingly, utilities of GAM26 include diagnosis and treatment of the abovementioned diseases and clinical conditions. The function and utilities of HIRA have been established by previous studies, as described hereinabove with to FIG. 26D.

Referring now to HIRA BINDING SITE. HIR (histone cell cycle regulation defective, S. cerevisiae) homolog A (HIRA) is a target gene of GAM26, corresponding to GAM26-TARGET GENE of FIG. 26A. HIRA BINDING SITE is a binding site found in an translated region of HIRA, corresponding to BINDING SITE of FIG. 26A. FIG. 26D illustrates the complementarity of the nucleotide sequence of HIRA BINDING SITE, designated SEQ ID:195850, to the nucleotide sequence of GAM26 RNA of FIG. 26A, designated SEQ ID:20604.

Yet a further function of GAM26 is therefore inhibition of HIR (histone cell cycle regulation defective, S. cerevisiae) homolog A (HIRA), a gene which encodes a transcription factor that could have a part in mechanisms of transcriptional regulation similar to that played by yeast hir1 and hir2 together, and is associated with DiGeorge syndrome. Accordingly, utilities of GAM26 include diagnosis and treatment of the abovementioned diseases and clinical conditions. The function and utilities of HIRA have been established by previous studies, as described hereinabove with reference to FIG. 26D.

Reference is now made to HMGA2 BINDING SITE (HMGA2) is a target gene of GAM26, corresponding to GAM26-TARGET GENE of FIG. 26A. HMGA2 BINDING SITE is a binding site found in an untranslated region of HMGA2, corresponding to BINDING SITE of FIG. 26A. FIG. 26D illustrates the complementarity of the nucleotide sequence of HMGA2 BINDING SITE, designated SEQ ID:197765, to the nucleotide sequence of GAM26 RNA of FIG. 26A, designated SEQ ID:20604.

Another function of GAM26 is therefore inhibition of (HMGA2), a gene which encodes a transcription factor that may affect transcription and cell differentiation; shares common DNA-binding motif with other HMG HMG I/Y family members, and is associated with lipoma. Accordingly, utilities of GAM26 include diagnosis and treatment of the abovementioned diseases and clinical conditions.

The function of HMGA2 has been established by previous studies. Ashar et al. (1995) considered the HMGIC gene a good candidate for involvement in lipoma for several reasons, including the facts that it encodes a transcriptional regulating factor, that the pygmy mouse had disproportionately less fat than normal litter mates, and that the mouse gene maps to a region of chromosome 10 with homology of synteny to human 12q14q15. Therefore, they cloned the human gene and investigated its possible role in lipomas. In FISH studies, Ashar et al. (1995) found apparent deletion of the 3-prime end of the HMGIC gene in translocations associated with lipoma. Chimeric transcripts were isolated from 2 lipomas in which HMGIC DNA-binding domains (AT hook motifs) were fused to either a LIM or an acidic transactivator domain. The identification of a gene rearranged in a benign neoplastic process suggests a role for HMGIC in adipogenesis and mesenchymal differentiation.

Animal model experiments lend further support to the function of HMGA2. To evaluate the role of the HMGIC component in the development of lipoma, Arlotta et al. (2000) expressed the DNA-binding domains of HMGIC in transgenic mice. Despite the ubiquitous expression of the truncated HMGIC protein, the transgenic mice developed a selective abundance of fat tissue early in life, showed marked adipose tissue inflammation, and had an abnormally high incidence of lipomas. These findings demonstrated that the DNA-binding domain of HMGIC, in the absence of a C-terminal fusion partner, are sufficient to perturb adipogenesis and predispose lipomas.

It is appreciated that the abovementioned animal model for HMGA2 is acknowledged by those skilled in the art as a scientifically valid animal model, as can be further appreciated from the publications sited hereinbelow.

Full details of the abovementioned studies are described in the following publications, the disclosure of which are hereby incorporated by reference:

Ashar, H. R.; Schoenberg Fejzo, M.; Tkachenko, A.; Zhou, X.; Fletcher, J. A.; Weremowicz, S.; Morton, C. C.; Chada, K.: Disruption of the architectural factor HMGI-C: DNA-binding AT hook motifs fused in lipomas to distinct transcriptional regulatory domains. Cell 82: 57-65, 1995. PubMed ID: 7606786 2. Arlotta, P.; Tai, A. K. -F.; Manfioletti, G.; Clifford, C.; Jay, G.; Ono, S. J.: Transgenic mice expressing a truncated form of the high mobility group I-C protein develop adiposity and an abnormally high prevalence of lipomas. J. Biol. Chem. 275: 14394-4400, 2000.

Further studies establishing the function and utilities of HMGA2 are found in John Hopkins OMIM database record ID 600698, and in references numbered 844-862 listed hereinbelow.

Referring now to HMGA2 BINDING (HMGA2) is a target gene of GAM26, corresponding to GAM26-TARGET GENE of FIG. 26A. HMGA2 BINDING SITE is a binding site found in an untranslated region of HMGA2, corresponding to BINDING SITE of FIG. 26A. FIG. 26D illustrates the complementarity of the nucleotide sequence of HMGA2 BINDING SITE, designated SEQ ID:197853, to the nucleotide sequence of GAM26 RNA of FIG. 26A, designated SEQ ID:20604.

Yet another function of GAM26 is therefore inhibition of (HMGA2), a gene which encodes a transcription factor that may affect transcription and cell differentiation; shares common DNA-binding motif with other HMG HMG I/Y family members and is associated with lipoma. Accordingly, utilities of GAM26 include diagnosis and treatment of the abovementioned diseases and clinical conditions. The function and utilities of HMGA2 have been established by previous studies, as described hereinabove with reference to FIG. 26D.

Reference is now made to HPCAL1 BINDING SITE. Hippocalcin-like 1 (HPCAL1) is a target gene of GAM26, corresponding to GAM26-TARGET GENE of FIG. 26A. HPCAL1 BINDING SITE is a binding site found in an untranslated region of HPCAL1, corresponding to BINDING SITE of FIG. 26A. FIG. 26D illustrates the complementarity of the nucleotide sequence of HPCAL1 BINDING SITE, designated SEQ ID:201019, to the nucleotide sequence of GAM26 RNA of FIG. 26A, designated SEQ ID:20604.

An additional function of GAM26 is therefore inhibition of hippocalcin-like 1 (HPCAL1), a gene which encodes a protein that is a neuron-specific Ca(2+)-binding proteins. Accordingly, utilities of GAM26 include diagnosis and treatment of the abovementioned diseases and clinical conditions.

The function of HPCAL1 has been established by previous studies. Hippocalcin-like-1 is a member of a family of neuron-specific Ca(2+)-binding proteins found in the retina and brain. Using rat hippocalcin (142622) cDNA as a probe in the screening of a human hippocampus cDNA library under low stringency conditions, Kobayashi et al. (1994) isolated a clone that encoded a novel calcium-binding protein structurally related to hippocalcin. They showed that this hippocalcin-like protein has a primary structure of 193 amino acids and contains 3 EF-hand structures and a possible NH2-terminal myristoylation site. A single transcript of 1.7 kb was detected only in the brain.

Full details of the abovementioned studies are described in the following publications, the disclosure of which are hereby incorporated by reference:

Kobayashi, M.; Takamatsu, K.; Fujishiro, M.; Saitoh, S.; Noguchi, T.: Molecular cloning of a novel calcium-binding protein structurally related to hippocalcin from human brain and chromosomal mapping of its gene. Biochim. Biophys. Acta 1222: 515-518, 1994.

Further studies establishing the function and utilities of HPCAL1 are found in John Hopkins OMIM record ID 600207, and in references numbered 863 listed hereinbelow.

Reference is now made to HRB BINDING SITE. HIV-1 Rev binding protein (HRB) is a target gene of GAM26, corresponding to GAM26-TARGET GENE of FIG. 26A. HRB BINDING SITE is a binding site found in an untranslated region of HRB, corresponding to BINDING SITE of FIG. 26A. FIG. 26D illustrates the complementarity of the nucleotide sequence of HRB BINDING SITE, designated SEQ ID:201812, to the nucleotide sequence of GAM26 RNA of FIG. 26A, designated SEQ ID:20604.

A further function of GAM26 is therefore inhibition of HIV-1 Rev binding protein (HRB), a gene which encodes a protein that may function as a cofactor for the Rev/Rex class of RNA export factors. Accordingly, utilities of GAM26 include diagnosis and treatment of the abovementioned diseases and clinical conditions.

The function of HRB has been established by previous studies. Fritz et al. (1995) reported the isolation of a gene they designated 'Rev-interacting protein' (RIP). The cDNA was isolated using the yeast 2-hybrid screening system in a study to identify proteins that interact with the Rev protein of HIV-1 and which thereby assist in HIV replication. A partial clone from the initial screen was used to obtain a full-length 2.4-kb RIP cDNA. The authors found that the predicted 562-amino acid protein is related to the nucleoporins (e.g., 114350), a class of proteins that mediate nucleocytoplasmic transport. The protein was detected in the nuclear extract of HeLa cells and by immunofluorescence on the nuclear surface. Expression studies showed that recombinant RIP did indeed lead to increased Rev activity Salcini et al. (1997) reported that both the RAB and RABR (604018) proteins bind to the EH protein-protein interaction domain found in EPS15 (600051) and other proteins. Coimmunoprecipitation studies demonstrated that RAB and EPS15 are associated in vivo.

Animal model experiments lend further support to the function of HRB. Kang-Decker et al. (2001) generated mice deficient in HRB by targeted disruption. Male mice with a null mutation in Hrb were infertile and displayed round-headed spermatozoa that lacked an acrosome. In wildtype spermatids, Hrb was associated with the cytosolic surface of proacrosomic transport vesicles that fuse to create a single large acrosomic vesicle at step 3 of spermiogenesis. Although proacrosomic vesicles for in spermatids that lack Hrb, the vesicles are unable to fuse, blocking acrosome development at step 2. Kang-Decker et al. (2001) concluded that HRB is required for docking and/or fusion of proacrosomic vesicles during acrosome biogenesis.

It is appreciated that the abovementioned animal model for HRB is acknowledged by those skilled in the art as a scientifically valid animal model, as can be further appreciated from the publications sited hereinbelow.

Full details of the abovementioned studies are described in the following publications, the disclosure of which are hereby incorporated by reference:

Jones, T.; Sheer, D.; Bevec, D.; Kappel, B.; Hauber, J.; Steinkasserer, A.: The human HIV-1 Rev binding-protein hRIP/Rab (HRB) maps to chromosome 2q36. Genomics 40: 198-199, 1997. PubMed ID: 9070945 4. Kang-Decker, N.; Mantchev, G. T.; Juneja, S. C.; McNiven, M. A.; van Deursen, J. M. A.: Lack of acrosome formation in Hrb-deficient mice. Science 294: 1531-1533, 2001.

Further studies establishing the function and utilities of HRB are found in John Hopkins OMIM database record ID 600862, and in references numbered 864-868 listed hereinbelow.

Reference is now made to HS3ST3B1 BINDING SITE. heparan sulfate (glucosamine) 3-O-sulfotransferase 3B1 (HS3ST3B1) is a target gene of GAM26, corresponding to GAM26-TARGET GENE of FIG. 26A. HS3ST3B1 BINDING SITE is a binding site found in an untranslated region of HS3ST3B1, corresponding to BINDING SITE of FIG. 26A. FIG. 26D illustrates the complementarity of the nucleotide sequence of HS3ST3B1 BINDING SITE, designated SEQ ID:202532, to the nucleotide sequence of GAM26 RNA of FIG. 26A, designated SEQ ID:20604.

Yet a further function of GAM26 is therefore inhibition of heparan sulfate (glucosamine) 3-O-sulfotransferase 3B1 (HS3ST3B1), a gene which encodes an enzyme that plays a role in the generation of heparan sulfate proteoglycan. Accordingly, utilities of GAM26 include diagnosis and treatment of the abovementioned diseases and clinical conditions.

The function of HS3ST3B1 has been established by previous studies. Heparan sulfate biosynthetic enzymes are key components in generating a myriad of distinct heparan sulfate fine structures that carry out multiple biologic activities. The heparan sulfate D-glucosaminyl 3-O-sulfotransferases (3OSTs) place the rare 3-O-sulfate group in various sequence contexts. See 3OST2 (604056). Shworak et al. (1999) isolated cDNAs encoding 3OST2, 3OST3A1 (604057), 3OST3B1, and 3OST4 (604059). Like 3OST2 and 3OST3A1, the predicted 390-amino acid 3OST3B1 protein is a type II integral membrane protein. Although the 3OST2 and 3OST3 enzymes have a similar regional organization, the homology between them is limited to their C-terminal sulfotransferase domains. In a companion paper, Liu et al. (1999) demonstrated that the 3OST3A and 3OST3B isoforms sulfate an identical disaccharide. By Southern blot analysis, Shworak et al. (1999) determined that the human genome contains 2 copies of the 3OST3A1 and 3OST3B1 genes; they named the duplicate genes 3OST3A2 and 3OST3B2. Northern blot analysis revealed that the 3OST3B gene was widely expressed as multiple transcripts, with the most abundant expression in liver and placenta. Using an interspecific backcross, Shworak et al. (1999) found that the mouse 3Ost3A and 3Ost3B genes are tightly linked on chromosome 11, suggesting that the 2 genes arose by a tandem duplication. By inclusion within mapped clones, the mapped the human 3OST3A1 and 3OST3B1 genes to 17p12-p11.2.

Full details of the abovementioned studies are described in the following publications, the disclosure of which are hereby incorporated by reference:

Liu, J.; Shworak N. W.; Sinay, P.; Schwartz, J. J.; Zhang, L.; Fritze, L. M.; Rosenberg, R. D.: Expression of heparan sulfate D-glucosaminyl 3-O-sulfotransferase isoforms reveals novel substrate specificities. J. Biol. Chem. 274: 5185-5192, 1999. PubMed ID: 9988768 Shworak, N. W.; Liu, J.; Petros, L. M.; Zhang, L.; Kobayashi, M.; Copeland, N. G.; Jenkins, N. A.; Rosenberg, R. D.: Multiple isoforms of heparan sulfate D-glucosaminyl 3-O-sulfotransferase: isolation, characterization, and expression of human cDNAs and identification of distinct genomic loci. J. Biol. Chem. 274: 5170-5184, 1999.

Further studies establishing the function and utilities of HS3ST3B1 are found in John Hopkins OMIM database record ID 604058, and in references numbered 869-870 listed hereinbelow.

Reference is now made to ING1L BINDING SITE. Inhibitor of growth family, member 1-like (ING1L) is a target gene of GAM26, corresponding to GAM26-TARGET GENE of FIG. 26A. ING1L BINDING SITE is a binding site found in an untranslated region of ING1L, corresponding to BINDING SITE of FIG. 26A. FIG. 26D illustrates the complementarity of the nucleotide sequence of ING1L BINDING SITE, designated SEQ ID:213784, to the nucleotide sequence of GAM26 RNA of FIG. 26A, designated SEQ ID:20604.

Another function of GAM26 is therefore inhibition of inhibitor of growth family, member 1-like (ING1L), a gene which encodes a protein that may interfere with signals transmitted through p53 and p33 (ING1), and is associated with colon tumors and hepatocellular carcinoma. Accordingly, utilities of GAM26 include diagnosis and treatment of the abovementioned diseases and clinical conditions.

The function of ING1L has been established by previous studies. The ING1 gene (601566) encodes a putative tumor suppressor. By searching a human EST database for cDNAs with sequence similarity to ING1, Shimada et al. (1998) identified a partial ING1-like (ING1L) cDNA. Using this partial cDNA, they isolated a full-length human fetal brain ING1L cDNA. The deduced 280-amino acid ING1L protein shares 58.9% sequence identity with ING1. ING1L contains a C-terminal PHD-type zinc finger domain. The PHD zinc finger was first identified in 2 closely related plant homeodomain-containing proteins. It is a cys4-his-cys3 (C4HC3)-type motif spanning 50 to 80 amino acids. PHD zinc fingers have been found in a number of proteins implicated in chromatin-mediated transcriptional control. Northern blot analysis of normal human tissues detected ubiquitous expression of 1.3- and 1.5-kb ING1L transcripts. The authors found that ING1L expression was significantly higher in colon tumors than in the adjacent normal colon tissue. Nagashima et al. (2001) cloned ING1L, which they termed p33ING2. Western blot analysis showed ubiquitous but variable expression of ING1, while p33ING2 expression was highly variable or absent in many cell lines. Highest expression of p33ING2 occurred in cell lines with null or mutant p53 (191170). The DNA-damaging agents etoposide and neocarzinostatin induced expression of p33ING2 but not ING1. Like ING1, p33ING2 was found to negatively regulate cell growth and survival in a p53-dependent manner through the induction of G1-phase cell-cycle arrest and apoptosis. p33ING2 enhanced the transcriptional transactivation activity of p53 and increased the acetylation of p53 at lys382. Western blot analysis detected ING1 but not p33ING2 in p53 immunoprecipitates. Nagashima et al. (2001) concluded that p33ING2 is a DNA damage-inducible gene that negatively regulates cell proliferation through activation of p53 by enhancing its acetylation.

Full details of the abovementioned studies are described in the following publications, the disclosure of which are hereby incorporated by reference:

Nagashima, M.; Shiseki, M.; Miura, K.; Hagiwara, K.; Linke, S. P.; Pedeux, R.; Wang, X. W.; Yokota, J.; Riabowol, K.; Harris, C. C.: DNA damage-inducible gene p33ING2 negatively regulates cell proliferation through acetylation of p53. Proc. Nat. Acad. Sci. 98: 9671-9676, 2001. PubMed ID: 11481424 2. Shimada, Y.; Saito, A.; Suzuki, M.; Takahashi, E.; Horie, M.: Cloning of a novel gene (ING1L) homologous to ING1, a candidate tumor suppressor. Cytogenet Cell Genet. 83: 232-235, 1998.

Further studies establishing the function and utilities of ING1L are found in John Hopkins OMIM database record ID 604215, and in references numbered 871-872 listed hereinbelow.

Referring now to ING1L BINDING SITE. Inhibitor of growth family, member 1-like (ING1L) is a target gene of GAM26, corresponding to GAM26-TARGET GENE of FIG. 26A. ING1L BINDING SITE is a binding site found in an untranslated region of ING1L, corresponding to BINDING SITE of FIG. 26A. FIG. 26D illustrates the complementarity of the nucleotide sequence of ING1L BINDING SITE, designated SEQ ID:213788, to the nucleotide sequence of GAM26 RNA of FIG. 26A, designated SEQ ID:20604.

Yet another function of GAM26 is therefore inhibition of inhibitor of growth family, member 1-like (ING1L), a gene which encodes a protein that may interfer with signals transmitted through p53 and p33 (ING1), and is associated with colon tumors and hepatocellular carcinoma. Accordingly, utilities of GAM26 include diagnosis and treatment of the abovementioned diseases and clinical conditions. The function and utilities of ING1L have been established by previous studies, as described hereinabove with reference to FIG. 26D.

Referring now to IRS1 BINDING SITE. Insulin receptor substrate 1 (IRS1) is a target gene GAM26, corresponding to GAM26-TARGET GENE of FIG. 26A. IRS1 BINDING SITE a binding site found in an untranslated region of IRS1, corresponding to BINDING SITE of FIG. 26A. FIG. 26D illustrates the complementarity of the nucleotide sequence of IRS1 BINDING SITE, designated SEQ ID:215707, to the nucleotide sequence of GAM26 RNA of FIG. 26A, designated SEQ ID:20604.

An additional function of GAM26 is therefore inhibition of insulin receptor substrate 1 (IRS1), a gene which encodes a receptor that may mediate the control of various cellular processes by insulin and is associated with DIABETES MELLITUS, TYPE II. Accordingly, utilities of GAM26 include diagnosis and treatment of the abovementioned diseases and clinical conditions. The function and utilities of IRS1 have been established by previous studies, as described hereinabove with reference to FIG. 26D.

Reference is now made to KCNA6 BINDING SITE. Potassium voltage-gated channel, shaker-related subfamily, member 6 (KCNA6) is a target gene of GAM26, corresponding to GAM26-TARGET GENE of FIG. 26. KCNA6 BINDING SITE is a binding site found in an untranslated region of KCNA6, corresponding to BINDING SITE of FIG. 26A. FIG. 26D illustrates the complementarity of the nucleotide sequence of KCNA6 BINDING SITE, designated SEQ ID:221336, to the nucleotide sequence of GAM26 RNA of FIG. 26A, designated SEQ ID:20604.

A further function of GAM26 is therefore inhibition of potassium voltage-gated channel, shaker-related subfamily, member 6 (KCNA6), a gene which encodes a protein that mediates the voltage-dependent potassium ion permeability of excitable membranes. Accordingly, utilities of GAM26 include diagnosis and treatment of the abovementioned diseases and clinical conditions.

The function of KCNA6 has been established by previous studies. By screening a human fetal cDNA library with a rat RCK3 potassium channel cDNA, Grupe et al. (1990) isolated cDNAs encoding a protein that they designated HBK2 (human brain potassium channel-2). The authors also cloned cDNAs corresponding to the rat homolog, RCK2. The predicted 52-amino acid HBK2 protein shares 94% identity with RCK2. HBK2 and RCK2 have the characteristic structure of voltage-gated ionic channels, with 6 potential membrane-spanning segments. When expressed in Xenopus oocytes, the HBK2/RCK2 channels exhibited the functional characteristics of a delayed-rectifier channel that acts especial in the more positive membrane voltage range. The functional and pharmacologic properties of HBK2/RCK2 potassium channels were distinct from those of previously characterized channels. Grupe et al. (1990) determined that the HBK2 gene did not contain introns. Using interspecific backcrosses between Mus musculus and Mus spretus, Klocke et al. (1993) mapped the mouse gene encoding the Kv1.6 potassium voltage-gated channel, Kcna6, to chromosome 6 in a cluster with Kcna1, Kcna5 (176267), and the homolog of human TPI1 (190450). Since human TPI1 is located on band 12p13, Klocke et al. (1993) predicted that the human KCNA6 gene is located on 12p near other genes of the Shaker-related subfamily, KCNA1 and 5. Albrecht et al. (1995) determined that a 300-kb cluster on chromosome 12p13 contains the human KCNA6, KCNA1, and KCNA5 genes arranged in tandem Full details of the abovementioned studies are described in the following publications, the disclosure of which are hereby incorporated by reference:

Albrecht, B.; Weber, K.; Pongs, O.: Characterization of a voltage-activated K-channel gene cluster on human chromosome 12p13. Receptors Channels 3: 213-220, 1995. PubMed ID: 8821794 2. Grupe, A.; Schroter, K. H.; Ruppersberg, J. P.; Stocker, M.; Drewes, T.; Beckh, S.; Pongs, O.: Cloning and expression of a human voltage-gated potassium channel: a novel member of the RCK potassium channel family. EMBO J. 9: 1749-1756, 1990.

Further studies establishing the function and utilities KCNA6 are found in John Hopkins OMIM database record ID 176257, and in references numbered 873-875 listed hereinbelow.

Reference is now made to KCNA7 BINDING SITE. Potassium voltage-gated channel, shaker-related subfamily, member 7 (KCNA7) is a target gene of GAM26, corresponding to GAM26-TARGET GENE of FIG. 26. KCNA7 BINDING SITE is a binding site found in an untranslated region of KCNA7, corresponding to BINDING SITE of FIG. 26A. FIG. 26D illustrates the complementarity of the nucleotide sequence of KCNA7 BINDING SITE, designated SEQ ID:221548, to the nucleotide sequence of GAM26 RNA of FIG. 26A, designated SEQ ID:20604.

Yet a further function of GAM26 is therefore inhibition of potassium voltage-gated channel, shaker-related subfamily, member 7 (KCNA7), a gene which encodes a protein allows nerve cells to efficiently repolarize following an action potential. Accordingly, utilities of GAM26 include diagnosis treatment of the abovementioned diseases and clinical conditions.

The function of KCNA7 has been established by previous studies. See 176260 for a general discussion of potassium voltage-gated ion channels. Using a probe from the mouse in the study of somatic cell hybrids, McPherson et al. (1991) found that a seventh member of the Shaker-related potassium voltage-gated channel is encoded by a gene on chromosome 19. Kalman et al. (1998) reported the isolation of the mouse voltage-gated Shaker-related potassium channel gene, Kv1.7 (Kcna7). Unlike other known Kv1 family genes that have intronless coding regions, the protein-coding region of Kv1.7 was interrupted by 1.9-kb intron. The gene was mapped to mouse chromosome 7 and human chromosome 19q13.3. The mouse Kv1.7 channel was voltage-dependent and exhibited cumulative inactivation. Northern blot analysis revealed transcripts of approximately 3 kb in mouse heart and skeletal muscle. Bardien Kruger et al. (2002) deduced the coding region of KCNA7 by aligning the mouse cDNA sequence with a human BAC clone and mouse EST sequences. The region encodes a protein of 456 amino acid residues containing cytoplasmic N- and C-termini, a central core domain composed of 6 transmembrane segments and the characteristic pore-loop. The human intron was 1153 bp in length and smaller than that of mouse (1929 bp). Using the deduced amino acid sequences, the potassium-channels of the 2 species were highly conserved (greater than 95%). The expression of KCNA7 in human adult heart was confirmed by RT-PCR studies. Bardien-Kruger et al. (2002) refined the location of the KCNA7 gene within chromosome 19q13.3 by bioinformatic in silico mapping and implicated it as a positional candidate gene for progressive familial heart block type I (604559), an autosomal dominant cardiac conduction disorder mapped to 19q13.3. In affected individuals, Bardien-Kruger et al. (2002) screened the coding region of KCNA7 by PCR-SSCP analysis and direct DNA sequencing, which did not reveal any pathogenic sequence changes Full details of the abovementioned studies are described in the following publications, the disclosure of which are hereby incorporated by reference:

Bardien-Kruger, S.; Wulff, H.; Arieff, Z.; Brink, P.; Chandy, K. G.; Corfield, V.: Characterisation of the human voltage-gated potassium channel gene, KCNA7, a candidate gene for inherited cardiac disorders, and its exclusion as cause of progressive familial heart block I (PFHBI). Europ. J. Hum. Genet. 10: 36-43, 2002. PubMed ID: 11896454 2. Kalman, K.; Nguyen, A.; Tseng-Crank, J.; Dukes, I. D.; Chandy, G.; Hustad, C. M.; Copeland, N. G.; Jenkins, N. A.; Mohrenweiser, H.; Brandriff, B.; Cahalan, M.; Gutman, G. A.; Chandy, K. G.: Genomic organization, chromosomal localization, tissue distribution, and biophysical characterization of a novel mammalian Shaker-related voltage-gated potassium channel, Kv1.7. J. Biol. Chem. 273: 5851-5857, 1998.

Further studies establishing the function and utilities of KCNA7 are found in John Hopkins OMIM database record ID 176268, and in references numbered 876-878 listed hereinbelow.

Referring now to KCNA7 BINDING SITE. Potassium voltage-gated channel, shaker-related subfamily, member 7 (KCNA7) is a target gene of GAM26, corresponding to GAM26-TARGET GENE of FIG. 26A. KCNA7 BINDING SITE is a binding site found in an untranslated region of KCNA7, corresponding to BINDING SITE of FIG. 26A. FIG. 26D illustrates the complementarity of the nucleotide sequence of KCNA7 BINDING SITE, designated SEQ ID:221616, to the nucleotide sequence of GAM26 RNA of FIG. 26A, designated SEQ ID:20604.

Another function of GAM26 is therefore inhibition of potassium voltage-gated channel, shaker-related subfamily, member 7 (KCNA7), a gene which encodes a protein that allows nerve cells to efficiently repolarize following an action potential. Accordingly, utilities of GAM26 include diagnosis and treatment of the abovementioned diseases and clinical conditions. The function and utilities of KCNA7 have been established by previous studies, as described hereinabove with reference to FIG. 26D.

Referring now to KCNA7 BINDING SITE. Potassium voltage-gated channel, shaker-related subfamily, member 7 (KCNA7) is a target gene of GAM26, corresponding to GAM26-TARGET GENE of FIG. 26A. KCNA7 BINDING SITE is a binding site found in an untranslated region of KCNA7, corresponding to BINDING SITE of FIG. 26A. FIG. 26D illustrates the complementarity of the nucleotide sequence of KCNA7 BINDING SITE, designated SEQ ID:221618, to the nucleotide sequence of GAM26 RNA of FIG. 26A, designated SEQ ID:20664.

Yet another function of GAM26 is therefore inhibition of potassium voltage-gated channel, shaker-related subfamily, member 7 (KCNA7), a gene which encodes a protein that allows nerve cells to efficiently repolarize following an action potential. Accordingly, utilities of GAM26 include diagnosis and treatment of the abovementioned diseases and clinical conditions. The function and utilities of KCNA7 have been established by previous studies, as described hereinabove, with reference to FIG. 26D.

Reference is now made to KCNF1 BINDING SITE. Potassium voltage-gated channel, subfamily F, member 1 (KCNF1) is a target gene of GAM26, corresponding to GAM26-TARGET GENE of FIG. 26A. KCNF1 BINDING SITE is a binding site found in an untranslated region of KCNF1, corresponding to BINDING SITE of FIG. 26A. FIG. 26D illustrates the complementarity of the nucleotide sequence of KCNF1 BINDING SITE, designated SEQ ID:222269, to the nucleotide sequence of GAM26 RNA of FIG. 26A, designated SEQ ID:20604.

An additional function of GAM26 is therefore inhibition of potassium voltage-gated channel, subfamily F, member 1 (KCNF1), a gene which encodes a protein that mediates the voltage-dependent potassium ion permeability of excitable membranes. Accordingly, utilities of GAM26 include diagnosis and treatment of the abovementioned diseases and clinical conditions.

The function of KCNF1 has been established by previous studies. Voltage-gated potassium channels are a family of plasma membrane proteins containing 6 putative transmembrane domains. See KCNA1 (176260). Su et al. (1997) identified ESTs encoding 2 novel putative potassium channels, KH1 and KH2 (603788). By screening a fetal brain library with a probe derived from the KH1 EST, they isolated cDNAs corresponding to the entire KH1 coding region. The KH1 gene shares 88% nucleotide homology with a rat potassium channel gene, IK8. The predicted 495-amino acid human protein contains 6 putative transmembrane domains. Northern blot analysis revealed that KH1 was expressed as a 5-kb mRNA in all tissues tested, with the highest levels in heart. A 2.4 kb transcript was detected only in brain. By fluorescence in situ hybridization, Su et al. (1997) mapped the KCNF1 gene to 2p25

Full details of the abovementioned studies are described in the following publications, the disclosure of which are hereby incorporated by reference:

u, K.; Kyaw, H.; Fan, P.; Zeng, Z.; Shell, B. K.; Carter, K. C.; Li, Y.: Isolation, characterization and mapping of two human potassium channels. Biochem. Biophys. Res. Commun. 241: 675-681, 1997.

Further studies establishing the function and utilities of KCNF1 are found in John Hopkins OMIM database record ID 603787, and in references numbered 879 listed hereinbelow.

Reference is now made to KCNK3 BINDING SITE. Potassium channel, subfamily K, member 3 (TASK-1) (KCNK3) is a target gene of GAM26, corresponding to GAM26-TARGET GENE of FIG. 26A. KCNK3 BINDING SITE is a binding site found in an untranslated region of KCNK3, corresponding to BINDING SITE of FIG. 26A. FIG. 26D illustrates the complementarity of the nucleotide sequence of KCNK3 BINDING SITE, designated SEQ ID:223599, to the nucleotide sequence of GAM26 RNA of FIG. 26, designated SEQ ID:20604.

A further function of GAM26 is therefore inhibition of potassium channel, subfamily K, member 3 (TASK-1) (KCNK3), a gene which encodes a protein that is a ph-dependent, voltage-insensitive, background potassium channel. Accordingly, utilities of GAM26 include diagnosis and treatment of the abovementioned diseases and clinical conditions.

The function of KCNK3 has been established by previous studies. Potassium channels are ubiquitous multisubunit membrane proteins that regulate membrane potential in numerous cell types. One family of mammalian K+ channels is characterized by the presence of 4 transmembrane domains and 2 P domains per subunit; this family includes TASK, TWIK (KCNK1; 601745), and TREK (KCNK2; 603219). Duprat et al. (1997) identified mouse expressed sequence tags with similarity to TREK and TWIK and cloned a corresponding cDNA from a mouse bra library. The mouse cDNA was used to clone the human counterpart from a kidney cDNA library. The human cDNA, designated TASK encodes a 394-amino acid polypeptide with 85% identity to the mouse ortholog. The sequence contains consensus sites for N-linked glycosylation and for phosphorylation at the C-terminal. Northern blot analysis showed that TASK is expressed in a variety of human tissues, with highest levels in pancreas and placenta. Expression of the TASK cDNA revealed that the functional protein creates currents that are K(+)-selective, instantaneous, and noninactivating. These currents showed an outward rectification when external K+ was low, but evinced absence of activation and inactivation kinetics as well as voltage independence, characteristics of so-called leak or background conductance. TASK currents were very sensitive to small changes in extracellular pH, suggesting that TASK has a role in cellular responses to changes in extracellular pH. Lesage and Lazdunski (1998) used a radiation hybrid mapping panel to map the human KCNK3 gene to chromosome 2p23 between markers WI13615 and WI11298. By fluorescene in situ hybridization, Manjunath et al. (1999) mapped the KCNK3 gene to 2p24.1-p23.3 and the mouse homolog to chromosome 5B.

Full details of the abovementioned studies are described in the following publications, the disclosure of which are hereby incorporated by reference:

Lesage, F.; Lazdunski, M.: Mapping of human potassium channel genes TREK-1 (KCNK2) and TASK (KCNK3) to chromosomes 1q41 and 2p23. Genomics 51: 478-479, 1998. PubMed ID: 9721223 3. Manjunath, N. A.; Bray-Ward, P.; Goldstein, S. A. N.; Gallagher, P. G.: Assignment of the 2P domain, acid-sensitive potassium channel OAT1 gene KCNK3 to human chromosome bands 2p24.1-p23.3 an murine 5B by in situ hybridization. Cytogenet. Cell Genet. 86: 242-243, 1999.

Further studies establishing the function and utilities of KCNK3 are found in John Hopkins OMIM database record ID 603220, and in references numbered 880-882 listed hereinbelow.

Referring now to KCNK3 BINDING SITE. Potassium channel, subfamily K, member 3 (TASK-1) (KCNK3) is a target gene of GAM26, corresponding to GAM26-TARGET GENE of FIG. 26A. KCNK3 BINDING SITE is a binding site found in an untranslated region of KCNK3, corresponding to BINDING SITE of FIG. 26A. FIG. 26D illustrates the complementarity of the nucleotide sequence of KCNK3 BINDING SITE, designated SEQ ID:223678, to the nucleotide sequence of GAM26 RNA of FIG. 26A, designated SEQ ID:20604.

Yet a further function of GAM26 is therefore inhibition of potassium channel, subfamily K, member 3 (TASK-1) (KCNK3), a gene which encodes a protein that is a ph-dependent voltage-insensitive, background potassium channel. Accordingly, utilities of GAM26 include diagnosis and treatment of the abovementioned diseases and clinical conditions. The function and utilities of KCNK3 have been established by previous studies, as described hereinabove with reference to FIG. 26D.

Referring now to KCNK3 BINDING SITE. Potassium channel, subfamily K, member 3 (TASK-1) (KCNK3) is a target gene of GAM26, corresponding to GAM26-TARGET GENE of FIG. 26A. KCNK3 BINDING SITE is a binding site found in an untranslated of KCNK3, corresponding to BINDING SITE of FIG. 26A. FIG. 26D illustrates the complementarity of the nucleotide sequence of KCNK3 BINDING SITE, designated SEQ ID:223685, to the nucleotide sequence of GAM26 RNA of FIG. 26A, designated SEQ ID:20604.

Another function of GAM26 is therefore inhibition of potassium channel, subfamily K, member 3 (TASK-1) (KCNK3), a gene which encodes a protein that is a ph-dependent, voltage-insensitive, background potassium channel. Accordingly, utilities of GAM26 include diagnosis and treatment of the abovementioned diseases and clinical conditions. The function and utilities of KCNK3 have been established by previous studies, as described hereinabove with reference to FIG. 26D.

Reference is now made to KCNMB4 BINDING SITE. Potassium large conductance calcium-activated channel, subfamily M, be (KCNMB4) is a target gene of GAM26, corresponding to GAM26-TARGET GENE of FIG. 26A. KCNMB4 BINDING SITE is a binding site found in an untranslated region of KCNMB4, corresponding to BINDING SITE of FIG. 26A. FIG. 26D illustrates the complementarity of the nucleotide sequence of KCNMB4 BINDING SITE, designated SEQ ID:224477, to the nucleotide sequence of GAM26 RNA of FIG. 26A, designated SEQ ID:20604.

Yet another function of GAM26 is therefore inhibition of potassium large conductance calcium-activated channel, subfamily M, be (KCNMB4), a gene which encodes a protein that regulates gating kinetics of slow K channels in a Ca-sensitive manner. Accordingly, utilities of GAM26 include diagnosis and treatment of the abovementioned diseases and clinical conditions.

The function of KCNMB4 has been established by previous studies. The large conductance, calcium-activated potassium (BK) channel is a member of the Shaker-related 6-transmembrane domain potassium channel superfamily that is sensitive to voltage and calcium. BK channels are composed of a pore-forming alpha subunit (KCNMA1, or HSLO; 600150) and, in some tissues, a beta subunit. The beta-1 subunit (KCNMB1; 603951) is expressed predominantly in smooth muscle cells, whereas the beta-2 subunit (KCNMB2; 605214) is expressed in endocrine tissue, such as adrenal chromaffin cells. By searching EST databases, Behrens et al. (2000) and Brenner et al. (2000) identified cDNAs encoding KCNMB4. Sequence analysis predicted that the 210-amino acid KCNMB4 protein contains 2 conserved transmembrane domains and an extracellular domain containing an N-glycosylation site and 4 cys residues; however, like KCNMB3 (605222), KCNMB4 lacks the putative charybdotoxin/iberiotoxin-binding site. RNA dot blot analysis by Behrens et al. (2000) revealed high and specific expression of KCNMB4 in central nervous system tissue, with no expression in nonneuronal tissue. Northern blot analysis by Behrens et al. (2000) and Brenner et al. (2000) detected major 1.9- and minor 3.0- and 6.1-kb KCNMB4 transcripts in all brain tissues. Functional analysis of the effects of KCNMB4 on KCNMA1 showed that KCNMB4 slows activation kinetics, leads to steeper calcium sensitivity, and shifts the voltage range of BK current activation to more negative potentials than does KCNMB1. KCNMA1/KCNMB4 channels were not blocked by charybdotoxin or iberiotoxin and were activated by 17-beta-estradiol (Behrens et al., 2000). By electronic PCR, Behrens et al. (2000) mapped the KCNMB4 gene to 12q14.1-q15

Full details of the abovementioned studies are described in the following publications, the disclosure of which are hereby incorporated by reference:

Behrens, R.; Nolting, A.; Reimann, F.; Schwarz, M.; Waldschutz, R.; Pongs, O.: hKCNMB3 and hKCNMB4, cloning and characterization of two members of the large-conductance calcium-activated potassium channel beta subunit family. FEBS Lett. 474: 99-106, 2000. PubMed ID:10828459 2. Brenner, R.; Jegla, T. J.; Wickenden, A.; Liu, Y.; Aldrich, R. W.: Cloning and functional characterization of novel large conductance calcium-activated potassium channel beta subunits, hKCNMB3 and hKCNMB4. J. Biol. Chem. 275: 6453-6461, 2000.

Further studies establishing the function and utilities of KCNMB4 are found in John Hopkins OMIM database record ID 605223, and references numbered 883-884 listed hereinbelow.

Referring now to KCNMB4 BINDING SITE. Potassium large conductance calcium-activated channel, subfamily M, be (KCNMB4) is a target gene of GAM26, corresponding to GAM26-TARGET GENE of FIG. 26A. KCNMB4 BINDING SITE is a binding site found in an untranslated region of KCNMB4, corresponding to BINDING SITE of FIG. 26A. FIG. 26D illustrates the complementarity of the nucleotide sequence of KCNMB4 BINDING SITE, designated SEQ ID:224480, to the nucleotide sequence of GAM26 RNA of FIG. 26A, designated SEQ ID:20604.

An additional function of GAM26 is therefore inhibition of potassium large conductance calcium-activated channel, subfamily M, be (KCNMB4), a gene which encodes a protein that regulates gating kinetics of slow K channels in a Ca-sensitive manner. Accordingly, utilities of GAM26 include diagnosis and treatment of the abovementioned diseases and clinical conditions. The function and utilities of KCNMB4 have been established by previous studies, as described hereinabove to FIG. 26D.

Reference is now made to KCNS2 BINDING SITE. Potassium voltage-gated channel, delayed-rectifier, subfamily S, membe (KCNS2) is a target gene of GAM26, corresponding to GAM26-TARGET GENE of FIG. 26A. KCNS2 BINDING SITE is a binding site found in an untranslated region of KCNS2, corresponding to BINDING SITE of FIG. 26A. FIG. 26D illustrates the complementarity of the nucleotide sequence of KCNS2 BINDING SITE, designated SEQ ID:224998, to the nucleotide sequence of GAM26 RNA of FIG. 26A, designated SEQ ID:20604.

A further function of GAM26 is therefore inhibition of potassium voltage-gated channel, delayed-rectifier, subfamily S, membe (KCNS2), a gene which encodes a protein that mediates the voltage-dependent potassium ion permeability of excitable membranes. Accordingly, utilities of GAM26 include diagnosis and treatment of the abovementioned diseases and clinical conditions.

The function of KCNS2 has been established by previous studies. See KCNS1 (602905). By searching an expressed sequence tag (EST) database with the peptide sequence of the silent Kv8.1 alpha subunit, Salinas et al. (1997) identified human cDNAs encoding KCNS2, which they called Kv9.2. Using these ESTs, the authors isolated a mouse Kcns2 cDNA from a brain cDNA library. The predicted 477-amino acid Kcns2 protein has all of the structural characteristics of an outward rectifier Kv alpha subunit, namely 6 transmembrane domains, a transmembrane region with 5 positively charged amino acids, and a conserved pore-forming region. Several putative phosphorylation sites are located in the cytoplasmic regions. Northern blot analysis showed that Kcns2 is expressed only in the brain. In situ hybridization detected high levels of Kcns2 mRNA in the olfactory bulb, cerebral cortex, hippocampal formation, habenula, basolateral amygdaloid nuclei, and cerebellum; expression was also found in the retina and spinal cord. Salinas et al. (1997) demonstrated that Kcns2 does not have potassium channel activity by itself but can modulate the activities of the Kv2.1 (see KCNB1; 600397) and Kv2.2 alpha subunits. By fluorescence in situ hybridization and radiation hybrid mapping, Banfi et al. (1996) mapped an EST (GenBank R19352) corresponding to the human KCNS2 gene (Salinas et al., 1997) to 8q22.

Full details of the abovementioned studies are described in the following publications, the disclosure of which are hereby incorporated by reference:

Banfi, S.; Borsani, G.; Rossi, E.; Bernard, L.; Guffanti, A.; Rubboli, F.; Marchitiello, A.; Giglio, S.; Coluccia, E.; Zollo, M.; Zuffardi, O.; Ballabio, A.: Identification and mapping of human cDNAs homologous to Drosophila mutant genes through EST database searching. Nature Genet. 13: 167-174, 1996. PubMed ID: 8640222 2. Salinas, M.; Duprat, F.; Heurteaux, C.; Hugnot, J. -P. Lazdunski, M.: New modulatory alpha subunits for mammalian Shab K(+) channels. J. Biol. Chem. 272: 24371-24379, 1997.

Further studies establishing the function and utilities of KCNS2 are found in John Hopkins OMIM database record ID 602906, and in references numbered 885-886 listed hereinbelow.

Reference is now made to KRAS2 BINDING SITE. V-Ki-ras2 Kirsten rat sarcoma 2 viral oncogene homolog (KRAS2) is a target gene of GAM26, corresponding to GAM26-TARGET GENE of FIG. 26A. KRAS2 BINDING SITE is a binding site found in an untranslated region of KRAS2, corresponding to BINDING SITE of FIG. 26A. FIG. 26D illustrates the complementarity of the nucleotide sequence of KRAS2 BINDING SITE, designated SEQ ID:229032, to the nucleotide sequence of GAM26 RNA of FIG. 26A, designated SEQ ID:20604.

Yet a further function of GAM26 is therefore inhibition of v-Ki-ras2 Kirsten rat sarcoma 2 viral oncogene homolog (KRAS2), a gene which encodes a protein that ras proteins bind gdp/gtp and possess intrinsic gtpase activity and is associated with LUNG CANCER and STOMACH CANCER. Accordingly, utilities of GAM26 include diagnosis and treatment of the abovementioned diseases and clinical conditions.

The function of KRAS2 has been established by previous studies. See 190020. KRAS2 is on chromosome 12; KRAS1P, a pseudogene, is on chromosome 6. Weinberg (1982) suggested that the then-recognized cellular oncogenes could be assigned to a small number of gene families; e.g., the ras family with at least 4 distinct oncogenes, and the src-yes-mos family with another 3. The probable role of at least 2 oncogenes in normal differentiation is indicated by the findings of transcription of KRAS and the McDonough strain of feline sarcoma virus (FMS) during mouse development (Muller et al., 1983). Furthermore, the differences in transcription in different tissues suggested a specific role for each: FMS was expressed in extraembryonic structures or in transport in these tissues, whereas KRAS was expressed ubiquitously. KRAS, with a length of more than 30 kb, is much larger than HRAS (190020) or NRAS (164790). Although the 3 ras genes, HRAS, KRAS, and NRAS, have different genetic structures, all code for proteins of 189 amino acid residues, generically designated p21. These genes acquire malignant properties by single point mutations that affect the incorporation of the 12th or 61st amino acid residue of their respective p21. KRAS is involved in malignancy much more often than is HRAS. In a study of 96 human tumors or tumor cell lines in the NIH 3T3 transforming system, Pulciani et al. (1982) found a mutated HRAS locus only in T24 bladder cancer cells, whereas transforming KRAS genes were identified in 8 different carcinomas and sarcomas. Holland et al. (2000) transferred, in a tissue-specific manner, genes encoding activated forms of Ras and Akt (164730) to astrocytes and neural progenitors in mice. Holland et al. (2000) found that although neither activated Ras nor Akt alone was sufficient to induce glioblastoma multiforme (GBM; 137800) formation, the combination of activated Ras and Akt induced high-grade gliomas with the histologic features of human GBMs. These tumors appeared to arise after gene transfer to neural progenitors, but not after transfer to differentiated astrocytes. Increased activity of RAS is found in many human GBMs, and Holland et al. (2000) demonstrated that Akt activity is increased in most of these tumors, implying that combined activation of these 2 pathways accurately models the biology of this disease. Bezieau et al. (2001) used ARMS (allele-specific amplification method) to evaluate the incidence of NRAS- and KRAS2-activating mutations in patients with multiple myeloma and related disorders. Mutations were more frequent in KRAS2 than in NRAS. The authors concluded that early mutations in these 2 oncogenes may play a major role in the oncogenesis of multiple myeloma and primary plasma cell leukemia. Rajagopalan et al. (2002) systematically evaluated mutation in BRAF (164757) and KRAS in 330 colorectal tumors. There were 32 mutations in BRAF, 28 with a V599E mutation (164757.0001) and 1 each with the R461I (164757.0002), I462S (164757.0003), G463E (164757.0004), or K600E (164757.0005) mutations. All but 2 mutations seemed to be heterozygous, and in all 20 cases for which normal tissue was available, the mutations were shown to be somatic. In the same set of tumors there were 169 mutations in KRAS. No tumor exhibited mutations in both BRAF and KRAS. There was also a striking difference in the frequency of BRAF mutations between cancers with and without mismatch repair deficiency. All but 1 of the 15 BRAF mutations identified in mismatch repair deficient cases resulted in a V599E substitution. Rajagopalan et al. (2002) concluded their results provide strong support for the hypothesis that BRAF and KRAS mutations are equivalent in their tumorigenic effects. Both genes seem to be mutated at a similar phase of tumorigenesis, after initiation but before malignant conversion. Moreover, no tumor concurrently contained both BRAF and KRAS mutations.

Animal model experiments lend further support to the function of KRAS2. Costa et al. (2002) crossed Nf1 heterozygote mice with mice heterozygous for a null mutation in the Kras gene and tested the Nf1 descendants. They found that the double heterozygotes with decreased Ras function had improved learning relative to Nf1 heterozygote mice. Costa et al. (2002) also showed that the Nf1 +/− mice have increased GABA-mediated inhibition and specific deficits in long-term potentiation, both of which can be reversed by decreasing Ras function. Costa et al. (2002) concluded that learning deficits associated with Nf1 may be caused by excessive Ras activity, which leads to impairments in long-term potentiation caused by increased GABA-mediated inhibition.

It is appreciated that the abovementioned animal model for KRAS2 is acknowledged by those skilled in the art as a scientifically valid animal model, as can be further appreciated from the publications sited hereinbelow.

Full details of the abovementioned studies are described in the following publications, the disclosure of which are hereby incorporated by reference:

Costa, R. M.; Federov, N. B.; Kogan, J. H.; Murphy, G. G.; Stern, J.; Ohno, M.; Kucherlapati, R.; Jacks, T.; Silva, A. J.: Mechanism for the learning deficits in a mouse model of neurofibromatosis type 1. Nature 415: 526-530, 2002. PubMed ID: 11793011 39. Rajagopalan, H.; Bardelli, A.; Lengauer, C.; Kinzler, K. W.; Vogelstein, B.; Velculescu, V. E.: RAF/RAS oncogenes and mismatch-repair status. (Letter) Nature 418: 934 only, 2002.

Further studies establishing the function and utilities of KRAS2 are found in John Hopkins OMIM database record ID 190070, and in references numbered 887-942 listed hereinbelow.

Referring now to KRAS2 BINDING SITE. V-Ki-ras2 Kirsten rat sarcoma 2 viral oncogene homolog (KRAS2) is a target gene of GAM26, corresponding to GAM26-TARGET GENE of FIG. 26A. KRAS2 BINDING SITE is a binding site found in an untranslated region of KRAS2, corresponding to BINDING SITE of FIG. 26A. FIG. 26D illustrates the complementarity of the nucleotide sequence of KRAS2 BINDING SITE, designated SEQ ID:229035, to the nucleotide sequence of GAM26 RNA of FIG. 26A, designated SEQ ID:20604.

Another function of GAM26 is therefore inhibition of v-Ki-ras2 Kirsten rat sarcoma 2 viral oncogene homolog (KRAS2), a gene which encodes a protein that ras proteins bind gdp/gtp and possess intrinsic gtpase activity and is associated with LUNG CANCER and STOMACH CANCER. Accordingly, utilities of GAM26 include diagnosis and treatment of the abovementioned diseases and clinical conditions. The function and utilities of KRAS2 have been established by previous studies, as described hereinabove with reference to FIG. 26D.

Referring now to KRAS2 BINDING SITE. V-Ki-ras2 Kirsten rat sarcoma 2 viral oncogen homolog (KRAS2) is a target gene of GAM26, corresponding to GAM26-TARGET GENE of FIG. 26A. KRAS2 BINDING SITE is a binding site found in an untranslated region of KRAS2, corresponding to BINDING SITE of FIG. 26A. FIG. 26D illustrates the complementarity of the nucleotide sequence of KRAS2

BINDING SITE, designated SEQ ID:229036, to the nucleotide sequence of GAM26 RNA of FIG. 26A, designated SEQ ID:20604.

Yet another function of GAM26 is therefore inhibition of v-Ki-ras2 Kirsten rat sarcoma 2 viral oncogene homolog (KRAS2), a gene which encodes a protein that ras proteins bind gdp/gtp and possess intrinsic gtpase activity and is associated with LUNG CANCER and STOMACH CANCER. Accordingly, utilities of GAM26 include diagnosis and treatment of the abovementioned diseases and clinical conditions. The function and utilities of KRAS2 have been established by previous studies, as described hereinabove with reference FIG. 26D.

Referring now to KRAS2 BINDING SITE. V-Ki-ras2 Kirsten rat sarcoma 2 viral oncogene homolog (KRAS2) is a target gene of GAM26, corresponding to GAM26-TARGET GENE of FIG. 26A. KRAS2 BINDING SITE is a binding site found in an untranslated region of KRAS2, corresponding to BINDING SITE of FIG. 26A. FIG. 26D illustrates the complementarity of the nucleotide sequence of KRAS2 BINDING SITE, designated SEQ ID:229050, to the nucleotide sequence of GAM26 RNA of FIG. 26A, designated SEQ ID:20604.

An additional function of GAM26 is therefore inhibition of v-Ki-ras2 Kirsten rat sarcoma 2 viral oncogene homolog (KRAS2), a gene which encodes a protein that ras proteins bind gdp/gtp and possess intrinsic gtpase activity, and is associated with LUNG CANCER and STOMACH CANCER. Accordingly, utilities of GAM26 include diagnosis and treatment of the abovementioned diseases and clinical conditions. The function and utilities of KRAS2 have been established by previous studies, as described hereinabove with reference to FIG. 26D.

Referring now to KRAS2 BINDING SITE. V-Ki-ras2 Kirsten rat sarcoma 2 viral oncogene homolog (KRAS2) is a target gene of GAM26, corresponding to GAM26-TARGET GENE of FIG. 26A. KRAS2 BINDING SITE is a binding site found in an untranslated region of KRAS2, corresponding to BINDING SITE of FIG. 26A. FIG. 26D illustrates the complementarity of the nucleotide sequence of KRAS2 BINDING SITE, designated SEQ ID:229059, to the nucleotide sequence of GAM26 RNA of FIG. 26A, designated SEQ ID:20604.

A further function of GAM26 is therefore inhibition of v-Ki-ras2 Kirsten rat sarcoma 2 viral oncogene homolog (KRAS2), a gene which encodes a protein that ras proteins bind gdp/gtp and possess intrinsic gtpase activity, and is associated with LUNG CANCER and STOMACH CANCER. Accordingly, utilities of GAM26 include diagnosis and treatment of the abovementioned diseases and clinical conditions. The function and utilities of KRAS2 have been established by previous studies, as described hereinabove with reference to FIG. 26D.

Reference is now made to LASS1 BINDING SITE. Longevity assurance (LAG1, *S. cerevisiae*) homolog 1 (LASS1) is a tar et gene of GAM26, corresponding to GAM26-TARGET GENE of FIG. 26A. LASS1 BINDING SITE is a binding site found in an untranslated region of LASS1, corresponding to BINDING SITE of FIG. 26A. FIG. 26D illustrates the complementarity of the nucleotide sequence of LASS1 BINDING SITE, designated SEQ ID:231693, to the nucleotide sequence of GAM26 RNA of FIG. 26A, designated SEQ ID:20604.

Yet a further function of GAM26 is therefore inhibition of longevity assurance (LAG1, *S. cerevisiae*) homolog 1 (LASS1), a gene which encodes an enzyme that may mediate cell differentiation events during embryonic development. Accordingly, utilities of GAM26 include diagnosis and treatment of the abovementioned diseases and clinical conditions.

The function of LASS1 has been established by previous studies. Longevity assurance gene-1 (Lag1) is preferentially expressed in young yeast, i.e., yeast cells that have undergone a small number of cell divisions. By screening genomic and cDNA libraries using a yeast Lag1 probe and degenerate PCR primers, followed by database searching, Jiang et al. (1998) identified a cDNA encoding LASS1. LASS1 had been identified previously by Lee (1991), who designated it UOG1 for upstream of GDF1 (602880). Lee (1991) showed that the potential 350-amino acid human and mouse UOG1 proteins are 81% identical. Jiang et al. (1998) determined that the deduced LASS1 protein contains a conserved 52-residue stretch termed the Lag1 motif, as well as a transmembrane domain. Complementation analysis indicated that LASS1, but not a similar gene, TRAM (605190), can replace yeast Lag1 in spite of limited amino acid homology. Northern blot analysis revealed expression of a 3.0-kb transcript in brain, skeletal muscle, and testis, as well as in glioblastoma and neuroblastoma cell lines. By PCR screening of a BAC library, Jiang et al. (1998) determined that the LASS1 gene contains 8 exons and spans approximately 30 kb. The translation start codon is in a GC-rich region. There are no TATA boxes.

Full details of the abovementioned studies are described in the following publications, the disclosure of which are hereby incorporated by reference:

Jiang, J. C.; Kirchman, P. A.; Zagulski, M.; Hunt, J.; Jazwinski, S. M.: Homologs of the yeast longevity gene LAG1 in *Caenorhabditis elegans* and human. Genome Res. 8: 1259-1272, 1998. PubMed ID: 9872981 2. Lee, S. -J.: Expression of growth/differentiation factor 1 in the nervous system: conservation of a bicistronic structure. Proc. Nat. Acad. Sci. 88: 4250-4254, 1991.

Further studies establishing the function and utilities of LASS1 are found in John Hopkins OMIM database record ID 606919, and in references numbered 943-944 listed hereinbelow.

Reference is now made to LASS2 BINDING SITE. (LASS2) is a target gene of GAM26, corresponding to GAM26-TARGET GENE of FIG. 26A. LASS2 BINDING SITE is a binding site found in an untranslated region of LASS2, corresponding to BINDING SITE of FIG. 26A. FIG. 26D illustrates the complementarity of the nucleotide sequence of LASS2 BINDING SITE, designated SEQ ID:231822, to the nucleotide sequence of GAM26 RNA of FIG. 26A, designated SEQ ID:20604.

Another function of GAM26 is therefore inhibition of (LASS2), a gene which encodes a protein that interacts with asialoglycoprotein receptor-1. Accordingly, utilities of GAM26 include diagnosis and treatment of the abovementioned diseases and clinical conditions.

The function of LASS2 has been established by previous studies. Longevity assurance gene-1 (Lag1) is preferentially expressed in young yeast, i.e., yeast cells that have undergone a small number of cell divisions. Yeast lifespan can be increased or decreased by mutation or overexpression of this gene. By EST database searching for homologs of Lag1, followed by 5-prime RACE, Pan et al. (2001) identified a cDNA encoding LASS2. The deduced 230-amino acid protein is 29% identical to LASS1 (606919) over 224 amino acids. It has 4 transmembrane helices (2 fewer than most Lag1 homologs), a Lag1 motif, and a C-terminal acidic domain. Northern blot analysis revealed expression of a 2.4-kb transcript in kidney and liver, with lower levels in brain, heart placenta, and lung. GENE FUNCTION By yeast 2-hybrid screening of liver and fetal brain cDNA libraries with LASS2 as bait, followed by GST pull-down assays, Pan et al. (2001) showed that LASS2 interacts with asialoglycoprotein receptor-1 (ASGR1; 108360) and -2 (ASGR2, 108361), the C-terminal half of OCT1 (SLC22A1; 602607), and ATP6L (108745). Expression of LASS2 in hepatocellular carcinoma cell lines led to suppression of cancer cell growth Full details of the abovementioned studies are described in the following publications, the disclosure of which are hereby incorporated by reference:

Pan, H.; Qin, W. -X.; Huo, K. -K.; Wan, D. -F.; Yu, Y.; Yu, Z. -G.; Hu, Q. -D.; Gu, K. T.; Zhou, X. -M.; Jiang, H. -Q.; Zhang, P. -P.; Huang, Y.; Li, Y. -Y.; Gu, J. -R.: Cloning, mapping, and characterization of a human homologue of the yeast longevity assurance gene LAG1. Genomics 77: 58-64, 2001.

Further studies establishing the function and utilities of LASS2 are found in John Hopkins OMIM database record ID 606920, and in references numbered 945 listed hereinbelow.

Reference is now made to LMO2 BINDING SITE. LIM domain only 2 (rhombotin-like 1) (LM 2) is a target gene of GAM26, corresponding to GAM26-TARGET GENE of FIG. 26A. LMO2 BINDING SITE is a binding site found in an untranslated region of LMO2, corresponding to BINDING SITE of FIG. 26A. FIG. 26D illustrates the complementarity of the nucleotide sequence of LMO2 BINDING SITE, designated SEQ ID:236309, to the nucleotide sequence of GAM26 RNA of FIG. 26A, designated SEQ ID:20604.

Yet another function of GAM26 is therefore inhibition of LIM domain only 2 (rhombotin-like 1) (LMO2), a gene which encodes a protein that binds to the basic helix-loop-helix protein tal-1, and is associated with lymphoblastic leukemia. Accordingly, utilities of GAM26 include diagnosis and treatment of the abovementioned diseases and clinical conditions.

The function of LMO2 has been established by previous studies. Rhombotin comprises multigene family. Rhombotin-1, implicated in an unusual subset of T-cell acute lymphoblastic leukemia, is located in the 11p15 region. A second member of the family, rhombotin-2, maps to 11p13 (see 186921). The known translocation breakpoints in the T-ALL cluster are at the 5-prime end of the RBTN2 gene within 25 kb of the presumed transcriptional start site Royer-Pokora et al. (1991) cloned 70 kb of DNA from 11p13 at the site of a recurrent translocation in T-cell leukemia: t(11;14)(p13;q11). The translocation involves the TCR-delta gene (186810) on 14q11 and a new site on 11p13. They found 2 new and 10 previously identified translocations mapping within 25 kb of each other on 11p13 and constituting the so-called 11p13. T-cell translocation cluster (11p13 ttc). A search for expressed sequences surrounding breakpoint cluster region identified a gene telomeric of all breakpoints that was overexpressed in 3 T-ALL samples with a t(11;14). This new gene, called T-cell translocation gene-2 (TTG2), encodes a small cysteine-rich protein. It showed 48% amino acid identity with T-cell translocation gene-1, or rhombotin (186921), in 11p15. Both proteins contain 2 copies of a cysteine-rich motif. The proteins encoded by these 2 translocation-deregulated genes belong to a class of cysteine-rich proteins with the LIM motif and are important in normal development.

Full detail of the abovementioned studies are described in the following publications, the disclosure of which are hereby incorporated by reference:

Royer-Pokora, B.; Loos, U.; Ludwig, W. -D.: TTG-2, a new gene encoding a cysteine-rich protein with the LIM motif, is overexpressed in acute T-cell leukaemia with the t(11; 14)(13;q11). Oncogene 6: 1887-1893, 1991.

Further studies establishing the function and utilities of LMO2 are found in John Hopkins OMIM database record ID 180385, and in referent numbered 946-950 listed hereinbelow.

Referring now to LMO2 BINDING SITE. LIM domain only 2 (rhombotin-like 1) (LMO2) is a target gene of GAM26, corresponding to GAM26-TARGET GENE of FIG. 26A. LMO2 BINDING SITE is a binding site found in; an untranslated region of LMO2, corresponding to BINDING SITE of FIG. 26A. FIG. 26D illustrates the complementarity of the nucleotide sequence of LMO2 BINDING SITE, designated SEQ ID:236311, to the nucleotide sequence of GAM26 RNA of FIG. 26A, designated SEQ ID:20604.

An additional function of GAM26 is therefore inhibition of LIM domain only 2 (rhombotin-like 1)(LMO2), a gene which encodes a protein that binds to the basic helix-loop-helix protein tal-1, and is associated with lymphoblastic leukemia. Accordingly, utilities of GAM26 include diagnosis and treatment of the abovementioned diseases and clinical conditions. The function and utilities of LMO2 have been established by previous studies, as described hereinabove with reference to FIG. 26D.

Referring now to LMO2 BINDING SITE. LIM domain only 2 (rhombotin-like 1) (LMO2) is a target gene of GAM26, corresponding to GAM26-TARGET GENE of FIG. 26A. LMO2 BINDING SITE is a binding site found in an untranslated region of LMO2, corresponding to BINDING SITE of FIG. 26A. FIG. 26D illustrates the complementarity of the nucleotide sequence of LMO2 BINDING SITE, designated SEQ ID:236328, to the nucleotide sequence of GAM26 RNA of FIG. 26A, designated SEQ ID:20604.

A further function of GAM26 is therefore inhibition of LIM domain only 2 (rhombotin-like 1) (LMO2), a gene which encodes a protein that binds to the basic helix-loop-helix protein tal-1 and is associated with lymphoblastic leukemia. Accordingly, utilities of GAM26 include diagnosis and treatment the abovementioned diseases and clinical conditions. The function and utilities of LMO2 have been established by previous studies, as described hereinabove with reference to FIG. 26D.

Referring now to LMO2 BINDING SITE. LIM domain only 2 (rhombotin-like 1) (LMO2) is a target gene of GAM26, corresponding to GAM26-TARGET GENE of FIG. 26A. LMO2 BINDING SITE is a binding site found in an untranslated region of LMO2, corresponding to BINDING SITE of FIG. 26A. FIG. 26D illustrates the complementarity of the nucleotide sequence of LMO2 BINDING SITE, designated SEQ ID:236380, to the nucleotide sequence of GAM26 RNA of FIG. 26A, designated SEQ ID:20604.

Yet a further function of GAM26 is therefore inhibition of LIM domain only 2 (rhombotin-like 1) (LMO2), a gene which encodes a protein that binds to the basic helix-loop-helix protein tal-1, and is associated with lymphoblastic leukemia. Accordingly, utilities of GAM26 include diagnosis and treatment of the abovementioned diseases and clinical conditions. The function and utilities of LMO2 have been established by previous studies, as described hereinabove with reference to FIG. 26D.

Referring now to LMO2 BINDING SITE. LIM domain only 2 (rhombotin-like 1) (LMO2) is a target gene of GAM26, corresponding to GAM26-TARGET GENE of FIG. 26A. LMO2 BINDING SITE is a binding site found in an untranslated region of LMO2, corresponding to BINDING SITE of FIG. 26A. FIG. 26D illustrates the complementarity of the nucleotide sequence of LMO2 BINDING SITE, designated SEQ ID:236383, to the nucleotide sequence of GAM26 RNA of FIG. 26A, designated SEQ ID:20604.

Another function of GAM26 is therefore inhibition of LIM domain only 2 (rhombotin-like 1) (LMO2), a gene which encodes a protein that binds to the basic helix-loop-helix protein tal-1, and is associated with lymphoblastic leukemia. Accordingly, utilities of GAM26 include diagnosis and treatment of the abovementioned diseases and clinical conditions. The function and utilities of LMO2 have been established by previous studies, as described hereinabove with reference to FIG. 26D.

Referring now to LMO2 BINDING SITE. LIM domain only 2 (rhombotin-like 1) (LMO2) is a target gene of GAM26, corresponding to GAM26-TARGET GENE of FIG. 26A. LMO2 BINDING SITE is a binding site found in an untranslated region of LMO2, corresponding to BINDING SITE of FIG. 26A. FIG. 26D illustrates the complementarity of the nucleotide sequence of LMO2 BINDING SITE, designated SEQ ID:236384, to the nucleotide sequence of GAM26 RNA of FIG. 26A, designated SEQ ID:20604.

Yet another function of GAM26 is therefore inhibition of LIM domain only 2 (rhombotin-like 1) (LMO2), a gene which encodes a protein that binds to the basic helix-loop-helix protein tal-1, and is associated with lymphoblastic leukemia. Accordingly, utilities of GAM26 include diagnosis and treatment the abovementioned diseases and clinical conditions. The function and utilities LMO2 have been established by previous studies, as described hereinabove with reference to FIG. 26D.

Referring now to LMO2 BINDING SITE. LIM domain only 2 (rhombotin-like 1) (LMO2) is a target gene of GAM26, corresponding to GAM26-TARGET GENE of FIG. 26A. LMO2 BINDING SITE is a binding site found in an untranslated region of LMO2, corresponding to BINDING SITE of FIG. 26A. FIG. 26D illustrates the complementarity of the nucleotide sequence of LMO2 BINDING SITE, designated SEQ ID:236385, to the nucleotide sequence of GAM26 RNA of FIG. 26A, designated SEQ ID:20604.

An additional function of GAM26 is therefore inhibition of LIM domain only 2 (rhombotin-like 1) (LMO2), a gene which encodes a protein that binds to the basic helix-loop-helix protein tal-1, and is associated with lymphoblastic leukemia. Accordingly, utilities of GAM26 include diagnosis and treatment of the abovementioned diseases and clinical conditions. The function and utilities of LMO2 have been established by previous studies, as described hereinabove with reference to FIG. 26D.

Reference is now made to LRP8 BINDING SITE. low density lipoprotein receptor-related protein 8, apolipoprotein e r (LRP8) is a target gene of GAM26, corresponding to GAM26-TARGET GENE of FIG. 26A. LRP8 BINDING SITE is a binding site found in an untranslated region of LRP8, corresponding to BINDING SITE of FIG. 26A. FIG. 26D illustrates the complementarity of the nucleotide sequence of LRP8 BINDING SITE, designated SEQ ID:238167, to the nucleotide sequence of GAM26 RNA of FIG. 26A, designated SEQ ID:20604.

A further function of GAM26 is therefore inhibition of low density lipoprotein receptor-related protein 8, apolipoprotein e r (LRP8), a gene which encodes a receptor that binds vldl and transports it into cells by endocytosis. Accordingly, utilities of GAM26 include diagnosis and treatment of the abovementioned diseases and clinical conditions.

The function of LRP8 has been established by previous studies. Apolipoprotein E (APOE; 107741) is a 34-kD lipophilic protein that mediates high-affinity binding of APOE-containing lipoproteins to the low density lipoprotein receptor (see LDLR; 606945) and the very low density lipoprotein receptor (VLDLR; 192977). By screening a human placenta cDNA library with degenerate oligonucleotides based on a highly conserved region between LDLR and VLDLR, Kim et al. (1996) identified a cDNA encoding APOE receptor-2 (APOER2). The predicted 963-amino acid protein contains a putative 41 amino acid signal sequence and 5 functional domains that resemble those of LDLR and VLDLR. APOER2 appears specific for APOE-containing ligands: LDLR-deficient mammalian cells expressing APOER bound APOE-rich beta-VLDL with high affinity, but bound LDL and VLDL with much lower affinities. Northern blot analysis revealed that APOER2 is expressed as 4.5- and 8.5-kb mRNAs in brain and placenta Kim et al. (1997) reported that the APOER2 gene contains 19 exons and spans approximately 60 kb. Alternative splicing generates multiple transcripts encoding receptors with different numbers of cysteine rich repeats in the ligand-binding domain.

Full details of the abovementioned studies are described in the following publications, the disclosure of which are hereby incorporated by reference:

Kim, D. -H.; Iijima, H.; Goto, K.; Sakai, J.; Ishii H.; Kim, H. -J.; Suzuki, H.; Kondo, H.; Saeki, S.; Yamamoto, T.: Human apolipoprotein E receptor 2: a novel lipoprotein receptor of the low density lipoprotein receptor family predominantly expressed in brain. J. Biol. Chem. 271: 8373-8380, 1996. PubMed ID: 8626535.: Kim, D. -H.; Magoori, K.; Inoue, T. R.; Mao, C. C.; Kim, H. -J.; Suzuki, H.; Fujita, T.; Endo, Y.; Saeki, S.; Yamamoto, T. T.: Exon/intron organization, chromosome localization, alternative splicing, and transcription units of the human apolipoprotein E receptor 2 gene. J. Biol. Chem. 272: 8498-8504, 1997.

Further studies establishing the function and utilities of LRP8 are found in John Hopkins OMIM database record ID 602600, and in references numbered 497, 951-952 and 504 listed herein below.

Referring now to LRP8 BINDING SITE. Low density lipoprotein receptor-related protein 8, apolipoprotein e r (LRP8) is a target gene of GAM26, corresponding to GAM26-TARGET GENE of FIG. 26A. LRP8 BINDING SITE is a binding site found in an untranslated region of LRP8, corresponding to BINDING SITE of FIG. 26A. FIG. 26D illustrates the complementarity of the nucleotide sequence of LRP8 BINDING SITE, designated SEQ ID:238167, to the nucleotide sequence of GAM26 RNA of FIG. 26A, designated SEQ ID:20604.

Yet a further function of GAM26 is therefore inhibition of low density lipoprotein receptor-related protein 8, apolipoprotein e r (LRP8), a gene which encodes a receptor that binds vldl and transports it into cells by endocytosis. Accordingly, utilities of GAM26 include diagnosis and treatment of the abovementioned diseases and clinical conditions. The function and utilities of LRP8 have been established by previous studies, as described hereinabove with reference to FIG. 26D.

Referring now to LRP8 BINDING SITE. Low density lipoprotein receptor-related protein 8, apolipoprotein e r (LRP8) is a target gene of GAM26, corresponding to GAM26-TARGET GENE of FIG. 26A. LRP8 BINDING SITE is a binding site found in an untranslated region of LRP8, corresponding to BINDING SITE of FIG. 26A. FIG. 26D illustrates the complementarity of the nucleotide sequence of LRP8 BINDING SITE, designated SEQ ID:238168, to the nucleotide sequence of GAM26 RNA of FIG. 26A, designated SEQ ID:20604.

Another function of GAM26 is therefore inhibition of low density lipoprotein receptor-related protein 8, apolipoprotein e r (LRP8), a gene which encodes a receptor that binds vldl and transports it into cells by endocytosis. Accordingly, utilities of GAM26 include diagnosis and treatment of the abovementioned diseases and clinical conditions. The function and utilities of LRP8 have been established by previous studies, as described hereinabove with reference to FIG. 26D.

Referring now to LRP8 BINDING SITE. Low density lipoprotein receptor-related protein 8, apolipoprotein e r (LRP8) is a target gene of GAM26, corresponding to GAM26-TARGET GENE of FIG. 26A. LRP8 BINDING SITE is a binding site found in an untranslated region of LRP8, corresponding to BINDING SITE of FIG. 26A. FIG. 26D illustrates the complementarity of the nucleotide sequence of LRP8 BINDING SITE, designated SEQ ID:238188, to the nucleotide sequence of GAM26 RNA of FIG. 26A, designated SEQ ID:20604.

Yet another function of GAM26 is therefore inhibition of low density lipoprotein receptor-related protein 8, apolipoprotein e r (LRP8), a gene which encodes a receptor that binds vldl and transports it into cells by endocytosis. Accordingly, utilities of GAM26 include diagnosis and treatment of the abovementioned diseases and clinical conditions. The function and utilities of LRP8 have been established by previous studies, as described hereinabove with reference to FIG. 26D.

Referring now to LRP8 BINDING SITE. Low density lipoprotein receptor-related protein 8, apolipoprotein e r (LRP8) is a target gene of GAM26, corresponding to GAM26-TARGET GENE of FIG. 26A. LRP8 BINDING SITE is a binding site found in an untranslated region of LRP8, corresponding to BINDING SITE of FIG. 26A. FIG. 26D illustrates the complementarity of the nucleotide sequence of LRP8 BINDING SITE, designated SEQ ID:238204, to the nucleotide sequence of GAM26 RNA of FIG. 26A, designated SEQ ID:20604.

An additional function of GAM26 is therefore inhibition of low density lipoprotein receptor-related protein 8, apolipoprotein e r (LRP8), a gene which encodes a receptor that binds vldl and transports it into cells by endocytosis. Accordingly, utilities of GAM26 include diagnosis and treatment of the abovementioned diseases and clinical conditions. The function and utilities of LRP8 have been established by previous studies, as described hereinabove with reference to FIG. 26D.

Referring now to LRP8 BINDING SITE. Low density lipoprotein receptor-related protein 8, apolipoprotein e r (LRP8) is a target gene of GAM26, corresponding to GAM26-TARGET GENE of FIG. 26A. LRP8 BINDING SITE is a binding site found in an untranslated region of LRP8, corresponding to BINDING SITE of FIG. 26A. FIG. 26D illustrates the complementarity of the nucleotide sequence of LRP8 BINDING SITE, designated SEQ ID:238208, to the nucleotide sequence of GAM26 RNA of FIG. 26A, designated SEQ ID:20604.

A further function of GAM26 is therefore inhibition of low density lipoprotein receptor-related protein 8, apolipoprotein e r (LRP8), a gene which encodes a receptor that binds vldl and transports it into cells by endocytosis. Accordingly, utilities of GAM26 include diagnosis and treatment of the abovementioned diseases and clinical conditions. The function and utilities of LRP8 have been established by previous studies, as described hereinabove with reference to FIG. 26D.

Referring now to LRP8 BINDING SITE. Low density lipoprotein receptor-related protein 8, apolipoprotein e r (LRP8) is a target gene of GAM26, corresponding to GAM26-TARGET GENE of FIG. 26A. LRP8 BINDING SITE is a binding site found in an untranslated region of LRP8, corresponding to BINDING SITE of FIG. 26A. FIG. 26D illustrates the complementarity of the nucleotide sequence of LRP8 BINDING SITE, designated SEQ ID:238239, to the nucleotide sequence of GAM26 RNA of FIG. 26A, designated SEQ ID:20604.

Yet a further function of GAM26 is therefore inhibition of low density lipoprotein receptor-related protein 8, apolipoprotein e r (LRP8), a gene which encodes a receptor that binds vldl and transports it into cells by endocytosis. Accordingly, utilities of GAM26 include diagnosis and treatment of the abovementioned diseases and clinical conditions. The function and utilities of LRP8 have been established by previous studies, as described hereinabove with reference to FIG. 26D.

Reference is now made to MAD BINDING SITE. MAX dimerization protein (MAD) is a target gene of GAM26, corresponding to GAM26-TARGET GENE of FIG. 26A. MAD BINDING SITE is a binding site found in an untranslated region of MAD, corresponding to BINDING SITE of FIG. 26A. FIG. 26D illustrates the complementarity of the nucleotide sequence of MAD BINDING SITE, designated SEQ ID:241104, to the nucleotide sequence of GAM26 RNA of FIG. 26A, designated SEQ ID:20604.

Another function of GAM26 is therefore inhibition of MAX dimerization protein (MAD), a gene which encodes a protein that forms a heterodimer with MAX and represses transcription, antagonizes c-Myc (MYC), and promotes cellular differentiation. Accordingly, utilities of GAM26 include diagnosis and treatment of the abovementioned diseases and clinical conditions.

The function of MAD has been established by previous studies. The MAD and MXI1 (600020) genes encode proteins that belong to a distinct subfamily of MAX-interacting proteins. The MAX protein (154950) specifically interacts with the MYC protein family (190080) by forming heterodimers mediated by their basic-helix-loop-helix-leucine zipper interaction domains. Binding to MAX is essential for MYC transcription and transforming activity; MYC homodimers are inactive. Both MAD and MXI1 bind MAX in vitro, forming a sequence-specific DNA-binding complex similar to the MYC-MAX heterodimer. MAD and MYC compete for binding to MAX. In addition, MAD acts as a transcriptional repressor, while MYC appears to function as an activator. MXI1 also appears to lack a transcriptional activation domain. Therefore, MXI1 and MAD might antagonize MYC function and are candidate tumor suppressor genes. Edelhoff et al. (1994) mapped the human MAD and MXI1 genes to 2p13 and 10q25, respectively, by fluorescence in situ hybridization. The homologous gene in the mouse was mapped to chromosome 6 by interspecific backcross analysis. Shapiro et al. (1994) confirmed the assignments of the MAD and MXI1 genes to chromosomes 2p13-p12 and 10q24-q25, respectively, by somatic cell mapping and fluorescene in situ hybridization. The designation MAD was derived from MAX dimerizer (Eisenman, 1994).

Full details of the abovementioned studies are described in the following publications, the disclosure of which are hereby incorporated by reference:

Edelhoff, S.; Ayer, D. E.; Zervos, A. S.; Steingrimsson, E.; Jenkins, N. A.; Copeland, N. G.; Eisenman, R. N.; Brent, R.; Disteche, C. M.: Mapping of two genes encoding members of a distinct subfamily of MAX interacting proteins: MAD to human chromosome 2 and mouse chromosome 6, and MXI1 to chromosome 10 and mouse chromosome 19. Oncogene 9: 665-668, 1994. PubMed ID: 8290278 Shapiro, D. N.; Valentine, V.; Eagle, L.; Yin, X.; Morris, S. W.; Prochownik, E. V.: Assignment of the human MAD and MXI1 genes to chromosomes 2p12-p13 and 10q24-q25. Genomics 23: 282-285, 1994.

Further studies establishing the function and utilities of MAD are found in John Hopkins OMIM database record ID 600021, and in references numbered 953-955 listed hereinbelow.

Reference is now made to MAD1L1 BINDING SITE. MAD1 (mitotic arrest deficient, yeast, homolog)-like 1 (MAD1L1) is a target gene of GAM26, corresponding to GAM26-TARGET GENE of FIG. 26A. MAD1L1 BINDING SITE is a binding site found in an untranslated region of MAD1L1, corresponding to BINDING SITE of FIG. 26A. FIG. 26D illustrates the complementarity of the nucleotide sequence of MAD1L1 BINDING SITE, designated SEQ ID:241126, to the nucleotide sequence of GAM26 RNA of FIG. 26A, designated SEQ ID:20604.

Yet another function of GAM26 is therefore inhibition of MAD1 (mitotic arrest deficient, yeast, homolog)-like 1 (MAD1L1), a gene which encodes a protein that appears to play a role in cytokinesis, cell shape, and specialized functions such as secretion and capping. Mitotic spindle checkpoint protein 1; may be a target for type 1 T cell leukemia virus oncoprotein Tax. Accordingly, utilities of GAM26 include diagnosis and treatment of the abovementioned diseases and clinical conditions.

The function of MAD1L1 has been established by previous studies. Aneuploidy is a characteristic of most human cancers, and defects of mitotic checkpoints appear to play a role in carcinogenesis. MAD1L1 is a checkpoint gene, and its dysfunction is associated with chromosomal instability. By RT PCR-SSCP and nucleotide sequencing, Tsukasaki et al. (2001) performed a mutation search on the MAD1L1 gene in a total of 44 cell lines (hematopoietic, prostate, osteosarcoma, breast, glioblastoma, and lung) and 133 fresh cancer cells (hematopoietic prostate, breast, and glioblastoma). Eight mutations consisting of missense, nonsense, and frameshift mutations were found, together with a number of nucleotide polymorphisms. All of the alterations in cell lines were heterozygous. The frequency of mutations was relatively high in prostate cancer (2 of 7 cell lines and 2 of 33 tumor specimens). Tsukasaki et al. (2001) placed a mutant truncated MAD1L1 gene from a lymphoma sample into 3 different cell lines and found that it was less inhibitory than wildtype MAD1L1 at decreasing cell proliferation. Coexpression experiments showed that the mutant form had a dominant-negative effect. Furthermore, this mutant impaired the mitotic checkpoint as shown by decreased mitotic indices in cells expressing mutant MAD1L1 after culture with the microtubule-disrupting agent nocodazole.

The results suggested a pathogenic role of mutations in the MAD1L1 gene in various types of human cancer Gene-specific targeting of the SIN3 corepressor complex (see 602949) by DNA-bound repressors is an important mechanism of gene silencing in eukaryotes. The SIN3 corepressor specifically associates with a diverse group of transcriptional repressors, including members of the MAD family, that play crucial roles in development. Brubaker et al. (2000) determined the nuclear magnetic resonance imaging structure of the complex formed by the PAH2 domain of mammalian Sin3a with the transrepression domain (SIN3-interaction domain, or SID) of human MAD1. They showed that the Sin3a PAH2 domain and the MAD1 SID undergo mutual folding transitions upon complex formation, generating an unusual left-handed, 4-helix bundle structure and an amphipathic alpha helix, respectively. The SID helix is wedged within a deep hydrophobic pocket defined by 2 PAH2 helices. Luo et al. (2002) showed that RNA interference-mediated suppression of MAD1 function in mammalian cells caused loss of MAD2 kinetochore localization and impairment of the spindle checkpoint. MAD1 and CDC20 (603618) contain MAD2-binding motifs that share a common consensus, and the authors identified a class of MAD2-binding peptides (MBPs) with a similar consensus. Binding of one of these ligands, MBP1, triggered an extensive rearrangement of the tertiary structure of MAD2. MAD2 also underwent a similar striking structural change upon binding to a MAD1 or CDC20 binding motif peptide. These data suggested that, upon checkpoint activation, MAD1 recruits MAD2 to unattached kinetochores and may promote binding of MAD2 to CDC20

Full details of the abovementioned studies are described in the following publications, the disclosure of which are hereby incorporated by reference:

Tsukasaki, K.; Miller, C. W.; Greenspun, E.; Eshaghian, S.; Kawabata, H.; Fujimoto, T.; Tomonaga, M.; Sawyers, C.; Said, J. W.; Koeffler, H. P.: Mutations in the mitotic check point gene, MAD1L1, in human cancers. Oncogene 120: 3301-3305, 2001. PubMed ID: 11423979 Luo, X.; Tang, Z.; Rizo, J.; Yu, H.: The Mad2 spindle checkpoint protein undergoes similar major conformational changes upon binding to either Mad1 or Cdc20. Molec. Cell 9: 59-71, 2002.

Further studies establishing the function and utilities of MAD1L1 are found in John Hopkins OMIM database record ID 602686, and in references numbered 956-960 listed hereinbelow.

Reference is now made to MAF BINDING SITE. V-maf musculoaponeurotic fibrosarcoma (avian) oncogene homolog (MAF) is a target gene of GAM26, corresponding to GAM26-TARGET GENE of FIG. 26A. MAF BINDING SITE is a binding site found in an untranslated region of MAF, corresponding to BINDING SITE of FIG. 26A. FIG. 26D illustrates the complementarity of the nucleotide sequence of MAF BINDING SITE, designated SEQ ID:241961, to the nucleotide sequence of GAM26 RNA of FIG. 26A, designated SEQ ID:20604.

An additional function of GAM26 is therefore inhibition of v-maf musculoaponeurotic fibrosarcoma (avian) oncogene homolog (MAF), a gene which encodes a transcription actor that is a transcription factor; contains a leucine zipper motif and is associated with hereditary congenital cataract. Accordingly, utilities of GAM26 include treatment of the abovementioned diseases and clinical conditions.

The function of MAF has been established by previous studies. Nishizawa et al. (1989) identified in the human genome a cellular analog of v-maf which was isolated from the provirus of the avian musculoaponeurotic fibrosarcoma virus AS42. The deduced amino acid sequence of the v-maf gene product contains a leucine zipper motif similar to that found in a number of DNA binding proteins, including the gene products of the FOS (164810), JUN (165160), and MYC (190080) oncogenes. Through the use of a cDNA probe for in situ hybridization, Yoshida et al. (1991) localized the MAF gene to 16q22-q23. Blank and Andrews (1997) reviewed the MAF transcription factors, a unique subclass of basic-leucine zipper transcription (bZIP) factors. Members of the MAF family appear to play important roles in the regulation of differentiation. Human congenital cataract and ocular anterior segment dysgenesis both demonstrate extensive genetic and phenotypic heterogeneity. Kim et al. (1999) demonstrated that the homozygous null mutant Maf mouse embryo exhibits defective lens formation and microphthalmia. Jamieson et al. (2002) identified a family where ocular developmental abnormalities (cataract, anterior segment dysgenesis, and microphthalmia) cosegregated with a translocation, t(5;16)(p15.3;q23.2), in both balanced and unbalanced forms. Cloning the 16q23.2 breakpoint demonstrated that it transected the genomic-control domain of MAF. The 16q23.2 breakpoint transected the common fragile site FRA16D (see 605131), providing a molecular demonstration of a germline break in a common fragile site. Through mutation screening of a panel of patients with hereditary congenital cataract, Jamieson et al. (2002) identified a mutation in the MAF gene in a 3-generation family with cataract, microcornea, and iris coloboma Full details of the abovementioned studies are described in the following publications, the disclosure of which are hereby incorporated by reference:

Jamieson, R. V.; Perveen, R.; Kerr, B.; Carette, M.; Yardley, J.; Heon, E.; Wirth, M. G.; van Heyningen, V.; Donnai, D.; Munier, F.; Black, C. M.: Domain disruption and mutation of the bZIP transcription factor, MAF, associated with cataract, ocular anterior segment dysgenesis and coloboma. Hum. Molec. Genet. 11: 33-42, 2002. PubMed ID: 11772997 Kim, J. I.; Li, T.; Ho, I. C.; Grusby, M. J.; Glimcher, L. H.: Requirement for the c-Maf transcription factor in crystallin gene regulation and lens development. Proc. Nat. Acad. Sci. 96: 3781-3785, 1999.

Further studies establishing the function and utilities of MAF are found in John Hopkins OMIM database record ID 177075, and in references numbered 961-965 listed hereinbelow.

Referring now to ADARB1 BINDING SITE. Adenosine deaminase, RNA-specific, B1 (homolog of rat RED1) (ADARB1) is a target gene of GAM26, corresponding GAM26-TARGET GENE of FIG. 26A. ADARB1 BINDING SITE is a binding site found in an untranslated region of ADARB1, corresponding to BINDING SITE of FIG. 26A. FIG. 26D illustrates the complementarity of the nucleotide sequence of ADARB1 BINDING SITE, designated SEQ ID:241978, to the nucleotide sequence of GAM26 RNA of FIG. 26A, designated SEQ ID:20604.

A further function of GAM26 is therefore inhibition of adenosine deaminase, RNA-specific, B1 (homolog of rat RED1) (ADARB1), a gene which encodes enzyme that RNA editing involves the deamination of adenosines at specific sites. Accordingly, utilities of GAM26 include diagnosis and treatment of the abovementioned diseases and clinical conditions. The function an utilities of ADARB1 have been established by previous studies, as described hereinabove with reference to FIG. 26D.

Referring now to BCL11B BINDING SITE. B-cell CLL/lymphoma 11B (zinc finger protein) (BCL11B) is a target gene of GAM26, corresponding to GAM26-TARGET GENE of FIG. 26A. BCL11B BINDING SITE is a binding site found in an untranslated region of BCL11B, corresponding to BINDING SITE of FIG. 26A. FIG. 26D illustrates the complementarity of the nucleotide sequence of BCL11B BINDING SITE, designated SEQ ID:241978, to the nucleotide sequence of GAM26 RNA of FIG. 26A, designated SEQ ID:20604.

Yet a further function of GAM26 is therefore inhibition of B-cell CLL/lymphoma 11B (zinc finger protein) (BCL11B), a gene which encodes a protein that is implicated in mouse and human leukemias and is associated with T-cell leukemia/lymphoma. Accordingly, utilities of GAM26 include diagnosis and treatment of the abovementioned diseases and clinical conditions. The function and utilities of BCL11B have been established by previous studies, as describe hereinabove with reference to FIG. 26D.

Referring now to FMR1 BINDING SITE. Fragile X mental retardation 1 (FMR1) is a target gene of GAM26, corresponding to GAM26-TARGET GENE of FIG. 26A. FMR1 BINDING SITE is a binding site found in an untranslated region of FMR1, corresponding to BINDING SITE of FIG. 26A. FIG. 26D illustrates the complementarity of the nucleotide sequence of FMR1 BINDING SITE, designated SEQ ID:241978, to the nucleotide sequence of GAM26 RNA of FIG. 26A, designated SEQ ID:20604.

Another function of GAM26 is therefore inhibition of fragile X mental retardation 1 (FMR1), a gene which encodes a protein that is associated with fragile x syndrome. Accordingly, utilities of GAM26 include diagnosis and treatment of the abovementioned diseases and clinical conditions. The function and utilities of FMR1 have been established by previous studies, as described hereinabove with reference to FIG. 26D.

Referring now to MAF BINDING SITE. V-maf musculoaponeurotic fibrosarcoma (avian) oncogene homolog (MAF) is a target gene of GAM26, corresponding to GAM26-TARGET GENE of FIG. 26A. MAF BINDING SITE is a binding site found in an untranslated region of MAF, corresponding to BINDING SITE of FIG. 26A. FIG. 26D illustrates the complementarity of the nucleotide sequence of MAF BINDING SITE, designated SEQ ID:241978, to the nucleotide sequence of GAM26 RNA of FIG. 26A, designated SEQ ID:20604.

Yet another function of GAM26 is therefore inhibition of v-maf musculoaponeurotic fibrosarcoma (avian) oncogene homolog (MAF), a gene which encodes a transcription factor that is a transcription factor; contains a leucine zipper motif and is associated with hereditary congenital cataract. Accordingly, utilities of GAM26 include diagnosis and treatment of the abovementioned diseases and clinical conditions. The function and utilities of MAF have been established by previous studies, as described hereinabove with reference to FIG. 26D.

Referring now to NPAS2 BINDING SITE. Neuronal PAS domain protein 2 (NPAS2) is a target gene of GAM26, corresponding to GAM26-TARGET GENE of FIG. 26A. NPAS2 BINDING SITE is a binding site found in an untranslated region of NPAS2, corresponding to BINDING SITE of FIG. 26A. FIG. 26D illustrates the complementarity of the nucleotide sequence of NPAS2 BINDING SITE, designated SEQ ID:241978, to the nucleotide sequence of GAM26 RNA of FIG. 26A, designated SEQ ID:20604.

An additional function of GAM26 is therefore inhibition of neuronal PAS domain protein 2 (NPAS2), a gene which encodes a protein that is a member of basic helix-loop-helix-PAS family of transcription factors. Accordingly, utilities of GAM26 include diagnosis and treatment of the abovementioned diseases and clinical conditions. The function and utilities of NPAS2 have been established by previous studies, as described hereinabove with reference to FIG. 26D.

Referring now to RELN BINDING SITE. Reelin (RELN) is a target gene of GAM26, corresponding to GAM26-TARGET GENE of FIG. 26A. RELN BINDING SITE is a binding site found in an untranslated region of RELN, corresponding to BINDING SITE of FIG. 26A. FIG. 26D illustrates the complementarity of the nucleotide sequence of RELN BINDING SITE, designated SEQ ID:241978, to the nucleotide sequence of GAM26 RNA of FIG. 26A, designated SEQ ID:20604.

A further function of GAM26 is therefore inhibition of reelin (RELN), a gene which encodes a transcription factor that is associated with Norman-Roberts syndrome. Accordingly, utilities of GAM26 include diagnosis and treatment of the abovementioned diseases and clinical conditions. The function and utilities of RELN have been established by previous studies, as described hereinabove with reference to FIG. 26D.

Referring now to ZNF6 BINDING SITE. Zinc finger protein 6 (CMPX1) (ZNF6) is a target gene of GAM26, corresponding to GAM26-TARGET GENE of FIG. 26A. ZNF6 BINDING SITE is a binding site found in an untranslated region of ZNF6, corresponding to BINDING SITE of FIG. 26A. FIG. 26D illustrates the complementarity of the nucleotide sequence of ZNF6 BINDING SITE, designated SEQ ID:241978, to the nucleotide sequence of GAM26 RNA of FIG. 26A, designated SEQ ID:20604.

Yet a further function of GAM26 is therefore inhibition of zinc finger protein 6 (CMPX1) (ZNF6), a gene which encodes a protein that is probably a transcriptional activator. Accordingly, utilities of GAM26 include diagnosis and treatment of the abovementioned diseases and clinical conditions. The function and utilities of ZNF6 have been established by previous studies, as described hereinabove with reference to FIG. 26D.

Reference is now made to MAFK BINDING SITE. V-maf musculoaponeurotic fibrosarcoma (avian) oncogene family, protein (MAFK) is a target gene of GAM26, corresponding to GAM26-TARGET GENE of FIG. 26A. MAFK BINDING SITE is a binding site found in an untranslated region of MAFK, corresponding to BINDING SITE of FIG. 26A. FIG. 26D illustrate the complementarity of the nucleotide sequence of MAFK BINDING SITE, designated SEQ ID:242287, to the nucleotide sequence of GAM26 RNA of FIG. 26A, designated SEQ ID:20604.

Another function of GAM26 is therefore inhibition of v-maf musculoaponeurotic fibrosarcoma (avian) oncogene family, protein (MAFK), a gene which encodes a transcription factor that is involved in regulation of transcription at NEF2 sites. Accordingly, utilities of GAM26 include diagnosis and treatment of the abovementioned diseases and clinical conditions.

The function of MAFK has been established by previous studies. The developmentally regulated expression of the globin genes depends on upstream regulatory elements termed locus control regions (LCRs). LCRs are associated with powerful enhancer activity that is mediated by the transcription factor NFE2 (nuclear factor erythroid-2). NFE2 recognition sites are also present in the gene promoters of 2 heme biosynthetic enzymes, porphobilinogen deaminase (PBGD; 176000) and ferrochelatase (FECH; 177000). NFE2 DNA-binding activity consists of a heterodimer containing an 18-kD Maf protein (MafF, MafG (602020), or MafK) and p45 (601490). Both subunits are members of the activator protein-1 superfamily of basic leucine zipper (bZip) proteins (see 165160). Maf homodimers suppress transcription at NFE2 sites. Toki et al. (1997) isolated a cDNA encoding human MAFK. The MAFK gene encodes a 156 amino acid polypeptide which is widely expressed, with highest levels seen in heart, placenta, skeletal muscle, and kidney. Toki et al. (1997) showed that MAFK could heterodimerize not only with p45, but also with NFE2-related factor 1 (NRF1; 163260) and NFE2-related factor 2 (600492); these heterodimers bound to NFE2 sites in vitro. In vivo, MAFK/p45 and MAFK/NRF1 heterodimers stimulated transcription from NFE2 sites. Similar results were found with MAFG. Iwata et al. (1998) showed that MAFK encoded by 3 exons spanning approximately 10 kb By use of 2 DNA mapping panels isolated from mice of a recombinant inbred strain set, Peters and Eicher (1994) demonstrated that the ubiquitous subunit is located on mouse chromosome 5. Since this region of the mouse genome shares linkage homology with human chromosome 7q, Peters and Eicher (1994) suggested that human NFE2U is probably located on 7q. Iwata et al. (1998) used FISH to map the MAFK gene to human chromosome 7p22. Motohashi et al. (2000) found that mouse embryos expressing abundant transgene-derived Mafk died of severe anemia, while lines expressing lower levels of small Maf lived to adulthood. Megakaryocytes from the latter overexpressing lines exhibited reduced proplatelet formation and MARE (Maf recognition element)-dependent transcription, phenocopying Mafg null mice (see Shavit et al. (1998)). When the Mafg null mice were bred to small Maf-overexpressing transgenic animals, both loss- and gain-of-function phenotypes were reversed Full details of the abovementioned studies are described in the following publications, the disclosure of which are hereby incorporated by reference:

Toki, T.; Itoh, J.; Kitazawa, J.; Arai, K.; Hatakeyama, K.; Akasaka, J.; Igarashi, K.; Nomura, N.; Yokoyama, M.; Yamamoto, M.; Ito, E.: Human small Maf proteins form heterodimers with CNC family transcription factors and recognize the NF-E2 motif. Oncogene 14: 1901-1910, 1997. PubMed ID: 9150357 Motohashi, H.; Katsuoka, F.; Shavit, J. A.; Engel, J. D.; Yamamoto, M.: Positive or negative MARE-dependent transcriptional regulation is determined by the abundance of small Maf proteins. Cell 103: 865-875, 2000.

Further studies establishing the function and utilities of MAFK are found in John Hopkins OMIM database record ID 600197, and in references numbered 966-970 listed hereinbelow.

Reference is now made to MAN2A1 BINDING SITE. Mannosidase alpha, class 2A, member 1 (MAN2A1) is a target gene of GAM26, corresponding to GAM26-TARGET GENE of FIG. 26A. MAN2A1 BINDING SITE is a binding site found in an untranslated region of MAN2A1, corresponding to BINDING SITE of FIG. 26A. FIG. 26D illustrates the complementarity of the nucleotide sequence of MAN2A1 BINDING SITE, designated SEQ ID:243405, to the nucleotide sequence of GAM26 RNA of FIG. 26A, designated SEQ ID:20604.

Yet another function of GAM26 is therefore inhibition of mannosidase, alpha, class 2A, member 1 (MAN2A1), a gene which encodes an enzyme that catalyzes the final hydrolytic step in the asparagine-linked oligosaccharide (N-glycan) maturation pathway and is associated with lupus erythematosus. Accordingly, utilities of GAM26 include diagnosis and treatment of the abovementioned diseases and clinical conditions.

The function of MAN2A1 has been established by previous studies. Alpha-mannosidase II catalyzes the first committed step in the biosynthesis of complex N-glycans. Genetic deficiency of this enzyme should abolish complex N-glycan production as reportedly does inhibition of the enzyme by swainsonine. Chui et al. (1997) found that mice in whom the alpha-mannosidase II gene had been disrupted developed a dyserythropoietic anemia concurrent with loss of erythrocyte complex N-glycans. Unexpectedly, nonerythroid cell types continued to produce complex N-glycans by an alternate pathway comprising a distinct alpha-mannosidase. These studies revealed cell type-specific variations in N-linked oligosaccharide biosynthesis and an essential role for alpha-mannosidase II in the formation of erythroid complex N-glycans. Alpha-mannosidase II deficiency elicited a phenotype in mice that corresponds to human congenital dyserythropoietic anemia type II. Although a genetic defect of MAN2A1 was thought to cause congenital dyserythropoietic anemia type II, or HEMPAS (224100), Gasparini et al. (1997) excluded it as a candidate gene by demonstrating linkage of the disorder to markers on chromosome 20. Protein glycosylation in the Golgi apparatus produces structural variation at the cell surface and contributes to immune self-recognition. Altered protein glycosylation and antibodies that recognize endogenous glycans have been associated with various autoimmune syndromes, with the possibility that such abnormalities may reflect genetic defects in glycan formation. Studying mice with a null allele for alpha-mannosidase II, Chui et al. (2001) showed that mutation in this gene, which regulates the hybrid to complex branching pattern of extracellular asparagine (N)-linked oligosaccharide chains (N-glycans), results in a systemic autoimmune disease similar to human systemic lupus erythematosus (152700). The findings demonstrated a genetic cause of autoimmune disease provoked by a defect in the pathway of protein N-glycosylation.

Full details of the abovementioned studies are described in the following publications, the disclosure of which are hereby incorporated by reference:

Chui, D.; Oh-Eda, M.; Liao, Y. -F.; Panneerselvam, K.; Lai, A.; Marek, K. W.; Freeze, H. H.; Moremen, K. W.; Fukuda, M. N.; Marth, J. D.: Alpha-mannosidase-II deficiency results in dyserythropoiesis and unveils an alternate pathway in oligosaccharide biosynthesis. Cell 90: 157-167, 1997. PubMed ID: 9230311 2. Chui, D.; Sellakumar, G.; Green, S.; Sutton-Smith, M.; McQuistan, T.; Marek, K. W.; Morris, H. R.; Dell, A.; Marth, J. D.: Genetic remodeling of protein glycosylation in vivo induces autoimmune disease. Proc. Nat. Acad. Sci. 98: 1142-1147, 2601.

Further studies establishing the function and utilities of MAN2A1 are found in John Hopkins OMIM database record ID 154582, and in references numbered 971-975 listed hereinbelow.

Reference is now made to MAP3K5 BINDING SITE. Mitogen-activated protein kinase kinase kinase 5 (MAP3K5) is a target gene of GAM26, corresponding to GAM26-TARGET GENE of FIG. 26A. MAP3K5 BINDING SITE is a binding site found in an untranslated region of MAP3K5, corresponding to BINDING SITE of FIG. 26A. FIG. 26D illustrates the complementarity of the nucleotide sequence of MAP3K5 BINDING SITE, designated SEQ ID:244540, to the nucleotide sequence of GAM26 RNA of FIG. 26A, designated SEQ ID:20604.

An additional function of GAM26 is therefore inhibition of mitogen-activated protein kinase kinase kinase 5 (MAP3K5), a gene which encodes an enzyme that phosphorylates and activates two different subgroups of map kinases, mkk4/sek1 and mkk3/mapkk6 (or mkk6) overexpression induces apoptotic cell death. Accordingly, utilities of GAM26 include diagnosis and treatment the abovementioned diseases and clinical conditions.

The function of MAP3K5 has been established by previous studies. Mitogen-activated protein kinase (MAPK) signaling cascades include MAPK or extracellular signal-regulated kinase (ERK), MAPK kinase (MAP2K, also called MKK or MEK), and MAPK kinase kinase (MAP3K, also called MAPKKK or MEKK). MAPKK kinase/MEKK phosphorylates and activates its downstream protein kinase, MAPK kinase/MEK, which in turn activates MAPK. The kinases of these signaling cascades are highly conserved, and homologs exist in yeast, *Drosophila*, and mammalian cells Ichijo et al. (1997) used a similar strategy to identify a nearly identical MAPKKK cDNA, termed ASK1 for apoptosis signal-regulating kinase. The deduced protein contains 1,375 amino acids, and is most closely related to yeast SSK2 and SSK22, which are upstream regulators of yeast HOG1 MAPK. ASK1 expression complements a yeast mutant lacking functional SSK2 and SSK22. ASK1 also activates MKK3 (60231), MKK4 (SEK1), and MKK6 (601254). Overexpression of ASK1 induces apoptotic cell death, and ASK1 is activated in cells treated with tumor necrosis factor-alpha (TNFA; 191160). Nishitoh et al. (1998) showed that ASK1 interacts with members of the TRAF family and is activated by TRAF2 (601895) in the TNF-signaling pathway. After activation by TRAF2, ASK1 activates MKK4, which in turn activates JNK. Thus, ASK1 is mediator of TRAF2-induced JNK activation.

Animal model experiments lend further support to the function of MAP3K5. Using a forward genetic screen of *C. elegans* mutants, Kim et al. (2002) showed that viable worms lacking esp2 and esp8, homologs of the mammalian MAP kinases SEK1 and ASK1, were highly susceptible to and died more rapidly from both a gram-negative bacterium, *P. aeruginosa*, and a gram-positive organism, *E. faecalis*, than wildtype worms. RNA-interference and biochemical analyses likewise implicated the p38 MAP kinase homolog, pmk1, in susceptibility to these pathogens. Kim et al. (2002) concluded that MAP kinase signaling, which is also involved in plant pathogen resistance, is a conserved element in innate metazoan immunity to diverse pathogens.

It is appreciated that the abovementioned animal model for MAP3K5 is acknowledged by those skilled in the art as a scientifically valid animal model, as can be further appreciated from the publications sited hereinbelow.

Full details of the abovementioned studies are described in the following publications, the disclosure of which are hereby incorporated by reference:

Kim D. H.; Feinbaum, R.; Alloing, G.; Emerson, F. E.; Garsin, D. A.; Inoue, H.; Tanaka-Hino, M.; Hisamoto, N.; Matsumoto, K.; Tan, M. W.; Ausubel, F. M.: A conserved p38 MAP kinase pathway in *Caenorhabditis elegans* innate immunity. Science 297: 623-626, 2002. PubMed ID: 12142542 Nishitoh, H.; Saitoh, M.; Mochida, Y.; Takeda, K.; Nakano H.; Rothe, M.; Miyazono, K.; Ichijo, H.: ASK1 is essential for JNK/SAPK activation by TRAF2. Molec. Cell 2: 389-395, 1998.

Further studies establishing the function and utilities MAP3K5 are found in John Hopkins OMIM database record ID 602448, and in references numbered 976-985 listed hereinbelow.

Reference is now made to MAP4K5 BINDING SITE. Mitogen-activated protein kinase kinase kinase kinase 5 (MAP4K5) is a target gene of GAM26, corresponding to GAM26-TARGET GENE of FIG. 26A. MAP4K5 BINDING SITE is a binding site found in an untranslated region of MAP4K5, corresponding to BINDING SITE of FIG. 26A. FIG. 26D illustrates the complementarity of the nucleotide sequence of MAP4K5 BINDING SITE, designate SEQ ID:245274, to the nucleotide sequence of GAM26 RNA of FIG. 26A, designated SEQ ID:20604.

A further function of GAM26 is therefore inhibition of mitogen-activated protein kinase kinase kinase kinase 5 (MAP4K5), a gene which encodes an enzyme that is a serine/threonine protein kinase required for spore wall development, activates Jun N-terminal kinase; member of the STE20 kinase family. Accordingly, utilities of GAM26 include diagnosis and treatment of the abovementioned diseases and clinical conditions.

The function of MAP4K5 has been established by previous studies. Protein kinases (PKs) are critical to the regulation of many cellular processes, including growth factor response, cytoskeletal changes, gene expression, and metabolism. Mitogen-activated PKs (MAPKs) are a family of serine/threonine involved in highly conserved cascades that control these processes. MAPKs are activated by MAPK kinases (MAP2Ks), which are activated by MAP2K kinases (MAP3Ks), which are activated by MAP3K kinases (MAP4Ks). (For example, ERK2 (MAPK1; 16948) is activated by phosphorylation of ser/thr residues by its upstream kinase, MEK1 (MAP2K1; 176872), which is itself activated by MEKK1 (MAP3K1; 600982). Another MAPK, JNK (MAPK8; 601158), is predominantly activated in response to stress. JNK expression is also regulated by upstream kinases (e.g., MAP2K4; 601335), which are activated by MAP3Ks. Homologs of the S. cerevisiae STE20 and SPS1 proteins are predicted to link the membrane with the cytoplasmic signaling machinery; see 602255. By screening a T-cell library with a PCR-derived probe that was similar to yeast STE20, Tung and Blenis (1997) obtained a cDNA encoding MAP4K5, which they called 'kinase homologous to SPS1/STE20,' or KHS. Sequence analysis revealed that the 846-amino acid MAP4K5 protein contains an N-terminal catalytic domain and shares 55% amino acid identity with MAP4K2 (603166). Northern blot analysis detected a 4.5-kb MAP4K5 transcript in all tissues tested, namely spleen, thymus, prostate, testis, ovary, small intestine, colon, and peripheral blood leukocytes. SDS-PAGE and immunoblot analyses determined that MAP4K5 is expressed as a 95-kD protein. Confocal laser microscopy demonstrated cytoplasmic expression MAP4K5. Functional analyses showed that MAP4K5 has kinase activity and that it activates JNK but not ERK1 (MAPK3; 601795) or MAPK14 (600289) through MAP2K4.

Full details of the abovementioned studies are described in the following publications, the disclosure of which are hereby incorporated by reference:

Tung, R. M.; Blenis, J.: A novel human SPS1/STE20 homologue, KHS, activates Jun N-terminal kinase. Oncogene 14: 653-659, 1997.

Further studies establishing the function and utilities of MAP4K5 are found in John Hopkins OMIM database record ID 604923, and in references numbered 986 listed hereinbelow.

Referring now to MAP4K5 BINDING SITE. Mitogen-activated protein kinase kinase kinase kinase 5 (MAP4K5) is a target gene of GAM26, corresponding to GAM26-TARGET GENE of FIG. 26A. MAP4K5 BINDING SITE is a binding site found in an untranslated region of MAP4K5, corresponding to BINDING SITE of FIG. 26A. FIG. 26D illustrates the complementarity of the nucleotide sequence of MAP4K5 BINDING SITE, designated SEQ ID:245277, to the nucleotide sequence of GAM26 RNA of FIG. 26A, designated SEQ ID:20604.

Yet a further function of GAM26 is therefore inhibition of mitogen-activated protein kinase kinase kinase kinase 5 (MAP4K5), a gene which encodes a an enzyme that is a serine/threonine protein kinase required for spore wall development activates Jun N-terminal kinase; member of the STE20 kinase family. Accordingly, utilities of GAM26 include diagnosis and treatment of the abovementioned diseases and clinical conditions. The function and utilities of MAP4K5 have been established by previous studies, as described hereinabove with reference to FIG. 26D.

Referring now to MAP4K5 BINDING SITE. Mitogen-activated protein kinase kinase kinase kinase 5 (MAP4K5) is a target gene of GAM26, corresponding to GAM26-TARGET GENE of FIG. 26A. MAP4K5 BINDING SITE is a binding site found in an untranslated region of MAP4K5, corresponding to BINDING SITE of FIG. 26A. FIG. 26D illustrates the complementarity of the nucleotide sequence of MAP4K5 BINDING SITE, designated SEQ ID:245293, to the nucleotide sequence of GAM26 RNA of FIG. 26A, designated SEQ ID:20604.

Another function of GAM26 is therefore inhibition of mitogen-activated protein kinase kinase kinase kinase 5 (MAP4K5), a gene which encodes an enzyme that is a serine/threonine protein kinase required for spore wall development, activates Jun N-terminal kinase; member of the STE20 kinase family. Accordingly, utilities of GAM26 include diagnosis and treatment of the abovementioned diseases and clinical conditions. The function and utilities of MAP4K5 have been established by previous studies, as described hereinabove with reference to FIG. 26D.

Referring now to MAP4K5 BINDING SITE. Mitogen-activated protein kinase kinase kinase kinase 5 (MAP4K5) is a target gene of GAM26, corresponding to GAM26-TARGET GENE of FIG. 26A. MAP4K5 BINDING SITE is a binding site found in an untranslated region of MAP4K5, corresponding to BINDING SITE of FIG. 26A. FIG. 26D illustrates the complementarity of the nucleotide sequence of MAP4K5 BINDING SITE, designated SEQ ID:245294, to the nucleotide sequence of GAM26 RNA of FIG. 26A, designated SEQ ID:20604.

Yet another function of GAM26 is therefore inhibition of mitogen-activated protein kinase kinase kinase kinase 5 (MAP4K5), a gene which encodes an enzyme that is a serine/threonine protein kinase required for spore wall development, activates Jun N-terminal kinase; member of the STE20 kinase family. Accordingly, utilities of GAM26 include diagnosis and treatment of the abovementioned diseases and clinical conditions. The function and utilities of MAP4K5 have been established by previous studies, as described hereinabove with reference to FIG. 26D.

Reference is now made to MAPK1 BINDING SITE. Mitogen-activated protein kinase 1 (MAPK1) is a target gene of GAM26, corresponding to GAM26-TARGET GENE of FIG. 26A. MAPK1 BINDING SITE is a binding site found in an untranslated region of MAPK1, corresponding to BINDING SITE of FIG. 26A. FIG. 26D illustrates the complementarity of the nucleotide sequence of MAPK1 BINDING SITE, designated SEQ ID:245382, to the nucleotide sequence of GAM26 RNA of FIG. 26A, designated SEQ ID:20604.

An additional function of GAM26 is therefore inhibition of mitogen-activated protein kinase 1 (MAPK1), a gene which encodes an enzyme that phosphorylates microtubule-associated protein-2 (map2) myelin basic protein (mbp), and elk-1; may promote entry in the cell cycle. Accordingly, utilities of GAM26 include diagnosis and treatment of the abovementioned diseases and clinical conditions.

The function of MAPK1 has been established by previous studies. Forcet et al. (2002) showed that in embryonic kidney cells expression full-length, but not cytoplasmic domain-truncated, DCC (120470), NTN1 (601614) causes increased transient phosphorylation and activity of ERK1 and ERK2, but not of JNK1 (601158), JNK2 (602896), or p38 (MAPK14; 600289). This phosphorylation was mediated by MEK1 and/or MEK2. NTN1 also activated the transcription factor ELK1 (311040) and serum response element-regulated gene expression. Immunoprecipitation analysis showed interaction of full-length DCC with MEK1/2 in the present or absence of NTN1. Forcet et al. (2002) showed that activation of Dcc by Ntn1 in rat embryonic day-13 dorsal spinal cord stimulates and is required for the outgrowth of commissural axons and Erk1/2 activation. Immunohistochemical analysis demonstrated expression of activated Erk1/2 in embryonic commissural axons, and this expression was diminished in Dcc or Ntn1 knockout animals. Forcet et al. (2002) concluded that the MAPK pathway is involved in responses to NTN1 and proposed that ERK activation affects axonal growth by phosphorylation of microtubule-associated proteins and neurofilaments. Stefanovsky et al. (2001) showed that epidermal growth factor (131530) induces immediate, ERK1/ERK2-dependent activation of endogenous ribosomal transcription, while inactivation of ERK1/ERK2 causes an equally immediate reversion to the basal transcription level. ERK1/ERK2 was found to phosphorylate the architectural transcription factor UBF (600673) at amino acids 117 and 201 within HMG boxes 1 and 2, preventing their interaction with DNA. Mutation of these sites inhibited transcription activation and abrogated the transcriptional response to ERK1/ERK2. Thus, growth factor regulation of ribosomal transcription likely acts by a cyclic modulation of DNA architecture. The data suggested a central role for ribosome biogenesis in growth regulation Full details of the abovementioned studies are described in the following publications, the disclosure of which are hereby incorporated by reference:

Forcet, C.; Stein, E.; Pays, L.; Corset, V.; Llambi, F.; Tessier-Lavigne, M.; Mehlen, P.: Netrin-1-mediated axon outgrowth requires deleted in colorectal cancer-dependent MAPK activation. Nature 417: 443-447, 2002. PubMed ID:11986622. Stefanovsky, V. Y.; Pelletier, G.; Hannan, R.; Gagnon-Kugler, T.; Rothblum, L. I.; Moss, T.: An immediate response of ribosomal transcription to growth factor stimulation in mammals is mediated by ERK phosphorylation of UBF. Molec. Cell 8: 1063-1073, 2001.

Further studies establishing the function and utilities of MAPK1 are found in John Hopkins OMIM database record ID 176948, and in references numbered 987-1001 listed hereinbelow.

Referring now to MAPK1 BINDING SITE. Mitogen-activated protein kinase 1 (MAPK1) is a target gene of GAM26, corresponding to GAM26-TARGET GENE of FIG. 26A. MAPK1 BINDING SITE is a binding site found in an untranslated region of MAPK1, corresponding to BINDING SITE of FIG. 26A. FIG. 26D illustrates the complementarity of the nucleotide sequence of MAPK1 BINDING SITE, designated SEQ ID:245394, to the nucleotide sequence of GAM26 RNA of FIG. 26A, designated SEQ ID:20604.

A further function of GAM26 is therefore inhibition of mitogen-activated protein kinase 1 (MAPK1), a gene which encodes an enzyme that phosphorylates microtubule-associated protein-2 (map2). myelin basic protein (mbp), and elk-1; may promote entry in the cell cycle. Accordingly, utilities of GAM26 include diagnosis and treatment of the abovementioned diseases and clinical conditions. The function and utilities of MAPK1 have been established by previous studies, as described hereinabove with reference to FIG. 26D.

Reference is now made to MATK BINDING SITE. Megakaryocyte-associated tyrosine kinase (MATK) is a target gene of GAM26, corresponding to GAM26-TARGET GENE of FIG. 26A. MATK BINDING SITE is a binding site found in an untranslated region of MATK, corresponding to BINDING SITE of FIG. 26A. FIG. 26D illustrates the complementarity of the nucleotide sequence of MATK BINDING SITE, designated SEQ ID:247365, to the nucleotide sequence of GAM26 RNA of FIG. 26A, designated SEQ ID:20604.

Yet a further function of GAM26 is therefore inhibition of megakaryocyte-associated tyrosine kinase (MATK), a gene which encodes an enzyme that can phosphorylate members of the SRC family of PTKs at the regulatory tyrosine residue. Accordingly, utilities of GAM26 include diagnosis and treatment of the abovementioned diseases and clinical conditions.

The function of MATK has been established by previous studies. In the mouse, Klages et al. (1994) reported the molecular cloning and preliminary functional characterization of a nonreceptor protein tyrosine kinase (PTK) that is related to CSK (124095). This PTK, designated Ctk for CSK-type protein-tyrosine kinase, was found to be a 52-kD protein expressed primarily in brain and predicted to be structurally similar to CSK. Klages et al. (1994) found that, like CSK, Ctk can phosphorylate members of the SRC family of PTKs at the regulatory tyrosine residue. Thus, Ctk and CSK define a family of kinases that phosphorylate carboxy-terminal regulatory tyrosine residues. Protein-tyrosine kinases play major roles in signal transduction pathways. Bennett et al. (1994) cloned a novel tyrosine kinase, termed megakaryocyte-associated tyrosine kinase (MATK) from a human megakaryocyte cDNA library using degenerate PCR. The MATK cDNA encodes a 527-amino acid protein that shows 50% amino acid identity to CSK and has the structural features of the CSK subfamily: SRC homology SH (2) and SH3 domains, a catalytic domain, a unique N terminus, lack of myristylation signals, lack of a negative regulatory phosphorylation site, and lack of an autophosphorylation site Bennett et al. (1994) localized the MATK protein to the cytoplasm of megakaryocytic cells using immunofluorescence and immunoblot analysis of subcellular fractions. They showed by Northern blotting that the MATK gene is expressed abundantly in megakaryocytes and at a lower level in adult brain as a 2.3-kb transcript; it was not delectably expressed in any other examined tissue. Bennett et al. (1994) found that MATK expression is upregulated in megakaryocytic cells that are induced to differentiate by phorbol ester. They suggested that MATK functions in signal transduction pathways that are important in megakaryocyte growth and/or differentiation. Avraham et al. (1995) showed that MATK can phosphorylate the SRC (176947) protein in vitro. Sakano et al. (1994) cloned the MATK cDNA, name HYL by them, and localized the gene to 19p13.3 using fluorescence in situ hybridization. Avraham et al. (1995) mapped the MATK gene to chromosome 19 using somatic cell hybrids and found that the murine Matk gene maps within a region of synteny on chromosome 10. Zrihan-Licht et al. (1997) reported that MATK is expressed in human breast cancer but not in the adjacent normal breast tissues, suggesting that MATK might be involved in signaling in some cases of breast cancer. Zrihan-Licht et al. (1997) demonstrated that MATK interacts with ErbB-2 (164870) in vivo upon heregulin stimulation and that this interaction occurs via the SH2 domain of MATK.

Full details of the abovementioned studies are described in the following publications, the disclosure of which are hereby incorporated by reference:

Klages, S.; Adam, D.; Class, K.; Fargnoli, J.; Bolen, J. B.; Penhallow, R. C.: Ctk: a protein-tyrosine kinase related to Csk that defies an enzyme family. Proc. Nat. Acad. Sci. 91: 2597-2601, 1994. PubMed ID: 7511815 1. Avraham, S.; Jiang, S.; Ota, S.; Fu, Y.; Deng, B.; Dowler, L. L.; White, R. A.; Avraham, H.: Structural and functional studies of the intracellular tyrosine kinase MATK gene and its translated product. J. Biol. Chem. 270: 1833-1842, 1995.

Further studies establishing the function and utilities of MATK are found in John Hopkins OMIM database record ID 600038, and in references numbered 1002-1006 listed hereinbelow.

Reference is now made to MID2 BINDING SITE. Midline 2 (MID2) is a target gene of GAM26, corresponding to GAM26-TARGET GENE of FIG. 26A. MID2 BINDING SITE is a binding site found in an untranslated region of MID2, corresponding to BINDING SITE of FIG. 26A. FIG. 26D illustrates the complementarity of the nucleotide sequence of MID2 BINDING SITE, designated SEQ ID:254906, to the nucleotide sequence of GAM26 RNA of FIG. 26A, designated SEQ ID:20604.

Another function of GAM26 is therefore inhibition of midline 2 (MID2), a gene which encodes a protein that has a fibronectin type III domain, similar to FXY/MID1. Accordingly, utilities of GAM26 include diagnosis and treatment of the abovementioned diseases and clinical conditions.

The function of MID2 has been established by previous studies. By searching an EST database to identify human homologs of the MID1 gene, Buchner et al. (1999) identified MID2, a transcript closely related to MID1. MID1 and MID2 display 84% similarity and 77% identity at the protein level, and 70% identity at the nucleotide level. Like MID1, MID2 displays a RING finger, 2 B-boxes, a coiled-coil, and a conserved RFP-like C-terminal domain. The mouse Mid2 protein shows 99.3% identity with human MID2. MID2 appears to be part of a linkage group conserved between mouse and man. Buchner et al. (1999) found that the MID2 gene contains 9 exons. The junction sequences were all in agreement with the 5-prime and 3-prime splice site consensus motifs, with the exception of the exon 6 5-prime splice site which showed the sequence GCAAGT instead of the consensus GT dinucleotide reported in all but 0.13% of donor splice site sequences (Shapiro and Senapathy, 1987). MID1 and MID2 have similar intron-exon structures, with the exception of MID2 exon 6 which had 30 additional amino acids as compared with MID1.

Full details of the abovementioned studies are described in the following publications, the disclosure of which are hereby incorporated by reference:

Buchner, G.; Montini, E.; Andolfi, G.; Quaderi, N.; Cainarca, S.; Messali, S.; Bassi, M. T.; Ballabio, A.; Meroni, G.; Franco, B.: MID2, a homologue of the Opitz syndrome gene MID1: similarities in subcellular localization and differences in expression during development. Hum. Molec. Genet 8: 1397-1407, 1999. PubMed ID: 10400986 3. Shapiro, M. B.; Senapathy, P.: RNA splice junctions of different classes of eukaryotes: sequence statistics and functional implications in gene expression. Nucleic Acids Res. 15: 7155-7174, 1987.

Further studies establishing the function and utilities of MID2 are found in John Hopkins OMIM database record ID 300204, and in reference numbered 1007-1009 listed hereinbelow.

Referring now to MID2 BINDING SITE. Midline 2 (MID2) is a target gene of GAM26, corresponding to GAM26-TARGET GENE of FIG. 26A. MID2 BINDING SITE is a binding site found in an untranslated region of MID2, corresponding to BINDING SITE of FIG. 26A. FIG. 26D illustrates the complementarity of the nucleotide sequence of MID2 BINDING SITE, designated SEQ ID:254911, to the nucleotide sequence of GAM26 RNA of FIG. 26A, designated SEQ ID:20604.

Yet another function of GAM26 is therefore inhibition of midline 2 (MID2), a gene which encodes a protein that has a fibronectin type III domain, similar to FXY/MID1. Accordingly, utilities of GAM26 include diagnosis and treatment of the abovementioned diseases and clinical conditions. The function and utilities of MID2 have been established by previous studies, as described hereinabove with reference to FIG. 26D.

Referring now to MID2 BINDING SITE. Midline 2 (MID2) is a target gene of GAM26, corresponding to GAM26-TARGET GENE of FIG. 26A. MID2 BINDING SITE is a binding site found in an untranslated region of MID2, corresponding to BINDING SITE of FIG. 26A. FIG. 26D illustrates the complementarity of the nucleotide sequence of MID2 BINDING SITE, designated SEQ ID:254918, to the nucleotide sequence of GAM26 RNA of FIG. 26A, designated SEQ ID:20604.

An additional function of GAM26 is therefore inhibition of midline 2 (MID2), a gene which encodes a protein that Has fibronectin type III domain. Also has fibronectin type III domain, similar to FXY/MID1. Accordingly, utilities of GAM26 include diagnosis and treatment of the abovementioned diseases and clinical conditions. The function and utilities of MID2 have been established by previous studies, as described hereinabove with reference to FIG. 26D.

Referring now to MID2 BINDING SITE. Midline 2 (MID2) is a target gene of GAM26, corresponding to GAM26-TARGET GENE of FIG. 26A. MID2 BINDING SITE is a binding site found in an untranslated region of MID2, corresponding to BINDING SITE of FIG. 26A. FIG. 26D illustrates the complementarity of the nucleotide sequence of MID2 BINDING SITE, designated SEQ ID:254922, to the nucleotide sequence of GAM26 RNA of FIG. 26A, designated SEQ ID:20604.

A further function of GAM26 is therefore inhibition of midline 2 (MID2), a gene which encodes a protein that has fibronectin type III domain, similar to FXY/MID1. Accordingly, utilities of GAM26 include diagnosis and treatment of the abovementioned diseases and clinical conditions. The function and utilities of MID2 have been established by previous studies, as described hereinabove with reference to FIG. 26D.

Referring now to MID2 BINDING SITE. Midline 2 (MID2) is a target gene of GAM26, corresponding to GAM26-TARGET GENE of FIG. 26A. MID2 BINDING SITE is a binding site found in an untranslated region of MID2, corresponding to BINDING SITE of FIG. 26A. FIG. 26D illustrates the complementarity of the nucleotide sequence of MID2 BINDING SITE, designated SEQ ID:254923, to the nucleotide sequence of GAM26 RNA of FIG. 26A, designated SEQ ID:20604.

Yet a further function of GAM26 is therefore inhibition of midline 2 (MID2), a gene which encodes a protein that has fibronectin type III domain, similar to FXY/MID1. Accordingly, utilities of GAM26 include diagnosis and treatment of the abovementioned diseases and clinical conditions. The function and utilities of MID2 have been established by previous studies, as described hereinabove with reference to FIG. 26D.

Referring now to MLLT1 BINDING SITE. Myeloid/lymphoid or mixed-lineage leukemia (trithorax (*Drosophila*) horn (MLLT1) is a target gene of GAM26, corresponding to GAM26-TARGET GENE of FIG. 26A. MLLT1 BINDING SITE is a binding site found in an untranslated region of MLLT1, corresponding to BINDING SITE of FIG. 26A. FIG. 26D illustrates the complementarity of the nucleotide sequence of MLLT1 BINDING SITE, designated SEQ ID:255942, to the nucleotide sequence of GAM26 RNA of FIG. 26A, designated SEQ ID:20604.

Another function of GAM26 is therefore inhibition of myeloid/lymphoid or mixed-lineage leukemia trithorax (*Drosophila*) horn (MLLT1), a gene which encodes a protein that is associated with acute leukemias. Accordingly, utilities of GAM26 include diagnosis and treatment of the abovementioned diseases and clinical conditions. The function and utilities of MLLT1 have been established by previous studies, as described hereinabove with reference to FIG. 26D.

Referring now to MLLT1 BINDING SITE. Myeloid/lymphoid or mixed-lineage leukemia (trithorax (*Drosophila*) horn (MLLT1) is a target gene of GAM26, corresponding to GAM26-TARGET GENE of FIG. 26A. MLLT1 BINDING SITE is a binding site found in an untranslated region of MLLT1, corresponding to BINDING SITE of FIG. 26A. FIG. 26D illustrates the complementarity of the nucleotide sequence of MLLT1 BINDING SITE, designated SEQ ID:255948, to the nucleotide sequence of GAM26 RNA of FIG. 26A, designated SEQ ID:20604.

Yet another function of GAM26 is therefore inhibition of myeloid/lymphoid or mixed-lineage leukemia (trithorax (*Drosophila*) horn (MLLT1), a gene which encodes a protein that is associated with acute leukemias. Accordingly, utilities of GAM26 include diagnosis and treatment of the abovementioned diseases and clinical conditions. The function and utilities of MLLT1 have been established by previous studies, as described hereinabove with reference to FIG. 26D.

Referring now to NTRK3 BINDING SITE. Neurotrophic tyrosine kinase, receptor, type 3 (NTRK3) is a target gene of GAM26, corresponding to GAM26-TARGET GENE of FIG. 26A. NTRK3 BINDING SITE is a binding site found in an untranslated region of NTRK3, corresponding to BINDING SITE of FIG. 26A. FIG. 26D illustrates the complementarity of the nucleotide sequence of NTRK3 BINDING SITE, designated SEQ ID:255948, to the nucleotide sequence of GAM26 RNA of FIG. 26A, designated SEQ ID:20604.

An additional function of GAM26 is therefore inhibition of neurotrophic tyrosine kinase, receptor, type 3 (NTRK3), a gene which encodes a protein that is a tyrosine-protein kinase receptor. Accordingly, utilities of GAM26 include diagnosis and treatment of the abovementioned diseases and clinical conditions. The function and utilities of NTRK3 have been established by previous studies, as described here above with reference to FIG. 26D.

Referring now to MLLT1 BINDING SITE. Myeloid/lymphoid or mixed-lineage leukemia (trithorax (*Drosophila*) horn (MLLT1) is a target gene of GAM26, corresponding to GAM26-TARGET GENE of FIG. 26A. MLLT1 BINDING SITE is a binding site found in an untranslated region of MLLT1, corresponding to BINDING SITE of FIG. 26A. FIG. 26D illustrates the complementarity of the nucleotide sequence of MLLT1 BINDING SITE, designated SEQ ID:255952, to the nucleotide sequence of GAM26 RNA of FIG. 26A, designated SEQ ID:20604.

A further function of GAM26 is therefore inhibition of myeloid/lymphoid or mixed-lineage leukemia (trithorax (*Drosophila*) horn (MLLT1), a gene which encodes a protein that is associated with acute leukemias. Accordingly, utilities of GAM26 include diagnosis and treatment of the abovementioned diseases and clinical conditions. The function and utilities of MLLT1 have been established by previous studies, as described hereinabove with reference to FIG. 26D.

Referring now to MLLT1 BINDING SITE. Myeloid/lymphoid or mixed-lineage leukemia (trithorax (*Drosophila*) horn (MLLT1) is a target gene of GAM26, corresponding to GAM26-TARGET GENE of FIG. 26A. MLLT1 BINDING SITE is a binding site found in an untranslated region of MLLT1, corresponding to BINDING SITE of FIG. 26A. FIG. 26D illustrates the complementarity of the nucleotide sequence of MLLT1 BINDING SITE, designated SEQ ID:255957, to the nucleotide sequence of GAM26 RNA of FIG. 26A, designated SEQ ID:20604.

Yet a further function of GAM26 is therefore inhibition of myeloid/lymphoid or mixed-lineage leukemia (trithorax (*Drosophila*) horn (MLLT1), a gene which encodes a protein that is associated with acute leukemias. Accordingly, utilities of GAM26 include diagnosis and treatment of the abovementioned diseases and clinical conditions. The function and utilities of MLLT1 have been established by previous studies, as described hereinabove with reference to FIG. 26D.

Reference is now made to MPP6 BINDING SITE. MEMBRANE PROTEIN, PALMITOYLATED 6; MPP6 (MPP6) is a target gene of GAM26, corresponding to GAM26-TARGET GENE of FIG. 26A. MPP6 BINDING SITE is a binding site found in an untranslated region of MPP6, corresponding to BINDING SITE of FIG. 26A. FIG. 26D illustrates the complementarity of the nucleotide sequence of MPP6 BINDING SITE, designated SEQ ID:259906, to the nucleotide sequence of GAM26 RNA of FIG. 26A, designated SEQ ID:20604.

Another function of GAM26 is therefore inhibition of MEMBRANE PROTEIN, PALMITOYLATED 6; MPP6 (MPP6), a gene which encodes a protein that may regulate transmembrane proteins that bind calcium, calmodulin, or nucleotides. Accordingly, utilities of GAM26 include diagnosis and treatment of the abovementioned diseases and clinical conditions.

The function of MPP6 has been established by previous studies. By searching an EST database with DLG2 (603583) as the probe, followed by PCR of a brain cDNA library and 5-prime RACE, Tseng et al. (2001) obtained a cDNA encoding MPP6, which they called VAM1 for VELI (603380) associated MAGUK-1. The deduced 540-amino acid protein has a single PDZ domain, a central SH3 domain, and a C-terminal GUK domain, resembling other members of the p55 MAGUK subfamily. Like MPP1, MPP6 also contains a protein 4.1 (EPB41; 130500)-binding domain with its characteristic KKKK sequence, as well as a leucine zipper and 2 phosphorylation sites. Northern blot analysis revealed expression of an abundant 2.3-kb transcript and a minor 4.2-kb transcript only in testis. RT-PCR analysis detected predominant expression in testis, with lower amounts in ovary, prostate, thymus, small intestine, and several other tissues; VELI has a similar expression pattern. GST pull-down and mutation analyses indicated that a domain N-terminal of the PDZ region of VAM1 contains the minimal VELI-binding sequence. No binding between VAM1 and EPB41 was detected. Kamberov et al. (2000) cloned and characterized the mouse Mpp5 (606958) and Mpp6 genes, which they called Pals1 and Pals2, respectively. The Pals proteins bind to mouse Lin7 (VELI) through a region N-terminal to their PDZ domains.

Full details of the abovementioned studies are described in the following publications, the disclose of which are hereby incorporated by reference:

amberov, E.; Makarova, O.; Roh, M.; Liu, A.; Karnak, D.; Straight, S.; Margolis, B.: Molecular cloning and characterization of Pals, proteins associated with mLin-7. J. Biol. Chem. 275: 11425-11431, 2000. PubMed ID: 10753959 2. Tseng, T. C.; Marfatia, S. M.; Bryant, P. J.; Pack, S.; Zhuang, A.; O'Brien, J. E.; Lin, L.; Hanada, T.; Chishti, A. H.: VAM-1: a new member of the MAGUK family binds to human Veli-1 through a conserved domain. Biochim. Biophys. Acta 1518: 249-259, 2001.

Further studies establishing the function and utilities of MPP6 are found in John Hopkins OMIM database record ID 606959, and in references numbered 1010-1011 listed hereinbelow.

Referring now to MPP6 BINDING SITE MEMBRANE PROTEIN, PALMITOYLATED 6; MPP6 (MPP6) is a target gene of GAM26, corresponding to GAM26-TARGET GENE of FIG. 26A. MPP6 BINDING SITE is a binding site found in an untranslated region of MPP6, corresponding to BINDING SITE of FIG. 26A. FIG. 26D illustrates the complementarity of the nucleotide sequence of MPP6 BINDING SITE, designated SEQ ID:259910, to the nucleotide sequence of GAM26 RNA of FIG. 26A, designated SEQ ID:20604.

Yet another function of GAM26 is therefore inhibition of MEMBRANE PROTEIN, PALMITOYLATED 6; MPP6 (MPP6), a gene which encodes a protein that may regulate transmembrane proteins that bind calcium, calmodulin, or nucleotides. Accordingly, utilities of GAM26 include diagnosis and treatment of the abovementioned diseases and clinical conditions. The function and utilities of MPP6 have been established by previous studies, as described hereinabove with to FIG. 26D.

Reference is now made to MTA1L1 BINDING SITE. Metastasis-associated 1-like 1 (MTA1L1) is a target gene of GAM26, corresponding to GAM26-TARGET GENE of FIG. 26A. MTA1L1 BINDING SITE is a binding site found in an untranslated region of MTA1L1, corresponding to BINDING SITE of FIG. 26A. FIG. 26D illustrates the complementarity of the nucleotide sequence of MTA1L1 BINDING SITE, designated SEQ ID:261852, to the nucleotide sequence of GAM26 RNA of FIG. 26A, designated SEQ ID:20604.

An additional function of GAM26 is therefore inhibition of metastasis-associated 1-like 1 (MTA1L1), a gene which encodes a protein that regulates histone deacetylase core complex enzymatic activity. Accordingly, utilities of GAM26 include diagnosis and treatment of the abovementioned diseases and clinical conditions.

The function of MTA1L1 has been established by studies. The p53 tumor suppressor (191170) is a transcriptional factor whose activity is modulated by protein stability and posttranslational modifications including acetylation. Luo et al. (2000) showed that deacetylation of p53 is mediated by a histone deacetylase-1 (HDAC1; 601241)-containing complex. They also purified a p53 target protein, which they named PID, in the deacetylase complexes. PID is identical to MTA1L1, also called MTA2, which had been identified as a component of the nucleosome remodeling and histone deacetylation (NURD) complex. The authors found that MTA1L1 specifically interacts with p53 both in vitro and in vivo, and its expression reduces significantly the steady-state levels of acetylated p53. MTA1L1 expression strongly represses p53-dependent transcriptional activation, and, notably, it modulates p53-mediated cell growth arrest and apoptosis. Luo et al. (2000) concluded that their results show that deacetylation and functional interactions between the MTA1L1-associated NURD complex may represent an important pathway to regulate p53 function. Zhang et al. (1999) showed that MTA2 and the 32-kD MBD3 (603573) proteins are subunits of the NURD complex. Immunoprecipitation analysis showed that MBD3 interacts with HDAC1, RBBP4 (602923), and RBBP7 (602922), but not with MI2 (CHD4; 603277), suggesting that MBD3 is embedded within the NURD complex. The authors found that MTA2 directs the assembly of an active histone deacetylase complex and that the association of MTA2 with the complex requires MBD3. Gel mobility shift analysis determined that both NURD and MBD3 are unable to bind to methylated DNA in the absence of MBD2 (603547). Zhang et al. (1999) proposed that NURD is involved in the transcriptional repression of methylated DNA. Wade et al. (1999) also identified MTA1, MTA1L, and MBD3 as components of the NURD complex, which they referred to as the MI2 complex.

Full details of the abovementioned studies are described in the following publications, the disclosure of which are hereby incorporated by reference:

Futamura, M.; Nishimori, H.; Shiratsuchi, T.; Saji, S.; Nakamura, Y.; Tokino, T.: Molecular cloning, mapping, and characterization of a novel human gene, MTA1-L1, showing homology to a metastasis-associated gene, MTA1. J. Hum. Genet 44: 52-56, 1999. PubMed ID: 9929979 2. Luo, J.; Su, F.; Chen, D.; Shiloh, A.; Gu, W.: Deacetylation of p53 modulates its effect on cell growth and apoptosis. Nature 408: 377-381, 2000.

Further studies establishing the function and utilities of MTA1L1 are found in John Hopkins OMIM database record ID 603947, and in references numbered 1012-1015 listed hereinbelow.

Reference is now made to MTMR1 BINDING SITE. Myotubularin related protein 1 (MTMR1) is a target gene of GAM26, corresponding to GAM26-TARGET GENE of FIG. 26A. MTMR1 BINDING SITE is a binding site found in an untranslated region of MTMR1, corresponding to BINDING SITE of FIG. 26A. FIG. 26D illustrates the complementarity of the nucleotide sequence of MTMR1 BINDING SITE, designated SEQ ID:262287, to the nucleotide sequence of GAM26 RNA of FIG. 26A, designated SEQ ID:20604.

A further unction of GAM26 is therefore inhibition of myotubularin related protein 1 (MTMR1), a gene which encodes a protein that is a member of the myotubularin family of dual specificity protein phosphatases and is associated with biopsy-proven myotubular myopathy. Accordingly, utilities of GAM26 include diagnosis and treatment of the abovementioned diseases and clinical conditions.

The function of MTMR1 has been established by previous studies. X-linked myotubular myopathy is caused by mutations in the MTMR1 (310400) gene. The corresponding protein, myotubularin, contains the consensus active site of tyrosine phosphatases (PTP) and is a dual-specific phosphatase (DSP), acting on both phosphotyrosine and phosphoserine. By searching an EST database, Laporte et al. (1996) identified partial cDNAs encoding MTMR1 (myotubularin-related protein-1), MTMR2 (603557), and (603558). Kioschis et al. (1998) isolated additional cDNAs corresponding to the entire MTMR1 coding region. The predicted MTMR1 protein contains 662 amino acids. The MTMR1 gene contains 16 exons and spans 71 kb. The authors identified 1 cDNA, MTMR1-alpha, that appeared to result from alternative splicing of exon 13. Laporte et al. (1998) identified cDNAs encoding 4 additional MTM1 related proteins, MTMR4 (603559), MTMR5 (603560), MTMR6 (603561), and MTMR7(603562). Phylogenetic analysis of the consensus PTP/DSP region indicated that MTM1, MTMR1, MTMR2, a zebrafish ortholog of MTMR2, and *Drosophila* Mtmh1 form distinct subgroup of the myotubularin protein family. Using Northern blot analysis, Laporte et al. (1998) found that the 3.7-kb MTMR1 mRNA is expressed ubiquitously. An additional 3.1-kb transcript was detected only in placenta. By inclusion within mapped clones, Laporte et al. (1996) localized the MTMR1 gene to Xq28, within the 100 kb telomeric to the MTM1 gene. Kioschis al. (1998) determined that the 2 genes are transcribed in the same direction and are separated by 20 kb. Analysis of the genomic region containing MTM1 and MTMR1 revealed that the 2 genes share a similar structure, suggesting that they are related and arose from an intrachromosomal gene duplication. The authors stated that other examples of intrachromosomal gene duplications in Xq28 include the IDS (309900) gene duplication and a cluster of MAGE genes (see 300016). The MTMR1 gene shares structural similarities with the MTM1 gene, and is also located in the same chromosomal region. Because no MTM1 mutation was found in approximately 20% of males with biopsy-proven myotubular myopathy, Copley et al. (2002) screened the MTMR1 gene for mutations in 14 patients for whom no mutation was found in MTM1. Two of the pedigrees were consistent with X-linked recessive inheritance. No mutations were found in MTMR1.

Full details of the abovementioned studies are described in the following publications, the disclose of which are hereby incorporated by reference:

Copley, L. M.; Zhao, W. D.; Kopacz, K.; Herman, G. E.; Kioschis, P.; Poustka, A.; Taudien, S.; Platzer, M.: Exclusion of mutations in the MTMR1 gene as a frequent cause of X-linked myotubular myopathy. (Letter) Am. J. Med. Genet. 107: 256-258, 2002. PubMed ID: 11807911 2. Kioschis, P.; Wiemann, S.; Heiss, N. S.; Francis, F.; Gotz, C.; Poustka, A.; Taudien, S.; Platzer, M.; Wiehe, T.; Beckmann, G.; Weber, J.; Nordsiek, G.; Rosenthal, A.: Genomic organization of a 225-kb region in Xq28 containing the gene for X-linked myotubular myopathy (MTM1) and a related gene (MTMR1). Genomics 54: 256-266, 1998.

Further studies establishing the function and utilities of MTMR1 are found in John Hopkins OMIM database record ID 300171, and in references numbered 1016-1019 listed hereinbelow.

Reference is now made to MVK BINDING SITE. Mevalonate kinase (mevalonic aciduria) (MVK) is a target gene of GAM26, corresponding to GAM26-TARGET GENE of FIG. 26A. MVK BINDING SITE is a binding site found in an untranslated region of MVK, corresponding to BINDING SITE of FIG. 26A. FIG. 26D illustrates the complementarity of the nucleotide sequence of MVK BINDING SITE, designated SEQ ID:264118, to the nucleotide sequence of GAM26 RNA of FIG. 26A, designated SEQ ID:20604.

Yet a further function of GAM26 is therefore inhibition of mevalonate kinase (mevalonic aciduria) (MVK), a gene which encodes an enzyme that is associated with Mevalonicaciduria and hyperimmunoglobulinemia d and periodic fever syndrome (hids). Accordingly, utilities of GAM26 include diagnosis and treatment of the abovementioned diseases and clinical conditions.

The function of MVK has been established by previous studies. Mevalonicaciduria, the first recognized defect in the biosynthesis of cholesterol and isoprenoids, is a consequence of a deficiency of mevalonate kinase (ATP:mevalonate 5-phosphotransferase; EC 2.7.1.36). Mevalonic acid accumulates because of failure of conversion to 5-phosphomevalonic acid, which is catalyzed by mevalonate kinase. Mevalonic acid is synthesized from 3-hydroxy-3-methylglutaryl-CoA, a reaction catalyzed by HMG-CoA reductase (142910). Cuisset et al. (2001) screened the entire coding region of the MVK gene in 25 unrelated patients with HIDS. The patients (22 Dutch, 1 British, 1 Czech, and 1 Spanish), had mevalonate kinase enzyme activity varying from 1.8 to 28%. A total of 13 different mutations were identified, 7 of which were novel. The most common mutation was V377I (251170.0002), detected in 20 patients, followed by I268T (251170.0004), detected in 7 patients. The frequency or severity of febrile attacks did not differ between V377I positive and negative patients. The data of Cuisset et al. (2001), combined with results from previous reports, showed that HIDS mutations were evenly distributed along the coding region of the MVK gene, in contrast to mutations causing mevalonicaciduria, which clustered between amino acids 243 and 334. Three of the HIDS patients illustrated genotypic and phenotypic overlap with mevalonicaciduria, suggesting that factors in addition to specific mutations are important for the resultant phenotype Full details of the abovementioned studies are described in the following publications, the disclosure of which are hereby incorporated by reference:

Cuisset, L.; Drenth, J. P. H.; Simon, A.; Vincent, M. F.; van der Velde Visser, S.; van der Meer, J. W. M.; Grateau, G.; Delpech, M.; International Hyper-IgD Study Group: Molecular analysis of MVK mutations and enzymatic activity in hyper-IgD and periodic fever syndrome. Europ. J. Hum. Genet. 9: 260-266, 2001. PubMed ID: 11313769 3. Drenth, J. P. H.; Cuisset, L.; Grateau, G.; Vasseur, C.; van de Velde-Visser, S. D.; de Jong, J. G. N.; Beckmann, J. S.; van der Meer, J. W. M.; Delpech, M.; International Hyper-IgD Study Group: Mutations in the gene encoding mevalonate kinase cause hyper-IgD and periodic fever syndrome. Nature Genet. 22: 178-181, 1999.

Further studies establishing the function and utilities of MVK are found in John Hopkins OMIM database record ID 251170, and in references numbered 1020-1037 listed hereinbelow.

Reference is now made to NCKAP1 BINDING SITE. NCK-ASSOCIATED PROTEIN 1 (NCKAP1) is a target gene of GAM26, corresponding to GAM26-TARGET GENE of FIG. 26A. NCKAP1 BINDING SITE is a binding site found in an untranslated region of NCKAP1, corresponding to BINDING SITE of FIG. 26A. FIG. 26D illustrates the complementarity of the nucleotide sequence of NCKAP1 BINDING SITE, designated SEQ ID:268447, to the nucleotide sequence of GAM26 RNA of FIG. 26A, designated SEQ ID:20604.

Another function of GAM26 is therefore inhibition of NCK-ASSOCIATED PROTEIN 1 (NCKAP1), a gene which encodes a protein that is an apoptosis-related protein and is associated with Alzheimer disease. Accordingly, utilities of GAM26 include diagnosis and treatment of the abovementioned diseases and clinical conditions.

The function of NCKAP1 has been established by previous studies. Alzheimer disease (AD; 104300), a major cause of senile dementia, is a progressive neurodegenerative disease of the central nervous system. To identify molecules involved in the AD process, Suzuki et al. (2000) used a modified differential display method to search for genes showing unique expression profiles at the transcriptional level in sporadic AD-affected brains compared to normal brains. Among 31 differentially expressed genes, 1 gene, NCKAP1, showed markedly reduced expression in most of the AD-affected brains examined. Suzuki et al. (2000) isolated a human cDNA containing a full-length NCKAP1 coding sequence. The deduced 1,128-amino acid NCKAP1 protein shares 99.2% amino acid sequence identity with rat Nck-associated protein-1 (Nap1); thus, the authors referred to NCKAP1 as NAP1. NCKAP1 also shares significant sequence homology with HEM1 (141180). NCKAP1 is predicted type II transmembrane protein, a C-terminal transmembrane domain Northern blot analysis detected an approximately 4.2-kb NCKAP1 transcript in all tissues examined except peripheral blood leukocytes, with highest expression in brain, heart, and skeletal muscle. In the brain, NCKAP1 transcripts were present in all subregions examined, with slightly higher expression in the amygdala and hippocampus, which have dense populations of neurons. Northern blot analysis showed that NCKAP1 was expressed at a higher level in adult brain than in fetal brain. In situ hybridization of human brain indicated that NCKAP1 is expressed predominantly in neuronal cells. Suzuki et al. (2000) demonstrated that suppression of NCKAP1 expression using an antisense NCKAP1 oligonucleotide induces apoptosis of neuronal cells. By somatic cell hybrid analysis, Suzuki et al. (2000) mapped the NCKAP1 gene to chromosome 2. They localized the NCKAP1 gene to 2q32.1-q32.2 using FISH.

Full details of the abovementioned studies are described in the following publications, the disclosure of which are hereby incorporated by reference:

Suzuki, T.; Nishiyama, K.; Yamamoto, A.; Inazawa, J.; Iwaki, T.; Yamada, T.; Kanazawa, I.; Sakaki, Y.: Molecular cloning of a novel apoptosis-related gene, human Nap1 (NCKAP1), and its possible relation to Alzheimer disease. Genomics 63: 246-254, 2000.

Further studies establishing the function and utilities of NCKAP1 are found in John Hopkins OMIM database record ID 604891, and in references numbered 1038 listed hereinbelow.

Reference is now made to NFYA BINDING SITE. nuclear transcription factor Y, alpha (NFYA) is a target gene of GAM26, corresponding to GAM26-TARGET GENE of FIG. 26A. NFYA BINDING SITE is a binding site found in an untranslated region of NFYA, corresponding to BINDING SITE of FIG. 26A. FIG. 26D illustrates the complementarity of the nucleotide sequence of NFYA BINDING SITE, designated SEQ ID:272973, to the nucleotide sequence of GAM26 RNA of FIG. 26A, designated SEQ ID:20604.

Yet another function of GAM26 is therefore inhibition of nuclear transcription factor Y, alpha (NFYA), a gene which encodes a protein that stimulates the transcription of various genes by recognizing and binding to a ccaat motif in promoters. Accordingly, utilities of GAM26 include diagnosis and treatment of the abovementioned diseases and clinical conditions.

The function of NFYA has been established by previous studies. NF-Y is a transcription factor thought to be essential for expression of the class II genes of the major histocompatibility complex (MHC; see 142800). It recognizes a CCAAT motif upstream of gene promoters and is probably involved in the regulation of a variety of genes, including those for albumin (103600), alpha-globin (141800), collagen (see 120150), and beta-actin (102630). NF-Y is composed of 2 subunits, NFYA and NFYB (189904), both of which are necessary for DNA binding. This 2-subunit DNA-binding unit has been well conserved during evolution. NFYA and NFYB show striking sequence similarity with the yeast transcription factors Hap2 and Hap3, both which are required for specific binding to a CCAAT-like motif. By in situ hybridization and analysis of somatic cell hybrids, Li et al. (1991) assigned the NFYA gene to 6p21 (close to MHC) and the NFYB gene to human chromosome 12. After in situ hybridization, the maximum concentration of grains was in the region 12q22-q23. By Southern blot analysis of recombinant inbred lines and by in situ hybridization, the Nfya and Nfyb genes were assigned to mouse chromosome 17 and mouse chromosome 10, respectively. CCAAT, an upstream sequence element found in a multitude of higher eukaryotic promoters, serves as the recognition sequence for a variety of mammalian transcription factors. There are at least 3 chromatographically separable CCAAT-binding factors in cells: CP1, CP2, and CTF/NF-1 (600729). These factors recognize overlapping but distinct subsets of known CCAAT-containing promoters and make distinguishable patterns of contacts with DNA in and around the CCAAT motif. Becker et al. (1991) noted that of these 3 factors, CP1 bears the greatest resemblance to the yeast Hap complex. This complex of 3 genes, Hap2, Hap3, and Hap4, is required for the expression of respiration in *Saccharomyces cerevisiae*—in particular, for expression of the principal isoform of cytochrome C (CYC1; 123980). In the yeast, 3 proteins are associated in a heteromeric complex that binds to an upstream activation sequence in the CYC1 promoter. Like Hap2/3/4, CYP in the human consists of a heteromeric association of at least 2 components, CP1A and CP1B, both of which are required for binding. Most strikingly, the subunits of CP1 and Hap2/3/4 can be interchanged in vitro. Thus, CP1 likely represents the human homolog of the yeast Hap complex, with the CP1B fraction containing the Hap2 homolog and the CP1A fraction containing a Hap3 equivalent. Becker et al. (1991) reported the isolation of a HeLa cDNA whose expression in *S. cerevisiae* corrected the respiratory defect in a strain bearing a Hap2 deletion. The cDNA encoding the human Hap2 homolog encodes a protein of 257 amino acids which has a 62-amino acid C-terminal region that shares 73% identity with the essential core region of Hap2.

Full details of the abovementioned studies are described in the following publications, the disclosure of which are hereby incorporated by reference:

Becker, D. M.; Fikes, J. D.; Guarente, L.: A cDNA encoding a human CCAAT-binding protein cloned by functional complementation in yeast Proc. Nat. Acad. Sci. 88: 1968-1972, 1991. PubMed ID: 2000400 2. Li, X. -Y.; Mattei, M. G.; Zaleska-Rutczynska, Z.; Hooft van Huijsduijnen, R.; Figueroa, F.; Nadeau, J.; Benoist, C.; Mathis, D.: One subunit of the transcription factor NF-Y maps close to the major histocompatibility complex in murine and human chromosomes. Genomics 11: 630-634, 1991.

Further studies establishing the function and utilities of NFYA are found in John Hopkins OMIM database record ID 189903, and in reference numbered 1039-1040 listed hereinbelow.

Referring now to NFYA BINDING SITE. Nuclear transcription factor Y, alpha (NFYA) is a target gene of GAM26, corresponding to GAM26-TARGET GENE of FIG. 26A. NFYA BINDING SITE is a binding site found in an untranslated region of NFYA, corresponding to BINDING SITE of FIG. 26A. FIG. 26D illustrates the complementarity of the nucleotide sequence of NFYA BINDING SITE, designated SEQ ID:272979, to the nucleotide sequence of GAM26 RNA of FIG. 26A, designated SEQ ID:20604.

An additional function of GAM26 is therefore inhibition of nuclear transcription factor Y, alpha (NFYA), a gene which encodes a protein that stimulates the transcription of various genes by recognizing and binding to a ccaat motif in promoters. Accordingly, utilities of GAM26 include diagnosis and treatment of the abovementioned diseases and clinical conditions. The function and utilities of NFYA have been established by previous studies, as described hereinabove with reference to FIG. 26D.

Referring now to NPAS2 BINDING SITE. Neuronal PAS domain protein 2 (NPAS2) is a target gene of GAM26, corresponding to GAM26-TARGET GENE of FIG. 26A. NPAS2 BINDING SITE is a binding site found in an untranslated region of NPAS2, corresponding to BINDING SITE of FIG. 26A. FIG. 26D illustrates the complementarity of the nucleotide sequence of NPAS2 BINDING SITE, designated SEQ ID:275935, to the nucleotide sequence of GAM26 RNA of FIG. 26A, designated SEQ ID:20604.

A further function of GAM26 is therefore inhibition of neuronal PAS domain protein 2 (NPAS2) a gene which encodes a protein that is a member of basic helix-loop-helix-PAS family of transcription factors. Accordingly, utilities of GAM26 include diagnosis and treatment of the abovementioned diseases and clinical conditions. The function and utilities of NPAS2 have been established by previous studies, as described hereinabove with reference to FIG. 26D.

Referring now to NPAS2 BINDING SITE. Neuronal PAS domain protein 2 (NPAS2) is a target gene of GAM26, corresponding to GAM26-TARGET GENE of FIG. 26A. NPAS2 BINDING SITE is a binding site found in an untranslated region of NPAS2, corresponding to BINDING SITE of FIG. 26A. FIG. 26D illustrates the complementarity of the nucleotide sequence of NPAS2 BINDING SITE, designated SEQ ID:275947, to the nucleotide sequence of GAM26 RNA of FIG. 26A, designated SEQ ID:20604.

Yet a further function of GAM26 is therefore inhibition of neuronal PAS domain protein 2 (NPAS2), a gene which encodes a protein that is a member of basic helix-loop-helix-PAS family of transcription factors. Accordingly, utilities of GAM26 include diagnosis and treatment of the abovementioned diseases and clinical conditions. The function and utilities of NPAS2 have been established by previous studies, as described here above with reference to FIG. 26D.

Reference is now made to NRG2 BINDING SITE. Neuregulin 2 (NRG2) is a target gene of GAM26, corresponding to GAM26-TARGET GENE of FIG. 26A. NRG2 BINDING SITE is a binding site found in an untranslated region of NRG2, corresponding to BINDING SITE of FIG. 26A. FIG. 26D illustrates the complementarity of the nucleotide sequence of NRG2 BINDING SITE, designated SEQ ID:279264, to the nucleotide sequence of GAM26 RNA of FIG. 26A, designated SEQ ID:20604.

Another function of GAM26 is therefore inhibition of neuregulin 2 (NRG2), a gene which encodes a protein that recruits erbb1 and erbb2 coreceptors resulting in ligand-stimulated tyrosine phosphorylation and activation of the erbb receptors. Accordingly, utilities of GAM26 include diagnosis and treatment of the abovementioned diseases and clinical conditions.

The function of NRG2 has been established by previous studies. Neuregulins are a family of growth and differentiation factors that are related to epidermal growth factor (EGF; 131530). The receptors for neuregulins are the ERBB family of tyrosine kinase transmembrane receptors, which includes the EGF receptor (EGFR; 131550), ERBB2 (164870), ERBB3 (190151), and ERBB4 (600543). Through interaction with ERBB receptors, neuregulins induce the growth and differentiation of epithelial, neuronal, glial, and other types of cells (Burden and Yarden, 1997). In particular, the neuregulin-ERBB signaling pathways play crucial roles in regulating the proliferation and differentiation of Schwann cells, the myelin-forming cells in the peripheral nervous system. For additional information about neuregulins, see NRG1 (142445). Using homologous mouse cDNA as probe, Busfield et al. (1997) cloned 2 NRG2 variants, which they called DON-1r and DON-1b, from a human fetal brain library. The clones predict mosaic proteins containing an N-terminal domain, an immunoglobulin-C2 loop, an EGF-like domain, a transmembrane sequence, and a large cytoplasmic tail showing a number of potential N-linked and O-linked glycosylation sites. DON-1b differs from DON-1r by an 8-amino acid insertion proximal to the transmembrane domain. Northern blot analysis of adult human tissues revealed expression of 3- and 4-kb transcripts restricted to the cerebellum. Expression was also detected in fetal brain and lung. In situ hybridization of mouse brain sections revealed restricted expression in the cerebellum and dentate gyrus.

Full detail of the abovementioned studies are described in the following publications, the disclosure of which are hereby incorporated by reference:

Burden, S.; Yarden, Y.: Neuregulins and their receptors: a versatile signaling module in organogenesis and oncogenesis. Neuron 18: 847-855, 1997. PubMed ID: 9208852 2. Busfield, S. J.; Michnick, D. A.; Chickering, T. W.; Revett, T. L.; Ma, J.; Woolf, E. A.; Comrack, C. A.; Dussault, B. J.; Woolf, J.; Goodearl, A. D. J.; Gearing, D. P.: Characterization of a neuregulin-related gene, Don-1, that is highly expressed in restricted regions of the cerebellum and hippocampus. Molec. Cell. Biol. 17: 4007-4014, 1997.

Further studies establishing the function and utilities of NRG2 are found in John Hopkins OMIM database record ID 603818, and in references numbered 1041-1046 listed hereinbelow.

Reference is now made to NUP98 BINDING SITE. Nucleoporin 98 kD (NUP98) is a target gene of GAM26, corresponding to GAM26-TARGET GENE of FIG. 26A. NUP98 BINDING SITE is a binding site found in an untranslated region of NUP98, corresponding to BINDING SITE of FIG. 26A. FIG. 26D illustrates the complementarity of the nucleotide sequence of NUP98 BINDING SITE, designated SEQ ID:281811, to the nucleotide sequence of GAM26 RNA of FIG. 26A, designated SEQ ID:20604.

Yet another function of GAM26 is therefore inhibition of nucleoporin 98 kD (NUP98), a gene which encodes a protein that functions in the nuclear transport of protein and RNA. Accordingly, utilities of GAM26 include diagnosis and treatment of the abovementioned diseases and clinical conditions.

The function of NUP98 has been established by previous studies. Nucleoporins are proteins that function in the nuclear transport of protein and RNA. Nakamura et al. (1996) showed that in 3 patients with t(7;11), the chromosome rearrangement created a genomic fusion between the HOXA9 gene (142956) and the nucleoporin gene NUP98 on 11p15. Expression of Hoxa7 and Hoxa9 is activated by proviral integration in BXH2 murine myeloid leukemias; this result, combined with the mapping of the HOXA cluster to 7p15, suggested that one of the HOXA genes may be involved in the human t(7;11)(p15;p15) translocation found in some myeloid leukemia patients. The translocation produced an invariant chimeric NUP98/HOXA9 transcript containing the amino terminal half of NUP98 fused in-frame to HOXA9. These studies identified HOXA9 as an important human myeloid leukemia gene and suggested an important role for nucleoporins in human myeloid leukemia, given that a second nucleoporin, NUP214 (114350), had also been implicated in human myeloid leukemia. The 11p15 gene was identified by exon trapping experiments. Borrow et al. (1996) likewise identified the HOXA9 and NUP98 genes as the parents of the fusion in t(7;11)(p15;p15) in acute myeloid leukemia of the FABM2 and M4 types. Borrow et al. (1996) suggested that the predicted NUP98/HOXA9 fusion protein may promote leukemogenesis through inhibition of HOXA9-mediated terminal differentiation and/or aberrant nucleocytoplasmic transport.

Full details of the abovementioned studies are described in the following publications, the disclosure of which are hereby incorporated by reference:

Borrow, J.; Shearman, A. M.; Stanton, V. P., Jr.; Becher, R.; Collins, T.; Williams, A. J.; Dube, I.; Katz, F.; Kwong, Y. L.; Morris, C.; Ohyashiki, K.; Toyama, K.; Rowley, J.; Housman, D. E.: The t(7;11)(p15;p15) translocation in acute myeloid leukaemia fuses the genes for nucleoporin NUP98 and class I homeoprotein HOXA9. Nature Genet. 12: 159-167, 1996. PubMed ID: 8563754 12. Nakamura, T.; Largaespada, D. A.; Lee, M. P.; Johnson, L. A.; Ohyashiki, K.; Toyama, K.; Chen, S. J.; Willman, C. L.; Chen, I. -M.; Feinberg A. P.; Jenkins, N. A.; Copeland, N. G.; Shaughnessy, J. D., Jr.: Fusion of the nucleoporin gene NUP98 to HOXA9 by the chromosome translocation t(7;11)(p15;p15) in human myeloid leukaemia. Nature Genet. 12: 154-158, 1996.

Further studies establishing the function and utilities of NUP98 are found in John Hopkins OMIM database record ID 601021, and in reference numbered 1047-1062 listed hereinbelow.

Referring now to NUP98 BINDING SITE. Nucleoporin 98 kD (NUP98) is a target gene GAM26, corresponding to GAM26-TARGET GENE of FIG. 26A. NUP98 BINDING SITE is a binding site found in an untranslated region of NUP98, corresponding to BINDING SITE of FIG. 26A. FIG. 26D illustrates the complementarity of the nucleotide sequence of NUP98 BINDING SITE, designated SEQ ID:281839, to the nucleotide sequence of GAM26 RNA of FIG. 26A, designated SEQ ID:20604.

An additional function of GAM26 is therefore inhibition of nucleoporin 98 kD (NUP98), a gene which encodes a protein that functions in the nuclear transport of protein and RNA. Accordingly, utilities of GAM26 include diagnosis and treatment of the abovementioned diseases and clinical conditions. The function and utilities of NUP98 have been established by previous studies, as described hereinabove with reference to FIG. 26D.

Reference is now made to OSR1 BINDING SITE. Oxidative-stress responsive 1 (OSR1) is a target gene of GAM26, corresponding to GAM26-TARGET GENE of FIG. 26A. OSR1 BINDING SITE is a binding site found in an untranslated region of OSR1, corresponding to BINDING SITE of FIG. 26A. FIG. 26D illustrates the complementarity of the nucleotide sequence of OSR1 BINDING SITE, designated SEQ ID:285281, to the nucleotide sequence of GAM26 RNA of FIG. 26A, designated SEQ ID:20604.

A further function of GAM26 is therefore inhibition of oxidative-stress responsive 1 (OSR1), a gene which encodes a protein that mediates stress-activated signals. Accordingly, utilities of GAM26 include diagnosis and treatment of the abovementioned diseases and clinical conditions.

The function of OSR1 has been established by previous studies. The 3p22-p21.3 chromosomal region is one of 3 regions of 3p that is commonly deleted in various carcinomas. By analyzing a cloned segment from this region, Tamari et al. (1999) identified a novel gene that they designated OSR1 (oxidative stress-responsive-1) because the predicted 527-amino acid protein shares 39% identity with Ste20/oxidant stress-response kinase-1 (602255). The OSR1 gene contains 18 exons and spans approximately 90 kb. Northern blot analysis revealed that OSR1 was expressed as a 4.6-kb major transcript in all tissues tested. A less abundant 7.5-kb mRNA was detected in heart and skeletal muscle. Daigo et al. (1999) reported that the OSR1 gene is located between the OCTL1 (604047) and MYD88 (602170) genes on 3p22-p21.3.

Full details of the abovementioned studies are described in the following publications, the disclosure of which are hereby incorporated by reference:

Tamari, M.; Daigo, Y.; Nakamura, Y.: Isolation characterization of a novel serine threonine kinase gene on chromosome 3q22-21.3. J. Hum. Genet. 44: 116-120, 1999. PubMed ID: 10083736 Daigo, Y.; Isomura, M.; Nishiwaki, T.; Tamari, M.; Ishikawa, S.; Kai, M.; Murata, Y.; Takeuchi, K.; Yamane, Y.; Hayashi, R.; Minami, M.; Fujino, M. A.; Hojo, Y.; Uchiyama, I.; Takagi, T.; Nakamura, Y.: Characterization of a 1200-kb genomic segment of chromosome 3p22-p21.3. DNA Res. 6: 37-44, 1999.

Further studies establishing the function and utilities of OSR1 are found in John Hopkins OMIM database record ID 604046, and in references numbered 1063-1064 listed hereinbelow.

Reference is now made to PACE4 BINDING SITE. Paired basic amino acid cleaving system 4 (PACE4) is a target gene of GAM26, corresponding to GAM26-TARGET GENE of FIG. 26A. PACE4 BINDING SITE is a binding site found in an untranslated region of PACE4, corresponding to BINDING SITE of FIG. 26A. FIG. 26D illustrates the complementarity of the nucleotide sequence of PACE4 BINDING SITE, designated SEQ ID:287686, to the nucleotide sequence of GAM26 RNA of FIG. 26A, designated SEQ ID:20604.

Yet a further function of GAM26 is therefore inhibition of paired basic amino acid cleaving system 4 (PACE4), a gene which encodes an enzyme that processes hormone precursors by cleaving paired basic amino acids. Accordingly, utilities of GAM26 include diagnosis and treatment of the abovementioned diseases and clinical conditions.

The function of PACE4 has been established by previous studies. Using PCR methods, Kiefer et al. (1991) identified a second human subtilisin-like protease gene on chromosome 15. PCR primers were designed to be specific for the subfamily of eukaryotic subtilisin-like proteases with specificity for paired basic amino acid residue processing motifs. The gene encoding this protease, designated PACE4, also encoded a smaller subtilisin-related polypeptide derived by alternative mRNA splicing. As with the product of the PACE gene (136950), the tissue distribution of PACE4 was widespread, with comparatively higher levels in the liver. By in situ hybridization using isolated cosmid clones, Kiefer et al. (1991) mapped the PACE4 gene to chromosome 15 in close proximity to the PACE gene at 15q25-q26. Double labeling in situ hybridization suggested that the 2 genes are within 5 megabases of each other. Mbikay et al. (1995) mapped the gene for PACE4 (Pcsk6) to mouse chromosome 7 by RFLP analysis of a DNA panel from an interspecific backcross. It was located at a distance of 13 cM from the Pcsk3 locus, which specifies furin (136950), another member of this family of enzymes previously mapped to mouse chromosome 7. This is in concordance with the known close proximity of these 2 loci in the homologous region on human 15q25-qter. Pcsk3 and Pcsk6 map to a region of mouse chromosome 7 that has been associated cytogenetically with post lethality in maternal disomy, suggesting that these genes may be imprinted.

Full details of the abovementioned studies are described in the following publications, the disclosure of which are hereby incorporated by reference:

Kiefer, M. C.; Tucker, J. E.; Joh, R.; Landsberg, K. E.; Saltman, D.; Barr, P. J.: Identification of a second human subtilisin-like protease gene in the fes/fps region of chromosome 15. DNA Cell Biol. 10: 757-769, 1991. PubMed ID: 1741956 2. Mbikay, M.; Seidah, N. G.; Chretien, M.; Simpson, E. M.: Chromosomal alignment of the genes for proprotein convertases PC4, PC5, and PACE 4 in mouse and Genomics 26: 123-129, 1995.

Further studies establishing the function and utilities PACE4 are found in John Hopkins OMIM record ID 167405, and in references numbered 1065-1066 listed hereinbelow.

Referring now to PACE4 BINDING SITE. Paired basic amino acid cleaving system 4 (PACE4) is a target gene of GAM26, corresponding to GAM26-TARGET GENE of FIG. 26A. PACE4 BINDING SITE is a binding site found in an untranslated region of PACE4, corresponding to BINDING SITE of FIG. 26A. FIG. 26D illustrates the complementarity of the nucleotide sequence of PACE4 BINDING SITE, designated SEQ ID:287698, to the nucleotide sequence of GAM26 RNA of FIG. 26A, designated SEQ ID:20604.

Another function of GAM26 is therefore inhibition of paired basic amino acid cleaving system 4 (PACE4), a gene which encodes an enzyme that processes hormone precursors by cleaving paired basic amino acids. Accordingly, utilities of GAM26 include diagnosis and treatment of the abovementioned diseases and clinical conditions. The function and utilities of PACE4 have been established by previous studies, as described hereinabove with reference to FIG. 26D.

Reference is now made to PACSIN1 BINDING SITE. protein kinase C and casein kinase substrate in neurons 1 (PACSIN1) is a target gene of GAM26, corresponding to GAM26-TARGET GENE of FIG. 26A. PACSIN1 BINDING SITE is a binding site found in an untranslated region of PACSIN1, corresponding to BINDING SITE of FIG. 26A. FIG. 26D illustrates the complementarity of the nucleotide sequence of PACSIN1 BINDING SITE, designated SEQ ID:287889, to the nucleotide sequence of GAM26 RNA of FIG. 26A, designated SEQ ID:20604.

Yet another function of GAM26 is therefore inhibition of protein kinase C and casein kinase substrate in neurons 1 (PACSIN1), a gene which encodes a protein that plays a role in vesicle formation and transport. Accordingly, utilities of GAM26 include diagnosis and treatment of the abovementioned diseases and clinical conditions.

The function of PACSIN1 has been established by previous studies. By screening brain cDNA libraries for sequences with the potential to encode large proteins, Nagase et al. (2000) identified a partial cDNA encoding PACSIN1, which they called KIAA1379. The deduced 434-amino acid protein was predicted to be a homolog of rat syndapin I. RT-PCR analysis detected expression only in brain, predominantly in hippocampus. By EST database searching with mouse Pacsin1 as the probe, followed by 5-prime RACE, Sumoy et al. (2001) obtained full-length cDNAs encoding PACSIN1 and PACSIN3 (606513). Sequence analysis predicted that the 444-amino acid PACSIN1 protein, which is 95% identical to the mouse protein, contains a conserved N-terminal Fes/CIP4 homology (FCH) domain (also called the RAEYL motif), a central coiled-coil region, and a C-terminal SH3 motif. Northern blot analysis revealed strong expression of a 4.4 kb PACSIN1 transcript in brain, with much lower levels in heart, pancreas, and liver. In contrast, PACSIN2 (604960) and PACSIN3 were found to have ubiquitous expression patterns.

Full details the abovementioned studies are described in the following publications, the disclosure of which are hereby incorporated by reference:

Sumoy, L.; Pluvinet, R.; Andreu, N.; Estivill, X.; Escarceller, M.: PACSIN 3 is a novel SH3 domain cytoplasmic adapter protein of the pacsin-syndapin-FAP52 gene family. Gene 262: 199-205, 2001.

Further studies establishing the function and utilities of PACSIN1 are found in John Hopkins OMIM database record ID 606512, and in references numbered 1067-1068 listed hereinbelow.

Reference is now made to PAPOLA BINDING SITE. poly(A) polymerase alpha (PAPOLA) is a target gene of GAM26, corresponding to GAM26-TARGET GENE of FIG. 26A. PAPOLA BINDING SITE is a binding site found in an untranslated region of PAPOLA, corresponding to BINDING SITE of FIG. 26A. FIG. 26D illustrates the complementarity of the nucleotide sequence of PAPOLA BINDING SITE, designated SEQ ID:288993, to the nucleotide sequence of GAM26 RNA of FIG. 26A, designated SEQ ID:20604.

An additional function of GAM26 is therefore inhibition of poly(A) polymerase alpha (PAPOLA), a gene which encodes an enzyme that creates the 3' poly(a) tail of mRNA's. Accordingly, utilities of GAM26 include diagnosis and treatment of the abovementioned diseases and clinical conditions.

The function of PAPOLA has been established by previous studies. Polyadenylation of the 3-prime ends of eukaryotic mRNAs is a key event that takes place in the nucleus during maturation of mRNA. The reaction occurs in 2 distinct steps: endoribonucleolytic cleavage of the pre-RNA at the poly(A) site, followed by synthesis of the poly(A) tail at the 3-prime end of the upstream cleavage product. The poly(A) polymerase (PAP) is required for the adenosine addition reaction. Using RT-PCR on cytoplasmic RNA from primary human fibroblasts, Thuresson et al. (1994) obtained a cDNA encoding PAP. The deduced 500-amino acid protein is 99% similar to the bovine sequence. Western blot analysis of HeLa cell extracts detected heat-resistant 100- and 106-kD proteins in both nuclear and cytoplasmic fractions, and a 90-kD heat-sensitive protein in nuclear fractions. The 106-kD protein is phosphorylated. Functional analysis of mutated peptides showed that the N-terminal region of PAP is required for nonspecific polymerase activity while the N and C termini are required for specific polymerase activity.

Full details of the abovementioned studies are described in the following publications, the disclosure of which are hereby incorporated by reference:

Thuresson, A. -C.; Astrom, J.; Astrom, A.; Gronvik, K. -O.; Virtanen, A.: Multiple forms of poly(A) polymerases in human cells. Proc. Nat. Acad. Sci. 91: 979-983, 1994. PubMed ID: 8302877 2. Yamauchi, T.; Sugimoto J.; Hatakeyama, T.; Asakawa, S.; Shimizu, N.; Isobe, M.: Assignment of the human poly(A) polymerase (PAP) gene to chromosome 14q32.1-q32.2 and isolation of a polymorphic CA repeat sequence. J. Hum. Genet. 14: 253-255, 1999.

Further studies establishing the function and utilities PAPOLA are found in John Hopkins OMIM database record ID 605553, and in references numbered 1069-1070 and 1070 listed here below.

Referring now to PEA15 BINDING SITE. Phosphoprotein enriched in astrocytes 15 (PEA15) is a target gene of GAM26, corresponding to GAM26-TARGET GENE of FIG. 26A. PEA15 BINDING SITE is a binding site found in an untranslated region of PEA15, corresponding to BINDING SITE FIG. 26A. FIG. 26D illustrates the complementarity of the nucleotide sequence of PEA15 BINDING SITE, designated SEQ ID:301501, to the nucleotide sequence of GAM26 RNA of FIG. 26A, designated SEQ ID:20604.

A further function of GAM26 is therefore inhibition of phosphoprotein enriched in astrocytes 15 (PEA15), a gene which encodes a protein that is a phosphoprotein and involved in glucose uptake. Accordingly, utilities of GAM26 include diagnosis and treatment of the abovementioned diseases and clinical conditions. The function and utilities of PEA15 have been established by previous studies, as described hereinabove with reference to FIG. 26D.

Referring now to PEA15 BINDING SITE. Phosphoprotein enriched in astrocytes 15 (PEA15) is a target gene of GAM26, corresponding to GAM26 TARGET GENE of FIG. 26A. PEA15 BINDING SITE is a binding site found in an untranslated region of PEA15, corresponding to BINDING SITE of FIG. 26A. FIG. 26D illustrates the complementarity of the nucleotide sequence of PEA15 BINDING SITE, designated SEQ ID:301508, to the nucleotide sequence of GAM26 RNA of FIG. 26A, designated SEQ ID:20604.

Yet a further function of GAM26 is therefore inhibition of phosphoprotein enriched in astrocytes 15 (PEA15), a gene which encodes a protein that is a phosphoprotein and involved in glucose uptake. Accordingly, utilities of GAM26 include diagnosis and treatment of the abovementioned diseases and clinical conditions. The function and utilities of PEA15 have been established by previous studies, as described hereinabove with reference to FIG. 26D.

Referring now to PEA15 BINDING SITE. Phosphoprotein enriched in astrocytes 15 (PEA 15) is a target gene of GAM26, corresponding to GAM26-TARGET GENE of FIG. 26A. PEA15 BINDING SITE is a binding site found in an untranslated region of PEA15, corresponding to BINDING SITE of FIG. 26A. FIG. 26D illustrates the complementarity of the nucleotide sequence of PEA15 BINDING SITE, designated SEQ ID:301547, to the nucleotide sequence of GAM26 RNA of FIG. 26A, designated SEQ ID:20604.

Another function of GAM26 is therefore inhibition of phosphoprotein enriched in astrocytes 15 (PEA15), a gene which encodes a protein that is a phosphoprotein and involved in glucose uptake. Accordingly, utilities of GAM26 include diagnosis and treatment of the abovementioned diseases and clinical conditions. The function and utilities of PEA15 have been established by previous studies, as described hereinabove with reference to FIG. 26D.

Referring now to PEA15 BINDING SITE. Phosphoprotein enriched in astrocytes 15 (PEA15) is a target gene of GAM26, corresponding to GAM26-TARGET GENE of FIG. 26A. PEA15 BINDING SITE is a binding site found in an untranslated region of PEA15, corresponding to BINDING SITE of FIG. 26A. FIG. 26D illustrates the complementarity of the nucleotide sequence of PEA15 BINDING SITE, designated SEQ ID:301572, to the nucleotide sequence of GAM26 RNA of FIG. 26A, designated SEQ ID:20604.

Yet another function of GAM26 is therefore inhibition of phosphoprotein enriched in astrocytes 15 (PEA15), a gene which encodes a protein that is a phosphoprotein and involve in glucose uptake. Accordingly, utilities of GAM26 include diagnosis and treatment of the abovementioned diseases and clinical conditions. The function and utilities of PEA15 have been established by previous studies, as described hereinabove with reference to FIG. 26D.

Reference is now made to PIM1 BINDING SITE. pim-1 oncogene (PIM1) is a target gene of GAM26, corresponding to GAM26-TARGET SITE GENE of FIG. 26A. PIM1 BINDING SITE is a binding site found in an untranslated region of PIM1, corresponding to BINDING SITE of FIG. 26A. FIG. 26D illustrates the complementarity of the nucleotide sequence of PIM1 BINDING SITE, designated SEQ ID:305922, to the nucleotide sequence of GAM26 RNA of FIG. 26A, designated SEQ ID:20604.

An additional function of GAM26 is therefore inhibition of pim-1 oncogene (PIM1), a gene which encodes an enzyme that is a protooncogene and is associated with prostate cancer. Accordingly, utilities of GAM26 include diagnosis and treatment of the abovementioned diseases and clinical conditions.

The function of PIM1 has been established by previous studies. Amson et al. (1989) showed that the 33-kD product of the PIM gene is highly expressed in the liver and spleen during fetal hematopoiesis. In contrast, it is only slightly expressed in circulating granulocytes in adults. It was overexpressed in hematopoietic malignancies, particularly in myeloid and lymphoid acute leukemias. The results implied a physiologic role of the PIM1 oncogene during hematopoietic development and a deregulation of the gene in various leukemias Animal model experiments lend further support to the function of PIM1. To understand the function of Pim1 and its role in hematopoietic development, Laird et al. (1993) generated mice deficient in Pim1 function. Pim1-deficient mice were ostensibly normal, healthy, and fertile; however, detailed analysis demonstrated a correlation of Pim1 deficiency with erythrocyte microcytosis, whereas overexpression of Pim1 in transgenic mice resulted in erythrocyte macrocytosis It is appreciated that the abovementioned animal model for PIM1 is acknowledged by those skilled in the art as a scientifically valid animal model, as can be further appreciated from the publications sited hereinbelow.

Full details of the abovementioned studies are described in the following publications, the disclosure of which are hereby incorporated by reference:

Laird, P. W.; van der Lugt, N. M. T.; Clarke, A.; Domen, J.; Linders, K.; McWhir, J.; Berns, A.; Hooper, M.: In vivo analysis of Pim-1 deficiency. Nucleic Acids Res. 21: 4750-4755, 1993. PubMed ID: 8233823 Amson, R.; Sigaux, F.; Przedborski, S.; Flandrin, G.; Givol, D.; Telerman, A.: The human protooncogene product p33pim is expressed during fetal hematopoiesis and in diverse leukemias. Proc. Nat. Acad. Sci. 86: 8857-8861, 1989.

Further studies establishing the function and utilities of PIM1 are found in John Hopkins OMIM database record ID 164960, and in references numbered 1071-1082 listed hereinbelow.

Referring now to PIM1 BINDING SITE. Pim-1 oncogene (PIM1) is a target gene of GAM26, corresponding to GAM26-TARGET GENE of FIG. 26A. PIM1 nucleotide sequence of PIM1 BINDING SITE, designated SEQ ID:305956, to the nucleotide sequence of GAM26 RNA of FIG. 26A, designated SEQ ID:20604.

A further function of GAM26 is therefore inhibition of pim-1 oncogene (PIM1), a gene which encodes an enzyme that is a protooncogene and is associated with prostate cancer. Accordingly, utilities of GAM26 include diagnosis and treatment of the abovementioned diseases and clinical conditions. The function and utilities of PIM1 have been established by previous studies, as described hereinabove with reference to FIG. 26D.

Reference is now made to PITPN BINDING SITE. Phosphotidylinositol transfer protein (PITPN) is a target gene of GAM26, corresponding to GAM26-TARGET GENE of FIG. 26. PITPN BINDING SITE is a binding site found in an untranslated region of PITPN, corresponding to BINDING SITE of FIG. 26A. FIG. 26D illustrates the complementarity of the nucleotide sequence of PITPN BIN DING SITE, designated SEQ ID:306515, to the nucleotide sequence of GAM26 RNA, of FIG. 26A, designated SEQ ID:20604.

Yet a further function of GAM26 is therefore inhibition of phosphotidylinositol transfer protein (PITPN), a gene which encodes a protein that catalyzes the transfer of ptdins and phosphatidylcholine between membranes. Accordingly, utilities of GAM26 include diagnosis and treatment of the abovementioned diseases and clinical conditions.

The function of PITPN has been established by previous studies. Phosphatidylinositol transfer protein is a member of a diverse set of cytosolic phospholipid transfer proteins that are distinguished by their ability to transfer phospholipids between membranes in vitro (Wirtz, 1991). The rat PITPN gene encodes a polypeptide of 271 amino acids and is expressed in a wide range of tissues (Dickeson et al., 1989). The protein predicted by the human PITPN gene cloned and sequenced by Dickeson et al. (1994) showed only 3 amino acid sequence differences from the rat protein, 2 of which represented conservative substitutions. Hay and Martin (1993) reported studies suggesting that PITPN is identical to priming-specific factor-3, one of the 3 priming factors involved in the ATP-dependent priming of Ca(2+)-activated secretion. Rat PITPN shares 40% amino acid homology over its entire length with the *Drosophila* retinal degeneration B (rdgB) protein (Vihtelic et al., 1993). Flies carrying the rdgB mutation undergo light-enhanced retinal degeneration.

Animal model experiments lend further support to the function of PITPN. The mouse 'vibrator' (vb) mutation causes an early-onset progressive action tremor, degeneration of brain stem and spinal cord neurons, and juvenile death. Hamilton et al. (1997) cloned the vb mutation using an in vivo positional complementation approach followed by complete resequencing of the resulting 76-kb critical region in vb and its progenitor strain. The authors showed that the vb mutation is an intracisternal. A particle retroposon insertion in intron 4 of the Pitpn gene, causing a 5-fold reduction in Pitpn RNA and protein levels. Expression of neurofilament light chain (NEFL; 162280) was also reduced in vb mice, suggesting 1 signaling pathway that may underlie vb pathology. The vb phenotype was suppressed in 1 intercross. By a complete genome scan, they mapped a major suppressor locus (Mvbl) to proximal mouse chromosome 19

It is appreciated that the abovementioned animal model for PITPN is acknowledged by those skilled in the art as a scientifically valid animal model, as can be further appreciated from the publications sited hereinbelow.

Full details of the abovementioned studies are described in the following publications, the disclosure of which are hereby incorporated by reference:

Hamilton, B. A.; Smith, D. J.; Mueller, K. L.; Kerrebrock, A. W.; Bronson, R. T.; van Berkel, V.; Daly, M. J.; Kruglyak, L.; Reeve, M. P.; Nemhauser, J. L.; Hawkins, T. L.; Rubin, E. M.; Lander, E. S.: The vibrator mutation causes neurodegeneration via reduced expression of PITP-alpha: positional complementation cloning and extragenic suppression. Neuron 18: 711-722, 1997. PubMed ID:9182797. Wirtz, K. W. A.: Phospholipid transfer proteins. Annu. Rev. Biochem. 60: 73-99, 1991. PubMed ID:1883207. Dickeson, S. K.; Lim, C. N.; Schuyler, G. T.; Dalton, T. P.; Helmkamp, G. M., Jr.; Yarbrough, L. R.: Isolation and sequence of cDNA clones encoding rat phosphatidylinositol transfer protein. Biol. Chem. 264: 16557-16564, 1989.

Further studies establishing the function and utilities PITPN are found in John Hopkins OMIM database record ID 600174, and in references numbered 1083-1089 listed hereinbelow.

Reference is now made to POLI BINDING SITE. Polymerase (DNA directed) iota (POLI) is a target gene of GAM26, corresponding to GAM26-TARGET GENE of FIG. 26A. POLI BINDING SITE is a binding site found in an untranslated region of POLI, corresponding to BINDING SITE of FIG. 26A. FIG. 26D illustrates the complementarity of the nucleotide sequence of POLI BINDING SITE, designated SEQ ID:312045, to the nucleotide sequence of GAM2 RNA of FIG. 26A, designated SEQ ID:20604.

Another function of GAM26 is therefore inhibition of polymerase (DNA directed) iota (POLI), a gene which encodes an enzyme that incorporates deoxynucleotides opposite DNA lesions. Accordingly, utilities of GAM26 include diagnosis and treatment of the abovementioned diseases and clinical conditions.

The function of POLI has been established by previous studies. The *S. cerevisiae* RAD30 and ha RAD30A genes encode Pol-eta, which bypasses a cis-syn thymine-thymine dimer efficiently and accurately. Johnson et al. (2000) showed that the related human gene RAD30B encodes the DNA polymerase Pol-iota, which misincorporates deoxynucleotides at a high rate. To bypass damage, Pol-iota specifically incorporates deoxynucleotides opposite highly distorting or noninstructional DNA lesions. This action is combined with that of DNA Pol-zeta (602776) which is essential for damaged-induced mutagenesis, to complete the lesion bypass. Pol-zeta is very inefficient in inserting deoxynucleotides opposite DNA lesions, but readily extends from such deoxynucleotides once they have been inserted. Thus, in a new model for mutagenic bypass of DNA lesions in eukaryotes, the 2 DNA polymerases act sequentially. Pol-iota incorporates deoxynucleotides opposite DNA lesions, and Pol-zeta functions as a mispair extender. Bebenek et al. (2001) reported that human Pol-iota has an intrinsic 5-prime-deoxyribose phosphate (dRP) lyase activity. In reactions reconstituted with uracil-DNA glycosylase (191525), apurinic/apyrimidinic (AP) endonuclease (107748), and DNA ligase I (126391), Pol-iota can use its dRP lyase and polymerase activities to repair G-U and A-U pairs in DNA. These data and 3 distinct catalytic properties of Pol-iota implicate it in specialized forms of base excision repair.

Full details of the abovementioned studies are described in the following publications, the disclosure which are hereby incorporated by reference:

Johnson, R. E.; Washington, M. T.; Haracska, L.; Prakash, S.; Prakash, L.: Eukaryotic polymerases iota and zeta act sequentially to bypass DNA lesions. Nature 406: 1015-1019, 2000. PubMed ID: 10984059 Bebenek, K.; Tissier, A.; Frank, E. G.; McDonald, J. P.; Prasad, R.; Wilson, S. R.; Woodgate, R.; Kunkel, T. A.: 5-prime-deoxyribose phosphate lyase activity of human DNA polymerase iota in vitro. Science 291: 2156-2159, 2001.

Further studies establishing the function and utilities of POLI are found in John Hopkins OMIM database record ID 605252, and in references numbered 1090-1092 listed hereinbelow.

Reference is now made to POLRMT BINDING SITE. Polymerase (RNA) mitochondrial (DNA directed) (POL-RMT) is a target gene of GAM26, corresponding to GAM26-TARGET GENE of FIG. 26A. POLRMT BINDING SITE is a binding site found in an untranslated region of POLRMT, corresponding to BINDING SITE of FIG. 26A. FIG. 26D illustrates the complementarity of the nucleotide sequence of POLRMT BINDING SITE, designated SEQ ID:312593, to the nucleotide sequence of GAM26 RNA of FIG. 26A, designated SEQ ID:20604.

Yet another function of GAM26 is therefore inhibition of polymerase (RNA) mitochondrial (DNA directed) (POL-RMT), a gene which encodes an enzyme that is a mitochondrial DNA-directed RNA polymerase. Accordingly, utilities of GAM26 include diagnosis and treatment of the abovementioned diseases and clinical conditions.

The function of POLRMT has been established by previous studies. Mitochondria of all organisms contain a genome that is distinct from that of the nucleus. The circular mitochondrial chromosome contains 37 genes that encode the RNA components of the mitochondrial translational apparatus, i.e., 22 transfer RNAs and 2 ribosomal RNA genes, as well as 13 polypeptide-encoding genes. All 13 polypeptides are essential components of 4 of the 5 complexes that form the mitochondrial oxidative phosphorylation (OXPHOS) pathway (complexes I, III, IV, and V). However, gene expression in mitochondria relies upon numerous nuclear genes that encode protein components required for transcription and translation of the mtDNA-encoded genes, as well as protein and RNA components required for replication of mtDNA. In addition, nuclear genes encode factors controlling the import, assembly, and turnover of OXPHOS complexes, and proteins acting as general regulators of mitochondrial function. Nuclear-encoded mitochondrial proteins are synthesized by cytoplasmic ribosomes, usually as precursors containing an N-terminal extension. Import into mitochondria is carried out by a complex, ATP-dependent transport system, followed by cleavage of the leader peptide, which eventually produce a mature, functional protein. Tiranti et al. (1997) noted that abnormalities in the nuclear genome repertoire controlling mitochondrial biogenesis were proposed as the cause of some human disorders characterized by the presence of mtDNA abnormalities and Mendelian transmission. Both autosomal dominant (157640) and autosomal recessive (601779) forms of chronic progressive external ophthalmoplegia are associated with the accumulation of multiple deletions of mtDNA in stable tissues. Another example is tissue-specific mtDNA depletion (251880), autosomal recessive disorder causing severe organ-specific syndromes in early infancy. Mendelian inheritance indicates the presence of transmissible mutations in nuclear genes that can ultimately damage the structural integrity of the mtDNA molecule or its copy number. Genes involved in the control of mtDNA replication and expression are considered attractive candidates for these disorders. The characterization of the collection of human proteins related to mitochondria, the so-called human mitochondrial proteome, is important in the elucidation of fundamental mechanisms of nucleo-mitochondrial intergenomic signaling, as well as to clinical researchers interested in mitochondrial disorders. Tiranti et al. (1997) used a gene cloning strategy based on the screening of the expressed sequence tags database (dbEST), using sequences of mitochondrial housekeeping proteins of yeast, to identify the cDNA encoding the precursor of the human mitochondrial RNA polymerase. They identified a 3,831-bp human cDNA predicted to encode a protein of 1,230 amino acid residues. The protein sequence showed significant homology with sequences corresponding to mitochondrial. RNA polymerases from lower eukaryotes and to RNA polymerases from several bacteriophages. Mitochondrial RNA polymerase carries out the central activity of mitochondrial gene expression and, by providing the RNA primers for initiation of replication, is also implicated in the maintenance and propagation of the mitochondrial genome. Thus, it is an attractive candidate for disorders of nucleo-mitochondrial intergenomic signaling.

Full details of the abovementioned studies are described in the following publications, the disclosure of which are hereby incorporated by reference:

Tiranti, V.; Savoia, A.; Forti, F.; D'Apolito, M. -F.; Centra, M.; Rocchi, M.; Zeviani, M.: Identification of the gene encoding the human mitochondrial RNA polymerase (h-mtRPOL) by cyberscreening of the Expressed Sequence Tags database. Hum. Molec. Genet. 6: 615-625, 1997. PubMed ID: 9097968 Tiranti, V.; Savoia, A.; Forti, F.; D'Apolito, M. -F.; Centra, M.; Rocchi, M.; Zeviani, M.: Identification of the gene encoding the human mitochondrial RNA polymerase (h-mtRPOL) by cyberscreening of the Expressed Sequence Tags database. Hum. Molec. Genet 6: 615-625, 1997.

Further studies establishing the function and utilities of POLRMT are found in John Hopkins OMIM database record ID 601778, and in references numbered 1093-1095 listed hereinbelow.

Reference is now made to PP BINDING SITE. Pyrophosphatase (inorganic) (PP) is a target of GAM26, corresponding to GAM26-TARGET GENE of FIG. 26A. PP BINDING SITE is a binding site found in an untranslated region of PP, corresponding to BINDING SITE of FIG. 26A. FIG. 26D illustrates the complementarity of the nucleotide sequence of PP BINDING SITE, designated SEQ ID:313812, to the nucleotide sequence of GAM26 RNA of FIG. 26A, designated SEQ ID:20604.

An additional function of GAM26 is therefore inhibition of pyrophosphatase (inorganic) (PP), a gene which encodes an enzyme that catalyzes the hydrolysis of pyrophosphate to inorganic phosphate. Accordingly, utilities of GAM26 include diagnosis and treatment of the abovementioned diseases and clinical conditions.

The function of PP has been established by previous studies. Among 3000 unrelated persons, Fisher et al. (1974) found no genetically determined variants of the enzyme in red cells. Assignment of the structural gene locus for inorganic pyrophosphatase to chromosome 10 was first reported by Van Cong et al. (1975) and confirmed by somatic cell hybrid studies in two other laboratories (McAlpine et al., 1976; Chem, 1976). From dosage studies in a patient trisomic for 10pter-10q11.1, Snyder et al. (1984) showed that PP is not on the short arm; red cell PP levels were normal.

Full details of the abovementioned studies are described in the following publications, the disclosure of which are hereby incorporated by reference:

Van Cong, N.; Rebourcet, R.; Weil, D.; Pangalos, C.; Frezal, J.: Localisation d'un locus de structure de la pyrophosphatase inorganique 'erythrocytaire' sur le chromosome 10 chez l'homme par la methode d'hypridation cellulaire homme-hamster. Comp. Rend. Acad. Sci. (Paris) 281: 435-438, 1975.

Further studies establishing the function and utilities of PP are found in John Hopkins OMIM data base record ID 179030, and in references numbered 1096-1102 listed hereinbelow.

Referring now to CACNA1A BINDING SITE. Calcium channel, voltage-dependent, P/Q type, alpha 1A subunit (CACNA1A) is a target gene of GAM26, corresponding to GAM26-TARGET GENE of FIG. 26A. CACNA1A BINDING SITE is a binding site found in an untranslated region of CACNA1A, corresponding to BINDING SITE of FIG. 26A. FIG. 26D illustrates the complementarity of the nucleotide sequence of CACNA1A BINDING SITE, designated SEQ ID:317209, to the nucleotide sequence of GAM26 RNA of FIG. 26A, designated SEQ ID:20604.

A further function of GAM26 is therefore inhibition of calcium channel, voltage-dependent, P/Q type, alpha 1A subunit (CACNA1A), a gene which encodes a protein that is associated with episodic ataxia type 2, familial hemiplegic migraine, spinocerebellar ataxia type 6, and idiopathic generalized epilepsy. Accordingly, utilities of GAM26 include diagnosis and treatment of the abovementioned diseases and clinical conditions. The function and utilities of CACNA1A have been established by previous studies, as described hereinabove with reference to FIG. 26D.

Referring now to CACNA1A BINDING SITE. Calcium channel, voltage-dependent, P/Q type, alpha 1A subunit (CACNA1A) is a target gene of GAM26, corresponding to GAM26-TARGET GENE of FIG. 26A. CACNA1A BINDING SITE is a binding site found in an untranslated region of CACNA1A, corresponding to BINDING SITE of FIG. 26A. FIG. 26D illustrates the complementarity of the nucleotide sequence of CACNA1A BINDING SITE, designated SEQ ID:317209, to the nucleotide sequence of GAM26 RNA of FIG. 26A, designated SEQ ID:20604.

Yet a further function of GAM26 is therefore inhibition of calcium channel, voltage-dependent, P/Q type, alpha 1A subunit (CACNA1A), a gene which encodes a protein that is associated with episodic ataxia type 2, familial hemiplegic migraine, spinocerebellar ataxia type 6, and idiopathic generalized epilepsy. Accordingly, utilities of GAM26 include diagnosis and treatment of the abovementioned diseases and clinical conditions. The function utilities of CACNA1A have been established by previous studies, as described hereinabove with reference to FIG. 26D.

Referring now to PPP3CA BINDING SITE. Protein phosphatase 3 (formerly 2B), catalytic subunit, alpha isoform (PPP3CA) is a target gene of GAM26, corresponding to GAM26-TARGET GENE of FIG. 26A. PPP3CA BINDING SITE is a binding site found in an untranslated region of PPP3CA, corresponding to BINDING SITE of FIG. 26A. FIG. 26D illustrates the complementarity of the nucleotide sequence of PPP3CA BINDING SITE, designated SEQ ID:317209, to the nucleotide sequence of GAM26 RNA of FIG. 26A, designated SEQ ID:20604.

Another function of GAM26 is therefore inhibition of protein phosphatase 3 (formerly 2B), catalytic subunit, alpha isoform (PPP3CA), a gene which encodes a Enzyme that is the catalytic subunit of calcium-dependent, calmodulin-stimulated protein phosphatase. Accordingly utilities of GAM26 include diagnosis and treatment of the abovementioned diseases and clinical conditions. The function an utilities of PPP3 CA have been established by previous studies, as described hereinabove with reference to FIG. 26D.

Referring now to GABRB3 BINDING SITE. Gamma-aminobutyric acid (GABA) A receptor, beta 3 (GABRB3) is a target gene of GAM26, corresponding to GAM26-TARGET GENE of FIG. 26A. GABRB3 BINDING SITE is a binding site found in an untranslated of GABRB3, corresponding to BINDING SITE of FIG. 26A. FIG. 26D illustrates the complementarity of the nucleotide sequence of GABRB3 BINDING SITE, designated SEQ ID:317210, to the nucleotide sequence of GAM26 RNA of FIG. 26A, designated SEQ ID:20604.

Yet another function of GAM26 is therefore inhibition of gamma-aminobutyric acid (GABA) A receptor, beta 3 (GABRB3), a gene which encodes a receptor that mediates neuronal inhibition by binding to the gaba/benzodiazepine receptor and opening an integral chloride channel and is associated with Angelman syndrome and Prader-Willi syndrome. Accordingly, utilities of GAM26 include diagnosis and treatment of the abovementioned diseases and clinical conditions. The fun ion and utilities of GABRB3 have been established by previous studies, as described hereinabove with reference to FIG. 26D.

Referring now to PPP3CA BINDING SITE. Protein phosphatase 3 (formerly 2B), catalytic subunit, alpha isoform (PPP3CA) is a target gene of GAM26, corresponding to GAM26-TARGET GENE of FIG. 26A. PPP3CA BINDING SITE is a binding site found in an untranslated region of PPP3CA, corresponding to BINDING SITE of FIG. 26A. FIG. 26D illustrates the complementarity of the nucleotide sequence of PPP3CA BINDING SITE, designated SEQ ID:317210, to the nucleotide sequence of GAM26 RNA of FIG. 26A, designated SEQ ID:20604.

An additional function of GAM26 is therefore inhibition of protein phosphatase 3 (formerly 2B), catalytic subunit, alpha isoform (PPP3CA), a gene which encodes a Enzyme that is the catalytic subunit of calcium-dependent, calmodulin-stimulated protein phosphatase. Accordingly, utilities of GAM26 include diagnosis and treatment of the abovementioned diseases and clinical conditions. The function and utilities of PPP3CA have been established by previous studies, as described hereinabove with reference to FIG. 26D.

Referring now to PPP3CA BINDING SITE. Protein phosphatase 3 (formerly 2B), catalytic subunit, alpha isoform (PPP3CA) is a target gene of GAM26, corresponding to GAM26-TARGET GENE of FIG. 26A. PPP3CA BINDING SITE is a binding site found in an untranslated region of PPP3CA, corresponding to BINDING SITE of FIG. 26A. FIG. 26D illustrates the complementarity of the nucleotide sequence of PPP3CA BINDING SITE, designated SEQ ID:317246, to the nucleotide sequence of GAM26 RNA of FIG. 26A, designated SEQ ID:20604.

A further function of GAM26 is therefore inhibition of protein phosphatase 3 (formerly 2B), catalytic subunit, alpha isoform (PPP3CA), a gene which encodes an enzyme that is the catalytic subunit of calcium-dependent, calmodulin-stimulated protein phosphatase. Accordingly, utilities of GAM26 include diagnosis and treatment of the abovementioned diseases and clinical conditions. The function and utilities of PPP3CA have been established by previous studies, as described hereinabove with reference to FIG. 26D.

Reference is now made to PRKAA2 BINDING SITE. Protein kinase, AMP-activated, alpha 2 catalytic subunit (PRKAA2) is a target gene of GAM26, corresponding to GAM26-TARGET GENE of FIG. 26A. PRKAA2 BINDING SITE is a binding site found in an untranslated region of PRKAA2, corresponding to BINDING SITE of FIG. 26A. FIG. 26D illustrates the complementarity of the nucleotide sequence of PRKAA2 BINDING SITE, designated SEQ ID:318787, to the nucleotide sequence of GAM26 RNA of FIG. 26A, designated SEQ ID:20604.

Yet a further function of GAM26 is therefore inhibition of protein kinase, AMP-activated, alpha 2 catalytic subunit (PRKAA2), a gene which encodes a protein that are responsible for the regulation of fatty acid synthesis by phosphorylation of acetyl-coa carboxylase. Accordingly, utilities of GAM26 include diagnosis and treatment of the abovementioned diseases and clinical conditions.

The function of PRKAA2 has been established by previous studies. AMP-activated protein kinase plays a key role in the regulation of fatty acid and cholesterol metabolism (Hardie, 1992 Hardie and MacKintosh, 1992). In vitro, it phosphorylates and inactivates 3-hydroxy-3-methylglutaryl-CoA reductase (HMGCR; 142910) and acetyl-CoA carboxylase (ACC; 200350), key enzymes involved in regulating de novo biosynthesis of cholesterol and fatty acids, respectively. See PRKAA1 (602739) for additional background. Beri et al. (1994) used a cDNA encoding rat liver AMPK to isolate human skeletal muscle AMPK cDNA clones. The human cDNA was more than 90% homologous to the rat sequence and predicted a protein of 62.3 kD that closely agreed with the mass of human AMPK observed in Western blots of human tissue extracts. A cDNA probe was used to identify a 9.5-kb transcript in several human tissues and to isolate human genomic clones. Stapleton et al. (1997) showed that rat liver Ampk-alpha-2 is associated with Ampk-beta-1 (PRKAB1; 602740) and Ampk-gamma-1 (PRKAG1; 602742). They noted that Ampk-alpha-1 (PRKAA1) is also associated with these beta and gamma isoforms. Beri et al. (1994) used PCR mapping of rodent/human hybrid cell lines to localize the human AMPK gene to chromosome 1, and they sublocalized the AMPK gene to 1p31 by fluorescence in situ hybridization with a human genomic clone. (The cDNA referred to as AMPK by Beri et al. (1994) encodes the alpha-2 subunit of AMPK) Tsujikawa et al. (1998) determined that PRKAA2 and the CDC-like kinase-2 gene (CLK2; 60,989) are located in the same interval of approximately 2.6 cM between D1S2890 and D1S2801. They suggested that CLK2 and PRKAA2 are possible candidate genes for gelatinous drop-like corneal dystrophy (204870). Mu et al. (2001) investigated the role of the metabolic sensor AMPK in the regulation of glucose transport in skeletal muscle. Expression in mouse muscle of a dominant inhibitory mutant of Ampk-alpha-2 completely blocked the ability of hypoxia and 5-aminoimidazole-4-carboxamide ribonucleoside (AICAR) to activate hexose uptake, while only partially reducing contraction-stimulated hexose uptake. These data indicated that AMPK transmits a portion of the signal by which muscle contraction increases glucose uptake, but other AMPK-independent pathways also contribute to the response. Minokoshi et al. (2002) demonstrated that leptin (164160) selectively stimulates phosphorylation and activation of AMPK-alpha-2 in skeletal muscle, thus establishing an additional signaling pathway for leptin. Early activation of AMPK occurs by leptin acting directly on muscle, whereas later activation depends on leptin functioning through the hypothalamic-sympathetic nervous system axis. In parallel with its activation of AMPK, leptin suppresses the activity of ACC (200350, 601557), thereby stimulating the oxidation of fatty acids in muscle. Blocking AMPK activation inhibits the phosphorylation of ACC stimulated by leptin. Minokoshi et al. (2002) concluded that their data identify AMPK as a principal mediator of the effects of leptin on fatty acid metabolism in muscle.

Full details of the abovementioned studies are described in the following publications, the disclosure of which are hereby incorporated by reference:

Minokoshi, Y.; Kim, Y. -B.; Peroni, O. D.; Fryer, L. G. D.; Muller, C.; Carling, D.; Kahn, B. B.: Leptin stimulates fatty-acid oxidation by activating AMP-activated protein kinase. Nature 415: 339-343, 2002. PubMed ID: 11797013 5. Mu, J.; Brozinick, J. T., Jr.; Valladares, O.; Bucan, M.; Birnbaum, M. J.: A role for AMP-activated protein kinase in contraction- and hypoxia-regulated glucose transport in skeletal muscle. Molec. Cell 7: 1085-1094, 2001.

Further studies establishing the function and utilities of PRKAA2 are found in John Hopkins OMIM database record ID 600497, and in references numbered 1103-1109 listed hereinbelow.

Referring now to PRKAA2 BINDING SITE. Protein kinase, AMP-activated, alpha 2 catalytic subunit (PRKAA2) is a target gene of GAM26, corresponding to GAM26-TARGET GENE of FIG. 26A. PRKAA2 BINDING SITE is a binding site found in an untranslated region of PRKAA2, corresponding to BINDING SITE of FIG. 26A. FIG. 26D illustrates the complementarity of the nucleotide sequence of PRKAA2 BINDING SITE, designated SEQ ID:318794, to the nucleotide sequence of GAM26 RNA of FIG. 26A, designated SEQ ID:20604.

Another function of GAM26 is therefore inhibition of protein kinase, AMP-activated, alpha 2 catalytic subunit (PRKAA2), a gene which encodes a protein that are responsible for the regulation of fatty acid synthesis by phosphorylation of acetyl-coa carboxylase. Accordingly utilities of GAM26 include diagnosis and treatment of the abovementioned diseases and clinical conditions. The function and utilities of PRKAA2 have been established by previous studies, as described hereinabove with reference to FIG. 26D.

Reference is now made to PSEN1 BINDING SITE. Presenilin 1 (Alzheimer disease 3) (PSEN1) is a target gene of GAM26, corresponding to GAM26-TARGET GENE of FIG. 26A. PSEN1 BINDING SITE is a binding site found in an untranslated region of PSEN1, corresponding to BINDING SITE of FIG. 26A. FIG. 26D illustrates the complementarity of the nucleotide sequence of PSEN1 BINDING SITE, designated SEQ ID:322696, to the nucleotide sequence of GAM26 RNA of FIG. 26A, designated SEQ ID:20604.

Yet another function of GAM26 is therefore inhibition of presenilin 1 (Alzheimer disease 3) (PSEN1), a gene which encodes a protein that is associated with ALZHEIMER DISEASE, FAMILIAL, TYPE 3. Accordingly, utilities of GAM26 include diagnosis and treatment of the abovementioned diseases and clinical diseases.

The function of PSEN1 has been established by previous studies. St. George-Hyslop et al. (1992), Van Broeckhoven et al. (1992), and Mullan et al. (1992) presented evidence of location of a mutation responsible for early-onset familial Alzheimer disease on 14q. Mullan et al. (1992) placed the gene proximal to that for alpha-1-antichymotrypsin (107280), thus excluding AACT, which is a component of plaque cores and a protease inhibitor, as a possible candidate gene or AD. In a subset of early-onset familial Alzheimer disease (FAD), mutations in the amyloid precursor protein (APP; 104760) have been identified; for example, 3 have been found in codon 717. However, the majority of early-onset FAD families do not show linkage to, or appear to have mutations in, the amyloid precursor protein gene. There may be an additional FAD locus on chromosome 21 separate from the APP locus (St. George-Hyslop et al., 1987; St. George-Hyslop et al., 1990; Tanzi et al., 1991), and a locus on chromosome 19 seemed quite definite (Pericak-Vance et al., 1991; Schellenberg et al., 1992). Schellenberg et al. (1992) indicated the existence of yet another locus for early-onset Alzheimer disease on chromosome 14; a total lod score of 9.15 at theta=0.01 was obtained with the marker D14S43 located at 14q24.3. A single early-onset family yielded a lod score of 4.89 (theta=0.0). When no assumptions were made about age-dependent penetrance, significant results were still obtained (maximum lod=5.94 at theta=0.0) despite the loss of power. Kamal et al. (2000) demonstrated that the axonal transport of APP in neurons is mediated by the direct binding of APP to the kinesin light chain (600025) subunit of kinesin-I. Kamal et al. (2001) identified an axonal membrane compartment that contains APP, beta-secretase (604252), and presenilin-1. The fast anterograde axonal transport of this compartment is mediated APP and kinesin-1. Proteolytic processing of APP can occur in the compartment in vitro and in vivo in axons. This proteolysis generates amyloid-beta and a carboxy-terminal fragment of APP, and liberates kinesin-I from the membrane. Kamal et al. (2001) concluded that APP functions as a kinesin-I membrane receptor, mediating the axonal transport of beta-secretase and presenilin-1, and that processing of APP to amyloid-beta by secretases can occur in an axonal membrane compartment transported by kinesin-I. Lambert et al. (2001) studied 287 individuals with Alzheimer disease. In addition, brain samples from a further 99 cases were studied. They carried out genotype analysis at the polymorphic site at position −48 in the PS1 gene promoter. Lambert et al. (2001) found an increased risk of developing Alzheimer disease associated with the −48 CC genotype (odds ratio=1.55; 95% CI 1.03 to 2.35). This appeared to be present in both familial and sporadic cases and independent of the APOE4 (see 107741) allele genotype. They also that the A-beta load in the brains of individuals with the −48 CC genotype was significantly increased (p less than 0.003). PS1 and PS2 have been suggested to be gamma-secretases responsible for the proteolytic cleavage of amyloid precursor protein (104760) to form amyloid beta. Wilson et al. (2002) examined whether these presenilins are required for the generation of multiple amyloid beta species by analyzing the production of secreted and intracellular amyloid beta in mouse cells lacking PS1, PS2 or both proteins. Although most amyloid beta species were abolished in PS1/PS2 −/− cells, the production of intracellular A-beta-42 generated in the endoplasmic reticulum/intermediate compartment was unaffected by the absence of these proteins, either singly or in combination. Wilson et al. (2002) concluded that production of this pool of amyloid beta occurs independently of PS1/PS2 and, therefore, another gamma-secretase activity must be responsible for cleavage of APP within the early secretory compartments Animal model experiments lend further support to the function of PSEN1. Handler et al. (2000) analyzed Psen1-deficient mouse embryos and observed that lack of Psen1 leads to premature differentiation of neural progenitor cells. They concluded that Psen1 has a role in a cell fate decision between postmitotic neurons and neural progenitor cells. Handler et al. (2000) also detected changes in expression of genes involved in Notch signaling. They concluded that Psen1 controls neuronal differentiation in association with the downregulation of Notch signaling during neurogenesis. Due to the perinatal lethality of Psen1 knockout mice, Yu et al. (2001) developed a conditional knockout mouse (cKO), in which Psen1 inactivation was restricted to the postnatal forebrain. The cKO mice were viable with no gross abnormalities, allowing Yu et al. (2001) to investigate the effects of Psen1 inactivation on amyloid precursor protein processing the Notch signaling pathway, and synaptic and cognitive function in the adult brain. They concluded from their studies that inactivation of Psen1 function in the adult cerebral cortex leads to reduced beta-amyloid generation and subtle cognitive deficits without affecting expression of Notch downstream target genes. Using 3 groups of transgenic mice carrying the presenilin A246E mutation (104311.0003), the amyloid precursor protein K670/M671L mutation (APP; 104760.0008), or both mutations, Dineley et al. (2002) showed that coexpression of both mutant transgenes resulted in accelerated beta-amyloid accumulation, first detected at 7 months in the cortex and hippocampus, compared to the APP or PS1 transgene alone. Contextual fear learning, a hippocampus-dependent associative learning task, but not cued fear learning, was impaired in mice carrying both mutations or the APP mutation, but not the PS1 mutation alone. The impairment manifested at 5 months of age, preceding detectable plaque deposition, and worsened with age. Dineley et al. (2002) also found increased levels of alpha-7 nicotinic acetylcholine receptor protein in the hippocampus, which they hypothesized contributes to disease progression via chronic activation of the ERK MAPK cascade.

It is appreciated that the abovementioned animal model for PSEN1 is acknowledged by those skilled in the art as a scientifically valid animal model, as can be further appreciated from the publications sited hereinbelow.

Full details of the abovementioned studies are described in the following publications, the disclosure of which are hereby incorporated by reference:

Dineley, K. T.; Xia, X.; Bui, D.; Sweatt, J. D.; Zhang, H.: Accelerated plaque accumulation, associative learning deficits, and up-regulation of alpha-7 nicotinic receptor protein in transgenic mice co-expressing mutant human presenilin 1 and amyloid precursor proteins. J. Biol. Chem. 277: 22768-22780, 2002. PubMed ID: 11912199

93. Yu, H.; Saura, C. A.; Choi, S. -Y.; Sun, L. D.; Yang, X.; Handler, M.; Kawarabayashi, T.; Younkin, L.; Fedeles, B.; Wilson, M. A.; Younkin, S.; Kandel, E. R.; Kirkwood, A.; Shen, J.: APP processing and synaptic plasticity in presenilin-1 conditional knockout mice. Neuron 31: 713-726, 2001.

Further studies establishing the function and utilities of PSEN1 are found in John Hopkins OMIM database record ID 104311, and in references numbered 1110-1114, 67, 1115-1124, 75, 1125, 1126-1133, 90, 1134, 1135, 1136-1152, 117 and 1153-1196 listed hereinbelow.

Reference is now made to PTEN BINDING SITE. Phosphatase and tensin homolog (mutated in multiple advanced cancers 1 (PTEN) is a target gene of GAM26, corresponding to GAM26-TARGET GENE of FIG. 26A. PTEN BINDING SITE is a binding site found in an untranslated region of PTEN, corresponding to BINDING SITE of FIG. 26A. FIG. 26D illustrates the complementarity of the nucleotide sequence of PTEN BINDING SITE, designated SEQ ID:324380, to the nucleotide sequence of GAM26 RNA of FIG. 26A, designated SEQ ID:20604.

An additional function of GAM26 is therefore inhibition of phosphatase and tensin homolog (mutated in multiple advanced cancers 1 (PTEN), a gene which encodes an enzyme that is associated with Cowden disease. Accordingly, utilities of GAM26 include diagnosis and treatment of the abovementioned diseases and clinical conditions.

The function of PTEN has been established by previous studies. As tumors progress to more advanced stages, they acquire an increasing of genetic alterations. Li et al. (1997) noted that one alteration which occurs at high frequency in a variety of human tumors is loss of heterozygosity (LOH) at 10q23. Although rarely seen in low-grade glial tumors and early-stage prostate cancers, LOH at 10q23 occurs in approximately 70% of glioblastomas (the most advanced form of glial tumor) and approximately 60% of advanced prostate cancers. This pattern of LOH and the finding that wildtype chromosome 10 suppresses the tumorigenicity of glioblastoma cells in mice suggested to Li et al. (1997) that 10q23 encodes a tumor suppressor gene. By mapping of homozygous deletions on 10q23, they isolated a candidate tumor suppressor gene that they called PTEN for 'phosphatase and tensin homolog deleted on chromosome ten.' Sequence analysis of the predicted 403-amino acid open reading frame (ORF) revealed a protein tyrosine phosphatase domain and a large region of homology (approximately 175 amino acids) to chicken tensin (600076; a protein that interacts with actin filaments at focal adhesions) and bovine auxilin. In preliminary screens, Li et al. (1997) detected mutations of PTEN in 31% (13 of 42) of glioblastoma cell lines and xenografts, 100% (4 of 4) of prostate cancer cell lines, 6% (4 of 65) of breast cancer cell lines and xenografts, and 17% (3 of 18) of primary glioblastomas. The homologies displayed by the structure of PTEN suggested to the investigators that it may suppress tumor cell growth by antagonizing protein tyrosine kinases and may regulate tumor cell invasion and metastasis through interactions at focal adhesions.

Animal model experiments lend further support to the function of PTEN. To examine the role of the dual-specificity phosphatase PTEN in ontogenesis and tumor suppression, Di Cristofano et al. (1998) disrupted mouse Pten by homologous recombination. Pten inactivation resulted in early embryonic lethality. Homozygous deficient ES (embryonic stem) cells formed aberrant embryoid bodies and displayed an altered ability to differentiate into endodermal, ectodermal, and mesodermal derivatives. Heterozygous knockout mice and chimeric mice derived from heterozygous ES cells showed hyperplastic/dysplastic changes in the prostate, skin, and colon, which are characteristic of Cowden disease, Lhermitte-Duclos disease, and Bannayan-Zonana syndrome. They also spontaneously developed germ cell, gonadostromal, thyroid, and colon tumors. In addition, Pten inactivation enhanced the ability of ES cells to generate tumors in nude and syngeneic mice, due to increased anchorage-independent growth and aberrant differentiation. These results supported the notion that PTEN haploinsufficiency plays a causal role in the 3 disorders in which mutations had been found, and demonstrated that Pten is a tumor suppressor essential for embryonic development.

It is appreciated that the abovementioned animal model for PTEN is acknowledged by those skilled in the art as a scientifically valid animal model as can be further appreciated from the publications sited hereinbelow.

Full details of the abovementioned studies are described in the following publications, the disclosure of which are hereby incorporated by reference:

Di Cristofano, A.; Pesce, B.; Cordon-Cardo, C.; Pandolfi, P. P.: Pten is essential for embryonic development and tumour suppression. Nature Genet. 19: 348-355, 1998. PubMed ID: 9697695 35. Li, J.; Yen, C.; Liaw, D.; Podsypanina, K.; Bose, S.; Wang, S. I.; Puc, J.; Miliaresis, C.; Rodgers, L.; McCombie, R.; Bigner, S. H.; Giovanella, B. C.; Ittmann, M.; Tycko, B.; Hibshoosh, H.; Wigler, M. H.; Parsons, R.: PTEN, a putative protein tyrosine phosphatase gene mutated in human brain, breast, and prostate cancer. Science 275: 1943-1946, 1997.

Further studies establishing the function and utilities of PTEN are found in John Hopkins OMIM database record ID 601728, and in references numbered 1197-1267 listed hereinbelow.

Referring now to PTEN BINDING SITE. Phosphatase and tensin homolog (mutated in multiple advanced cancers 1 (PTEN) is a target gene of GAM26, corresponding to GAM26-TARGET GENE of FIG. 26A. PTEN BINDING SITE is a binding site found in an untranslated region of PTEN, corresponding to BINDING SITE of FIG. 26A. FIG. 26D illustrates the complementarity of the nucleotide sequence of PTEN BINDING SITE, designated SEQ ID:324398, to the nucleotide sequence of GAM26 RNA of FIG. 26A, designated SEQ ID:20604.

A further function of GAM26 is therefore inhibition of phosphatase and tensin homolog (mutated in multiple advanced cancers 1 (PTEN), a gene which encodes a Enzyme that is associated with Cowden disease. Accordingly, utilities of GAM26 include diagnosis and treatment of the abovementioned diseases and clinical conditions. The function and utilities of PTEN have been established by previous studies, as described hereinabove with reference to FIG. 26D.

Referring now to PTEN BINDING SITE. Phosphatase and tensin homolog (mutated in multiple advanced cancers 1 (PTEN) is a target gene of GAM26, corresponding to GAM26-TARGET GENE of FIG. 26A. PTEN BINDING SITE is a binding site found in an untranslated region of PTEN, corresponding to BINDING SITE of FIG. 26A. FIG. 26D illustrates the complementarity of the nucleotide sequence of PTEN BINDING SITE, designated SEQ ID:324399, to the nucleotide sequence of GAM26 RNA of FIG. 26A, designated SEQ ID:20604.

Yet a further function of GAM26 is therefore inhibition of phosphatase and tensin homolog (mutated in multiple advanced cancers 1 (PTEN), a gene which encodes a Enzyme that is associated with Cowden disease. Accordingly, utilities of GAM26 include diagnosis and treatment of the abovementioned diseases and clinical conditions. The function and utilities of PTEN have been established by previous studies, as described hereinabove with reference to FIG. 26D.

Referring now to PTEN BINDING SITE. Phosphatase and tensin homolog (mutated in multiple advanced cancers 1 (PTEN) is a target gene of GAM26, corresponding to GAM26-TARGET GENE of FIG. 26A. PTEN BINDING SITE is a binding site found in an untranslated region of PTEN, corresponding to BINDING SITE of FIG. 26A. FIG. 26D illustrates the complementarity of the nucleotide sequence of PTEN BINDING SITE, designated SEQ ID:324417, to the nucleotide sequence of GAM26 RNA of FIG. 26A, designated SEQ ID:20604.

Another function of GAM26 is therefore inhibition of phosphatase and tensin homolog (mutated in multiple advanced cancers 1 (PTEN), a gene which encodes a Enzyme that is associated with Cowden disease. Accordingly, utilities of GAM26 include diagnosis and treatment of the abovementioned diseases and clinical conditions. The function and utilities of PTEN have been established by previous studies, as described hereinabove with reference to FIG. 26D.

Referring now to PTEN BINDING SITE. Phosphatase and tensin homolog (mutated in multiple advanced cancers 1 (PTEN is a target gene of GAM26, corresponding to GAM26-TARGET GENE of FIG. 26A. PTEN BINDING SITE is a binding site found in an untranslated region of PTEN, corresponding to BINDING SITE of FIG. 26A. FIG. 26D illustrates the complementarity of the nucleotide sequence of PTEN BINDING SITE, designated SEQ ID:324417, to the nucleotide sequence of GAM26 RNA of FIG. 26A, designated SEQ ID:20604.

Yet another function of GAM26 is therefore inhibition of phosphatase and tensin homolog (mutated in multiple advanced cancers 1 (PTEN), a gene which encodes an enzyme that associated with Cowden disease. Accordingly, utilities of GAM26 include diagnosis and treatment of the abovementioned diseases and clinical conditions. The function and utilities of PTEN have been established by previous studies, as described hereinabove with reference to FIG. 26D.

Referring now to PTEN BINDING SITE. Phosphatase and tensin homolog (mutated in multiple advanced cancers 1 (PTEN) is a target gene of GAM26, corresponding to GAM26-TARGET GENE of FIG. 26A. PTEN BINDING SITE is a binding site found in an untranslated region of PTEN, corresponding to BINDING SITE of FIG. 26A. FIG. 26D illustrates the complementarity of the nucleotide sequence of PTEN BINDING SITE, designated SEQ ID:324452, to the nucleotide sequence of GAM26 RNA of FIG. 26A, designated SEQ ID:20604.

An additional function of GAM26 is therefore inhibition of phosphatase and tensin homolog (mutated in multiple advanced cancers 1 (PTEN), a gene which encodes an enzyme that is associated with Cowden disease. Accordingly, utilities of GAM26 include diagnosis and treatment of the abovementioned diseases and clinical conditions. The function and utilities of PTEN have been established by previous studies, as described hereinabove with reference to FIG. 26D.

Reference is now made to PTP4A2 BINDING SITE. Protein tyrosine phosphatase type IVA, member 2 (PTP4A2) is a target gene of GAM26, corresponding to GAM26-TARGET GENE of FIG. 26A. PTP4A2 BINDING SITE is a binding site found in an untranslated region of PTP4A2, corresponding to BINDING SITE of FIG. 26A. FIG. 26D illustrates the complementarity of the nucleotide sequence of PTP4A2 BINDING SITE, designated SEQ ID:326495, to the nucleotide sequence of GAM26 RNA of FIG. 26A, designated SEQ ID:20604.

A further function of GAM26 is therefore inhibition of protein tyrosine phosphatase type IVA, member 2 (PTP4A2), a gene which encodes an enzyme that is a protein tyrosine phosphatase which has a C-terminal prenylation site. Accordingly, utilities of GAM26 include diagnosis and treatment of the abovementioned diseases and clinical conditions.

The function of PTP4A2 has been established by previous studies. The rat Prl1 (phosphatase of regenerating liver-1; 601585) protein is a 20-kD nuclear protein tyrosine phosphatase (PTPase) that is not homologous to previously characterized dual-specificity PTPases or the monospecific PTPases. Montagna et al., (1995) identified a cDNA encoding a human PRL1-like protein, which they designated OV1. By using an in vitro prenylation screen, Cates et al. (1996) found that human PRL1 and OV1, which they referred to as PTP(CAAX1) and PTP(CAAX2), respectively, are farnesylated in vitro by mammalian farnesyl:protein transferase. Overexpression of these PTPs in epithelial cells caused a transformed phenotype in cultured cells and tumor growth in nude mice. Cates et al. (1996) concluded that PTP(CAAX1) and PTP(CAAX2) represent a novel class of isoprenylated, oncogenic PTPs. Zhao et al. (1996) isolated both cDNA and genomic clones as part of a screen for genes with CTG repeats. Among these were 2 cDNAs, HH13 and HH7-2, that were identical in their coding regions but differed primarily in their 5-prime untranslated regions (UTRs). The predicted 167-amino acid sequence from each was 89% identical to rat Prl1 but was unrelated to other PTPs except for the active site. The protein contains a large number of basic residues and has a predicted isoelectric point of 8.33. Northern blot analysis using a probe from the common 3-prime UTR of HH13 and HH7-2 identified transcripts of 2 and 4 kb in all human tissues examined. Zeng et al. (1998) identified cDNAs encoding the mouse homolog of human PTP (CAAX2), or PRL2. The predicted human and mouse PRL2 proteins are identical. Zhao et al. (1996) used the HH13 cDNA to identify a YAC that was mapped to 1p35 by fluorescence in situ hybridization. They found a third cDNA (designated HH18) which contains a large deletion in the reading frame and may be a splice variant of either HH13 or HH7-2. Furthermore, a processed pseudogene with 96% sequence identity was found in the BRCA1 (113705) region of 17q21.

Full details of the abovementioned studies are described in the following publications, the disclosure of which are hereby incorporated by reference:

ates, C. A.; Michael, R. L.; Stayrook, K. R.; Harvey K. A.; Burke, Y. D.; Randall, S. K.; Crowell, P. L.; Crowell, D. N.: Prenylation of oncogenic human PTP(CAAX) protein tyrosine phosphatases. Cancer Lett. 110: 49-55, 1996. PubMed ID: 9018080 4. Zhao, Z.; Lee, C. -C.; Monckton, D. G.; Yazdani, A.; Coolbaugh, M. I.; Li, X.; Bailey, J.; Shen, Y.; Caskey, C. T.: Characterization and genomic mapping of genes and pseudogenes of a new human protein tyrosine phosphatase. Genomics 35: 172-181, 1996.

Further studies establishing the function and utilities of PTP4A2 are found in John Hopkins OMIM database record ID 601584, and in references numbered 1268-1269, 1271 and 1273 listed hereinbelow.

Referring now to PTP4A2 BINDING SITE. Protein tyrosine phosphatase type IVA, member 2 (PTP4A2) is a target gene of GAM26, corresponding to GAM26-TARGET GENE of FIG. 26A. PTP4A2 BINDING SITE is a binding site found in an untranslated region of PTP4A2, corresponding to BINDING SITE of FIG. 26A. FIG. 26D illustrates the complementarity of the nucleotide sequence of PTP4A2 BINDING SITE, designated SEQ ID:326499, to the nucleotide sequence of GAM26 RNA of FIG. 26A, designated SEQ ID:20604.

Yet a further function of GAM26 is therefore inhibition of protein tyrosine phosphatase type IVA, member 2 (PTP4A2), a gene which encodes an enzyme that is a protein tyrosine phosphatase which has a C-terminal prenylation site. Accordingly, utilities of GAM26 include diagnosis and treatment of the abovementioned diseases and clinical conditions. The function and utilities of PTP4A2 have been established by previous studies, as described hereinabove with reference to FIG. 26D.

Referring now to PTP4A2 BINDING SITE. Protein tyrosine phosphatase type IVA, member 2 (PTP4A2) is a target gene of GAM26, corresponding to GAM26-TARGET GENE of FIG. 26A. PTP4A2 BINDING SITE is a binding site found in an untranslated region of PTP4A2, corresponding to BINDING SITE of FIG. 26A. FIG. 26D illustrates the complementarity of the nucleotide sequence of PTP4A2 BINDING SITE, designated SEQ ID:326500, to the nucleotide sequence of GAM26 RNA of FIG. 26A, designated SEQ ID:20604.

Another function of GAM26 is therefore inhibition of protein tyrosine phosphatase type IVA, member 2 (PTP4A2), a gene which encode an enzyme that is a protein tyrosine phosphatase which has a C-terminal prenylation site. Accordingly, utilities of GAM26 include diagnosis and treatment of the abovementioned diseases and clinical conditions. The function and utilities of PTP4A2 have been established by previous studies, as described hereinabove with reference to FIG. 26D.

Referring now to PTP4A2 BINDING SITE. Protein tyrosine phosphatase type IVA, member 2 (PTP4A2) is a target gene of GAM26, corresponding to GAM26-TARGET GENE of FIG. 26A. PTP4A2 BINDING SITE is a binding site found in an untranslated region of PTP4A2, corresponding to BINDING SITE of FIG. 26A. FIG. 26D illustrates the complementarity of the nucleotide sequence of PTP 4A2 BINDING SITE, designated SEQ ID:326502, to the nucleotide sequence of GAM26 RNA of FIG. 26A, designated SEQ ID:20604.

Yet another function of GAM26 is therefore inhibition of protein tyrosine phosphatase type IVA, member 2 (PTP4A2), a gene which encodes an enzyme that is a protein tyrosine phosphatase which has a C-terminal prenylation site. Accordingly, utilities of GAM26 include diagnosis and treatment of the abovementioned diseases and clinical conditions. The function and utilities of PTP4A2 have been established by previous studies, as described hereinabove with reference to FIG. 26D.

Referring now to PTP4A2 BINDING SITE. Protein tyrosine phosphatase type IVA, member 2 (PTP4A2) is a target gene of GAM26, corresponding to GAM26-TARGET GENE of FIG. 26A. PTP4A2 BINDING SITE is a binding site found in an untranslated region of PTP4A2, corresponding to BINDING SITE of FIG. 26A. FIG. 26D illustrates the complementarity of the nucleotide sequence of PTP4A2 BINDING SITE, designated SEQ ID:326511, to the nucleotide sequence of GAM26 RNA of FIG. 26A, designated SEQ ID:20604.

An additional function of GAM26 is therefore inhibition of protein tyrosine phosphatase type IVA, member 2 (PTP4A2), a gene which encode an enzyme that is a protein tyrosine phosphatase which has a C-terminal prenylation site. Accordingly, utilities of GAM26 include diagnosis and treatment of the abovementioned diseases and clinical conditions. The function and utilities of PTP4A2 have been established by previous studies, as described hereinabove with reference to FIG. 26D.

Referring now to PTP4A2 BINDING SITE. Protein tyrosine phosphatase type IVA, member 2 (PTP4A2) is a target gene of GAM26, corresponding to GAM26-TARGET GENE of FIG. 26A. PTP4A2 BINDING SITE is a binding site found in an untranslated region of PTP4A2, corresponding to BINDING SITE of FIG. 26A. FIG. 26D illustrates the complementarity of the nucleotide sequence of PTP4A2 BINDING SITE, designated SEQ ID:326515, to the nucleotide sequence of GAM26 RNA of FIG. 26A, designated SEQ ID:20604.

A further function of GAM26 is therefore inhibition of protein tyrosine phosphatase type IVA, member 2 (PTP4A2), a gene which encodes an enzyme that is a protein tyrosine phosphatase which has a C-terminal prenylation site. Accordingly, utilities of GAM26 include diagnosis and treatment of the above-mentioned diseases and clinical conditions. The function and utilities of PTP4A2 have been established by previous studies, as described hereinabove with reference to FIG. 26D.

Reference is now made to PTPN1 BINDING SITE. Protein tyrosine phosphatase, non-receptor type 1 (PTPN1) is a target gene of GAM26, corresponding to GAM26-TARGET GENE of FIG. 26A. PTPN1 BINDING SITE is a binding site found in an untranslated region of PTPN1, corresponding to BINDING SITE of FIG. 26A. FIG. 26D illustrates the complementarity of the nucleotide sequence of PTPN1 BINDING SITE, designated SEQ ID:326697, to the nucleotide sequence of GAM26 RNA of FIG. 26A, designated SEQ ID:20604.

Yet a further function of GAM26 is therefore inhibition of protein tyrosine phosphatase, non-receptor type 1 (PTPN1), a gene which encodes an enzyme that is a non-receptor type 1 protein tyrosine phosphatase and inhibits insulin signaling. Accordingly, utilities of GAM26 include diagnosis and treatment of the abovementioned diseases and clinical conditions.

The function of PTPN1 has been established by previous studies. PTP1B inhibits insulin signaling and, when overexpressed, plays a role in insulin resistance (Ahmad et al., 1997). In the 3-prime untranslated region of the PTP1B gene, Di Paola et al. (2002) identified a 1484insG variation (176885.0001) that, in 2 different populations, was associated with several features of insulin resistance. Similar data were obtained in a family-based association study by use of sib pairs discordant for genotype (Gu et al., 2000). Subjects carrying the 1484insG variant showed PTP1B mRNA overexpression in skeletal muscle. PTP1B mRNA stability was significantly higher in human embryonic kidney cells transfected with 1484insG PTP1B as compared with those transfected with wildtype PTP1B. The data indicated that the 1484insG allele causes PTP1B overexpression and plays a role in insulin resistance. Therefore, individuals carrying the 1484insG variant might particularly benefit from PTP1B inhibitors in the treatment of insulin resistance (Kennedy and Ramachandran, 2000).

Animal model experiments lend further support to the function of PTPN1. Elchebly et al. (1999) generated PTP1B-deficient mice by targeted disruption of the mouse homolog of the PTP1B gene. Mice were phenotypically and pathologically normal and had normal life span. In the fed state, homozygous mutant mice had slightly lower blood glucose concentrations, and half the circulating insulin concentrations, of wildtype littermates. The enhanced insulin sensitivity of PTP1B-deficient mice was also evident in glucose- and insulin-tolerance tests. After insulin injection, deficient mice showed increased phosphorylation of the insulin receptor in liver and muscle tissue compared to wildtype mice. On a high-fat diet, PTP1B-deficient mice were resistant to weight gain and remained insulin sensitive, while wildtype mice rapidly gained weight and became insulin resistant. These results suggested a major role for PTP1B in modulation of insulin sensitivity and fuel metabolism. The authors proposed PTP1B as a potential therapeutic target for the treatment of type 2 diabetes and obesity.

It is appreciated that the abovementioned animal model for PTPN1 is acknowledged by those skilled in the art as a scientifically valid animal model, as can be further appreciated from the publications sited hereinbelow.

Full details of the abovementioned studies are described in the following publications, the disclosure of which are hereby incorporated by reference:

Elchebly, M.; Payette, P.; Michaliszyn, E.; Cromlish, W.; Collins, S.; Loy, A. L.; Normandin, D.; Cheng, A.; Himms-Hagen, J.; Chan, C.; Ramachandran, C.; Gresser, M. J.; Tremblay, M. L.; Kennedy, B. P.: Increased insulin sensitivity and obesity resistance in mice lacking the protein tyrosine phosphatase-1B gene. Science 283: 1544-1548, 1999. PubMed ID: 10066179 5. Di Paola, R.; Frittitta, L.; Miscio, G.; Bozzali, M.; Baratta, R.; Centra, M.; Spampinato, D.; Santagati, M. G.; Ercolino, T.; Cisternino, C.; Soccio, T. Mastroianno, S.; Tassi, V.; Almgren, P.; Pizzuti, A.; Vigneri, R.; Trischitta, V.: A variation in 3-prime UTR of hPTP1B increases specific gene expression and associates with insulin resistance. Am. J. Hum. Genet. 70: 806-812, 2002.

Further studies establishing the function and utilities of PTPN1 are found in John Hopkins OMIM data base record ID 176885, and in references numbered 1274-1288 listed hereinbelow.

Reference is now made to PTPRF BINDING SITE. Protein tyrosine phosphatase, receptor type, F (PTPRF) is a target gene of GAM26, corresponding to GAM26-TARGET GENE of FIG. 26A. PTPRF BINDING SITE is a binding site found in an untranslated region of PTPRF, corresponding to BINDING SITE of FIG. 26A. FIG. 26D illustrates the complementarity of the nucleotide sequence of PTPRF BINDING SITE, designated SEQ ID:327695, to the nucleotide sequence of GAM26 RNA of FIG. 26A, designated SEQ ID:20604.

Another function of GAM26 is therefore inhibition of protein tyrosine phosphatase, receptor type, F (PTPRF), a gene which encodes an enzyme that negatively regulates the insulin signaling pathway. Accordingly, utilities of GAM26 include diagnosis and treatment of the abovementioned diseases and clinical conditions.

The function of PTPRF has been established by previous studies. The LAR gene (symbolized PTPRF) encodes a membrane protein that has a cytoplasmic domain with homology to protein-tyrosine phosphatase 1B (176885) and an extracellular domain homologous to the neural cellular adhesion molecule NCAM (116930). The human LAR molecule closely resembles cell adhesion molecules, which suggests that it may be involved in the regulation of phosphotyrosine levels through cell-cell or cell-matrix interactions. As a first stop toward site-directed mutagenesis studies of LAR function, Schaapveld et al. (1995) characterized the mouse Ptprf gene. They found that its cytoplasmic region is encoded by 11 exons that span only 4.5 kb of genomic DNA. Compared to the known exon-intron structures of other mammalia receptor-like protein tyrosine phosphatase genes such as Ptpra (encoding LRP; 176884) and Ptprc (coding for Ly-5; 151460), the portion of the Ptprf gene encoding the cytoplasmic region of murine LAR contained not only smaller, but also fewer introns. O'Grady et al. (1994) demonstrated that the human LAR gene is composed of 33 exons spanning over 85 kb. Exon 2 encodes the signal sequence and the first 4 amino acids in the mature LAR protein. The 3 immunoglobulin-like domains are encoded by exons 3 to 7, and the 8 fibronectin type III (FN-III) domains by exons 8 to 17. Exons 18 to 22 encode the juxtamembrane and transmembrane domains, and exons 23 to 33 encode the 2 conserved tyrosine phosphatase domains and the entire 3-prime untranslated region. Alternative splicing of LAR mRNA was revealed by RT-PCR analysis.

Full details of the abovementioned studies are described in the following publications, the disclosure of which are hereby incorporated by reference:

Schaapveld, R. Q. J.; van den Maagdenberg, A. M. J. M.; Schepens, J. T. G.; Olde Weghuis, D.; Geurts van Kessel, A.; Wieringa, B.; Hendriks, W. J. A. J.: The mouse gene Ptprf encoding the leukocyte common antigen-related molecule LAR: cloning, characterization, and chromosomal localization. Genomics 27: 124-130, 1995. PubMed ID: 7665159 6. O'Grady, P.; Krueger, N. X.; Streuli, M.; Saito, H.: Genomic organization of the human LAR protein tyrosine phosphatase gene and alternative splicing in the extracellular fibronectin type-III domains. J. Biol. Chem. 269: 25193-25199, 1994. PubMed ID: 7929208 9. Tsujikawa, K.; Kawakami, N.; Uchino, Y.; Ichijo, T.; Furukawa, T.; Saito, H.; Yamamoto, H.: Distinct functions of two protein tyrosine phosphatase domains of LAR (leukocyte common antigen-related) on tyrosine dephosphorylation of insulin receptor. Molec. Endocr. 15: 271-280, 2001.

Further studies establishing the function and utilities of PTPRF are found in John Hopkins OMIM database record ID 179590, and in references numbered 1289-1297 listed hereinbelow.

Reference is now made to PURA BINDING SITE. Purine-rich element binding protein A (PURA) is a target gene of GAM26, corresponding to GAM26-TARGET GENE of FIG. 26A. PURA BINDING SITE is a binding site found in an untranslated region of PURA, corresponding to BINDING SITE of FIG. 26A. FIG. 26D illustrates the complementarity of the nucleotide sequence of PURA BINDING SITE, designated SEQ ID:328884, to the nucleotide sequence of GAM26 RNA of FIG. 26A, designated SEQ ID:20604.

Yet another function of GAM26 is therefore inhibition of purine-rich element binding protein A (PURA), a gene which encodes a protein that is a probable transcription activator. Accordingly, utilities of GAM26 include diagnosis and treatment of the abovementioned diseases and clinical conditions.

The function of PURA has been established by previous studies. Kennedy and Rutter (1992) identified a transcription factor, which they referred to as Pur-1 because of its ability to bind to purine-rich sequences. Such purine-rich stretches of nucleotides (GAGA boxes) are often found just upstream of transcription start sites in many genes, including insulin (INS; 176730). Mutational analysis suggested that the GAGA box plays an important role in transcription of the rat insulin I gene. Kennedy and Rutter (1992) identified at least 4 different proteins that bind specifically to the insulin GAGA box. Using a GAGA oligonucleotide, they isolated a cDNA encoding a sequence-specific protein from a lambda-gt11 expression library made from a hamster insulinoma cell line. This was the protein that they designated Pur-1. They found that it binds to the GAGA boxes of the rat insulin I and II genes and the human islet amyloid polypeptide gene. Pur-1 is a potent transactivator in both pancreatic and nonpancreatic cells. Furthermore, Pur-1 is able to activate an intact insulin promoter in HeLa cells, where it is normally inactive. Pur-alpha is a single-stranded DNA-binding protein with specific affinity for a purine-rich element of the configuration (GGN)n present in several initiation zones of eukaryotic DNA replication. It interacts with large T-antigen and cellular protein YB-1 (154030) to activate JC viral DNA transcription in human cells (Chen et al., 1995). The functional activities of Pur-alpha, together with its evolutionary conservation, suggested it may represent an important link between DNA replication and differential gene expression. Using a 16-kb genomic probe together with hybridization of a cDNA probe to blots of DNA from human/hamster cell lines, Ma et al. (1995) mapped the PURA gene to 5q31. This region is frequently deleted in myelogenous leukemias in hematologic malignancies and other cancers. Sequences with homology to the PURA gene were also present at 6q14.

Full details of the abovementioned studies are described in the following publications, the disclosure of which are hereby incorporated by reference:

Gallia, G. L.; Johnson, E. M.; Khalili, K.: Pur-alpha: a multifunctional single-stranded DNA- and RNA-binding protein. Nucleic Acids Res. 28: 3197-3205, 2000. PubMed ID: 10954586 3. Kennedy, G. C.; Rutter, W. J.: Pur-1, a zinc-finger protein that binds to purine-rich sequences, transactivates an insulin promoter in heterologous cells. Proc. Nat. Acad. Sci. 89: 11498-11502, 1992. PubMed ID: 1454839 4. Ma, Z. -W.; Pejovic, T.; Najfeld, V.; Ward, D. C.; Johnson, M.: Localization of PURA, the gene encoding the sequence-specific single-stranded-DNA-binding protein Pur-alpha, to chromosome band 5q31. Cytogenet. Cell Genet, 71: 64-67, 1995.

Further studies establishing the function and utilities of PURA are found in John Hopkins OMIM database record ID 600473, and in references numbered 1298-1301 listed hereinbelow.

Referring now to PURA BINDING SITE. Purine-rich element binding protein A (PURA) is a target gene of GAM26, corresponding to GAM26-TARGET GENE of FIG. 26A. PURA BINDING SITE is a binding site found in an untranslated region of PURA, corresponding to BINDING SITE of FIG. 26A. FIG. 26D illustrates the complementarity of the nucleotide sequence of PURA BINDING SITE, designated SEQ ID:328886, to the nucleotide sequence of GAM26 RNA of FIG. 26A, designated SEQ ID:20604.

An additional function of GAM26 is therefore inhibition of purine-rich element binding protein A (PURA), a gene which encodes a protein that is a probable transcription activator. Accordingly, utilities of GAM26 include diagnosis and treatment of the abovementioned diseases and clinical condition. The function and utilities of PURA have been established by previous studies, as described hereinabove with reference to FIG. 26D.

Reference is now made to PX19 BINDING SITE. (PX19) is a target gene of GAM26, corresponding to GAM26-TARGET GENE of FIG. 26A. PX19 BINDING SITE is a binding site found in an untranslated region of PX19, corresponding to BINDING SITE of FIG. 26A. FIG. 26D illustrates the complementarity of the nucleotide sequence of PX19 BINDING SITE, designated SEQ ID:329171, to the nucleotide sequence of GAM26 RNA of FIG. 26A, designated SEQ ID:20604.

A further function of GAM26 is therefore inhibition of (PX9), a gene which encodes a protein that plays a role in hemopoiesis. Accordingly, utilities of GAM26 include diagnosis and treatment of the abovementioned diseases and clinical conditions.

The function of PX19 has been established by previous studies. The late embryogenesis abundant (LEA) motif is found in plant proteins that protect against desiccation and other type of stress affecting plant embryo development. In chicken, a LEA motif-containing protein termed Px19 plays a role in hemopoiesis. By gene motif-targeted RT-PCR differential display of tonsillar B-lymphocyte subpopulations purified and sorted by flow cytometry, Guzman-Rojas et al. (2000) isolated a cDNA encoding human PX19, which they termed PRELI for 'protein of relevant evolutionary and lymphoid interest.' Sequence analysis predicted that the 219-amino acid human protein is 85% identical to the avian protein. PX19 contains 2 alpha helices with amphipathic domains in opposite orientation, and the LEA motifs (A/TAEKAK) are clustered within this region. Northern blot analysis detected 1.0- and 1.2-kb transcripts predominantly in fetal liver, with much lower levels in other fetal tissues. Expression was significantly reduced in adult liver, but was higher in other adult organs. Expression was low in bone marrow and thymus, but high in adult spleen, lymph node, and peripheral blood leukocytes. Further analysis of B-cell lines indicated that expression is higher in mature B cells, predominantly from germinal centers, and absent in progenitor and precursor B-cell lines. Guzman-Rojas et al. (2000) inferred from these data that PX19 expression is more important in B- than in T-lymphocyte differentiation and early lymphopoiesis, and that PX19 may be more significant for mature B lymphocytes during secondary immune responses, a stage of stressful selection pressure.

Full details of the abovementioned studies are described in the following publications, the disclosure of which are hereby incorporated by reference:

Guzman-Rojas, L.; Sims, J. C.; Rangel, R.; Guret, C.; Sun, Y.; Alcocer, J. M.; Martinez-Valdez, H.: PRELI, the human homologue of the avian px19, is expressed by germinal center B lymphocytes. Int. Immun. 12: 607-612, 2000.

Further studies establishing the function and utilities of PX19 are found in John Hopkins OMIM database record ID 605733, and in references numbered 1302 listed hereinbelow.

Referring now to PX19 BINDING SITE. (PX19) is a target gene of GAM26, corresponding to GAM26-TARGET GENE of FIG. 26A. PX19 BINDING SITE is a binding site found in an untranslated region of PX19, corresponding to BINDING SITE of FIG. 26A. FIG. 26D illustrates the complementarity of the nucleotide sequence of PX19 BINDING SITE, designated SEQ ID:329172, to the nucleotide sequence of GAM26 RNA of FIG. 26D designated SEQ ID:20604.

Yet a further function of GAM26 is therefore inhibition of (PX19), a gene which encodes a protein that plays a role in hemopoiesis. Accordingly, utilities of GAM26 include diagnosis and treatment of the abovementioned diseases and clinical conditions. The function and utilities of PX19 have been established by previous studies, as described hereinabove with reference to FIG. 26D.

Referring now to PX19 BINDING SITE. (PX19) is a target gene of GAM26, corresponding to GAM26-TARGET GENE of FIG. 26A. PX19 BINDING SITE is a binding site found translated region of PX19, corresponding to BINDING SITE of FIG. 26A. FIG. 26D illustrates the complementarity of the nucleotide sequence of PX19 BINDING SITE, designated SEQ ID:329182, to the nucleotide sequence of GAM26 RNA of FIG. 26, designated SEQ ID:20604.

Another function of GAM26 is therefore inhibition of (PX19), a gene which encodes a protein that plays a role in hemopoiesis. Accordingly, utilities of GAM26 include diagnosis and treatment of the abovementioned diseases and clinical conditions. The function and utilities of PX19 have been established by previous studies, as described hereinabove with reference to FIG. 26D.

Reference is now made to RAB1A BINDING SITE. (RAB1A) is a target gene of GAM26, corresponding to GAM26-TARGET GENE of FIG. 26A. RAB1A BINDING SITE is a binding site found in an untranslated region of RAB1A, corresponding to BINDING SITE of FIG. 26A. FIG. 26D illustrates the complementarity of the nucleotide sequence of RAB1A BINDING SITE, designated SEQ ID:330375, to the nucleotide sequence of GAM26 RNA of FIG. 26A, designated SEQ ID:20604.

Yet another function of GAM26 is therefore inhibition of (RAB1A), a gene which encodes a protein that is involved in vesicle transport. Accordingly, utilities of GAM26 include diagnosis and treatment of the abovementioned diseases and clinical conditions.

The function of RAB1A has been established by previous studies. RAB proteins have been postulated to regulate the targeting and fusion of membranous vesicles during organelle assembly and transport. RAB proteins undergo regulated exchange of GTP for GDP, and they slowly hydrolyze the bound GTP in a reaction that is thought to regulate the timing and unidirectional nature of these assembly events. All of the known RAB proteins terminate in sequences such as cys-X-cys (e.g., RAB3A, 179490), cys-cys (e.g., RAB1A), or a closely related sequence, and all are believed to be geranylgeranylated. From a human pheochromocytoma cDNA library, Zahraoui et al. (1989) isolated 7 cDNA clones corresponding to genes encoding the Ras-associated GTP-binding proteins. See RAB5A (179512). The predicted 205-amino acid human and rat RAB1 proteins are identical and share 75% identity with YPT1, the *S. cerevisiae* homolog. Northern blot analysis revealed that the RAB1 gene was expressed as a major (2.7 kb) and a minor (1.7 kb) mRNA in a human fibroblast cell line. The 'wobbler' spinal muscular atrophy gene (wr) maps to proximal mouse chromosome 11, tightly linked to Rab1 and Glns-ps1, an intronless pseudogene of the glutamine synthetase gene (138290). Wedemeyer et al. (1996) used these markers to construct a 1.3-Mb YAC contig of the Rab1 region on mouse chromosome 11. Two overlapping YACS were identified that contained a 150-kb region of human chromosome 2p, comprising the RAB1 locus as well as a newly discovered STS (AHY1.1) and a trapped exon (ETG1.1). The region was mapped to 2p14-p13.4 using somatic cell hybrids and a radiation hybrid panel, thus extending a known region of conserved synteny between mouse chromosome 11 and human 2p. The gene for limb-girdle muscular dystrophy type 2B (LGMD2B; 253601) maps to 2p16-p13. The authors noted that conservation between the mouse Rab1 and human RAB1 regions will be helpful in identifying candidate genes for the 'wobbler' spinal muscular atrophy and in clarifying a possible relationship between wr and LGMD2B.

Full details of the abovementioned studies are described in the following publications, the disclosure of which are hereby incorporated by reference:

Allan, B. B.; Moyer, B. D.; Balch, W. E.: Rab1 recruitment of p115 into a cis-SNARE complex: programming budding COPII vesicles for fusion. Science 289: 444-448, 2000. PubMed ID: 10903204 2. Wedemeyer, N.; Lengeling, A.; Ronsiek, M.; Korthaus, D.; Baer, K.; Wuttke, M.; Jockusch, H.: YAC contigs of the Rab1 and wobbler (wr) spinal muscular atrophy gene region on proximal mouse chromosome 11 and of the homologous region on human chromosome 2p. Genomics 32: 447-454, 1996. PubMed ID: 8838809 3. Zahraoui, A.; Touchot, N.; Chardin, P.;

Tavitian, A.: The human Rab genes encode a family of GTP-binding proteins related to yeast YPT1 and SEC4 products involved in secretion. J. Biol. Chem. 264: 12399-12401, 1989.

Further studies establishing the function and utilities of RAB1A are found in John Hopkins OMIM database record ID 179508, and in references numbered 1303-1305 listed hereinbelow.

Referring now to RAB1A BINDING SITE. (RAB1A) is a target gene of GAM26, corresponding to GAM26-TARGET GENE of FIG. 26A. RAB1A BINDING SITE is a binding site found in an untranslated region of RAB1A, corresponding to BINDING SITE of FIG. 26A. FIG. 26D illustrates the complementarity of the nucleotide sequence of RAB1A BINDING SITE, designated SEQ ID:330388, to the nucleotide sequence of GAM26 RNA of FIG. 26A, designated SEQ ID:20604.

An additional function of GAM26 is therefore inhibition of (RAB1A), a gene which encodes a protein that is involved in vesicle transport. Accordingly, utilities of GAM26 include diagnosis and treatment of the abovementioned diseases and clinical conditions. The function and utilities of RAB1A have been established by previous studies, as described hereinabove with reference to FIG. 26D.

Referring now to RAB1A BINDING SITE. (RAB1A) is a target gene of GAM26, corresponding to GAM26-TARGET GENE of FIG. 26. RAB1A BINDING SITE is a binding site found in an untranslated region of RAB1A, corresponding to BINDING SITE of FIG. 26A. FIG. 26D illustrates the complementarity of the nucleotide sequence of RAB1A BINDING SITE, designated SEQ ID:330410, to the nucleotide sequence of GAM26 RNA of FIG. 26A, designated SEQ ID:20604.

A further function of GAM26 is therefore inhibition of (RAB1A), a gene which encodes a protein that is involved in vesicle transport. Accordingly, utilities of GAM26 include diagnosis and treatment of the abovementioned diseases and clinical conditions. The function and utilities of RAB1A have been established by previous studies, as described hereinabove with reference to FIG. 26D.

Reference is now made to RAB33A BINDING SITE. RAB33A, member RAS oncogene family (RAB33A) is a target gene of GAM26, corresponding to GAM26-TARGET GENE of FIG. 26A. RAB33A BINDING SITE is a binding site found in an untranslated region of RAB33A, corresponding to BINDING SITE of FIG. 26A. FIG. 26D illustrates the complementarity of the nucleotide sequence of RAB33A BINDING SITE, designated SEQ ID:330765, to the nucleotide sequence of GAM26 RNA of FIG. 26A, designated SEQ ID:20604.

Yet a further function of GAM26 is therefore inhibition of RAB33A, member RAS oncogene family (RAB33A), a gene which encodes a protein that is an GTP-binding protein. Accordingly, utilities of GAM26 include diagnosis and treatment of the abovementioned diseases and clinical conditions.

The function of RAB33A has been established by previous studies. Small GTP-binding proteins re involved in many cellular functions, including signal transduction, vesicular transport, and control of cytoskeleton and chromatin structure. These proteins all contain conserved regions, termed G1 through G5, that are involved in GTP/GDP binding and GTPase activity. By RT-PCR analysis using degenerate primers from conserved regions of small GTP-binding proteins and screening a Jurkat T-lymphocyte cDNA library, Koda and Kakinuma (1993) isolated a cDNA encoding RAB33A, which they called S10. The deduced 237-amino acid RAB33A protein belongs to the RAB subfamily of small GTPases (see RAB1; 179508), other members of which are involved in vesicular transport. Northern blot analysis showed that expression of RAB33A is restricted to lymphoid and monocytic lineage.

Full details of the abovementioned studies are described in the following publications, the disclosure of which are hereby incorporated by reference:

Koda, T.; Kakinuma, M.: Molecular cloning of a cDNA encoding a novel small GTP-binding protein. FEBS Lett. 328: 21-24, 1993. PubMed ID: 7688322 3. Zheng, J. Y.; Koda, T.; Arimura, Y.; Kishi, M.; Kakinuma, M.: Structure and expression of the mouse S10 gene. Biochim. Biophys. Acta 1351: 47-50, 1997.

Further studies establishing the function and utilities of RAB33A are found in John Hopkins OMIM database record ID 300333, and in references numbered 1306-1308 listed hereinbelow.

Reference is now made to RAD21 BINDING SITE. RAD21 (*S. pombe*) homolog (RAD21) is a target gene of GAM26, corresponding to GAM26-TARGET GENE of FIG. 26A. RAD21 BINDING SITE is a binding site found in an untranslated region of RAD21, corresponding to BINDING SITE of FIG. 26A. FIG. 26D illustrates the complementarity of the nucleotide sequence of RAD21 BINDING SITE, designated SEQ ID:333078, to the nucleotide sequence of GAM26 RNA of FIG. 26A, designated SEQ ID:20604.

Another function of GAM26 is therefore inhibition of RAD21 (*S. pombe*) homolog (RAD21), a gene which encodes a protein that may act in double strand break repair. Accordingly, utilities of GAM26 include diagnosis and treatment of the abovementioned diseases and clinical conditions.

The function of RAD21 has been established by previous studies. Eukaryotic sister chromatids remain connected from the time of synthesis until they are separated in anaphase. This cohesion depends on a complex of proteins known as cohesins. In vertebrates, unlike in yeast, the cohesins dissociate from chromosome arms earlier in M phase, during prophase. Small amounts of cohesin remain near the centromere until metaphase, with complete removal at the beginning of anaphase. Cohesin complexes contain SMC1 (300040), SMC3 (CSPG6; 60602), SCC1 (RAD21), and either SA1 (STAG1; 604358) or SA2 (STAG2; 604359). The complexes, in turn, interact with PDS5, a protein implicated in chromosome cohesion, condensation, and recombination in yeast (Sumara et al., 2000). By sequencing cDNAs randomly selected from a cDNA library derived from a human immature myeloid cell line, Nomura et al. (1994) identified a cDNA encoding a homolog of *S. pombe* Rad21 that they termed KIAA0078. The deduced KIAA0078 protein has 631 amino acids. Northern blot analysis detected equivalent expression of KIAA0078 in all tissues tested.

Full details of the abovementioned studies are described in the following publications, the disclosure of which are hereby incorporated by reference:

Sumara, I.; Vorlaufer, E.; Gieffers, C.; Peters, B. H.; Peters, J. -M.: Characterization of vertebrate cohesin complexes and their regulation in prophase. J. Cell Biol. 151: 749-761, 2000. PubMed ID: 11076961 5. Nomura, N.; Nagase, T.; Miyajima, N.; Sazuka, T.; Tanaka, A.; Sato, S.; Seki, N.; Kawarabayasi, Y.; Ishikawa, K.; Tabata, S.: Prediction of the coding sequences of unidentified human genes. II. The coding sequences of 40 new genes (KIAA0041-KIAA0080) deduced by analysis of cDNA clones from human cell line KG-1. DNA Res. 1: 223-229, 1994.

Further studies establishing the function and utilities of RAD21 are found in John Hopkins OMIM database record ID 606462, and in references numbered 1309-1315 listed hereinbelow.

Reference is now made to RASGRP1 BINDING SITE. RAS guanyl releasing protein 1 (calcium and DAG-regulated) (RASGRP1) is a target gene of GAM26, corresponding to GAM26-TARGET GENE of FIG. 26A. RASGRP1 BINDING SITE is a binding site found in an untranslated region of RASGRP1, corresponding to BINDING SITE of FIG. 26A. FIG. 26D illustrates the complementarity of the nucleotide sequence of RASGRP1 BINDING SITE, designated SEQ ID:336440, to the nucleotide sequence of GAM26 RNA of FIG. 26A, designated SEQ ID:20604.

Yet another function of GAM26 is therefore inhibition of RAS guanyl releasing protein 1 (calcium and DAG-regulated) (RASGRP1), a gene which encodes a protein that is a RAS guanyl releasing protein. Accordingly, utilities of GAM26 include diagnosis and treatment of the abovementioned diseases and clinical conditions.

The function of RASGRP1 has been established by previous studies. The basal ganglia are implicated in the central control of movement and in forms of procedural learning related to habit formation. The basal ganglia have a unique double-inhibitory pathway design combined with abundant expression of neuromodulators in striatal neurons. Genes with differentially high expression in the striatum include genes encoding proteins with signaling functions, such as adenylate cyclase-5 (ADCY5; 600293). In a search for striatum-enriched transcripts by a differential display method, Kawasaki et al. (1998) found a family of genes characterized by the presence of a Ras superfamily guanine nucleotide exchange factor (GEF) domain. Kawasaki et al. (1998) characterized the calcium- and diacylglycerol (DAG)-regulated GEFI. They showed that the calcium- and DAG-regulated GEFII, which was cloned by Ebinu et al. (1998), exhibited a different brain expression pattern. Bottorff et al. (1999) proposed that the Ras activator GEFII represented a 5-prime and 3-prime truncated version of a larger normal transcript that encodes a predicted 90-kD protein, which they called RAS guanyl nucleotide-releasing protein (RASGRP). Bottorff et al. (1999) studied the structure of the mouse and human sequences and confirmed their conclusions about the nature of the 5-prime truncation. They localized the human RASGRP1 gene to 15q15 by in situ hybridization, and positioned the mouse gene on chromosome 2 near thrombospondin by linkage analysis.

Full details of the abovementioned studies are described in the following publications, the disclosure of which are hereby incorporated by reference:

Further studies establishing the function and utilities of RASGRP1 are found in John Hopkins OMIM database record ID 603962, and in references numbered 1316-1318 listed hereinbelow.

Reference is now made to LAF4 BINDING SITE. Lymphoid nuclear protein related to AF4 (LAF4) is a target gene of GAM26, corresponding to GAM26-TARGET GENE of FIG. 26A. LAF4 BINDING SITE is a binding site found in an untranslated region of LAF4, corresponding to BINDING SITE of FIG. 26A. FIG. 26D illustrates the complementarity of the nucleotide sequence of LAF4 BINDING SITE, designated SEQ ID:338574, to the nucleotide sequence of GAM26 RNA of FIG. 26A, designated SEQ ID:20604.

An additional function of GAM26 is therefore inhibition of lymphoid nuclear protein related to AF4 (LAF4), a gene which encodes a protein that may function in lymphoid development and oncogenesis, and is associated with leukemias. Accordingly, utilities of GAM26 include diagnosis and treatment of the abovementioned diseases and clinical conditions.

The function of LAF4 has been established by previous studies. The translocation t(4;11)(q21;q23) is present in approximately 50% of children under 1 year of age suffering from acute lymphoblastic leukemia (ALL). Lymphoid nuclear protein related to AF4 (LAF4) is related to MLLT2 (159557), also referred to as AF4, which is the gene that is fused to the MLL gene (159555), also termed ALL1, HRX, and HTRX, in t(4;11)(q21;q23). Ma and Staudt (1996) isolated a human cDNA encoding LAF4 from a subtracted cDNA library enriched for genes expressed in the Raji Burkitt's lymphoma cell line and not in the K562 erythroleukemia cell line. LAF4 is a 1,227-amino acid protein with a mass of 135 kD in B-cell lines. It is similar to MLLT2 throughout its length, with the greatest similarity in the N-terminal and C-terminal regions. LAF4 is a tissue-restricted nuclear transcriptional activator that is preferentially expressed in lymphoid tissue. Northern blot analysis detected a major 8.5-kb transcript in lymphoid cell lines. By interspecific backcross lysis, Liao et al. (1996) determined that the mouse Laf4 gene is located on chromosome 1. By fluorescence in situ hybridization, they assigned the human LAF4 gene to 2q11.2-q12. Liao et al. (1996) stated that the isolation of LAF4 has defined a highly conserved LAF4/MLLT2 gene family of nuclear transcription factors that may function in lymphoid development and oncogenesis.

Full details of the abovementioned studies are described in the following publications, the disclosure of which are hereby incorporated by reference:
Liao, X.; Ma, C.; Trask, B.; Massa, H.; Gilbert, D. J.; Staudt, L. M.; Jenkins, N. A.; Copeland, N. G.: LAF4 maps to mouse chromosome 1 and human chromosome 2q11.2-q12. Mammalian Genome 7: 467-468, 1996. PubMed ID: 8662235 2. Ma, C.; Staudt, L. M.: LAF-4 encodes a lymphoid nuclear protein with transactivation potential that is homologous to AF-4, the gene fused to MLL in t(4;11) leukemias. Blood 87: 734-745, 1996.

Further studies establishing the function and utilities of LAF4 are found in John Hopkins OMIM database record ID 601464, and in references numbered 1319-1320 listed hereinbelow.

Reference is now made to RECK BINDING SITE. Reversion-inducing-cysteine-rich protein with kazal motifs (RECK) is a target gene of GAM26, corresponding to GAM26-TARGET GENE of FIG. 26A. RECK BINDING SITE is a binding site found in an untranslated region of RECK, corresponding to BINDING SITE of FIG. 26A. FIG. 26D illustrates the complementarity of the nucleotide sequence of RECK BINDING SITE, designated SEQ ID:338574, to the nucleotide sequence of GAM26 RNA of FIG. 26A, designated SEQ ID:20604.

A further function of GAM26 is therefore inhibition of reversion-inducing-cysteine-rich protein with kazal motifs (RECK), a gene which encodes a protein that plays a role in regulation of cancer progression and tumor angiogenesis and is associated with cancerous tumors. Accordingly, utilities of GAM26 include diagnosis and treatment of the abovementioned diseases and clinical conditions.

The function of RECK has been established by previous studies. Transformed malignant cell lines frequently lose a flat morphology and acquire a round morphology. Genes that induce flat reversion may be useful in the control of cancer. By screening a fibroblast expression library for reversion inducing cDNAs, Takahashi et al. (1998) isolated a cDNA encoding RECK (reversion-inducing, cysteine-rich protein with Kazal motifs). Sequence analysis predicted that the 971-amino acid RECK protein, which shares 93% amino acid identity with mouse Reck, is 9% cysteine and contains an N-terminal signal sequence; 5 putative cysteine knot motifs; 5 potential N-glycosylation sites; 3 central serine protease inhibitor domains with either complete or incomplete Kazal-type, 4-cys motifs; 2 regions with weak homology to EGF-like repeats; and a C-terminal hydrophobic glycosylphosphatidylinositol-anchoring signal. Immunoblot analysis showed that RECK is expressed as a 110-kD protein that is reduced to approximately 100 kD after deglycosylation. Northern blot analysis detected a 4.6-kb RECK transcript in a wide variety of tissues and normal cell lines, but no expression was detected in tumor cell lines. Restoration of RECK expression in tumor cell lines did not affect growth but did significantly suppress matrix invasion and metastatic activity. SDS-PAGE and gelatin zymography analysis demonstrated that due to a posttranscriptional event(s), secretion of MMP9 (120361), a key enzyme in tumor invasion and metastasis, is decreased in cells expressing RECK. An RECK mutant lack in the C-terminal 23 residues retained the ability to suppress tumor cell invasion and MMP9 proteolytic activity but lost the ability to inhibit MMP9 release.

Animal model experiments lend further support to the function of RECK. Oh et al. (2001) showed that in addition to MMP9, RECK also regulates MMP2 (120360) and MT1-MMP (MMP14; 600754), which are known to be involved in cancer progression. Mice lacking a functional Reck gene died around embryonic day 10.5 with defects in collagen fibrils, the basal lamina, and vascular development; this phenotype could be partially suppressed by Mmp2 null mutation. Vascular sprouting was dramatically suppressed in tumors derived from Reck-expressing fibrosarcoma cells grown in nude mice. These results supported a role for RECK in the regulation of MMP2 in vivo and implicated RECK downregulation in tumor angiogenesis.

It is appreciated that the abovementioned anima model for RECK is acknowledged by those skilled in the art as a scientifically valid animal model, as can be further appreciated from the publications sited hereinbelow.

Full details of the abovementioned studies are described in the following publications, the disclosure of which are hereby incorporated by reference:
Takahashi, C.; Sheng, Z.; Horan, T. P.; Kitayama, H.; Maki, M.; Hitomi, K.; Kitaura, Y.; Takai, S.; Sasahara, R. M.; Horimoto, A.; Ikawa, Y.; Ratzkin, B. J.; Arakawa, T.; Noda, M.: Regulation of matrix metalloproteinase-9 and inhibition of tumor invasion by the membrane-anchored glycoprotein RECK. Proc. Nat. Acad. Sci. 95: 13221-13226, 1998. PubMed ID: 9789069 1. Oh, J.; Takahashi, R.; Kondo, S.; Mizoguchi, A.; Adachi, E.; Sasahara, R. M.; Nishimura, S.; Imamura, Y.; Kitayama, H.; Alexander, D. B.; Ide, C.; Horan, T. P.; Arakawa, T.; Yoshida, H.; Nishikawa, S.; Itoh, Y.; Seiki, M.; Itohara, S.; Takahashi, C.; Noda, M.: The membrane-anchored MMP inhibitor RECK is a key regulator of extracellular matrix integrity and angiogenesis. Cell 107: 789-800, 2001.

Further studies establishing the function and utilities of RECK are found in John Hopkins OMIM database record ID 605227, and in references numbered 1321-1322 listed hereinbelow.

Referring now to RECK BINDING SITE. Reversion-inducing-cysteine-rich protein with kazal motifs (RECK) is a target gene of GAM26, corresponding to GAM26-TARGET GENE of FIG. 26A. RECK BINDING SITE is a binding site found in an untranslated region of RECK, corresponding to BINDING SITE of FIG. 26A. FIG. 26D illustrates the complementarity of the nucleotide sequence of RECK BINDING SITE, designated SEQ ID:338574, to the nucleotide sequence of GAM26 RNA of FIG. 26A, designated SEQ ID:20604.

Yet a further function of GAM26 is therefore inhibition of reversion-inducing-cysteine-rich protein with kazal motifs (RECK), a gene which encodes a protein that plays a role in regulation of cancer progression and tumor angiogenesis and is associated with cancerous tumors. Accordingly, utilities of GAM26 include diagnosis and treatment of the abovementioned diseases and clinical conditions. The function and utilities of RECK have been established by previous studies, as described hereinabove with reference to FIG. 26D.

Referring now to RECK BINDING SITE. Reversion-inducing-cysteine-rich protein with kazal motifs (RECK) is a target gene of GAM26, corresponding to GAM26-TARGET GENE of FIG. 26A. RECK BINDING SITE is a binding site found in an untranslated region of RECK, corresponding to BINDING SITE of FIG. 26A. FIG. 26D illustrates the complementarity of the nucleotide sequence of RECK BINDING SITE, designated SEQ ID:338585, to the nucleotide sequence of GAM26 RNA of FIG. 26A, designated SEQ ID:20604.

Another function of GAM26 is therefore inhibition of reversion-inducing-cysteine-rich protein with kazal motifs (RECK), a gene which encodes a protein that plays a role in regulation of cancer progression and tumor angiogenesis, and is associated with cancerous tumors. Accordingly, utilities of GAM26 include diagnosis and treatment of the abovementioned diseases and clinical conditions. The function and utilities of RECK have been established by previous studies, as described hereinabove with reference to FIG. 26D.

Reference is now made to RENT1 BINDING SITE. Regulator of nonsense transcripts 1 (RENT1) is a target gene of GAM26, corresponding to GAM26-TARGET GENE of FIG. 26A. RENT1 BINDING SITE is a binding site found in an untranslated region of RENT1, corresponding to BINDING SITE of FIG. 26A. FIG. 26D illustrates the complementarity of the nucleotide sequence of RENT1 BINDING SITE, designated SEQ ID:339175, to the nucleotide sequence of GAM26 RNA of FIG. 26A, designated SEQ ID:20604.

Yet another function of GAM26 is therefore inhibition of regulator of nonsense transcripts 1 (RENT1), a gene which encodes a protein that eliminates the production of nonsense-containing RNAs in mammalian cells. Accordingly, utilities of GAM26 include diagnosis and treatment of the abovementioned diseases and clinical conditions.

The function of RENT1 has been established by previous studies. Sun et al. (1998) provided evidence for a factor that functions to eliminate production of nonsense-containing RNAs in mammalian cells. They identified the factor, variously referred to as RENT1 and HUPF1, by isolating cDNA for a human homolog of S. cerevisiae Upf1p, which is a group I RNA helicase that functions in the nonsense-mediated decay of mRNA in yeast. Using monkey COS cells and human HeLa cells, Sun et al. (1998) demonstrated that expression of human Upf1 protein harboring an arginine-to-cysteine mutation at residue 844 within the RNA helicase domain acts in a dominant-negative fashion to abrogate the decay of nonsense-containing mRNA that takes place in association with nuclei or in the cytoplasm. These findings provided evidence that nonsense-mediated mRNA decay is related mechanistically in yeast and in mammalian cells, regardless of the cellular site of decay.

Animal model experiments lend further support to the function of RENT1. Medghalchi et al. (2001) explored the consequences of loss of NMRD function in vertebrates through targeted disruption of the Rent1 gene, which encodes a mammalian ortholog of Upf1p, in murine embryonic stem cells. Mice heterozygous for the targeted allele showed no apparent phenotypic abnormalities but homozygosity was never observed, demonstrating that Rent1 is essential for embryonic ability. Homozygous targeted embryos showed complete loss of NMRD and were viable in the preimplantation period, but resorbed shortly after implantation. Furthermore, Rent1 −/− blastocysts isolated at 3.5 days postcoitum underwent apoptosis in culture following a brief phase of cellular expansion. The authors hypothesized that NMRD is essential for mammalian cellular viability and supports a critical role for the pathway in the regulated expression of selected physiologic transcripts.

It is appreciated that the abovementioned animal model for RENT1 is acknowledged by those skilled in the art as a scientifically valid animal model, as can be further appreciated from the publications sited hereinbelow.

Full details of the abovementioned studies are described in the following publications, the disclosure of which are hereby incorporated by reference:

Sun, X.; Perlick, H. A.; Dietz, H. C.; Maquat, L. E.: A mutated human homologue to yeast Upf1 protein has a dominant-negative effect on the decay of nonsense-containing mRNAs in mammalian cells. Proc. Nat. Acad. Sci. 95: 10009-10014, 1998. PubMed ID: 9707591 2. Medghalchi, S. M.; Frischmeyer, P. A.; Mendell, J. T.; Kelly, A. G.; Lawler, A. M.; Dietz, H. C.: Rent1, a trans-effector of nonsense-mediated mRNA decay, is essential for mammalian embryonic viability. Hum. Molec. Genet. 10: 99-105, 2001.

Further studies establishing the function and utilities of RENT1 are found in John Hopkins OMIM database record ID 601430, and in references numbered 1323-1328 listed hereinbelow.

Referring now to REPS2 BINDING SITE. RALBP1 associated Eps domain containing 2 (REPS2) is a target gene of GAM26, corresponding to GAM26-TARGET GENE of FIG. 26A. REPS2 BINDING SITE is a binding site found in an untranslated region of REPS2, corresponding to BINDING SITE of FIG. 26A. FIG. 26D illustrates the complementarity of the nucleotide sequence of REPS2 BINDING SITE, designated SEQ ID:339240, to the nucleotide sequence of GAM26 RNA of FIG. 26A, designated SEQ ID:20604.

An additional function of GAM26 is therefore inhibition of RALBP1 associated Eps domain containing 2 (REPS2), a gene which encodes a protein that interacts with the active form of RAS with adaptor protein GRB2 and binds calcium. Accordingly, utilities of GAM26 include diagnosis and treatment of the abovementioned diseases and clinical conditions. The function and utilities of REPS2 have been established by previous studies, as described hereinabove with reference to FIG. 26D.

Referring now to REPS2 BINDING SITE. RALBP1 associated Eps domain containing 2 (REPS2) is a target gene of GAM26, corresponding to GAM26-TARGET GENE of FIG. 26A. REPS2 BINDING SITE is a binding site found in an untranslated region of REPS2, corresponding to BINDING SITE of FIG. 26A. FIG. 26D illustrates the complementarity of the nucleotide sequence of REPS2 BINDING SITE, designated SEQ ID:339246, to the nucleotide sequence of GAM26 RNA of FIG. 26A, designated SEQ ID:20604.

A further function of GAM26 is therefore inhibition of RALBP1 associated Eps domain containing 2 (REPS2), a gene which encodes a protein that interacts with the active form of RAS with adaptor protein GRB2 and binds calcium. Accordingly, utilities of GAM26 include diagnosis and treatment of the abovementioned diseases and clinical conditions. The function and utilities of REPS2 have been established by previous studies, as described hereinabove with reference to FIG. 26D.

Referring now to REPS2 BINDING SITE. RALBP1 associated Eps domain containing 2 (REPS2) is a target gene of GAM26, corresponding to GAM26-TARGET GENE of FIG. 26A. REPS2 BINDING SITE is a binding site found in an untranslated region of REPS2, corresponding to BINDING SITE of FIG. 26A. FIG. 26D illustrates the complementarity of the nucleotide sequence of REPS2 BINDING SITE, designated SEQ ID:339265, to the nucleotide sequence of GAM26 RNA of FIG. 26A, designated SEQ ID:20604.

Yet a further function of GAM26 is therefore inhibition of RALBP1 associated Eps domain containing 2 (REPS2), a gene which encodes a protein that interacts with the active form of RAS with adaptor protein GRB2 and binds calcium. Accordingly, utilities of GAM26 include diagnosis and treatment of the abovementioned diseases and clinical conditions. The function and utilities of REPS2 have been established by previous studies, as described hereinabove with reference to FIG. 26D.

Referring now to REPS2 BINDING SITE. RALBP1 associated Eps domain containing 2 (REPS2) is a target gene of GAM26, corresponding to GAM26-TARGET GENE of FIG. 26A. REPS2 BINDING SITE is a binding site found in an untranslated region of REPS2, corresponding to BINDING SITE of FIG. 26A. FIG. 26D illustrates the complementarity of the nucleotide sequence of REPS2 BINDING SITE, designated SEQ ID:339278, to the nucleotide sequence of GAM26 RNA of FIG. 26A, designated SEQ ID:20604.

Another function of GAM26 is therefore inhibition of RALBP1 associated Eps domain containing 2 (REPS2), a gene which encodes a protein that interacts with the active form of RAS with adaptor protein GRB2 and binds calcium. Accordingly, utilities of GAM26 include diagnosis and treatment of the abovementioned diseases and clinical conditions. The function and utilities of REPS2 have been established by previous studies, as described hereinabove with reference to FIG. 26D.

Referring now to REPS2 BINDING SITE. RALBP1 associated Eps domain containing 2 (REPS2) is a target gene of GAM26, corresponding to GAM26-TARGET GENE of FIG. 26A. REPS2 BINDING SITE is a binding site found in an untranslated region of REPS2, corresponding to BINDING SITE of FIG. 26A. FIG. 26D illustrates the complementarity of the nucleotide sequence of REPS2 BINDING SITE, designated SEQ ID:339279, to the nucleotide sequence of GAM26 RNA of FIG. 26A, designated SEQ ID:20604.

Yet another function of GAM26 is therefore inhibition of RALBP1 associated Eps domain containing 2 (REPS2), a gene which encodes a protein that interacts with the active form of RAS with adaptor protein GRB2 and binds calcium. Accordingly, utilities of GAM26 include diagnosis and treatment of the abovementioned diseases and clinical conditions. The function and utilities of REPS2 have been established by previous studies, as described hereinabove with reference to FIG. 26D.

Reference is now made to REV3L BINDING SITE. REV3 (yeast homolog)-like, catalytic subunit of DNA polymerase zeta (REV3L) is a target gene of GAM26, corresponding to GAM26-TARGET GENE of FIG. 26A. REV3L BINDING SITE is a binding site found in an untranslated region of REV3L, corresponding to BINDING SITE of FIG. 26A. FIG. 26D illustrates the complementarity of the nucleotide sequence of REV3L BINDING SITE, designated SEQ ID:339991, to the nucleotide sequence of GAM26 RNA of FIG. 26A, designated SEQ ID:20604.

An additional function of GAM26 is therefore inhibition of REV3 (yeast homolog)-like, catalytic subunit of DNA polymerase zeta (REV3L), a gene which encodes an enzyme that is a catalytic subunit of DNA polymerase zeta and acts in translation replication and mutagenesis. Accordingly, utilities of GAM26 include diagnosis and treatment of the abovementioned diseases and clinical conditions.

The function of REV3L has been established by previous studies. To get a better understanding of mutagenic mechanisms in humans, Gibbs et al. (1998) cloned and sequenced the human homolog of the *Saccharomyces cerevisiae* REV3 gene. The yeast gene encodes the catalytic subunit DNA polymerase zeta, a nonessential enzyme that is thought to carry out translation replication and is responsible for virtually all DNA damage-induced mutagenisis and the majority of spontaneous mutagenesis. The human gene encodes an expected protein of 3,130 residues, about twice the size of the yeast protein, which has 1,504 amino acids. The 2 proteins are 29% identical in an amino-terminal region of approximately 340 residues, 39% identical in a carboxy-terminal region of approximately 850 residues, and 29% identical in a 55-residue region in the middle of the 2 genes. The sequence of the expected protein strongly predicted that it is the catalytic subunit of DNA polymerase of the polymerase-zeta type; the carboxy-terminal domain possesses, in the right order, the 6 motifs characteristic of eukaryotic DNA polymerases, most closely resembles yeast polymerase-zeta among all polymerases in the GenBank database, and is different from the human alpha (POLA; 312040), delta (POLD1; 174761), and epsilon (POLE; 174762) enzymes. Human cells expressing high levels of an REV3 antisense RNA fragment grow normally, but show little or no UV-induced mutagenesis and re slightly more sensitive to killing by UV. The human gene therefore appears to carry out a function similar to that of its yeast counterpart. Xiao et al. (1998) identified human cDNA clones from 3 different libraries whose deduced amino acid sequences bore remarkable homology to yeast REV3. By in situ hybridization, they mapped the human REV3 gene to 1p33-p32. The gene encodes an mRNA of more than 10 kb. Its expression varies in different tissues and appeared to be elevated in some but not all of the tumor cell lines examined. In a study of genes involved in tumor suppression from 6q21, Morelli et al. (1998) identified the same sequence as that reported by Gibbs et al. (1998). The REV3L gene contains 33 exons (3 noncoding at the 5-prime end) and spans approximately 200 kb of genomic DNA. The chromosome 6 assignment is the more likely (AFS).

Full details of the abovementioned studies are described in the following publications, the disclosure of which are hereby incorporated by reference:

Gibbs, P. E. M.; McGregor, W. G.; Maher, V. M.; Nisson. P.; Lawrence, C. W.: A human homolog of the *Saccharomyces cerevisiae* REV3 gene, which encodes the catalytic subunit of DNA polymerase zeta. Proc. Nat. Acad. Sci. 195: 6876-6880, 1998. PubMed ID: 9618506 3. Xiao, W.; Lechler, T.; Chow, B. L.; Fontanie, T.; Agustus, M.;

Carter, K. C.; Wei, Y. -F.: Identification, chromosomal mapping and tissue-specific expression of hREV3 encoding a putative human DNA polymerase zeta. Carcinogenesis 19: 945-949, 1998.

Further studies establishing the function and utilities of REV3L are found in John Hopkins OMIM database record ID 602776, and in references numbered 1329-1331 listed hereinbelow.

Referring now to RGS19IP1 BINDING SITE. (RGS19IP1) is a target gene of GAM26, corresponding to GAM26-TARGET GENE of FIG. 26A. RGS19IP1 BINDING SITE is a binding site found in an untranslated region of RGS19IP1, corresponding to BINDING SITE of FIG. 26A. FIG. 26D illustrates the complementarity of the nucleotide sequence of RGS19IP1 BINDING SITE, designated SEQ ID:341338, to the nucleotide sequence of GAM26 RNA of FIG. 26A, designated SEQ ID:20604.

A further function of GAM26 is therefore inhibition of (RGS19IP1), a gene which encodes a protein that is involved in g protein-linked signaling. Accordingly, utilities of GAM26 include diagnosis and treatment of the abovementioned diseases and clinical conditions. The function and utilities of RGS19IP1 have been established by previous studies, as described hereinabove with reference to FIG. 26D.

Referring now to RGS19IP1 BINDING SITE. (RGS19IP1) is a target gene of GAM26, corresponding to GAM26-TARGET GENE of FIG. 26A. RGS19IP1 BINDING SITE is a binding site found in an untranslated region of RGS19IP1, corresponding to BINDING SITE of FIG. 26A. FIG. 26D illustrates the complementarity of the nucleotide sequence of RGS19IP1 BINDING SITE, designed SEQ ID:341352, to the nucleotide sequence of GAM26 RNA of FIG. 26A, designated SEQ ID:20604.

Yet a further function of GAM26 is therefore inhibition of (RGS19IP1), a gene which encodes a protein that is involved in g protein-linked signaling. Accordingly, utilities of GAM26 include diagnosis and treatment the abovementioned diseases and clinical conditions. The function and utilities of RGS19IP1 have been established by previous studies, as described hereinabove with reference to FIG. 26D.

Reference is now made to RNF14 BINDING SITE. Ring finger protein 14 (RNF14) is a target gene of GAM26, corresponding to GAM26-TARGET GENE of FIG. 26A. RNF14 BINDING SITE is a binding site found in an untranslated region of RNF14, corresponding to BINDING SITE of FIG. 26A. FIG. 26D illustrates the complementarity of the nucleotide sequence of RNF14 BINDING SITE, designated SEQ ID:342895, to the nucleotide sequence of GAM26 RNA of FIG. 26A, designated SEQ ID:20604.

Another function of GAM26 is therefore inhibition of ring finger protein 14 (RNF14), a gene which encodes a transcription factor that associates with the androgen receptor (AR); functions as a transcriptional coactivator. Accordingly, utilities of GAM26 include diagnosis and treatment of the abovementioned diseases and clinical conditions.

The function of RNF14 has been established by previous studies. The RING finger motif is a unique zinc-chelating domain involved in mediating protein-DNA and protein-protein interactions. Using the sequence of the partial cDNA clone HFB30 isolated by Ueki et al. (1998) to screen a human fetal brain cDNA library, Ueki et al. (1999) cloned the full-length cDNA, which encoded a novel ring finger protein, RNF14. The deduced 474-amino acid protein has a calculated molecular mass of approximately 53 kD. RT-PCR analysis revealed ubiquitous expression of RNF14 in a wide variety of human tissues. Kang et al. (1999) independently cloned RNF14, which they called ARA54 (androgen receptor-associated protein-54), by a yeast 2-hybrid screen of a prostate cDNA library. Northern blot analysis detected a major 3-kb transcript, with highest expression in testis, followed by thymus, spleen, colon, prostate, and uterus. Low expression was detected in small intestine and blood leukocytes. The RNF14 transcript was also strongly detected in 2 other prostate cell lines. A second transcript of 2 kb was detected in testis only. Kang et al. (1999) demonstrated that RNF14 can function as a coactivator for androgen-dependent transcription on both wildtype and mutant androgen receptor (313700). They also showed that in the presence of a certain amount of 17-beta-estradiol or hydroxyflutamide, the transcriptional activity of a specific AR mutant was significantly enhanced, whereas that of wildtype and another AR mutant was not. The authors suggested that both RNF14 and the positions of the AR mutation might contribute to the specificity of AR-mediated transactivation. Ueki et al. (1999) determined that the RNF14 gene contains 9 exons and spans approximately 20 kb of genomic DNA. By somatic cell hybrid and radiation hybrid analyses, Ueki et al. (1999) mapped the RNF14 gene to chromosome 5q23.3-q31.1.

Full details the abovementioned studies are described in the following publications, the disclosure of which are hereby incorporated by reference:

Ueki, N.; Seki, N.; Yano, K.; Masuho, Y.; Saito T.; Muramatsu, M.: Isolation and characterization of a novel human gene (HFB30) which encodes a protein with a RING finger motif. Biochim. Biophys. Acta 232-236, 1999. PubMed ID: 10320776. Kan, H. -Y.; Yeh, S.; Fujimoto, N.; Chang, C.: Cloning and characterization of human prostate coactivator ARA54, a novel protein that associates with the androgen receptor. J. Biol. Chem. 274: 8570-8576, 1999.

Further studies establishing the function and utilities of RNF14 are found in John Hopkins OMIM database record ID 605675, and in references numbered 1332-1334 listed hereinbelow.

Reference is now made to ROCK2 BINDING SITE. Rho-associated, coiled-coil containing protein kinase 2 (ROCK2) is a target gene of GAM26, corresponding to GAM26-TARGET GENE of FIG. 26A. ROCK2 BINDING SITE is a binding site found in an untranslated region of ROCK2, corresponding to BINDING SITE of FIG. 26A. FIG. 26D illustrates the complementarity of the nucleotide sequence of ROCK2 BINDING SITE, designated SEQ ID:344223, to the nucleotide sequence of GAM26 RNA of FIG. 26A, designated SEQ ID:20604.

Yet another function of GAM26 is therefore inhibition of Rho-associated, coiled-coil containing protein kinase 2 (ROCK2), a gene which encodes an enzyme that regulates cytokinesis, smooth muscle contraction, the formation of actin stress fibers and focal adhesions. Accordingly, utilities of GAM26 include diagnosis and treatment of the abovementioned diseases and clinical conditions.

The function of ROCK2 has been established by previous studies. ROCK2 is a serine/threonine kinase that regulates cytokinesis, smooth muscle contraction, the formation of actin stress fibers and focal adhesions, and the activation of the c-fos (164810) serum response element ROCK2, which is an isozyme of ROCK1 (601702), is a target for the small GTPase Rho (e.g., 165390). Nakamura et al. (2001) studied the role of Rho in the migration of corneal epithelial cells in rabbit. They detected both ROCK1 (601702) and ROCK2 in the corneal epithelium at protein and mRNA levels. They found that exoenzyme C3, a Rho inhibitor, inhibits corneal epithelial migration in a dose-dependent manner and prevents the stimulatory effect of the Rho activator lysophosphatidic acid (LPA). Both cytochalasin B, an inhibitor of actin filament assembly, and ML7, an inhibitor of myosin light chain kinase, also prevent LPA stimulation of epithelial migration. The authors suggested that Rho mediates corneal epithelial migration in response to external stimuli by regulating the organization of the actin cytoskeleton. Rao et al. (2001) investigated the role of Rho kinase in the modulation of aqueous humor outflow facility. The treatment of human trabecular meshwork and canal of Schlemm cells with a Rho kinase-specific inhibitor led to significant but reversible changes in cell shape and decreased actin stress fibers, focal adhesions, and protein phosphotyrosine staining. Based on the Rho kinase inhibitor-induced changes in myosin light chain phosphorylation and actomyosin organization, the authors suggested that cellular relaxation and loss of cell-substratum adhesions in the human trabecular meshwork and canal of Schlemm cells could result in either increased paracellular fluid flow across the canal of Schlemm or altered flow pathway through the juxtacanalicular tissue, thereby lowering resistance to outflow. They suggested Rho kinase as a potential target for the development of drugs to modulate intraocular pressure in glaucoma patients.

Full details of the abovementioned studies are described in the following publications, the disclosure of which are hereby incorporated by reference:

Nakamura, M.; Nagano, T.; Chikama, T.; Nishida, T.: Role of the small GTP-binding protein Rho in epithelial cell migration in the rabbit cornea. Invest. Ophthal. Vis. Sci. 42: 941-947, 2001. PubMed ID:11274070. Rao, P. V.; Deng, P. -F.; Kumar, J.; Epstein, D. L.: Modulation of aqueous humor outflow facility by the Rho kinase-specific inhibitor Y-27632. Invest. Ophthal. Vis. Sci. 42: 1029-1037, 2001.

Further studies establishing the function and utilities of ROCK2 are found in John Hopkins OMIM database record ID 604002, and in references numbered 1335-1338 listed hereinbelow.

Referring now to ROCK2 BINDING SITE. Rho-associated, coiled-coil containing protein kinase 2 (ROCK2) is a target gene of GAM26, corresponding to GAM26-TARGET GENE of FIG. 26A. ROCK2 BINDING SITE is a binding site found in an untranslated region of ROCK2, corresponding to BINDING SITE of FIG. 26A. FIG. 26D illustrates the complementarity of the nucleotide sequence of ROCK2 BINDING SITE, designated SEQ ID:344231, to the nucleotide sequence of GAM26 RNA of FIG. 26A, designated SEQ ID:20604.

An additional function of GAM26 is therefore inhibition of Rh-associated, coiled-coil containing protein kinase 2 (ROCK2), a gene which encodes an enzyme that regulates cytokinesis, smooth muscle contraction, the formation of actin stress fibers and focal adhesions. Accordingly, utilities of GAM26 include diagnosis and treatment of the abovementioned diseases and clinical conditions. The function and utilities of ROCK2 have been established by previous studies, as described hereinabove with reference to FIG. 26D.

Reference is now made to RORA BINDING SITE. RAR-related orphan receptor A (RORA) is a target gene of GAM26, corresponding to GAM26-TARGET GENE of FIG. 26A. RORA BINDING SITE is a binding site found in an untranslated region of RORA, corresponding to BINDING SITE of FIG. 26A. FIG. 26D illustrates the complementarity of the nucleotide sequence of RORA BINDING SITE, designated SEQ ID:344515, to the nucleotide sequence of GAM26 RNA of FIG. 26A, designated SEQ ID:20604.

A further function of GAM26 is therefore inhibition of RAR-related orphan receptor A (RORA), a gene which encodes a receptor that binds DNA as a monomer to hormone response elements (hre) containing a single core motif half-site preceded by a short a-t rich sequences. Accordingly, utilities of GAM26 include diagnosis and treatment of the abovementioned diseases and clinical conditions.

The function of RORA has been established by previous studies. Meyer et al. (2000) showed that the RORA gene and the RORC (602943) gene, but not the RORB gene, are expressed in mesenchymal stem cells derived from bone marrow. Cells undergoing osteogenic differentiation showed increased messenger signal expression. They found that homozygous 'staggerer' mutants have thin long bones compared with heterozygous animals and wildtype littermates and that the bones of sg/sg animals are osteopenic. They concluded that the product of the Rora gene most likely acts by direct modulation of a bone matrix component Animal model experiments lend further support to the function of RORA. The recessive mouse mutation 'staggerer' (sg) is associated with severe cerebellar ataxia due to a cell-autonomous defect in the development of Purkinje cells. These cells are reduced in numbers and show immature morphology, synaptic arrangement, biochemical properties, and gene expression. In addition, sg heterozygotes show accelerated dendritic atrophy and cell loss, suggesting that sg has a role in mature Purkinje cells. Certain functions of the immune system are also affected. Hamilton et al. (1996) mapped sg to a 160-kb interval on mouse chromosome 9 that was found to contain the gene encoding Rora, a member of the nuclear hormone receptor superfamily. Furthermore, sg mice were found to carry a deletion within the Rora gene that prevents translation of the ligand-binding homology domain. Based on these results, they proposed a model in which Rora interacts with the thyroid hormone signaling pathway to induce Purkinje cell maturation. Of the 4 different isoforms of the Rora gene that are generated by a combination of alternative promoter usage and exon splicing and that differ in their DNA-binding properties, Matysiak-Scholze and Nehls (1997) found that isoforms Rora1 and Rora4 are specifically coexpressed in the murine cerebellum and human cerebellum. Thus, at least isoforms of the murine Rora gene are affected by the genomic deletion associated with the sg phenotype. The finding of cerebellum-specific coregulation of Rora1 and Rora4 suggested that distinct sets of target genes regulated by the Rora1 and Rora4 isoforms are required for Purkinje cell development It is appreciated that the abovementioned animal model for RORA is acknowledged by those skilled in the art as a scientifically valid animal model, as can be further appreciated from the publications sited hereinbelow.

Full detail of the abovementioned studies are described in the following publications, the disclosure of which are hereby incorporated by reference:

Meyer, T.; Kneissel, M.; Mariani, J.; Fournier, B.: In vitro and in vivo evidence for orphan nuclear receptor ROR-alpha function in bone metabolism. Proc. Nat. Acad. Sci. 97: 9197-9202, 2000. PubMed ID: 10900268 Matysiak-Scholze, U.; Nehls, M.: The structural integrity of ROR-alpha isoforms is mutated in staggerer mice: cerebellar coexpression of ROR-alpha-1 and ROR-alpha-4. Genomics 43: 78-84, 1997.

Further studies establishing the function and utilities of RORA are found in John Hopkins OMIM record ID 600825, and in references numbered 1339-1348 listed hereinbelow.

Reference is now made to RPS6KA1 BINDING SITE. Ribosomal protein S6 kinase, 90 kD, polypeptide 1 (RPS6KA1) is a target gene of GAM26, corresponding to GAM26-TARGET GENE of FIG. 26A. RPS6KA1 BINDING SITE is a binding site found in an untranslated region of RPS6KA1, corresponding to BINDING SITE of FIG. 26A. FIG. 26D illustrates the complementarity of the nucleotide sequence of RPS6KA1 BINDING SITE, designated SEQ ID:346249, to the nucleotide sequence of GAM26 RNA of FIG. 26A, designated SEQ ID:20604.

Yet a further function of GAM26 is therefore inhibition of ribosomal protein S6 kinase, 90 kD, polypeptide 1 (RPS6KA1), a gene which encodes an enzyme that is an effector of the phosphatidylinositide-3-OH kinase signaling pathway and is associated with type II diabetes mellitus. Accordingly, utilities of GAM26 include diagnosis and treatment of the abovementioned diseases and clinical conditions.

The function of RPS6KA1 has been established by previous studies. Moller et al. (1994) described the cloning and characterization of 3 genes encoding 3 isoforms of ribosomal protein S6 kinase (RSK), which they called HU1 (RPS6KA1), HU2 (RPS6KA2; 601685), and HU3 (RPS6KA3; 300075). The HU1 cDNA (GenBank L07597) encodes a predicted 735-amino acid protein containing 2 distinct consensus ATP-binding site sequences. Northern blot and RNase protection analyses detected an approximately 3.5-kb HU1 transcript in lymphocytes, skeletal muscle, liver, and adipose tissue.

Animal model experiments lend further support to the function of RPS6KA1. Shima et al. (1998) generated mice deficient in S6 kinase-1 by targeted disruption. These mice are viable and fertile, but exhibit a conspicuous reduction in body size during embryogenesis, an effect that was mostly overcome by adulthood. Shima et al. (1998) hypothesized that the weak penetrance of the phenotype may arise from increased expression in S6k1-deficient mice of the highly homologous gene S6K2 (601685). Pende et al. (2000) showed that mice deficient for S6 kinase-1, a known effector of the phosphatidylinositide-3-OH kinase signaling pathway, are hypoinsulinemic and glucose intolerant. Whereas insulin resistance was not observed in isolated muscle, such mice exhibit a sharp reduction in glucose-induced insulin secretion and in pancreatic insulin content. This is not due a lesion in glucose sensing or insulin production, but to a reduction in pancreatic endocrine mass, which is accounted for by a selective decrease in beta-cell size. Pende et al. (2000) concluded that the observed phenotype closely parallels those of preclinical type II diabetes mellitus, in which malnutrition-induced hypoinsulinemia prediposes individuals to glucose intolerance.

It is appreciated that the abovementioned animal model for RPS6KA1 is acknowledged by those skilled in the art as a scientifically valid animal model, as can be further appreciated from the publications sited hereinbelow.

Full details of the abovementioned studies are described in the following publications, the disclosure of which are hereby incorporated by reference:

Moller, D. E.; Xia, C. H.; Tang, W.; Zhu, A. X.; Jakubowski, M.: Human rsk isoforms: cloning and characterization of tissue-specific expression. Am. J. Physiol. 266: C351-C359, 1994.

Further studies establishing the function and utilities of RPS6KA1 are found in John Hopkins OMIM database record ID 601684, and references numbered 1349-1355 listed hereinbelow.

Reference is now made to RRAS BINDING SITE. Related RAS viral (r-ras) oncogene homolog (RRAS) is a target gene of GAM26, corresponding to GAM26-TARGET GENE of FIG. 26A. RRAS BINDING SITE is a binding site found in an untranslated region of RRAS, corresponding to BINDING SITE of FIG. 26A. FIG. 26D illustrates the complementarity of the nucleotide sequence of RRAS BINDING SITE, designated SEQ ID:346568, to the nucleotide sequence of GAM26 RNA of FIG. 26A, designated SEQ ID:20604.

Another function of GAM26 is therefore inhibition of related RAS viral (r-ras) oncogene homolog (RRAS), a gene which encodes an enzyme that is a member of the ras family of GTP binding proteins. Accordingly, utilities of GAM26 include diagnosis and treatment of the abovementioned diseases and clinical conditions.

The function of RRAS has been established by previous studies. Lowe et al. (1987) isolated the human RRAS gene by low-stringency hybridization with a Harvey-ras probe. They found that the predicted 218-amino acid RRAS protein has an amino-terminal extension of 26 residues compared with HRAS p21 (190020) and shares 55% sequence identity with it. The cloned mouse Rras cDNA encode a predicted protein sharing 94.5% sequence identity with the human protein. Lowe et al. (1987) determined that the RRAS gene has at least 6 exons.

Full details of the abovementioned studies are described in the following publications, the disclosure of which are hereby incorporated by reference:

Lowe, D. G.; Capon, D. J.; Delwart, E.; Sakaguchi, A. Y.; Naylor, S. L.; Goeddel, D. V.: Structure of the human and murine R-ras genes, novel genes closely related to ras proto-oncogenes. Cell 48: 137-146, 1987.

Further studies establishing the function and utilities of RRAS are found in John Hopkins OMIM database record ID 165090, and in references numbered 1356 listed hereinbelow.

Reference is now made to RRAS2 BINDING SITE. RELATED RAS VIRAL ONCOGENE HOMOLOG 2 (RRAS2) is a target gene of GAM26, corresponding to GAM26-TARGET GENE of FIG. 26A. RRAS2 BINDING SITE is a binding site found in an untranslated region of RRAS2, corresponding to BINDING SITE of FIG. 26A. FIG. 26D illustrates the complementarity of the nucleotide sequence of RRAS2 BINDING SITE, designated SEQ ID:346598, to the nucleotide sequence of GAM26 RNA of FIG. 26A, designated SEQ ID:20604.

Yet another function of GAM26 is therefore inhibition of RELATED RAS VIRAL ONCOGENE HOMOLOG 2 (RRAS2), a gene which encodes an enzyme that is a member the ras family of GTP binding proteins and is associated with OVARIAN CARCINOMA. Accordingly, utilities of GAM26 include diagnosis and treatment of the abovementioned diseases and clinical conditions.

The function of RRAS2 has been established by previous studies. The TC21 oncogene, a member of the RAS superfamily, was initially cloned from a human teratocarcinoma cDNA library by PCR methods using degenerate oligonucleotides corresponding to the conserved region of the RAS genes (Drivas et al., 1990). Chan et al. (1994) found the same oncogene when they generated an expression cDNA library from an ovarian carcinoma line. They found, furthermore, that a single point mutation substituting glutamine for leucine at position 72 was responsible for activation of transforming properties. While the cDNA clone possessed high transforming activity, the ovarian tumor genomic DNA, which contained the mutated TC21 allele, failed to induce transformed foci. Thus, expression cDNA cloning made it possible identify and isolate a human oncogene that had evaded detection by conventional approaches. The International Radiation Hybrid Mapping Consortium mapped the RRAS2 gene to chromosome 11pter-p15.5 (RH40056).

Full details of the abovementioned studies are described in the following publications, the disclosure of which are hereby incorporated by reference:

Chan, A. M. -L.; Miki, T.; Meyers, K. A.; Aaronson, S. A.: A human oncogene of the RAS superfamily unmasked by expression cDNA cloning. Proc. Nat. Acad. Sci. 91: 7558-7562, 1994.

Further studies establishing the function and utilities of RRAS2 are found in John Hopkins OMIM database record ID 600098, and in references numbered 1357-1358 listed hereinbelow.

Reference is now made to RTN4 BINDING SITE. Reticulon 4 (RTN4) is a target gene of GAM26, corresponding to GAM26-TARGET GENE of FIG. 26A. RTN4 BINDING SITE is a binding site found in an untranslated region of RTN4, corresponding to BINDING SITE of FIG. 26A. FIG. 26D illustrates the complementarity of the nucleotide sequence of RTN4 BINDING SITE, designated SEQ ID:347317, to the nucleotide sequence of GAM26 RNA of FIG. 26A, designated SEQ ID:20604.

An additional function of GAM26 is therefore inhibition of reticulon 4 (RTN4), a gene which encodes a protein that plays a central role in limiting axonal regeneration after central nervous system injury. Accordingly, utilities of GAM26 include diagnosis and treatment of the abovementioned diseases and clinical conditions.

The function of RTN4 has been established by previous studies. NOGO has been identified as a component of the central nervous system myelin that prevents axonal regeneration in the adult vertebrate central nervous system. Analysis of NOGOA has shown that an axon-inhibiting domain of 66 amino acids is expressed at the extracellular surface and at the endoplasmic reticulum lumen of transfected cells and oligodendrocytes. The acidic amino terminus of NOGOA is detected at the cytosolic face of cellular membranes and may contribute to inhibition of axon regeneration at sites of oligodendrocyte injury. Fournier et al. (2001) showed that the extracellular domain of NOGO (NOGO-66) inhibits axonal extension but does not alter nonneuronal cell morphology. In contrast, a multivalent form of the N terminus NOGOA affects the morphology of both neurons and other cell types. Fournier et al. (2001) identified a brain-specific, leucine-rich-repeat protein with high affinity for soluble NOGO-66. Cleavage of the NOGO-66 receptor (605566) and other glycosylphosphatidylinositol-linked proteins from axonal surfaces renders neurons insensitive to NOGO-66. NOGO-66 receptor expression is sufficient to impart NOGO-66 axonal inhibition to unresponsive neurons. Disruption of the interaction between NOGO-66 and its receptor provides the potential for enhanced recovery after human central nervous system injury. GrandPre et al. (2002) identified competitive antagonists of the NOGO receptor derived from amino-terminal peptide fragments of NOGO-66. The NOGO-66(1-40) antagonist peptide blocks NOGO-66 or central nervous system myelin inhibition of axonal outgrowth in vitro, demonstrating that the NOGO receptor mediates a significant portion of axonal outgrowth inhibition by myelin. Intrathecal administration of the amino-terminal antagonist peptide to rats with midthoracic spinal cord hemisection resulted in significant axon outgrowth of the corticospinal tract, a improved functional recovery. Thus, GrandPre et al. (2002) concluded that NOGO-66 and the NOGO receptor have central roles in limiting axonal regeneration after central nervous system injury. Axonal regeneration in the adult central nervous system (CNS) is limited by 2 proteins in myelin, NOGO and myelin-associated glycoprotein (MAG; 159640). The receptor for Nogo (NgR) had been identified as an axonal glycosylphosphatidylinositol (GPI)-anchored protein, whereas the MAG receptor had remained elusive. Liu et al (2002) demonstrated that MAG binds directly, with high affinity, to NgR Cleavage of GPI-linked proteins from axons protects growth cones from MAG-induced collapse, and dominant-negative NgR eliminate MAG inhibition of neurite outgrowth. MAG resistant embryonic neurons were rendered MAG-sensitive by expression of NgR. MAG and NOGO-66 activate NgR independently and serve as redundant NgR ligands that may limit axonal regeneration after CNS injury.

Full details of the abovementioned studies are described in the following publications, the disclosure of which are hereby incorporated by reference:

Fournier, A. E.; GrandPre, T.; Strittmatter, S. M.: Identification of a receptor mediating Nogo-66 inhibition of axonal regeneration. Nature 409: 341-346, 2001. PubMed ID: 11201742 3. GrandPre, T.; Li, S.; Strittmatter, S. M.: Nogo-66 receptor antagonist peptide promotes axonal regeneration. Nature 417: 547-551, 2002.

Further studies establishing the function and utilities RTN4 are found in John Hopkins OMIM database record ID 604475, and in reference numbered 1359-1367 listed hereinbelow.

Referring now to RTN4 BINDING SITE. Reticulon 4 (RTN4) is a target gene of GAM26, corresponding to GAM26-TARGET GENE of FIG. 26A. RTN4 BINDING SITE is a binding site found in an untranslated region of RTN4, corresponding to BINDING SITE of FIG. 26A. FIG. 26D illustrates the complementarity of the nucleotide sequence of RTN4 BINDING SITE, designated SEQ ID:347318, to the nucleotide sequence of GAM26 RNA of FIG. 26A, designated SEQ ID:20604.

A further function of GAM26 is therefore inhibition of reticulon 4 (RTN4), a gene which encodes a protein that plays a central role in limiting axonal regeneration after central nervous system injury. Accordingly, utilities of GAM26 include diagnosis and treatment the abovementioned diseases and clinical conditions. The function and utilities of RTN4 have been established by previous studies, as described hereinabove with reference to FIG. 26D.

Reference is now made to SAS BINDING SITE. Sarcoma amplified sequence (SAS) is a target gene of GAM26, corresponding to GAM26-TARGET GENE of FIG. 26A. SAS BINDING SITE is a binding site found in an untranslated region of SAS, corresponding to BINDING SITE of FIG. 26A. FIG. 26D illustrates the complementarity of the nucleotide sequence of SAS BINDING SITE, designated SEQ ID:349188, to the nucleotide sequence of GAM26 RNA of FIG. 26A, designated SEQ ID:20604.

Yet a further function of GAM26 is therefore inhibition of sarcoma amplified sequence (SAS), a gene which encodes a protein that is a member of the transmembrane 4 superfamily (TM4SF) and may be involved in growth-related cellular processes T. Accordingly, utilities of GAM26 include diagnosis treatment of the abovementioned disease and clinical conditions.

The function of SAS has been established by previous studies. SAS is a member of the transmembrane 4 superfamily, all members of which have 4 hydrophobic domains. This family includes various tumor-associated antigens such as CO-029 (600769), L6 (M3S1; 191155), and ME491 (CD63; 155740), hematopoietic cell antigens such as CD9 (143030), CD53 (151525), CD37 (151523), and TAPA1 (186845), as well as the parasitic trematode surface proteins Sm23 and Sj23. Meltzer et al. (1991) identified and partially cloned a gene that is amplified in human malignant fibrous histiocytoma. They demonstrated that the gene, designated sarcoma amplified sequence, is located on chromosome 12 by hybridization to a rodent/human somatic cell hybrid mapping panel. They further regionalized the assignment to 12q13-q14 by fluorescence in situ hybridization. This chromosomal region is commonly involved in rearrangements in myxoid liposarcoma, benign lipoma, and uterine leiomyoma. Meltzer et al. (1991) identified SAS amplification in 5 of 29 malignant fibrous histiocytoma biopsies, 4 of 12 liposarcoma biopsies, and 1 osteogenic sarcoma cell line. Since amplification of cellular oncogenes occurs frequently in human cancers, identification of amplified genes in tumor cells is a useful approach for understanding genetic alterations. Jankowski et al. (1995) characterized the genomic structure of SAS and showed that it has 6 exons spanning approximately 3.2 kb.

Full details of the abovementioned studies are described in the following publications, the disclosure of which are hereby incorporated by reference:

Jankowski, S. A.; De Jong, P.; Meltzer, P. S.: Genomic structure of SAS, a member of the transmembrane 4 superfamily amplified in human sarcomas. Genomics 25: 501-506, 1995. PubMed ID: 7789984 2. Meltzer, P. S.; Jankowski, S. A.; Dal Cin, P.; Sandberg, A. A.; Paz, I. B.; Coccia, M. A.; Smith, S. H.: Identification and cloning of a novel amplified DNA sequence in human malignant fibrous histiocytoma derived from a region of chromosome 12 frequently rearranged in soft tissue tumors. (Abstract) Cytogenet. Cell Genet. 58: 1979 only, 1991.

Further studies establishing the function and utilities of SAS are found in John Hopkins OMIM database record ID 181035, and in reference numbered 1368-1369 listed hereinbelow.

Referring now to SERPINB8 BINDING SITE. Serine (or cysteine) proteinase inhibitor, clade B (ovalbumin), member (SERPINB8) is a target gene of GAM26, corresponding to GAM26-TARGET GENE of FIG. 26A. SERPINB8 BINDING SITE is a binding site found in an untranslated region of SERPINB8, corresponding to BINDING SITE of FIG. 26A, FIG. 26D illustrates the complementarity of the nucleotide sequence of SERPINB8 BINDING SITE, designated SEQ ID:353985, to the nucleotide sequence of GAM26 RNA of FIG. 26A, designated SEQ ID:20604.

Another function of GAM26 is therefore inhibition of serine (or cysteine) proteinase inhibitor, clade B (ovalbumin), member (SERPINB8), a gene which encodes a protein that protease inhibitors; may be a serpin serine protease inhibitor that binds thrombin. Accordingly, utilities of GAM26 include diagnosis and treatment of the abovementioned diseases and clinical conditions. The function and utilities of SERPINB8 have been established by previous studies, as described hereinabove with reference to FIG. 26D.

Referring now to REPS2 BINDING SITE. RALBP1 associated Eps domain containing 2 (REPS2) is a target gene of GAM26, corresponding to GAM26-TARGET GENE of FIG. 26A. REPS2 BINDING SITE is a binding site found in an untranslated region of REPS2, corresponding to BINDING SITE of FIG. 26A. FIG. 26D illustrates the complementarity of the nucleotide sequence of REPS2 BINDING SITE, designated SEQ ID:353987, to the nucleotide sequence of GAM26 RNA of FIG. 26A, designated SEQ ID:20604.

Yet another function of GAM26 is therefore inhibition of RALBP1 associated Eps domain containing 2 (REPS2), a gene which encodes a protein that interacts with the active form of RAS with adaptor protein GRB2 and binds calcium. Accordingly, utilities of GAM26 include diagnosis and treatment of the abovementioned diseases and clinical conditions. The function and utilities of REPS2 have been established by previous studies, as described hereinabove with reference to FIG. 26D.

Referring now to SERPINB8 BINDING SITE. Serine (or cysteine) proteinase inhibitor, clade B (ovalbumin), member (SERPINB8) is a target gene of GAM26, corresponding to GAM26-TARGET GENE of FIG. 26A. SERPINB8 BINDING SITE is a binding site found in an untranslated region of SERPINB8, corresponding to BINDING SITE of FIG. 26A. FIG. 26D illustrates the complementarity of the nucleotide sequence of SERPINB8 BINDING SITE, designated SEQ ID:353987, to the nucleotide sequence of GAM26 RNA of FIG. 26A, designated SEQ ID:20604.

An additional function of GAM26 is therefore inhibition of serine (or cysteine) proteinase inhibitor, clade B (ovalbumin), member (SERPINB8), a gene which encodes a protein that protease inhibitors; may be a serpin serine protease inhibitor that binds thrombin. Accordingly, utilities of GAM26 include diagnosis and treatment of the abovementioned diseases and clinical conditions. The function and utilities of SERPINB8 have been established by previous studies, as described hereinabove with reference to FIG. 26D.

Referring now to GABRB3 BINDING SITE. Gamma-aminobutyric acid (GABA) A receptor, beta 3 (GABRB3) is a target gene of GAM26, corresponding to GAM26-TARGET GENE of FIG. 26A. GABRB3 BINDING SITE is a binding site found in an untranslated region of GABRB3, corresponding to BINDING SITE of FIG. 26A. FIG. 26D illustrates the complementarity of the nucleotide sequence of GABRB3 BINDING SITE, designated SEQ ID:353989, to the nucleotide sequence of GAM26 RNA of FIG. 26A, designated SEQ ID:20604.

A further function of GAM26 is therefore inhibition of gamma-aminobutyric acid (GABA) A receptor, beta 3 (GABRB3), a gene which encodes a receptor that mediates neuronal inhibition by binding to the gaba/benzodiazepine receptor and opening an integral chloride channel, and is associated with Angelman syndrome and Prader-Willi syndrome. Accordingly, utilities of GAM26 include diagnosis and treatment of the abovementioned diseases and clinical conditions. The function and utilities of GABRB3 have been established by previous studies, as described hereinabove with reference to FIG. 26D.

Referring now to SERPINB8 BINDING SITE. Serine (or cysteine) proteinase inhibitor, clade B (ovalbumin), member (SERPINB8) is a target gene of GAM26, corresponding to GAM26-TARGET GENE of FIG. 26A. SERPINB8 BINDING SITE is a binding site found in an untranslated region of SERPINB8, corresponding to BINDING SITE of FIG. 26A. FIG. 26D illustrates the complementarity of the nucleotide sequence of SERPINB8 BINDING SITE, designated SEQ ID:353989, to the nucleotide sequence of GAM26 RNA of FIG. 26A, designated SEQ ID:20604.

Yet a further function of GAM26 is therefore inhibition of serine (or cysteine) proteinase inhibitor, clade B (ovalbumin), member (SERPINB8), a gene which encodes a protein that protease inhibitors; may be a serpin serine protease inhibitor that binds thrombin. Accordingly, utilities of GAM26 include diagnosis and treatment of the abovementioned diseases and clinical conditions. The function and utilities of SERPINB8 have been established by previous studies, as described hereinabove with reference to FIG. 26D.

Reference is now made to SFRP5 BINDING SITE. Secreted frizzled-related protein 5 (SFRP5) is a target gene of GAM26, corresponding to GAM26-TARGET GENE of FIG. 26A. SFRP5 BINDING SITE is a binding site found in an untranslated region of SFRP5, corresponding to BINDING SITE of FIG. 26A. FIG. 26D illustrates the complementarity of the nucleotide sequence of SFRP5 BINDING SITE, designated SEQ ID:355430, to the nucleotide sequence of GAM26 RNA of FIG. 26A, designated SEQ ID:20604.

Another function of GAM26 is therefore inhibition of secreted frizzled-related protein 5 (SFRP5), a gene which encodes a protein that receptor for wnt proteins that may modulate Wnt protein function and retinal cell polarization. Accordingly, utilities of GAM26 include diagnosis and treatment of the abovementioned diseases and clinical conditions.

The function of SFRP5 has been established by previous studies. Members of the 'frizzled' (FZ) transmembrane protein family (see 600667) are receptors for Wnt family members, cysteine-rich glycosylated ligands implicated in a variety of cellular processes, including control of cell polarity in a number of systems, including the *Drosophila* retina. See 16975. The secreted frizzled-related proteins (SFRPs) appear to act as soluble modulators of Wnt signaling by competing with membrane-bound frizzled receptors for the binding of secreted Wnt ligands. Chang et al. (1999) isolated bovine cDNAs encoding SFRP5, an SFRP highly expressed in the retinal pigment epithelium (RPE). By screening human genomic and RPE/retina libraries, they identified human SFRP5 genomic and cDNA clones. The SFRP5 gene contains 3 coding exons. The predicted 317-amino acid human protein shares 98% and 95% sequence identity with bovine and mouse Sfrp5, respectively. Like other SFRPs, SFRP5 contains an N-terminal signal peptide followed by a region homologous to the frizzled cysteine-rich domain (CRD). In an assay based on Wnt8 (see 601396)-induced axis duplication in *Xenopus* embryos, SFRP5 inhibited Wnt signaling. Chang et al. (1999) reported that although human SFRP5 is expressed in the RPE, SFRP2 (604157) is highly and preferentially expressed in bovine retina throughout the inner nuclear layer. Thus, photoreceptors appear to be bathed by complementary gradients of SFRP signaling molecules/modulators. The authors speculated that these putative inverse gradients of SFRP2 and SFRP5 might be involved in determining the polarity of photoreceptors and perhaps other cells in the retina.

Full details of the abovementioned studies are described in the following publications, the disclosure of which are hereby incorporated by reference:

Chang, J. T.; Esumi, N.; Moore, K.; Li, Y.; Zhang, S.; Chew, C.; Goodman, B.; Rattner, A.; Moody, S.; Stetten, G.; Campochiaro, P. A.; Zack, D. J.: Cloning and characterization of a secreted fizzled-related protein that is expressed by the retinal pigment epithelium. Hum. Molec. Genet. 8: 575-583, 1999.

Further studies establishing the function and utilities of SFRP5 are found in John Hopkins OMIM database record ID 604158, and in references numbered 1370-1371 listed hereinbelow.

Reference is now made to SGCB BINDING SITE. sarcoglycan, beta (43 kD dystrophin-associated glycoprotein) (SGCB) is a target gene of GAM26, corresponding to GAM26-TARGET GENE of FIG. 26A. SGCB BINDING SITE is a binding site found in an untranslated region of SGCB, corresponding to BINDING SITE of FIG. 26A. FIG. 26D illustrates the complementarity of the nucleotide sequence of SGCB BINDING SITE, designated SEQ ID:356034, to the nucleotide sequence of GAM26 RNA of FIG. 26A, designated SEQ ID:20604.

Yet another function of GAM26 is therefore inhibition of sarcoglycan, beta (43 kD dystrophin-associated glycoprotein) (SGCB), a gene which encodes a protein that is associated with limb-girdle muscular dystrophy type 2e. Accordingly, utilities of GAM26 include diagnosis and treatment of the abovementioned diseases and clinical conditions.

The function of SGCB has been established by previous studies. The dystrophin-glycoprotein complex (DGC) is a large oligomeric complex of sarcolemmal proteins and glycoproteins that acts as a structural link between the cytoskeleton of muscle and the extracellular matrix, and is believed to confer stability to the sarcolemma and protect muscle cells from contraction-induced damage. Lim et al. (1995) cloned and characterized human beta-sarcoglycan, a 43-kD component of the dystrophin-glycoprotein complex, and demonstrated its involvement in a form of muscular dystrophy, designated LGMD2E (604286). They showed that beta-sarcoglycan colocalizes with the DGC at the sarcolemma and is expressed ubiquitously, although predominantly in muscle. By PCR analysis of DNA from a panel of human/rodent somatic cell hybrids, they assigned the gene to chromosome 4 and then further narrowed the localization by study of DNA from somatic cell hybrids containing various fragments of chromosome 4. This involved assignment to the region 4p14-q21.2, which overlaps the centromere. By fluorescence in situ hybridization, they further narrowed the assignment to 4q12. Using pericentromeric markers and an intragenic polymorphic CA repeat, they demonstrated perfect cosegregation with autosomal recessive limb-girdle muscular dystrophy in Amish families from southern Indiana. A thr151-to-arg missense mutation (600900.0001) was identified in the beta-sarcoglycan gene that led to a dramatically reduced expression of beta-sarcoglycan in the sarcolemma and a concomitant loss of adhalin (600119) and 35-DAG (SGCD; 601411), which was interpreted as representing a disruption of a functional subcomplex within the dystrophin-glycoprotein complex. Durbeej et al. (2000) engineered Sgcb-null mice to analyze the biologic role of beta-sarcoglycan in the pathogenesis of LGMD2E. These mice developed severe muscular dystrophy and cardiomyopathy with focal areas of necrosis. The sarcoglycan-sarcospan and dystroglycan complexes were disrupted in skeletal, cardiac, and smooth muscle membranes. Epsilon-sarcoglycan (SGCE; 604149) was also reduced in membrane preparations of striated and smooth muscle. Loss of the sarcoglycan-sarcospan complex in vascular smooth muscle resulted in vascular irregularities in heart, diaphragm, and kidneys. Further biochemical characterization suggested the presence of a distinct epsilon-sarcoglycan complex in skeletal muscle that was disrupted in Sgcb-null mice. Thus, the authors concluded that perturbation of vascular function together with disruption of the epsilon-sarcoglycan-containing complex contribute to the pathogenesis of LGMD2E.

Full details of the abovementioned studies are described in the following publications, the disclosure of which are hereby incorporated by reference:

Lim, L. E.; Duclos, F.; Broux, O.; Bourg, N.; Sunada, Y.; Allamand, V.; Meyer, J.; Richard, I.; Moomaw, C.; Slaughter, C.; Tome, F. M. S.; Fardeau, M.; Jackson, C. E.; Beckmann, J. S.; Campbell, K. P.: Beta-sarcoglycan: characterization and role in limb-girdle muscular dystrophy linked to 4q12. Nature Genet 11: 257-265, 1995. PubMed ID: 7581448 Durbeej, M.; Cohn, R. D.; Hrstka, R. F.; Moore, S. A.; Allamand, V.; Davidson, B. L.; Williamson, R. A.; Campbell, K. P.: Disruption of the beta-sarcoglycan gene reveals pathogenetic complexity of limb-girdle muscular dystrophy type 2E. Molec. Cell 5: 141-151, 2000.

Further studies establishing the function and utilities of SGCB are found in John Hopkins OMIM database record ID 600900, and in reference numbered 1372-1378 listed hereinbelow.

Reference is now made to SLC1A1 BINDING SITE. solute carrier family 1 (neuronal/epithelial high affinity glutamate t (SLC1A1) is a target gene of GAM26, corresponding to GAM26-TARGET GENE of FIG. 26A. SLC1A1 BINDING SITE is a binding site found in an untranslated region of SLC1A1, corresponding to BINDING SITE of FIG. 26A. FIG. 26D illustrates the complementarity of the nucleotide sequence of SLC1A1 BINDING SITE, designated SEQ ID:362965, to the nucleotide sequence of GAM26 RNA of FIG. 26A, designated SEQ ID:20604.

An additional function of GAM26 is therefore inhibition of solute carrier family 1 (neuronal/epithelial high affinity glutamate t (SLC1A1), a gene which encodes a protein that is a glutamate transporter, essential for terminating the postsynaptic action of glutamate by rapidly removing it from the synaptic cleft and is associated with amyotrophic lateral sclerosis; dicarboxylicaminoaciduria; familial ALS; neurodegenerative disorders. Accordingly, utilities of GAM26 include diagnosis and treatment of the abovementioned diseases and clinical conditions.

The function of SLC1A1 has been established by previous studies. High-affinity glutamate transporters play an essential role in transporting glutamate across plasma membranes. In brain, these transporters are crucial in terminating the action of the excitatory neurotransmitter glutamate and in maintaining extracellular glutamate concentrations below neurotoxic levels. Functional defects of high-affinity glutamate transporters have been suggested to be involved in the pathophysiology of amyotrophic lateral sclerosis (105400). In small intestine and kidney, in which the high-affinity glutamate transporter mediates net absorption of glutamate and aspartate across epithelial cells, an inborn error of glutamate transport is thought to cause dicarboxylicaminoaciduria (222730). Kanai and Hediger (1992) isolated a cDNA encoding a high-affinity glutamate transporter, designated EAAC1, that also transports aspartate but not other amino acids. EAAC1 was found to be uniquely expressed throughout the body, particularly in brain (neurons), intestine, and kidney. By Southern analysis of a panel of human/rodent somatic cell hybrids and by fluorescence in situ hybridization (FISH), Smith et al. (1994) mapped the EAAC1 gene to 9p24. They suggested that mutations in this gene may be responsible for dicarboxylicaminoaciduria or for a form of familial ALS separate from the form due to mutation in the SOD1 gene (147450) on chromosome 21.

Lin et al. (2001) used a yeast 2-hybrid assay to identify a protein that interacts with EAAC1. This protein, termed GTRAP3-18 (605709), is expressed in numerous tissues, localizes the cell membrane and cytoplasm, and specifically interacts with the carboxy-terminal intracellular domain of EAAC1. Increasing the expression of GTRAP3-18 in cells reduces EAAC1-mediated glutamate transport by lowering substrate affinity. The expression of GTRAP3-18 can be upregulated by retinoic acid, which results in a specific reduction of EAAC1-mediated glutamate transport. Lin et al. (2001) concluded that glutamate transport proteins can be regulated potently and that GTRAP can modulate the transport functions ascribed to EAAC1. GTRAP3-18 may be important in regulating the metabolic functions of EAAC1.

Full detail of the abovementioned studies are described in the following publications, the disclosure of which are hereby incorporated by reference:

Kanai, Y. Hediger, M. A.: Primary structure and functional characterization of a high-affinity glutamate transporter. Nature 360: 467-471, 1992. PubMed ID: 1280334 3. Smith, C. P.; Weremowicz, S.; Kanai, Y.; Stelzner, M.; Morton, C. C.; Hediger, M. A.: Assignment of the gene coding for the human high-affinity glutamate transporter EAAC1 to 9p24: potential role in dicarboxylic aminoaciduria and neurodegenerative disorders. Genomics 20: 335-336, 1994. PubMed ID: 8020993 2. Lin, C. G.; Orlov, I.; Ruggiero, A. M.; Dykes-Hoberg, M.; Lee, A.; Jackson, M.; Rothstein, J. D.: Modulation of the neuronal glutamate transporter EAAC1 by the interacting protein GTRAP3-18. Nature 410: 84-88, 2001.

Further studies establishing the function and utilities of SLC1A1 are found in John Hopkins OMIM database record ID 133550, and in references numbered 1379-1381 listed hereinbelow.

Referring now to SLC1A1 BINDING SITE. Solute carrier family 1 (neuronal/epithelial high affinity glutamate t (SLC1A1) is a tar et gene of GAM26, corresponding to GAM26-TARGET GENE of FIG. 26A. SLC1A1 BINDING SITE is a binding site found in an untranslated region of SLC1A1, corresponding to BINDING SITE of FIG. 26A. FIG. 26D illustrates the complementarity of the nucleotide sequence of SLC1A1 BINDING SITE, designated SEQ ID:362996, to the nucleotide sequence of GAM26 RNA of FIG. 26A, designated SEQ ID:20604.

A further function of GAM26 is therefore inhibition of solute carrier family 1 (neuronal/epithelial high affinity glutamate t (SLC1A1), a gene which encodes a protein that is a glutamate transporter, essential for terminating the postsynaptic action of glutamate by rapidly removing it from the synaptic cleft and is associated with amyotrophic lateral sclerosis; dicarboxylicaminoaciduria; familial ALS; neurodegenerative disorders. Accordingly, utilities of GAM26 include diagnosis and treatment of the abovementioned diseases and clinical conditions. The function and utilities of SLC1A1 have been established by previous studies, as described hereinabove with reference to FIG. 26D.

Reference is now made to SMARCB1 BINDING SITE. SWI/SNF related, matrix associated, actin dependent regulator of chrom (SMARCB1) is a target gene of GAM26, corresponding to GAM26-TARGET GENE of FIG. 26A. SMARCB1 BINDING SITE is a binding site found in an untranslated region of SMARCB1, corresponding to BINDING SITE of FIG. 26A. FIG. 26D illustrates the complementarity of the nucleotide sequence of SMARCB1 BINDING SITE, designated SEQ ID:370333, to the nucleotide sequence of GAM26 RNA of FIG. 26A, designated SEQ ID:20604.

Yet a further function of GAM26 is therefore inhibition of SWI/SNF related, matrix associated actin dependent regulator of chrom (SMARCB1), a gene which encodes a protein that is associated with malignant rhabdoid tumors (mrt). Accordingly, utilities of GAM26 include diagnosis and treatment of the abovementioned diseases and clinical conditions.

The function of SMARCB1 has been established by previous studies. Versteege et al. (1998) found that the SNF5/INI1 gene contains 9 exons and spans approximately 50 kb. They concluded that biallelic, somatic alteration of SNF5/INI1, arising through a combination of complete deletions of the gene, frameshift alterations, and nonsense mutations, is a frequent, if not constant, feature of MRTs. This was considered fully consistent with the paradigm of the 2-hit recessive model of oncogenesis and supported the hypothesis that SNF5/INI1 is the MRT tumor suppressor gene. Although constitutional mutations were not detected in this study, which was based on sporadic tumors, previous reports of multifocal and/or familial MRTs indicated that constitutional inactivation of 1 allele of SNF5/INI1 could be responsible for hereditary cases. Given the low incidence of MRT and its aggressive evolution, which frequently leads to death at a young age, familial cases, if existing, would be expected to be rare. Altered chromatin organization at specific DNA sites may be crucial in the process of oncogenesis. The SWI/SNF complexes, which have been identified in organisms from yeast to humans, are thought to be important in the remodeling of chromatin structure. Most samples and cell lines from malignant rhabdoid tumors show biallelic inactivating mutations of the SNF5 gene, suggesting that SNF5 may act as a tumor suppressor. Roberts et al. (2000) examined the role of Snf5 in development and cancer in a mouse model. They found that Snf5 is widely expressed during embryogenesis with focal areas of high-level expression in the mandibular portion of the first branchial arch and central nervous system. Homozygous knockout of Snf5 resulted in lethality by embryonic day 7, whereas heteroygous mice were born at the expected frequency and appeared normal. However, beginning as early as 5 weeks of age, heterozygous mice developed tumors consistent with malignant rhabdoid tumor. Most tumors arose in soft tissues derived from the first branchial arch. Most samples and cell lines from malignant rhabdoid tumors show biallelic inactivating mutations of the SNF5 gene, suggesting that SNF5 may act as a tumor suppressor. Roberts et al. (2000) examined the role of Snf5 in development and cancer in a mouse model. They found that Snf5 is widely expressed during embryogenesis with focal areas of high-level expression in the mandibular portion of the first branchial arch and central nervous system. Homozygous knockout of Snf5 resulted in lethality by embryonic day 7, whereas heterozygous mice were born at the expected frequency and appeared normal. However, beginning as early as 5 weeks of age, heterozygous mice developed tumors consistent with malignant rhabdoid tumor. Most tumors arose in soft tissues derived from the first branchial arch.

Full details of the abovementioned studies are described in the following publications, the disclosure of which are hereby incorporated by reference:

Versteege, I.; Sevenet, N.; Lange, J.; Rousseau-Merck, M. -F.; Ambros, P.; Handgretinger, R.; Aurias, A.; Delattre, O.: Truncating mutations of hSNF5/INI1 in aggressive paediatric cancer. Nature 394: 203-206, 1998. PubMed ID:9671307. Roberts, C. W. M.; Galusha, S. A.; McMenamin, M. E.; Fletcher, C. D. M.; Orkin, S. H.: Haploinsufficiency of Snf5 (integrase interactor 1) predisposes to malignant rhabdoid tumors in mice. Proc. Nat. Acad. Sci. 97: 13796-13800, 2000.

Further studies establishing the function and utilities of SMARCB1 are found in John Hopkins OMIM database record ID 601607, and in references numbered 1382-1397 listed hereinbelow.

Reference is now made to SMARCC1 BINDING SITE. SWI/SNF-RELATED, MATRIX-ASSOCIATED, ACTIN-DEPENDENT REGULATOR OF CHROMATIN, SUB-FAMILY C, MEMBER 1 (SMARCC1) is a target gene of GAM26, corresponding to GAM26-TARGET GENE of FIG. 26A. SMARCC1 BINDING SITE is a binding site found in an untranslated region of SMARCC1, corresponding to BINDING SITE of FIG. 26A. FIG. 26D illustrates the complementarity of the nucleotide sequence of SMARCC1 BINDING SITE designated SEQ ID:370474, to the nucleotide sequence of GAM26 RNA of FIG. 26A, designated SEQ ID:20604.

Another function of GAM26 is therefore inhibition of SWI/SNF-RELATED, MATRIX-ASSOCIATED, ACTIN-DEPENDENT REGULATOR OF CHROMATIN, SUB-FAMILY C, MEMBER 1 (SMARCC1), a gene which encodes a protein that is involved in chromatin remodeling. Accordingly, utilities of GAM26 include diagnosis and treatment of the abovementioned diseases and clinical conditions.

The function of SMARCC1 has been established by previous studies. Chromatin is actively remodeled during development. Chromatin remodeling of certain genes appears to precede their transcriptional activation. In yeast, the multisubunit SWI/SNF complex is thought to be responsible for chromatin remodeling. Wang et al. (1996) isolated an analogous SWI/SNF complex from human YT cells. They found that the resultant complexes are composed of 9 to 12 polypeptides, which they termed BAFs (for BRG1-associated factors). Wang et al. (1996) isolated BAF155 from a human Jurkat T-cell cDNA library. This gene encodes a polypeptide of 1,104 amino acids, and is homologous both to the yeast SWI3 gene and to BAF170, another of the proteins in this chromatin remodeling complex (601734). SWI3, BAF155, and BAF170 all contain a predicted leucine zipper region (a dimerization motif for a variety of transcription factors) and a myb-like tryptophan-repeat domain. Western blot analysis and EST database analysis revealed that BAF155 is expressed in many tissues Full details of the abovementioned studies are described in the following publications, the disclosure of which are hereby incorporated by reference:

Ring, H. Z.; Vameghi-Meyers, V.; Wang, W.; Crabtree, G. R.; Francke, U.: Five SWI/SNF-related, matrix-associated, actin-dependent regulator of chromatin (SMARC) genes are dispersed in the human genome. Genomics 51: 140-143, 1998. PubMed ID: 9693044 2. Wang, W.; Xue, Y.; Zhou, S.; Kuo, A.; Cairns, B. R.; Crabtree, G. R.: Diversity and specialization of mammalian SWI/SNF complexes. Genes Dev. 10: 2117-2130, 1996.

Further studies establishing the function and utilities of SMARCC1 are found in John Hopkins OMIM database record ID 601732, and in references numbered 1398-1399 listed hereinbelow.

Reference is now made to SNX3 BINDING SITE. sorting nexin 3 (SNX3) is a target gene of GAM26, corresponding to GAM26-TARGET GENE of FIG. 26A. SNX3 BINDING SITE is a binding site found in an untranslated region of SNX3, corresponding to BINDING SITE of FIG. 26A. FIG. 26D illustrates the complementarity of the nucleotide sequence of SNX3 BINDING SITE, designated SEQ ID:373083, to the nucleotide sequence of GAM26 RNA of FIG. 26A, designated SEQ ID:20604.

Yet another function of GAM26 is therefore inhibition of sorting nexin 3 (SNX3), a gene which encodes a protein that may associate with late-Golgi resident proteins rather than cell surface receptors. Accordingly, utilities of GAM26 include diagnosis and treatment of the abovementioned diseases and clinical conditions.

The function of SNX3 has been established by previous studies. By database searching with the sequence of sorting nexin-1 (SNX1; 601272), Haft et al. (1998) obtained several human EST clones, determined their nucleotide sequences, and constructed full-length cDNAS corresponding to an isoform of SNX1 (SNX1A), SNX2 (605929), SNX3, and SNX4 (605931). The SNX3 cDNA encode a deduced 162-amino acid protein. Northern blot analysis detected an approximately 1.9-kb SNX3 transcript in all tissues tested, with highest expression in peripheral leukocytes, spleen, heart, and skeletal muscle, and low expression in kidney. Western blot analysis showed that SNX3 is found mainly in the cytosol, whereas SNX1, SNX1A, SNX2, and SNX4 are associated predominantly with membranes. Coimmunoprecipitation studies detected no association of SNX3 with any receptors studied. Because SNX3 is the human ortholog of yeast Grd19p, Haft et al. (1998) suggested that SNX3 may associate with late-Golgi resident proteins rather than cell surface receptors. Based on the functions of their yeast homologs, Haft et al. (1998) suggested that mammalian sorting nexins function in intracellular trafficking of proteins to various organelles.

Full details of the abovementioned studies are described in the following publications, the disclosure of which are hereby incorporated by reference:

Haft, C. R.; de la Luz Sierra, M.; Barr, V. A.; Haft, D. H.; Taylor, S. I.: Identification of a family of sorting nexin molecules and characterization of their association with receptors. Molec. Cell. Biol. 18: 7278-7287, 1998.

Further studies establishing the function and utilities of SNX3 are found in John Hopkins OMIM database record ID 605930, and in references numbered 1400 listed hereinbelow.

Reference is now made to SOX10 BINDING SITE. SRY (sex determining region Y)-box 10 (SOX10) is a target gene of GAM26, corresponding to GAM26-TARGET GENE of FIG. 26A. SOX10 BINDING SITE is a binding site found in an untranslated region of SOX10, corresponding to BINDING SITE of FIG. 26A. FIG. 26D illustrates the complementarity of the nucleotide sequence of SOX10 BINDING SITE, designated SEQ ID:374793, to the nucleotide sequence of GAM26 RNA of FIG. 26A, designated SEQ ID:20604.

An additional function of GAM26 is therefore inhibition of SRY (sex determining region Y)-box 10 (SOX10), a gene which encodes a transcription factor that is associated with Waardenburg syndrome type 4. Accordingly, utilities of GAM26 include diagnosis and treatment of the abovementioned diseases and clinical conditions.

The function of SOX10 has been established by previous studies. Waardenburg syndrome combines deafness with pigmentary abnormalities and Hirschsprung disease (aganglionic megacolon). Both are congenital disorders caused by defective function of the embryonic neural crest. The disorders are associated in patients with Waardenburg-Shah syndrome (WS4; 277580) in which the manifestations are reminiscent of the white coat-spotting and aganglionic megacolon displayed by the mouse mutants Dom, piebald-lethal, and lethal spotting (ls). The last 2 phenotypes are caused by mutations in the genes encoding the endothelin-B receptor and its ligand, endothelin-3, respectively, in the mouse, and mutations in either of these 2 genes can result in the Waardenburg-Shah syndrome in humans. The identification of Sox10 as the gene mutated in Dom mice prompted Pingault et al. (1998) to analyze the role of its human homolog in neural crest defects. In 4 families with Waardenburg-Shah syndrome, they found mutations in the SOX10 gene (e.g., 602229.0001). These mutations probably result in haploinsufficiency of the SOX10 product.

Animal model experiments lend further support to the function of SOX10. Mouse model of Hirschsprung disease (HSCR; 142623), dominant megacolon (Dom), arose spontaneously at the Jackson Laboratory (Lane and Liu, 1984). Megacolon was associated with dominantly inherited spotting. While Dom/+ heterozygous mice displayed regional deficiencies of neural crest-derived enteric ganglia in the distal colon, Dom/Dom homozygous animals were embryonic lethal. Linkage analysis indicated that the Dom mutation is located in the mid-terminal region of mouse chromosome 15. Pingault et al. (1997) noted that, in mice, natural and in vitro-induced mutations affecting the Ret (164761), Ednrb (131242), and Edn3 (131244) genes generated phenotypes similar to human Hirschsprung disease. Using polymorphisms for conserved human/mouse genes, Pingault et al. (1997) established homology between the Dom locus and human chromosome 22q12-q13. Two genes, Smstr3 and Ads1 (103050), not previously mapped in the mouse genome, were also mapped to mouse chromosome 15. The investigators stated that 3 genes, Smstr3, Lgals1 (150570), and Pdgfb (190040), are possible Dom candidates, as they did not recombine with the Dom mutation in a backcross.

It is appreciated that the abovementioned animal model for SOX10 is acknowledged by those skilled in the art as a scientifically valid animal model, as can be further appreciated from the publications sited hereinbelow.

Full details of the abovementioned studies are described in the following publications, the disclosure of which are hereby incorporated by reference:

Touraine, R. L.; Attie-Bitach, T.; Manceau, E.; Korsch, E.; Sarda, P.; Pingault, V.; Encha-Razai, F.; Pelet, A.; Auge, J.; Nivelon-Chevallier, A.; Holschneider, A. M.; Munnes, M.; Deer, W.; Goossens, M.; Munnich, A.; Vekemans, M.; Lyonnet, S.: Neurological phenotype in Waardenburg syndrome type 4 correlates with novel SOX10 truncating mutations and expression in developing brain. Am. J. Hum. Gene 66: 1496-1503, 2000. Note: Erratum: Am. J. Hum. Genet. 66: 2020 only 2000. PubMed ID: 10762540

Bondurand, N.; Kuhlbrodt, K.; Pingault, V.; Enderich J.; Sajus, M.; Tommerup, N.; Warburg, M.; Hennekam, R. C. M.; Read, A. P.; Wegner, M.; Goossens, M.: A molecular analysis of the Yemenite deaf-blind hypopigmentation syndrome: SOX10 dysfunction causes different neurocristopathies. Hum. Molec. Genet. 8: 1785-1789, 1999.

Further studies establishing the function and utilities of SOX10 are found in John Hopkins OMIM database record ID 602229, and in references numbered 1401-1422 listed hereinbelow.

Referring now to SOX10 BINDING SITE. SRY (sex determining region Y)-box 10 (SOX10) is a target gene of GAM26, corresponding to GAM26-TARGET GENE of FIG. 26A. SOX10 BINDING SITE is a binding site found in an untranslated region of SOX10, corresponding to BINDING SITE of FIG. 26A. FIG. 26D illustrates the complementarity of the nucleotide sequence of SOX10

BINDING SITE, designated SEQ ID:374849, to the nucleotide sequence of GAM26 RNA of FIG. 26A, designated SEQ ID:20604.

A further function of GAM26 is therefore inhibition of SRY (sex determining region Y)-box 10 (SOX10), a gene which encodes a transcription factor that is associated with Waardenburg syndrome type 4. Accordingly, utilities of GAM26 include diagnosis and treatment of the abovementioned diseases and clinical conditions. The function and utilities of SOX10 have been established by previous studies, as described hereinabove with reference to FIG. 26D.

Reference is now made to SOX11 BINDING SITE. SRY (sex determining region Y)-box 11 (SOX11) is a target gene of GAM26, corresponding to GAM26-TARGET GENE of FIG. 26A. SOX11 BINDING SITE is a binding site found in an untranslated region of SOX11, corresponding to BINDING SITE of FIG. 26A. FIG. 26D illustrates the complementarity of the nucleotide sequence of SOX11 BINDING SITE, designated SEQ ID:375242, to the nucleotide sequence of GAM26 RNA of FIG. 26A, designated SEQ ID:20604.

Yet a further function of GAM26 is therefore inhibition of SRY (sex determining region Y)-box 11 (SOX11), a gene which encodes a transcription factor that is probably important in the developing nervous system. Accordingly, utilities of GAM26 include diagnosis and treatment of the abovementioned diseases and clinical conditions.

The function of SOX11 has been established by previous studies. SRY (480000) is the testis-determining gene located on the Y chromosome of mammals. It encodes a protein whose most striking feature is a motif of 78 amino acids conserved with respect to the DNA binding domain of the high mobility group (HMG) proteins. Jay et al. (1995) noted that more than 100 HMG box-containing proteins had been reported at that time and are classified in 2 distinct subgroups according to the sequence-specificity of the binding, the number of DNA binding domains, and phylogenetic considerations (Laudet et al., 1993). An important subgroup of HMG box-containing proteins includes SRY and SRY box-related (SOX) sequences. They contain only 1 DNA-binding domain, and they bind to DNA in a sequence-specific manner. They are all potential transcription factors implicated in the developmental control of gene expression. Degenerate PCR-based methods enabled the cloning and sequencing of a great number of new SRY-related box sequences in both vertebrates and invertebrates. Only a few have been further characterized and, except for SOX4 (184430), which has been shown to be a transcriptional activator in lymphocytes, and for SOX9 (114290), which is the site of mutations causing campomelic dysplasia (a disorder of bone and sex determination), the functions of the SOX proteins were as yet unknown. Jay et al. (1995) cloned and characterized the human SOX11 gene using the partial clones of both human and mouse SOX11 genes and mapped the gene to 2p25 by fluorescence in situ hybridization. The SOX11 sequence is strongly conserved with the chicken homolog and is related to SOX4. It contains several putative transcriptional activator or repressor domains. The authors observed that the SOX11 expression pattern is consistent with the hypothesis that this gene is important in the developing nervous system.

Full details of the abovementioned studies are described in the following publications, the disclosure of which are hereby incorporated by reference:
Jay, P.; Goze, C.; Marsollier, C.; Taviaux, S.; Hardelin, J. -P.; Koopman, P.; Berta, P.: The human SOX11 gene: cloning, chromosomal assignment and tissue expression. Genomics 29: 541-545, 1995.

Further studies establishing the function and utilities of SOX11 are found in John Hopkins OMIM database record ID 600898, and in referent numbered 1423-1424 listed hereinbelow.

Reference is now made to SPG4 BINDING SITE spastic paraplegia 4 (autosomal dominant; spastin) (SPG4) is a target gene of GAM26, corresponding to GAM26-TARGET GENE of FIG. 26A. SPG4 BINDING SITE is a binding site found in an untranslated region of SPG4, corresponding to BINDING SITE of FIG. 26A. FIG. 26D illustrates the complementarity of the nucleotide sequence of BINDING SITE, designated SEQ ID:376880, to the nucleotide sequence of GAM26 RNA of FIG. 26A, designated SEQ ID:20604.

Another function of GAM26 is therefore inhibition of spastic paraplegia 4 (autosomal dominant; spastin) (SPG4), a gene which encodes a protein that is probably an ATPase involved in the assembly or function of nuclear protein complexes and is associated with spastic paraparesis. Accordingly, utilities of GAM26 include diagnosis and treatment of the abovementioned diseases and clinical conditions.

The function of SPG4 has been established by previous studies. SPG4 is ubiquitously expressed in human adult and fetal tissue, showing slightly higher expression in fetal brain. Hazan et al. (1999) cloned the mouse ortholog of SPG4, which between amino acids 113 and 616 has 96% identity with human SPG4. Spg4 transcripts are ubiquitously expressed in adult tissues and from embryonic day 7 to 17 in mouse. Interaction with the cytoskeleton was mediated by the N-terminal region of spastin and was regulated through the ATPase activity of the AAA domain. Expression of missense mutations (including 604277.0001, 604277.0002, and 604277.0004) into the AAA domain led to constitutive binding to microtubules in transfected cells and induced the disappearance of the aster and the formation of thick perinuclear bundles, suggesting a role of spastin in microtubule dynamics. Consistently, wildtype spastin promoted microtubule disassembly in transfected cells. The authors suggested that spastin may be involved in microtubule dynamics similarly to the highly homologous microtubule-severing protein katanin (606696). The authors hypothesized that impairment of fine regulation of the microtubule cytoskeleton in long axons, due to spastin mutations, may underlie the pathogenesis of hereditary spastic paraplegia Full details of the abovementioned studies are described in the following publications, the disclosure of which are hereby incorporated by reference:
Hazan, J.; Fonknechten, N.; Mavel, D.; Paternotte, C.; Samson, D.; Artiguenave, F.; Davoine, C. -S.; Cruaud, C.; Durr, A.; Wincker, P.; Brottier, P.; Cattolico, L.; Barbe, V.; Burgunder, J. -M.; Prud'homme, J. -F.; Brice, A.; Fontaine, B.; Heilig, R.; Weissenbach, J.: Spastin, a new AAA protein, is altered in the most frequent form of autosomal dominant spastic paraplegia. Nature Genet. 23: 296-303, 1999. PubMed ID: 10610178 Errico, A.; Ballabio, A.; Rugarli, E. I.: Spastin, the protein mutated in autosomal dominant hereditary spastic paraplegia, is involved in microtubule dynamics. Hum. Molec. Genet. 11: 153-163, 2002.

Further studies establishing the function and utilities SPG4 are found in John Hopkins OMIM database record ID 604277, and in references numbered 1425-1437 listed hereinbelow.

Reference is now made to ST7 BINDING SITE. Suppression of tumorigenicity 7 (ST7) is a target gene of GAM26, corresponding GAM26-TARGET GENE of FIG. 26A. ST7 BINDING SITE is a binding site found in an untranslated region of ST7, corresponding to BINDING SITE of FIG. 26A. FIG. 26D illustrates the complementarity of the nucleotide sequence of ST7 BINDING SITE, designated SEQ ID:380179, to the nucleotide sequence of GAM26 RNA of FIG. 26A, designated SEQ ID:20604.

Yet another function of GAM26 is therefore inhibition of suppression of tumorigenicity 7 (ST7), a gene which encodes a protein that has a role in regulating cell-environment or cell-cell interactions and is associated with a variety of human tumors. Accordingly, utilities of GAM26 include diagnosis and treatment of the abovementioned diseases and clinical conditions.

The function of S17 has been established by previous studies. A distinct tumor suppressor gene involved in primary ovarian carcinomas was suggested by the finding of Zenklusen et al. (1995) of allelic loss at 7q31.1 in such carcinomas. In 17 of 19 informative cases (73%), loss of heterozygosity (LOH) was detected in D7S522 at 7q31.1. The smallest common deleted region covered about 1 cM. Previous microcell fusion transfer of human chromosome 7 to a murine squamous cell carcinoma cell line indicated that the inserted chromosome can delay the onset of tumors and in some cases completely repress the tumorigenic potential. In situ hybridization showed that the clones that reverted to the malignant phenotype had expelled the inserted chromosome. The authors stated that LOH of 7q31.1 had frequently been found in squamous cell carcinomas of the head and neck and in colon and prostate carcinomas. Vincent et al. (2000) studied an individual with autism (209850) who carried the translocation t(7;13)(q31.3;q21). The chromosomal 7 breakpoint is located in the region of 7q in which a susceptibility locus for autism had been postulated. Using a combination of DNA sequence analysis and cDNA screening of human colon carcinoma and fetal brain cDNA libraries, Vincent et al. (2000) cloned the ST7 gene, which they designated RAY1 (or FAM4A1), which spanned the translocation breakpoint. The gene contains 16 exons and extends more than 220 kb at 7q31.3. Alternatively spliced transcripts differing at exon 7 and having 2 different exon 16s encode deduced proteins of 554 and 585 amino acids. Apparent homologs of RAY1 had been identified in mouse, rat, pig, chicken, fruit fly, and nematode. Vincent et al. (2000) determined that the human and mouse RAY1 genes share similar splicing patterns, and that their predicted protein products are 98% identical.

Full details of the abovementioned studies are described in the following publications, the disclosure of which are hereby incorporated by reference:

Vincent, J. B.; Herbrick, J. -A.; Gurling, H. M. D.; Bolton, P. F.; Roberts, W.; Scherer, S. W.: Identification of a novel gene chromosome 7q31 that is interrupted by a translocation breakpoint in an autistic individual. Am. J. Hum. Genet. 67: 510-514, 2000. PubMed ID: 10889047 6.

Zenklusen, J. C.; Weitzel, J. N.; Ball, H. G.; Conti, C. J.: Allelic loss at 7q31.1 in human primary ovarian carcinomas suggests the existence of a tumor suppressor gene. Oncogene 11: 359-363, 1995.

Further studies establishing the function and utilities of S17 are found in John Hopkins OMIM database record ID 600833, and in references numbered 1438-1443 listed hereinbelow.

Reference is now made to STAR BINDING SITE. Steroidogenic acute regulatory protein (STAR) is a target gene of GAM26, corresponding to GAM26-TARGET GENE of FIG. 26A. STAR BINDING SITE is a binding site found in an untranslated region of STAR, corresponding to BINDING SITE of FIG. 26A. FIG. 26D illustrates the complementarity of the nucleotide sequence of STAR BINDING SITE, designated SEQ ID:380380, to the nucleotide sequence of GAM26 RNA of FIG. 26A, designated SEQ ID:20604.

An additional function of GAM26 is therefore inhibition of steroidogenic acute regulatory protein (STAR), a gene which encodes a protein that is associated with congenital lipoid adrenal hyperplasia (clah). Accordingly, utilities of GAM26 include diagnosis and treatment of the abovementioned diseases and clinical conditions.

The function of STAR has been established by previous studies. Steroidogenic acute regulatory protein appears to mediate the rapid increase in pregnenolone synthesis stimulated by tropic hormones. Sugawara et al. (1995) isolated cDNAs encoding this protein from a human adrenal cortex library; the authors symbolized the protein STAR. When coexpressed in COS-1 cells with cytochrome P450scc (118485) and adrenodoxin (103260), STAR increased pregnenolone synthesis more than 4-fold. A major STAR transcript of 1.6 kb and less abundant transcripts of 4.4 and 7.5 kb were detected in ovary and testis. Kidney had a lower amount of the 1.6-kb message. STAR mRNA was not detected in other tissues, including placenta. Sugawara et al. (1995) concluded that STAR expression is restricted to tissues that carry out mitochondrial sterol oxidations subject to acute regulation by cAMP and that STAR mRNA levels are regulated by cAMP.

Animal model experiments lend further support to the function of STAR. Caron et al. (1997) used targeted gene disruption to produce STAR knockout mice. Initially, the knockout mice were indistinguishable from wildtype littermates, except that males and females had female external genitalia. After birth, they failed to grow normally and died from adrenocortical insufficiency. Hormone assays confirmed severe defects in adrenal steroids—with loss of negative feedback regulation at hypothalamic-pituitary levels—whereas hormone constituting the gonadal axis did not differ significantly from levels in wildtype littermates. Histologically, the adrenal cortex of STAR knockout mice contained florid lipid deposits, with lesser deposits in the steroidogenic compartment of the testis and none in the ovary. The sex-specific differences in gonadal involvement supported a 2-stage model of the pathogenesis of STAR deficiency, with trophic hormone stimulation inducing progressive accumulation of lipids within the steroidogenic cells and ultimately causing their death.

It is appreciated that the abovementioned animal model for STAR is acknowledged by those skilled in the art as a scientifically valid animal model, as can be further appreciated from the publications sited hereinbelow.

Full details of the abovementioned studies are described in the following publications, the disclosure of which are hereby incorporated by reference:

Caron, K. M.; Soo, S. -C.; Wetsel, W. C.; Stocco, D. M.; Clark, B. J.; Parker, K. L.: Targeted disruption of the mouse gene encoding steroidogenic acute regulatory protein provides insights into congenital lipoid adrenal hyperplasia. Proc. Nat. Acad. Sci. 94: 11540-11545, 1997. PubMed ID: 9326645 11. Sugawara, T.; Holt, J. A.; Driscoll, D.; Strauss, J. F., III; Lin, D.; Miller, W. L.; Patterson, D.; Clancy, K. P.; Hart, I. M.; Clark, B. J.; Stocco, I. M.: Human steroidogenic acute regulatory protein: functional activity in COS-1 cells, tissue-specific expression, and mapping of the structural gene to 8p11.2 and a pseudogene to chromosome 13. Proc. Nat. Acad. Sci. 2: 4778-4782, 1995.

Further studies establishing the function and utilities of STAR are found in John Hopkins OMIM database record ID 600617, and in references numbered 1444-1455 listed hereinbelow.

Referring now to STAR BINDING SITE. Steroidogenic acute regulatory protein (STAR) is a target gene of GAM26, corresponding to GAM26-TARGET GENE of FIG. 26A. STAR BINDING SITE is a binding site found in an untranslated region of STAR, corresponding to BINDING SITE of FIG. 26A, FIG. 26D illustrates the complementarity of the nucleotide sequence of STAR BINDING SITE, designated SEQ ID:380387, to the nucleotide sequence of GAM26 RNA of FIG. 26A, designated SEQ ID:20604.

A further function of GAM26 is therefore inhibition of steroidogenic acute regulatory protein (STAR), a gene which encodes a protein that is associated with congenital lipoid adrenal hyperplasia (clah). Accordingly, utilities of GAM26 include diagnosis and treatment of the abovementioned diseases and clinical conditions. The function and utilities of STAR have been established by previous studies, as described hereinabove with reference to FIG. 26D.

Reference is now made to STC1 BINDING SITE. Stanniocalcin 1 (STC1) is a target gene of GAM26, corresponding to GAM26-TARGET GENE of FIG. 26A. STC1 BINDING SITE is a binding site found in an untranslated region of STC1, corresponding to BINDING SITE of FIG. 26A. FIG. 26D illustrates the complementarity of the nucleotide sequence of STC1 BINDING SITE, designated SEQ ID:381482, to the nucleotide sequence of GAM26 RNA of FIG. 26A, designated SEQ ID:20604.

Yet a further function of GAM26 is therefore inhibition of stanniocalcin 1 (STC1), a gene which encodes a protein that stimulates renal phosphate reabsorption, and could therefore prevent hypercalcemia. Accordingly, utilities of GAM26 include diagnosis and treatment of the abovementioned diseases and clinical conditions.

The function of STC1 has been established by previous studies. Stanniocalcin (STC) is a calcium-regulated hormone in bony fishes. The hormone was so named because it is synthesized by the corpuscles of Stannius, endocrine glands that are associated with the kidneys of all fishes with a bony skeleton. The primary function of STC in fishes is the prevention of hypercalcemia; Olsen et al. (1996) noted that a rise in serum calcium levels is the primary stimulus for secretion. Upon release into the circulation, STC lowers calcium transport by the gills, thereby reducing its rate of influx from the environment into the extracellular compartment. A second equally important action of STC is stimulation of phosphate reabsorption by renal proximal tubules. The consequence of this renal effect is increased levels of plasma phosphate, which combines with excess calcium and promotes its disposal into bone and scales. Wagner et al. (1995) found evidence of STC immunoreactivity in human kidney and serum, suggesting the existence of the hormone in mammals. Olsen et al. (1996) isolated a human cDNA clone encoding the mammalian homolog of STC. Human STC was found to be 247 amino acids long and to share 73% amino acid sequence similarity with fish STC. Polyclonal antibodies to recombinant human STC localized to a distinct cell type in the nephron tubule, suggesting kidney as a possible site of synthesis. Recombinant human STC inhibited the gill transport of calcium when administered to fish and stimulated renal phosphate reabsorption in the rat.

Full details of the abovementioned studies are described in the following publications, the disclosure of which are hereby incorporated by reference:

Olsen H. S.; Cepeda, M. A.; Zhang, Q. -Q.; Rosen, C. A.; Vozzolo, B. L.; Wagner, G. F.: Human stanniocalcin: a possible hormonal regulator of mineral metabolism. Proc. Nat. Acad. Sci. 93: 1792-1796, 1996. PubMed ID: 8700837 6. Wagner, G. F.; Guiraudon, C. C.; Milliken, C.; Copp, D. H.: Immunological and biological evidence for a stanniocalcin-like hormone in human kidney. Proc. Nat. Acad. Sci. 92: 1871-1875, 1995.

Further studies establishing the function and utilities of STC1 are found in John Hopkins OMIM database record ID 601185, and in references numbered 1456-1463 listed hereinbelow.

Referring now to STC1 BINDING SITE. Stanniocalcin 1 (STC1) is a target gene GAM26, corresponding to GAM26-TARGET GENE of FIG. 26A. STC1 BINDING SITE is a binding site found in an untranslated region of STC1, corresponding to BINDING SITE of FIG. 26A. FIG. 26D illustrates the complementarity of the nucleotide sequence of STC1 BINDING SITE, designated SEQ ID:381506, to the nucleotide sequence of GAM26 RNA of FIG. 26A, designated SEQ ID:20604.

Another function of GAM26 is therefore inhibition of stanniocalcin 1 (STC1), a gene which encodes a protein that stimulates renal phosphate reabsorption, and could therefore prevent hypercalcemia. Accordingly, utilities of GAM26 include diagnosis and treatment of the abovementioned diseases and clinical conditions. The function and utilities of STC1 have been established by previous studies, as described hereinabove with reference to FIG. 26D.

Referring now to STC1 BINDING SITE. Stanniocalcin 1 (STC1) is a target gene of GAM26, corresponding to GAM26-TARGET GENE of FIG. 26A. STC1 BINDING SITE is a binding site found in an untranslated region of STC1, corresponding to BINDING SITE of FIG. 26A. FIG. 26D illustrate the complementarity of the nucleotide sequence of STC1 BINDING SITE, designated SEQ ID:381507, to the nucleotide sequence of GAM26 RNA of FIG. 26A, designated SEQ ID:20604.

Yet another function of GAM26 is therefore inhibition of stanniocalcin 1 (STC1), a gene which encodes a protein that stimulates renal phosphate reabsorption, and could therefore prevent hypercalcemia. Accordingly, utilities of GAM26 include diagnosis and treatment of the abovementioned diseases and clinical conditions. The function and utilities of STC1 have been established by previous studies, as described hereinabove with reference to FIG. 26D.

Referring now to STAR BINDING SITE. Steroidogenic acute regulatory protein (STAR) is a target gene of GAM26, corresponding to GAM26-TARGET GENE of FIG. 26A. STAR BINDING SITE is a binding site found in an untranslated region of STAR, corresponding to BINDING SITE of FIG. 26A. FIG. 26D illustrates the complementarity of the nucleotide sequence of STAR BINDING SITE, designated SEQ ID:381508, to the nucleotide sequence of GAM26 RNA of FIG. 26A, designated SEQ ID:20604.

An additional function of GAM26 is therefore inhibition of steroidogenic acute regulatory protein (STAR), a gene which encodes a protein that is associated with congenital lipoid a renal hyperplasia (clah). Accordingly, utilities of GAM26 include diagnosis and treatment of the abovementioned diseases and clinical conditions. The function and utilities of STAR have been established by previous studies, as described hereinabove with reference to FIG. 26D.

Referring now to STC1 BINDING SITE. Stanniocalcin 1 (STC1) is a target gene of GAM26, corresponding to GAM26-TARGET GENE of FIG. 26A. STC1 BINDING SITE is a binding site found in an untranslated region of STC1, corresponding to BINDING SITE of FIG. 26A. FIG. 26D illustrates the complementarity of the nucleotide sequence of STC1 BINDING SITE, designated SEQ ID:381508, to the nucleotide sequence of GAM26 RNA of FIG. 26A, designated SEQ ID:20604.

A further function of GAM26 is therefore inhibition of stanniocalcin 1 (STC1), a gene which encodes a protein that stimulates renal phosphate reabsorption, and could therefore prevent hypercalcemia. Accordingly, utilities of GAM26 include diagnosis and treatment of the abovementioned diseases and clinical conditions. The function and utilities of STC1 have been established by previous studies, as described hereinabove with reference to FIG. 26D.

Reference is now made to SYK BINDING SITE. Spleen tyrosine kinase (SYK) is a target gene of GAM26, corresponding to GAM26-TARGET GENE of FIG. 26A. SYK BINDING SITE is a binding site found in an untranslated region of SYK, corresponding to BINDING SITE of FIG. 26A. FIG. 26D illustrates the complementarity of the nucleotide sequence of SYK BINDING SITE, designated SEQ ID:384918, to the nucleotide sequence of GAM26 RNA of FIG. 26A, designated SEQ ID:20604.

Yet a further function of GAM26 is therefore inhibition of spleen tyrosine kinase (SYK), a gene which encodes a protein that may participate in signaling pathways and play a role in lymphocyte activation. Accordingly, utilities of GAM26 include diagnosis and treatment of the abovementioned diseases and clinical conditions.

The function of SYK has been established by previous studies. The pig protein-tyrosine kinase SYK, with a relative molecular mass of 72,000, was first described as a protein predominantly expressed in the spleen and thymus (Zioncheck et al., 1988). The nucleotide and deduced amino acid sequence indicated that SYK is a member of the family of nonreceptor type kinases (Taniguchi et al., 1991). Muller et al. (1994) cloned the human homolog. They found an open reading frame of 1,890 bp encoding a protein of 630 amino acids, in comparison with the pig SYK of 628 amino acids. In the human protein the N-terminal SH2 domain spans amino acids 10-102, the C-terminal SH2 domain spans amino acids 163-254, and the kinase domain includes amino acids 366-621. On the amino acid level, the overall similarity between human and pig SYK is 93%. The similarity was highest in the kinase domain.

Animal model experiments lend further support to the function of SYK. Colucci et al. (2002) noted that humans with mutations in ZAP70 have T-cell immunodeficiency, that mice lacking Zap70 have blocked T-cell development, and that mice lacking Syk have a failure of B-cell development. NK cells express both molecules, which associate with immunoreceptor tyrosine-based activation motifs (ITAMs). Using mice deficient in both Zap70 and Syk, Colucci et al. (2002) observed NK cell activity comparable to that in wildtype mice. The mutant cells expressed Nkg2d (602893) and were able to lyse targets with and without Nkg2d ligands in vitro and in vivo. However, wildtype cells, but not the double-deficient cells, responded to CD16 (146740) and Ly49d (see 604274) cross-linking with increased cytotoxicity, suggesting that these 2 ITAM-bearing receptors are unable to signal in the mutant cells. Inhibitors of PI3K (see 601232) or Src kinases blocked and, in combination, abrogated cytotoxic activity in the mutant cells, whereas inhibition of both kinases was required to reduce wildtype NK activity. Colucci et al. (2002) concluded that intracellular signaling in the adaptive immune system, i.e., in B and T cells, is fundamentally different from that in the NK cells of the innate immune system.

It is appreciated that the abovementioned animal model for SYK is acknowledged by those skilled in the art as a scientifically valid animal model, as can be further appreciated from the publications sited hereinbelow.

Full details of the abovementioned studies are described in the following publications, the disclosure of which are hereby incorporated by reference:

Colucci, F.; Schweighoffer, E.; Tomasello, E.; Turner, M.; Ortaldo, J. R.; Vivier, E.; Tybulewicz, V. L. J.; Di Santo, J. P.: Natural cytotoxicity uncoupled from the Syk and ZAP-70 intracellular kinases. Nature Immun. 3: 288-294, 2002. PubMed ID: 11836527 6. Muller, B.; Cooper, L.; Terhorst, C.: Molecular cloning of the human homologue to the pig protein-tyrosine kinase syk. Immunogenetics: 9: 359-362, 1994.

Further studies establishing the function and utilities of SYK are found in John Hopkins OMIM database record ID 600085, and in references numbered 1464-1472 listed hereinbelow.

Reference is now made to SYNGR2 BINDING SITE. Synaptogyrin 2 (SYNGR2) is a target gene of GAM26, corresponding to GAM26-TARGET GENE of FIG. 26A, SYNGR2 BINDING SITE is a binding site found in an untranslated region of SYNGR2, corresponding to BINDING SITE of FIG. 26A. FIG. 26D illustrates the complementarity of the nucleotide sequence of SYNGR2 BINDING SITE, designated SEQ ID:385461, to the nucleotide sequence of GAM26 RNA of FIG. 26A, designated SEQ ID:20604.

Another function of GAM26 is therefore inhibition of synaptogyrin 2 (SYNGR2), a gene which encodes a protein that may play a role in regulating membrane traffic in non-neuronal cells. Accordingly, utilities of GAM26 include diagnosis and treatment of the abovementioned diseases and clinical conditions.

The function of SYNGR2 has been established by previous studies. Synaptic vesicles represent specialized secretory organelles that store neurotransmitters in nerve terminals, and release them by fusing with the presynaptic plasma membrane during exocytosis. Synaptogyrin (SYNGR1; 603925) and synaptophysins I (see 313475) and II (synaptoporin) contain 4 transmembrane regions with cytoplasmic C and N termini, and are among the most abundant synaptic vesicle proteins. Janz and Sudhof (1998) identified a rat gene encoding cellugyrin, a protein related to synaptogyrin. Western blot analysis revealed that cellugyrin and synaptogyrin are expressed in mirror-image patterns in rat tissues: cellugyrin is ubiquitous with the lowest levels in brain, while synaptogyrin is detectable only in the brain. Subcellular fractionation of rat brain cells indicated that both synaptogyrin and cellugyrin are associated with microsomes; however, only synaptogyrin is found in synaptic vesicles. The authors suggested that synaptogyrin is a specialized version of the ubiquitous cellugyrin, supporting the concept that synaptic vesicles are a simplified and specialized form of a generic trafficking organelle. Independently, Kedra et al. (1998) identified cDNAs encoding the mouse and human homologs of cellugyrin, which they called synaptogyrin-2 (SYNGR2). Like SYNGR1, the predicted 224-amino a id human SYNGR2 protein contains 4 transmembrane regions. Northern blot analysis revealed that the 1.6 kb SYNGR2 mRNA was expressed at high levels in all tissues tested except brain.

Full details of the abovementioned studies are described in the following publications, the disclosure of which are hereby incorporated by reference:

Janz, R.; Sudhof, T. C.: Cellugyrin, a novel ubiquitous form of synaptogyrin that is phosphorylated by pp60(c-src). J. Biol. Chem. 273: 2851-2857, 1998. PubMed ID: 9446595
2. Kedra, D.; Pan, H. -Q.; Seroussi, E.; Fransson, I.; Guilbaud, C.; Collins, J. E.; Dunham, I.; Blennow, E.; Roe, B. A.; Piehl, F.; Dumanski, J. P.: Characterization of the synaptogyrin gene family. Hum. 103: 131-141, 1998.

Further studies establishing the function and utilities of SYNGR2 are found in John Hopkins OMIM database record ID 603926, and in references 1473-1474 listed hereinbelow.

Referring now to SYNGR2 BINDING SITE. Synaptogyrin 2 (SYNGR2) is a target gene of GAM26, corresponding to GAM26-TARGET GENE of FIG. 26A. SYNGR4 BINDING SITE is a binding site found in an untranslated region of SYNGR2, corresponding to BINDING SITE of FIG. 26A. FIG. 26D illustrates the complementarity of the nucleotide sequence of SYNGR2 BINDING SITE, designated SEQ ID:385484, to the nucleotide sequence of GAM26 RNA of FIG. 26A, designated SEQ ID:20604.

Yet another function of GAM26 is therefore inhibition of synaptogyrin 2 (SYNGR2), a gene which encodes a protein that may play a role in regulating membrane traffic in non-neuronal cells. Accordingly, utilities of GAM26 include diagnosis and treatment of the abovementioned diseases and clinical conditions. The function and utilities of SYNGR2 have been established by previous studies, as described hereinabove with reference to FIG. 26D.

Referring now to SYNGR2 BINDING SITE. Synaptogyrin 2 (SYNGR2) is a target gene of GAM26, corresponding to GAM26-TARGET GENE of FIG. 26A. SYNGR2 BINDING SITE is a binding site found in an untranslated region of SYNGR2, corresponding to BINDING SITE of FIG. 26A. FIG. 26D illustrates the complementarity of the nucleotide sequence of SYNGR2 BINDING SITE, designated SEQ ID:385485, to the nucleotide sequence of GAM26 RNA of FIG. 26A, designated SEQ ID:20604.

An additional function of GAM26 is therefore inhibition of synaptogyrin 2 (SYNGR2), a gene which encodes a protein that may play a role in regulating membrane traffic in non-neuronal cells. Accordingly, utilities of GAM26 include diagnosis and treatment of the abovementioned diseases and clinical conditions. The function and utilities of SYNGR2 have been established by previous studies, as described hereinabove with reference to FIG. 26D.

Reference is now made to TBL3 BINDING SITE. Transducin (beta)-like 3 (TBL3) is a target gene of GAM26, corresponding to GAM26-TARGET GENE of FIG. 26A. TBL3 BINDING SITE is a binding site found in an untranslated region of TBL3, corresponding to BINDING SITE of FIG. 26A. FIG. 26D illustrates the complementarity of the nucleotide sequence of TBL3 BINDING SITE, designated SEQ ID:388909, to the nucleotide sequence of GAM26 RNA of FIG. 26A, designated SEQ ID:20604.

A further function of GAM26 is therefore inhibition of transducin (beta)-like 3 (TBL3), a gene which encodes a protein that belongs to members of the beta-transducin superfamily. Accordingly, utilities of GAM26 include diagnosis and treatment of the abovementioned diseases and clinical conditions.

The function of TBL3 has been established by previous studies. Weinstat-Saslow et al. (1993) isolated cDNAs that map to chromosome 16p in the region of the autosomal dominant polycystic kidney disease locus (601313). Sequence analysis of one of these cDNAs, TBL3, which was designated SAZD by the authors, revealed a similarity to members of the beta-transducin superfamily. The full-length TBL3 cDNA encodes a 519-amino acid protein with 7 WD40 (beta-transducin) motifs, each of which contains 40 to 45 amino acids with an invariant tryptophan residue. TBL3 shares 18 to 25% sequence identity with G protein beta subunits, with homology occurring predominantly in the conserved repeated WD40 motifs. By somatic cell and radiation hybrid analyses, Weinstat-Saslow et al. (1993) assigned the TBL3 gene to chromosome 16p13.3.

Full details of the abovementioned studies are described in the following publications, the disclosure of which are hereby incorporated by reference:

Weinstat-Saslow, D. L.; Germino, G. G.; Somlo, S.; Reeders, S. T.: A transducin-like gene maps to the autosomal dominant polycystic kidney disease gene region. Genomics 18: 709-711, 1993.

Further studies establishing the function and utilities of TBL3 are found in John Hopkins OMIM database record ID 605915, and in references numbered 1475 listed hereinbelow.

Reference is now made to TCF4 BINDING SITE. Transcription factor 4 (TCF4) is a target gene of GAM26, corresponding to GAM26-TARGET GENE of FIG. 26A. TCF4 BINDING SITE is a binding site found in an untranslated region of TCF4, corresponding to BINDING SITE of FIG. 26A. FIG. 26D illustrates the complementarity of the nucleotide sequence of TCF4 BINDING SITE, designated SEQ ID:390926, to the nucleotide sequence of GAM RNA of FIG. 26A, designated SEQ ID:20604.

Yet a further function of GAM26 is therefore inhibition of transcription factor 4 (TCF4), a gene which encodes a protein that is a transcriptional activator; interacts with ITF1 (TCF3); and contains basic helix-loop-helix domain. Accordingly, utilities of GAM26 include diagnosis and treatment of the abovementioned diseases and clinical conditions.

The function of TCF4 has been established by previous studies. The high mobility group (HMG) box is a DNA-binding domain. TCF7 (189908), also called TCF1; and LEF1 (153245), also called TCF1-alpha, are human lymphoid transcription factors that contain a virtually identical HMG box. By PCR of human genomic DNA using degenerate oligonucleotides based on the HMG boxes of TCF7 and LEF1, Castrop et al. (1992) identified the TCF7L1 (604652) and TCF7L2 genes, which they called TCF3 and TCF4, respectively. TCF7L1 and TCF7L2 were not expressed in cells of the lymphoid lineage. The deduced amino acid sequences of the HMG boxes of TCF7L1, TCF7L2, and TCF7 show striking homology. The authors suggested the existence of a subfamily of TCF7-like HMG box-containing transcription factors.

Animal model experiments lend further support to the function of TCF4. To study the physiologic role of Tcf4 (which is encoded by the Tcf7l2 gene), Korinek et al. (1998) disrupted Tcf7l2 by homologous recombination. The homozygous null mice died shortly after birth. A single histopathologic abnormality was observed. An apparently normal transition of intestinal endoderm into epithelium occurred at approximately embryonic day (E) 14.5. However, no proliferative compartments were maintained in the prospective crypt regions between the villi. As a consequence, the neonatal epithelium was composed entirely of differentiated, nondividing villus cells. Korinek et al. (1998) concluded that the genetic program controlled by Tcf712 maintains the crypt stem cells of the small intestine. The constitutive activity of Tcf4 in APC-deficient epithelial cells may contribute to their malignant transformation by maintaining stem cell characteristics.

It is appreciated that the abovementioned animal model for TCF4 is acknowledged by those skilled in the art as a scientifically valid animal model, as can be further appreciated from the publications sited hereinbelow.

Full details of the abovementioned studies are described in the following publications, the disclosure of which are hereby incorporated by reference:

Castrop, J.; van Norren, K.; Clevers, H.: A gene family of HMG-box transcription factors with homology to TCF-1. Nucleic Acids Res. 20: 611 only, 1992. PubMed ID: 1741298 5. Korinek, V.; Barker, N.; Moerer, P.; van Donselaar, E.; Huls, G.; Peters, P. J.; Clevers, H.: Depletion of epithelial stem cell compartments in the small intestine of mice lacking Tcf-4. Nature Genet 19: 379-383, 1998.

Further studies establishing the function and utilities of TCF4 are found in John Hopkins OMIM database record ID 602228, and in references numbered 1477-1478, 1478, 1480, 1483-1484, 1484, 1486-1487, 1487-1488 and 1488 listed hereinbelow.

Referring now to TCF4 BINDING SITE. Transcription factor 4 (TCF4) is a target gene of GAM26, corresponding to GAM26-TARGET GENE of FIG. 26A. TCF4 BINDING SITE is a binding site found in an untranslated region of TCF4, corresponding to BINDING SITE of FIG. 26A. FIG. 26D illustrates the complementarity of the nucleotide sequence of TCF4 BINDING SITE, designated SEQ ID:390929, to the nucleotide sequence of GAM26 RNA of FIG. 26A, designated SEQ ID:20604.

Another function of GAM26 is therefore inhibition of transcription factor 4 (TCF4), a gene which encodes a protein that is a transcriptional activator; interacts with ITF1 (TCF3); and contains basic helix-loop-helix domain. Accordingly, utilities of GAM26 include diagnosis and treatment of the abovementioned diseases and clinical conditions. The function and utilities of TCF4 have been established by previous studies, as described hereinabove with reference to FIG. 26D.

Referring now to TCF4 BINDING SITE. Transcription factor 4 (TCF4) is a target gene of GAM26, corresponding to GAM26-TARGET GENE of FIG. 26A. TCF4 BINDING SITE is a binding site found in an untranslated region of TCF4, corresponding to BINDING SITE of FIG. 26A. FIG. 26D illustrates the complementarity of the nucleotide sequence of TCF4 BINDING SITE, designated SEQ ID:390953, to the nucleotide sequence of GAM26 RNA of FIG. 26A, designated SEQ ID:20604.

Yet another function of GAM26 is therefore inhibition of transcription factor 4 (TCF4), a gene which encodes a protein that is a transcriptional activator; interacts with ITF1 (TCF 3); and contains basic helix-loop-helix domain. Accordingly, utilities of GAM26 include diagnosis and treatment of the abovementioned diseases and clinical conditions. The function and utilities of TCF4 have been established by previous studies, as described hereinabove with reference to FIG. 26D.

Referring now to TCF4 BINDING SITE. Transcription factor 4 (TCF4) is a target gene of GAM26, corresponding to GAM26-TARGET GENE of FIG. 26A. TCF4 BINDING SITE is a binding site found in an untranslated region of TCF4, corresponding to BINDING SITE of FIG. 26A. FIG. 26D illustrates the complementarity of the nucleotide sequence of TCF4 BINDING SITE, designated SEQ ID:390956, to the nucleotide sequence of GAM26 RNA of FIG. 26A, designated SEQ ID:20604.

An additional function of GAM26 is therefore inhibition of transcription factor 4 (TCF4), a gene which encodes a protein that is a transcriptional activator; interacts with ITF1 (TCF3); and contains basic helix-loop-helix domain. Accordingly, utilities of GAM26 include diagnosis and treatment of the abovementioned diseases and clinical conditions. The function and utilities of TCF4 have been established by previous studies, as described hereinabove with reference to FIG. 26D.

Reference is now made to THOP1 BINDING SITE. Thimet oligopeptidase 1 (THOP1) is a target gene of GAM26, corresponding to GAM26-TARGET GENE of FIG. 26A. THOP1 BINDING SITE is a binding site found in an untranslated region of THOP1, corresponding to BINDING SITE of FIG. 26A. FIG. 26D illustrates the complementarity of the nucleotide sequence of THOP1 BINDING SITE, designated SEQ ID:396604, to the nucleotide sequence of GAM26 RNA of FIG. 26A, designated SEQ ID:20604.

A further function of GAM26 is therefore inhibition of thimet oligopeptidase 1 (THOP1), a gene which encodes an enzyme that involves in the metabolism of neuropeptide and in cytoplasmic peptide degradation. Accordingly, utilities of GAM26 include diagnosis and treatment of the abovementioned diseases and clinical conditions.

The function of THOP1 has been established by previous studies. Papastoitsis et al. (1994) purified and characterized the metalloprotease from human Alzheimer disease brain that is able to cleave a synthetic peptide encompassing the amino-terminus of amyloid beta peptide and generate amyloidogenic fragments from recombinant human APP. Sequence comparison revealed that this enzyme has high homology to the previously described rat metalloendopeptidase 24.15 (EC 3.4.24.15). The beta-secretase-like activity of the human enzyme in vitro in combination with its localization in neurons its co-localization with APP in transport vesicles purified from rabbit optic nerve rendered this enzyme an interesting candidate for amyloidogenic processing of APP. Using a cDNA encoding the rat enzyme, Meckelein et al. (1996) assigned the human gene, symbolized THOP1, to chromosome 19 by hybridization to DNA from human/rodent somatic cell hybrids. By fluorescence in situ hybridization, they localized the gene to 19q13.3. However, after localizing the THOP1 gene to the high-resolution cosmid contig map of human chromosome 19, Torres et al. (1998) found that the FISH mapping to 19q13.3 by Meckelein et al. (1996) was incorrect. Results of the hybridization and FISH mapping of positive clones indicated localization of THOP1 to 19p13.3, thus excluding THOP1 as a candidate gene for AD2.

Full details of the abovementioned studies are described in the following publications, the disclosure of which are hereby incorporated by reference:

Papastoitsis, G.; Siman, R.; Scott, R.; Abraham, C. R.: Identification of a metalloprotease from Alzheimer's disease brain able to degrade the beta-amyloid precursor protein and generate amyloidogenic fragments. Biochemistry 33: 192-199, 1994. PubMed ID: 8286339 1. Meckelein, B.; Rohan de Silva, H. A.; Roses, A. D.; Rao, P. N.; Pettenati, M. J.; Xu, P. -T.; Hodge, R.; Glucksman, M. J.; Abraham, C. R.: Human endopeptidase (THOP1) is localized on chromosome 19 within the linkage region for the late-onset Alzheimer disease AD2 locus. Genomics 31: 246-249, 1996.

Further studies establishing the function and utilities of THOP1 are found in John Hopkins OMIM database record ID 601117, and in references numbered 1489-1491 listed hereinbelow.

Reference is now made to TIF1 BINDING SITE. Transcriptional intermediary factor 1 (TIF1) is a target gene of GAM26, corresponding to GAM26-TARGET GENE of FIG. 26A. TIF1 BINDING SITE is a binding site found in an untranslated region of TIF1, corresponding to BINDING SITE of FIG. 26A. FIG. 26D illustrates the complementarity of the nucleotide sequence of TIF1 BINDING SITE, designated SEQ ID:397065, to the nucleotide sequence of GAM26 RNA of FIG. 26A, designated SEQ ID:20604.

Yet a further function of GAM26 is therefore inhibition of transcriptional intermediary factor 1 (TIF1), a gene which encodes a transcription factor that mediates the activation function (AF-2) of nuclear estrogen receptor. Accordingly, utilities of GAM26 include diagnosis and treatment of the abovementioned diseases and clinical conditions.

The function of TIF1 has been established by previous studies. Hormonal regulation of gene activity is mediated by nuclear receptors acting as ligand-activated transcription factors. The activity of the ligand-dependent activation function, or AF2, of the receptors requires intermediary factors that interact with the AF2-activating domain, a C-terminal region that is highly conserved in the nuclear receptor family. Thenot et al. (1997) isolated human breast cancer cell cDNAs that encode transcription intermediary factor-1 (TIF1), a protein that is able to bind to the AF2-activating domain of the estrogen receptor (ESR; e.g., 133430). The deduced 1,013-amino acid TIF1 protein, which is more than 92% conserved with mouse Tif1, contains several domains: a RING finger, B-box fingers, a coiled-coil domain, a PHD homeodomain finger, and a bromodomain. A 26-amino acid region of TIF1 is sufficient for its hormone-dependent binding to the ESR. Thenot et al. (199% demonstrated that the AF2-activating domain of ESR is required but not sufficient for the binding of TIF1, that TIF1 association with DNA-bound ESR requires the presence of estradiol, and that TIF1 interacts selectively with different nuclear receptors. The authors identified a cDNA variant that encodes a TIF1 isoform containing a 34-amino acid insertion. Northern blot analysis detected a major 4.5-kb transcript in MCF7 breast cancer cells. Fusion of PML (102578) and TIF1A to RARA (180240) and BRAF (164757), respectively, results in the production of PML RAR-alpha and TIF1-alpha-B-RAF (T18) oncoproteins. Zhong et al. (1999) showed that PML, TIF1-alpha, and RXR-alpha (180245)/RAR-alpha function together in a retinoic acid-dependent transcription complex. Zhong et al. (1999) found that PML acts as a ligand-dependent coactivator of RXR-alpha/RARA-alpha. PML interacts with TIF1-alpha and CREB-binding protein (CBP; 600140). In PML −/− cells, the retinoic acid-dependent induction of genes such as RARB2 and the ability of TIF1-alpha and CBP to act as transcriptional coactivators on retinoic acid are impaired. Zhong et al. (1999) showed that both PML and TIF1-alpha are growth suppressors required for the growth-inhibitory activity of retinoic acid. T18, similar to PML-RAR-alpha, disrupts the retinoic acid-dependent activity of this complex in a dominant-negative manner, resulting in a growth advantage. PML-RAR-alpha was the first example of an oncoprotein generated by the fusion of 2 molecules participating in the same pathway, specifically the fusion of a transcription factor to one of its own cofactors. Since the PML and RAR-alpha pathways converge at the transcriptional level, there is no need for a double-dominant-negative product to explain the pathogenesis of acute promyelocytic leukemia, or APL. Beckstead et al. (2001) found that the *Drosophila* 'bonus' (bon) gene encodes a homolog of the vertebrate TIF1 transcriptional cofactors. Bon is required for male viability, molting, and numerous events in metamorphosis, including leg elongation, bristle development, and pigmentation. Most of these processes are associated with genes that are implicated in the ecdysone pathway, a nuclear hormone receptor pathway required throughout *Drosophila* development. Bon is associated with sites on the polytene chromosomes and can interact with numerous *Drosophila* nuclear receptor proteins. In vivo, bon behaves as a transcriptional inhibitor.

Full details of the abovementioned studies are described in the following publications, the disclosure of which are hereby incorporated by reference:

Zhong, S.; Delva, L.; Rachez, C.; Cenciarelli, C.; Gandini, D.; Zhang, H.; Kalantry, S.; Freedman, L. P.; Pandolfi, P. P.: A RA-dependent, tumour-growth suppressive transcription complex is the target of the PML-RAR-alpha and T18 oncoproteins. Nature Genet 23: 287-295, 1999. PubMed ID: 106101771. Beckstead, R.; Ortiz, J. A.; Sanchez, C.; Prokopenko, S. N.; Chambon, P.; Losson, R.; Bellen, H. J.: Bonus, a *Drosophila* homolog of TIF1 proteins, interacts with nuclear receptors and can inhibit beta-FTZ-F1-dependent transcription. Molec. Cell 7: 753-765, 2001.

Further studies establishing the function and utilities of TIF1 are found in John Hopkins OMIM database record ID 603406, and in references numbered 1492-1497 listed hereinbelow.

Reference is now made to TIMP3 BINDING SITE. Tissue inhibitor of metalloproteinase 3 (Sorsby fundus dystrophy, pseu (TIMP3) is a target gene of GAM26, corresponding to GAM26-TARGET GENE of FIG. 26A. TIMP3 BINDING SITE is a binding site found in an untranslated region of TIMP3, corresponding to BINDING SITE of FIG. 26A. FIG. 26D illustrates the complementarity of the nucleotide sequence of TIMP3 BINDING SITE, designated SEQ ID:397666, to the nucleotide sequence of GAM26 RNA of FIG. 26A, designated SEQ ID:20604.

Another function of GAM26 is therefore inhibition of tissue inhibitor of metalloproteinase 3 (Sorsby fundus dystrophy, pseu (TIMP3), a gene which encodes a protein that is associated with Sorsby's fundus dystrophy. Accordingly, utilities of GAM26 include diagnosis and treatment of the abovementioned diseases and clinical conditions.

The function of TIMP3 has been established by previous studies. Osman et al. (2002) showed that mature dendritic cells (DCs) produce more (120361) than do immature DCs, facilitating their hydroxaminic acid-inhibitable migration through gel in vitro and, presumably, through the extracellular matrix to monitor the antigenic environment in vivo. RT-PCR analysis indicated that the enhanced expression of MMP9 is correlated with a downregulation of TIMP1 and, particularly, TIMP2, while expression of TIMP3 is upregulated. The authors concluded that the balance of MMP and TIMP determines the net migratory capacity of DCs. They proposed that TIMP3 may be a marker for mature DCs. Langton et al. (1998) found that wildtype TIMP3 is localized entirely to the extracellular matrix (ECM) in both its glycosylated (27 kD) and unglycosylated (24 kD) forms. A COOH-terminally truncated TIMP3 molecule was found to be a non-ECM bound matrix metalloproteinase (MMP)

inhibitor, whereas a chimeric TIMP molecule, consisting of the NH2-terminal domain of TIMP2 fused to the COOH-terminal domain of TIMP3, displayed ECM binding, albeit with a lower affinity than the wildtype TIMP3 molecule. Thus, as in TIMP1 and TIMP2, the NH2-terminal domain is responsible for MMP inhibition, whereas the COOH-terminal domain is most important in mediating the specific functions of the molecule. A mutant TIMP3 in which serine-181 was changed to cysteine (188826.0001), found in Sorsby fundus dystrophy, gave rise to an additional 48-kD species (possibly a TIMP3 dimer) that retained its ability to inhibit MMPs and localize to the ECM when expressed in COS-7 cells. These data favored the hypothesis that the TIMP3 mutation seen in Sorsby fundus dystrophy contributes to disease progression by accumulation of mutant protein rather than by loss of functional TIMP3. Weber et al. (1994), who had mapped the gene for Sorsby fundus dystrophy (SFD; 1136900) to 22q13-qter, examined the TIMP3 gene as a possible site of causative mutations in SFD on the basis of its chromosomal location and its pivotal role in extracellular matrix remodeling. They identified point mutations in TIMP3 in affected members of 2 SFD pedigrees. These mutations were predicted to disrupt the tertiary structure and thus the functional properties of the mature protein.

Full details of the abovementioned studies are described in the following publications, the disclosure of which are hereby incorporated by reference:

Osman, M.; Tortorella, M.; Londei, M.; Quaratino, S.: Expression of matrix metalloproteinases and tissue inhibitors of metalloproteinases define the migratory characteristics of human monocyte-derived dendritic cells. Immunology 105: 73-82, 2002. PubMed ID: 11849317 11. Weber, B. H. F.; Vogt, G.; Pruett, R. C.; Stohr, H.; Felbor, U.: Mutations in the tissue inhibitor metalloproteinases-3 (TIMP3) in patients with Sorsby's fundus dystrophy. Nature Genet 8: 352-356, 1994.

Further studies establishing the function and utilities of TIMP3 are found in John Hopkins OMIM database record ID 188826, and in references numbered 1498-1510 listed hereinbelow.

Referring now to TIMP3 BINDING SITE. Tissue inhibitor of metalloproteinase 3 (Sorsby fundus dystrophy, pseu (TIMP3) is a target gene of GAM26, corresponding to GAM26-TARGET GENE of FIG. 26A. TIMP3 BINDING SITE is a binding site found in an untranslated region of TIMP3, corresponding to BINDING SITE of FIG. 26A. FIG. 26D illustrates the complementarity of the nucleotide sequence of TIMP3 BINDING SITE, designated SEQ ID:397672, to the nucleotide sequence of GAM26 RNA of FIG. 26A, designated SEQ ID:20604.

Yet another function of GAM26 is therefore inhibition of tissue inhibitor of metalloproteinase 3 (Sorsby fundus dystrophy, pseu (TIMP3), a gene which encodes a protein that is associated with Sorsby's fundus dystrophy. Accordingly, utilities of GAM26 include diagnosis and treatment of the abovementioned diseases and clinical conditions. The function and utilities of TIMP3 have been established by previous studies, as described hereinabove with reference to FIG. 26D.

Reference is now made to TMPO BINDING SITE. Thymopoietin (TMPO) is a target gene of GAM26, corresponding to GAM26-TARGET GENE of FIG. 26A. TMPO BINDING SITE is a binding site found in an untranslated region of TMPO, corresponding to BINDING SITE of FIG. 26A. FIG. 26D illustrates the complementarity of the nucleotide sequence of TMPO BINDING SITE, designated SEQ ID:400315, to the nucleotide sequence of GAM26 RNA of FIG. 26A, designated SEQ ID:20604.

An additional function of GAM26 is therefore inhibition of thymopoietin (TMPO), a gene which encodes a protein that plays important roles in T-cell development and function. Accordingly, utilities of GAM26 include diagnosis and treatment of the abovementioned diseases and clinical conditions.

The function of TMPO has been established by previous studies. A single TMPO gene encodes 3 thymopoietins: alpha (75 kD), beta (51 kD), and gamma (39 kD). TMPO-alpha is present diffusely throughout the nucleus, whereas TMPOs beta and gamma are localized to the nuclear membrane. Harris et al. (1995) cloned the TMPO gene. The 8 exons of the gene are spread over approximately 35 kb. The 3 isoforms are produced by alternative mRNA splicing. Exon 4, which is spliced into TMPO-alpha mRNA, contains sequences that encode a putative basic nuclear localization motif. Exon 8, which is spliced into TMPO-beta and TMPO-gamma mRNAs, encodes a hydrophobic putative membrane-spanning domain that is thought to target these 2 gene products to the nuclear membrane. Harris et al. (1995) pointed out that TMPO-beta appears to be the human homolog of the rat protein LAP (lamina-associated polypeptide 2), which is thought to play an important role in the regulation of nuclear architecture by binding lamin B1 and chromosomes, in a manner regulated by phosphorylation during mitosis.

Full details of the abovementioned studies are described in the following publications, the disclosure of which are hereby incorporated by reference:

Audhya, T.; Schlesinger, D. H.; Goldstein, G.: Isolation and complete amino acid sequence of human thymopoietin and splenin. Proc. Nat. Acad. Sci. 84: 3545-3549, 1987. PubMed ID: 3473468 3. Harris, C. A.; Andryuk, P. J.; Cline, S. W.; Mathew, S.; Siekierka, J. J.; Goldstein, G.: Structure and mapping of the human thymopoietin (TMPO) gene and relationship of human TMPO beta to rat lamin-associated polypeptide 2. Genomics 28: 198-205, 1995.

Further studies establishing the function and utilities of TMPO are found in John Hopkins OMIM database record ID 188380, and in reference numbered 1511-1513 listed hereinbelow.

Reference is now made to U2AF1 BINDING SITE. U2(RNU2) small nuclear RNA auxiliary factor 1 (non-standard symbol) (U2AF1) is a target gene of GAM26, corresponding to GAM26-TARGET GENE of FIG. 26A. U2AF1 BINDING SITE is a binding site found in an untranslated region of U2AF1, corresponding to BINDING SITE of FIG. 26A. FIG. 26D illustrates the complementarity of the nucleotide sequence of U2AF1 BINDING SITE, designated SEQ ID:411863, to the nucleotide sequence of GAM26 RNA of FIG. 26A, designated SEQ ID:20604.

A further function of GAM26 is therefore inhibition of U2(RNU2) small nuclear RNA auxillary factor 1 (non-standard symbol) (U2AF1), a gene which encodes a protein that plays a critical role in both splicing constitutive and enhancer-dependent splicing. Accordingly, utilities of GAM26 include diagnosis and treatment of the abovementioned diseases and clinical conditions.

The function of U2AF1 has been established by previous studies. In vitro experiments demonstrate that pre-mRNA splicing begins with the assembly of a multicomponent complex on the pre-mRNA. This complex, the spliceosome, contains 2 types of factors: small nuclear ribonucleoprotein particles (snRNPs) and proteins. Binding of U2 snRNP (180690) the pre-mRNA branch site requires, in addition to U2 snRNP itself, U1 snRNP (180680) and at least 3 protein factors: SF1, SF3, and U2 snRNP auxiliary factor (U2AF). Purified HeLa cell U2AF comprises 2 polypeptides of 65 (U2AF65; 191318) and 35 kD. U2AF35 is evolutionarily conserved and copurifies with U2AF65. Zhang et al. (1992) isolated a cDNA encoding U2AF35. They showed directly the interaction between the 65-kD and 35-kD proteins. With anti-peptide antibodies, they showed that the proteins have the same intranuclear location in coiled bodies, subnuclear organelles first identified by light microscopy in 1903. Lalioti et al. (1996) cloned portions of the UAF35 gene, or U2AF1, by exon trapping. The cDNA was then hybridized to a cosmid which maps to 21q22.3 near the cystathionine beta-synthase gene (236200). The map position was confirmed by fluorescence in situ hybridization.

Full details of the abovementioned studies are described in the following publications, the disclosure of which are hereby incorporated by reference:

Zhang, M.; Zamore, P. D.; Carmo-Fonseca, M.; Lamond, A. I.; Green, M. R.: Cloning and intracellular localization of the U2 small nuclear ribonucleoprotein auxiliary factor small subunit. Proc. Nat. Acad. Sci. 89: 8769-8773, 1992. PubMed ID:1388271. Lalioti, M. D.; Gos, A.; Green, M. R.; Rossier, C.; Morris, M. A.; Antonarakis, S. E.: The gene for human U2 snRNP auxiliary factor small 35-kDa subunit (U2AF1) maps to the progressive myoclonus epilepsy (EPM1) critical region on chromosome 21q22.3. Genomics 33: 298-300, 1996.

Further studies establishing the function and utilities of U2AF1 are found in John Hopkins OMIM database record ID 191317, and in references numbered 1514-1517 listed hereinbelow.

Referring now to UBE2B BINDING SITE. Ubiquitin-conjugating enzyme E2B, (RAD6 homolog) (UBE2B) is a target gene of GAM26, corresponding to GAM26-TARGET GENE of FIG. 26A. UBE2B BINDING SITE is a binding site found in an untranslated region of UBE2B, corresponding to BINDING SITE of FIG. 26A. FIG. 26D illustrates the complementarity of the nucleotide sequence of UBE2B BINDING SITE, designated SEQ ID:412149, to the nucleotide sequence of GAM26 RNA of FIG. 26A, designated SEQ ID:20604.

Yet a further function of GAM26 is therefore inhibition of ubiquitin-conjugating enzyme E2B (RAD6 homolog) (UBE2B), a gene which encodes a Enzyme that catalyzes the covalent attachment of ubiquitin to other proteins and is required for postreplication repair of uv-damaged DNA. Accordingly, utilities of GAM26 include diagnosis and treatment of the abovementioned diseases and clinical conditions. The function and utilities of UBE2B have been established by previous studies, as described hereinabove with reference to FIG. 26D.

Referring now to MLLT1 BINDING SITE. Myeloid/lymphoid or mixed-lineage leukemia (trithorax (*Drosophila*) horn (MLLT1) is a target gene of GAM26, corresponding to GAM26-TARGET GENE of FIG. 26A. MLLT1 BINDING SITE is a binding site found in an untranslated region of MLLT1, corresponding to BINDING SITE of FIG. 26A. FIG. 26D illustrates the complementarity of the nucleotide sequence of MLLT1 BINDING SITE, designated SEQ ID:412156, to the nucleotide sequence of GAM26 RNA of FIG. 26A, designated SEQ ID:20604.

Another function of GAM26 is therefore inhibition of myeloid/lymphoid or mixed-lineage leukemia (trithorax (*Drosophila*) horn (MLLT1), a gene which encodes a protein that is associated with acute leukemias. Accordingly, utilities of GAM26 include diagnosis and treatment of the abovementioned diseases and clinical conditions. The function and utilities of MLLT1 have been established by previous studies, as described hereinabove with reference to FIG. 26D.

Referring now to UBE2B BINDING SITE. Ubiquitin-conjugating enzyme E2B (RAD6 homolog) (UBE2B) is a target gene of GAM26, corresponding to GAM26-TARGET GENE of FIG. 26A. UBE2B BINDING SITE is a binding site found in an untranslated region of UBE2B, corresponding to BINDING SITE of FIG. 26A. FIG. 26D illustrates the complementarity of the nucleotide sequence of UBE2B BINDING SITE, designated SEQ ID:412156, to the nucleotide sequence of GAM26 RNA of FIG. 26A, designated SEQ ID:20604.

Yet another function of GAM26 is therefore inhibition of ubiquitin-conjugating enzyme E2B (RAD6 homolog) (UBE2B), a gene which encodes a Enzyme that catalyzes the covalent attachment of ubiquitin to other proteins and is required for postreplication repair of uv-damaged DNA. Accordingly, utilities of GAM26 include diagnosis and treatment of the abovementioned diseases and clinical conditions. The function and utilities of UBE2B have been established by previous studies, as described hereinabove with reference to FIG. 26D.

Referring now to UBE2B BINDING SITE. Ubiquitin-conjugating enzyme E2B (RAD6 homolog) (UBE2B) is a target gene of GAM26, corresponding to GAM26-TARGET GENE of FIG. 26A. UBE2B BINDING SITE is a binding site found in an untranslated region of UBE2B, corresponding to BINDING SITE of FIG. 26A. FIG. 26D illustrates the complementarity of the nucleotide sequence of UBE2B BINDING SITE, designated SEQ ID:412157, to the nucleotide sequence of GAM26 RNA of FIG. 26A, designated SEQ ID:20604.

An additional function of GAM26 is therefore inhibition of ubiquitin-conjugating enzyme E2B(RAD6 homolog) (UBE2B), a gene which encodes a Enzyme that catalyzes the covalent attachment of ubiquitin to other proteins and is required for postreplication repair of uv-damaged DNA. Accordingly, utilities of GAM26 include diagnosis and treatment of the abovementioned diseases and clinical conditions. The function and utilities of UBE2B have been established by previous studies, as described hereinabove with reference to FIG. 26D.

Reference is now made to UFD1L BINDING SITE. Ubiquitin fusion degradation 1-like (UFD1L) is a target gene of GAM26, corresponding to GAM26-TARGET GENE of FIG. 26A. UFD1L BINDING SITE is a binding site found in an untranslated region of UFD1L, corresponding to BINDING SITE of FIG. 26A. FIG. 26D illustrates the complementarity of the nucleotide sequence of UFD1L BINDING SITE, designated SEQ ID:414051, to the nucleotide sequence of GAM26 RNA of FIG. 26A, designated SEQ ID:20604.

A further function of GAM26 is therefore inhibition of ubiquitin fusion degradation 1-like (UFD1L), a gene which encodes a protein that is an essential component of the ubiquitin-dependent proteolytic pathway and is associated with some of the CATCH22-associated developmental defects. Accordingly, utilities of GAM26 include diagnosis and treatment of the abovementioned diseases and clinical conditions.

The function of UFD1L has been established by previous studies. In a search for genes in the 22q11.2 region possibly implicated in the DiGeorge syndrome (188400), Pizutti et al. (1997) identified a gene whose functional features and tissue-specific expression suggested a distinct role in embryogenesis. Symbolized UFD1L by them (for ubiquitin fusion degradation 1-like), the gene encodes the human homolog of the yeast ubiquitin fusion degradation 1 (UFD1) protein that is involved in the degradation of ubiquitin fusion proteins (see 191320). Cloning and characterization of the murine homolog (Ufd1l) showed it to be expressed during embryogenesis in the eyes and in the inner ear primordia. These findings suggested to Pizutti al. (1997) that the proteolytic pathway recognizing ubiquitin fusion proteins for degradation is conserved in vertebrates and that UFD1L gene hemizygosity may be the cause of some of the CATCH22-associated developmental defects. The basic helix-loop-helix transcription factor dHAND (HAND2, 602407) is required for survival of cells in the neural crest-derived branchial and aortic arch arteries and the right ventricle. Mice lacking endothelin-1 (EDN1; 131240) have cardiac and cranial neural crest defects typical of the 22q11 deletion syndrome and display downregulation of dHAND, suggesting that a molecular pathway involving dHAND may be disrupted in that syndrome. The HAND2, EDN1, and ET1 receptor (EDNRA; 131243) genes do not map to 21q11, the DiGeorge syndrome critical region, in humans a screen for mouse genes dependent on dHAND, Yamagishi et al. (1999) identified Ufd1, which maps to human 22q11 and encodes a protein involved in degradation of ubiquitinated proteins. Mouse Ufd1 was specifically expressed in most tissues affected in patients with the DiGeorge (22q11 deletion) syndrome. Yamagishi et al. (1999) found, furthermore that the human UFD1L gene was deleted in all 182 patients studied with the 22q11 deletion, and a smaller deletion of approximately 20 kb that removed exons 1 to 3 of UFD1L was found in 1 individual with features typical of 22q11 deletion syndrome. In the individual with the smaller deletion, patient J. F., Yamagishi et al. (1999) found that the CDC45L gene (603465), which is immediately telomeric of UFD1L, was the site of the deletion in the region between exons 5 and 6 of the 5-prime breakpoint. They considered that the deletion in CDC45L may act as a modifier of the phenotype in patient J. F. UFD1L and CDC45L are transcribed in opposite directions. The deletion left exons 4 to 12 of UFD1L intact; the first 5 exons of CDC45L were deleted. Patient J. F. had nearly all of the features commonly associated with the 2-Mb 22q11 deletion. Four days after birth the patient was diagnosed with interrupted aortic arch, persistent truncus arteriosus, cleft palate, small mouth, low-set ears, broad nasal bridge, neonatal hypocalcemia, T-lymphocyte deficiency, and syndactyly of her toes. The deletion was not present in her parents or in 100 control subjects.

Full details of the abovementioned studies are described in the following publications, the disclosure of which are hereby incorporated by reference:

izutti, A.; Novelli, G.; Ratti, A.; Amati, F.; Mari, A.; Calabrese, G.; Nicolis, S.; Silani, V.; Marino, B.; Scarlato, G.; Ottolenghi, S.; Dallapiccola, B.: UFD1L, a developmentally expressed ubiquitination gene, is deleted in CATCH22 syndrome. Hum. Molec. Genet. 6: 259-265, 1997. PubMed ID: 9063746 2. Yamagishi, H.; Garg, V.; Matsuoka, R.; Thomas, T.; Srivastava, D.: A molecular pathway revealing a genetic basis for human cardiac and craniofacial defects. Science 283: 1158-1161, 1999.

Further studies establishing the function and utilities of UFD1L are found in John Hopkins OMIM database record ID 601754, and in references numbered 1518-1519 listed hereinbelow.

Referring now to UFD1L BINDING SITE. Ubiquitin fusion degradation 1-like (UFD1L) is a target gene of GAM26, corresponding to GAM26-TARGET GENE of FIG. 26A. UFD1L BINDING SITE is a binding site found in an untranslated region of UFD1L, corresponding to BINDING SITE of FIG. 26A. FIG. 26D illustrates the complementarity of the nucleotide sequence of UFD1L BINDING SITE, designated SEQ ID:414052, to the nucleotide sequence of GAM26 RNA of FIG. 26A, designated SEQ ID:20604.

Yet a further function of GAM26 is therefore inhibition of ubiquitin fusion degradation 1-like (UFD1L), a gene which encodes a protein that is an essential component of the ubiquitin-dependent proteolytic pathway and is associated with some of the CATCH22-associated developmental defects. Accordingly, utilities of GAM26 include diagnosis and treatment of the abovementioned diseases and clinical conditions. The function and utilities of UFD1L have been established by previous studies, as described hereinabove with reference to FIG. 26D.

Referring now to UFD1L BINDING SITE. Ubiquitin fusion degradation 1-like (UFD1L) is a target gene of GAM26, corresponding to GAM26-TARGET GENE of FIG. 26A. UFD1L BINDING SITE is a binding site found in an untranslated region of UFD1L, corresponding to BINDING SITE of FIG. 26A. FIG. 26D illustrates the complementarity of the nucleotide sequence of UFD1L BINDING SITE, designated SEQ ID:414064, to the nucleotide sequence of GAM26 RNA of FIG. 26A, designated SEQ ID:20604.

Another function of GAM26 is therefore inhibition of ubiquitin fusion degradation 1-like (UFD1L), a gene which encodes a protein that is essential component of the ubiquitin-dependent proteolytic pathway and is associated with some of the CATCH22-associated developmental defects. Accordingly utilities of GAM26 include diagnosis and treatment of the abovementioned diseases and clinical conditions. The function and utilities of UFD1L have been established by previous studies, as described hereinabove with reference to FIG. 26D.

Reference is now made to UNC119 BINDING SITE. unc119 (C. elegans) homolog (UNC119) is a target gene of GAM26, corresponding to GAM26-TARGET GENE of FIG. 26A. UNC119 BINDING SITE is a binding site found in an untranslated region of UNC119, corresponding to BINDING SITE of FIG. 26A. FIG. 26D illustrates the complementarity of the nucleotide sequence of UNC119 BINDING SITE, designated SEQ ID:414673, to the nucleotide sequence of GAM26 RNA of FIG. 26A, designated SEQ ID:20604.

Yet another function of GAM26 is therefore inhibition of unc119 (C. elegans) homolog (UNC119), a gene which encodes a protein that is expressed in the retina and may play a role in the mechanism of photoreceptor neurotransmitter release through the synaptic vesicle cycle. Accordingly, utilities of GAM26 include diagnosis and treatment of the abovementioned diseases and clinical conditions.

The function of UNC119 has been established by previous studies. Using a subtractive hybridization strategy, Higashide et al. (1996) identified a retina-specific cDNA that they designated HRG4 (human retinal gene-4). Northern blot analysis revealed that the approximately 1.4-kb HRG4 mRNA is expressed specifically in human retina. The authors also cloned a cDNA encoding RRG4, the rat HRG4 homolog. The predicted 240-amino acid human and rat proteins both contain an N-terminal region rich in proline and glycine followed by a region with a mixture of alpha helices, beta sheets, and turns. Sequence comparisons indicated that the proline-glycine domains of RRG4 and HRG4 share only 67% homology, while the rest of the sequence is 100% identical. By in situ hybridization, Higashide et al. (1996) demonstrated that the HRG4 gene is expressed specifically in photoreceptors, both rods and cones, in human retina. In rat, the authors observed high levels of RRG4 expression in the outer retina beginning around postnatal day 5, when the photoreceptors begin to differentiate, and expression increased rapidly to reach the adult level by postnatal day 23. Mutations in the C. elegans unc119 gene lead to defects in locomotion, feeling behavior, and chemosensation. Both Swanson et al. (1998) and Higashide et al. (1998) observed that HRG4 shares strong homology with the C. elegans unc119 protein, leading Swanson et al. (1998) to designate the human protein UNC119. Swanson et al. (1998) stated that a human UNC119 cDNA functionally complemented the C. elegans unc119 mutation. Using immunofluorescence, Higashide et al. (1998) localized HRG4 to the outer plexiform layer of the retina in the synaptic termini of rod and cone photoreceptors. Electron microscopic immunolocalization showed that the protein is present in the cytoplasm and on the presynaptic membranes of the photoreceptor synapses. The authors suggested that HRG4 may play a role in the mechanism of photoreceptor neurotransmitter release through the synaptic vesicle cycle. They noted that the homology of HRG4 and unc119 is consistent with a possible role of HRG4 in the synaptic vesicle cycle, because the broad effects of unc119 on neuronal function are consistent with a defect in neurotransmission.

Full details of the abovementioned studies are described in the following publications, the disclosure of which are hereby incorporated by reference:

Higashide, T.; Murakami, A.; McLaren, M. J.; Inana, G.: Cloning of the cDNA for a novel photoreceptor protein. J. Biol. Chem. 271: 1797-1804, 1996. PubMed ID: 8576185 4. Swanson, D. A.; Chang, J. T.; Campochiaro, P. A.; Zack, D. J.; Valle, D.: Mammalian orthologs of C. elegans unc-119 highly express in photoreceptors. Invest Ophthal. Vis. Sci. 39: 2085-2094, 1998.

Further studies establishing the function and utilities of UNC119 are found in John Hopkins OMIM database record ID 604011, and in referee numbered 1520-1523 listed hereinbelow.

Referring now to UNC119 BINDING SITE. unc119 (C. elegans) homolog (UNC119) is a target gene of GAM26, corresponding to GAM26-TARGET GENE of FIG. 26A. UNC119 BINDING SITE is a binding site found in an untranslated region of UNC119, corresponding to BINDING SITE of FIG. 26A. FIG. 26D illustrates the complementarity of the nucleotide sequence of UNC119 BINDING SITE, designated SEQ ID:414674, to the nucleotide sequence of GAM26 RNA of FIG. 26A, designated SEQ ID:20604.

An additional function of GAM26 is therefore inhibition of unc119 (C. elegans) homolog (UNC119), a gene which encodes a protein that is expressed in the retina and may play a role in the mechanism of photoreceptor neurotransmitter release through the synaptic vesicle cycle. Accordingly, utilities of GAM26 include diagnosis and treatment the abovementioned diseases and clinical conditions. The function and utilities of UNC119 have been established by previous studies, as described hereinabove with reference to FIG. 26D.

Referring now to UNC119 BINDING SITE. unc119 (C. elegans) homolog (UNC119) is a target gene of GAM26, corresponding to GAM26-TARGET GENE of FIG. 26A. UNC119 BINDING SITE is a binding site found in an untranslated region of UNC119, corresponding to BINDING SITE of FIG. 26A. FIG. 26 illustrates the complementarity of the nucleotide sequence of UNC119 BINDING SITE, designated SEQ ID:414696, to the nucleotide sequence of GAM26 RNA of FIG. 26A, designated SEQ ID:20604.

A further function of GAM26 is therefore inhibition of unc119 (C. elegans) homolog (UNC119), a gene which encodes a protein that is expressed in the retina and may play a role in the mechanism of photoreceptor neurotransmitter release through the synaptic vesicle cycle. Accordingly, utilities of GAM26 include diagnosis and treatment of the abovementioned diseases and clinical conditions. The function and utilities of UNC119 have been established by previous studies, as described hereinabove with reference to FIG. 26D.

Reference is now made to USP11 BINDING SITE. Ubiquitin specific protease 11 (USP11) is a target gene of GAM26, corresponding to GAM26-TARGET GENE of FIG. 26A. USP11 BINDING SITE is a binding site found in an untranslated region of USP11, corresponding to BINDING SITE of FIG. 26A. FIG. 26D illustrates the complementarity of the nucleotide sequence of USP11 BINDING SITE, designated SEQ ID:415547, to the nucleotide sequence of GAM26 RNA of FIG. 26A, designated SEQ ID:20604.

Yet a further function of GAM26 is therefore inhibition of ubiquitin specific protease 11 (USP11), a gene which encodes an enzyme that removes ubiquitin from ubiquitin-conjugated proteins. Accordingly, utilities of GAM26 include diagnosis and treatment of the abovementioned diseases and clinical conditions.

The function of USP11 has been established by previous studies. Swanson et al. (1996) used a differential hybridization screen to isolate a novel cDNA from a human retina library. The cDNA encodes a protein of 690 amino acids and has strong homology to the proteins encoded by a variety of ubiquitin hydrolases (p values ranging between 2.4e-265 and 1.4e-13). Swanson et al. (1996) reviewed the role of ubiquitination in protein degradation and presented evidence that disturbances in protein processing and turnover can lead to retinal degeneration. They noted that there are at least 4 X-linked retinal diseases that map to a region within or overlapping the UHX1 interval. They cited evidence indicating that ubiquitin hydrolases play a role in oncogenesis (oncogenes and tumor suppressor gene products are degraded in ubiquitin-dependent pathways) and that the region of loss of heterozygosity in ovarian cancer lies within the mapping interval defined for UHX1. Swanson et al. (1996) mapped the structural gene encoding this cDNA, which they designated UHX1, to Xp21.2-p11.2 by somatic cell hybridization. Stoddart et al. (1999) mapped the UHX1 gene to Xp11.3 by inclusion within a YAC contig Full details of the abovementioned studies are described in the following publications, the disclosure of which are hereby incorporated by reference:

Swanson, D. A.; Freund, C. L.; Ploder, L.; McInnes, R. R.; Valle, D.: A ubiquitin C-terminal hydrolase gene on the proximal short arm of the X chromosome: implications for X-linked retinal disorders. Hum. Molec. Genet. 5: 533-538, 1996. PubMed ID: 8845848 1. Stoddart, K. L.; Jermak, C.; Nagaraja, R.; Schlessinger, D.; Bech-Hansen, N. T.: Physical map covering a 2 Mb region in human Xp11.3 distal to DX6849. Gene 227: 111-116, 1999.

Further studies establishing the function and utilities of USP11 are found in John Hopkins OMIM database record ID 300050, and in references numbered 1524-1525 listed hereinbelow.

Reference is now made to UVRAG BINDING SITE. UV radiation resistance associated gene (UVRAG) is a target gene of GAM26, corresponding to GAM26-TARGET GENE of FIG. 26A. UVRAG BINDING SITE is a binding site found in an untranslated region of UVRAG, corresponding to BINDING SITE of FIG. 26A. FIG. 26D illustrates the complementarity of the nucleotide sequence of UVRAG BINDING SITE, designated SEQ ID:416390, to the nucleotide sequence of GAM26 RNA of FIG. 26A, designated SEQ ID:20604.

Another function of GAM26 is therefore inhibition of UV radiation resistance associated gene (UVRAG), a gene which encodes a protein that confers UV radiation resistance a xeroderma pigmentosum cell line. Accordingly, utilities of GAM26 include diagnosis and treatment of the abovementioned diseases and clinical conditions.

The function of UVRAG has been established by previous studies. Teitz et al. (1990) identified a cDNA that partially complements the ultraviolet (UV) sensitivity of xeroderma pigmentosum complementation group C (see XPC; 278720) cells. Perelman et al. (1997) named this gene 'UV radiation resistance-associated gene' (UVRAG) and reported that the 4.0 kb UVRAG mRNA encodes a predicted 648-amino acid protein. Using cell fractionation studies, they found that the UVRAG protein either is localized within an organelle or is part of the cytoskeleton. Northern blotting showed that UVRAG is expressed ubiquitously in humans; it was also present in most of the vertebrate species tested. By fluorescence in situ hybridization and PCR analysis of somatic cell hybrids, Perelman et al. (1997) mapped the UVRAG gene to 11q13, between D11S916 and D11S906

Full details of the abovementioned studies are described in the following publications, the disclosure of which are hereby incorporated by reference:

Perelman, B.; Dafni, N.; Naiman, T.; Eli, D.; Yaakov, M.; Yang Feng, T. L.; Sinha, S.; Weber, G.; Khodaei, S.; Sancar, A.; Dotan, I.; Canaani, D.: Molecular cloning of a novel human gene encoding a 63-kDa protein and its sublocalization within the 11q13 locus. Genomics 41: 397-405, 1997.

Further studies establishing the function and utilities of UVRAG are found in John Hopkins OMIM database record ID 602493, and in references numbered 1526-1527 listed hereinbelow.

Referring now to UVRAG BINDING SITE. UV radiation resistance associated gene (UVRAG) is a target gene of GAM26, corresponding to GAM26-TARGET GENE of FIG. 26A. UVRAG BINDING SITE is a binding site found in an untranslated region of UVRAG, corresponding to BINDING SITE of FIG. 26A. FIG. 26D illustrates the complementarity of the nucleotide sequence of UVRAG BINDING SITE, designated SEQ ID:416391, to the nucleotide sequence of GAM26 RNA of FIG. 26A, designated SEQ ID:20604.

Yet another function of GAM26 is therefore inhibition of UV radiation resistance associated gene (UVRAG), a gene which encodes a protein that confers UV radiation resistance to a xeroderma pigmentosum cell line. Accordingly, utilities of GAM26 include diagnosis and treatment of the abovementioned diseases and clinical conditions. The function and utilities of UVRAG have been established by previous studies, as described hereinabove with reference to FIG. 26D.

Referring now to UVRAG BINDING SITE. UV radiation resistance associated gene (UVRAG) is a target gene of GAM26, corresponding to GAM26-TARGET GENE of FIG. 26A. UVRAG BINDING SITE is a binding site found in an untranslated region of UVRAG, corresponding to BINDING SITE of FIG. 26A. FIG. 26D illustrates the complementarity of the nucleotide sequence of UVRAG BINDING SITE, designated SEQ ID:416392, to the nucleotide sequence of GAM26 RNA of FIG. 26A, designated SEQ ID:20604.

An additional function of GAM26 is therefore inhibition of UV radiation resistance associated gene (UVRAG), a gene which encodes a protein that confers UV radiation resistance to a xeroderma pigmentosum cell line. Accordingly, utilities of GAM26 include diagnosis and treatment of the abovementioned diseases and clinical conditions. The function and utilities of UVRAG have been established by previous studies, as described hereinabove with reference to FIG. 26D.

Referring now to UVRAG BINDING SITE. UV radiation resistance associated gene (UVRAG) is a target gene of GAM26, corresponding to GAM26-TARGET GENE of FIG. 26A. UVRAG BINDING SITE is a bi ding site found in an untranslated region of UVRAG, corresponding to BINDING SITE of FIG. 26A. FIG. 26D illustrates the complementarity of the nucleotide sequence of UVRAG BINDING SITE, designated SEQ ID:416394, to the nucleotide sequence of GAM26 RNA of FIG. 26A, designated SEQ ID:20604.

A further function of GAM26 is therefore inhibition of UV radiation resistance associated gene (UVRAG), a gene which encodes a protein that confers UV radiation resistance to a xeroderma pigmentosum cell line. Accordingly, utilities of GAM26 include diagnosis and treatment of the abovementioned diseases and clinical conditions. The function and utilities of UVRAG have been established by previous studies, as described hereinabove with reference to FIG. 26D.

Referring now to UVRAG BINDING SITE. UV radiation resistance associated gene (UVRAG) is a target gene of GAM26, corresponding to GAM26-TARGET GENE of FIG. 26A. UVRAG BINDING SITE is a binding site found in an untranslated region of UVRAG, corresponding to BINDING SITE of FIG. 26A. FIG. 26D illustrates the complementarity of the nucleotide sequence of UVRAG BINDING SITE, designated SEQ ID:416396, to the nucleotide sequence of GAM26 RNA of FIG. 26A, designated SEQ ID:20604.

Yet a further function of GAM26 is therefore inhibition of UV radiation resistance associated gene (UVRAG), a gene which encodes a protein that confers UV radiation resistance to a xeroderma pigmentosum cell line. Accordingly, utilities of GAM26 include diagnosis and treatment of the abovementioned diseases and clinical conditions. The function and utilities of UVRAG have been established by previous studies, as described hereinabove with reference to FIG. 26D.

Referring now to UVRAG BINDING SITE. UV radiation resistance associated gene (UVRAG) is a target gene of GAM26, corresponding to GAM26-TARGET GENE of FIG. 26A. UVRAG BINDING SITE is a binding site found in an untranslated region of UVRAG, corresponding to BINDING SITE FIG. 26A. FIG. 26D illustrates the complementarity of the nucleotide sequence of UVRAG BINDING SITE, designated SEQ ID:416411, to the nucleotide sequence of GAM26 RNA of FIG. 26A, designated SEQ ID:20604.

Another function of GAM26 is therefore inhibition of UV radiation resistance associated gene (UVRAG), a gene which encodes a protein that confers UV radiation resistance to a xeroderma pigmentosum cell line. Accordingly, utilities of GAM26 include diagnosis and treatment of the abovementioned diseases and clinical conditions. The function and utilities of UVRAG have been established by previous studies, as described hereinabove with reference to FIG. 26D.

Referring now to UVRAG BINDING SITE. UV radiation resistance associated gene (UVRAG) is a target gene of GAM26, corresponding to GAM26-TARGET GENE of FIG. 26A. UVRAG BINDING SITE is a binding site found in an untranslated region of UVRAG, corresponding to BINDING SITE of FIG. 26A. FIG. 26D illustrates the complementarity of the nucleotide sequence of UVRAG BINDING SITE, designated SEQ ID:416412, to the nucleotide sequence of GAM26 RNA of FIG. 26A, designated SEQ ID:20604.

Yet another function of GAM26 is therefore inhibition of UV radiation resistance associated gene (UVRAG), a gene which encodes a protein that confers UV radiation resistance to a xeroderma pigmentosum cell line. Accordingly, utilities of GAM26 include diagnosis and treatment of the abovementioned diseases and clinical conditions. The function and utilities of UVRAG have been established by previous studies, as described hereinabove with reference to FIG. 26D.

Reference is now made to VAMP5 BINDING SITE. Vesicle-associated membrane protein 5 (myobrevin) (VAMP5) is a target gene of GAM26, corresponding to GAM26-TARGET GENE of FIG. 26A. VAMP5 BINDING SITE is a binding site found in an untranslated region of VAMP5, corresponding to BINDING SITE of FIG. 26A. FIG. 26D illustrates the complementarity of the nucleotide sequence of VAMP5 BINDING SITE, designated SEQ ID:416481, to the nucleotide sequence of GAM26 RNA of FIG. 26A, designated SEQ ID:20604.

An additional function of GAM26 is therefore inhibition of vesicle-associated membrane protein 5 (myobrevin) (VAMP5), a gene which encodes a protein that may participate in trafficking events that are associated with myogenesis. Accordingly, utilities of GAM26 include diagnosis and treatment of the abovementioned diseases and clinical conditions.

The function of VAMP5 has been established by previous studies. By database searching with the mouse synaptobrevin/Vamp2 (185881) sequence as query, Zeng et al. (1998) identified a mouse EST clone for Vamp5. The deduced 102-amino acid protein is predicted to contain a cytoplasmic coiled-coil structure at the N terminus, a hydrophobic domain, and a short hydrophilic C-terminal sequence. Vamp5 shares 33% sequence identity with cellubrevin (VAMP3; 603657) and synaptobrevin/Vamp2. Northern blot analysis detected a major 700-bp transcript in skeletal muscle and heart, with much lower expression in spleen, lung, liver, kidney, and testis, and no expression in brain. An approximately 1.5-kb transcript was detected in testis. By Northern blot analysis of mouse muscle cells in culture, Zeng et al. (1998) found that Vamp5 expression was 8- to 10-fold higher in multinucleated myotubes than in undifferentiated myoblasts. Western blot analysis revealed protein levels 6-fold higher in myotubes than in myoblasts. Immunofluorescence and electron microscopy indicated that Vamp5 localizes to intracellular perinuclear and peripheral vesicular structures of myotubes as well as to the plasma membrane. Vamp5 staining did not colocalize with a Golgi marker, GS28 (GOSR1; 604026), upon treatment of the cell with Golgi-disrupting agents.

Full details of the abovementioned studies are described in the following publications, the disclosure of which are hereby incorporated by reference:

Zeng, Q.; Subramaniam, V. N.; Wong, S. H.; Tang B. L.; Parton, R. G.; Rea, S.; James, D. E.; Hong, W.: A novel synaptobrevin/VAMP homologous protein (VAMP5) is increased during in vitro myogenesis and present in the plasma membrane. Molec. Biol. Cell 9: 2423-2437, 1998.

Further studies establishing the function and utilities of VAMP5 are found in John Hopkins OMIM database record ID 607029, and in references numbered 1528 listed hereinbelow.

Reference is now made to VEGF BINDING SITE. Vascular endothelial growth factor (VEGF) is a target gene of GAM26; corresponding to GAM26-TARGET GENE of FIG. 26A. VEGF BINDING SITE is a binding site found in an untranslated region of VEGF, corresponding to BINDING SITE of FIG. 26A. FIG. 26D illustrates the complementarity of the nucleotide sequence of VEGF BINDING SITE, designated SEQ ID:417797, to the nucleotide sequence of GAM26 RNA of FIG. 26A, designated SEQ ID:20604.

A further function of GAM26 is therefore inhibition of vascular endothelial growth factor (VEGF), a gene which encodes a protein that induces endothelial cell proliferation and vascular permeability and is associated with tumors. Accordingly, utilities of GAM26 include diagnosis and treatment of the abovementioned diseases and clinical conditions.

The function of VEGF has been established by previous studies. To explore the possibility that VEGF and angiopoietins (see ANG2, 60192) collaborate during tumor angiogenesis, Holash et al. (1999) analyzed several different murine and human tumor models. Holash et al. (1999) noted that angiopoietin-1 (ANG1; 601667) was antiapoptotic for cultured endothelial cells and expression of its antagonist angiopoietin-2 was induced in the endothelium of co-opted tumor vessels before their regression. In contrast, marked induct on of VEGF expression occurred much later in tumor progression, in the hypoxic periphery of tumor cells surrounding the few remaining internal vessels, as well as adjacent to the robust plexus of vessels at the tumor margin. Expression of Ang2 in the few surviving internal vessels and in the angiogenic vessels at the tumor margin suggested that the destabilizing action of angiopoietin-2 facilitates the angiogenic action of VEGF at the tumor rim. Holash et al. (1999) implanted rat RBA mammary adenocarcinoma cells into rat brains. Tumor cells rapidly associated with and migrated along cerebral blood vessels. There was minimal upregulation of VEGF. Holash et al. (1999) suggested that a subset of tumors rapidly co-opts existing host vessels to form an initially well vascularized tumor mass. Perhaps as part of a host defense mechanism there is widespread regression of these initially co-opted vessels, leading to a secondarily avascular tumor and a massive tumor cell loss. However, the remaining tumor is ultimately rescued by robust angiogenesis at the tumor margin.

Animal model experiments lend further support to the function of VEGF. De Fraipont et al. (2000) measured the cytosolic concentrations of 3 proteins involved in angiogenesis, namely, platelet-derived endothelial cell growth factor (PDECGF; 131222), VEGFA, and thrombospondin-1 (THBS1; 188060) in a series of 43 human sporadic adrenocortical tumors. The tumors were classified as adenomas, transitional tumors, or carcinomas. PDECGF/thymidine phosphorylase levels were not significantly different among these 3 groups. One hundred percent of the adenomas and 73% of the transitional tumors showed VEGFA concentrations under the threshold value of 107 ng/g protein, whereas 75% of the carcinomas had VEGFA concentrations above this threshold value. Similarly, 89% of the adenomas showed THBS1 concentrations above the threshold value of 57 microg/g protein, whereas only 25% of the carcinomas and 33% of the transitional tumor samples did so. IGF2 (147470) overexpression, a common genetic alteration of adrenocortical carcinomas, was significantly correlated with higher VEGFA and lower THBS1 concentrations. The authors concluded that a decrease in THBS1 expression is an event that precedes an increase in VEGFA expression during adrenocortical tumor progression. The population of premalignant tumors with low THBS1 and normal VEGFA levels could represent a selective target for antiangiogenic therapies.

It is appreciated that the abovementioned animal model for VEGF is acknowledged by those skilled in the art as a scientifically valid animal model, as can be further appreciated from the publications sited hereinbelow.

Full details of the abovementioned studies are described in the following publications, the disclosure of which are hereby incorporated by reference:

Holash, J.; Maisonpierre, P. C.; Compton, D.; Boland, P.; Alexander, C. R.; Zagzag, D.; Yancopoulos, G. D.; Wiegand, S. J.: Vessel cooption, regression, and growth in tumors mediated by angiopoietins and VEGF. Science 284: 1994-1998, 1999. PubMed ID: 10373119 de Fraipont, F.; El Atifi, M.; Gicquel, C.; Bertagna, X.; Chambaz, E. M.; Feige, J. J.: Expression of the angiogenesis markers vascular endothelial growth factor-A, thrombospondin-1, and platelet-derived endothelial cell growth factor in human sporadic adrenocortical tumors: correlation with genotypic alterations. J. Clin. Endocr. Metab. 85: 4734-4741, 2000.

Further studies establishing the function and utilities of VEGF are found in John Hopkins OMIM data base record ID 192240, and in references numbered 1529-1566 listed hereinbelow.

Reference is now made to WHSC1L1 BINDING SITE. Wolf-Hirschhorn syndrome candidate 1-like 1 (WHSC1L1) is a target gene of GAM26, corresponding to GAM26-TARGET GENE of FIG. 26A. WHSC1L1 BINDING SITE is a binding site found in an untranslated region of WHSC1L1, corresponding to BINDING SITE of FIG. 26A. FIG. 26D illustrates the complementarity of the nucleotide sequence of WHSC1L1 BINDING SITE, designated SEQ ID:422800, to the nucleotide sequence of GAM26 RNA of FIG. 26A, designated SEQ ID:20604.

Yet a further function of GAM26 is therefore inhibition of Wolf-Hirschhorn syndrome candidate 1-like 1 (WHSC1L1), a gene which encodes a protein that restores repair of base-base and single-nucleotide insertion-deletion mismatches, and increases the proficiency to process heteroduplexes with insertion-deletion mismatches. Accordingly, utilities of GAM26 include diagnosis and treatment of the abovementioned diseases and clinical conditions.

The function of WHSC1L1 has been established by previous studies. By EST database searching with mouse Nsd1 (606681) and human NSD2 (WHSC1; 602952) as probe and screening of an amnion cell cDNA library, Angrand et al. (2001) cloned a partial sequence for WHSC1L1, which they called NSD3. They obtained the full-length cDNA by 5-prime RACE. The deduced 1,437- amino acid protein contains 2 PWWP domains involved in protein-protein interaction, 5 PHD-type zinc finger motifs found in chromatin-associated proteins, a SAC (SET-associated cys-rich) domain, a SET domain, and a C-terminal C5HCH domain. They also identified a variant, arising from alternative polyadenylation and exon splicing, that encodes a deduced 645-amino acid peptide. The short isoform contains a single PWWP domain. By PCR analysis, Angrand et al. (2001) found the 2 variants, as well as a third, 1,388-amino acid peptide, in HeLa cells. WHSC1L1 shares 68% and 55% identity with mouse Nsd1 (606681) and human WHSC1 (602952), respectively, over a 700-amino acid block containing the SAC, SET, and C5HCH domains. Northern blot analysis detected an 8.5-kb transcript in all tissues examined, with highest expression in brain, heart, and skeletal muscle, and lower expression in liver and lung. Angrand et al. (2001) determined that the WHSC1L1 gene contains 24 exons and spans over 90 kb. By FISH, Angrand et al. (2001) mapped the WHSC1L1 gene to chromosome 8p12. Stec et al. (2001) identified a pseudogene (WHSC1L2P) on chromosome 17q21. Rosati et al. (2002) described fusion between the NUP98 gene (601021) and the NSD3 gene in a patient with acute myeloid leukemia associated with t(8;11)(p11.2;p15). FISH analysis revealed a split of a specific BAC which showed the fusion partner at 8p11.2 to be NSD3.

Full details of the abovementioned studies are described in the following publications, the disclosure of which are hereby incorporated by reference:

Angrand, P. -O.; Apiou, F.; Stewart, A. F.; Dutrillaux, B.; Losson, R.; Chambon, P.: NSD3, a new SET domain-containing gene, maps to 8p12 and is amplified in human breast cancer ell lines. Genomics 74: 79-88, 2001. PubMed ID: 11374904 2. Rosati, R.; La Starza, R.; Veronese, A.; Aventin, A.; Schwienbacher, C.; Vallespi, T.; Negrini, M.; Martelli, M. F.; Mecucci, C.: NUP98 is fused to the NSD3 gene in acute myeloid leukemia associated with t(8;11)(p11.2;p15). Blood 99: 3857-3860, 2002.

Further studies establishing the function and utilities of WHSC1L1 are found in John Hopkins OMIM database record ID 607083, and in references numbered 1567 and 1568 listed hereinbelow.

Referring now to WHSC1L1 BINDING SITE. Wolf-Hirschhorn syndrome candidate 1-like 1 (WHSC1L1) is a target gene of GAM26, corresponding to GAM26-TARGET GENE of FIG. 26A. WHSC1L1 BINDING SITE is a binding site found in an untranslated region of WHSC1L1, corresponding to BINDING SITE of FIG. 26A. FIG. 26D illustrates the complementarity of the nucleotide sequence of WHSC1L1 BINDING SITE, designated SEQ ID:422801, to the nucleotide sequence of GAM26 RNA of FIG. 26A, designated SEQ ID:20604.

Another function of GAM26 is therefore inhibition of Wolf-Hirschhorn syndrome candidate 1-like 1 (WHSC1L1), a gene which encode a protein that restores repair of base-base and single-nucleotide insertion-deletion mismatches, and increases the proficiency to process heteroduplexes with insertion deletion mismatches. Accordingly, utilities of GAM26 include diagnosis and treatment of the abovementioned diseases and clinical conditions. The function and utilities of WHSC1L1 have been established by previous studies, as described hereinabove with reference to FIG. 26D.

Referring now to WHSC1L1 BINDING SITE. Wolf-Hirschhorn syndrome candidate 1-like 1 (WHSC1L1) is a target gene of GAM26, corresponding to GAM26-TARGET GENE of FIG. 26A. WHSC1L1 BINDING SITE is a binding site found in an untranslated region of WHSC1L1, corresponding to BINDING SITE of FIG. 26A. FIG. 26D illustrates the complementarity of the nucleotide sequence of WHSC1L1 BINDING SITE, designated SEQ ID:422875, to the nucleotide sequence of GAM26 RNA of FIG. 26A, designated SEQ ID:20604.

Yet another function of GAM26 is therefore inhibition of Wolf-Hirschhorn syndrome candidate 1-like 1 (WHSC1L1), a gene which encodes a protein that restores repair of base-base and single-nucleotide insertion-deletion mismatches, and increases the proficiency to process heteroduplexes with insertion deletion mismatches. Accordingly, utilities of GAM26 include diagnosis and treatment of the abovementioned diseases and clinical conditions. The function and utilities of WHSC1L1 have been established by previous studies, as described hereinabove with reference to FIG. 26D.

Reference is now made to YWHAH BINDING SITE. Tyrosine 3-monooxygenase/tryptophan 5-monooxygenase activation protein (YWHAH) is a target gene of GAM26, corresponding to GAM26-TARGET GENE of FIG. 26A. YWHAH BINDING SITE is a binding site found in an untranslated region of YWHAH, corresponding to BINDING SITE of FIG. 26A. FIG. 26D illustrates the complementarity of the nucleotide sequence of YWHAH BINDING SITE, designate SEQ ID:426949, to the nucleotide sequence of GAM26 RNA of FIG. 26A, designated SEQ ID:20604.

An additional function of GAM26 is therefore inhibition of tyrosine 3-monooxygenase/tryptophan 5-monooxygenase activation protein (YWHAH), a gene which encodes a protein that activates tyrosine and tryptophan hydroxylases in the presence of and strongly activates protein kinase c. Accordingly, utilities of GAM26 include diagnosis and treatment of the abovementioned diseases and clinical conditions.

The function of YWHAH has been established by previous studies. Protein 14-3-3 is a protein kinase-dependent activator of tyrosine and tryptophan hydroxylases (191290, 191060) and an endogenous inhibitor of protein kinase C (176960). It was first described as a brain-specific bovine protein. It consists of acidic dimeric subunits of about 27 kD. Immunohistochemical analyses showed that the 14-3-3 protein is located exclusively in the cytoplasm of neurons in the cerebral cortex and is axonally transported to the nerve terminals. Electrophoresis and chromatography demonstrated that the 14-3-3 protein exists in at least 7 distinct forms: alpha, beta, gamma, delta, epsilon, zeta, and eta. Watanabe et al. (1994) found mRNA corresponding to an eighth subtype, which they termed theta, in rat brain. The mRNA theta subtype was found in the gray matter of cerebellar cortex and the hippocampus, as well as in white matter where cell bodies of glial cells predominate. In contrast, mRNA of the zeta subtype was distributed widely in the brain gray matter with high levels of transcripts in the neocortex, hippocampus, caudate-putamen, thalamus, cerebellar cortex, and several brain stem nuclei. A human protein with phospholipase A2 activity was shown to be the zeta subtype of the 14-3-3 protein (Zupan et al., 1992). The gene is also symbolized YWHAH. Muratake et al. (1996) determined that the human YWHAH gene has 2 exons separated by an intron of approximately 8 kb. Using S1 nuclease mapping, primer extension, and RACE PCR, Muratake et al. (1996) identified the transcription initiation site. They also identified several regulatory element sequences, including CRE, in the 5-prime noncoding region. Muratake et al. (1996) noted that the presence of a CRE binding element may indicate that this gene is involved in brain responses to narcotics. The authors also found changes in a 7-bp repeat sequence (GCCTGCA) located in the noncoding region of exon 1 and they speculated that these changes, or other changes in the sequence of this gene, may be associated with neuropsychiatric disorders.

Full details of the abovementioned studies are described in the following publications, the disclosure of which are hereby incorporated by reference:

Muratake, T.; Hayashi, S.; Ichikawa, T.; Kumanishi, T.; Ichimura, Y.; Kuwano, R.; Isobe, T.; Wang, Y.; Minoshima, S.; Shimizu, N.; Takahashi, Y.: Structural organization and chromosomal assignment of the human 14-3-3-eta chain gene (YWHAH). Genomics 36: 63-69, 1996. PubMed ID: 8812417 6. Zupan, L. A.; Steffens, D. L.; Berry, C. A.; Landt, M.; Gross, R. W.: Cloning and express on of a human 14-3-3 protein mediating phospholipolysis. J. Biol. Chem. 267: 8707-8710, 1992.

Further studies establishing the function and utilities of YWHAH are found in John Hopkins OMIM database record ID 113508, and in references numbered 1569-1574 listed hereinbelow.

Referring now to ZNF6 BINDING SITE. Zinc finger protein 6 (CMPX1) (ZNF6) is a target gene of GAM26, corresponding to GAM26-TARGET GENE of FIG. 26A. ZNF6 BINDING SITE is a binding site found in an untranslated region of ZNF6, corresponding to BINDING SITE of FIG. 26A. FIG. 26D illustrates the complementarity of the nucleotide sequence of ZNF6 BINDING SITE, designated SEQ ID:432632, to the nucleotide sequence of GAM26 RNA of FIG. 26A, designated SEQ ID:20604.

A further function of GAM26 is therefore inhibition of zinc finger protein 6 (CMPX1) (ZNF6), a gene which encodes a protein that is probably a transcriptional activator. Accordingly, utilities of GAM26 include diagnosis and treatment of the abovementioned diseases and clinical conditions. The function and utilities of ZNF6 have been established by previous studies, as described hereinabove with reference to FIG. 26D.

Referring now to ZNF6 BINDING SITE. Zinc finger protein 6 (CMPX1) (ZNF6) is a target gene of GAM26, corresponding to GAM26-TARGET GENE of FIG. 26A. ZNF6 BINDING SITE is a binding site found in an untranslated region of ZNF6, corresponding to BINDING SITE of FIG. 26A. FIG. 26D illustrates the complementarity of the nucleotide sequence of ZNF6 BINDING SITE, designated SEQ ID:432637, to the nucleotide sequence of GAM26 RNA of FIG. 26A, designated SEQ ID:20604.

Yet a further function of GAM26 is therefore inhibition of zinc finger protein 6 (CMPX1) (ZNF6), a gene which encodes a protein that is probably a transcriptional activator. Accordingly, utilities of GAM26 include diagnosis and treatment of the abovementioned diseases and clinical conditions. The function and utilities of ZNF6 have been established by previous studies, as described hereinabove with reference to FIG. 26D.

Referring now to ADARB1 BINDING SITE. Adenosine deaminase, RNA-specific, B1 (homolog of rat RED1) (ADARB1) is a target gene of GAM26, corresponding to GAM26-TARGET GENE of FIG. 26A. ADARB1 BINDING SITE is a binding site found in an untranslated region of ADARB1, corresponding to BINDING SITE of FIG. 26A. FIG. 26D illustrates the complementarity of the nucleotide sequence of ADARB1 BINDING SITE, designated SEQ ID:432641, to the nucleotide sequence of GAM26 RNA of FIG. 26A, designated SEQ ID:20604.

Another function of GAM26 is therefore inhibition of adenosine deaminase, RNA-specific, B1 (homolog of rat RED1) (ADARB1), a gene which encodes an enzyme that RNA editing involves the deamination of adenosines at specific sites. Accordingly, utilities of GAM26 include diagnosis and treatment of the abovementioned diseases and clinical conditions. The function and utilities of ADARB1 have been established by previous studies, as described hereinabove with reference to FIG. 26D.

Referring now to BCL11B BINDING SITE. B-cell CLL/lymphoma 11B (zinc finger protein) (BCL11B) is a target gene of GAM26, corresponding to GAM26-TARGET GENE of FIG. 26A. BCL11B BINDING SITE is a binding site found in an untranslated region of BCL11B, corresponding to BINDING SITE of FIG. 26A. FIG. 26D illustrates the complementarity of the nucleotide sequence of BCL11B BINDING SITE, designated SEQ ID:432641, to the nucleotide sequence of GAM25 RNA of FIG. 26A, designated SEQ ID:20604.

Yet another function of GAM26 is therefore inhibition of B-cell CLL/lymphoma 11B (zinc finger protein) (BCL11B), a gene which encodes a protein that is implicated in mouse and human leukemias and is associated with T-cell leukemia/lymphoma. Accordingly, utilities of GAM26 include diagnosis and treatment of the abovementioned diseases and clinical conditions. The function and utilities of BCL11B have been established by previous studies, as described hereinabove with reference to FIG. 26D.

Referring now to BCR BINDING SITE. Breakpoint cluster region (BCR) is a target gene of GAM26, corresponding to GAM26-TARGET GENE of FIG. 26A. BCR BINDING SITE is a binding site found in an untranslated region of BCR, corresponding to BINDING SITE of FIG. 26A. FIG. 26D illustrates the complementarity of the nucleotide sequence of BCR BINDING SITE, designated SEQ ID:432641, to the nucleotide sequence of GAM26 RNA of FIG. 26A, designated SEQ ID:20604.

An additional function of GAM26 is therefore inhibition of breakpoint cluster region (BCR), a gene which encodes a protein that is a serine/threonine kinase that involves in the t(9;22) translocation (Philadelphia chromosome) and is associated with chronic myeloid leukemia (cml), acute myeloid leukemia (aml), acute lymphoblastic leukemia (all). Accordingly, utilities of GAM26 include diagnosis and treatment of the abovementioned diseases and clinical conditions. The function and utilities of BCR have been established by previous studies, as described hereinabove with reference to FIG. 26D.

Referring now to BCR BINDING SITE. Breakpoint cluster region (BCR) is a target gene of GAM26, corresponding to GAM26-TARGET GENE of FIG. 26A. BCR BINDING SITE is a binding site found in an untranslated region of BCR, corresponding to BINDING SITE of FIG. 26A. FIG. 26D illustrate the complementarity of the nucleotide sequence of BCR BINDING SITE, designated SEQ ID:432641, to the nucleotide sequence of GAM26 RNA of FIG. 26A, designated SEQ ID:20604.

A further function of GAM26 is therefore inhibition of breakpoint cluster region (BCR), a gene which encodes a protein that is a serine/threonine kinase that involves in the t(9;22) translocation (Philadelphia chromosome) and is associated with chronic myeloid leukemia (cml), acute myeloid leukemia (aml) acute lymphoblastic leukemia (all). Accordingly, utilities of GAM26 include diagnosis and treatment of the abovementioned diseases and clinical conditions. The function and utilities of BCR have been established by previous studies, as described hereinabove with reference to FIG. 26D.

Referring now to ZNF6 BINDING SITE. Zinc finger protein 6 (CMPX1) (ZNF6) is a target gene of GAM26, corresponding to GAM26-TARGET GENE of FIG. 26A. ZNF6 BINDING SITE is a binding site found in an untranslated region of ZNF6, corresponding to BINDING SITE of FIG. 26A. FIG. 26D illustrates the complementarity of the nucleotide sequence of ZNF6 BINDING SITE, designated SEQ ID:432641, to the nucleotide sequence of GAM26 RNA of FIG. 26A, designated SEQ ID:20604.

Yet a further function of GAM26 is therefore inhibition of zinc finger protein 6 (CMPX1) (ZNF6), a gene which encodes a protein that is probably a transcriptional activator. Accordingly, utilities of GAM26 include diagnosis and treatment of the abovementioned diseases and clinical conditions. The function and utilities of ZNF6 have been established by previous studies, as described hereinabove with reference to FIG. 26D.

Referring now to ZNF6 BINDING SITE. Zinc finger protein 6 (CMPX1) (ZNF6) is a get gene of GAM26, corresponding to GAM2-TARGET GENE of FIG. 26A. ZNF6 BINDING SITE is a binding site found in an untranslated region of ZNF6, corresponding to BINDING SITE of FIG. 26A. FIG. 26D illustrates the complementarity of the nucleotide sequence of ZNF6 BINDING SITE, designated SEQ ID:432642, to the nucleotide sequence of GAM26 RNA of FIG. 26A, designated SEQ ID:20604.

Another function of GAM26 is therefore inhibition of zinc finger protein 6 (CMPX1) (ZNF6), a gene which encodes a protein that is probably a transcriptional activator. Accordingly, utilities of GAM26 include diagnosis and treatment of the abovementioned diseases and clinical conditions. The function and utilities of ZNF6 have been established by previous studies, as described hereinabove, with reference to FIG. 26D.

Referring now to ADARB1 BINDING SITE. Adenosine deaminase, RNA-specific, B1 (homolog of rat RED1) (ADARB1) is a target gene of GAM26, corresponding to GAM26-TARGET GENE of FIG. 26A. ADARB1 BINDING SITE is a binding site found in an untranslated region of ADARB1, corresponding to BINDING SITE of FIG. 26A. FIG. 26D illustrates the complementarity of the nucleotide sequence of ADARB1 BINDING SITE, designated SEQ ID:432644, to the nucleotide sequence of GAM26 RNA of FIG. 26A, designated SEQ ID:20604.

Yet another function of GAM26 is therefore inhibition of adenosine deaminase, RNA-specific, B1 (homolog of rat RED1) (ADARB1), a gene which encodes a Enzyme that RNA editing involves the deamination of adenosines at specific sites. Accordingly, utilities of GAM26 include diagnosis and treatment of the abovementioned diseases and clinical conditions. The function and utilities of ADARB1 have been established by previous studies, as described hereinabove with reference to FIG. 26D.

Referring now to BCL11B BINDING SITE. B-cell CLL/lymphoma 11B (zinc finger protein) (BCL11B) is a target gene of GAM26, corresponding to GAM26-TARGET GENE of FIG. 26A. BCL11B BINDING SITE is a binding site found in an untranslated region of BCL11B, corresponding to BINDING SITE of FIG. 26A. FIG. 26D illustrates the complementarity of the nucleotide sequence of BCL11B BINDING SITE, designated SEQ ID:432644, to the nucleotide sequence of GAM26 RNA of FIG. 26A, designated SEQ ID:20604.

An additional function of GAM26 is therefore inhibition of B-cell CLL/lymphoma 11B (zinc finger protein) (BCL11B), a gene which encodes a protein that is implicated in mouse and human leukemias and is associated with T-cell leukemia/lymphoma. Accordingly, utilities of GAM26 include diagnosis and treatment of the abovementioned diseases and clinical conditions. The function and utilities of BCL11B have been established by previous studies, as described hereinabove with reference to FIG. 26D.

Referring now to BCR BINDING SITE. Breakpoint cluster region (BCR) is a target gene of GAM26, corresponding to GAM26-TARGET GENE of FIG. 26A. BCR BINDING SITE is a binding site found in an untranslated region of BCR, corresponding to BINDING SITE of FIG. 26A. FIG. 26D illustrates the complementarity of the nucleotide sequence of BCR BINDING SITE, designated SEQ ID:432644, to the nucleotide sequence of GAM26 RNA of FIG. 26A, designated SEQ ID:20604.

A further function of GAM26 is therefore inhibition of breakpoint cluster region (BCR), a gene which encodes a protein that is a serine/threonine kinase that involves in the t(9;22) translocation (Philadelphia chromosome) and is associated with chronic myeloid leukemia (cml), acute myeloid leukemia (aml), acute lymphoblastic leukemia (all). Accordingly, utilities of GAM26 include diagnosis and treatment of the abovementioned diseases and clinical conditions. The function and utilities of BCR have been established by previous studies, as described hereinabove with reference to FIG. 26D.

Referring now to BCR BINDING SITE. Breakpoint cluster region (BCR) is a target gene of GAM26, corresponding to GAM26-TARGET GENE of FIG. 26A. BCR BINDING SITE is a binding site found in an untranslated region of BCR, corresponding to BINDING SITE of FIG. 26A. FIG. 26D illustrates the complementarity of the nucleotide sequence of BCR BINDING SITE, designated SEQ ID:432644, to the nucleotide sequence of GAM26 RNA of FIG. 26A, designated SEQ ID:20604.

Yet a further function of GAM26 is therefore inhibition of breakpoint cluster region (BCR), a gene which encodes a protein that is a serine/threonine kinase that involves in the t(9;22) translocation (Philadelphia chromosome) and is associated with chronic myeloid leukemia (cml), acute myeloid leukemia (aml), acute lymphoblastic leukemia (all). Accordingly, utilities of GAM26 include diagnosis and treatment of the abovementioned diseases and clinical conditions. The function and utilities of BCR have been established by previous studies, as described hereinabove with reference to FIG. 26D.

Referring now to REPS2 BINDING SITE. RALBP1 associated Eps domain containing 2 (REPS2) is a target gene of GAM26, corresponding to GAM26-TARGET GENE of FIG. 26A. REPS2 BINDING SITE is a binding site found in an untranslated region of REPS2, corresponding to BINDING SITE of FIG. 26A. FIG. 26D illustrates the complementarity of the nucleotide sequence of REPS2 BINDING SITE, designated SEQ ID:432644, to the nucleotide sequence of GAM26 RNA of FIG. 26A, designated SEQ ID:20604.

Another function of GAM26 is therefore inhibition of RALBP1 associated Eps domain containing 2 (REPS2), a gene which encodes a protein that interacts with the active form of RAS with adaptor protein GRB2 and binds calcium. Accordingly, utilities of GAM26 include diagnosis and treatment of the abovementioned diseases and clinical conditions. The function and utilities of REPS2 have been established by previous studies, as described hereinabove with reference to FIG. 26D.

Referring now to ZNF6 BINDING SITE. Zinc finger protein 6 (CMPX1) (ZNF6) is a target gene of GAM26, corresponding to GAM26-TARGET GENE of FIG. 26A. ZNF6 BINDING SITE is a binding site found in an untranslated region of ZNF6, corresponding to BINDING SITE of FIG. 26A. FIG. 26D illustrates the complementarity of the nucleotide sequence of ZNF6 BINDING SITE, designated SEQ ID:432644, to the nucleotide sequence of GAM26 RNA of FIG. 26A, designated SEQ ID:20604.

Yet another function of GAM26 is therefore inhibition of zinc finger protein 6 (CMPX1) (ZNF6), a gene which encodes a protein that is probably a transcriptional activator. Accordingly, utilities of GAM26 include diagnosis and treatment of the abovementioned diseases and clinical conditions. The function and utilities of ZNF6 have been established by previous studies, as described hereinabove with reference to FIG. 26D.

Referring now to ZNF6 BINDING SITE. Zinc finger protein 6 (CMPX1) (ZNF6) is a target gene of GAM26, corresponding to GAM26-TARGET GENE of FIG. 26A. ZNF6 BINDING SITE is a binding site found in an untranslated region of ZNF6, corresponding to BINDING SITE of FIG. 26A. FIG. 26D illustrates the complementarity of the nucleotide sequence of ZNF6 BINDING SITE, designated SEQ ID:432645, to the nucleotide sequence of GAM26 RNA of FIG. 26A, designated SEQ ID:20604.

An additional function of GAM26 is therefore inhibition of zinc finger protein 6 (CMPX1) (ZNF6), a gene which encodes a protein that is probably a transcriptional activator. Accordingly, utilities of GAM26 include diagnosis and treatment of the abovementioned diseases and clinical conditions. The function and utilities of ZNF6 have been established by previous studies, as described hereinabove with reference to FIG. 26D.

Referring now to ZNF6 BINDING SITE. Zinc finger protein 6 (CMPX1) (ZNF6) is a target gene of GAM26, corresponding to GAM26-TARGET GENE of FIG. 26A. ZNF6 BINDING SITE is a binding site found in an untranslated region of ZNF6, corresponding to BINDING SITE of FIG. 26A. FIG. 26D illustrates the complementarity of the nucleotide sequence of ZNF6 BINDING SITE, designated SEQ ID:432654, to the nucleotide sequence of GAM26 RNA of FIG. 26A, designated SEQ ID:20604.

A further function of GAM26 is therefore inhibition of zinc finger protein 6 (CMPX1) (ZNF6), a gene which encodes a protein that is probably a transcriptional activator. Accordingly, utilities of GAM26 include diagnosis and treatment of the abovementioned diseases and clinical conditions. The function and utilities of ZNF6 have been established by previous studies, as described hereinabove with reference to FIG. 26D.

Referring now to ZNF6 BINDING SITE. Zinc finger protein 6 (CMPX1) (ZNF6) is a target gene of GAM26, corresponding to GAM26-TARGET GENE of FIG. 26A. ZNF6 BINDING SITE is a binding site found in an untranslated region of ZNF6, corresponding to BINDING SITE of FIG. 26A. FIG. 26D illustrates the complementarity of the nucleotide sequence of ZNF6 BINDING SITE, designated SEQ ID:432654, to the nucleotide sequence of GAM26 RNA of FIG. 26A, designated SEQ ID:20604.

Yet a further function of GAM26 is therefore inhibition of zinc finger protein 6 (CMPX1) (ZNF16), a gene which encodes a protein that is probably a transcriptional activator. Accordingly, utilities of GAM26 include diagnosis and treatment of the abovementioned diseases and clinical conditions. The function and utilities of ZNF6 have been established by previous studies, as described hereinabove with reference to FIG. 26D.

Referring now to ZNF6 BINDING SITE. Zinc finger protein 6 (CMPX1) (ZNF6) is a target gene of GAM26, corresponding to GAM26-TARGET GENE of FIG. 26A. ZNF6 BINDING SITE is a binding site found in an untranslated region of ZNF6, corresponding to BINDING SITE of FIG. 26A. FIG. 26D illustrates the complementarity of the nucleotide sequence of ZNF6 BINDING SITE, designated SEQ ID:432655, to the nucleotide sequence of GAM26 RNA of FIG. 26A, designated SEQ ID:20604.

Another function of GAM26 is therefore inhibition of zinc finger protein 6 (CMPX1) (ZNF6), a gene which encodes a protein is probably a transcriptional activator. Accordingly, utilities of GAM26 include diagnosis and treatment of the abovementioned diseases and clinical condition. The function and utilities of ZNF6 have been established by previous studies, as described hereinabove with reference to FIG. 26D.

Referring now to RELN BINDING SITE. Reelin (RELN) is a target gene of GAM26, corresponding to GAM26-TARGET GENE of FIG. 26A. RELN BINDING SITE is a binding site found in an untranslated region of RELN, corresponding to BINDING SITE of FIG. 26A. FIG. 26D illustrates the complementarity of the nucleotide sequence of RELN BINDING SITE, designated SEQ ID:547115, to the nucleotide sequence of GAM26 RNA of FIG. 26A, designated SEQ ID:20604.

Yet another function of GAM26 is therefore inhibition of reelin (RELN), a gene which encodes transcription factor that is associated with Norman-Roberts syndrome. Accordingly, utilities of GAM26 include diagnosis and treatment of the abovementioned diseases and clinical conditions. The function and utilities of RELN have been established by previous studies, as described hereinabove with reference to FIG. 26D.

Referring now to DR1 BINDING SITE. Down-regulator of transcription 1, TBP-binding (negative cofactor 2) (DR1) is a et gene of GAM26, corresponding to GAM26-TARGET GENE of FIG. 26A. DR1 BINDING SITE is a binding site found in an untranslated region of DR1, corresponding to BINDING SITE of FIG. 26A. FIG. 26D illustrates the complementarity of the nucleotide sequence of DR1 BINDING SITE, designated SEQ ID:625767, to the nucleotide sequence of GAM26 RNA of FIG. 26A, designated SEQ ID:20604.

An additional function of GAM26 is therefore inhibition of down-regulator of transcription 1, TBP-binding (negative cofactor 2) (DR1), a gene which encodes a protein that influences functional repression of both activated and basal transcription of class II genes. Accordingly, utilities of GAM26 include diagnosis and treatment of the abovementioned diseases and clinical conditions. The function and utilities of DR1 have been established by previous studies, as described hereinabove with reference to FIG. 26D.

Referring now to SOX10 BINDING SITE. SRY (sex determining region Y)-box 10 (SOX10) is a target gene of GAM26, corresponding to GAM26-TARGET GENE of FIG. 26A. SOX10 BINDING SITE is a binding site found in an untranslated region of SOX10, corresponding to BINDING SITE of FIG. 26A. FIG. 26D illustrates the complementarity of the nucleotide sequence of SOX10 BINDING SITE, designated SEQ ID:717573, to the nucleotide sequence of GAM26 RNA of FIG. 26A, designated SEQ ID:20604.

A further function of GAM26 is therefore inhibition of SRY (sex determining region Y)-box 10 (SOX10), a gene which encodes a transcription factor that is associated with Waardenburg syndrome type 4. Accordingly utilities of GAM26 include diagnosis and treatment of the abovementioned diseases and clinical conditions. The function and utilities of SOX10 have been established by previous studies, as described hereinabove with reference to FIG. 26D.

Referring now to ADRBK1 BINDING SITE. Adrenergic beta, receptor kinase 1 (ADRBK1) is a target gene of GAM26, corresponding to GAM26-TARGET GENE of FIG. 26A. ADRBK1 BINDING SITE is a binding site found in an untranslated region of ADRBK1, corresponding to BINDING SITE of FIG. 26A. FIG. 26D illustrates the complementarity of the nucleotide sequence of ADRBK1 BINDING SITE, designated SEQ ID:816521, to the nucleotide sequence of GAM26 RNA of FIG. 26A, designated SEQ ID:20604.

Yet a further function of GAM26 is therefore inhibition of adrenergic, beta, receptor kinase 1 (ADRBK1), a gene which encodes a Enzyme that regulates desensitization of b-adrenergic receptors and related GPCRs. Accordingly, utilities of GAM26 include diagnosis and treatment of the abovementioned diseases and clinical conditions. The function and utilities of ADRBK1 have been established by previous studies, as described hereinabove with reference to FIG. 26D.

Referring now to PEA15 BINDING SITE. Phosphoprotein enriched in astrocytes 15 (PEA15) is a target gene of GAM26, corresponding to GAM26-TARGET GENE of FIG. 26A. PEA15 BINDING SITE is a binding site found in an untranslated region of PEA15, corresponding to BINDING SITE of FIG. 26A. FIG. 26D illustrates the complementarity of the nucleotide sequence of PEA15 BINDING SITE, designated SEQ ID:816521, to the nucleotide sequence of GAM26 RNA of FIG. 26A, designated SEQ ID:20604.

Another function of GAM26 is therefore inhibition of phosphoprotein enriched in astrocytes 15 (PEA15), a gene which encodes a protein that is a phosphoprotein and involved in glucose uptake. Accordingly, utilities of GAM26 include diagnosis and treatment of the abovementioned diseases and clinical conditions. The function and utilities of PEA15 have been established by previous studies, as described hereinabove with reference to FIG. 26D.

Referring now to ADRBK1 BINDING SITE. Adrenergic beta, receptor kinase 1 (ADRBK1) is a target gene of GAM26, corresponding to GAM26-TARGET GENE of FIG. 26A. ADRBK1 BINDING SITE is a binding site found in an untranslated region of ADRBK1, corresponding to BINDING SITE of FIG. 26A. FIG. 26D illustrates the complementarity of the nucleotide sequence of ADRBK1 BINDING SITE, designated SEQ ID:844404, to the nucleotide sequence of GAM26 RNA of FIG. 26A, designated SEQ ID:20604.

Yet another function of GAM26 is therefore inhibition of adrenergic, beta, receptor kinase 1 (ADRBK1), a gene which encodes an enzyme that regulates desensitization of b-adrenergic receptors and related GPCRs. Accordingly, utilities of GAM26 include diagnosis and treatment of the abovementioned diseases and clinical conditions. The function and utilities of ADRBK1 have been established by previous studies, as described hereinabove with reference to FIG. 26D.

Referring now to FOXF1 BINDING SITE. Forkhead box F1 (FOXF1) is a target gene of GAM26, corresponding to GAM26-TARGET GENE of FIG. 26A FOXF1 SITE is a binding site found in an untranslated region of FOXF1, corresponding to BINDING SITE of FIG. 26A. FIG. 26D illustrates the complementarity of the nucleotide sequence of FOXF1 BINDING SITE, designated SEQ ID:844404, to the nucleotide sequence of GAM26 RNA of FIG. 26A, designated SEQ ID:20604.

An additional function of GAM26 is therefore inhibition of forkhead box F1 (FOXF1), a gene which encodes a transcription factor that is probable transcription activator for a number of lung-specific genes. Accordingly, utilities of GAM26 include diagnosis and treatment the abovementioned diseases and clinical conditions. The function and utilities of FOXF1 have been established by previous studies, as described hereinabove with reference to FIG. 26D.

Reference is now made to CHIC2 BINDING SITE. Cystein-rich hydrophobic domain 2 (CHIC2) is a target gene of GAM26, corresponding to GAM26-TARGET GENE of FIG. 26A. CHIC2 BINDING SITE is a binding site found in an untranslated region CHIC2, corresponding to BINDING SITE of FIG. 26A. FIG. 26D illustrates the complementarity of the nucleotide sequence of CHIC2 BINDING SITE, designated SEQ ID:893635, to the nucleotide sequence of GAM26 RNA of FIG. 26A, designated SEQ ID 20604.

A further function of GAM26 is therefore inhibition of cystein-rich hydrophobic domain 2 (CHIC2), a gene which encodes a protein that is a Cysteine-rich hydrophobic protein 2, and is associated with acute myeloid leukemia. Accordingly, utilities of GAM26 include diagnosis and treatment of the abovementioned diseases and clinical conditions.

The function of CHIC2 has been established by previous studies. The ETV6 gene (600618), also known as TEL, is the main target of chromosomal translocations affecting 12p3. The rearrangements fuse ETV6 to a wide variety of partner genes in both myeloid and lymphoid malignancies. Cools al. (1999) reported 4 cases of acute myeloid leukemia with very immature myeloblasts and a t(4;12)(q11-q12;p13). In all cases, ETV6 was found to be recombined with a novel gene homologous to the mouse Brx gene the authors therefore named the gene 'Brx-like translocated in leukemia,' or BTL. RT-PCR Experiments indicated that expression of the BTL-ETV6 transcript but not of the reciprocal ETV6-BTL transcript is a common finding in these leukemias. In contrast to most of the other ETV6 fusions, both the complete helix-loop-helix and ETS DNA-binding domains of ETV6 are present in the predicted BTL-ETV6 fusion protein, and a chimeric gene is transcribed from the BTL promoter.

Full details of the abovementioned studies are described in the following publications, the disclosure of which are hereby incorporated by reference:

Cools, J.; Bilhou-Nabera, C.; Wlodarska, I.; Cabrol, C.; Talmant, P.; Bernard, P.; Hagemeijer, A.; Marynen, P.: Fusion of a novel gene, BTL, to ETV6 in acute myeloid leukemias with a t(4;12)(q11-q12;p13). Blood 94: 1820-1824, 1999.

Further studies establishing the function and utilities of CHIC2 are found in John Hopkins OMIM database record ID 604332, and in references numbered 1575 listed hereinbelow.

Referring now to MAP4K5 BINDING SITE. Mitogen-activated protein kinase kinase kinase kinase 5 (MAP4K5) is a target gene of GAM26, corresponding to GAM26-TARGET GENE of FIG. 26A. MAP4K5 BINDING SITE is a binding site found in an untranslated region of MAP4K5, corresponding to BINDING SITE of FIG. 26A. FIG. 26D illustrates the complementarity of the nucleotide sequence of MAP4K5 BINDING SITE, designated SEQ ID:918189, to the nucleotide sequence of GAM26 RNA of FIG. 26A, designated SEQ ID:20604.

Yet a further function of GAM26 is therefore inhibition of mitogen-activated protein kinase kinase kinase kinase 5 (MAP4K5), a gene which encodes an enzyme that is a serine/threonine protein kinase required for spore wall development, activates Jun N-terminal kinase, a member of the STE20 kinase family. Accordingly, utilities of GAM26 include diagnosis and treatment of the abovementioned diseases and clinical conditions. The function and utilities of MAP4K5 have been established by previous studies, as described hereinabove with reference to FIG. 26D.

Referring now to ATP2B2 BINDING SITE. ATPase, Ca++ transporting, plasma membrane 2 (NOTE: redefinition of sy (ATP2B2) is a target gene of GAM26, corresponding to GAM26-TARGET GENE of FIG. 26A. ATP2B2 BINDING SITE is a binding site found in an untranslated region of ATP2B2, corresponding to BINDING SITE of FIG. 26A. FIG. 2 illustrates the complementarity of the nucleotide sequence of ATP2B2 BINDING SITE designated SEQ ID:947819, to the nucleotide sequence of GAM26 RNA of FIG. 26A, designated SEQ ID:20604.

Another function of GAM26 is therefore inhibition of ATPase, Ca++ transporting, plasma membrane 2 (NOTE: redefinition of sy (ATP2B2), a gene which encodes a Enzyme that catalyzes the hydrolysis of ATP coupled with the transport of calcium out of the cell. Accordingly, utilities of GAM26 include diagnosis and treatment of the abovementioned diseases and clinical conditions. The function and utilities of ATP2B2 have been established by previous studies, as described hereinabove with reference to FIG. 26D.

Referring now to SERPINB8 BINDING SITE. Serine (or cysteine) proteinase inhibitor, clade B (ovalbumin), member (SERPINB8) is a target gene of GAM26, corresponding to GAM26-TARGET GENE of FIG. 26A. SERPINB8 BINDING SITE is a binding site found in an untranslated region of SERPINB8, corresponding to BINDING SITE of FIG. 26A. FIG. 26D illustrates the complementarity of the nucleotide sequence of SERPINB8 BINDING SITE, designated SEQ ID:950359, to the nucleotide sequence of GAM26 RNA of FIG. 26A, designated SEQ ID:20604.

Yet another function of GAM26 is therefore inhibition of serine (or cysteine) proteinase inhibitor, clade B (ovalbumin), member (SERPINB8), a gene which encodes a protein protease inhibitors; may be a serpin serine protease inhibitor that binds thrombin. Accordingly, utilities of GAM26 include diagnosis and treatment of the abovementioned diseases and clinical conditions. The fun on and utilities of SERPINB8 have been established by previous studies, as described hereinabove with reference to FIG. 26D.

Referring now to SERPINB8 BINDING SITE. Serine (or cysteine) proteinase inhibitor, clade B (ovalbumin), member (SERPINB8) is a target gene of GAM26, corresponding to GAM26-TARGET GENE of FIG. 26A. SERPINB8 BINDING SITE is a binding site found in an untranslated region of SERPINB8, corresponding to BINDING SITE of FIG. 26A. FIG. 26D illustrates the complementarity of the nucleotide sequence of SERPINB8 BINDING SITE, designated SEQ ID:950360, to the nucleotide sequence of GAM26 RNA of FIG. 26A, designated SEQ ID:20604.

An additional function of GAM26 is therefore inhibition of serine (or cysteine) proteinase inhibitor, clade B (ovalbumin), member (SERPINB8), a gene which encodes a protein protease inhibitors; may be a serpin serine protease inhibitor that binds thrombin. Accordingly, utilities of GAM26 include diagnosis and treatment of the abovementioned diseases and clinical conditions. The function and utilities of SERPINB8 have been established by previous studies, as described hereinabove with reference to FIG. 26D.

Referring now to FOXF1 BINDING SITE. Forkhead box F1 (FOXF1) is a target gene of GAM26, corresponding to GAM26-TARGET GENE of FIG. 26A. FOXF1 BINDING SITE is a binding site found in an untranslated region of FOXF1, corresponding to BINDING SITE of FIG. 26A. FIG. 26D illustrates the complementarity of the nucleotide sequence of FOXF1 BINDING SITE, designated SEQ ID:969275, to the nucleotide sequence of GAM26 RNA of FIG. 26A, designated SEQ ID:20604.

A further function of GAM26 is therefore inhibition of forkhead box F1 (FOXF1), a gene which encodes a transcription factor that is a probable transcription activator for a number of lung-specific genes. Accordingly, utilities of GAM26 include diagnosis and treatment of the abovementioned diseases and clinical conditions. The function and utilities of FOXF1 have been established by previous studies, as described hereinabove with reference to FIG. 26D.

Reference is now made to MMP2 BINDING SITE. Matrix metalloproteinase 2 (gelatinase A, 72 kD gelatinase, 72 kD type I (MMP2) is a target gene of GAM26, corresponding to GAM26-TARGET GENE of FIG. 26A. MMP2 BINDING SITE is a binding site found in an untranslated region of MMP2, corresponding to BINDING SITE of FIG. 26A. FIG. 26D illustrates the complementarity of the nucleotide sequence of MMP2 BINDING SITE, designated SEQ ID:969275, to the nucleotide sequence of GAM26 RNA of FIG. 26A, designated SEQ ID:20604.

Yet a further function of GAM26 is therefore inhibition of matrix metalloproteinase 2 (gelatinase A, 72 kD gelatinase, 72 kD type I (MMP2), a gene which encodes an enzyme that prevents trom binding to alpha-V/beta-3 and blocks cell surface collagenolytic activity and is associated with OSTEOLYSIS, IDIOPATHIC. Accordingly, utilities of GAM26 include diagnosis and treatment of the abovementioned diseases and clinical conditions.

The function of MMP2 has been established by previous studies. Angiogenesis depends both cell adhesion and proteolytic mechanisms. Matrix metalloproteinase-2 and integrin alpha-V/beta-3 are functionally associated on the surface of angiogenic blood vessels. Brooks et al. (1998) found that a fragment of MMP2, which comprises the C-terminal hemopexin-like domain (amino acids 445-635) and is termed PEX, prevents this enzyme from binding to alpha-V/beta-3 and blocks cell surface collagenolytic activity in melanoma and endothelial cells. PEX blocks MMP2 activity on the chick chorioallantoic membrane where it disrupts angiogenesis and tumor growth. Brooks et al. (1998) also found that a naturally occurring form of PEX can be detected in vivo in conjunction with alpha-V/beta-3 expression in tumors and during developmental retinal neovascularization. Levels of PEX in these vascularized tissues suggest that it interacts with endothelial cell alpha-V/beta-3 where it serves as a natural inhibitor of MMP2 activity, thereby regulating the invasive behavior of new blood vessels. The authors concluded that recombinant PEX may provide a potentially novel therapeutic approach for diseases associated with neovascularization.

Animal model experiments lend further support to the function of MMP2. To study the role of Mmp2 in angiogenesis, Kato et al. (2001) analyzed the Mmp2-deficient mice generated by Itoh et al. (1998). To determine whether corneal vascularization was altered in Mmp2-deficient mice, they implanted basic fibroblast growth factor (FGF) containing micropellets into the cornea of mice and observed that Mmp2-deficient mice had decreased corneal neovascularization. The angiogenetic response normally induced by basic FGF is markedly reduced in mice lacking functional Mmp2. To determine the role of Mmp2 in vascular endothelial cell migration and tube formation in vitro, the authors prepared aortic rings from Mmp2-deficient mice. They observed that Mmp2-deficient mice showed a significant reduction of endothelial outgrowth compared to wildtype mice after stimulation with basic FGF. Kato et al. (2001) concluded that Mmp2 may play an important role in the regulation of corneal angiogenesis.

It is appreciated that the abovementioned animal model for MMP2 is acknowledged by those skilled in the art as a scientifically valid animal model, as can be further appreciated from the publications sited hereinbelow.

Full details of the abovementioned studies are described in the following publications, the disclosure of which are hereby incorporated by reference:

Brooks, P. C.; Silletti, S.; von Schalscha, T. L.; Friedlander, M.; Cheresh, D. A.: Disruption of angiogenesis by PEX, a noncatalytic metalloproteinase fragment with integrin binding activity. Cell 92: 391-400, 1998 Kato, T.; Kure, T.; Chang, J. -H., Gabison, E. E.; Itoh, T.; Itohara, S.; Azar, D. T.: Diminished corneal angiogenesis in gelatinase A-deficient mice. FEBS Lett. 508: 187-190, 2001.

Further studies establishing the function and utilities of MMP2 are found in John Hopkins OMIM database record ID 120360, and in reference numbered 1576-1593 listed hereinbelow.

Referring now to CACNA1A BINDING SITE. Calcium channel, voltage-dependent, P/Q type, alpha 1A subunit (CACNA1A) is a target gene of GAM26, corresponding to GAM26-TARGET GENE of FIG. 26A. CACNA1A BINDING SITE is a binding site found in an untranslated region of CACNA1A, corresponding to BINDING SITE of FIG. 26A. FIG. 2 5D illustrates the complementarity of the nucleotide sequence of CACNA1A BINDING SITE, designated SEQ ID:969284, to the nucleotide sequence of GAM26 RNA of FIG. 26A, designated SEQ ID:20604.

Another function of GAM26 is therefore inhibition of calcium channel, voltage-dependent, P/Q type, alpha 1A subunit (CACNA1A), a gene which encodes a protein that is associated with episodic ataxia type 2, familial hemiplegic migraine, spinocerebellar ataxia type 6, and idiopathic generalized epilepsy. Accordingly, utilities of GAM26 include diagnosis and treatment of the abovementioned diseases and clinical conditions. The function and utilities of CACNA1A have been established by previous studies, as described hereinabove with reference to FIG. 26D.

Referring now to CAMK4 BINDING SITE. Calcium/calmodulin-dependent protein kinase IV (CAMK4) is a target gene of GAM26, corresponding to GAM26-TARGET GENE of FIG. 26A. CAMK4 BINDING SITE is a binding site found in an untranslated region of CAMK4, corresponding to BINDING SITE of FIG. 26A. FIG. 26D illustrates the complementarity of the nucleotide sequence of CAMK4 BINDING SITE, designated SEQ ID:969284, to the nucleotide sequence of GAM26 RNA of FIG. 26A, designated SEQ ID:20604.

Yet another function of GAM26 is therefore inhibition of calcium/calmodulin-dependent protein kinase IV (CAMK4), a gene which encodes a Enzyme that is a heat-sable, acidic, calmodulin-binding protein. Accordingly, utilities of GAM26 include diagnosis and treatment of the abovementioned diseases and clinical conditions. The function and utilities of CAMK4 have been established by previous studies, as described hereinabove with reference to FIG. 26D.

Referring now to FGF18 BINDING SITE. Fibroblast growth factor 18 (FGF18) is a target gene of GAM26, corresponding to GAM26-TARGET GENE of FIG. 26A. FGF18 BINDING SITE is a binding site found in an untranslated region of FGF18, corresponding to BINDING SITE of FIG. 26A. FIG. 26D illustrates the complementarity of the nucleotide sequence of FGF18 BINDING SITE, designated SEQ ID:969284, to the nucleotide sequence of GAM26 RNA of FIG. 26A, designated SEQ ID:20604.

An additional function of GAM26 is therefore inhibition of fibroblast growth factor 18 (FGF18), a gene which encodes a protein that stimulates hepatic and intestinal proliferation. Accordingly, utilities of GAM26 include diagnosis and treatment of the abovementioned diseases and clinical conditions. The function and utilities of FGF18 have been established by previous studies, as described hereinabove with reference to FIG. 26D.

Referring now to RGS19IP1 BINDING SITE. (RGS19IP1) is a target gene of GAM26, corresponding to GAM26-TARGET GENE of FIG. 26A. RGS19IP1 BINDING SITE is a binding site found in an untranslated region of RGS19IP1, corresponding to BINDING SITE of FIG. 26A. FIG. 26D illustrates the complementarity of the nucleotide sequence of RGS19IP1 BINDING SITE, designated SEQ ID:969284, to the nucleotide sequence of GAM26 RNA of FIG. 26A, designated SEQ ID:20604.

A further function of GAM26 is therefore inhibition of (RGS19IP1), a gene which encodes a protein that is involved in g protein-linked signaling. Accordingly, utilities of GAM26 include diagnosis and treatment of the abovementioned diseases and clinical conditions. The function and utilities of RGS19IP1 have been established by previous studies, as described hereinabove with reference to FIG. 26D.

Referring now to LRP8 BINDING SITE. Low density lipoprotein receptor-related protein 8, apolipoprotein e r (LRP8) is a target gene of GAM26, corresponding to GAM26-TARGET GENE of FIG. 26A. LRP8 BINDING SITE is a binding site found in an untranslated region of LRP8, corresponding to BINDING SITE of FIG. 26A. FIG. 26D illustrates the complementarity of the nucleotide sequence of LRP8 BINDING SITE, designated SEQ ID:969288, to the nucleotide sequence of GAM26 RNA of FIG. 26A, designated SEQ ID:20604.

Yet a further function of GAM26 is therefore inhibition of low density lipoprotein receptor-related protein 8, apolipoprotein e r (LRP8), a gene which encodes a receptor that binds vldl and transports it into cells by endocytosis. Accordingly, utilities of GAM26 include diagnosis and treatment of the abovementioned diseases and clinical conditions. The function and utilities of LRP8 have been established by previous studies, as described hereinabove with reference to FIG. 26D.

Referring now to REPS2 BINDING SITE. RALBP1 associated Eps domain containing 2 (REPS2) is a target gene of GAM26, corresponding to GAM26-TARGET GENE of FIG. 26A. REPS2 BINDING SITE is a binding site found in an untranslated region of REPS2, corresponding to BINDING SITE of FIG. 26A. FIG. 26D illustrates the complementarity of the nucleotide sequence of REPS2 BINDING SITE, designated SEQ ID:969288, to the nucleotide sequence of GAM26 RNA of FIG. 26A, designated SEQ ID:20604.

Another function of GAM26 is therefore inhibition RALBP1 associated Eps domain containing 2 (REPS2), a gene which encodes a protein that interacts with the active form of RAS with adaptor protein GRB2 and binds calcium. Accordingly, utilities of GAM26 include diagnosis and treatment of the abovementioned diseases and clinical conditions. The unction and utilities of REPS2 have been established by previous studies, as described hereinabove with reference to FIG. 26D.

Reference is now made to CRAT BINDING SITE. carnitine acetyltransferase (CRAT) target gene of GAM26, corresponding to GAM26-TARGET GENE of FIG. 26A. CRAT BINDING SITE is a binding site found in an untranslated region of CRAT, corresponding to BINDING SITE FIG. 26A. FIG. 26D illustrates the complementarity of the nucleotide sequence of CRAT BINDING SITE, designated SEQ ID:982983, to the nucleotide sequence of GAM26 RNA of FIG. 26A, designated SEQ ID:20604.

Yet another function of GAM26 is therefore inhibition of carnitine acetyltransferase (CRAT), a gene which encodes an enzyme that catalyzes the reversible transfer of acyl groups from an acyl-CoA thioester to carnitine, and is associated with Alzheimer's disease. Accordingly, utilities of GAM26 include diagnosis and treatment of the abovementioned diseases and clinical condition.

The function of CRAT has been established by previous studies. Carnitine acyltransferases are a group of enzymes that catalyze the reversible transfer of acyl groups from an acyl-CoA thioester to carnitine, thus forming the corresponding acylcarnitine. These enzymes can be distinguished according to their substrate specificity in carnitine palmitoyltransferase (see CPT1, 600528 and CPT2, 600650), carnitine octanoyltransferase (CROT; 606090), and carnitine acetyltransferase (EC 2.3.1.7). CRAT is a key enzyme for metabolic pathways involved with the control of the acyl-CoA/CoA ratio in mitochondria, peroxisomes, and endoplasmic reticulum Acetylcarnitine, which can be a precursor for acetylcholine synthesis catalyzed by choline acetyltransferase, is thought to slow the rate of mental deterioration in Alzheimer patients, and Kalaria and Harik (1992) found decreased function of CRAT in the brain of Alzheimer patients Full details of the abovementioned studies are described in the following publications, the disclosure of which are hereby incorporated by reference:

Kalaria, R. N.; Harik, S. I.: Carnitine acetyltransferase activity in the human brain and its microvessels is decreased in Alzheimer's disease. Ann. Neurol. 32: 583-586, 1992. PubMed ID: 1456745 3. van der Leij, F. R.; Huijkman, N. C. A.; Boomsma, C.; Kuipers, J. R. G.; Bartelds, B.: Genomics of the human carnitine acyltransferase genes. Molec. Genet. Metab. 71: 139-153, 2000

Further establishing the function and utilities found in John Hopkins OMIM record ID 600184, and in references numbered 1591-1596 listed hereinbelow.

Referring now to PX19 BINDING SITE. (PX19) is a target gene of GAM26, corresponding to GAM26-TARGET GENE of FIG. 26A. PX19 BINDING SITE is a binding site found in an untranslated region of PX19, corresponding to BINDING SITE of FIG. 26A. FIG. 2D illustrates the complementarity of the nucleotide sequence of PX19 BINDING SITE, designated SEQ ID:993966, to the nucleotide sequence of GAM26 RNA of FIG. 26A, designated SEQ ID:20604.

An addition function of GAM26 is therefore inhibit of (PX19), a gene which encodes a protein that plays a role in hemopoiesis. Accordingly, utilities of GAM26 include diagnosis and treatment of the abovementioned diseases and clinical conditions. The function and utilities of PX19 have been established by previous studies, as described hereinabove with reference to FIG. 26D.

Reference is now made to ADAM10 BINDING SITE. A disintegrin and metalloproteinase domain 10 (ADAM10) is a target gene of GAM26, corresponding to GAM26-TARGET GENE of FIG. 26A. ADAM10 BINDING SITE is a binding site found in an untranslated region of ADAM10, corresponding to BINDING SITE of FIG. 26A. FIG. 26D illustrates the complementarity of the nucleotide sequence of ADAM10 BINDING SITE, designated SEQ ID:993970, to the nucleotide sequence of GAM26 RNA of FIG. 26A, designated SEQ ID:20604.

A further function of GAM26 is therefore inhibition of a disintegrin and metalloproteinase domain 10 (ADAM10), a gene which encodes an enzyme that Member of ADAM family of zinc metalloproteases. Accordingly, utilities of GAM26 include diagnosis and treatment of the abovementioned diseases and clinical conditions.

The function of ADAM10 has been established by previous studies. Wolfsberg et al. (1995) identified a family of proteins containing a disintegrin and metalloproteinase (ADAM) domain. Members of this family are cell surface proteins with a unique structure possessing both potential adhesion and protease domains. Tumor necrosis factor-alpha (TNFA; 191160) is synthesized as a proinflammatory cytokine from a 233-amino acid precursor. Conversion of the membrane-bound precursor to a secreted mature protein is mediated by a protease termed TNFA convertase. Lunn et al. (1997) found that ADAM10 possesses TNFA convertase activity. TNFA is involved in a variety of diseases. To elucidate whether the ADAM10 locus maps to the same region as a disease susceptibility, Yamazaki et al. (1997) mapped the ADAM10 locus. Using a radiation hybrid mapping method, they showed that ADAM10 is located on 15q21.3-q23. Although ephrins form a high-affinity multivalent complex with their receptors present on axons, axons can be rapidly repelled rather than being bound. Hattori et al. (2000) showed that ephrin-A2 (602756) forms a stable complex with the metalloproteinase Kuzbanian (ADAM10) involving interactions outside the cleavage region and the protease domain. Eph receptor binding triggered ephrin-A2 cleavage in a localized reaction specific to the cognate ligand. The cleavage-inhibiting mutation in ephrin-A2 delayed axon withdrawal. Hattori et al. (2000) concluded that their studies reveal mechanisms for protease recognition and control of cell surface proteins, and, for ephrin-A2, they may provide a means for efficient axon detachment and termination of signaling.

Full details of the abovementioned studies are described in the following publications, the disclosure of which are hereby incorporated by reference:

Lunn, C. A.; Fan, X.; Dalie, B.; Miller, K.; Zavodny, P. J.; Narula, S. K.; Lundell, D.: Purification of ADAM 10 from bovine spleen as a TNFalpha convertase. FEBS Lett. 400: 333-335, 1997. PubMed ID: 9009225 1. Hattori, M.; Osterfield, M.; Flanagan, J. G.: Regulated cleavage of a contact-mediated axon repellent. Science 289: 1360-1365, 2000.

Further studies establishing the function and utilities of ADAM10 are found in John Hopkins OMIM database record ID 602192, and in references numbered 1597-1600 listed hereinbelow.

Referring now to REPS2 BINDING SITE. RALBP1 associated Eps domain containing 2 (REPS2) is a target gene of GAM26, corresponding to GAM26-TARGET GENE of FIG. 26A. REPS2 BINDING SITE is a binding site found in an untranslated region of REPS2, corresponding to BINDING SITE of FIG. 26A. FIG. 26D illustrates the complementarity of the nucleotide sequence of REPS2 BINDING SITE, designated SEQ ID:993970, to the nucleotide sequence of GAM26 RNA of FIG. 26A, designated SEQ ID:20604.

Yet a further function of GAM26 is therefore inhibition of RALBP1 associated Eps domain containing 2 (REPS2), a gene which encodes a protein that interacts with the active form of RAS with adaptor protein GRB2 and binds calcium. Accordingly, utilities of GAM26 include diagnosis and treatment of the abovementioned diseases and clinical conditions. The function and utilities of REPS2 have been established by previous studies, as described hereinabove with reference to FIG. 26D.

Reference is now made to EXTL3 BINDING SITE. Exostoses (multiple)-like 3 (EXTL3) is a target gene of GAM26, corresponding to GAM26-TARGET GENE of FIG. 26A. EXTL3 BINDING SITE is a binding site found in an untranslated region of EXTL3, corresponding to BINDING SITE of FIG. 26A. FIG. 26D illustrates the complementarity of the nucleotide sequence of EXTL3 BINDING SITE, designated SEQ ID:1065873, to the nucleotide sequence of GAM26 RNA of FIG. 26A, designated SEQ ID:20604.

Another function of GAM26 is therefore inhibition of exostoses (multiple)-like 3 (EXTL3), a gene which encodes a protein that a member of the multiple exostoses gene family. Accordingly, utilities of GAM26 include diagnosis and treatment of the abovementioned diseases and clinical conditions.

The function of EXTL3 has been established by previous studies. By EST database searching with the sequences of EXT1 (133700), EXT2 (133701), and EXTL1 (601738), followed by 5-prime and 3-prime RACE, Saito et al. (1998) cloned full-length cDNAs for 2 new members of the EXT family, EXTL2 (602411) and EXTL3, which they called EXTR2 and EXTR1, respectively. The deduced 919-amino acid EXTL3 protein contains a highly conserved region in the C terminus common to other EXT proteins. Northern blot analysis detected expression of 6.2- and 4.7-kb EXTR1 transcripts in all tissues tested except ovary. The larger transcript was predominant in brain, skeletal muscle, and testis, and the shorter transcript in heart, liver, thymus, and prostate. Kobayashi et al. (2000) isolated a cDNA for a REG protein (see 167770) receptor from a rat islet cDNA library. Cells into which the cDNA had been introduced bound REG protein with high affinity. When the cDNA was introduced into a pancreatic beta-cell line that showed REG-dependent growth, the transformants exhibited a significant increase in the incorporation of 5-prime-bromo-2-prime-deoxyuridine as well as in the cell numbers in response to REG protein. A homology search revealed that the rat REG protein receptor cDNA is a homolog of EXTL3. The rat and human proteins share 97% sequence identity. Kobayashi et al. (2000) found that REG receptor mRNA in the rat is detectable in liver, kidney, stomach, small intestine, colon, adrenal gland, pituitary gland, and brain, but not in heart, suggesting the possible involvement of the REG-REG protein receptor signal system in a variety of cell types other than pancreatic beta cells. By somatic cell hybrid and radiation hybrid analyses, Saito et al. (1998) mapped the human EXTL3 gene to chromosome 8p21. By FISH, radiation hybrid analysis, and inclusion within a mapped contig, Van Hul et al. (1998) mapped the gene to 8p21-p12.

Full details of the abovementioned studies are described in the following publications, the disclosure of which are hereby incorporated by reference:
Saito T.; Seki, N.; Yamauchi, M.; Tsuji, S.; Hayashi, A.; Kozuma, S.; Hori, T.: Structure, chromosomal location, and expression profile of EXTR1 and EXTR2, new members of the multiple exostoses gene family. Biochem. Biophys. Res. Commun. 243: 61-66, 1998. PubMed ID: 9473480 3. Van Hul, W.; Wuyts, W.; Hendrickx, J.; Speleman, F.; Wauters, J.; De Boulle, K.; Van Roy, N.; Bossuyt, P.; Willems, P. J.: Identification of a third EXT-like gene (EXTL3) belonging to the EXT gene family. Genomics 47: 230-237, 1998.

Further studies establishing the function and utilities of EXTL3 are found in John Hopkins OMIM database record ID 605744, and in references numbered 1601-1603 listed hereinbelow.

Referring now to CAMK4 BINDING SITE. Calcium/calmodulin-dependent protein kinase IV (CAMK4) is a target gene of GAM26, corresponding to GAM26-TARGET GENE of FIG. 26A. CAMK4 BINDING SITE is a binding site found in an untranslated region of CAMK4, corresponding to BINDING SITE of FIG. 26A. FIG. 26D illustrates the complementarity of the nucleotide sequence of CAMK4 BINDING SITE, designated SEQ ID:1295963, to the nucleotide sequence of GAM26 RNA of FIG. 26A, designated SEQ ID:20604.

Yet another function of GAM26 is therefore inhibition of calcium/calmodulin-dependent protein kinase IV (CAMK4), a gene which encodes a Enzyme that is a heat-stable, acidic, calmodulin-binding protein. Accordingly, utilities of GAM26 include diagnosis and treatment of the abovementioned diseases and clinical conditions. The function and utilities of CAMK4 have been established by previous studies, as described hereinabove with reference to FIG. 26D.

Referring now to EXTL3 BINDING SITE. Exostoses (multiple)-like 3 (EXTL3) is a target gene of GAM26, corresponding to GAM26-TARGET GENE of FIG. 26A. EXTL3 BINDING SITE is a binding site found in an untranslated region of EXTL3, corresponding to BINDING SITE of FIG. 26A. FIG. 26D illustrates the complementarity of the nucleotide sequence of EXTL3 BINDING SITE, designated SEQ ID:1310953, to the nucleotide sequence of GAM26 RNA of FIG. 26A, designated SEQ ID:20604.

An additional function of GAM26 is therefore inhibition of exostoses (multiple)-like 3 (EXTL3), a gene which encodes a protein a member of the multiple exostoses gene family. Accordingly, utilities of GAM26 include diagnosis and treatment of the abovementioned diseases and clinical conditions. The function and utilities of EXTL3 have seen established by previous studies, as described hereinabove with reference to FIG. 26D.

Referring now to REPS2 BINDING SITE. RALBP1 associated Eps domain containing 2 (REPS2) is a target gene of GAM26, corresponding to GAM26-TARGET GENE of FIG. 26A. REPS2 BINDING SITE is a binding site found in an untranslated region of REPS2, corresponding to BINDING SITE of FIG. 26A. FIG. 26D illustrates the complementarity of the nucleotide sequence of REPS2 BINDING SITE, designated SEQ ID:1323750, to the nucleotide sequence of GAM26 RNA of FIG. 26A, designated SEQ ID:20604.

A further function of GAM26 is therefore inhibition of RALBP1 associated Eps domain containing 2 (REPS2), a gene which encodes a protein that interacts with the active form of RAS with adaptor protein GRB2 and binds calcium. Accordingly, utilities of GAM26 include diagnosis and treatment of the abovementioned diseases and clinical conditions. The function and utilities of REPS2 have been established by previous studies, as described hereinabove with reference to FIG. 26D.

Reference is now made to FAF1 BINDING SITE. FAF1 is a target gene of GAM26, corresponding to GAM26-TARGET GENE of FIG. 26A. FAF1 BINDING SITE is a binding site found in an untranslated region of FAF1, corresponding to BINDING SITE of FIG. 26A. FIG. 26D illustrates the complementarity of the nucleotide sequence of FAF1 BINDING SITE, designated SEQ ID:46198, to the nucleotide sequence of GAM26 RNA of FIG. 26A, designated SEQ ID:20604. Yet a further function of GAM26 is therefore inhibition of (FAF1). Accordingly, utilities of GAM26 include diagnosis and treatment of diseases and clinical conditions with which FAF1 is associated.

Reference is now made to FLJ12377 BINDING SITE. FLJ12377 is a target gene of GAM26, corresponding to GAM26-TARGET GENE of FIG. 26A. FLJ12377 BINDING SITE is a binding site found in an untranslated region of FLJ12377, corresponding to BINDING SITE of FIG. 26A. FIG. 26D illustrates the complementarity of the nucleotide sequence of FLJ12377 BINDING SITE, designated SEQ ID:46198, to the nucleotide sequence of GAM26 RNA of FIG. 26A, designated SEQ ID:20604. Another function of GAM26 is therefore inhibition of (FLJ12377). Accordingly, utilities of GAM26 include diagnosis and treatment of diseases and clinical conditions with which FLJ12377 is associated.

Reference is now made to CHSY1 BINDING SITE. CHSY1 is a target gene of GAM26, corresponding to GAM26-TARGET GENE of FIG. 26A. CHSY1 BINDING SITE is a binding site found in an untranslated region of CHSY1, corresponding to BINDING SITE of FIG. 26A. FIG. 26D illustrates the complementarity of the nucleotide sequence of CHSY1 BINDING SITE, designated SEQ ID:94853, to the nucleotide sequence of GAM26 RNA of FIG. 26A, designated SEQ ID:20604. Yet another function of GAM26 is therefore inhibition of (CHSY1). Accordingly, utilities of GAM26 include diagnosis and treatment of diseases and clinical conditions with which CHSY1 is associated.

Reference is now made to CHSY1 BINDING SITE. CHSY1 is a target gene of GAM26, corresponding to GAM26-TARGET GENE of FIG. 26A. CHSY1. BINDING SITE is a binding site found in an untranslated region of CHSY1, corresponding to BINDING SITE of FIG. 26A. FIG. 26D illustrates the complementarity of the nucleotide sequence of CHSY1 BINDING SITE, designated SEQ ID:94853, to the nucleotide sequence of GAM26 RNA of FIG. 26A, designates SEQ ID:20604. An additional function of GAM26 is therefore inhibition of (CHSY1). Accordingly, utilities of GAM26 include diagnosis and treatment of diseases and clinical conditions with which CHSY1 is associated.

Reference is now made to FLJ21588 BINDING SITE. FLJ21588 is a target gene of GAM26, corresponding to GAM26-TARGET GENE of FIG. 26A. FLJ21588 BINDING SITE is a binding site found in an untranslated region of FLJ21588, corresponding to BINDING SITE of FIG. 26A. FIG. 26D illustrates the complementarity of the nucleotide sequence of FLJ21588 BINDING SITE, designated SEQ ID:94853, to the nucleotide sequence of GAM26 RNA of FIG. 26A, designated SEQ ID:20604. A further function of GAM26 is therefore inhibition of (FLJ21588). Accordingly, utilities of GAM26 include diagnosis and treatment of diseases and clinical conditions with which FLJ21588 is associated.

Reference is now made to MGC10702 BINDING SITE. MGC10702 is a target gene of GAM26, corresponding to GAM26-TARGET GENE of FIG. 26A. MGC10702 BINDING SITE is a binding site found in an untranslated region of MGC10702, corresponding to BINDING SITE of FIG. 26A. FIG. 26D illustrates the complementarity of the nucleotide sequence of MGC10702 BINDING SITE, designated SEQ ID:94853, to the nucleotide sequence of GAM26 RNA of FIG. 26A, designated SEQ ID:20604. Yet a further function of GAM26 is therefore inhibition of (MGC10702). Accordingly, utilities of GAM26 include diagnosis and treatment of diseases and clinical conditions with which MGC10702 is associated.

Reference is now made to QKI BINDING SITE. QKI is a target gene of GAM26, corresponding to GAM26-TARGET GENE of FIG. 26A. QKI BINDING SITE is a binding site found in an untranslated region of QKI, corresponding to BINDING SITE of FIG. 26A. FIG. 26D illustrates the complementarity of the nucleotide sequence of QKI BINDING SITE, designated SEQ ID:94853, to the nucleotide sequence of GAM26 RNA of FIG. 26A, designated SEQ ID:20604. Another function of GAM26 is therefore inhibition of (QKI). Accordingly, utilities of GAM26 include diagnosis and treatment of diseases and clinical conditions with which QKI is associated.

Reference is now made to STK39 BINDING SITE. STK39 is a target gene of GAM26, corresponding to GAM26-TARGET GENE of FIG. 26A. STK39 BINDING SITE is a binding site found in an untranslated region of STK39, corresponding to BINDING SITE of FIG. 26A. FIG. 26D illustrates the complementarity of the nucleotide sequence of STK39 BINDING SITE, designated SEQ ID:94853, to the nucleotide sequence of GAM26 RNA of FIG. 26A, designated SEQ ID:20604. Yet another function of GAM26 is therefore inhibition of (STK39). Accordingly, utilities of GAM26 include diagnosis and treatment of diseases and clinical conditions with which STK39 is associated.

Reference is now made to STK39 BINDING SITE. STK39 is a target gene of GAM26, corresponding to GAM26-TARGET GENE of FIG. 26A. STK39 BINDING SITE is a binding site found in an untranslated region of STK39, corresponding to BINDING SITE of FIG. 26A. FIG. 26D illustrates the complementarity of the nucleotide sequence of STK39 BINDING SITE, designated SEQ ID:94853, to the nucleotide sequence of GAM26 RNA of FIG. 26A, designated SEQ ID:20604. An additional function of GAM26 is therefore inhibition of (STK39). Accordingly, utilities of GAM26 include diagnosis and of diseases and clinical conditions STK39 is associated.

Reference is now made to STK39 BINDING SITE. STK39 is a target gene of GAM26, corresponding to GAM26-TARGET GENE of FIG. 26A. STK39 BINDING SITE is a binding site found in an untranslated region of STK39, corresponding to BINDING SITE of FIG. 26A. FIG. 26D illustrates the complementarity of the nucleotide sequence of STK39 BINDING SITE, designated SEQ ID:94853, to the nucleotide sequence of GAM26 RNA of FIG. 26A, designated SEQ ID:20604. A further function of GAM26 is therefore inhibition of (STK39). Accordingly, utilities of GAM26 include diagnosis and treatment of diseases and clinical conditions with which STK39 is associated.

Reference is now made to FLJ10996 BINDING SITE. FLJ10996 is a target gene of GAM26, corresponding to GAM26-TARGET GENE of FIG. 26A. FLJ10996 BINDING SITE is a binding site found in an untranslated region of FLJ10996, corresponding to BINDING SITE of FIG. 26A. FIG. 26D illustrates the complementarity of the nucleotide sequence of FLJ10996 BINDING SITE, designated SEQ ID:94860, to the nucleotide sequence of GAM26 RNA of FIG. 26A, designated SEQ ID:20604. Yet a further function of GAM26 is therefore inhibition of (FLJ10996). Accordingly, utilities of GAM26 include diagnosis and treatment of diseases and clinical conditions with which FLJ10996 is associated.

Reference is now made to FLJ21588 BINDING SITE. FLJ21588 is a target gene of GAM26, corresponding to GAM26-TARGET GENE of FIG. 26A. FLJ21588 BINDING SITE is a binding site found in an untranslated region of FLJ21588, corresponding to BINDING SITE of FIG. 26A, FIG. 26D illustrates the complementarity of the nucleotide sequence of FLJ21588 BINDING SITE, designated SEQ ID:94860, to the nucleotide sequence of GAM26 RNA of FIG. 26A, designated SEQ ID:20604. Another function of GAM26 is therefore inhibition of (FLJ21588). Accordingly, utilities of GAM26 include diagnosis and treatment of diseases and clinical conditions with which FLJ21588 is associated.

Reference is now made to MGC4796 BINDING SITE. MGC4796 is a target gene of GAM26, corresponding to GAM26-TARGET GENE of FIG. 26A. MGC4796 BINDING SITE is a binding site found in an untranslated region of MGC4796, corresponding to BINDING SITE of FIG. 26A. FIG. 26D illustrates the complementarity of the nucleotide sequence of MGC4796 BINDING SITE, designated SEQ ID:94860, to the nucleotide sequence of GAM26 RNA of FIG. 26A, designated SEQ ID:20604. Yet another function of GAM26 is therefore inhibition of (MGC4796). Accordingly, utilities of GAM26 include diagnosis and treatment of diseases and clinical conditions with which MGC4796 is associated.

Reference is now made to OATPRP4 BINDING SITE. OATPRP4 is a target gene of GAM26, corresponding to GAM26-TARGET GENE of FIG. 26A. OATPRP4 BINDING SITE is a binding site found in an untranslated region of OATPRP4, corresponding to BINDING SITE of FIG. 26A. FIG. 26D illustrates the complementarity of the nucleotide sequence of OATPRP4 BINDING SITE, designated SEQ ID:163380, to the nucleotide sequence of GAM26 RNA of FIG. 26A, designated SEQ ID:20604. An additional function of GAM26 is therefore inhibition of (OATPRP4). Accordingly, utilities of GAM26 include diagnosis and treatment of diseases and clinical conditions with which OATPRP4 is associated.

Reference is now made to FLJ10996 BINDING SITE. FLJ10996 is a target gene of GAM26, corresponding to GAM26-TARGET GENE of FIG. 26A. FLJ10996 BINDING SITE is a binding site found in an untranslated region of FLJ10996, corresponding to BINDING SITE of FIG. 26A. FIG. 26D illustrates the complementarity of the nucleotide sequence of FLJ10996 BINDING SITE, designated SEQ ID:167722, to the nucleotide sequence of GAM26 RNA of FIG. 26A, designate SEQ ID:20604. A further function of GAM26 is therefore inhibition of (FLJ10996). Accordingly, utilities of GAM26 include diagnosis and treatment of diseases and clinical conditions with which FLJ10996 is associated.

Reference is now made to KIAA1483 BINDING SITE. KIAA1483 is a target gene of GAM26, corresponding to GAM26-TARGET GENE of FIG. 26A. KIAA1483 BINDING SITE is a binding site found in an untranslated region of KIAA1483, corresponding to BINDING SITE of FIG. 26A. FIG. 26D illustrates the complementarity of the nucleotide sequence of KIAA1483 BINDING SITE, designated SEQ ID:193594, to the nucleotide sequence of GAM26 RNA of FIG. 26A, designated SEQ ID:20604. Yet a further function of GAM26 is therefore inhibition of (KIAA1483). Accordingly, utilities of GAM26 include diagnosis and treatment of diseases and clinical conditions with which KIAA1483 is associated.

Reference is now made to FLJ20539 BINDING SITE. FLJ20539 is a target gene of GAM26, corresponding to GAM26-TARGET GENE of FIG. 26A. FLJ20539 BINDING SITE is a binding site found in an untranslated region of FLJ20539, corresponding to BINDING SITE of FIG. 26A. FIG. 26D illustrates the complementarity of the nucleotide sequence of FLJ20539 BINDING SITE, designated SEQ ID:241978, to the nucleotide sequence of GAM26 RNA of FIG. 26A, designated SEQ ID:20604. Another function of GAM26 is therefore inhibition of (FLJ20539). Accordingly, utilities of GAM26 include diagnosis and treatment of diseases and clinical conditions with which FLJ20539 is associated.

Reference is now made to MGC2599 BINDING SITE. MGC2599 is a target gene of GAM26, corresponding to GAM26-TARGET GENE of FIG. 26A. MGC2599 BINDING SITE is a binding site found in an untranslated region of MGC2599, corresponding to BINDING SITE of FIG. 26A. FIG. 26D illustrates the complementarity of the nucleotide sequence of MGC2599 BINDING SITE, designated SEQ ID:241978, to the nucleotide sequence of GAM26 RNA of FIG. 26A, designated SEQ ID:20604. Yet another function of GAM26 is therefore inhibition of (MGC2599). Accordingly, utilities of GAM26 include diagnosis and treatment of diseases and clinical conditions with which MGC2599 is associated.

Reference is now made to TSLL2 BINDING SITE. TSLL2 is a target gene of GAM26, corresponding to GAM26-TARGET GENE of FIG. 26A. TSLL2 BINDING SITE is a binding site found in an untranslated region of TSLL2, corresponding to BINDING SITE of FIG. 26A. FIG. 26D illustrates the complementarity of the nucleotide sequence of TSLL2 BINDING SITE, designated SEQ ID:241978, to the nucleotide sequence of GAM26 RNA of FIG. 26A, designated SEQ ID:20604. An additional function of GAM26 is therefore inhibition of (TSLL2). Accordingly, utilities of GAM26 include diagnosis and treatment of diseases and clinical conditions with which TSLL2 is associated.

Reference is now made to KIAA0995 BINDING SITE. KIAA0995 is a target gene of GAM26, corresponding to GAM26-TARGET GENE of FIG. 26A. KIAA0995 BINDING SITE is a binding site found in an untranslated region of KIAA0995, corresponding to BINDING SITE of FIG. 26A. FIG. 26D illustrates the complementarity of the nucleotide sequence of KIAA0995 BINDING SITE, designated SEQ ID:245294, to the nucleotide sequence of GAM26 RNA of FIG. 26A, designated SEQ ID:20604. A further function of GAM26 is therefore inhibition of (KIAA0995). Accordingly, utilities of GAM26 include diagnosis and treatment of diseases and clinical conditions with which KIAA0995 is associated.

Reference is now made to PMX2B BINDING SITE. PMX2B is a target gene of GAM26, corresponding to GAM26-TARGET GENE of FIG. 26A. PMX2B BINDING SITE is a binding site found in an untranslated region of PMX2B, corresponding to BINDING SITE of FIG. 26A. FIG. 26D illustrates the complementarity of the nucleotide sequence of PMX2B BINDING SITE, designated SEQ ID:245294, to the nucleotide sequence of GAM26 RNA of FIG. 26A, designated SEQ ID:20604. Yet a further function of GAM26 is therefore inhibition of (PMX2B). Accordingly, utilities of GAM26 include diagnosis and treatment of diseases and clinical conditions with which PMX2B is associated.

Reference is now made to CLSTN1 BINDING SITE. CLSTN1 is a target gene of GAM26, corresponding to GAM26-TARGET GENE of FIG. 26A. CLSTN1 BINDING SITE is a binding site found in an untranslated region of CLSTN1, corresponding to BINDING SITE of FIG. 26A. FIG. 26D illustrates the complementarity of the nucleotide sequence of CLSTN1 BINDING SITE, designated SEQ ID:324417, to the nucleotide sequence of GAM26 RNA of FIG. 26A, designated SEQ ID:20604. Another function of GAM26 is therefore inhibition of (CLSTN1). Accordingly, utilities of GAM26 include diagnosis and treatment of diseases and clinical conditions with which CLSTN1 is associated.

Reference is now made to FLJ10996 BINDING SITE. FLJ10996 is a target gene of GAM26, corresponding to GAM26-TARGET GENE of FIG. 26A. FLJ10996 BINDING SITE is a binding site found in an untranslated region of FLJ10996, corresponding to BINDING SITE of FIG. 26A. FIG. 26D illustrates the complementarity of the nucleotide sequence of FLJ10996 BINDING SITE, designated SEQ ID:324417, to the nucleotide sequence of GAM26 RNA of FIG. 26A, designated SEQ ID:20604. Yet another function of GAM26 is therefore inhibition of (FLJ10996). Accordingly, utilities of GAM26 include diagnosis and treatment of diseases and clinical conditions with which FLJ10996 is associated.

Reference is now made to MGC4170 BINDING SITE. MGC4170 is a target gene of GAM26, corresponding to GAM26-TARGET GENE of FIG. 26A. MGC4170 BINDING SITE is a binding site found in an untranslated region of MGC4170, corresponding to BINDING SITE of FIG. 26A. FIG. 26D illustrates the complementarity of the nucleotide sequence of MGC4170 BINDING SITE, designated SEQ ID:324417, to the nucleotide sequence of GAM26 RNA of FIG. 26A, designated SEQ ID:20604. An additional function of GAM26 is therefore inhibition of (MGC4170). Accordingly, utilities of GAM26 include diagnosis and treatment of diseases and clinical conditions with which MGC4170 is associated.

Reference is now made to SSBP3 BINDING SITE. SSBP3 is a target gene of GAM26, corresponding to GAM26-TARGET GENE of FIG. 26A. SSBP3 BINDING SITE is a binding site found in an untranslated region of SSBP3, corresponding to BINDING SITE of FIG. 26A. FIG. 26D illustrates the complementarity of the nucleotide sequence of SSBP3 BINDING SITE, designated SEQ ID:412156, to the nucleotide sequence of GAM26 RNA of FIG. 26A, designated SEQ ID:20604. A further function of GAM26 is therefore inhibition of (SSBP3). Accordingly, utilities of GAM26 include diagnosis and treatment of diseases and clinical conditions with which SSBP3 is associated.

Reference is now made to ADAR3 BINDING SITE. ADAR3 is a target gene of GAM26, corresponding to GAM26-TARGET GENE of FIG. 26A. ADAR3 BINDING SITE is a binding site found in an untranslated region of ADAR3, corresponding to BINDING SITE of FIG. 26A. FIG. 26D illustrates the complementarity of the nucleotide sequence of ADAR3 BINDING SITE, designated SEQ ID:436814, to the nucleotide sequence of GAM26 RNA of FIG. 26A, designated SEQ ID:20604. Yet a further function of GAM26 is therefore inhibition of (ADAR3). Accordingly, utilities of GAM26 include diagnosis and treatment of diseases and clinical conditions with which ADAR3 is associated.

Reference is now made to ADPRTL2 BINDING SITE. ADPRTL2 is a target gene of GAM26, corresponding to GAM26-TARGET GENE of FIG. 26A. ADPRTL2 BINDING SITE is a binding site found in an untranslated region of ADPRTL2, corresponding to BINDING SITE of FIG. 26A. FIG. 26D illustrates the complementarity of the nucleotide sequence of ADPRTL2 BINDING SITE, designated SEQ ID:437139, to the nucleotide sequence of GAM26 RNA of FIG. 26A, designated SEQ ID:20604. Another function of GAM26 is therefore inhibition of (ADPRTL2). Accordingly, utilities of GAM26 include diagnosis and treatment of diseases and clinical conditions with which ADPRTL2 is associated.

Reference is now made to ADPRTL2 BINDING SITE. ADPRTL2 is a target gene of GAM26, corresponding to GAM26-TARGET GENE of FIG. 26A. ADPRTL2 BINDING SITE is a binding site found in an untranslated region of ADPRTL2, corresponding to BINDING SITE of FIG. 26A. FIG. 26D illustrates the complementarity of the nucleotide sequence of ADPRTL2 BINDING SITE, designated SEQ ID:437144, to the nucleotide sequence of GAM26 RNA of FIG. 26A, designated SEQ ID:20604. Yet another function of GAM26 is therefore inhibition of (ADPRTL2). Accordingly, utilities of GAM26 include diagnosis and treatment of diseases and clinical conditions with which ADPRTL2 is associated.

Reference is now made to AKAP9 BINDING SITE, AKAP9 is a target gene of GAM26, corresponding to GAM26-TARGET GENE of FIG. 26A. AKAP9 BINDING SITE is a binding site found in an untranslated region of AKAP9, corresponding to BINDING SITE of FIG. 26A. FIG. 26D illustrates the complementarity of the nucleotide sequence of AKAP9 BINDING SITE, designated SEQ ID:439691, to the nucleotide sequence if GAM26 RNA of FIG. 26A, designates SEQ ID:20604. An additional function of GAM26 is therefore inhibition of (AKAP9). Accordingly, utilities of GAM26 include diagnosis and treatment of diseases and clinical conditions with which AKAP9 is associated.

Reference is now made to ALTE BINDING SITE. ALTE is a target gene of GAM26, corresponding to GAM26-TARGET GENE of FIG. 26A. ALTE BINDING SITE is a binding site found in an untranslated region of ALTE corresponding to BINDING SITE of FIG. 26A. FIG. 26D illustrates the complementarity of the nucleotide sequence of ALTE BINDING SITE, designated SEQ ID:440959, to the nucleotide sequence of GAM26 RNA of FIG. 26A, designated SEQ ID:20604. A further function of GAM26 is therefore inhibition of (ALTE). Accordingly, utilities of GAM26 include diagnosis and treatment of diseases and clinical conditions with which ALTE is associated.

Reference is now made to AP1GBP1 BINDING SITE. AP1GBP1 is a target gene of GAM26, corresponding to GAM26-TARGET GENE of FIG. 26A. AP1GBP1 BINDING SITE is a binding site found in an untranslated region of AP1GBP1, corresponding to BINDING SITE of FIG. 26A. FIG. 26D illustrates the complementarity of the nucleotide sequence of AP1GBP1 BINDING SITE, designated SEQ ID:442346, to the nucleotide sequence of GAM26 RNA of FIG. 26A, designated SEQ ID:20604. Yet a further function of GAM26 is therefore inhibition of (AP1GBP1). Accordingly, utilities of include diagnosis and treatment of diseases and clinical conditions with which AP1GBP1 is associated.

Reference is now made to AP4E1 BINDING SITE. AP4E1 is a target gene of GAM26, corresponding to GAM26-TARGET GENE of FIG. 26A. AP4E1 BINDING SITE is a binding site found in an untranslated region of AP4E1, corresponding to BINDING SITE of FIG. 26A. FIG. 26D illustrates the complementarity of the nucleotide sequence of AP4E1 BINDING SITE, designated SEQ ID:443308, to the nucleotide sequence of GAM26 RNA of FIG. 26A, designated SEQ ID:20604. Another function of GAM26 is therefore inhibition of (AP4E1). Accordingly, utilities of GAM26 include diagnosis and treatment of diseases and clinical conditions with which AP4E1 is associated.

Reference is now made to ARF6 BINDING SITE. ARF6 is a target gene of GAM26, corresponding to GAM26-TARGET GENE of FIG. 26A. ARF6 BINDING SITE is a binding site found in an untranslated region of ARF6, corresponding to BINDING SITE of FIG. 26A. FIG. 26D illustrates the complementarity of the nucleotide sequence of ARF6 BINDING SITE, designated SEQ ID:445874, to the nucleotide sequence of GAM26 RNA of FIG. 26A, designated SEQ ID:20604. Yet another function of GAM26 is therefore inhibition of (ARF6). Accordingly, utilities of GAM26 include diagnosis and treatment of diseases and clinical conditions with which ARF6 is associated.

Reference is now made to ARF6 BINDING SITE. ARF6 is a target gene of GAM26, corresponding to GAM26-TARGET GENE of FIG. 26A. ARF6 BINDING SITE is a binding site found in an untranslated region of ARF6, corresponding to BINDING SITE of FIG. 26A. FIG. 26D illustrates the complementarity of the nucleotide sequence of ARF6 BINDING SITE, designated SEQ ID:445885, to the nucleotide sequence of GAM26 RNA of FIG. 26A, designated SEQ ID:20604. An additional function of GAM26 is therefore inhibition of (ARF6). Accordingly, utilities of GAM26 include diagnosis and treatment of diseases and clinical condition with which ARF6 is associated.

Reference is now made to ARTS-1 BINDING SITE. ARTS-1 is a target gene of GAM26, corresponding to GAM26-TARGET GENE of FIG. 26A. ARTS-1 BINDING SITE is a binding site found in an untranslated region of ARTS-1, corresponding to BINDING SITE of FIG. 26A. FIG. 26D illustrates the complementarity of the nucleotide sequence of ARTS-1 BINDING SITE, designated SEQ ID:449602, to the nucleotide sequence of GAM26 RNA of FIG. 26A, designated SEQ ID:20604. A further function of GAM26 is therefore inhibition of (ARTS-1). Accordingly, utilities of GAM26 include diagnosis and treatment of diseases and clinical conditions with which ARTS-1 is associated.

Reference is now made to ATE1 BINDING SITE. ATE1 is a target gene of GAM26, corresponding to GAM26-TARGET GENE of FIG. 26A. ATE1 BINDING SITE is a binding site found in an untranslated region of ATE1, corresponding to BINDING SITE of FIG. 26A. FIG. 26D illustrates the complementarity of the nucleotide sequence of ATE1 BINDING SITE, designated SEQ ID:450724, to the nucleotide sequence of GAM26 RNA of FIG. 26A, designated SEQ ID:20604. Yet a further function of GAM26 is therefore inhibition of (ATE1). Accordingly, utilities of GAM26 include diagnosis and treatment of diseases and clinical conditions with which ATE1 is associated.

Reference is now made to ATP6V1B2 BINDING SITE. ATP6V1B2 is a target gene of GAM26, corresponding to GAM26-TARGET GENE of FIG. 26A. ATP6V1B2 BINDING SITE is a binding site found in an untranslated region of ATP6V1B2, corresponding to BINDING SITE of FIG. 26A. FIG. 26D illustrates the complementarity of the nucleotide sequence of ATP6V1B2 BINDING SITE, designated SEQ ID:451749, to the nucleotide sequence of GAM26 RNA of FIG. 26A, designated SEQ ID:20604. Another function of GAM26 is therefore inhibition of (ATP6V1B2). Accordingly, utilities of GAM26 include diagnosis and treatment of diseases and clinical conditions with which ATP6V1B2 is associated.

Reference is now made to AWP1 BINDING SITE. AWP1 is a target gene of GAM26, corresponding to GAM26-TARGET GENE of FIG. 26A. AWP1 BINDING SITE is a binding site found in an untranslated region of AWP1, corresponding to BINDING SITE of FIG. 26A. FIG. 26D illustrates the complementarity of the nucleotide sequence of AWP1 BINDING SITE, designated SEQ ID:452398, to the nucleotide sequence of GAM26 RNA of FIG. 26A, designated SEQ ID:20604. Yet another function of GAM26 is therefore inhibition of (AWP1). Accordingly, utilities of GAM26 include diagnosis and treatment of diseases and clinical conditions with which AWP1 is associated.

Reference is now made to AWP1 BINDING SITE. AWP1 is a target gene of GAM26, correspondingly to GAM26-TARGET GENE of FIG. 26A. AWP1 BINDING SITE is a binding site found in an untranslated region of AWP1, corresponding to BINDING SITE of FIG. 26A. FIG. 26D illustrates the complementarity of the nucleotide sequence of AWP1 BINDING SITE, designated SEQ ID:452399, to the nucleotide sequence of GAM26 RNA of FIG. 26A, designated SEQ ID:20604. An additional function of GAM26 is therefore inhibition of (AWP1). Accordingly, utilities of GAM26 include diagnosis and treatment of diseases and clinical conditions with which AWP1 is associated.

Reference is now made to BA108L7.2 BINDING SITE. BA108L7.2 is a target gene of GAM26, corresponding to GAM26-TARGET GENE of FIG. 26A. BA108L7.2 BINDING SITE is a binding site found in an untranslated region of BA108L7.2, corresponding to BINDING SITE of FIG. 26A. FIG. 26D illustrates the complementarity of the nucleotide sequence of BA108L7.2 BINDING SITE, designated SEQ ID:453226, to the nucleotide sequence of GAM26 RNA of FIG. 26A, designated SEQ ID:20604. A further function of GAM26 is therefore inhibition of (BA108L7.2). Accordingly, utilities of GAM26 include diagnosis and treatment of diseases and clinical conditions with which BA108L7.2 is associated.

Reference is now made to BC-2 BINDING SITE. BC-2 is a target gene of GAM26, corresponding to GAM26-TARGET GENE of FIG. 26A. BC-2 BINDING SITE is a binding site found in an untranslated region of BC-2, corresponding to BINDING SITE of FIG. 26A. FIG. 26D illustrates the complementarity of the nucleotide sequence of BC-2 BINDING SITE designated SEQ ID:454363, to the nucleotide sequence of GAM26 RNA of FIG. 26A, designated SEQ ID:20604. Yet a further function of GAM26 is therefore inhibition of (BC-2). Accordingly, utilities of GAM26 include diagnosis and treatment of diseases and clinical conditions with which BC-2 is associated.

Reference is now made to BEX1 BINDING SITE. BEX1 is a target gene of GAM26, corresponding to GAM26-TARGET GENE of FIG. 26A. BEX1 BINDING SITE is a binding site found in an untranslated region of BEX1, corresponding to BINDING SITE of FIG. 26A. FIG. 26D illustrates the complementarity of the nucleotide sequence of BEX1 BINDING SITE, designated SEQ ID:455564, to the nucleotide sequence of GAM26 RNA of FIG. 26A, designated SEQ ID:20604. Another function of GAM26 is therefore inhibition of (BEX1). Accordingly, utilities of GAM26 include diagnosis and treatment of diseases and clinical conditions with which BEX1 is associated.

Reference is now made to BLCAP BINDING SITE. BLCAP is a target gene of GAM26, corresponding to GAM26-TARGET GENE of FIG. 26A. BLCAP BINDING SITE is a binding site found in an untranslated region of BLCAP, corresponding to BINDING SITE of FIG. 26A. FIG. 26D illustrate the complementarity of the nucleotide sequence of BLCAP BINDING SITE, designated SEQ ID:457198, to the nucleotide sequence of GAM26 RNA of FIG. 26A, designated SEQ ID:20604. Yet another function of GAM26 is therefore inhibition of (BLCAP). Accordingly, utilities of GAM26 include diagnosis and treatment of diseases and clinical conditions with which BLCAP is associated.

Reference is now made to BLCAP BINDING SITE. BLCAP is a target gene of GAM26, corresponding to GAM26-TARGET GENE of FIG. 26A. BLCAP BINDING SITE is a binding site found in an untranslated region of BLCAP, corresponding to BINDING SITE of FIG. 26A. FIG. 26D illustrates the complementarity of the nucleotide sequence of BLCAP BINDING SITE, designate SEQ ID:457204, to the nucleotide sequence of GAM26 RNA of FIG. 26A, designated SEQ ID:20604. An additional function of GAM26 is therefore inhibition of (BLCAP). Accordingly, utilities of GAM26 include diagnosis and treatment of diseases and clinical conditions with which BLCAP is associated.

Reference is now made to BTBD1 BINDING SITE. BTBD1 is a target gene of GAM26, corresponding to GAM26-TARGET GENE of FIG. 26A. BTBD1 BINDING SITE is a binding site found in an untranslated region of BTBD1, corresponding to BINDING SITE of FIG. 26A. FIG. 26D illustrates the complementarity of the nucleotide sequence of BTBD1 BINDING SITE, designate SEQ ID:460514, to the nucleotide sequence of GAM26 RNA of FIG. 26A, designate SEQ ID:20604. A further function of GAM26 is therefore inhibition of (BTBD1). Accordingly, utilities of GAM26 include diagnosis and treatment of diseases and clinical conditions with which BTBD1 is associated.

Reference is now made to C12orf22 BINDING SITE. C12orf22 is a target gene of GAM26, corresponding to GAM26-TARGET GENE of FIG. 26A. C12orf22 BINDING SITE is a binding site found in an untranslated region of C12orf22, corresponding to BINDING SITE of FIG. 26A. FIG. 26D illustrates the complementarity of the nucleotide sequence of C12orf22 BINDING SITE, designated SEQ ID:463154, to the nucleotide sequence of GAM26 RNA of FIG. 26A, designated SEQ ID:20604. Yet a further function of GAM26 is therefore inhibition of (C12orf22). Accordingly, utilities of GAM26 include diagnosis and treatment of diseases and clinical conditions with which C12orf22 is associated.

Reference is now made to C12orf22 BINDING SITE. C12orf22 is a target gene of GAM26, corresponding to GAM26-TARGET GENE of FIG. 26A. C12orf22 BINDING SITE is a binding site found in an untranslated region of C12orf22, corresponding to BINDING SITE of FIG. 26A. FIG. 26D illustrates the complementarity of the nucleotide sequence of C12orf22 BINDING SITE, designated SEQ ID:463178, to the nucleotide sequence of GAM26

RNA of FIG. 26A, designated SEQ ID:20604. Another function of GAM26 is therefore inhibition of (C12orf22). Accordingly, utilities of GAM26 include diagnosis and treatment of diseases and clinical conditions with which C12orf22 is associated.

Reference is now made to C20orf124 BINDING SITE. C20orf124 is a target gene of GAM26, corresponding to GAM26-TARGET GENE of FIG. 26A. C20orf124 BINDING SITE is a binding site found in an untranslated region of C20orf124, corresponding to BINDING SITE of FIG. 26A. FIG. 26D illustrates the complementarity of the nucleotide sequence of C20orf124 BINDING SITE, designated SEQ ID:468753, to the nucleotide sequence of GAM26 RNA of FIG. 26A, designated SEQ ID:20604. Yet another function of GAM26 is therefore inhibition of (C20orf124). Accordingly, utilities of GAM26 include diagnosis and treatment of diseases and clinical conditions with which C20orf124 is associated.

Reference is now made to C20orf139 BINDING SITE. C20orf139 is a target gene of GAM26, corresponding to GAM26-TARGET GENE of FIG. 26A. C20orf139 BINDING SITE is a binding site found in an untranslated region of C20orf139, corresponding to BINDING SITE of FIG. 26A. FIG. 26D illustrates the complementarity of the nucleotide sequence of C20orf139 BINDING SITE, designated SEQ ID:469119, to the nucleotide sequence of GAM26 RNA of FIG. 26A, designated SEQ ID:20604. An additional function of GAM26 is therefore inhibition of (C20orf139). Accordingly, utilities of GAM26 include diagnosis and treatment of diseases and clinical conditions with which C20orf139 is associated.

Reference is now made to C20orf178 BINDING SITE. C20orf178 is a target gene of GAM26, corresponding to GAM26-TARGET GENE of FIG. 26A. C20orf178 BINDING SITE is a binding site found in an untranslated region of C20orf178, corresponding to BINDING SITE of FIG. 26A. FIG. 26D illustrates the complementarity of the nucleotide sequence of C20orf178 BINDING SITE, designated SEQ ID:470891, to the nucleotide sequence of GAM26 RNA of FIG. 26A, designated SEQ ID:20604. A further function of GAM26 is therefore inhibition of (C20orf178). Accordingly, utilities of GAM26 include diagnosis and treatment of diseases and clinical conditions with which C20orf178 is associated.

Reference is now made to C2orf7 BINDING SITE. C2orf7 is a target gene of GAM26, corresponding to GAM26-TARGET GENE of FIG. 26A. C2orf7 BINDING SITE is a binding site found in an untranslated region of C2orf7, corresponding to BINDING SITE of FIG. 26A. FIG. 26D illustrates the complementarity of the nucleotide sequence of C2orf7 BINDING SITE, designated SEQ ID:476575, to the nucleotide sequence of GAM26 RNA of FIG. 26A, designated SEQ ID:20604. Yet a further function of GAM26 is therefore inhibition of (C2orf7). Accordingly, utilities of GAM26 include diagnosis and treatment of diseases and clinical conditions with which C2orf7 is associated.

Reference is now made to C4S-2 BINDING SITE. C4S-2 is a target gene of GAM26, corresponding to GAM26-TARGET GENE of FIG. 26A. C4S-2 BINDING SITE is a binding site fund in an untranslated region of C4S-2, corresponding to BINDING SITE of FIG. 26D illustrates the complementarity of the nucleotide sequence of C4S-2 BINDING SITE, designated SEQ ID:477108, to the nucleotide sequence of GAM26 RNA of FIG. 26A, designated SEQ ID:20604. Another function of GAM26 is therefore inhibition of (C4S-2). Accordingly, utilities of GAM26 include diagnosis and treatment of diseases and clinical conditions with which C4S-2 is associated.

Reference is now made to CAMTA1 BINDING SITE. CAMTA1 is a target gene of GAM26, corresponding to GAM26-TARGET GENE of FIG. 26A. CAMTA1 BINDING SITE is a binding site found in an untranslated region of CAMTA1, corresponding to BINDING SITE of FIG. 26A. FIG. 26D illustrates the complementarity of the nucleotide sequence of CAMTA1 BINDING SITE, designated SEQ ID:483028, to the nucleotide sequence of GAM26 RNA of FIG. 26A, designate SEQ ID:20604. Yet another function of GAM26 is therefore inhibition of (CAMTA1). Accordingly, utilities of GAM26 include diagnosis and treatment of diseases and clinical conditions with which CAMTA1 is associated.

Reference is now made to CARM1 BINDING SITE. CARM1 is a target gene of GAM26, corresponding to GAM26-TARGET GENE of FIG. 26A. CARM1 BINDING SITE is a binding site found in an untranslated region of CARM1, corresponding to BINDING SITE of FIG. 26A. FIG. 26D illustrates the complementarity of the nucleotide sequence of CARM1 BINDING SITE, designated SEQ ID:483979, to the nucleotide sequence GAM26 RNA of FIG. 26A, designate SEQ ID:20604. An additional function of GAM26 is therefore inhibition of (CARM1). Accordingly, utilities of GAM26 include diagnosis and treatment of diseases and clinical conditions with which CARM1 is associated.

Reference is now made to CARM1 BINDING SITE. CARM1 is a target gene of GAM26, corresponding to GAM26-TARGET GENE of FIG. 26A. CARM1 BINDING SITE is a binding site found in an untranslated region of CARM1, corresponding to BINDING SITE of FIG. 26A. FIG. 26D illustrates the complementarity of the nucleotide sequence of CARM1 BINDING SITE, designate SEQ ID:483989, to the nucleotide sequence of GAM26 RNA of FIG. 26A, designate SEQ ID:20604. A further function of GAM26 is therefore inhibition of (CARM1). Accordingly, utilities of GAM26 include diagnosis and treatment of diseases and clinical conditions with which CARM1 is associated.

Reference is now made to CBLN1 BINDING SITE. CBLN1 is a target gene of GAM26, corresponding to GAM26-TARGET GENE of FIG. 26A. CBLN1 BINDING SITE is a binding site found in an untranslated region of CBLN1, corresponding to BINDING SITE of FIG. 26A. FIG. 26D illustrates the complementarity of the nucleotide sequence of CBLN1 BINDING SITE, designated SEQ ID:485030, to the nucleotide sequence of GAM26 RNA of FIG. 26A, designated SEQ ID:20604. Yet a further function of GAM26 is therefore inhibition of (CBLN1). Accordingly, utilities of GAM26 include diagnosis and treatment of diseases and clinical conditions with which CBLN1 is associated.

Reference is now made to CBLN1 BINDING SITE. CBLN1 is a target gene of GAM26, corresponding to GAM26-TARGET GENE of FIG. 26A. CBLN1 BINDING SITE is a binding site found in an untranslated region of CBLN1, corresponding to BINDING SITE of FIG. 26A. FIG. 26D illustrated the complementarity of the nucleotide sequence of CBLN1 BINDING SITE, designated SEQ ID:485054, to the nucleotide sequence of GAM26 RNA of FIG. 26A, designated SEQ ID:20604. Another function of GAM26 is therefore inhibition of (CBLN1). Accordingly, utilities of GAM26 include diagnosis and treatment of diseases and clinical conditions with which CBLN1 is associated.

Reference is now made to CDC14A BINDING SITE. CDC14A is a target gene of GAM26, corresponding to GAM26-TARGET GENE of FIG. 26A. CDC14A BINDING SITE is a binding site found in an untranslated region of CDC14A, corresponding to BINDING SITE of FIG. 26A. FIG. 26D illustrates the complementarity of the nucleotide sequence of CDC14A BINDING SITE, designated SEQ ID:487263, to the nucleotide sequence of GAM26 RNA of FIG. 26A, designated SEQ ID:20604. Yet another function of GAM26 is therefore inhibition of (CDC14A). Accordingly, utilities of GAM26 include diagnosis and treatment of diseases and clinical conditions with which CDC14A is associated.

Reference is now made to CDC14A BINDING SITE. CDC14A is a target gene of GAM26, corresponding to GAM26-TARGET GENE of FIG. 26A. CDC14A BINDING SITE is a binding site found in an untranslated region of CDC14A, corresponding to BINDING SITE of FIG. 26A. FIG. 26D illustrates the complementarity of the nucleotide sequence of CDC14A BINDING SITE, designated SEQ ID:487263, to the nucleotide sequence of GAM26 RNA of FIG. 26A, designated SEQ ID:20604. An additional function of GAM26 is therefore inhibition of (CDC14A). Accordingly, utilities of GAM26 include diagnosis and treatment of diseases and clinical conditions with which CDC14A is associated.

Reference is now made to CDC16 BINDING SITE. CDC16 is a target gene of GAM26, corresponding to GAM26-TARGET GENE of FIG. 26A. CDC16 BINDING SITE is a binding site found in an untranslated region of CDC16, corresponding to BINDING SITE of FIG. 26A. FIG. 26D illustrates the complementarity of the nucleotide sequence of CDC16 BINDING SITE, designated SEQ ID:487765, to the nucleotide sequence of GAM26 RNA of FIG. 26A, designated SEQ ID:20604. A further function of GAM26 is therefore inhibition of (CDC16). Accordingly, utilities of GAM26 include diagnosis and treatment of diseases and clinical conditions with which CDC16 is associated.

Reference is now made to CDC42BPB BINDING SITE. CDC42BPB is a target gene of GAM26, corresponding to GAM26-TARGET GENE of FIG. 26A. CDC42BPB BINDING SITE is a binding site found in an untranslated region of CDC42BPB, corresponding to BINDING SITE of FIG. 26A. FIG. 26D illustrates the complementarity of the nucleotide sequence of CDC42BPB BINDING SITE, designated SEQ ID:487991, to the nucleotide sequence of GAM26 RNA of FIG. 26A, designated SEQ ID:20604. Yet a further function of GAM26 is therefore inhibition of (CDC42BPB). Accordingly, utilities of GAM26 include diagnosis and treatment of diseases and clinical conditions with which CDC42BPB is associated.

Reference is now made to CDCA4 BINDING SITE. CDCA4 is a target gene of GAM26, corresponding to GAM26-TARGET GENE of FIG. 26A. CDCA4 BINDING SITE is a binding site found in an untranslated region of CDCA4, corresponding to BINDING SITE of FIG. 26A. FIG. 26D illustrates the complementarity of the nucleotide sequence of CDCA4 BINDING SITE, designated SEQ ID:488095, to the nucleotide sequence of GAM26 RNA of FIG. 26A, designated SEQ ID:20604. Another function of GAM26 is therefore inhibition of (CDCA4). Accordingly, utilities of GAM26 include diagnosis and treatment of diseases and clinical conditions with which CDCA4 is associated.

Reference is now made to CECR2 BINDING SITE. CECR2 is a target gene of GAM26, corresponding to GAM26-TARGET GENE of FIG. 26A. CECR2 BINDING SITE is a binding site found in an untranslated region of CECR2, corresponding to BINDING SITE of FIG. 26A. FIG. 26D illustrate the complementarity of the nucleotide sequence of CECR2 BINDING. SITE, designate SEQ ID:489555, to the nucleotide sequence GAM26 RNA of FIG. 26A, designated SEQ ID:20604. Yet another function of GAM26 is therefore inhibition of (CECR2). Accordingly, utilities of GAM26 include diagnosis and treatment of diseases and clinical conditions with which CECR2 is associated.

Reference is now made to CGGBP1 BINDING SITE. CGGBP1 is a target gene of GAM26, corresponding to GAM26-TARGET GENE of FIG. 26A. CGGBP1 BINDING SITE is a binding site found in an untranslated region of CGGBP1, corresponding to BINDING SITE of FIG. 26A. FIG. 26D illustrates the complementarity of the nucleotide sequence of CGGBP1 BINDING SITE, designate SEQ ID:492176, to the nucleotide sequence of GAM26 RNA of FIG. 26A, designate SEQ ID:20604. An additional function of GAM26 is therefore inhibition of (CGGBP1). Accordingly, utilities of GAM26 include diagnosis and treatment of diseases and clinical conditions with which CGGBP1 is associated.

Reference is now made to CGGBP1 BINDING SITE. CGGBP1 is a target gene of GAM26, corresponding to GAM26-TARGET GENE of FIG. 26A. CGGBP1 BINDING SITE is a binding site found in an untranslated region of CGGBP1, corresponding to BINDING SITE of FIG. 26A. FIG. 26D illustrates the complementarity of the nucleotide sequence of CGGBP1 BINDING SITE, designated SEQ ID:492221, to the nucleotide sequence of GAM26 RNA of FIG. 26A, designate SEQ ID:20604. A further function of GAM26 is therefore inhibition of (CGGBP1). Accordingly, utilities of GAM26 include diagnosis and treatment of diseases and clinical conditions with which CGGBP1 is associated.

Reference is now made to CHSY1 BINDING SITE. CHSY1 is a target gene of GAM26, corresponding to GAM26-TARGET GENE of FIG. 26A. CHSY1 BINDING SITE is a binding site found in an untranslated region of CHSY1, corresponding to BINDING SITE of FIG. 26A. FIG. 26D illustrates the complementarity of the nucleotide sequence of CHSY1 BINDING SITE, designated SEQ ID:494504, to the nucleotide sequence of GAM26 RNA of FIG. 26A, designated SEQ ID:20604. Yet a further function of GAM26 is therefore inhibition of (CHSY1). Accordingly, utilities of GAM26 include diagnosis and treatment of diseases and clinical conditions with which CHSY1 is associated.

Reference is now made to CHSY1 BINDING SITE. CHSY1 is a target gene of GAM26, corresponding to GAM26-TARGET GENE of FIG. 26A. CHSY1 BINDING SITE is a binding site found in an untranslated region of CHSY1, corresponding to BINDING SITE of FIG. 26A. FIG. 26D illustrates the complementarity of the nucleotide sequence of CHSY1 BINDING SITE, designate SEQ ID:494516, to the nucleotide sequence of GAM26 RNA of FIG. 26A, designated SEQ ID:20604. Another function of GAM26 is therefore inhibition of (CHSY1). Accordingly, utilities of GAM26 include diagnosis and treatment of diseases and clinical conditions with which CHSY1 is associated.

Reference is now made to CHSY1 BINDING SITE. CHSY1 is a target gene of GAM26, corresponding to GAM26-TARGET GENE of FIG. 26A. CHSY1 BINDING SITE is a binding site found in an untranslated region of CHSY1, corresponding to BINDING SITE of FIG. 26A. FIG. 26D illustrates the complementarity of the nucleotide sequence of CHSY1 BINDING SITE, designated SEQ ID:494532, to the nucleotide sequence of GAM26 RNA of FIG. 26A, designated SEQ ID:20604. Yet another function of GAM26 is therefore inhibition of (CHSY1). Accordingly, utilities of GAM26 include diagnosis and treatment of diseases and clinical conditions with which CHSY1 is associated.

Reference is now made to CHSY1 BINDING SITE. CHSY1 is a target gene of GAM26, corresponding to GAM26-TARGET GENE of FIG. 26A. CHSY1 BINDING SITE is a binding site found in an untranslated region of CHSY1, corresponding to BINDING SITE of FIG. 26A. FIG. 26D illustrates the complementarity of the nucleotide sequence of CHSY1 BINDING SITE, designated SEQ ID:494603, to the nucleotide sequence of GAM26 RNA of FIG. 26A, designated SEQ ID:20604. An additional function of GAM26 is therefore inhibition of (CHSY1). Accordingly, utilities of GAM26 include diagnosis and treatment of diseases and clinical conditions with which CHSY1 is associated.

Reference is now made to CLSTN1 BINDING SITE. CLSTN1 is a target gene of GAM26, corresponding to GAM26-TARGET GENE of FIG. 26A. CLSTN1 BINDING SITE is a binding site found in an untranslated region of CLSTN1, corresponding to BINDING SITE of FIG. 26A. FIG. 26D illustrates the complementarity of the nucleotide sequence of CLSTN1 BINDING SITE, designated SEQ ID:496944, to the nucleotide sequence of GAM26 RNA of FIG. 26A, designated SEQ ID:20604. A further function of GAM26 is therefore inhibition of (CLSTN1). Accordingly, utilities of GAM26 include diagnosis and treatment of diseases and clinical conditions with which CLSTN1 is associated.

Reference is now made to CNNM3 BINDING SITE. CNNM3 is a target gene of GAM26, corresponding to GAM26-TARGET GENE of FIG. 26A. CNNM3 BINDING SITE is a binding site found in an untranslated region of CNNM3, corresponding to BINDING SITE of FIG. 26A. FIG. 26D illustrates the complementarity of the nucleotide sequence of CNNM3 BINDING SITE, designate SEQ ID:498002, to the nucleotide sequence of GAM26 RNA of FIG. 26A, designated SEQ ID:20604. Yet a further function of GAM26 is therefore inhibition of (CNNM3). Accordingly, utilities of GAM26 include diagnosis and treatment of diseases and clinical conditions with which CNNM3 is associated.

Reference is now made to COASTER BINDING SITE. COASTER is a target gene of GAM26, corresponding to GAM26-TARGET GENE of FIG. 26A. COASTER BINDING SITE is a binding site found in an untranslated region of COASTER, corresponding to BINDING SITE of FIG. 26A. FIG. 26D illustrates the complementarity of the nucleotide sequence of COASTER BINDING SITE, designated SEQ ID:498924, to the nucleotide sequence of GAM26 RNA of FIG. 26A, designated SEQ ID:20604. Another function of GAM26 is therefore inhibition of (COASTER). Accordingly, utilities of include diagnosis and treatment of diseases and clinical conditions with which COASTER is associated.

Reference is now made to COL4A3BP BINDING SITE. COL4A3BP is a target gene of GAM26, corresponding to GAM26-TARGET GENE of FIG. 26A. COL4A3BP BINDING SITE is a binding site found in an untranslated region of COL4A3BP, corresponding to BINDING SITE of FIG. 26A. FIG. 26D illustrates the complementarity of the nucleotide sequence of COL4A3BP BINDING SITE, designated SEQ ID:499352, to the nucleotide sequence of GAM26 RNA of FIG. 26A, designated SEQ ID:20604. Yet another function of GAM26 is therefore inhibition of (COL4A3BP). Accordingly, utilities of GAM26 include diagnosis and treatment of diseases and clinical conditions with which COL4A3BP is associated.

Reference is now made to CTCF BINDING SITE. CTCF is a target gene of GAM26, corresponding to GAM26-TARGET GENE of FIG. 2A. CTCF BINDING SITE is a binding site found in an untranslated region of CTF, corresponding to BINDING SITE of FIG. 26A. FIG. 26D illustrates the complementarity of the nucleotide sequence of CTCF BINDING SITE, designated SEQ ID:503528, to the nucleotide sequence of GAM26 RNA of FIG. 26A, designated SEQ ID:20604. An additional function of GAM26 is therefore inhibition of (CTCF). Accordingly, utilities of GAM26 include diagnosis and treatment of diseases and clinical conditions with which CTCF is associated.

Reference is now made to CTCF BINDING SITE. CTCF is a target gene of GAM26, corresponding to GAM26-TARGET GENE of FIG. 26A. CTCF BINDING SITE is a binding site fund in an untranslated region of CTCF, corresponding to BINDING SITE of FIG. 26A. FIG. 26D illustrates the complementarity of the nucleotide sequence of CTCF BINDING SITE, designated SEQ ID:503529, to the nucleotide sequence of GAM26 RNA of FIG. 26A, designated SEQ ID:20604. A further function of GAM26 is therefore inhibition of (CTCF). Accordingly, utilities of GAM26 include diagnosis and treatment of diseases and clinical conditions with which CTCF is associated.

Reference is now made to DDM36 BINDING SITE. DDM36 is a target gene of GAM26, corresponding to GAM26-TARGET GENE of FIG. 26A. DDM36 BINDING SITE is a binding site found in an untranslated region of DDM36, corresponding to BINDING SITE of FIG. 26A. FIG. 26D illustrate the complementarity of the nucleotide sequence of DDM36 BINDING SITE, designated SEQ ID:508506, to the nucleotide sequence of GAM26 RNA of FIG. 26A, designated SEQ ID:20604. Yet a further function of GAM26 is therefore inhibition of (DDM36). Accordingly, utilities of GAM26 include diagnosis and treatment of diseases and clinical conditions with which DDM36 is associated.

Reference is now made to DDM36 BINDING SITE. DDM36 is a target gene of GAM26, corresponding to GAM26-TARGET GENE of FIG. 26A. DDM36 BINDING SITE is a binding site found in an untranslated region of DDM36, corresponding to BINDING SITE of FIG. 26A. FIG. 26D illustrates the complementarity of the nucleotide sequence of DDM36 BINDING SITE, designate SEQ ID:508575, to the nucleotide sequence of GAM26 RNA of FIG. 26A, designated SEQ ID:20604. Another function of GAM26 is therefore inhibition of (DDM36). Accordingly, utilities of GAM26 include diagnosis and treatment of diseases and clinical conditions with which DDM36 is associated.

Reference is now made to DKFZP434D1335 BINDING SITE. DKFZP434D1335 is a target gene of GAM26, corresponding GAM26-TARGET GENE of FIG. 26A. DKFZP434D1335 BINDING SITE is a binding site found in an untranslated region of DKFZP434D1335, corresponding to BINDING SITE of FIG. 26A. FIG. 26D illustrates the complementarity of the nucleotide sequence of DKFZP434D1335 BINDING SITE, designated SEQ ID:516151, to the nucleotide sequence of GAM26 RNA of FIG. 26A, designated SEQ ID:20604. Yet another function of GAM26 is therefore inhibition of (DKFZP434D1335). Accordingly, utilities of GAM26 include diagnosis and treatment of diseases and clinical conditions with which DKFZP434D1335 is associated.

Reference is now made to DKFZP434J154 BINDING SITE. DKFZP434J154 is a target gene of GAM26, corresponding to GAM26-TARGET GENE of FIG. 26A. DKFZP434J154 BINDING SITE is a binding site found in an untranslated region of DKFZP434J154, corresponding to BINDING SITE of FIG. 26A. FIG. 26D illustrates the complementarity of the nucleotide sequence of DKFZP434J154 BINDING SITE, designated SEQ ID:520474, to the nucleotide sequence of GAM26 RNA of FIG. 26A, designated SEQ ID:20604. An additional function of GAM26 is therefore inhibition of (DKFZP434J154). Accordingly utilities of GAM26 include diagnosis and treatment of diseases and clinical conditions with which DKFZP434J154 is associated.

Reference is now made to DKFZP434N093 BINDING SITE. DKFZP434N093 is a target gene of GAM26, corresponding to GAM26-TARGET GENE of FIG. 26A. DKFZP434N093 BINDING SITE is a binding site found in an untranslated region of DKFZP434N093, corresponding to BINDING SITE of FIG. 26A. FIG. 26D illustrates the complementarity of the nucleotide sequence of DKFZP434N093 BINDING SITE, designated SEQ ID:522414, to the nucleotide sequence of GAM26 RNA of FIG. 26A, designated SEQ ID:20604. A further function of GAM26 is therefore inhibition of (DKFZP434N093). Accordingly, utilities of GAM26 include diagnosis and treatment of diseases and clinical conditions with which DKFZP434N093 is associated.

Reference is now made to DKFZP434P106 BINDING SITE. DKFZP434P106 is a target gene of GAM26, corresponding to GAM26-TARGET GENE of FIG. 26A. DKFZP434P106 BINDING SITE is a binding site found in an untranslated region of DKFZP434P106, corresponding to BINDING SITE of FIG. 26A. FIG. 26D illustrates the complementarity of the nucleotide sequence of DKFZP434P106 BINDING SITE, designated SEQ ID:523992, to the nucleotide sequence of GAM26 RNA of FIG. 26A, designated SEQ ID:20604. Yet a further function of GAM26 therefore inhibition of (DKFZP434P106). Accordingly, utilities of GAM26 include diagnosis and treatment of diseases and clinical conditions with which DKFZP434P106 is associated.

Reference is now made to DKFZP566A1524 BINDING SITE. DKFZP566A1524 is a target gene of GAM26, corresponding of GAM26-TARGET GENE of FIG. 26A. DKFZP566A1524 BINDING SITE is a binding site found in an untranslated region of DKFZP566A1524, corresponding to BINDING SITE of FIG. 26A. FIG. 26D illustrates the complementarity of the nucleotide sequence DKFZP566A1524 BINDING SITE, designated SEQ ID:531199, to the nucleotide sequence of GAM26 RNA of FIG. 26A, designated SEQ ID:20604. Another function of GAM26 is therefore inhibition of (DKFZP566A1524). Accordingly, utilities of GAM26 include diagnosis and treatment of diseases and clinical conditions with which DKFZP566A1524 is associated.

Reference is now made to DKFZP566K1924 BINDING SITE. DKFZP566K1924 is a target gene of GAM26, corresponding to GAM26-TARGET GENE of FIG. 26A. DKFZP566K1924 BINDING SITE is a binding site found in an untranslated region of DKFZP566K1924, corresponding to BINDING SITE of FIG. 26A. FIG. 26D illustrates the complementarity of the nucleotide sequence of DKFZP566K1924 BINDING SITE, designated SEQ ID:532863, to the nucleotide sequence of GAM26 RNA of FIG. 26A, designated SEQ ID:20604. Yet another function of GAM26 is therefore inhibition of (DKFZP566K1924). Accordingly, utilities of GAM26 include diagnosis and treatment of diseases and clinical conditions with which DKFZP566K1924 is associated.

Reference is now made to DKFZp761B0514 BINDING SITE. DKFZp761B0514 is a target gene of GAM26, corresponding to GAM26-TARGET GENE of FIG. 26A. DKFZp761B0514 BINDING SITE is a binding site found in an untranslated region of DKFZp761B0514, corresponding to BINDING SITE of FIG. 26A. FIG. 26D illustrates the complementarity of the nucleotide sequence of DKFZp761B0514 BINDING SITE, designated SEQ ID:536448, to the nucleotide sequence of GAM26 RNA of FIG. 26A, designated SEQ ID:20604. An additional function of GAM26 is therefore inhibition of (DKFZp761B0514). Accordingly, utilities of GAM26 include diagnosis and treatment of diseases and clinical conditions with which DKFZp761B0514 is associated.

Reference is now made to DKFZp762E1511 BINDING SITE. DKFZp762E1511 is a target gene of GAM26, corresponding to GAM26-TARGET GENE of FIG. 26A. DKFZp762E1511 BINDING SITE is a binding site found in an untranslated region of DKFZp762E1511, corresponding to BINDING SITE of FIG. 26A. FIG. 26D illustrates the complementarity of the nucleotide sequence of DKFZp762E1511 BINDING SITE, designated SEQ ID:539970, to the nucleotide sequence of GAM26 RNA of FIG. 26A, designated SEQ ID:20604. A further function of GAM26 is therefore inhibition of (DKFZp762E1511). Accordingly, utilities of GAM26 include diagnosis and treatment of diseases and clinical conditions with which DKFZp762E1511 is associated.

Reference is now made to Dlc2 BINDING SITE. Dlc2 is a target gene of GAM26, corresponding to GAM26-TARGET GENE of FIG. 26A. Dlc2 BINDING SITE is a binding site found in an untranslated region of Dlc2, corresponding to BINDING SITE of FIG. 26A. FIG. 26D illustrates the complementarity of the nucleotide sequence of Dlc2 BINDING SITE, designated SEQ ID:540962, to the nucleotide sequence of GAM26 RNA of FIG. 26A, designated SEQ ID:20604. Yet a further function of GAM26 is therefore inhibition of (Dlc2). Accordingly, utilities of GAM26 include diagnosis and treatment of diseases and clinical conditions with which Dlc2 is associated.

Reference is now made to E46L BINDING SITE. E46L is a target gene of GAM26, corresponding to GAM26-TARGET GENE of FIG. 26A. E46L BINDING SITE is a binding site found in an untranslated region of E46L, corresponding to BINDING SITE of FIG. 26A. FIG. 26D illustrates the complementarity of the nucleotide sequence of E46L BINDING SITE, designated SEQ ID:545962, to the nucleotide sequence of GAM26 RNA of FIG. 26A, designated SEQ ID:20604. Another function of GAM26 is therefore inhibition of (E46L). Accordingly, utilities of GAM26 include diagnosis and treatment of diseases and clinical conditions with which E46L is associated.

Reference is now made to E46L BINDING SITE. E46L is a target gene of GAM26, corresponding to GAM26-TARGET GENE of FIG. 26A. E46L BINDING SITE is a binding site found in an untranslated region of E46L, corresponding to BINDING SITE of FIG. 26A. FIG. 26D illustrates the complementarity of the nucleotide sequence of E46L BINDING SITE, designated SEQ ID:545966, to the nucleotide sequence of GAM26 RNA of FIG. 26A, designated SEQ ID:20604. Yet another function of GAM26 is therefore inhibition of (E46L). Accordingly, utilities of GAM26 include diagnosis and treatment of diseases and clinical conditions with which E46L is associated.

Reference is now made to EHM2 BINDING SITE. EHM2 is a target gene of GAM26, corresponding to GAM26-TARGET GENE of FIG. 26A. EHM2 BINDING SITE is a binding site found in an untranslated region of EHM2, corresponding to BINDING SITE of FIG. 26A. FIG. 26D illustrates the complementarity of the nucleotide sequence of EHM2 B DING SITE, designated SEQ ID:547115, to the nucleotide sequence of GAM26 RNA of FIG. 26A, designated SEQ ID:20604. An additional function of GAM26 is therefore inhibition of (EHM2). Accordingly, utilities of GAM26 include diagnosis and treatment of diseases and clinical conditions with which EHM2 is associated.

Reference is now made to EHM2 BINDING SITE. EHM2 is a target gene of GAM26, corresponding to GAM26-TARGET GENE of FIG. 26A. EHM2 BINDING SITE is a binding site found in an untranslated region of EHM2, corresponding to BINDING SITE of FIG. 26A. FIG. 26D illustrates the complementarity of the nucleotide sequence of EHM2 BINDING SITE, designated SEQ ID:547149, to the nucleotide sequence of GAM26 RNA of FIG. 26A, designated SEQ ID:20604, A further function of GAM26 is therefore inhibition of (EHM2). Accordingly, utilities of GAM26 include diagnosis and treatment of diseases and clinical conditions with which EHM2 is associated.

Reference is now made to EHM2 BINDING SITE. EHM2 is a target gene of GAM26, corresponding to GAM26-TARGET GENE of FIG. 26A. EHM2 BINDING SITE is a binding site found in an untranslated region of EHM2, corresponding to BINDING SITE of FIG. 26A. FIG. 26D illustrates the complementarity of the nucleotide sequence of EHM2 BINDING SITE, designated SEQ ID:547151, to the nucleotide sequence of GAM26 RNA of FIG. 26A, designated SEQ ID:20604. Yet a further function of GAM26 is therefore inhibition of (EHM2). Accordingly, utilities of GAM26 include diagnosis and treatment of diseases and clinical conditions with which EHM2 is associated.

Reference is now made to ELKS BINDING SITE. ELKS is a target gene of GAM26, corresponding to GAM26-TARGET GENE of FIG. 26A. ELKS BINDING SITE is a binding site found in an untranslated region of ELKS, corresponding to BINDING SITE of FIG. 26A. FIG. 26D illustrates the complementarity of the nucleotide sequence of ELKS BINDING SITE, designated SEQ ID:548280, to the nucleotide sequence of GAM26 RNA of FIG. 26A, designated SEQ ID:20604. Another function of GAM26 is therefore inhibition of (ELKS). Accordingly, utilities of GAM26 include diagnosis and treatment of diseases and clinical conditions with which ELKS is associated.

Reference is now made to ELKS BINDING SITE. ELKS is a target gene of GAM26, corresponding to GAM26-TARGET GENE of FIG. 26A. ELKS BINDING SITE is a binding site found in an untranslated region of ELKS, corresponding to BINDING SITE of FIG. 26A. FIG. 26D illustrates the complementarity of the nucleotide sequence of ELKS BINDING SITE, designated SEQ ID:548281, to the nucleotide sequence of GAM26 RNA of FIG. 26A, designated SEQ ID:20604. Yet another function of GAM26 is therefore inhibition of (ELKS). Accordingly, utilities of GAM26 include diagnosis and treatment of diseases and clinical conditions with which ELKS is associated.

Reference is now made to ELKS BINDING SITE. ELKS is a target gene of GAM26, corresponding to GAM26-TARGET GENE of FIG. 26A. ELKS BINDING SITE is a binding site found in an untranslated region of ELKS, corresponding to BINDING SITE of FIG. 26. FIG. 26D illustrates the complementarity of the nucleotide sequence of ELKS BINDING SITE, designated SEQ ID:548286, to the nucleotide sequence of GAM26 RNA of FIG. 26A, designated SEQ ID:20604. An additional function of GAM26 is therefore inhibition of (ELKS). Accordingly, utilities of GAM26 include diagnosis and treatment of diseases and clinical conditions with which ELKS is associated.

Reference is now made to ELKS BINDING SITE. ELKS is a target gene of GAM26, corresponding to GAM26-TARGET GENE of FIG. 26A. ELKS BINDING SITE is a binding site found in an untranslated region of ELKS, corresponding to BINDING SITE of FIG. 26A. FIG. 26D illustrates the complementarity of the nucleotide sequence of ELKS BINDING SITE, designated SEQ ID:548299, to the nucleotide sequence of GAM26 RNA of FIG. 26A, designated SEQ ID:20604. A further function of GAM26 is therefore inhibition of (ELKS). Accordingly, utilities of GAM26 include diagnosis and treatment of diseases and clinical conditions with which ELKS is associated.

Reference is now made to ELL2 BINDING SITE. ELL2 is a target gene of GAM26, corresponding to GAM26-TARGET GENE of FIG. 26A. ELL2 BINDING SITE is a binding site found in an untranslated region of ELL2, corresponding to BINDING SITE of FIG. 26A. FIG. 26D illustrates the complementarity of the nucleotide sequence of ELL2 BINDING SITE, designated SEQ ID:548421, to the nucleotide sequence of GAM26 RNA of FIG. 26A, designated SEQ ID:20604. Yet a further function of GAM26 is therefore inhibition of (ELL2). Accordingly, utilities of GAM26 include diagnosis and treatment of diseases and clinical conditions with which ELL2 is associated.

Reference is now made to ELL2 BINDING SITE. ELL2 is a target gene of GAM26, corresponding to GAM26-TARGET GENE of FIG. 26A. ELL2 BINDING SITE is a binding site found in an untranslated region of ELL2, corresponding to BINDING SITE of FIG. 26A. FIG. 26D illustrates the complementarity of the nucleotide sequence of ELL2 BINDING SITE, designated SEQ ID:548442, to the nucleotide sequence of GAM26 RNA of FIG. 26A, designated SEQ ID:20604. Another function of GAM26 is therefore inhibition of (ELL2). Accordingly, utilities of GAM26 include diagnosis and treatment of diseases and clinical conditions with which ELL2 is associated.

Reference is now made to FAF1 BINDING SITE. FAF1 is a target gene of GAM26, corresponding to GAM26-TARGET GENE of FIG. 26A. FAF1 BINDING SITE is a binding site found in an untranslated region of FAF1, corresponding to BINDING SITE of FIG. 26A. FIG. 26D illustrates the complementarity of the nucleotide sequence of FAF1 BINDING SITE, designated SEQ ID:552942, to the nucleotide sequence of GAM26 RNA of FIG. 26A, designated SEQ ID:20604. Yet another function of GAM26 is therefore inhibition of (FAF1). Accordingly, utilities of GAM26 include diagnosis and treatment of diseases and clinical conditions with which FAF1 is associated.

Reference is now made to FAF1 BINDING SITE. FAF1 is a target gene of GAM26, corresponding to GAM26-TARGET GENE of FIG. 26A. FAF1 BINDING SITE is a binding site found in an untranslated region of FAF1, corresponding to BINDING SITE of FIG. 26A. FIG. 26D illustrates the complementarity of the nucleotide sequence of FAF1 BINDING SITE, designated SEQ ID:552963, to the nucleotide sequence of GAM26 RNA of FIG. 26A, designated SEQ ID:20604. An additional function of GAM26 is therefore inhibition of (FAF1). Accordingly, utilities of GAM26 include diagnosis and treatment of diseases and clinical conditions with which FAF1 is associated.

Reference is now made to FEM1B BINDING SITE. FEM1B is a target gene of GAM26, corresponding to GAM26-TARGET GENE of FIG. 26A. FEM1B BINDING SITE is a binding site found in an untranslated region of FEM1B, corresponding to BINDING SITE of FIG. 26A. FIG. 26D illustrate the complementarity of the nucleotide sequence of FEM1B BINDING SITE, designated SEQ ID:556003, to the nucleotide sequence of GAM26 RNA of FIG. 26A, designated SEQ ID:20604. A further function of GAM26 is therefore inhibition of (FEM1B). Accordingly, utilities of GAM26 include diagnosis and treatment of diseases and clinical conditions with which FEM1B is associated.

Reference is now made to FJX1 BINDING SITE. FJX1 is a target gene of GAM26, corresponding to GAM26-TARGET GENE of FIG. 26A. FJX1 BINDING SITE is a binding site found in an untranslated region of FJX1, corresponding to BINDING SITE of FIG. 26A. FIG. 26D illustrates the complementarity of the nucleotide sequence of FJX1 BINDING SITE, designated SEQ ID:557158, to the nucleotide sequence of GAM26 RNA of FIG. 26A, designated SEQ ID:20604. Yet a further function of GAM26 is therefore inhibition of (FJX1). Accordingly, utilities of GAM26 include diagnosis and treatment of diseases and clinical conditions with which FJX1 is associated.

Reference is now made to FLJ10211 BINDING SITE. FLJ0211 is a target gene of GAM26, corresponding to GAM26-TARGET GENE of FIG. 26A. FLJ10211 BINDING SITE is a binding site found in an untranslated region of FLJ10211, corresponding to BINDING SITE of FIG. 26A. FIG. 26D illustrates the complementarity of the nucleotide sequence of FLJ10211 BINDING SITE, designated SEQ ID:562466, to the nucleotide sequence of GAM26 RNA of FIG. 26A, designated SEQ ID:20604. Another function of GAM26 is therefore inhibition of (FLJ10211). Accordingly, utilities of GAM26 include diagnosis and treatment of diseases and clinical conditions with which FLJ10211 is associated.

Reference is now made to FLJ10211 BINDING SITE. FLJ10211 is a target gene of GAM26, corresponding to GAM26-TARGET GENE of FIG. 26A. FLJ0211 BINDING SITE is a binding site found in an untranslated region of FLJ10211, corresponding to BINDING SITE of FIG. 26A. FIG. 26D illustrates the complementarity of the nucleotide sequence of FLJ10211 BINDING SITE, designated SEQ ID:562496, to the nucleotide sequence of GAM26 RNA of FIG. 26A, designated SEQ ID:20604. Yet another function of GAM26 is therefore inhibition of (FLJ10211). Accordingly, utilities of GAM26 include diagnosis and treatment of diseases and clinical conditions with which FLJ10211 is associated.

Reference is now made to FLJ10211 BINDING SITE. FLJ10211 is a target gene of GAM26, corresponding to GAM26-TARGET GENE of FIG. 26A. FLJ10211 BINDING SITE is a binding site found in an untranslated region of FLJ10211, corresponding to BINDING SITE of FIG. 26A. FIG. 26D illustrates the complementarity of the nucleotide sequence of FLJ10211 BINDING SITE, designate SEQ ID:562509, to the nucleotide sequence of GAM26 RNA of FIG. 26A, designate SEQ ID:20604. An additional function of GAM26 is therefore inhibition of (FLJ10211). Accordingly, utilities of GAM26 include diagnosis and treatment of diseases and clinical conditions with which FLJ10211 is associated.

Reference is now made to FLJ10244 BINDING SITE. FLJ10244 is a target gene of GAM26, corresponding to GAM26-TARGET GENE of FIG. 26A. FLJ10244 BINDING SITE is a binding site found in an untranslated region of FLJ10244, corresponding to BINDING SITE of FIG. 26A. FIG. 26D illustrates the complementarity of the nucleotide sequence of FLJ10244 BINDING SITE, designated SEQ ID:562895, to the nucleotide sequence of GAM26 RNA of FIG. 26A, designated SEQ ID:20604. A further function of GAM2 is therefore inhibition of (FLJ10244). Accordingly, utilities of GAM26 include diagnosis and treatment of diseases and clinical conditions with which FLJ10244 is associated.

Reference is now made to FLJ10244 BINDING SITE. FLJ10244 is a target gene of GAM26, corresponding to GAM26-TARGET GENE of FIG. 26A. FLJ10244 BINDING SITE is a binding site found in an untranslated region of FLJ10244, corresponding to BINDING SITE of FIG. 26A. FIG. 26D illustrate the complementarity of the nucleotide sequence of FLJ10244 BINDING SITE, designate SEQ ID:562897, to the nucleotide sequence of GAM26 RNA of FIG. 26A, designated SEQ ID:20604. Yet a further function of GAM26 is therefore inhibition of (FLJ10244). Accordingly, utilities of GAM26 include diagnosis and treatment of diseases and clinical conditions with which FLJ10244 is associated.

Reference is now made to FLJ10244 BINDING SITE. FLJ10244 is a target gene of GAM26, corresponding to GAM26-TARGET GENE of FIG. 26A. FLJ10244 BINDING SITE is a binding site found in an untranslated region of FLJ10244, corresponding to BINDING SITE of FIG. 26A. FIG. 26D illustrates the complementarity of the nucleotide sequence of FLJ10244 BINDING SITE, designated SEQ ID:562906, to the nucleotide sequence of GAM26 RNA of FIG. 26A, designated SEQ ID:20604. Another function of GAM26 is therefore inhibition of (FLJ10244). Accordingly, utilities of GAM26 include diagnosis and treatment of diseases and clinical conditions with which FLJ10244 is associated.

Reference is now made to FLJ10244 BINDING SITE. FLJ10244 is a target gene of GAM26, corresponding to GAM26-TARGET GENE of FIG. 26A. FLJ10244 BINDING SITE, is a binding site found in an untranslated region of FLJ10244, corresponding to BINDING SITE of FIG. 26A. FIG. 26D illustrates the complementarity of the nucleotide sequence of FLJ10244 BINDING SITE, designated SEQ ID:562923, to the nucleotide sequence of GAM26 RNA of FIG. 26A, designated SEQ ID:20604. Yet another function of GAM26 is therefore inhibition of (FLJ10244). Accordingly, utilities of GAM26 include diagnosis and treatment of diseases and clinical conditions with which FLJ10244 is associated.

Reference is now made to FLJ10244 BINDING SITE. FLJ10244 is a target gene of GAM26, corresponding to GAM26-TARGET GENE of FIG. 26A. FLJ10244 BINDING SITE is a binding site found in an untranslated region of FLJ10244, corresponding to BINDING SITE of FIG. 26A. FIG. 26D illustrates the complementarity of the nucleotide sequence of FLJ10244 BINDING SITE, designated SEQ ID:562943, to the nucleotide sequence of GAM26 RNA of FIG. 26A, designate SEQ ID:20604. An additional function of GAM26 is therefore inhibition of (FLJ10244).

Accordingly, utilities of GAM26 include diagnosis and treatment of diseases and clinical conditions with which FLJ10244 is associated.

Reference is now made to FLJ10342 BINDING SITE. FLJ10342 is a target gene of GAM26, corresponding to GAM26-TARGET GENE of FIG. 26A. FLJ10342 BINDING SITE is a binding site found in an untranslated region of FLJ10342, corresponding to BINDING SITE of FIG. 26A. FIG. 26D illustrates the complementarity of the nucleotide sequence of FLJ10342 BINDING SITE, designated SEQ ID:564347, to the nucleotide sequence of GAM26 RNA of FIG. 26A, designated SEQ ID:20604. A further function of GAM26 is therefore inhibition of (FLJ10342). Accordingly, utilities of GAM26 include diagnosis and treatment of diseases and clinical conditions with which FLJ10342 is associated.

Reference is now made to FLJ10648 BINDING SITE. FLJ10648 is a target gene of GAM26, corresponding to GAM26-TARGET GENE of FIG. 26A. FLJ10648 BINDING SITE is a binding site found in an untranslated region of FLJ10648, corresponding to BINDING SITE of FIG. 26A. FIG. 26D illustrates the complementarity of the nucleotide sequence of FLJ10648 BINDING SITE, designated SEQ ID:569200, to the nucleotide sequence of GAM26 RNA of FIG. 26A, designated SEQ ID:20604. Yet a further function of GAM26 is therefore inhibition of (FLJ10648). Accordingly, utilities of GAM26 include diagnosis and treatment of diseases and clinical conditions with which FLJ10648 is associated.

Reference is now made to FLJ10709 BINDING SITE. FLJ10709 is a target gene of GAM26, corresponding to GAM26-TARGET GENE of FIG. 26A. FLJ10709 BINDING SITE is a binding site found in an untranslated region of FLJ10709, corresponding to BINDING SITE of FIG. 26A. FIG. 26D illustrates the complementarity of the nucleotide sequence of FLJ10709 BINDING SITE, designated SEQ ID:570431, to the nucleotide sequence of GAM26 RNA of FIG. 26A, designated SEQ ID:20604. Another function of GAM26 is therefore inhibition of (FLJ10709). Accordingly, utilities of GAM26 include diagnosis and treatment of diseases and clinical conditions with which FLJ10709 is associated.

Reference is now made to FLJ10856 BINDING SITE. FLJ10856 is a target gene of GAM26, corresponding to GAM2 TARGET GENE of FIG. 26A. FLJ10856 BINDING SITE is a binding site found in an untranslated region of FLJ10856, corresponding to BINDING SITE of FIG. 26A. FIG. 26D illustrates the complementarity of the nucleotide sequence of FLJ10856 BINDING SITE, designated SEQ ID:574295, to the nucleotide sequence of GAM26 RNA of FIG. 26A, designated SEQ ID:20604. Yet another function of GAM26 is therefore inhibition of (FLJ10856). Accordingly, utilities of GAM26 include diagnosis and treatment of diseases and clinical conditions with which FLJ10856 is associated.

Reference is now made to FLJ10925 BINDING SITE. FLJ10925 is a target gene of GAM26, corresponding to GAM26-TARGET GENE of FIG. 26A. FLJ10925 BINDING SITE is a binding site found in an untranslated region of FLJ10925, corresponding to BINDING SITE of FIG. 26A. FIG. 26D illustrate the complementarity of the nucleotide sequence of FLJ10925 BINDING SITE, designated SEQ ID:575621, to the nucleotide sequence of GAM26 RNA of FIG. 26A, designated SEQ ID:20604. An additional function of GAM26 is therefore inhibition of (FLJ0925). Accordingly, utilities of GAM26 include diagnosis and treatment of diseases and clinical conditions with which FLJ10925 is associated.

Reference is now made to FLJ10996 BINDING SITE. FLJ10996 is a target gene of GAM26, corresponding to GAM26-TARGET GENE of FIG. 26A. FLJ10996 BINDING SITE is a binding site found in an untranslated region of FLJ10996, corresponding to BINDING SITE of FIG. 26A. FIG. 26D illustrates the complementarity of the nucleotide sequence of FLJ10996 BINDING SITE, designated SEQ ID:576651, to the nucleotide sequence of GAM26 RNA of FIG. 26A, designated SEQ ID:20604. A further function of GAM26 is therefore inhibition of (FLJ10996). Accordingly, utilities of GAM26 include diagnosis and treatment of diseases and clinical conditions with which FLJ10996 is associated.

Reference is now made to FLJ11700 BINDING SITE. FLJ11700 is a target gene of GAM26, corresponding to GAM26-TARGET GENE of FIG. 26A. FLJ11700 BINDING SITE is a binding site found in an untranslated region of FLJ11700, corresponding to BINDING SITE of FIG. 26A. FIG. 26D illustrates the complementarity of the nucleotide sequence of FLJ11700 BINDING SITE, designated SEQ ID:582367, to the nucleotide sequence of GAM26 RNA of FIG. 26A, designated SEQ ID:20604. Yet a further function of GAM26 is therefore inhibition of (FLJ11700). Accordingly, utilities of GAM26 include diagnosis and treatment of diseases and clinical conditions with which FLJ11700 is associated.

Reference is now made to FLJ12363 BINDING SITE. FLJ12363 is a target gene of GAM26, corresponding to GAM26-TARGET GENE of FIG. 26A. FLJ12363 BINDING SITE is a binding site found in an untranslated region of FLJ12363, corresponding to BINDING SITE of FIG. 26A. FIG. 26D illustrates the complementarity of the nucleotide sequence of FLJ12363 BINDING SITE, designated SEQ ID:587504, to the nucleotide sequence of GAM26 RNA of FIG. 26A, designated SEQ ID:20604. Another function of GAM26 is therefore inhibition of (FLJ12363). Accordingly, utilities of GAM26 include diagnosis and treatment of diseases and clinical conditions with which FLJ12363 is associated.

Reference is now made to FLJ12363 BINDING SITE. FLJ12363 is a target gene of GAM26, corresponding to GAM26-TARGET GENE of FIG. 26A. FLJ12363 BINDING SITE is a binding site found in an untranslated region of FLJ12363, corresponding to BINDING SITE of FIG. 26A. FIG. 26D illustrates the complementarity of the nucleotide sequence of FLJ12363 BINDING SITE, designated SEQ ID:587507, to the nucleotide sequence of GAM26 RNA of FIG. 26A, designated SEQ ID:20604. Yet another function of GAM26 is therefore inhibition of (FLJ12363). Accordingly, utilities of GAM26 include diagnosis and treatment of diseases and clinical conditions with which FLJ12363 is associated.

Reference is now made to FLJ12377 BINDING SITE. FLJ12377 is a target gene of GAM26, corresponding to GAM26-TARGET GENE of FIG. 26A. FLJ12377 BINDING SITE is a binding site found in an untranslated region of FLJ12377, corresponding to BINDING SITE of FIG. 26A. FIG. 26D illustrates the complementarity of the nucleotide sequence of FLJ12377 BINDING SITE, designated SEQ ID:587654, to the nucleotide sequence of GAM26 RNA of FIG. 26A, designated SEQ ID:20604. An additional function of GAM26 is therefore inhibition of (FLJ12377).

Accordingly, utilities of GAM26 include diagnosis and treatment of diseases and clinical conditions with which FLJ12377 is associated.

Reference is now made to FLJ12697 BINDING SITE. FLJ12697 is a target gene of GAM26, corresponding to GAM26-TARGET GENE of FIG. 26A. FLJ12697 BINDING SITE is a binding site found in an untranslated region of FLJ12697, corresponding to BINDING SITE of FIG. 26A. FIG. 26D illustrates the complementarity of the nucleotide sequence of FLJ12697 BINDING SITE, designated SEQ ID:592585, to the nucleotide sequence of GAM26 RNA of FIG. 26A, designated SEQ ID:20604. A further function of GAM26 is therefore inhibition of (FLJ12697). Accordingly, utilities of GAM26 include diagnosis and treatment of diseases and clinical conditions with which FLJ12697 is associated.

Reference is now made to FLJ12750 BINDING SITE. FLJ12750 is a target gene of GAM26, corresponding to GAM26-TARGET GENE of FIG. 26A. FLJ12750 BINDING SITE is a binding site found in an untranslated region of FLJ12750, corresponding to BINDING SITE of FIG. 26A. FIG. 26D illustrates the complementarity of the nucleotide sequence of FLJ12750 BINDING SITE, designate SEQ ID:593299, to the nucleotide sequence of GAM26 RNA of FIG. 26A, designated SEQ ID:20604. Yet a further function of GAM26 is therefore inhibition of (FLJ12750). Accordingly, utilities of GAM26 include diagnosis and treatment of diseases and clinical conditions with which FLJ12750 is associated.

Reference is now made to FLJ13189 BINDING SITE. FLJ13189 is a target gene of GAM26, corresponding to GAM26-TARGET GENE of FIG. 26A. FLJ13189 BINDING SITE is a binding site found in an untranslated region of FLJ13189, corresponding to BINDING SITE of FIG. 26A. FIG. 26D illustrates the complementarity of the nucleotide sequence of FLJ13189 BINDING SITE, designated SEQ ID:599594, to the nucleotide sequence of GAM26 RNA of FIG. 26A, designated SEQ ID:20604. Another function of GAM26 is therefore inhibition of (FLJ13189). Accordingly, utilities of GAM26 include diagnosis and treatment of diseases and clinical conditions with which FLJ13189 is associated.

Reference is now made to FLJ13189 BINDING SITE. FLJ13189 is a target gene of GAM26, corresponding to GAM26-TARGET GENE of FIG. 26A. FLJ13189 BINDING SITE is a binding site found in an untranslated region of FLJ13189, corresponding to BINDING SITE of FIG. 26A. FIG. 26D illustrates the complementarity of the nucleotide sequence of FLJ13189 BINDING SITE, designated SEQ ID:599628, to the nucleotide sequence of GAM26 RNA of FIG. 26A, designated SEQ ID:20604. Yet another function of GAM26 is therefore inhibition of (FLJ13189). Accordingly, utilities of GAM26 include diagnosis and treatment of diseases and clinical conditions with which FLJ13189 is associated.

Reference is now made to FLJ13194 BINDING SITE. FLJ13194 is a target gene of GAM26, corresponding to GAM26-TARGET GENE of FIG. 26A. FLJ3194 BINDING SITE is a binding site found in an untranslated region of FLJ13194, corresponding to BINDING SITE of FIG. 26A. FIG. 26D illustrates the complementarity of the nucleotide sequence of FLJ13194 BINDING SITE, designated SEQ ID:600122, to the nucleotide sequence of GAM26 RNA of FIG. 26A, designated SEQ ID:20604. An additional function of GAM26 is therefore inhibition of (FLJ13194). Accordingly, utilities of GAM26 include diagnosis and treatment of diseases and clinical conditions with which FLJ13194 is associated.

Reference is now made to FLJ13340 BINDING SITE. FLJ13340 is a target gene of GAM26, corresponding to GAM26-TARGET GENE of FIG. 26A. FLJ13340 BINDING SITE is a binding site found in an untranslated region of FLJ13340, corresponding to BINDING SITE of FIG. 26A. FIG. 26D illustrates the complementarity of the nucleotide sequence of FLJ13340 BINDING SITE, designated SEQ ID:601522, to the nucleotide sequence of GAM26 RNA of FIG. 26A, designated SEQ ID:20604. A further function of GAM26 is therefore inhibition of (FLJ13340). Accordingly, utilities of GAM26 include diagnosis and treatment of diseases and clinical conditions with which FLJ13340 is associated.

Reference is now made to TBDN100 BINDING SITE. TBDN100 is a target gene of GAM26, corresponding to GAM26-TARGET GENE of FIG. 26A. TBDN100 BINDING SITE is a binding site found in an untranslated region of TBDN100, corresponding to BINDING SITE of FIG. 26A. FIG. 26D illustrates the complementarity of the nucleotide sequence of TBDN100 BINDING SITE, designated SEQ ID:601522, to the nucleotide sequence of GAM26 RNA of FIG. 26A, designated SEQ ID:20604. Yet a further function of GAM26 is therefore inhibition of (TBDN100). Accordingly, utilities of GAM26 include diagnosis and treatment of diseases and clinical conditions with which TBDN100 is associated.

Reference is now made to FLJ13855 BINDING SITE. FLJ13855 is a target gene of GAM26, corresponding to GAM26-TARGET GENE of FIG. 26A. FIJI 3855 BINDING SITE is a binding site found in an untranslated region of FLJ13855, corresponding to BINDING SITE of FIG. 26A. FIG. 26D illustrates the complementarity of the nucleotide sequence of FLJ13855 BINDING SITE, designated SEQ ID:605857, to the nucleotide sequence of GAM26 RNA of FIG. 26A, designated SEQ ID:20604. Another function of GAM26 is therefore inhibition of (FLJ13855). Accordingly, utilities of GAM26 include diagnosis and treatment of diseases and clinical conditions with which FLJ13855 is associated.

Reference is now made to FLJ13855 BINDING SITE. FLJ13855 is a target gene of GAM26, corresponding to GAM26-TARGET GENE of FIG. 26A. FLJ13855 BINDING SITE is a binding site found in an untranslated region of FLJ13855, corresponding to BINDING SITE of FIG. 26A. FIG. 26D illustrates the complementarity of the nucleotide sequence of FLJ13855 BINDING SITE, designate SEQ ID:605858, to the nucleotide sequence of GAM26 RNA of FIG. 26A, designated SEQ ID:20604. Yet another function of GAM26 is therefore inhibition of (FLJ13855). Accordingly, utilities of GAM26 include diagnosis and treatment of diseases and clinical conditions with which FLJ13855 is associated.

Reference is now made to FLJ14299 BINDING SITE. FLJ14299 is a target gene of GAM26, corresponding to GAM26-TARGET GENE of FIG. 26A. FLJ14299 BINDING SITE is a binding site found in an untranslated region of FLJ14299, corresponding to BINDING SITE of FIG. 26A. FIG. 26D illustrates the complementarity of the nucleotide sequence of FLJ14299 BINDING SITE, designated SEQ ID:610393, to the nucleotide sequence of GAM26 RNA of FIG. 26A, designated SEQ ID:20604. An additional function of GAM26 is therefore inhibition of (FLJ14299).

Accordingly, utilities of GAM26 include diagnosis and treatment of diseases and clinical conditions with which FLJ14299 is associated.

Reference is now made to FLJ14451 BINDING SITE. FLJ14451 is a target gene of GAM26, corresponding to GAM26-TARGET GENE of FIG. 26A. FLJ14451 BINDING SITE is a binding site found in an untranslated region of FLJ14451, corresponding to BINDING SITE of FIG. 26A. FIG. 26D illustrates the complementarity of the nucleotide sequence of FLJ14451 BINDING SITE, designated SEQ ID:612603, to the nucleotide sequence of GAM26 RNA of FIG. 26A, designated SEQ ID:20604. A further function of GAM2 is therefore inhibition of (FLJ14451). Accordingly, utilities of GAM26 include diagnosis and treatment of diseases and clinical conditions with which FLJ14451 is associated.

Reference is now made to FLJ14451 BINDING SITE. FLJ14451 is a target gene of GAM26, corresponding to GAM26-TARGET GENE of FIG. 26A. FLJ14451 BINDING SITE is a binding site found in an untranslated region of FLJ14451, corresponding to BINDING SITE of FIG. 26A. FIG. 26D illustrates the complementarity of the nucleotide sequence of FLJ14451 BINDING SITE, designated SEQ ID:612607, to the nucleotide sequence of GAM26 RNA of FIG. 26A, designated SEQ ID:20604. Yet a further function of GAM26 is therefore inhibition of (FLJ14451). Accordingly, utilities of GAM26 include diagnosis and treatment of diseases and clinical conditions with which FLJ14451 is associated.

Reference is now made to FLJ20288 BINDING SITE. FLJ20288 is a target gene of GAM26, corresponding to GAM26-TARGET GENE of FIG. 26A. FLJ20288 BINDING SITE is a binding site found in an untranslated region of FLJ20288, corresponding to BINDING SITE of FIG. 26A. FIG. 26D illustrates the complementarity of the nucleotide sequence of FLJ20288 BINDING SITE, designate SEQ ID:625741, to the nucleotide sequence of GAM26 RNA of FIG. 26A, designated SEQ ID:20604. Another function of GAM26 is therefore inhibition of (FLJ20288). Accordingly, utilities of GAM26 include diagnosis and treatment of diseases and clinical conditions with which FLJ20288 is associated.

Reference is now made to FLJ20288 BINDING SITE. FLJ20288 is a target gene of GAM26, corresponding to GAM26-TARGET GENE of FIG. 26A. FLJ20288 BINDING SITE is a binding site found in an untranslated region of FLJ20288, corresponding to BINDING SITE of FIG. 26A. FIG. 26D illustrates the complementarity of the nucleotide sequence of FLJ20288 BINDING SITE, designated SEQ ID:625764, to the nucleotide sequence of GAM26 RNA of FIG. 26A, designated SEQ ID:20604. Yet another function of GAM26 is therefore inhibition of (FLJ20288). Accordingly, utilities of GAM26 include diagnosis and treatment of diseases and clinical conditions with which FLJ20288 is associated.

Reference is now made to PCAF BINDING SITE. PCAF is a target gene of GAM26, corresponding to GAM26-TARGET GENE of FIG. 26A. PCAF BINDING SITE is a binding site found in an untranslated region of PCAF, corresponding to BINDING SITE of FIG. 26A. FIG. 26D illustrates the complementarity of the nucleotide sequence of PCAF BINDING SITE, designated SEQ ID:625767, to the nucleotide sequence of GAM26 RNA of FIG. 26A, designated SEQ ID:29604. An additional function of GAM26 is therefore inhibition of (PCAF). Accordingly, utilities of GAM26 include diagnosis and treatment of diseases and clinical conditions with which PCAF is associated.

Reference is now made to FLJ20288 BINDING SITE. FLJ20288 is a target gene of GAM26, corresponding to GAM26-TARGET GENE of FIG. 26A. FLJ20288 BINDING SITE is a binding site found in an untranslated region of FLJ20288, corresponding to BINDING SITE of FIG. 26A. FIG. 26D illustrates the complementarity of the nucleotide sequence of FLJ20288 BINDING SITE, designated SEQ ID:625783, to the nucleotide sequence of GAM26 RNA of FIG. 26A, designated SEQ ID:20604. A further function of GAM26 is therefore inhibition of (FLJ20288). Accordingly, utilities of GAM26 include diagnosis and treatment of diseases and clinical conditions with which FLJ20288 is associated.

Reference is now made to FLJ20288 BINDING SITE. FLJ20288 is a target gene of GAM26, corresponding to GAM26-TARGET GENE of FIG. 26A. FLJ20288 BINDING SITE is a binding site found in an untranslated region of FLJ20288, corresponding to BINDING SITE of FIG. 26A. FIG. 26D illustrates, the complementarity of the nucleotide sequence of FLJ20288 BINDING SITE, designated SEQ ID:625785, to the nucleotide sequence of GAM26 RNA of FIG. 26A, designated SEQ ID:20604. Yet a further function of GAM26 is therefore inhibition of (FLJ20288). Accordingly, utilities of GAM26 include diagnosis and treatment of diseases and clinical conditions with which FLJ20288 is associated.

Reference is now made to FLJ20288 BINDING SITE. FLJ20288 is a target gene of GAM26, corresponding to GAM26-TARGET GENE of FIG. 26A. FLJ20288 BINDING SITE is a binding site found in an untranslated region of FLJ20288, corresponding to BINDING SITE of FIG. 26A. FIG. 26D illustrates the complementarity of the nucleotide sequence of FLJ20288 BINDING SITE, designated SEQ ID:625802, to the nucleotide sequence of GAM26 RNA of FIG. 26A, designated SEQ ID:20604. Another function of GAM26 is therefore inhibition of (FLJ20288). Accordingly, utilities of GAM26 include diagnosis and treatment of diseases and clinical conditions with which FLJ20288 is associated.

Reference is now made to FLJ20400 BINDING SITE. FLJ20400 is a target gene of GAM26, corresponding to GAM26-TARGET GENE of FIG. 26A. FLJ20400 BINDING SITE is a binding site found in an untranslated region of FLJ20400, corresponding to BINDING SITE of FIG. 26A. FIG. 26D illustrates the complementarity of the nucleotide sequence of FLJ20400 BINDING SITE, designated SEQ ID:629258, to the nucleotide sequence of GAM26 RNA of FIG. 26A, designated SEQ ID:20604. Yet another function of GAM26 is therefore inhibition of (FLJ20400). Accordingly, utilities of GAM26 include diagnosis and treatment of diseases and clinical conditions with which FLJ20400 is associated.

Reference is now made to FLJ20421 BINDING SITE. FLJ20421 is a target gene of GAM26, corresponding to GAM26-TARGET GENE of FIG. 26A. FLJ20421 BINDING SITE is a binding site found in an untranslated region of FLJ20421, corresponding to BINDING SITE of FIG. 26A. FIG. 26D illustrates the complementarity of the nucleotide sequence of FLJ20421 BINDING SITE, designated SEQ ID:629645, to the nucleotide sequence of GAM26 RNA of FIG. 26A, designated SEQ ID:20604. An additional function of GAM26 is therefore inhibition of (FLJ20421). Accordingly, utilities of GAM26 include diagnosis and treatment of diseases and clinical conditions with which FLJ20421 is associated.

Reference is now made to FLJ20421 BINDING SITE. FLJ20421 is a target gene of GAM26, corresponding to GAM26-TARGET GENE of FIG. 26A. FLJ20421 BINDING SITE is a binding site found in an untranslated region of FLJ20421, corresponding to BINDING SITE of FIG. 26A. FIG. 26D illustrates the complementarity of the nucleotide sequence of FLJ20421 BINDING SITE, designated SEQ ID:629655, to the nucleotide sequence of GAM26 RNA of FIG. 26A, designated SEQ ID:20604. A further function of GAM26 is therefore inhibition of (FLJ20421). Accordingly, utilities of GAM26 include diagnosis and treatment of diseases and clinical conditions with which FLJ20421 is associated.

Reference is now made to FLJ20421 BINDING SIT. FLJ20421 is a target gene of GAM26, corresponding to GAM26-TARGET GENE of FIG. 26A. FLJ20421 BINDING SITE is a binding site found in an untranslated region of FLJ20421, corresponding to BINDING SITE of FIG. 26A. FIG. 26D illustrates the complementarity of the nucleotide sequence of FLJ20421 BINDING SITE, designated SEQ ID:629660, to the nucleotide sequence of GAM26 RNA of FIG. 26A, designated SEQ ID:20604. Yet a further function of GAM26 is therefore inhibition of (FLJ20421). Accordingly, utilities of GAM26 include diagnosis and treatment of diseases and clinical conditions with which FLJ20421 is associated.

Reference is now made to FLJ20425 BINDING SITE. FLJ20425 is a target gene of GAM26, corresponding to GAM26-TARGET GENE of FIG. 26A. FLJ20425 BINDING SITE is a binding site found in an untranslated region of FLJ20425, corresponding to BINDING SITE of FIG. 26A. FIG. 26D illustrate the complementarity of the nucleotide sequent of FLJ20425 BINDING SITE, designated SEQ ID:629739, to the nucleotide sequence of GAM26 RNA of FIG. 26A, designated SEQ ID:20604. Another function of GAM26 is therefore inhibition of (FLJ20425). Accordingly, utilities of GAM26 include diagnosis and treatment of diseases and clinical conditions with which FLJ20425 is associated.

Reference is now made to FLJ20539 BINDING SITE. FLJ20539 is a target gene of GAM26, corresponding to GAM26-TARGET GENE of FIG. 26A. FLJ20539 BINDING SITE is a binding site found in an untranslated region of FLJ20539, corresponding to BINDING SITE of FIG. 26A. FIG. 26D illustrates the complementarity of the nucleotide sequence of FLJ20539 BINDING SITE, designated SEQ ID:632084, to the nucleotide sequence GAM26 RNA of FIG. 26A, designated, SEQ ID:20604. Yet another function of GAM26 is therefore inhibition of (FLJ20539). Accordingly, utilities of GAM26 include diagnosis and treatment of diseases and clinical conditions with which FLJ20539 is associated.

Reference is now made to FLJ20718 BINDING SITE. FLJ20718 is a target gene of GAM26, corresponding to GAM26-TARGET GENE of FIG. 26A. FLJ20718 BINDING SITE is a binding site found in an untranslated region of FLJ20718, corresponding to BINDING SITE of FIG. 26A. FIG. 26D illustrates the complementarity of the nucleotide sequence of FLJ20718 BINDING SITE, designated SEQ ID:635286, to the nucleotide sequence of GAM26 RNA of FIG. 26A, designated SEQ ID:20604. An additional function of GAM26 is therefore inhibition of (FLJ20718). Accordingly, utilities of GAM26 include diagnosis and treatment of diseases and clinical conditions with which FLJ20718 is associated.

Reference is now made to FLJ21588 BINDING SITE. FLJ21588 is a target gene of GAM26, corresponding to GAM26-TARGET GENE of FIG. 26A. FLJ21588 BINDING SITE is a binding site found in an untranslated region of FLJ21588, corresponding to BINDING SITE of FIG. 26A. FIG. 26D illustrates the complementarity of the nucleotide sequence of FLJ21588 BINDING SITE, designated SEQ ID:641646, to the nucleotide sequence of GAM26 RNA of FIG. 26A, designated SEQ ID:20604. A further function of GAM25 is therefore inhibition of (FLJ21588). Accordingly, utilities of GAM26 include diagnosis and treatment of diseases and clinical conditions with which FLJ21588 is associated.

Reference is now made to FLJ21613 BINDING SITE. FLJ21613 is a target gene of GAM26, corresponding to GAM26-TARGET GENE of FIG. 26A. FLJ21613 BINDING SITE is a binding site found in an untranslated region of FLJ21613; corresponding to BINDING SITE of FIG. 26A. FIG. 26D illustrates the complementarity of the nucleotide sequence of FLJ21613 BINDING SITE, designated SEQ ID:641999, to the nucleotide sequence of GAM26 RNA of FIG. 26A, designated SEQ ID:20604. Yet a further function of GAM26 is therefore inhibition of (FLJ21613). Accordingly, utilities of GAM26 include diagnosis and treatment of diseases and clinical conditions with which FLJ21613 is associated.

Reference is now made to FLJ22393 BINDING SITE. FLJ22393 is a target gene of GAM26, corresponding to GAM26-TARGET GENE of FIG. 26A. FLJ22393 BINDING SITE is a binding site found in an untranslated region of FLJ22393, corresponding to BINDING SITE of FIG. 26A. FIG. 26D illustrates the complementarity of the nucleotide sequence of FLJ22393 BINDING SITE, designated SEQ ID:649088, to the nucleotide sequence of GAM26 RNA of FIG. 26A, designated SEQ ID:20604. Another function of GAM26 is therefore inhibition of (FLJ22393). Accordingly, utilities of GAM26 include diagnosis and treatment of diseases and clinical conditions with which FLJ22393 is associated.

Reference is now made to FLJ23251 BINDING SITE. FLJ23251 is a target gene of GAM26, corresponding to GAM26-TARGET GENE of FIG. 26A. FLJ23251 BINDING SITE is a binding site found in an untranslated region of FLJ23251, corresponding to BINDING SITE of FIG. 26A. FIG. 26D illustrates the complementarity of the nucleotide sequence of FLJ23251 BINDING SITE, designated SEQ ID:657789, to the nucleotide sequence of GAM26 RNA of FIG. 26A, designate SEQ ID:20604. Yet another function of GAM26 is therefore inhibition of (FLJ23251). Accordingly, utilities of GAM26 include diagnosis and treatment of diseases and clinical conditions with which FLJ23251 is associated.

Reference is now made to FLJ31564 BINDING SITE. FLJ31564 is a target gene of GAM26, corresponding to GAM26-TARGET GENE of FIG. 26A. FLJ31564 BINDING SITE is a binding site found in an untranslated region of FLJ31564, corresponding to BINDING SITE of FIG. 26A. FIG. 26D illustrates the complementarity of the nucleotide sequence of FLJ31564 BINDING SITE, designated SEQ ID:665686, to the nucleotide sequence of GAM26 RNA of FIG. 26A, designated SEQ ID:20604. An additional function of GAM26 is therefore inhibition of (FLJ31564). Accordingly, utilities of GAM26 include diagnosis and treatment of diseases and clinical conditions with which FLJ31564 is associated.

Reference is now made to FLJ31978 BINDING SITE. FLJ31978 is a target gene of GAM26, corresponding to GAM26-TARGET GENE of FIG. 26A. FLJ31978 BINDING SITE is a binding site found in an untranslated region of FLJ31978, corresponding to BINDING SITE of FIG. 26A. FIG. 26D illustrates the complementarity of the nucleotide sequence of FLJ31978 BINDING SITE, designated SEQ ID:666546, to the nucleotide sequence of GAM26 RNA of FIG. 26A, designated SEQ ID:20604. A further function of GAM26 is therefore inhibition of (FLJ31978). Accordingly, utilities of GAM26 include diagnosis and treatment of diseases and clinical conditions with which FLJ31978 is associated.

Reference is now made to FOXO3A BINDING SITE. FOXO3A is a target gene of GAM26, corresponding to GAM26-TARGET GENE of FIG. 26A. FOXO3A BINDING SITE is a binding site found in an untranslated region of FOXO3A, corresponding to BINDING SITE of FIG. 26A. FIG. 26D illustrates the complementarity of the nucleotide sequence of FOXO3A BINDING SITE, designated SEQ ID:669368, to the nucleotide sequence of GAM26 RNA of FIG. 26A, designated SEQ ID:20604. Yet a further function of GAM26 is therefore inhibition of (FOXO3A). Accordingly, utilities of GAM26 include diagnosis and treatment of diseases and clinical conditions with which FOXO3A is associated.

Reference is now made to FUBP3 BINDING SITE. FUBP3 is a target gene of GAM26, corresponding to GAM26-TARGET GENE FIG. 26A. FUBP3 BINDING SITE is a binding site found in an untranslated region of FUBP3, corresponding to BINDING SITE of FIG. 26A. FIG. 26D illustrates the complementarity of the nucleotide sequence of FUBP3 BINDING SITE, designated SEQ ID:670361, to the nucleotide sequence of GAM26 RNA of FIG. 26A, designated SEQ ID:20604. Another function of GAM26 is therefore inhibition of (FUBP3). Accordingly, utilities of GAM26 include diagnosis and treatment of diseases and clinical conditions with which FUBP3 is associated.

Reference is now made to FUBP3 BINDING SITE. FUBP3 is a target gene of GAM26, corresponding to GAM26-TARGET GENE of FIG. 26A. FUBP3 BINDING SITE is a binding site found in an untranslated region of FUBP3, corresponding to BINDING SITE of FIG. 26A. FIG. 26D illustrates the complementarity of the nucleotide sequence of FUBP3 BINDING SITE, designated SEQ ID:670394, to the nucleotide sequence of GAM26 RNA of FIG. 26A, designated SEQ ID:20604. Yet another function of GAM26 is therefore inhibition of (FUBP3). Accordingly, utilities of GAM26 include diagnosis and treatment of diseases and clinical conditions with which FUBP3 is associated.

Reference is now made to GIOT-3 BINDING SITE. GIOT-3 is a target gene of GAM26, corresponding to GAM26-TARGET GENE of FIG. 26A. GIOT-3 BINDING SITE is a binding site found in an untranslated region of GIOT-3, corresponding to BINDING SITE of FIG. 26A. FIG. 26D illustrates the complementarity of the nucleotide sequence of GIOT-3 BINDING SITE, designated SEQ ID:674988, to the nucleotide sequence of GAM26 RNA of FIG. 26A, designated SEQ ID:20604. An additional function of GAM26 is therefore inhibition of (GIOT-3). Accordingly, utilities of GAM26 include diagnosis and treatment of diseases and clinical conditions with which GIOT-3 is associated.

Reference is now made to GIOT-3 BINDING SITE. GIOT-3 is a target gene of GAM26, corresponding to GAM26-TARGET GENE of FIG. 26A. GIOT-3 BINDING SITE is a binding site found in an untranslated region of GIOT-3, corresponding to BINDING SITE of FIG. 26A. FIG. 26D illustrates the complementarity of the nucleotide sequence of GIOT-3 BINDING SITE, designated SEQ ID:674995, to the nucleotide sequence of GAM26 RNA of FIG. 26A, designated SEQ ID:20604. A further function of GAM26 is therefore inhibition of (GIOT-3). Accordingly, utilities of GAM26 include diagnosis and treatment of diseases and clinical conditions with which GIOT-3 is associated.

Reference is now made to MGC14425 BINDING SITE. MGC14425 is a target gene of GAM26, corresponding to GAM26-TARGET GENE of FIG. 26A. MGC14425 BINDING SITE is a binding site found in an untranslated region of MGC14425, corresponding to BINDING SITE of FIG. 26A. FIG. 26D illustrates the complementarity of the nucleotide sequence of MGC14425 BINDING SITE, designated SEQ ID:676856, to the nucleotide sequence of GAM26 RNA of FIG. 26A, designated SEQ ID:20604. Yet a further function of GAM26 is therefore inhibition of (MGC14425). Accordingly, utilities of GAM26 include diagnosis and treatment of diseases and clinical conditions with which MGC14425 is associated.

Reference is now made to GNA13 BINDING SITE. GNA13 is a target gene of GAM26, corresponding to GAM26-TARGET GENE of FIG. 26A. GNA13 BINDING SITE is a binding site found in an untranslated region of GNA13, corresponding to BINDING SITE of FIG. 26A. FIG. 26D illustrate the complementarity of the nucleotide sequence of GNA13 BINDING SITE, designated SEQ ID:676857, to the nucleotide sequence of GAM26 RNA of FIG. 26A, designated SEQ ID:20604. Another function of GAM26 is therefore inhibition of (GNA13). Accordingly, utilities of GAM26 include diagnosis and treatment of diseases and clinical conditions with which GNA13 is associated.

Reference is now made to GOLPH2 BINDING SITE. GOLPH2 is a target gene of GAM26, corresponding to GAM26-TARGET GENE of FIG. 26A. GOLPH2 BINDING SITE is a binding site found in an untranslated region of GOLPH2, corresponding to BINDING SITE of FIG. 26A. FIG. 26D illustrates the complementarity of the nucleotide sequence of GOLPH2 BINDING SITE, designated SEQ ID:677940, to the nucleotide sequence of GAM26 RNA of FIG. 26A, designated SEQ ID:20604. Yet another function of GAM26 is therefore inhibition of (GOLPH2). Accordingly, utilities of GAM26 include diagnosis and treatment of diseases and clinical conditions with which GOLPH2 is associated.

Reference is now made to GSK3A BINDING SITE. GSK3A is a target gene of GAM26, corresponding to GAM26-TARGET GENE of FIG. 26A. GSK3A BINDING SITE is a binding site found in an untranslated region of GSK3A, corresponding to BINDING SITE of FIG. 26A. FIG. 26D illustrates the complementarity of the nucleotide sequence of GSK3A BINDING SITE, designated SEQ ID:681389, to the nucleotide sequence GAM26 RNA of FIG. 26A, designated SEQ ID:20604. An additional function of GAM26 is therefore inhibition of (GSK3A). Accordingly, utilities of GAM26 include diagnosis and treatment of diseases and clinical conditions with which GSK3A is associated.

Reference is now made to GSK3A BINDING SITE. GSK3A is a target gene of GAM26, corresponding to GAM26-TARGET GENE of FIG. 26A. GSK3A BINDING SITE is a binding site found in an untranslated region of GSK3A, corresponding to BINDING SITE of FIG. 26A. FIG. 26D illustrate the complementarity of the nucleotide sequence of GSK3A BINDING SITE, designate SEQ ID:681400, to the nucleotide sequence of GAM26 RNA of FIG. 26A, designated SEQ ID:20604. A further function of GAM26 is therefore inhibition of (GSK3A). Accordingly, utilities of GAM26 include diagnosis and treatment of diseases and clinical conditions with which GSK3A is associated.

Reference is now made to GTF2A1 BINDING SITE. GTF2A1 is a target gene of GAM26, corresponding to GAM26-TARGET GENE of FIG. 26A. GTF2A1 BINDING SITE is a binding site found in an untranslated region of GTF2A1, corresponding to BINDING SITE of FIG. 26A. FIG. 26D illustrates the complementarity of the nucleotide sequence of GTF2A1 BINDING SITE, designated SEQ ID:681625, to the nucleotide sequence of GAM26 RNA of FIG. 26A, designated SEQ ID:20604. Yet a further function of GAM26 is therefore inhibition of (GTF2A1). Accordingly, utilities of GAM26 include diagnosis and treatment of diseases and clinical conditions with which GTF2A1 is associated.

Reference is now made to GTF2A1 BINDING SITE GTF2A1 is a target gene of GAM26, corresponding to GAM26-TARGET GENE of FIG. 26A. GTF2A1 BINDING SITE is a binding site found in an untranslated region of GTF2A1, corresponding to BINDING SITE of FIG. 26A. FIG. 26D illustrates the complementarity of the nucleotide sequence of GTF2A1 BINDING SITE, designated SEQ ID:681632, to the nucleotide sequence of GAM26 RNA of FIG. 26A, designated SEQ ID:20604. Another function of GAM26 is therefore inhibition of (GTF2A1). Accordingly, utilities of GAM26 include diagnosis and treatment of diseases and clinical conditions with which GTF2A1 is associated.

Reference is now made to H2AV BINDING SITE. H2AV is a target gene of GAM26, corresponding to GAM26-TARGET GENE of FIG. 26A. H2AV BINDING SITE is a binding site found in an untranslated region of H2AV, corresponding to BINDING SITE of FIG. 26A. FIG. 26D illustrates the complementarity of the nucleotide sequence of H2AV BINDING SITE, designated SEQ ID:683857, to the nucleotide sequence of GAM26 RNA of FIG. 26A, designated SEQ ID:20604. Yet another function of GAM26 is therefore inhibition of (H2AV). Accordingly, utilities of GAM26 include diagnosis and treatment of diseases and clinical conditions with which H2AV is associated.

Reference is now made to H2AV BINDING SITE. H2AV is a target gene of GAM26, corresponding to GAM26-TARGET GENE of FIG. 26A. H2AV BINDING SITE is a binding site found in an untranslated region of H2AV, corresponding to BINDING SITE of FIG. 26A. FIG. 26D illustrates the complementarity of the nucleotide sequence of H2AV BINDING SITE, designated SEQ ID:683934, to the nucleotide sequence of GAM26 RNA of FIG. 26A, designated SEQ ID:20604. An additional function of GAM26 is therefore inhibition of (H2AV). Accordingly, utilities of GAM26 include diagnosis and treatment of diseases and clinical conditions with which H2AV is associated.

Reference is now made to HNRPA0 BINDING SITE. HNRPA0 is a target gene of GAM26, corresponding to GAM26-TARGET GENE of FIG. 26A. HNRPA0 BINDING SITE is a binding site found in an untranslated region of HNRPA0, corresponding to BINDING SITE of FIG. 26A. FIG. 26D illustrates the complementarity of the nucleotide sequence of HNRPA0 BINDING SITE, designated SEQ ID:689726, to the nucleotide sequence of GAM26 RNA of FIG. 26A, designated SEQ ID:20604. A further function of GAM26 is therefore inhibition of (HNRPA0). Accordingly, utilities of GAM26 include diagnosis and treatment of diseases and clinical conditions with which HNRPA0 is associated.

Reference is now made to HRIHFB2122 BINDING SITE. HRIHFB2122 is a target gene of GAM126, corresponding to GAM26-TARGET GENE of FIG. 26A. HRIHFB2122 BINDING SITE is a binding site found in an untranslated region of HRIHFB2122, corresponding to BINDING SITE of FIG. 26A. FIG. 26D illustrates the complementarity of the nucleotide sequence of HRIHFB2122 BINDING SITE, designated SEQ ID:691356, to the nucleotide sequence of GAM26 RNA of FIG. 26A, designated SEQ ID:20604. Yet a further function of GAM26 is therefore inhibition of (HRIHFB2122). Accordingly, utilities of GAM26 include diagnosis and treatment of diseases and clinical conditions with which HRIHFB2122 is associated.

Reference is now made to HS6ST1 BINDING SITE. HS6ST1 is a target gene of GAM26, corresponding to GAM26-TARGET GENE of FIG. 26A. HS6ST1 BINDING SITE is a binding site found in an untranslated region of HS6ST1, corresponding to BINDING SITE of FIG. 26A. FIG. 26D illustrates the complementarity of the nucleotide sequent of HS6ST1 BINDING SITE, designated SEQ ID:691939, to the nucleotide sequence of GAM26 RNA of FIG. 26A, designated SEQ ID:20604. Another function of GAM26 is therefore inhibition of (HS6ST1). Accordingly, utilities of GAM26 include diagnosis and treatment of diseases and clinical conditions with which HS6ST1 is associated.

Reference is now made to HSPC195 BINDING SITE. HSPC195 is a target gene of GAM26, corresponding to GA 6-TARGET GENE of FIG. 26A. HSPC195 BINDING SITE is a binding site found in an untranslated region of HSPC195, corresponding to BINDING SITE of FIG. 26A. FIG. 26D illustrates the complementarity of the nucleotide sequence of HSPC195 BINDING SITE, designated SEQ ID:696302, to the nucleotide sequence of GAM26 RNA of FIG. 26A, designated SEQ ID:20604. Yet another function of GAM26 is therefore inhibition of (HSPC195). Accordingly, utilities of GAM26 include diagnosis and treatment of diseases and clinical conditions with which HSPC195 is associated.

Reference is now made to HSPC195 BINDING SITE. HSPC195 is a target gene of GAM26, corresponding to GAM26-TARGET GENE of FIG. 26A. HSPC195 BINDING SITE is a binding site found in an untranslated region of HSPC195, corresponding to BINDING SITE of FIG. 26A. FIG. 26D illustrates the complementarity of the nucleotide sequence of HSPC195 BINDING SITE, designated SEQ ID:696329, to the nucleotide sequence of GAM26 RNA of FIG. 26A, designated SEQ ID:20604. An additional function of GAM26 is therefore inhibition of (HSPC195). Accordingly, utilities of GAM26 include diagnosis and treatment of diseases and clinical conditions with which HSPC195 is associated.

Reference is now made to HSPC195 BINDING SITE. HSPC195 is a target gene of GAM26, corresponding to GAM26-TARGET GENE of FIG. 26A. HSPC195 BINDING SITE is a binding site found in an untranslated region of HSPC195, corresponding to BINDING SITE of FIG. 26A. FIG. 26D illustrates the complementarity of the nucleotide sequence of HSPC195 BINDING SITE, designated SEQ ID:696330, to the nucleotide sequence of GAM26 RNA of FIG. 26A, designated SEQ ID:20604. A further function of GAM26 is therefore inhibition of (HSPC195). Accordingly, utilities of GAM26 include diagnosis and treatment of diseases and clinical conditions with which HSPC195 is associated.

Reference is now made to HSPC195 BINDING SITE. HSPC195 is a target gene of GAM26, corresponding to GAM26-TARGET GENE of FIG. 26A. HSPC195 BINDING SITE is a binding site found in an untranslated region of HSPC195, corresponding to BINDING SITE of FIG. 26A. FIG. 26D illustrates the complementarity of the nucleotide sequence of HSPC195 BINDING SITE, designated SEQ ID:696332, to the nucleotide sequence of GAM26 RNA of FIG. 26A, designated SEQ ID:20604. Yet a further function of GAM26 is therefore inhibition of (HSPC195). Accordingly, utilities of GAM26 include diagnosis and treatment of diseases and clinical conditions with which HSPC195 is associated.

Reference is now made to HSPC195 BINDING SITE. HSPC195 is a target gene of GAM26, corresponding to GAM26-TARGET GENE of FIG. 26A. HSPC195 BINDING SITE is a binding site found in an untranslated region of HSPC195, corresponding to BINDING SITE of FIG. 26A. FIG. 26D illustrates the complementarity of the nucleotide sequence of HSPC195 BINDING SITE, designated SEQ ID:696333, to the nucleotide sequence of GAM26 RNA of FIG. 26A, designated SEQ ID:20604. Another function of GAM26 is therefore inhibition of (HSPC195). Accordingly, utilities of GAM26 include diagnosis and treatment of diseases and clinical conditions with which HSPC195 is associated.

Reference is now made to HUMAGCGB BINDING SITE. HUMAGCGB is a target gene of GAM26, corresponding to GAM26-TARGET GENE of FIG. 26A. HUMAGCGB BINDING SITE is a binding site found in an untranslated region of HUMAGCGB, corresponding to BINDING SITE of FIG. 26A. FIG. 26D illustrates the complementarity of the nucleotide sequence of HUMAGCGB BINDING SITE, designated SEQ ID:698714, to the nucleotide sequence of GAM26 RNA of FIG. 26A, designated SEQ ID:20604. Yet another function of GAM26 is therefore inhibition of (HUMAGCGB). Accordingly, utilities of GAM26 include diagnosis and treatment of diseases and clinical conditions with which HUMAGCGB is associated.

Reference is now made to ILF3 BINDING SITE. ILF3 is a target gene of GAM26, corresponding to GAM26-TARGET GENE of FIG. 26A. ILF3 BINDING SITE is a binding site found in an untranslated region of ILF3, corresponding to BINDING SITE of FIG. 26A. FIG. 26D illustrates the complementarity of the nucleotide sequence of ILF3 BINDING SITE, designated SEQ ID:701811, to the nucleotide sequence of GAM26 RNA of FIG. 26A, designated SEQ ID:20604. An additional function of GAM26 is therefore inhibition of (ILF3). Accordingly, utilities of GAM26 include diagnosis and treatment of diseases and clinical conditions with which ILF3 is associated.

Reference is now made to ITPK1 BINDING SITE. ITPK1 is a target gene of GAM26, corresponding to GAM26-TARGET GENE of FIG. 26A. ITPK1 BINDING SITE is a binding site found in an untranslated region of ITPK1, corresponding to BINDING SITE of FIG. 26A. FIG. 26D illustrates the complementarity of the nucleotide sequence of ITPK1 BINDING SITE, designated SEQ ID:704065, to the nucleotide sequence of GAM26 RNA of FIG. 26A, designated SEQ ID:20604. A further function of GAM26 is therefore inhibition of (ITPK1). Accordingly, utilities of GAM26 include diagnosis and treatment of diseases and clinical conditions with which ITPK1 is associated.

Reference is now made to KCNT1 BINDING SITE. KCNT1 is a target gene of GAM26, corresponding to GAM26-TARGET GENE of FIG. 26A. KCNT1 BINDING SITE is a binding site found in an untranslated region of KCNT1, corresponding to BINDING SITE of FIG. 26A. FIG. 26D illustrates the complementarity of the nucleotide sequence of KCNT1 BINDING SITE, designated SEQ ID:707411, to the nucleotide sequence of GAM26 RNA of FIG. 26A, designated SEQ ID:20604. Yet a further function of GAM26 is therefore inhibition of (KCNT1). Accordingly, utilities of GAM26 include diagnosis and treatment of diseases and clinical conditions with which KCNT1 is associated.

Reference is now made to KIAA0082 BINDING SITE. KIAA0082 is a target gene of GAM26, corresponding to GAM26-TARGET GENE of FIG. 26A. KIAA0082 BINDING SITE is a binding site found in an untranslated region of KIAA0082, corresponding to BINDING SITE of FIG. 26A. FIG. 26D illustrates the complementarity of the nucleotide sequence of KIAA0082 BINDING SITE, designated SEQ ID:710416, to the nucleotide sequence of GAM26 RNA of FIG. 26A, designated SEQ ID:20604. Another function of GAM26 is therefore inhibition of (KIAA0082). Accordingly, utilities of GAM26 include diagnosis and treatment of diseases and clinical conditions with which KIAA0082 is associated.

Reference is now made to KIAA0082 BINDING SITE. KIAA0082 is a target gene of GAM26, corresponding to GAM26-TARGET GENE of FIG. 26A. KIAA0082 BINDING SITE is a binding site found in an untranslated region of KIAA0082, corresponding to BINDING SITE of FIG. 26A. FIG. 26D illustrates the complementarity of the nucleotide sequence of KIAA0082 BINDING SITE, designated SEQ ID:710439, to the nucleotide sequence of GAM26 RNA of FIG. 26A, designated SEQ ID:20604. Yet another function of GAM26 is therefore inhibition of (KIAA0082). Accordingly, utilities of GAM26 include diagnosis and treatment of diseases and clinical conditions with which KIAA0082 is associated.

Reference is now made to KIAA0084 BINDING SITE. KIAA0084 is a target gene of GAM26, corresponding to GAM26-TARGET GENE of FIG. 26A. KIAA0084 BINDING SITE is a binding site found in an untranslated region of KIAA0084, corresponding to BINDING SITE of FIG. 26A. FIG. 26D illustrates the complementarity of the nucleotide sequence of KIAA0084 BINDING SITE, designated SEQ ID:710507, to the nucleotide sequence of GAM26 RNA of FIG. 26A, designated SEQ ID:20604. An additional function of GAM26 is therefore inhibition of (KIAA0084). Accordingly, utilities of GAM26 include diagnosis and treatment of diseases and clinical conditions with which KIAA0084 is associated.

Reference is now made to KIAA0084 BINDING SITE. KIAA0084 is a target gene of GAM26, corresponding to GAM26-TARGET GENE of FIG. 26A. KIAA0084 BINDING SITE is a binding site found in an untranslated region of KIAA0084, corresponding to BINDING SITE of FIG. 26A. FIG. 26D illustrates the complementarity of the nucleotide sequence of KIAA0084 BINDING SITE, designated SEQ ID:710522, to the nucleotide sequence of GAM26 RNA of FIG. 26A, designated SEQ ID:20604. A further function of GAM26 is therefore inhibition of (KIAA0084). Accordingly, utilities of GAM26 include diagnosis and treatment of diseases and clinical conditions with which KIAA0084 is associated.

Reference is now made to KIAA0191 BINDING SITE. KIAA0191 is a target gene of GAM26, corresponding to GAM26-TARGET GENE of FIG. 26A. KIAA0191 BINDING SITE is a binding site found in an untranslated region of KIAA0191, corresponding to BINDING SITE of FIG. 26A. FIG. 26D illustrates the complementarity of the nucleotide sequence of KIAA0191 BINDING SITE, designated SEQ ID:715434, to the nucleotide sequence of GAM26 RNA of FIG. 26A, designated SEQ ID:20604. Yet a further function of GAM26 is therefore inhibition of (KIAA0191). Accordingly, utilities of GAM26 include diagnosis and treatment of diseases and clinical conditions with which KIAA0191 is associated.

Reference is now made to KIAA0191 BINDING SITE. KIAA0191 is a target gene of GAM26, corresponding to GAM26-TARGET GENE of FIG. 26A. KIAA0191 BINDING SITE is a binding site found in an untranslated region of KIAA0191, corresponding to BINDING SITE of FIG. 26A. FIG. 26D illustrates the complementarity of the nucleotide sequence of KIAA0191 BINDING SITE, designated SEQ ID:715436, to the nucleotide sequence of GAM26 RNA of FIG. 26A, designated SEQ ID:20604. Another function of GAM26 is therefore inhibition of (KIAA0191). Accordingly, utilities of GAM26 include diagnosis and treatment of diseases and clinical conditions with which KIAA0191 is associated.

Reference is now made to KIAA0191 BINDING SITE. KIAA0191 is a target gene of GAM26, corresponding to GAM26-TARGET GENE of FIG. 26A. KIAA0191 BINDING SITE is a binding site found in an untranslated region of KIAA0191, corresponding to BINDING SITE of FIG. 26A. FIG. 26D illustrates the complementarity of the nucleotide sequence of KIAA0191 BINDING SITE, designated SEQ ID:715438, to the nucleotide sequence of GAM26 RNA of FIG. 26A, designated SEQ ID:20604. Yet another function of GAM26 is therefore inhibition of (KIAA0191). Accordingly, utilities of GAM26 include diagnosis and treatment of diseases and clinical conditions with which KIAA0191 is associated.

Reference is now made to KIAA0191 BINDING SITE. KIAA0191 is a target gene of GAM26, corresponding to GAM26-TARGET GENE of FIG. 26A. KIAA0191 BINDING SITE is a binding site found in an untranslated region of KIAA0191, corresponding to BINDING SITE of FIG. 26A. FIG. 26D illustrates the complementarity of the nucleotide sequence of KIAA0191 BINDING SITE, designated SEQ ID:715439, to the nucleotide sequence of GAM26 RNA of FIG. 26A, designated SEQ ID:20604. An additional function of GAM26 is therefore inhibition of (KIAA0191). Accordingly, utilities of GAM26 include diagnosis and treatment of diseases and clinical conditions with which KIAA0191 is associated.

Reference is now made to KIAA0191 BINDING SITE. KIAA0191 is a target gene of GAM26, corresponding to GAM26-TARGET GENE of FIG. 26A. KIAA0191 BINDING SITE is a binding site found in an untranslated region of KIAA0191, corresponding to BINDING SITE of FIG. 26A. FIG. 26D illustrates the complementarity of the nucleotide sequence of KIAA0191 BINDING SITE, designated SEQ ID:715444, to the nucleotide sequence of GAM26 RNA of FIG. 26A, designated SEQ ID:20604. A further function of GAM26 is therefore inhibition of (KIAA0191). Accordingly, utilities of GAM26 include diagnosis and treatment of diseases and clinical conditions with which KIAA0191 is associated.

Reference is now made to KIAA0191 BINDING SITE. KIAA0191 is a target gene of GAM26, corresponding to GAM26-TARGET GENE of FIG. 26A. KIAA0191 BINDING SITE is a binding site found in an untranslated region of KIAA0191, corresponding to BINDING SITE of FIG. 26A. FIG. 26D illustrates the complementarity of the nucleotide sequence of KIAA0191 BINDING SITE, designated SEQ ID:715447, to the nucleotide sequence of GAM26 RNA of FIG. 26A, designated SEQ ID:20604. Yet a further function of GAM26 is therefore inhibition of (KIAA0191). Accordingly, utilities of GAM26 include diagnosis and treatment of diseases and clinical conditions with which KIAA0191 is associated.

Reference is now made to KIAA0227 BINDING SITE. KIAA0227 is a target gene of GAM26, corresponding to GAM26-TARGET GENE of FIG. 26A. KIAA0227 BINDING SITE is a binding site found in an untranslated region of KIAA0227, corresponding to BINDING SITE of FIG. 26A. FIG. 26D illustrates the complementarity of the nucleotide sequence of KIAA0227 BINDING SITE, designated SEQ ID:717573, to the nucleotide sequence of GAM26 RNA of FIG. 26A, designated SEQ ID:20604. Another function of GAM26 is therefore inhibition of (KIAA0227). Accordingly, utilities of GAM26 include diagnosis and treatment of diseases and clinical conditions with which KIAA0227 is associated.

Reference is now made to KIAA0227 BINDING SITE. KIAA0227 is a target gene of GAM26, corresponding to GAM26-TARGET GENE of FIG. 26A. KIAA0227 BINDING SITE is a binding site found in an untranslated region of KIAA0227, corresponding to BINDING SITE of FIG. 26A. FIG. 26D illustrates the complementarity of the nucleotide sequence of KIAA0227 BINDING SITE, designated SEQ ID:717578, to the nucleotide sequence of GAM26 RNA of FIG. 26A, designated SEQ ID:20604. Yet another function of GAM26 is therefore inhibition of (KIAA0227). Accordingly, utilities of GAM26 include diagnosis and treatment of diseases and clinical conditions with which KIAA0227 is associated.

Reference is now made to KIAA0227 BINDING SITE. KIAA0227 is a target gene of GAM26, corresponding to GAM26-TARGET GENE of FIG. 26A. KIAA0227 BINDING SITE is a binding site found in an untranslated region of KIAA0227, corresponding to BINDING SITE of FIG. 26A. FIG. 26D illustrates the complementarity of the nucleotide sequence of KIAA0227 BINDING SITE, designated SEQ ID:717615, to the nucleotide sequence of GAM26 RNA of FIG. 26A, designated SEQ ID:20604. An additional function of GAM26 is therefore inhibition of (KIAA0227). Accordingly, utilities of GAM26 include diagnosis and treatment of diseases and clinical conditions with which KIAA0227 is associated.

Reference is now made to KIAA0252 BINDING SITE. KIAA0252 is a target gene of GAM26, corresponding to GAM26-TARGET GENE of FIG. 26A. KIAA0252 BINDING SITE is a binding site found in an untranslated region of KIAA0252, corresponding to BINDING SITE of FIG. 26A. FIG. 26D illustrates the complementarity of the nucleotide sequence of KIAA0252 BINDING SITE, designated SEQ ID:718931, to the nucleotide sequence of GAM26 RNA of FIG. 26A, designated SEQ ID:20604. A further function of GAM26 is therefore inhibition of (KIAA0252). Accordingly, utilities of GAM26 include diagnosis and treatment of diseases and clinical conditions with which KIAA0252 is associated.

Reference is now made to KIAA0252 BINDING SITE. KIAA0252 is a target gene of GAM26, corresponding to GAM26-TARGET GENE of FIG. 26A. KIAA0252 BINDING SITE is a binding site found in an untranslated region of KIAA0252, corresponding to BINDING SITE of FIG. 26A. FIG. 26D illustrates the complementarity of the nucleotide sequence of KIAA0252 BINDING SITE, designated SEQ ID:718993, to the nucleotide sequence of GAM26

RNA of FIG. 26A, designated SEQ ID:20604. Yet a further function of GAM26 is therefore inhibition of (KIAA0252). Accordingly, utilities of GAM26 include diagnosis and treatment of diseases and clinical conditions with which KIAA0252 is associated.

Reference is now made to KIAA0252 BINDING SITE. KIAA0252 is a target gene of GAM26, corresponding to GAM26-TARGET GENE of FIG. 26A. KIAA0252 BINDING SITE is a binding site found in an untranslated region of KIAA0252, corresponding to BINDING SITE of FIG. 26A. FIG. 26D illustrates the complementarity of the nucleotide sequence of KIAA0252 BINDING SITE, designated SEQ ID:719014, to the nucleotide sequence of GAM26 RNA of FIG. 26A, designated SEQ ID:20604. Another function of GAM26 is therefore inhibition of (KIAA0252). Accordingly, utilities of GAM26 include diagnosis and treatment of diseases and clinical conditions with which KIAA0252 is associated.

Reference is now made to KIAA0336 BINDING SITE. KIAA0336 is a target gene of GAM26, corresponding to GAM26-TARGET GENE of FIG. 26A. KIAA0336 BINDING SITE is a binding site found in an untranslated region of KIAA0336, corresponding to BINDING SITE of FIG. 26A. FIG. 26D illustrates the complementarity of the nucleotide sequence of KIAA0336 BINDING SITE, designated SEQ ID:724234, to the nucleotide sequence of GAM26 RNA of FIG. 26A, designated SEQ ID:20604. Yet another function of GAM26 is therefore inhibition of (KIAA0336). Accordingly, utilities of GAM26 include diagnosis and treatment of diseases and clinical conditions with which KIAA0336 is associated.

Reference is now made to KIAA0397 BINDING SITE. KIAA0397 is a target gene of GAM26, corresponding to GAM26-TARGET GENE of FIG. 26A. KIAA0397 BINDING SITE is a binding site found in an untranslated region of KIAA0397, corresponding to BINDING SITE of FIG. 26A. FIG. 26D illustrates the complementarity of the nucleotide sequence of KIAA0397 BINDING SITE, designated SEQ ID:726863, to the nucleotide sequence of GAM26 RNA of FIG. 26A, designated SEQ ID:20604. An additional function of GAM26 is therefore inhibition of (KIAA0397). Accordingly, utilities of GAM26 include diagnosis and treatment of diseases and clinical conditions with which KIAA0397 is associated.

Reference is now made to KIAA0406 BINDING SITE. KIAA0406 is a target gene of GAM26, corresponding to GAM26-TARGET GENE of FIG. 26A. KIAA0406 BINDING SITE is a binding site found in an untranslated region of KIAA0406, corresponding to BINDING SITE of FIG. 26A. FIG. 26D illustrates the complementarity of the nucleotide sequence of KIAA0406 BINDING SITE, designated SEQ ID:726937, to the nucleotide sequence of GAM26 RNA of FIG. 26A, designated SEQ ID:20604. A further function of GAM26 is therefore inhibition of (KIAA0406). Accordingly, utilities of GAM26 include diagnosis and treatment of diseases and clinical conditions with which KIAA0406 is associated.

Reference is now made to KIAA0441 BINDING SITE. KIAA0441 is a target gene of GAM26, corresponding to GAM26-TARGET GENE of FIG. 26A. KIAA0441 BINDING SITE is a binding site found in an untranslated region of KIAA0441, corresponding to BINDING SITE of FIG. 26A. FIG. 26D illustrates the complementarity of the nucleotide sequence of KIAA0441 BINDING SITE, designated SEQ ID:730328, to the nucleotide sequence of GAM26 RNA of FIG. 26A, designated SEQ ID:20604. Yet a further function of GAM26 is therefore inhibition of (KIAA0441). Accordingly, utilities of include diagnosis and treatment of diseases and clinical conditions with which KIAA0441 is associated.

Reference is now made to KIAA0475 BINDING SITE. KIAA0475 is a target gene of GAM26, corresponding to GAM26-TARGET GENE of FIG. 26A. KIAA0475 BINDING SITE is a binding site found in an untranslated region of KIAA0475, corresponding to BINDING SITE of FIG. 26A. FIG. 26D illustrates the complementarity of the nucleotide sequence of KIAA0475 BINDING SITE, designated SEQ ID:734620, to the nucleotide sequence of GAM26 RNA of FIG. 26A, designated SEQ ID:20604. Another function of GAM26 is therefore inhibition of (KIAA0475). Accordingly, utilities of GAM26 include diagnosis and treatment of diseases and clinical conditions with which KIAA0475 is associated.

Reference is now made to KIAA0633 BINDING SITE. KIAA0633 is a target gene of GAM26, corresponding to GAM26-TARGET GENE of FIG. 26A. KIAA0633 BINDING SITE is a binding site found in an untranslated region of KIAA0633, corresponding to BINDING SITE of FIG. 26A. FIG. 26D illustrates the complementarity of the nucleotide sequence of KIAA0633 BINDING SITE, designated SEQ ID:744516, to the nucleotide sequence of GAM26 RNA of FIG. 26A, designated SEQ ID:20604. Yet another function of GAM26 is therefore inhibition of (KIAA0633). Accordingly, utilities of GAM26 include diagnosis and treatment of diseases and clinical conditions with which KIAA0633 is associated.

Reference is now made to KIAA0649 BINDING SITE. KIAA0649 is a target gene of GAM26, corresponding to GAM26-TARGET GENE of FIG. 26A. KIAA0649 BINDING SITE is a binding site found in an untranslated region of KIAA0649, corresponding to BINDING SITE of FIG. 26A. FIG. 26D illustrates the complementarity of the nucleotide sequence of KIAA0649 BINDING SITE, designated SEQ ID:745411, to the nucleotide sequence of GAM26 RNA of FIG. 26A, designated SEQ ID:20604. An additional function of GAM26 is therefore inhibition of (KIAA0649). Accordingly, utilities of GAM26 include diagnosis and treatment of diseases and clinical conditions with which KIAA0649 is associated.

Reference is now made to KIAA0649 BINDING SITE. KIAA0649 is a target gene of GAM26, corresponding to GAM26-TARGET GENE of FIG. 26A. KIAA0649 BINDING SITE is a binding site found in an untranslated region of KIAA0649, corresponding to BINDING SITE of FIG. 26A. FIG. 26D illustrates the complementarity of the nucleotide sequence of KIAA0649 BINDING SITE, designated SEQ ID:745444, to the nucleotide sequence of GAM26 RNA of FIG. 26A, designated SEQ ID:20604. A further function of GAM26 is therefore inhibition of (KIAA0649). Accordingly, utilities of GAM26 include diagnosis and treatment of diseases and clinical conditions with which KIAA0649 is associated.

Reference is now made to KIAA0700 BINDING SITE. KIAA0700 is a target gene of GAM26, corresponding to GAM26-TARGET GENE of FIG. 26A. KIAA0700 BINDING SITE is a binding site found in an untranslated region of KIAA0700, corresponding to BINDING SITE of FIG. 26A. FIG. 26D illustrates the complementarity of the nucleotide sequence of KIAA0700 BINDING SITE, designated SEQ ID:747790, to the nucleotide sequence of GAM26 RNA of FIG. 26A, designated SEQ ID:20604. Yet a further function of GAM26 is therefore inhibition of (KIAA0700).

Accordingly, utilities of GAM26 include diagnosis and treatment of diseases and clinical conditions with which KIAA0700 is associated.

Reference is now made to KIAA0844 BINDING SITE. KIAA0844 is a target gene of GAM26, corresponding to GAM26-TARGET GENE of FIG. 26A. KIAA0844 BINDING SITE is a binding site found in an untranslated region of KIAA0844, corresponding to BINDING SITE of FIG. 26A. FIG. 26D illustrates the complementarity of the nucleotide sequence of KIAA0844 BINDING SITE, designated SEQ ID:754642, to the nucleotide sequence of GAM26 RNA of FIG. 26A, designated SEQ ID:20604. Another function of GAM26 is therefore inhibition of (KIAA0844). Accordingly, utilities of GAM26 include diagnosis and treatment of diseases and clinical conditions with which KIAA0844 is associated.

Reference is now made to KIAA0960 BINDING SITE. KIAA0960 is a target gene of GAM26, corresponding to GAM26-TARGET GENE of FIG. 26A. KIAA0960 BINDING SITE is a binding site found in an untranslated region of KIAA0960, corresponding to BINDING SITE of FIG. 26A. FIG. 26D illustrates the complementarity of the nucleotide sequence of KIAA0960 BINDING SITE, designated SEQ ID:760740, to the nucleotide sequence of GAM26 RNA of FIG. 26A, designated SEQ ID:20604. Yet another function of GAM26 is therefore inhibition of (KIAA0960). Accordingly, utilities of GAM26 include diagnosis and treatment of diseases and clinical conditions with which KIAA0960 is associated.

Reference is now made to KIAA0963 BINDING SITE. KIAA0963 is a target gene of GAM26, corresponding to GAM26-TARGET GENE of FIG. 26A. KIAA0963 BINDING SITE is a binding site found in an untranslated region of KIAA0963, corresponding to BINDING SITE of FIG. 26A. FIG. 26D illustrates the complementarity of the nucleotide sequence of KIAA0963 BINDING SITE, designated SEQ ID:761105, to the nucleotide sequence of GAM26 RNA of FIG. 26A, designated SEQ ID:20604. An additional function of GAM26 is therefore inhibition of (KIAA0963). Accordingly, utilities of GAM26 include diagnosis and treatment of diseases and clinical conditions with which KIAA0963 is associated.

Reference is now made to KIAA0979 BINDING SITE. KIAA0979 is a target gene of GAM26, corresponding to GAM26-TARGET GENE of FIG. 26A. KIAA0979 BINDING SITE is a binding site found in an untranslated region of KIAA0979, corresponding to BINDING SITE of FIG. 26A. FIG. 26D illustrates the complementarity of the nucleotide sequence of KIAA0979 BINDING SITE, designated SEQ ID:762065, to the nucleotide sequence of GAM26 RNA of FIG. 26A, designated SEQ ID:20604. A further function of GAM26 is therefore inhibition of (KIAA0979). Accordingly, utilities of GAM26 include diagnosis and treatment of diseases and clinical conditions with which KIAA0979 is associated.

Reference is now made to FUBP3 BINDING SITE. FUBP3 is a target gene of GAM26, corresponding to GAM26-TARGET GENE of FIG. 26A. FUBP3 BINDING SITE is a binding site found in an untranslated region of FUBP3, corresponding to BINDING SITE of FIG. 26A. FIG. 26D illustrates the complementarity of the nucleotide sequence of FUBP3 BINDING SITE, designated SEQ ID:763022, to the nucleotide sequence of GAM26 RNA of FIG. 26A, designated SEQ ID:20604. Yet a further function of GAM26 is therefore inhibition of (FUBP3). Accordingly, utilities of GAM26 include diagnosis and treatment of diseases and clinical conditions with which FUBP3 is associated.

Reference is now made to KIAA0995 BINDING SITE. KIAA0995 is a target gene of GAM26, corresponding to GAM26-TARGET GENE of FIG. 26A. KIAA0995 BINDING SITE is a binding site found in an untranslated region of KIAA0995, corresponding to BINDING SITE of FIG. 26A. FIG. 26D illustrates the complementarity of the nucleotide sequence of KIAA0995 BINDING SITE, designated SEQ ID:763022, to the nucleotide sequence of GAM26 RNA of FIG. 26A, designated SEQ ID:20604. Another function of GAM26 is therefore inhibition of (KIAA0995). Accordingly, utilities of GAM26 include diagnosis and treatment of diseases and clinical conditions with which KIAA0995 is associated.

Reference is now made to KIAA0995 BINDING SITE. KIAA0995 is a target gene of GAM26, corresponding to GAM26-TARGET GENE of FIG. 26A. KIAA0995 BINDING SITE is a binding site found in an untranslated region of KIAA0995, corresponding to BINDING SITE of FIG. 26A. FIG. 26D illustrates the complementarity of the nucleotide sequence of KIAA0995 BINDING SITE, designated SEQ ID:763026, to the nucleotide sequence of GAM26 RNA of FIG. 26A, designated SEQ ID:20604. Yet another function of GAM26 is therefore inhibition of (KIAA0995). Accordingly, utilities of GAM26 include diagnosis and treatment of diseases and clinical conditions with which KIAA0995 is associated.

Reference is now made to KIAA0995 BINDING SITE. KIAA0995 is a target gene of GAM26, corresponding to GAM26-TARGET GENE of FIG. 26A. KIAA0995 BINDING SITE is a binding site found in an untranslated region of KIAA0995, corresponding to BINDING SITE of FIG. 26A. FIG. 26D illustrates the complementarity of the nucleotide sequence of KIAA0995 BINDING SITE, designated SEQ ID:763030, to the nucleotide sequence of GAM26 RNA of FIG. 26A, designated SEQ ID:20604. An additional function of GAM26 is therefore inhibition of (KIAA0995). Accordingly, utilities of GAM26 include diagnosis and treatment of diseases and clinical conditions with which KIAA0995 is associated.

Reference is now made to KIAA0995 BINDING SITE. KIAA0995 is a target gene of GAM26, corresponding to GAM26-TARGET GENE of FIG. 26A. KIAA0995 BINDING SITE is a binding site found in an untranslated region of KIAA0995, corresponding to BINDING SITE of FIG. 26A. FIG. 26D illustrates the complementarity of the nucleotide sequence of KIAA0995 BINDING SITE, designated SEQ ID:763031, to the nucleotide sequence of GAM26 RNA of FIG. 26A, designated SEQ ID:20604. A function of GAM26 is therefore inhibition of (KIAA0995). Accordingly, utilities of GAM26 include diagnosis and treatment of diseases and clinical conditions with which KIAA0995 is associated.

Reference is now made to KIAA0995 BINDING SITE. KIAA0995 is a target gene of GAM26, corresponding to GAM26-TARGET GENE of FIG. 26A. KIAA0995 BINDING SITE is a binding site found in an untranslated region of KIAA0995, corresponding to BINDING SITE of FIG. 26A. FIG. 26D illustrates the complementarity of the nucleotide sequence of KIAA0995 BINDING SITE, designated SEQ ID:763039, to the nucleotide sequence of GAM26 RNA of FIG. 26A, designated SEQ ID:20604. Yet a further function of GAM26 is therefore inhibition of (KIAA0995).

Accordingly, utilities of GAM26 include diagnosis and treatment of diseases and clinical conditions with which KIAA0995 is associated.

Reference is now made to KIAA1016 BINDING SITE. KIAA1016 is a target gene of GAM26, corresponding to GAM26-TARGET GENE of FIG. 26A. KIAA1016 BINDING SITE is a binding site found in an untranslated region of KIAA1016, corresponding to BINDING SITE of FIG. 26A. FIG. 26D illustrates the complementarity of the nucleotide sequence of KIAA1016 BINDING SITE, designated SEQ ID:764057, to the nucleotide sequence of GAM26 RNA of FIG. 26A, designated SEQ ID:20604. Another function of GAM26 is therefore inhibition of (KIAA1016). Accordingly, utilities of GAM26 include diagnosis and treatment of diseases and clinical conditions with which KIAA1016 is associated.

Reference is now made to KIAA1061 BINDING SITE. KIAA1061 is a target gene of GAM26, corresponding to GAM26-TARGET GENE of FIG. 26A. KIAA1061 BINDING SITE is a binding site found in an untranslated region of KIAA1061, corresponding to BINDING SITE of FIG. 26A. FIG. 26D illustrates the complementarity of the nucleotide sequence of KIAA1061 BINDING SITE, designated SEQ ID:768364, to the nucleotide sequence of GAM26 RNA of FIG. 26A, designated SEQ ID:20604. Yet another function of GAM26 is therefore inhibition of (KIAA1061). Accordingly, utilities of GAM26 include diagnosis and treatment of diseases and clinical conditions with which KIAA1061 is associated.

Reference is now made to KIAA1079 BINDING SITE. KIAA1079 is a target gene of GAM26, corresponding to GAM26-TARGET GENE of FIG. 26A. KIAA1079 BINDING SITE is a binding site found in an untranslated region of KIAA1079, corresponding to BINDING SITE of FIG. 26A. FIG. 26D illustrates the complementarity of the nucleotide sequence of KIAA1079 BINDING SITE, designated SEQ ID:769234, to the nucleotide sequence of GAM26 RNA of FIG. 26A, designated SEQ ID:20604. An additional function of GAM26 is therefore inhibition of (KIAA1079). Accordingly, utilities of GAM26 include diagnosis and treatment of diseases and clinical conditions with which KIAA1079 is associated.

Reference is now made to KIAA1091 BINDING SITE. KIAA1091 is a target gene of GAM26, corresponding to GAM26-TARGET GENE of FIG. 26A. KIAA1091 BINDING SITE is a binding site found in an untranslated region of KIAA1091, corresponding to BINDING SITE of FIG. 26A. FIG. 26D illustrates the complementarity of the nucleotide sequence of KIAA1091 BINDING SITE, designated SEQ ID:769882, to the nucleotide sequence of GAM26 RNA of FIG. 26A, designated SEQ ID:20604. A further function of GAM26 is therefore inhibition of (KIAA1091). Accordingly, utilities of GAM26 include diagnosis and treatment of diseases and clinical conditions with which KIAA1091 is associated.

Reference is now made to KIAA1140 BINDING SITE. KIAA1140 is a target gene of GAM26, corresponding to GAM26-TARGET GENE of FIG. 26A. KIAA1140 BINDING SITE is a binding site found in an untranslated region of KIAA1140, corresponding to BINDING SITE of FIG. 26A. FIG. 26D illustrates the complementarity of the nucleotide sequence of KIAA1140 BINDING SITE, designated SEQ ID:771839, to the nucleotide sequence of GAM26 RNA of FIG. 26A, designated SEQ ID:20604. Yet a further function of GAM26 is therefore inhibition of (KIAA1140). Accordingly, utilities of GAM26 include diagnosis and treatment of diseases and clinical conditions with which KIAA1140 is associated.

Reference is now made to KIAA1140 BINDING SITE. KIAA11140 is a target gene of GAM26, corresponding to GAM26-TARGET GENE of FIG. 26A.

KIAA1140 BINDING SITE is a binding site found in an untranslated region of KIAA1140, corresponding to BINDING SITE of FIG. 26A. FIG. 26D illustrates the complementarity of the nucleotide sequence of KIAA1140 BINDING SITE, designated SEQ ID:771842, to the nucleotide sequence of GAM26 RNA of FIG. 26A, designated SEQ ID:20604. Another function of GAM26 is therefore inhibition of (KIAA1140). Accordingly, utilities of GAM26 include diagnosis and treatment of diseases and clinical conditions with which KIAA1140 is associated.

Reference is now made to KIAA1194 BINDING SITE. KIAA1194 is a target gene of GAM26, corresponding to GAM26-TARGET GENE of FIG. 26A. KIAA1194 BINDING SITE is a binding site found in an untranslated region of KIAA1194, corresponding to BINDING SITE of FIG. 26A. FIG. 26D illustrates the complementarity of the nucleotide sequence of KIAA1194 BINDING SITE, designated SEQ ID:776042, to the nucleotide sequence of GAM26 RNA of FIG. 26A, designated SEQ ID:20604. Yet another function of GAM26 is therefore inhibition of (KIAA1194). Accordingly, utilities of GAM26 include diagnosis and treatment of diseases and clinical conditions with which KIAA1194 is associated.

Reference is now made to KIAA1233 BINDING SITE. KIAA1233 is a target gene of GAM26, corresponding to GAM26-TARGET GENE of FIG. 26A. KIAA1233 BINDING SITE is a binding site found in an untranslated region of KIAA1233, corresponding to BINDING SITE of FIG. 26A. FIG. 26D illustrates the complementarity of the nucleotide sequence of KIAA1233 BINDING SITE, designated SEQ ID:779098, to the nucleotide sequence of GAM26 RNA of FIG. 26A, designated SEQ ID:20604. An additional function of GAM26 is therefore inhibition of (KIAA1233). Accordingly, utilities of GAM26 include diagnosis and treatment of diseases and clinical conditions with which KIAA1233 is associated.

Reference is now made to KIAA1332 BINDING SITE. KIAA1332 is a target gene of GAM26, corresponding to GAM26-TARGET GENE of FIG. 26A. KIAA1332 BINDING SITE is a binding site found in an untranslated region of KIAA1332, corresponding to BINDING SITE of FIG. 26A. FIG. 26D illustrates the complementarity of the nucleotide sequence of KIAA1332 BINDING SITE, designated SEQ ID:785691, to the nucleotide sequence of GAM26 RNA of FIG. 26A, designated SEQ ID:20604. A further function of GAM26 is therefore inhibition of (KIAA1332). Accordingly, utilities of GAM26 include diagnosis and treatment of diseases and clinical conditions with which KIAA1332 is associated.

Reference is now made to KIAA1458 BINDING SITE. KIAA1458 is a target gene of GAM26, corresponding to GAM26-TARGET GENE of FIG. 26A. KIAA1458 BINDING SITE is a binding site found in an untranslated region of KIAA1458, corresponding to BINDING SITE of FIG. 26A. FIG. 26D illustrates the complementarity of the nucleotide sequence of KIAA1458 BINDING SITE, designated SEQ ID:791465, to the nucleotide sequence of GAM26 RNA of FIG. 26A, designated SEQ ID:20604. Yet a further function of GAM26 is therefore inhibition of (KIAA1458).

Accordingly, utilities of GAM26 include diagnosis and treatment of diseases and clinical conditions with which KIAA1458 is associated.

Reference is now made to KIAA1458 BINDING SITE. KIAA1458 is a target gene of GAM26, corresponding to GAM26-TARGET GENE of FIG. 26A. KIAA1458 BINDING SITE is a binding site found in an untranslated region of KIAA1458, corresponding to BINDING SITE of FIG. 26A. FIG. 26D illustrates the complementarity of the nucleotide sequence of KIAA1458 BINDING SITE, designated SEQ ID:791473, to the nucleotide sequence of GAM26 RNA of FIG. 26A, designated SEQ ID:20604. Another function of GAM26 is therefore inhibition of (KIAA1458). Accordingly, utilities of GAM26 include diagnosis and treatment of diseases and clinical conditions with which KIAA1458 is associated.

Reference is now made to KIAA1483 BINDING SITE. KIAA1483 is a target gene of GAM26, corresponding to GAM26-TARGET GENE of FIG. 26A. KIAA1483 BINDING SITE is a binding site found in an untranslated region of KIAA1483, corresponding to BINDING SITE of FIG. 26A. FIG. 26D illustrates the complementarity of the nucleotide sequence of KIAA1483 BINDING SITE, designated SEQ ID:792995, to the nucleotide sequence of GAM26 RNA of FIG. 26A, designated SEQ ID:20604. Yet another function of GAM26 is therefore inhibition of (KIAA1483). Accordingly, utilities of GAM26 include diagnosis and treatment of diseases and clinical conditions with which KIAA1483 is associated.

Reference is now made to KIAA1483 BINDING SITE. KIAA1483 is a target gene of GAM26, corresponding to GAM26-TARGET GENE of FIG. 26A. KIAA1483 BINDING SITE is a binding site found in an untranslated region of KIAA1483, corresponding to BINDING SITE of FIG. 26A. FIG. 26D illustrates the complementarity of the nucleotide sequence of KIAA1483 BINDING SITE, designated SEQ ID:793014, to the nucleotide sequence of GAM26 RNA of FIG. 26A, designated SEQ ID:20604. An additional function of GAM26 is therefore inhibition of (KIAA1483). Accordingly, utilities of GAM26 include diagnosis and treatment of diseases and clinical conditions with which KIAA1483 is associated.

Reference is now made to KIAA1542 BINDING SITE. KIAA1542 is a target gene of GAM26, corresponding to GAM26-TARGET GENE of FIG. 26A. KIAA1542 BINDING SITE is a binding site found in an untranslated region of KIAA1542, corresponding to BINDING SITE of FIG. 26A. FIG. 26D illustrates the complementarity of the nucleotide sequence of KIAA1542 BINDING SITE, designated SEQ ID:795954, to the nucleotide sequence of GAM26 RNA of FIG. 26A, designated SEQ ID:20604. A further function of GAM26 is therefore inhibition of (KIAA1542). Accordingly, utilities of GAM26 include diagnosis and treatment of diseases and clinical conditions with which KIAA1542 is associated.

Reference is now made to KIAA1542 BINDING SITE. KIAA1542 is a target gene of GAM26, corresponding to GAM26-TARGET GENE of FIG. 26A. KIAA1542 BINDING SITE is a binding site found in an untranslated region of KIAA1542, corresponding to BINDING SITE of FIG. 26A. FIG. 26D illustrates the complementarity of the nucleotide sequence of KIAA1542 BINDING SITE, designated SEQ ID:795958, to the nucleotide sequence of GAM26 RNA of FIG. 26A, designated SEQ ID):20604. Yet a further function of GAM26 is therefore inhibition of (KIAA1542).

Accordingly, utilities of GAM26 include diagnosis and treatment of diseases and clinical conditions with which KIAA1542 is associated.

Reference is now made to KIAA1542 BINDING SITE. KIAA1542 is a target gene of GAM26, corresponding to GAM26-TARGET GENE of FIG. 26A. KIAA1542 BINDING SITE is a binding site found in an untranslated region of KIAA1542, corresponding to BINDING SITE of FIG. 26A. FIG. 26D illustrates the complementarity of the nucleotide sequence of KIAA1542 BINDING SITE, designated SEQ ID:795963, to the nucleotide sequence of GAM26 RNA of FIG. 26A, designated SEQ ID:20604. Another function of GAM26 is therefore inhibition of (KIAA1542). Accordingly, utilities of GAM26 include diagnosis and treatment of diseases and clinical conditions with which KIAA1542 is associated.

Reference is now made to KIAA1608 BINDING SITE. KIAA1608 is a target gene of GAM26, corresponding to GAM26-TARGET GENE of FIG. 26A. KIAA1608 BINDING SITE is a binding site found in an untranslated region of KIAA1608, corresponding to BINDING SITE of FIG. 26A. FIG. 26D illustrates the complementarity of the nucleotide sequence of KIAA1608 BINDING SITE, designated SEQ ID:799200, to the nucleotide sequence of GAM26 RNA of FIG. 26A, designated SEQ ID:20604. Yet another function of GAM26 is therefore inhibition of (KIAA1608). Accordingly, utilities of GAM26 include diagnosis and treatment of diseases and clinical conditions with which KIAA1608 is associated.

Reference is now made to KIAA1608 BINDING SITE. KIAA1608 is a target gene of GAM26, corresponding to GAM26-TARGET GENE of FIG. 26A. KIAA1608 BINDING SITE is a binding site found in an untranslated region of KIAA1608, corresponding to BINDING SITE of FIG. 26A. FIG. 26D illustrates the complementarity of the nucleotide sequence of KIAA1608 BINDING SITE, designated SEQ ID:799201, to the nucleotide sequence of GAM26 RNA of FIG. 26A, designated SEQ ID:20604. An additional function of GAM26 is therefore inhibition of (KIAA1608). Accordingly, utilities of GAM26 include diagnosis and treatment of diseases and clinical conditions with which KIAA1608 is associated.

Reference is now made to KIAA1766 BINDING SITE. KIAA1766 is a target gene of GAM26, corresponding to GAM26-TARGET GENE of FIG. 26A. KIAA1766 BINDING SITE is a binding site found in an untranslated region of KIAA1766, corresponding to BINDING SITE of FIG. 26A. FIG. 26D illustrates the complementarity of the nucleotide sequence of KIAA1766 BINDING SITE, designated SEQ ID:808833, to the nucleotide sequence of GAM26 RNA of FIG. 26A, designated SEQ ID:20604. A further function of GAM26 is therefore inhibition of (KIAA1766). Accordingly, utilities of GAM26 include diagnosis and treatment of diseases and clinical conditions with which KIAA1766 is associated.

Reference is now made to KIAA1893 BINDING SITE. KIAA1893 is a target gene of GAM26, corresponding to GAM26-TARGET GENE of FIG. 26A. KIAA1893 BINDING SITE is a binding site found in an untranslated region of KIAA1893, corresponding to BINDING SITE of FIG. 26A. FIG. 26D illustrates the complementarity of the nucleotide sequence of KIAA1893 BINDING SITE, designated SEQ ID:816521, to the nucleotide sequence of GAM26 RNA of FIG. 26A, designated SEQ ID:20604. Yet a further function of GAM26 is therefore inhibition of (KIAA1893).

Accordingly, utilities of GAM26 include diagnosis and treatment of diseases and clinical conditions with which KIAA1893 is associated.

Reference is now made to KIAA1966 BINDING SITE. KIAA1966 is a target gene of GAM26, corresponding to GAM26-TARGET GENE of FIG. 26A. KIAA1966 BINDING SITE is a binding site found in an untranslated region of KIAA1966, corresponding to BINDING SITE of FIG. 26A. FIG. 26D illustrates the complementarity of the nucleotide sequence of KIAA1966 BINDING SITE, designated SEQ ID:822274, to the nucleotide sequence of GAM26 RNA of FIG. 26A, designated SEQ ID:20604. Another function of GAM26 is therefore inhibition of (KIAA1966). Accordingly, utilities of GAM26 include diagnosis and treatment of diseases and clinical conditions with which KIAA1966 is associated.

Reference is now made to KIAA1966 BINDING SITE. KIAA1966 is a target gene of GAM26, corresponding to GAM26-TARGET GENE of FIG. 26A. KIAA1966 BINDING SITE is a binding site found in an untranslated region of KIAA1966, corresponding to BINDING SITE of FIG. 26A. FIG. 26D illustrates the complementarity of the nucleotide sequence of KIAA1966 BINDING SITE, designated SEQ ID:822277, to the nucleotide sequence of GAM26 RNA of FIG. 26A, designated SEQ ID:20604. Yet another function of GAM26 is therefore inhibition of (KIAA1966). Accordingly, utilities of GAM26 include diagnosis and treatment of diseases and clinical conditions with which KIAA1966 is associated.

Reference is now made to KIAA1981 BINDING SITE. KIAA1981 is a target gene of GAM26, corresponding to GAM26-TARGET GENE of FIG. 26A. KIAA1981 BINDING SITE is a binding site found in an untranslated region of KIAA1981, corresponding to BINDING SITE of FIG. 26A. FIG. 26D illustrates the complementarity of the nucleotide sequence of KIAA1981 BINDING SITE, designated SEQ ID:823610, to the nucleotide sequence of GAM26 RNA of FIG. 26A, designated SEQ ID:20604. An additional function of GAM26 is therefore inhibition of (KIAA1981). Accordingly, utilities of GAM26 include diagnosis and treatment of diseases and clinical conditions with which KIAA1981 is associated.

Reference is now made to LANCL2 BINDING SITE. LANCL2 is a target gene of GAM26, corresponding to GAM26-TARGET GENE of FIG. 26A. LANCL2 BINDING SITE is a binding site found in an untranslated region of LANCL2, corresponding to BINDING SITE of FIG. 26A. FIG. 26D illustrates the complementarity of the nucleotide sequence of LANCL2 BINDING SITE, designated SEQ ID:828560, to the nucleotide sequence of GAM26 RNA of FIG. 26A, designated SEQ ID:20604. A further function of GAM26 is therefore inhibition of (LANCL2). Accordingly, utilities of GAM26 include diagnosis and treatment of diseases and clinical conditions with which LANCL2 is associated.

Reference is now made to LANO BINDING SITE. LANO is a target gene of GAM26, corresponding to GAM26-TARGET GENE of FIG. 26A. LANO BINDING SITE is a binding site found in an untranslated region of LANO, corresponding to BINDING SITE of FIG. 26A. FIG. 26D illustrates the complementarity of the nucleotide sequence of LANO BINDING SITE, designated SEQ ID:828789, to the nucleotide sequence of GAM26 RNA of FIG. 26A, designated SEQ ID:20604. Yet a further function of GAM26 is therefore inhibition of (LANO). Accordingly, utilities of GAM26 include diagnosis and treatment of diseases and clinical conditions with which LANO is associated.

Reference is now made to LAP1B BINDING SITE. LAP1B is a target gene of GAM26, corresponding to GAM26-TARGET GENE of FIG. 26A. LAP1B BINDING SITE is a binding site found in an untranslated region of LAP1B, corresponding to BINDING SITE of FIG. 26A. FIG. 26D illustrates the complementarity of the nucleotide sequence of LAP1B BINDING SITE, designated SEQ ID:828926, to the nucleotide sequence of GAM26 RNA of FIG. 26A, designated SEQ ID:20604. Another function of GAM26 is therefore inhibition of (LAP1B). Accordingly, utilities of GAM26 include diagnosis and treatment of diseases and clinical conditions with which LAP1B is associated.

Reference is now made to LSM4 BINDING SITE. LSM4 is a target gene of GAM26, corresponding to GAM26-TARGET GENE of FIG. 26A. LSM4 BINDING SITE is a binding site found in an untranslated region of LSM4, corresponding to BINDING SITE of FIG. 26A. FIG. 26D illustrates the complementarity of the nucleotide sequence of LSM4 BINDING SITE, designated SEQ ID:834693, to the nucleotide sequence of GAM26 RNA of FIG. 26A, designated SEQ ID:20604. Yet another function of GAM26 is therefore inhibition of (LSM4). Accordingly, utilities of GAM26 include diagnosis and treatment of diseases and clinical conditions with which LSM4 is associated.

Reference is now made to MAP2K7 BINDING SITE. MAP2K7 is a target gene of GAM26, corresponding to GAM26-TARGET GENE of FIG. 26A. MAP2K7 BINDING SITE is a binding site found in an untranslated region of MAP2K7, corresponding to BINDING SITE of FIG. 26A. FIG. 26D illustrates the complementarity of the nucleotide sequence of MAP2K7 BINDING SITE, designated SEQ ID:838581, to the nucleotide sequence of GAM26 RNA of FIG. 26A, designated SEQ ID:20604. An additional function of GAM26 is therefore inhibition of (MAP2K7). Accordingly, utilities of GAM26 include diagnosis and treatment of diseases and clinical conditions with which MAP2K7 is associated.

Reference is now made to MAPK8IP3 BINDING SITE. MAPK8IP3 is a target gene of GAM26, corresponding to GAM26-TARGET GENE of FIG. 26A. MAPK8IP3 BINDING SITE is a binding site found in an untranslated region of MAPK8IP3, corresponding to BINDING SITE of FIG. 26A. FIG. 26D illustrates the complementarity of the nucleotide sequence of MAPK8IP3 BINDING SITE, designated SEQ ID:839431, to the nucleotide sequence of GAM26 RNA of FIG. 26A, designated SEQ ID:20604. A further function of GAM26 is therefore inhibition of (MAPK8IP3). Accordingly, utilities of GAM26 include diagnosis and treatment of diseases and clinical conditions with which MAPK8IP3 is associated.

Reference is now made to MESDC1 BINDING SITE. MESDC1 is a target gene of GAM26, corresponding to GAM26-TARGET GENE of FIG. 26A. MESDC1 BINDING SITE is a binding site found in an untranslated region of MESDC1, corresponding to BINDING SITE of FIG. 26A. FIG. 26D illustrates the complementarity of the nucleotide sequence of MESDC1 BINDING SITE, designated SEQ ID:842805, to the nucleotide sequence of GAM26 RNA of FIG. 26A, designated SEQ ID:20604. Yet a further function of GAM26 is therefore inhibition of (MESDC1). Accordingly, utilities of GAM26 include diagnosis and treatment of diseases and clinical conditions with which MESDC1 is associated.

Reference is now made to MESDC1 BINDING SITE. MESDC1 is a target gene of GAM26, corresponding to GAM26-TARGET GENE of FIG. 26A. MESDC1 BINDING SITE is a binding site found in an untranslated region of MESDC1, corresponding to BINDING SITE of FIG. 26A. FIG. 26D illustrates the complementarity of the nucleotide sequence of MESDC1 BINDING SITE, designated SEQ ID:842838, to the nucleotide sequence of GAM26 RNA of FIG. 26A, designated SEQ ID:20604. Another function of GAM26 is therefore inhibition of (MESDC1). Accordingly, utilities of GAM26 include diagnosis and treatment of diseases and clinical conditions with which MESDC1 is associated.

Reference is now made to OATPRP4 BINDING SITE. OATPRP4 is a target gene of GAM26, corresponding to GAM26-TARGET GENE of FIG. 26A. OATPRP4 BINDING SITE is a binding site found in an untranslated region of OATPRP4, corresponding to BINDING SITE of FIG. 26A. FIG. 26D illustrates the complementarity of the nucleotide sequence of OATPRP4 BINDING SITE, designated SEQ ID:844404, to the nucleotide sequence of GAM26 RNA of FIG. 26A, designated SEQ ID:20604. Yet another function of GAM26 is therefore inhibition of (OATPRP4). Accordingly, utilities of GAM26 include diagnosis and treatment of diseases and clinical conditions with which OATPRP4 is associated.

Reference is now made to SLC21A11 BINDING SITE. SLC21A11 is a target gene of GAM26, corresponding to GAM26-TARGET GENE of FIG. 26A. SLC21A11 BINDING SITE is a binding site found in an untranslated region of SLC21A11, corresponding to BINDING SITE of FIG. 26A. FIG. 26D illustrates the complementarity of the nucleotide sequence of SLC21A11 BINDING SITE, designated SEQ ID:844404, to the nucleotide sequence of GAM26 RNA of FIG. 26A, designated SEQ ID:20604. An additional function of GAM26 is therefore inhibition of (SLC21A11). Accordingly, utilities of GAM26 include diagnosis and treatment of diseases and clinical conditions with which SLC21A11 is associated.

Reference is now made to MGC10702 BINDING SITE. MGC10702 is a target gene of GAM26, corresponding to GAM26-TARGET GENE of FIG. 26A. MGC10702 BINDING SITE is a binding site found in an untranslated region of MGC10702, corresponding to BINDING SITE of FIG. 26A. FIG. 26D illustrates the complementarity of the nucleotide sequence of MGC10702 BINDING SITE, designated SEQ ID:844408, to the nucleotide sequence of GAM26 RNA of FIG. 26A, designated SEQ ID:20604. A further function of GAM26 is therefore inhibition of (MGC10702). Accordingly, utilities of GAM26 include diagnosis and treatment of diseases and clinical conditions with which MGC10702 is associated.

Reference is now made to MGC13159 BINDING SITE. MGC13159 is a target gene of GAM26, corresponding to GAM26-TARGET GENE of FIG. 26A. MGC13159 BINDING SITE is a binding site found in an untranslated region of MGC13159, corresponding to BINDING SITE of FIG. 26A. FIG. 26D illustrates the complementarity of the nucleotide sequence of MGC13159 BINDING SITE, designated SEQ ID:851324, to the nucleotide sequence of GAM26 RNA of FIG. 26A, designated SEQ ID:20604. Yet a further function of GAM26 is therefore inhibition of (MGC13159). Accordingly, utilities of GAM26 include diagnosis and treatment of diseases and clinical conditions with which MGC13159 is associated.

Reference is now made to MGC14425 BINDING SITE. MGC14425 is a target gene of GAM26, corresponding to GAM26-TARGET GENE of FIG. 26A. MGC14425 BINDING SITE is a binding site found in an untranslated region of MGC14425, corresponding to BINDING SITE of FIG. 26A. FIG. 26D illustrates the complementarity of the nucleotide sequence of MGC14425 BINDING SITE, designated SEQ ID:852921, to the nucleotide sequence of GAM26 RNA of FIG. 26A, designated SEQ ID:20604. Another function of GAM26 is therefore inhibition of (MGC14425). Accordingly, utilities of GAM26 include diagnosis and treatment of diseases and clinical conditions with which MGC14425 is associated.

Reference is now made to MGC15396 BINDING SITE. MGC15396 is a target gene of GAM26, corresponding to GAM26-TARGET GENE of FIG. 26A. MGC15396 BINDING SITE is a binding site found in an untranslated region of MGC15396, corresponding to BINDING SITE of FIG. 26A. FIG. 26D illustrates the complementarity of the nucleotide sequence of MGC15396 BINDING SITE, designated SEQ ID:853827, to the nucleotide sequence of GAM26 RNA of FIG. 26A, designated SEQ ID:20604. Yet another function of GAM26 is therefore inhibition of (MGC15396). Accordingly, utilities of GAM26 include diagnosis and treatment of diseases and clinical conditions with which MGC15396 is associated.

Reference is now made to MGC15396 BINDING SITE. MGC15396 is a target gene of GAM26, corresponding to GAM26-TARGET GENE of FIG. 26A. MGC15396 BINDING SITE is a binding site found in an untranslated region of MGC15396, corresponding to BINDING SITE of FIG. 26A. FIG. 26D illustrates the complementarity of the nucleotide sequence of MGC15396 BINDING SITE, designated SEQ ID:853851, to the nucleotide sequence of GAM26 RNA of FIG. 26A, designated SEQ ID:20604. An additional function of GAM26 is therefore inhibition of (MGC15396). Accordingly, utilities of GAM26 include diagnosis and treatment of diseases and clinical conditions with which MGC15396 is associated.

Reference is now made to MGC17347 BINDING SITE. MGC17347 is a target gene of GAM26, corresponding to GAM26-TARGET GENE of FIG. 26A. MGC17347 BINDING SITE is a binding site found in an untranslated region of MGC17347, corresponding to BINDING SITE of FIG. 26A. FIG. 26D illustrates the complementarity of the nucleotide sequence of MGC17347 BINDING SITE, designated SEQ ID:858358, to the nucleotide sequence of GAM26 RNA of FIG. 26A, designated SEQ ID:20604. A further function of GAM26 is therefore inhibition of (MGC17347). Accordingly, utilities of GAM26 include diagnosis and treatment of diseases and clinical conditions with which MGC17347 is associated.

Reference is now made to MGC17347 BINDING SITE. MGC17347 is a target gene of GAM26, corresponding to GAM26-TARGET GENE of FIG. 26A. MGC17347 BINDING SITE is a binding site found in an untranslated region of MGC17347, corresponding to BINDING SITE of FIG. 26A. FIG. 26D illustrates the complementarity of the nucleotide sequence of MGC17347 BINDING SITE, designated SEQ ID:858360, to the nucleotide sequence of GAM26 RNA of FIG. 26A, designated SEQ ID:20604. Yet a further function of GAM26 is therefore inhibition of (MGC17347). Accordingly, utilities of GAM26 include diagnosis and treatment of diseases and clinical conditions with which MGC117347 is associated.

Reference is now made to MGC1842 BINDING SITE. MGC1842 is a target gene of GAM26, corresponding to GAM26-TARGET GENE of FIG. 26A. MGC1842 BINDING SITE is a binding site found in an untranslated region of MGC1842, corresponding to BINDING SITE of FIG. 26A. FIG. 26D illustrates the complementarity of the nucleotide sequence of MGC1842 BINDING SITE, designated SEQ ID:858800, to the nucleotide sequence of GAM26 RNA of FIG. 26A, designated SEQ ID:20604. Another function of GAM26 is therefore inhibition of (MGC1842). Accordingly, utilities of GAM26 include diagnosis and treatment of diseases and clinical conditions with which MGC1842 is associated.

Reference is now made to MGC22679 BINDING SITE. MGC22679 is a target gene of GAM26, corresponding to GAM26-TARGET GENE of FIG. 26A. MGC22679 BINDING SITE is a binding site found in an untranslated region of MGC22679, corresponding to BINDING SITE of FIG. 26A. FIG. 26D illustrates the complementarity of the nucleotide sequence of MGC22679 BINDING SITE, designated SEQ ID:861565, to the nucleotide sequence of GAM26 RNA of FIG. 26A, designated SEQ ID:20604. Yet another function of GAM26 is therefore inhibition of (MGC22679). Accordingly, utilities of GAM26 include diagnosis and treatment of diseases and clinical conditions with which MGC22679 is associated.

Reference is now made to MGC2594 BINDING SITE. MGC2594 is a target gene of GAM26, corresponding to GAM26-TARGET GENE of FIG. 26A. MGC2594 BINDING SITE is a binding site found in an untranslated region of MGC2594, corresponding to BINDING SITE of FIG. 26A. FIG. 26D illustrates the complementarity of the nucleotide sequence of MGC2594 BINDING SITE, designated SEQ ID:864289, to the nucleotide sequence of GAM26 RNA of FIG. 26A, designated SEQ ID:20604. An additional function of GAM26 is therefore inhibition of (MGC2594). Accordingly, utilities of GAM26 include diagnosis and treatment of diseases and clinical conditions with which MGC2594 is associated.

Reference is now made to MGC26684 BINDING SITE. MGC26684 is a target gene of GAM26, corresponding to GAM26-TARGET GENE of FIG. 26A. MGC26684 BINDING SITE is a binding site found in an untranslated region of MGC26684, corresponding to BINDING SITE of FIG. 26A. FIG. 26D illustrates the complementarity of the nucleotide sequence of MGC26684 BINDING SITE, designated SEQ ID:865556, to the nucleotide sequence of GAM26 RNA of FIG. 26A, designated SEQ ID:20604. A further function of GAM26 is therefore inhibition of (MGC26684). Accordingly, utilities of GAM26 include diagnosis and treatment of diseases and clinical conditions with which MGC26684 is associated.

Reference is now made to MGC3222 BINDING SITE. MGC3222 is a target gene of GAM26, corresponding to GAM26-TARGET GENE of FIG. 26A. MGC3222 BINDING SITE is a binding site found in an untranslated region of MGC3222, corresponding to BINDING SITE of FIG. 26A. FIG. 26D illustrates the complementarity of the nucleotide sequence of MGC3222 BINDING SITE, designated SEQ ID:870434, to the nucleotide sequence of GAM26 RNA of FIG. 26A, designated SEQ ID:20604. Yet a further function of GAM26 is therefore inhibition of (MGC3222). Accordingly, utilities of GAM26 include diagnosis and treatment of diseases and clinical conditions with which MGC3222 is associated.

Reference is now made to MGC4170 BINDING SITE. MGC4170 is a target gene of GAM26, corresponding to GAM26-TARGET GENE of FIG. 26A. MGC4170 BINDING SITE is a binding site found in an untranslated region of MGC4170, corresponding to BINDING. SITE of FIG. 26A. FIG. 26D illustrates the complementarity of the nucleotide sequence of MGC4170 BINDING SITE, designated SEQ ID:872011, to the nucleotide sequence of GAM26 RNA of FIG. 26A, designated SEQ ID:20604. Another function of GAM26 is therefore inhibition of (MGC4170). Accordingly, utilities of GAM26 include diagnosis and treatment of diseases and clinical conditions with which MGC4170 is associated.

Reference is now made to MGC4172 BINDING SITE. MGC4172 is a target gene of GAM26, corresponding to GAM26-TARGET GENE of FIG. 26A. MGC4172 BINDING SITE is a binding site found in an untranslated region of MGC4172, corresponding to BINDING SITE of FIG. 26A. FIG. 26D illustrates the complementarity of the nucleotide sequence of MGC4172 BINDING SITE, designated SEQ ID:872115, to the nucleotide sequence of GAM26 RNA of FIG. 26A, designated SEQ ID:20604. Yet another function of GAM26 is therefore inhibition of (MGC4172). Accordingly, utilities of GAM26 include diagnosis and treatment of diseases and clinical conditions with which MGC4172 is associated.

Reference is now made to MGC4172 BINDING SITE. MGC4172 is a target gene of GAM26, corresponding to GAM26-TARGET GENE of FIG. 26A. MGC4172 BINDING SITE is a binding site found in an untranslated region of MGC4172, corresponding to BINDING SITE of FIG. 26A. FIG. 26D illustrates the complementarity of the nucleotide sequence of MGC4172 BINDING SITE, designated SEQ ID:872142, to the nucleotide sequence of GAM26 RNA of FIG. 26A, designated SEQ ID:20604. An additional function of GAM26 is therefore inhibition of (MGC4172). Accordingly, utilities of GAM26 include diagnosis and treatment of diseases and clinical conditions with which MGC4172 is associated.

Reference is now made to MGC5466 BINDING SITE. MGC5466 is a target gene of GAM26, corresponding to GAM26-TARGET GENE of FIG. 26A. MGC5466 BINDING SITE is a binding site found in an untranslated region of MGC5466, corresponding to BINDING SITE of FIG. 26A. FIG. 26D illustrates the complementarity of the nucleotide sequence of MGC5466 BINDING SITE, designated SEQ ID:877031, to the nucleotide sequence of GAM26 RNA of FIG. 26A, designated SEQ ID:20604. A further function of GAM26 is therefore inhibition of (MGC5466). Accordingly, utilities of GAM26 include diagnosis and treatment of diseases and clinical conditions with which MGC5466 is associated.

Reference is now made to MIP-T3 BINDING SITE. MIP-T3 is a target gene of GAM26, corresponding to GAM26-TARGET GENE of FIG. 26A. MIP-T3 BINDING SITE is a binding site found in an untranslated region of MIP-T3, corresponding to BINDING SITE of FIG. 26A. FIG. 26D illustrates the complementarity of the nucleotide sequence of MIP-T3 BINDING SITE, designated SEQ ID:879055, to the nucleotide sequence of GAM26 RNA of FIG. 26A, designated SEQ ID:20604. Yet a further function of GAM26 is therefore inhibition of (MIP-T3). Accordingly, utilities of GAM26 include diagnosis and treatment of diseases and clinical conditions with which MIP-T3 is associated.

Reference is now made to MIR BINDING SITE. MIR is a target gene of GAM26, corresponding to GAM26-TARGET GENE of FIG. 26A. MIR BINDING SITE is a binding site found in an untranslated region of MIR, corresponding to BINDING SITE of FIG. 26A. FIG. 26D illustrates the complementarity of the nucleotide sequence of MIR BINDING SITE, designated SEQ ID:879086, to the nucleotide sequence of GAM26 RNA of FIG. 26A, designated SEQ ID:20604. Another function of GAM26 is therefore inhibition of (MIR). Accordingly, utilities of GAM26 include diagnosis and treatment of diseases and clinical conditions with which MIR is associated.

Reference is now made to MOV34-34KD BINDING SITE. MOV34-34KD is a target gene of GAM26, corresponding to GAM26-TARGET GENE of FIG. 26A. MOV34-34KD BINDING SITE is a binding site found in an untranslated region of MOV34-34KD, corresponding to BINDING SITE of FIG. 26A. FIG. 26D illustrates the complementarity of the nucleotide sequence of MOV34-34KD BINDING SITE, designated SEQ ID:881891, to the nucleotide sequence of GAM26 RNA of FIG. 26A, designated SEQ ID:20604. Yet another function of GAM26 is therefore inhibition of (MOV34-34KD). Accordingly, utilities of GAM26 include diagnosis and treatment of diseases and clinical conditions with which MOV34-34KD is associated.

Reference is now made to MOV34-34KD BINDING SITE. MOV34-34KD is a target gene of GAM26, corresponding to GAM26-TARGET GENE of FIG. 26A. MOV34-34KD BINDING SITE is a binding site found in an untranslated region of MOV34-34KD, corresponding to BINDING SITE of FIG. 26A. FIG. 26D illustrates the complementarily of the nucleotide sequence of MOV34-34KD BINDING SITE, designated SEQ ID:881892, to the nucleotide sequence of GAM26 RNA of FIG. 26A, designated SEQ ID:20604. An additional function of GAM26 is therefore inhibition of (MOV34-34KD). Accordingly, utilities of GAM26 include diagnosis and treatment of diseases and clinical conditions with which MOV34-34KD is associated.

Reference is now made to MOV34-34KD BINDING SITE. MOV34-34KD is a target gene of GAM26, corresponding to GAM26-TARGET GENE of FIG. 26A. MOV34-34KD BINDING SITE is a binding site found in an untranslated region of MOV34-34KD, corresponding to BINDING SITE of FIG. 26A. FIG. 26D illustrates the complementarity of the nucleotide sequence of MOV34-34KD BINDING SITE, designated SEQ ID:881894, to the nucleotide sequence of GAM26 RNA of FIG. 26A, designated SEQ ID:20604. A further function of GAM26 is therefore inhibition of (MOV34-34KD). Accordingly, utilities of GAM26 include diagnosis and treatment of diseases and clinical conditions with which MOV34-34KD is associated.

Reference is now made to MPZL1 BINDING SITE. MPZL1 is a target gene of GAM26, corresponding to GAM26-TARGET GENE of FIG. 26A. MPZL1 BINDING SITE is a binding site found in an untranslated region of MPZL1, corresponding to BINDING SITE of FIG. 26A. FIG. 26D illustrates the complementarity of the nucleotide sequence of MPZL1 BINDING SITE, designated SEQ ID:882046, to the nucleotide sequence of GAM26 RNA of FIG. 26A, designated SEQ ID:20604. Yet a further function of GAM26 is therefore inhibition of (MPZL1). Accordingly, utilities of GAM26 include diagnosis and treatment of diseases and clinical conditions with which MPZL1 is associated.

Reference is now made to MPZL1 BINDING SITE. MPZL1 is a target gene of GAM26, corresponding to GAM26-TARGET GENE of FIG. 26A. MPZL1 BINDING SITE is a binding site found in an untranslated region of MPZL1, corresponding to BINDING SITE of FIG. 26A. FIG. 26D illustrates the complementarity of the nucleotide sequence of MPZL1 BINDING SITE, designated SEQ ID:882049, to the nucleotide sequence of GAM26 RNA of FIG. 26A, designated SEQ ID:20604. Another function of GAM26 is therefore inhibition of (MPZL1). Accordingly, utilities of GAM26 include diagnosis and treatment of diseases and clinical conditions with which MPZL1 is associated.

Reference is now made to NCOR1 BINDING SITE. NCOR1 is a target gene of GAM26, corresponding to GAM26-TARGET GENE of FIG. 26A. NCOR1 BINDING SITE is a binding site found in an untranslated region of NCOR1, corresponding to BINDING SITE of FIG. 26A. FIG. 26D illustrates the complementarity of the nucleotide sequence of NCOR1 BINDING SITE, designated SEQ ID:889437, to the nucleotide sequence of GAM26 RNA of FIG. 26A, designated SEQ ID:20604. Yet another function of GAM26 is therefore inhibition of (NCOR1). Accordingly, utilities of GAM26 include diagnosis and treatment of diseases and clinical conditions with which NCOR1 is associated.

Reference is now made to NCOR1 BINDING SITE. NCOR1 is a target gene of GAM26, corresponding to GAM26-TARGET GENE of FIG. 26A. NCOR1 BINDING SITE is a binding site found in an untranslated region of NCOR1, corresponding to BINDING SITE of FIG. 26A. FIG. 26D illustrates the complementarity of the nucleotide sequence of NCOR1 BINDING SITE, designated SEQ ID:889452, to the nucleotide sequence of GAM26 RNA of FIG. 26A, designated SEQ ID:20604. An additional function of GAM26 is therefore inhibition of (NCOR1). Accordingly, utilities of GAM26 include diagnosis and treatment of diseases and clinical conditions with which NCOR1 is associated.

Reference is now made to NFAT5 BINDING SITE. NFAT5 is a target gene of GAM26, corresponding to GAM26-TARGET GENE of FIG. 26A. NFAT5 BINDING SITE is a binding site found in an untranslated region of NFAT5, corresponding to BINDING SITE of FIG. 26A. FIG. 26D illustrates the complementarity of the nucleotide sequence of NFAT5 BINDING SITE, designated SEQ ID:892135, to the nucleotide sequence of GAM26 RNA of FIG. 26A, designated SEQ ID:20604. A further function of GAM26 is therefore inhibition of (NFAT5). Accordingly, utilities of GAM26 include diagnosis and treatment of diseases and clinical conditions with which NFAT5 is associated.

Reference is now made to NIR1 BINDING SITE. NIR1 is a target gene of GAM26, corresponding to GAM26-TARGET GENE of FIG. 26A. NIR1 BINDING SITE is a binding site found in an untranslated region of NIR1, corresponding to BINDING SITE of FIG. 26A. FIG. 26D illustrates the complementarity of the nucleotide sequence of NIR1 BINDING SITE, designated SEQ ID:893156, to the nucleotide sequence of GAM26 RNA of FIG. 26A, designated SEQ ID:20604. Yet a further function of GAM26 is therefore inhibition of (NIR1). Accordingly, utilities of GAM26 include diagnosis and treatment of diseases and clinical conditions with which NIR1 is associated.

Reference is now made to NIR1 BINDING SITE. NIR1 is a target gene of GAM26, corresponding to GAM26-TARGET GENE of FIG. 26A. NIR1 BINDING SITE is a binding site found in an untranslated region of NIR1, corresponding to BINDING SITE of FIG. 26A. FIG. 26D illustrates the complementarity of the nucleotide sequence of NIR1 BINDING SITE, designated SEQ ID:893162, to the nucleotide sequence of GAM26 RNA of FIG. 26A, designated SEQ ID:20604. Another function of GAM26 is therefore inhibition of (NIR1). Accordingly, utilities of GAM26 include diagnosis and treatment of diseases and clinical conditions with which NIR1 is associated.

Reference is now made to NKX2B BINDING SITE. NKX2B is a target gene of GAM26, corresponding to GAM26-TARGET GENE of FIG. 26A. NKX2B BINDING SITE is a binding site found in an untranslated region of NKX2B, corresponding to BINDING SITE of FIG. 26A. FIG. 26D illustrates the complementarity of the nucleotide sequence of NKX2B BINDING SITE, designated SEQ ID:893635, to the nucleotide sequence of GAM26 RNA of FIG. 26A, designated SEQ ID:20604. Yet another function of GAM26 is therefore inhibition of (NKX2B). Accordingly, utilities of GAM26 include diagnosis and treatment of diseases and clinical conditions with which NKX2B is associated.

Reference is now made to NS1-BP BINDING SITE. NS1-BP is a target gene of GAM26, corresponding to GAM26-TARGET GENE of FIG. 26A. NS1-BP BINDING SITE is a binding site found in an untranslated region of NS1-BP, corresponding to BINDING SITE of FIG. 26A. FIG. 26D illustrates the complementarity of the nucleotide sequence of NS1-BP BINDING SITE, designated SEQ ID:896538, to the nucleotide sequence of GAM26 RNA of FIG. 26A, designated SEQ ID:20604. An additional function of GAM26 is therefore inhibition of (NS1-BP). Accordingly, utilities of GAM26 include diagnosis and treatment of diseases and clinical conditions with which NS1-BP is associated.

Reference is now made to NTN4 BINDING SITE. NTN4 is a target gene of GAM26, corresponding to GAM26-TARGET GENE of FIG. 26A. NTN4 BINDING SITE is a binding site found in an untranslated region of NTN4, corresponding to BINDING SITE of FIG. 26A. FIG. 26D illustrates the complementarity of the nucleotide sequence of NTN4 BINDING SITE, designated SEQ ID:896979, to the nucleotide sequence of GAM26 RNA of FIG. 26A, designated SEQ ID:20604. A further function of GAM26 is therefore inhibition of (NTN4). Accordingly, utilities of GAM26 include diagnosis and treatment of diseases and clinical conditions with which NTN4 is associated.

Reference is now made to OAZ1 BINDING SITE. OAZ1 is a target gene of GAM26, corresponding to GAM26-TARGET GENE of FIG. 26A. OAZ1 BINDING SITE is a binding site found in an untranslated region of OAZ1, corresponding to BINDING SITE of FIG. 26A. FIG. 26D illustrates the complementarity of the nucleotide sequence of OAZ1 BIN DING SITE, designated SEQ ID:899518, to the nucleotide sequence of GAM26 RNA of FIG. 26A, designated SEQ ID:20604. Yet a further function of GAM26 is therefore inhibition of (OAZ1). Accordingly, utilities of GAM26 include diagnosis and treatment of diseases and clinical conditions with which OAZ1 is associated.

Reference is now made to OAZ1 BINDING SITE. OAZ1 is a target gene of GAM26, corresponding to GAM26-TARGET GENE of FIG. 26A. OAZ1 BINDING SITE is a binding site found in an untranslated region of OAZ1, corresponding to BINDING SITE of FIG. 26A. FIG. 26D illustrates the complementarity of the nucleotide sequence of OAZ1 BINDING SITE, designated SEQ ID:899526, to the nucleotide sequence of GAM26 RNA of FIG. 26A, designated SEQ ID:20604. Another function of GAM26 is therefore inhibition of (OAZ1). Accordingly, utilities of GAM26 include diagnosis and treatment of diseases and clinical conditions with which OAZ1 is associated.

Reference is now made to OAZ2 BINDING SITE. OAZ2 is a target gene of GAM26, corresponding to GAM26-TARGET GENE of FIG. 26A. OAZ2 BINDING SITE is a binding site found in an untranslated region of OAZ2, corresponding to BINDING SITE of FIG. 26A. FIG. 26D illustrates the complementarity of the nucleotide sequence of OAZ2 BINDING SITE, designated SEQ ID:899599, to the nucleotide sequence of GAM26 RNA of FIG. 26A, designated SEQ ID:20604. Yet another function of GAM26 is therefore inhibition of (OAZ2). Accordingly, utilities of GAM26 include diagnosis and treatment of diseases and clinical conditions with which OAZ2 is associated.

Reference is now made to OAZ2 BINDING SITE. OAZ2 is a target gene of GAM26, corresponding to GAM26-TARGET GENE of FIG. 26A. OAZ2 BINDING SITE is a binding site found in an untranslated region of OAZ2, corresponding to BINDING SITE of FIG. 26A. FIG. 26D illustrates the complementarity of the nucleotide sequence of OAZ2 BINDING SITE, designated SEQ ID:899619, to the nucleotide sequence of GAM26 RNA of FIG. 26A, designated SEQ ID:20604. An additional function of GAM26 is therefore inhibition of (OAZ2). Accordingly, utilities of GAM26 include diagnosis and treatment of diseases and clinical conditions with which OAZ2 is associated.

Reference is now made to OSBPL1A BINDING SITE. OSBPL1A is a target gene of GAM26, corresponding to GAM26-TARGET GENE of FIG. 26A. OSBPL1A BINDING SITE is a binding site found in an untranslated region of OSBPL1A, corresponding to BINDING SITE of FIG. 26A. FIG. 26D illustrates the complementarity of the nucleotide sequence of OSBPL1A BINDING SITE, designated SEQ ID:902150, to the nucleotide sequence of GAM26 RNA of FIG. 26A, designated SEQ ID:20604. A further function of GAM26 is therefore inhibition of (OSBPL1A). Accordingly, utilities of GAM26 include diagnosis and treatment of diseases and clinical conditions with which OSBPL1A is associated.

Reference is now made to PARG1 BINDING SITE. PARG1 is a target gene of GAM26, corresponding to GAM26-TARGET GENE of FIG. 26A. PARG1 BINDING SITE is a binding site found in an untranslated region of PARG1, corresponding to BINDING SITE of FIG. 26A. FIG. 26D illustrates the complementarity of the nucleotide sequence of PARG1 BINDING SITE, designated SEQ ID:907038, to the nucleotide sequence of GAM26 RNA of FIG. 26A, designated SEQ ID:20604. Yet a further function of GAM26 is therefore inhibition of (PARG1). Accordingly, utilities of GAM26 include diagnosis and treatment of diseases and clinical conditions with which PARG1 is associated.

Reference is now made to PCAF BINDING SITE. PCAF is a target gene of GAM26, corresponding to GAM26-TARGET GENE of FIG. 26A. PCAF BINDING SITE is a binding site found in an untranslated region of PCAF, corresponding to BINDING SITE of FIG. 26A. FIG. 26D illustrates the complementarity of the nucleotide sequence of PCAF BINDING SITE, designated SEQ ID:908148, to the nucleotide sequence of GAM26 RNA of FIG. 26A, designated SEQ ID:20604. Another function of GAM26 is therefore inhibition of (PCAF). Accordingly, utilities of GAM26 include diagnosis and treatment of diseases and clinical conditions with which PCAF is associated.

Reference is now made to PCCX2 BINDING SITE. PCCX2 is a target gene of GAM26, corresponding to GAM26-TARGET GENE of FIG. 26A. PCCX2 BINDING SITE is a binding site found in an untranslated region of PCCX2, corresponding to BINDING SITE of FIG. 26A. FIG. 26D illustrates the complementarity of the nucleotide sequence of PCCX2 BINDING SITE, designated SEQ ID:908515, to the nucleotide sequence of GAM26 RNA of FIG. 26A, designated SEQ ID:20604. Yet another function of GAM26 is therefore inhibition of (PCCX2). Accordingly, utilities of GAM26 include diagnosis and treatment of diseases and clinical conditions with which PCCX2 is associated.

Reference is now made to PELI2 BINDING SITE. PELI2 is a target gene of GAM26, corresponding to GAM26-TARGET GENE of FIG. 26A. PELI2. BINDING SITE is a binding site found in an untranslated region of PELI2, corresponding to BINDING SITE of FIG. 26A. FIG. 26D illustrates the complementarity of the nucleotide sequence of PELI2 BINDING SITE, designated SEQ ID:912193, to the nucleotide sequence of GAM26 RNA of FIG. 26A, designated SEQ ID:20604. An additional function of GAM26 is therefore inhibition of (PELI2). Accordingly, utilities of GAM26 include diagnosis and treatment of diseases and clinical conditions with which PELI2 is associated.

Reference is now made to PELI2 BINDING SITE. PELI2 is a target gene of GAM26, corresponding to GAM26-TARGET GENE of FIG. 26A. PELI2 BINDING SITE is a binding site found in an untranslated region of PELI2, corresponding to BINDING SITE of FIG. 26A. FIG. 26D illustrates the complementarity of the nucleotide sequence of PELI2 BIN DING SITE, designated SEQ ID:912206, to the nucleotide sequence of GAM26 RNA of FIG. 26A, designated SEQ ID:20604. A further function of GAM26 is therefore inhibition of (PELI2). Accordingly, utilities of GAM26 include diagnosis and treatment of diseases and clinical conditions with which PELI2 is associated.

Reference is now made to PF1 BINDING SITE. PF1 is a target gene of GAM26, corresponding to GAM26-TARGET GENE of FIG. 26A. PF1 BINDING SITE is a binding site found in untranslated region of PF1, corresponding to BINDING SITE of FIG. 26A. FIG. 26D illustrates the complementarity of the nucleotide sequence of PF1 BINDING SITE, designated SEQ ID:912812, to the nucleotide sequence of GAM26 RNA of FIG. 26A, designated SEQ ID:20604. Yet a further function of GAM26 is therefore inhibition of (PF1). Accordingly, utilities of GAM26 include diagnosis and treatment of diseases and clinical conditions with which PF1 is associated.

Reference is now made to PLCL2 BINDING SITE. PLCL2 is a target gene of GAM26, corresponding to GAM26-TARGET GENE of FIG. 26A. PLCL2 BINDING SITE is a binding site found in an untranslated region of PLCL2, corresponding to BINDING SITE of FIG. 26A. FIG. 26D illustrates the complementarity of the nucleotide sequence of PLCL2 BINDING SITE, designated SEQ ID:917013, to the nucleotide sequence of GAM26 RNA of FIG. 26A, designated SEQ ID:20604. Another function of GAM26 is therefore inhibition of (PLCL2). Accordingly, utilities of GAM26 include diagnosis and treatment of diseases and clinical conditions with which PLCL2 is associated.

Reference is now made to PM5 BINDING SITE. PM5 is a target gene of GAM26, corresponding to GAM26-TARGET GENE of FIG. 26A. PM5 BINDING SITE is a binding site found in an untranslated region of PM5, corresponding to BINDING SITE of FIG. 26A. FIG. 26D illustrates the complementarity of the nucleotide sequence of PM5 BINDING SITE, designated SEQ ID:917719, to the nucleotide sequence of GAM26 RNA of FIG. 26A, designated SEQ ID:20604. Yet another function of GAM26 is therefore inhibition of (PM5). Accordingly, utilities of GAM26 include diagnosis and treatment of diseases and clinical conditions with which PM5 is associated.

Reference is now made to PMX2B BINDING SITE. PMX2B is a target gene of GAM26, corresponding to GAM26-TARGET GENE of FIG. 26A. PMX2B BINDING SITE is a binding site found in an untranslated region of PMX2B, corresponding to BINDING SITE of FIG. 26A. FIG. 26D illustrates the complementarity of the nucleotide sequence of PMX2B BINDING SITE, designated SEQ ID:918145, to the nucleotide sequence of GAM26 RNA of FIG. 26A, designated SEQ ID:20604. An additional function of GAM26 is therefore inhibition of (PMX2B). Accordingly, utilities of GAM26 include diagnosis and treatment of diseases and clinical conditions with which PMX2B is associated.

Reference is now made to PMX2B BINDING SITE. PMX2B is a target gene of GAM26, corresponding to GAM26-TARGET GENE of FIG. 26A. PMX2B BINDING SITE is a binding site found in an untranslated region of PMX2B, corresponding to BINDING SITE of FIG. 26A. FIG. 26D illustrates the complementarity of the nucleotide sequence of PMX2B BINDING SITE, designated SEQ ID:918187, to the nucleotide sequence of GAM26 RNA of FIG. 26A, designated SEQ ID:20604. A further function of GAM26 is therefore inhibition of (PMX2B). Accordingly, utilities of GAM26 include diagnosis and treatment of diseases and clinical conditions with which PMX2B is associated.

Reference is now made to PMX2B BINDING SITE. PMX2B is a target gene of GAM26, corresponding to GAM26-TARGET GENE of FIG. 26A. PMX2B BINDING SITE is a binding site found in an untranslated region of PMX2B, corresponding to BINDING SITE of FIG. 26A. FIG. 26D illustrates the complementarity of the nucleotide sequence of PMX2B BINDING SITE, designated SEQ ID:918189, to the nucleotide sequence of GAM26 RNA of FIG. 26A, designated SEQ ID:20604. Yet a further function of GAM26 is therefore inhibition of (PMX2B). Accordingly, utilities of GAM26 include diagnosis and treatment of diseases and clinical conditions with which PMX2B is associated.

Reference is now made to PRDM8 BINDING SITE. PRDM8 is a target gene of GAM26, corresponding to GAM26-TARGET GENE of FIG. 26A. PRDM8 BINDING SITE is a binding site found in an untranslated region of PRDM8, corresponding to BINDING SITE of FIG. 26A. FIG. 26D illustrates the complementarity of the nucleotide sequence of PRDM8 BINDING SITE, designated SEQ ID:924600, to the nucleotide sequence of GAM26 RNA of FIG. 26A, designated SEQ ID:20604. Another function of GAM26 is therefore inhibition of (PRDM8). Accordingly, utilities of GAM26 include diagnosis and treatment of diseases and clinical conditions with which PRDM8 is associated.

Reference is now made to PSIP2 BINDING SITE. PSIP2 is a target gene of GAM26, corresponding to GAM26-TARGET GENE of FIG. 26A. PSIP2 BINDING SITE is a binding site found in an untranslated region of PSIP2, corresponding to BINDING SITE of FIG. 26A. FIG. 26D illustrates the complementarity of the nucleotide sequence of PSIP2 BINDING SITE, designated SEQ ID:933689, to the nucleotide sequence of GAM26 RNA of FIG. 26A, designated SEQ ID:20604. Yet another function of GAM26 is therefore inhibition of (PSIP2). Accordingly, utilities of GAM26 include diagnosis and treatment of diseases and clinical conditions with which PSIP2 is associated.

Reference is now made to PSIP2 BINDING SITE. PSIP2 is a target gene of GAM26, corresponding to GAM26-TARGET GENE of FIG. 26A. PSIP2 BINDING SITE is a binding site found in an untranslated region of PSIP2, corresponding to BINDING SITE of FIG. 26A. FIG. 26D illustrates the complementarity of the nucleotide sequence of PSIP2 BINDING SITE, designated SEQ ID:933709, to the nucleotide sequence of GAM26 RNA of FIG. 26A, designated SEQ ID:20604. An additional function of GAM26 is therefore inhibition of (PSIP2). Accordingly, utilities of GAM26 include diagnosis and treatment of diseases and clinical conditions with which PSIP2 is associated.

Reference is now made to PTR4 BINDING SITE. PTR4 is a target gene of GAM26, corresponding to GAM26-TARGET GENE of FIG. 26A. PTR4 BINDING SITE is a binding site found in an untranslated region of PTR4, corresponding to BINDING SITE of FIG. 26A. FIG. 26D illustrates the complementarity of the nucleotide sequence of PTR4 BINDING SITE, designated SEQ ID:937407, to the nucleotide sequence of GAM26 RNA of FIG. 26A, designated SEQ ID:20604. A further function of GAM26 is therefore inhibition of (PTR4). Accordingly, utilities of GAM26 include diagnosis and treatment of diseases and clinical conditions with which PTR4 is associated.

Reference is now made to QKI BINDING SITE. QKI is a target gene of GAM26, corresponding to GAM26-TARGET GENE of FIG. 26A. QKI BINDING SITE is a binding site found in an untranslated region of QKI, corresponding to BINDING SITE of FIG. 26A. FIG. 26D illustrates the complementarity of the nucleotide sequence of QKI BINDING SITE, designated SEQ ID:938140, to the nucleotide sequence of GAM26 RNA of FIG. 26A, designated SEQ ID:20604. Yet a further function of GAM26 is therefore inhibition of (QKI). Accordingly, utilities of GAM26 include diagnosis and treatment of diseases and clinical conditions with which QKI is associated.

Reference is now made to QKI BINDING SITE. QKI is a target gene of GAM26, corresponding to GAM26-TARGET GENE of FIG. 26A. QKI BINDING SITE is a binding site found in an untranslated region of QKI, corresponding to BINDING SITE of FIG. 26A. FIG. 26D illustrates the complementarity of the nucleotide sequence of QKI BINDING SIT, designated SEQ ID:938170, to the nucleotide sequence of GAM26 RNA of FIG. 26A, designated SEQ ID:20604. Another function of GAM26 is therefore inhibition of (QKI). Accordingly, utilities of GAM26 include diagnosis and treatment of diseases and clinical conditions with which QKI is associated.

Reference is now made to QKI BINDING SITE. QKI is a target gene of GAM26, corresponding to GAM26-TARGET GENE of FIG. 26A. QKI BINDING SITE is a binding site found in an untranslated region of QKI, corresponding to BINDING SITE of FIG. 26A. FIG. 26D illustrates the complementarity of the nucleotide sequence of QKI BINDING SITE, designated SEQ ID:938172, to the nucleotide sequence of GAM26 RNA of FIG. 26A, designated SEQ ID:20604. Yet another function of GAM26 is therefore inhibition of (QKI). Accordingly, utilities of GAM26 include diagnosis and treatment of diseases and clinical conditions with which QKI is associated.

Reference is now made to QKI BINDING SITE. QKI is a target gene of GAM26, corresponding to GAM26-TARGET GENE of FIG. 26A. QKI BINDING SITE is a binding site found in an untranslated region of QKI, corresponding to BINDING SITE of FIG. 26A. FIG. 26D illustrates the complementarity of the nucleotide sequence of QKI BINDING SITE, designated SEQ ID:938196, to the nucleotide sequence of GAM26 RNA of FIG. 26A, designated SEQ ID:20604. An additional function of GAM26 is therefore inhibition of (QKI). Accordingly, utilities of GAM26 include diagnosis and treatment of diseases and clinical conditions with which QKI is associated.

Reference is now made to RAB2 BINDING SITE. RAB2 is a target gene of GAM26, corresponding to GAM26-TARGET GENE of FIG. 26A. RAB2 BINDING SITE is a binding site found in an untranslated region of RAB2, corresponding to BINDING SITE of FIG. 26A. FIG. 26D illustrates the complementarity of the nucleotide sequence of RAB2 BINDING SITE, designated SEQ ID:939662, to the nucleotide sequence of GAM26 RNA of FIG. 26A, designated SEQ ID:20604. A further function of GAM26 is therefore inhibition of (RAB2). Accordingly, utilities of GAM26 include diagnosis and treatment of diseases and clinical conditions with which RAB2 is associated.

Reference is now made to RAB2 BINDING SITE. RAB2 is a target gene of GAM26, corresponding to GAM26-TARGET GENE of FIG. 26A. RAB2 BINDING SITE is a binding site found in an untranslated region of RAB2, corresponding to BINDING SITE of FIG. 26A. FIG. 26D illustrates the complementarity of the nucleotide sequence of RAB2 BINDING SITE, designated SEQ ID:939672, to the nucleotide sequence of GAM26 RNA of FIG. 26A, designated SEQ ID:20604. Yet a further function of GAM26 is therefore inhibition of (RAB2). Accordingly, utilities of GAM26 include diagnosis and treatment of diseases and clinical conditions with which RAB2 is associated.

Reference is now made to RAB2 BINDING SITE. RAB2 is a target gene of GAM26, corresponding to GAM26-TARGET GENE of FIG. 26A. RAB2 BINDING SITE is a binding site found in an untranslated region of RAB2, corresponding to BINDING SITE of FIG. 26A. FIG. 26D illustrates the complementarity of the nucleotide sequence of RAB2 BINDING SITE, designated SEQ ID:939672, to the nucleotide sequence of GAM26 RNA of FIG. 26A, designated SEQ ID:20604. Another function of GAM26 is therefore inhibition of (RAB2). Accordingly, utilities of GAM26 include diagnosis and treatment of diseases and clinical conditions with which RAB2 is associated.

Reference is now made to RAB22A BINDING SITE. RAB22A is a target gene of GAM26, corresponding to GAM26-TARGET GENE of FIG. 26A. RAB22A BINDING SITE is a binding site found in an untranslated region of RAB22A, corresponding to BINDING SITE of FIG. 26A. FIG. 26D illustrates the complementarity of the nucleotide sequence of RAB22A BINDING SITE, designated SEQ ID:939920, to the nucleotide sequence of GAM26 RNA of FIG. 26A, designated SEQ ID:20604. Yet another function of GAM26 is therefore inhibition of (RAB22A). Accordingly, utilities of GAM26 include diagnosis and treatment of diseases and clinical conditions with which RAB22A is associated.

Reference is now made to RAB22A BINDING SITE. RAB22A is a target gene of GAM26, corresponding to GAM26-TARGET GENE of FIG. 26A. RAB22A BINDING SITE is a binding site found in an untranslated region of RAB22A, corresponding to BINDING SITE of FIG. 26A. FIG. 26D illustrates the complementarity of the nucleotide sequence of RAB22A BINDING SITE, designated SEQ ID:939925, to the nucleotide sequence of GAM26 RNA of FIG. 26A, designated SEQ ID:20604. An additional function of GAM26 is therefore inhibition of (RAB22A). Accordingly, utilities of GAM26 include diagnosis and treatment of diseases and clinical conditions with which RAB22A is associated.

Reference is now made to RAB5EP BINDING SITE. RAB5EP is a target gene of GAM26, corresponding to GAM26-TARGET GENE of FIG. 26A. RAB5EP BINDING SITE is a binding site found in an untranslated region of RAB5EP, corresponding to BINDING SITE of FIG. 26A. FIG. 26D illustrates the complementarity of the nucleotide sequence of RAB5EP BINDING SITE, designated SEQ ID:941423, to the nucleotide sequence of GAM26 RNA of FIG. 26A, designated SEQ ID:20604. A further function of GAM26 is therefore inhibition of (RAB5EP). Accordingly, utilities of GAM26 include diagnosis and treatment of diseases and clinical conditions with which RAB5EP is associated.

Reference is now made to RALY BINDING SITE. RALY is a target gene of GAM26, corresponding to GAM26-TARGET GENE of FIG. 26A. RALY BINDING SITE is a binding site found in an untranslated region of RALY, corresponding to BINDING SITE of FIG. 26A. FIG. 26D illustrates the complementarity of the nucleotide sequence of RALY BINDING SITE, designated SEQ ID:943042, to the nucleotide sequence of GAM26 RNA, of FIG. 26A, designated SEQ ID:20604. Yet a further function of GAM26 is therefore inhibition of (RALY). Accordingly, utilities of GAM26 include diagnosis and treatment of diseases and clinical conditions with which RALY is associated.

Reference is now made to RALY BINDING SITE. RALY is a target gene of GAM26, corresponding to GAM26-TARGET GENE of FIG. 26A. RALY BINDING SITE is a binding site found in an untranslated region of RALY, corresponding to BINDING SITE of FIG. 26A. FIG. 26D illustrates the complementarity of the nucleotide sequence of RALY BINDING SITE, designated SEQ ID:943043, to the nucleotide sequence of GAM26 RNA of FIG. 26A, designated SEQ ID:20604. Another function of GAM26 is therefore inhibition of (RALY). Accordingly, utilities of GAM26 include diagnosis and treatment of diseases and clinical conditions with which RALY is associated.

Reference is now made to RALY BINDING SITE. RALY is a target gene of GAM26, corresponding to GAM26-TARGET GENE of FIG. 26A. RALY BINDING SITE is a binding site found in an untranslated region of RALY, corresponding to BINDING SITE of FIG. 26A. FIG. 26D illustrates the complementarity of the nucleotide sequence of RALY BINDING SITE, designated SEQ ID:943044, to the nucleotide sequence of GAM26 RNA of FIG. 26A, designated SEQ ID:20604. Yet another function of GAM26 is therefore inhibition of (RALY). Accordingly, utilities of GAM26 include diagnosis and treatment of diseases and clinical conditions with which RALY is associated.

Reference is now made to RC3 BINDING SITE. RC3 is a target gene of GAM26, corresponding to GAM26-TARGET GENE of FIG. 26A. RC3 BINDING SITE is a binding site found in an untranslated region of RC3, corresponding to BINDING SITE of FIG. 26A. FIG. 26D illustrates the complementarity of the nucleotide sequence of RC3 BINDING SITE, designated SEQ ID:945022, to the nucleotide sequence of GAM26 RNA of FIG. 26A, designated SEQ ID:20604. An additional function of GAM26 is therefore inhibition of (RC3). Accordingly, utilities of GAM26 include diagnosis and treatment of diseases and clinical conditions with which RC3 is associated.

Reference is now made to RNPC2 BINDING SITE. RNPC2 is a target gene of GAM26, corresponding to GAM26-TARGET GENE of FIG. 26A. RNPC2 BINDING SITE is a binding site found in an untranslated region of RNPC2, corresponding to BINDING SITE of FIG. 26A. FIG. 26D illustrates the complementarity of the nucleotide sequence of RNPC2 BINDING SITE, designated SEQ ID:950359, to the nucleotide sequence of GAM26 RNA of FIG. 26A, designated SEQ ID:20604. A further function of GAM26 is therefore inhibition of (RNPC2). Accordingly, utilities of GAM26 include diagnosis and treatment of diseases and clinical conditions with which RNPC2 is associated.

Reference is now made to RNPC2 BINDING SITE. RNPC2 is a target gene of GAM26, corresponding to GAM26-TARGET GENE of FIG. 26A. RNPC2 BINDING SITE is a binding site found in an untranslated region of RNPC2, corresponding to BINDING SITE of FIG. 26A. FIG. 26D illustrates the complementarity of the nucleotide sequence of RNPC2 BINDING SITE, designated SEQ ID:950360, to the nucleotide sequence of GAM26 RNA of FIG. 26A, designated SEQ ID:20604. Yet a further function of GAM26 is therefore inhibition of (RNPC2). Accordingly, utilities of GAM26 include diagnosis and treatment of diseases and clinical conditions with which RNPC2 is associated.

Reference is now made to RPS6KC1 BINDING SITE. RPS6KC1 is a target gene of GAM26, corresponding to GAM26-TARGET GENE of FIG. 26A. RPS6KC1 BINDING SITE is a binding site found in an untranslated region of RPS6KC1, corresponding to BINDING SITE of FIG. 26A. FIG. 26D illustrates the complementarity of the nucleotide sequence of RPS6KC1 BINDING SITE, designated SEQ ID:952575, to the nucleotide sequence of GAM26 RNA of FIG. 26A, designated SEQ ID:20604. Another function of GAM26 is therefore inhibition of (RPS6KC1). Accordingly, utilities of GAM26 include diagnosis and treatment of diseases and clinical conditions with which RPS6KC1 is associated.

Reference is now made to SERP1 BINDING SITE. SERP1 is a target gene of GAM26, corresponding to GAM26-TARGET GENE of FIG. 26A. SERP1 BINDING SITE is a binding site found in an untranslated region of SERP1, corresponding to BINDING SITE of FIG. 26A. FIG. 26D illustrates the complementarity of the nucleotide sequence of SERP1 BINDING SITE, designated SEQ ID:963975, to the nucleotide sequence of GAM26 RNA of FIG. 26A, designated SEQ ID:20604. Yet another function of GAM26 is therefore inhibition of (SERP1). Accordingly, utilities of GAM26 include diagnosis and treatment of diseases and clinical conditions with which SERP1 is associated.

Reference is now made to SERP1 BINDING SITE. SERP1 is a target gene of GAM26, corresponding to GAM26-TARGET GENE of FIG. 26A. SERP1 BINDING SITE is a binding site found in an untranslated region of SERP1, corresponding to BINDING SITE of FIG. 26A. FIG. 26D illustrates the complementarity of the nucleotide sequence of SERP1 BINDING SITE, designated SEQ ID:963978, to the nucleotide sequence of GAM26 RNA of FIG. 26A, designated SEQ ID:20604. An additional function of GAM26 is therefore inhibition of (SERP1). Accordingly, utilities of GAM26 include diagnosis and treatment of diseases and clinical conditions with which SERP1 is associated.

Reference is now made to SERP1 BINDING SITE. SERP1 is a target gene of GAM26, corresponding to GAM26-TARGET GENE of FIG. 26A. SERP1 BINDING SITE is a binding site found in an untranslated region of SERP1, corresponding to BINDING SITE of FIG. 26A. FIG. 26D illustrates the complementarity of the nucleotide sequence of SERP1 BINDING SITE, designated SEQ ID:964015, to the nucleotide sequence of GAM26 RNA of FIG. 26A, designated SEQ ID:20604. A further function of GAM26 is therefore inhibition of (SERP1). Accordingly, utilities of GAM26 include diagnosis and treatment of diseases and clinical conditions with which SERP1 is associated.

Reference is now made to SFRS9 BINDING SITE. SFRS9 is a target gene of GAM26, corresponding to GAM26-TARGET GENE of FIG. 26A. SFRS9 BINDING SITE is a binding site found in an untranslated region of SFRS9, corresponding to BINDING SITE of FIG. 26A. FIG. 26D illustrates the complementarity of the nucleotide sequence of SFRS9 BINDING SITE, designated SEQ ID:964985, to the nucleotide sequence of GAM26 RNA of FIG. 26A, designated SEQ ID:20604. Yet a further function of GAM26 is therefore inhibition of (SFRS9). Accordingly, utilities of GAM26 include diagnosis and treatment of diseases and clinical conditions with which SFRS9 is associated.

Reference is now made to SH2D3C BINDING SITE. SH2D3C is a target gene of GAM26, corresponding to GAM26-TARGET GENE of FIG. 26A. SH2D3C BINDING SITE is a binding site found in an untranslated region of SH2D3C, corresponding to BINDING SITE of FIG. 26A. FIG. 26D illustrates the complementarity of the nucleotide sequence of SH2D3C BINDING SITE, designated SEQ ID:965802, to the nucleotide sequence of GAM26 RNA of FIG. 26A, designated SEQ ID:20604. Another function of GAM26 is therefore inhibition of (SH2D3C). Accordingly, utilities of GAM26 include diagnosis and treatment of diseases and clinical conditions with which SH2D3C is associated.

Reference is now made to SHANK3 BINDING SITE. SHANK3 is a target gene of GAM26, corresponding to GAM26-TARGET GENE of FIG. 26A. SHANK3 BINDING SITE is a binding site found in an untranslated region of SHANK3, corresponding to BINDING SITE of FIG. 26A. FIG. 26D illustrates the complementarity of the nucleotide sequence of SHANK3 BINDING SITE, designated SEQ ID:966276, to the nucleotide sequence of GAM26 RNA of FIG. 26A, designated SEQ ID:20604. Yet another function of GAM26 is therefore inhibition of (SHANK3). Accordingly, utilities of GAM26 include diagnosis and treatment of diseases and clinical conditions with which SHANK3 is associated.

Reference is now made to SHARP BINDING SITE. SHARP is a target gene of GAM26, corresponding to GAM26-TARGET GENE of FIG. 26A. SHARP BINDING SITE is a binding site found in an untranslated region of SHARP, corresponding to BINDING SITE of FIG. 26A. FIG. 26D illustrates the complementarity of the nucleotide sequence of SHARP BINDING SITE, designated SEQ ID:966487, to the nucleotide sequence of GAM26 RNA of FIG. 26A, designated SEQ ID:20604. An additional function of GAM26 is therefore inhibition of (SHARP). Accordingly, utilities of GAM26 include diagnosis and treatment of diseases and clinical conditions with which SHARP is associated.

Reference is now made to SIAT8A BINDING SITE. SIAT8A is a target gene of GAM26, corresponding to GAM26-TARGET GENE of FIG. 26A. SIAT8A BINDING SITE is a binding site found in an untranslated region of SIAT8A, corresponding to BINDING SITE of FIG. 26A. FIG. 26D illustrates the complementarity of the nucleotide sequence of SIAT8A BINDING SITE, designated SEQ ID:966899, to the nucleotide sequence of GAM26 RNA of FIG. 26A, designated SEQ ID:20604. A further function of GAM26 is therefore inhibition of (SIAT8A). Accordingly, utilities of GAM26 include diagnosis and treatment of diseases and clinical conditions with which SIAT8A is associated.

Reference is now made to SLC16A3 BINDING SITE. SLC16A3 is a target gene of GAM26, corresponding to GAM26-TARGET GENE of FIG. 26A. SLC16A3 BINDING SITE is a binding site found in an untranslated region of SLC16A3, corresponding to BINDING SITE of FIG. 26A. FIG. 26D illustrates the complementarity of the nucleotide sequence of SLC16A3 BINDING SITE, designated SEQ ID:968639, to the nucleotide sequence of GAM26 RNA of FIG. 26A, designated SEQ ID:20604. Yet a further function of GAM26 is therefore inhibition of (SLC16A3). Accordingly, utilities of GAM26 include diagnosis and treatment of diseases and clinical conditions with which SLC16A3 is associated.

Reference is now made to SLC21A11 BINDING SITE. SLC21A11 is a target gene of GAM26, corresponding to GAM26-TARGET GENE of FIG. 26A. SLC21A11 BINDING SITE is a binding site found in an untranslated region of SLC21A11, corresponding to BINDING SITE of FIG. 26A. FIG. 26D illustrates the complementarity of the nucleotide sequence of SLC21A11 BINDING SITE, designated SEQ ID:969275, to the nucleotide sequence of GAM26 RNA of FIG. 26A, designated SEQ ID:20604. Another function of GAM26 is therefore inhibition of (SLC21A11). Accordingly, utilities of GAM26 include diagnosis and treatment of diseases and clinical conditions with which SLC21A11 is associated.

Reference is now made to OATPRP4 BINDING SITE. OATPRP4 is a target gene of GAM26, corresponding to GAM26-TARGET GENE of FIG. 26A. OATPRP4 BINDING SITE is a binding site found in an untranslated region of OATPRP4, corresponding to BINDING SITE of FIG. 26A. FIG. 26D illustrates the complementarity of the nucleotide sequence of OATPRP4 BINDING SITE, designated SEQ ID:969284, to the nucleotide sequence of GAM26 RNA of FIG. 26A, designated SEQ ID:20604. Yet another function of GAM26 is therefore inhibition of (OATPRP4). Accordingly, utilities of GAM26 include diagnosis and treatment of diseases and clinical conditions with which OATPRP4 is associated.

Reference is now made to SLC21A11 BINDING SITE. SLC21A11 is a target gene of GAM26, corresponding to GAM26-TARGET GENE of FIG. 26A. SLC21A11 BINDING SITE is a binding site found in an untranslated region of SLC21A11, corresponding to BINDING SITE of FIG. 26A. FIG. 26D illustrates the complementarity of the nucleotide sequence of SLC21A11 BINDING SITE, designated SEQ ID:969284, to the nucleotide sequence of GAM26 RNA of FIG. 26A, designated SEQ ID:20604. An additional function of GAM26 is therefore inhibition of (SLC21A11). Accordingly, utilities of GAM26 include diagnosis and treatment of diseases and clinical conditions with which SLC21A11 is associated.

Reference is now made to SLC21A11 BINDING SITE. SLC21A11 is a target gene of GAM26, corresponding to GAM26-TARGET GENE of FIG. 26A. SLC21A11 BINDING SITE is a binding site found in an untranslated region of SLC21A11, corresponding to BINDING SITE of FIG. 26A. FIG. 26D illustrates the complementarity of the nucleotide sequence of SLC21A11 BINDING SITE, designated SEQ ID:969288, to the nucleotide sequence of GAM26 RNA of FIG. 26A, designated SEQ ID:20604. A further function of GAM26 is therefore inhibition of (SLC21A11).

Accordingly, utilities of GAM26 include diagnosis and treatment of diseases and clinical conditions with which SLC21A11 is associated.

Reference is now made to SLC21A11 BINDING SITE. SLC21A11 is a target gene of GAM26, corresponding to GAM26-TARGET GENE of FIG. 26A. SLC21A11 BINDING SITE is a binding site found in an untranslated region of SLC21A11, corresponding to BINDING SITE of FIG. 26A. FIG. 26D illustrates the complementarity of the nucleotide sequence of SLC21A11 BINDING SITE, designated SEQ ID:969292, to the nucleotide sequence of GAM26 RNA of FIG. 26A, designated SEQ ID:20604. Yet a further function of GAM26 is therefore inhibition of (SLC21A11). Accordingly, utilities of GAM26 include diagnosis and treatment of diseases and clinical conditions with which SLC21A11 is associated.

Reference is now made to SLC21A11 BINDING SITE. SLC21A11 is a target gene of GAM26, corresponding to GAM26-TARGET GENE of FIG. 26A. SLC21A11 BINDING SITE is a binding site found in an untranslated region of SLC21A11, corresponding to BINDING SITE of FIG. 26A. FIG. 26D illustrates the complementarity of the nucleotide sequence of SLC21A11 BINDING SITE, designated SEQ ID:969328, to the nucleotide sequence of GAM26 RNA of FIG. 26A, designated SEQ ID:20604. Another function of GAM26 is therefore inhibition of (SLC21A11). Accordingly, utilities of GAM26 include diagnosis and treatment of diseases and clinical conditions with which SLC21A11 is associated.

Reference is now made to SLC21A11 BINDING SITE. SLC21A11 is a target gene of GAM26, corresponding to GAM26-TARGET GENE of FIG. 26A. SLC21A11 BINDING SITE is a binding site found in an untranslated region of SLC21A11, corresponding to BINDING SITE of FIG. 26A. FIG. 26D illustrates the complementarity of the nucleotide sequence of SLC21A11 BINDING SITE, designated SEQ ID:969329, to the nucleotide sequence of GAM26 RNA of FIG. 26A, designated SEQ ID:20604. Yet another function of GAM26 is therefore inhibition of (SLC21A11). Accordingly, utilities of GAM26 include diagnosis and treatment of diseases and clinical conditions with which SLC2A11 is associated.

Reference is now made to SRF BINDING SITE. SRF is a target gene of GAM26, corresponding to GAM26-TARGET GENE of FIG. 26A. SRF BINDING SITE is a binding site found in an untranslated region of SRF, corresponding to BINDING SITE of FIG. 26A. FIG. 26D illustrates the complementarity of the nucleotide sequence of SRF BINDING SITE designated SEQ ID:979150, to the nucleotide sequence of GAM26 RNA of FIG. 26A, designated SEQ ID:20604. An additional function of GAM26 is therefore inhibition of (SRF). Accordingly, utilities of GAM26 include diagnosis and treatment of diseases and clinical conditions with which SRF is associated.

Reference is now made to SSBP3 BINDING SITE. SSBP3 is a target gene of GAM26, corresponding to GAM26-TARGET GENE of FIG. 26A. SSBP3 BINDING SITE is a binding site found in an untranslated region of SSBP3, corresponding to BINDING SITE of FIG. 26A. FIG. 26D illustrates the complementarity of the nucleotide sequence of SSBP3 BINDING SITE, designated SEQ ID:980403, to the nucleotide sequence of GAM26 RNA of FIG. 26A, designated SEQ ID:20604. A further function of GAM26 is therefore inhibition of (SSBP3). Accordingly, utilities of GAM26 include diagnosis and treatment of diseases and clinical conditions with which SSBP3 is associated.

Reference is now made to SSBP3 BINDING SITE. SSBP3 is a target gene of GAM26, corresponding to GAM26-TARGET GENE of FIG. 26A. SSBP3 BINDING SITE is a binding site found in an untranslated region of SSBP3, corresponding to BINDING SITE of FIG. 26A. FIG. 26D illustrates the complementarity of the nucleotide sequence of SSBP3 BINDING SITE, designated SEQ ID:980404, to the nucleotide sequence of GAM26 RNA of FIG. 26A, designated SEQ ID:20604. Yet a further function of GAM26 is therefore inhibition of (SSBP3). Accordingly, utilities of GAM26 include diagnosis and treatment of diseases and clinical conditions with which SSBP3 is associated.

Reference is now made to SSBP3 BINDING SITE. SSBP3 is a target gene of GAM26, corresponding to GAM26-TARGET GENE of FIG. 26A. SSBP3 BINDING SITE is a binding site found in an untranslated region of SSBP3, corresponding to BINDING SITE of FIG. 26A. FIG. 26D illustrates the complementarity of the nucleotide sequence of SSBP3 BINDING SITE, designated SEQ ID:980415, to the nucleotide sequence of GAM26 RNA of FIG. 26A, designated SEQ ID:20604. Another function of GAM26 is therefore inhibition of (SSBP3). Accordingly, utilities of GAM26 include diagnosis and treatment of diseases and clinical conditions with which SSBP3 is associated.

Reference is now made to SSBP4 BINDING SITE. SSBP4 is a target gene of GAM26, corresponding to GAM26-TARGET GENE of FIG. 26A. SSBP4 BINDING SITE is a binding site found in an untranslated region of SSBP4, corresponding to BINDING SITE of FIG. 26A. FIG. 26D illustrates the complementarity of the nucleotide sequence of SSBP4 BINDING SITE, designated SEQ ID:980450, to the nucleotide sequence of GAM26 RNA of FIG. 26A, designated SEQ ID:20604. Yet another function of GAM26 is therefore inhibition of (SSBP4). Accordingly, utilities of GAM26 include diagnosis and treatment of diseases and clinical conditions with which SSBP4 is associated.

Reference is now made to STIM2 BINDING SITE. STIM2 is a target gene of GAM26, corresponding to GAM26-TARGET GENE of FIG. 26A. STIM2 BINDING SITE is a binding site found in an untranslated region of STIM2, corresponding to BINDING SITE of FIG. 26A. FIG. 26D illustrates the complementarity of the nucleotide sequence of STIM2 BINDING SITE, designated SEQ ID:982983, to the nucleotide sequence of GAM26 RNA of FIG. 26A, designated SEQ ID:20604. An additional function of GAM26 is therefore inhibition of (STIM2). Accordingly, utilities of GAM26 include diagnosis and treatment of diseases and clinical conditions with which STIM2 is associated.

Reference is now made to STK39 BINDING SITE. STK39 is a target gene of GAM26, corresponding to GAM26-TARGET GENE of FIG. 26A. STK39 BINDING SITE is a binding site found in an untranslated region of STK39, corresponding to BINDING SITE of FIG. 26A. FIG. 26D illustrates the complementarity of the nucleotide sequence of STK39 BINDING SITE, designated SEQ ID:983798, to the nucleotide sequence of GAM26 RNA of FIG. 26A, designated SEQ ID:20604. A further function of GAM26 is therefore inhibition of (STK39). Accordingly, utilities of GAM26 include diagnosis and treatment of diseases and clinical conditions with which STK39 is associated.

Reference is now made to STK39 BINDING SITE. STK39 is a target gene of GAM26, corresponding to GAM26-TARGET GENE of FIG. 26A. STK39 BINDING SITE is a binding site found in an untranslated region of STK39, corresponding to BINDING SITE of FIG. 26A. FIG. 26D illustrates the complementarity of the nucleotide sequence of STK39 BINDING SITE, designated SEQ ID:983808, to the nucleotide sequence of GAM26 RNA of FIG. 26A, designated SEQ ID:20604. Yet a further function of GAM26 is therefore inhibition of (STK39). Accordingly, utilities of GAM26 include diagnosis and treatment of diseases and clinical conditions with which STK39 is associated.

Reference is now made to KIAA0995 BINDING SITE. KIAA0995 is a target gene of GAM26, corresponding to GAM26-TARGET GENE of FIG. 26A. KIAA0995 BINDING SITE is a binding site found in an untranslated region of KIAA0995, corresponding to BINDING SITE of FIG. 26A. FIG. 26D illustrates the complementarity of the nucleotide sequence of KIAA0995 BINDING SITE, designated SEQ ID:983814, to the nucleotide sequence of GAM26 RNA of FIG. 26A, designated SEQ ID:20604. Another function of GAM26 is therefore inhibition of (KIAA0995). Accordingly, utilities of GAM26 include diagnosis and treatment of diseases and clinical conditions with which KIAA0995 is associated.

Reference is now made to STK39 BINDING SITE. STK39 is a target gene of GAM26, corresponding to GAM26-TARGET GENE of FIG. 26A. STK39 BINDING SITE is a binding site found in an untranslated region of STK139, corresponding to BINDING SITE of FIG. 26A. FIG. 26D illustrates the complementarity of the nucleotide sequence of STK39 BINDING SITE, designated SEQ ID:983814, to the nucleotide sequence of GAM26 RNA of FIG. 26A, designated SEQ ID:20604. Yet another function of GAM26 is therefore inhibition of (STK39). Accordingly, utilities of GAM26 include diagnosis and treatment of diseases and clinical conditions with which STK39 is associated.

Reference is now made to STRBP BINDING SITE. STRBP is a target gene of GAM26, corresponding to GAM26-TARGET GENE of FIG. 26A. STRBP BINDING SITE is a binding site found in an untranslated region of STRBP, corresponding to BINDING SITE of FIG. 26A. FIG. 26D illustrates the complementarity of the nucleotide sequence of STRBP BINDING SITE, designated SEQ ID:984349, to the nucleotide sequence of GAM26 RNA of FIG. 26A, designated SEQ ID:20604. An additional function of GAM26 is therefore inhibition of (STRBP). Accordingly, utilities of GAM26 include diagnosis and treatment of diseases and clinical conditions with which STRBP is associated.

Reference is now made to SULT4A1 BINDING SITE. SULT4A1 is a target gene of GAM26, corresponding to GAM26-TARGET GENE of FIG. 26A. SULT4A1 BINDING SITE is a binding site found in an untranslated region of SULT4A1, corresponding to BINDING SITE of FIG. 26A. FIG. 26D illustrates the complementarity of the nucleotide sequence of SULT4A1 BINDING SITE, designated SEQ ID:985480, to the nucleotide sequence of GAM26 RNA of FIG. 26A, designated SEQ ID:20604. A further function of GAM26 is therefore inhibition of (SULT4A1). Accordingly, utilities of GAM26 include diagnosis and treatment of diseases and clinical conditions with which SULT4A1 is associated.

Reference is now made to SULT4A1 BINDING SITE. SULT4A1 is a target gene of GAM26, corresponding to GAM26-TARGET GENE of FIG. 26A. SULT4A1 BINDING SITE is a binding site found in an untranslated region of SULT4A1, corresponding to BINDING SITE of FIG. 26A. FIG. 26D illustrates the complementarity of the nucleotide sequence of SULT4A1 BINDING SITE, designated SEQ ID:985482, to the nucleotide sequence of GAM26 RNA of FIG. 26A, designated SEQ ID:20604. Yet a further function of GAM26 is therefore inhibition of (SULT4A1). Accordingly, utilities of GAM26 include diagnosis and treatment of diseases and clinical conditions with which SULT4A1 is associated.

Reference is now made to SULT4A1 BINDING SITE. SULT4A1 is a target gene of GAM26, corresponding to GAM26-TARGET GENE of FIG. 26A. SULT4A1 BINDING SITE is a binding site found in an untranslated region of SULT4A1, corresponding to BINDING SITE of FIG. 26A. FIG. 26D illustrates the complementarity of the nucleotide sequence of SULT4A1 BINDING SITE, designated SEQ ID:985499, to the nucleotide sequence of GAM26 RNA of FIG. 26A, designated SEQ ID:20604. Another function of GAM26 is therefore inhibition of (SULT4A1). Accordingly, utilities of GAM26 include diagnosis and treatment of diseases and clinical conditions with which SULT4A1 is associated.

Reference is now made to SULT4A1 BINDING SITE. SULT4A1 is a target gene of GAM26, corresponding to GAM26-TARGET GENE of FIG. 26A. SULT4A1 BINDING SITE is a binding site found in an untranslated region of SULT4A1, corresponding to BINDING SITE of FIG. 26A. FIG. 26D illustrates the complementarity of the nucleotide sequence of SULT4A1 BINDING SITE, designated SEQ ID:985516, to the nucleotide sequence of GAM26 RNA of FIG. 26A, designated SEQ ID:20604. Yet another function of GAM26 is therefore inhibition of (SULT4A1). Accordingly, utilities of GAM26 include diagnosis and treatment of diseases and clinical conditions with which SULT4A1 is associated.

Reference is now made to TBLR1 BINDING SITE. TBLR1 is a target gene of GAM26, corresponding to GAM26-TARGET GENE of FIG. 26A. TBLR1 BINDING SITE is a binding site found in an untranslated region of TBLR1, corresponding to BINDING SITE of FIG. 26A. FIG. 26D illustrates the complementarity of the nucleotide sequence of TBLR1 BINDING SITE, designated SEQ ID:989703, to the nucleotide sequence of GAM26 RNA of FIG. 26A, designated SEQ ID:20604. An additional function of GAM26 is therefore inhibition of (TBLR1). Accordingly, utilities of GAM26 include diagnosis and treatment of diseases and clinical conditions with which TBLR1 is associated.

Reference is now made to TIEG BINDING SITE. TIEG is a target gene of GAM26, corresponding to GAM26-TARGET GENE of FIG. 26A. TIEG BINDING SITE is a binding site found in an untranslated region of TIEG, corresponding to BINDING SITE of FIG. 26A. FIG. 26D illustrates the complementarity of the nucleotide sequence of TIEG BINDING SITE, designated SEQ ID:993412, to the nucleotide sequence of GAM26 RNA of FIG. 26A, designated SEQ ID:20604. A further function of GAM26 is therefore inhibition of (TIEG). Accordingly, utilities of GAM26 include diagnosis and treatment of diseases and clinical conditions with which TIEG is associated.

Reference is now made to TIEG BINDING SITE. TIEG is a target gene of GAM26, corresponding to GAM26-TARGET GENE of FIG. 26A. TIEG BINDING SITE is a binding site found in an untranslated region of TIEG, corresponding to BINDING SITE of FIG. 26A. FIG. 26D illustrates the complementarity of the nucleotide sequence of TIEG BINDING SITE, designated SEQ ID:993414, to the nucleotide sequence of GAM26 RNA of FIG. 26A, designated SEQ ID:20604. Yet a further function of GAM26 is therefore inhibition of (TIEG). Accordingly, utilities of GAM26 include diagnosis and treatment of diseases and clinical conditions with which TIEG is associated.

Reference is now made to FLJ20288 BINDING SITE. FLJ20288 is a target gene of GAM26, corresponding to GAM26-TARGET GENE of FIG. 26A. FLJ20288 BINDING SITE is a binding site found in an untranslated region of FLJ20288, corresponding to BINDING SITE of FIG. 26A. FIG. 26D illustrates the complementarity of the nucleotide sequence of FLJ20288 BINDING SITE, designated SEQ ID:993970, to the nucleotide sequence of GAM26 RNA of FIG. 26A, designated SEQ ID:20604. Another function of GAM26 is therefore inhibition of (FLJ20288). Accordingly, utilities of GAM26 include diagnosis and treatment of diseases and clinical conditions with which FLJ20288 is associated.

Reference is now made to TIP120A BINDING SITE. TIP120A is a target gene of GAM26, corresponding to GAM26-TARGET GENE of FIG. 26A. IP120A BINDING SITE is a binding site found in an untranslated region of TIP120A, corresponding to BINDING SITE of FIG. 26A. FIG. 26D illustrates the complementarity of the nucleotide sequence of TIP120A BINDING SITE, designated SEQ ID:993970, to the nucleotide sequence of GAM26 RNA of FIG. 26A, designated SEQ ID:20604. Yet another function of GAM26 is therefore inhibition of (TIP120A). Accordingly, utilities of GAM26 include diagnosis and treatment of diseases and clinical conditions with which TIP120A is associated.

Reference is now made to TIP120A BINDING SITE. TIP120A is a target gene of GAM26, corresponding to GAM26-TARGET GENE of FIG. 26A. TIP120A BINDING SITE is a binding site found in an untranslated region of TIP120A, corresponding to BINDING SITE of FIG. 26A. FIG. 26D illustrates the complementarity of the nucleotide sequence of TIP120A BINDING SITE, designated SEQ ID:993979, to the nucleotide sequence of GAM26 RNA of FIG. 26A, designated SEQ ID:20604. An additional function of GAM26 is therefore inhibition of (TIP120A). Accordingly, utilities of GAM26 include diagnosis and treatment of diseases and clinical conditions with which TIP120A is associated.

Reference is now made to TIP120A BINDING SITE. TIP120A is a target gene of GAM26, corresponding to GAM26-TARGET GENE of FIG. 26A. TIP120A BINDING SITE is a binding site found in an untranslated region of TIP120A, corresponding to BINDING SITE of FIG. 26A. FIG. 26D illustrates the complementarity of the nucleotide sequence of TIP120A BINDING SITE, designated SEQ ID:993980, to the nucleotide sequence of GAM26 RNA of FIG. 26A, designated SEQ ID:20604. A further function of GAM26 is therefore inhibition of (TIP120A). Accordingly, utilities of GAM26 include diagnosis and treatment of diseases and clinical conditions with which TIP120A is associated.

Reference is now made to TLK2 BINDING SITE. TLK2 is a target gene of GAM26, corresponding to GAM26-TARGET GENE of FIG. 26A. TLK2 BINDING SITE is a binding site found in an untranslated region of TLK2, corresponding to BINDING SITE of FIG. 26A. FIG. 26D illustrates the complementarity of the nucleotide sequence of TLK2 BINDING SITE, designated SEQ ID:994634, to the nucleotide sequence of GAM26 RNA of FIG. 26A, designated SEQ ID:20604. Yet a further function of GAM26 is therefore inhibition of (TLK2). Accordingly, utilities of GAM26 include diagnosis and treatment of diseases and clinical conditions with which TLK2 is associated.

Reference is now made to TPARL BINDING SITE. TPARL is a target gene of GAM26, corresponding to GAM26-TARGET GENE of FIG. 26A. TPARL BINDING SITE is a binding site found in an untranslated region of TPARL, corresponding to BINDING SITE of FIG. 26A. FIG. 26D illustrates the complementarity of the nucleotide sequence of TPARL BINDING SITE, designated SEQ ID:997782, to the nucleotide sequence of GAM26 RNA of FIG. 26A, designated SEQ ID:20604. Another function of GAM26 is therefore inhibition of (TPARL). Accordingly, utilities of GAM26 include diagnosis and treatment of diseases and clinical conditions with which TPARL is associated.

Reference is now made to TRIM28 BINDING SITE. TRIM28 is a target gene of GAM26, corresponding to GAM26-TARGET GENE of FIG. 26A. TRIM28 BINDING SITE is a binding site found in an untranslated region of TRIM28, corresponding to BINDING SITE of FIG. 26A. FIG. 26D illustrates the complementarity of the nucleotide sequence of TRIM28 BINDING SITE, designated SEQ ID:1000325, to the nucleotide sequence of GAM26 RNA of FIG. 26A, designated SEQ ID:20604. Yet another function of GAM26 is therefore inhibition of (TRIM28). Accordingly, utilities of GAM26 include diagnosis and treatment of diseases and clinical conditions with which TRIM28 is associated.

Reference is now made to TRIM28 BINDING SITE. TRIM28 is a target gene of GAM26, corresponding to GAM26-TARGET GENE of FIG. 26A. TRIM28 BINDING SITE is a binding site found in an untranslated region of TRIM28, corresponding to BINDING SITE of FIG. 26A. FIG. 26D illustrates the complementarity of the nucleotide sequence of TRIM28 BINDING SITE, designated SEQ ID:1000339, to the nucleotide sequence of GAM26 RNA of FIG. 26A, designated SEQ ID:20604. An additional function of GAM26 is therefore inhibition of (TRIM28). Accordingly, utilities of GAM26 include diagnosis and treatment of diseases and clinical conditions with which TRIM28 is associated.

Reference is now made to TRIM28 BINDING SITE. TRIM28 is a target gene of GAM26, corresponding to GAM26-TARGET GENE of FIG. 26A. TRIM28 BINDING SITE is a binding site found in an untranslated region of TRIM28, corresponding to BINDING SITE of FIG. 26A. FIG. 26D illustrates the complementarity of the nucleotide sequence of TRIM28 BINDING SITE, designated SEQ ID:1000350, to the nucleotide sequence of GAM26 RNA of FIG. 26A, designated SEQ ID:20604. A further function of GAM26 is therefore inhibition of (TRIM28). Accordingly, utilities of GAM26 include diagnosis and treatment of diseases and clinical conditions with which TRIM28 is associated.

Reference is now made to TRIM33 BINDING SITE. TRIM33 is a target gene of GAM26, corresponding to GAM26-TARGET GENE of FIG. 26A. TRIM33 BINDING SITE is a binding site found in an untranslated region of TRIM33, corresponding to BINDING SITE of FIG. 26A. FIG. 26D illustrates the complementarity of the nucleotide sequence of TRIM33 BINDING SITE, designated SEQ ID:1000528, to the nucleotide sequence of GAM26 RNA of FIG. 26A, designated SEQ ID:20604. Yet a further function of GAM26 is therefore inhibition of (TRIM33). Accordingly, utilities of GAM26 include diagnosis and treatment of diseases and clinical conditions with which TRIM33 is associated.

Reference is now made to TRIM33 BINDING SITE. TRIM33 is a target gene of GAM26, corresponding to GAM26-TARGET GENE of FIG. 26A. TRIM33 BINDING SITE is a binding site found in an untranslated region of TRIM33, corresponding to BINDING SITE of FIG. 26A. FIG. 26D illustrates the complementarity of the nucleotide sequence of TRIM33 BINDING SITE, designated SEQ ID:1000533, to the nucleotide sequence of GAM26 RNA of FIG. 26A, designated SEQ ID:20604. Another function of GAM26 is therefore inhibition of (TRIM33). Accordingly, utilities of GAM26 include diagnosis and treatment of diseases and clinical conditions with which TRIM33 is associated.

Reference is now made to TRIP10 BINDING SITE. TRIP10 is a target gene of GAM26, corresponding to GAM26-TARGET GENE of FIG. 26A. TRIP10 BINDING SITE is a binding site found in an untranslated region of TRIP10, corresponding to BINDING SITE of FIG. 26A. FIG. 26D illustrates the complementarity of the nucleotide sequence of TRIP10 BINDING SITE, designated SEQ ID:1001537, to the nucleotide sequence of GAM26 RNA of FIG. 26A, designated SEQ ID:20604. Yet another function of GAM26 is therefore inhibition of (TRIP10). Accordingly, utilities of GAM26 include diagnosis and treatment of diseases and clinical conditions with which TRIP10 is associated.

Reference is now made to ZDHHC3 BINDING SITE. ZDHHC3 is a target gene of GAM26, corresponding to GAM26-TARGET GENE of FIG. 26A. ZDHHC3 BINDING SITE is a binding site found in an untranslated region of ZDHHC3, corresponding to BINDING SITE of FIG. 26A. FIG. 26D illustrates the complementarity of the nucleotide sequence of ZDHHC3 BINDING SITE, designated SEQ ID:1001537, to the nucleotide sequence of GAM26 RNA of FIG. 26A, designated SEQ ID:20604. An additional function of GAM26 is therefore inhibition of (ZDHHC3). Accordingly, utilities of GAM26 include diagnosis and treatment of diseases and clinical conditions with which ZDHHC3 is associated.

Reference is now made to WBSCR21 BINDING SITE. WBSCR21 is a target gene of GAM26, corresponding to GAM26-TARGET GENE of FIG. 26A. WBSCR21 BINDING SITE is a binding site found in an untranslated region of WBSCR21, corresponding to BINDING SITE of FIG. 26A. FIG. 26D illustrates the complementarity of the nucleotide sequence of WBSCR21 BINDING SITE, designated SEQ ID:1012104, to the nucleotide sequence of GAM26 RNA of FIG. 26A, designated SEQ ID:20604. A further function of GAM26 is therefore inhibition of (WBSCR21). Accordingly, utilities of GAM26 include diagnosis and treatment of diseases and clinical conditions with which WBSCR21 is associated.

Reference is now made to WBSCR21 BINDING SITE. WBSCR21 is a target gene of GAM26, corresponding to GAM26-TARGET GENE of FIG. 26A. WBSCR21 BINDING SITE is a binding site found in an untranslated region of WBSCR21, corresponding to BINDING SITE of FIG. 26A. FIG. 26D illustrates the complementarity of the nucleotide sequence of WBSCR21 BINDING SITE, designated SEQ ID:1012156, to the nucleotide sequence of GAM26 RNA of FIG. 26A, designated SEQ ID:20604. Yet a further function of GAM26 is therefore inhibition of (WBSCR21). Accordingly, utilities of GAM26 include diagnosis and treatment of diseases and clinical conditions with which WBSCR21 is associated.

Reference is now made to ZDHHC5 BINDING SITE. ZDHHC5 is a target gene of GAM26, corresponding to GAM26-TARGET GENE of FIG. 26A. ZDHHC5 BINDING SITE is a biding site found in an untranslated region of ZDHHC5, corresponding to BINDING SITE of FIG. 26A. FIG. 26D illustrates the complementarity of the nucleotide sequence of ZDHHC5 BINDING SITE, designated SEQ ID:1016404, to the nucleotide sequence of GAM26 RNA of FIG. 26A, designated SEQ ID:20604. Another function of GAM26 is therefore inhibition of (ZDHHC5). Accordingly, utilities of GAM26 include diagnosis and treatment of diseases and clinical conditions with which ZDHHC5 is associated.

Reference is now made to ZDHHC5 BINDING SITE. ZDHHC5 is a target gene of GAM26, corresponding to GAM26-TARGET GENE of FIG. 26A. ZDHHC5 BINDING SITE is a binding site found in an untranslated region of ZDHHC5, corresponding to BINDING SITE of FIG. 26A. FIG. 26D illustrates the complementarity of the nucleotide sequence of ZDHHC5 BINDING SITE, designated SEQ ID:1016478, to the nucleotide sequence of GAM26 RNA of FIG. 26A, designated SEQ ID:20604. Yet another function of GAM26 is therefore inhibition of (ZDHHC5). Accordingly, utilities of GAM26 include diagnosis and treatment of diseases and clinical conditions with which ZDHHC5 is associated.

Reference is now made to ZER6 BINDING SITE. ZER6 is a target gene of GAM26, corresponding to GAM26-TARGET GENE of FIG. 26A. ZER6 BINDING SITE is a binding site found in an untranslated region of ZER6, corresponding to BINDING SITE of FIG. 26A. FIG. 26D illustrates the complementarity of the nucleotide sequence of ZER6 BINDING SITE, designated SEQ ID:1016788, to the nucleotide sequence of GAM26 RNA of FIG. 26A, designated SEQ ID:20604. An additional function of GAM26 is therefore inhibition of (ZER6). Accordingly, utilities of GAM26 include diagnosis and treatment of diseases and clinical conditions with which ZER6 is associated.

Reference is now made to ZER6 BINDING SITE. ZER6 is a target gene of GAM26, corresponding to GAM26-TARGET GENE of FIG. 26A. ZER6 BINDING SITE is a binding site found in an untranslated region of ZER6, corresponding to BINDING SITE of FIG. 26A. FIG. 26D illustrates the complementarity of the nucleotide sequence of ZER6 BINDING SITE, designated SEQ ID:1016846, to the nucleotide sequence of GAM26 RNA of FIG. 26A, designated SEQ ID:20604. A further function of GAM26 is therefore inhibition of (ZER6). Accordingly, utilities of GAM26 include diagnosis and treatment of diseases and clinical conditions with which ZER6 is associated.

Reference is now made to ZF BINDING SITE. ZF is a target gene of GAM26, corresponding to GAM26-TARGET GENE of FIG. 26A. ZF BINDING SITE is a binding site found in an untranslated region of ZF, corresponding to BINDING SITE of FIG. 26A. FIG. 26D illustrates the complementarity of the nucleotide sequence of ZF BINDING SITE, designated SEQ ID:1016945, to the nucleotide sequence of GAM26 RNA of FIG. 26A, designated SEQ ID:20604. Yet a further function of GAM26 is therefore inhibition of (ZF). Accordingly, utilities of GAM26 include diagnosis and treatment of diseases and clinical conditions with which ZF is associated.

Reference is now made to ZNF364 BINDING SITE. ZNF364 is a target gene of GAM26, corresponding to GAM26-TARGET GENE of FIG. 26A. ZNF364 BINDING SITE is a binding site found in an untranslated region of ZNF364, corresponding to BINDING SITE of FIG. 26A. FIG. 26D illustrates the complementarity of the nucleotide sequence of ZNF364 BINDING SITE, designated SEQ ID:1023294, to the nucleotide sequence of GAM26 RNA of FIG. 26A, designated SEQ ID:20604. Another function of GAM26 is therefore inhibition of (ZNF364). Accordingly, utilities of GAM26 include diagnosis and treatment of diseases and clinical conditions with which ZNF364 is associated.

Reference is now made to ZNF364 BINDING SITE. ZNF364 is a target gene of GAM26, corresponding to GAM26-TARGET GENE of FIG. 26A. ZNF364 BINDING SITE is a binding site found in an untranslated region of ZNF364, corresponding to BINDING SITE of FIG. 26A. FIG. 26D illustrates the complementarity of the nucleotide sequence of ZNF364 BINDING SITE, designated SEQ ID:1023303, to the nucleotide sequence of GAM26 RNA of FIG. 26A, designated SEQ ID:20604. Yet another function of GAM26 is therefore inhibition of (ZNF364). Accordingly, utilities of GAM26 include diagnosis and treatment of diseases and clinical conditions with which ZNF364 is associated.

Reference is now made to ZTL1 BINDING SITE. ZTL1 is a target gene of GAM26, corresponding to GAM26-TARGET GENE of FIG. 26A. ZTL1 BINDING SITE is a binding site found in an untranslated region of ZTL1, corresponding to BINDING SITE of FIG. 26A. FIG. 26D illustrates the complementarity of the nucleotide sequence of ZTL1 BINDING SITE, designated SEQ ID:1023979, to the nucleotide sequence of GAM26 RNA of FIG. 26A, designated SEQ ID:20604. An additional function of GAM26 is therefore inhibition of (ZTL1). Accordingly, utilities of GAM26 include diagnosis and treatment of diseases and clinical conditions with which ZTL1 is associated.

Reference is now made to ZTL1 BINDING SITE. ZTL1 is a target gene of GAM26, corresponding to GAM26-TARGET GENE of FIG. 26A. ZTL1 BINDING SITE is a binding site found in an untranslated region of ZTL1, corresponding to BINDING SITE of FIG. 26A. FIG. 26D illustrates the complementarity of the nucleotide sequence of ZTL1 BINDING SITE, designated SEQ ID:1023979, to the nucleotide sequence of GAM26 RNA of FIG. 26A, designated SEQ ID:20604. A further function of GAM26 is therefore inhibition of (ZTL1). Accordingly, utilities of GAM26 include diagnosis and treatment of diseases and clinical conditions with which ZTL1 is associated.

Reference is now made to CTCF BINDING SITE. CTCF is a target gene of GAM26, corresponding to GAM26-TARGET GENE of FIG. 26A. CTCF BINDING SITE is a binding site found in an untranslated region of CTCF, corresponding to BINDING SITE of FIG. 26A. FIG. 26D illustrates the complementarity of the nucleotide sequence of CTCF BINDING SITE, designated SEQ ID:1037665, to the nucleotide sequence of GAM26 RNA of FIG. 26A, designated SEQ ID:20604. Yet a further function of GAM26 is therefore inhibition of (CTCF). Accordingly, utilities of GAM26 include diagnosis and treatment of diseases and clinical conditions with which CTCF is associated.

Reference is now made to HRIHFB2122 BINDING SITE. HRIHFB2122 is a target gene of GAM26, corresponding to GAM26-TARGET GENE of FIG. 26A. HRIHFB2122 BINDING SITE is a binding site found in an untranslated region of HRIHFB2122, corresponding to BINDING SITE of FIG. 26A. FIG. 26D illustrates the complementarity of the nucleotide sequence of HRIHFB2122 BINDING SITE, designated SEQ ID:1065873, to the nucleotide sequence of GAM26 RNA of FIG. 26A, designated SEQ ID:20604. Another function of GAM26 is therefore inhibition of (HRIHFB2122). Accordingly, utilities of GAM26 include diagnosis and treatment of diseases and clinical conditions with which HRIHFB2122 is associated.

Reference is now made to KIAA0397 BINDING SITE. KIAA0397 is a target gene of GAM26, corresponding to GAM26-TARGET GENE of FIG. 26A. KIAA0397 BINDING SITE is a binding site found in an untranslated region of KIAA0397, corresponding to BINDING SITE of FIG. 26A. FIG. 26D illustrates the complementarity of the nucleotide sequence of KIAA0397 BINDING SITE, designated SEQ ID:1065873, to the nucleotide sequence of GAM26 RNA of FIG. 26A, designated SEQ ID:20604. Yet another function of GAM26 is therefore inhibition of (KIAA0397). Accordingly, utilities of GAM26 include diagnosis and treatment of diseases and clinical conditions with which KIAA0397 is associated.

Reference is now made to FUBP3 BINDING SITE. FUBP3 is a target gene of GAM26, corresponding to GAM26-TARGET GENE of FIG. 26A. FUBP3 BINDING SITE is a binding site found in an untranslated region of FUBP3, corresponding to BINDING SITE of FIG. 26A. FIG. 26D illustrates the complementarity of the nucleotide sequence of FUBP3 BINDING SITE, designated SEQ ID:1190283, to the nucleotide sequence of GAM26 RNA of FIG. 26A, designated SEQ ID:20604. An additional function of GAM26 is therefore inhibition of (FUBP3). Accordingly, utilities of GAM26 include diagnosis and treatment of diseases and clinical conditions with which FUBP3 is associated.

Reference is now made to H2AV BINDING SITE. H2AV is a target gene of GAM26, corresponding to GAM26-TARGET GENE of FIG. 26A. H2AV BINDING SITE is a binding site found in an untranslated region of H2AV, corresponding to BINDING SITE of FIG. 26A. FIG. 26D illustrates the complementarity of the nucleotide sequence of H2AV BINDING SITE, designated SEQ ID:1303366, to the nucleotide sequence of GAM26 RNA of FIG. 26A, designated SEQ ID:20604. A further function of GAM26 is therefore inhibition of (H2AV). Accordingly, utilities of GAM26 include diagnosis and treatment of diseases and clinical conditions with which H2AV is associated.

Reference is now made to FLJ20539 BINDING SITE. FLJ20539 is a target gene of GAM26, corresponding to GAM26-TARGET GENE of FIG. 26A. FLJ20539 BINDING SITE is a binding site found in an untranslated region of FLJ20539, corresponding to BINDING SITE of FIG. 26A. FIG. 26D illustrates the complementarity of the nucleotide sequence of FLJ20539 BINDING SITE, designated SEQ ID:1310953, to the nucleotide sequence of GAM26 RNA of FIG. 26A, designated SEQ ID:20604. Yet a further function of GAM26 is therefore inhibition of (FLJ20539). Accordingly, utilities of GAM26 include diagnosis and treatment of diseases and clinical conditions with which FLJ20539 is associated.

Reference is now made to KIAA1893 BINDING SITE. KIAA1893 is a target gene of GAM26, corresponding to GAM26-TARGET GENE of FIG. 26A. KIAA1893 BINDING SITE is a binding site found in an untranslated region of KIAA1893, corresponding to BINDING SITE of FIG. 26A. FIG. 26D illustrates the complementarity of the nucleotide sequence of KIAA1893 BINDING SITE, designated SEQ ID:1310953, to the nucleotide sequence of GAM26 RNA of FIG. 26A, designated SEQ ID:20604. Another function of GAM26 is therefore inhibition of (KIAA1893). Accordingly, utilities of GAM26 include diagnosis and treatment of diseases and clinical conditions with which KIAA1893 is associated.

Reference is now made to RINZF BINDING SITE. RINZF is a target gene of GAM26, corresponding to GAM26-TARGET GENE of FIG. 26A. RINZF BINDING SITE is a binding site found in an untranslated region of RINZF, corresponding to BINDING SITE of FIG. 26A. FIG. 26D illustrates the complementarity of the nucleotide sequence of RINZF BINDING SITE, designated SEQ ID:1310953, to the nucleotide sequence of GAM26 RNA of FIG. 26A, designated SEQ ID:20604. Yet another function of GAM26 is therefore inhibition of (RINZF). Accordingly, utilities of GAM26 include diagnosis and treatment of diseases and clinical conditions with which RINZF is associated.

Reference is now made to TIP120A BINDING SITE. TIP120A is a target gene of GAM26, corresponding to GAM26-TARGET GENE of FIG. 26A. TIP120A BINDING SITE is a binding site found in an untranslated region of TIP120A, corresponding to BINDING SITE of FIG. 26A. FIG. 26D illustrates the complementarity of the nucleotide sequence of TIP120A BINDING SITE, designated SEQ ID:1323750, to the nucleotide sequence of GAM26 RNA of FIG. 26A, designated SEQ ID:20604. An additional function of GAM26 is therefore inhibition of (TIP120A). Accordingly, utilities of GAM26 include diagnosis and treatment of diseases and clinical conditions with which TIP120A is associated.

Reference is now made to LOC146223 BINDING SITE. LOC146223 is a target gene of GAM26, corresponding to GAM26-TARGET GENE of FIG. 26A. LOC146223 BINDING SITE is a binding site found in an untranslated region of LOC146223, corresponding to BINDING SITE of FIG. 26A. FIG. 26D illustrates the complementarity of the nucleotide sequence of LOC146223 BINDING SITE, designated SEQ ID:94853, to the nucleotide sequence of GAM26 RNA of FIG. 26A, designated SEQ ID:20604. A further function of GAM26 is therefore inhibition of (LOC146223). Accordingly, utilities of GAM26 include diagnosis and treatment of diseases and clinical conditions with which LOC146223 is associated.

Reference is now made to LOC255426 BINDING SITE. LOC255426 is a target gene of GAM26, corresponding to GAM26-TARGET GENE of FIG. 26A. LOC255426 BINDING SITE is a binding site found in an untranslated region of LOC255426, corresponding to BINDING SITE of FIG. 26A. FIG. 26D illustrates the complementarity of the nucleotide sequence of LOC255426 BINDING SITE, designated SEQ ID:94853, to the nucleotide sequence of GAM26 RNA of FIG. 26A, designated SEQ ID:20604. Yet a further function of GAM26 is therefore inhibition of (LOC255426). Accordingly, utilities of GAM26 include diagnosis and treatment of diseases and clinical conditions with which LOC255426 is associated.

Reference is now made to LOC255426 BINDING SITE. LOC255426 is a target gene of GAM26, corresponding to GAM26-TARGET GENE of FIG. 26A. LOC255426 BINDING SITE is a binding site found in an untranslated region of LOC255426, corresponding to BINDING SITE of FIG. 26A. FIG. 26D illustrates the complementarity of the nucleotide sequence of LOC255426 BINDING SITE, designated SEQ ID:94853, to the nucleotide sequence of GAM26 RNA of FIG. 26A, designated SEQ ID:20604. Another function of GAM26 is therefore inhibition of (LOC255426). Accordingly, utilities of GAM26 include diagnosis and treatment of diseases and clinical conditions with which LOC255426 is associated.

Reference is now made to LOC255426 BINDING SITE. LOC255426 is a target gene of GAM26, corresponding to GAM26-TARGET GENE of FIG. 26A. LOC255426 BINDING SITE is a binding site found in an untranslated region of LOC255426, corresponding to BINDING SITE of FIG. 26A. FIG. 26D illustrates the complementarity of the nucleotide sequence of LOC255426 BINDING SITE, designated SEQ ID:94853, to the nucleotide sequence of GAM26 RNA of FIG. 26A, designated SEQ ID:20604. Yet another function of GAM26 is therefore inhibition of (LOC255426). Accordingly, utilities of GAM26 include diagnosis and treatment of diseases and clinical conditions with which LOC255426 is associated.

Reference is now made to LOC255426 BINDING SITE. LOC255426 is a target gene of GAM26, corresponding to GAM26-TARGET GENE of FIG. 26A. LOC255426 BINDING SITE is a binding site found in an untranslated region of LOC255426, corresponding to BINDING SITE of FIG. 26A. FIG. 26D illustrates the complementarity of the nucleotide sequence of LOC255426 BINDING SITE, designated SEQ ID:94853, to the nucleotide sequence of GAM26 RNA of FIG. 26A, designated SEQ ID:20604. An additional function of GAM26 is therefore inhibition of (LOC255426). Accordingly, utilities of GAM26 include diagnosis and treatment of diseases and clinical conditions with which LOC255426 is associated.

Reference is now made to LOC255426 BINDING SITE. LOC255426 is a target gene of GAM21, corresponding to GAM26-TARGET GENE of FIG. 26A. LOC255426 BINDING SITE is a binding site found in an untranslated region of LOC255426, corresponding to BINDING SITE of FIG. 26A. FIG. 26D illustrates the complementarity of the nucleotide sequence of LOC255426 BINDING SITE, designated SEQ ID:94853, to the nucleotide sequence of GAM26 RNA of FIG. 26A, designated SEQ ID:20604. A further function of GAM26 is therefore inhibition of (LOC255426). Accordingly, utilities of GAM26 include diagnosis and treatment of diseases and clinical conditions with which LOC255426 is associated.

Reference is now made to LOC255426 BINDING SITE. LOC255426 is a target gene of GAM26, corresponding to GAM26-TARGET GENE of FIG. 26A. LOC255426 BINDING SITE is a binding site found in an untranslated region of LOC255426, corresponding to BINDING SITE of FIG. 26A. FIG. 26D illustrates the complementarity of the nucleotide sequence of LOC255426 BINDING SITE, designated SEQ ID:94853, to the nucleotide sequence of GAM26 RNA of FIG. 26A, designated SEQ ID:20604. Yet a further function of GAM26 is therefore inhibition of (LOC255426). Accordingly, utilities of GAM26 include diagnosis and treatment of diseases and clinical conditions with which LOC255426 is associated.

Reference is now made to LOC122525 BINDING SITE. LOC122525 is a target gene of GAM26, corresponding to GAM26-TARGET GENE of FIG. 26A. LOC122525 BINDING SITE is a binding site found in an untranslated region of LOC122525, corresponding to BINDING SITE of FIG. 26A. FIG. 26D illustrates the complementarity of the nucleotide sequence of LOC122525 BINDING SITE, designated SEQ ID:173934, to the nucleotide sequence of GAM26 RNA of FIG. 26A, designated SEQ ID:20604. Another function of GAM26 is therefore inhibition of (LOC122525). Accordingly, utilities of GAM26 include diagnosis and treatment of diseases and clinical conditions with which LOC122525 is associated.

Reference is now made to LOC122525 BINDING SITE. LOC122525 is a target gene of GAM26, corresponding to GAM26-TARGET GENE of FIG. 26A. LOC122525 BINDING SITE is a binding site found in an untranslated region of LOC122525, corresponding to BINDING SITE of FIG. 26A. FIG. 26D illustrates the complementarity of the nucleotide sequence of LOC122525 BINDING SITE, designated SEQ ID:241978, to the nucleotide sequence of GAM26 RNA of FIG. 26A, designated SEQ ID:20604. Yet another function of GAM26 is therefore inhibition of (LOC122525). Accordingly, utilities of GAM26 include diagnosis and treatment of diseases and clinical conditions with which LOC122525 is associated.

Reference is now made to LOC146057 BINDING SITE. LOC146057 is a target gene of GAM26, corresponding to GAM26-TARGET GENE of FIG. 26A. LOC146057 BINDING SITE is a binding site found in an untranslated region of LOC146057, corresponding to BINDING SITE of FIG. 26A. FIG. 26D illustrates the complementarity of the nucleotide sequence of LOC146057 BINDING SITE, designated SEQ ID:264106, to the nucleotide sequence of GAM26 RNA of FIG. 26A, designated SEQ ID:20604. An additional function of GAM26 is therefore inhibition of (LOC146057). Accordingly, utilities of GAM26 include diagnosis and treatment of diseases and clinical conditions with which LOC146057 is associated.

Reference is now made to LOC203197 BINDING SITE. LOC203197 is a target gene of GAM26, corresponding to GAM26-TARGET GENE of FIG. 26A. LOC203197 BINDING SITE is a binding site found in an untranslated region of LOC203197, corresponding to BINDING SITE of FIG. 26A. FIG. 26D illustrates the complementarity of the nucleotide sequence of LOC203197 BINDING SITE, designated SEQ ID:317209, to the nucleotide sequence of GAM26 RNA of FIG. 26A, designated SEQ ID:20604. A further function of GAM26 is therefore inhibition of (LOC203197). Accordingly, utilities of GAM26 include diagnosis and treatment of diseases and clinical conditions with which LOC203197 is associated.

Reference is now made to LOC146223 BINDING SITE. LOC146223 is a target gene of GAM26, corresponding to GAM26-TARGET GENE of FIG. 26A. LOC146223 BINDING SITE is a binding site found in an untranslated region of LOC146223, corresponding to BINDING SITE of FIG. 26A. FIG. 26D illustrates the complementarity of the nucleotide sequence of LOC146223 BINDING SITE, designated SEQ ID:412156, to the nucleotide sequence of GAM26 RNA of FIG. 26A, designated SEQ ID:20604. Yet a further function of GAM26 is therefore inhibition of (LOC146223). Accordingly, utilities of GAM26 include diagnosis and treatment of diseases and clinical conditions with which LOC146223 is associated.

Reference is now made to LOC256905 BINDING SITE. LOC256905 is a target gene of GAM26, corresponding to GAM26-TARGET GENE of FIG. 26A. LOC256905 BINDING SITE is a binding site found in an untranslated region of LOC256905, corresponding to BINDING SITE of FIG. 26A. FIG. 26D illustrates the complementarity of the nucleotide sequence of LOC256905 BINDING SITE, designated SEQ ID:432644, to the nucleotide sequence of GAM26 RNA of FIG. 26A, designated. SEQ ID:20604. Another function of GAM26 is therefore inhibition of (LOC256905). Accordingly, utilities of GAM26 include diagnosis and treatment of diseases and clinical conditions with which LOC256905 is associated.

Reference is now made to LOC158301 BINDING SITE. LOC158301 is a target gene of GAM26, corresponding to GAM26-TARGET GENE of FIG. 26A. LOC158301 BINDING SITE is a binding site found in an untranslated region of LOC158301, corresponding to BINDING SITE of FIG. 26A. FIG. 26D illustrates the complementarity of the nucleotide sequence of LOC158301 BINDING SITE, designated SEQ ID:670361, to the nucleotide sequence of GAM26 RNA of FIG. 26A, designated SEQ ID:20604. Yet another function of GAM26 is therefore inhibition of (LOC158301). Accordingly, utilities of GAM26 include diagnosis and treatment of diseases and clinical conditions with which LOC158301 is associated.

Reference is now made to LOC158301 BINDING SITE. LOC158301 is a target gene of GAM26, corresponding to GAM26-TARGET GENE of FIG. 26A. LOC158301 BINDING SITE is a binding site found in an untranslated region of LOC158301, corresponding to BINDING SITE of FIG. 26A. FIG. 26D illustrates the complementarity of the nucleotide sequence of LOC158301 BINDING SITE, designated SEQ ID:670394, to the nucleotide sequence of GAM26 RNA of FIG. 26A, designated SEQ ID:20604. An additional function of GAM26 is therefore inhibition of (LOC158301). Accordingly, utilities of GAM26 include diagnosis and treatment of diseases and clinical conditions with which LOC158301 is associated.

Reference is now made to LOC254573 BINDING SITE. LOC254573 is a target gene of GAM26, corresponding to GAM26-TARGET GENE of FIG. 26A. LOC254573 BINDING SITE is a binding site found in an untranslated region of LOC254573, corresponding to BINDING SITE of FIG. 26A. FIG. 26D illustrates the complementarity of the nucleotide sequence of LOC254573 BINDING SITE, designated SEQ ID:683857, to the nucleotide sequence of GAM26 RNA of FIG. 26A, designated SEQ ID:20604. A further function of GAM26 is therefore inhibition of (LOC254573). Accordingly, utilities of GAM26 include diagnosis and treatment of diseases and clinical conditions with which LOC254573 is associated.

Reference is now made to LOC158301 BINDING SITE. LOC158301 is a target gene of GAM26, corresponding to GAM26-TARGET GENE of FIG. 26A. LOC158301 BINDING SITE is a binding site found in an untranslated region of LOC158301, corresponding to BINDING SITE of FIG. 26A. FIG. 26D illustrates the complementarity of the nucleotide sequence of LOC158301 BINDING SITE, designated SEQ ID:763022, to the nucleotide sequence of GAM26 RNA of FIG. 26A, designated SEQ ID:20604. Yet a further function of GAM26 is therefore inhibition of (LOC158301). Accordingly, utilities of GAM26 include diagnosis and treatment of diseases and clinical conditions with which LOC158301 is associated.

Reference is now made to LOC57795 BINDING SITE. LOC57795 is a target gene of GAM26, corresponding to GAM26-TARGET GENE of FIG. 26A. LOC57795 BINDING SITE is a binding site found in an untranslated region of LOC57795, corresponding to BINDING SITE of FIG. 26A. FIG. 26D illustrates the complementarity of the nucleotide sequence of LOC57795 BINDING SITE, designated SEQ ID:865556, to the nucleotide sequence of GAM26 RNA of FIG. 26A, designated SEQ ID:20604. Another function of GAM26 is therefore inhibition of (LOC57795). Accordingly, utilities of GAM26 include diagnosis and treatment of diseases and clinical conditions with which LOC57795 is associated.

Reference is now made to LOC122525 BINDING SITE. LOC122525 is a target gene of GAM26, corresponding to GAM26-TARGET GENE of FIG. 26A. LOC122525 BINDING SITE is a binding site found in an untranslated region of LOC122525, corresponding to BINDING SITE of FIG. 26A. FIG. 26D illustrates the complementarity of the nucleotide sequence of LOC122525 BINDING SITE, designated SEQ ID:969284, to the nucleotide sequence of GAM26

RNA of FIG. 26A, designated SEQ ID:20604. Yet another function of GAM26 is therefore inhibition of (LOC122525). Accordingly, utilities of GAM26 include diagnosis and treatment of diseases and clinical conditions with which LOC122525 is associated.

Reference is now made to LOC112609 BINDING SITE. LOC112609 is a target gene of GAM26, corresponding to GAM26-TARGET GENE of FIG. 26A. LOC112609 BINDING SITE is a binding site found in an untranslated region of LOC112609, corresponding to BINDING SITE of FIG. 26A. FIG. 26D illustrates the complementarity of the nucleotide sequence of LOC112609 BINDING SITE, designated SEQ ID:1024445, to the nucleotide sequence of GAM26 RNA of FIG. 26A, designated SEQ ID:20604. An additional function of GAM26 is therefore inhibition of (LOC112609). Accordingly, utilities of GAM26 include diagnosis and treatment of diseases and clinical conditions with which LOC112609 is associated.

Reference is now made to LOC121536 BINDING SITE. LOC121536 is a target gene of GAM26, corresponding to GAM26-TARGET GENE of FIG. 26A. LOC121536 BINDING SITE is a binding site found in an untranslated region of LOC121536, corresponding to BINDING SITE of FIG. 26A. FIG. 26D illustrates the complementarity of the nucleotide sequence of LOC121536 BINDING SITE, designated SEQ ID:1036323, to the nucleotide sequence of GAM26 RNA of FIG. 26A, designated SEQ ID:20604. A further function of GAM26 is therefore inhibition of (LOC121536). Accordingly, utilities of GAM26 include diagnosis and treatment of diseases and clinical conditions with which LOC121536 is associated.

Reference is now made to LOC121536 BINDING SITE. LOC121536 is a target gene of GAM26, corresponding to GAM26-TARGET GENE of FIG. 26A. LOC121536 BINDING SITE is a binding site found in an untranslated region of LOC121536, corresponding to BINDING SITE of FIG. 26A. FIG. 26D illustrates the complementarity of the nucleotide sequence of LOC121536 BINDING SITE, designated SEQ ID:1036334, to the nucleotide sequence of GAM26 RNA of FIG. 26A, designated SEQ ID:20604. Yet a further function of GAM26 is therefore inhibition of (LOC121536). Accordingly, utilities of GAM26 include diagnosis and treatment of diseases and clinical conditions with which LOC121536 is associated.

Reference is now made to LOC121536 BINDING SITE. LOC121536 is a target gene of GAM26, corresponding to GAM26-TARGET GENE of FIG. 26A. LOC121536 BINDING SITE is a binding site found in an untranslated region of LOC121536, corresponding to BINDING SITE of FIG. 26A. FIG. 26D illustrates the complementarity of the nucleotide sequence of LOC121536 BINDING SITE, designated SEQ ID:1036375, to the nucleotide sequence of GAM26 RNA of FIG. 26A, designated SEQ ID:20604. Another function of GAM26 is therefore inhibition of (LOC121536). Accordingly, utilities of GAM26 include diagnosis and treatment of diseases and clinical conditions with which LOC121536 is associated.

Reference is now made to LOC122525 BINDING SITE. LOC122525 is a target gene of GAM26, corresponding to GAM26-TARGET GENE of FIG. 26A. LOC122525 BINDING SITE is a binding site found in an untranslated region of LOC122525, corresponding to BINDING SITE of FIG. 26A. FIG. 26D illustrates the complementarity of the nucleotide sequence of LOC122525 BINDING SITE, designated SEQ ID:1036926, to the nucleotide sequence of GAM26 RNA of FIG. 26A, designated SEQ ID:20604. Yet another function of GAM26 is therefore inhibition of (LOC122525). Accordingly, utilities of GAM26 include diagnosis and treatment of diseases and clinical conditions with which LOC122525 is associated.

Reference is now made to LOC124944 BINDING SITE. LOC124944 is a target gene of GAM26, corresponding to GAM26-TARGET GENE of FIG. 26A. LOC124944 BINDING SITE is a binding site found in an untranslated region of LOC124944, corresponding to BINDING SITE of FIG. 26A. FIG. 26D illustrates the complementarity of the nucleotide sequence of LOC124944 BINDING SITE, designated SEQ ID:1041522, to the nucleotide sequence of GAM26 RNA of FIG. 26A, designated SEQ ID:20604. An additional function of GAM26 is therefore inhibition of (LOC124944). Accordingly, utilities of GAM26 include diagnosis and treatment of diseases and clinical conditions with which LOC124944 is associated.

Reference is now made to LOC125228 BINDING SITE. LOC125228 is a target gene of GAM26, corresponding to GAM26-TARGET GENE of FIG. 26A. LOC125228 BINDING SITE is a binding site found in an untranslated region of LOC125228, corresponding to BINDING SITE of FIG. 26A. FIG. 26D illustrates the complementarity of the nucleotide sequence of LOC125228 BINDING SITE, designated SEQ ID:1042173, to the nucleotide sequence of GAM26 RNA of FIG. 26A, designated SEQ ID:20604. A further function of GAM26 is therefore inhibition of (LOC125228). Accordingly, utilities of GAM26 include diagnosis and treatment of diseases and clinical conditions with which LOC125228 is associated.

Reference is now made to LOC125228 BINDING SITE. LOC125228 is a target gene of GAM26, corresponding to GAM26-TARGET GENE of FIG. 26A. LOC125228 BINDING SITE is a binding site found in an untranslated region of LOC125228, corresponding to BINDING SITE of FIG. 26A. FIG. 26D illustrates the complementarity of the nucleotide sequence of LOC125228 BINDING SITE, designated SEQ ID:1042179, to the nucleotide sequence of GAM26 RNA of FIG. 26A, designated SEQ ID:20604. Yet a further function of GAM26 is therefore inhibition of (LOC125228). Accordingly, utilities of GAM26 include diagnosis and treatment of diseases and clinical conditions with which LOC1125228 is associated.

Reference is now made to LOC126432 BINDING SITE. LOC126432 is a target gene of GAM26, corresponding to GAM26-TARGET GENE of FIG. 26A. LOC126432 BINDING SITE is a binding site found in an untranslated region of LOC126432, corresponding to BINDING SITE of FIG. 26A. FIG. 26D illustrates the complementarity of the nucleotide sequence of LOC126432 BINDING SITE, designated SEQ ID:1044359, to the nucleotide sequence of GAM26 RNA of FIG. 26A, designated SEQ ID:20604. Another function of GAM26 is therefore inhibition of (LOC126432). Accordingly, utilities of GAM26 include diagnosis and treatment of diseases and clinical conditions with which LOC126432 is associated.

Reference is now made to LOC126917 BINDING SITE. LOC126917 is a target gene of GAM26, corresponding to GAM26-TARGET. GENE of FIG. 26A. LOC126917 BINDING SITE is a binding site found in an untranslated region of LOC126917, corresponding to BINDING SITE of FIG. 26A. FIG. 26D illustrates the complementarity of the nucleotide sequence of LOC126917 BINDING SITE, designated SEQ ID:1045771, to the nucleotide sequence of GAM26 RNA of FIG. 26A, designated SEQ ID:20604. Yet another function of GAM26 is therefore inhibition of (LOC126917). Accordingly, utilities of GAM26 include diagnosis and treatment of diseases and clinical conditions with which LOC126917 is associated.

Reference is now made to LOC130367 BINDING SITE. LOC130367 is a target gene of GAM26, corresponding to GAM26-TARGET GENE of FIG. 26A. LOC130367 BINDING SITE is a binding site found in an untranslated region of LOC130367, corresponding to BINDING SITE of FIG. 26A. FIG. 26D illustrates the complementarity of the nucleotide sequence of LOC130367 BINDING SITE, designated SEQ ID:1051475, to the nucleotide sequence of GAM26 RNA of FIG. 26A, designated SEQ ID:20604. An additional function of GAM26 is therefore inhibition of (LOC130367). Accordingly, utilities of GAM26 include diagnosis and treatment of diseases and clinical conditions with which LOC130367 is associated.

Reference is now made to LOC143243 BINDING SITE. LOC143243 is a target gene of GAM26, corresponding to GAM26-TARGET GENE of FIG. 26A. LOC143243 BINDING SITE is a binding site found in an untranslated region of LOC143243, corresponding to BINDING SITE of FIG. 26A. FIG. 26D illustrates the complementarity of the nucleotide sequence of LOC143243 BINDING SITE, designated SEQ ID:1065873, to the nucleotide sequence of GAM26 RNA of FIG. 26A, designated SEQ ID:20604. A further function of GAM26 is therefore inhibition of (LOC143243). Accordingly, utilities of GAM26 include diagnosis and treatment of diseases and clinical conditions with which LOC143243 is associated.

Reference is now made to LOC143891 BINDING SITE. LOC143891 is a target gene of GAM26, corresponding to GAM26-TARGET GENE of FIG. 26A. LOC143891 BINDING SITE is a binding site found in an untranslated region of LOC143891, corresponding to BINDING SITE of FIG. 26A. FIG. 26D illustrates the complementarity of the nucleotide sequence of LOC143891 BINDING SITE, designated SEQ ID:1068561, to the nucleotide sequence of GAM26 RNA of FIG. 26A, designated SEQ ID:20604. Yet a further function of GAM26 is therefore inhibition of (LOC143891). Accordingly, utilities of GAM26 include diagnosis and treatment of diseases and clinical conditions with which LOC143891 is associated.

Reference is now made to LOC145173 BINDING SITE. LOC145173 is a target gene of GAM26, corresponding to GAM26-TARGET GENE of FIG. 26A. LOC145173 BINDING SITE is a binding site found in an untranslated region of LOC145173, corresponding to BINDING SITE of FIG. 26A. FIG. 26D illustrates the complementarity of the nucleotide sequence of LOC145173 BINDING SITE, designated SEQ ID:1077948, to the nucleotide sequence of GAM26 RNA of FIG. 26A, designated SEQ ID:20604. Another function of GAM26 is therefore inhibition of (LOC145173). Accordingly, utilities of GAM26 include diagnosis and treatment of diseases and clinical conditions with which LOC145173 is associated.

Reference is now made to LOC145173 BINDING SITE. LOC145173 is a target gene of GAM26, corresponding to GAM26-TARGET GENE of FIG. 26A. LOC145173 BINDING SITE is a binding site found in an untranslated region of LOC145173, corresponding to BINDING SITE of FIG. 26A. FIG. 26D illustrates the complementarity of the nucleotide sequence of LOC145173 BINDING SITE, designated SEQ ID:1077952, to the nucleotide sequence of GAM26 RNA of FIG. 26A, designated SEQ ID:20604. Yet another function of GAM26 is therefore inhibition of (LOC145173). Accordingly, utilities of GAM26 include diagnosis and treatment of diseases and clinical conditions with which LOC145173 is associated.

Reference is now made to LOC145581 BINDING SITE. LOC145581 is a target gene of GAM26, corresponding to GAM26-TARGET GENE of FIG. 26A. LOC145581 BINDING SITE is a binding site found in an untranslated region of LOC145581, corresponding to BINDING SITE of FIG. 26A. FIG. 26D illustrates the complementarity of the nucleotide sequence of LOC145581 BINDING SITE, designated SEQ ID:1081817, to the nucleotide sequence of GAM26 RNA of FIG. 26A, designated SEQ ID:20604. An additional function of GAM26 is therefore inhibition of (LOC145581). Accordingly, utilities of GAM26 include diagnosis and treatment of diseases and clinical conditions with which LOC145581 is associated.

Reference is now made to LOC145990 BINDING SITE. LOC145990 is a target gene of GAM26, corresponding to GAM26-TARGET GENE of FIG. 26A. LOC145990 BINDING SITE is a binding site found in an untranslated region of LOC145990, corresponding to BINDING SITE of FIG. 26A. FIG. 26D illustrates the complementarity of the nucleotide sequence of LOC145990 BINDING SITE, designated SEQ ID:1089127, to the nucleotide sequence of GAM26 RNA of FIG. 26A, designated SEQ ID:20604. A further function of GAM26 is therefore inhibition of (LOC145990). Accordingly, utilities of GAM26 include diagnosis and treatment of diseases and clinical conditions with which LOC145990 is associated.

Reference is now made to LOC145990 BINDING SITE. LOC145990 is a target gene of GAM26, corresponding to GAM26-TARGET GENE of FIG. 26A. LOC145990 BINDING SITE is a binding site found in an untranslated region of LOC145990, corresponding to BINDING SITE of FIG. 26A. FIG. 26D illustrates the complementarity of the nucleotide sequence of LOC145990 BINDING SITE, designated SEQ ID:1089148, to the nucleotide sequence of GAM26 RNA of FIG. 26A, designated SEQ ID:20604. Yet a further function of GAM26 is therefore inhibition of (LOC145990). Accordingly, utilities of GAM26 include diagnosis and treatment of diseases and clinical conditions with which LOC145990 is associated.

Reference is now made to LOC145990 BINDING SITE. LOC145990 is a target gene of GAM26, corresponding to GAM26-TARGET GENE of FIG. 26A. LOC145990 BINDING SITE is a binding site found in an untranslated region of LOC145990, corresponding to BINDING SITE of FIG. 26A. FIG. 26D illustrates the complementarity of the nucleotide sequence of LOC145990 BINDING SITE, designated SEQ ID:1089170, to the nucleotide sequence of GAM26 RNA of FIG. 26A, designated SEQ ID:20604. Another function of GAM26 is therefore inhibition of (LOC145990). Accordingly, utilities of GAM26 include diagnosis and treatment of diseases and clinical conditions with which LOC145990 is associated.

Reference is now made to LOC145990 BINDING SITE. LOC145990 is a target gene of GAM26, corresponding to GAM26-TARGET GENE of FIG. 26A. LOC145990 BINDING SITE is a binding site found in an untranslated region of LOC145990, corresponding to BINDING SITE of FIG. 26A. FIG. 26D illustrates the complementarity of the nucleotide sequence of LOC145990 BINDING SITE, designated SEQ ID:1089181, to the nucleotide sequence of GAM26 RNA of FIG. 26A, designated SEQ ID:20604. Yet another function of GAM26 is therefore inhibition of (LOC145990). Accordingly, utilities of GAM26 include diagnosis and treatment of diseases and clinical conditions with which LOC145990 is associated.

Reference is now made to LOC146057 BINDING SITE. LOC146057 is a target gene of GAM26, corresponding to GAM26-TARGET GENE of FIG. 26A. LOC146057 BINDING SITE is a binding site found in an untranslated region of LOC146057, corresponding to BINDING SITE of FIG. 26A. FIG. 26D illustrates the complementarity of the nucleotide sequence of LOC146057 BINDING SITE, designated SEQ ID:1089542, to the nucleotide sequence of GAM26 RNA of FIG. 26A, designated SEQ ID:20604. An additional function of GAM26 is therefore inhibition of (LOC146057). Accordingly, utilities of GAM26 include diagnosis and treatment of diseases and clinical conditions with which LOC146057 is associated.

Reference is now made to LOC146057 BINDING SITE. LOC146057 is a target gene of GAM26, corresponding to GAM26-TARGET GENE of FIG. 26A. LOC146057 BINDING SITE is a binding site found in an untranslated region of LOC146057, corresponding to BINDING SITE of FIG. 26A. FIG. 26D illustrates the complementarity of the nucleotide sequence of LOC146057 BINDING SITE, designated SEQ ID:1089568, to the nucleotide sequence of GAM26 RNA of FIG. 26A, designated SEQ ID:20604. A further function of GAM26 is therefore inhibition of (LOC146057). Accordingly, utilities of GAM26 include diagnosis and treatment of diseases and clinical conditions with which LOC146057 is associated.

Reference is now made to LOC146223 BINDING SITE. LOC146223 is a target gene of GAM26, corresponding to GAM26-TARGET GENE of FIG. 26A. LOC146223 BINDING SITE is a binding site found in an untranslated region of LOC146223, corresponding to BINDING SITE of FIG. 26A. FIG. 26D illustrates the complementarity of the nucleotide sequence of LOC146223 BINDING SITE, designated SEQ ID:1090768, to the nucleotide sequence of GAM26 RNA of FIG. 26A, designated SEQ ID:20604. Yet a further function of GAM26 is therefore inhibition of (LOC146223). Accordingly, utilities of GAM26 include diagnosis and treatment of diseases and clinical conditions with which LOC46223 is associated.

Reference is now made to LOC147057 BINDING SITE. LOC147057 is a target gene of GAM26, corresponding to GAM26-TARGET GENE of FIG. 26A. LOC147057 BINDING SITE is a binding site found in an untranslated region of LOC147057, corresponding to BINDING SITE of FIG. 26A. FIG. 26D illustrates the complementarity of the nucleotide sequence of LOC147057 BINDING SITE, designated SEQ ID:1102464, to the nucleotide sequence of GAM26 RNA of FIG. 26A, designated SEQ ID:20604. Another function of GAM26 is therefore inhibition of (LOC147057). Accordingly, utilities of GAM26 include diagnosis and treatment of diseases and clinical conditions with which LOC147057 is associated.

Reference is now made to LOC147409 BINDING SITE. LOC147409 is a target gene of GAM26, corresponding to GAM26-TARGET GENE of FIG. 26A. LOC147409 BINDING SITE is a binding site found in an untranslated region of LOC147409, corresponding to BINDING SITE of FIG. 26A. FIG. 26D illustrates the complementarity of the nucleotide sequence of LOC147409 BINDING SITE, designated SEQ ID:1105742, to the nucleotide sequence of GAM26 RNA of FIG. 26A, designated SEQ ID:20604. Yet another function of GAM26 is therefore inhibition of (LOC147409). Accordingly, utilities of GAM26 include diagnosis and treatment of diseases and clinical conditions with which LOC147409 is associated.

Reference is now made to LOC147808 BINDING SITE. LOC147808 is a target gene of GAM26, corresponding to GAM26-TARGET GENE of FIG. 26A. LOC147808 BINDING SITE is a binding site found in an untranslated region of LOC147808, corresponding to BINDING SITE of FIG. 26A. FIG. 26D illustrates the complementarity of the nucleotide sequence of LOC147808 BINDING SITE, designated SEQ ID:1108755, to the nucleotide sequence of GAM26 RNA of FIG. 26A, designated SEQ ID:20604. An additional function of GAM26 is therefore inhibition of (LOC147808). Accordingly, utilities of GAM26 include diagnosis and treatment of diseases and clinical conditions with which LOC147808 is associated.

Reference is now made to LOC150984 BINDING SITE. LOC150984 is a target gene of GAM26, corresponding to GAM26-TARGET GENE of FIG. 26A. LOC150984 BINDING SITE is a binding site found in an untranslated region of LOC150984, corresponding to BINDING SITE of FIG. 26A. FIG. 26D illustrates the complementarity of the nucleotide sequence of LOC150984 BINDING SITE, designated SEQ ID:1144920, to the nucleotide sequence of GAM26 RNA of FIG. 26A, designated SEQ ID:20604. A further function of GAM26 is therefore inhibition of (LOC150984). Accordingly, utilities of GAM26 include diagnosis and treatment of diseases and clinical conditions with which LOC150984 is associated.

Reference is now made to LOC151517 BINDING SITE. LOC151517 is a target gene of GAM26, corresponding to GAM26-TARGET GENE of FIG. 26A. LOC151517 BINDING SITE is a binding site found in an untranslated region of LOC151517, corresponding to BINDING SITE of FIG. 26A. FIG. 26D illustrates the complementarity of the nucleotide sequence of LOC151517 BINDING SITE, designated SEQ ID:1151083, to the nucleotide sequence of GAM26 RNA of FIG. 26A, designated SEQ ID:20604. Yet another function of GAM26 is therefore inhibition of (LOC151517). Accordingly, utilities of GAM26 include diagnosis and treatment of diseases and clinical conditions with which LOC151517 is associated.

Reference is now made to LOC152048 BINDING SITE. LOC152048 is a target gene of GAM26, corresponding to GAM26-TARGET GENE of FIG. 26A. LOC152048 BINDING SITE is a binding site found in an untranslated region of LOC152048, corresponding to BINDING SITE of FIG. 26A. FIG. 26D illustrates the complementarity of the nucleotide sequence of LOC152048 BINDING SITE, designated SEQ ID:1155173, to the nucleotide sequence of GAM26 RNA of FIG. 26A, designated SEQ ID:20604. Another function of GAM26 is therefore inhibition of (LOC152048). Accordingly, utilities of GAM26 include diagnosis and treatment of diseases and clinical conditions with which LOC152048 is associated.

Reference is now made to LOC154743 BINDING SITE. LOC154743 is a target gene of GAM26, corresponding to GAM26-TARGET GENE of FIG. 26A. LOC154743 BINDING SITE is a binding site found in an untranslated region of LOC154743, corresponding to BINDING SITE of FIG. 26A. FIG. 26D illustrates the complementarity of the nucleotide sequence of LOC154743 BINDING SITE, designated SEQ ID:1174818, to the nucleotide sequence of GAM26 RNA of FIG. 26A, designated SEQ ID:20604. Yet another function of GAM26 is therefore inhibition of (LOC154743). Accordingly, utilities of GAM26 include diagnosis and treatment of diseases and clinical conditions with which LOC154743 is associated.

Reference is now made to LOC154807 BINDING SITE. LOC154807 is a target gene of GAM26, corresponding to GAM26-TARGET GENE of FIG. 26A. LOC154807 BINDING SITE is a binding site found in an untranslated region of LOC154807, corresponding to BINDING SITE of FIG. 26A. FIG. 26D illustrates the complementarity of the nucleotide sequence of LOC154807 BINDING SITE, designated SEQ ID:1175671, to the nucleotide sequence of GAM26 RNA of FIG. 26A, designated SEQ ID:20604. An additional function of GAM26 is therefore inhibition of (LOC154807). Accordingly, utilities of GAM26 include diagnosis and treatment of diseases and clinical conditions with which LOC154807 is associated.

Reference is now made to LOC154807 BINDING SITE. LOC154807 is a target gene of GAM26, corresponding to GAM26-TARGET GENE of FIG. 26A. LOC154807 BINDING SITE is a binding site found in an untranslated region of LOC154807, corresponding to BINDING SITE of FIG. 26A. FIG. 26D illustrates the complementarity of the nucleotide sequence of LOC154807 BINDING SITE, designated SEQ ID:1175672, to the nucleotide sequence of GAM26 RNA of FIG. 26A, designated SEQ ID:20604. A further function of GAM26 is therefore inhibition of (LOC154807). Accordingly, utilities of GAM26 include diagnosis and treatment of diseases and clinical conditions with which LOC154807 is associated.

Reference is now made to LOC158301 BINDING SITE. LOC158301 is a target gene of GAM26, corresponding to GAM26-TARGET GENE of FIG. 26A. LOC158301 BINDING SITE is a binding site found in an untranslated region of LOC158301, corresponding to BINDING SITE of FIG. 26A. FIG. 26D illustrates the complementarity of the nucleotide sequence of LOC158301 BINDING SITE, designated SEQ ID:1190223, to the nucleotide sequence of GAM26 RNA of FIG. 26A, designated SEQ ID:20604. Yet a further function of GAM26 is therefore inhibition of (LOC158301). Accordingly, utilities of GAM26 include diagnosis and treatment of diseases and clinical conditions with which LOC158301 is associated.

Reference is now made to LOC158301 BINDING SITE. LOC158301 is a target gene of GAM26, corresponding to GAM26-TARGET GENE of FIG. 26A. LOC158301 BINDING SITE is a binding site found in an untranslated region of LOC158301, corresponding to BINDING SITE of FIG. 26A. FIG. 26D illustrates the complementarity of the nucleotide sequence of LOC158301 BINDING SITE, designated SEQ ID:1190283, to the nucleotide sequence of GAM26 RNA of FIG. 26A, designated SEQ ID:20604. Another function of GAM26 is therefore inhibition of (LOC158301). Accordingly, utilities of GAM26 include diagnosis and treatment of diseases and clinical conditions with which LOC158301 is associated.

Reference is now made to LOC158856 BINDING SITE. LOC158856 is a target gene of GAM26, corresponding to GAM26-TARGET GENE of FIG. 26A. LOC158856 BINDING is a binding site found in an untranslated region of LOC158856, corresponding to BINDING SITE of FIG. 26A. FIG. 26D illustrates the complementarity of the nucleotide sequence of LOC158856 BINDING SITE, designated SEQ ID:1195246, to the nucleotide sequence of GAM26 RNA of FIG. 26A, designated SEQ ID:20604. Yet another function of GAM26 is therefore inhibition of (LOC158856). Accordingly, utilities of GAM26 include diagnosis and treatment of diseases and clinical conditions with which LOC158856 is associated.

Reference is now made to LOC161635 BINDING SITE. LOC161635 is a target gene of GAM26, corresponding to GAM26-TARGET GENE of FIG. 26A. LOC161635 BINDING SITE is a binding site found in an untranslated region of LOC161635, corresponding to BINDING SITE of FIG. 26A. FIG. 26D illustrates the complementarity of the nucleotide sequence of LOC161635 BINDING SITE, designated SEQ ID:1199731, to the nucleotide sequence of GAM26 RNA of FIG. 26A, designated SEQ ID:20604. An additional function of GAM26 is therefore inhibition of (LOC161635). Accordingly, utilities of GAM26 include diagnosis and treatment of diseases and clinical conditions with which LOC161635 is associated.

Reference is now made to LOC162417 BINDING SITE. LOC162417 is a target gene of GAM26, corresponding to GAM26-TARGET GENE of FIG. 26A. LOC162417 BINDING SITE is a binding site found in an untranslated region of LOC162417, corresponding to BINDING SITE of FIG. 26A. FIG. 26D illustrates the complementarity of the nucleotide sequence of LOC162417 BINDING SITE, designated SEQ ID:1201175, to the nucleotide sequence of GAM26 RNA of FIG. 26A, designated SEQ ID:20604. A further function of GAM26 is therefore inhibition of (LOC162417). Accordingly, utilities of GAM26 include diagnosis and treatment of diseases and clinical conditions with which LOC162417 is associated.

Reference is now made to LOC162762 BINDING SITE. LOC162762 is a target gene of GAM26, corresponding to GAM26-TARGET GENE of FIG. 26A. LOC162762 BINDING SITE is a binding site found in an untranslated region of LOC162762, corresponding to BINDING SITE of FIG. 26A. FIG. 26D illustrates the complementarity of the nucleotide sequence of LOC162762 BINDING SITE, designated SEQ ID:1201432, to the nucleotide sequence of GAM26 RNA of FIG. 26A, designated SEQ ID:20604. Yet a further function of GAM26 is therefore inhibition of (LOC162762). Accordingly, utilities of GAM26 include diagnosis and treatment of diseases and clinical conditions with which LOC162762 is associated.

Reference is now made to LOC162762 BINDING SITE. LOC162762 is a target gene of GAM26, corresponding to GAM26-TARGET GENE of FIG. 26A. LOC162762 BINDING SITE is a binding site found in an untranslated region of LOC162762, corresponding to BINDING SITE of FIG. 26A. FIG. 26D illustrates the complementarity of the nucleotide sequence of LOC162762 BINDING SITE, designated SEQ ID:1201436, to the nucleotide sequence of GAM26 RNA of FIG. 26A, designated SEQ ID:20604. Another function of GAM26 is therefore inhibition of (LOC162762). Accordingly, utilities of GAM26 include diagnosis and treatment of diseases and clinical conditions with which LOC162762 is associated.

Reference is now made to LOC163126 BINDING SITE. LOC163126 is a target gene of GAM26, corresponding to GAM26-TARGET GENE of FIG. 26A. LOC163126 BINDING SITE a binding site found in an untranslated region of LOC163126, corresponding to BINDING SITE of FIG. 26A. FIG. 26D illustrates the complementarity of the nucleotide sequence of LOC163126 BINDING SITE, designated SEQ ID:1201784, to the nucleotide sequence of GAM26 RNA of FIG. 26A, designated SEQ ID:20604. Yet another function of GAM26 is therefore inhibition of (LOC163126). Accordingly, utilities of GAM26 include diagnosis and treatment of diseases and clinical conditions with which LOC163126 is associated.

Reference is now made to LOC163126 BINDING SITE. LOC163126 is a target gene of GAM26, corresponding to GAM26-TARGET GENE of FIG. 26A. LOC163126 BINDING SITE is a binding site found in an untranslated region of LOC163126, corresponding to BINDING SITE of FIG. 26A. FIG. 26D illustrates the complementarity of the nucleotide sequence of LOC163126 BINDING SITE, designated SEQ ID:1201817, to the nucleotide sequence of GAM26 RNA of FIG. 26A, designated SEQ ID:20604. An additional function of GAM26 is therefore inhibition of (LOC163126).

Accordingly, utilities of GAM26 include diagnosis and treatment of diseases and clinical conditions with which LOC163126 is associated.

Reference is now made to LOC165257 BINDING SITE. LOC165257 is a target gene of GAM26, corresponding to GAM26-TARGET GENE of FIG. 26A. LOC165257 BINDING SITE is a binding site found in an untranslated region of LOC165257, corresponding to BINDING SITE of FIG. 26A. FIG. 26D illustrates the complementarity of the nucleotide sequence of LOC165257 BINDING SITE, designated SEQ ID:1205008, to the nucleotide sequence of GAM26 RNA of FIG. 26A, designated SEQ ID:20604. A further function of GAM26 is therefore inhibition of (LOC165257). Accordingly, utilities of GAM26 include diagnosis and treatment of diseases and clinical conditions with which LOC165257 is associated.

Reference is now made to LOC165333 BINDING SITE. LOC165333 is a target gene of GAM26, corresponding to GAM26-TARGET GENE of FIG. 26A. LOC165333 BINDING SITE is a binding site found in an untranslated region of LOC165333, corresponding to BINDING SITE of FIG. 26A. FIG. 26D illustrates the complementarity of the nucleotide sequence of LOC165333 BINDING SITE, designated SEQ ID:1205096, to the nucleotide sequence of GAM26 RNA of FIG. 26A, designated SEQ ID:20604. Yet a further function of GAM26 is therefore inhibition of (LOC165333). Accordingly, utilities of GAM26 include diagnosis and treatment of diseases and clinical conditions with which LOC165333 is associated.

Reference is now made to LOC165552 BINDING SITE. LOC165552 is a target gene of GAM26, corresponding to GAM26-TARGET GENE of FIG. 26A. LOC165552 BINDING SITE is a binding site found in an untranslated region of LOC165552, corresponding to BINDING SITE of FIG. 26A. FIG. 26D illustrates the complementarity of the nucleotide sequence of LOC165552 BINDING SITE, designated SEQ ID:1205248, to the nucleotide sequence of GAM26 RNA of FIG. 26A, designated SEQ ID:20604. Another function of GAM26 is therefore inhibition of (LOC165552). Accordingly, utilities of GAM26 include diagnosis and treatment of diseases and clinical conditions with which LOC165552 is associated.

Reference is now made to LOC196549 BINDING SITE. LOC196549 is a target gene of GAM26, corresponding to GAM26-TARGET GENE of FIG. 26A. LOC196549 BINDING SITE is a binding site found in an untranslated region of LOC196549, corresponding to BINDING SITE of FIG. 26A. FIG. 26D illustrates the complementarity of the nucleotide sequence of LOC196549 BINDING SITE, designated SEQ ID:1213581, to the nucleotide sequence of GAM26 RNA of FIG. 26A, designated SEQ ID:20604. Yet another function of GAM26 is therefore inhibition of (LOC196549). Accordingly, utilities of GAM26 include diagnosis and treatment of diseases and clinical conditions with which LOC196549 is associated.

Reference is now made to LOC202020 BINDING SITE. LOC202020 is a target gene of GAM26, corresponding to GAM26-TARGET GENE of FIG. 26A. LOC202020 BINDING SITE is a binding site found in an untranslated region of LOC202020, corresponding to BINDING SITE of FIG. 26A. FIG. 26D illustrates the complementarity of the nucleotide sequence of LOC202020 BINDING SITE, designated SEQ ID:1240261, to the nucleotide sequence of GAM26 RNA of FIG. 26A, designated SEQ ID:20604. An additional function of GAM26 is therefore inhibition of (LOC202020). Accordingly, utilities of GAM26 include diagnosis and treatment of diseases and clinical conditions with which LOC202020 is associated.

Reference is now made to LOC203197 BINDING SITE. LOC203197 is a target gene of GAM26, corresponding to GAM26-TARGET GENE of FIG. 26A. LOC203197 BINDING SITE is a binding site found in an untranslated region of LOC203197, corresponding to BINDING SITE of FIG. 26A. FIG. 26D illustrates the complementarity of the nucleotide sequence of LOC203197 BINDING SITE, designated SEQ ID:1245216, to the nucleotide sequence of GAM26 RNA of FIG. 26A, designated SEQ ID:20604. A further function of GAM26 is therefore inhibition of (LOC203197). Accordingly, utilities of GAM26 include diagnosis and treatment of diseases and clinical conditions with which LOC203197 is associated.

Reference is now made to LOC203197 BINDING SITE. LOC203197 is a target gene of GAM26, corresponding to GAM26-TARGET GENE of FIG. 26A. LOC203197 BINDING SITE is a binding site found in an untranslated region of LOC203197, corresponding to BINDING SITE of FIG. 26A. FIG. 26D illustrates the complementarity of the nucleotide sequence of LOC203197 BINDING SITE, designated SEQ ID:1245218, to the nucleotide sequence of GAM26 RNA of FIG. 26A, designated SEQ ID:20604. Yet a further function of GAM26 is therefore inhibition of (LOC203197). Accordingly, utilities of GAM26 include diagnosis and treatment of diseases and clinical conditions with which LOC203197 is associated.

Reference is now made to LOC203197 BINDING SITE. LOC203197 is a target gene of GAM26, corresponding to GAM26-TARGET GENE of FIG. 26A. LOC203197 BINDING SITE is a binding site found in an untranslated region of LOC203197, corresponding to BINDING SITE of FIG. 26A. FIG. 26D illustrates the complementarity of the nucleotide sequence of LOC203197 BINDING SITE, designated SEQ ID:1245270, to the nucleotide sequence of GAM26 RNA of FIG. 26A, designated SEQ ID:20604. Another function of GAM26 is therefore inhibition of (LOC203197). Accordingly, utilities of GAM26 include diagnosis and treatment of diseases and clinical conditions with which LOC203197 is associated.

Reference is now made to LOC203668 BINDING SITE. LOC203668 is a target gene of GAM26, corresponding to GAM26-TARGET GENE of FIG. 26A. LOC203668 BINDING SITE is a binding site found in an untranslated region of LOC203668, corresponding to BINDING SITE of FIG. 26A. FIG. 26D illustrates the complementarity of the nucleotide sequence of LOC203668 BINDING SITE, designated SEQ ID:1249923, to the nucleotide sequence of GAM26 RNA of FIG. 26A, designated SEQ ID:20604. Yet another function of GAM26 is therefore inhibition of (LOC203668). Accordingly, utilities of GAM26 include diagnosis and treatment of diseases and clinical conditions with which LOC203668 is associated.

Reference is now made to LOC219333 BINDING SITE. LOC219333 is a target gene of GAM26, corresponding to GAM26-TARGET GENE of FIG. 26A. LOC219333 BINDING SITE is a binding site found in an untranslated region of LOC219333, corresponding to BINDING SITE of FIG. 26A. FIG. 26D illustrates the complementarity of the nucleotide sequence of LOC219333 BINDING SITE, designated SEQ ID:1253262, to the nucleotide sequence of GAM26 RNA of FIG. 26A, designated SEQ ID:20604. An additional function of GAM26 is therefore inhibition of (LOC219333).

Accordingly, utilities of GAM26 include diagnosis and treatment of diseases and clinical conditions with which LOC219333 is associated.

Reference is now made to LOC219333 BINDING SITE. LOC219333 is a target gene of GAM26, corresponding to GAM26-TARGET GENE of FIG. 26A. LOC219333 BINDING SITE is a binding site found in an untranslated region of LOC219333, corresponding to BINDING SITE of FIG. 26A. FIG. 26D illustrates the complementarity of the nucleotide sequence of LOC219333 BINDING SITE, designated SEQ ID:1253264, to the nucleotide sequence of GAM26 RNA of FIG. 26A, designated SEQ ID:20604. A further function of GAM26 is therefore inhibition of (LOC219333). Accordingly, utilities of GAM26 include diagnosis and treatment of diseases and clinical conditions with which LOC219333 is associated.

Reference is now made to LOC219654 BINDING SITE. LOC219654 is a target gene of GAM26, corresponding to GAM26-TARGET GENE of FIG. 26A. LOC219654 BINDING SITE is a binding site found in an untranslated region of LOC219654, corresponding to BINDING SITE of FIG. 26A. FIG. 26D illustrates the complementarity of the nucleotide sequence of LOC219654 BINDING SITE, designated SEQ ID:1256056, to the nucleotide sequence of GAM26 RNA of FIG. 26A, designated SEQ ID:20604. Yet a further function of GAM26 is therefore inhibition of (LOC219654). Accordingly, utilities of GAM26 include diagnosis and treatment of diseases and clinical conditions with which LOC219654 is associated.

Reference is now made to LOC219899 BINDING SITE. LOC219899 is a target gene of GAM26, corresponding to GAM26-TARGET GENE of FIG. 26A. LOC219899 BINDING SITE is a binding site found in an untranslated region of LOC219899, corresponding to BINDING SITE of FIG. 26A. FIG. 26D illustrates the complementarity of the nucleotide sequence of LOC219899 BINDING SITE, designated SEQ ID:1258777, to the nucleotide sequence of GAM26 RNA of FIG. 26A, designated SEQ ID:20604. Another function of GAM26 is therefore inhibition of (LOC219899). Accordingly, utilities of GAM26 include diagnosis and treatment of diseases and clinical conditions with which LOC219899 is associated.

Reference is now made to LOC219899 BINDING SITE. LOC219899 is a target gene of GAM26, corresponding to GAM26-TARGET GENE of FIG. 26A. LOC219899 BINDING SITE is a binding site found in an untranslated region of LOC219899, corresponding to BINDING SITE of FIG. 26A. FIG. 26D illustrates the complementarity of the nucleotide sequence of LOC219899 BINDING SITE, designated SEQ ID:1258810, to the nucleotide sequence of GAM26 RNA of FIG. 26A, designated SEQ ID:20604. Yet another function of GAM26 is therefore inhibition of (LOC219899). Accordingly, utilities of GAM26 include diagnosis and treatment of diseases and clinical conditions with which LOC219899 is associated.

Reference is now made to LOC220058 BINDING SITE. LOC220058 is a target gene of GAM26, corresponding to GAM26-TARGET GENE of FIG. 26A. LOC220058 BINDING is a binding site found in an untranslated region of LOC220058, corresponding to BINDING SITE of FIG. 26A. FIG. 26D illustrates the complementarity of the nucleotide sequence of LOC220058 BINDING SITE, designated SEQ ID:1261177, to the nucleotide sequence of GAM26 RNA of FIG. 26A, designated SEQ ID:20604. An additional function of GAM26 is therefore inhibition of (LOC220058).

Accordingly, utilities of GAM26 include diagnosis and treatment of diseases and clinical conditions with which LOC220058 is associated.

Reference is now made to LOC245726 BINDING SITE. LOC245726 is a target gene of GAM26, corresponding to GAM26-TARGET GENE of FIG. 26A. LOC245726 BINDING SITE is a binding site found in an untranslated region of LOC245726, corresponding to BINDING SITE of FIG. 26A. FIG. 26D illustrates the complementarity of the nucleotide sequence of LOC245726 BINDING SITE, designated SEQ ID:1287683, to the nucleotide sequence of GAM26 RNA of FIG. 26A, designated SEQ ID:20604. A further function of GAM26 is therefore inhibition of (LOC245726). Accordingly, utilities of include diagnosis and treatment of diseases and clinical conditions with which LOC245726 is associated.

Reference is now made to LOC253943 BINDING SITE. LOC253943 is a target gene of GAM26, corresponding to GAM26-TARGET GENE of FIG. 26A. LOC253943 BINDING SITE is a binding site found in an untranslated region of LOC253943, corresponding to BINDING SITE of FIG. 26A. FIG. 26D illustrates the complementarity of the nucleotide sequence of LOC253943 BINDING SITE, designated SEQ ID:1295954, to the nucleotide sequence of GAM26 RNA of FIG. 26A, designated SEQ ID:20604. Yet a further function of GAM26 is therefore inhibition of (LOC253943). Accordingly, utilities of GAM26 include diagnosis and treatment of diseases and clinical conditions with which LOC253943 is associated.

Reference is now made to LOC253943 BINDING SITE. LOC253943 is a target gene of GAM26, corresponding to GAM26-TARGET GENE of FIG. 26A. LOC253943 BINDING SITE is a binding site found in an untranslated region of LOC253943, corresponding to BINDING SITE of FIG. 26A. FIG. 26D illustrates the complementarity of the nucleotide sequence of LOC253943 BINDING SITE, designated SEQ ID:1295956, to the nucleotide sequence of GAM26 RNA of FIG. 26A, designated SEQ ID:20604. Another function of GAM26 is therefore inhibition of (LOC253943). Accordingly, utilities of GAM26 include diagnosis and treatment of diseases and clinical conditions with which LOC253943 is associated.

Reference is now made to LOC253943 BINDING SITE. LOC253943 is a target gene of GAM26, corresponding to GAM26-TARGET GENE of FIG. 26A. LOC253943 BINDING SITE is a binding site found in an untranslated region of LOC253943, corresponding to BINDING SITE of FIG. 26A. FIG. 26D illustrates the complementarity of the nucleotide sequence of LOC253943 BINDING SITE, designated SEQ ID:1295963, to the nucleotide sequence of GAM26 RNA of FIG. 26A, designated SEQ ID:20604. Yet another function of GAM26 is therefore inhibition of (LOC253943). Accordingly, utilities of GAM26 include diagnosis and treatment of diseases and clinical conditions with which LOC253943 is associated.

Reference is now made to LOC253943 BINDING SITE. LOC253943 is a target gene of GAM26, corresponding to GAM26-TARGET GENE of FIG. 26A. LOC253943 BINDING SITE is a binding site found in an untranslated region of LOC253943, corresponding to BINDING SITE of FIG. 26A. FIG. 26D illustrates the complementarity of the nucleotide sequence of LOC253943 BINDING SITE, designated SEQ ID:1295964, to the nucleotide sequence of GAM26 RNA of FIG. 26A, designated SEQ ID:20604. An additional function of GAM26 is therefore inhibition of (LOC253943).

Accordingly, utilities of GAM26 include diagnosis and treatment of diseases and clinical conditions with which LOC253943 is associated.

Reference is now made to LOC254102 BINDING SITE. LOC254102 is a target gene of GAM26, corresponding to GAM26-TARGET GENE of FIG. 26A. LOC254102 BINDING SITE is a binding site found in an untranslated region of LOC254102, corresponding to BINDING SITE of FIG. 26A. FIG. 26D illustrates the complementarity of the nucleotide sequence of LOC254102 BINDING SITE, designated SEQ ID:1298522, to the nucleotide sequence of GAM26 RNA of FIG. 26A, designated SEQ ID:20604. A further function of GAM26 is therefore inhibition of (LOC254102). Accordingly, utilities of GAM26 include diagnosis and treatment of diseases and clinical conditions with which LOC254102 is associated.

Reference is now made to LOC254102 BINDING SITE. LOC254102 is a target gene of GAM26, corresponding to GAM26-TARGET GENE of FIG. 26A. LOC254102 BINDING SITE is a binding site found in an untranslated region of LOC254102, corresponding to BINDING SITE of FIG. 26A. FIG. 26D illustrates the complementarity of the nucleotide sequence of LOC254102 BINDING SITE, designated SEQ ID:1298528, to the nucleotide sequence of GAM26 RNA of FIG. 26A, designated SEQ ID:20604. Yet a further function of GAM26 is therefore inhibition of (LOC254102). Accordingly, utilities of GAM26 include diagnosis and treatment of diseases and clinical conditions with which LOC254102 is associated.

Reference is now made to LOC254107 BINDING SITE. LOC254107 is a target gene of GAM26, corresponding to GAM26-TARGET GENE of FIG. 26A. LOC254107 BINDING SITE is a binding site found in an untranslated region of LOC254107, corresponding to BINDING SITE of FIG. 26A. FIG. 26D illustrates the complementarity of the nucleotide sequence of LOC254107 BINDING SITE, designated SEQ ID:1298621, to the nucleotide sequence of GAM26 RNA of FIG. 26A, designated SEQ ID:20604. Another function of GAM26 is therefore inhibition of (LOC254107). Accordingly, utilities of GAM26 include diagnosis and treatment of diseases and clinical conditions with which LOC254107 is associated.

Reference is now made to LOC254573 BINDING SITE. LOC254573 is a target gene of GAM26, corresponding to GAM26-TARGET GENE of FIG. 26A. LOC254573 BINDING SITE is a binding site found in an untranslated region of LOC254573, corresponding to BINDING SITE of FIG. 26A. FIG. 26D illustrates the complementarity of the nucleotide sequence of LOC254573 BINDING SITE, designated SEQ ID:1303366, to the nucleotide sequence of GAM26 RNA of FIG. 26A, designated SEQ ID:20604. Yet another function of GAM26 is therefore inhibition of (LOC254573). Accordingly, utilities of GAM26 include diagnosis and treatment of diseases and clinical conditions with which LOC254573 is associated.

Reference is now made to LOC255028 BINDING SITE. LOC255028 is a target gene of GAM26, corresponding to GAM26-TARGET GENE of FIG. 26A. LOC255028 BINDING SITE is a binding site found in an untranslated region of LOC255028, corresponding to BINDING SITE of FIG. 26A. FIG. 26D illustrates the complementarity of the nucleotide sequence of LOC255028 BINDING SITE, designated SEQ ID:1306373, to the nucleotide sequence of GAM26 RNA of FIG. 26A, designated SEQ ID:20604. An additional function of GAM26 is therefore inhibition of (LOC255028). Accordingly, utilities of GAM26 include diagnosis and treatment of diseases and clinical conditions with which LOC255028 is associated.

Reference is now made to LOC255056 BINDING SITE. LOC255056 is a target gene of GAM26, corresponding to GAM26-TARGET GENE of FIG. 26A. LOC255056 BINDING SITE is a binding site found in an untranslated region of LOC255056, corresponding to BINDING SITE of FIG. 26A. FIG. 26D illustrates the complementarity of the nucleotide sequence of LOC255056 BINDING SITE, designated SEQ ID:1307405, to the nucleotide sequence of GAM26 RNA of FIG. 26A, designated SEQ. ID:20604. A further function of GAM26 is therefore inhibition of (LOC255056). Accordingly, utilities of GAM26 include diagnosis and treatment of diseases and clinical conditions with which LOC255056 is associated.

Reference is now made to LOC255426 BINDING SITE. LOC255426 is a target gene of GAM26, corresponding to GAM26-TARGET GENE of FIG. 26A. LOC255426 BINDING SITE is a binding site found in an untranslated region of LOC255426, corresponding to BINDING SITE of FIG. 26A. FIG. 26D illustrates the complementarity of the nucleotide sequence of LOC255426 BINDING SITE, designated SEQ ID:1310952, to the nucleotide sequence of GAM26 RNA of FIG. 26A, designated SEQ ID:20604. Yet a further function of GAM26 is therefore inhibition of (LOC255426). Accordingly, utilities of GAM26 include diagnosis and treatment of diseases and clinical conditions with which LOC255426 is associated.

Reference is now made to LOC255426 BINDING SITE. LOC255426 is a target gene of GAM26, corresponding to GAM26-TARGET GENE of FIG. 26A. LOC255426 BINDING SITE is a binding site found in an untranslated region of LOC255426, corresponding to BINDING SITE of FIG. 26A. FIG. 26D illustrates the complementarity of the nucleotide sequence of LOC255426 BINDING SITE, designated SEQ ID:1310952, to the nucleotide sequence of GAM26 RNA of FIG. 26A, designated SEQ ID:20604. Another function of GAM26 is therefore inhibition of (LOC255426). Accordingly, utilities of GAM26 include diagnosis and treatment of diseases and clinical conditions with which LOC255426 is associated.

Reference is now made to LOC146223 BINDING SITE. LOC146223 is a target gene of GAM26, corresponding to GAM26-TARGET GENE of FIG. 26A. LOC146223 BINDING SITE is a binding site found in an untranslated region of LOC146223, corresponding to BINDING SITE of FIG. 26A. FIG. 26D illustrates the complementarity of the nucleotide sequence of LOC146223 BINDING SITE, designated SEQ ID:1310953, to the nucleotide sequence of GAM26 RNA of FIG. 26A, designated SEQ ID:20604. Yet another function of GAM26 is therefore inhibition of (LOC146223). Accordingly, utilities of GAM26 include diagnosis and treatment of diseases and clinical conditions with which LOC146223 is associated.

Reference is now made to LOC255426 BINDING SITE. LOC255426 is a target gene of GAM26, corresponding to GAM26-TARGET GENE of FIG. 26A. LOC255426 BINDING SITE is a binding site found in an untranslated region of LOC255426, corresponding to BINDING SITE of FIG. 26A. FIG. 26D illustrates the complementarity of the nucleotide sequence of LOC255426 BINDING SITE, designated SEQ ID:1310953, to the nucleotide sequence of GAM26 RNA of FIG. 26A, designated SEQ ID:20604. An additional function of GAM26 is therefore inhibition of (LOC255426).

Accordingly, utilities of GAM26 include diagnosis and treatment of diseases and clinical conditions with which LOC255426 is associated.

Reference is now made to LOC201780 BINDING SITE. LOC201780 is a target gene of GAM26, corresponding to GAM26-TARGET GENE of FIG. 26A. LOC201780 BINDING SITE is a binding site found in an untranslated region of LOC201780, corresponding to BINDING SITE of FIG. 26A. FIG. 26D illustrates the complementarity of the nucleotide sequence of LOC201780 BINDING SITE, designated SEQ ID:1317863, to the nucleotide sequence of GAM26 RNA of FIG. 26A, designated SEQ ID:20604. A further function of GAM26 is therefore inhibition of (LOC201780). Accordingly, utilities of GAM26 include diagnosis and treatment of diseases and clinical conditions with which LOC201780 is associated.

Reference is now made to LOC256160 BINDING SITE. LOC256160 is a target gene of GAM26, corresponding to GAM26-TARGET GENE of FIG. 26A. LOC256160 BINDING SITE is a binding site found in an untranslated region of LOC256160, corresponding to BINDING SITE of FIG. 26A. FIG. 26D illustrates the complementarity of the nucleotide sequence of LOC256160 BINDING SITE, designated SEQ ID:1317863, to the nucleotide sequence of GAM26 RNA of FIG. 26A, designated SEQ ID:20604. Yet a further function of GAM26 is therefore inhibition of (LOC256160). Accordingly, utilities of GAM26 include diagnosis and treatment of diseases and clinical conditions with which LOC256160 is associated.

Reference is now made to LOC256537 BINDING SITE. LOC256537 is a target gene of GAM26, corresponding to GAM26-TARGET GENE of FIG. 26A. LOC256537 BINDING SITE is a binding site found in an untranslated region of LOC256537, corresponding to BINDING SITE of FIG. 26A. FIG. 26D illustrates the complementarity of the nucleotide sequence of LOC256537 BINDING SITE, designated SEQ ID:1321461, to the nucleotide sequence of GAM26 RNA of FIG. 26A, designated SEQ ID:20604. Another ion of GAM26 is therefore inhibition of (LOC256537). Accordingly, utilities of GAM26 include diagnosis and treatment of diseases and clinical conditions with which LOC256537 is associated.

Reference is now made to LOC256586 BINDING SITE. LOC256586 is a target gene of GAM26, corresponding to GAM26-TARGET GENE of FIG. 26A. LOC256586 BINDING SITE is a binding site found in an untranslated region of LOC256586, corresponding to BINDING SITE of FIG. 26A. FIG. 26D illustrates the complementarity of the nucleotide sequence of LOC256586 BINDING SITE, designated SEQ ID:1321729, to the nucleotide sequence of GAM26 RNA of FIG. 26A, designated SEQ ID:20604. Yet another function of GAM26 is therefore inhibition of (LOC256586). Accordingly, utilities of GAM26 include diagnosis and treatment of diseases and clinical conditions with which LOC256586 is associated.

Reference is now made to LOC256812 BINDING SITE. LOC256812 is a target gene of GAM26, corresponding to GAM26-TARGET. GENE of FIG. 26A. LOC256812 BINDING SITE is a binding site found in an untranslated region of LOC256812, corresponding to BINDING SITE of FIG. 26A. FIG. 26D illustrates the complementarity of the nucleotide sequence of LOC256812. BINDING SITE, designated SEQ ID:1322939, to the nucleotide sequence of GAM26 RNA of FIG. 26A, designated SEQ ID:20604. An additional function of GAM26 is therefore inhibition of (LOC256812). Accordingly, utilities of GAM26 include diagnosis and treatment of diseases and clinical conditions with which LOC256812 is associated.

Reference is now made to LOC256905 BINDING SITE. LOC256905 is a target gene of GAM26, corresponding to GAM26-TARGET GENE of FIG. 26A. LOC256905 BINDING SITE is a binding site found in an untranslated region of LOC256905, corresponding to BINDING SITE of FIG. 26A. FIG. 26D illustrates the complementarity of the nucleotide sequence of LOC256905 BINDING SITE, designated SEQ ID:1323732, to the nucleotide sequence of GAM26 RNA of FIG. 26A, designated SEQ ID:20604. A further function of GAM26 is therefore inhibition of (LOC256905). Accordingly, utilities of GAM26 include diagnosis and treatment of diseases and clinical conditions with which LOC256905 is associated.

Reference is now made to LOC256905 BINDING SITE. LOC256905 is a target gene of GAM26, corresponding to GAM26-TARGET GENE of FIG. 26A. LOC256905 BINDING SITE is a binding site found in an untranslated region of LOC256905, corresponding to BINDING SITE of FIG. 26A. FIG. 26D illustrates the complementarity of the nucleotide sequence of LOC256905 BINDING SITE, designated SEQ ID:1323749, to the nucleotide sequence of GAM26 RNA of FIG. 26A, designated SEQ ID:20604. Yet a further function of GAM26 is therefore inhibition of (LOC256905). Accordingly, utilities of GAM26 include diagnosis and treatment of diseases and clinical conditions with which LOC256905 is associated.

Reference is now made to LOC256905 BINDING SITE. LOC256905 is a target gene of GAM26, corresponding to GAM26-TARGET GENE of FIG. 26A. LOC256905 BINDING SITE is a binding site found in an untranslated region of LOC256905, corresponding to BINDING SITE of FIG. 26A. FIG. 26D illustrates the complementarity of the nucleotide sequence of LOC256905 BINDING SITE, designated SEQ ID:1323750, to the nucleotide sequence of GAM26 RNA of FIG. 26A, designated SEQ ID:20604. Another function of GAM26 is therefore inhibition of (LOC256905). Accordingly, utilities of GAM26 include diagnosis and treatment of diseases and clinical conditions with which LOC256905 is associated.

Reference is now made to LOC257222 BINDING SITE. LOC257222 is a target gene of GAM26, corresponding to GAM26-TARGET GENE of FIG. 26A. LOC257222 BINDING SITE is a binding site found in an untranslated region of LOC257222, corresponding to BINDING SITE of FIG. 26A. FIG. 26D illustrates the complementarity of the nucleotide sequence of LOC257222 BINDING SITE, designated SEQ ID:1326885, to the nucleotide sequence of GAM26 RNA of FIG. 26A, designated SEQ ID:20604. Yet another function of GAM26 is therefore inhibition of (LOC257222). Accordingly, utilities of GAM26 include diagnosis and treatment of diseases and clinical conditions with which LOC257222 is associated.

Reference is now made to LOC257479 BINDING SITE. LOC257479 is a target gene of GAM26, corresponding to GAM26-TARGET GENE of FIG. 26A. LOC257479 BINDING SITE is a binding site found in an untranslated region of LOC257479, corresponding to BINDING SITE of FIG. 26A. FIG. 26D illustrates the complementarity of the nucleotide sequence of LOC257479 BINDING SITE, designated SEQ ID:1330681, to the nucleotide sequence of GAM26 RNA of FIG. 26A, designated SEQ ID:20604. An additional function of GAM26 is therefore inhibition of (LOC257479). Accordingly, utilities of GAM26 include diagnosis and treatment of diseases and clinical conditions with which LOC257479 is associated.

Reference is now made to LOC257479 BINDING SITE. LOC257479 is a target gene of GAM26, corresponding to GAM26-TARGET GENE of FIG. 26A. LOC257479 BINDING SITE is a binding site found in an untranslated region of LOC257479, corresponding to BINDING SITE of FIG. 26A. FIG. 26D illustrates the complementarily of the nucleotide sequence of LOC257479 BINDING SITE, designated SEQ ID:1330687, to the nucleotide sequence of GAM26 RNA of FIG. 26A, designated SEQ ID:20604. A further function of GAM26 is therefore inhibition of (LOC257479). Accordingly, utilities of GAM26 include diagnosis and treatment of diseases and clinical conditions with which LOC257479 is associated.

Reference is now made to LOC257479 BINDING SITE. LOC257479 is a target gene of GAM26, corresponding to GAM26-TARGET GENE of FIG. 26A. LOC257479 BINDING SITE is a binding site found in an untranslated region of LOC257479, corresponding to BINDING SITE of FIG. 26A. FIG. 26D illustrates the complementarity of the nucleotide sequence of LOC257479 BINDING SITE, designated SEQ ID:1330706, to the nucleotide sequence of GAM26 RNA of FIG. 26A, designated SEQ ID:20604. Yet a further function of GAM26 is therefore inhibition of (LOC257479). Accordingly, utilities of GAM26 include diagnosis and treatment of diseases and clinical conditions with which LOC257479 is associated.

Reference is now made to LOC257479 BINDING SITE. LOC257479 is a target gene of GAM26, corresponding to GAM26-TARGET GENE of FIG. 26A. LOC257479 BINDING SITE is a binding site found in an untranslated region of LOC257479, corresponding to BINDING SITE of FIG. 26A. FIG. 26D illustrates the complementarity of the nucleotide sequence of LOC257479 BINDING SITE, designated SEQ ID:1330708, to the nucleotide sequence of GAM26 RNA of FIG. 26A, designated SEQ ID:20604. Another function of GAM26 is therefore inhibition of (LOC257479). Accordingly, utilities of GAM26 include diagnosis and treatment of diseases and clinical conditions with which LOC257479 is associated.

Reference is now made to LOC51061 BINDING SITE. LOC51061 is a target gene of GAM26, corresponding to GAM26-TARGET GENE of FIG. 26A. LOC51061 BINDING is a binding site found in an untranslated region of LOC51061, corresponding to BINDING SITE of FIG. 26A. FIG. 26D illustrates the complementarity of the nucleotide sequence of LOC51061 BINDING SITE, designated SEQ ID:1335336, to the nucleotide sequence of GAM26 RNA of FIG. 26A, designated SEQ ID:20604. Yet another function of GAM26 is therefore inhibition of (LOC51061). Accordingly, utilities of GAM26 include diagnosis and treatment of diseases and clinical conditions with which LOC51061 is associated.

Reference is now made to LOC55829 BINDING SITE. LOC55829 is a target gene of GAM2, corresponding to GAM26-TARGET GENE of FIG. 26A. LOC55829 BINDING SITE is a binding site found in an untranslated region of LOC55829, corresponding to BINDING SITE of FIG. 26A. FIG. 26D illustrates the complementarity of the nucleotide sequence of LOC55829 BINDING SITE, designated SEQ ID:1343670, to the nucleotide sequence of GAM26 RNA of FIG. 26A, designated SEQ ID:20604. An additional function of GAM26 is therefore inhibition of (LOC55829). Accordingly, utilities of GAM26 include diagnosis and treatment of diseases and clinical conditions with which LOC55829 is associated.

Reference is now made to LOC55829 BINDING SITE. LOC55829 is a target gene of GAM26, corresponding to GAM26-TARGET GENE of FIG. 26A. LOC55829 BINDING SITE is a binding site found in an untranslated region of LOC55829, corresponding to BINDING SITE of FIG. 26A. FIG. 26D illustrates the complementarity of the nucleotide sequence of LOC55829 BINDING SITE, designated SEQ ID:1343683, to the nucleotide sequence of GAM26 RNA of FIG. 26A, designated SEQ ID:20604. A further function of GAM26 is therefore inhibition of (LOC55829). Accordingly, utilities of GAM26 include diagnosis and treatment of diseases and clinical conditions with which LOC55829 is associated.

Reference is now made to LOC57795 BINDING SITE. LOC57795 is a target gene of GAM26, corresponding to GAM26-TARGET GENE of FIG. 26A. LOC57795 BINDING SITE is a binding site found in an untranslated region of LOC57795, corresponding to BINDING SITE of FIG. 26A. FIG. 26D illustrates the complementarity of the nucleotide sequence of LOC57795 BINDING SITE, designated SEQ ID:1347000, to the nucleotide sequence of GAM26 RNA of FIG. 26A, designated SEQ ID:20604. Yet a further function of GAM26 is therefore inhibition of (LOC57795). Accordingly, utilities of GAM26 include diagnosis and treatment of diseases and clinical conditions with which LOC57795 is associated.

Reference is now made to LOC84548 BINDING SITE. LOC84548 is a target gene of GAM26, corresponding to GAM26-TARGET GENE of FIG. 26A. LOC84548 BINDING SITE is a binding site found in an untranslated region of LOC84548, corresponding to BINDING SITE of FIG. 26A. FIG. 26D illustrates the complementarity of the nucleotide sequence of LOC84548 BINDING SITE, designated SEQ ID:1349247, to the nucleotide sequence of GAM26 RNA of FIG. 26A, designated SEQ ID:20604. Another function of GAM26 is therefore inhibition of (LOC84548). Accordingly, utilities of include diagnosis and treatment of diseases and clinical conditions with which LOC84548 is associated.

Reference is now made to LOC84548 BINDING SITE. LOC84548 is a target gene of GAM26, corresponding to GAM26-TARGET GENE of FIG. 26A. LOC84548 BINDING SITE is a binding site found in an untranslated region of LOC84548, corresponding to BINDING SITE of FIG. 26A. FIG. 26D illustrates the complementarity of the nucleotide sequence of LOC84548 BINDING SITE, designated SEQ ID:1349248, to the nucleotide sequence of GAM26 RNA of FIG. 26A, designated SEQ ID:20604. Yet another function of GAM26 is therefore inhibition of (LOC84548). Accordingly, utilities of GAM26 include diagnosis and treatment of diseases and clinical conditions with which LOC84548 is associated.

Reference is now made to LOC84548 BINDING SITE. LOC84548 is a target gene of GAM26, corresponding to GAM26-TARGET GENE of FIG. 26A. LOC84548 BINDING SITE is a binding site found in an untranslated region of LOC84548, corresponding to BINDING SITE of FIG. 26A. FIG. 26D illustrates the complementarity of the nucleotide sequence of LOC84548 BINDING SITE, designated SEQ ID:1349283, to the nucleotide sequence of GAM26 RNA of FIG. 26A, designated SEQ ID:20604. An additional function of GAM26 is therefore inhibition of (LOC84548). Accordingly, utilities of 4M26 include diagnosis and treatment of diseases and clinical conditions with which LOC84548 is associated.

Reference is now made to LOC84548 BINDING SITE. LOC84548 is a target gene of GAM26, corresponding to GAM26-TARGET GENE of FIG. 26A. LOC84548 BINDING SITE is a binding site found in an untranslated region of LOC84548, corresponding to BINDING SITE of FIG. 26A. FIG. 26D illustrates the complementarity of the nucleotide sequence of LOC84548 BINDING SITE, designated SEQ ID:1349284, to the nucleotide sequence of GAM26 RNA of FIG. 26A, designated SEQ ID:20604. A further function of GAM26 is therefore inhibition of (LOC84548). Accordingly, utilities of GAM26 include diagnosis and treatment of diseases and clinical conditions with which LOC84548 is associated.

Reference is now made to LOC86010 BINDING SITE. LOC86010 is a target gene of GAM26, corresponding to GAM26-TARGET GENE of FIG. 26A. LOC86010 BINDING SITE is a binding site found in an untranslated region of LOC86010, corresponding to BINDING SITE of FIG. 26A. FIG. 26D illustrates the complementarity of the nucleotide sequence of LOC86010 BINDING SITE, designated SEQ ID:1349829, to the nucleotide sequence of GAM26 RNA of FIG. 26A, designated SEQ ID:20604. Yet a further function of GAM26 is therefore inhibition of (LOC86010). Accordingly, utilities of GAM26 include diagnosis and treatment of diseases and clinical conditions with which LOC86010 is associated.

Reference is now made to LOC86010 BINDING SITE. LOC86010 is a target gene of GAM26, corresponding to GAM26-TARGET GENE of FIG. 26A. LOC86010 BINDING SITE is a binding site found in an untranslated region of LOC86010, corresponding to BINDING SITE of FIG. 26A. FIG. 26D illustrates the complementarity of the nucleotide sequence of LOC86010 BINDING SITE, designated SEQ ID:1349832, to the nucleotide sequence of GAM26 RNA of FIG. 26A, designated SEQ ID:20604. Another function of GAM26 is therefore inhibition of (LOC86010). Accordingly, utilities of GAM26 include diagnosis and treatment of diseases and clinical conditions with which LOC86010 is associated.

Reference is now made to LOC90379 BINDING SITE. LOC90379 is a target gene of GAM26, corresponding to GAM26-TARGET GENE of FIG. 26A. LOC90379 BINDING SITE is a binding site found in an untranslated region of LOC90379, corresponding to BINDING SITE of FIG. 26A. FIG. 26D illustrates the complementarity of the nucleotide sequence of LOC90379 BINDING SITE, designated SEQ ID:1356590, to the nucleotide sequence of GAM26 RNA of FIG. 26A, designated SEQ ID:20604. Yet another function of GAM26 is therefore inhibition of (LOC90379). Accordingly, utilities of GAM26 include diagnosis and treatment of diseases and clinical conditions with which LOC90379 is associated.

Reference is now made to LOC90835 BINDING SITE. LOC90835 is a target gene of GAM26, corresponding to GAM26-TARGET GENE of FIG. 26A. LOC90835 BINDING SITE is a binding site found in an untranslated region of LOC90835, corresponding to BINDING SITE of FIG. 26A. FIG. 26D illustrates the complementarity of the nucleotide sequence of LOC90835 BINDING SITE, designated SEQ ID:1362330, to the nucleotide sequence of GAM26 RNA of FIG. 26A, designated SEQ ID:20604. An additional function of GAM26 is therefore inhibition of (LOC90835). Accordingly, utilities of GAM26 include diagnosis and treatment of diseases and clinical conditions with which LOC90835 is associated.

Reference is now made to LOC90835 BINDING SITE. LOC90835 is a target gene of GAM26, corresponding to GAM26-TARGET GENE of FIG. 26A. LOC90835 BINDING SITE is a binding site found in an untranslated region of LOC90835, corresponding to BINDING SITE of FIG. 26A. FIG. 26D illustrates the complementarity of the nucleotide sequence of LOC90835 BINDING SITE, designated SEQ ID:1362338, to the nucleotide sequence of GAM26 RNA of FIG. 26A, designated SEQ ID:20604. A further function of GAM26 is therefore inhibition of (LOC90835). Accordingly, utilities of GAM26 include diagnosis and treatment of diseases and clinical conditions with which LOC90835 is associated.

Reference is now made to LOC90874 BINDING SITE. LOC90874 is a target gene of GAM26, corresponding to GAM26-TARGET GENE of FIG. 26A. LOC90874 BINDING SITE is a binding site found in an untranslated region of LOC90874, corresponding to BINDING SITE of FIG. 26A. FIG. 26D illustrates the complementarity of the nucleotide sequence of LOC90874 BINDING SITE, designated SEQ ID:1362769, to the nucleotide sequence of GAM26 RNA of FIG. 26A, designated SEQ ID:20604. Yet a further function of GAM26 is therefore inhibition of (LOC90874). Accordingly, utilities of GAM26 include diagnosis and treatment of diseases and clinical conditions with which LOC90874 is associated.

Reference is now made to LOC91050 BINDING SITE. LOC91050 is a target gene of GAM26, corresponding to GAM26-TARGET GENE of FIG. 26A. LOC91050 BINDING SITE is a binding site found in an untranslated region of LOC91050, corresponding to BINDING SITE of FIG. 26A. FIG. 26D illustrates the complementarity of the nucleotide sequence of LOC91050 BINDING SITE, designated SEQ ID:1364688, to the nucleotide sequence of GAM26 RNA of FIG. 26A, designated SEQ ID:20604. Another function of GAM26 is therefore inhibition of (LOC91050). Accordingly, utilities of GAM26 include diagnosis and treatment of diseases and clinical conditions with which LOC91050 is associated.

Reference is now made to LOC91050 BINDING SITE. LOC91050 is a target gene of GAM26, corresponding to GAM26-TARGET GENE of FIG. 26A. LOC91050 BINDING SITE is a binding site found in an untranslated region of LOC91050, corresponding to BINDING SITE of FIG. 26A. FIG. 26D illustrates the complementarity of the nucleotide sequence of LOC91050 BINDING SITE, designated SEQ ID:1364726, to the nucleotide sequence of GAM26 RNA of FIG. 26A, designated SEQ ID:20604. Yet another function of GAM26 is therefore inhibition of (LOC91050). Accordingly, utilities of include diagnosis and treatment of diseases and clinical conditions with which LOC91050 is associated.

Reference is now made to LOC91050 BINDING SITE. LOC91050 is a target gene of GAM26, corresponding to GAM26-TARGET GENE of FIG. 26A. LOC91050 BINDING SITE is a binding site found in an untranslated region of LOC91050, corresponding to BINDING SITE of FIG. 26A. FIG. 26D illustrates the complementarity of the nucleotide sequence of LOC91050 BINDING SITE, designated SEQ ID:1364727, to the nucleotide sequence of GAM26 RNA of FIG. 26A, designated SEQ ID:20604. An additional function of GAM26 is therefore inhibition of (LOC91050). Accordingly, utilities of GAM26 include diagnosis and treatment of diseases and clinical conditions with which LOC91050 is associated.

Reference is now made to LOC91300 BINDING SITE. LOC91300 is a target gene of GAM26, corresponding to GAM26-TARGET GENE of FIG. 26A. LOC91300 BINDING SITE is a binding site found in an untranslated region of LOC91300, corresponding to BINDING SITE of FIG. 26A. FIG. 26D illustrates the complementarity of the nucleotide sequence of LOC91300 BINDING SITE, designated SEQ ID:1367936, to the nucleotide sequence of GAM26

RNA of FIG. 26A, designated SEQ ID:20604. A further function of GAM26 is therefore inhibition of (LOC91300). Accordingly, utilities of GAM6 include diagnosis and treatment of diseases and clinical conditions with which LOC91300 is associated.

Reference is now made to LOC91300 BINDING SITE. LOC91300 is a target gene of GAM26, corresponding to GAM26-TARGET GENE of FIG. 26A. LOC91300 BINDING SITE is a binding site found in an untranslated region of LOC91300, corresponding to BINDING SITE of FIG. 26A. FIG. 26D illustrates the complementarity of the nucleotide sequence of LOC91300 BINDING SITE, designated SEQ ID:1367936, to the nucleotide sequence of GAM26 RNA of FIG. 26A, designated SEQ ID:20604. Yet a further function of GAM26 is therefore inhibition of (LOC91300). Accordingly, utilities of GAM26 include diagnosis and treatment of diseases and clinical conditions with which LOC91300 is associated.

Reference is now made to LOC91978 BINDING SITE. LOC91978 is a target gene of GAM26, corresponding to GAM26-TARGET GENE of FIG. 26A. LOC91978 BINDING SITE is a binding site found in an untranslated region of LOC91978, corresponding to BINDING SITE of FIG. 26A. FIG. 26D illustrates the complementarity of the nucleotide sequence of LOC91978 BINDING SITE, designated SEQ ID:1375053, to the nucleotide sequence of GAM26 RNA of FIG. 26A, designated SEQ ID:20604. Another function of GAM26 is therefore inhibition of (LOC91978). Accordingly, utilities of include diagnosis and treatment of diseases and clinical conditions with which LOC91978 is associated.

Reference is now made to LOC92181 BINDING SITE. LOC92181 is a target gene of GAM26, corresponding to GAM26-TARGET GENE of FIG. 26A. LOC92181 BINDING SITE is a binding site found in an untranslated region of LOC92181, corresponding to BINDING SITE of FIG. 26A. FIG. 26D illustrates the complementarity of the nucleotide sequence of LOC92181 BINDING SITE, designated SEQ ID:1376487, to the nucleotide sequence of GAM26 RNA of FIG. 26A, designated SEQ ID:20604. Yet another function of GAM26 is therefore inhibition of (LOC92181). Accordingly, utilities of GAM26 include diagnosis and treatment of diseases and clinical conditions with which LOC92181 is associated.

Reference is now made to LOC92299 BINDING SITE. LOC92299 is a target gene of GAM26, corresponding to GAM26-TARGET GENE of FIG. 26A. LOC92299 BINDING SITE is a binding site found in an untranslated region of LOC92299, corresponding to BINDING SITE of FIG. 26A. FIG. 26D illustrates the complementarity of the nucleotide sequence of LOC92299 BINDING SITE, designated SEQ ID:1377998, to the nucleotide sequence of GAM26 RNA of FIG. 26A, designated SEQ ID:20604. An additional function of GAM26 is therefore inhibition of (LOC92299). Accordingly, utilities of GAM26 include diagnosis and treatment of diseases and clinical conditions with which LOC92299 is associated.

Figures 27A, 27B, 27C:
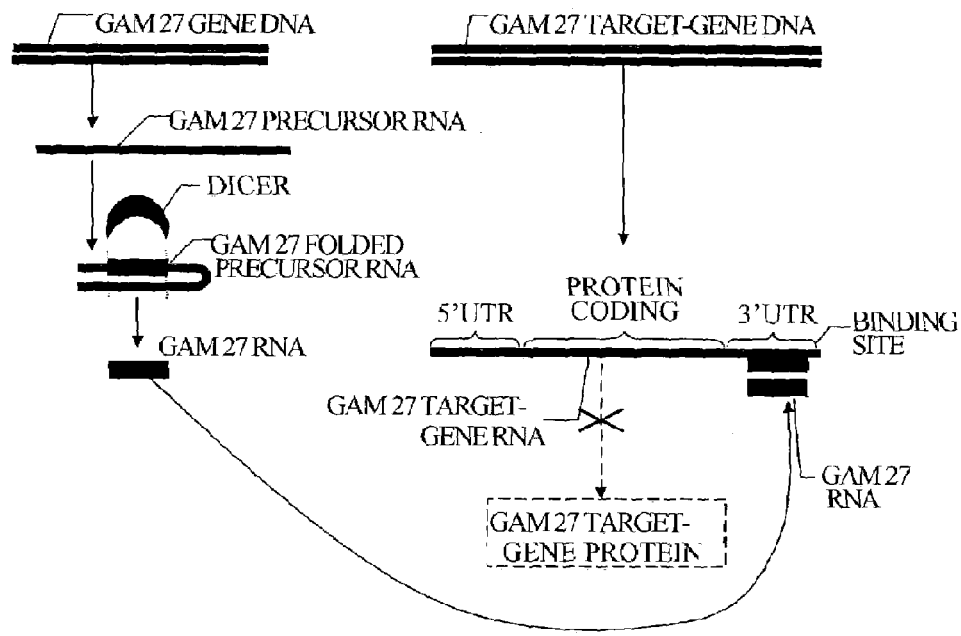

Reference is now made to FIG. 27A, which is a simplified diagram providing a conceptual explanation of the mode by which a novel bioinformatically detected gene, referred to here as GAM27 modulates expression of target genes thereof, the function and utility of which target genes is known in the art.

GAM27 (Genomic Address Messenger 27) is a novel bioinformatically detected regulatory, non protein coding, micro RNA (miRNA) gene. The method by which GAM27 was detected is described hereinabove with reference to FIGS. 6-15.

GAM27 GENE and GAM27-TARGET GENE are two human genes contained in the human genome.

GAM27 GENE encodes a GAM27 PRECURSOR RNA. Similar to other miRNA genes, and unlike most ordinary genes, the RNA transcribed by GAM27, GAM27 PRECURSOR RNA, does not encode a protein.

GAM27 PRECURSOR RNA folds onto itself, forming GAM27 FOLDED PRECURSOR RNA. As FIG. 27 illustrates, GAM27 FOLDED PRECURSOR RNA forms a 'hairpin structure', folding onto itself. As is well known in the art, this 'hairpin structure', is typical of RNA encoded by miRNA genes, and is due to the fact that the nucleotide sequence of the first half of the RNA encoded by a miRNA gene is an accurate or partial inversed-reversed sequence of the nucleotide sequence of the second half thereof. By "inversed-reversed" is meant a sequence which is reversed and wherein each nucleotide is replaced by a complimentary nucleotide, as is well known in the art (e.g. ATGGC is the inversed-reversed sequence of GCCAT).

An enzyme complex designated DICER COMPLEX, 'dices' the GAM27 FOLDED PRECURSOR RNA into a single stranded ~22 nt long RNA segment, designated GAM27 RNA. As is known in the art, 'dicing' of a hairpin structured RNA precursor product into short a ~22 nt RNA segment is catalyzed by an enzyme complex comprising an enzyme called Dicer together with other necessary proteins.

GAM27-TARGET GENE encodes a corresponding messenger RNA, designated GAM27-TARGET RNA. GAM27-TARGET RNA comprises three regions, as is typical of mRNA of a protein coding gene: a 5' untranslated region, a protein coding region and a 3' untranslated region, designated 5'UTR, PROTEIN CODING and 3'UTR respectively.

GAM27 RNA binds complimentarily to a BINDING SITE, located on an untranslated region of GAM27-TARGET RNA. This complimentarily binding is due to the fact that the nucleotide sequence of GAM27 RNA is an accurate or a partial inversed-reversed sequence of the nucleotide sequence of BINDING SITE. It is appreciated that while FIG. 27A depicts the BINDING SITE on the 3'UTR region, this is meant as an example only—the BINDING SITE nay be located on the 5'UTR region as well.

The complimentary binding of GAM27 RNA to BINDING SITE inhibits translation of GAM27-TARGET RNA into GAM27-TARGET PROTEIN. GAM27-TARGET PROTEIN is therefore outlined by a broken line.

It is appreciated that GAM27-TARGET GENE in fact represents a plurality of target genes of GAM27. The mRNA of each of this plurality of target genes of GAM27 comprises a BINDING SITE, having a nucleotide sequence which is at least partly complementary to GAM27 RNA, and which when bound by GAM27 RNA causes inhibition of translation of one of a plurality of target proteins of GAM27. The plurality of target genes of GAM27 and their respective binding sites, are described hereinbelow with reference to FIG. 27D.

It is appreciated by one skilled in the art that the mode of translational inhibition illustrated by FIG. 27 with specific reference to translational inhibition exerted by GAM27 on one or more target genes of GAM27, is in fact common to other known miRNA genes. As mentioned hereinabove with reference to the background section, although a specific complimentary binding site has been demonstrated only for miRNA genes Lin-4 and Let-7, all other recently discovered miRNA genes are also believed by those skilled in the art to modulate expression of other genes by complimentary binding, although specific complimentary binding sites of these genes have not yet been found (Ruvkun G., 'Perspective: Glimpses of a tiny RNA world', Science 294, 779 (2001)).

Reference is now made to FIG. 27B which shows the nucleotide sequence of GAM27 PRECURSOR RNA of FIG. 27A, designated SEQ ID:4, and a probable nucleotide sequence of GAM27 RNA of FIG. 27A, designated SEQ ID:20605. The nucleotide sequence of SEQ ID:20605, which is highly likely (over 0.887508%) to be identical or highly similar to that of GAM27, is marked by an underline within the sequence of GAM27 PRECURSOR RNA.

Reference is now made to FIG. 27C, which shows the secondary folding of GAM27 PRECURSOR RNA forming a 'hairpin structure' designated GAM27 FOLDED PRECURSOR RNA, both of FIG. 27A. A probable (>0.887508%) nucleotide sequence of GAM27 RNA, designated SEQ ID:20605 of FIG. 27B, is marked by an underline on GAM27 FOLDED PRECURSOR RNA. It is appreciated that the complimentary base-paring is not perfect, with 'bulges', as is well known in the art with respect to the RNA folding of all known miRNA genes.

Reference is now made to FIG. 27D, which is a table showing binding sites found in untranslated regions of a plurality of target genes of GAM27, each binding site corresponding to BINDING SITE of FIG. 27A, and their complementarity to SEQ ID:20605, which is highly likely (>0.887508%) to be identical or highly similar to the nucleotide sequence of GAM27 RNA of FIG. 27A.

It is appreciated that the functions, and accordingly the utilities, of GAM27 correlate with, and may be deduced from, the identity of the target genes which GAM27 binds and inhibits, and the function of these target genes, as elaborated hereinbelow.

Reference is now made to DEC1 BINDING SITE. Deleted in esophageal cancer 1 (DEC1) is a target gene of GAM27, corresponding to GAM27-TARGET GENE of FIG. 27A. DEC1 BINDING SITE is a binding site found in an untranslated region of DEC1, corresponding to BINDING SITE of FIG. 27A. FIG. 27D illustrates the complementarity of the nucleotide sequence of DEC1 BINDING SITE, designated SEQ ID:131107, to the nucleotide sequence of GAM27 RNA of FIG. 27A, designated SEQ ID:20605.

A function of GAM27 is therefore inhibition of deleted in esophageal cancer 1 (DEC1), a gene which encodes a protein that acts as a tumor suppressor associated with esophageal cancer, and is associated with esophageal cancer. Accordingly, utilities of GAM27 include diagnosis and treatment of the abovementioned diseases and clinical conditions.

The function of DEC1 has been established by previous studies. Loss of heterozygosity (LOH) is often shown at 9q31 in esophageal squamous cell carcinomas (133239) as well as in squamous cell carcinomas of developmentally related tissues such as bladder (109800), lung (211980), and head and neck. Miura et al. (1996) delineated a region commonly deleted in esophageal squamous cell carcinomas to a 200-kb segment at 9q32. Nishiwaki et al. (2000) sequenced overlapping clones in this commonly deleted region and identified a possible candidate gene, which they named 'deleted in esophageal cancer-1' (DEC1). The DEC1 gene encodes a deduced 70-amino acid protein. Northern blot analysis detected a 1.4-kb DEC1 transcript in all tissues tested, with highest expression in prostate and testis. DEC1 expression was lower than normal and often absent in more than half of the esophageal carcinomas examined. Furthermore, DEC1 cDNA was able to exert growth suppressive activity in vitro. Although expression was reduced, no genetic alteration was detected in the DEC1 gene in any of the cancers examined.

Full details of the abovementioned studies are described in the following publications, the disclose of which are hereby incorporated by reference:

Miura, K.; Suzuki, K.; Tokino, T.; Isomura, M.; Inazawa, J.; Matsuno, S.; Nakamura, Y.: Detailed deletion mapping in squamous cell carcinomas of the esophagus narrows a region containing a putative tumor suppressor gene to about 200 kilobases on distal chromosome 9q. Cancer Res. 56: 1629-1634, 1996. PubMed ID: 8603412 2.

Nishiwaki, T.; Daigo, Y.; Kawasoe, T.; Nakamura, Y.: Isolation and mutational analysis of a novel human cDNA, DEC1 (deleted in esophageal cancer 1), derived from the tumor suppressor locus in 9q32. Genes Chromosomes Cancer 27: 169-176, 2000.

Further studies establishing the function and utilities of DEC1 are found in John Hopkins OMIM database record ID 604767, and in references numbered 1604-1605 listed hereinbelow.

Reference is now made to HD BINDING SITE. Huntingtin (Huntington disease) (HD) is a target gene of GAM27, corresponding to GAM27-TARGET GENE of FIG. 27A. HD BINDING SITE is a binding site found in an untranslated region of HD, corresponding to BINDING SITE of FIG. 27A. FIG. 27D illustrates the complementarity of the nucleotide sequence of HD BINDING SITE, designated SEQ ID:193353, to the nucleotide sequence of GAM27 RNA of FIG. 27A, designated SEQ ID:20605.

Yet another function of GAM27 is therefore inhibition of huntingtin (Huntington disease) (HD), a gene which encodes an enzyme that is associated with Huntington disease (HD). Accordingly, utilities of GAM27 include diagnosis and treatment of the abovementioned diseases and clinical conditions.

The function of HD has been established by previous studies. Relative to the mechanisms by which the mutant huntingtin protein cause neurodegeneration, Panov et al. (2002) showed that lymphoblast mitochondria from patients with HD have a lower membrane potential and depolarize at lower calcium loads than do mitochondria from controls. They found a similar defect in brain mitochondria from transgenic mice expressing full-length mutant huntingtin, and this defect preceded the onset of pathologic or behavioral abnormalities by months. By electron microscopy, they identified N-terminal mutant huntingtin on neuronal mitochondrial membranes, and by incubating normal mitochondria with a fusion protein containing an abnormally long polyglutamine repeat, they reproduced the mitochondrial calcium defect seen in human patients and transgenic animals. Thus, mitochondrial calcium abnormalities occur early in HD pathogenesis and may be a direct effect of mutant huntingtin on the organelle.

Animal model experiments lend further support to the function of HD. To distinguish between 'loss-of-function' and 'gain-of-function' models of HD, Duyao et al. (1995) inactivated the mouse Hdh by gene targeting. Mice heterozygous for Hdh inactivation were phenotypically normal, whereas homozygosity resulted in embryonic death. Homozygotes displayed abnormal gastrulation at embryonic day 7.5 and were resorbing by day 8.5. Thus, they concluded that huntingtin is critical early in embryonic development, before the emergence of the nervous system. That Hdh inactivation does not mimic adult HD neuropathology suggested to the authors that the human disease involves a gain of function.

It is appreciated that the abovementioned animal model for HD is acknowledged by those skilled in the art as a scientifically valid animal model, as can be further appreciated from the publications sited hereinbelow.

Full details of the abovementioned studies are described in the following publications, the disclosure of which are hereby incorporated by reference:

Duyao, M. P.; Auerbach, A. B.; Ryan, A.; Persichetti, F.; Barnes, G. T.; McNeil, S. M.; Ge, P.; Vonsattel, J. -P.; Gusella, J. F.; Joyner, A. L.; MacDonald, M. E.: Inactivation of the mouse Huntington's disease gene homolog Hdh. Science 269: 407-410, 1995. PubMed ID: 7618107 204. Panov, A. V.; Gutekunst, C. -A.; Leavitt, B. R.; Hayden, M. R.; Burke, J. R.; Strittmatter, W. J.; Greenamyre, J. T.: Early mitochondrial calcium defects in Huntington's disease are a direct effect of polyglutamines. Nature Neurosci. 5: 731-736, 2002.

Further studies establishing the function and utilities of HD are found in John Hopkins OMIM database record ID 143100, and in references numbered 1606-1704 listed hereinbelow.

Reference is now made to HPN BINDING SITE. hepsin (transmembrane protease, serine 1) (HPN) is a target gene of GAM27, corresponding to GAM27-TARGET GENE of FIG. 27A. HPN BINDING SITE is a binding site found in an untranslated region of HPN, corresponding to BINDING SITE of FIG. 27A. FIG. 27D illustrates the complementarity of the nucleotide sequence of HPN BINDING SITE, designated SEQ ID:201170, to the nucleotide sequence of GAM27 RNA of FIG. 27A, designated SEQ ID:20605.

An additional function of GAM27 is therefore inhibition of hepsin (transmembrane protease, serine 1) (HPN), a gene which encodes an enzyme that is a cell surface serine protease. Accordingly, utilities of GAM27 include diagnosis and treatment of the abovementioned diseases and clinical conditions.

The function of HPN has been established by previous studies. Hepsin is a cell surface serine protease. From cDNA libraries prepared from human liver and hepatoma cell line mRNA, Leytus et al. (1988) isolated cDNA clones coding for a serine protease called hepsin. The proteolytic enzymes of the serine protease family exist as single- or 2-chain zymogenes that are activated by a specific and limited proteolytic cleavage. They contain 3 principal active-site amino acids, his, asp, and ser, that participate in peptide bond hydrolysis. Among the best-studied serine proteases are those found in plasma. These enzymes are involved in processes such as blood coagulation, fibrinolysis, and complement activation. Tsuji et al. (1991) showed that the hepsin mRNA is 1.85 kb in size and present in most tissues, with the highest level in liver. It is present in the plasma membrane in a molecular orientation of type II membrane associated proteins, with its catalytic subunit (C-terminal half) at the cell surface and its N terminus facing the cytosol. Hepsin is not found in cytosol. See also TMPRSS2 (602060), a related serine protease.

Animal model experiments lend further support to the function of HPN. To determine the functional importance of hepsin, Wu et al. (1998) generated hepsin-deficient mice by homologous recombination. The homozygous deficient mice were viable and fertile, and grew normally. In functional assays, including tail bleeding time, plasma clotting times, and tissue factor- or LPS-induced disseminated intravascular coagulation models, no significant difference was found between hepsin −/− and wildtype littermates. Liver weight and serum concentrations of liver-derived proteins and enzymes were similar. Serum concentrations of bone-derived alkaline phosphatase were approximately 2-fold higher in hepsin −/− mice of both sexes when compared with wildtype littermates. No obvious abnormalities were found in major organs in hepsin −/− mice on histologic examination. The results indicated that hepsin is not essential for embryonic development and normal hemostasis.

It is appreciated that the abovementioned animal model for HPN is acknowledged by those skilled in the art as a scientifically valid animal model, as can be further appreciated from the publications sited hereinbelow.

Full details of the abovementioned studies are described in the following publications, the disclosure of which are hereby incorporated by reference:

Leytus, S. P.; Loeb, K. R.; Hagen, F. S.; Kurachi, K.; Davie, E. W.: A novel trypsin-like serine protease (hepsin) with a putative transmembrane domain expressed by human liver and hepatoma cells. Biochemistry 27: 1067-1074, 1988. PubMed ID: 2835076 3. Tsuji, A.; Torres-Rosado, A.; Arai, T.; Le Beau, M. M.; Lemons, R. S.; Chou, S. -H.; Kurachi, K.: Hepsin, a cell membrane-associated protease: characterization, tissue distribution, and gene localization J. Biol. Chem. 266: 16948-16953, 1991.

Further studies establishing the function and utilities of HPN are found in John Hopkins OMIM database record ID 142440, and in references numbered 1074 and 1705-1707 listed hereinbelow.

Reference is now made to C20orf11 BINDING SITE. C20orf11 is a target gene of GAM27, corresponding to GAM27-TARGET GENE of FIG. 27A. C20orf11 BINDING SITE is a binding site found in an untranslated region of C20orf11, corresponding to BINDING SITE of FIG. 27A. FIG. 27D illustrates the complementarity of the nucleotide sequence of C20orf11 BINDING SITE, designated SEQ ID:468069, to the nucleotide sequence of GAM27 RNA of FIG. 27A, designated SEQ ID:20605. A further function of GAM27 is therefore inhibition of (C20orf11). Accordingly, utilities of GAM27 include diagnosis and treatment of diseases and clinical conditions with which C20orf11 is associated.

Reference is now made to FAF1 BINDING SITE. FAF1 is a target gene of GAM27, corresponding to GAM27-TARGET GENE of FIG. 27A. FAF1 BINDING SITE is a binding site found in an untranslated region of FAF1, corresponding to BINDING SITE of FIG. 27A. FIG. 27D illustrates the complementarity of the nucleotide sequence of FAF1 BINDING SITE, designated SEQ ID:552947, to the nucleotide sequence of GAM27 RNA of FIG. 27A, designated SEQ ID:20605. Yet a further function of GAM27 is therefore inhibition of (FAF1). Accordingly, utilities of GAM27 include diagnosis and treatment of diseases and clinical conditions with which FAF1 is associated.

Reference is now made to FLJ23878 BINDING SITE. FLJ23878 is a target gene of GAM27 corresponding to GAM27-TARGET GENE of FIG. 27A. FLJ23878 BINDING SITE is a binding site found in an untranslated region of FLJ23878, corresponding to BINDING SITE of FIG. 27A. FIG. 27D illustrates the complementarity of the nucleotide sequence of FLJ23878 BINDING SITE, designated SEQ ID:662582, to the nucleotide sequence of GAM27 RNA of FIG. 27A, designated SEQ ID:20605. Another function of GAM27 is therefore inhibition of (FLJ23878). Accordingly, utilities of GAM27 include diagnosis and treatment of diseases and clinical conditions with which FLJ23878 is associated.

Reference is now made to ODZ2 BINDING SITE. ODZ2 is a target gene of GAM27, corresponding to GAM27-TARGET GENE of FIG. 27A. ODZ2 BINDING SITE is a binding site found in an untranslated region of ODZ2, corresponding to BINDING SITE of FIG. 27A. FIG. 27D illustrates the complementarity of the nucleotide sequence of ODZ2 BINDING SITE, designated SEQ ID:900303, to the nucleotide sequence of GAM27 RNA of FIG. 27A, designated SEQ ID:20605. Yet another function of GAM27 is therefore inhibition of (ODZ2). Accordingly, utilities of GAM27 include diagnosis and treatment of diseases and clinical conditions with which ODZ2 is associated.

Reference is now made to LOC144231 BINDING SITE. LOC144231 is a target gene of GAM27, corresponding to GAM27-TARGET GENE of FIG. 27A. LOC144231 BINDING SITE is a binding site found in an untranslated region of LOC144231, corresponding to BINDING SITE of FIG. 27A. FIG. 27D illustrates the complementarity of the nucleotide sequence of LOC144231 BINDING SITE, designated SEQ ID:1069942, to the nucleotide sequence of GAM27 RNA of FIG. 27A, designated SEQ ID:20605. An additional function of GAM27 is therefore inhibition of (LOC144231). Accordingly, utilities of GAM27 include diagnosis and treatment of diseases and clinical conditions with which LOC144231 is associated.

Reference is now made to LOC158156 BINDING SITE. LOC158156 is a target gene of GAM27, corresponding to GAM27-TARGET GENE of FIG. 27A. LOC158156 BINDING SITE is a binding site found in an untranslated region of LOC158156, corresponding to BINDING SITE of FIG. 27A. FIG. 27D illustrates the complementarity of the nucleotide sequence of LOC158156 BINDING SITE, designated SEQ ID:1187897, to the nucleotide sequence of GAM27 RNA of FIG. 27A, designated SEQ ID:20605. A further function of GAM27 is therefore inhibition of (LOC158156). Accordingly, utilities of GAM27 include diagnosis and treatment of diseases and clinical conditions with which LOC158156 is associated.

GR1 GENE (Genomic Record 1 Gene) is a novel bioinformatically detected viral regulatory, non protein coding, RNA gene. The method by which GR1 was detected is described hereinabove with reference to FIGS. 6-15.

GR1 GENE encodes an RNA molecule, typically several hundred nucleotides long, designated GR1 PRECURSOR RNA.

GR1 PRECURSOR RNA folds spatially, as illustrated by GR1 FOLDED PRECURSOR RNA, into a plurality of what is known in the art as 'hair-pin' structures. The nucleotide sequence of GR1 PRECURSOR RNA comprises a plurality of segments, the first half of each such segment having a nucleotide sequence which is at least a partial inversed-reversed sequence of the second half thereof, thereby causing formation of a plurality of 'hairpin' structures, as is well known in the art.

GR1 FOLDED PRECURSOR RNA is naturally processed by cellular enzymatic activity, into at least 2 separate hairpin shaped RNA segments, each corresponding to GAM PRECURSOR RNA, designated GAM27 PRECURSOR and GAM26 PRECURSOR respectively.

The above mentioned GAM precursors are diced by Dicer of FIG. 8, yielding short RNA segments of about 22 nucleotides in length, each corresponding to GAM RNA of FIG. 8, designated GAM27 and GAM26 respectively.

GAM26 binds complimentarily to a binding site located in an untranslated region of GAM26-TARGET RNA, which binding site corresponds to BINDING SITE of FIG. 26A, thereby inhibiting translation of GAM26-TARGET RNA into GAM26-TARGET PROTEIN, both of FIG. 26A. The target genes of GAM26 and their respective functions, and accordingly the function and utility of GAM26 are described hereinabove with reference to FIG. 26D.

GAM27 in complimentarily to a binding site located in an untranslated region of GAM27-TARGET RNA, which binding site corresponds to BINDING SITE of FIG. 27A, thereby inhibiting translation of GAM27-TARGET RNA into GAM27-TARGET PROTEIN, both of FIG. 27A. The target genes of GAM27 and their respective functions, and accordingly the function and utility of GAM27 are described hereinabove with reference to FIG. 27D.

Reference is now made to FIG. 28A, which is a simplified diagram providing a conceptual explanation of the mode by which a novel bioinformatically detected gene, referred to here as Genomic Address Messenger 12026 (GAM12026) modulates expression of target genes thereof, the function and utility of which target genes is known in the art.

GAM12026 is a novel bioinformatically detected regulatory, non protein coding, micro RNA (miRNA) gene. The method by which GAM12026 was detected is described hereinabove with reference to FIGS. 6-15.

GAM12026 GENE and GAM12026-TARGET GENE are human genes contained in the human genome.

GAM12026 GENE encodes a GAM12026 PRECURSOR RNA. Similar to other miRNA genes, and unlike most ordinary genes, the RNA transcribed by GAM12026, GAM12026 PRECURSOR RNA, does not encode a protein.

GAM12026 PRECURSOR RNA folds onto itself, forming a 'hairpin structure' designated GAM12026 FOLDED PRECURSOR RNA. As is well known in the art, this 'hairpin structure', is typical of RNA encoded by miRNA genes, and is due to the fact that the nucleotide sequence of the first half of the RNA encoded by a miRNA gene is an accurate or partial inversed-reversed sequence of the nucleotide sequence of the second half thereof. By "inversed-reversed" is meant a sequence which is reversed and wherein each nucleotide is replaced by a complementary nucleotide, as is well known in the art (e.g. ATGGC is the inversed-reversed sequence of GCCAT).

An enzyme complex designated DICER COMPLEX, 'dices' the GAM12026 FOLDED PRECURSOR RNA into a single stranded ~22 nt long RNA segment, designated GAM12026 RNA. As is known in the art, 'dicing' of a hairpin structured RNA precursor product into a short ~22 nt RNA segment is catalyzed by an enzyme complex comprising an enzyme called Dicer together with other necessary proteins.

GAM12026-TARGET GENE encodes a corresponding messenger RNA, designated GAM12026-TARGET RNA. GAM12026-TARGET RNA comprises three regions, as is typical of mRNA of a protein coding gene: a 5' untranslated region, a protein coding region and a 3' untranslated region, designated 5'UTR PROTEIN CODING and 3'UTR respectively.

GAM12026 RNA binds complementarily to one or more binding sites located in untranslated regions of GAM12026-TARGET RNA. This complementary binding is due to the fact that the nucleotide sequence of GAM12026 RNA is an accurate or a partial inversed-reversed sequence of the nucleotide sequence of each of the binding sites. As an illustration, FIG. 28A shows 3 such binding sites, designated BINDING SITE-I, BINDING SITE-II and BINDING SITE-III respectively. It is appreciated that the number of binding sites shown in FIG. 28A is meant as an illustration only, and is not meant to be limiting—GAM12026 may have a different number of binding sites in untranslated regions of a GAM12026-TARGET RNA. It is further appreciated that while FIG. 28A depicts the binding sites in the 3'UTR region, this is meant as an example only—the binding sites may be located in the 3'UTR region, the 5'UTR region, or in both 3'UTR and 5'UTR regions.

The complementary binding of GAM12026 RNA to target gene binding sites such as BINDING SITE-I, BINDING SITE-II and BINDING SITE-III inhibits translation of GAM12026-TARGET RNA into GAM12026-TARGET PROTEIN. GAM12026-TARGET PROTEIN is therefore outlined by a broken line.

It is appreciated that GAM12026-TARGET GENE in fact represents a plurality of target genes of GAM12026. The mRNA of each of this plurality of target genes of GAM12026 comprises one more binding sites, each having a nucleotide sequence which is at least partly complementary to GAM12026 RNA, and which when bound by GAM12026 RNA causes inhibition of translation of one of a plurality of target proteins of GAM12026. Target genes of GAM12026 and their respective binding sites, are described hereinbelow with reference to FIG. 28D.

It is further appreciated by one skilled in the art that the mode of translational inhibition illustrated by FIG. 28A with specific reference to translational inhibition exerted by GAM12026 on one or more target genes of GAM12026, is in fact common to other known miRNA genes. As mentioned hereinabove with reference to the background section, although a specific complementary binding site has been demonstrated only for miRNA genes Lin-4 and Let-7, all other recently discovered miRNA genes are also believed by those skilled in the art to modulate expression of other genes by complementary binding, although specific complementary binding sites of these genes have not yet been found (Ruvkun G., 'Perspective: Glimpses of a tiny RNA world', Science 294, 779 (2001)).

It is yet further appreciated that specific functions, and accordingly utilities, of GAM12026 correlate with, and may be deduced from, the identity of the target genes which GAM12026 binds and inhibits, and the function of these target genes, as elaborated hereinbelow with reference to FIG. 28D.

Reference is now made to FIG. 28B which shows the nucleotide sequence of GAM12026 PRECURSOR RNA of FIG. 28A, designated SEQ ID:12003, and a probable (over 0.833813%) nucleotide sequence of GAM12026 RNA of FIG. 28A, designated SEQ ID:42079. The nucleotide sequence of SEQ ID:42079 is marked by an underline within the sequence of GAM12026 PRECURSOR RNA.

Reference is now made to FIG. 28C, which shows the secondary folding of GAM12026 PRECURSOR RNA, forming a 'hairpin structure' designated GAM12026 FOLDED PRECURSOR RNA, both of FIG. 28A. The nucleotide sequence of SEQ ID:42079, which is highly likely (>0.833813%) to be identical or highly similar to the nucleotide sequence of GAM12026 RNA is marked on GAM12026 FOLDED PRECURSOR RNA by a solid underline. It is appreciated that the complementary basepairing is not perfect, with 'bulges', as is well the art with respect to the RNA folding of all known miRNA genes.

Reference is now made to FIG. 28D, which is a table showing complementarity of binding sites of GAM12026, found in untranslated regions of target genes of GAM12026, to SEQ ID:42079, which is highly likely (>0.833813%) to be identical or highly similar to the nucleotide sequence of GAM12026 RNA of FIG. 28A. Each of the binding sites described hereinbelow corresponds to a binding site, such as BINDING SITE-I, BINDING SITE-II or BINDING SITE-III all of FIG. 28A, and each of the target genes of GAM12026 described hereinbelow corresponds to GAM TARGET GENE of FIG. 28A.

As mentioned hereinabove with reference to FIG. 28A a function of GAM12026 is inhibition of expression of target genes. It is appreciated that specific functions, and accordingly utilities, of GAM12026 correlate with, and may be deduced from, the identity of the target genes which GAM12026 binds and inhibits, and the function of these target genes, as elaborated hereinbelow.

Reference is now made to DDEF2 BINDING SITE. development and differentiation enhancing factor 2 (DDEF2 Accession NM_003887) is a target gene of GAM12026, corresponding to GAM12026-TARGET GENE of FIG. 28A. DDEF2 BINDING SITE is a binding site found in the 3 untranslated region of DDEF2, corresponding to a binding site such as BINDING SITE-I, BINDING SITE-II or BINDING SITE-III, all of FIG. 28A. FIG. 28D illustrates the complementarity of the nucleotide sequence of DDEF2 BINDING SITE, designated SEQ ID:228939, to the nucleotide sequence of GAM12026 RNA of FIG. 28A, designated SEQ ID:42079.

Accordingly, utilities of GAM12026 include diagnosis, prevention and treatment of diseases and clinical conditions associated with DDEF2. The function of DDEF2 and its association with various diseases and clinical conditions, has been established by previous studies, as described hereinabove with reference to FIG. 29D.

Reference is now made to ELK4 BINDING SITE. ELK4, ETS-domain protein (SRF accessory protein 1) (Accession NM_001973) is a target gene of GAM12026, corresponding to GAM12026-TARGET GENE of FIG. 28A. ELK4 BINDING SITE is a binding site found in the 3' untranslated region of ELK4, corresponding to a binding site such as BINDING SITE-I, BINDING SITE-II or BINDING SITE-III, all of FIG. 28A. FIG. 28D illustrates the complementarity of the nucleotide sequence of ELK4 BINDING SITE, designated SEQ ID:228939, to the nucleotide sequence of GAM12026 RNA of FIG. 28A, designated SEQ ID:42079.

Accordingly, utilities of GAM12026 include diagnosis, prevention and treatment of diseases and clinical conditions associated with ELK4. The function of ELK4 and its association with various diseases and clinical conditions, has been established by previous studies, as described hereinabove with reference to FIG. 22SD.

Reference is now made to MEF2C BINDING SITE. MADS box transcription enhancer factor 2, polypeptide C (myocyte enhancer factor 2C) (MEF2C, Accession NM_002397) is a target gene of GAM12026, corresponding to GAM12026-TARGET GENE of FIG. 28A. MEF2C BINDING SITE is a binding site found in the 3' untranslated region of MEF2C, corresponding to binding site such as BINDING SITE-I, BINDING SITE-II or BINDING SITE-III, all of FIG. 28A. FIG. 28D illustrates the complementarity of the nucleotide sequence of MEF2C BINDING SITE, designated SEQ ID:228939, to the nucleotide sequence of GAM12026 RNA of FIG. 28A, designated SEQ ID:42079.

Accordingly, utilities of GAM12026 include diagnosis, prevention and treatment of diseases and clinical conditions associated with MEF2C. The function of MEF2C and its association with various diseases and clinical conditions, has been established by previous studies, as described hereinabove with reference to FIG. 31D.

Reference is now made to MRE11A BINDING SITE. MRE11 meiotic recombination 11 homolog A (S. cerevisiae) (MRE11A, Accession NM_005590) is a target gene of GAM12026, corresponding to GAM12026-TARGET GENE of FIG. 28A. MRE11A BINDING SITE is a binding site found in the 3' untranslated region of MRE11A, corresponding to a binding site such as BINDING SITE-I, BINDING SITE-II or BINDING SITE-III, all of FIG. 28A. FIG. 28D illustrates the complementarity of the nucleotide sequence of MRE11A BINDING SITE, designated SEQ ID:228939, to the nucleotide sequence of GAM12026 RNA of FIG. 28A, designated SEQ ID:42079.

Accordingly, utilities of GAM12026 include diagnosis, prevention and treatment of diseases and clinical conditions associated with MRE11A. The function of MRE11A and its association with various diseases and clinical conditions, has been established by previous studies, as described hereinabove with reference to FIG. 225D.

Reference is now made to NEU3 BINDING SITE. sialidase 3 (membrane sialidase) (NEU3, Accession NM_006656) is a target gene of GAM12026, corresponding to GAM12026-TARGET GENE of FIG. 28A. NEU3 BINDING SITE is a binding site found in the 3' untranslated region of NEU3, corresponding to a binding site such as BINDING SITE-I, BINDING SITE-II or BINDING SITE-III, all of FIG. 28A FIG. 28D illustrates the complementarity of the nucleotide sequence of NEU3 BINDING SITE, designated SEQ ID:228939, to the nucleotide sequence of GAM12026 RNA of FIG. 28A, designated SEQ ID:42079.

Accordingly, utilities of GAM12026 include diagnosis, prevention and treatment of diseases and clinical conditions associated with NEU3. The function of NEU3 and its association with various diseases and clinical conditions, has been established by previous studies, as described hereinabove with reference to FIG. 225D.

Reference is now made to NLGN1 BINDING SITE. neuroligin 1 (NLGN1, Accession NM_014932) is a target gene of GAM12026, corresponding to GAM12026-TARGET GENE of FIG. 28A. NLGN1 BINDING SITE is a binding site found in the 3' untranslated region of NLGN1, corresponding to a binding site such as BINDING SITE-I, BINDING SITE-II or BINDING SITE-III, all of FIG. 28A. FIG. 28D illustrates the complementarity of the nucleotide sequence of NLGN1 BINDING SITE, designated SEQ ID:228939, to the nucleotide sequence of GAM12026 RNA of FIG. 28A, designated SEQ ID:42079.

Accordingly, utilities of GAM12026 include diagnosis, prevention and treatment of diseases and clinical conditions associated with NLGN1. The function of NLGN1 and its association with various diseases and clinical conditions, has been established by previous studies, as described hereinabove with reference to FIG. 136D.

Reference is now made to PODXL BINDING SITE. podocalyxin-like (PODXL, Accession NM_005397) is target gene of GAM12026, corresponding to GAM12026-TARGET GENE of FIG. 28A. PODXL BINDING SITE is a binding site found in the 3' untranslated region of PODXL, corresponding to a binding site such as BINDING SITE-I, BINDING SITE-II or BINDING SITE-III, all of FIG. 28A. FIG. 28D illustrates the complementarity of the nucleotide sequence of PODXL BINDING SITE, designated SEQ ID:228939, to the nucleotide sequence of GAM12026 RNA of FIG. 28A, designated SEQ ID:42079.

Accordingly, utilities of GAM12026 include diagnosis, prevention and treatment of diseases and clinical conditions associated with PODXL. The function of PODXL and its association with various diseases and clinical conditions, has been established by previous studies, as described hereinabove with reference to FIG. 160D.

Reference is now made to TDE1 BINDING SITE. tumor differentially expressed 1 (TDE1, Accession NM_006811) is a target gene of GAM12026, corresponding to GAM12026-TARGET GENE of FIG. 28A. TDE1 BINDING SITE is a binding site found in the 3' untranslated region of TDE1, corresponding to a binding site such as BINDING SITE-I, BINDING SITE-II or BINDING SITE-III, all of FIG. 28A. FIG. 28D illustrates the complementarity of the nucleotide sequence of TDE1 BINDING SITE, designated SEQ ID:228939, to the nucleotide sequence of GAM12026 RNA of FIG. 28A, designated SEQ ID:42079.

Accordingly, utilities of GAM12026 include diagnosis, prevention and treatment of diseases and clinical conditions associated with TDE1. The function of TDE1 and its association with various diseases and clinical conditions, has been established by previous studies, as described hereinabove with reference to FIG. 116D.

Reference is now made to AD-020 BINDING SITE. AD-020 (Accession XM_002161) is a target gene of GAM12026, corresponding to GAM12026-TARGET GENE of FIG. 28A. AD-020 BINDING SITE is a binding site found in the Three' untranslated region of AD-020, corresponding to a binding site such as BINDING SITE-I, BINDING SITE-II or BINDING SITE-III, all of FIG. 28A. FIG. 28D illustrates the complementarity of the nucleotide sequence of AD-020 BINDING SITE, designated SEQ ID:228939, to the nucleotide sequence of GAM12026 RNA of FIG. 28A, designated SEQ ID:42079.

A further function of GAM12026 is therefore inhibition of (AD-020). Accordingly, utilities of GAM12026 include diagnosis and treatment of diseases and clinical conditions with which AD-020 is associated.

Reference is now made to AKL3L BINDING SITE. AKL3L (Accession NM_016282) is a target gene of GAM12026, corresponding to GAM12026-TARGET GENE of FIG. 28A. AKL3 BINDING SITE is a binding site found in the Three' untranslated region of AKL3L, corresponding to a binding site such as BINDING SITE-I, BINDING SITE-II or BINDING SITE-III, all of FIG. 28A. FIG. 28D illustrates the complementarity of the nucleotide sequence of AKL3L BINDING SITE, designated SEQ ID:228939, to the nucleotide sequence of GAM12026 RNA of FIG. 28A, designated SEQ ID:42079.

Yet a further function of GAM12026 is therefore inhibition of (AKL3L). Accordingly, utilities of GAM12026 include diagnosis and treatment of diseases and clinical conditions with which AKL3L is associated.

Reference is now made to B3GNT1 BINDING SITE. UDP-GlcNAc:betaGal beta-1,3-N-acetylglucosaminyltransferase 1 (B3GNT1, Accession NM_006577) is a target gene of GAM12026, corresponding to GAM12026-TARGET GENE of FIG. 28A. B3GNT1 BINDING SITE is a binding site found in the Three' untranslated region of B3GNT1, corresponding to a binding site such as BINDING SITE-I, BINDING SITE-II or BINDING SITE-III, all of FIG. 28A. FIG. 28D illustrates the complementarity of the nucleotide sequence of B3GNT1 BINDING SITE, designated SEQ ID:228939, to the nucleotide sequence of GAM12026 RNA of FIG. 28A, designated SEQ ID:42079.

Another function of GAM12026 is therefore inhibition of UDP-GlcNAc:betaGal beta-1,3-N-acetylglucosaminyltransferase 1 (B3GNT1). Accordingly, utilities of GAM12026 include diagnosis and treatment of diseases and clinical conditions with which B3GNT1 is associated.

Reference is now made to CDC14B BINDING SITE. CDC14 cell division cycle 14 homolog B (*S. cerevisiae*) (CDC14B, Accession NM_003671) is a target gene of GAM12026, corresponding GAM12026-TARGET GENE of FIG. 28A. CDC14B BINDING SITE is a binding site found in the Three' untranslated region of CDC14B, corresponding to a binding site such as BINDING SITE-I, BINDING SITE-II or BINDING SITE-III, all of FIG. 28A. FIG. 28D illustrates the complementarity of the nucleotide sequence of CDC14B BINDING SITE designated SEQ ID:228939, to the nucleotide sequence of GAM12026 RNA of FIG. 28A, designated SEQ ID:42079.

Yet another function of GAM12026 is therefore inhibition of CDC14 cell division cycle 14 homolog B (S. cerevisiae) (CDC14B). Accordingly, utilities of GAM12026 include diagnosis and treatment of diseases and clinical conditions with which CDC14B is associated.

Reference is now made to DKFZP434J214 BINDING SITE. DKFZP434J214 (Accession XM_027639) is a target gene of GAM12026, corresponding to GAM12026-TARGET GENE of FIG. 28A. DKFZP434J214 BINDING SITE is a binding site found in the Three' untranslated region of DKFZP434J214, corresponding to a binding site such as BINDING SITE-I, BINDING SITE-II or BINDING SITE-III, all of FIG. 28A. FIG. 28D illustrates the complementarity of the nucleotide sequence of DKFZP434J214 BINDING SITE, designated SEQ ID:228939, to the nucleotide sequence of GAM12026 RNA of FIG. 28A, designated SEQ ID:42079.

An additional function of GAM12026 is therefore inhibition of (DKFZP434J214). Accordingly, utilities of GAM12026 include diagnosis and treatment of diseases and clinical conditions with which DKFZP434J214 is associated.

Reference is now made to DKFZP434N161 BINDING SITE. DKFZP434N161 (Accession XM_085920) is a target gene of GAM12026, corresponding to GAM12026-TARGET GENE of FIG. 28A. DKFZP434N161 BINDING SITE is a binding site found in the Three' untranslated region of DKFZP434N161, corresponding to a binding site such as BINDING SITE-I, BINDING SITE-II or BINDING SITE-III, all of FIG. 28A. FIG. 28D illustrates the complementarity of the nucleotide sequence of DKFZP434N161 BINDING SITE, designated SEQ ID:28939, to the nucleotide sequence of GAM12026 RNA of FIG. 28A, designated SEQ ID:42079.

A further function of GAM12026 is therefore inhibition of (DKFZP434N161). Accordingly, utilities of GAM12026 include diagnosis and treatment of diseases and clinical conditions with which DKFZP434N161 is associated.

Reference is now made to FLJ10103 BINDING SITE. FLJ10103 (Accession NM_017996) is a target gene of GAM12026, corresponding to GAM12026-TARGET GENE of FIG. 28A. FLJ10103 BINDING SITE is a binding site found in the Three' untranslated region of FLJ10103, corresponding to a binding site such as BINDING SITE-I, BINDING SITE-II or BINDING SITE-III, all of FIG. 28A. FIG. 28D illustrates the complementarity of the nucleotide sequence of FLJ10103 BINDING SITE, designated SEQ ID:228939, to the nucleotide sequence of GAM12026 RNA of FIG. 28A, designated SEQ ID:42079.

Yet a further function of GAM12026 is therefore inhibition of (FLJ10103). Accordingly, utilities of GAM12026 include diagnosis and treatment of diseases and clinical conditions with which FLJ10103 is associated.

Reference is now lade to HSPC195 BINDING SITE. HSPC195 (Accession XM_087785) is a target gene of GAM12026, corresponding to GAM12026-TARGET GENE of FIG. 28A. HSPC195 BINDING SITE is a binding site found in the Three' untranslated region of HSPC195, corresponding to a binding site such as BINDING SITE-I, BINDING SITE-II or BINDING SITE-III, all of FIG. 28A. FIG. 28D illustrates the complementarity of the nucleotide sequence of HSPC195 BENDING SITE, designated SEQ ID:228939, to the nucleotide sequence of GAM12026 RNA of FIG. 28A, designated SEQ ID:42079.

Another function of GAM12026 is therefore inhibition of (HSPC195). Accordingly, utilities of GAM12026 include diagnosis and treatment of diseases and clinical conditions with which HSPC195 is associated.

Reference is now made to KIAA0210 BINDING SITE. KIAA0210 (Accession NM_014744) is a target gene of GAM12026, corresponding to GAM12026-TARGET GENE of FIG. 28A. KIAA0210 BINDING SITE is a binding site found in the Three' untranslated region of KIAA0210, corresponding to a binding site such as BINDING SITE-I, BINDING SITE-II or BINDING SITE-III, all of FIG. 28A. FIG. 28D illustrates the complementarity of the nucleotide sequence of KIAA0210 BINDING SITE, designated SEQ ID:228939, to the nucleotide sequence of GAM12026 RNA of FIG. 28A, designated SEQ ID:42079.

Yet another function of GAM12026 is therefore inhibition of (KIAA0210). Accordingly, utilities of GAM12026 include diagnosis and treatment of diseases and clinical conditions with which KIAA0210 is associated.

Reference is now made to KIAA0747 BINDING SITE. KIAA0747 (Accession NM_015292) is a target gene of GAM12026, corresponding to GAM12026-TARGET GENE of FIG. 28A. KIAA0747 BINDING SITE is a binding site found in the Three' untranslated region of KIAA0747, corresponding to a binding site such as BINDING SITE-I, BINDING SITE-II or BINDING SITE-III, all of FIG. 28A. FIG. 28D illustrates the complementarity of the nucleotide sequence of KIAA0747 BINDING SITE, designated SEQ ID:228939, to the nucleotide sequence of GAM12026 RNA of FIG. 28A, designated SEQ ID:42079.

An additional function of GAM12026 is therefore inhibition of (KIAA0747). Accordingly, utilities of GAM12026 include diagnosis and treatment of diseases and clinical conditions with which KIAA0747 is associated.

Reference is now made to KIAA0977 BINDING SITE. KIAA0977 (Accession NM_014900) is a target gene of GAM12026, corresponding to GAM12026-TARGET GENE of FIG. 28A. KIAA0977 BENDING SITE is a binding site found in the Three' untranslated region of KIAA0977, corresponding to a binding site such as BINDING SITE-I, BINDING SITE-II or BINDING SITE-III, all of FIG. 28A. FIG. 28D illustrates the complementarity of the nucleotide sequence of KIAA0977 BINDING SITE, designated SEQ ID:228939, to the nucleotide sequence of GAM12026 RNA of FIG. 28A, designated SEQ ID:42079.

A further function of GAM12026 is therefore inhibition of (KIAA0977). Accordingly, utilities of GAM12026 include diagnosis and treatment of diseases and clinical conditions with which KIAA0977 is associated.

Reference is now made to MIC2L1 BINDING SITE. MIC2 like 1 (MIC2L1, Accession NM_031462) is a target gene of GAM12026, corresponding to GAM12026-TARGET GENE of FIG. 28A. MIC2L1 BINDING SITE is a binding site found in the Three' untranslated region of MIC2L1, corresponding to a binding site such as BINDING SITE-I, BINDING SITE-II or BINDING SITE-III, all of FIG. 28A. FIG. 28D illustrates the complementarity of the nucleotide sequence of MIC2L1 BINDING SITE, designated SEQ ID:228939, to the nucleotide sequence of GAM12026 RNA of FIG. 28A, designated SEQ ID:42079.

Yet a further function of GAM12026 is therefore inhibition of MIC2 like 1 (MIC2L1). Accordingly, utilities of GAM12026 include diagnosis and treatment of diseases and clinical conditions with which MIC2L1 is associated.

Reference is now made to LOC143187 BINDING SITE. LOC143187 (Accession NM_145206) is a target gene of GAM12026, corresponding to GAM12026-TARGET GENE of FIG. 28A. LOC143187 BINDING SITE is a binding site found in the Three' untranslated region of LOC143187, corresponding to a binding site such as BINDING SITE-I, BINDING SITE-II or BINDING SITE-III, all of FIG. 28A. FIG. 28D illustrates the complementarity of the nucleotide sequence of LOC143187 BINDING SITE, designated SEQ ID:228939, to the nucleotide sequence of GAM12026 RNA of FIG. 28A, designated SEQ ID:42079.

Another function of GAM12026 is therefore inhibition of (LOC143187). Accordingly, utilities of a GAM12026 include diagnosis and treatment of diseases and clinical conditions with which LOC143187 is associated.

Reference is now made to LOC148604 BINDING SITE. LOC148604 (Accession XM_086249) is a target gene of GAM12026, corresponding to GAM12026-TARGET GENE of FIG. 28A. LOC148604 BINDING SITE is a binding site found in the Three' untranslated region of LOC148604, corresponding to a binding site such as BINDING SITE-I, BINDING SITE-II or BINDING SITE-III, all of FIG. 28A. FIG. 28D illustrates the complementarity of the nucleotide sequence of LOC148604 BINDING SITE, designated SEQ ID:228939, to the nucleotide sequence of GAM12026 RNA of FIG. 28A, designated SEQ ID:42079.

Yet another function of GAM12026 is therefore inhibition of (LOC148604). Accordingly, utilities of GAM12026 include diagnosis and treatment of diseases and clinical conditions with which LOC148604 is associated.

Reference is now made to LOC151248 BINDING SITE. LOC151248 (Accession XM_087143) is a target gene of GAM12026, corresponding to GAM12026-TARGET GENE of FIG. 28A. LOC151248 ENDING SITE is a binding site found in the Three' untranslated region of LOC151248, corresponding to a binding site such as BINDING SITE-I, BINDING SITE-II or BINDING SITE-III, all of FIG. 28A. FIG. 28D illustrates the complementarity of the nucleotide sequence of LOC151248 BINDING SITE, designated SEQ ID:228939, to the nucleotide sequence of GAM12026 RNA of FIG. 28A, designated SEQ ID:42079.

An additional function of GAM12026 is therefore inhibition of (LOC151248). Accordingly, utilities of GAM12026 include diagnosis and treatment of diseases and clinical conditions with which LOC151248 is associated.

Reference is now made to LOC253221 BINDING SITE. LOC253221 (Accession XM_173010) is a target gene of GAM12026, corresponding to GAM12026-TARGET GENE of FIG. 28A. LOC253221 BINDING SITE is a binding site found in the Three' untranslated region of LOC253221, corresponding to a binding site such as BINDING SITE-I, BINDING SITE-II or BINDING SITE-III, all of FIG. 28A. FIG. 28D illustrates the complementarity of the nucleotide sequence of LOC253221 BINDING SITE, designated SEQ ID:228939, to the nucleotide sequence of GAM12026 RNA of FIG. 28A, designated SEQ ID:42079.

A further function GAM12026 is therefore inhibition of (LOC253221). Accordingly, utilities of GAM12026 include diagnosis and treatment of diseases and clinical conditions with which LOC253221 is associated.

Reference is now made to LOC253927 BINDING SITE. LOC253927 (Accession XM_170785) is a target gene of GAM12026, corresponding to GAM12026-TARGET GENE of FIG. 28A. LOC253927 BINDING SITE is a binding site found in the Three' untranslated region of LOC253927, corresponding to a binding site such as BINDING SITE-I, BINDING SITE-II or BINDING SITE-III, all of FIG. 28A. FIG. 28D illustrates the complementarity of the nucleotide sequence of LOC253927 BINDING SITE, designated SEQ ID:228939, to the nucleotide sequence of GAM12026 RNA of FIG. 28A, designated SEQ ID:42079.

Yet a further function of GAM12026 is therefore inhibition of (LOC253927). Accordingly, utilities of GAM12026 include diagnosis and treatment of diseases and clinical conditions with which LOC253927 is associated.

It is appreciated by persons skilled in the art that the present invention is not limited by what has been particularly shown and described hereinabove. Rather the scope of the present invention includes both combinations and sub-combinations of the various features describe hereinabove as well as variations and modifications which would occur to persons skilled in the art upon reading the specifications and which are not in the prior art.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07250496B2). An electronic copy of the "Sequence Listing" will also be available from the USPTO upon request and payment of the fee set forth in 37 CFR 1.19(b)(3).

What is claimed is:

1. An isolated nucleic acid wherein the sequence of the nucleic acid consists of the sequence of SEQ ID NO: 12003.

2. A vector comprising, a human insert wherein an insert consists of the nucleic acid of claim 1.

3. An isolated first nucleic acid that is the complement of the nucleic acid according to claim 1.

4. A vector comprising an insert, wherein an insert is the nucleic acid of claim 3.

* * * * *